US009617268B2

(12) United States Patent
Woll et al.

(10) Patent No.: US 9,617,268 B2
(45) Date of Patent: Apr. 11, 2017

(54) COMPOUNDS FOR TREATING SPINAL MUSCULAR ATROPHY

(71) Applicants: PTC Therapeutics Inc., South Plainfield, NJ (US); F. Hoffmann-La Roche AG, Basel (CH)

(72) Inventors: Matthew G. Woll, Dunellen, NJ (US); Guangming Chen, Bridgewater, NJ (US); Soongyu Choi, Belle Mead, NJ (US); Amal Dakka, Whitehouse Station, NJ (US); Song Huang, San Leandro, NJ (US); Gary Mitchell Karp, Princeton Junction, NJ (US); Chang-Sun Lee, Belle Mead, NJ (US); Chunshi Li, East Brunswick, NJ (US); Jana Narasimhan, Scotch Plains, NJ (US); Nikolai Naryshkin, East Brunswick, NJ (US); Sergey Paushkin, Belle Mead, NJ (US); Hongyan Qi, Plainsboro, NJ (US); Anthony A. Turpoff, Hillsborough, NJ (US); Marla L. Weetall, Morristown, NJ (US); Ellen Welch, Califon, NJ (US); Tianle Yang, Mountainside, NJ (US); Nanjing Zhang, Princeton, NJ (US); Xiaoyan Zhang, Belle Mead, NJ (US); Xin Zhao, Belle Mead, NJ (US); Emmanuel Pinard, Linsdort (FR); Hasane Ratni, Habsheim (FR)

(73) Assignees: PTC Therapeutics, Inc., South Plainfield, NJ (US); F. Hoffmann-La Roche AG, Basel (CH)

( * ) Notice: Subject to any disclaimer, the term of this patent is extended or adjusted under 35 U.S.C. 154(b) by 0 days.

(21) Appl. No.: 14/369,294

(22) PCT Filed: Dec. 28, 2012

(86) PCT No.: PCT/US2012/071899
§ 371 (c)(1),
(2) Date: Jun. 27, 2014

(87) PCT Pub. No.: WO2013/101974
PCT Pub. Date: Jul. 4, 2013

(65) Prior Publication Data
US 2015/0119380 A1 Apr. 30, 2015

Related U.S. Application Data

(60) Provisional application No. 61/582,064, filed on Dec. 30, 2011.

(51) Int. Cl.
*A01N 43/00* (2006.01)
*C07D 487/04* (2006.01)
*C07D 405/14* (2006.01)
*C07D 413/14* (2006.01)
*C07D 311/16* (2006.01)
*C07D 405/04* (2006.01)
*C07D 405/12* (2006.01)
*C07D 413/04* (2006.01)
(Continued)

(52) U.S. Cl.
CPC ......... *C07D 487/04* (2013.01); *C07D 231/12* (2013.01); *C07D 311/16* (2013.01); *C07D 311/18* (2013.01); *C07D 405/04* (2013.01); *C07D 405/12* (2013.01); *C07D 405/14* (2013.01); *C07D 413/04* (2013.01); *C07D 413/14* (2013.01); *C07D 417/04* (2013.01); *C07D 417/14* (2013.01); *C07D 471/04* (2013.01); *C07D 491/04* (2013.01); *C07D 495/04* (2013.01); *C07D 513/04* (2013.01); *C07D 519/00* (2013.01)

(58) Field of Classification Search
CPC .................................................. C07D 487/04
USPC ..................................................... 514/210.21
See application file for complete search history.

(56) References Cited

U.S. PATENT DOCUMENTS 3,242,177 A    3/1966  Carl-wolfgang et al.
3,311,636 A *  3/1967  Moffett ................ C07D 405/04
                                                              252/392
(Continued)

FOREIGN PATENT DOCUMENTS

CN    1448431    * 10/2003    ............... A61K 8/49
CN    1448431 A    10/2003
(Continued)

OTHER PUBLICATIONS

Sreenivasulu, Proceedings—Indian Academy of Sciences, Section A (1974), 79(1), 41-7.*
Sreenivasulu, Proceedings—Indian Academy of Sciences, Section A (1973), 78(4), 159-68.*
Steyer Applied Physics (Berlin) (1975), 7(2), 113-22.*
Czerney, Journal fuer Praktische Chemie (Leipzig) (1982), 324(2), 255-66.*
(Continued)

*Primary Examiner* — Nizal Chandrakumar
(74) *Attorney, Agent, or Firm* — Jones Day

(57) ABSTRACT

Provided herein are compounds, compositions thereof and uses therewith for treating spinal muscular atrophy. In a specific embodiment, provided herein are compounds of a form that may be used to modulate the inclusion of exon 7 of SMN2 into mRNA that is transcribed from the SMN2 gene. In another specific embodiment, provided herein are compounds of a form that may be used to modulate the inclusion of exon 7 of SMN1 into mRNA that is transcribed from the SMN1 gene. In yet another embodiment, provided herein are compounds of a form that may be used to modulate the inclusion of exon 7 of SMN1 and SMN2 into mRNA that is transcribed from the SMN1 and SMN2 genes, respectively.

5 Claims, 23 Drawing Sheets

(51) Int. Cl.
    *C07D 417/04*     (2006.01)
    *C07D 417/14*     (2006.01)
    *C07D 471/04*     (2006.01)
    *C07D 491/04*     (2006.01)
    *C07D 495/04*     (2006.01)
    *C07D 513/04*     (2006.01)
    *C07D 519/00*     (2006.01)
    *C07D 231/12*     (2006.01)
    *C07D 311/18*     (2006.01)

(56) References Cited

U.S. PATENT DOCUMENTS

| | | | |
|---|---|---|---|
| 3,646,052 A | | 2/1972 | Otto et al. |
| 3,681,397 A | * | 8/1972 | Knupfer et al. ............ 549/288 |
| 4,141,900 A | | 2/1979 | Schlapfer |
| 4,284,787 A | * | 8/1981 | Knupfer et al. ............ 548/256 |
| 4,404,389 A | | 9/1983 | Vamvakaris et al. |
| 4,426,530 A | | 1/1984 | Berneth et al. |
| 5,194,393 A | | 3/1993 | Hugl et al. |
| 7,569,337 B2 | * | 8/2009 | Auberson ............ C07D 405/04 435/1.1 |
| 2006/0205741 A1 | | 9/2006 | Zhang et al. |
| 2007/0208033 A1 | * | 9/2007 | Yamazaki et al. ....... 514/255.05 |
| 2010/0004233 A1 | | 1/2010 | Iikura et al. |
| 2010/0035279 A1 | | 2/2010 | Gubernator et al. |
| 2011/0086833 A1 | | 4/2011 | Paushkin et al. |

FOREIGN PATENT DOCUMENTS

| | | | | |
|---|---|---|---|---|
| DE | 1020636 B | | 12/1957 | |
| DE | 2950291 | * | 12/1979 | ............ C07D 417/04 |
| DE | WO 2009124800 | * | 10/2009 | ............ A61K 8/49 |
| EP | 0030703 A1 | | 6/1981 | |
| EP | 0448241 | | 9/1991 | |
| FR | 2361680 | | 3/1978 | |
| GB | 991202 A | | 5/1965 | |
| JP | S4891129 | | 11/1973 | |
| JP | S56140990 | | 11/1981 | |
| JP | 7-3179 A | | 1/1995 | |
| JP | 0700317 | * | 6/1995 | ............ C09B 67/40 |
| WO | WO 03074519 | | 9/2003 | |
| WO | WO 2009/151546 | | 5/2009 | |
| WO | WO 2010/019236 | | 8/2009 | |
| WO | WO 2009/124800 A1 | | 10/2009 | |
| WO | WO 2010/049044 A1 | | 5/2010 | |

OTHER PUBLICATIONS

U.S. Appl. No. 14/373,937, filed Jul. 23, 2014, Chen et al.
U.S. Appl. No. 14/377,531, filed Aug. 8, 2014, Qi et al.
U.S. Appl. No. 14/380,385, filed Aug. 22, 2014, Lee et al.
U.S. Appl. No. 14/386,524, filed Sep. 19, 2014, Yang et al.
Le et al., (2005) "SMND7, the major product of the centromeric survival motor neuron (SMN2) gene, extends survival in mice with spinal muscular atrophy and associates with full-length SMN," *Human Molecular Genetics*, vol. 14(6) pp. 845-857 (2005).
Passini et al., (2001) "Antisense Oligonucleotides Delivered to the Mouse CNS Ameliorate Symptoms of Severe Spinal Muscular Atrophy," Sci Transl Med., vol. 3(72) (2001).
Hua et al., (2012) "Peripheral SMN restoration is essential for long-term rescue of a severe SMA mouse model," Nature, vol. 478(7367): pp. 123-126 (2012).
Coady et al., (2010) "Trans-splicing-mediated improvement in a severe mouse model of spinal muscular atrophy," J Neurosci., vol. 30(1), pp. 126-130 (2010).
Greene et al, (1991) Protective Groups in Organic Synthesis (1991), Wiley, New York.
Higuchi and W. Stella, (1987) "Pro-drugs as Novel Delivery Systems," vol. 14 of the A.C.S. Symposium Series, and in Bioreversible Carriers in Drug Design, ed. Edward B. Roche, American Pharmaceutical Association and Pergamon Press (1987).
Liu et al., (1996) "A novel nuclear structure containing the survival of motor neurons protein," EMBO J., vol. 15(14), pp. 3555-3565 (1996).
PCT International Search Report Issued Apr. 18, 2013 in connection with PCT/US2012/071899.
PCT International Preliminary Report Issued Jul. 10, 2014 in connection with PCT/US2012/071899.
Czerney et al., "Heterocyclisch Substituierte Cumarine Aus Beta-Chloropropeniminiumsalzen Heterocyclic Substituted Coumarines From Beta-Chloropropeniminium Salts," Journal Fuer Praktische Chemie, Wiley VCH, Weinheim, DE, vol. 324, No. 2, Jan. 1, 1982, pp. 255-266, XP009045598 (English abstract included).
English translation of Chinese Office Action for Chinese Patent Application Serial No. 201280071056.5 (PCT/US2012/071899) (This Office Action cites references G01, H01-H04 and I02 listed here.).
"Medicinal Chemistry", Chief editor is Qidong You, Chemical Industry Press, Jul. 2008, pp. 27-29.

* cited by examiner tagcttcttacccgtactccaccgttggcagcacgatcgcacgtcccacgtgaaccattggtaaaccctgatgggatccataattcccccacc
acctcccatatgtccagattctcttgatgatgctgatgctttgggaagtatgttaatttcatggtacatgagtggctatcatactggctattatatgg
taagtaatcactcagcatcttttcctgacaatttttttgtagttatgtgactttgttttgtaaatttataaaatactacttgcttctctctttatattactaaa
aaataaaaataaaaaaatacaactgtctgaggcttaaattactcttgcattgtccctaagtataattttagttaattttaaaaagctttcatgctattgt
tagattattttgattatacacttttgaattgaaattatactttttctaaataatgttttaatctctgatttgaaattgattgtagggaatggaaaagatggg
ataattttcataaatgaaaaatgaaattctttttttttttttttttttttgagacggagtcttgctctgttgcccaggctggagtgcaatggcgtgatct
tggctcacagcaagctctgcctcctggattcacgccattctcctgcctcagcctcagaggtagctgggactacaggtgcctgccaccacgcc
tgtctaattttttgtattttttgtaaagacagggtttcactgtgttagccaggatggtctcaatctcctgaccccgtgatccacccgcctcggcctt
ccaagagaaatgaaattttttaatgcacaaagatctggggtaatgtgtaccacattgaaccttggggagtatggcttcaaacttgtcactttata
cgttagtctcctacggacatgttctattgtattttagtcagaacatttaaaattatttatttttatttttttttttttttgagacggagtctcgctctgt
cacccaggctggagtacagtggcgcagtctcggctcactgcaagctccgcctcccgggttcacgccattctcctgcctcagcctctccgagt
agctgggactacaggcgcccgccaccacgcccggctaattttttttatttttagtagagacggggtttcaccgtggtctcgatctcctgacctc
gtgatccacccgcctcggcctcccaaagtgctgggattacaagcgtgagccaccgcgcccggcctaaaattatttttaaaagtaagctcttgt
gccctgctaaaattatgatgtgatattgtaggcacttgtattttagtaaattaatatagaagaaacaactgacttaaaggtgtatgtttttaaatgta
tcatctgtgtgtgcccccattaatattcttatttaaaagttaaggccagacatggtggcttacaactgtaatcccaacagtttgtgaggccgaggc
aggcagatcacttgaggtcaggagtttgagaccagcctggccaacatgatgaaaccttgtctctactaaaaataccaaaaaaaatttagcca
ggcatggtggcacatgcctgtaatcccagctacttgggaggctgtggcaggaaaattgctttaatctgggaggcagaggttgcagtgagttg
agattgtgccactgcactccacccttggtgacagagtgagattccatctcaaaaaaagaaaaaggcctggcacggtggctcacacctataat
cccagtactttgggaggtagaggcaggtggatcacttgaggttaggagttcaggaccagcctggccaacatggtgactactccatttctacta
aatacacaaaacttagcccagtggcgggcagttgtaatcccagctacttgagaggttgaggcaggagaatcacttgaacctgggaggcag
aggttgcagtgagccgagatcacaccgctgcactctagcctggccaacagagtgagaatttgcggagggaaaaaaaagtcacgcttcagt
tgttgtagtataaccttggtatattgtatgtatcatgaattcctcatttaatgaccaaaaagtaataaatcaacagcttgtaatttgttttgagatcag
ttatctgactgtaacactgtaggcttttgtgttttttaaattatgaaatatttgaaaaaaatacataatgtatatataaagtattggtataatttatgttct
aaataactttcttgagaaataattcacatggtgtgcagtttacctttgaaagtatacaagttggctgggcacaatggctcacgcctgtaatccca
gcactttgggaggccagggcaggtggatcacgaggtcaggagatcgagaccatcctggctaacatggtgaaaccccgtctctactaaaag
tacaaaaacaaattagccgggcatgttggcgggcaccttttgtcccagctgctcgggaggctgaggcaggagagtggcgtgaacccagg
aggtggagcttgcagtgagccgagattgtgccagtgcactccagcctgggcgacagagcgagactctgtctcaaaaaataaaataaaaaa
gaaagtatacaagtcagtggttttggttttcagttatgcaaccatcactacaatttaagaacattttcatcaccccaaaaagaaaccctgttaccttcattttccccagccctaggcagtcagtacactttctgtctctatgaatttgtctattttagatattatatataaacggaattatacgatatgtggtctttt
gtgtctggcttctttcacttagcatgctattttcaagattcatccatgctgtagaatgcaccagtactgcattccttcttattgctgaatattctgttgtt
tggttatatcacatttatccattcatcagttcatggacatttaggttgttttattttgggctataatgaataatgttgctatgaacattcgtttgtgttc
tttttgtttttttggtttttttgggtttttttgtttttgttttgttttgagacagtcttgctctgtctcctaagctggagtgcagtggcatgatcttggcttact
gcaagctctgcctcccgggttcacaccattctcctgcctcagcccgacaagtagctgggactacaggcgtgtgccaccatgcacggctaatt
ttttgtattttagtagagatggggtttcaccgtgttagccaggatggtctcgatctcctgacctcgtgatctgcctgccaggcctcccaaagtg
ctgggattacaggcgtgagccactgcacctggcctaagtgttttaatacgtcattgccttaagctaacaattcttaacctttgttctactgaagc
cacgtggttgagataggctctgagtctagcttttaacctctatctttttgtcttagaaatctaagcagaatgcaaatgactaagaataatgttgttga
aataacataaaataggttataactttgatactcattagtaacaaatctttcaatacatcttacggtctgttaggtgtagattagtaatgaagtgggaa
gccactgcaagctagtatacatgtagggaaagatagaaagcattgaagccagaagagagacagaggacatttgggctagatctgacaaga
aaaacaaatgtttagtattaattttgactttaaatttttttttttatttagtgaatactggtgtttaatggtctcattttaataagtatgacacaggtagttt
aaggtcatatatttatttgatgaaaataaggtataggccgggcacggtggctcacacctgtaatcccagcactttgggaggccgaggcagg
cggatcacctgaggtcgggagttagagactagcctcaacatggagaaaccccgtctctactaaaaaaaatacaaaattaggcgggcgtggt

Figure 2a ggtgcatgcctgtaatcccagctactcaggaggctgaggcaggagaattgcttgaacctgggaggtggaggttgcggtgagccgagatca
cctcattgcactccagcctgggcaacaagagcaaaactccatctcaaaaaaaaaaaataaggtataagcgggctcaggaacatcattgga
catactgaaagaagaaaaatcagctgggcgcagtggctcacgccggtaatcccaacactttgggaggccaaggcaggcgaatcacctga
agtcgggagttccagatcagcctgaccaacatggagaaaccctgtctctactaaaaatacaaaactagccgggcatggtggcgcatgcctg
taatcccagctacttgggaggctgaggcaggagaattgcttgaaccgagaaggcggaggttgcggtgagccaagattgcaccattgcact
ccagcctgggcaacaagagcgaaactccgtctcaaaaaaaaaaggaagaaaaatattttttaaattaattagtttatttatttttaagatggagt
tttgccctgtcacccaggctggggtgcaatggtgcaatctcggctcactgcaacctccgcctcctgggttcaagtgattctcctgcctcagctt
cccgagtagctgtgattacagccatatgccaccacgcccagccagttttgtgttttgttttgttttttgttttttttttttgagagggtgtcttgctctgt
cccccaagctggagtgcagcggcgcgatcttggctcactgcaagctctgcctcccaggttcacaccattctcttgcctcagcctcccgagta
gctgggactacaggtgcccgccaccacacccggctaattttttgtgttttagtagagatggggtttcactgtgttagccaggatggtctcgat
ctcctgaccttttgatccacccgcctcagcctccccaagtgctgggattataggcgtgagccactgtgcccggcctagtcttgtatttttagtag
agtcgggatttctccatgttggtcaggctgttctccaaatccgacctcaggtgatccgcccgccttggcctccaaaagtgcaaggcaaggcat
tacaggcatgagccactgtgaccggcaatgttttaaatttttacatttaaattttattttttagagaccaggtctcactctattgctcaggctggag
tgcaagggcacattcacagctcactgcagccttgacctccagggctcaagcagtcctctcacctcagtttcccgagtagctgggactacagt
gataatgccactgcacctggctaattttttattttatttatttattttttttgagacagagtcttgctctgtcacccaggctggagtgcagtggtgtaa
atctcagctcactgcagcctccgcctcctgggttcaagtgattctcctgcctcaacctcccaagtagctgggattagaggtccccaccaccat
gcctggctaattttttgtactttcagtagaaacggggttttgccatgttggccaggctgttctcgaactcctgagctcaggtgatccaactgtctc
ggcctcccaaagtgctgggattacaggcgtgagccactgtgcctagcctgagccaccacgccggcctaattttttaattttttgtagagacag
ggtctcattatgttgcccagggtggtgtcaagctccaggtctcaagtgatcccctacctccgcctcccaaagttgtgggattgtaggcatga
gccactgcaagaaaacccttaactgcagcctaataattgttttctttgggataacttttaaagtacattaaaagactatcaacttaatttctgatcatat
tttgttgaataaaataagtaaaatgtcttgtgaaacaaaatgcttttaacatccatataaagctatctatatatagctatctatatctatatagctattt
tttttaacttccttttattttccttacagggttttagacaaaatcaaaaagaaggaaggtgctcacattccttaaatataaggagtaagtctgccagc
attatgaaagtgaatcttacttttgtaaaactttatggtttgtggaaaacaaatgttttgaacatttaaaaagttcagatgttagaaagttgaaaggt
taatgtaaaacaatcaatattaaagaattttgatgccaaaactattagataaaaggttaatctacatccctactagaattctcatacttaactggttg
gttgtgtggaagaaacatactttcacaataaagagctttaggatatgatgccatttatatcactagtaggcagaccagcagactttttttattgtg
atatgggataacctaggcatactgcactgtacactctgacatatgaagtgctctagtcaagtttaactggtgtccacagaggacatggtttaact
ggaattcgtcaagcctctggttctaatttctcatttgcaggaaatgctggcatagagcagcacggatccgaagacgccaaaaacataaagaa
aggcccggcgccattctatcctctagaggatggaaccgctggagagcaactgcataaggctatgaagagatacgccctggttcctggaac
aattgcttttacagatgcacatatcgaggtgaacatcacgtacgcggaatacttcgaaatgtccgttcggttggcagaagctatgaaacgatat
gggctgaatacaaatcacagaatcgtcgtatgcagtgaaaactctcttcaattctttatgccggtgttgggcgcgttatttatcggagttgcagtt
gcgcccgcgaacgacatttataatgaacgtgaattgctcaacagtatgaacatttcgcagcctaccgtagtgtttgtttcaaaaaggggttgc
aaaaaattttgaacgtgcaaaaaaaattaccaataatccagaaaattattatcatggattctaaaacggattaccagggatttcagtcgatgtac
acgttcgtcacatctcatctacctcccggttttaatgaatacgattttgtaccagagtcctttgatcgtgacaaaacaattgcactgataatgaatt
cctctggatctactgggttacctaagggtgtggcccttccgcatagaactgcctgcgtcagattctcgcatgccagagatcctattttggcaat
caaatcattccggatactgcgattttaagtgttgttccattccatcacggttttggaatgtttactacactcggatatttgatatgtggatttcgagtc
gtcttaatgtatagatttgaagaagagctgtttttacgatcccttcaggattacaaaattcaaagtgcgttgctagtaccaacccctattttcattcttc
gccaaaagcactctgattgacaaatacgatttatctaatttacacgaaattgcttctggggggcgcacctctttcgaaagaagtcggggaagcg
gttgcaaaacgcttccatcttccaggatacgacaaggatatgggctcactgagactacatcagctattctgattacacccgagggggatgat
aaaccgggcgcggtcggtaaagttgttccatttttgaagcgaaggttgtggatctggataccgggaaaacgctgggcgttaatcagagagg
cgaattatgtgtcagaggacctatgattatgtccggttatgtaaacaatccggaagcgaccaacgccttgattgacaaggatggatggctaca
ttctggagacatagcttactgggacgaagacgaacacttcttcatagttgaccgcttgaagtctttaattaaatacaaaggatatcaggtggcc cccgctgaattggaatcgatattgttacaacaccccaacatcttcgacgcgggcgtggcaggtcttcccgacgatgacgccggtgaacttcc
cgccgccgttgttgttttggagcacggaaagacgatgacggaaaaagagatcgtggattacgtcgccagtcaagtaacaaccgcgaaaaa
gttgcgcggaggagttgtgtttgtggacgaagtaccgaaaggtcttaccggaaaactcgacgcaagaaaaatcagagagatcctcataaag
gccaagaagggcggaaagtccaaattgcgcggccgctaaatcgaaagtacaggactagccttcctagcaaccgcgggctgggagtctga
gacatcactcaagatatatgctcggtaacgtatgctctagccatctaactattccctatgtcttataggg

SEQ ID NO. 21

Figure 2a (continued)

SEQUENCE LISTING

```
<160> NUMBER OF SEQ ID NOS: 21

<210> SEQ ID NO 1
<211> LENGTH: 19
<212> TYPE: DNA
<213> ORGANISM: Artificial Sequence
<220> FEATURE:
<223> OTHER INFORMATION: SMN Forward Primer A

<400> SEQUENCE: 1
gaaggaaggt gctcacatt                                              19

<210> SEQ ID NO 2
<211> LENGTH: 22
<212> TYPE: DNA
<213> ORGANISM: Artificial Sequence
<220> FEATURE:
<223> OTHER INFORMATION: SMN Reverse Primer A

<400> SEQUENCE: 2
tctttatgtt tttggcgtct tc                                          22

<210> SEQ ID NO 3
<211> LENGTH: 26
<212> TYPE: DNA
<213> ORGANISM: Artificial Sequence
<220> FEATURE:
<223> OTHER INFORMATION: SMN Forward Probe A

<400> SEQUENCE: 3
```

```
aaggagaaat gctggcatag agcagc                                          26

<210> SEQ ID NO 4
<211> LENGTH: 21
<212> TYPE: DNA
<213> ORGANISM: Artificial Sequence
<220> FEATURE:
<223> OTHER INFORMATION: hGAPDH Forward Probe

<400> SEQUENCE: 4
cgcctggtca ccagggctgc t                                               21

<210> SEQ ID NO 5
<211> LENGTH: 21
<212> TYPE: DNA
<213> ORGANISM: Artificial Sequence
<220> FEATURE:
<223> OTHER INFORMATION: hGAPDH Forward Primer

<400> SEQUENCE: 5
caacggattt ggtcgtattg g                                               21

<210> SEQ ID NO 6
<211> LENGTH: 25
<212> TYPE: DNA
<213> ORGANISM: Artificial Sequence
<220> FEATURE:
<223> OTHER INFORMATION: hGAPDH Reverse Primer

<400> SEQUENCE: 6
tgatggcaac aatatccact ttacc                                           25

<210> SEQ ID NO 7
<211> LENGTH: 27
<212> TYPE: DNA
<213> ORGANISM: Artificial Sequence
<220> FEATURE:
<223> OTHER INFORMATION: SMN FL Forward Primer B

<400> SEQUENCE: 7
gctcacattc cttaaattaa ggagaaa                                         27

<210> SEQ ID NO 8
<211> LENGTH: 28
<212> TYPE: DNA
<213> ORGANISM: Artificial Sequence
<220> FEATURE:
<223> OTHER INFORMATION: SMN delta-7 Forward Primer B

<400> SEQUENCE: 8
tggctatcat actggctatt atatggaa                                        28

<210> SEQ ID NO 9
<211> LENGTH: 24
<212> TYPE: DNA
<213> ORGANISM: Artificial Sequence
<220> FEATURE:
<223> OTHER INFORMATION: SMN Reverse Primer B

<400> SEQUENCE: 9
tccagatctg tctgatcgtt tctt                                            24

<210> SEQ ID NO 10
<211> LENGTH: 30
<212> TYPE: DNA
<213> ORGANISM: Artificial Sequence
```

```
<220> FEATURE:
<223> OTHER INFORMATION: SMN Forward Probe B

<400> SEQUENCE: 10
ctggcataga gcagcactaa atgacaccac                                          30

<210> SEQ ID NO 11
<211> LENGTH: 21
<212> TYPE: DNA
<213> ORGANISM: Artificial Sequence
<220> FEATURE:
<223> OTHER INFORMATION: SMN Forward C

<400> SEQUENCE: 11
gatgctgatg ctttgggaag t                                                   21

<210> SEQ ID NO 12
<211> LENGTH: 22
<212> TYPE: DNA
<213> ORGANISM: Artificial Sequence
<220> FEATURE:
<223> OTHER INFORMATION: SMN Reverse C

<400> SEQUENCE: 12
cgcttcacat tccagatctg tc                                                  22

<210> SEQ ID NO 13
<211> LENGTH: 25
<212> TYPE: DNA
<213> ORGANISM: Artificial Sequence
<220> FEATURE:
<223> OTHER INFORMATION: SMN Forward D

<400> SEQUENCE: 13
atatgtccag attctcttga tgatg                                               25

<210> SEQ ID NO 14
<211> LENGTH: 11
<212> TYPE: DNA
<213> ORGANISM: Artificial Sequence
<220> FEATURE:
<223> OTHER INFORMATION: 5-prime end of exon 6 of the SMN2 gene

<400> SEQUENCE: 14
ataattcccc c                                                              11

<210> SEQ ID NO 15
<211> LENGTH: 6
<212> TYPE: DNA
<213> ORGANISM: Artificial Sequence
<220> FEATURE:
<223> OTHER INFORMATION: nucleic acid residue 23 of exon 8 of the SMN2
      gene

<400> SEQUENCE: 15 cagcac                                                                     6

<210> SEQ ID NO 16
<211> LENGTH: 28
<212> TYPE: DNA
<213> ORGANISM: Artificial Sequence
<220> FEATURE:
<223> OTHER INFORMATION: PCR forward primer

<400> SEQUENCE: 16
cgcggatcca taattccccc accacctc                                            28
```

```
<210> SEQ ID NO 17
<211> LENGTH: 28
<212> TYPE: DNA
<213> ORGANISM: Artificial Sequence
<220> FEATURE:
<223> OTHER INFORMATION: PCR reverse primer

<400> SEQUENCE: 17
cgcggatccg tgctgctcta tgccagca                                         28

<210> SEQ ID NO 18
<211> LENGTH: 6
<212> TYPE: DNA
<213> ORGANISM: Artificial Sequence
<220> FEATURE:
<223> OTHER INFORMATION: BamHI restriction endonuclease recognition
      sequence

<400> SEQUENCE: 18 ggatcc                                                                  6

<210> SEQ ID NO 19
<211> LENGTH: 70
<212> TYPE: DNA
<213> ORGANISM: Artificial Sequence
<220> FEATURE:
<223> OTHER INFORMATION: 5-prime DEG UTR

<400> SEQUENCE: 19
tagcttctta cccgtactcc accgttggca gcacgatcgc acgtcccacg tgaaccattg       60
gtaaaccctg                                                             70

<210> SEQ ID NO 20
<211> LENGTH: 120
<212> TYPE: DNA
<213> ORGANISM: Artificial Sequence
<220> FEATURE:
<223> OTHER INFORMATION: 3-prime DEG UTR

<400> SEQUENCE: 20
atcgaaagta caggactagc cttcctagca accgcgggct gggagtctga gacatcactc       60
aagatatatg ctcggtaacg tatgctctag ccatctaact attccctatg tcttataggg      120

<210> SEQ ID NO 21
<211> LENGTH: 8266
<212> TYPE: DNA
<213> ORGANISM: Artificial Sequence
<220> FEATURE:
<223> OTHER INFORMATION: DNA sequence of SMN2-A minigene

<400> SEQUENCE: 21
tagcttctta cccgtactcc accgttggca gcacgatcgc acgtcccacg tgaaccattg       60
gtaaaccctg atgggatcca taattccccc accacctccc atatgtccag attctcttga     120
tgatgctgat gctttgggaa gtatgttaat tcatggtac atgagtggct atcatactgg      180
ctattatatg gtaagtaatc actcagcatc ttttcctgac aatttttttg tagttatgtg     240
actttgtttt gtaaatttat aaaatactac ttgcttctct cttatatta ctaaaaaata      300 aaataaaaa aatacaactg tctgaggctt aaattactct tgcattgtcc ctaagtataa      360
ttttagttaa ttttaaaaag ctttcatgct attgttagat tatttgatt atacactttt      420 gaattgaaat tatactttttt ctaaataatg ttttaatctc tgatttgaaa ttgattgtag    480
```

```
ggaatggaaa agatgggata attttcata aatgaaaat gaaattcttt ttttttttt       540 tttttttttg agacggagtc ttgctctgtt gcccaggctg gagtgcaatg gcgtgatctt    600
ggctcacagc aagctctgcc tcctggattc acgccattct cctgcctcag cctcagaggt    660
agctgggact acaggtgcct gccaccacgc ctgtctaatt ttttgtattt ttttgtaaag    720
acagggtttc actgtgttag ccaggatggt ctcaatctcc tgaccccgtg atccacccgc    780
ctcggccttc aagagaaat gaatttttt taatgcacaa agatctgggg taatgtgtac      840
cacattgaac cttggggagt atggcttcaa acttgtcact ttatacgtta gtctcctacg    900
gacatgttct attgtatttt agtcagaaca tttaaaatta ttttatttta ttttattttt    960
tttttttttt tgagacggag tctcgctctg tcacccaggc tggagtacag tggcgcagtc   1020
tcggctcact gcaagctccg cctcccgggt tcacgccatt ctcctgcctc agcctctccg   1080
agtagctggg actacaggcg cccgccacca cgcccggcta attttttttt attttagta    1140 gagacggggt ttcaccgtgg tctcgatctc ctgacctcgt gatccacccg cctcggcctc   1200
ccaaagtgct gggattacaa gcgtgagcca ccgcgcccgg cctaaaatta tttttaaaag   1260
taagctcttg tgccctgcta aaattatgat gtgatattgt aggcacttgt atttttagta   1320
aattaatata gaagaaacaa ctgacttaaa ggtgtatgtt tttaaatgta tcatctgtgt   1380
gtgcccccat taatattctt atttaaaagt taaggccaga catggtggct tacaactgta   1440
atcccaacag tttgtgaggc cgaggcaggc agatcacttg aggtcaggag tttgagacca   1500
gcctggccaa catgatgaaa ccttgtctct actaaaaata ccaaaaaaaa tttagccagg   1560
catggtggca catgcctgta atccgagcta cttgggaggc tgtggcagga aaattgcttt   1620
aatctgggag gcagaggttg cagtgagttg agattgtgcc actgcactcc acccttggtg   1680
acagagtgag attccatctc aaaaaagaa aaaggcctgg cacggtggct cacacctata   1740
atcccagtac tttgggaggt agaggcaggt ggatcacttg aggttaggag ttcaggacca   1800
gcctggccaa catggtgact actccatttc tactaaaatac acaaaactta gcccagtggc   1860
gggcagttgt aatcccagct acttgagagg ttgaggcagg agaatcactt gaacctggga   1920
ggcagaggtt gcagtgagcc gagatcacac cgctgcactc tagcctggcc aacagagtga   1980
gaatttgcgg agggaaaaaa aagtcacgct tcagttgttg tagtataacc ttggtatatt   2040
gtatgtatca tgaattcctc attttaatga ccaaaagta taaatcaac agcttgtaat    2100 ttgttttgag atcagttatc tgactgtaac actgtaggct tttgtgtttt ttaaattatg   2160
aaatatttga aaaaatacaa taatgtatat ataaagtatt ggtataattt atgttctaaa   2220
taactttctt gagaaataat tcacatggtg tgcagtttac ctttgaaagt atacaagttg   2280
gctgggcaca atggctcacg cctgtaatcc cagcactttg ggaggccagg caggtggat    2340 cacgaggtca ggagatcgag accatcctgg ctaacatggt gaaacccgt ctctactaaa    2400 agtacaaaaa caattagcc gggcatgttg gcgggcacct tttgtcccag ctgctcggga    2460
ggctgaggca ggagagtggc gtgaacccag gaggtggagc ttgcagtgag ccgagattgt   2520
gccagtgcac tccagcctgg gcgacagagc gagactctgt ctcaaaaaat aaaataaaaa   2580
agaaagtata caagtcagtg gttttggttt tcagttatgc aaccatcact acaatttaag   2640
aacattttca tcaccccaaa agaaaccct gttaccttca ttttccccag ccctaggcag    2700
tcagtacact ttctgtctct atgaatttgt ctattttaga tattatatat aaacggaatt   2760
atacgatatg tggtcttttg tgtctggctt ctttcactta gcatgctatt ttcaagattc   2820
```

```
atccatgctg tagaatgcac cagtactgca ttccttctta ttgctgaata ttctgttgtt   2880
tggttatatc acattttatc cattcatcag ttcatggaca tttaggttgt ttttattttt   2940
gggctataat gaataatgtt gctatgaaca ttcgtttgtg ttcttttgt tttttggtt    3000 ttttgggttt ttttttgtttt gttttttgttt tgagacagt cttgctctgt ctcctaagct  3060
ggagtgcagt ggcatgatct tggcttactg caagctctgc ctcccgggtt cacaccattc   3120
tcctgcctca gcccgacaag tagctgggac tacaggcgtg tgccaccatg cacggctaat   3180 ttttttgtatt tttagtagag atggggtttc accgtgttag ccaggatggt ctcgatctcc   3240
tgacctcgtg atctgcctgc ctaggcctcc caaagtgctg ggattacagg cgtgagccac   3300
tgcacctggc cttaagtgtt tttaatacgt cattgcctta agctaacaat tcttaacctt   3360
tgttctactg aagccacgtg gttgagatag gctctgagtc tagcttttaa cctctatctt   3420
tttgtcttag aaatctaagc agaatgcaaa tgactaagaa taatgttgtt gaaataacat   3480
aaaataggtt ataactttga tactcattag taacaaatct ttcaatacat cttacggtct   3540
gttaggtgta gattagtaat gaagtgggaa gccactgcaa gctagtatac atgtaggggaa  3600 agatagaaag cattgaagcc agaagagaga cagaggacat ttgggctaga tctgacaaga   3660
aaaacaaatg ttttagtatt aatttttgac tttaaatttt tttttattt agtgaatact     3720 ggtgtttaat ggtctcattt taataagtat gacacaggta gtttaaggtc atatatttta    3780
tttgatgaaa ataaggtata ggccgggcac ggtggctcac acctgtaatc ccagcacttt    3840
gggaggccga ggcaggcgga tcacctgagg tcgggagtta gagactagcc tcaacatgga    3900 gaaacccgt ctctactaaa aaaatacaa aattaggcgg gcgtggtggt gcatgcctgt      3960
aatcccagct actcaggagg ctgaggcagg agaattgctt gaacctggga ggtggaggtt    4020
gcggtgagcc gagatcacct cattgcactc cagcctgggc aacaagagca aaactccatc    4080
tcaaaaaaaa aaaataagg tataagcggg ctcaggaaca tcattggaca tactgaaaga     4140
agaaaaatca gctgggcgca gtggctcacg ccggtaatcc caacactttg ggaggccaag    4200
gcaggcgaat cacctgaagt cgggagttcc agatcagcct gaccaacatg gagaaaccct    4260
gtctctacta aaaatacaaa actagccggg catggtggcg catgcctgta atcccagcta    4320
cttgggaggc tgaggcagga gaattgcttg aaccgagaag gcggaggttg cggtgagcca    4380
agattgcacc attgcactcc agcctgggca acaagagcga aactccgtct caaaaaaaaa    4440
aggaagaaaa atattttttt aaattaatta gtttattat tttttaagat ggagttttgc     4500
cctgtcaccc aggctggggt gcaatggtgc aatctcggct cactgcaacc tccgcctcct    4560
gggttcaagt gattctcctg cctcagcttc ccgagtagct gtgattacag ccatatgcca    4620
ccacgcccag ccagttttgt gttttgtttt gttttttgtt ttttttttt gagagggtgt     4680 cttgctctgt cccccaagct ggagtgcagc ggcgcgatct tggctcactg caagctctgc    4740
ctcccaggtt cacaccattc tcttgcctca gcctcccgag tagctgggac tacaggtgcc    4800
cgccaccaca cccggctaat tttttttgtgt ttttagtaga gatggggttt cactgtgtta    4860
gccaggatgg tctcgatctc ctgacctttt gatccacccg cctcagcctc ccaagtgct     4920 gggattatag gcgtgagcca ctgtgccggg cctagtcttg tattttagt agagtcggga     4980 tttctccatg ttggtcaggc tgttctccaa atccgacctc aggtgatccg cccgccttgg    5040
cctccaaaag tgcaaggcaa ggcattacag gcatgagcca ctgtgaccgg caatgttttt    5100
aaatttttta catttaaatt ttatttttta gagaccaggt ctcactctat tgctcaggct    5160
ggagtgcaag ggcacattca cagctcactg cagccttgac ctccagggct caagcagtcc    5220
```

```
tctcacctca gtttcccgag tagctgggac tacagtgata atgccactgc acctggctaa    5280
tttttatttt tatttattta ttttttttg agacagagtc ttgctctgtc acccaggctg      5340
gagtgcagtg gtgtaaatct cagctcactg cagcctccgc ctcctgggtt caagtgattc    5400
tcctgcctca acctcccaag tagctgggat tagaggtccc caccaccatg cctggctaat    5460
tttttgtact ttcagtagaa acggggtttt gccatgttgg ccaggctgtt ctcgaactcc    5520
tgagctcagg tgatccaact gtctcggcct cccaaagtgc tgggattaca ggcgtgagcc    5580
actgtgccta gcctgagcca ccacgccggc ctaattttta aattttttgt agagacaggg    5640
tctcattatg ttgcccaggg tggtgtcaag ctccaggtct caagtgatcc cctacctcc     5700 gcctcccaaa gttgtgggat tgtaggcatg agccactgca agaaaacctt aactgcagcc    5760
taataattgt tttctttggg ataactttta aagtacatta aaagactatc aacttaattt    5820
ctgatcatat tttgttgaat aaaataagta aaatgtcttg tgaaacaaaa tgcttttaa     5880 catccatata aagctatcta tatatagcta tctatatcta tatagctatt ttttttaact    5940
tcctttattt tccttacagg gttttagaca aaatcaaaaa gaaggaaggt gctcacattc    6000
cttaaatata aggagtaagt ctgccagcat tatgaaagtg aatcttactt ttgtaaaact    6060
ttatggtttg tggaaaacaa atgttttga acatttaaaa agttcagatg ttagaaagtt     6120
gaaaggttaa tgtaaaacaa tcaatattaa agaattttga tgccaaaact attagataaa    6180
aggttaatct acatccctac tagaattctc atacttaact ggttggttgt gtggaagaaa    6240
catactttca caataaagag ctttaggata tgatgccatt ttatatcact agtaggcaga    6300
ccagcagact tttttttatt gtgatatggg ataacctagg catactgcac tgtacactct    6360
gacatatgaa gtgctctagt caagtttaac tggtgtccac agaggacatg gtttaactgg    6420
aattcgtcaa gcctctggtt ctaatttctc atttgcagga aatgctggca tagagcagca    6480
cggatccgaa gacgccaaaa acataaagaa aggcccggcg ccattctatc ctctagagga    6540
tggaaccgct ggagagcaac tgcataaggc tatgaagaga tacgccctgg ttcctggaac    6600
aattgctttt acagatgcac atatcgaggt gaacatcacg tacgcggaat acttcgaaat    6660
gtccgttcgg ttggcagaag ctatgaaacg atatgggctg aatacaaatc acagaatcgt    6720
cgtatgcagt gaaaactctc ttcaattctt tatgccggtg ttgggcgcgt tatttatcgg    6780
agttgcagtt gcgcccgcga acgacattta taatgaacgt gaattgctca acagtatgaa    6840
catttcgcag cctaccgtag tgtttgtttc caaaaagggg ttgcaaaaaa ttttgaacgt    6900
gcaaaaaaaa ttaccaataa tccagaaaat tattatcatg gattctaaaa cggattacca    6960
gggatttcag tcgatgtaca cgttcgtcac atctcatcta cctcccggtt taatgaata     7020 cgattttgta ccagagtcct ttgatcgtga caaaacaatt gcactgataa tgaattcctc    7080
tggatctact gggttaccta agggtgtggc ccttccgcat agaactgcct gcgtcagatt    7140
ctcgcatgcc agagatccta ttttggcaa tcaaatcatt ccggatactg cgattttaag    7200
tgttgttcca ttccatcacg gttttggaat gtttactaca ctcggatatt tgatatgtgg    7260
atttcgagtc gtcttaatgt atagatttga agaagagctg ttttttacgat cccttcagga    7320 ttacaaaatt caaagtgcgt tgctagtacc aaccctattt tcattcttcg ccaaaagcac    7380
tctgattgac aaatacgatt tatctaattt acacgaaatt gcttctgggg gcgcacctct    7440
ttcgaaagaa gtcggggaag cggttgcaaa acgcttccat cttccaggga tacgacaagg    7500
atatgggctc actgagacta catcagctat tctgattaca cccgaggggg atgataaacc    7560
```

```
gggcgcggtc ggtaaagttg ttccattttt tgaagcgaag gttgtggatc tggataccgg    7620
gaaaacgctg ggcgttaatc agagaggcga attatgtgtc agaggaccta tgattatgtc    7680
cggttatgta aacaatccgg aagcgaccaa cgccttgatt gacaaggatg gatggctaca    7740
ttctggagac atagcttact gggacgaaga cgaacacttc ttcatagttg accgcttgaa    7800
gtctttaatt aaatacaaag gatatcaggt ggccccgct gaattggaat cgatattgtt    7860
acaacacccc aacatcttcg acgcgggcgt ggcaggtctt cccgacgatg acgccggtga    7920
acttcccgcc gccgttgttg ttttggagca cggaaagacg atgacggaaa aagagatcgt    7980
ggattacgtc gccagtcaag taacaaccgc gaaaaagttg cgcggaggag ttgtgtttgt    8040
ggacgaagta ccgaaaggtc ttaccggaaa actcgacgca agaaaaatca gagagatcct    8100
cataaaggcc aagaagggcg gaaagtccaa attgcgcggc cgctaaatcg aaagtacagg    8160
actagccttc ctagcaaccg cgggctggga gtctgagaca tcactcaaga tatatgctcg    8220
gtaacgtatg ctctagccat ctaactattc cctatgtctt ataggg                   8266
```

COMPOUNDS FOR TREATING SPINAL MUSCULAR ATROPHY

CROSS-REFERENCE TO RELATED APPLICATIONS

This application is a U.S. national stage application of International Patent Application No. PCT/US2012/071899, filed Dec. 28, 2012, which claims the benefit of U.S. Provisional Application No. 61/582,064, Dec. 30, 2011, each of which is incorporated by reference herein in its entirety.

STATEMENT REGARDING FEDERALLY SPONSORED RESEARCH OR DEVELOPMENT

The technology described herein has not been made with U.S. Government support.

THE NAMES OF THE PARTIES TO A JOINT RESEARCH AGREEMENT

PCT Therapeutics, Inc. and F. Hoffmann-La Roche AG.

STATEMENT ON JOINT RESEARCH AGREEMENT

The subject matter disclosed was developed and the claimed invention was made by, or on behalf of, one or more parties to a joint research agreement that was in effect on or before the effective filing date of the claimed invention;

the claimed invention was made as a result of activities undertaken within the scope of the joint research agreement; and the application for patent for the claimed invention discloses or is amended to disclose the names of the parties to the joint research agreement.

INTRODUCTION

Provided herein are compounds, compositions thereof and uses therewith for treating Spinal Muscular Atrophy.

BACKGROUND

Spinal muscular atrophy (SMA), in its broadest sense, describes a collection of inherited and acquired central nervous system (CNS) diseases characterized by progressive motor neuron loss in the spinal cord and brainstem causing muscle weakness and muscle atrophy. The most common form of SMA is caused by mutations in the Survival Motor Neuron (SMN) gene and manifests over a wide range of severity affecting infants through adults (Crawford and Pardo, Neurobiol. Dis., 1996, 3:97).

Infantile SMA is the most severe form of this neurodegenerative disorder. Symptoms include muscle weakness, poor muscle tone, weak cry, limpness or a tendency to flop, difficulty sucking or swallowing, accumulation of secretions in the lungs or throat, feeding difficulties, and increased susceptibility to respiratory tract infections. The legs tend to be weaker than the arms and developmental milestones, such as lifting the head or sitting up, cannot be reached. In general, the earlier the symptoms appear, the shorter the lifespan. As the motor neuron cells deteriorate, symptoms appear shortly afterward. The severe forms of the disease are fatal and all forms have no known cure. The course of SMA is directly related to the rate of motor neuron cell deterioration and the resulting severity of weakness. Infants with a severe form of SMA frequently succumb to respiratory disease due to weakness in the muscles that support breathing. Children with milder forms of SMA live much longer, although they may need extensive medical support, especially those at the more severe end of the spectrum. The clinical spectrum of SMA disorders has been divided into the following five groups.

(a) Type 0 SMA (In Utero SMA) is the most severe form of the disease and begins before birth. Usually, the first symptom of Type 0 SMA is reduced movement of the fetus that can first be observed between 30 and 36 weeks of pregnancy. After birth, newborns have little movement and difficulties with swallowing and breathing.

(b) Type 1 SMA (Infantile SMA or Werdnig-Hoffmann disease) presents the first symptoms between 0 and 6 months: This type of SMA is also very severe. Patients never achieve the ability to sit, and death usually occurs within the first 2 years without respiratory support.

(c) Type 2 SMA (Intermediate SMA) has an age of onset at 7-18 months. Patients achieve the ability to sit unsupported, but never stand or walk unaided. Prognosis in this group is largely dependent on the degree of respiratory involvement.

(d) Type 3 SMA (Juvenile SMA or Kugelberg-Welander disease) is generally diagnosed after 18 months. Type 3 SMA individuals are able to walk independently at some point during the course of the disease but often become wheelchair-bound during youth or adulthood.

(e) Type 4 SMA (Adult onset SMA). Weakness usually begins in late adolescence in the tongue, hands or feet, then progresses to other areas of the body. The course of adult onset SMA is much slower and has little or no impact on life expectancy.

The SMN gene has been mapped by linkage analysis to a complex region in chromosome 5q. In humans, this region contains an approximately 500 thousand base pairs (kb) inverted duplication resulting in two nearly identical copies of the SMN gene. SMA is caused by an inactivating mutation or deletion of the telomeric copy of the gene (SMN1) in both chromosomes, resulting in the loss of SMN1 gene function. However, all patients retain the centromeric copy of the gene (SMN2), and the copy number of the SMN2 gene in SMA patients generally correlates inversely with the disease severity; i.e., patients with less severe SMA have more copies of SMN2. Nevertheless, SMN2 is unable to compensate completely for the loss of SMN1 function due to alternative splicing of exon 7 caused by a translationally silent C to T mutation in exon 7. As a result, the majority of transcripts produced from SMN2 lack exon 7 (SMN2 Δ7), and encode a truncated Smn protein that has an impaired function and is rapidly degraded.

Smn is thought to play a role in RNA processing and metabolism, having a well characterized function of mediating the assembly of a specific class of RNA-protein complexes termed snRNPs. Smn may have other functions in motor neurons, however its role in preventing the selective degeneration of motor neurons is not well established.

In most cases, SMA is diagnosed based on clinical symptoms and by the presence of at least on copy of the SMN1 gene test. However, in approximately 5% of cases SMA is caused by mutation in genes other than the inactivation of SMN1, some known and others not yet defined. In some cases, when the SMN1 gene test is not feasible or does not show any abnormality, other tests such as an electromyography (EMG) or muscle biopsy may be indicated.

Medical care for SMA patients at present is limited to supportive therapy including respiratory, nutritional and rehabilitation care; there is no drug known to address the cause of the disease. Current treatment for SMA consists of prevention and management of the secondary effects of chronic motor unit loss. The major management issue in Type 1 SMA is the prevention and early treatment of pulmonary problems, which are the cause of death in the majority of the cases. While some infants afflicted with SMA grow to be adults, those with Type 1 SMA have a life expectancy of less than two years.

Several mouse models of SMA have been developed. In particular, the SMNΔ7 model (Le et al., Hum. Mol. Genet., 2005, 14:845) carries both the SMN2 gene and several copies of the SMN2Δ7 cDNA and recapitulates many of the phenotypic features of Type 1 SMA. The SMNΔ7 model can be used for both SMN2 expression studies as well as the evaluation of motor function and survival. The C/C-allele mouse model (Jackson Laboratory strain #008714) provides a less severe SMA disease model, with mice having reduced levels of both SMN2 FL mRNA and Smn protein. The C/C-allele mouse phenotype has the SMN2 gene and a hybrid mSmn1-SMN2 gene that undergoes alternative splicing, but does not have overt muscle weakness. The C/C-allele mouse model is used for SMN2 expression studies.

As a result of improved understanding of the genetic basis for SMA, several strategies for treatment have been explored, but none have yet demonstrated success in the clinic.

Gene replacement of SMN1, using viral delivery vectors, and cell replacement, using differentiated SMN1$^{+/+}$ stem cells, have demonstrated efficacy in animal models of SMA. More research is needed to determine the safety and immune response and to address the requirement for the initiation of treatment at the neonatal stage before these approaches can be applied to humans.

Correction of alternative splicing of SMN2 in cultured cells has also been achieved using synthetic nucleic acids as therapeutic agents: (i) antisense oligonucleotides that target sequence elements in SMN2 pre-mRNA and shift the outcome of the splicing reaction toward the generation of full length SMN2 mRNA (Passini et al., Sci. Transl. Med., 2011, 3:72ra18; and, Hua et al., Nature, 2011, 478:123) and (ii) trans-splicing RNA molecules that provide a fully functional RNA sequence that replace the mutant fragment during splicing and generate a full length SMN1 mRNA (Coady and Lorson, J Neurosci., 2010, 30:126).

Other approaches under exploration include searching for drugs that increase Smn levels, enhance residual Smn function, or compensate for loss of Smn. Aminoglycosides have been shown to enhance expression of stabilized Smn produced from SMN2 Δ7 mRNA by promoting the translational read-through of the aberrant stop codon, but have poor central nervous system penetration and are toxic after repeated dosing. Chemotherapeutic agents, such as aclarubicin, have been shown to increase Smn in cell culture; however, the toxicity profile of these drugs prohibits long-term use in SMA patients. Some drugs under clinical investigation for the treatment of SMA include transcription activators such as histone deacetylase ("HDAC") inhibitors (e.g., butyrates, valproic acid, and hydroxyurea), and mRNA stabilizers (mRNA decapping inhibitor RG3039 from Repligen), intended to increase the amount of total RNA transcribed from the SMN2 gene. However, the use of HDAC inhibitors or mRNA stabilizers does not address the underlying cause of SMA and may result in a global increase in transcription and gene expression with potential safety problems in humans.

In an alternative approach, neuroprotective agents such as olesoxime have been chosen for investigation. Such strategies are not aimed at producing functional Smn for the treatment of SMA, but instead are being explored to protect the Smn-deficient motor neurons from neurodegeneration.

A system designed to identify compounds that increase the inclusion of exon 7 of SMN into RNA transcribed from the SMN2 gene and certain benzooxazole and benzoisoxazole compounds identified thereby have been described in International Application PCT/US2009/003238 filed May 27, 2009 (published as International Publication Number WO2009/151546 and United States Publication Number US2011/0086833). A system designed to identify compounds that produce a stabilized Smn protein from SMN2 Δ7 mRNA and certain isoindolinone compounds identified thereby have been described in International Application PCT/US2009/004625 filed Aug. 13, 2009 (published as International Publication Number WO2010/019236 and United States Publication Number US2011/0172284). Each of the foregoing documents is herein incorporated in their entirety and for all purposes.

All other documents referred to herein are incorporated by reference into the present application as though fully set forth herein.

Despite the progress made in understanding the genetic basis and pathophysiology of SMA, there remains a need to identify compounds that alter the course of spinal muscular atrophy, one of the most devastating childhood neurological diseases.

SUMMARY

In one aspect, provided herein are compounds of Formula (I):

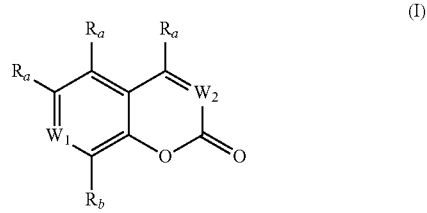

or a form thereof, wherein: $w_1$, $w_2$, $R_a$ and $R_b$ are as defined herein. In one embodiment, provided herein is a pharmaceutical composition comprising a compound of Formula (I) or a form thereof, and a pharmaceutically acceptable carrier, excipient or diluent. In a specific embodiment, provided herein is a compound of Formula (I) or a form thereof, or a pharmaceutical composition thereof for treating spinal muscular atrophy (SMA).

SMA is caused by deletion or mutation of the SMN1 gene, resulting in selective degeneration of Smn-deficient motor neurons. Although human subjects retain several copies of the SMN2 gene, the small amount of functional Smn protein expressed from SMN2 does not fully compensate for the loss of Smn that would have been expressed from the SMN1 gene. The compounds, compositions thereof and uses therewith described herein are based, in part, on the Applicants discovery that a compound of Formula (I) increases the inclusion of exon 7 of SMN2 into mRNA that is transcribed from an SMN2 minigene. The minigene reproduces the alternative splicing reaction of exon 7 of SMN2 which results in the loss of exon 7 in the majority of SMN2 transcripts. Thus, compounds of Formula (I) or a form thereof may be used to modulate inclusion of exon 7 of SMN2 into mRNA that is transcribed from the SMN2 gene. Applicants have also discovered that a compound of Formula (I) increases the inclusion of exon 7 of SMN1 into mRNA that is transcribed from an SMN1 minigene. Thus, compounds of Formula (I) or a form thereof may be used to modulate the inclusion of exon 7 of SMN1 into mRNA that is transcribed from the SMN1 gene.

In a specific embodiment, provided herein are compounds of Formula (I) or a form thereof that may be used to modulate the inclusion of exon 7 of SMN2 into mRNA that is transcribed from the SMN2 gene. In another specific embodiment, provided herein are compounds of Formula (I) or a form thereof that may be used to modulate the inclusion of exon 7 of SMN1 into mRNA that is transcribed from the SMN1 gene. In yet another embodiment, provided herein are compounds of Formula (I) or a form thereof that may be used to modulate the inclusion of exon 7 of SMN1 and SMN2 into mRNA that is transcribed from the SMN1 and SMN2 genes, respectively.

In another aspect, provided herein is the use of a compound of Formula (I) or a form thereof for treating SMA. In a specific embodiment, provided herein is a method for treating SMA in a human subject in need thereof, comprising administering to the subject an effective amount of a compound of Formula (I) or a form thereof. The compound of Formula (I) or a form thereof is preferably administered to a human subject in a pharmaceutical composition. In another specific embodiment, provided herein is the use of a compound of Formula (I) for treating SMA, wherein the compound enhances the inclusion of exon 7 of SMN2 into mRNA that is transcribed from the SMN2 gene. Without being limited by theory, compounds of Formula (I) enhance inclusion of exon 7 of SMN2 into mRNA that is transcribed from the SMN2 gene and increase levels of Smn protein produced from the SMN2 gene, and thus can be used to treat SMA in a human subject in need thereof.

In another aspect, provided herein are primers and/or probes described below in the Biological Examples (e.g., SMN primers such as SEQ ID NO. 1, 7, 8, 11 or 13, and/or SEQ ID NO. 2, 9 or 12, and/or SMN probes such as a SEQ ID NO. 3 or 10) and the use of those primers and/or probes. In a specific embodiment, provided herein is an isolated nucleotide sequence comprising SEQ ID NOs: 1, 2, 3, 7, 8, 9, 10, 11, 12 or 13. In another specific embodiment, provided herein is an isolated nucleotide sequence consisting essentially of SEQ ID NOs: 1, 2, 3, 7, 8, 9, 10, 11, 12 or 13. In another specific embodiment, provided herein is an isolated nucleotide sequence consisting of SEQ ID NOs: 1, 2, 3, 7, 8, 9, 10, 11, 12 or 13.

In certain embodiments, the amount of mRNA that is transcribed from the SMN1 gene and/or SMN2 gene and does not include exon 7 of SMN1 and/or SMN2 may be used as a biomarker for SMA, such as disclosed herein. In other embodiments, the amount of mRNA that is transcribed from the SMN1 and/or SMN2 gene and includes exon 7 of SMN1 and/or SMN2 may be used as a biomarker for treating a patient with a compound, such as disclosed herein. In a specific embodiment, the patient is an SMA patient.

In certain embodiments, the amount of mRNA that is transcribed from the SMN1 and/or SMN2 gene and includes exon 7 of SMN1 and/or SMN2 as well as the amount of mRNA that is transcribed from the SMN1 and/or SMN2 gene and does not include exon 7 of SMN1 and/or SMN2 may be used as biomarkers for treating a patient with a compound, such as disclosed herein. In a specific embodiment, the patient is an SMA patient.

In accordance with these embodiments, an SMN primer(s) and/or an SMN probe described below may be used in assays, such as PCR (e.g., qPCR), rolling circle amplification, and RT-PCR (e.g., endpoint RT-PCR and/or RT-qPCR) to assess and/or quantify the amount of mRNA that is transcribed from the SMN1 gene and/or SMN2 gene and does or does not include exon 7 of SMN1 and/or SMN2.

In a specific embodiment, a primer and/or probe described below in the Biological Examples (e.g., SMN primers such as SEQ ID NO. 1, 7, 8, 11 or 13 and/or SEQ ID NO. 2, 9 or 12, and/or SMN probes such as a SEQ ID NO. 3 or 10) is used in an assay, such as RT-PCR, RT-qPCR, endpoint RT-PCR, PCR, qPCR, rolling circle amplification, Northern blot or Southern blot (e.g., an assay such as described below in the Biological Examples), to determine whether a compound (e.g., a compound of Formula (I) or a form thereof) enhances the inclusion of exon 7 of SMN2 into mRNA that is transcribed from an SMN2 gene.

In a specific embodiment, a primer and/or probe described below in the Biological Examples (e.g., SMN primers such as SEQ ID NO. 1, 7, 8, 11 or 13 and/or SEQ ID NO. 2, 9 or 12, and/or SMN probes such as a SEQ ID NO. 3 or 10) is used in an assay, such as RT-PCR, RT-qPCR, endpoint RT-PCR, PCR, qPCR, rolling circle amplification, Northern blot or Southern blot (e.g., an assay such as described below in the Biological Examples), to determine whether a compound (e.g., a compound of Formula (I) or a form thereof) enhances the inclusion of exon 7 of SMN1 into mRNA that is transcribed from an SMN1 gene.

In a specific embodiment, a primer and/or probe described below in the Biological Examples (e.g., SMN primers such as SEQ ID NO. 1, 7, 8, 11 or 13 and/or SEQ ID NO. 2, 9 or 12, and/or SMN probes such as a SEQ ID NO. 3 or 10) is used in an assay, such as RT-PCR, RT-qPCR, endpoint RT-PCR, PCR, qPCR, rolling circle amplification, Northern blot or Southern blot (e.g., an assay such as described below in the Biological Examples), to determine whether a compound (e.g., a compound of Formula (I) or a form thereof) enhances the inclusion of exon 7 of SMN1 and/or SMN2 into mRNA that is transcribed from an SMN1 and/or SMN2 gene.

In another embodiment, a primer and/or probe described below in the Biological Examples (e.g., SMN primers such as SEQ ID NO. 7, 11 or 13 and/or SEQ ID NO. 9 or 12, and/or SMN probes such as a SEQ ID NO. 3 or 10) is used in an assay, such as RT-PCR, RT-qPCR, endpoint RT-PCR, PCR, qPCR, rolling circle amplification, Northern blot or Southern blot (e.g., an assay such as described below in the Biological Examples), to monitor the amount of mRNA that is transcribed from the SMN2 gene and includes exon 7 of SMN2 in a patient sample. In a specific embodiment, the patient is an SMA patient.

In another embodiment, a primer and/or probe described below in the Biological Examples (e.g., SMN primers such as SEQ ID NO. 7, 11 or 13 and/or SEQ ID NO. 9 or 12, and/or SMN probes such as a SEQ ID NO. 3 or 10) is used in an assay, such as RT-PCR, RT-qPCR, endpoint RT-PCR, PCR, qPCR, rolling circle amplification, Northern blot or Southern blot (e.g., an assay such as described below in the Biological Examples), to monitor the amount of mRNA that is transcribed from the SMN1 gene and includes exon 7 of SMN1 in a patient sample. In a specific embodiment, the patient is an SMA patient.

In another embodiment, a primer and/or probe described below in the Biological Examples (e.g., SMN primers such as SEQ ID NO. 7, 11 or 13 and/or SEQ ID NO. 9 or 12, and/or SMN probes such as a SEQ ID NO. 3 or 10) is used in an assay, such as RT-PCR, RT-qPCR, endpoint RT-PCR, PCR, qPCR, rolling circle amplification, Northern blot or Southern blot (e.g., an assay such as described below in the Biological Examples), to monitor the amount of mRNA that is transcribed from the SMN1 and/or SMN2 gene and includes exon 7 of SMN1 and/or SMN2 in a patient sample. In a specific embodiment, the patient is an SMA patient.

In another embodiment, a primer and/or probe described below in the Biological Examples (e.g., SMN primers such as SEQ ID NO. 7, 8, 11 or 13 and/or SEQ ID NO. 9 or 12, and/or SMN probes such as a SEQ ID NO. 3 or 10) is used in an assay, such as RT-PCR, RT-qPCR, endpoint RT-PCR, PCR, qPCR, rolling circle amplification, Northern blot or Southern blot (e.g., an assay such as described below in the Biological Examples), to monitor a patient's response to a compound (e.g., a compound of Formula (I) or a form thereof). In a specific embodiment, the patient is an SMA patient.

In another embodiment, provided herein is a method for determining whether a compound (e.g., a compound of Formula (I) disclosed herein) enhances the inclusion of exon 7 of SMN2 into mRNA that is transcribed from the SMN2 gene, comprising (a) contacting mRNA that is transcribed from an SMN2 minigene described herein or in International Application PCT/US2009/004625, filed Aug. 13, 2009 (published as International Publication Number WO2010/019236) or United States Publication Number US2011/0172284 in the presence of a compound (e.g., a compound of Formula (I) disclosed herein) with a primer(s) described herein (e.g., SEQ ID NO. 1 and/or 2) along with applicable components for, e.g., RT-PCR, RT-qPCR, PCR, endpoint RT-PCR, qPCR or rolling circle amplification; and (b) detecting the amount of mRNA that is transcribed from the minigene and includes exon 7 of the SMN2, wherein (1) an increase in the amount of mRNA that is transcribed from the minigene and includes exon 7 of SMN2 in the presence of the compound relative to the amount of mRNA that is transcribed from the minigene and includes exon 7 of SMN2 in the absence of the compound indicates that the compound enhances inclusion of exon 7 of SMN2 into mRNA that is transcribed from the SMN2 gene; and (2) no change or no substantial change in the amount of mRNA that is transcribed from the minigene and includes exon 7 of SMN2 in the presence of the compound relative to the amount of mRNA that is transcribed from the minigene and includes exon 7 of SMN2 in the absence of the compound indicates that the compound does not enhance the inclusion of exon 7 of SMN2 into mRNA that is transcribed from the SMN2 gene.

In another embodiment, provided herein is a method for determining whether a compound (e.g., a compound of Formula (I) disclosed herein) enhances the inclusion of exon 7 of SMN1 into mRNA that is transcribed from the SMN1 gene, comprising (a) contacting mRNA that is transcribed from an SMN1 minigene described in International Application PCT/US2009/004625, filed Aug. 13, 2009 (published as International Publication Number WO2010/019236) or United States Publication Number US2011/0172284 in the presence of a compound (e.g., a compound of Formula (I) disclosed herein) with a primer(s) described herein (e.g., SEQ ID NO. 1 and/or 2) along with applicable components for, e.g., RT-PCR, RT-qPCR, PCR, endpoint RT-PCR, qPCR or rolling circle amplification; and (b) detecting the amount of mRNA that is transcribed from the minigene and includes exon 7 of the SMN1, wherein (1) an increase in the amount of mRNA that is transcribed from the minigene and includes exon 7 of SMN1 in the presence of the compound relative to the amount of mRNA that is transcribed from the minigene and includes exon 7 of SMN1 in the absence of the compound indicates that the compound enhances inclusion of exon 7 of SMN1 into mRNA that is transcribed from the SMN1 gene; and (2) no change or no substantial change in the amount of mRNA that is transcribed from the minigene and includes exon 7 of SMN1 in the presence of the compound relative to the amount of mRNA that is transcribed from the minigene and includes exon 7 of SMN1 in the absence of the compound indicates that the compound does not enhance the inclusion of exon 7 of SMN1 into mRNA that is transcribed from the SMN1 gene.

In another embodiment, provided herein is a method for determining whether a compound (e.g., a compound of Formula (I) disclosed herein) enhances the inclusion of exon 7 of SMN2 into mRNA that is transcribed from the SMN2 gene, comprising (a) contacting mRNA that is transcribed from an SMN2 minigene described herein or in International Application PCT/US2009/004625, filed Aug. 13, 2009 (published as International Publication Number WO2010/019236) or United States Publication Number US2011/0172284 in the presence of a compound (e.g., a compound of Formula (I) disclosed herein) with a probe described herein (e.g., SEQ ID NO. 3 or 10) along with applicable components for, e.g., RT-PCR, RT-qPCR, endpoint RT-PCR, PCR, qPCR, rolling circle amplification and, as applicable, Northern blot or Southern blot; and (b) detecting the amount of mRNA that is transcribed from the minigene and includes exon 7 of the SMN2, wherein (1) an increase in the amount of mRNA that is transcribed from the minigene and includes exon 7 of SMN2 in the presence of the compound relative to the amount of mRNA that is transcribed from the minigene and includes exon 7 of SMN2 in the absence of the compound indicates that the compound enhances inclusion of exon 7 of SMN2 into mRNA that is transcribed from the SMN2 gene; and (2) no change or no substantial change in the amount of mRNA that is transcribed from the minigene and includes exon 7 of SMN2 in the presence of the compound relative to the amount of mRNA that is transcribed from the minigene and includes exon 7 of SMN2 in the absence of the compound indicates that the compound does not enhance the inclusion of exon 7 of SMN2 into mRNA that is transcribed from the SMN2 gene.

In another embodiment, provided herein is a method for determining whether a compound (e.g., a compound of Formula (I) disclosed herein) enhances the inclusion of exon 7 of SMN1 into mRNA that is transcribed from the SMN1 gene, comprising (a) contacting mRNA that is transcribed from an SMN1 minigene described in International Application PCT/US2009/004625, filed Aug. 13, 2009 (published as International Publication Number WO2010/019236) or United States Publication Number US2011/0172284 in the presence of a compound (e.g., a compound of Formula (I) disclosed herein) with a probe described herein (e.g., SEQ ID NO. 3 or 10) along with applicable components for, e.g., RT-PCR, RT-qPCR, endpoint RT-PCR, PCR, qPCR, rolling circle amplification and, as applicable, Northern blot or Southern blot; and (b) detecting the amount of mRNA that is transcribed from the minigene and includes exon 7 of the SMN1, wherein (1) an increase in the amount of mRNA that is transcribed from the minigene and includes exon 7 of SMN1 in the presence of the compound relative to the amount of mRNA that is transcribed from the minigene and includes exon 7 of SMN1 in the absence of the compound indicates that the compound enhances inclusion of exon 7 of SMN1 into mRNA that is transcribed from the SMN1 gene; and (2) no change or no substantial change in the amount of mRNA that is transcribed from the minigene and includes exon 7 of SMN1 in the presence of the compound relative to the amount of mRNA that is transcribed from the minigene and includes exon 7 of SMN1 in the absence of the compound indicates that the compound does not enhance the inclusion of exon 7 of SMN2 into mRNA that is transcribed from the SMN2 gene.

In another embodiment, provided herein is a method for determining whether a compound (e.g., a compound of Formula (I) disclosed herein) enhances the inclusion of exon 7 of SMN2 into mRNA that is transcribed from the SMN2 gene, comprising (a) contacting mRNA that is transcribed from an SMN2 minigene described herein or in International Application PCT/US2009/004625, filed Aug. 13, 2009 (published as International Publication Number WO2010/019236) or United States Publication Number US2011/0172284 in the presence of a compound (e.g., a compound of Formula (I) disclosed herein) with a primer(s) (e.g., SEQ ID NO. 1 or 2) and/or a probe described herein (e.g., SEQ ID NO. 3 or 10) along with applicable components for, e.g, RT-PCR, RT-qPCR, endpoint RT-PCR, PCR, qPCR, rolling circle amplification and, as applicable, Northern blot or Southern blot; and (b) detecting the amount of mRNA that is transcribed from the minigene and includes exon 7 of the SMN2, wherein (1) an increase in the amount of mRNA that is transcribed from the minigene and includes exon 7 of SMN2 in the presence of the compound relative to the amount of mRNA that is transcribed from the minigene and includes exon 7 of SMN2 in the absence of the compound indicates that the compound enhances inclusion of exon 7 of SMN2 into mRNA that is transcribed from the SMN2 gene; and (2) no change or no substantial change in the amount of mRNA that is transcribed from the minigene and includes exon 7 of SMN2 in the presence of the compound relative to the amount of mRNA that is transcribed from the minigene and includes exon 7 of SMN2 in the absence of the compound indicates that the compound does not enhance the inclusion of exon 7 of SMN2 into mRNA that is transcribed from the SMN2 gene.

In another embodiment, provided herein is a method for determining whether a compound (e.g., a compound of Formula (I) disclosed herein) enhances the inclusion of exon 7 of SMN1 into mRNA that is transcribed from the SMN1 gene, comprising (a) contacting mRNA that is transcribed from an SMN1 minigene described in International Application PCT/US2009/004625, filed Aug. 13, 2009 (published as International Publication Number WO2010/019236) or United States Publication Number US2011/0172284 in the presence of a compound (e.g., a compound of Formula (I) disclosed herein) with a primer(s) (e.g., SEQ ID NO. 1 or 2) and/or a probe described herein (e.g., SEQ ID NO. 3 or 10) along with applicable components for, e.g, RT-PCR, RT-qPCR, endpoint RT-PCR, PCR, qPCR, rolling circle amplification and, as applicable, Northern blot or Southern blot; and (b) detecting the amount of mRNA that is transcribed from the minigene and includes exon 7 of the SMN1, wherein (1) an increase in the amount of mRNA that is transcribed from the minigene and includes exon 7 of SMN1 in the presence of the compound relative to the amount of mRNA that is transcribed from the minigene and includes exon 7 of SMN1 in the absence of the compound indicates that the compound enhances inclusion of exon 7 of SMN1 into mRNA that is transcribed from the SMN1 gene; and (2) no change or no substantial change in the amount of mRNA that is transcribed from the minigene and includes exon 7 of SMN1 in the presence of the compound relative to the amount of mRNA that is transcribed from the minigene and includes exon 7 of SMN1 in the absence of the compound indicates that the compound does not enhance the inclusion of exon 7 of SMN1 into mRNA that is transcribed from the SMN1 gene.

In another aspect, provided herein are kits comprising a primer and/or probe described below in the Biological Examples (e.g., SMN primers such as SEQ ID NO. 1, 7, 8, 11 or 13 and/or SEQ ID NO. 2, 9 or 12, and/or SMN probes such as a SEQ ID NO. 3 or 10) and the use thereof.

BRIEF DESCRIPTION OF THE FIGURES

FIG. 2, referenced in Biological Example 1, provides the DNA sequence of the minigene from the SMN2-A minigene construct SEQ ID NO. 21 (FIG. 2a).

FIG. 11, referenced in Biological Example 11, shows increased Smn protein expression in tissues (Brain.

FIG. 12, referenced in Biological Example 12, shows a dose dependent increase in Smn protein expression in tissues (Brain.

FIG. 16, referenced in Biological Example 15, shows increased Smn protein expression in tissues (Brain.

DETAILED DESCRIPTION

Figure 1:
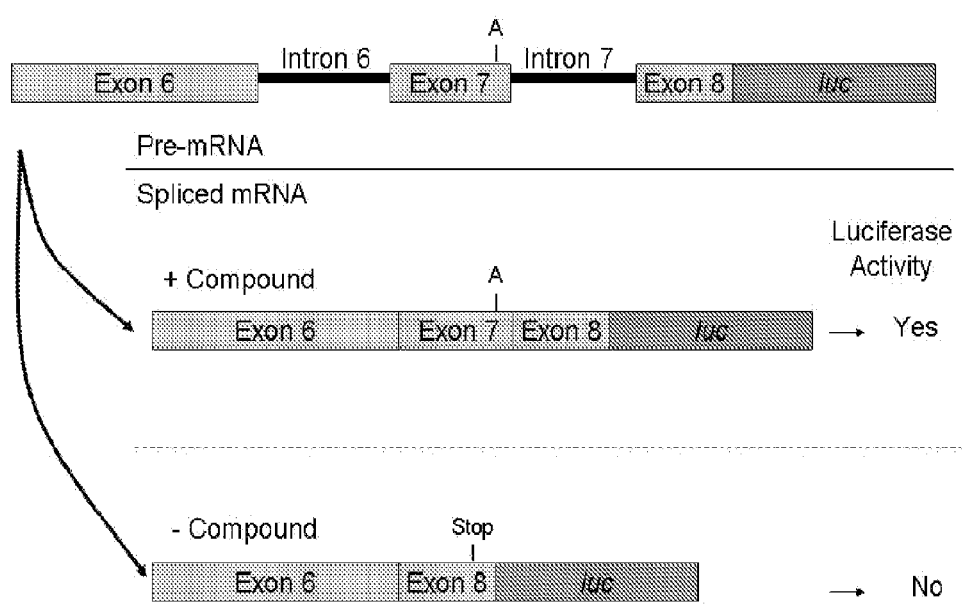
FIG. 1, referenced in Biological Example 1, is a schematic drawing of the SMN2 minigene construct, which features the two alternatively spliced mRNA transcripts. The nucleotide added to exon 7 of SMN2 after nucleic residue 48 is indicated by the letter "A," which could be adenine, cytosine, or thymine. The presence of one or more stop codon(s) generated in Exon 8 is indicated by "Stop."

Provided herein are compounds of Formula (I):

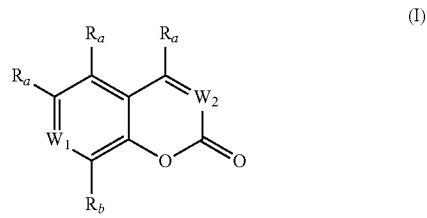

or a form thereof, wherein:
$w_1$ and $w_2$ are C—$R_1$ or C—$R_2$; wherein, one of $w_1$ and $w_2$ is C—$R_1$ and the other is C—$R_2$, provided that, when $w_1$ is C—$R_1$, then $w_2$ is C—$R_2$; or, when $w_1$ is C—$R_2$, then $w_2$ is C—$R_1$;
$R_1$ is $C_{1-8}$alkyl, amino, $C_{1-8}$alkyl-amino, ($C_{1-8}$alkyl)$_2$-amino, $C_{1-8}$alkoxy-$C_{1-8}$alkyl-amino, ($C_{1-8}$alkoxy-$C_{1-8}$alkyl)$_2$-amino, ($C_{1-8}$alkoxy-$C_{1-8}$alkyl)($C_{1-8}$alkyl)amino, amino-$C_{1-8}$alkyl, $C_{1-8}$alkyl-amino-$C_{1-8}$alkyl, ($C_{1-8}$alkyl)$_2$-amino-$C_{1-8}$alkyl, $C_{1-8}$alkoxy-$C_{1-8}$alkyl-amino-$C_{1-8}$alkyl, ($C_{1-8}$alkoxy-$C_{1-8}$alkyl)$_2$-amino-$C_{1-8}$alkyl, ($C_{1-8}$alkoxy-$C_{1-8}$alkyl)($C_{1-8}$alkyl)amino-$C_{1-8}$alkyl, amino-$C_{1-8}$alkyl-amino, (amino-$C_{1-8}$alkyl)$_2$-amino, (amino-$C_{1-8}$alkyl)($C_{1-8}$alkyl)amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl-amino-$C_{1-8}$alkyl)($C_{1-8}$alkyl)amino, ($C_{1-8}$alkyl)$_2$-amino-$C_{1-8}$alkyl-amino, [($C_{1-8}$alkyl)$_2$-amino-$C_{1-8}$alkyl]($C_{1-8}$alkyl)amino, amino-$C_{1-8}$alkoxy, $C_{1-8}$alkyl-amino-$C_{1-8}$alkoxy, ($C_{1-8}$alkyl)$_2$-amino-$C_{1-8}$alkoxy, $C_{1-8}$alkoxy-$C_{1-8}$alkyl-amino-$C_{1-8}$alkoxy, ($C_{1-8}$alkoxy-$C_{1-8}$alkyl)$_2$-amino-$C_{1-8}$alkoxy, ($C_{1-8}$alkoxy-$C_{1-8}$alkyl)($C_{1-8}$alkyl)amino-$C_{1-8}$alkoxy, amino-$C_{2-8}$alkenyl, $C_{1-8}$alkyl-amino-$C_{2-8}$alkenyl, ($C_{1-8}$alkyl)$_2$-amino-$C_{2-8}$alkenyl, amino-$C_{2-8}$alkynyl, $C_{1-8}$alkyl-amino-$C_{2-8}$alkynyl, ($C_{1-8}$alkyl)$_2$-amino-$C_{2-8}$alkynyl, halo-$C_{1-8}$alkyl-amino, (halo-$C_{1-8}$alkyl)$_2$-amino, (halo-$C_{1-8}$alkyl)($C_{1-8}$alkyl)amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino, (hydroxy-$C_{1-8}$alkyl)($C_{1-8}$alkyl)amino, hydroxy-$C_{1-8}$alkyl-amino-$C_{1-8}$alkyl, (hydroxy-$C_{1-8}$alkyl)$_2$-amino-$C_{1-8}$alkyl, (hydroxy-$C_{1-8}$alkyl)($C_{1-8}$alkyl)amino-$C_{1-8}$alkyl, hydroxy-$C_{1-8}$alkyl-amino-$C_{1-8}$alkoxy, (hydroxy-$C_{1-8}$alkyl)$_2$-amino-$C_{1-8}$alkoxy, (hydroxy-$C_{1-8}$alkyl)($C_{1-8}$alkyl)amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl)$_2$-amino, (hydroxy-$C_{1-8}$alkyl-amino-$C_{1-8}$alkyl)($C_{1-8}$alkyl)amino, (hydroxy-$C_{1-8}$alkyl)$_2$-amino-$C_{1-8}$alkyl-amino, (hydroxy-$C_{1-8}$alkyl)($C_{1-8}$alkyl)amino-$C_{1-8}$alkyl-amino, [(hydroxy-$C_{1-8}$alkyl)$_2$-amino-$C_{1-8}$alkyl]

($C_{1-8}$alkyl)amino, [(hydroxy-$C_{1-8}$alkyl)($C_{1-8}$alkyl)amino-$C_{1-8}$alkyl]($C_{1-8}$alkyl)amino, heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl;

wherein, each instance of heterocyclyl and heteroaryl is optionally substituted with one, two or three $R_3$ substituents and one additional, optional $R_4$ substituent; and, wherein, alternatively, each instance of heterocyclyl and heteroaryl is optionally substituted with one, two, three or four $R_3$ substituents;

$R_2$ is aryl, aryl-amino, aryl-amino-carbonyl, heterocyclyl, heteroaryl or heteroaryl-amino;

wherein, each instance of aryl, heterocyclyl and heteroaryl is optionally substituted with one, two or three $R_6$ substituents and one additional, optional $R_7$ substituent;

$R_a$ is, in each instance, independently selected from hydrogen, halogen or $C_{1-8}$alkyl;

$R_b$ is hydrogen, halogen, $C_{1-8}$alkyl or $C_{1-8}$alkoxy;

$R_3$ is, in each instance, independently selected from cyano, halogen, hydroxy, oxo, $C_{1-8}$alkyl, halo-$C_{1-8}$alkyl, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$alkoxy-carbonyl, amino, $C_{1-8}$alkyl-amino, ($C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl, amino-$C_{1-8}$alkyl-amino, $C_{1-8}$alkyl-amino-$C_{1-8}$alkyl-amino, ($C_{1-8}$alkyl)$_2$-amino-$C_{1-8}$alkyl-amino, $C_{1-8}$alkoxy-$C_{1-8}$alkyl-amino, $C_{1-8}$alkyl-carbonyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$ alkyl-amino, (hydroxy-$C_{1-8}$alkyl)$_2$-amino or (hydroxy-$C_{1-8}$alkyl)($C_{1-8}$alkyl)amino;

$R_4$ is $C_{3-14}$cycloalkyl, $C_{3-14}$cycloalkyl-$C_{1-8}$alkyl, $C_{3-14}$cycloalkyl-amino, aryl-$C_{1-8}$alkyl, aryl-$C_{1-8}$alkoxy-carbonyl, aryl-sulfonyloxy-$C_{1-8}$alkyl, heterocyclyl or heterocyclyl-$C_{1-8}$alkyl; wherein, each instance of $C_{3-14}$cycloalkyl, aryl and heterocyclyl is optionally substituted with one, two or three $R_5$ substituents;

$R_5$ is, in each instance, independently selected from halogen, hydroxy, cyano, nitro, $C_{1-8}$alkyl, halo-$C_{1-8}$alkyl, $C_{1-8}$alkoxy, halo-$C_{1-8}$alkoxy, amino, $C_{1-8}$alkyl-amino, ($C_{1-8}$alkyl)$_2$-amino or $C_{1-8}$alkyl-thio;

$R_6$ is, in each instance, independently selected from halogen, hydroxy, cyano, nitro, $C_{1-8}$alkyl, $C_{2-8}$alkenyl, halo-$C_{1-8}$alkyl, hydroxy-$C_{1-8}$alkyl, $C_{1-8}$alkoxy, halo-$C_{1-8}$alkoxy, amino, $C_{1-8}$alkyl-amino, ($C_{1-8}$alkyl)$_2$-amino or $C_{1-8}$alkyl-thio; and, $R_7$ is $C_{3-14}$cycloalkyl, $C_{3-14}$cycloalkyl-oxy, aryl, heterocyclyl or heteroaryl.

Embodiments

In one embodiment of a compound of Formula (I), $R_1$ is $C_{1-8}$alkyl, amino, $C_{1-8}$alkyl-amino, ($C_{1-8}$alkyl)$_2$-amino, $C_{1-8}$alkoxy-$C_{1-8}$alkyl-amino, ($C_{1-8}$alkoxy-$C_{1-8}$alkyl)$_2$-amino, ($C_{1-8}$alkoxy-$C_{1-8}$alkyl)($C_{1-8}$alkyl)amino, amino-$C_{1-8}$alkyl, $C_{1-8}$alkyl-amino-$C_{1-8}$alkyl, ($C_{1-8}$alkyl)$_2$-amino-$C_{1-8}$alkyl, $C_{1-8}$alkoxy-$C_{1-8}$alkyl-amino-$C_{1-8}$alkyl, ($C_{1-8}$alkoxy-$C_{1-8}$alkyl)$_2$-amino-$C_{1-8}$alkyl, ($C_{1-8}$alkoxy-$C_{1-8}$alkyl)($C_{1-8}$alkyl)amino-$C_{1-8}$alkyl, amino-$C_{1-8}$alkyl-amino, (amino-$C_{1-8}$ alkyl)$_2$-amino, (amino-$C_{1-8}$alkyl)($C_{1-8}$alkyl)amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl-amino-$C_{1-8}$alkyl)($C_{1-8}$alkyl)amino, ($C_{1-8}$alkyl)$_2$-amino-$C_{1-8}$alkyl-amino, [($C_{1-8}$alkyl)$_2$-amino-$C_{1-8}$alkyl]($C_{1-8}$alkyl)amino, amino-$C_{1-8}$alkoxy, $C_{1-8}$alkyl-amino-$C_{1-8}$alkoxy, ($C_{1-8}$alkyl)$_2$-amino-$C_{1-8}$alkoxy, $C_{1-8}$alkoxy-$C_{1-8}$alkyl-amino-$C_{1-8}$alkoxy, ($C_{1-8}$alkoxy-$C_{1-8}$alkyl)$_2$-amino-$C_{1-8}$alkoxy, ($C_{1-8}$alkoxy-$C_{1-8}$alkyl)($C_{1-8}$alkyl)amino-$C_{1-8}$alkoxy, amino-$C_{2-8}$alkenyl, $C_{1-8}$alkyl-amino-$C_{2-8}$alkenyl, ($C_{1-8}$alkyl)$_2$-amino-$C_{2-8}$alkenyl, amino-$C_{2-8}$alkynyl, $C_{1-8}$alkyl-amino-$C_{2-8}$alkynyl, ($C_{1-8}$ alkyl)$_2$-amino-$C_{2-8}$alkynyl, halo-$C_{1-8}$alkyl-amino, (halo-$C_{1-8}$alkyl)$_2$-amino, (halo-$C_{1-8}$alkyl)($C_{1-8}$alkyl)amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino, (hydroxy-$C_{1-8}$alkyl)($C_{1-8}$alkyl)amino, hydroxy-$C_{1-8}$alkyl-amino-$C_{1-8}$alkyl, (hydroxy-$C_{1-8}$alkyl)$_2$-amino-$C_{1-8}$alkyl, (hydroxy-$C_{1-8}$alkyl)($C_{1-8}$alkyl)amino-$C_{1-8}$alkyl, hydroxy-$C_{1-8}$alkyl-amino-$C_{1-8}$alkoxy, (hydroxy-$C_{1-8}$alkyl)$_2$-amino-$C_{1-8}$alkoxy, (hydroxy-$C_{1-8}$alkyl)($C_{1-8}$alkyl)amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl)$_2$-amino, (hydroxy-$C_{1-8}$alkyl-amino-$C_{1-8}$alkyl)($C_{1-8}$alkyl)amino, (hydroxy-$C_{1-8}$alkyl)$_2$-amino-$C_{1-8}$alkyl-amino, (hydroxy-$C_{1-8}$alkyl)($C_{1-8}$alkyl)amino-$C_{1-8}$alkyl-amino, [(hydroxy-$C_{1-8}$alkyl)$_2$-amino-$C_{1-8}$alkyl]($C_{1-8}$alkyl)amino, [(hydroxy-$C_{1-8}$alkyl)($C_{1-8}$alkyl)amino-$C_{1-8}$alkyl]($C_{1-8}$alkyl)amino, heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl; wherein, each instance of heterocyclyl and heteroaryl is optionally substituted.

In one embodiment of a compound of Formula (I), $R_1$ is $C_{1-8}$alkoxy-$C_{1-8}$alkyl-amino, ($C_{1-8}$alkoxy-$C_{1-8}$alkyl)$_2$-amino, ($C_{1-8}$alkoxy-$C_{1-8}$alkyl)($C_{1-8}$alkyl)amino, amino-$C_{1-8}$alkyl, $C_{1-8}$alkyl-amino-$C_{1-8}$alkyl, ($C_{1-8}$alkyl)$_2$-amino-$C_{1-8}$alkyl, $C_{1-8}$alkoxy-$C_{1-8}$alkyl-amino-$C_{1-8}$alkyl, ($C_{1-8}$alkoxy-$C_{1-8}$alkyl)$_2$-amino-$C_{1-8}$alkyl, ($C_{1-8}$alkoxy-$C_{1-8}$alkyl)($C_{1-8}$alkyl)amino-$C_{1-8}$alkyl, amino-$C_{1-8}$alkyl-amino, (amino-$C_{1-8}$ alkyl)$_2$-amino, (amino-$C_{1-8}$alkyl)($C_{1-8}$alkyl)amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl-amino-$C_{1-8}$alkyl)($C_{1-8}$alkyl)amino, ($C_{1-8}$alkyl)$_2$-amino-$C_{1-8}$alkyl-amino, [($C_{1-8}$alkyl)$_2$-amino-$C_{1-8}$alkyl]($C_{1-8}$alkyl)amino, amino-$C_{1-8}$alkoxy, $C_{1-8}$alkyl-amino-$C_{1-8}$alkoxy, ($C_{1-8}$alkyl)$_2$-amino-$C_{1-8}$ alkoxy, $C_{1-8}$alkoxy-$C_{1-8}$alkyl-amino-$C_{1-8}$alkoxy, ($C_{1-8}$alkoxy-$C_{1-8}$alkyl)$_2$-amino-$C_{1-8}$alkoxy, ($C_{1-8}$alkoxy-$C_{1-8}$alkyl)($C_{1-8}$alkyl)amino-$C_{1-8}$alkoxy, amino-$C_{2-8}$alkenyl, $C_{1-8}$alkyl-amino-$C_{2-8}$alkenyl, ($C_{1-8}$alkyl)$_2$-amino-$C_{2-8}$alkenyl, amino-$C_{2-8}$alkynyl, $C_{1-8}$alkyl-amino-$C_{2-8}$alkynyl, ($C_{1-8}$ alkyl)$_2$-amino-$C_{2-8}$alkynyl, halo-$C_{1-8}$alkyl-amino, (halo-$C_{1-8}$alkyl)$_2$-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino, (hydroxy-$C_{1-8}$alkyl)($C_{1-8}$alkyl)amino, hydroxy-$C_{1-8}$ alkyl-amino-$C_{1-8}$alkyl, (hydroxy-$C_{1-8}$alkyl)$_2$-amino-$C_{1-8}$alkyl, (hydroxy-$C_{1-8}$alkyl)($C_{1-8}$alkyl)amino-$C_{1-8}$alkyl, hydroxy-$C_{1-8}$alkyl-amino-$C_{1-8}$alkoxy, (hydroxy-$C_{1-8}$alkyl)$_2$-amino-$C_{1-8}$alkoxy, (hydroxy-$C_{1-8}$alkyl)($C_{1-8}$alkyl)amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl)$_2$-amino, (hydroxy-$C_{1-8}$alkyl-amino-$C_{1-8}$alkyl)($C_{1-8}$alkyl)amino, (hydroxy-$C_{1-8}$alkyl)$_2$-amino-$C_{1-8}$alkyl-amino, (hydroxy-$C_{1-8}$ alkyl)($C_{1-8}$alkyl)amino-$C_{1-8}$alkyl-amino, [(hydroxy-$C_{1-8}$alkyl)$_2$-amino-$C_{1-8}$alkyl]($C_{1-8}$alkyl)amino, [(hydroxy-$C_{1-8}$alkyl)($C_{1-8}$alkyl)amino-$C_{1-8}$alkyl]($C_{1-8}$alkyl)amino, heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$ alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$ alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$ alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl; wherein, each instance of heterocyclyl and heteroaryl is optionally substituted.

In another embodiment of a compound of Formula (I), $R_1$ is heterocyclyl selected from azetidinyl, tetrahydrofuranyl, pyrrolidinyl, piperidinyl, piperazinyl, 1,4-diazepanyl, 1,2,5,6-tetrahydropyridinyl, 1,2,3,6-tetrahydropyridinyl, hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, hexahydropyrrolo[3,4-c]pyrrol-(1H)-yl, (3aR,6aS)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(1H)-yl, (7R,8aS)-hexahydropyrrolo[1,2-a]pyrazin-(1H)-yl, (8aS)-hexahydropyrrolo[1,2-a]pyrazin-(1H)-yl, (8aR)-hexahydropyrrolo[1,2-a]pyrazin-(1H)-yl, (8aS)-octahydropyrrolo[1,2-a]pyrazin-(1H)-yl, (8aR)-octahydropyrrolo[1,2-a]pyrazin-(1H)-yl, hexahydropyrrolo[1,2-a]pyrazin-(2H)-one, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 2,6-diazaspiro[3.3]heptyl, 2,7-diazaspiro[3.5]nonyl, 5,8-diazaspiro[3.5]nonyl, 2,7-diazaspiro[4.4]nonyl or 6,9-diazaspiro[4.5]decyl; wherein, each instance of heterocyclyl is optionally substituted.

In another embodiment of a compound of Formula (I), $R_1$ is heterocyclyl selected from azetidin-1-yl, tetrahydrofuran-3-yl, pyrrolidin-1-yl, piperidin-1-yl, piperidin-4-yl, piperazin-1-yl, 1,4-diazepan-1-yl, 1,2,5,6-tetrahydropyridin-3-yl, 1,2,3,6-tetrahydropyridin-4-yl, hexahydropyrrolo[3,4-b]pyrrol-1(2H)-yl, (3aS,6aS)-hexahydropyrrolo[3,4-b]pyrrol-1(2H)-yl, (3aS,6aS)-hexahydropyrrolo[3,4-b]pyrrol-5(1H)-yl, (3aR,6aR)-hexahydropyrrolo[3,4-b]pyrrol-5(1H)-yl, hexahydropyrrolo[3,4-c]pyrrol-2(1H)-yl, (3aR,6aS)-hexahydropyrrolo[3,4-c]pyrrol-2(1H)-yl, octahydro-5H-pyrrolo[3,2-c]pyridin-5-yl, octahydro-6H-pyrrolo[3,4-b]pyridin-6-yl, (4aR,7aR)-octahydro-6H-pyrrolo[3,4-b]pyridin-6-yl, (4aS,7aS)-octahydro-6H-pyrrolo[3,4-b]pyridin-6-yl, hexahydropyrrolo[1,2-a]pyrazin-2(1H)-yl, hexahydropyrrolo[1,2-a]pyrazin-6(2H)-one, (7R,8aS)-hexahydropyrrolo[1,2-a]pyrazin-2(1H)-yl, (8aS)-hexahydropyrrolo[1,2-a]pyrazin-2(1H)-yl, (8aR)-hexahydropyrrolo[1,2-a]pyrazin-2(1H)-yl, (8aS)-octahydropyrrolo[1,2-a]pyrazin-2(1H)-yl, (8aR)-octahydropyrrolo[1,2-a]pyrazin-2(1H)-yl, octahydro-2H-pyrido[1,2-a]pyrazin-2-yl, 3-azabicyclo[3.1.0]hex-3-yl, 8-azabicyclo[3.2.1]oct-3-yl, (1R,5S)-8-azabicyclo[3.2.1]oct-3-yl, 8-azabicyclo[3.2.1]oct-2-en-3-yl, (1R,5S)-8-azabicyclo[3.2.1]oct-2-en-3-yl, 9-azabicyclo[3.3.1]non-3-yl, (1R,5S)-9-azabicyclo[3.3.1]non-3-yl, 2,5-diazabicyclo[2.2.1]hept-2-yl, (1S,4S)-2,5-diazabicyclo[2.2.1]hept-2-yl, 2,5-diazabicyclo[2.2.2]oct-2-yl, 3,8-diazabicyclo[3.2.1]oct-3-yl, (1R,5S)-3,8-diazabicyclo[3.2.1]oct-3-yl, 1,4-diazabicyclo[3.2.2]non-4-yl, azaspiro[3.3]hept-2-yl, 2,6-diazaspiro[3.3]hept-2-yl, 2,7-diazaspiro[3.5]non-7-yl, 5,8-diazaspiro[3.5]non-8-yl, 2,7-diazaspiro[4.4]non-2-yl or 6,9-diazaspiro[4.5]dec-9-yl; wherein, each instance of heterocyclyl is optionally substituted.

In another embodiment of a compound of Formula (I), $R_1$ is substituted heterocyclyl selected from (3aS,6aS)-1-methylhexahydropyrrolo[3,4-b]pyrrol-5(1H)-yl, (3aS,6aS)-5-methylhexahydropyrrolo[3,4-b]pyrrol-1(2H)-yl, (3aR,6aR)-1-methylhexahydropyrrolo[3,4-b]pyrrol-5(1H)-yl, (3aR,6aS)-5-methylhexahydropyrrolo[3,4-c]pyrrol-2(1H)-yl, (3aR,6aS)-5-(2-hydroxyethyl)hexahydropyrrolo[3,4-c]pyrrol-2(1H)-yl, (3aR,6aS)-5-(propan-2-yl)hexahydropyrrolo[3,4-c]pyrrol-2(1H)-yl, (3aR,6aS)-5-ethylhexahydropyrrolo[3,4-c]pyrrol-2(1H)-yl, (4aR,7aR)-1-methyloctahydro-6H-pyrrolo[3,4-b]pyridin-6-yl, (4aR,7aR)-1-ethyloctahydro-6H-pyrrolo[3,4-b]pyridin-6-yl, (4aR,7aR)-1-(2-hydroxyethyl)octahydro-6H-pyrrolo[3,4-b]pyridin-6-yl, (4aS,7aS)-1-methyloctahydro-6H-pyrrolo[3,4-b]pyridin-6-yl, (4aS,7aS)-1-(2-hydroxyethyl)octahydro-6H-pyrrolo[3,4-b]pyridin-6-yl, (7R,8aS)-7-hydroxyhexahydropyrrolo[1,2-a]pyrazin-2(1H)-yl, (8aS)-8a-methyloctahydropyrrolo[1,2-a]pyrazin-2(1H)-yl, (8aR)-8a-methyloctahydropyrrolo[1,2-a]pyrazin-2(1H)-yl, (1R,5S,6s)-6-(dimethylamino)-3-azabicyclo[3.1.0]hex-3-yl, (1R,5S)-8-methyl-8-azabicyclo[3.2.1]oct-3-yl, 9-methyl-9-azabicyclo[3.3.1]non-3-yl, (3-exo)-9-methyl-9-azabicyclo[3.3.1]non-3-yl, (1R,5S)-9-methyl-9-azabicyclo[3.3.1]non-3-yl, (1S,4S)-5-methyl-2,5-diazabicyclo[2.2.1]hept-2-yl or (1S,4S)-5-ethyl-2,5-diazabicyclo[2.2.1]hept-2-yl.

In one embodiment of a compound of Formula (I), $R_1$ is heterocyclyl-$C_{1-8}$alkyl, wherein heterocyclyl is selected from morpholinyl, piperidinyl, piperazinyl, imidazolyl or pyrrolidinyl; and, wherein, each instance of heterocyclyl is optionally substituted.

In one embodiment of a compound of Formula (I), $R_1$ is heterocyclyl-$C_{1-8}$alkyl selected from morpholin-4-yl-methyl, morpholin-4-yl-ethyl, morpholin-4-yl-propyl, piperidin-1-yl-methyl, piperazin-1-yl-methyl, piperazin-1-yl-ethyl, piperazin-1-yl-propyl, piperazin-1-yl-butyl, imidazol-1-yl-methyl, imidazol-1-yl-ethyl, imidazol-1-yl-propyl, imidazol-1-yl-butyl, pyrrolidin-1-yl-methyl, pyrrolidin-1-yl-ethyl, pyrrolidin-1-yl-propyl or pyrrolidin-1-yl-butyl; wherein, each instance of heterocyclyl is optionally substituted.

In one embodiment of a compound of Formula (I), $R_1$ is heterocyclyl-$C_{1-8}$alkoxy, wherein heterocyclyl is selected from pyrrolidinyl, piperidinyl or morpholinyl; and, wherein, each instance of heterocyclyl is optionally substituted.

In one embodiment of a compound of Formula (I), $R_1$ is heterocyclyl-$C_{1-8}$alkoxy selected from pyrrolidin-2-yl-methoxy, pyrrolidin-2-yl-ethoxy, pyrrolidin-1-yl-methoxy, pyrrolidin-1-yl-ethoxy, piperidin-1-yl-methoxy, piperidin-1-yl-ethoxy, morpholin-4-yl-methoxy or morpholin-4-yl-ethoxy; wherein, each instance of heterocyclyl is optionally substituted.

In one embodiment of a compound of Formula (I), $R_1$ is heterocyclyl-amino, wherein heterocyclyl is selected from azetidinyl, pyrrolidinyl, piperidinyl, 9-azabicyclo[3.3.1]nonyl or (1R,5S)-9-azabicyclo[3.3.1]nonyl; and, wherein, each instance of heterocyclyl is optionally substituted.

In one embodiment of a compound of Formula (I), $R_1$ is heterocyclyl-amino selected from azetidin-3-yl-amino, pyrrolidin-3-yl-amino, piperidin-4-yl-amino, 9-azabicyclo[3.3.1]non-3-yl-amino, (1R,5S)-9-azabicyclo[3.3.1]non-3-yl-amino, 9-methyl-9-azabicyclo[3.3.1]non-3-yl-amino, (3-exo)-9-methyl-9-azabicyclo[3.3.1]non-3-yl-amino or (1R,5S)-9-methyl-9-azabicyclo[3.3.1]non-3-yl-amino; wherein, each instance of heterocyclyl is optionally substituted.

In one embodiment of a compound of Formula (I), $R_1$ is (heterocyclyl)($C_{1-8}$alkyl)amino, wherein heterocyclyl is selected from pyrrolidinyl or piperidinyl; and, wherein, each instance of heterocyclyl is optionally substituted.

In one embodiment of a compound of Formula (I), $R_1$ is (heterocyclyl)($C_{1-8}$alkyl)amino selected from (pyrrolidin-3-yl)(methyl)amino or (piperidin-4-yl)(methyl)amino; wherein, each instance of heterocyclyl is optionally substituted.

In one embodiment of a compound of Formula (I), $R_1$ is heterocyclyl-amino-$C_{1-8}$alkyl, wherein heterocyclyl is selected from tetrahydrofuranyl; and, wherein, each instance of heterocyclyl is optionally substituted.

In one embodiment of a compound of Formula (I), $R_1$ is heterocyclyl-amino-$C_{1-8}$alkyl, selected from 3-(tetrahydrofuran-3-yl-amino)propyl; wherein, each instance of heterocyclyl is optionally substituted.

In one embodiment of a compound of Formula (I), $R_1$ is heterocyclyl-$C_{1-8}$alkyl-amino-$C_{1-8}$alkyl, wherein heterocyclyl is selected from tetrahydrofuranyl, thienyl or pyridinyl; and, wherein, each instance of heterocyclyl is optionally substituted.

In one embodiment of a compound of Formula (I), $R_1$ is heterocyclyl-$C_{1-8}$alkyl-amino-$C_{1-8}$alkyl, selected from 3-[(tetrahydrofuran-2-ylmethyl)amino]propyl, 3-[(thiophenyl-3-ylmethyl)amino]propyl, 3-[(pyridin-2-ylmethyl)amino]propyl or 3-[(pyridin-4-ylmethyl)amino]propyl; wherein, each instance of heterocyclyl is optionally substituted.

In one embodiment of a compound of Formula (I), $R_1$ is heterocyclyl-oxy, wherein heterocyclyl is selected from pyrrolidinyl or piperidinyl; and, wherein, each instance of heterocyclyl is optionally substituted.

In one embodiment of a compound of Formula (I), $R_1$ is heterocyclyl-oxy selected from pyrrolidin-3-yl-oxy or piperidin-4-yl-oxy; wherein, each instance of heterocyclyl is optionally substituted.

In one embodiment of a compound of Formula (I), $R_1$ is heterocyclyl-carbonyl, wherein heterocyclyl is selected from piperazinyl; and, wherein, each instance of heterocyclyl is optionally substituted.

In one embodiment of a compound of Formula (I), $R_1$ is heterocyclyl-carbonyl selected from piperazin-1-yl-carbonyl; wherein, each instance of heterocyclyl is optionally substituted.

In one embodiment of a compound of Formula (I), $R_1$ is heterocyclyl-carbonyl-oxy, wherein heterocyclyl is selected from piperazinyl; and, wherein, each instance of heterocyclyl is optionally substituted.

In one embodiment of a compound of Formula (I), $R_1$ is heterocyclyl-carbonyl-oxy selected from piperazin-1-yl-carbonyl-oxy; wherein, each instance of heterocyclyl is optionally substituted.

In one embodiment of a compound of Formula (I), $R_1$ is aryl-$C_{1-8}$alkyl-amino-$C_{1-8}$alkyl, wherein aryl is selected from phenyl; wherein, each instance of aryl is optionally substituted.

In one embodiment of a compound of Formula (I), $R_1$ is aryl-$C_{1-8}$alkyl-amino-$C_{1-8}$alkyl selected from 3-(benzylamino)propyl; wherein, each instance of aryl is optionally substituted.

In one embodiment of a compound of Formula (I), $R_1$ is heteroaryl, wherein heteroaryl is selected from pyridinyl; and, wherein, each instance of heteroaryl is optionally substituted.

In one embodiment of a compound of Formula (I), $R_1$ is heteroaryl selected from pyridin-4-yl; wherein, each instance of heteroaryl is optionally substituted.

In one embodiment of a compound of Formula (I), $R_1$ is heteroaryl-$C_{1-8}$alkyl, wherein heteroaryl is selected from 1H-imidazolyl; and, wherein, each instance of heteroaryl is optionally substituted.

In one embodiment of a compound of Formula (I), $R_1$ is heteroaryl-$C_{1-8}$alkyl selected from 1H-imidazol-1-yl-methyl; wherein, each instance of heteroaryl is optionally substituted.

In one embodiment of a compound of Formula (I), $R_1$ is (heteroaryl-$C_{1-8}$alkyl)($C_{1-8}$alkyl)amino, wherein heteroaryl is selected from pyridinyl; and, wherein, each instance of heteroaryl is optionally substituted.

In one embodiment of a compound of Formula (I), $R_1$ is (heteroaryl-$C_{1-8}$alkyl)($C_{1-8}$alkyl)amino selected from (pyridin-3-yl-methyl)(methyl)amino; wherein, each instance of heteroaryl is optionally substituted.

In one embodiment of a compound of Formula (I), $R_1$ is heteroaryl-$C_{1-8}$alkyl-amino-$C_{1-8}$alkyl, wherein heteroaryl is selected from thienyl or pyridinyl; and, wherein, each instance of heteroaryl is optionally substituted.

In one embodiment of a compound of Formula (I), $R_1$ is heteroaryl-$C_{1-8}$alkyl-amino-$C_{1-8}$alkyl selected from thien-3-yl-methyl-amino-propyl, pyridin-2-yl-methyl-amino-propyl, pyridin-3-yl-methyl-amino-propyl or pyridin-4-yl-methyl-amino-propyl; wherein, each instance of heteroaryl is optionally substituted.

In one embodiment of a compound of Formula (I), $R_3$ is selected from cyano, halogen, hydroxy, oxo, $C_{1-8}$alkyl, halo-$C_{1-8}$alkyl, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$alkoxy-carbonyl, amino, $C_{1-8}$alkyl-amino, ($C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl, amino-$C_{1-8}$alkyl-amino, $C_{1-8}$alkyl-amino-$C_{1-8}$alkyl-amino, ($C_{1-8}$alkyl)$_2$-amino-$C_{1-8}$alkyl-amino, $C_{1-8}$alkoxy-$C_{1-8}$alkyl-amino, $C_{1-8}$alkyl-carbonyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)($C_{1-8}$alkyl) amino or (hydroxy-$C_{1-8}$alkyl)$_2$-amino.

In one embodiment of a compound of Formula (I), $R_3$ is selected from cyano, halogen, hydroxy, oxo, $C_{1-8}$alkyl, halo-$C_{1-8}$alkyl, $C_{1-8}$alkoxy, $C_{1-8}$alkoxy-$C_{1-8}$alkyl, $C_{1-8}$alkoxy-carbonyl, amino, $C_{1-8}$alkyl-amino, ($C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl, $C_{1-8}$alkyl-amino-$C_{1-8}$alkyl-amino, $C_{1-8}$alkoxy-$C_{1-8}$alkyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)($C_{1-8}$alkyl) amino or (hydroxy-$C_{1-8}$alkyl)$_2$-amino.

In one embodiment of a compound of Formula (I), $R_3$ is $C_{1-8}$alkyl selected from methyl, ethyl, propyl, isopropyl or tert-butyl.

In one embodiment of a compound of Formula (I), $R_3$ is $C_{1-8}$alkyl selected from ethyl, propyl, isopropyl or tert-butyl.

In one embodiment of a compound of Formula (I), $R_3$ is halo-$C_{1-8}$alkyl selected from trihalo-methyl, dihalo-methyl, halo-methyl, trihalo-ethyl, dihalo-ethyl, halo-ethyl, trihalo-propyl, dihalo-propyl or halo-propyl; wherein, halo is selected from fluoro, chloro, bromo or iodo.

In one embodiment of a compound of Formula (I), $R_3$ is halo-$C_{1-8}$alkyl selected from trihalo-methyl, dihalo-methyl, halo-methyl, trihalo-ethyl, dihalo-ethyl, trihalo-propyl or dihalo-propyl; wherein, halo is selected from fluoro, chloro, bromo or iodo.

In one embodiment of a compound of Formula (I), $R_3$ is hydroxy-$C_{1-8}$alkyl selected from hydroxy-methyl, hydroxy-ethyl, hydroxy-propyl, dihydroxy-propyl, hydroxy-butyl or dihydroxy-butyl.

In one embodiment of a compound of Formula (I), $R_3$ is hydroxy-$C_{1-8}$alkyl selected from hydroxy-methyl, dihydroxy-propyl, hydroxy-butyl or dihydroxy-butyl.

In one embodiment of a compound of Formula (I), $R_3$ is $C_{1-8}$alkoxy selected from methoxy, ethoxy, propoxy or isopropoxy.

In one embodiment of a compound of Formula (I), $R_3$ is halo-$C_{1-8}$alkoxy selected from trihalo-methoxy, dihalo-methoxy, halo-methoxy, trihalo-ethoxy, dihalo-ethoxy, halo-ethoxy, trihalo-propoxy, dihalo-propoxy or halo-propoxy; wherein, halo is selected from fluoro, chloro, bromo or iodo.

In one embodiment of a compound of Formula (I), $R_3$ is $C_{1-8}$alkoxy-carbonyl-amino selected from methoxy-carbonyl-amino, ethoxy-carbonyl-amino, propoxy-carbonyl-amino, isopropoxy-carbonyl-amino, tert-butoxy-carbonyl-amino.

In one embodiment of a compound of Formula (I), $R_4$ is $C_{3-14}$cycloalkyl selected from cyclopropyl, cyclobutyl, cyclopentyl, cyclohexyl or cycloheptyl; wherein, each instance of $C_{3-14}$cycloalkyl is optionally substituted.

In one embodiment of a compound of Formula (I), $R_4$ is $C_{3-8}$cycloalkyl selected from cyclopropyl, cyclobutyl, cyclopentyl, cyclohexyl or cycloheptyl; wherein, each instance of $C_{3-8}$cycloalkyl is optionally substituted.

In one embodiment of a compound of Formula (I), $R_4$ is $C_{3-14}$cycloalkyl-$C_{1-8}$alkyl, wherein $C_{3-14}$cycloalkyl is selected from cyclopropyl, cyclobutyl, cyclopentyl, cyclohexyl or cycloheptyl; and, wherein, each instance of $C_{3-14}$cycloalkyl is optionally substituted.

In one embodiment of a compound of Formula (I), $R_4$ is $C_{3-8}$cycloalkyl-$C_{1-8}$alkyl, wherein $C_{3-8}$cycloalkyl is selected from cyclopropyl, cyclobutyl, cyclopentyl, cyclohexyl or cycloheptyl; and, wherein, each instance of $C_{3-8}$cycloalkyl is optionally substituted.

In one embodiment of a compound of Formula (I), $R_4$ is $C_{3-14}$cycloalkyl-amino, wherein $C_{3-14}$cycloalkyl is selected from cyclopropyl, cyclobutyl, cyclopentyl, cyclohexyl or cycloheptyl; and, wherein, each instance of $C_{3-14}$cycloalkyl is optionally substituted.

In one embodiment of a compound of Formula (I), $R_4$ is $C_{3-8}$cycloalkyl-amino, wherein $C_{3-8}$cycloalkyl is selected from cyclopropyl, cyclobutyl, cyclopentyl, cyclohexyl or cycloheptyl; and, wherein, each instance of $C_{3-8}$cycloalkyl is optionally substituted.

In one embodiment of a compound of Formula (I), $R_4$ is aryl-$C_{1-8}$alkyl, aryl-$C_{1-8}$alkoxy-carbonyl or aryl-sulfonyloxy-$C_{1-8}$alkyl, wherein each instance of aryl is selected from phenyl; and, wherein, each instance of aryl is optionally substituted.

In one embodiment of a compound of Formula (I), $R_4$ is aryl-$C_{1-8}$alkyl or aryl-$C_{1-8}$alkoxy-carbonyl, wherein each instance of aryl is selected from phenyl; and, wherein, each instance of aryl is optionally substituted.

In one embodiment of a compound of Formula (I), $R_4$ is heterocyclyl selected from oxetanyl, pyrrolidinyl, piperidinyl, piperazinyl, 1,3-dioxanyl or morpholinyl; wherein, each instance of heterocyclyl is optionally substituted.

In one embodiment of a compound of Formula (I), $R_4$ is heterocyclyl selected from oxetan-3-yl, pyrrolidin-1-yl, piperidin-1-yl, piperazin-1-yl, 1,3-dioxan-5-yl or morpholin-4-yl; wherein, each instance of heterocyclyl is optionally substituted.

In one embodiment of a compound of Formula (I), $R_4$ is heterocyclyl-$C_{1-8}$alkyl, wherein each instance of heterocyclyl is selected from pyrrolidinyl or piperidinyl; and, wherein, each instance of heterocyclyl is optionally substituted.

In one embodiment of a compound of Formula (I), $R_4$ is heterocyclyl-$C_{1-8}$alkyl selected from pyrrolidin-1-yl-$C_{1-8}$alkyl or piperidin-1-yl-$C_{1-8}$alkyl; wherein, each instance of heterocyclyl is optionally substituted.

In one embodiment of a compound of Formula (I), $R_5$ is selected from halogen, hydroxy, cyano, nitro, halo-$C_{1-8}$alkyl, $C_{1-8}$alkoxy, halo-$C_{1-8}$alkoxy, amino, $C_{1-8}$alkyl-amino, ($C_{1-8}$alkyl)$_2$-amino or $C_{1-8}$alkyl-thio.

In one embodiment of a compound of Formula (I), $R_5$ is hydroxy.

In one embodiment of a compound of Formula (I), $R_5$ is $C_{1-8}$alkyl selected from methyl, ethyl, propyl, isopropyl, n-butyl or tert-butyl.

In one embodiment of a compound of Formula (I), $R_5$ is $C_{1-8}$alkyl selected from ethyl, propyl, isopropyl or tert-butyl.

In one embodiment of a compound of Formula (I), $R_5$ is halo-$C_{1-8}$alkyl selected from trihalo-methyl, dihalo-methyl, halo-methyl, trihalo-ethyl, dihalo-ethyl, halo-ethyl, trihalo-propyl, dihalo-propyl or halo-propyl; wherein, halo is selected from fluoro, chloro, bromo or iodo.

In one embodiment of a compound of Formula (I), $R_5$ is $C_{1-8}$alkoxy selected from methoxy, ethoxy, propoxy or isopropoxy.

In one embodiment of a compound of Formula (I), $R_5$ is halo-$C_{1-8}$alkoxy selected from trihalo-methoxy, dihalo-methoxy, halo-methoxy, trihalo-ethoxy, dihalo-ethoxy, halo-ethoxy, trihalo-propoxy, dihalo-propoxy or halo-propoxy; wherein, halo is selected from fluoro, chloro, bromo or iodo.

In one embodiment of a compound of Formula (I), $R_2$ is aryl selected from phenyl; wherein, each instance of aryl is optionally substituted.

In one embodiment of a compound of Formula (I), $R_2$ is aryl-amino, wherein aryl is selected from phenyl; and, wherein, each instance of aryl is optionally substituted.

In one embodiment of a compound of Formula (I), $R_2$ is aryl-amino selected from phenyl-amino; wherein, each instance of aryl is optionally substituted.

In one embodiment of a compound of Formula (I), $R_2$ is aryl-amino-carbonyl, wherein aryl is selected from phenyl; wherein, each instance of aryl is optionally substituted.

In one embodiment of a compound of Formula (I), $R_2$ is aryl-amino-carbonyl selected from phenyl-amino-carbonyl; wherein, each instance of aryl is optionally substituted.

In one embodiment of a compound of Formula (I), $R_2$ is heterocyclyl selected from 1,2,3,6-tetrahydropyridinyl, 1,3-benzodioxolyl, 3a,7a-dihydrooxazolo[4,5-b]pyridinyl or 2,3-dihydro-1,4-benzodioxinyl; wherein, each instance of heterocyclyl is optionally substituted.

In another embodiment of a compound of Formula (I), $R_2$ is heterocyclyl selected from 1,2,3,6-tetrahydropyridin-4-yl, 1,3-benzodioxol-5-yl or 2,3-dihydro-1,4-benzodioxin-6-yl; wherein, each instance of heterocyclyl is optionally substituted.

In one embodiment of a compound of Formula (I), $R_2$ is heteroaryl selected from thienyl, 1H-pyrazolyl, 1H-imidazolyl, 1,3-thiazolyl, 1,2,4-oxadiazolyl, 1,3,4-oxadiazolyl, pyridinyl, pyrimidinyl, indolyl, 1H-indazolyl, 2H-indazolyl, indolizinyl, benzofuranyl, benzothienyl, 1H-benzimidazolyl, 1,3-benzothiazolyl, 1,3-benzooxazolyl, 9H-purinyl, furo[3,2-b]pyridinyl, furo[3,2-c]pyridinyl, furo[2,3-c]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, [1,3]oxazolo[4,5-b]pyridinyl, imidazo[1,2-a]pyrimidinyl, imidazo[1,2-a]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl or quinoxalinyl; wherein, each instance of heteroaryl is optionally substituted.

In another embodiment of a compound of Formula (I), $R_2$ is heteroaryl selected from thien-2-yl, thien-3-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,2,4-oxadiazol-3-yl, 1,3,4-oxadiazol-2-yl, pyridin-2-yl, pyridin-3-yl, pyridin-4-yl, pyrimidin-4-yl, 1H-indol-3-yl, 1H-indol-4-yl, indol-5-yl, indol-6-yl, 1H-indazol-5-yl, 2H-indazol-5-yl, indolizin-2-yl, benzofuran-2-yl, benzothien-2-yl, benzothien-3-yl, 1H-benzimidazol-2-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1,3-benzothiazol-6-yl, 9H-purin-8-yl, furo[3,2-b]pyridin-2-yl, furo[3,2-c]pyridin-2-yl, furo[2,3-c]pyridin-2-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrrolo[1,2-b]pyridazin-6-yl, pyrazolo[1,5-a]pyridin-2-yl, pyrazolo[1,5-a]pyrazin-2-yl, imidazo[2,1-b][1,3]thiazol-6-yl, imidazo[2,1-b][1,3,4]thiadiazol-6-yl, [1,3]oxazolo[4,5-b]pyridin-2-yl imidazo[1,2-a]pyridin-2-yl, imidazo[1,2-a]pyridin-6-yl, imidazo[1,2-a]pyrimidin-2-yl, imidazo[1,2-a]pyrimidin-6-yl, imidazo[1,2-c]pyrimidin-2-yl, imidazo[1,2-b]pyridazin-2-yl, imidazo[1,2-a]pyrazin-2-yl or quinoxalin-2-yl; wherein, each instance of heteroaryl is optionally substituted.

In another embodiment of a compound of Formula (I), $R_2$ is substituted heteroaryl selected from 4-methylthiophen-2-yl, 1-methyl-1H-pyrazol-3-yl, 4-methyl-1H-pyrazol-3-yl, 1-phenyl-1H-pyrazol-3-yl, 1-phenyl-1H-imidazol-4-yl, 2-methyl-1-(pyridin-2-yl)-1H-imidazol-4-yl, 4-methyl-1,3-thiazol-2-yl, 4-(trifluoromethyl)-1,3-thiazol-2-yl, 4-phenyl-1,3-thiazol-2-yl, 5-phenyl-1,2,4-oxadiazol-3-yl, 3-fluoropyridin-4-yl, 6-fluoropyridin-2-yl, 2-chloropyridin-4-yl, 4-chloropyridin-3-yl, 5-chloropyridin-2-yl, 6-methylpyridin-3-yl, 2-(trifluoromethyl)pyridin-3-yl, 4-(trifluoromethyl)pyridin-2-yl, 6-(trifluoromethyl)pyridin-2-yl, 2-methoxypyridin-4-yl, 4-methoxypyridin-3-yl, 6-methoxypyridin-2-yl, 2-ethoxypyridin-3-yl, 6-ethoxypyridin-2-yl, 6-(propan-2-yloxy)pyridin-2-yl, 6-(dimethylamino)pyridin-3-yl, 6-(methylsulfanyl)pyridin-2-yl, 6-(cyclobutyloxy)pyridin-2-yl, 6-(pyrrolidin-1-yl)pyridin-2-yl, 2-methylpyrimidin-4-yl, 2-(propan-2-yl)pyrimidin-4-yl, 2-cyclopropylpyrimidin-4-yl, 1-methyl-1H-indol-3-yl, 2-methyl-2H-indazol-5-yl, 1-methyl-1H-benzimidazol-2-yl, 4-methyl-1H-benzimidazol-2-yl 5-fluoro-1H-benzimidazol-2-yl, 4-fluoro-1,3-benzoxazol-2-yl, 5-fluoro-1,3-benzoxazol-2-yl, 4-chloro-1,3-benzoxazol-2-yl, 4-iodo-1,3-benzoxazol-2-yl, 2-methyl-1,3-benzoxazol-6-yl, 4-methyl-1,3-benzoxazol-2-yl, 4-(trifluoromethyl)-1,3-benzoxazol-2-yl, 7-(trifluoromethyl)-1,3-benzoxazol-2-yl, 4-chloro-1,3-benzothiazol-2-yl, 7-chloro-1,3-benzothiazol-2-yl, 2-methyl-1,3-benzothiazol-2-yl, 4-(trifluoromethyl)-1,3-benzothiazol-2-yl, 5-methylfuro[3,2-b]pyridin-2-yl, 4,6-dimethylfuro[3,2-c]pyridin-2-yl, 5,7-dimethylfuro[2,3-c]pyridin-2-yl, 4,6-dimethylthieno[3,2-c]pyridin-2-yl, 2,4-dimethylthieno[2,3-d]pyrimidin-6-yl, 1-methylpyrrolo[1,2-a]pyrazin-7-yl, 3-methylpyrrolo[1,2-a]pyrazin-7-yl, 1,3-dimethylpyrrolo[1,2-a]pyrazin-7-yl, 2-methylpyrrolo[1,2-b]pyridazin-6-yl, 5-methylpyrazolo[1,5-a]pyridin-2-yl, 4,6-dimethylpyrazolo[1,5-a]pyrazin-2-yl, 2-chloroimidazo[2,1-b][1,3]thiazol-6-yl, 2-methylimidazo[2,1-b][1,3]thiazol-6-yl, 3-methylimidazo[2,1-b][1,3]thiazol-6-yl, 2-ethylimidazo[2,1-b][1,3]thiazol-6-yl, 2-methylimidazo[2,1-b][1,3,4]thiadiazol-6-yl, 6-cyanoimidazo[1,2-c]pyridin-2-yl (also referred to as 2-imidazo[1,2-a]pyridine-6-carbonitrile), 6-fluoroimidazo[1,2-a]pyridin-2-yl, 8-fluoroimidazo[1,2-a]pyridin-2-yl, 6,8-difluoroimidazo[1,2-a]pyridin-2-yl, 7-(trifluoromethyl)imidazo[1,2-a]pyridin-2-yl, 8-(trifluoromethyl)imidazo[1,2-a]pyridin-2-yl, 6-chloroimidazo[1,2-a]pyridin-2-yl, 7-chloroimidazo[1,2-a]pyridin-2-yl, 8-chloroimidazo[1,2-a]pyridin-2-yl, 8-bromoimidazo[1,2-a]pyridin-2-yl, 2-methylimidazo[1,2-a]pyridin-2-yl, 5-methylimidazo[1,2-a]pyridin-2-yl, 6-methylimidazo[1,2-a]pyridin-2-yl, 7-methylimidazo[1,2-a]pyridin-2-yl, 8-methylimidazo[1,2-a]pyridin-2-yl, 7-ethylimidazo[1,2-a]pyridin-2-yl, 8-ethylimidazo[1,2-a]pyridin-2-yl, 6,8-dimethylimidazo[1,2-a]pyridin-2-yl, 8-ethyl-6-methylimidazo[1,2-a]pyridin-2-yl, 7-methoxyimidazo[1,2-a]pyridin-2-yl, 8-methoxyimidazo[1,2-a]pyridin-2-yl, 6-fluoro-8-methylimidazo[1,2-a]pyridin-2-yl, 8-fluoro-6-methylimidazo[1,2-a]pyridin-2-yl, 8-chloro-6-methylimidazo[1,2-a]pyridin-2-yl, 6-methyl-8-nitroimidazo[1,2-a]pyridin-2-yl, 8-cyclopropylimidazo[1,2-a]pyridin-2-yl, 2-methylimidazo[1,2-a]pyridin-6-yl, 2-ethylimidazo[1,2-a]pyridin-6-yl, 2,3-dimethylimidazo[1,2-a]pyridin-6-yl, 2,8-dimethylimidazo[1,2-a]pyridin-6-yl, 2-(trifluoromethyl)imidazo[1,2-a]pyridin-6-yl, 8-chloro-2-methylimidazo[1,2-a]pyridin-6-yl, 8-fluoro-2-methylimidazo[1,2-a]pyridin-6-yl, 6-fluoroimidazo[1,2-a]pyrimidin-2-yl, 6-chloroimidazo[1,2-a]pyrimidin-2-yl, 6-methylimidazo[1,2-a]pyrimidin-2-yl, 7-methylimidazo[1,2-a]pyrimidin-2-yl, 2-methylimidazo[1,2-a]pyrimidin-6-yl, 6-methylimidazo[1,2-b]pyridazin-2-yl, 2-methyl-3-(1,2,3,6-tetrahydropyridin-4-yl)imidazo[1,2-b]pyridazin-6-yl, 6-methylimidazo[1,2-a]pyrazin-2-yl, 8-methylimidazo[1,2-a]pyrazin-2-yl, 6,8-dimethylimidazo[1,2-c]pyrazin-2-yl, 6-chloro-8-methylimidazo[1,2-a]

pyrazin-2-yl, 6-methyl-8-(trifluoromethyl)imidazo[1,2-a]pyrazin-2-yl or 8-(methylsulfanyl)imidazo[1,2-a]pyrazin-2-yl.

In one embodiment of a compound of Formula (I), $R_2$ is heteroaryl-amino, wherein heteroaryl is selected from pyridinyl or pyrimidinyl; and, wherein, each instance of heteroaryl is optionally substituted.

In another embodiment of a compound of Formula (I), $R_2$ is heteroaryl-amino selected from pyridin-2-yl-amino, pyridin-3-yl-amino or pyrimidin-2-yl-amino; wherein, each instance of heteroaryl is optionally substituted.

In one embodiment of a compound of Formula (I), $R_6$ is selected from halogen, hydroxy, cyano, nitro, $C_{1-8}$alkyl, halo-$C_{1-8}$alkyl, hydroxy-$C_{1-8}$alkyl, $C_{1-8}$alkoxy, halo-$C_{1-8}$alkoxy, $(C_{1-8}$alkyl$)_2$-amino or $C_{1-8}$alkyl-thio In one embodiment of a compound of Formula (I), $R_6$ is $C_{1-8}$alkyl selected from methyl, ethyl, propyl, isopropyl or tert-butyl.

In one embodiment of a compound of Formula (I), $R_6$ is $C_{1-8}$alkyl selected from ethyl, propyl, isopropyl or tert-butyl.

In one embodiment of a compound of Formula (I), $R_6$ is $C_{2-8}$alkenyl selected from ethenyl, allyl or buta-1,3-dienyl.

In one embodiment of a compound of Formula (I), $R_6$ is $C_{2-8}$alkenyl selected from ethenyl or allyl.

In one embodiment of a compound of Formula (I), $R_6$ is halo-$C_{1-8}$alkyl selected from trihalo-methyl, dihalo-methyl, halo-methyl, trihalo-ethyl, dihalo-ethyl, halo-ethyl, trihalo-propyl, dihalo-propyl or halo-propyl; wherein, halo is selected from fluoro, chloro, bromo or iodo.

In one embodiment of a compound of Formula (I), $R_6$ is hydroxy-$C_{1-8}$alkyl selected from hydroxy-methyl, hydroxy-ethyl, hydroxy-propyl, dihydroxy-propyl, hydroxy-butyl or dihydroxy-butyl.

In one embodiment of a compound of Formula (I), $R_6$ is hydroxy-$C_{1-8}$alkyl selected from hydroxy-methyl, dihydroxy-propyl, hydroxy-butyl or dihydroxy-butyl.

In one embodiment of a compound of Formula (I), $R_6$ is $C_{1-8}$alkoxy selected from methoxy, ethoxy, propoxy or isopropoxy.

In one embodiment of a compound of Formula (I), $R_6$ is halo-$C_{1-8}$alkoxy selected from trihalo-methoxy, dihalo-methoxy, halo-methoxy, trihalo-ethoxy, dihalo-ethoxy, halo-ethoxy, trihalo-propoxy, dihalo-propoxy or halo-propoxy; wherein, halo is selected from fluoro, chloro, bromo or iodo.

In one embodiment of a compound of Formula (I), $R_7$ is $C_{3-14}$cycloalkyl, $C_{3-14}$cycloalkyl-oxy, aryl, heterocyclyl or heteroaryl; wherein $C_{3-14}$cycloalkyl is selected from cyclopropyl or cyclobutoxy; wherein aryl is selected from phenyl; wherein heterocyclyl is selected from pyrrolidinyl or 1,2,3,6-tetrahydropyridinyl; and, wherein heteroaryl is selected from thienyl or pyridinyl.

In one embodiment of a compound of Formula (I), $R_7$ is $C_{3-14}$cycloalkyl or $C_{3-14}$cycloalkyl-oxy, wherein each instance of $C_{3-14}$cycloalkyl is selected from cyclopropyl, cyclobutyl, cyclopentyl, cyclohexyl or cycloheptyl.

In one embodiment of a compound of Formula (I), $R_7$ is $C_{3-8}$cycloalkyl or $C_{3-8}$cycloalkyl-oxy, wherein each instance of $C_{3-8}$cycloalkyl is selected from cyclopropyl, cyclobutyl, cyclopentyl, cyclohexyl or cycloheptyl.

In one embodiment of a compound of Formula (I), $R_7$ is aryl selected from phenyl.

In one embodiment of a compound of Formula (I), $R_7$ is heterocyclyl selected from pyrrolidinyl or 1,2,3,6-tetrahydropyridinyl.

In one embodiment of a compound of Formula (I), $R_7$ is heterocyclyl selected from pyrrolidin-1-yl or 1,2,3,6-tetrahydropyridin-4-yl.

In one embodiment of a compound of Formula (I), $R_7$ is heteroaryl selected from thienyl or pyridinyl.

In one embodiment of a compound of Formula (I), $R_7$ is heteroaryl selected from pyridinyl.

In one embodiment of a compound of Formula (I), $R_7$ is heteroaryl selected from thien-2-yl or pyridin-2-yl.

In one embodiment of a compound of Formula (I), $R_7$ is heteroaryl selected from pyridin-2-yl.

In one embodiment of a compound of Formula (I), the compound is selected from Formula (Ia) or Formula (Ib):

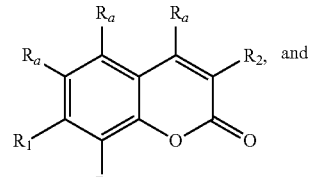

(Ia)

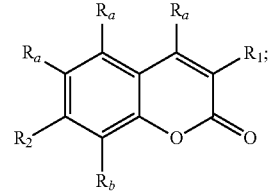

(Ib)

or a form thereof, wherein all variables are as previously defined.

In one embodiment of a compound of Formula (I), when $w_1$ is C—$R_1$, $w_2$ is C—$R_2$ and $R_1$ is selected from (methyl)$_2$-amino and $R_2$ is benzothiazol-2-yl optionally substituted with one $R_6$ substituent, then $R_6$ is other than chloro.

In one embodiment of a compound of Formula (I), when $w_1$ is C—$R_1$, $w_2$ is C—$R_2$ and $R_1$ is selected from (methyl)$_2$-amino or (2-fluoro-ethyl)(methyl)amino, then $R_2$ is benzothiazol-2-yl substituted with one, two or three $R_6$ substituents and one additional, optional $R_7$ substituent.

In one embodiment of a compound of Formula (I), when $w_1$ is C—$R_1$, $w_2$ is C—$R_2$ and $R_1$ is piperazin-1-yl substituted with one $R_3$ substituent selected from methyl, 2-fluoro-ethyl, 2-hydroxy-ethyl or 3-hydroxy-propyl; or, one $R_4$ substituent selected from 3-(4-methyl-phenyl-sulfonyloxy)-propyl, then $R_2$ is benzothiazol-2-yl substituted with one, two or three $R_6$ substituents and one additional, optional $R_7$ substituent.

In one embodiment of a compound of Formula (I), when $w_1$ is C—$R_1$, $w_2$ is C—$R_2$ and $R_1$ is piperazin-1-yl substituted with one $R_3$ substituent selected from 2-fluoro-ethyl and $R_2$ is imidazo[1,2-a]pyridin-2-yl optionally substituted with one $R_6$ substituent, then $R_6$ is other than chloro.

In one embodiment of a compound of Formula (I), when $w_1$ is C—$R_1$, $w_2$ is C—$R_2$ and $R_1$ is (2-fluoro-ethyl)(methyl)amino and $R_2$ is [1,3,4]oxadiazol-2-yl optionally substituted with one $R_7$ substituent, then $R_7$ is other than thien-2-yl.

In one embodiment of a compound of Formula (I), when $w_1$ is C—$R_1$, $w_2$ is C—$R_2$ and $R_1$ is piperazin-1-yl substituted with one $R_3$ substituent selected from 3-fluoro-propyl and $R_2$ is thiazol-2-yl optionally substituted with two $R_6$ substituents, then $R_6$ is not simultaneously methyl and buta-1,3-dienyl.

In one embodiment of a compound of Formula (I), when $w_1$ is C—$R_1$, $w_2$ is C—$R_2$ and $R_1$ is selected from methyl-amino or (methyl)$_2$-amino, then $R_2$ is benzooxazol-2-yl substituted with one, two or three $R_6$ substituents and one additional, optional $R_7$ substituent.

In one embodiment of a compound of Formula (I), when $w_1$ is C—$R_1$, $w_2$ is C—$R_2$ and $R_1$ is selected from (methyl)$_2$-amino and $R_2$ is benzooxazol-2-yl optionally substituted with one $R_6$ substituent, then $R_6$ is other than chloro.

In one embodiment of a compound of Formula (I), when $w_1$ is C—$R_1$, $w_2$ is C—$R_2$ and $R_1$ is piperazin-1-yl substituted with one $R_3$ substituent selected from methyl, then $R_2$ is benzooxazol-2-yl substituted with one, two or three $R_6$ substituents and one additional, optional $R_7$ substituent.

In one embodiment of a compound of Formula (I), when $w_1$ is C—$R_1$, $w_2$ is C—$R_2$ and $R_1$ is selected from (methyl)$_2$-amino, then $R_2$ is 1H-benzoimidazol-2-yl substituted with one, two or three $R_6$ substituents and one additional, optional $R_7$ substituent.

In one embodiment of a compound of Formula (I), when $w_1$ is C—$R_1$, $w_2$ is C—$R_2$ and $R_1$ is selected from (methyl)$_2$-amino and $R_2$ is 1H-benzoimidazol-2-yl substituted with one $R_6$ substituent, then $R_6$ is other than methyl.

In certain embodiments, the compound of Formula (I) is other than:

3-benzothiazol-2-yl-7-[4-(2-fluoro-ethyl)-piperazin-1-yl]-chromen-2-one, 3-benzothiazol-2-yl-7-[4-(2-hydroxy-ethyl)-piperazin-1-yl]-chromen-2-one, 3-(6-chloro-imidazo[1,2-a]pyridin-2-yl)-7-[4-(2-fluoro-ethyl)-piperazin-1-yl]-chromen-2-one, 3-benzothiazol-2-yl-7-(4-methyl-piperazin-1-yl)-chromen-2-one, 3-benzothiazol-2-yl-7-[(2-fluoro-ethyl)-methyl-amino]-chromen-2-one, 7-[(2-fluoro-ethyl)-methyl-amino]-3-(5-thiophene-2-yl-[1,3,4]oxadiazol-2-yl)-chromen-2-one, 3-(4-buta-1,3-dienyl-5-methyl-thiazol-2-yl)-7-[4-(3-fluoro-propyl)-piperazin-1-yl]-chromen-2-one, toluene-4-sulfonic acid 3-[4-(3-benzothiazol-2-yl-2-oxo-2H-chromen-7-yl)-piperazin-1-yl]-propyl ester, 3-benzothiazol-2-yl-7-[4-(3-hydroxy-propyl)-piperazin-1-yl]-chromen-2-one, 3-benzooxazol-2-yl-7-(4-methyl-piperazin-1-yl)-chromen-2-one, 7-dimethylamino-3-(1-methyl-1H-benzoimidazol-2-yl)-chromen-2-one, 3-(1H-benzoimidazol-2-yl)-7-dimethylamino-chromen-2-one, 3-(6-chloro-benzothiazol-2-yl)-7-dimethylamino-chromen-2-one, 3-benzothiazol-2-yl-7-dimethylamino-chromen-2-one, 3-benzooxazol-2-yl-7-dimethylamino-chromen-2-one, 3-benzooxazol-2-yl-7-methylamino-chromen-2-one, and 3-(5-chloro-benzooxazol-2-yl)-7-dimethylamino-chromen-2-one.

Further provided herein are compounds of Formula (I):

(I)

or a form thereof, wherein:

$w_1$ and $w_2$ are C—$R_1$ or C—$R_2$; wherein, one of $w_1$ and $w_2$ is C—$R_1$ and the other is C—$R_2$, provided that, when $w_1$ is C—$R_1$, then $w_2$ is C—$R_2$; or, when $w_1$ is C—$R_2$, then $w_2$ is C—$R_1$;

$R_1$ is amino, $C_{1-8}$alkoxy-$C_{1-8}$alkyl-amino, ($C_{1-8}$alkoxy-$C_{1-8}$alkyl)$_2$-amino, ($C_{1-8}$alkoxy-$C_{1-8}$alkyl)($C_{1-8}$alkyl)amino, amino-$C_{1-8}$alkyl, $C_{1-8}$alkyl-amino-$C_{1-8}$alkyl, ($C_{1-8}$alkyl)$_2$-amino-$C_{1-8}$alkyl, $C_{1-8}$alkoxy-$C_{1-8}$alkyl-amino-$C_{1-8}$alkyl, ($C_{1-8}$alkoxy-$C_{1-8}$alkyl)$_2$-amino-$C_{1-8}$alkyl, ($C_{1-8}$alkoxy-$C_{1-8}$alkyl)($C_{1-8}$alkyl)amino-$C_{1-8}$alkyl, amino-$C_{1-8}$alkyl-amino, (amino-$C_{1-8}$alkyl)$_2$-amino, (amino-$C_{1-8}$alkyl)($C_{1-8}$alkyl)amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl-amino-$C_{1-8}$alkyl)($C_{1-8}$alkyl)amino, ($C_{1-8}$alkyl)$_2$-amino-$C_{1-8}$alkyl-amino, [($C_{1-8}$alkyl)$_2$-amino-$C_{1-8}$alkyl]($C_{1-8}$alkyl)amino, amino-$C_{1-8}$alkoxy, $C_{1-8}$alkyl-amino-$C_{1-8}$alkoxy, ($C_{1-8}$alkyl)$_2$-amino-$C_{1-8}$alkoxy, $C_{1-8}$alkoxy-$C_{1-8}$alkyl-amino-$C_{1-8}$alkoxy, ($C_{1-8}$alkoxy-$C_{1-8}$alkyl)$_2$-amino-$C_{1-8}$alkoxy, ($C_{1-8}$alkoxy-$C_{1-8}$alkyl)($C_{1-8}$alkyl)amino-$C_{1-8}$alkoxy, amino-$C_{2-8}$alkenyl, $C_{1-8}$alkyl-amino-$C_{2-8}$alkenyl, ($C_{1-8}$alkyl)$_2$-amino-$C_{2-8}$alkenyl, amino-$C_{2-8}$alkynyl, $C_{1-8}$alkyl-amino-$C_{2-8}$alkynyl, ($C_{1-8}$alkyl)$_2$-amino-$C_{2-8}$alkynyl, halo-$C_{1-8}$alkyl-amino, (halo-$C_{1-8}$alkyl)$_2$-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino, (hydroxy-$C_{1-8}$alkyl)($C_{1-8}$alkyl)amino, hydroxy-$C_{1-8}$alkyl-amino-$C_{1-8}$alkyl, (hydroxy-$C_{1-8}$alkyl)$_2$-amino-$C_{1-8}$alkyl, (hydroxy-$C_{1-8}$alkyl)($C_{1-8}$alkyl)amino-$C_{1-8}$alkyl, hydroxy-$C_{1-8}$alkyl-amino-$C_{1-8}$alkoxy, (hydroxy-$C_{1-8}$alkyl)$_2$-amino-$C_{1-8}$alkoxy, (hydroxy-$C_{1-8}$alkyl)($C_{1-8}$alkyl)amino-$C_{1-8}$alkoxy, (hydroxy-$C_{1-8}$alkyl)$_2$-amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl)$_2$-amino, (hydroxy-$C_{1-8}$alkyl-amino-$C_{1-8}$alkyl)($C_{1-8}$alkyl)amino, (hydroxy-$C_{1-8}$alkyl)$_2$-amino-$C_{1-8}$alkyl-amino, (hydroxy-$C_{1-8}$alkyl)($C_{1-8}$alkyl)amino-$C_{1-8}$alkyl-amino, [(hydroxy-$C_{1-8}$alkyl)$_2$-amino-$C_{1-8}$alkyl]($C_{1-8}$alkyl)amino, [(hydroxy-$C_{1-8}$alkyl)($C_{1-8}$alkyl)amino-$C_{1-8}$alkyl]($C_{1-8}$alkyl)amino, heterocyclyl, heterocyclyl-$C_{1-8}$ alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$ alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)

amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl;

wherein, each instance of heterocyclyl and heteroaryl is optionally substituted with one, two or three $R_3$ substituents and one additional, optional $R_4$ substituent; and, wherein, alternatively, each instance of heterocyclyl and heteroaryl is optionally substituted with one, two, three or four $R_3$ substituents;

$R_2$ is aryl, aryl-amino, aryl-amino-carbonyl, heterocyclyl, heteroaryl or heteroaryl-amino;

wherein, each instance of aryl, heterocyclyl and heteroaryl is optionally substituted with one, two or three $R_6$ substituents and one additional, optional $R_7$ substituent;

$R_a$ is, in each instance, independently selected from hydrogen, halogen or $C_{1-8}$alkyl;

$R_b$ is hydrogen, halogen, $C_{1-8}$alkyl or $C_{1-8}$alkoxy;

$R_3$ is, in each instance, independently selected from cyano, halogen, hydroxy, oxo, $C_{1-8}$alkyl, halo-$C_{1-8}$alkyl, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$alkoxy-carbonyl, amino, $C_{1-8}$alkyl-amino, ($C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl, amino-$C_{1-8}$alkyl-amino, $C_{1-8}$alkyl-amino-$C_{1-8}$alkyl-amino, ($C_{1-8}$alkyl)$_2$-amino-$C_{1-8}$alkyl-amino, $C_{1-8}$alkoxy-$C_{1-8}$alkyl-amino, $C_{1-8}$alkyl-carbonyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$ alkyl-amino, (hydroxy-$C_{1-8}$alkyl)$_2$-amino or (hydroxy-$C_{1-8}$alkyl)($C_{1-8}$alkyl)amino;

$R_4$ is $C_{3-14}$cycloalkyl, $C_{3-14}$cycloalkyl-$C_{1-8}$alkyl, $C_{3-14}$cycloalkyl-amino, aryl-$C_{1-8}$alkyl, aryl-$C_{1-8}$alkoxy-carbonyl, heterocyclyl or heterocyclyl-$C_{1-8}$alkyl; wherein, each instance of $C_{3-14}$cycloalkyl, aryl and heterocyclyl is optionally substituted with one, two or three $R_5$ substituents;

$R_5$ is, in each instance, independently selected from halogen, hydroxy, cyano, nitro, $C_{1-8}$alkyl, halo-$C_{1-8}$alkyl, $C_{1-8}$alkoxy, halo-$C_{1-8}$alkoxy, amino, $C_{1-8}$alkyl-amino, ($C_{1-8}$alkyl)$_2$-amino or $C_{1-8}$alkyl-thio;

$R_6$ is, in each instance, independently selected from halogen, hydroxy, cyano, nitro, $C_{1-8}$alkyl, halo-$C_{1-8}$alkyl, hydroxy-$C_{1-8}$alkyl, $C_{1-8}$alkoxy, halo-$C_{1-8}$alkoxy, amino, $C_{1-8}$alkyl-amino, ($C_{1-8}$alkyl)$_2$-amino or $C_{1-8}$alkyl-thio; and, $R_7$ is $C_{3-14}$cycloalkyl, $C_{3-14}$cycloalkyl-oxy, aryl, heterocyclyl or heteroaryl.

In one embodiment of a compound of Formula (I), $R_3$ is, in each instance, independently selected from cyano, halogen, hydroxy, oxo, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$alkoxy-carbonyl, amino, $C_{1-8}$alkyl-amino, ($C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl, amino-$C_{1-8}$alkyl-amino, $C_{1-8}$alkyl-amino-$C_{1-8}$alkyl-amino, ($C_{1-8}$alkyl)$_2$-amino-$C_{1-8}$alkyl-amino, $C_{1-8}$alkoxy-$C_{1-8}$alkyl-amino, $C_{1-8}$alkyl-carbonyl-amino, $C_{1-8}$alkoxy-carbonyl-amino, hydroxy-$C_{1-8}$alkoxy-$C_{1-8}$alkyl, hydroxy-$C_{1-8}$ alkyl-amino, (hydroxy-$C_{1-8}$alkyl)$_2$-amino or (hydroxy-$C_{1-8}$alkyl)($C_{1-8}$alkyl)amino.

In one embodiment of a compound of Formula (I), $R_6$ is, in each instance, independently selected from hydroxy, cyano, nitro, halo-$C_{1-8}$alkyl, hydroxy-$C_{1-8}$alkyl, $C_{1-8}$alkoxy, halo-$C_{1-8}$ alkoxy, amino, $C_{1-8}$alkyl-amino, ($C_{1-8}$alkyl)$_2$-amino or $C_{1-8}$alkyl-thio.

In one embodiment of a compound of Formula (I), $R_7$ is $C_{3-14}$cycloalkyl, $C_{3-14}$cycloalkyl-oxy, aryl or heterocyclyl.

In one embodiment of a compound of Formula (I), the compound is selected from the group consisting of:

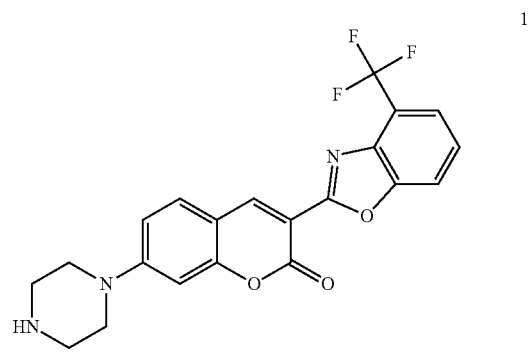

1

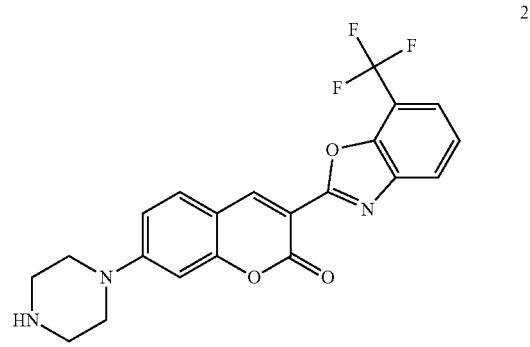

2

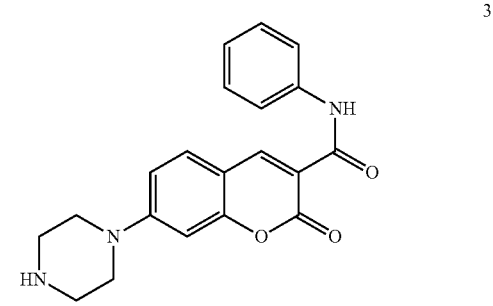

3

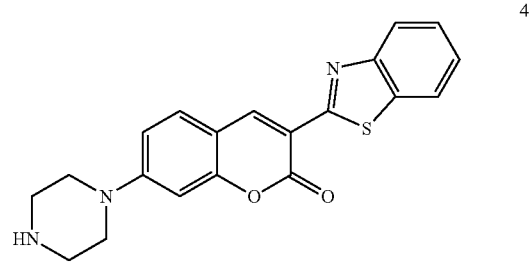

4

-continued
5
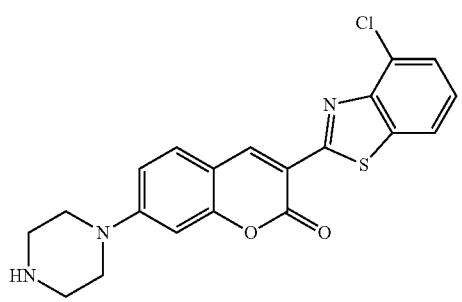
6
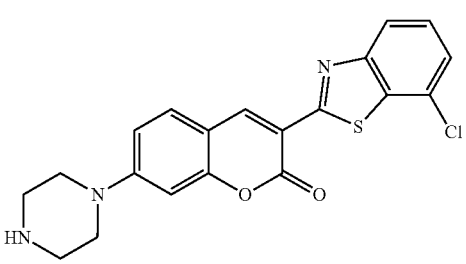
7
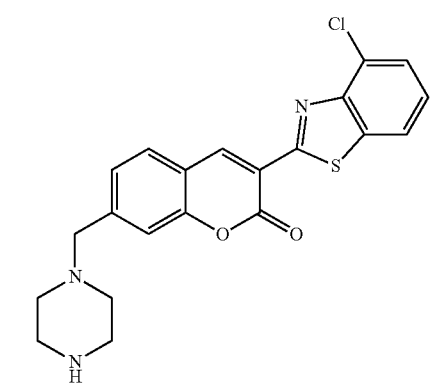
8
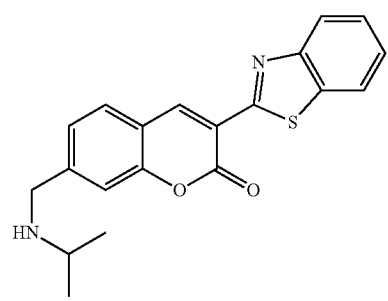
9
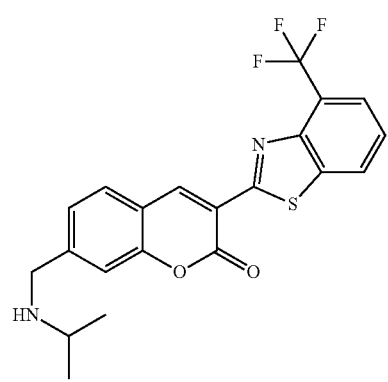
-continued
10
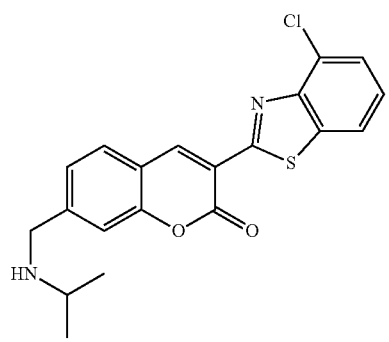
11
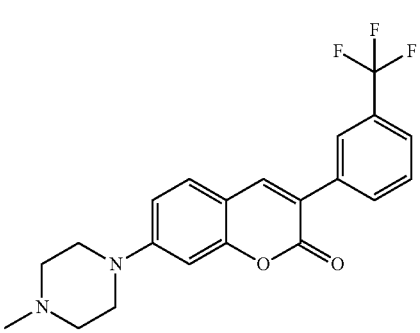
12
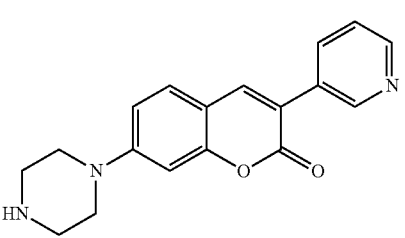
13
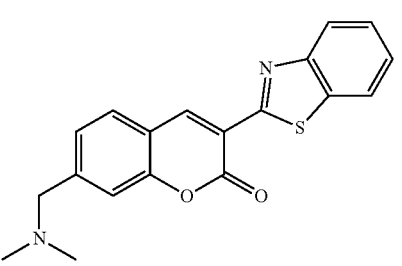
14
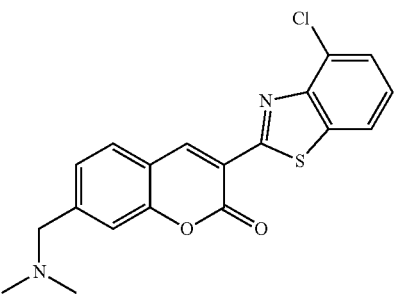

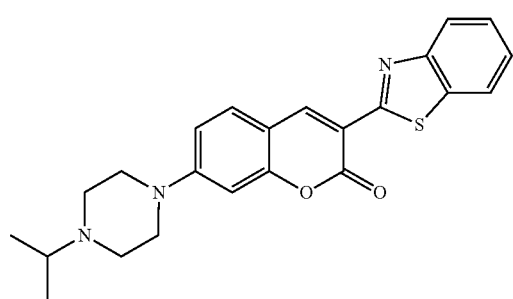
15
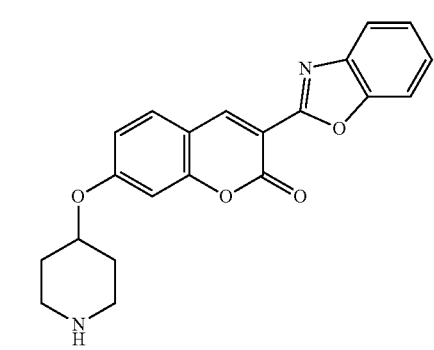
20
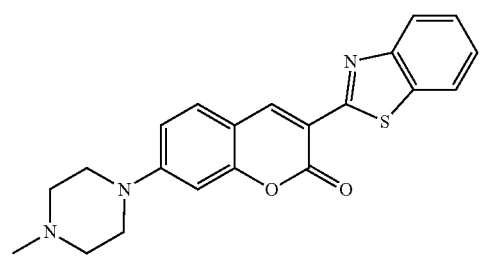
16
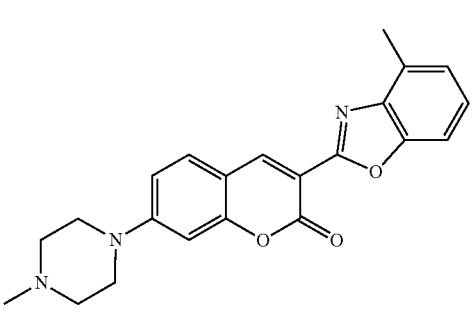
21
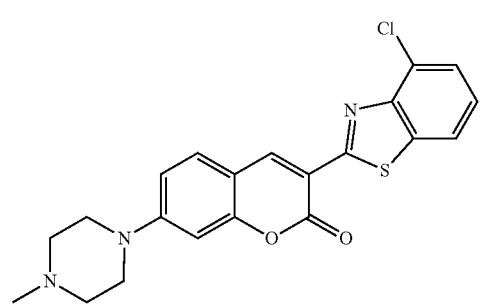
17
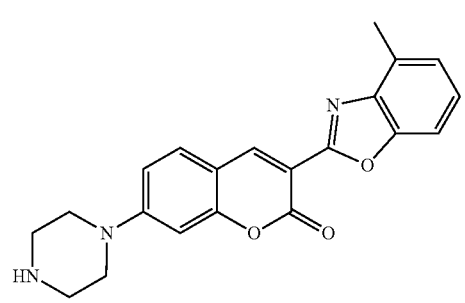
22
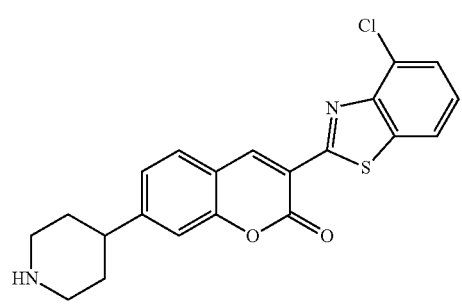
18
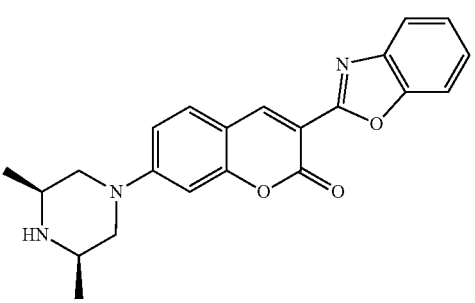
23
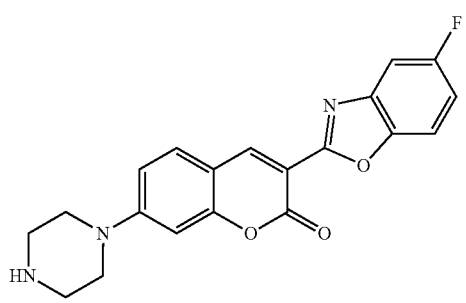
19
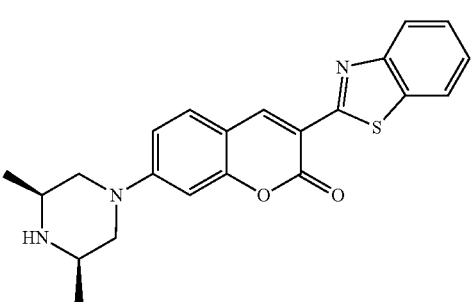
24

33
-continued
25
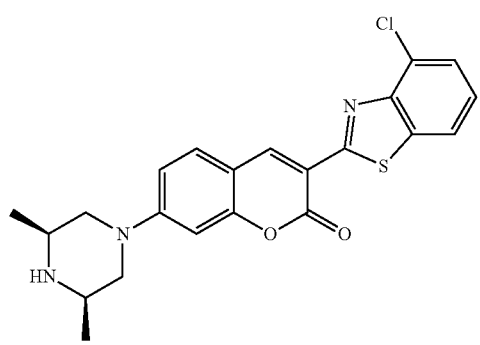
26
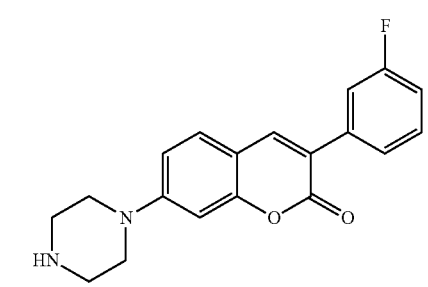
27
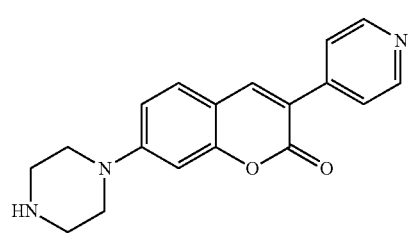
28
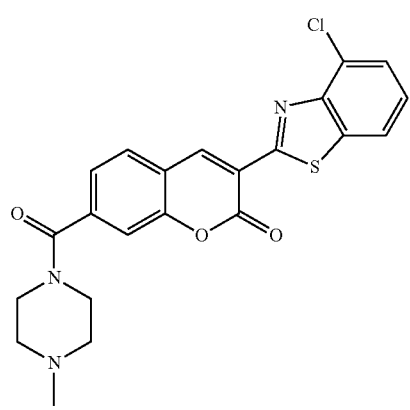
29
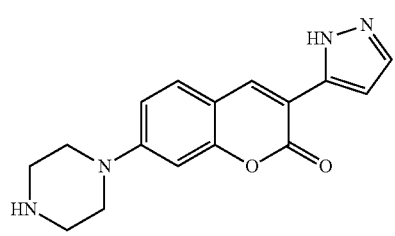
34
-continued
30
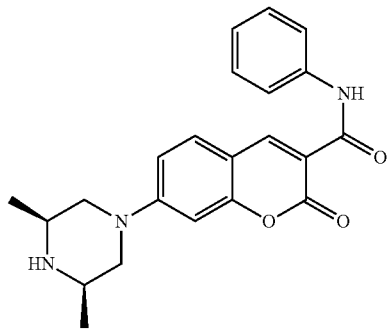
31
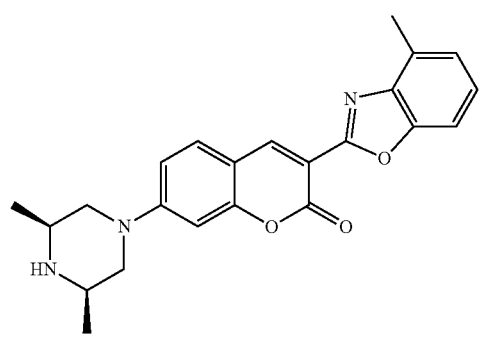
32
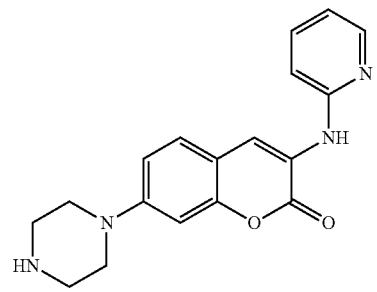
33
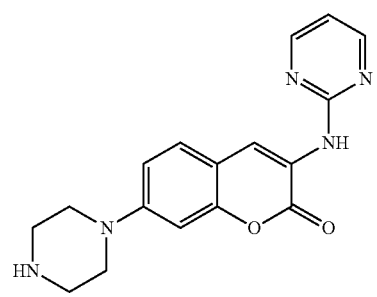
34
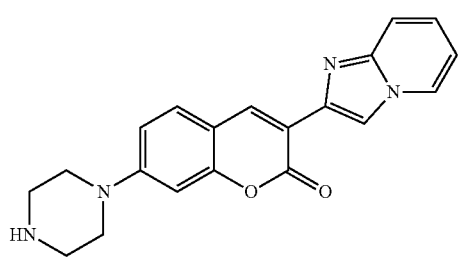

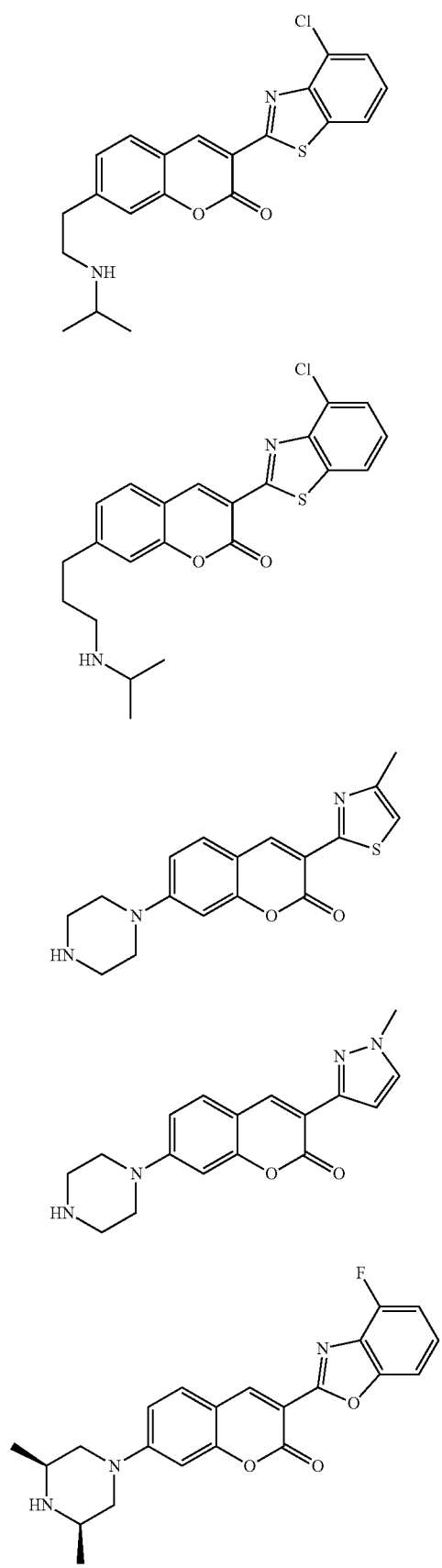

-continued
44
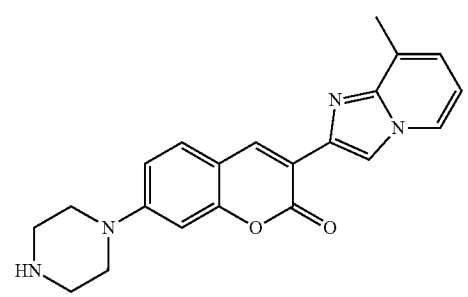
45
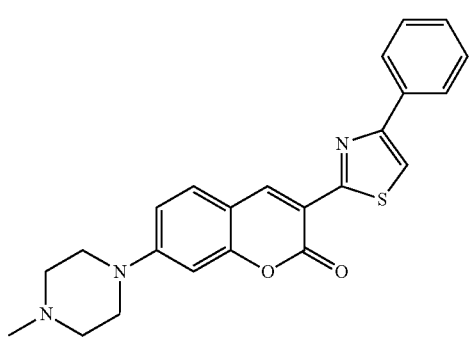
46
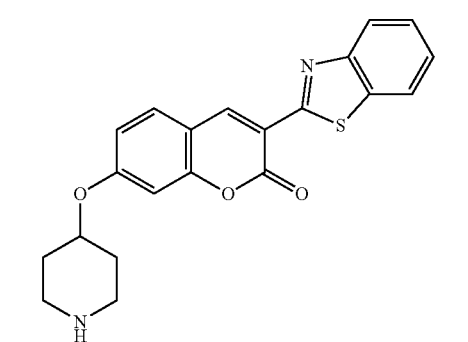
47
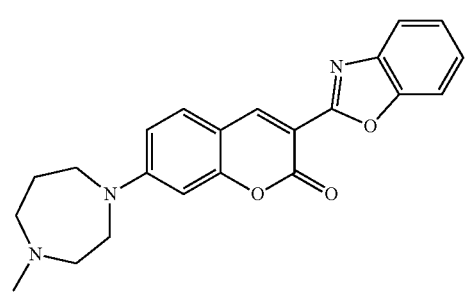
48
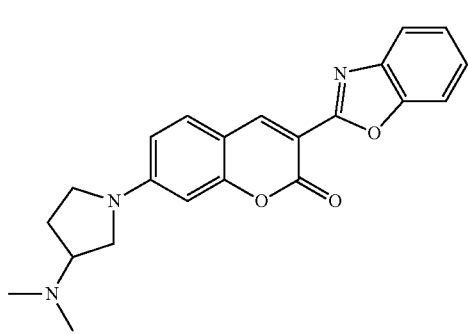
-continued
49
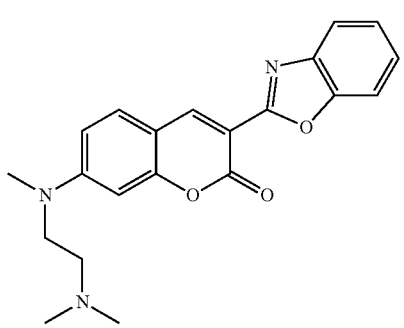
50
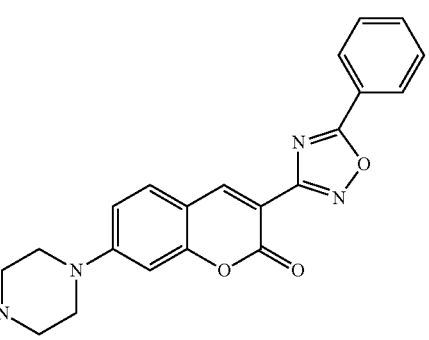
51
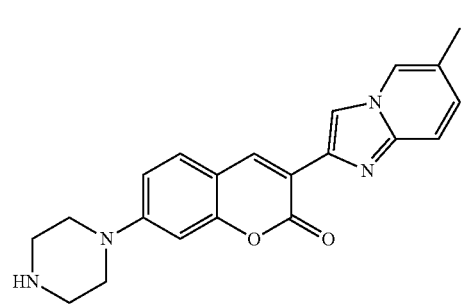
52
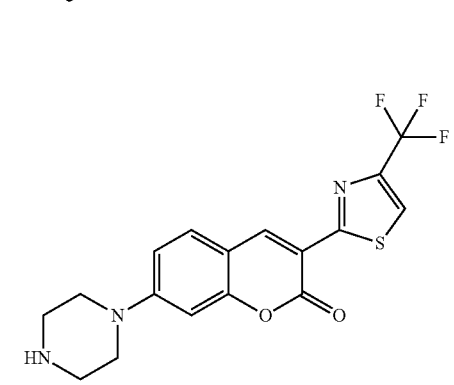
53
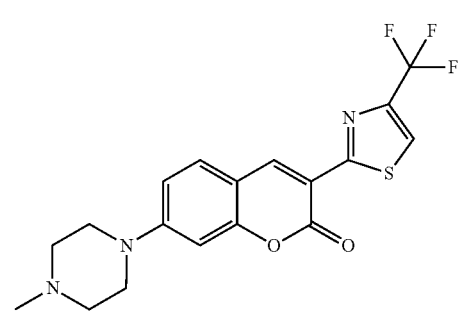

54
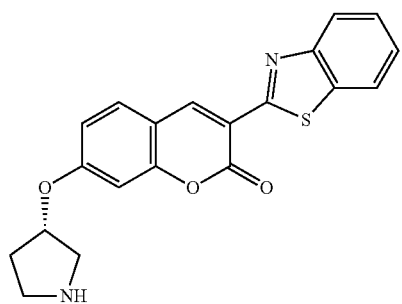
55
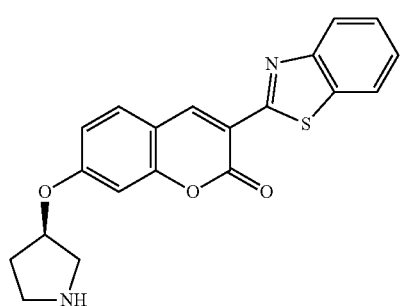
56
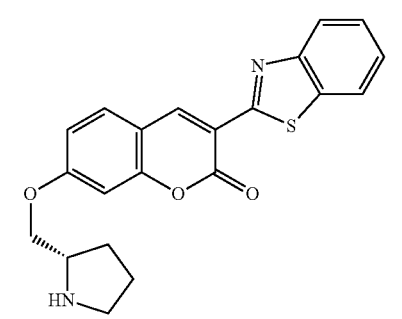
57
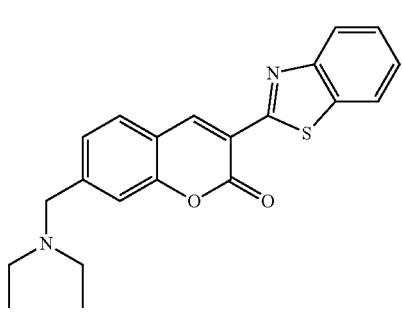
58
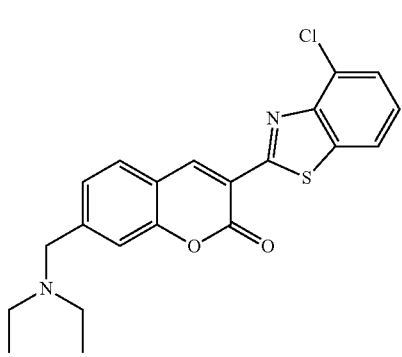
59
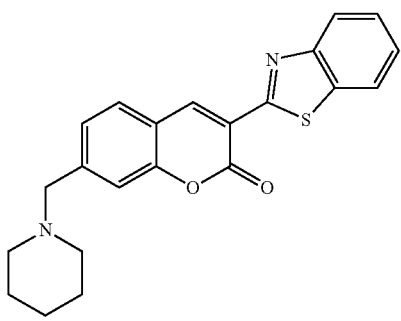
60
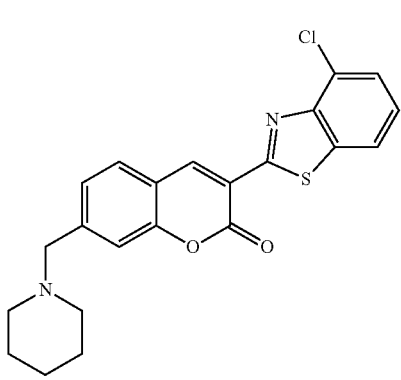
61
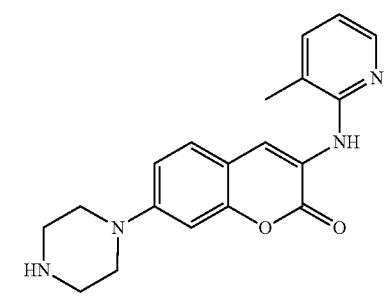
62
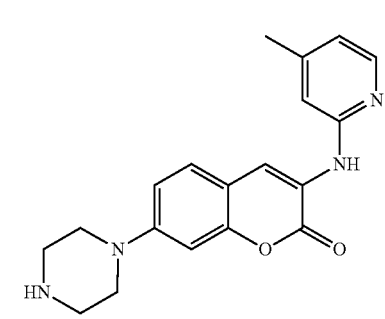
63
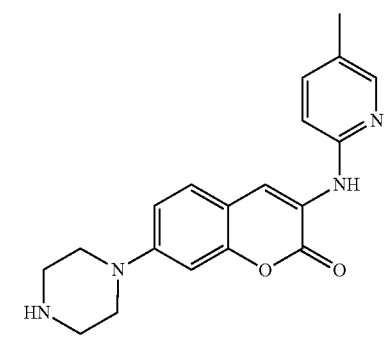

-continued
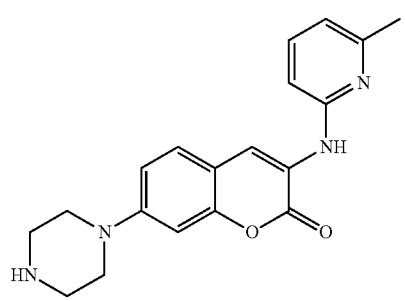
64
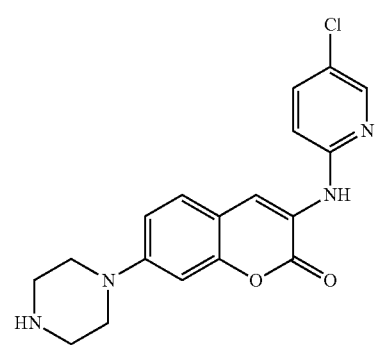
65
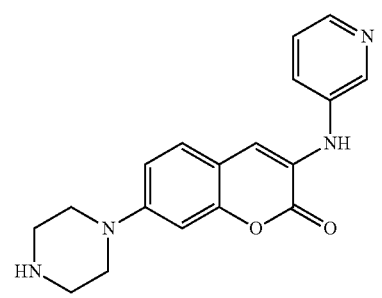
66
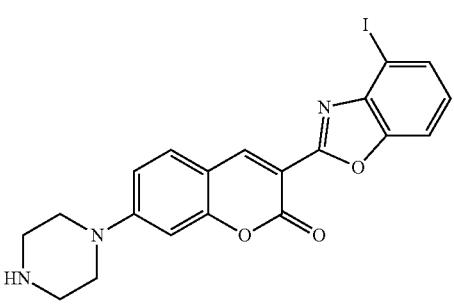
67
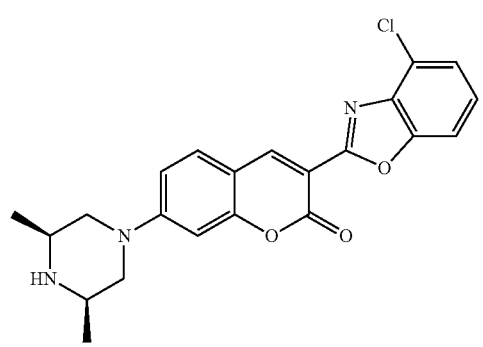
69
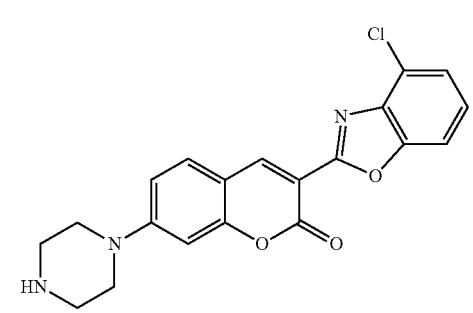
70
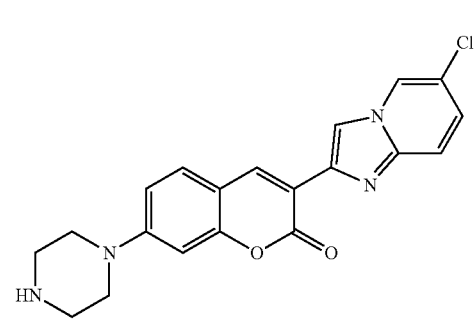
71
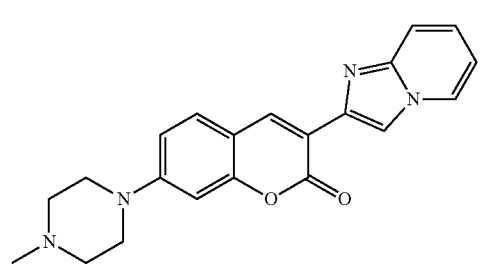
72
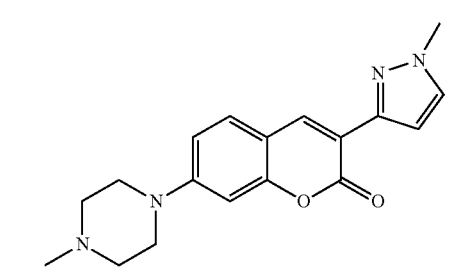
73

-continued
74
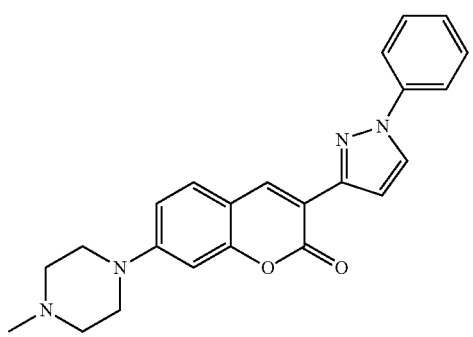
75
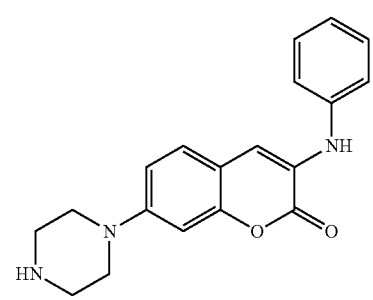
76
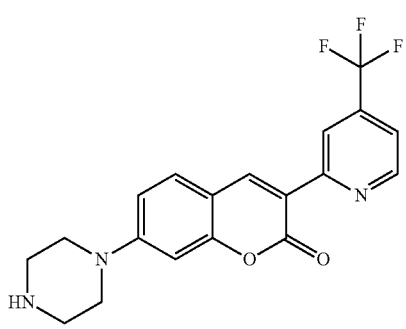
77
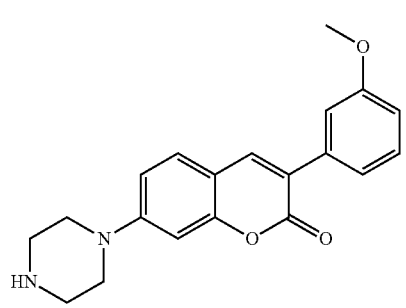
78
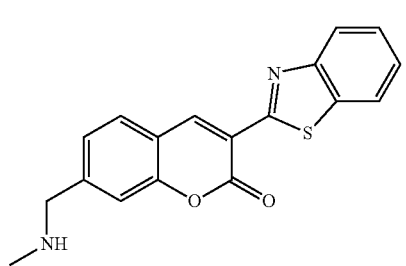
-continued
79
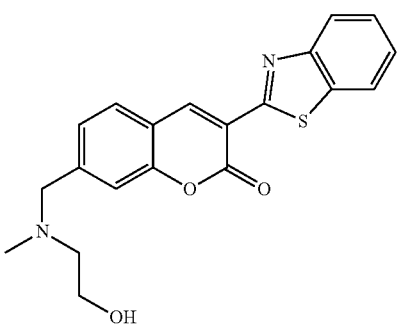
80
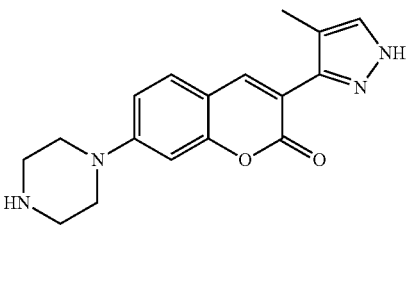
81
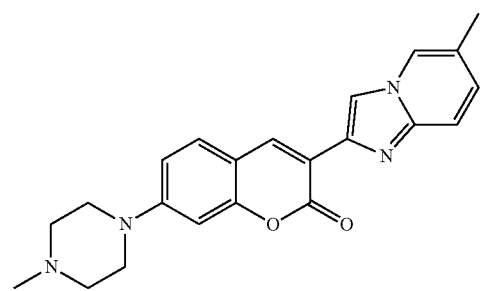
82
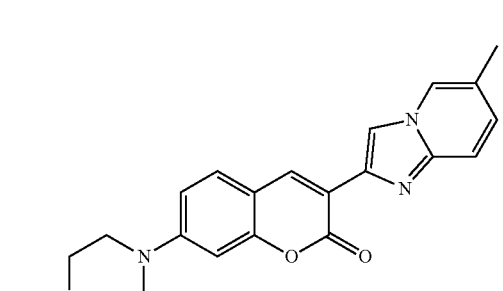
83
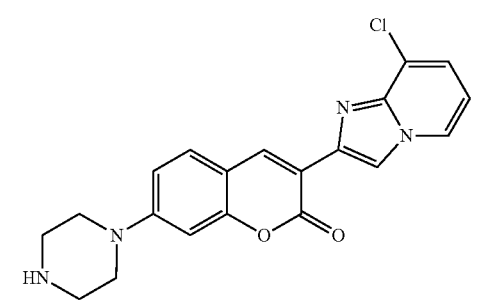

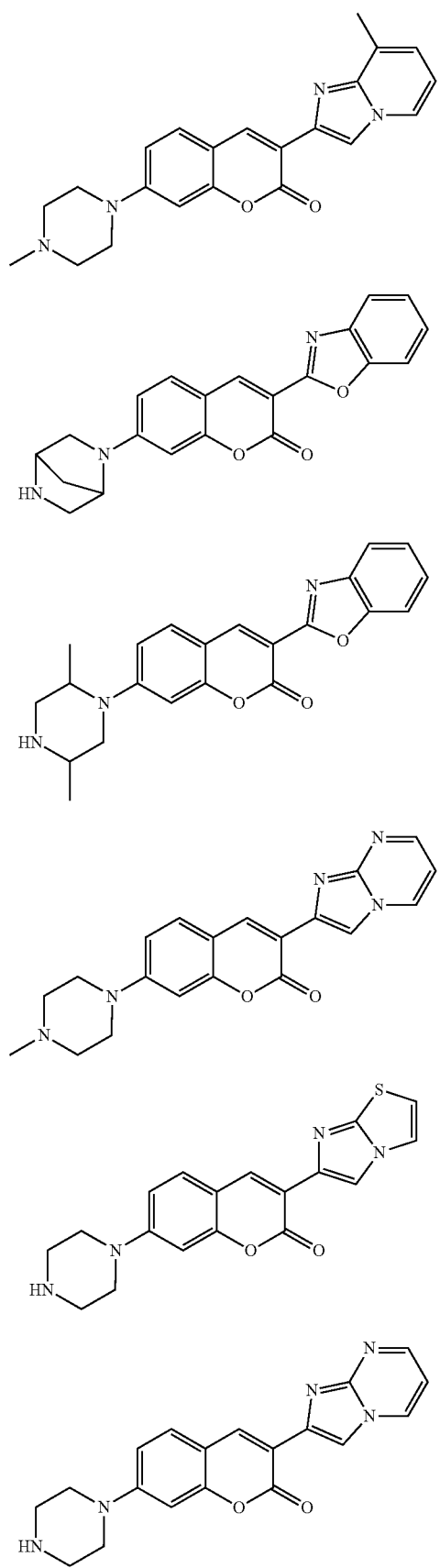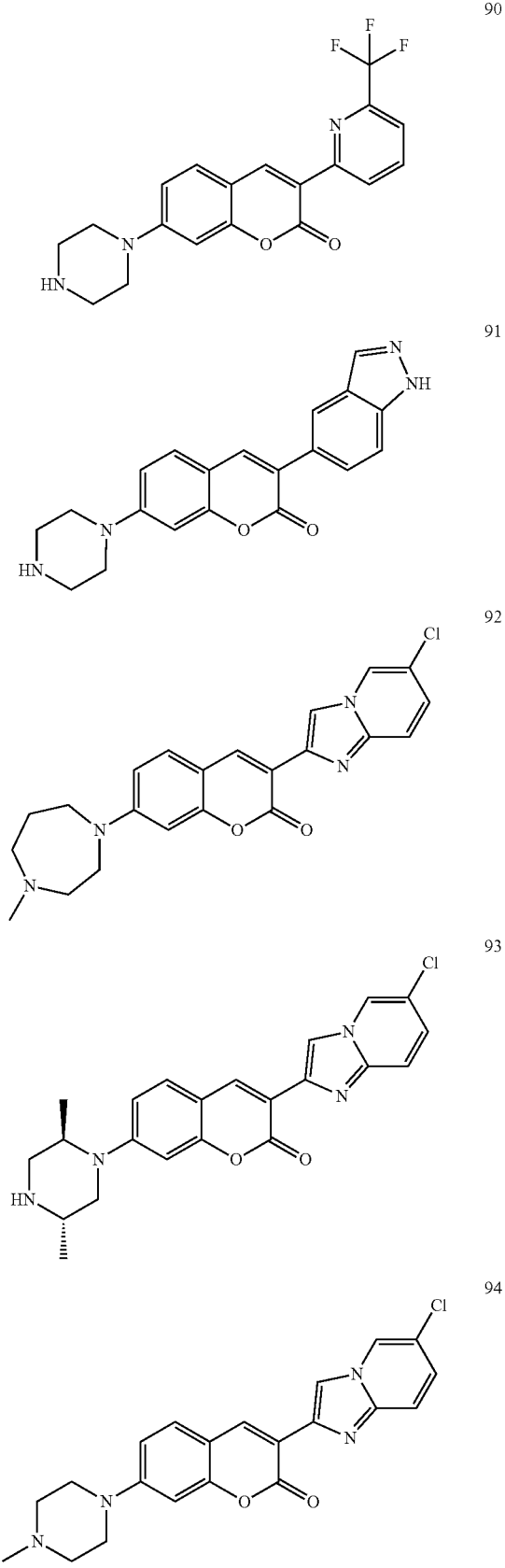

95 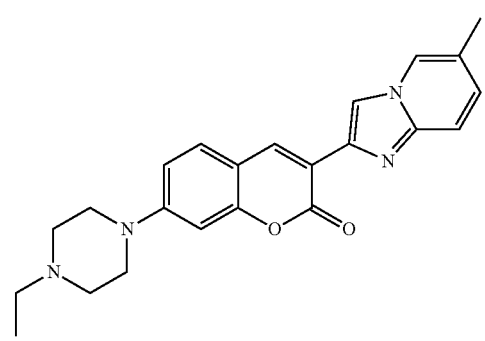
96 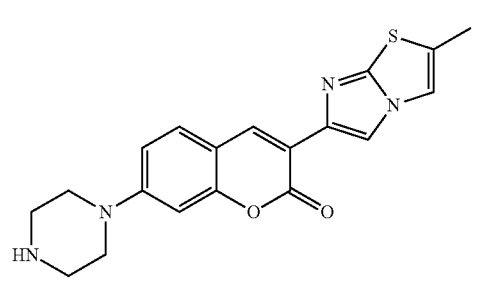
97 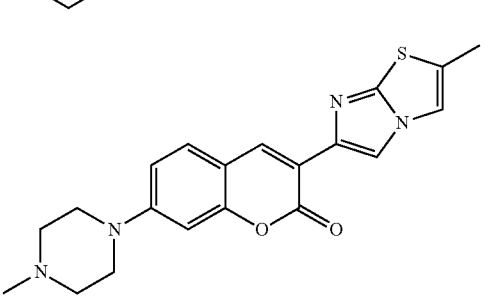
98 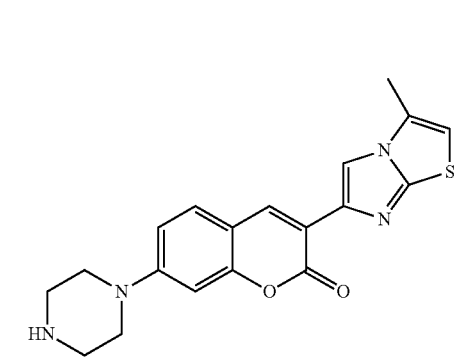
99 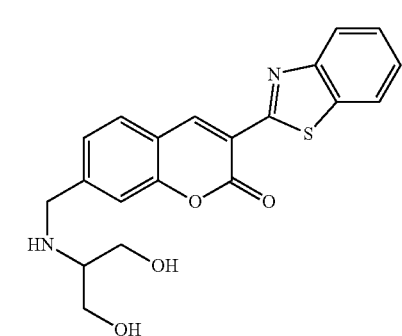
100 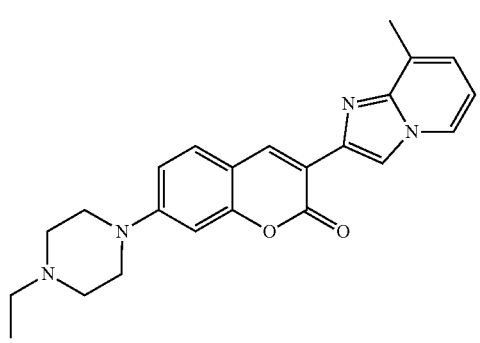
101 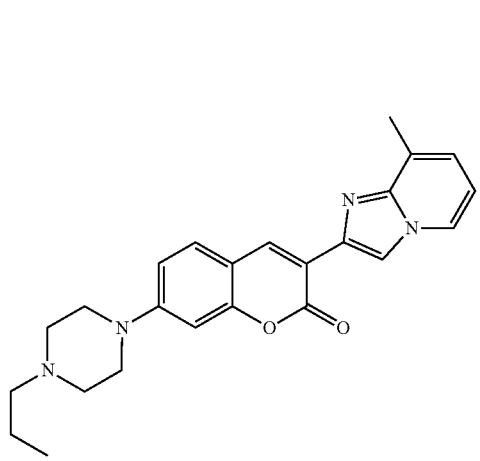
102 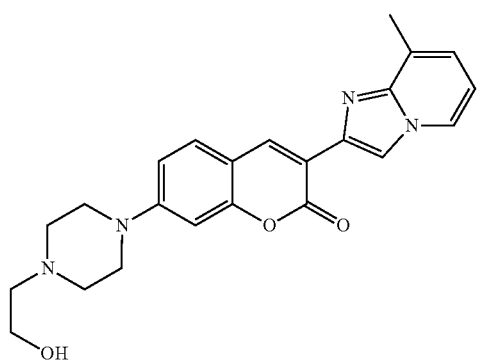
103 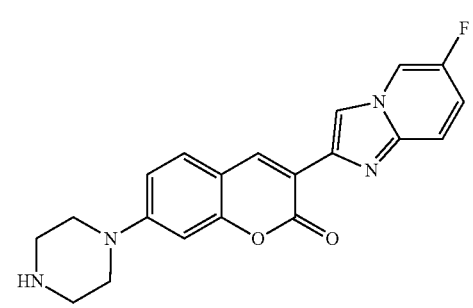

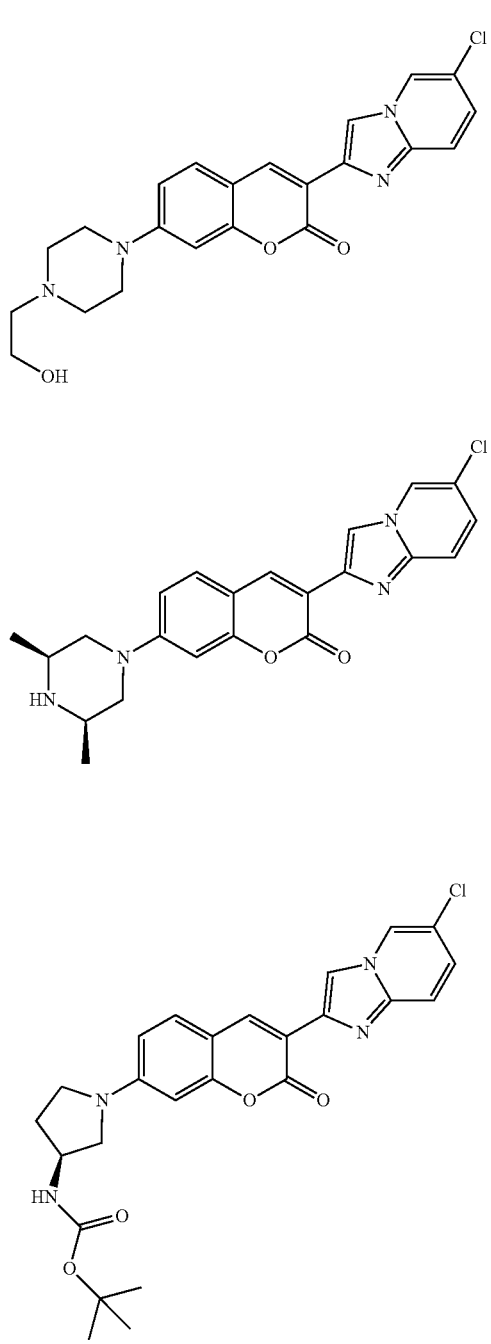
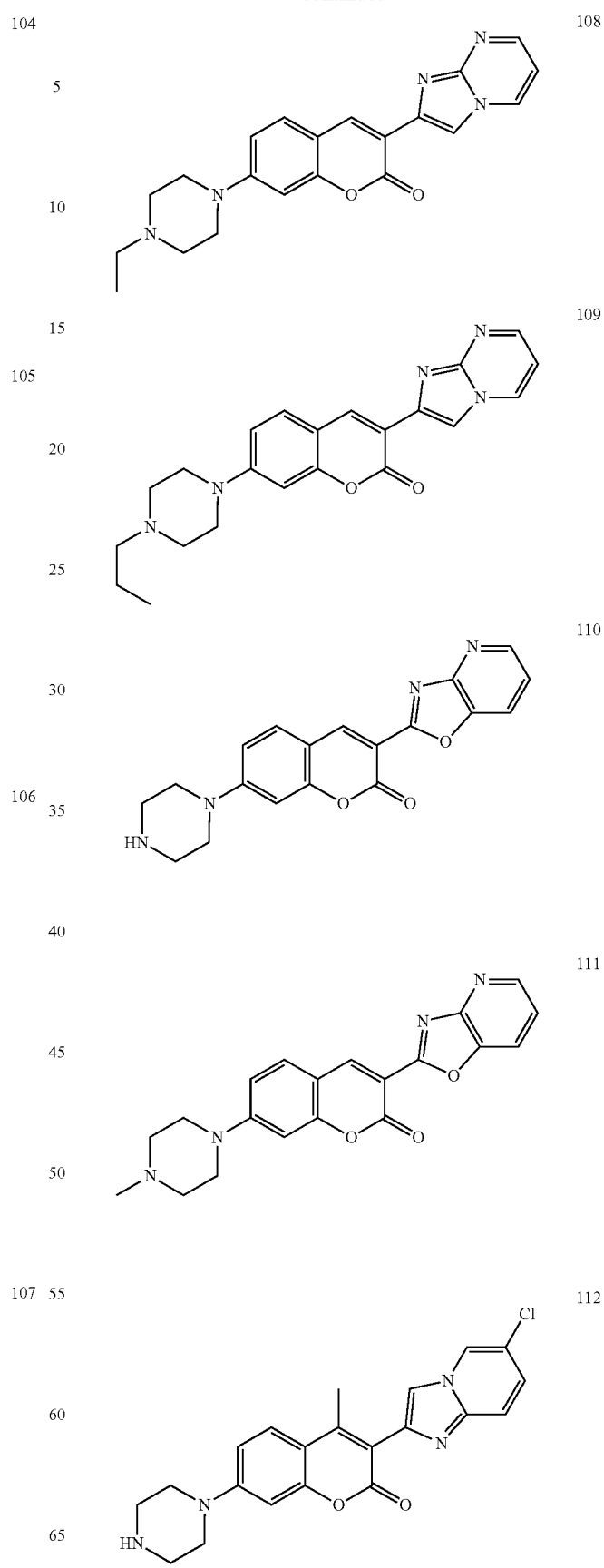

-continued
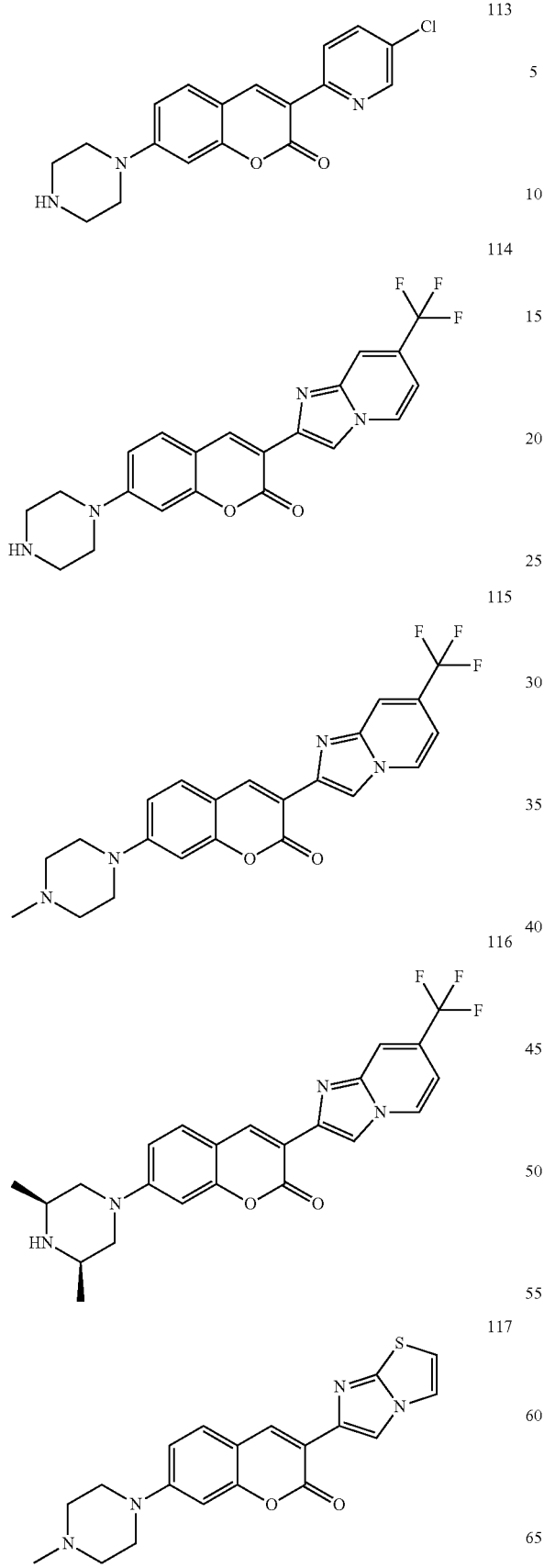
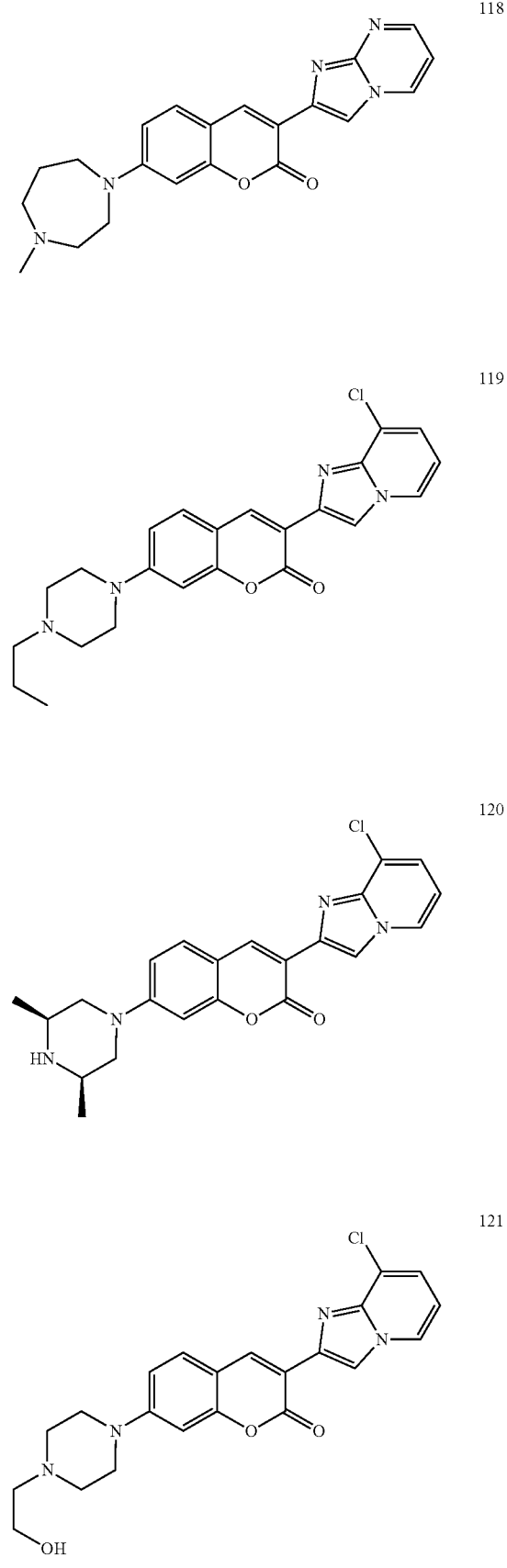

122 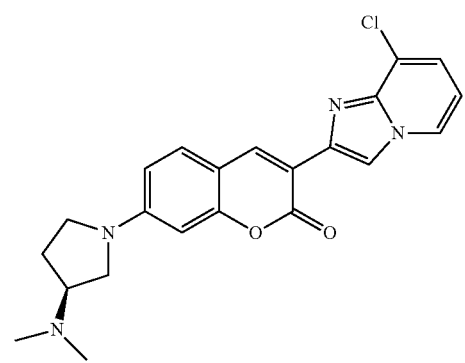
123 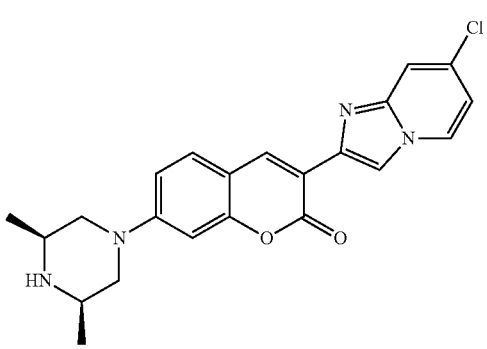
124 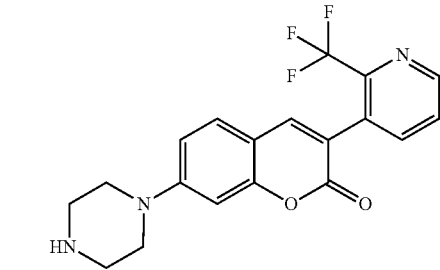
125 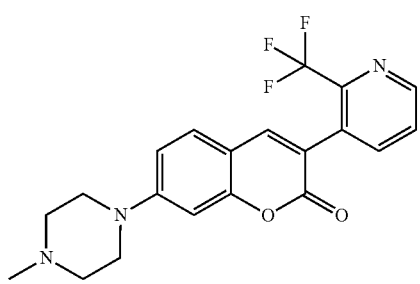
126 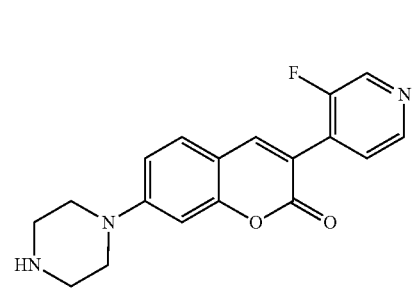
127 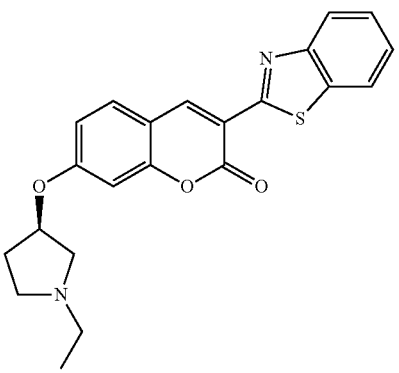
128 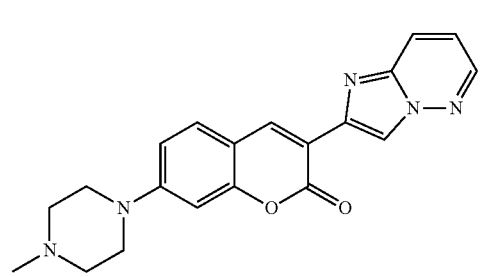
129 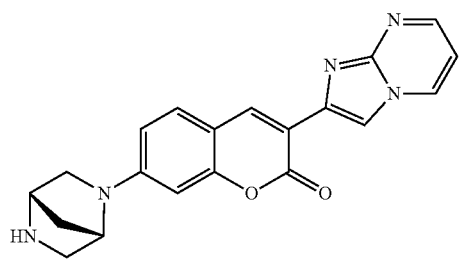
130 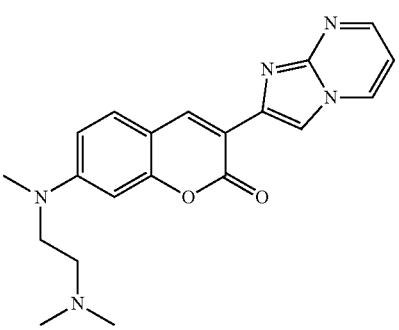
131 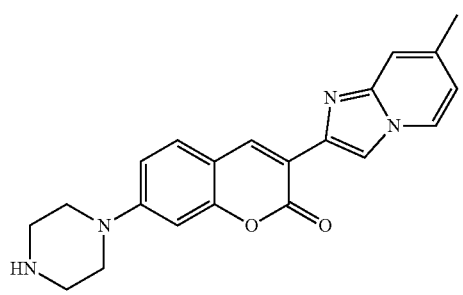

132 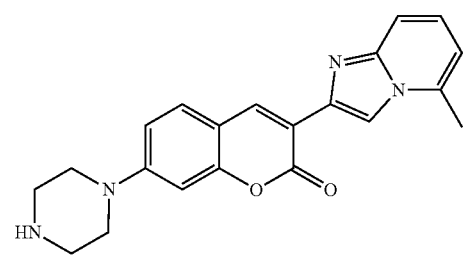
133 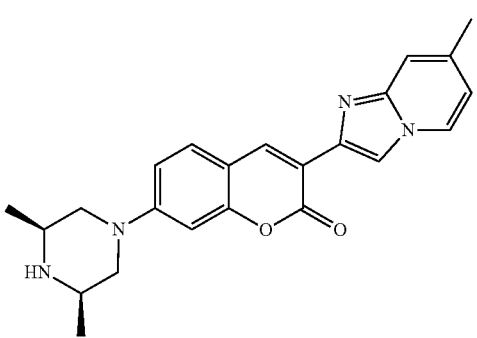
134 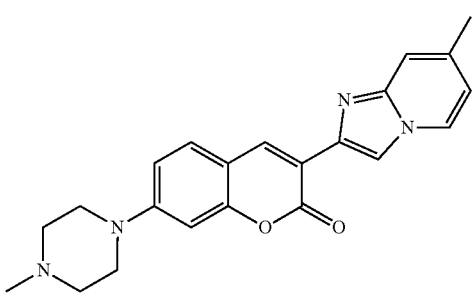
135 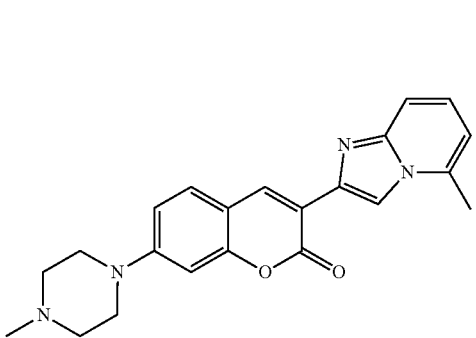
136 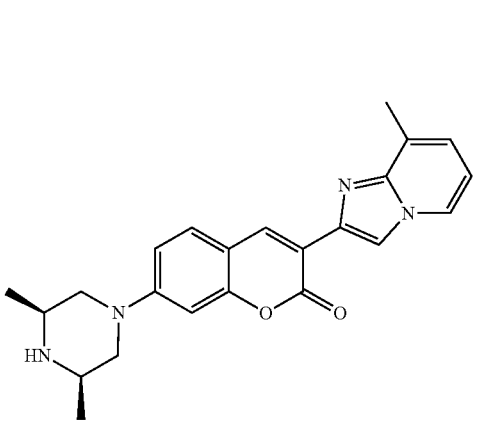
137 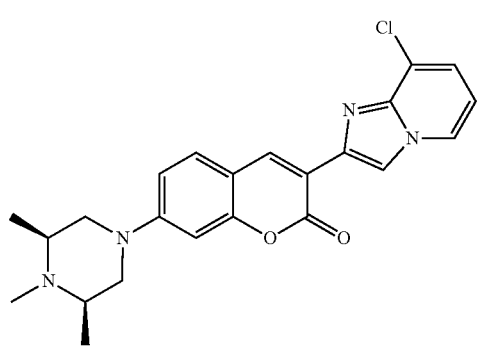
138 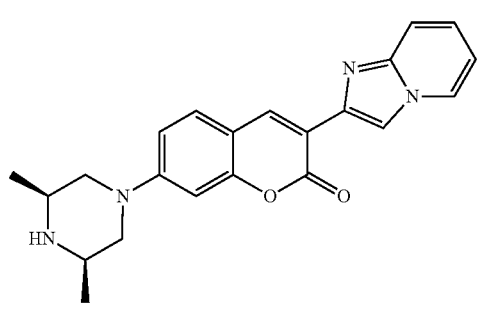
139 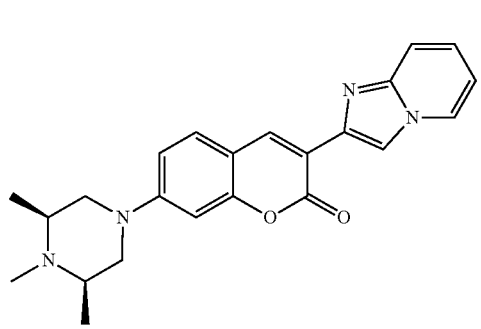
140 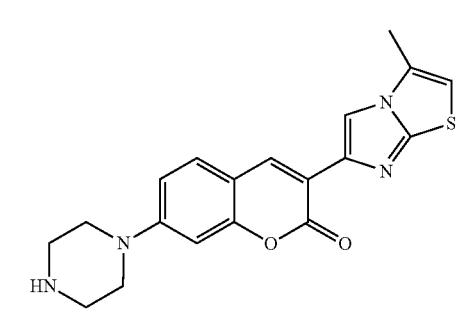
141 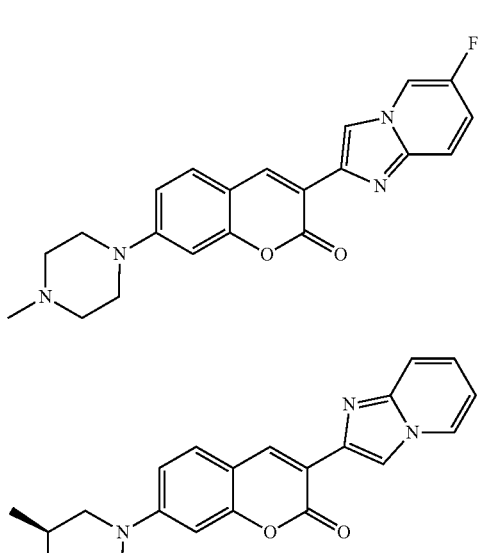

142
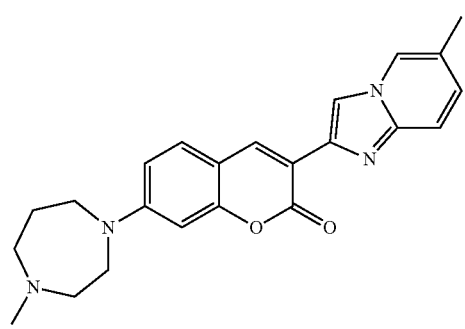
143
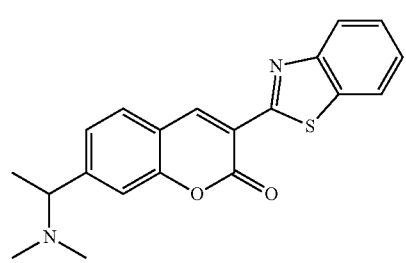
144
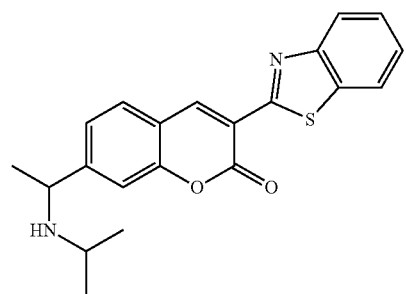
145
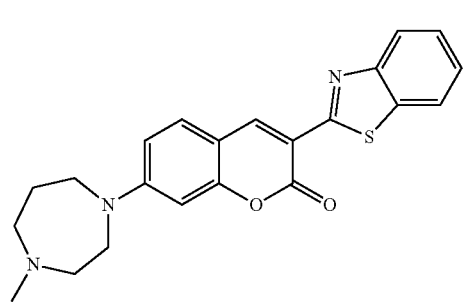
146
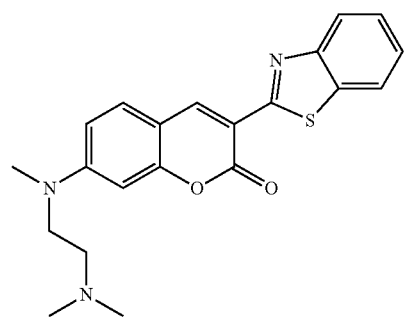
147
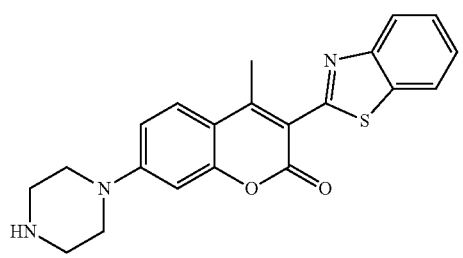
148
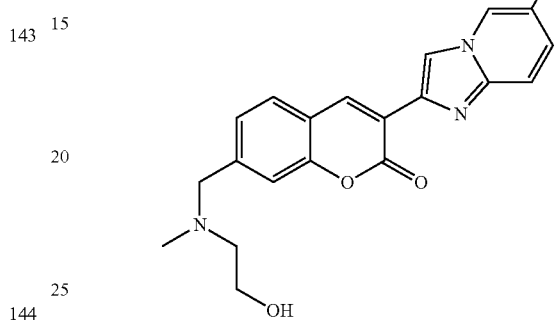
149
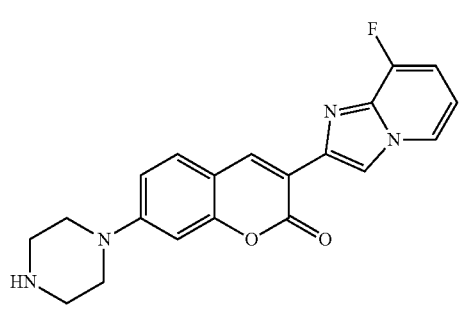
150
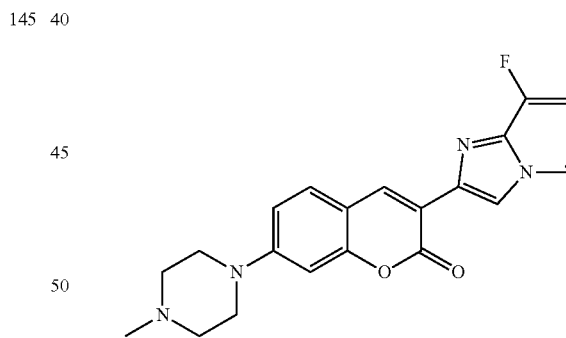
151
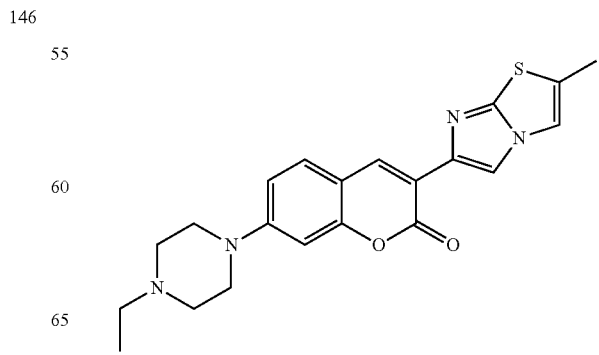

152 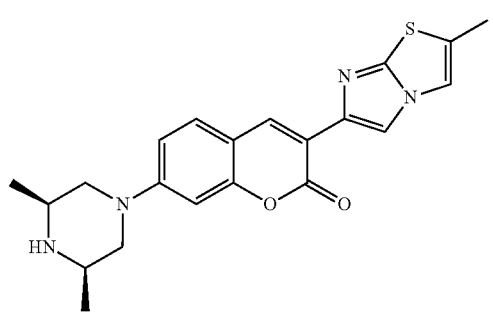
153 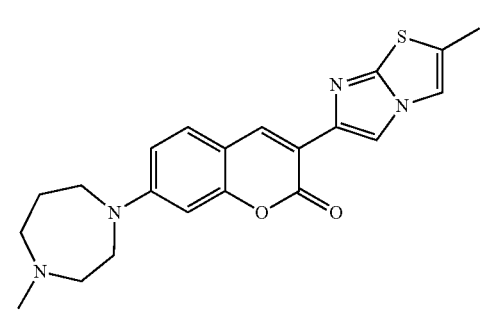
154 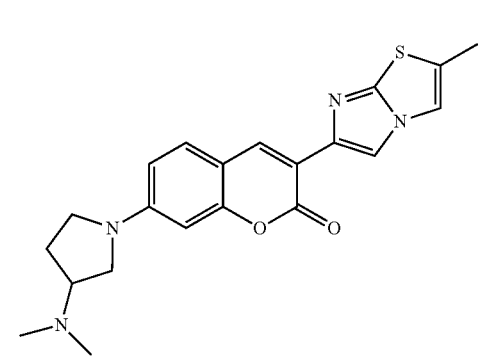
155 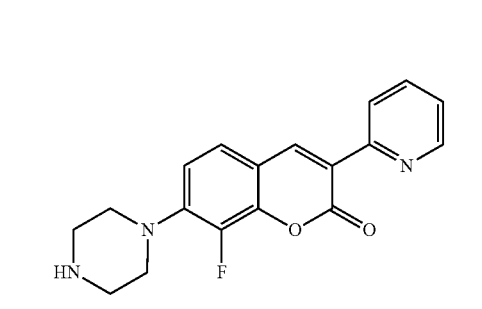
156 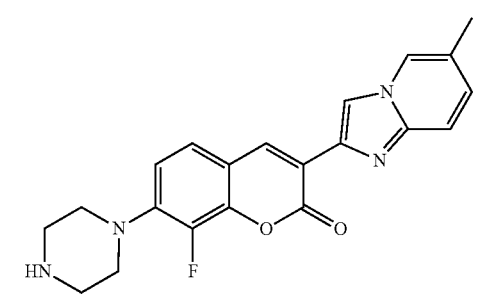
157 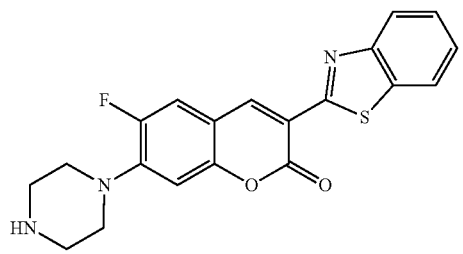
158 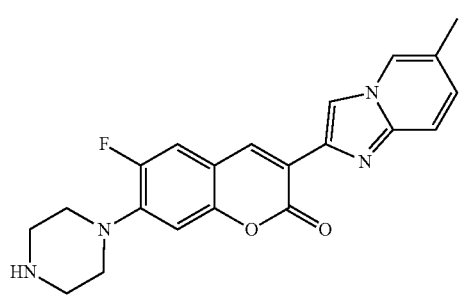
159 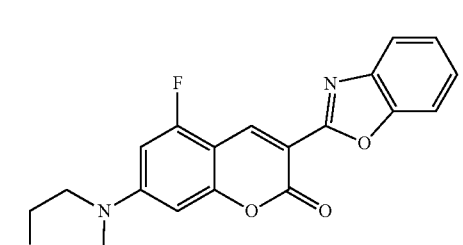
160 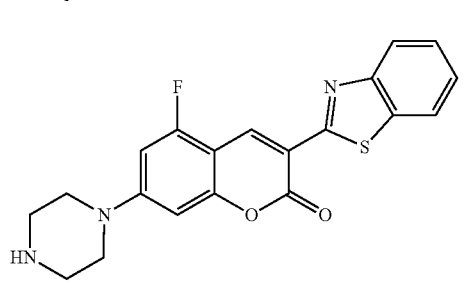
161 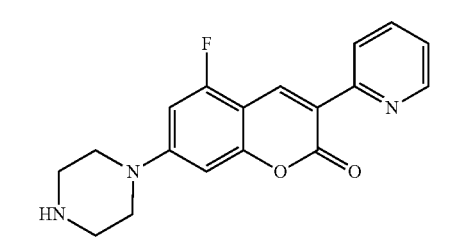
162 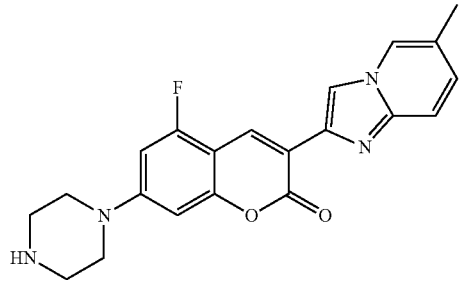

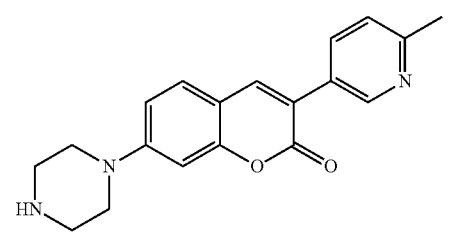
163
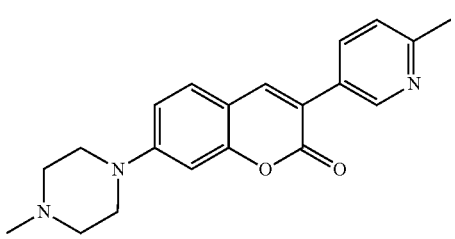
164
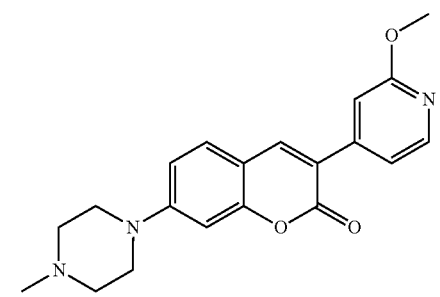
165
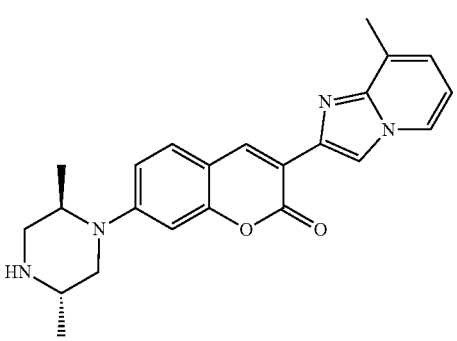
166
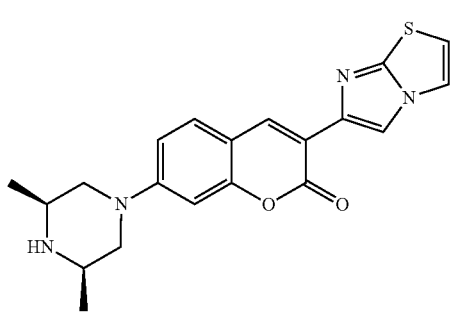
167
168
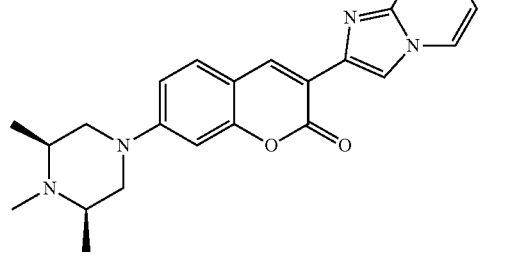
169
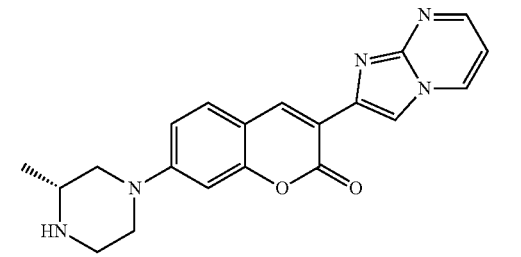
170
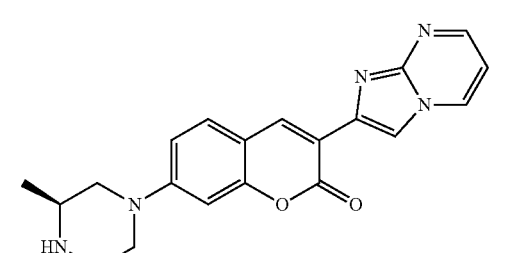
173
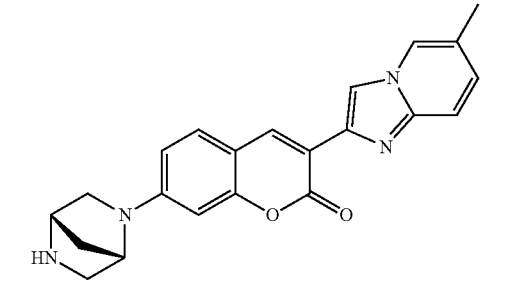
174
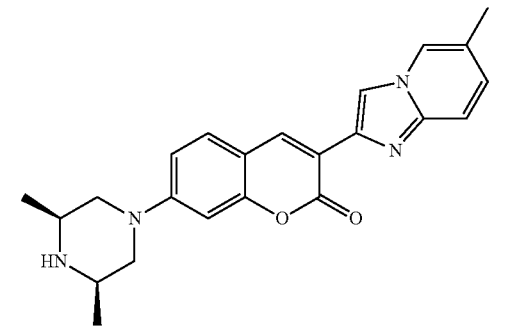

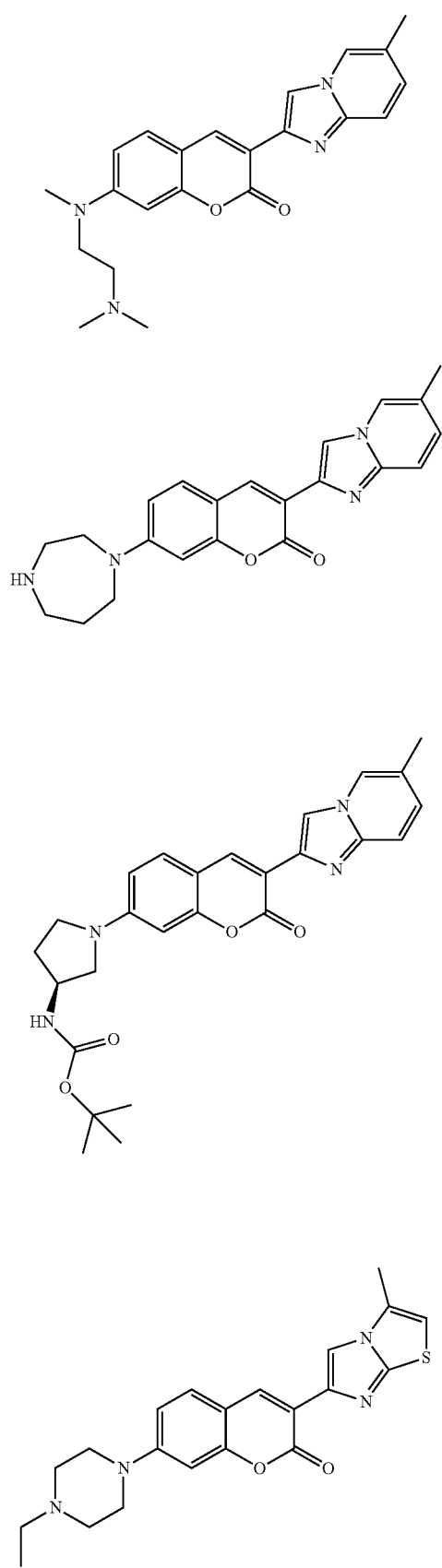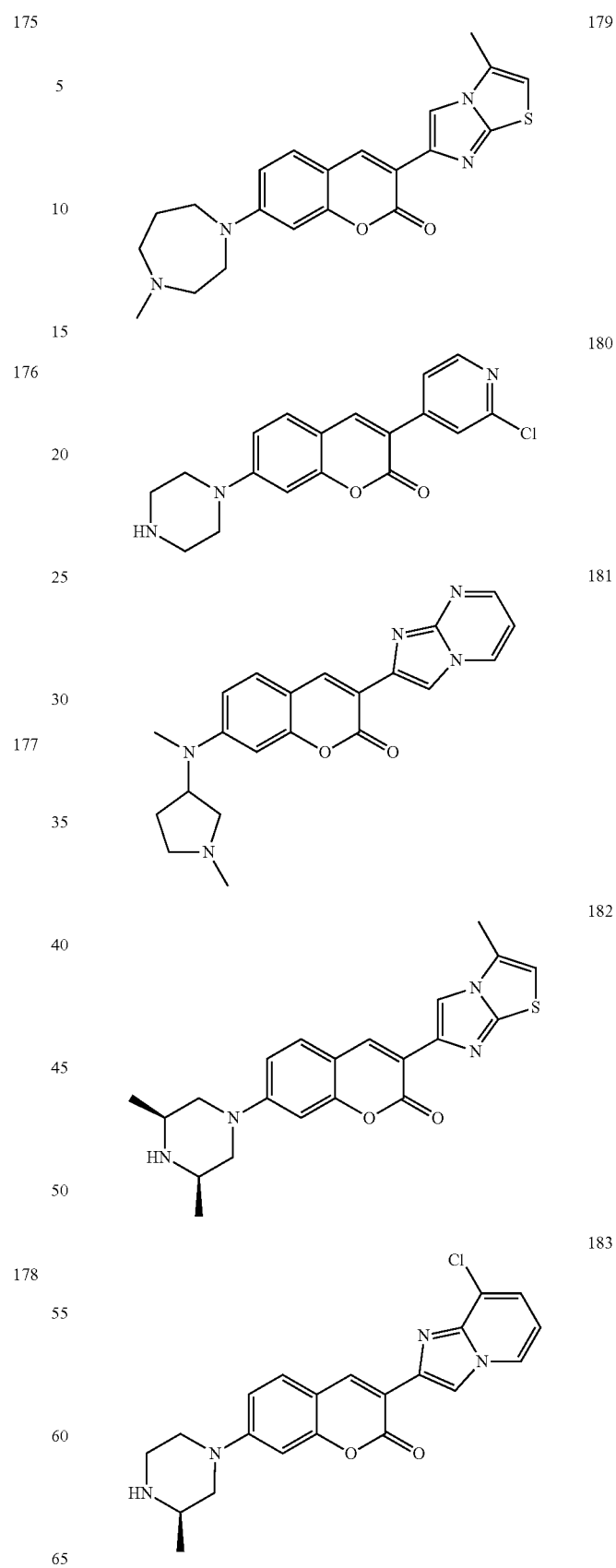

-continued
184
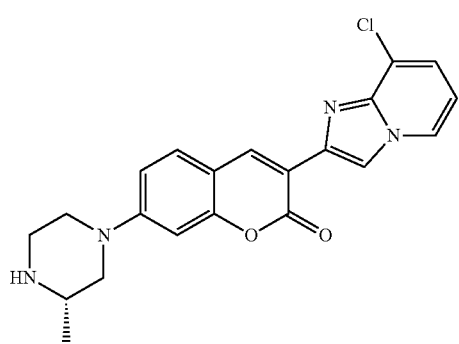
185
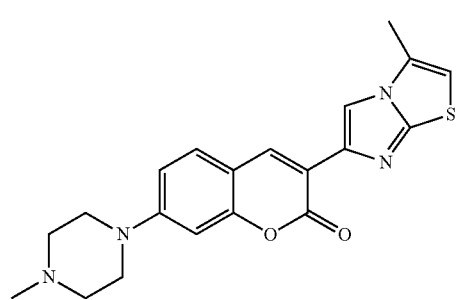
186
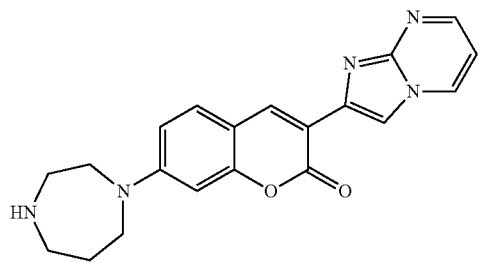
187
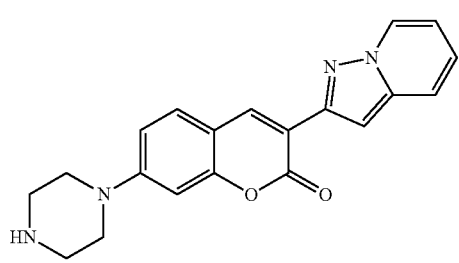
188
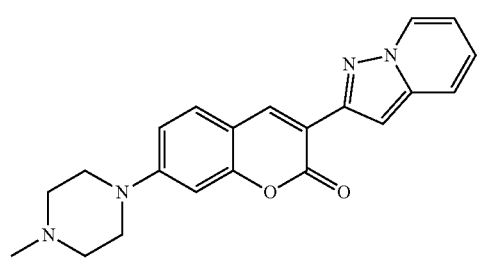
-continued
189
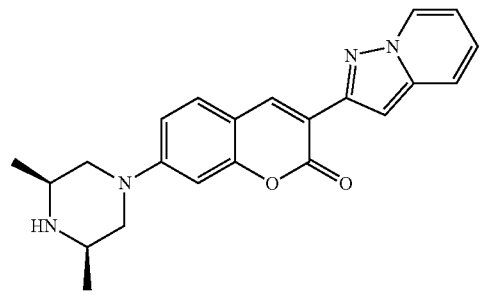
190
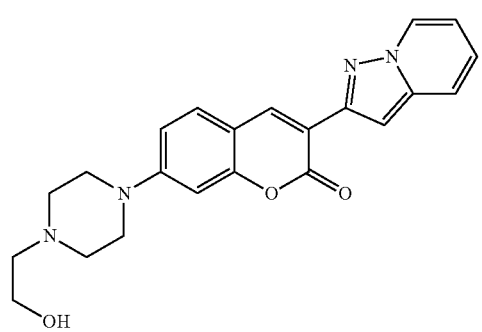
191
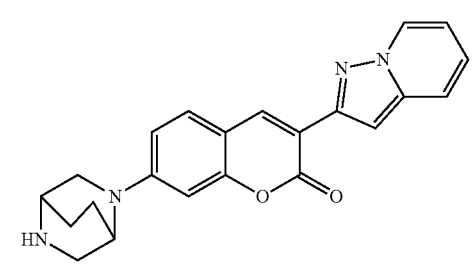
192
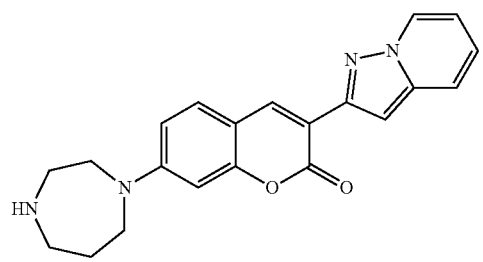
193
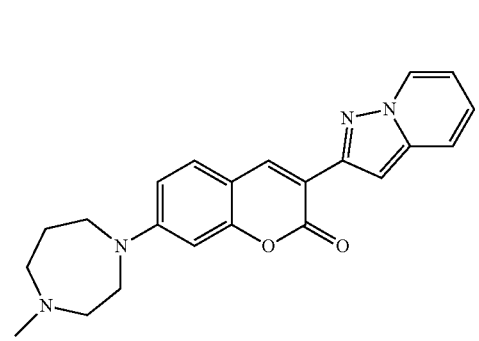

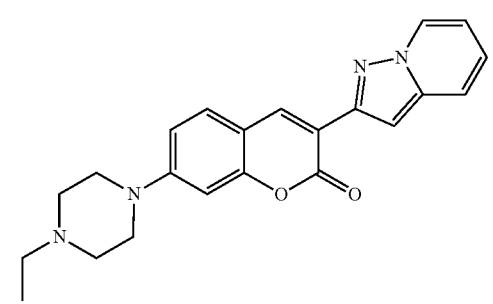 194
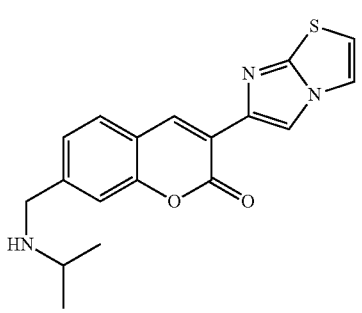 199
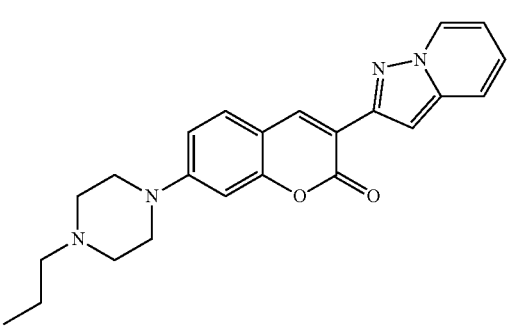 195
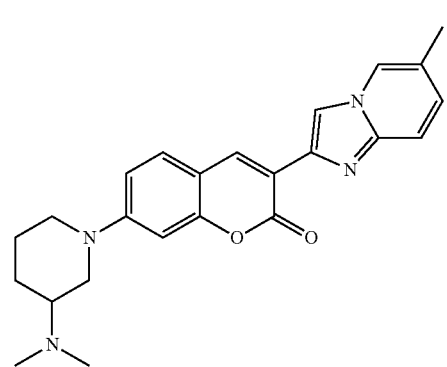 200
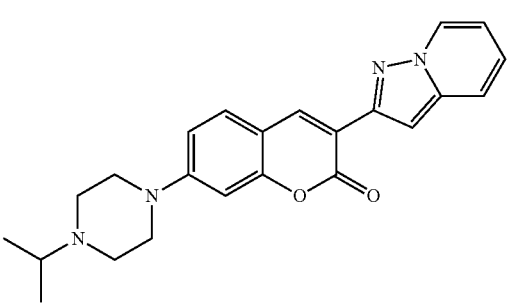 196
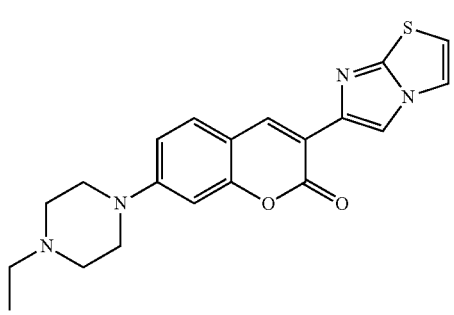 201
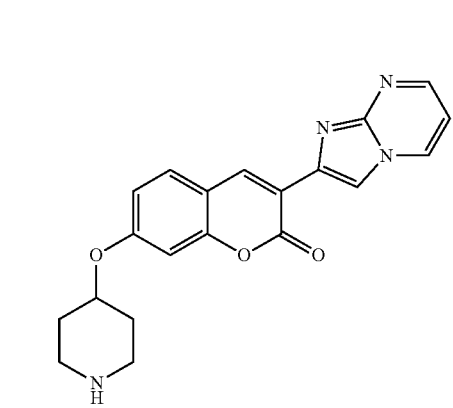 197
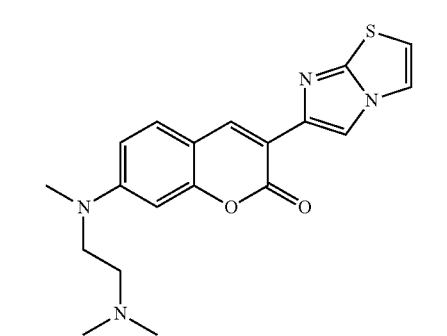 202
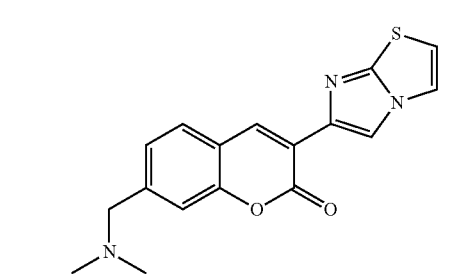 198
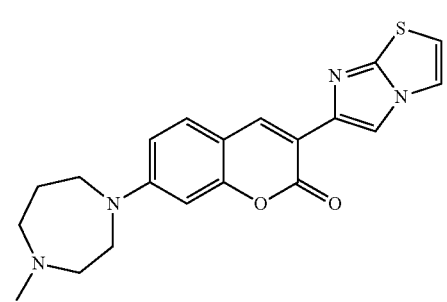 203

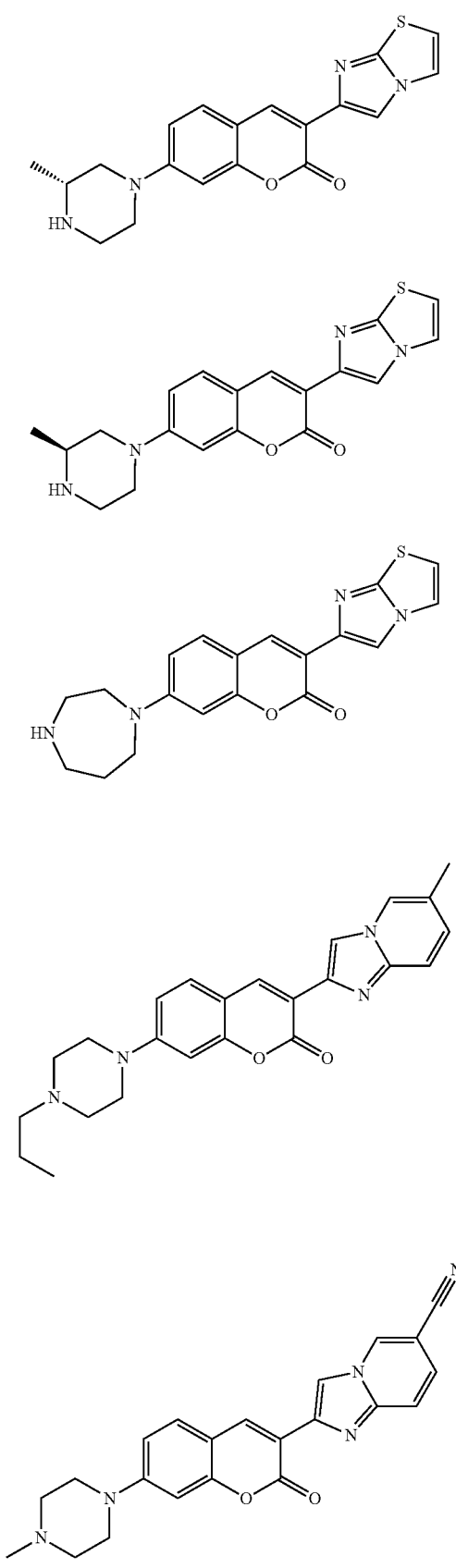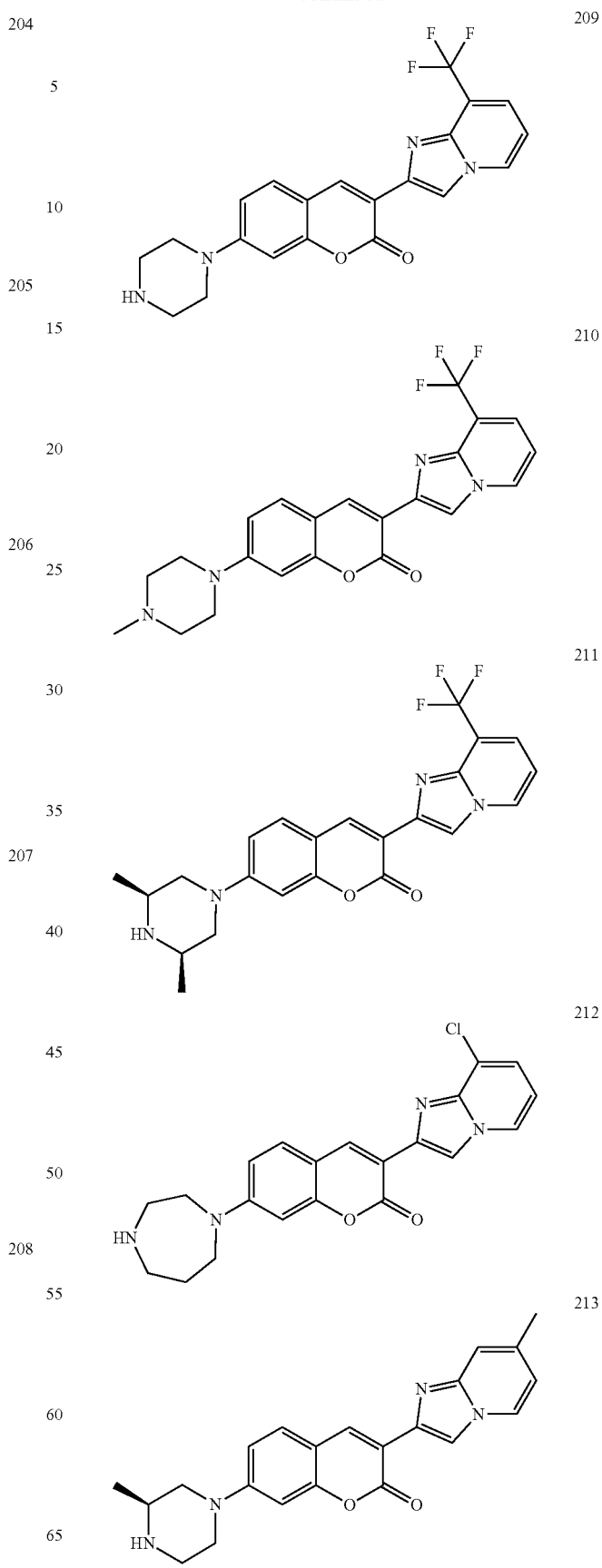

214 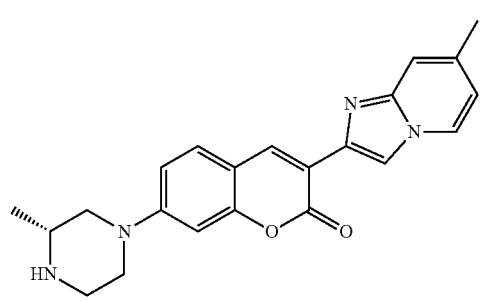
215 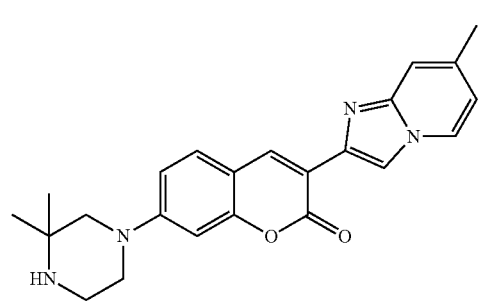
216 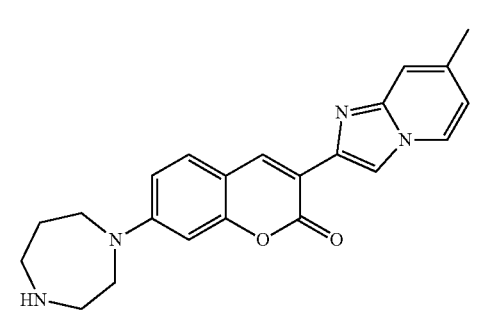
217 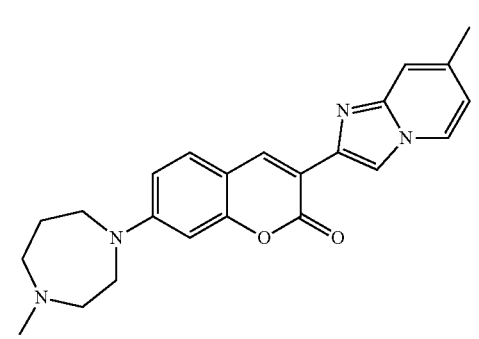
218 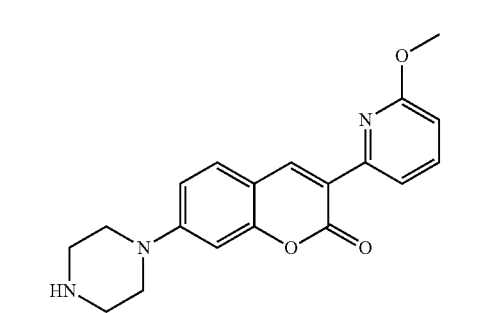
219 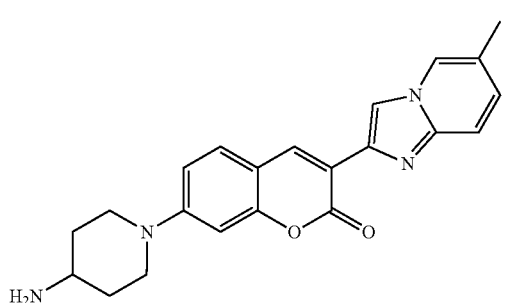
220 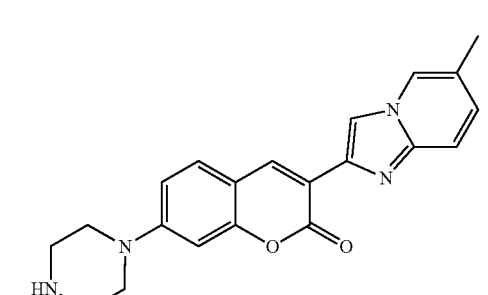
221 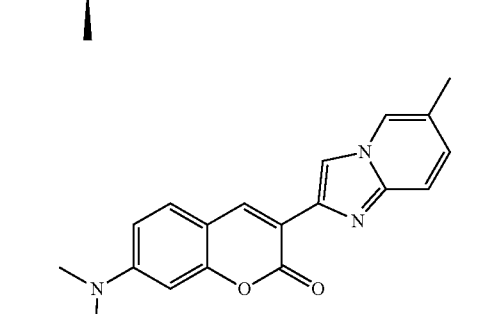
222 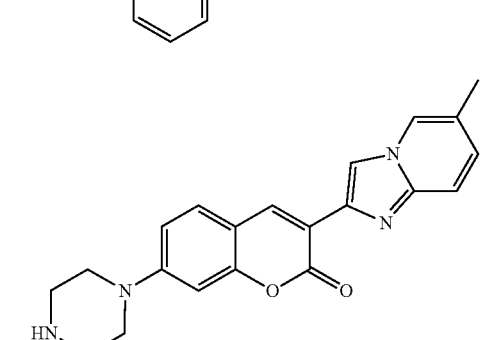
223 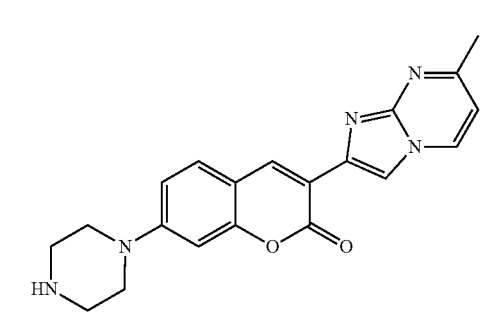

-continued
224
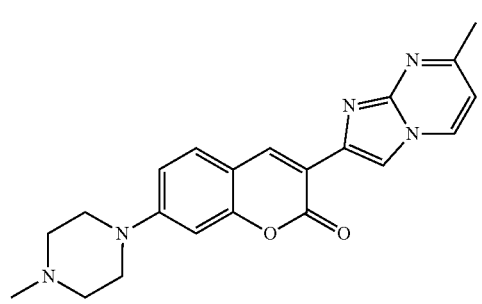
225
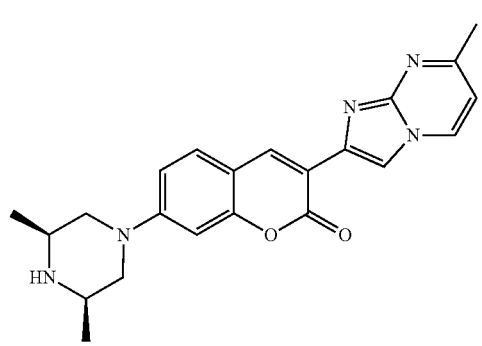
226
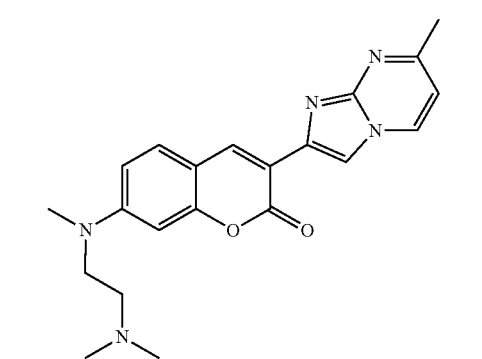
227
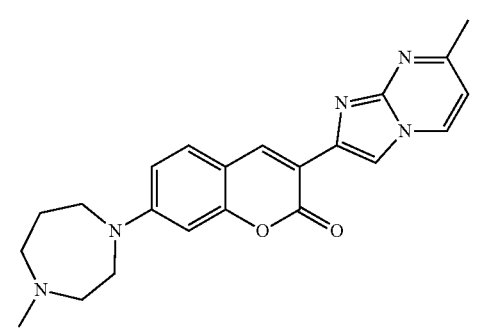
228
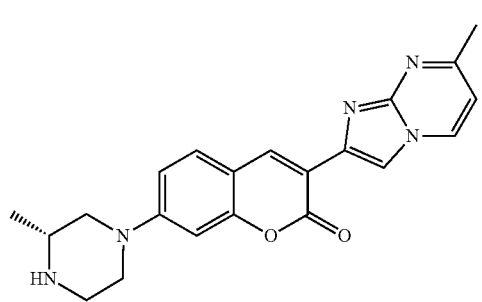
229
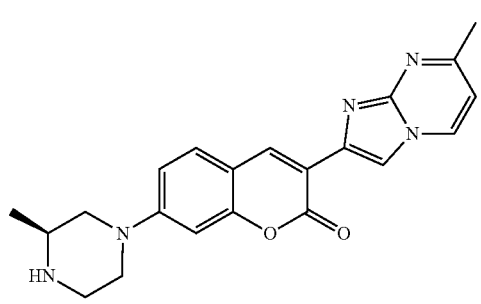
230
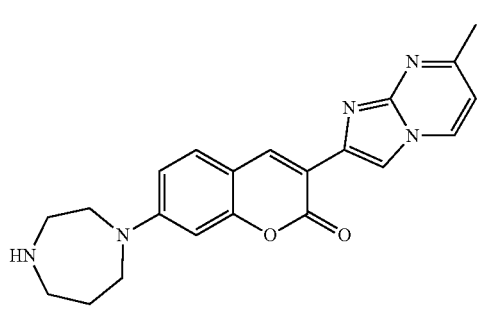
231
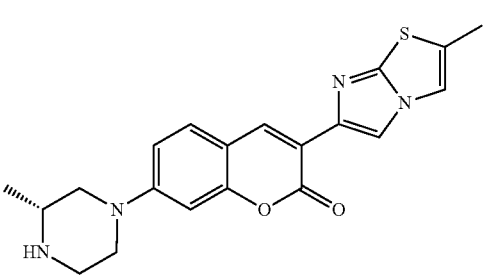
232
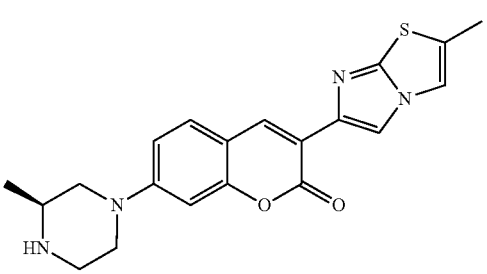
233
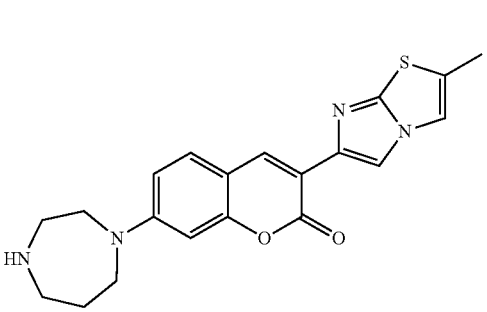

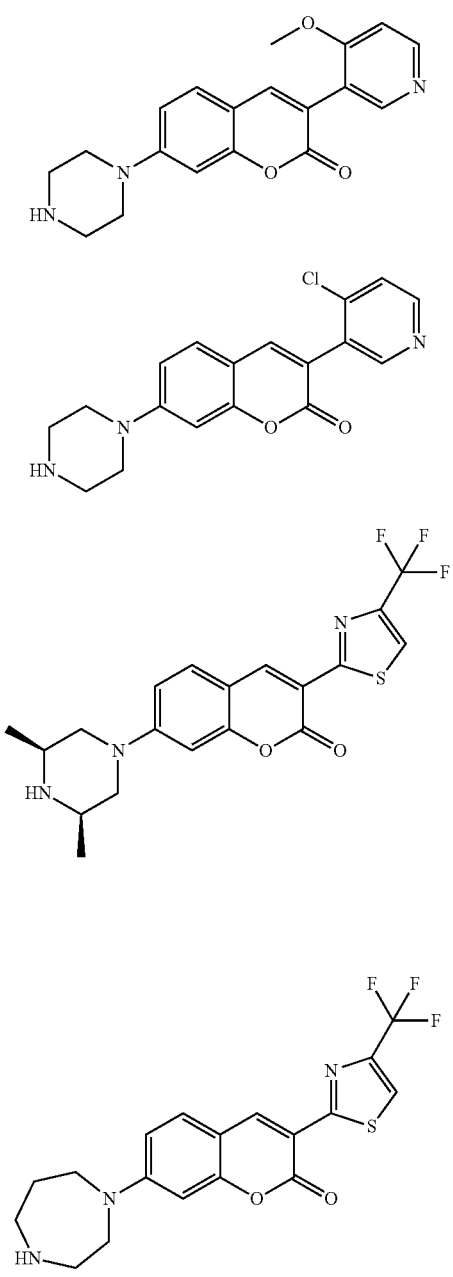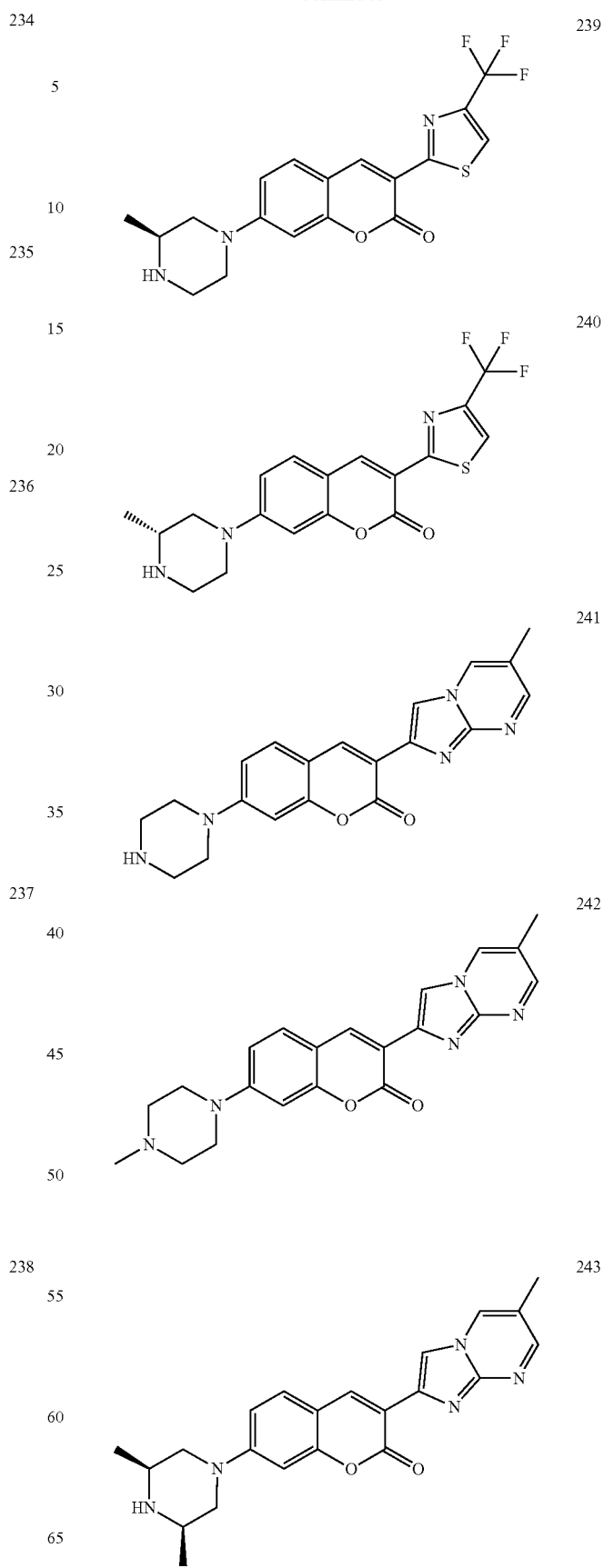

244 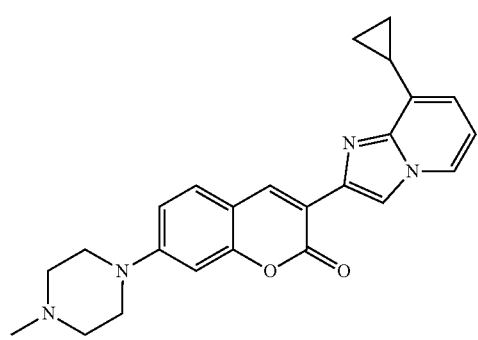
245 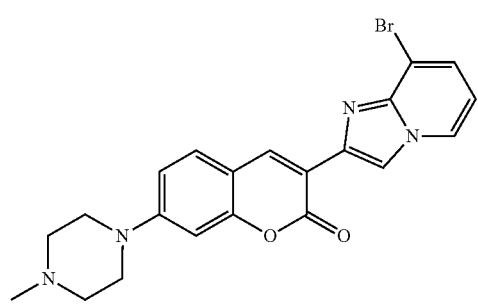
246 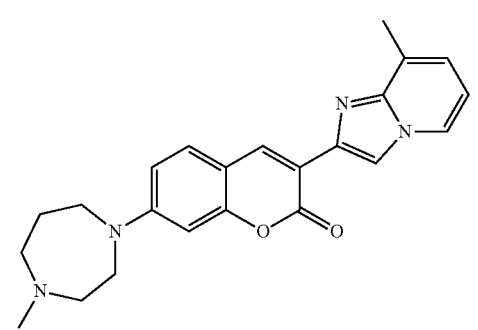
247 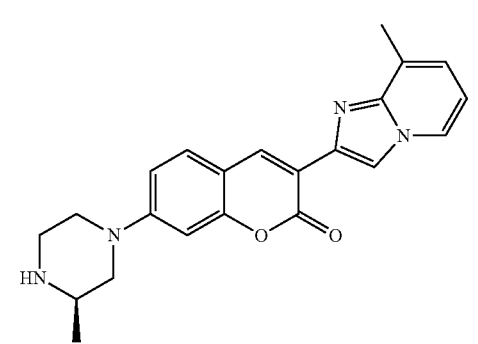
248 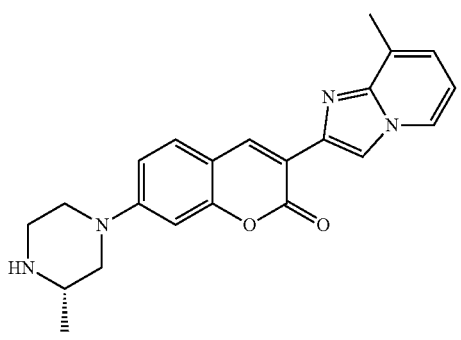
249 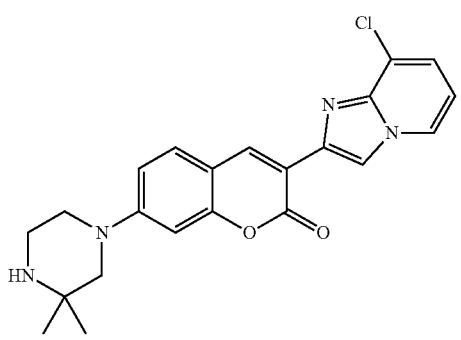
250 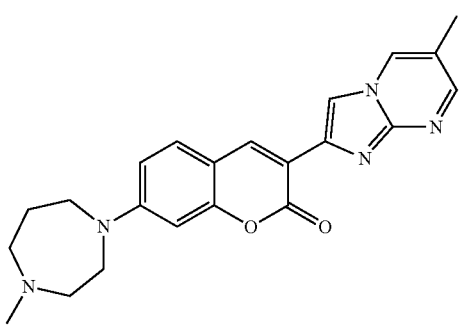
251 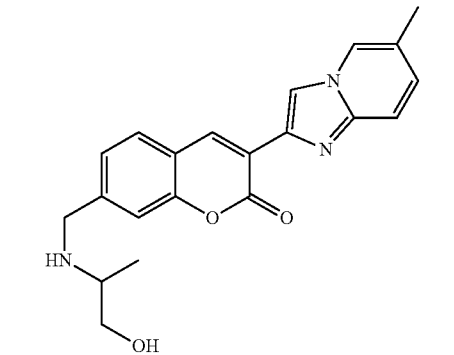

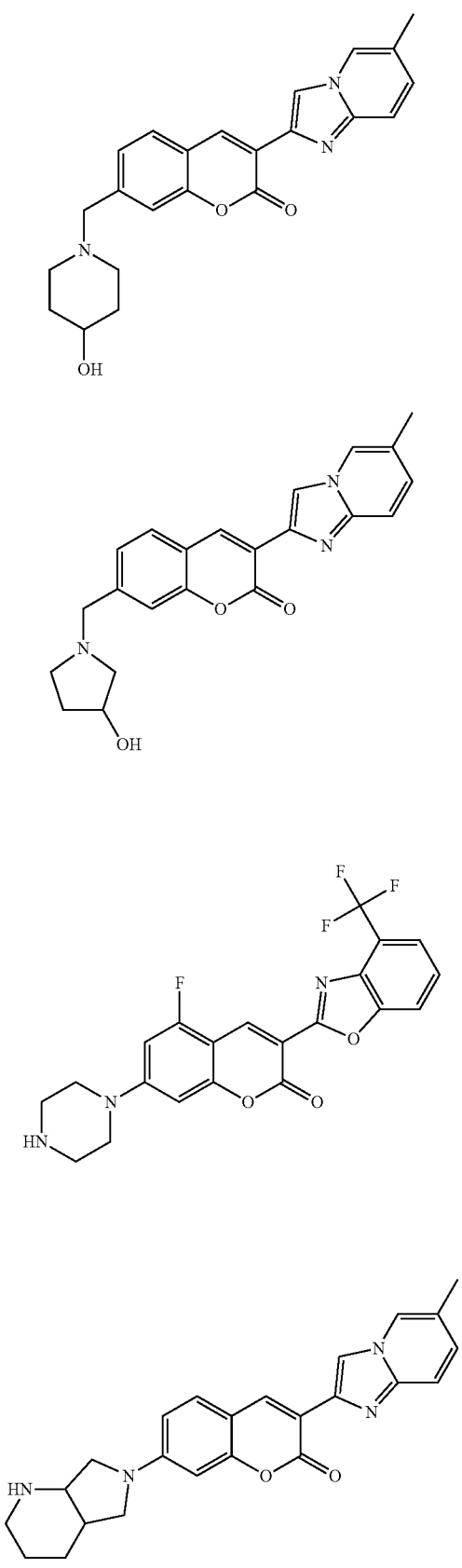
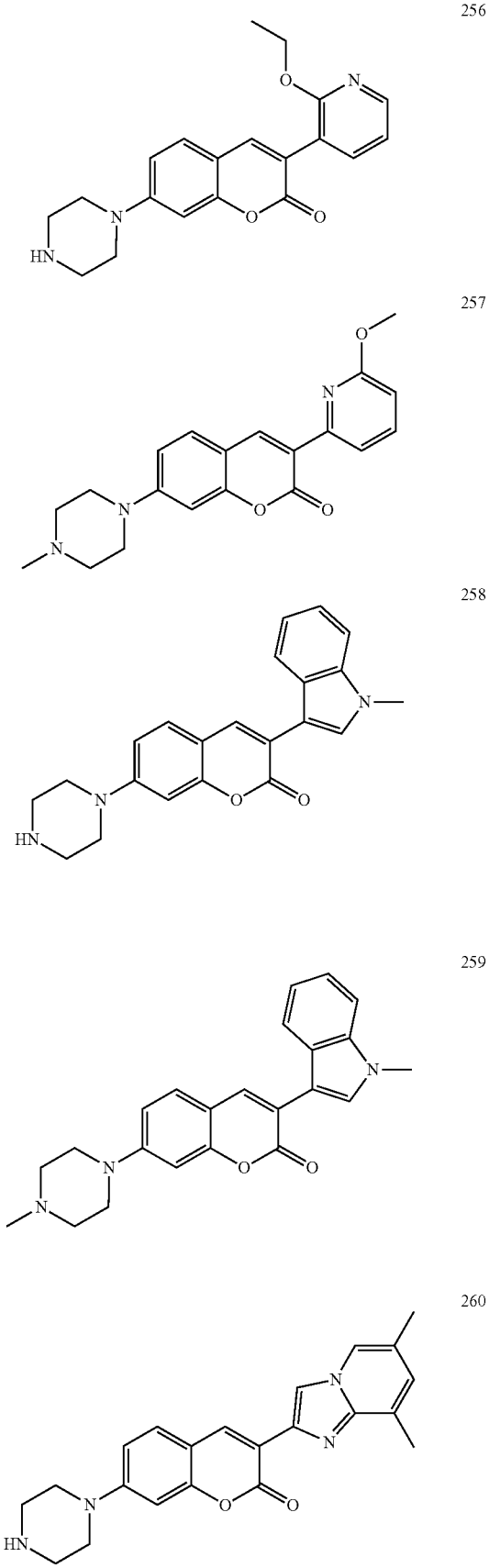

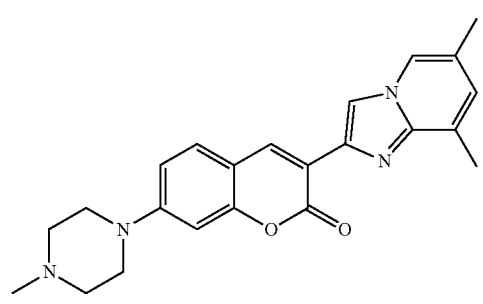
261
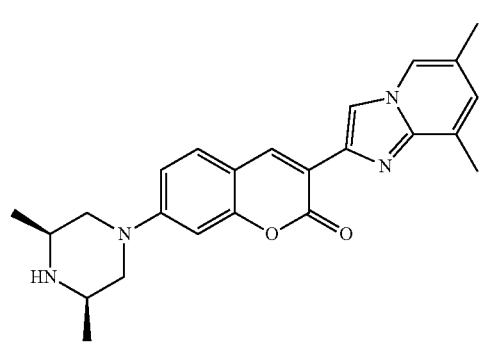
262
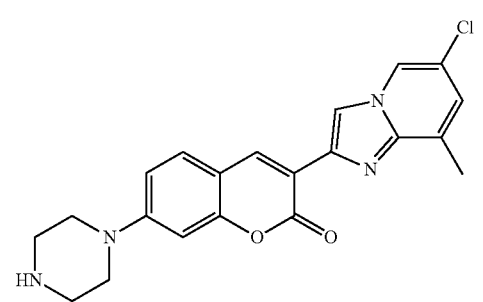
263
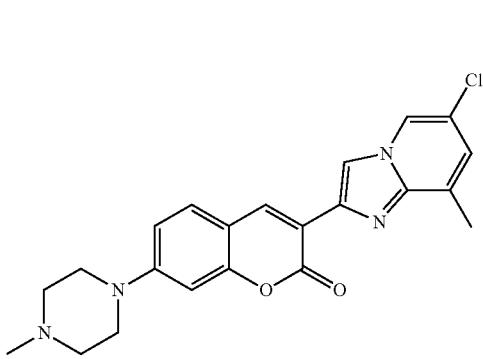
264
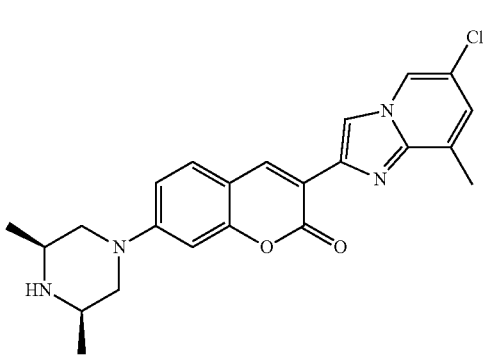
265
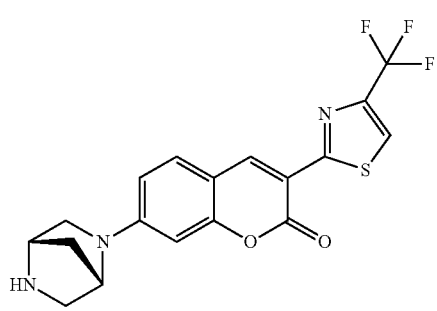
266
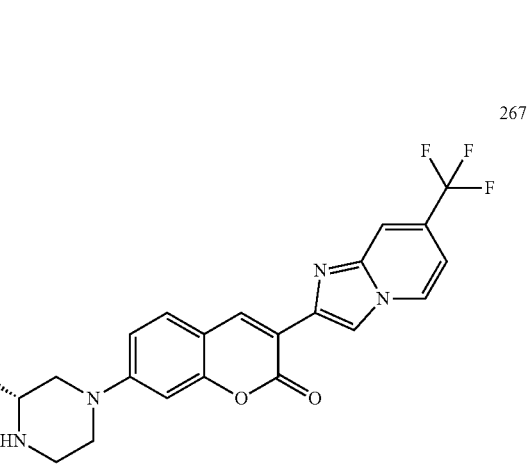
267
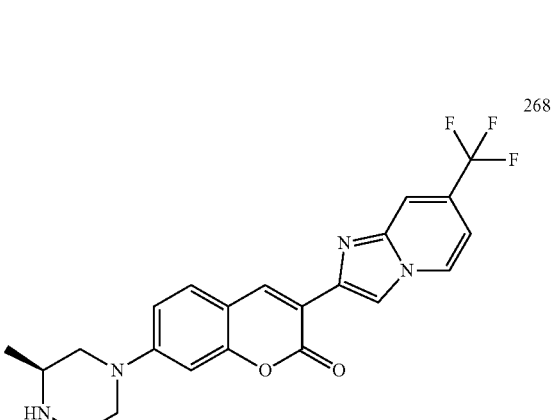
268
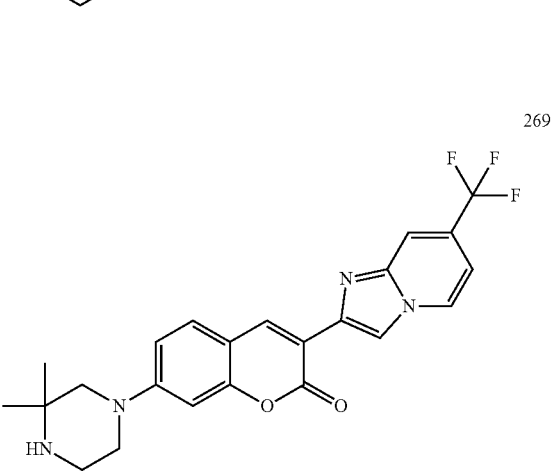
269

270 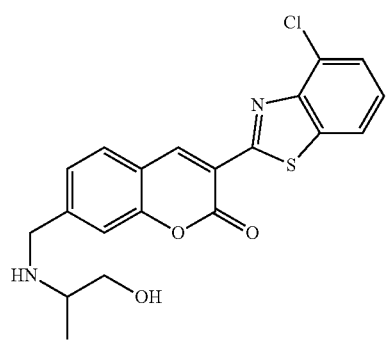
271 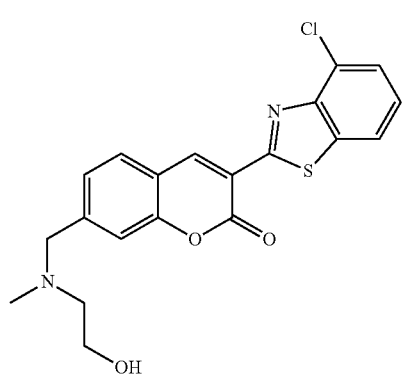
272 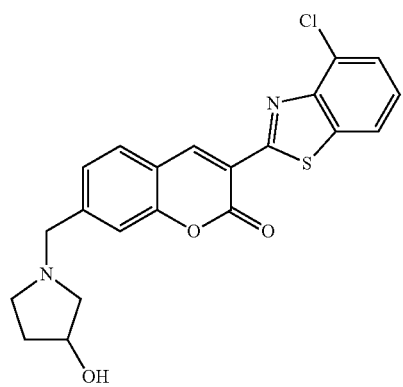
273 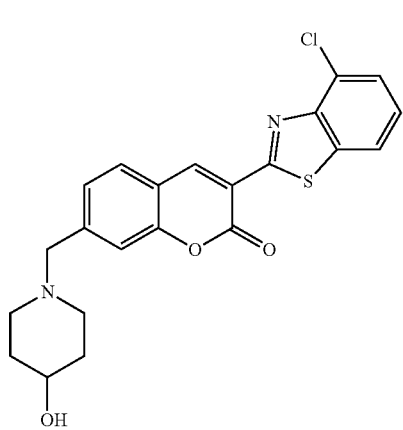
274 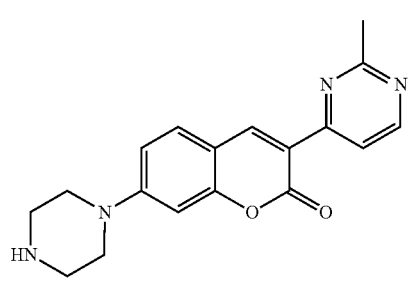
275 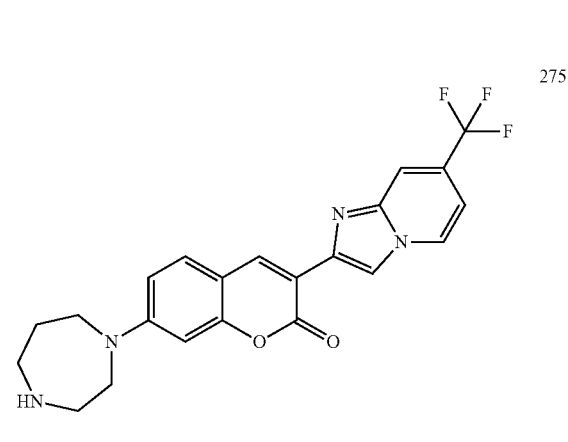
276 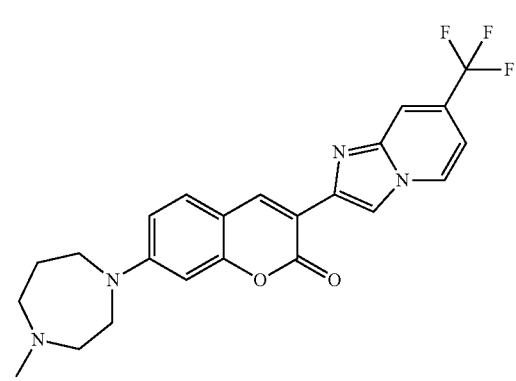
277 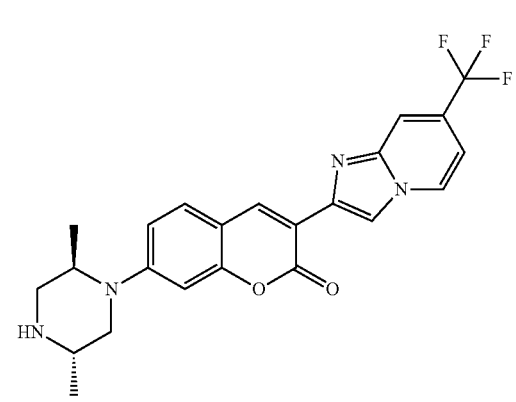

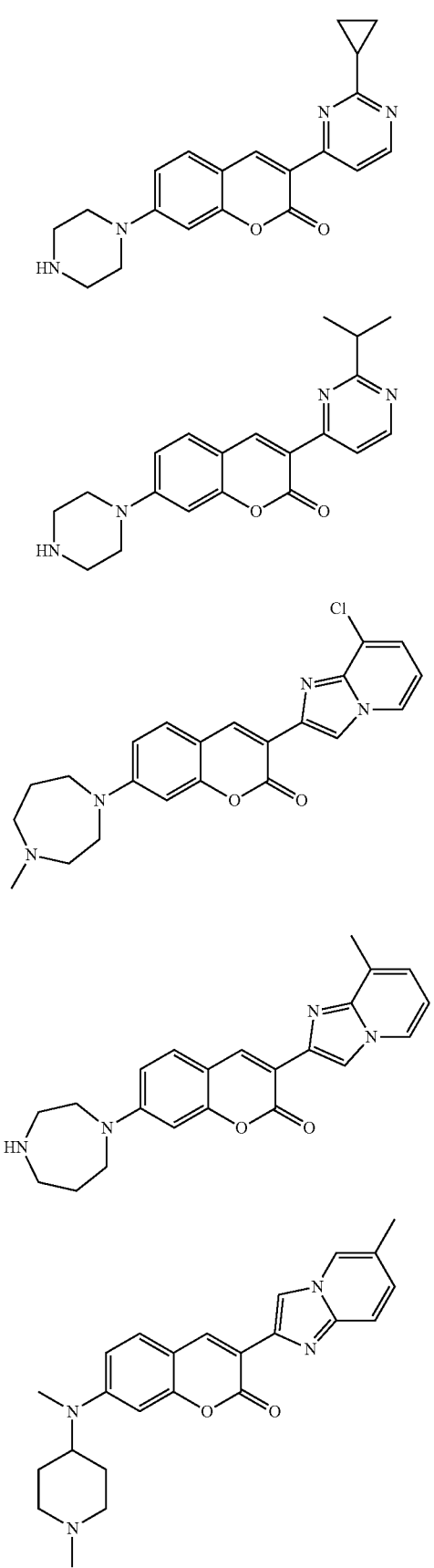
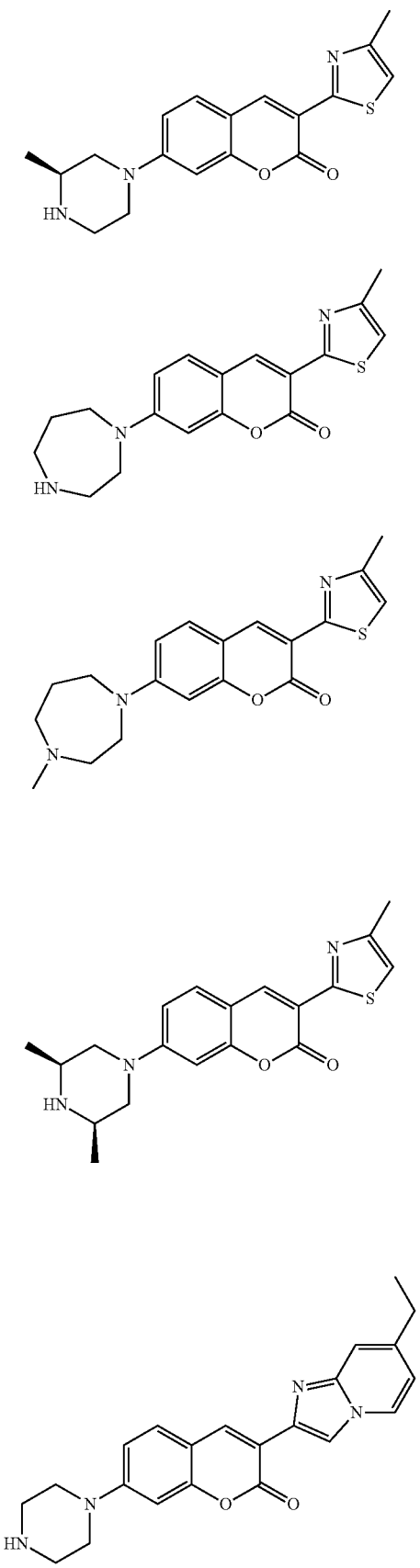

288
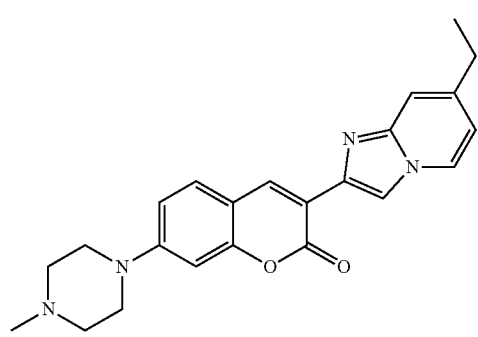
289
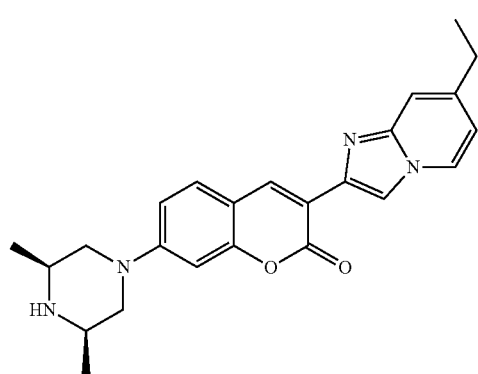
290
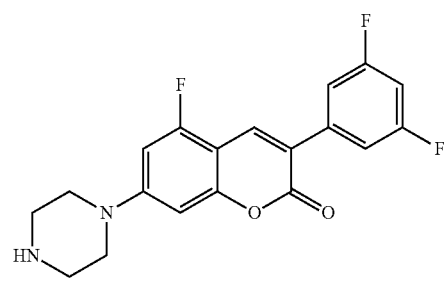
291
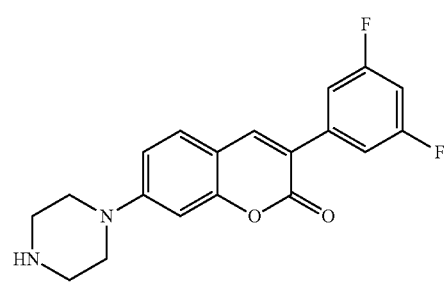
292
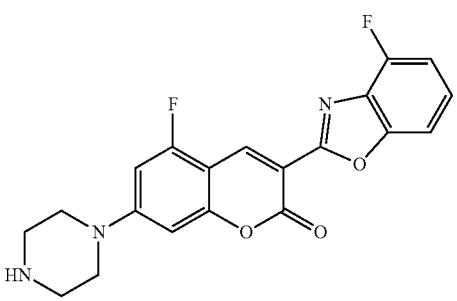
293
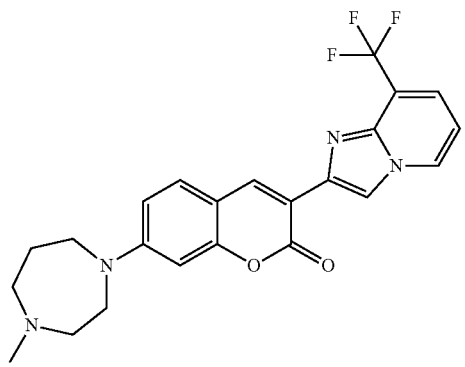
294
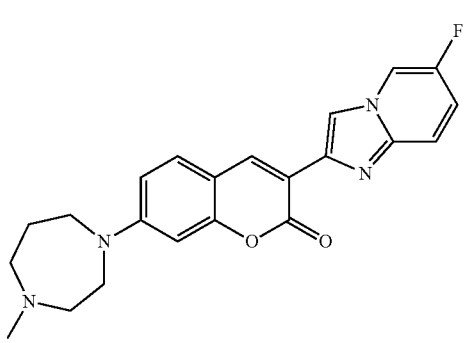
295
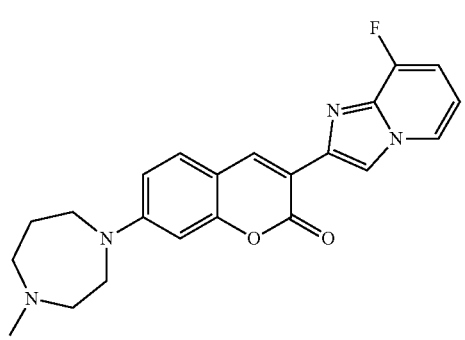
296
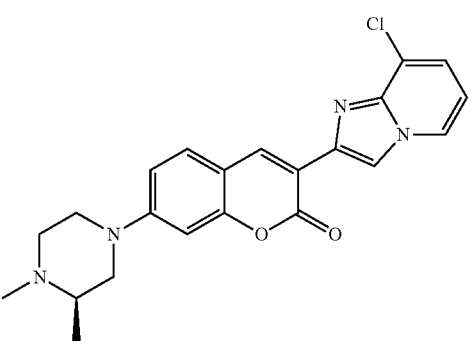
297
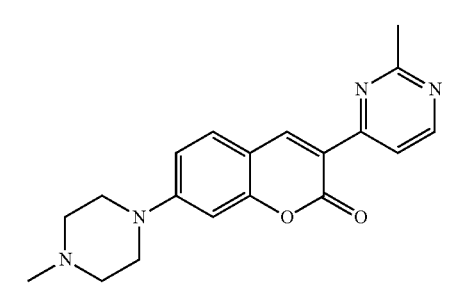

298
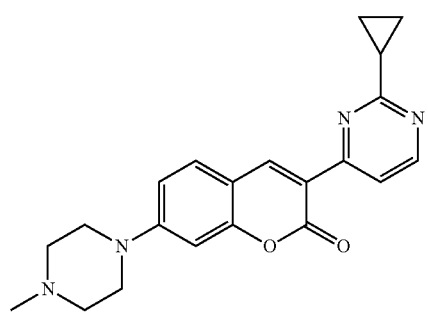
299
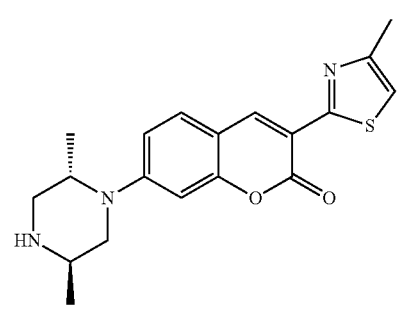
300
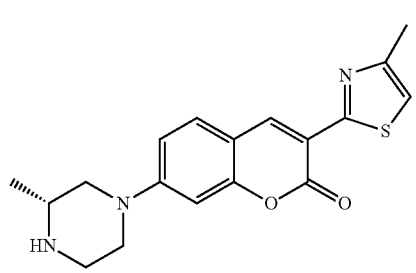
301
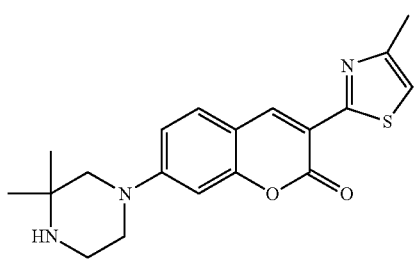
302
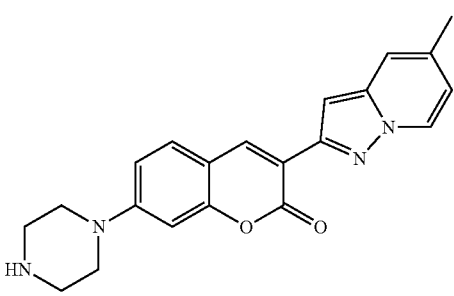
303
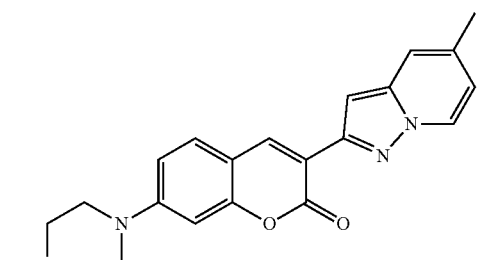
304
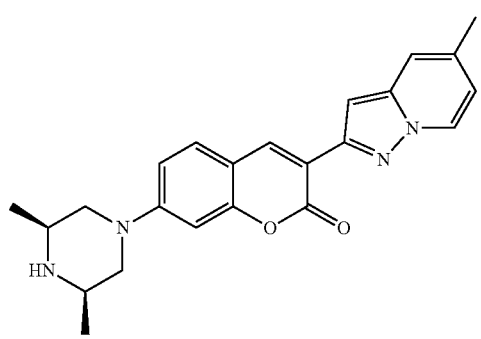
305
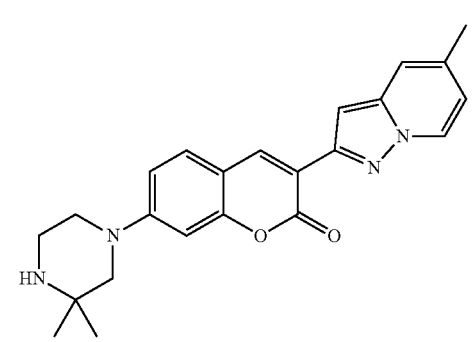
306
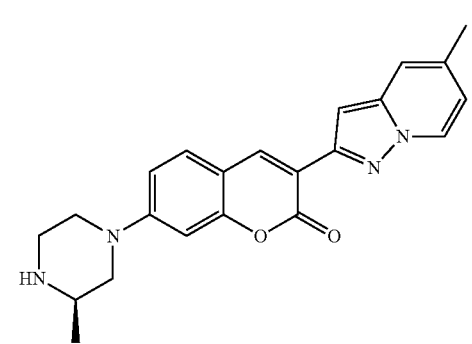
307
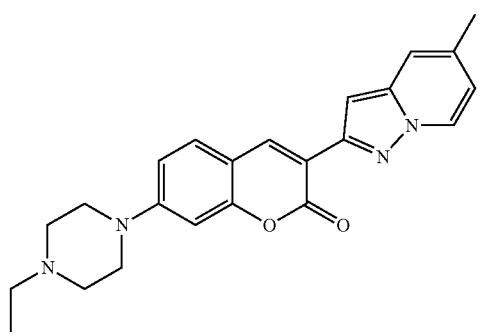

-continued
308
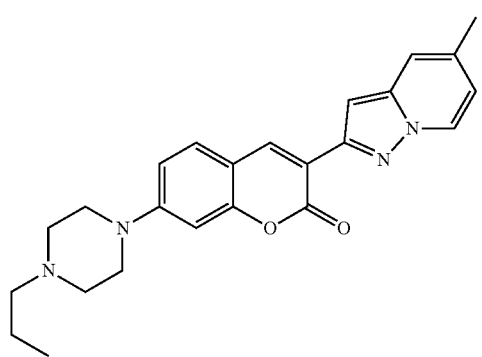
309
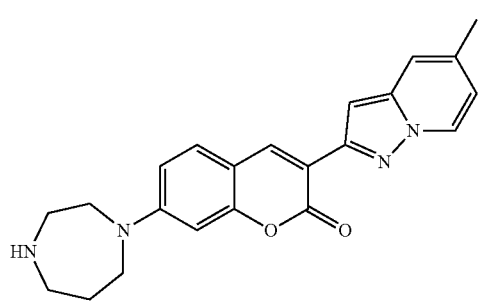
310
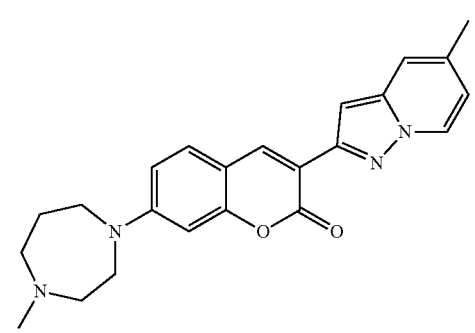
311
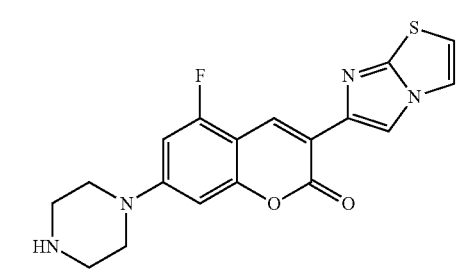
312
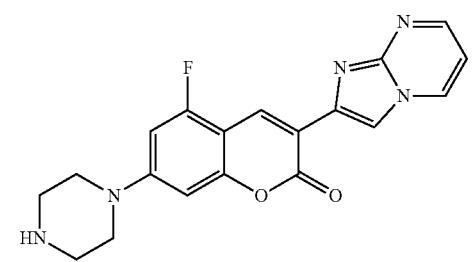
-continued
313
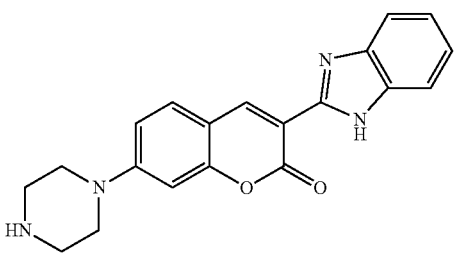
314
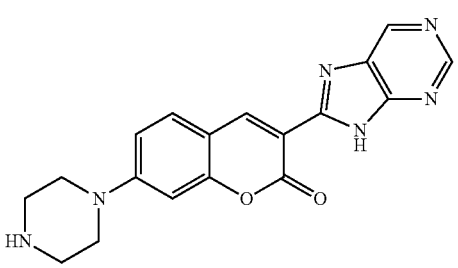
315
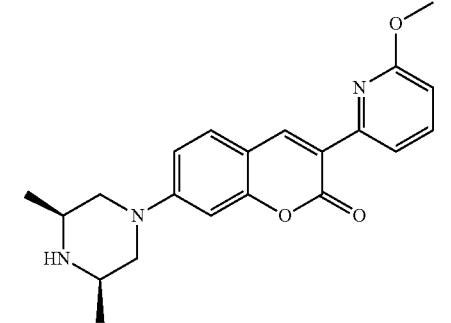
316
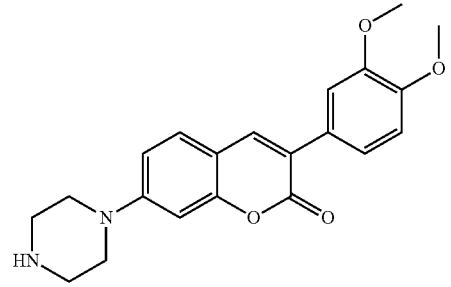
317
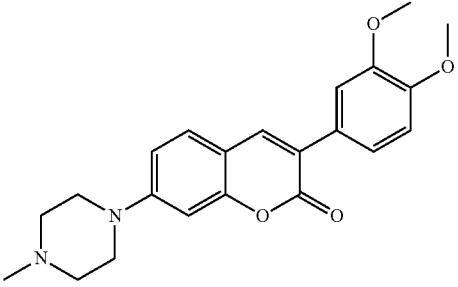

318
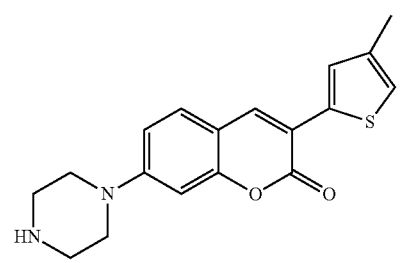
319
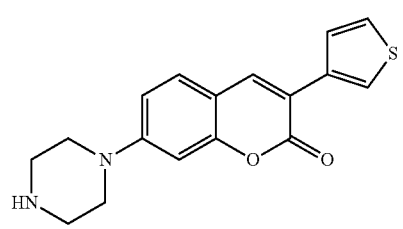
320
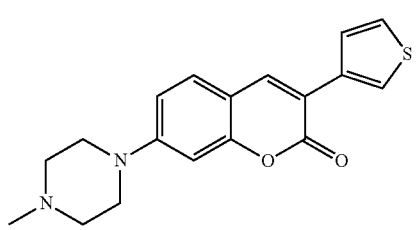
321
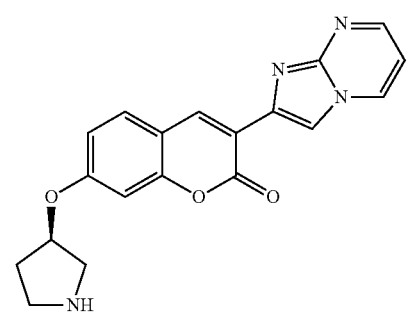
322
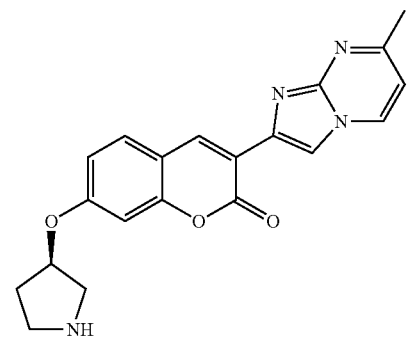
323
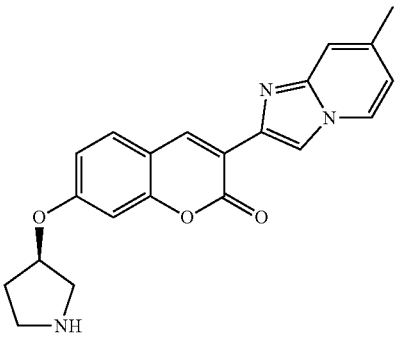
324
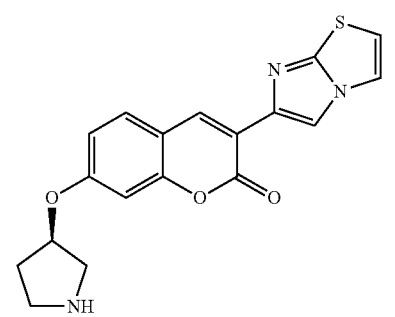
325
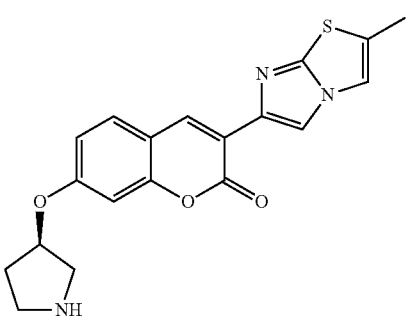
326
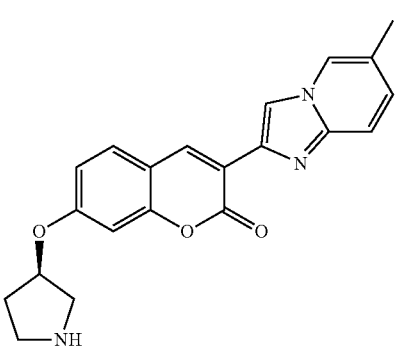
327
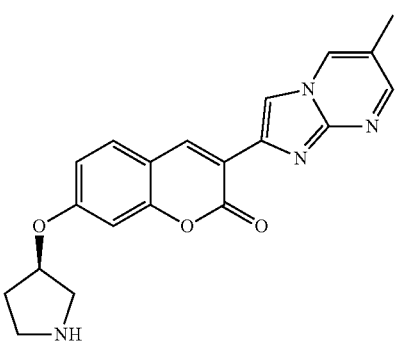

328 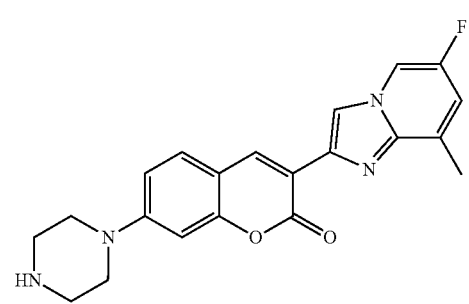
329 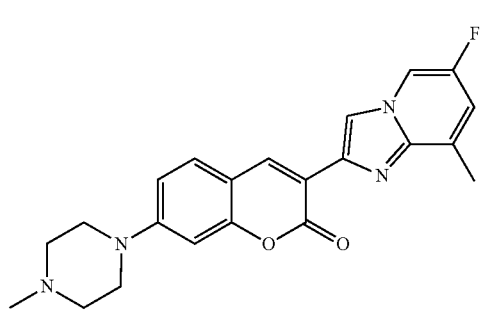
330 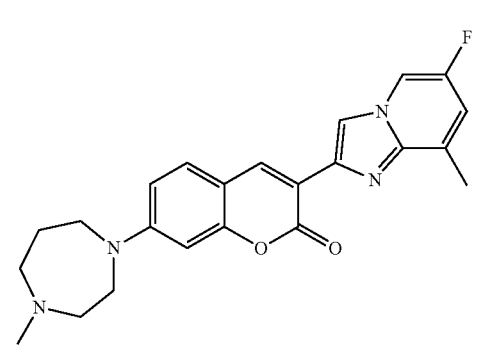
331 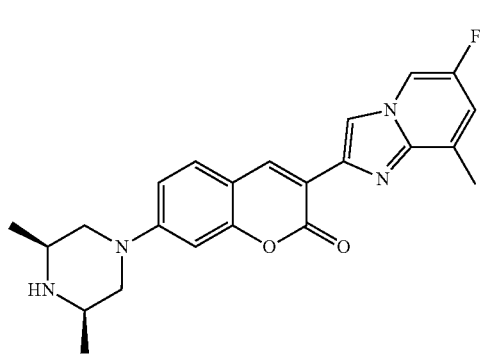
332 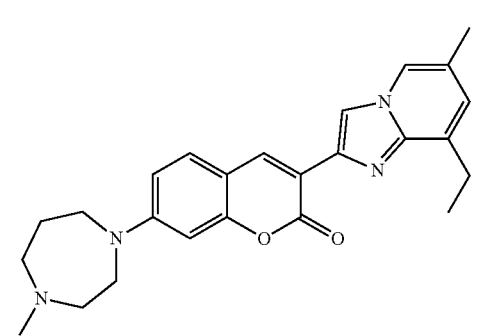
333 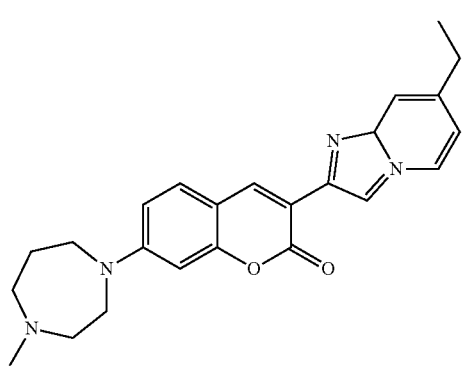
334 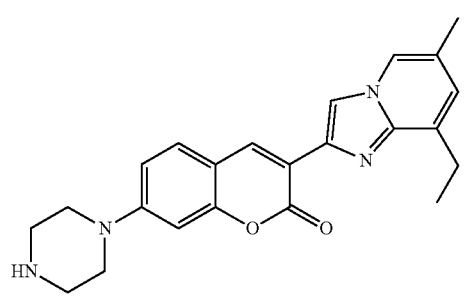
335 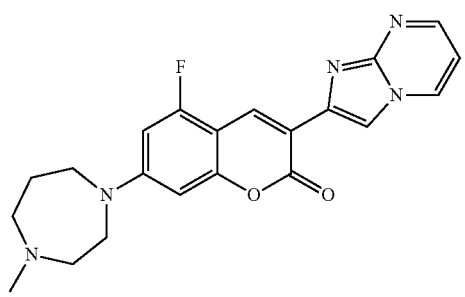
336 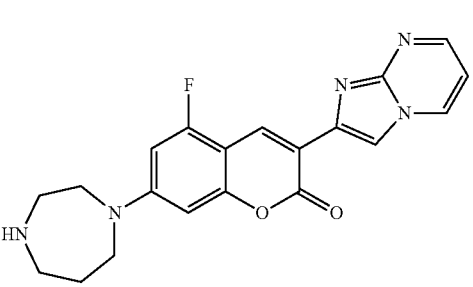
337 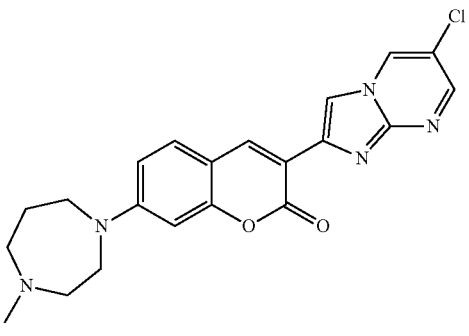

338 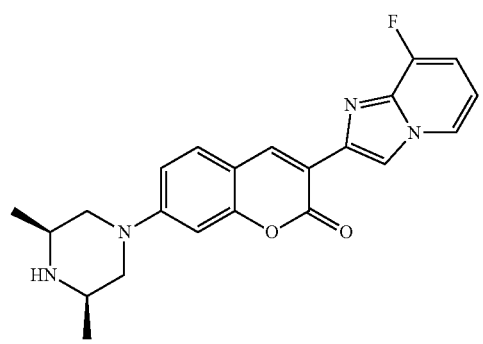
339 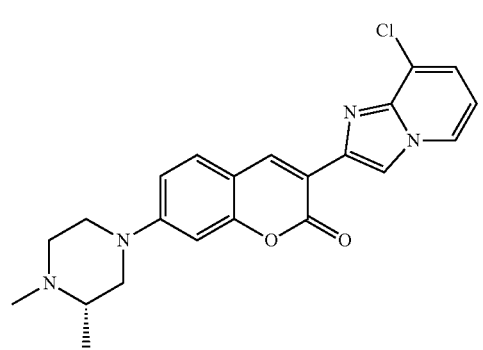
340 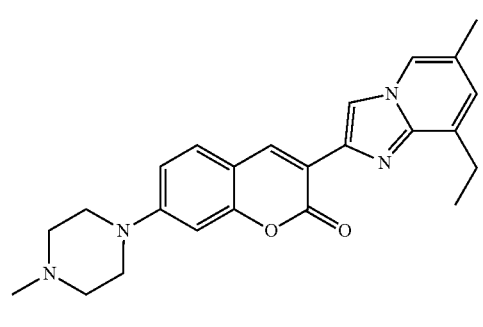
341 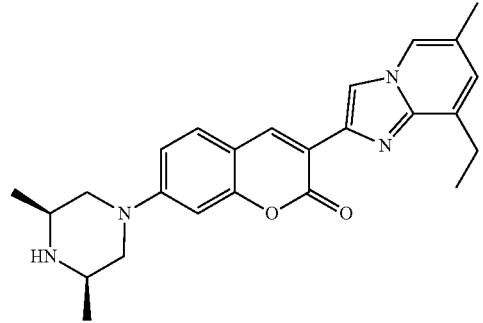
342 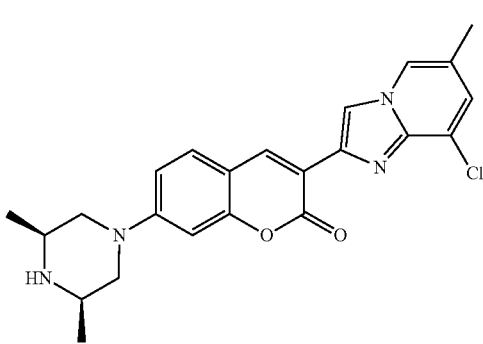
343 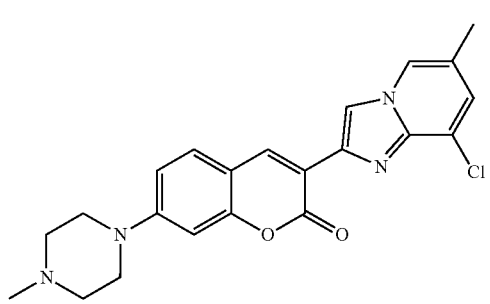
344 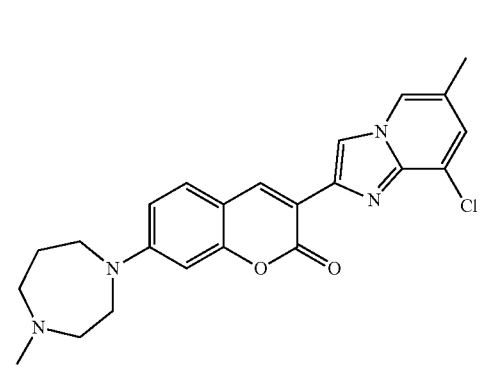
345 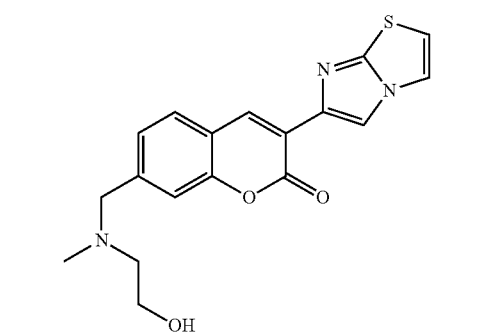
346 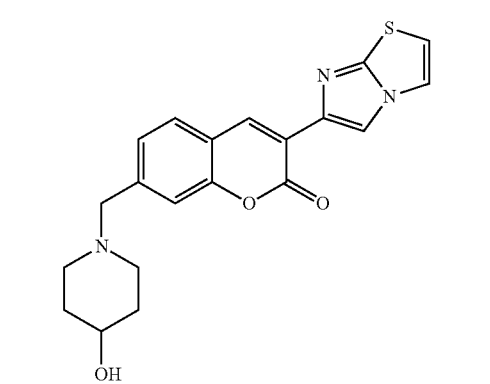

-continued
347
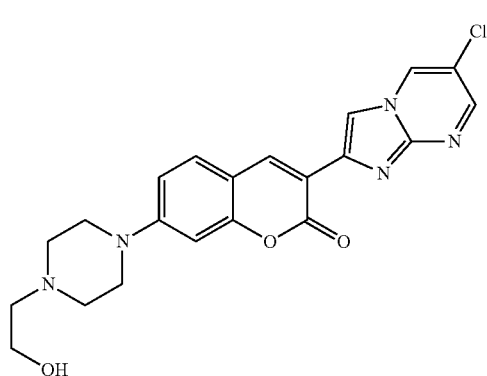
348
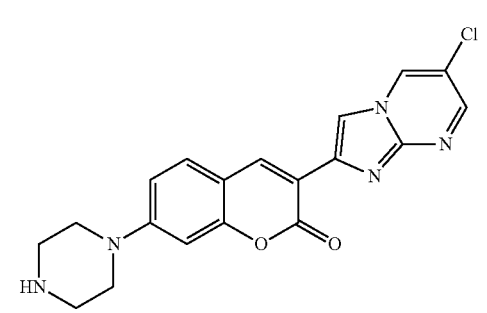
349
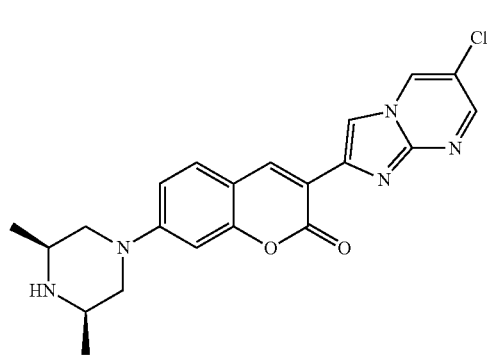
350
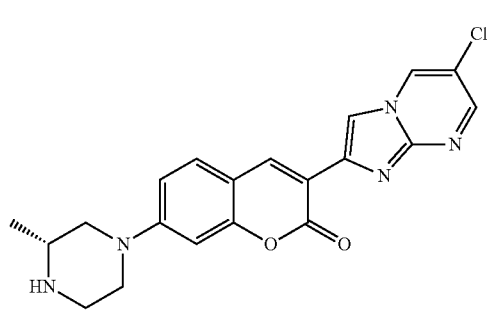
351
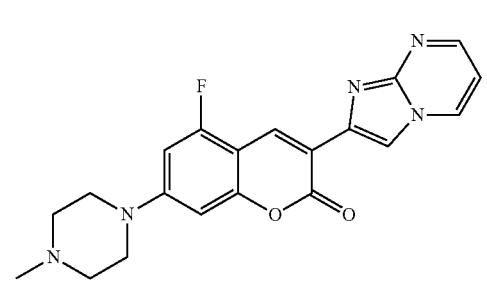
-continued
352
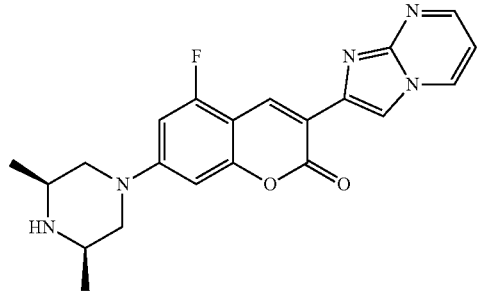
353
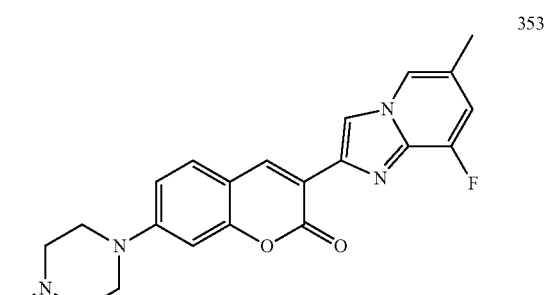
354
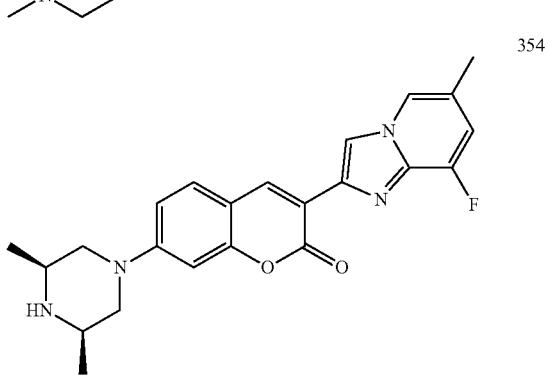
355
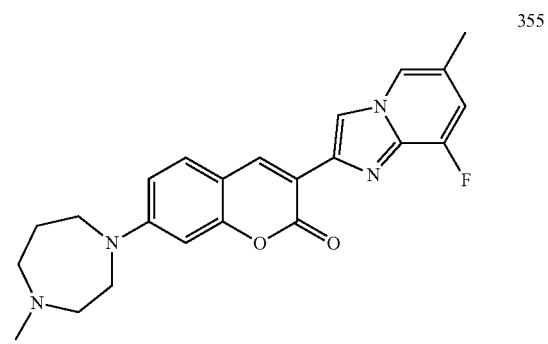
356
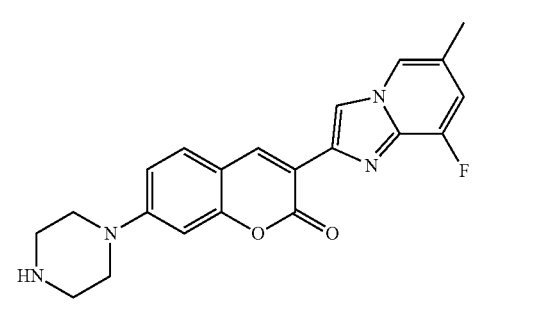

357 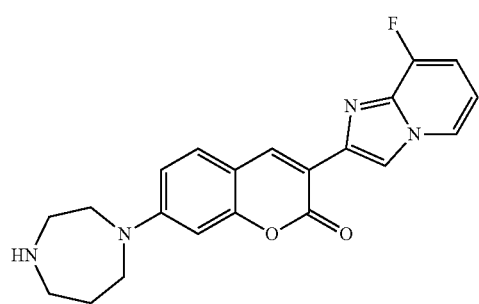
358 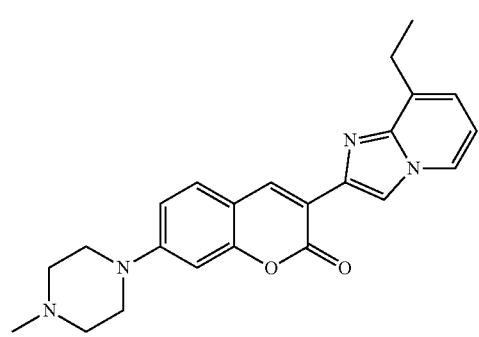
359 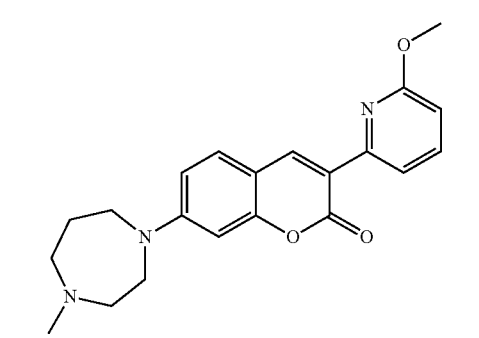
360 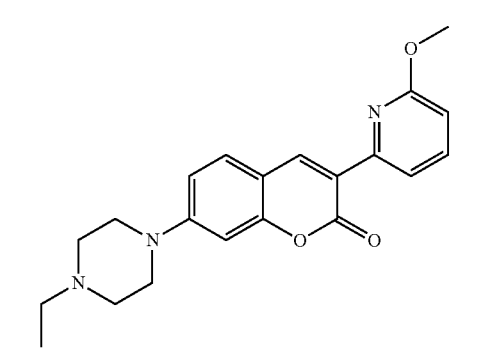
361 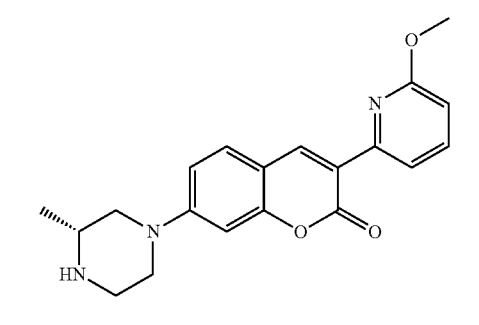
362 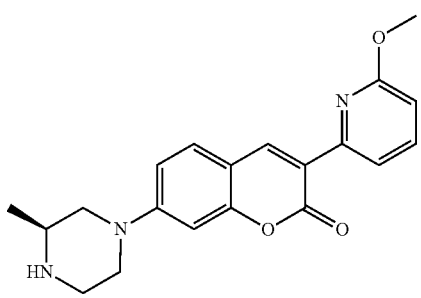
363 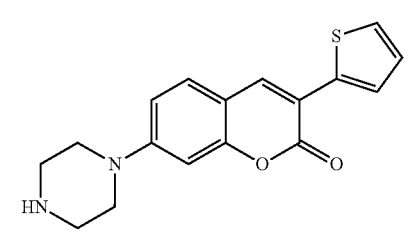
364 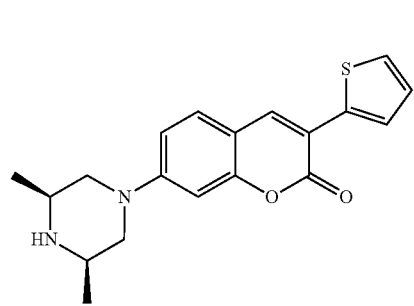
365 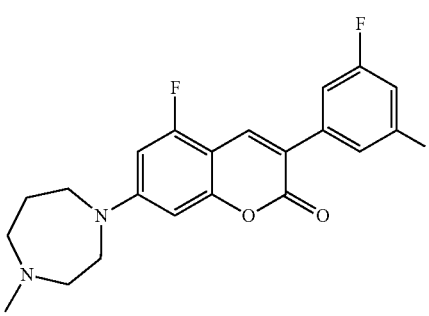
366 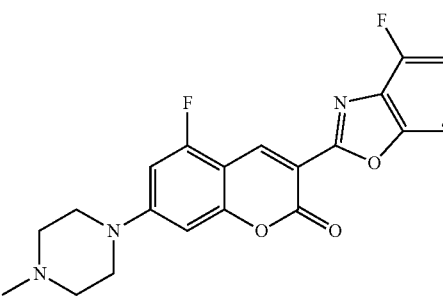

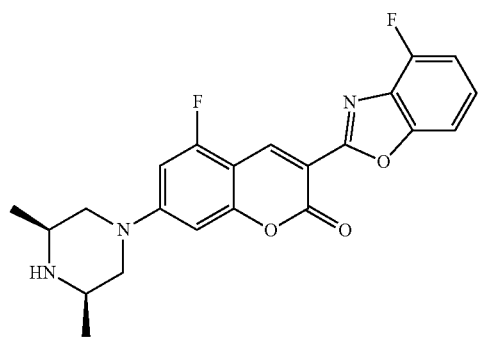
367
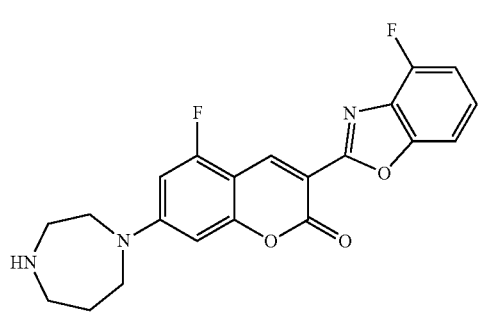
368
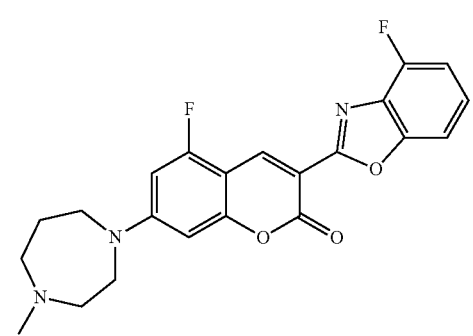
369
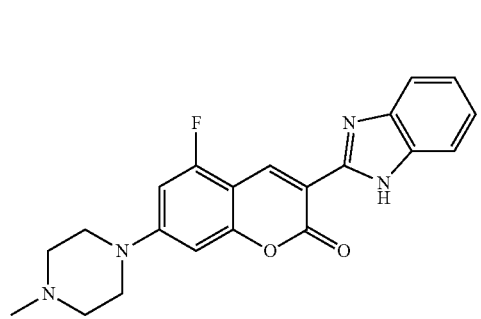
370
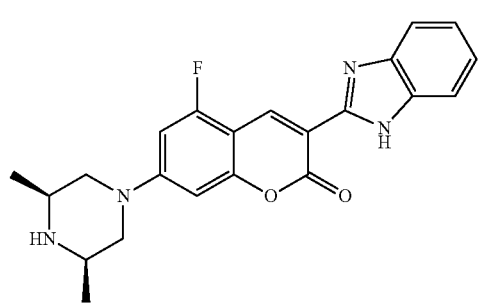
371
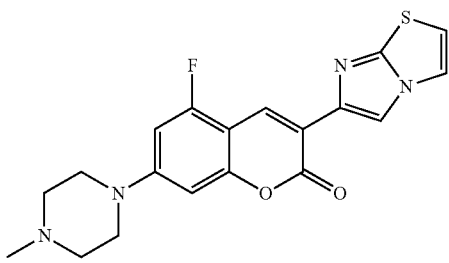
372
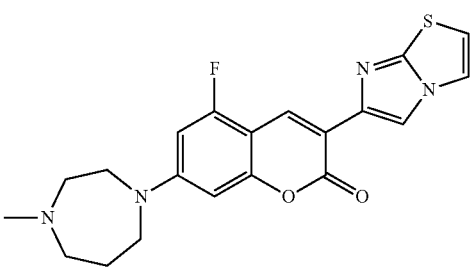
373
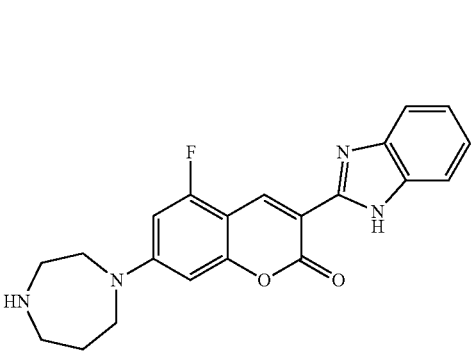
374
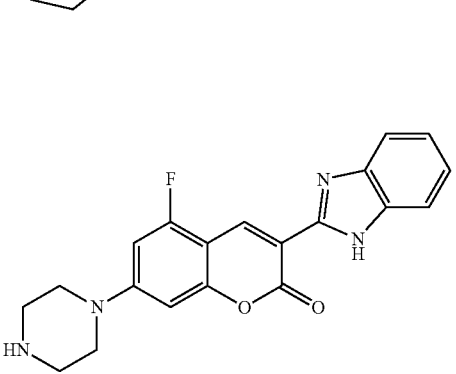
375
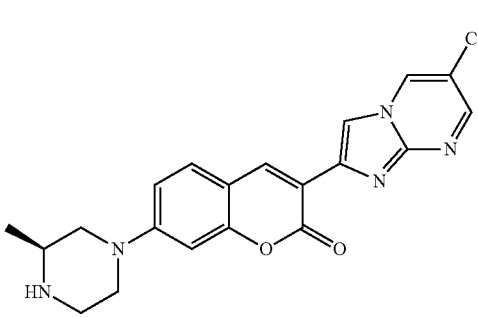
376

377 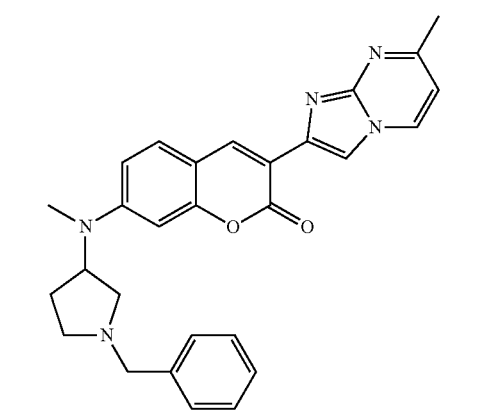
378 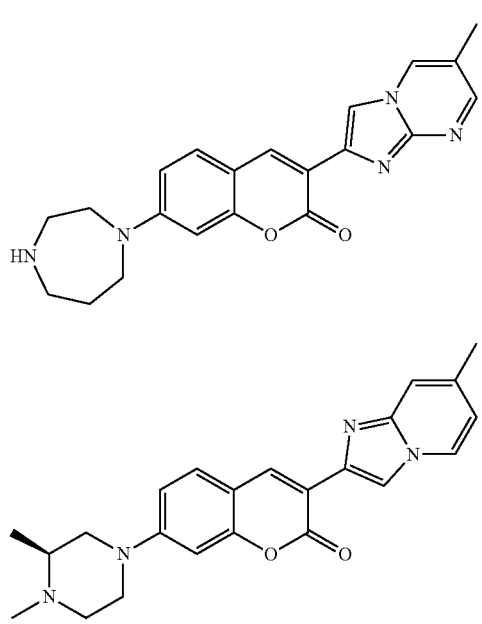
379 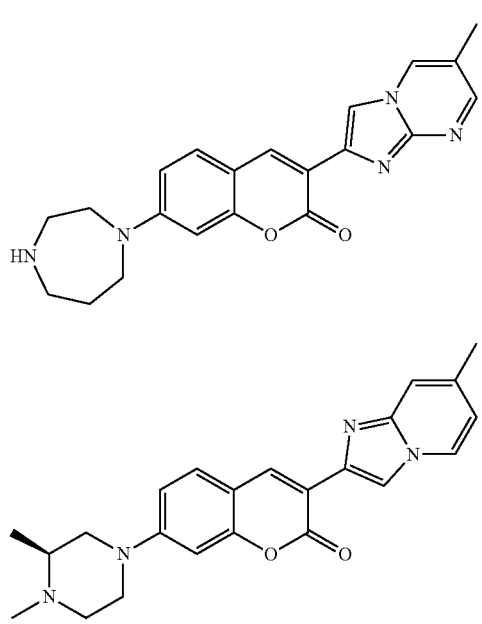
380 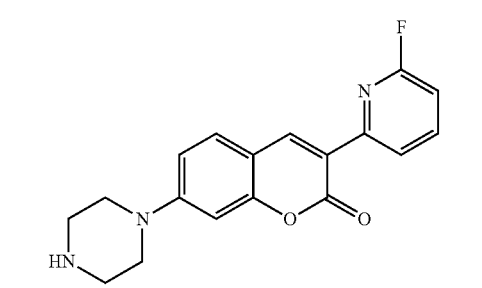
381 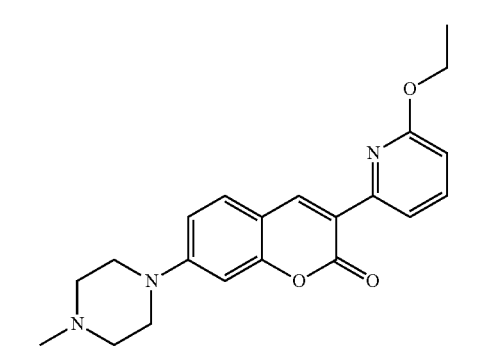
382 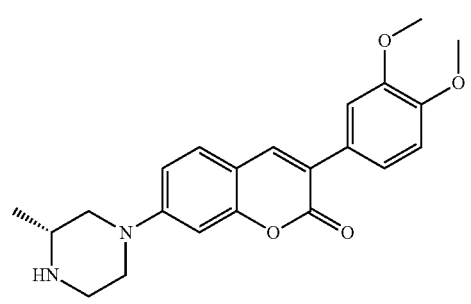
383 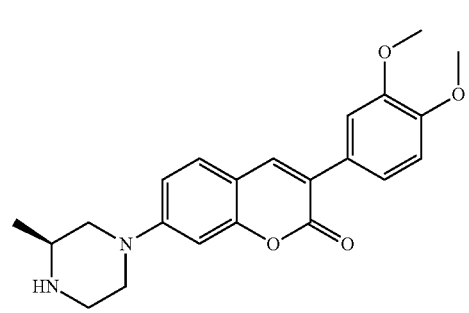
384 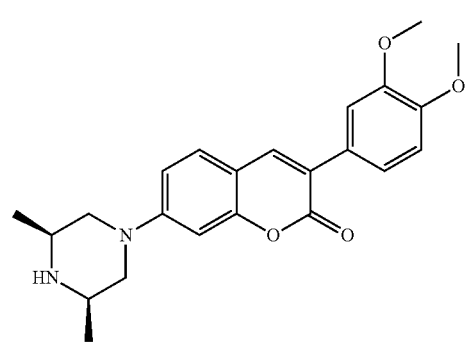
385 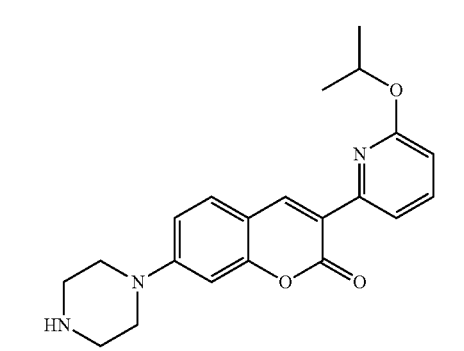
386 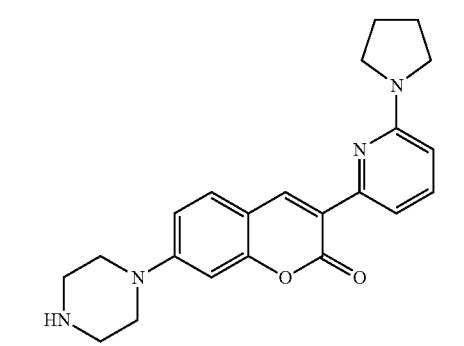

387 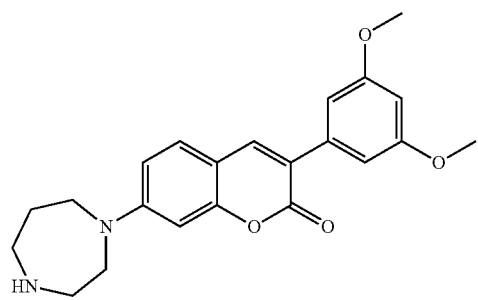
388 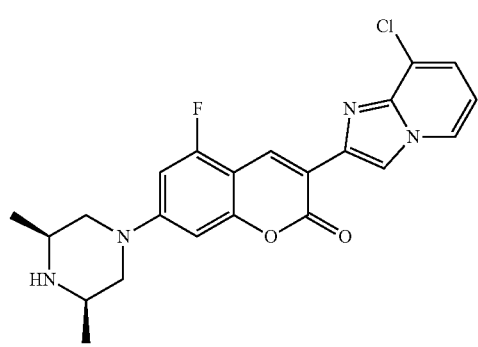
389 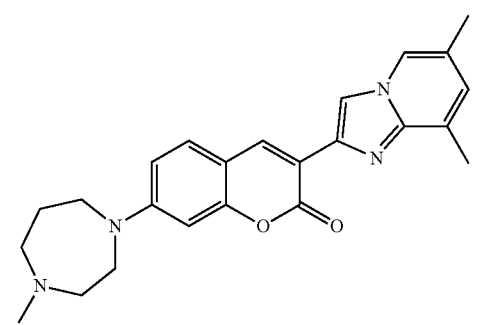
390 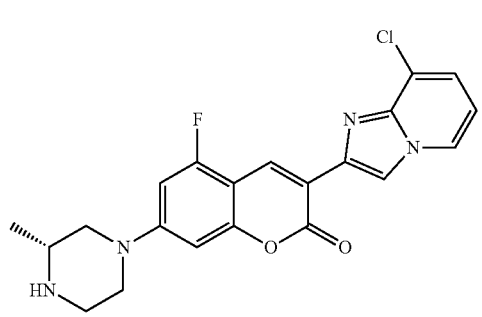
391 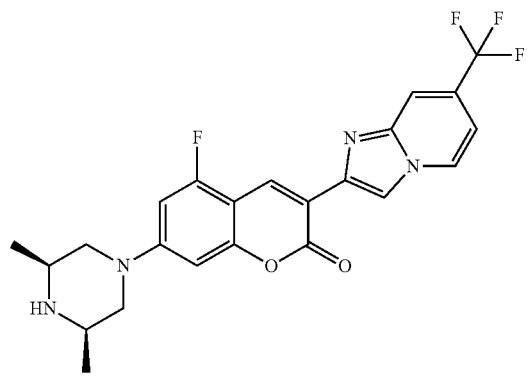
392 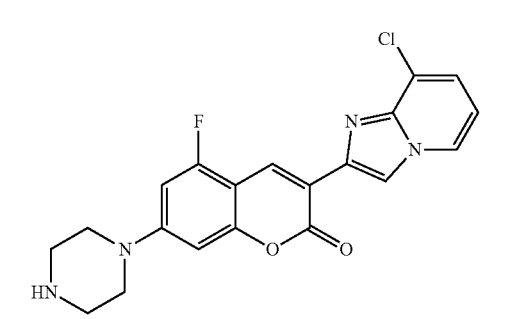
393 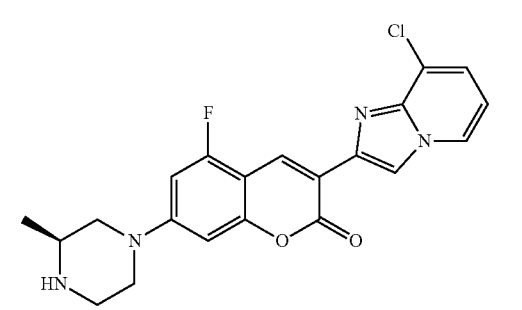
394 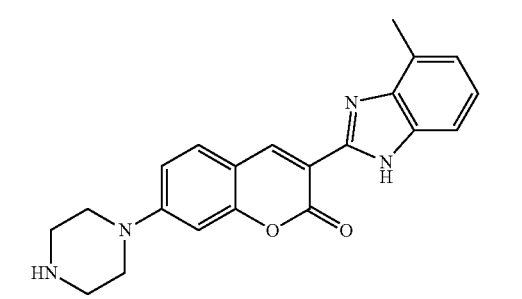
395 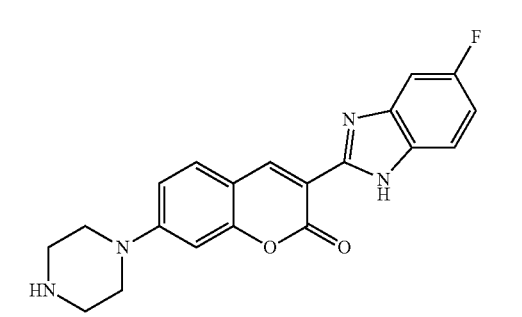

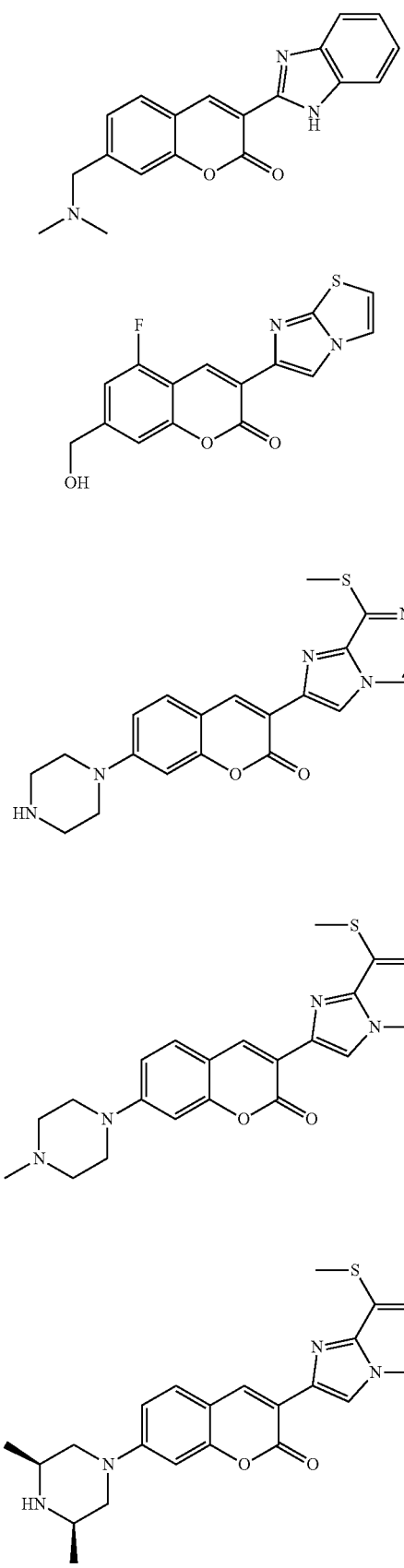
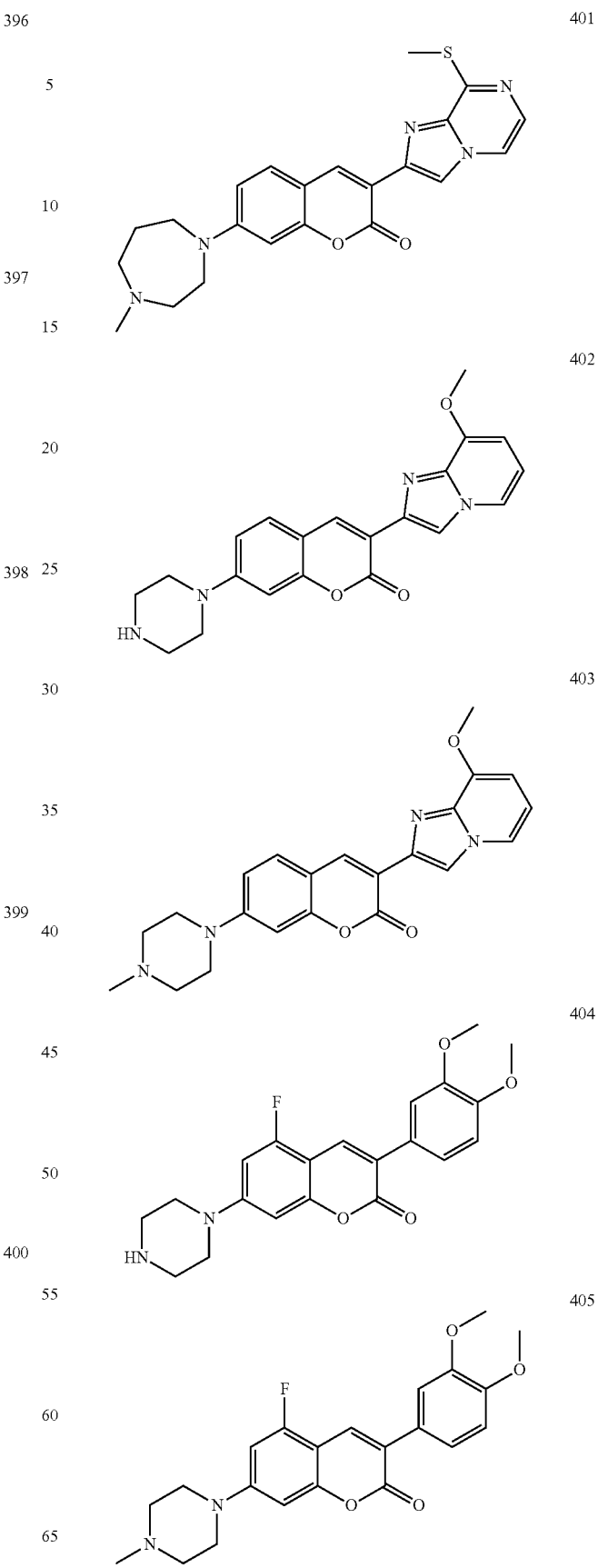

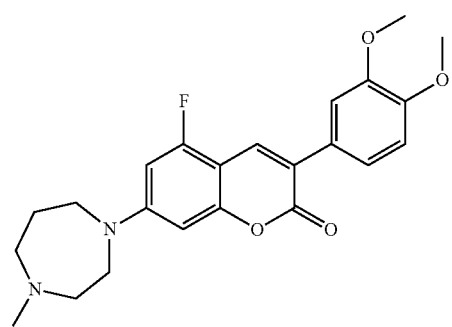
406
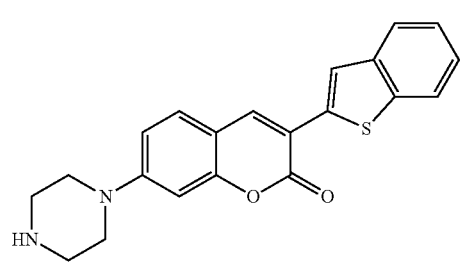
407
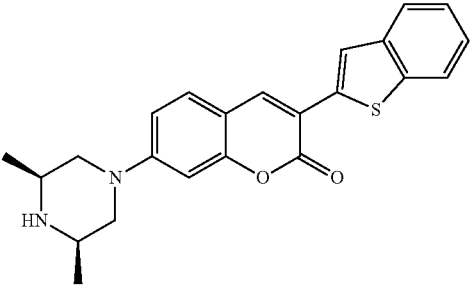
408
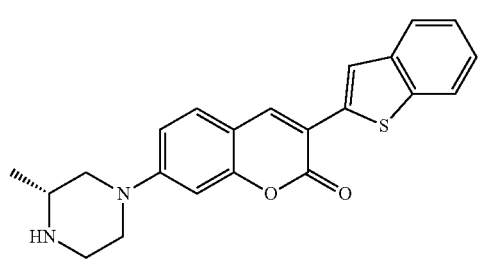
409
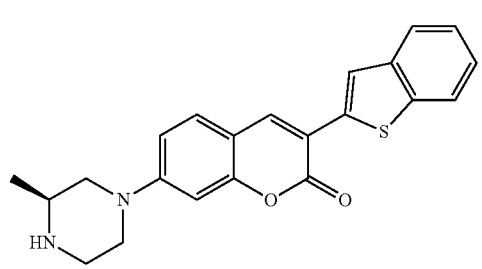
410
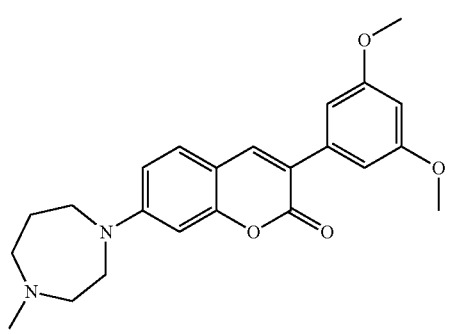
411
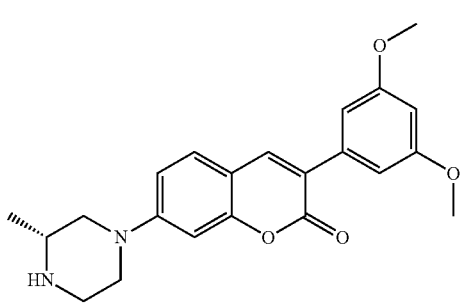
412
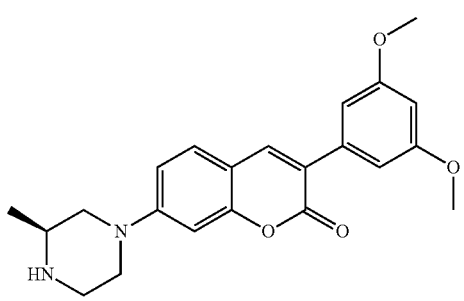
413
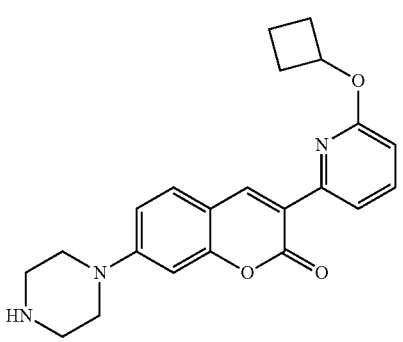
414
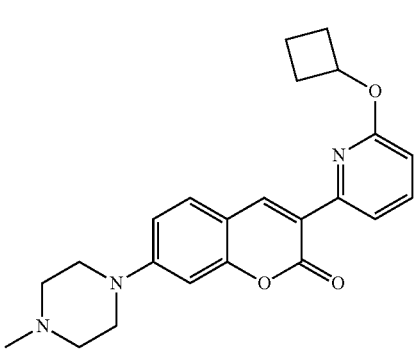
415

416 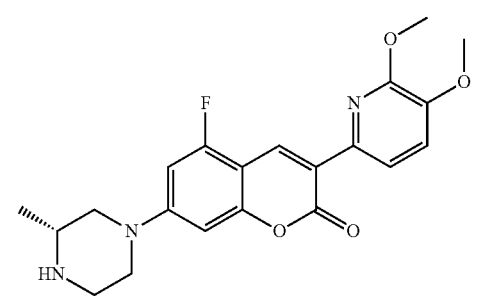
417 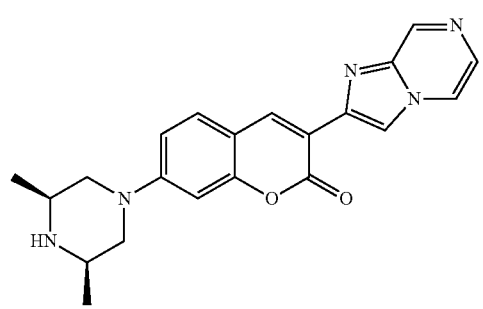
418 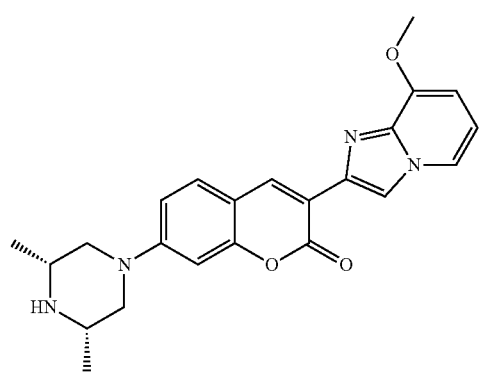
419 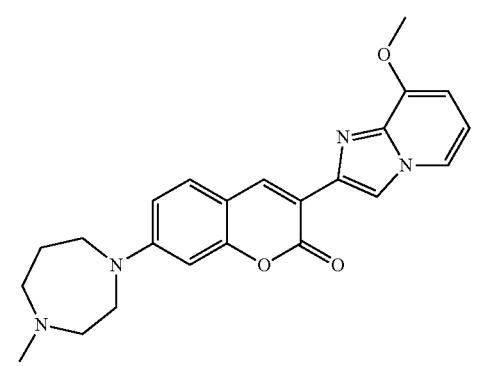
420 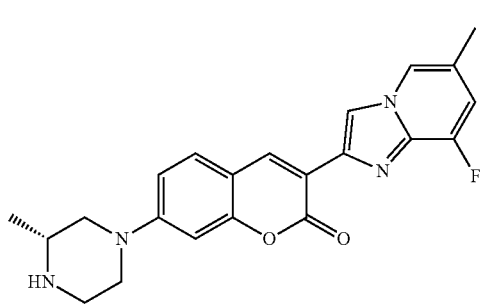
421 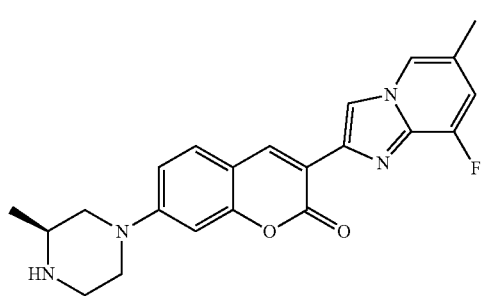
422 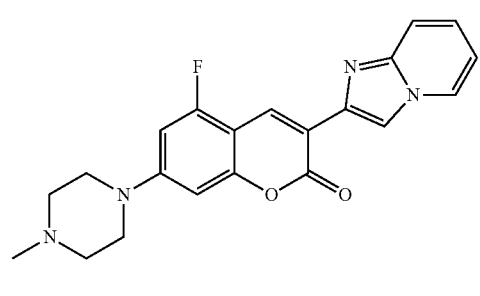
423 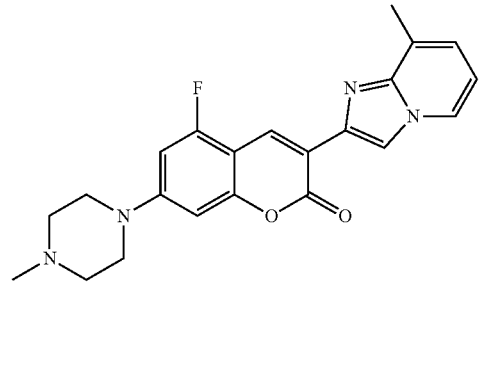
424 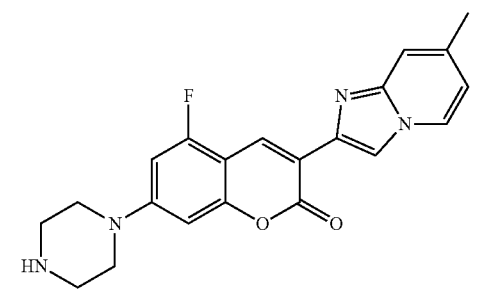
425 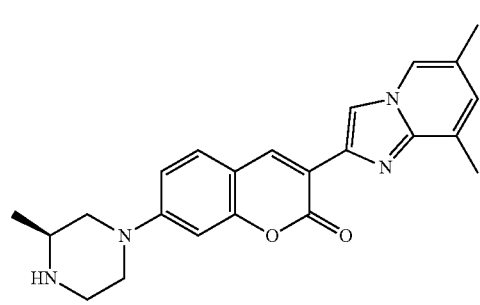

426
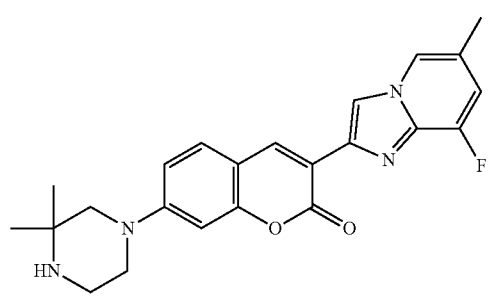
427
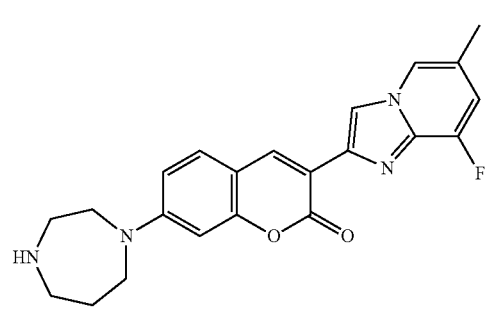
428
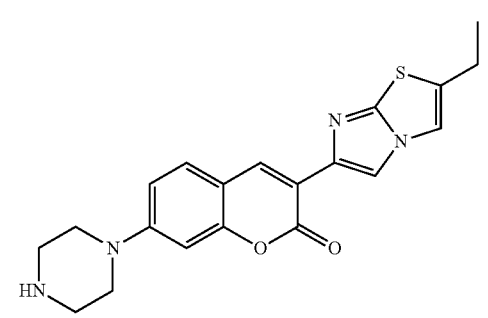
429
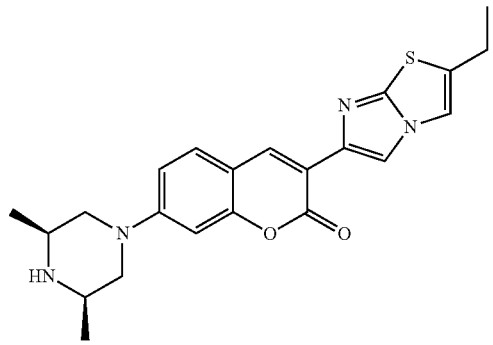
430
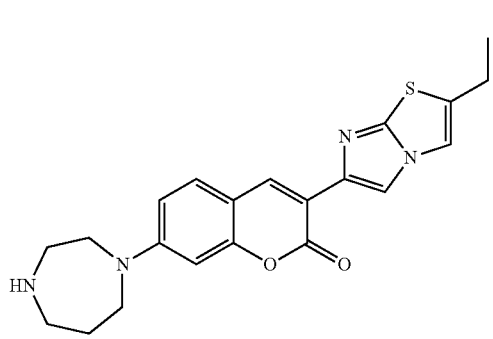
431
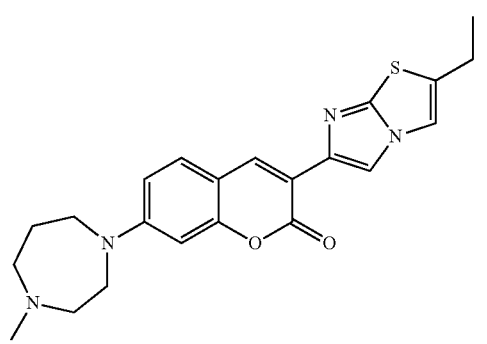
432
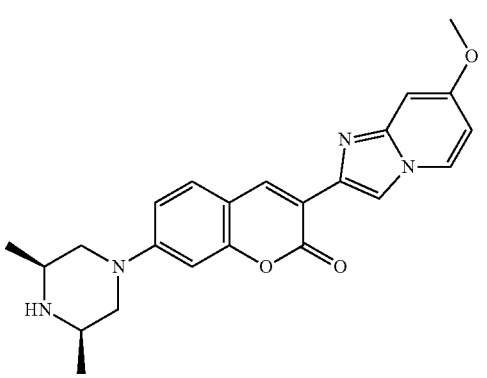
433
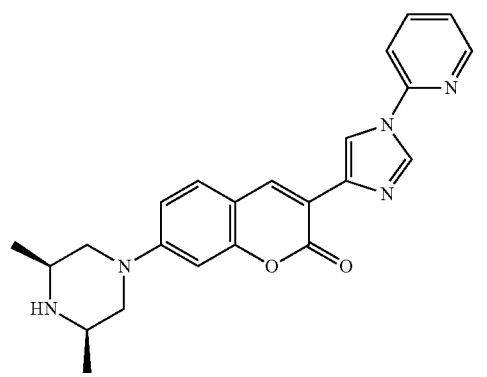
434
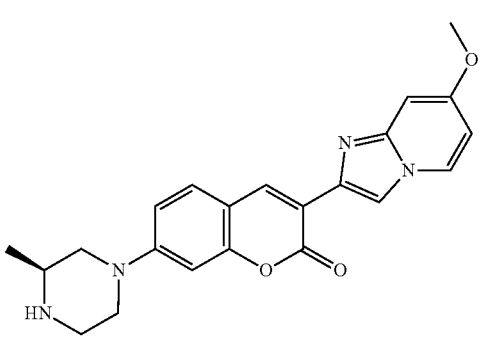

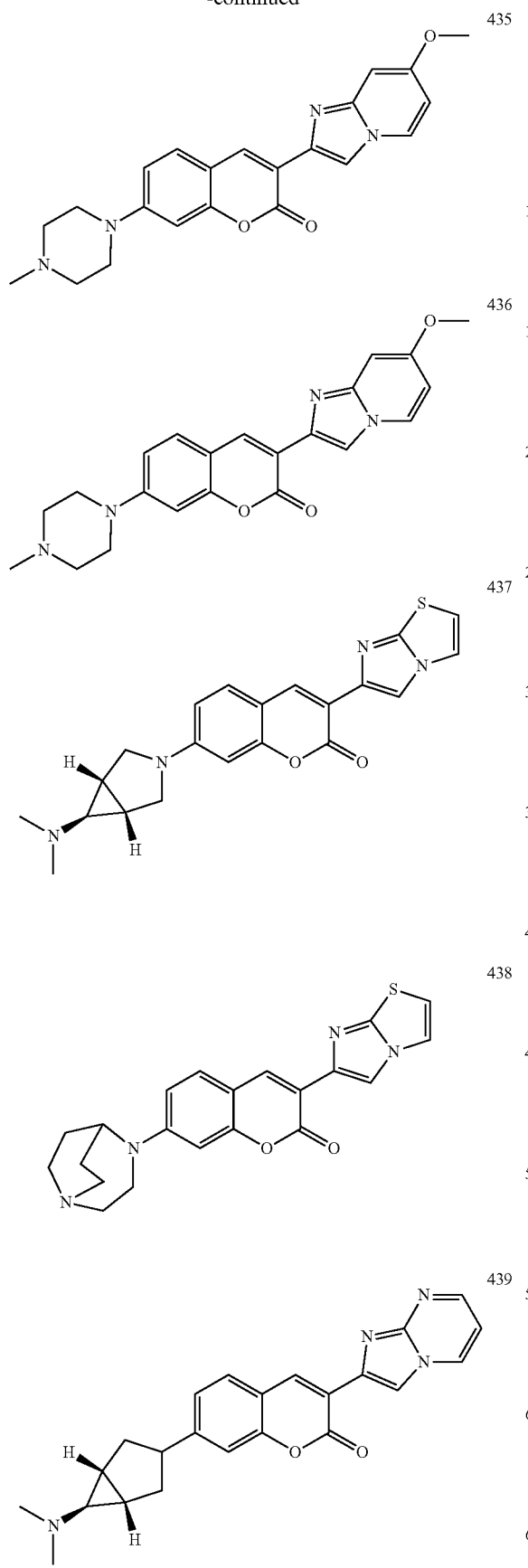
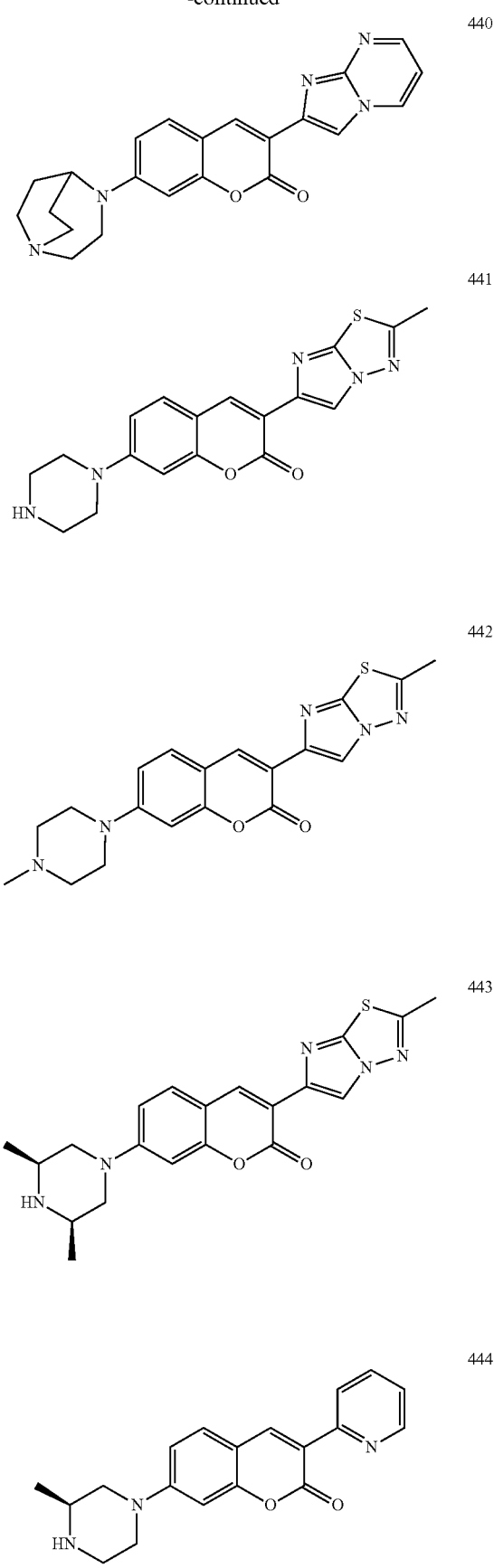

| | |
|---|---|
| 445 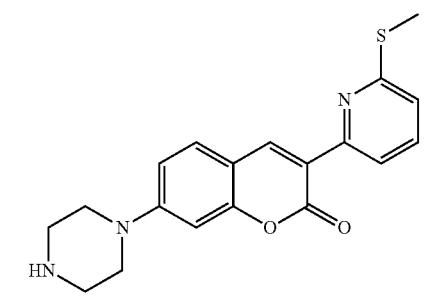 | 450 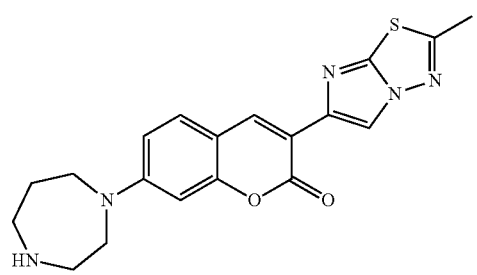 |
| 446 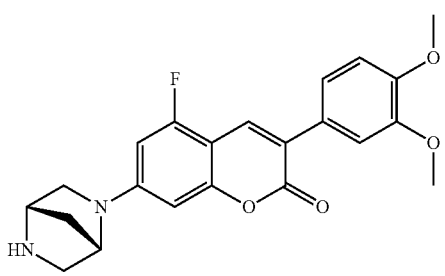 | 451 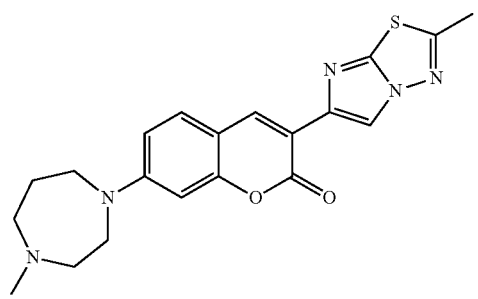 |
| 447 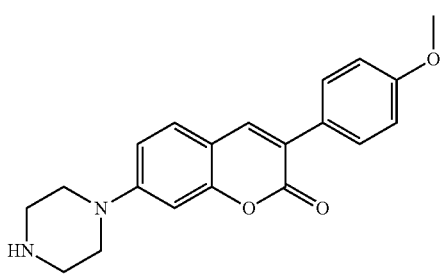 | 452 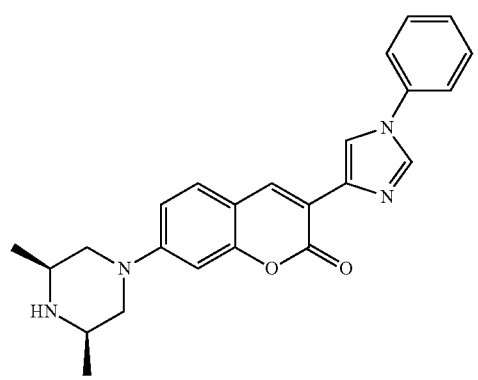 |
| 448 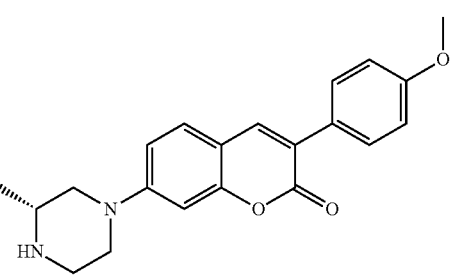 | 453 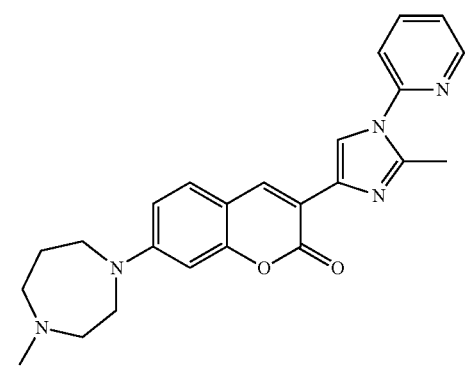 |
| 449 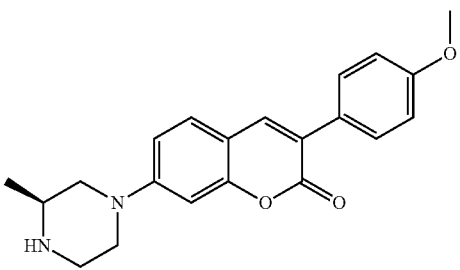 | 454 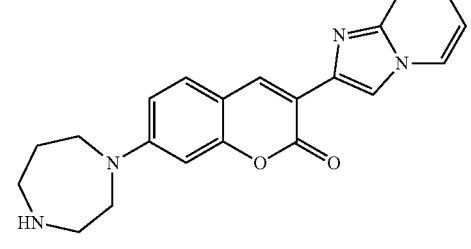 |

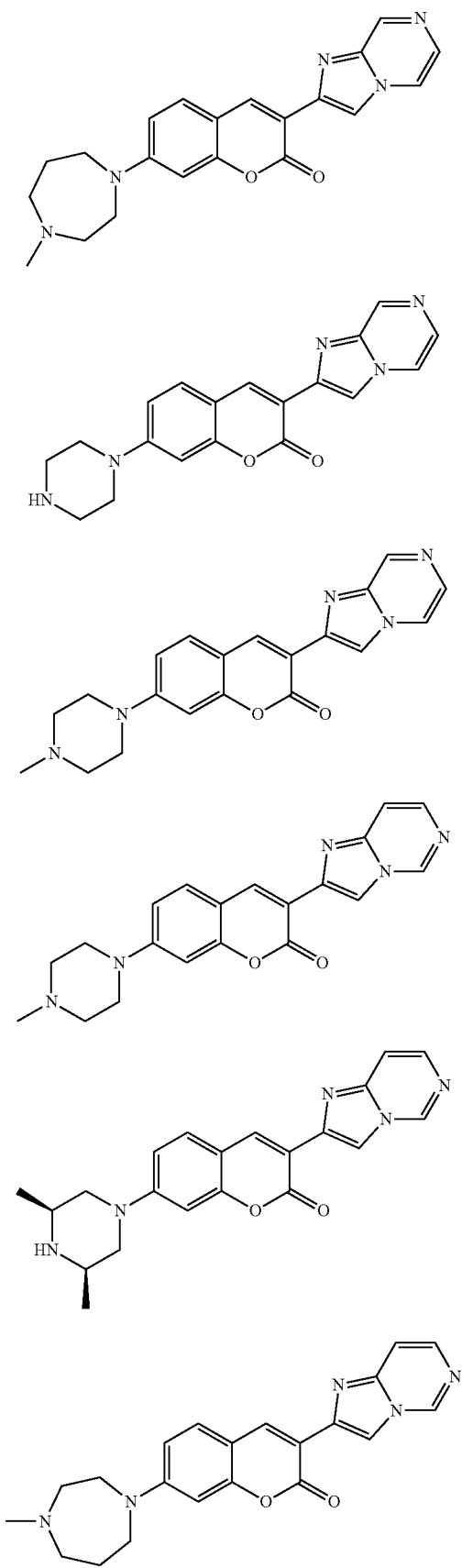
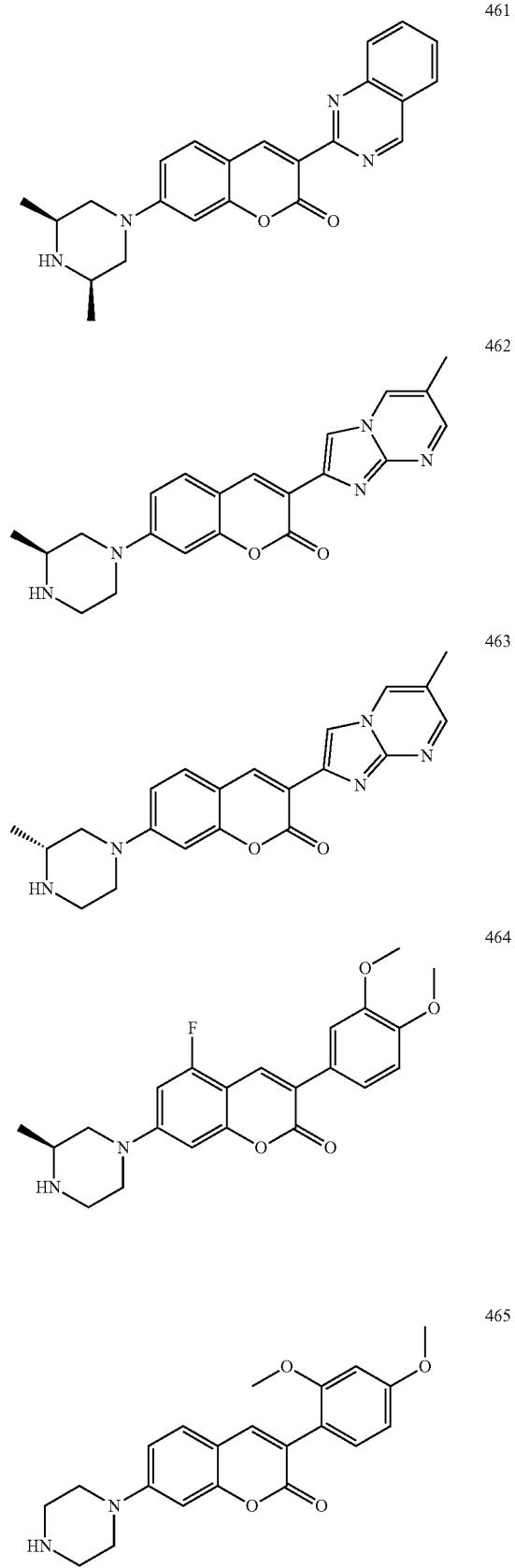

466
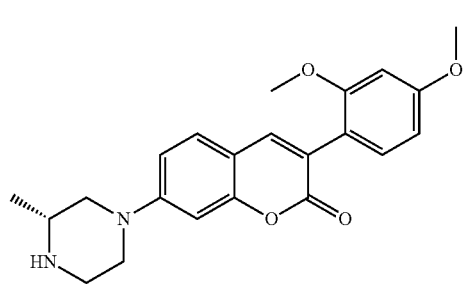
467
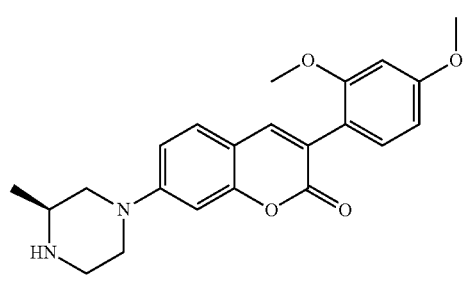
468
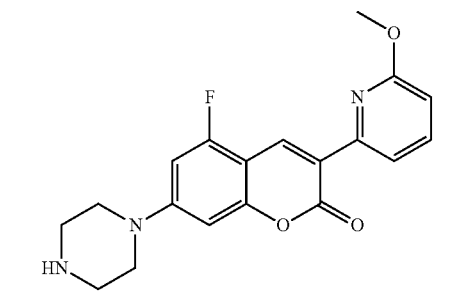
469
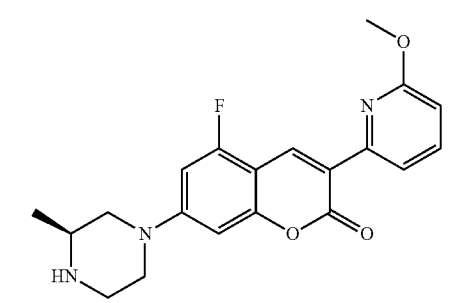
470
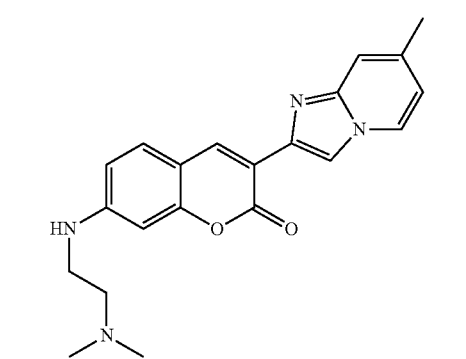
471
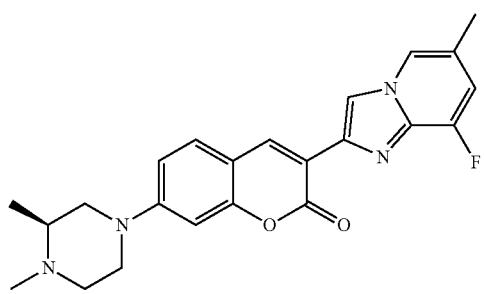
472
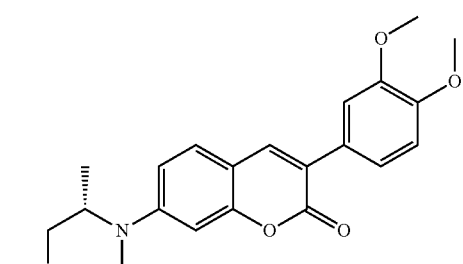
473
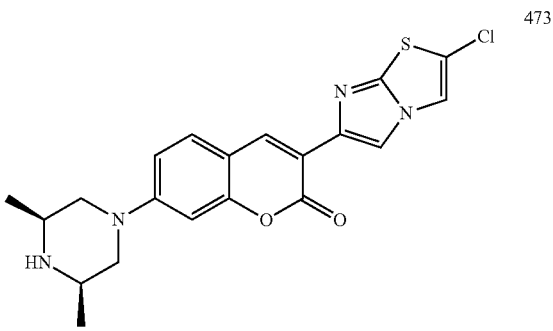
474
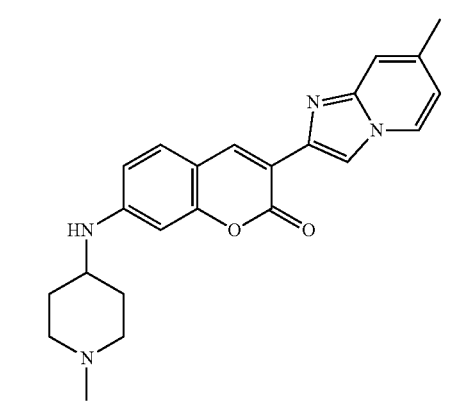

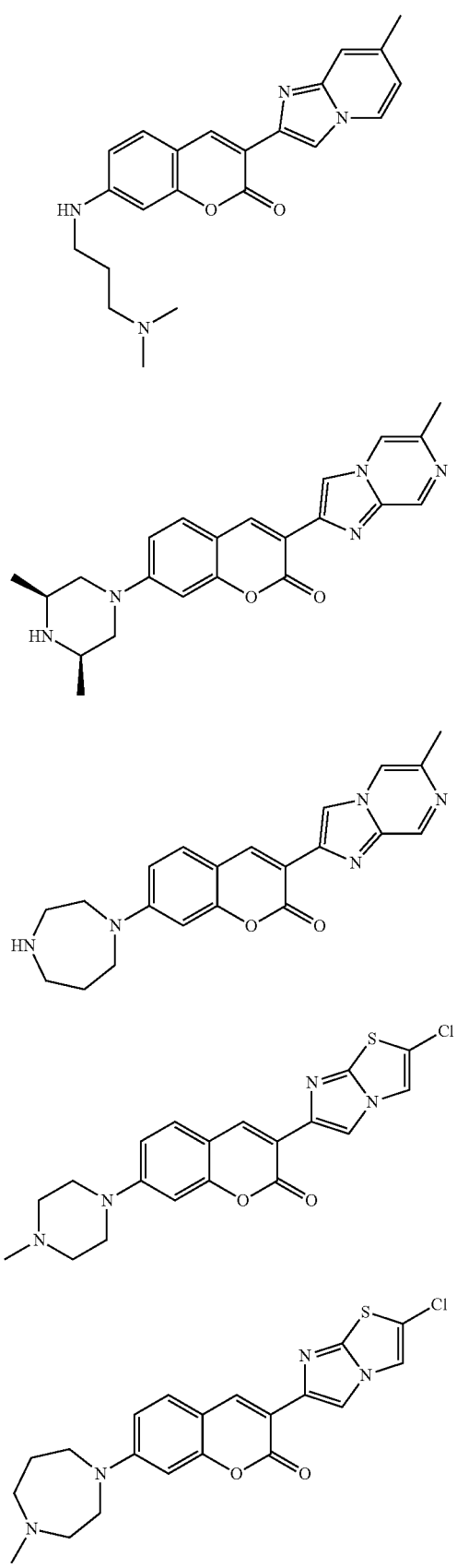
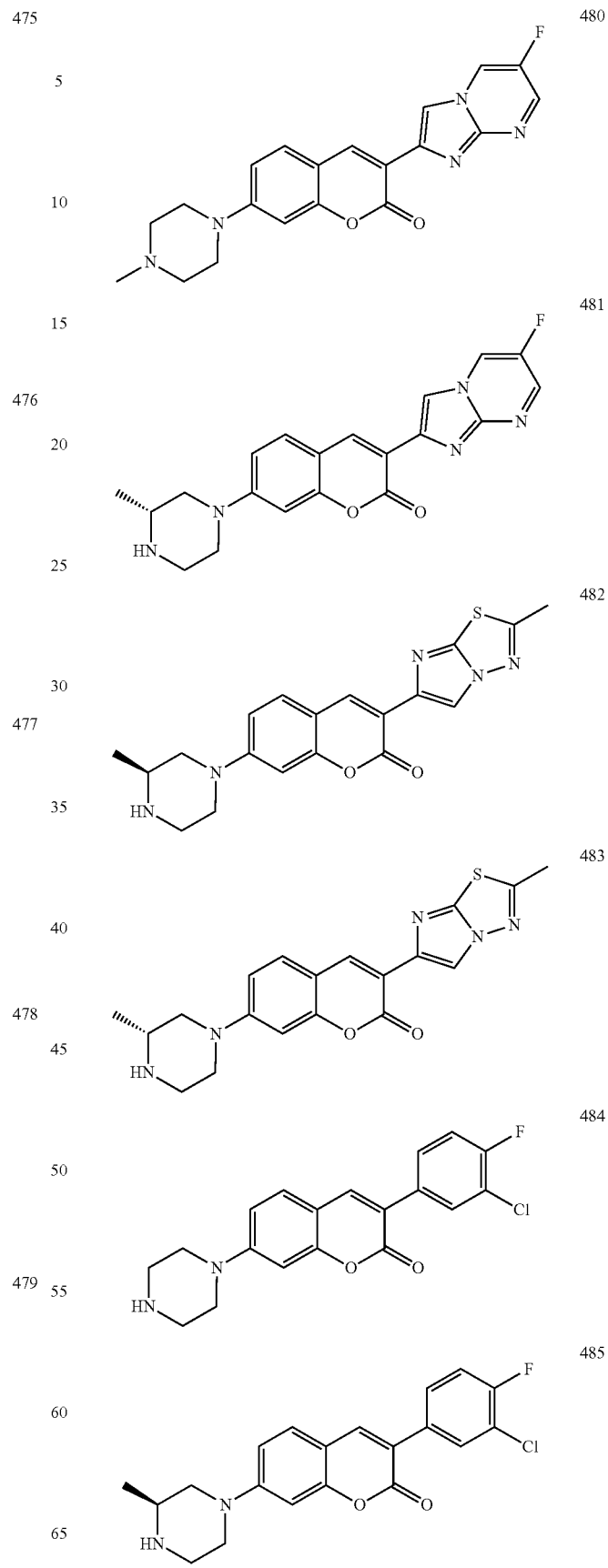

486 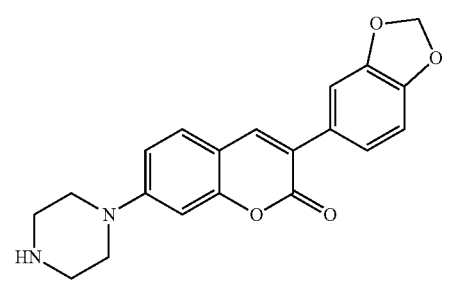
487 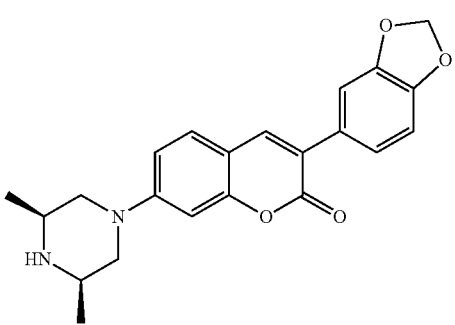
488 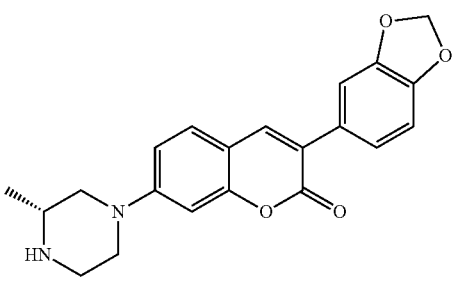
489 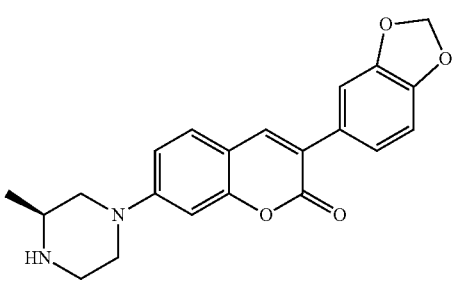
490 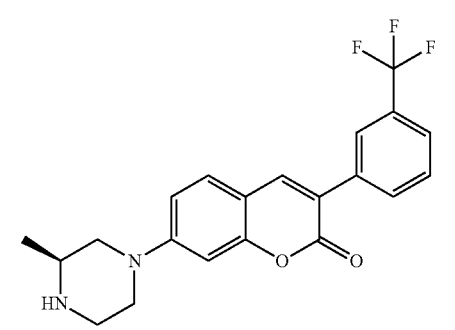
491 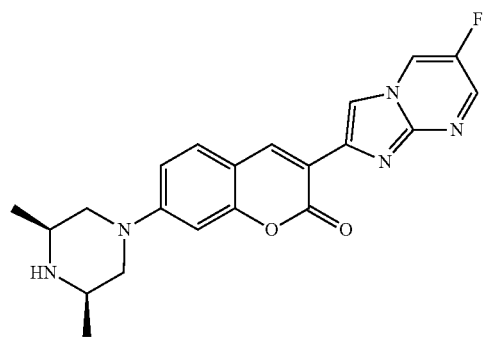
492 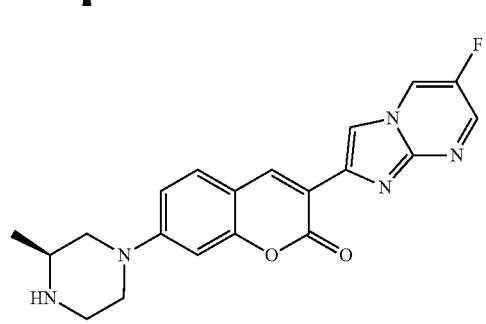
493 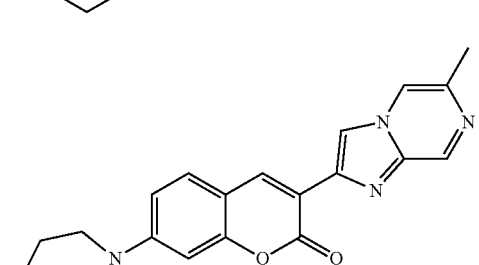
494 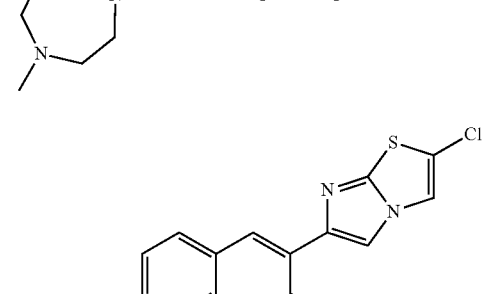
495 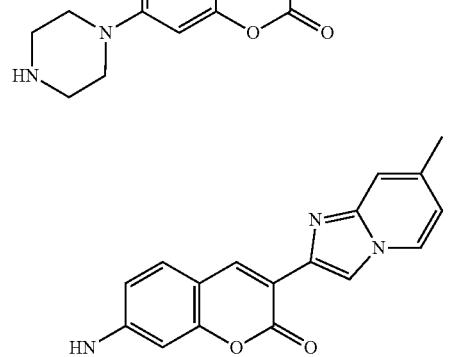

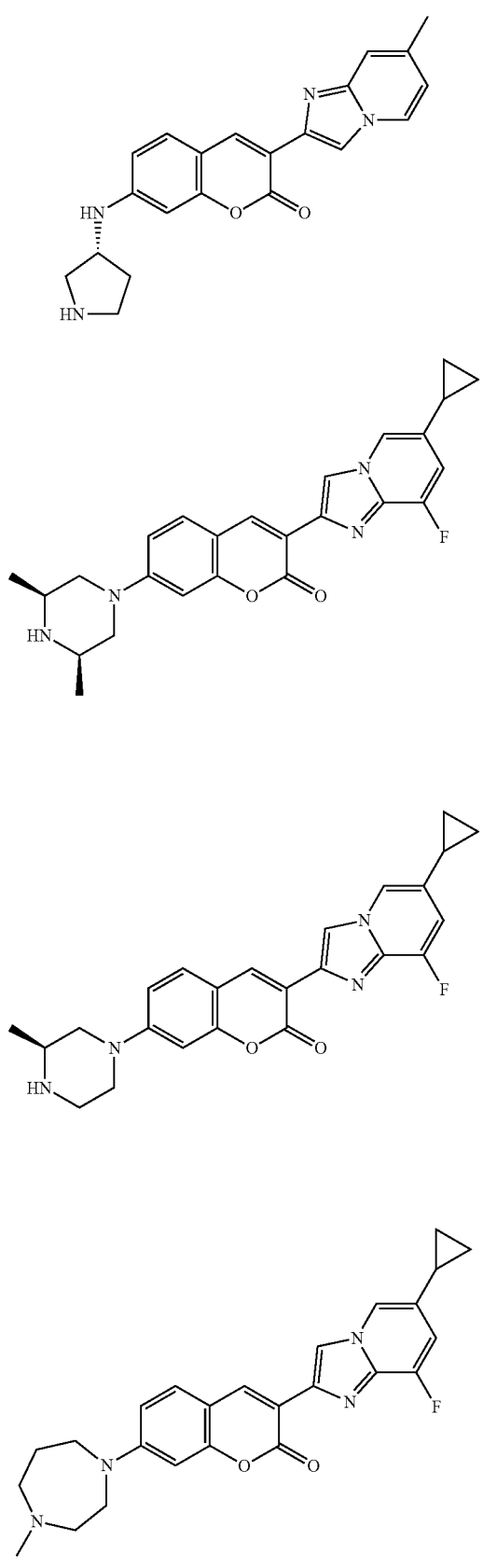
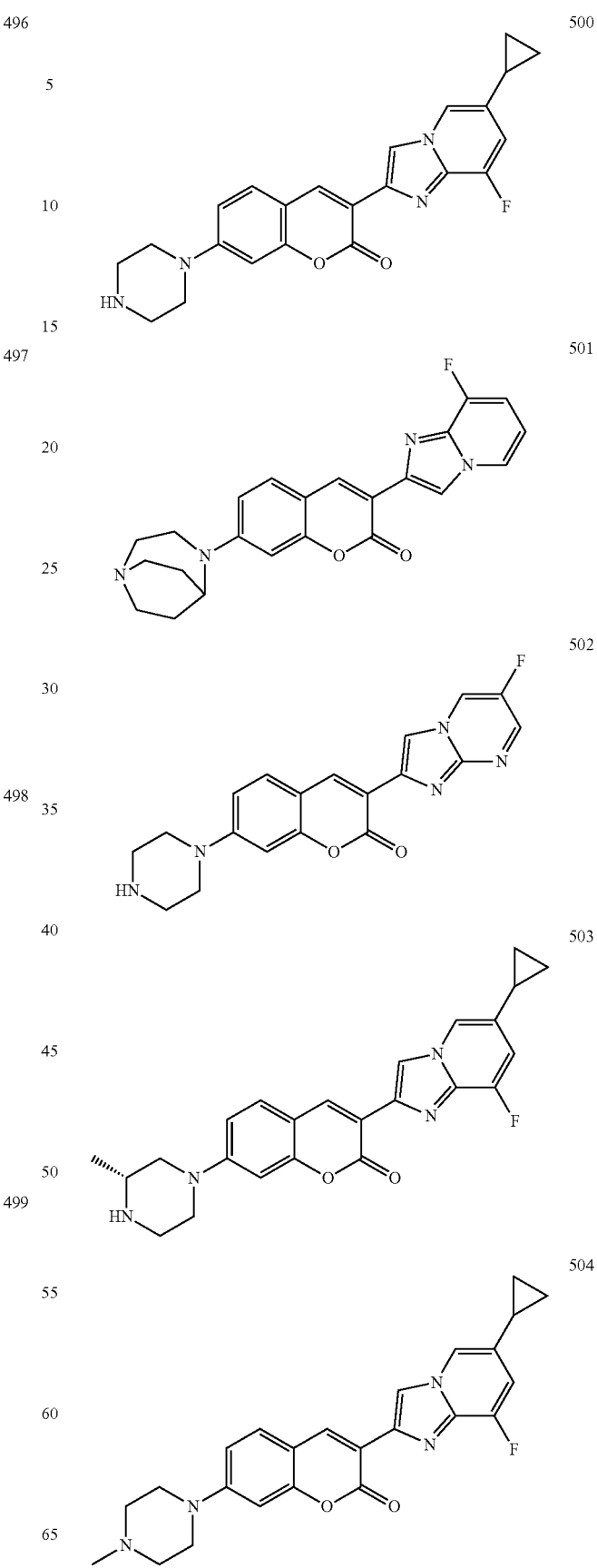

505 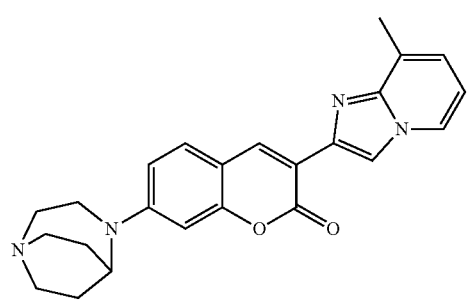
506 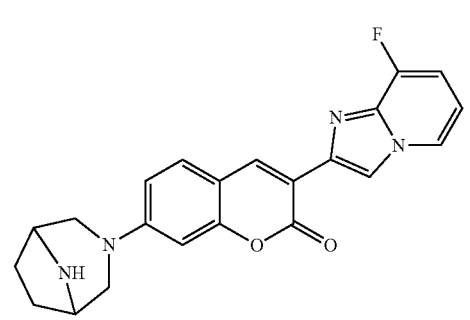
507 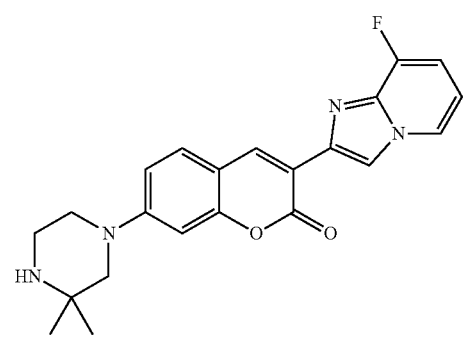
508 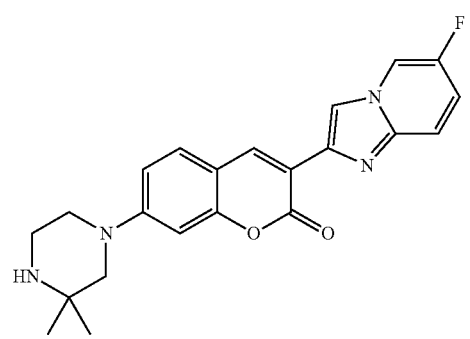
509 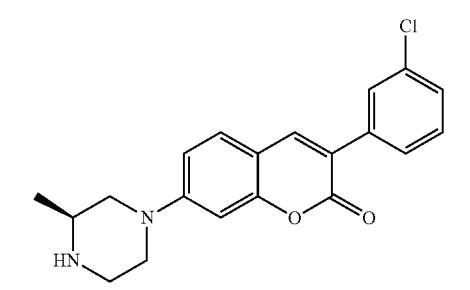
510 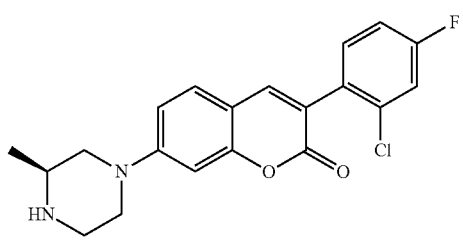
511 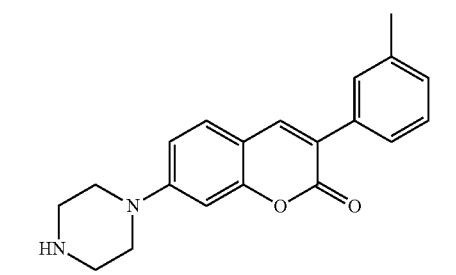
512 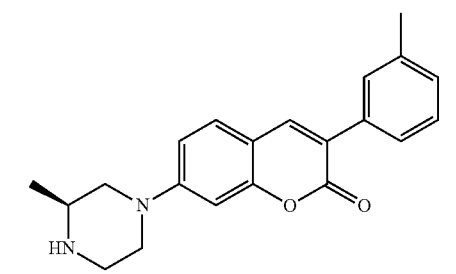
513 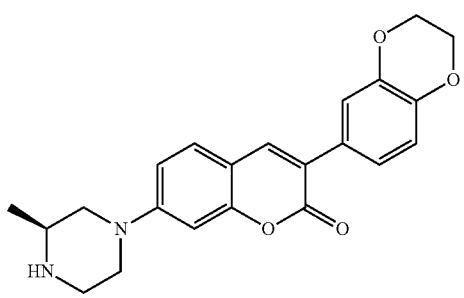
514 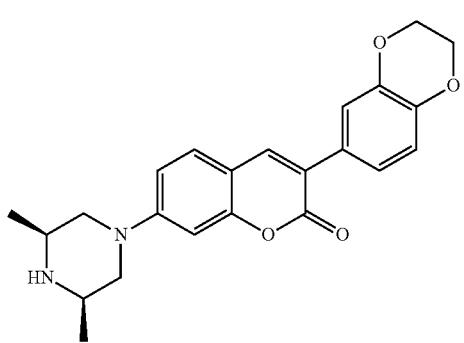

515 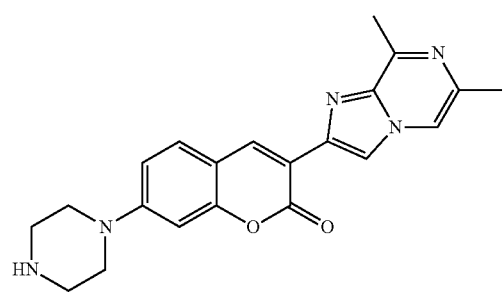
516 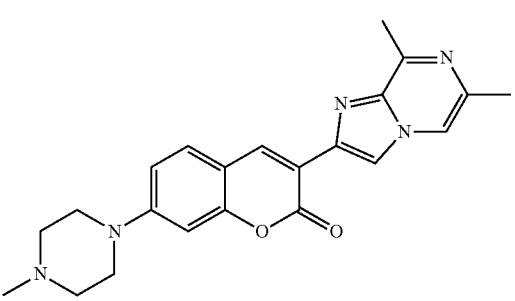
517 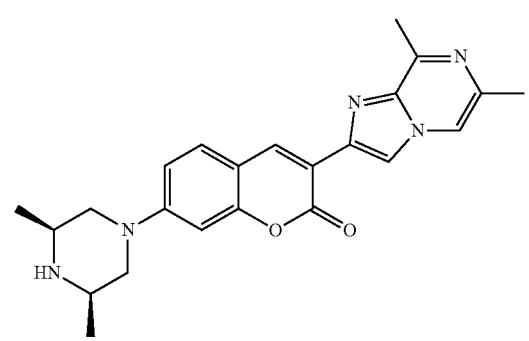
518 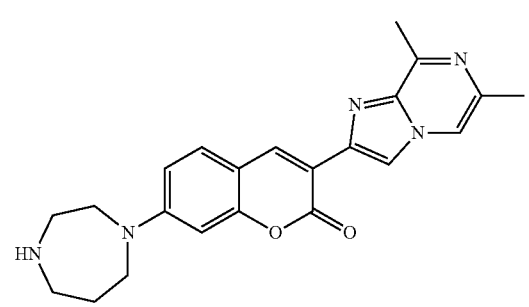
519 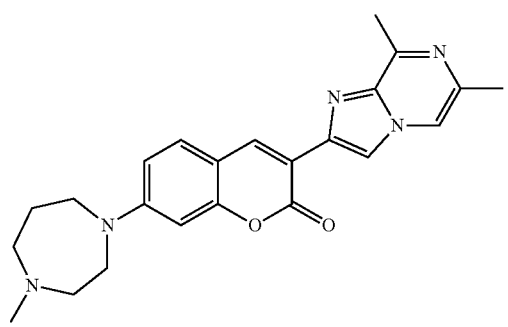
520 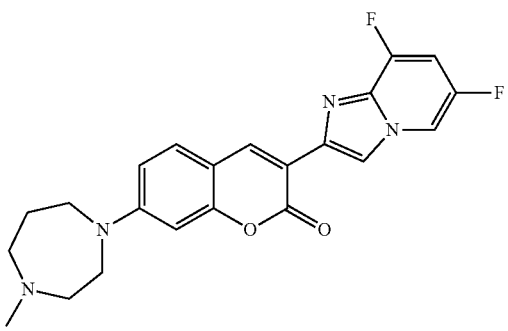
521 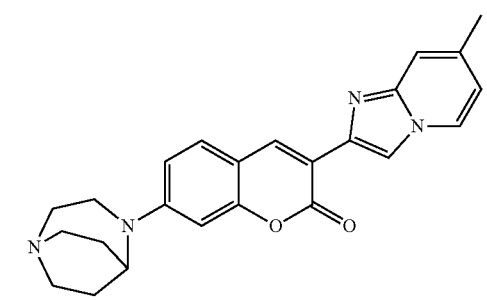
522 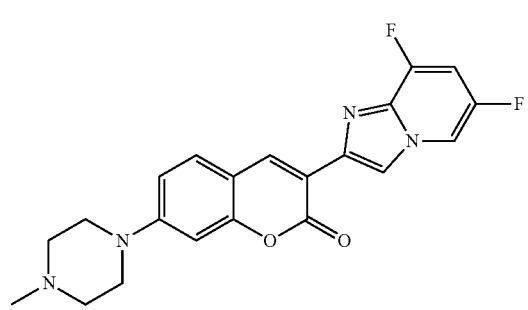
523 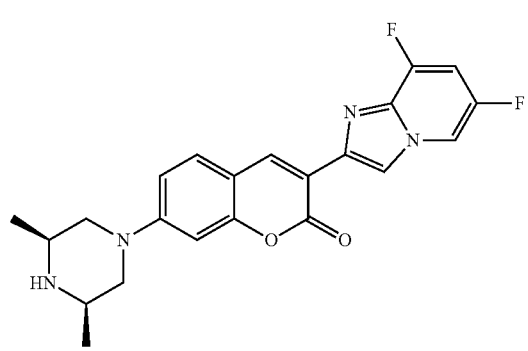
524 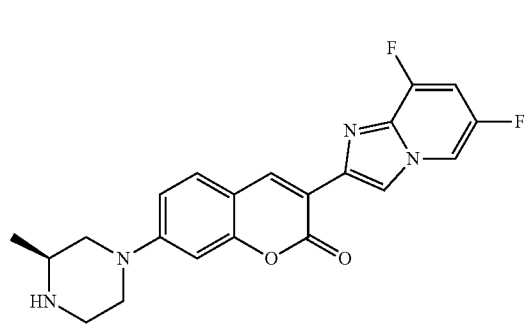

135
-continued
525
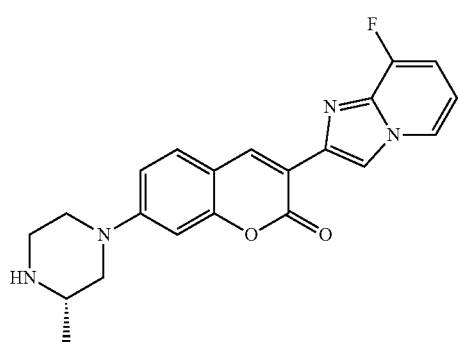
526
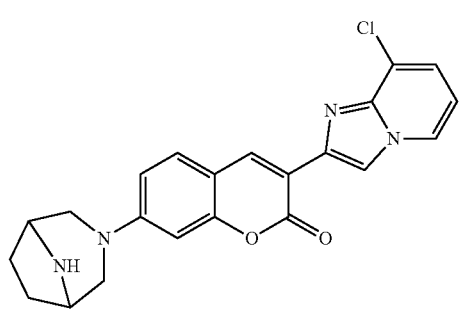
527
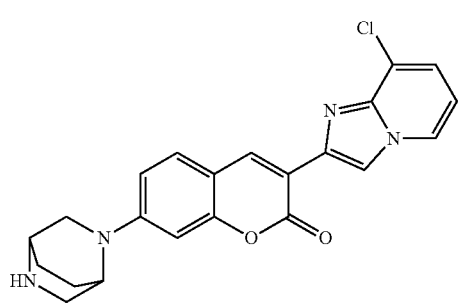
528
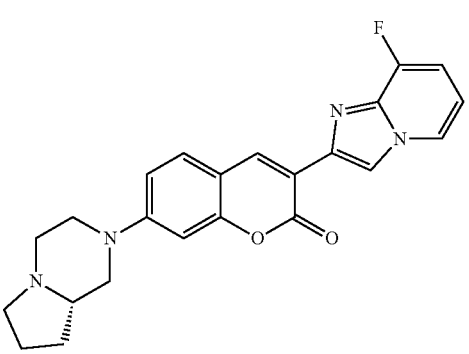
529
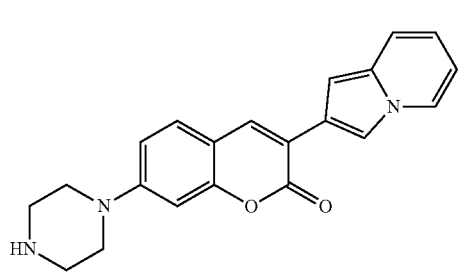
136
-continued
530
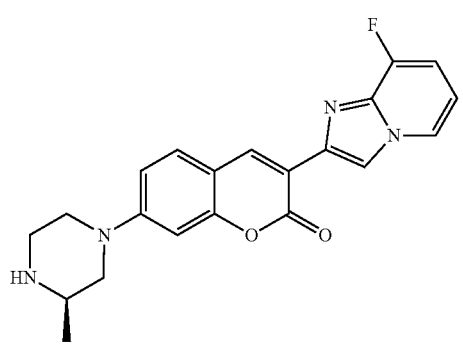
531
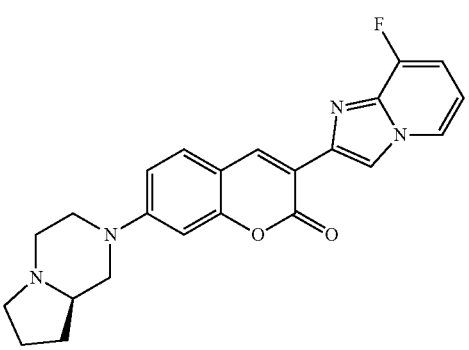
532
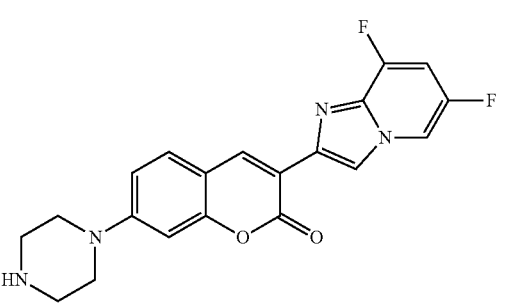
533
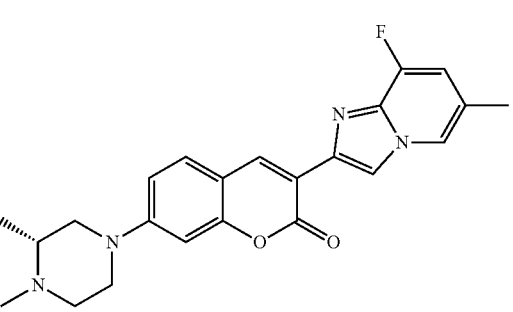

-continued
534 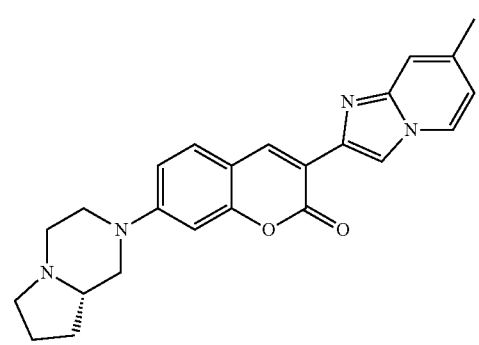
535 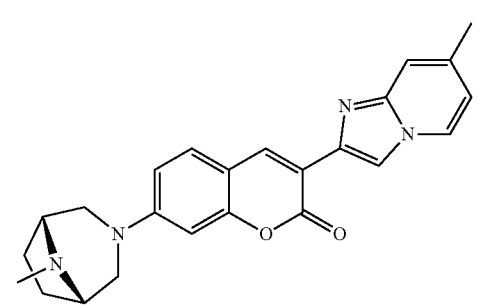
536 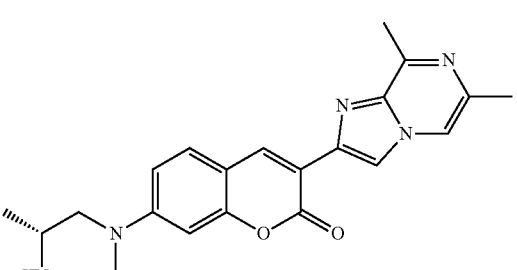
537 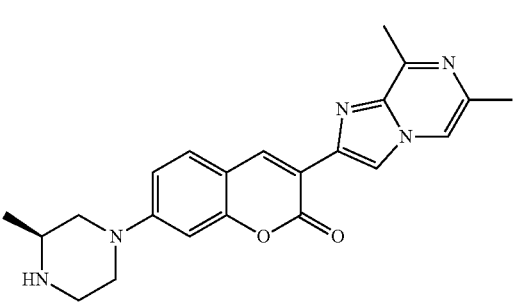
538 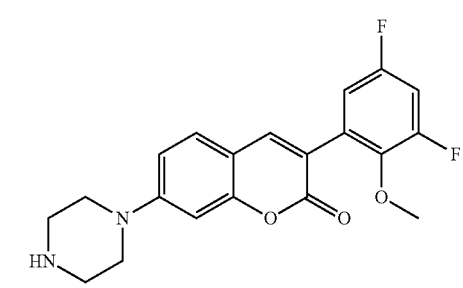
-continued
539 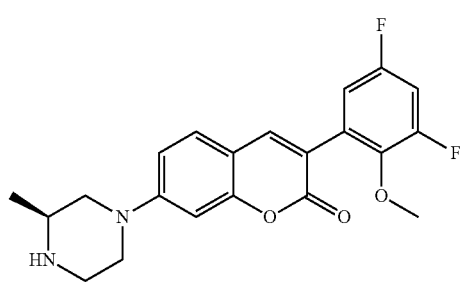
540 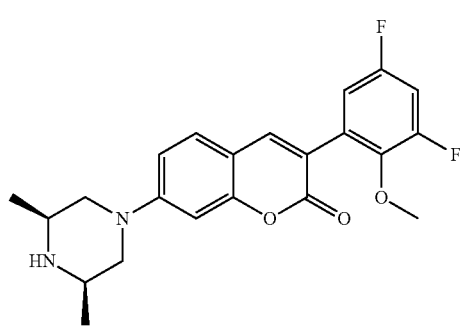
541 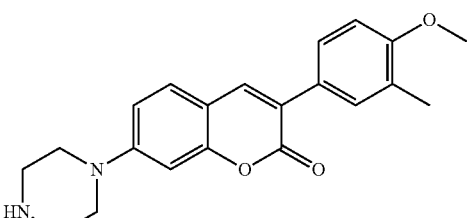
542 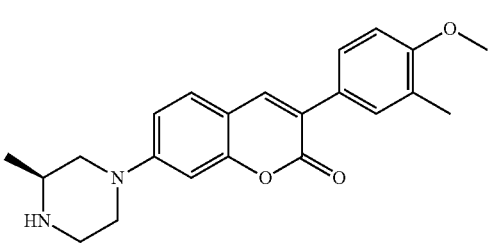
543 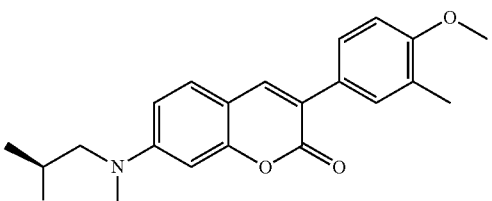
544 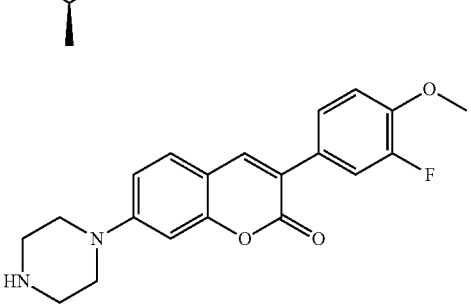

545 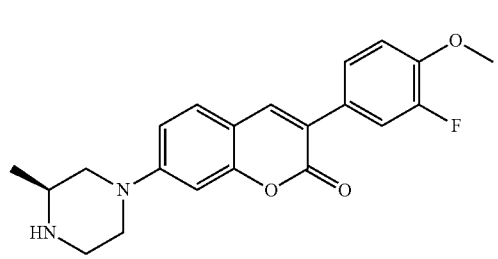
546 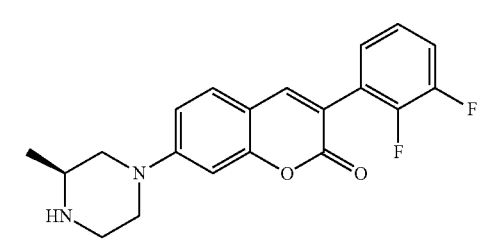
547 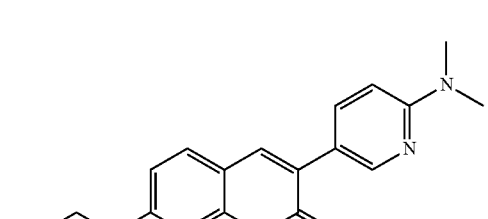
548 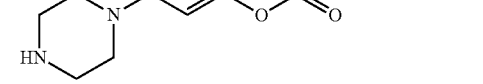
549 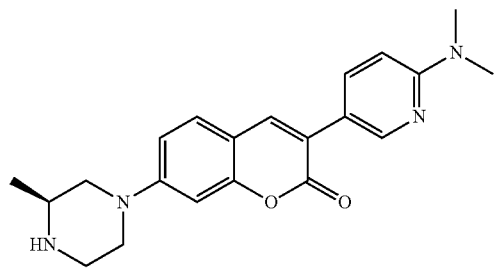
550 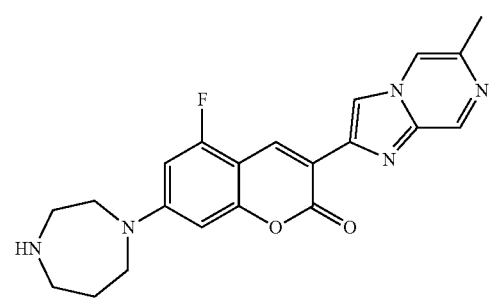
551 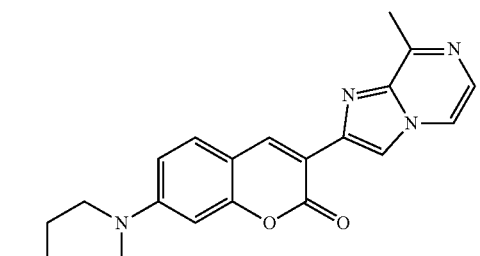
552 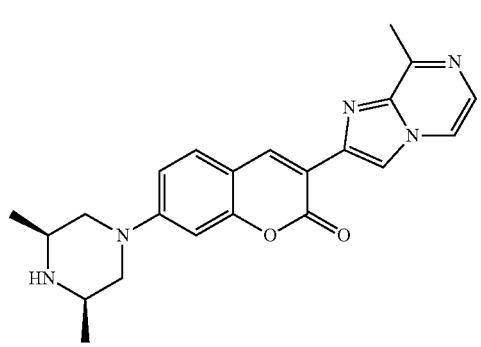
553 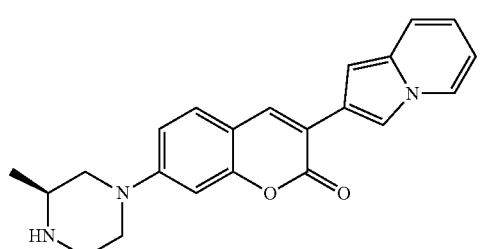
554 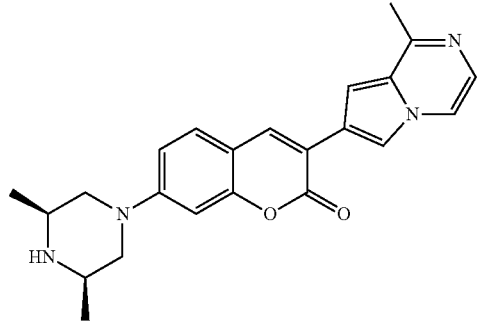
555 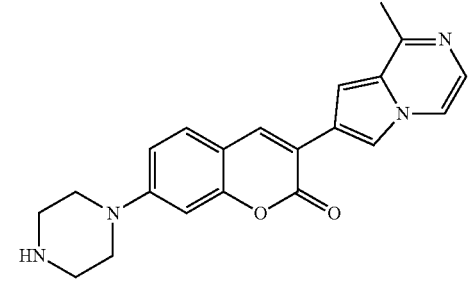

556
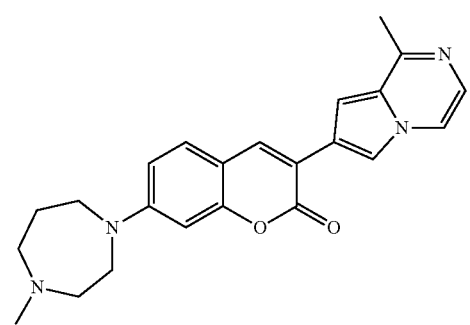
557
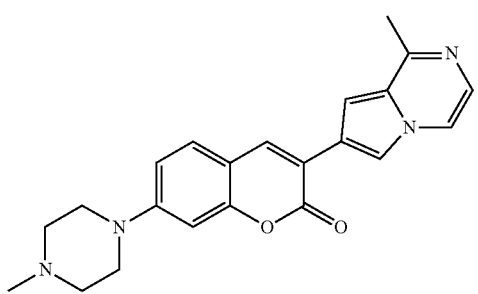
558
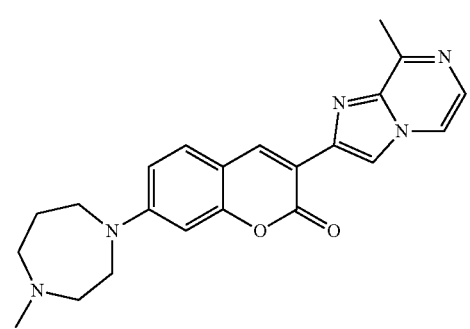
559
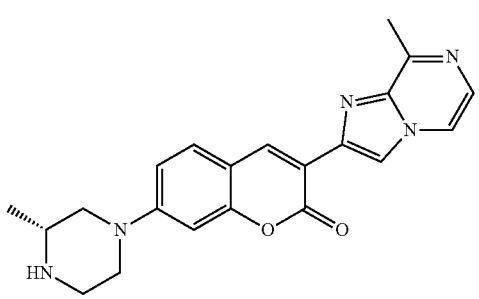
560
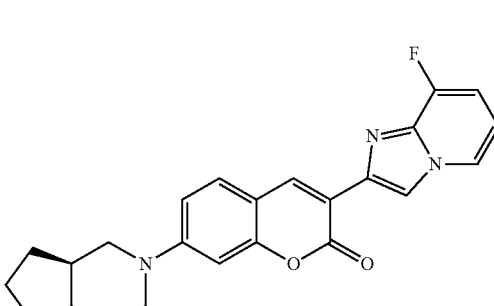
561
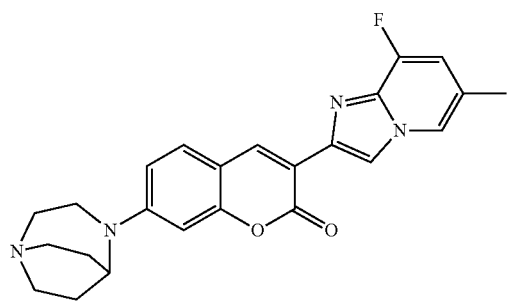
562
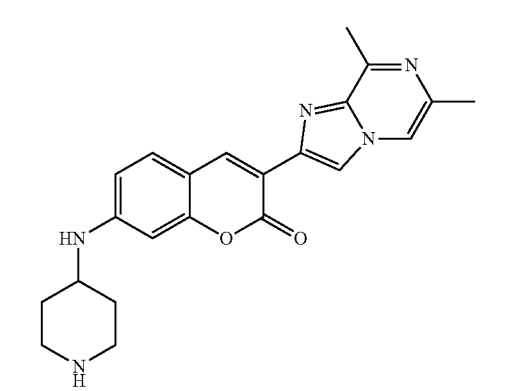
563
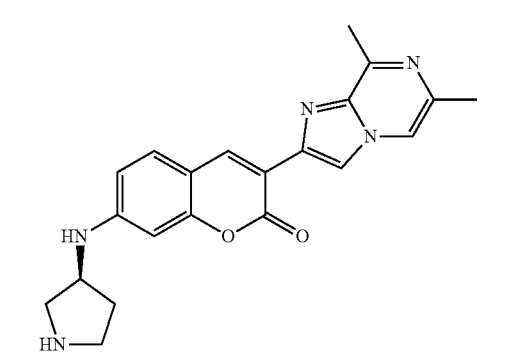
564
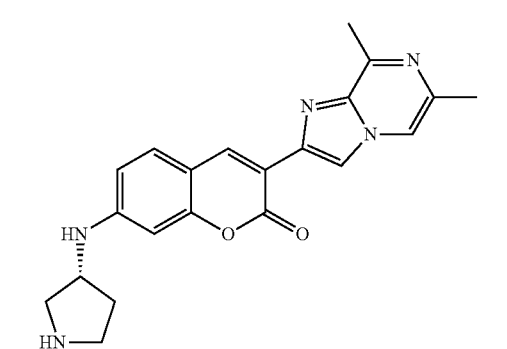

565 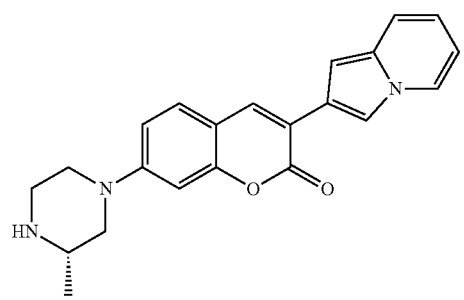
566 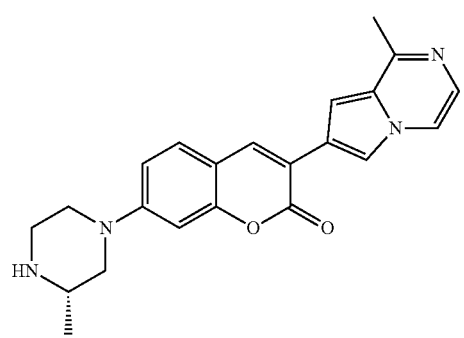
567 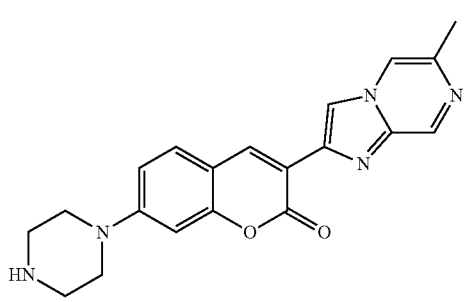
568 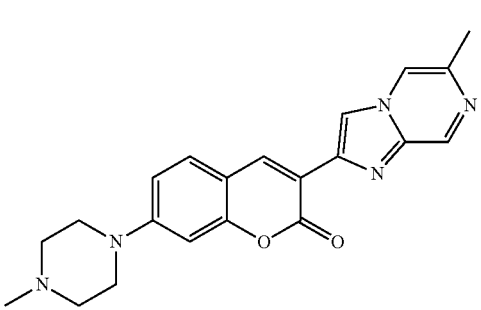
569 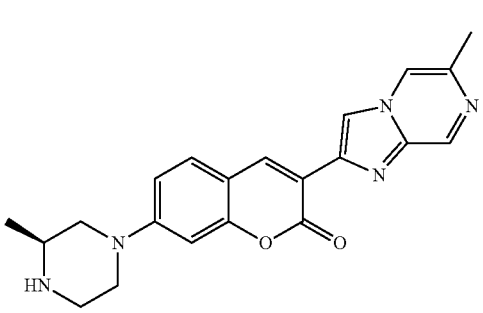
570 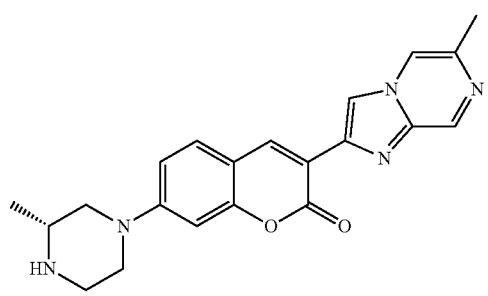
571 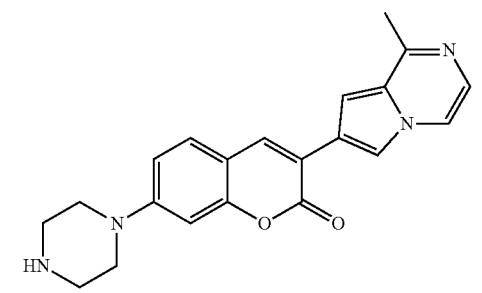
572 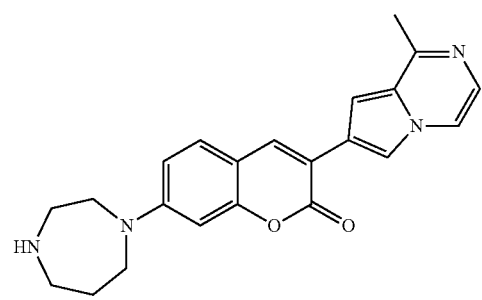
573 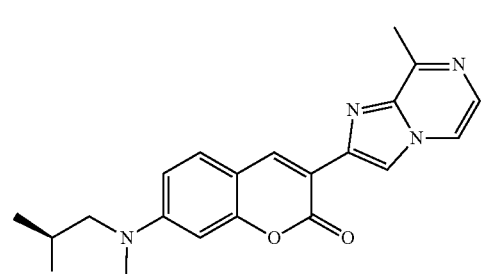
574 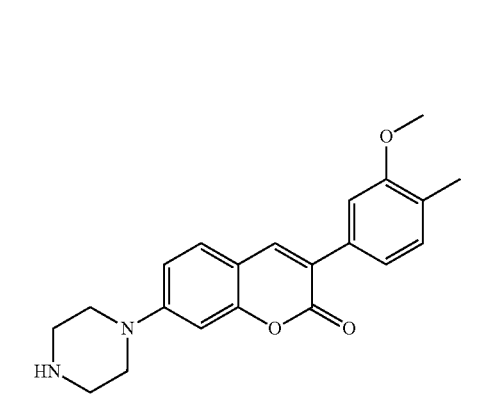

575 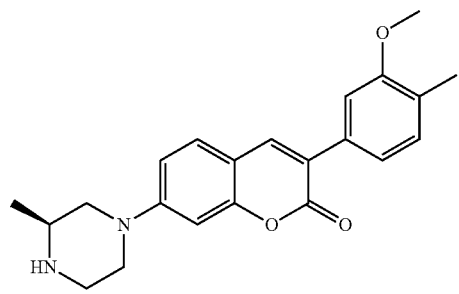
576 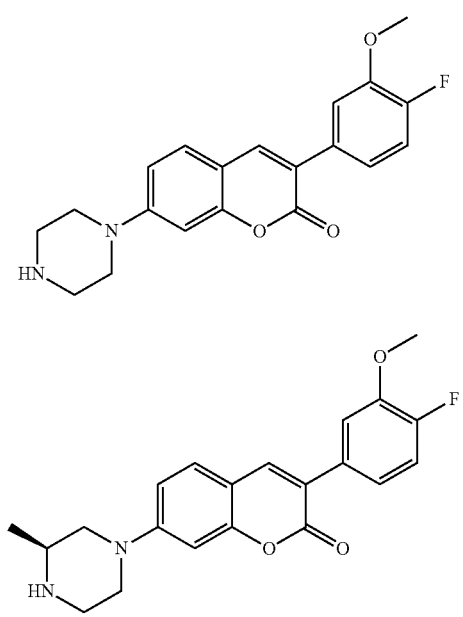
577
578 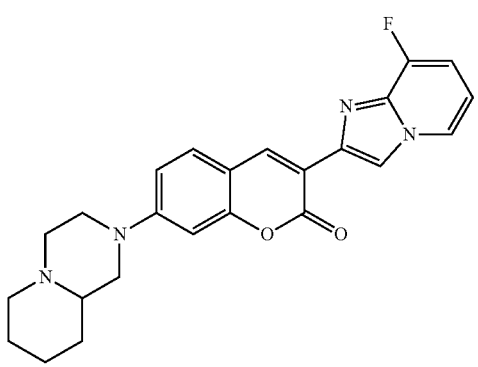
579 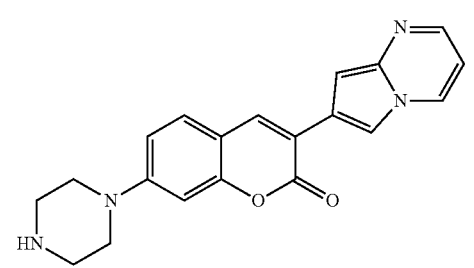
580 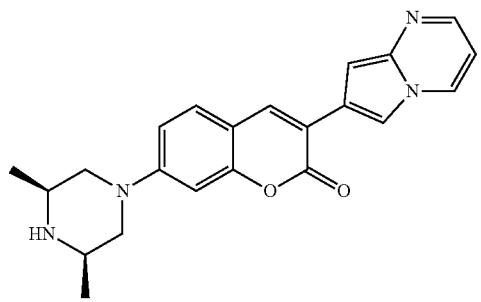
581 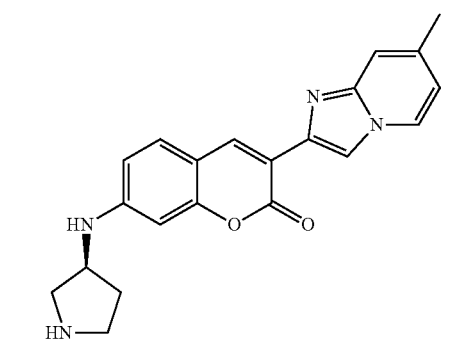
582 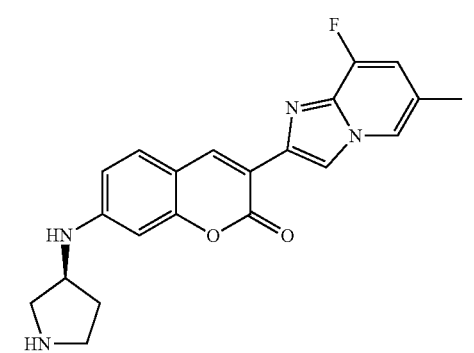
583 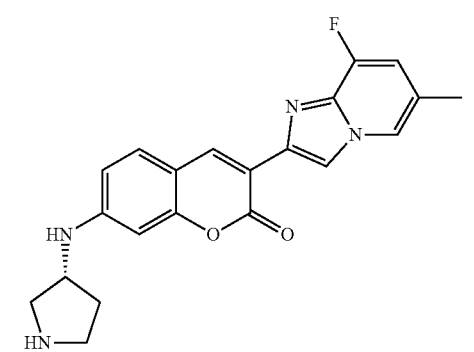

584
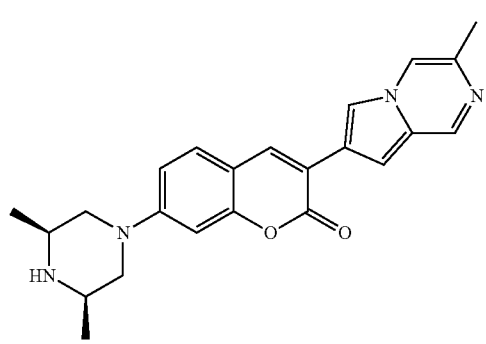
585
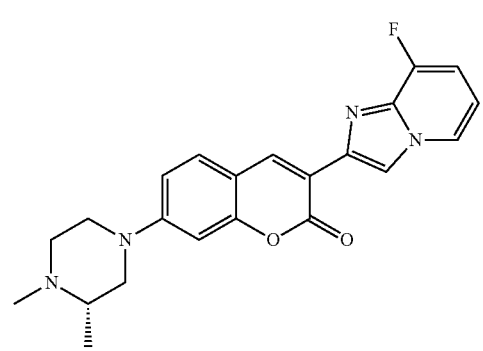
586
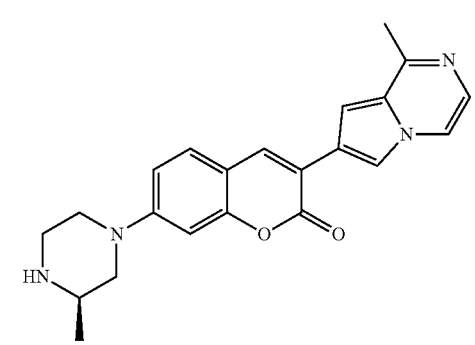
587
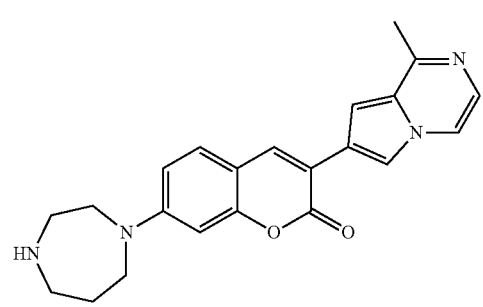
588
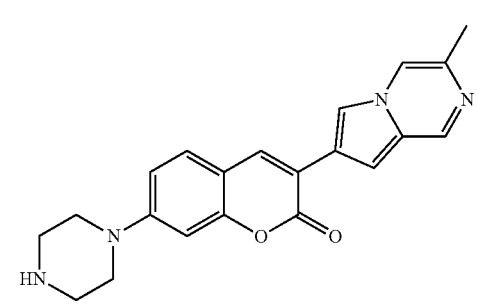
589
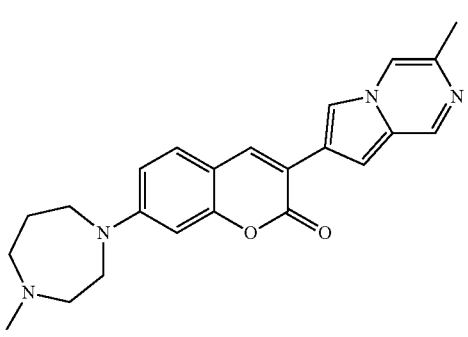
590
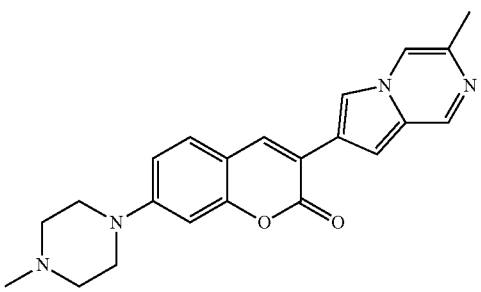
591
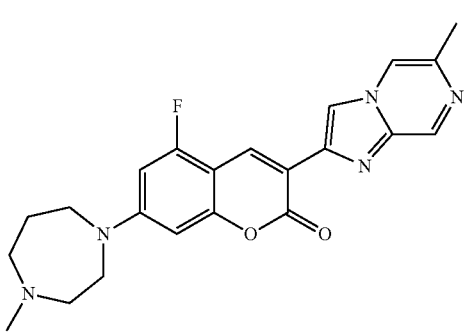
592
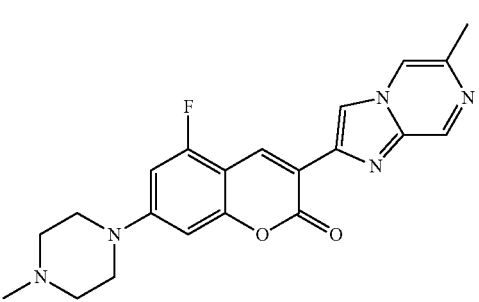
593
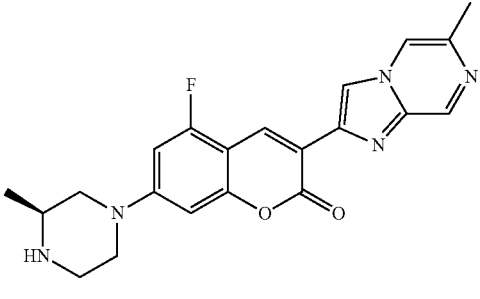

594
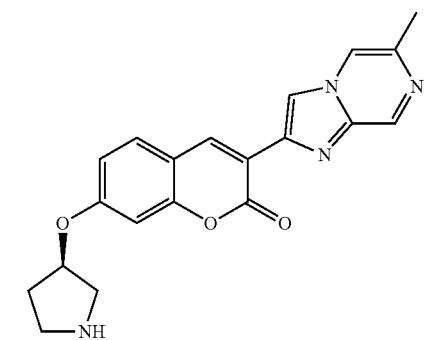
595
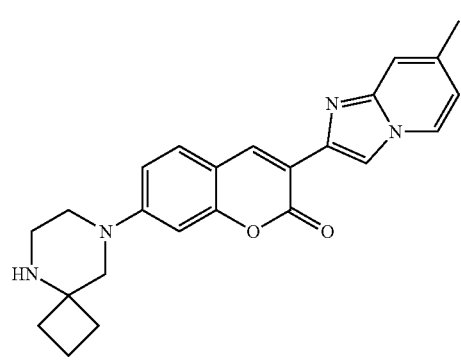
596

597
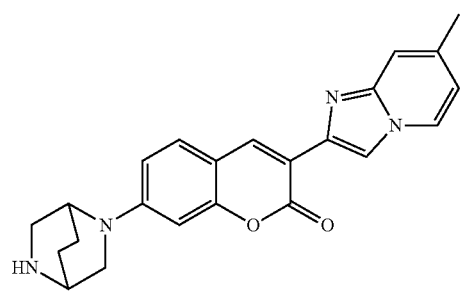
598
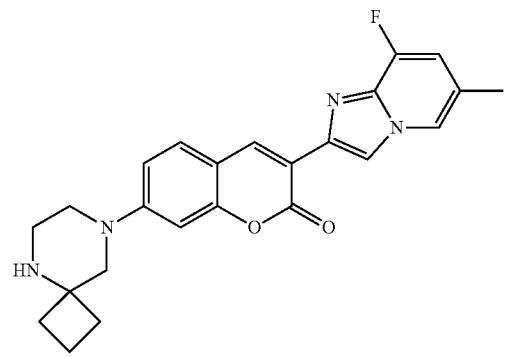
599
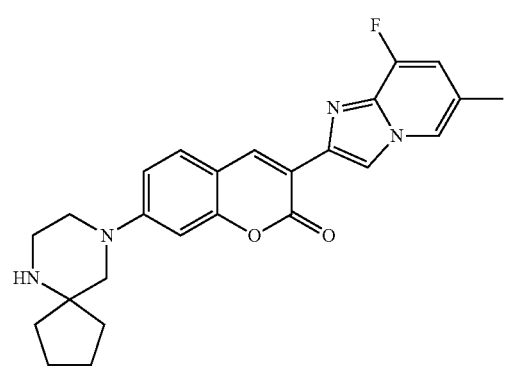
600
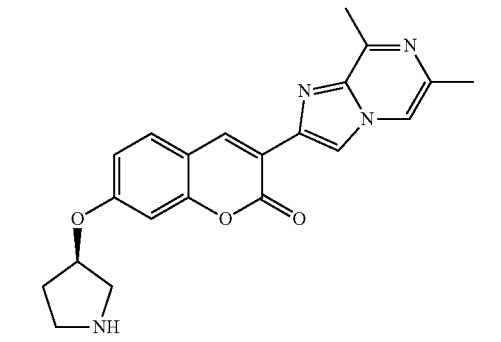
601
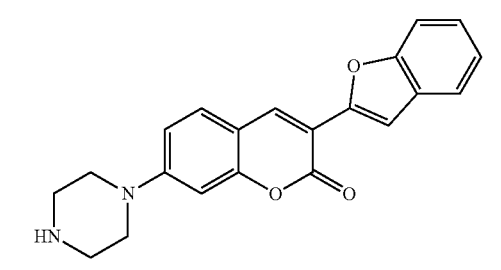
602
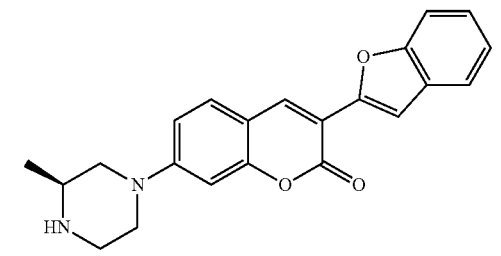

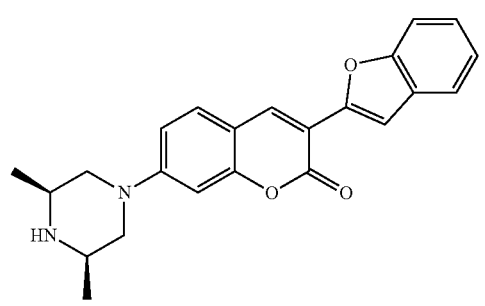
603
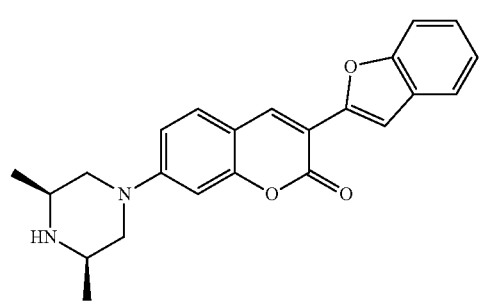
604
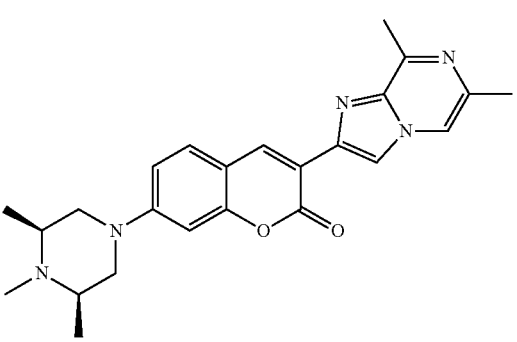
605
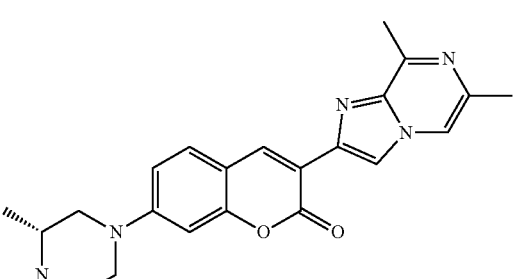
606
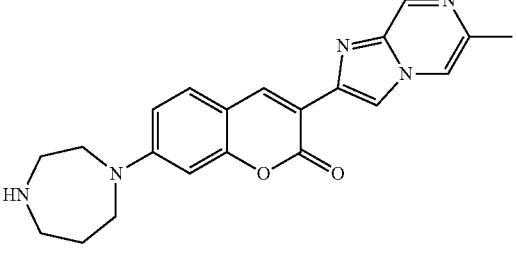
607
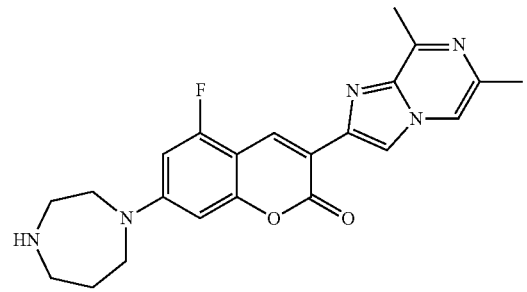
608
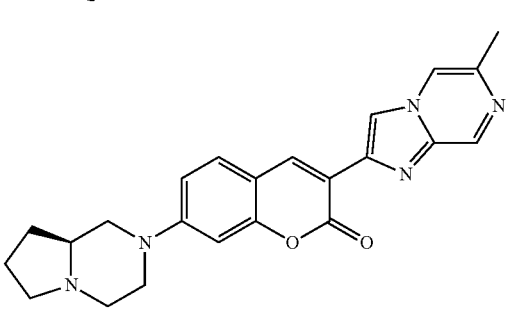
609
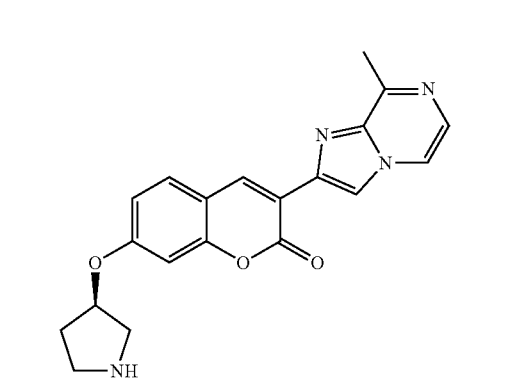
610
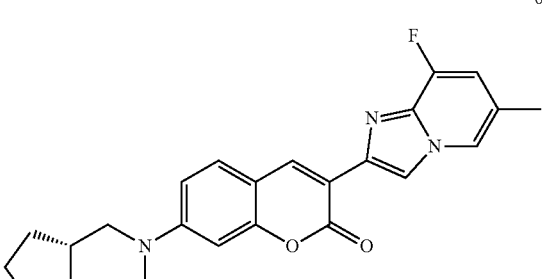
611
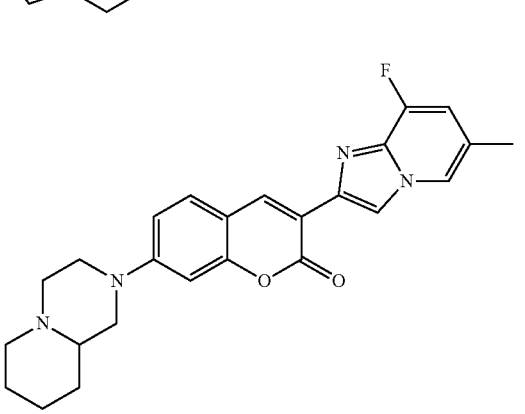
612

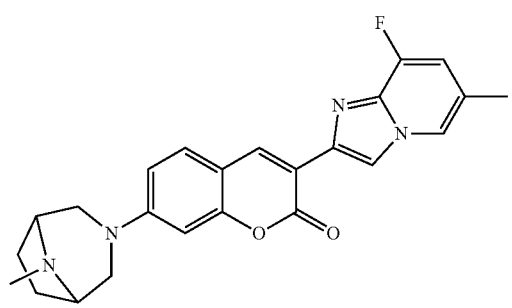
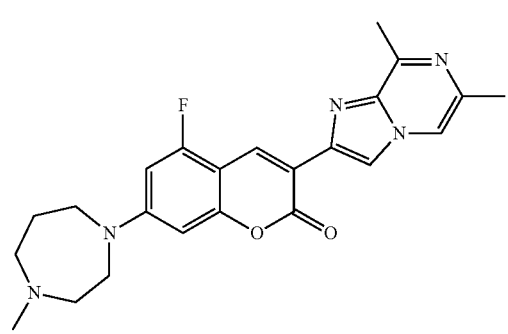
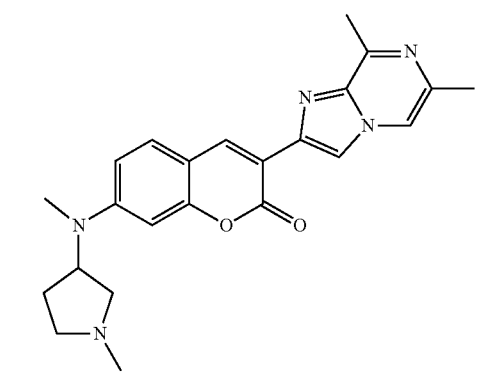
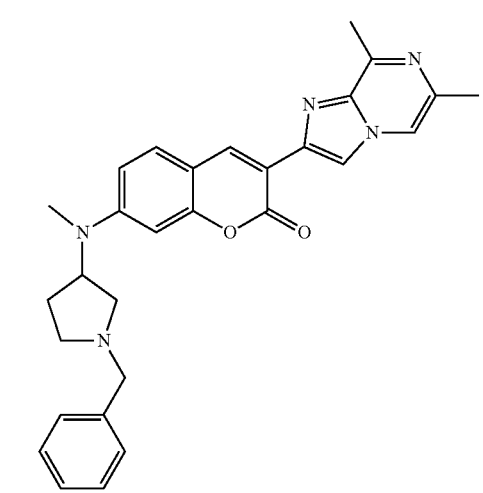
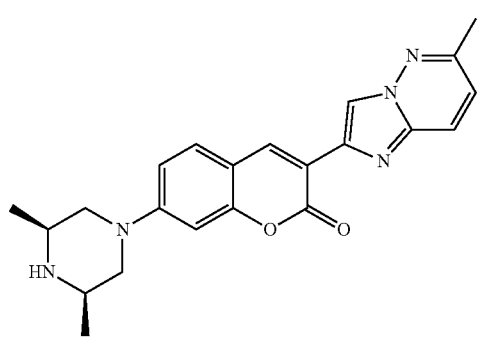
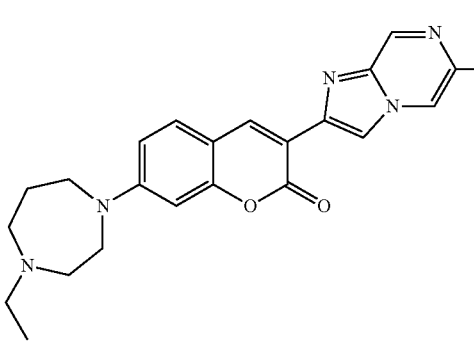
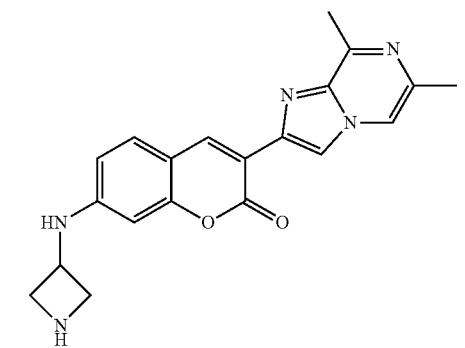
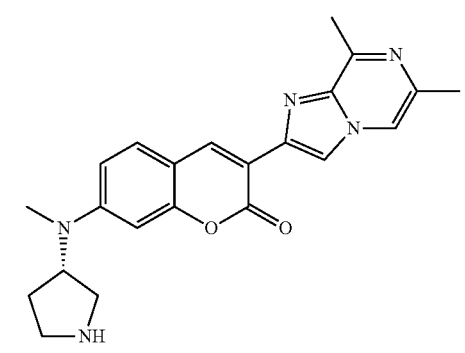

US 9,617,268 B2
-continued
621 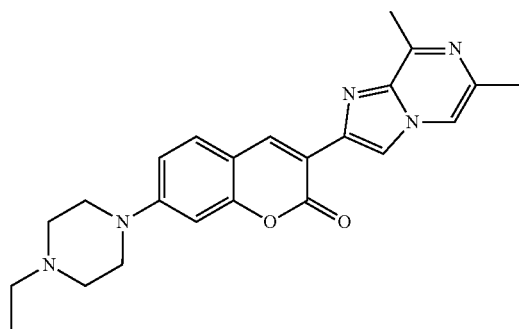
622 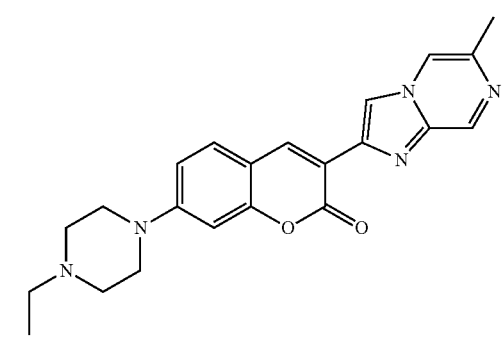
623 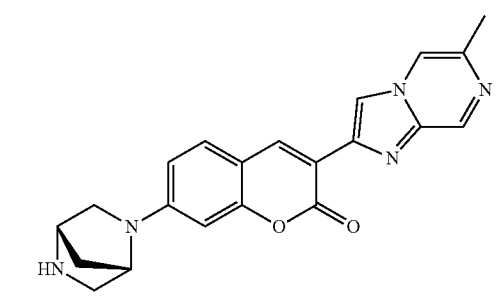
624 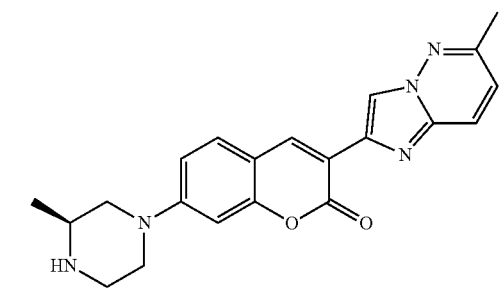
625 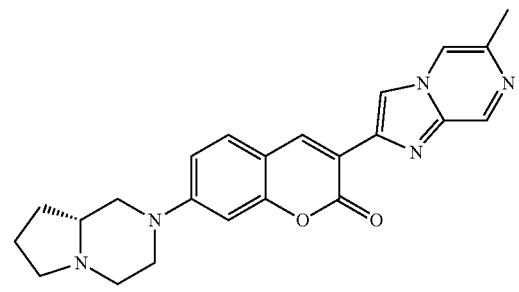
-continued
626 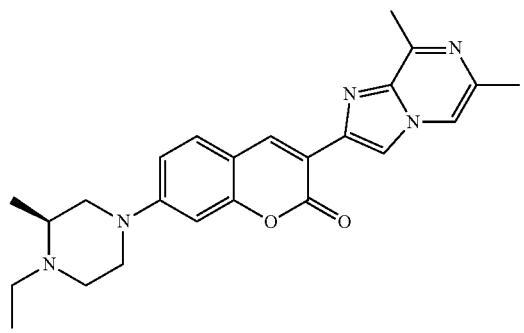
627 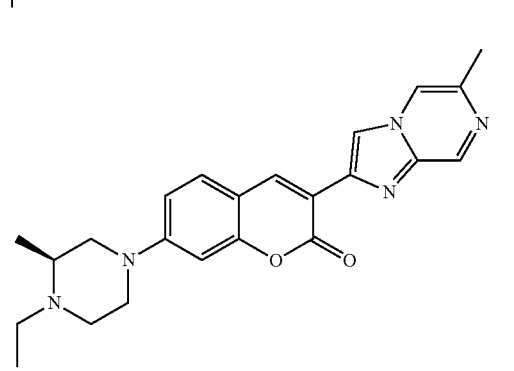
628 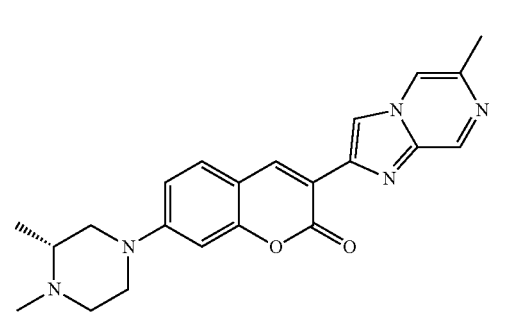
629 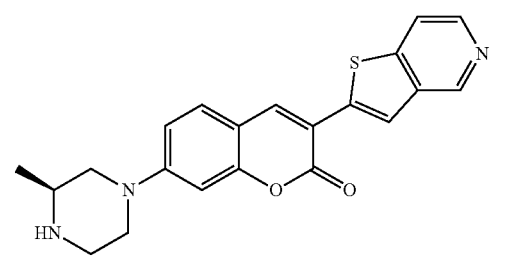
630 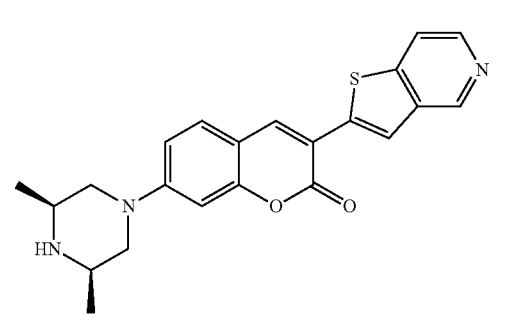

-continued
631
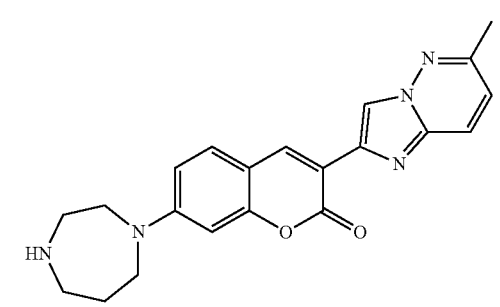
632
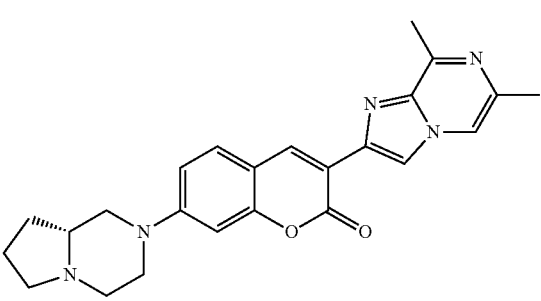
633
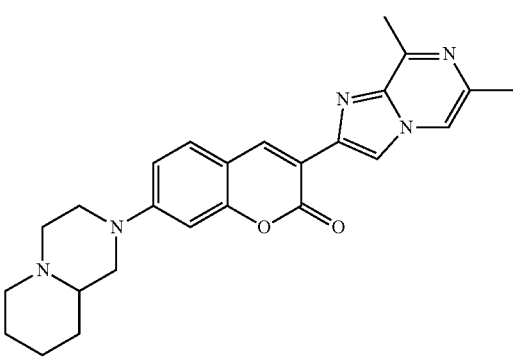
634
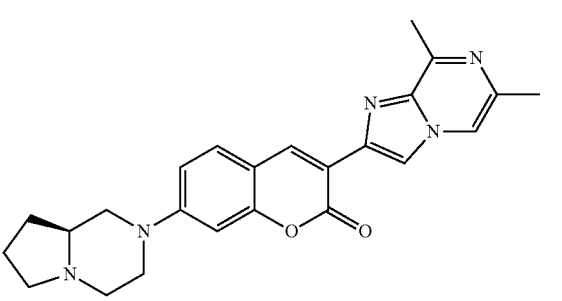
635
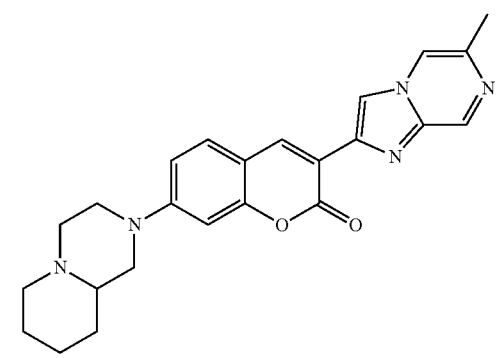
-continued
636
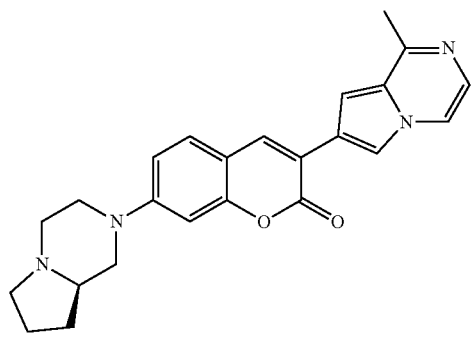
637
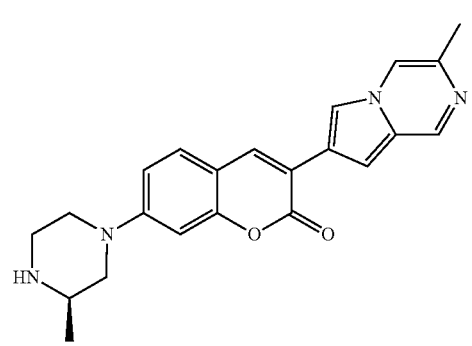
638
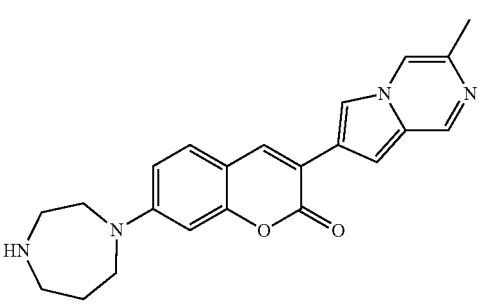
639
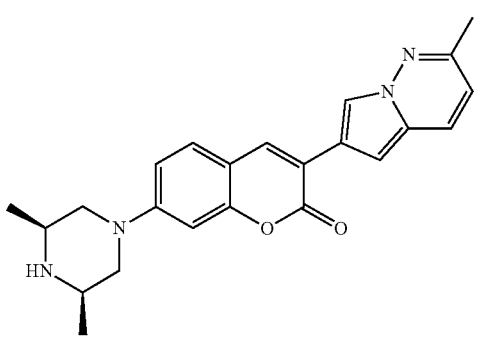
640
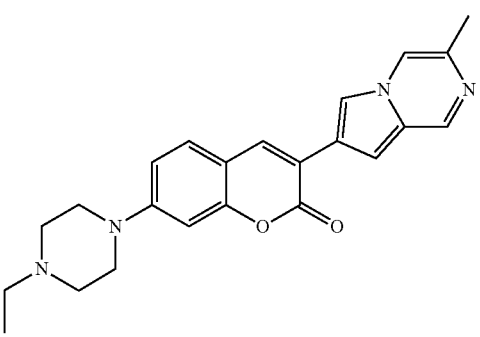

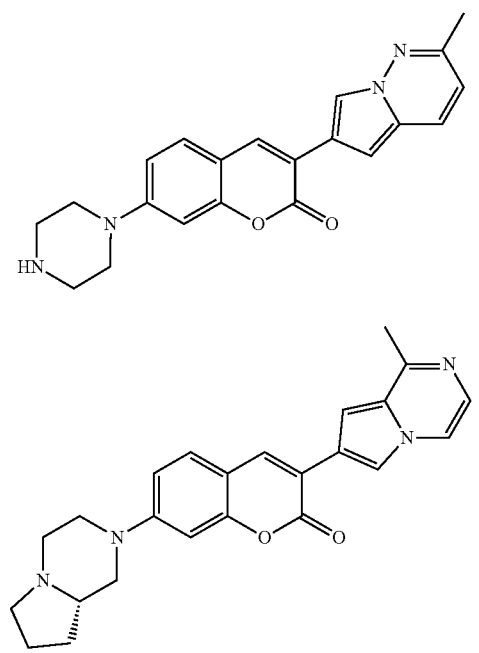
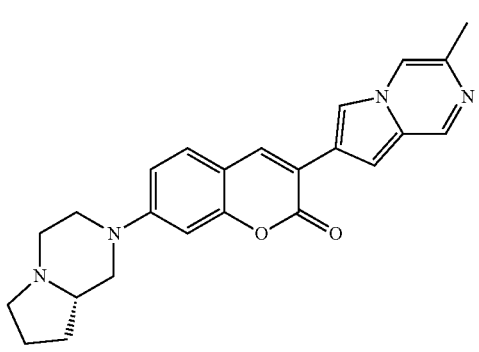
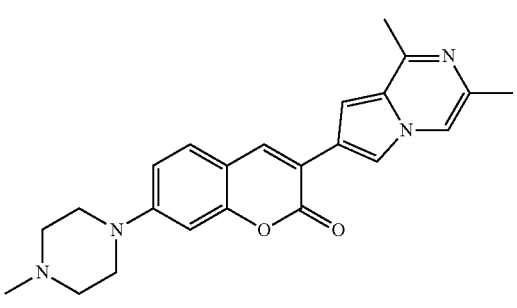
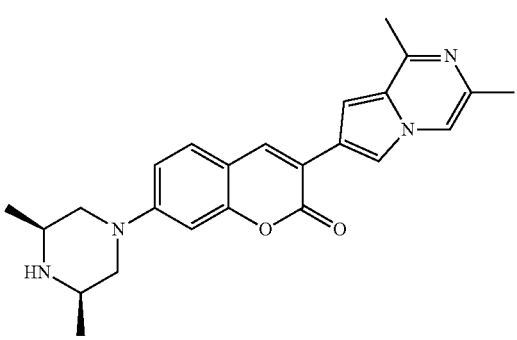
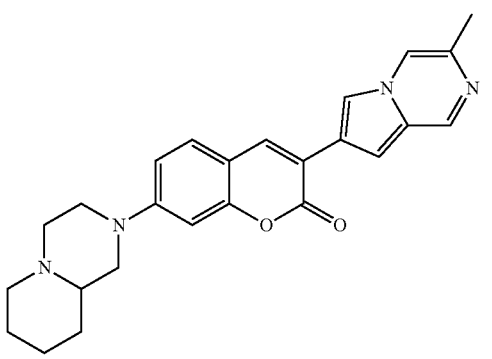
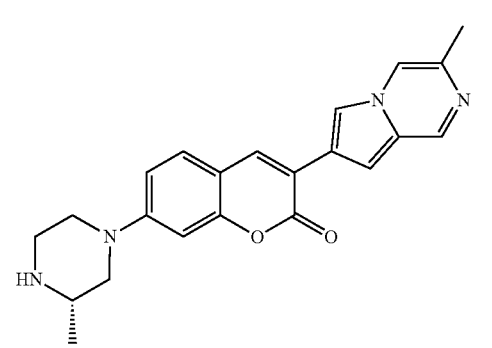
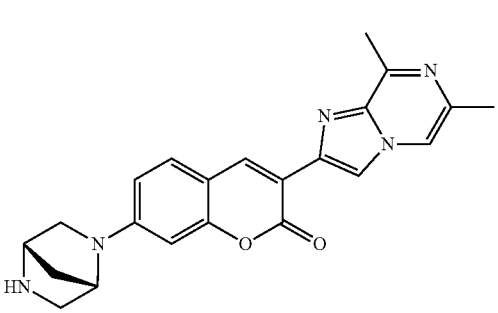
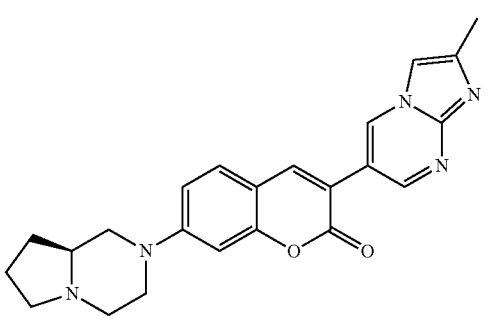
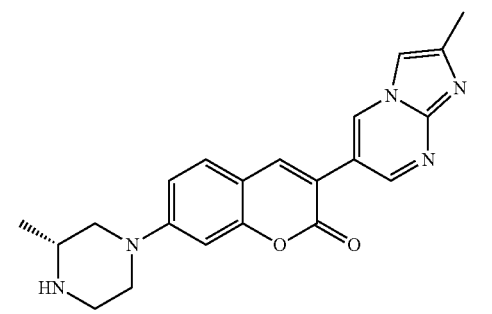

651
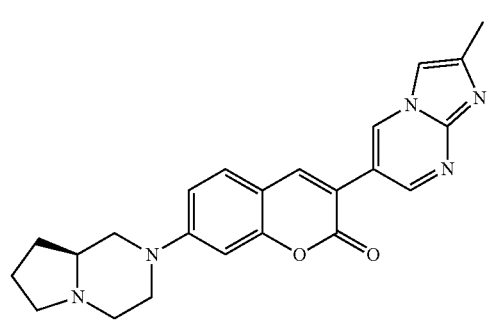
652
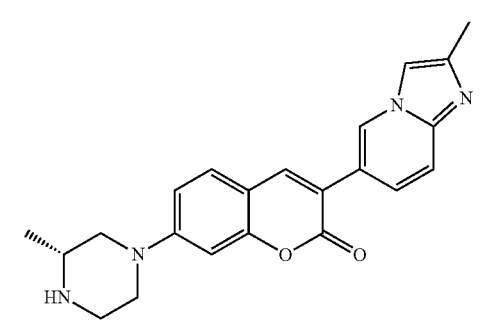
653
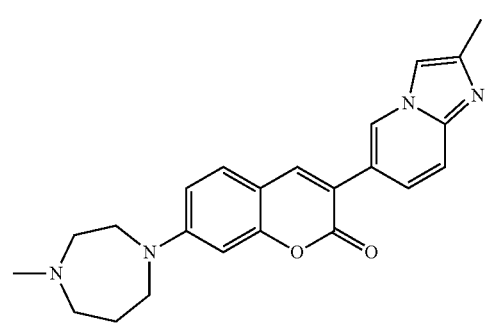
654
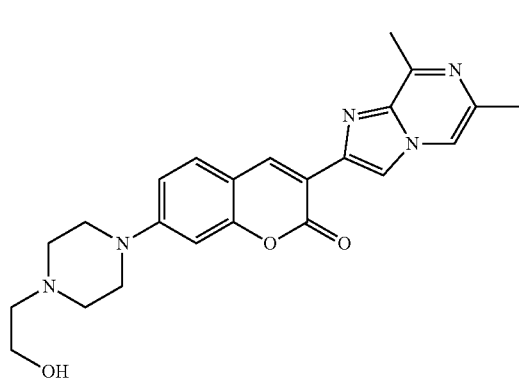
655
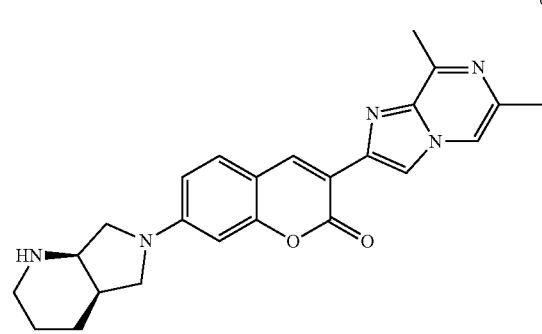
656
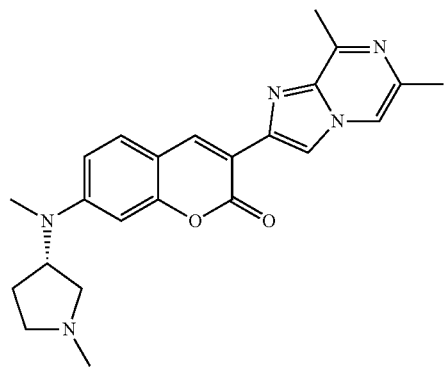
657
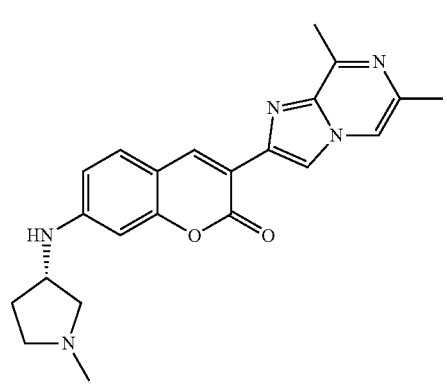
658
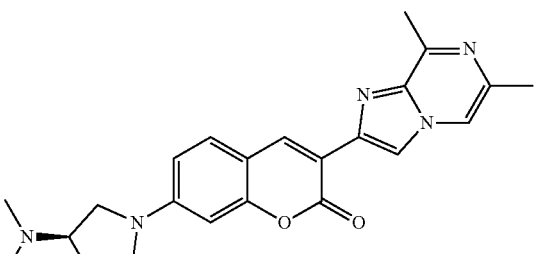
659
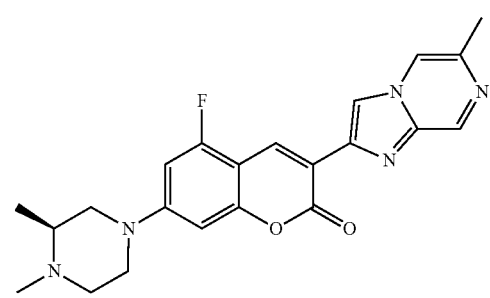

163
-continued
660
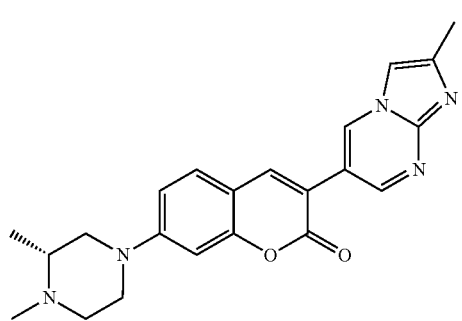
661
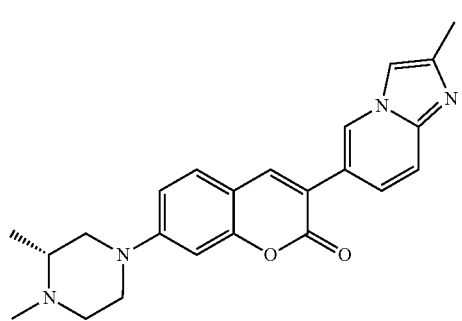
662
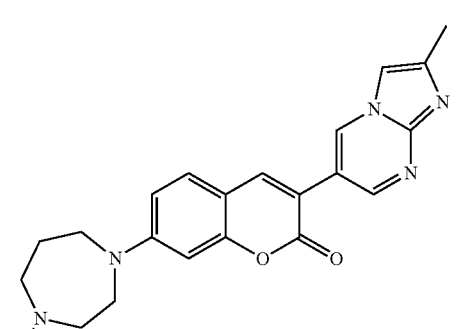
663
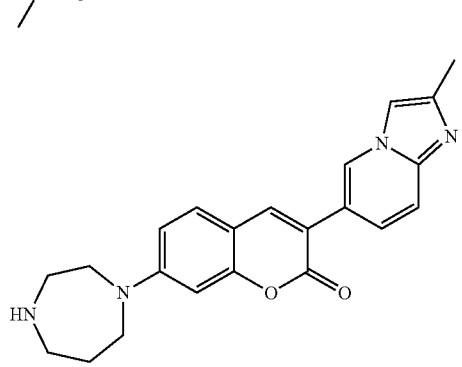
664
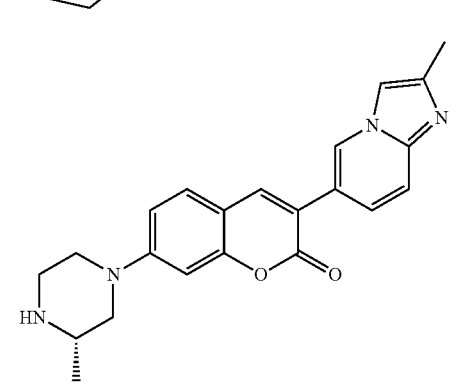
164
-continued
665
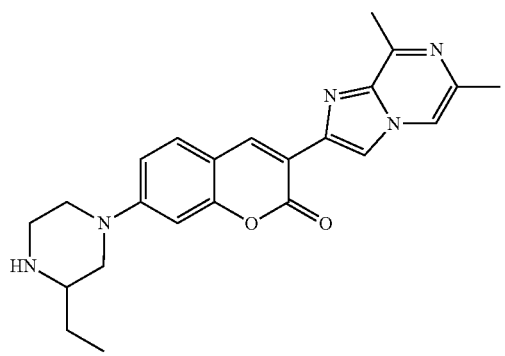
666
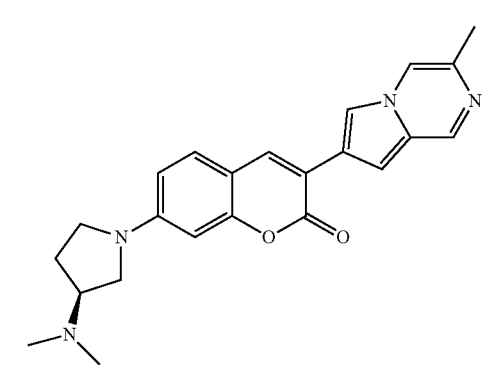
667
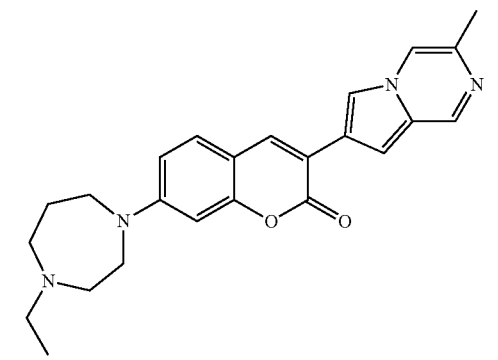
668
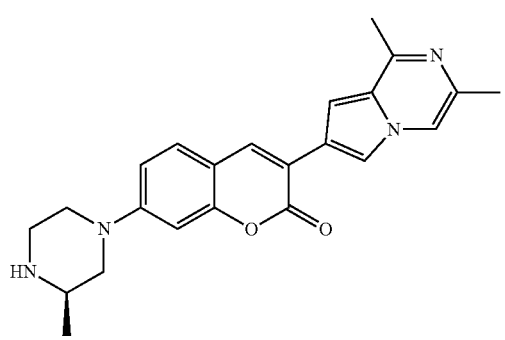

669
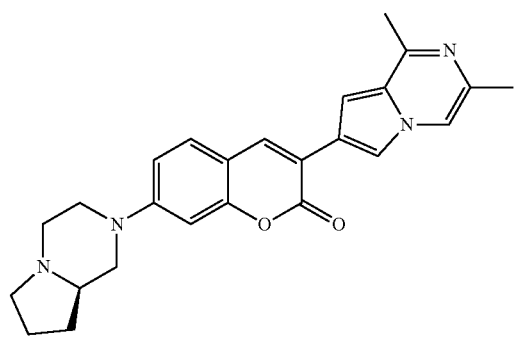
670
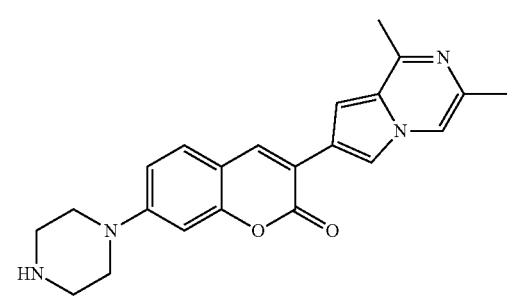
671
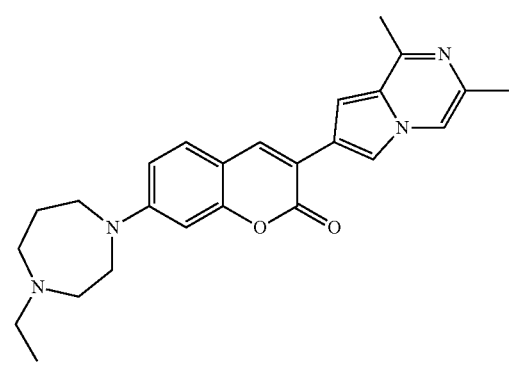
672
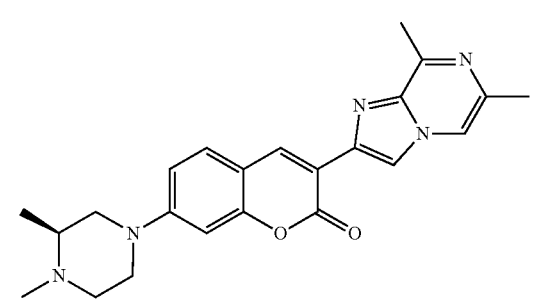
673
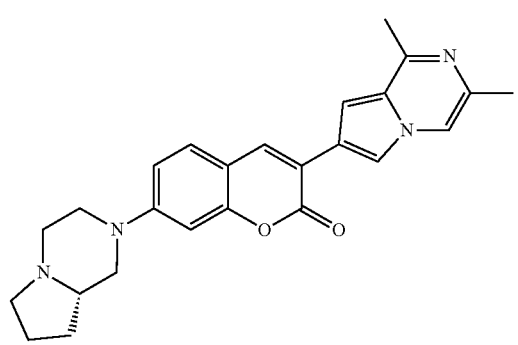
674
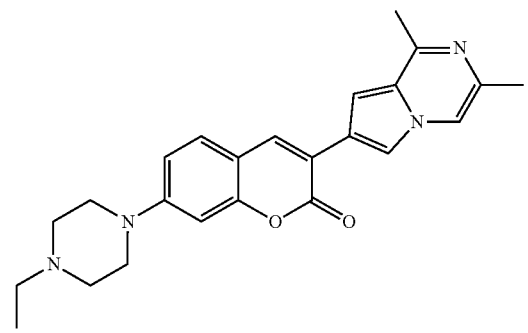
675
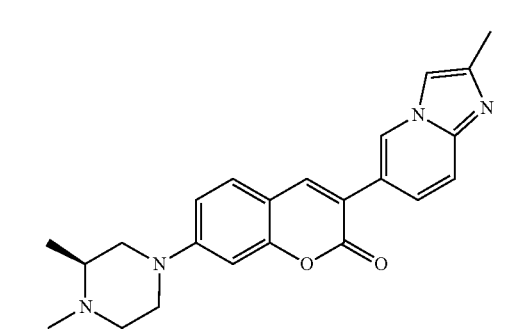
676
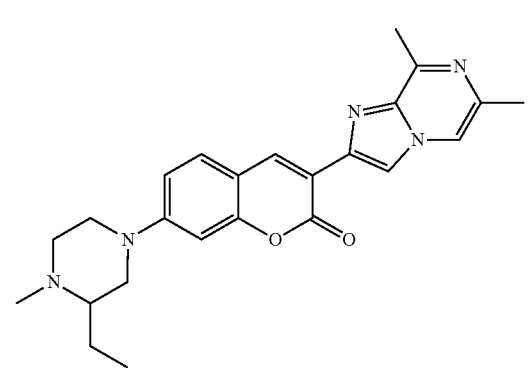
677
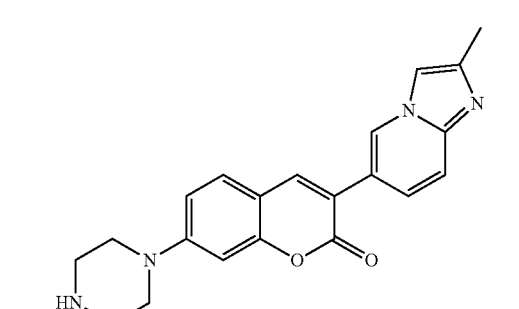
678
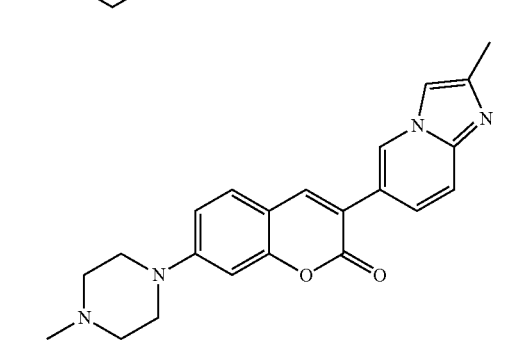

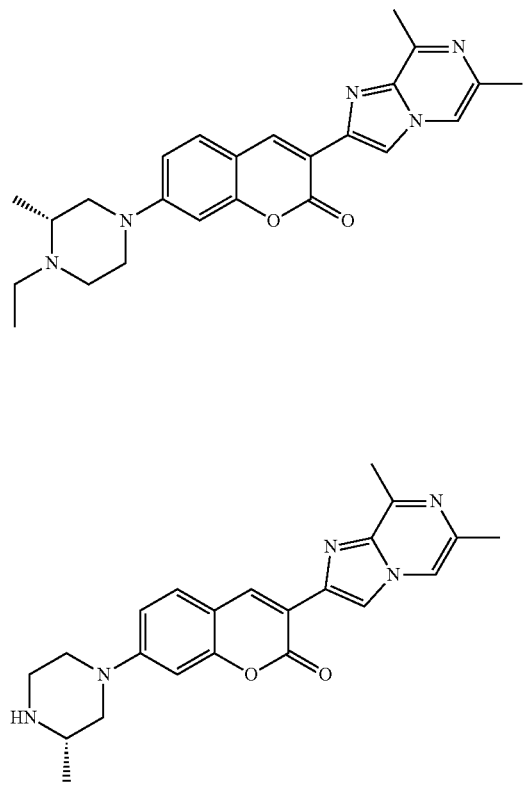
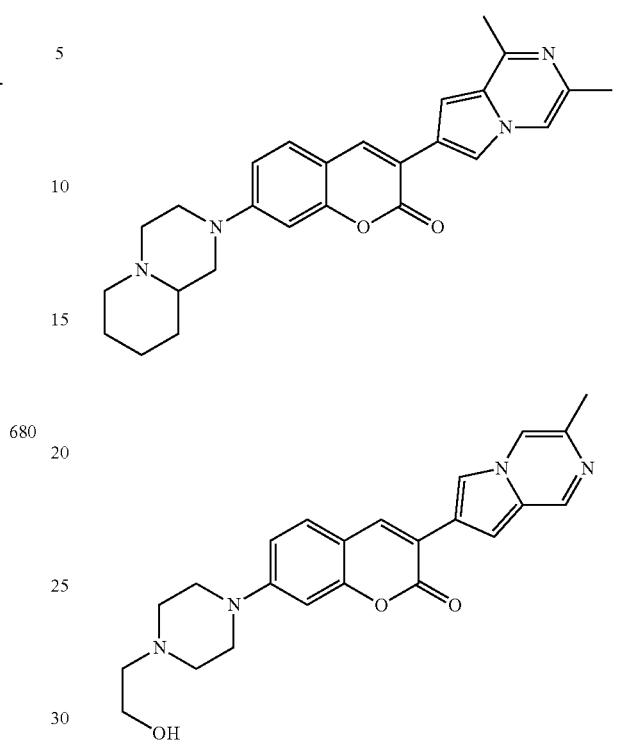
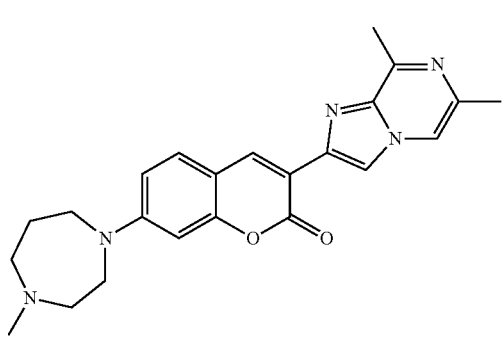
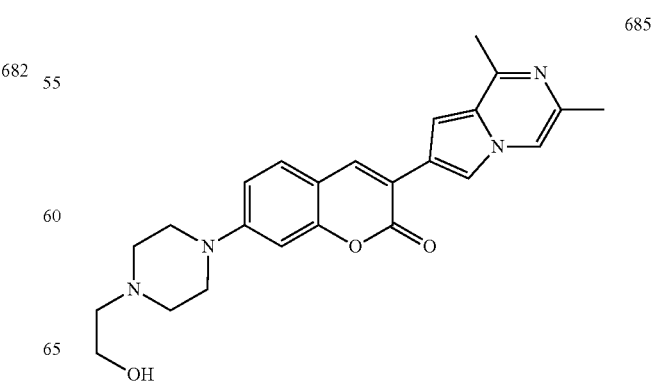

169
-continued
686
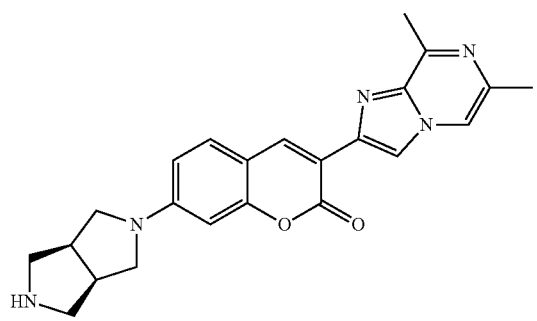
687
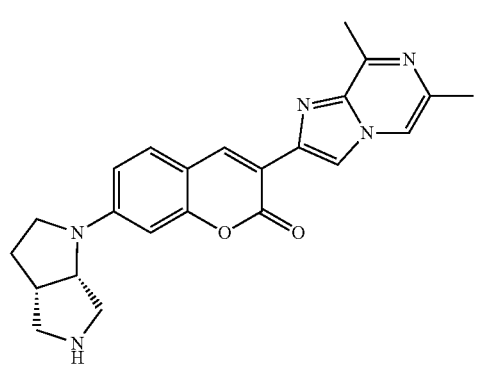
688
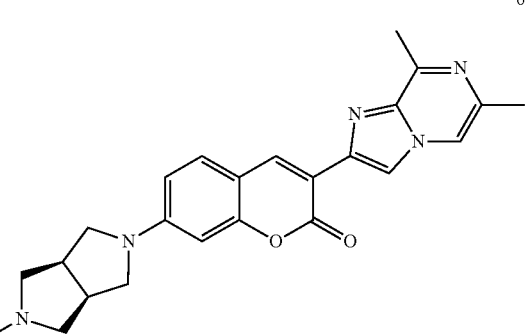
689
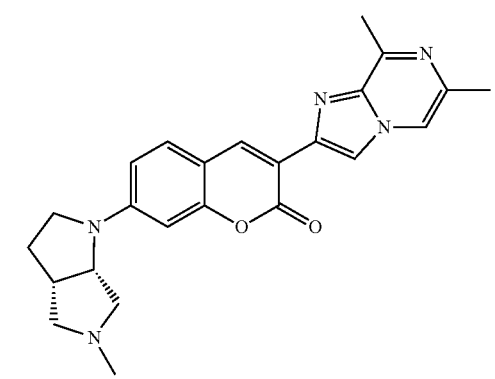
170
-continued
690
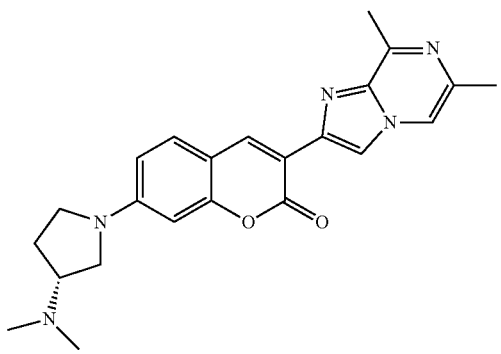
691
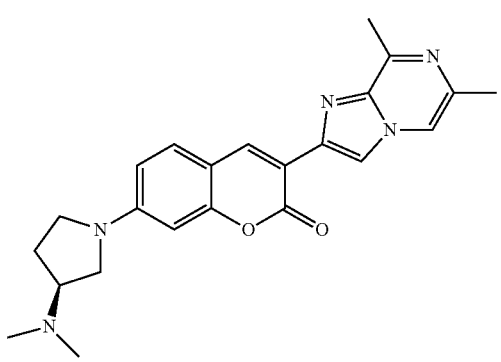
692
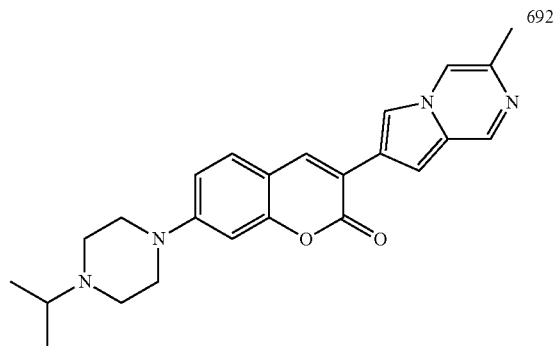
693
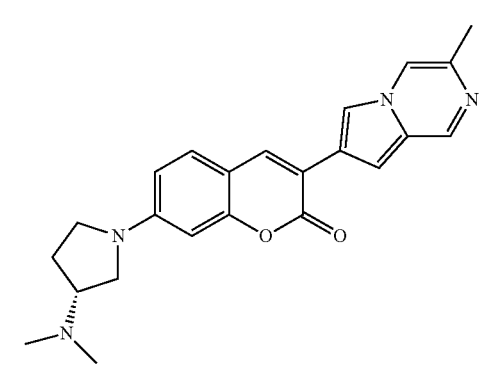

-continued
694
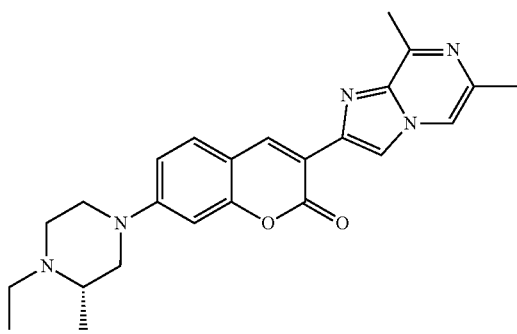
695
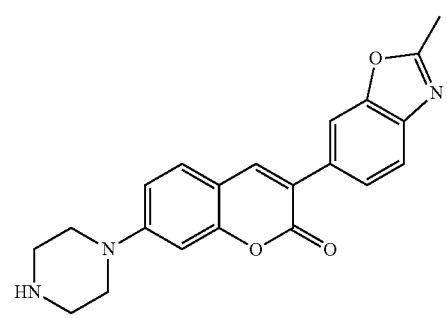
696
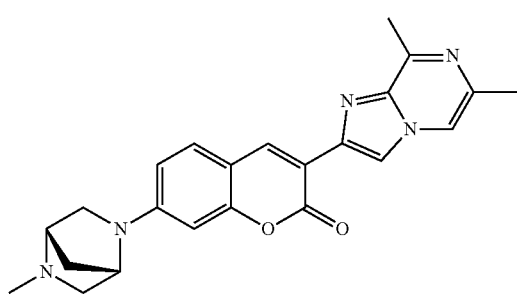
697
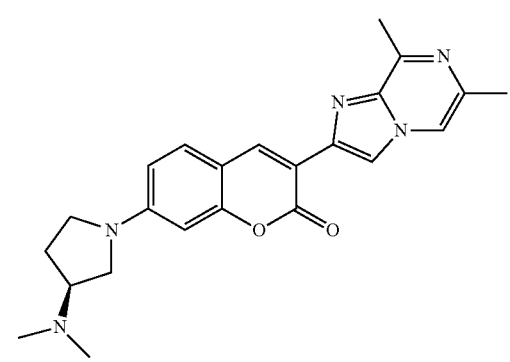
698
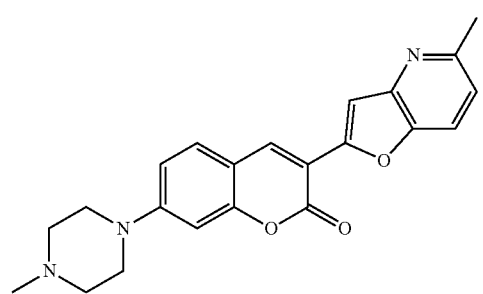
-continued
699
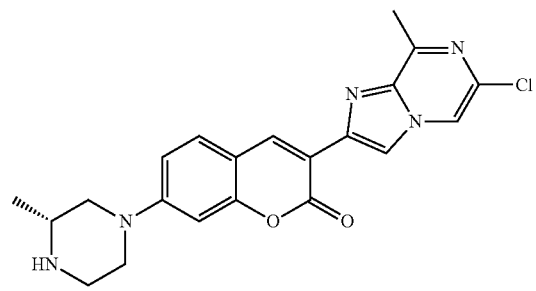
700
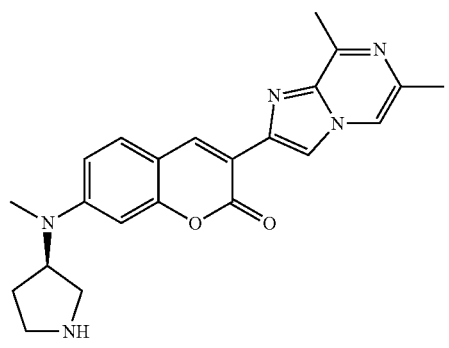
701
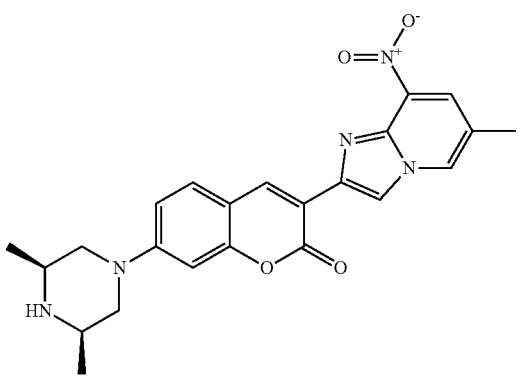
702
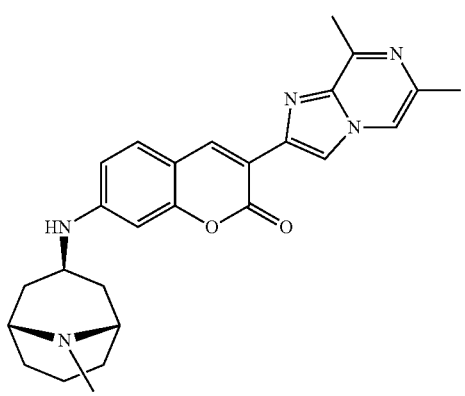

-continued
703
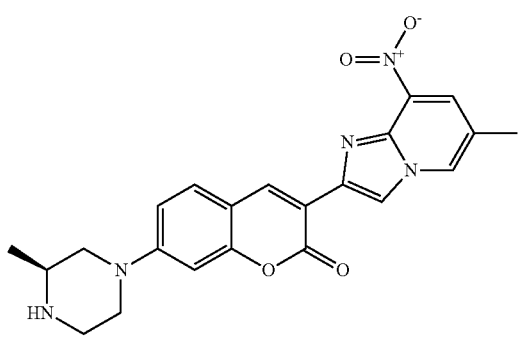
704
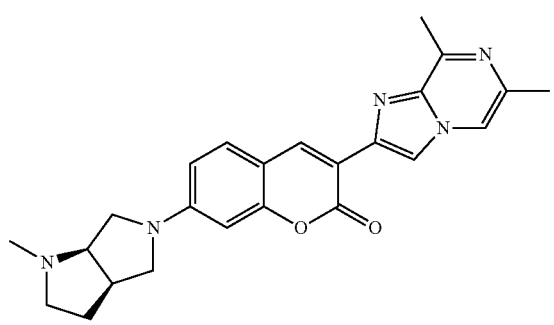
705
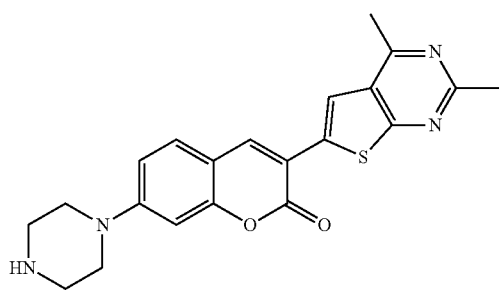
706
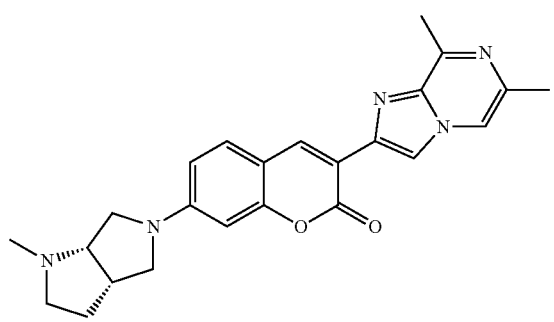
-continued
707
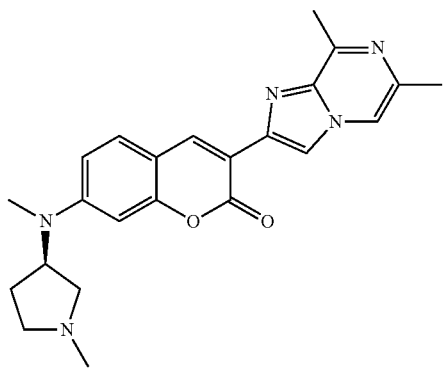
708
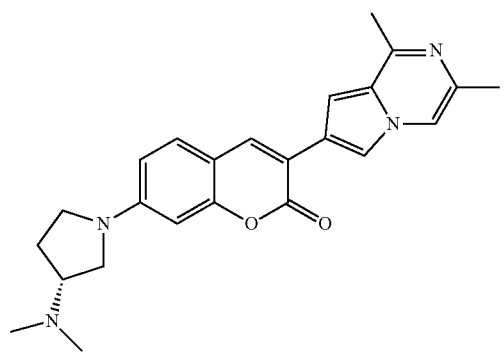
709
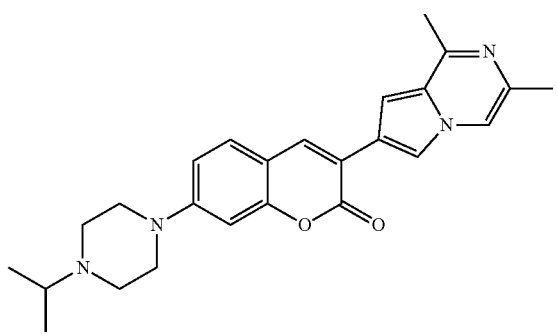
710
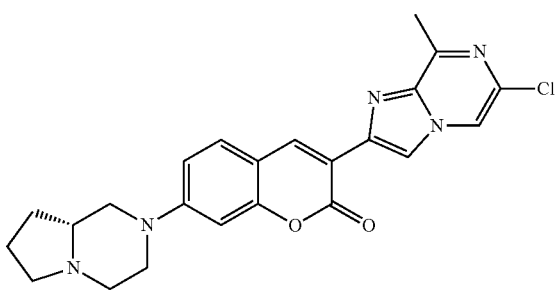

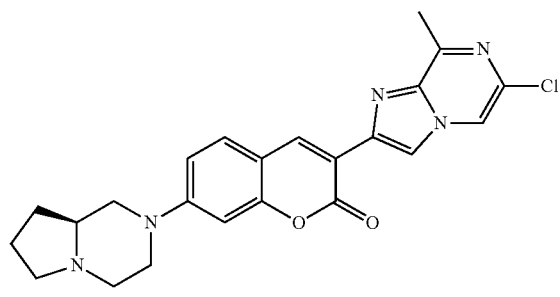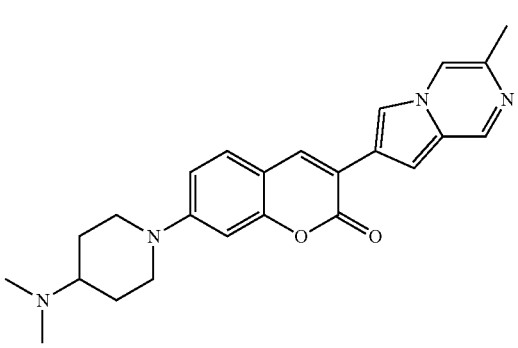

720 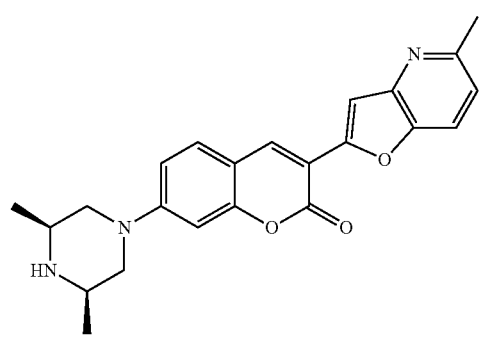
721 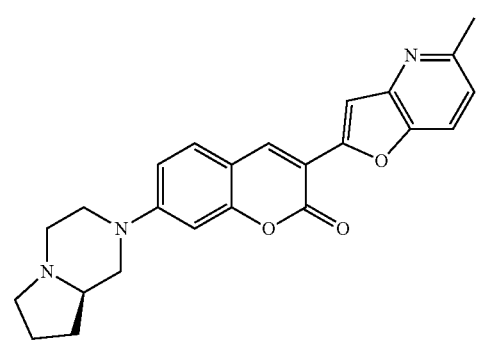
722 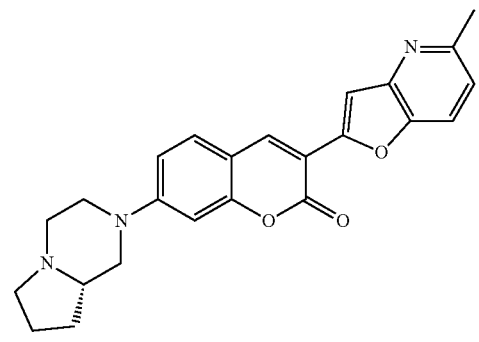
723 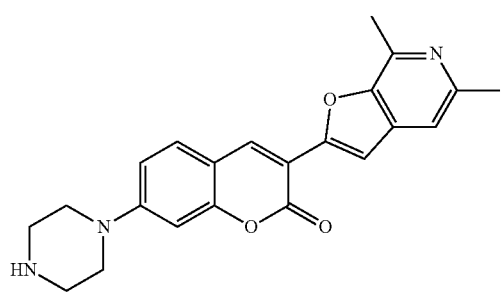
724 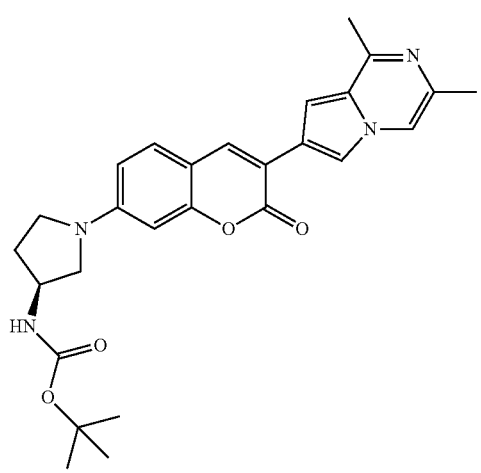
725 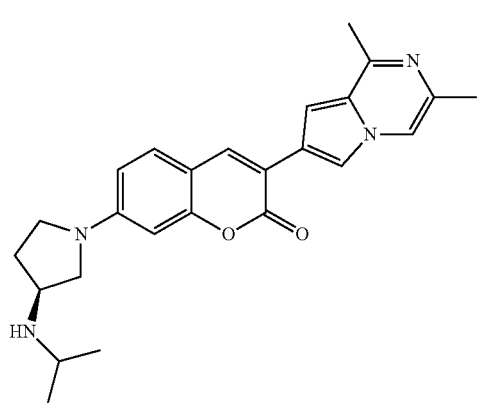
726 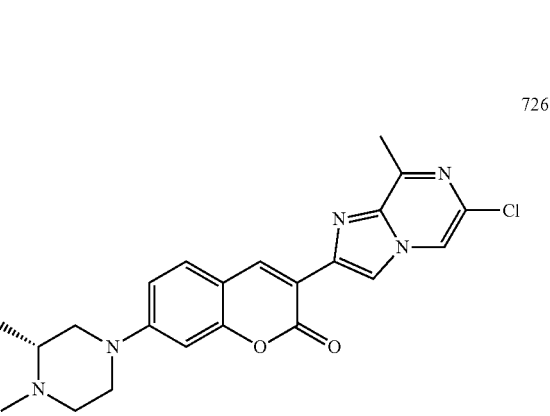
727 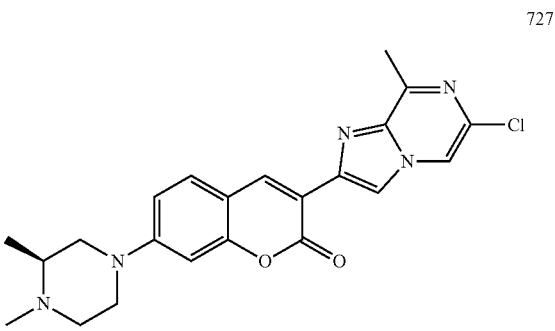

-continued
728
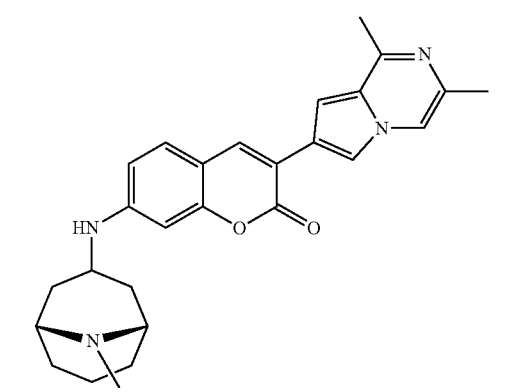
729
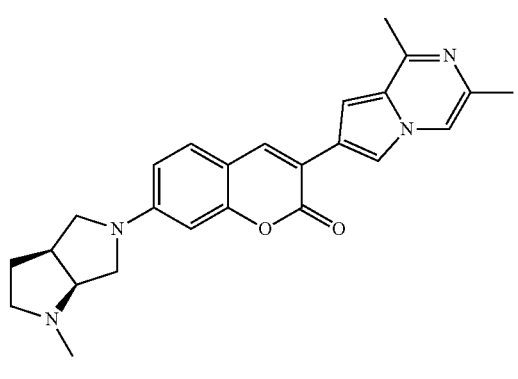
730
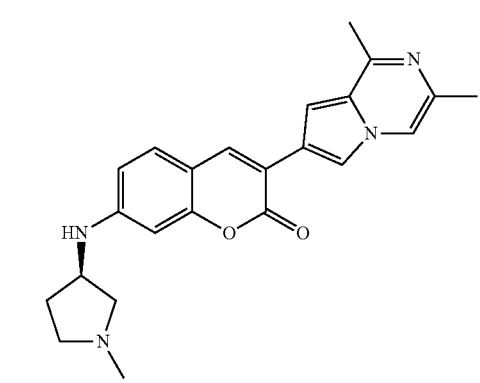
731
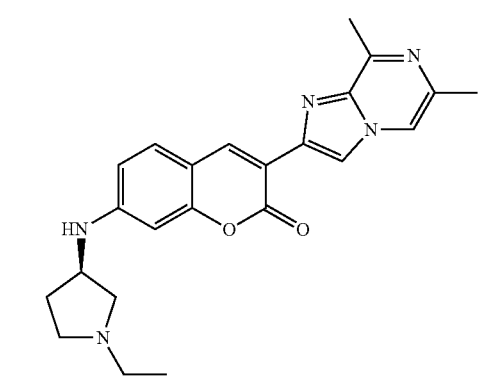
-continued
732
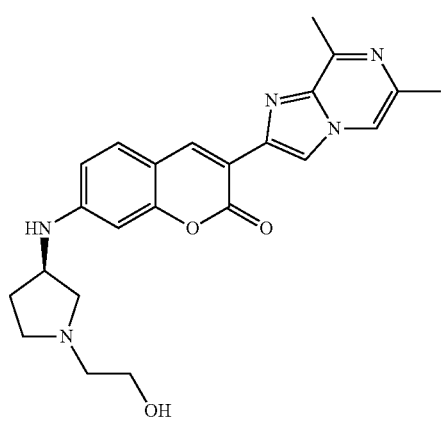
733
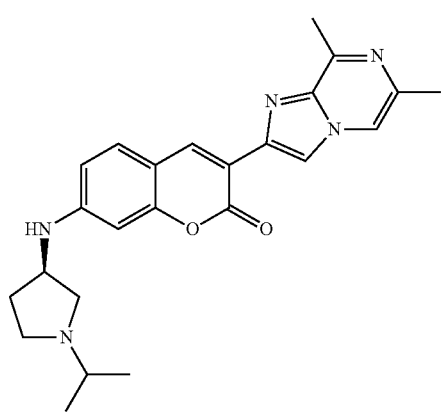
734
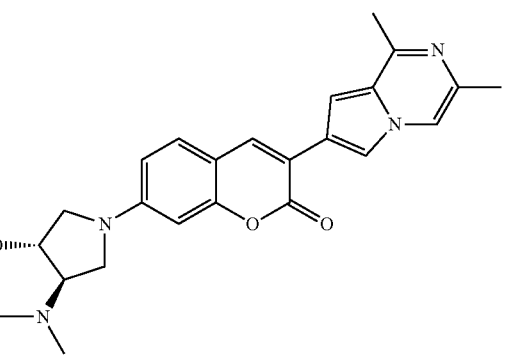
735
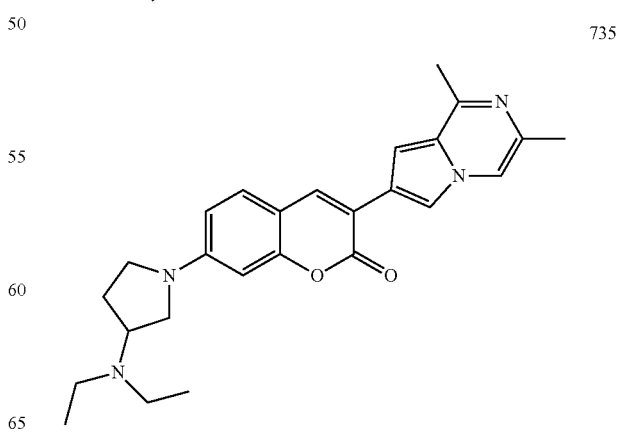

-continued
736
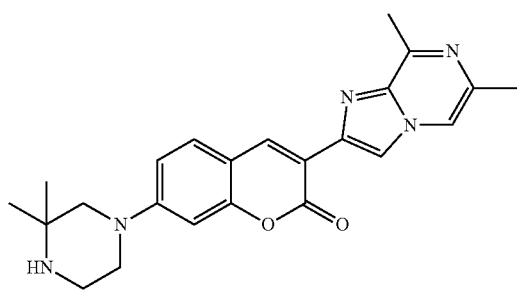
737
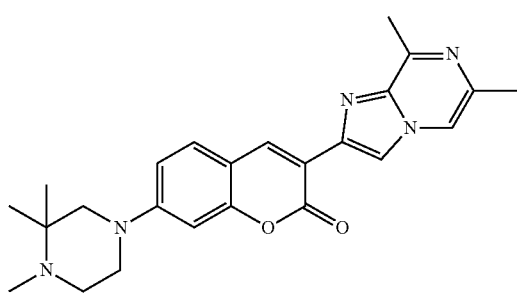
738
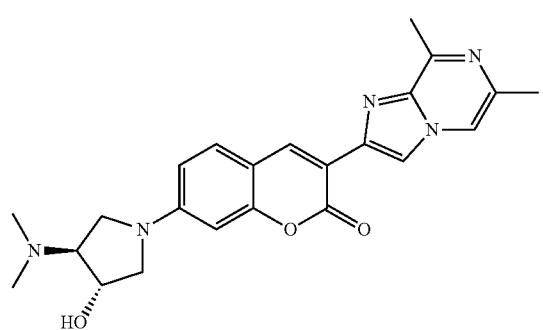
739
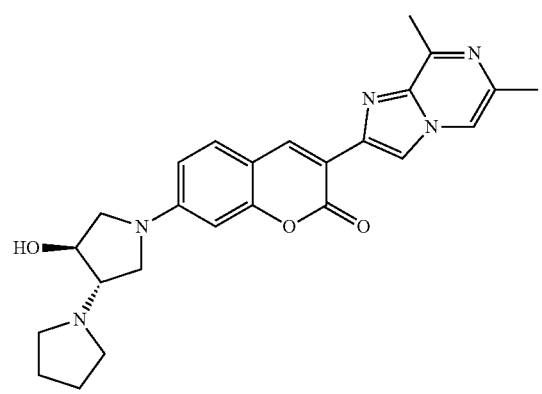
-continued
740
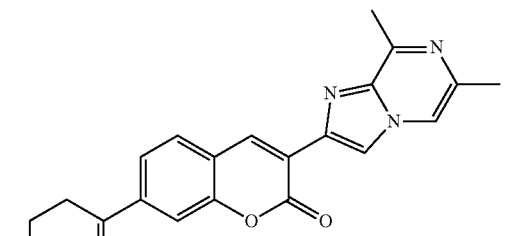
741
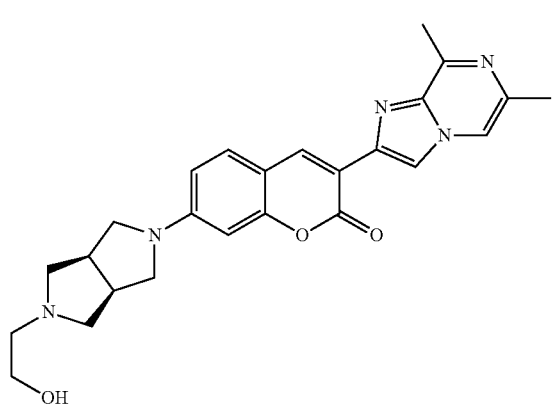
742
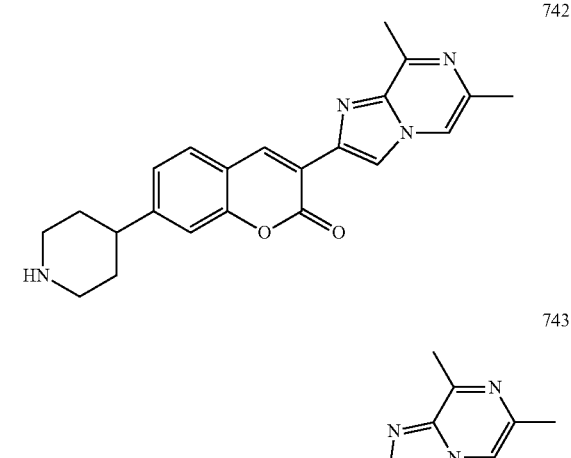
743
744
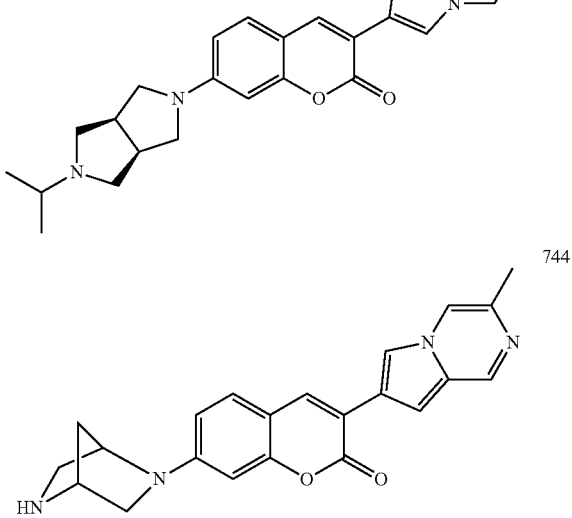

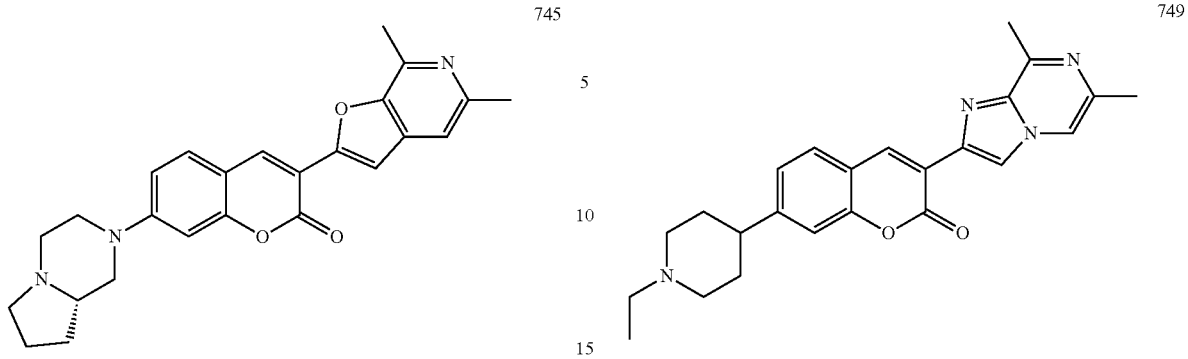
745
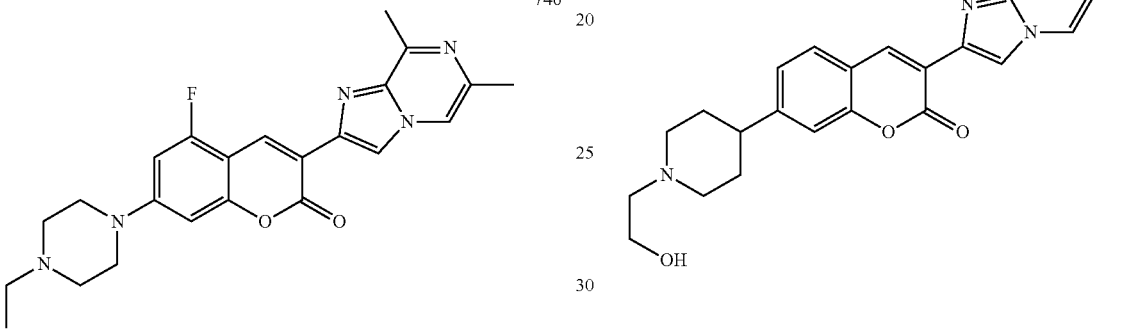
746
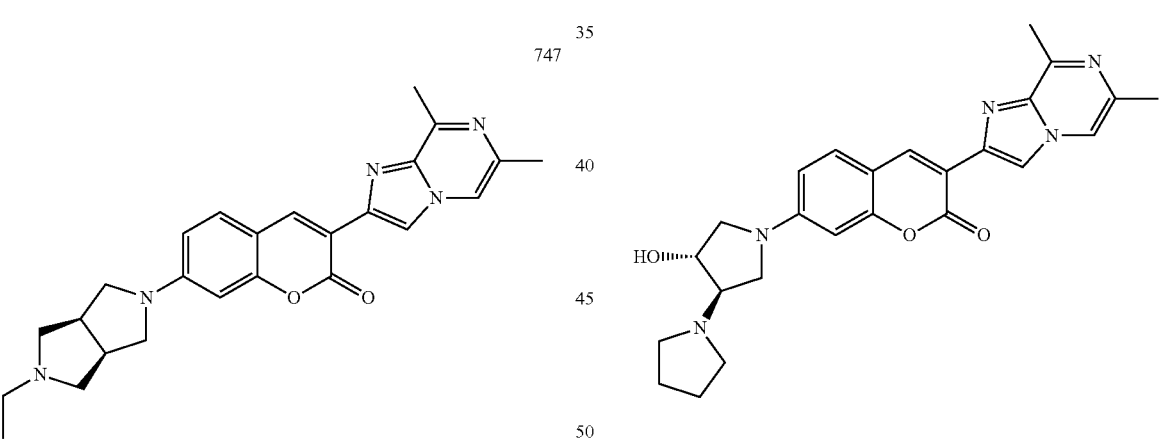
747
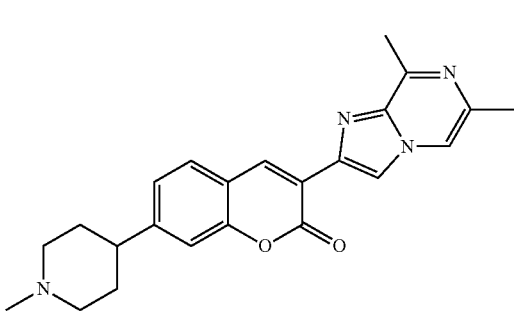
748
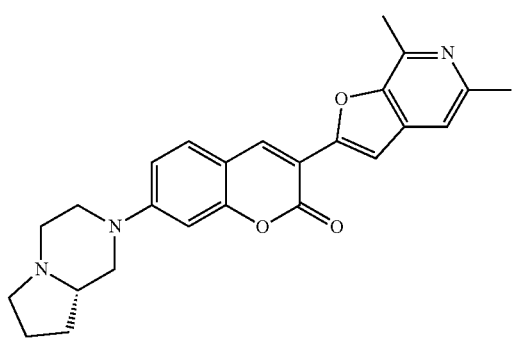
749
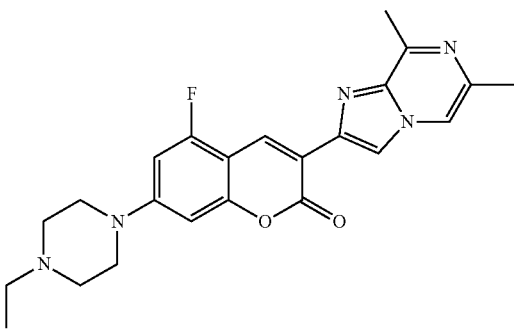
750
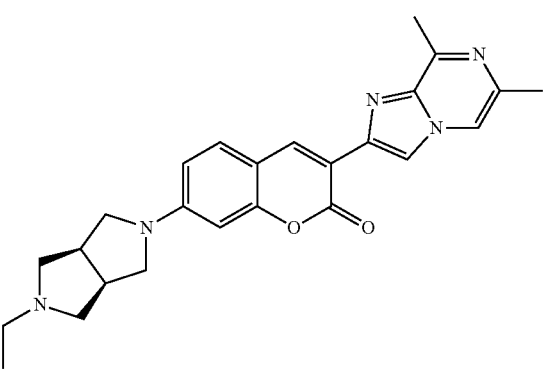
751
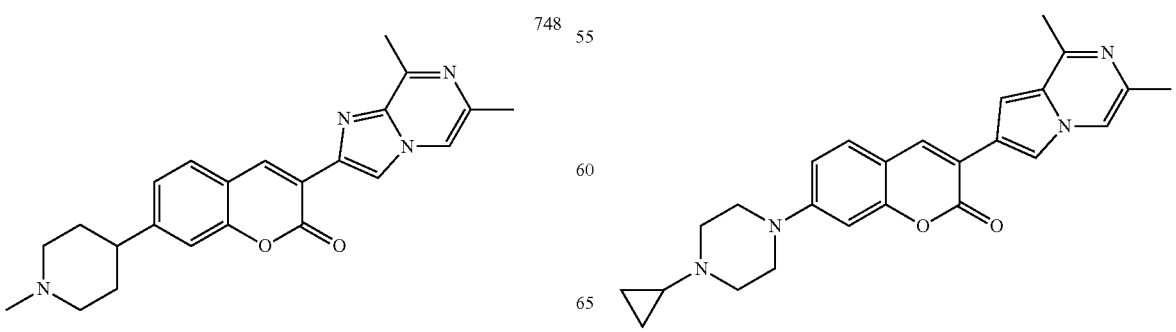
752

-continued
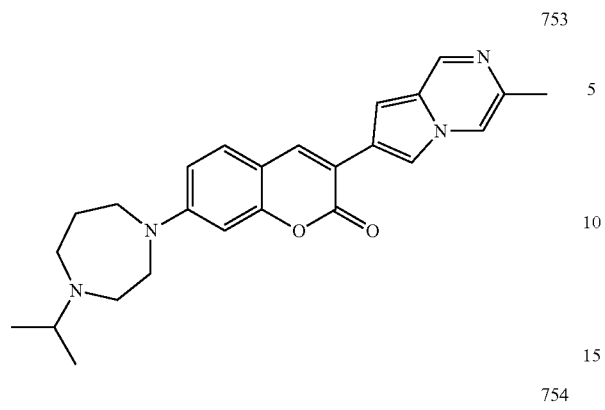
753
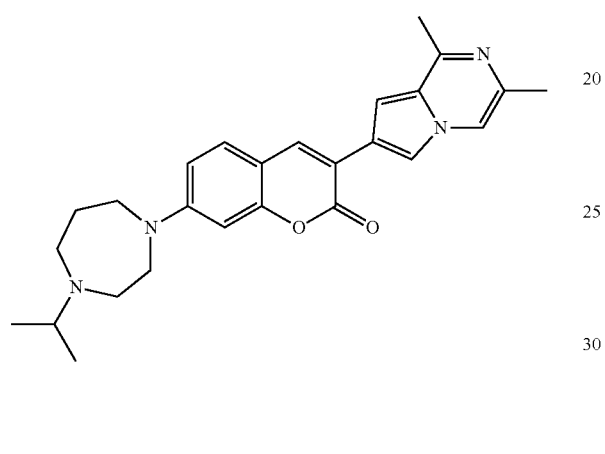
754
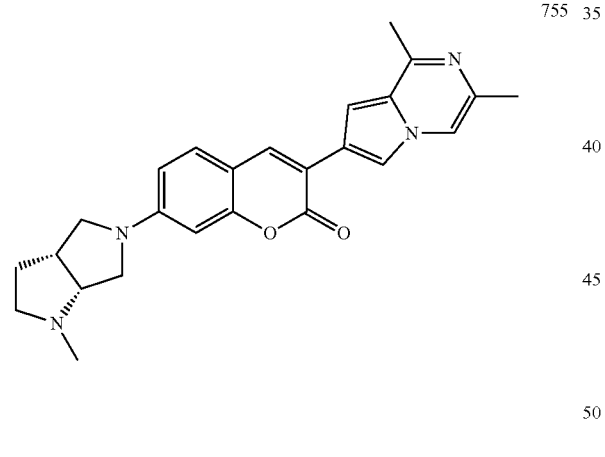
755
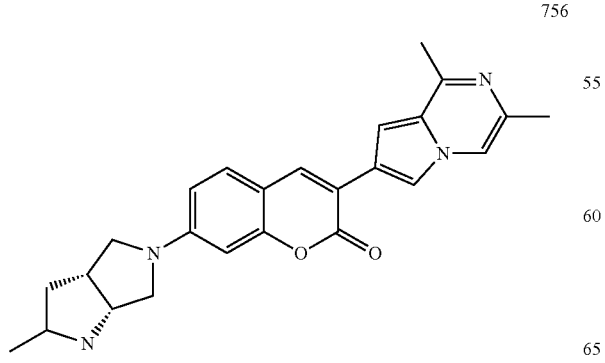
756
-continued
757
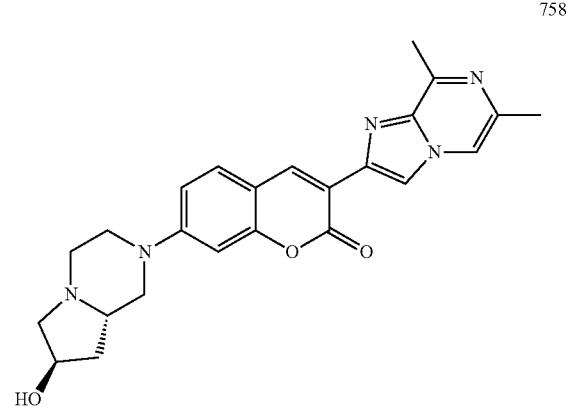
758
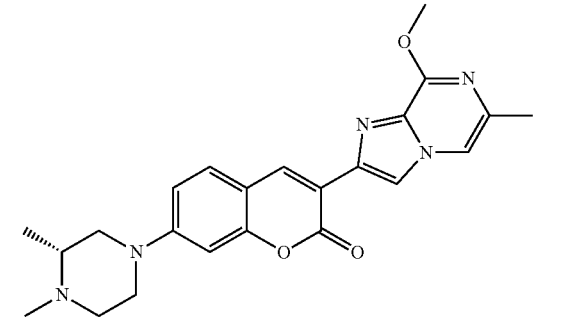
759
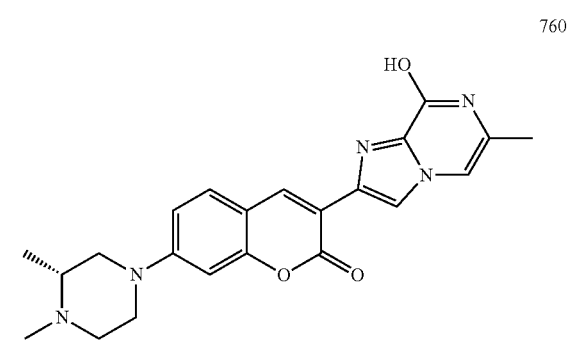
760

187
-continued
761
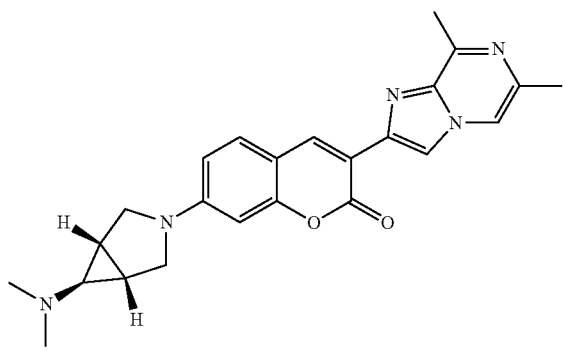
762
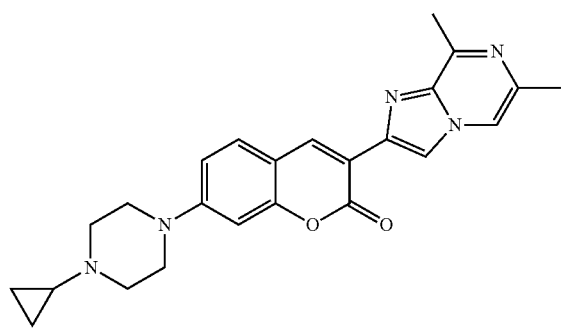
763
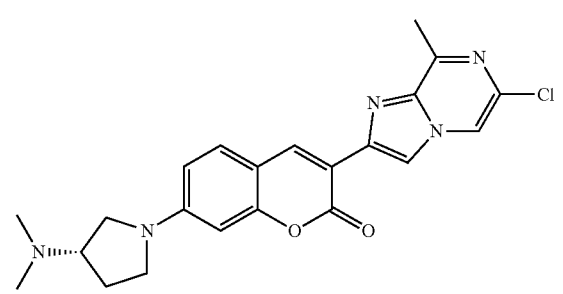
764
765
188
-continued
766
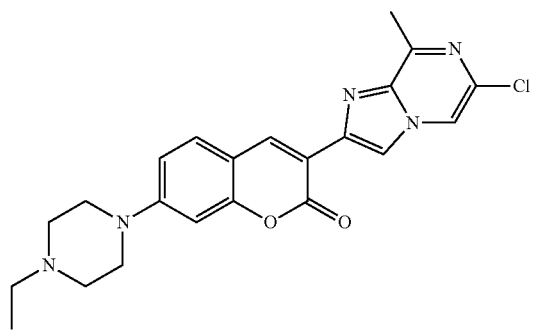
767
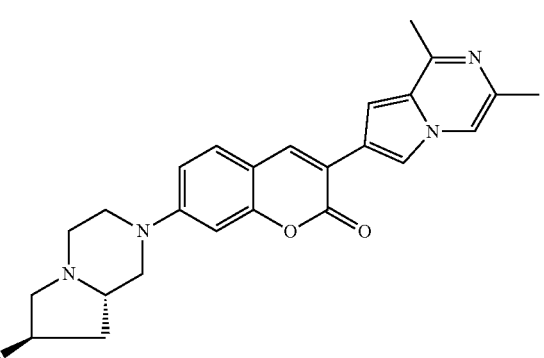
768
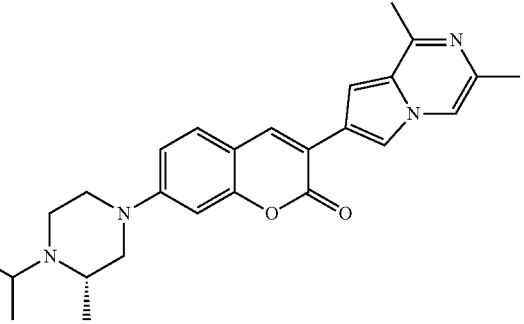
769
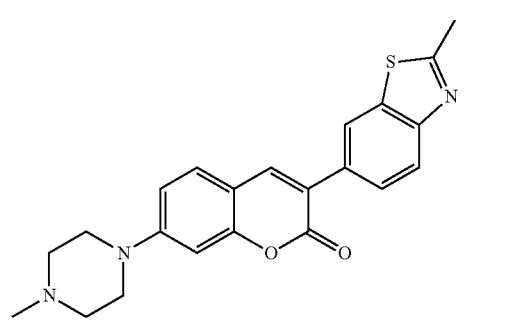

| 770 | 775 |
|---|---|
| 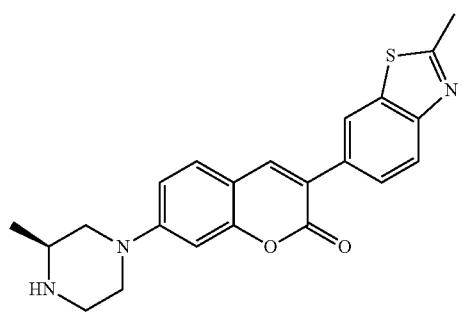 | 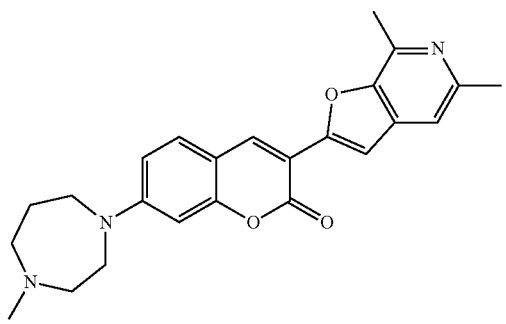 |
| 771 | 776 |
| 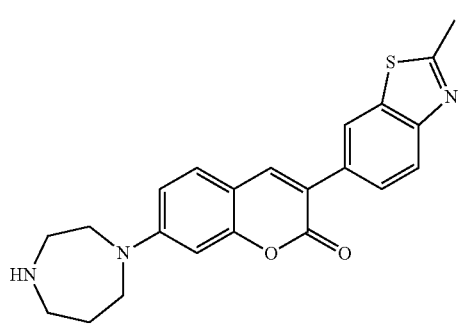 | 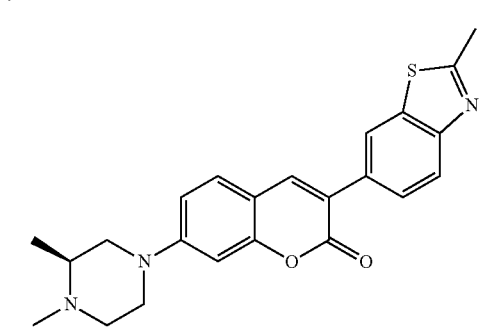 |
| 772 | 777 |
| 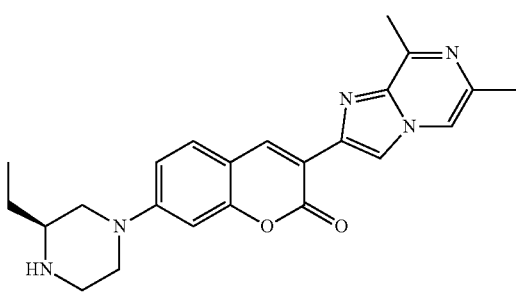 | 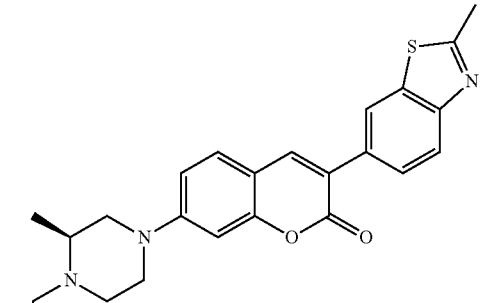 |
| 773 | 778 |
| 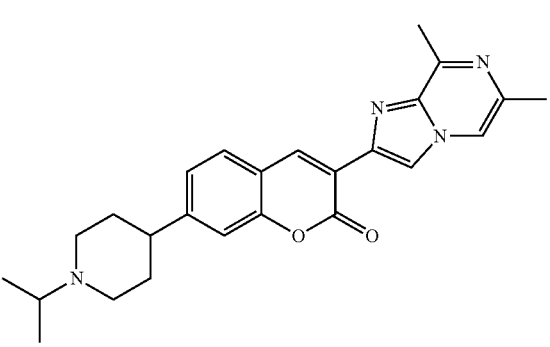 | 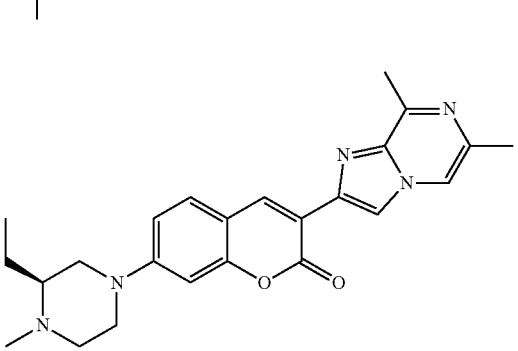 |
| 774 | 779 |
| 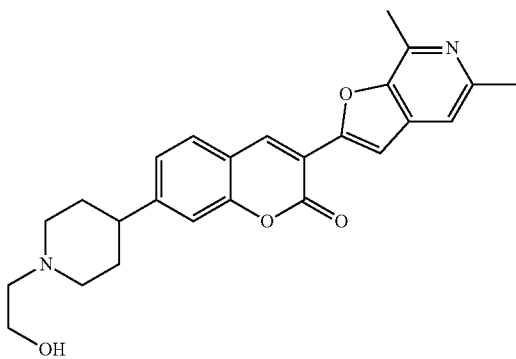 | 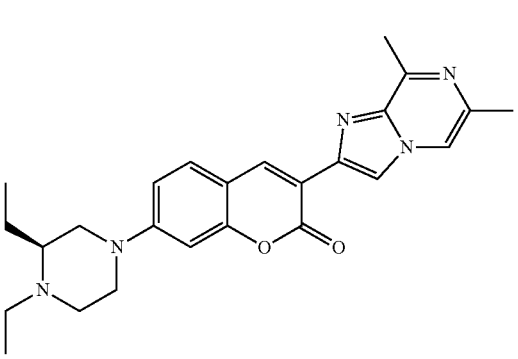 |

-continued
780
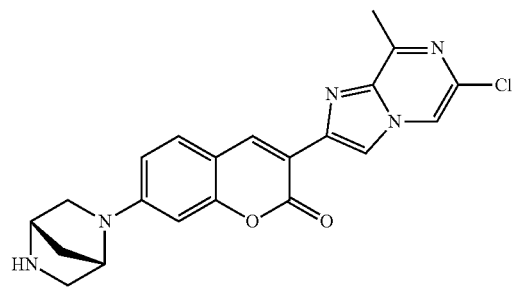
781
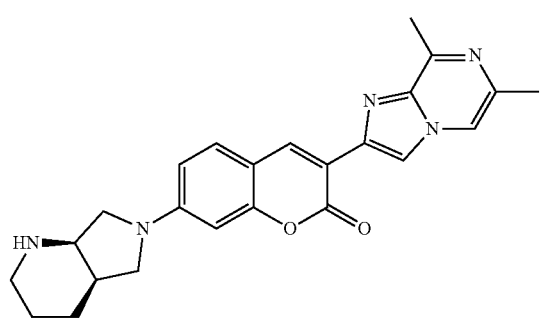
782
783
784
-continued
785
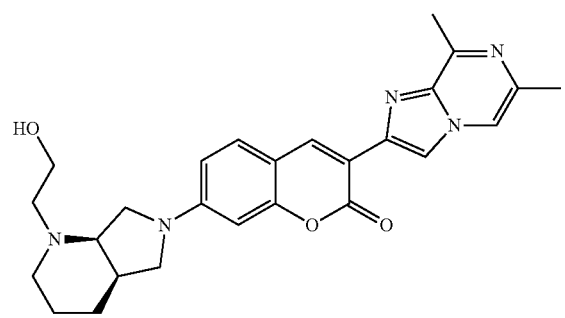
786
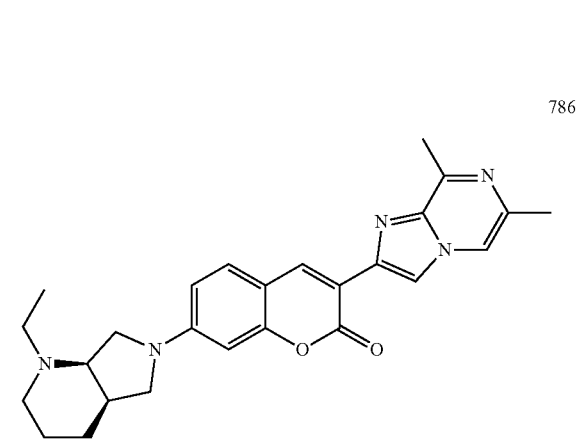
787
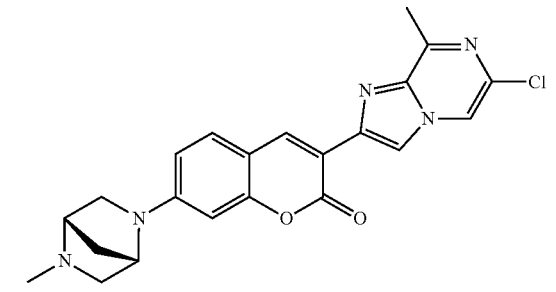
788
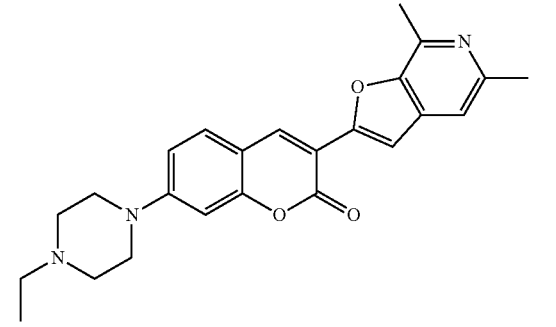

193
-continued
794
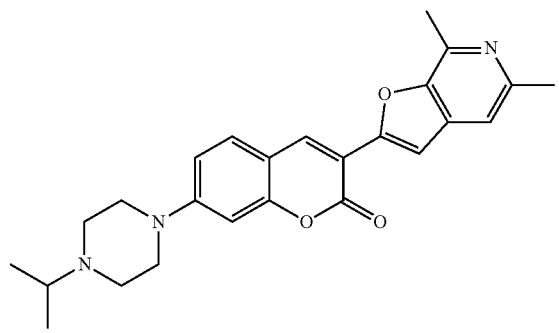
790
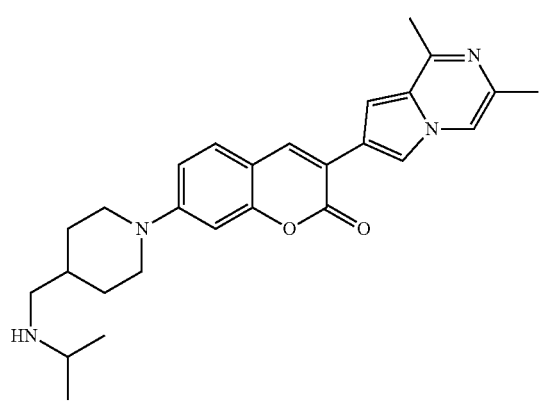
791
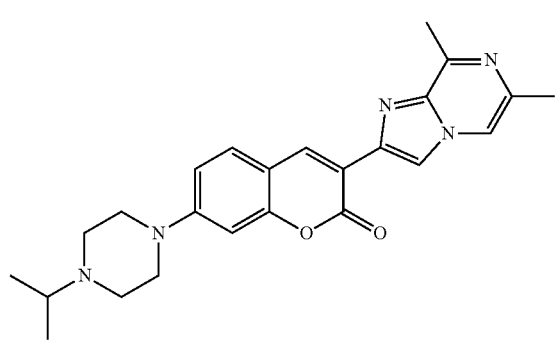
792
194
-continued
793
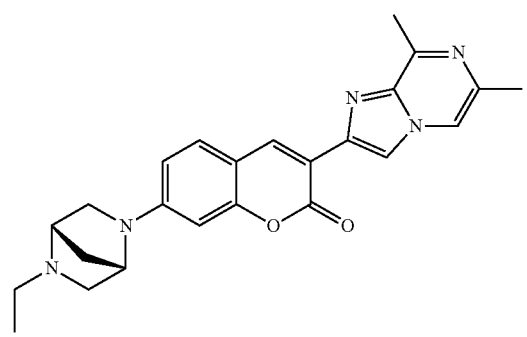
794
795
796
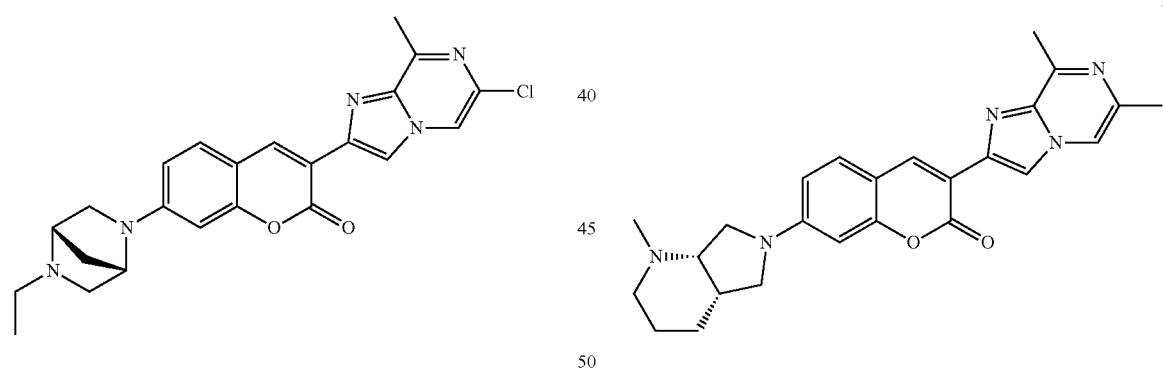
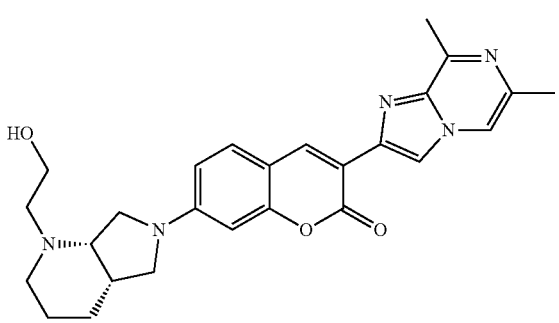

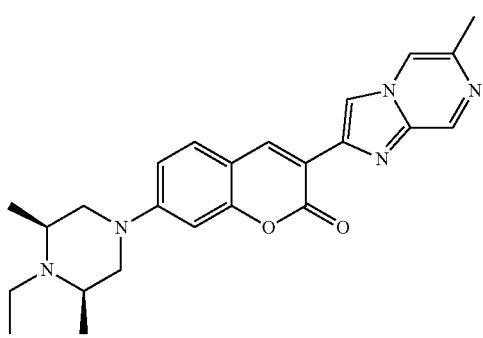
797
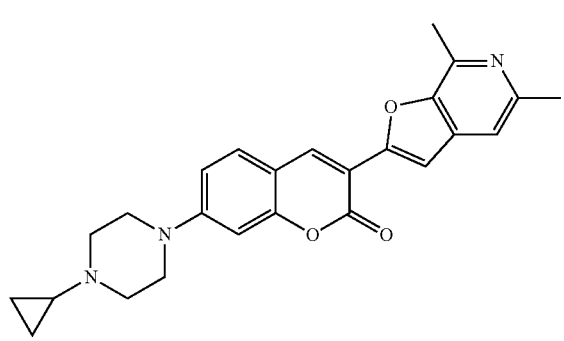
798
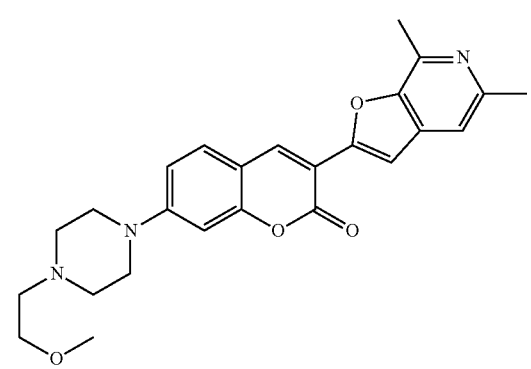
799
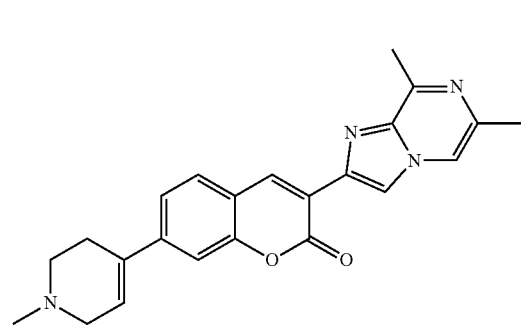
800
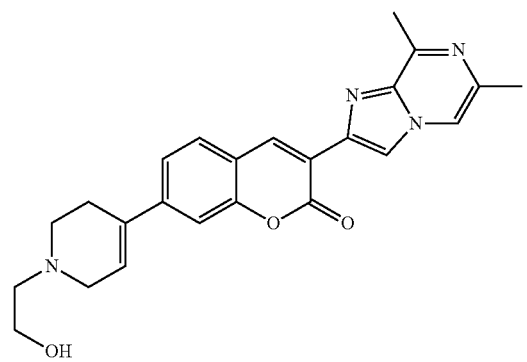
801
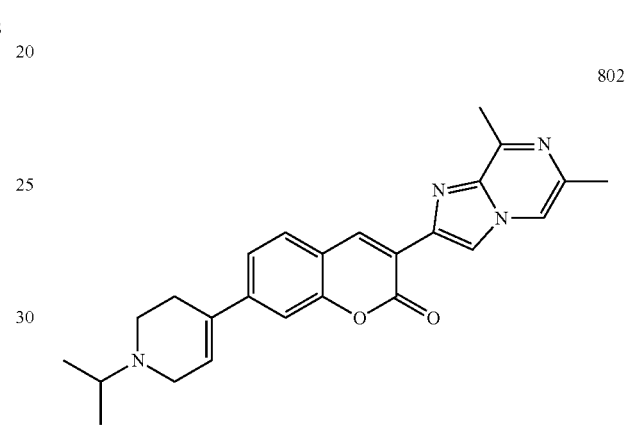
802
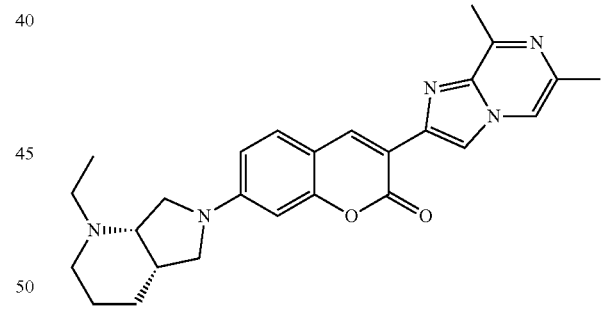
803
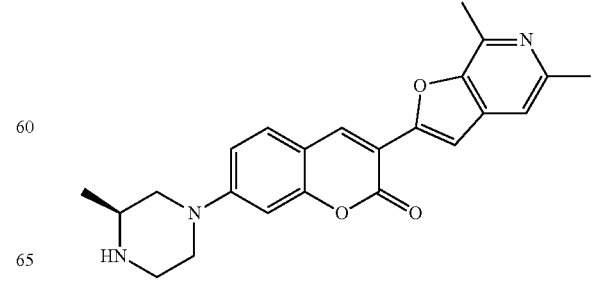
804

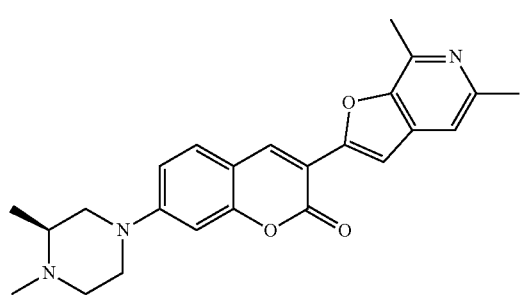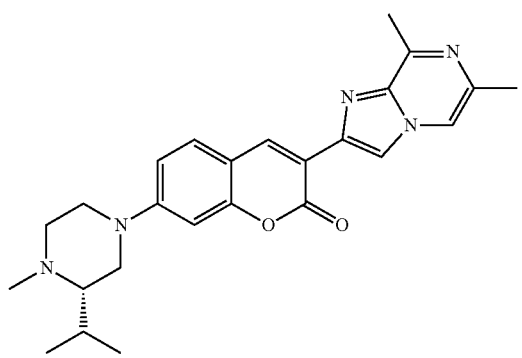

| 813 | 817 |
|---|---|
| 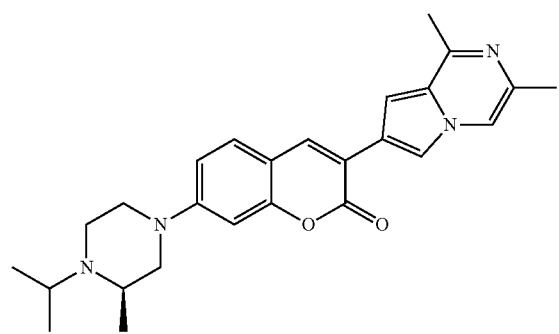 | 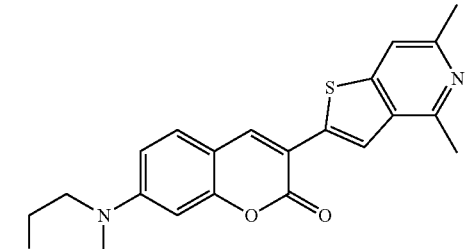 |
| 814 | 818 |
| 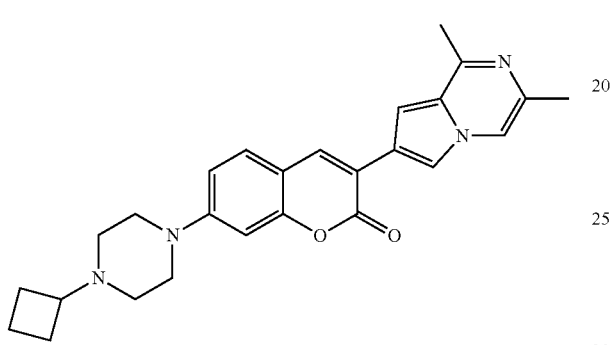 | 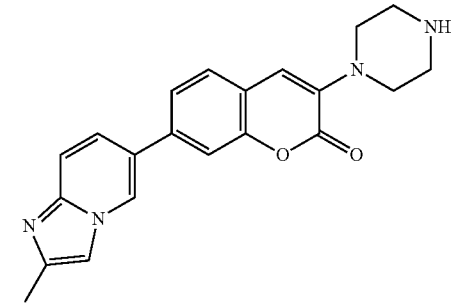 |
| 815 | 819 |
| 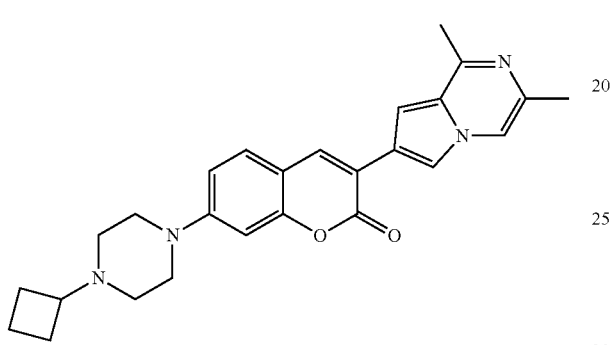 | 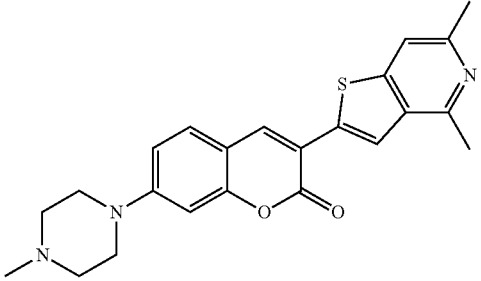 |
| 816 | 820 |
|  | 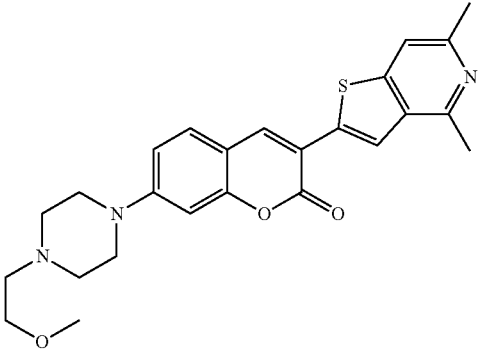 |
|  | 821 |
|  | 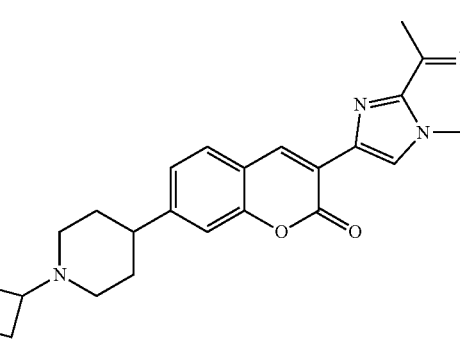 |

-continued
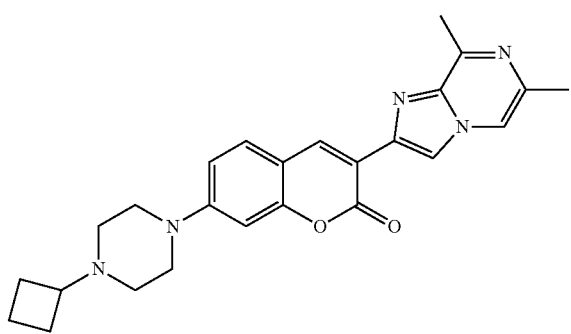
822
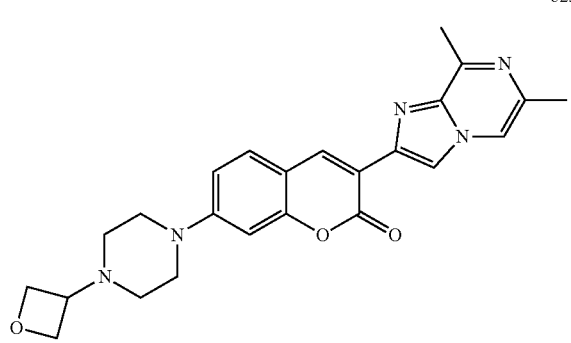
823
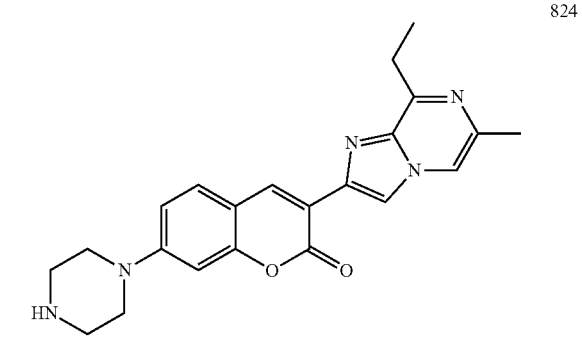
824
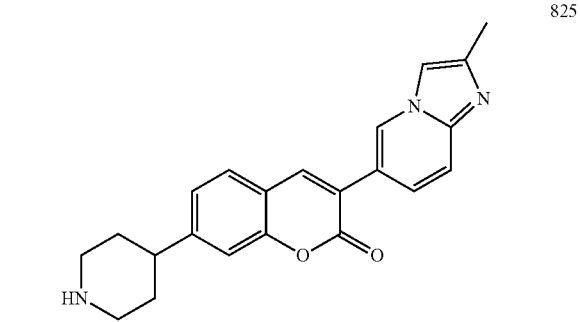
825
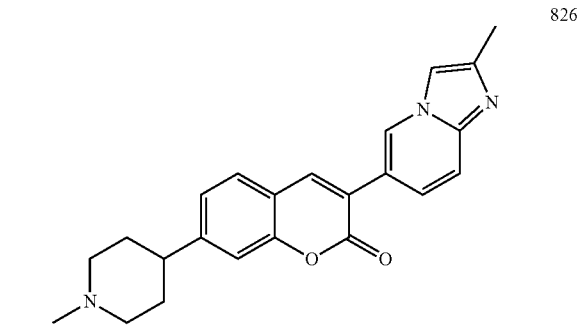
826
-continued
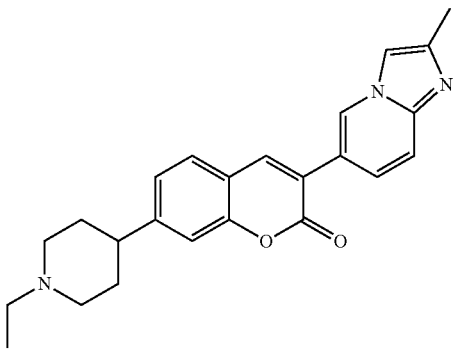
827
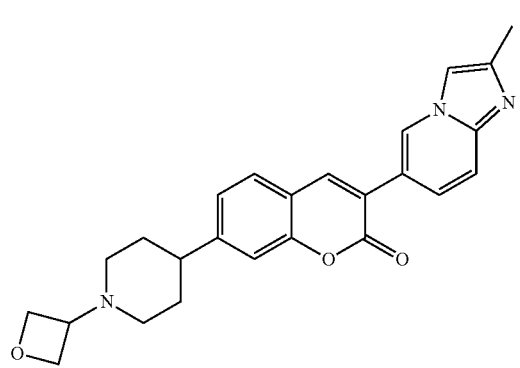
828
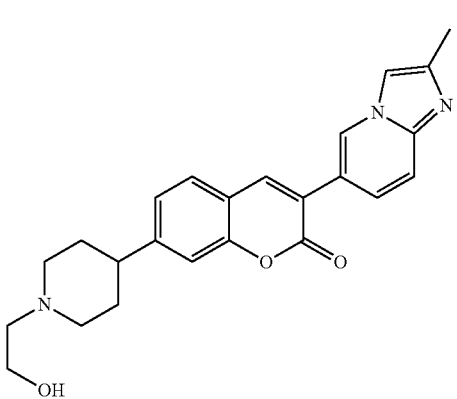
829
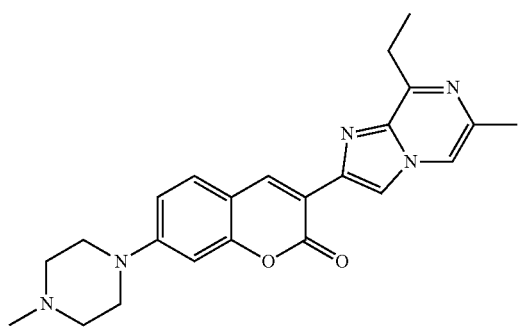
830

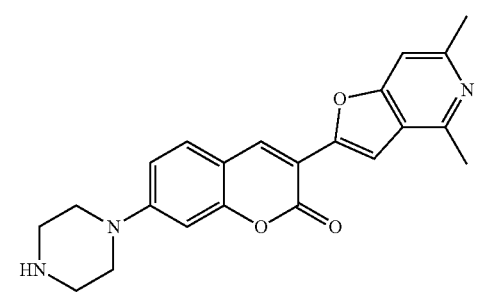
831
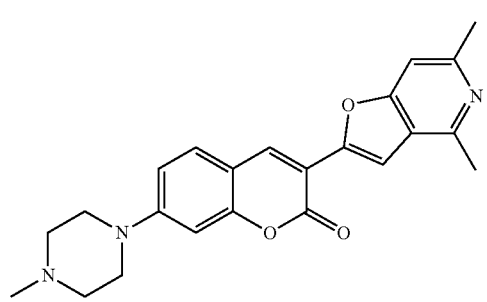
832
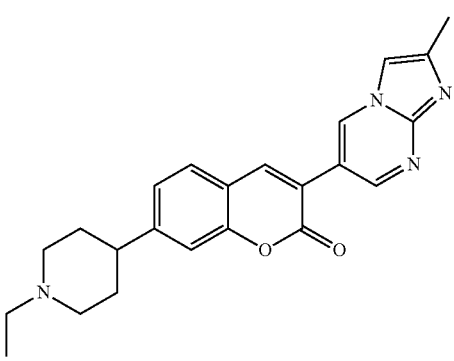
836
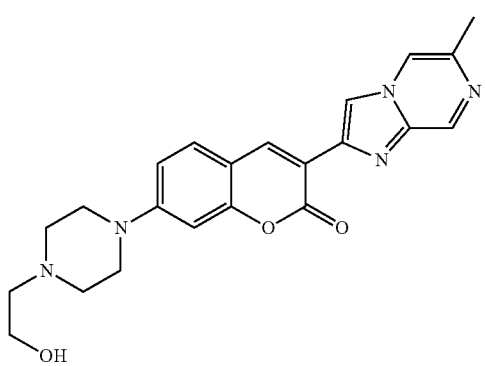
837
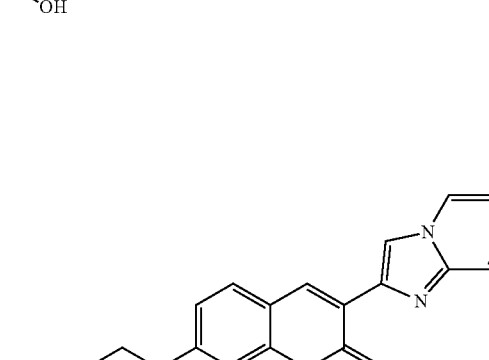
833
838
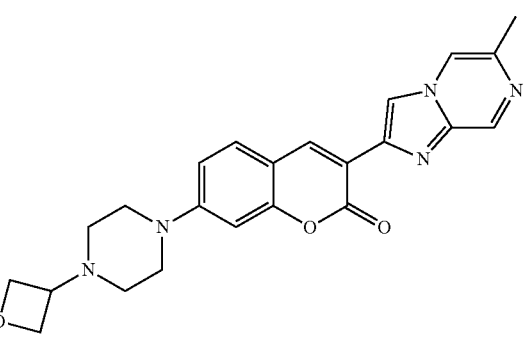
839

-continued
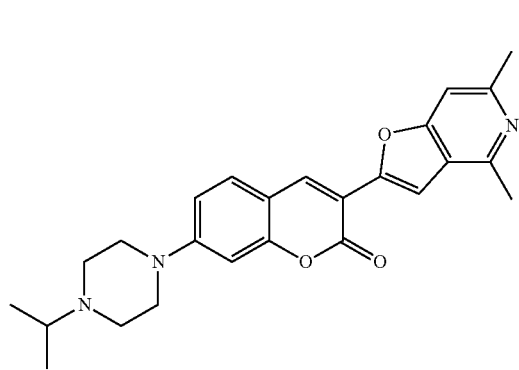
840
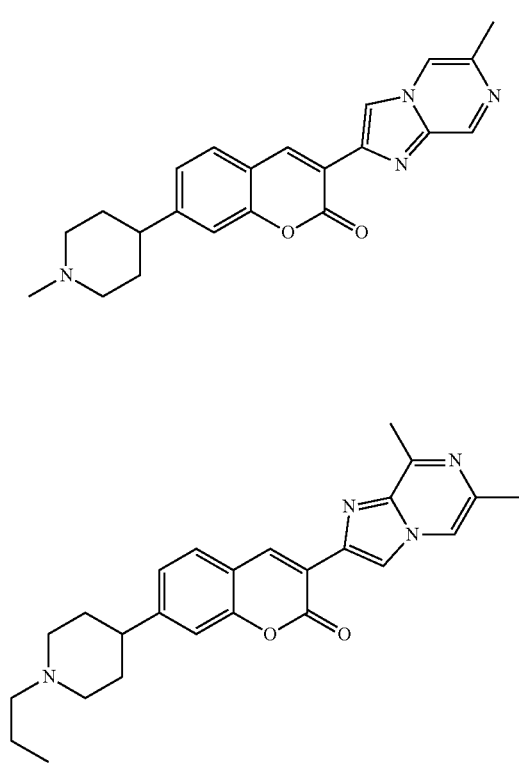
841
842
843
-continued
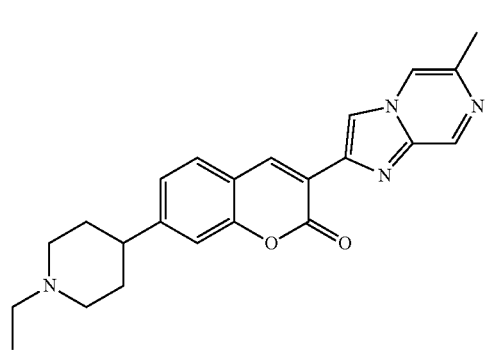
844
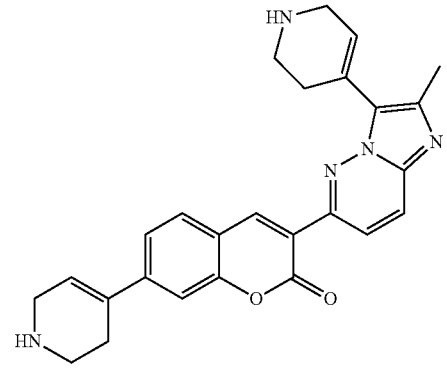
845
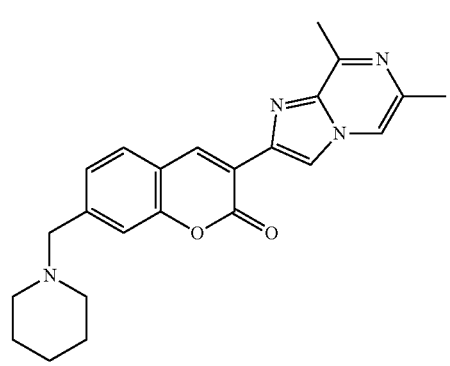
846
847

-continued
848
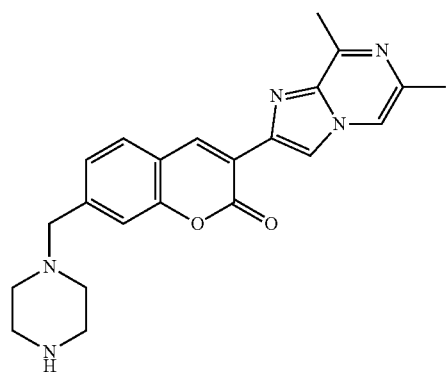
849
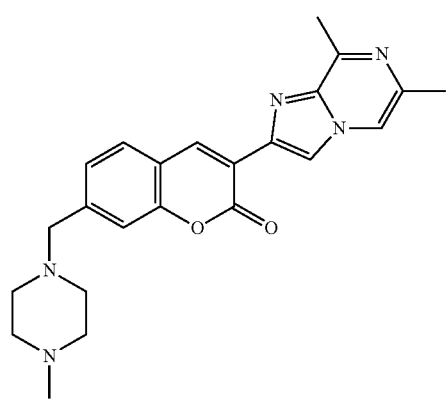
850
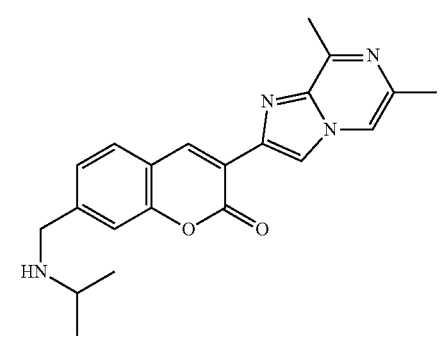
851
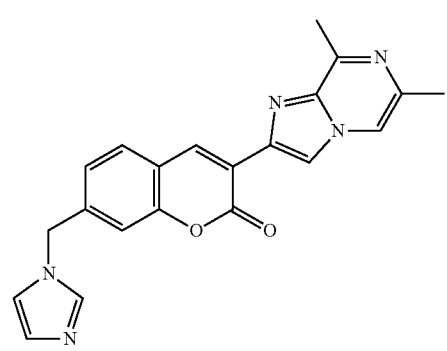
-continued
852
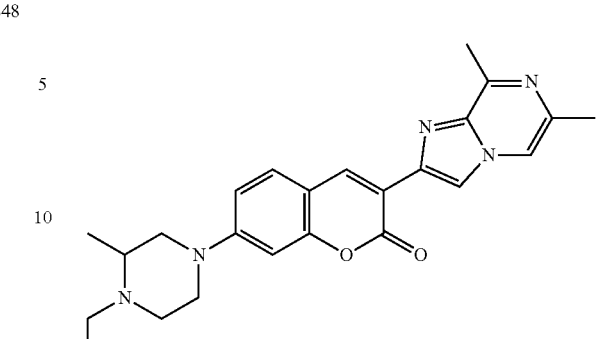
853
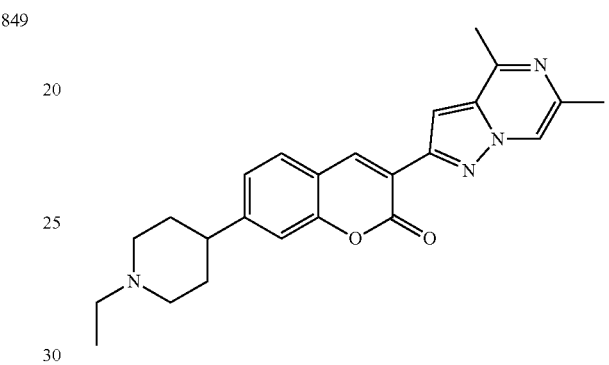
854
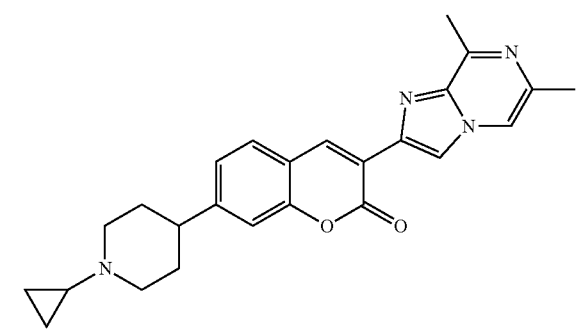
855
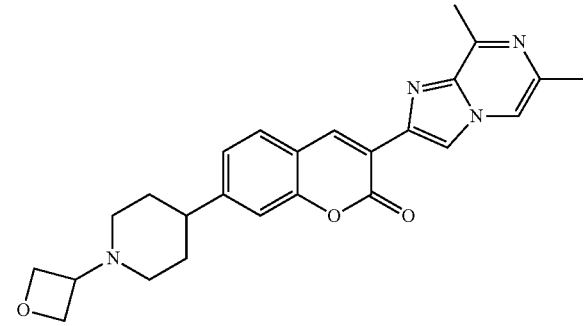

856 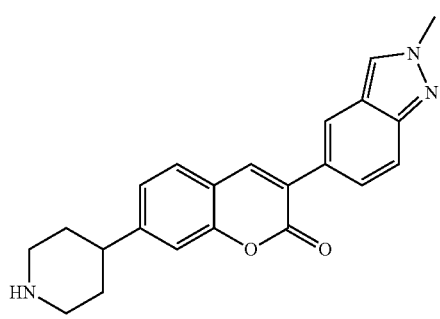
857 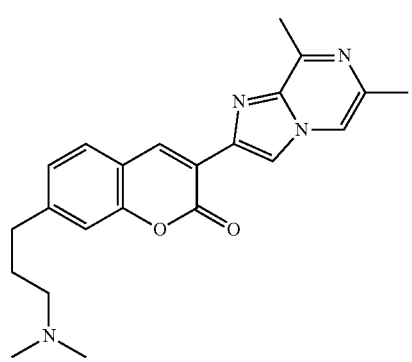
858 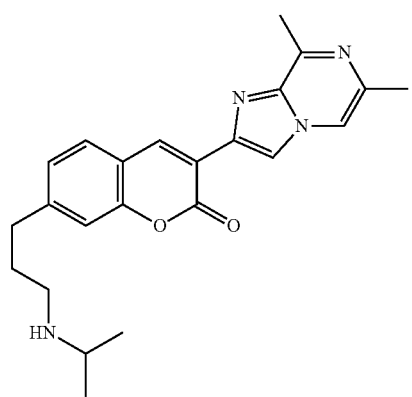
859 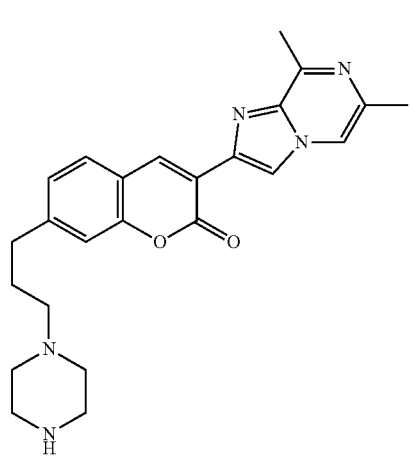
860 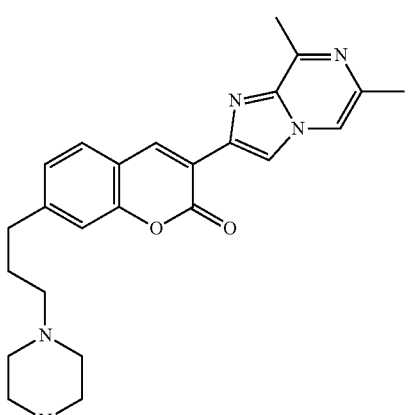
861 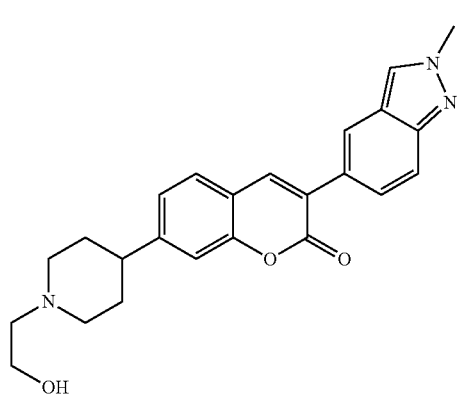
862 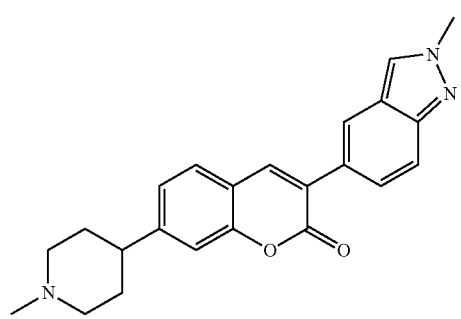
863 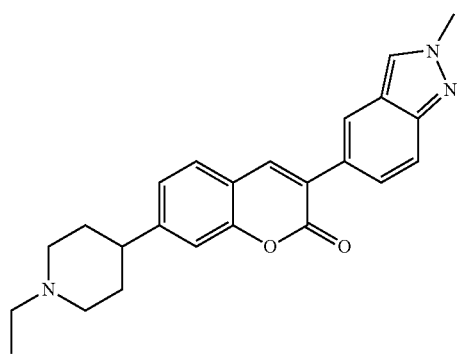

864 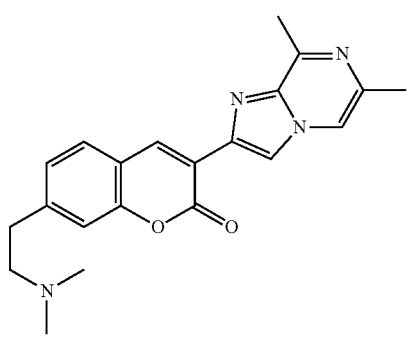
865 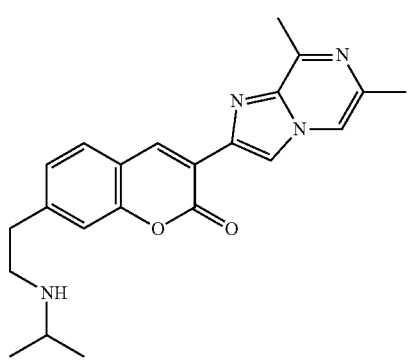
866 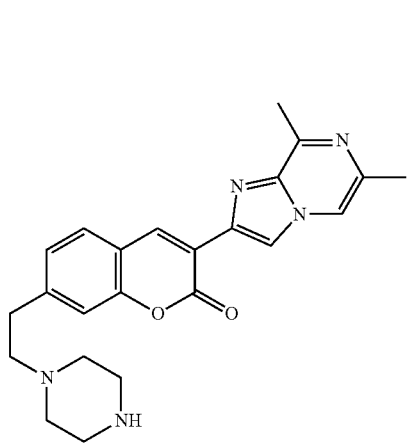
867 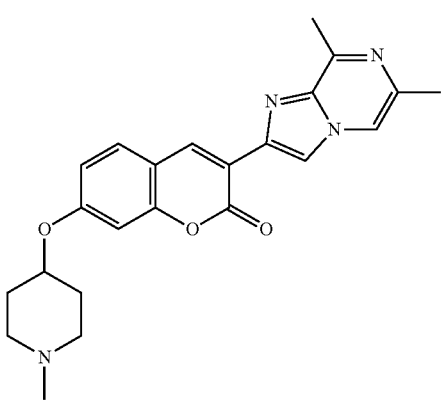
868 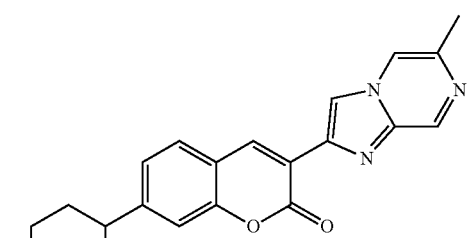
869 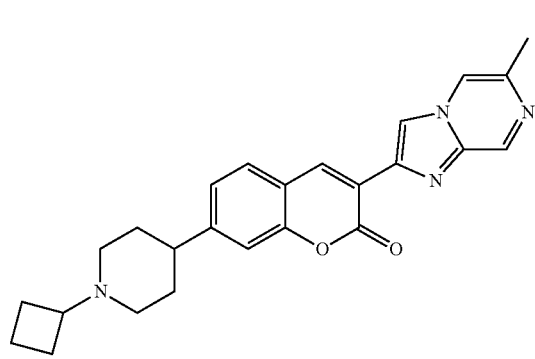
870 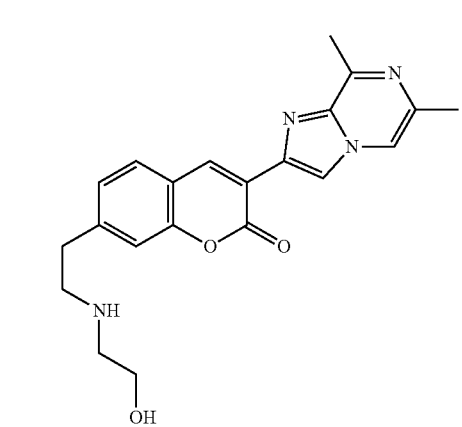
871 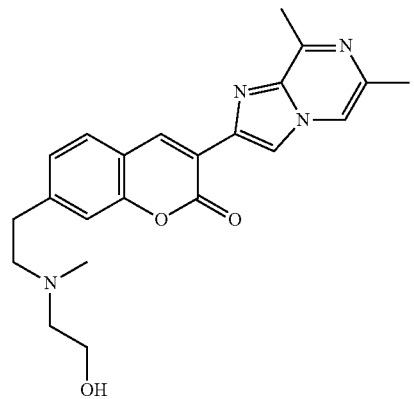

| | |
|---|---|
| 872 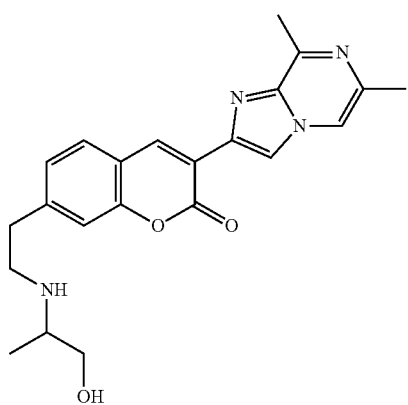 | 876 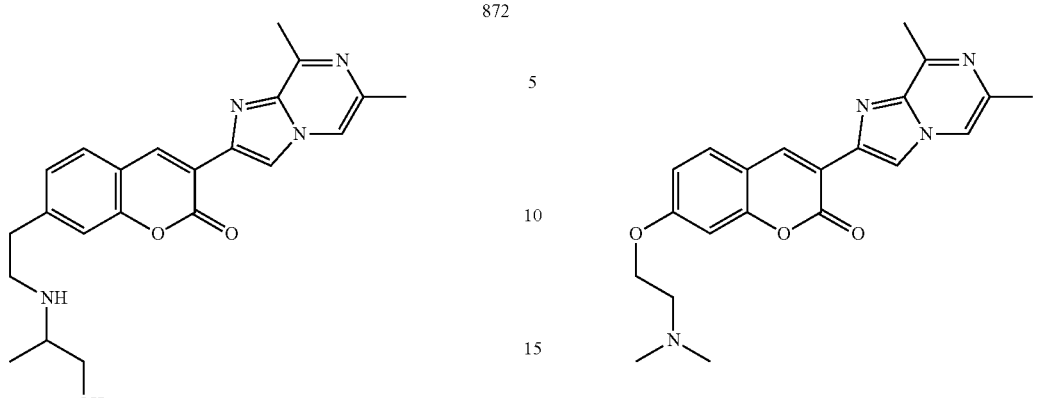 |
| 873 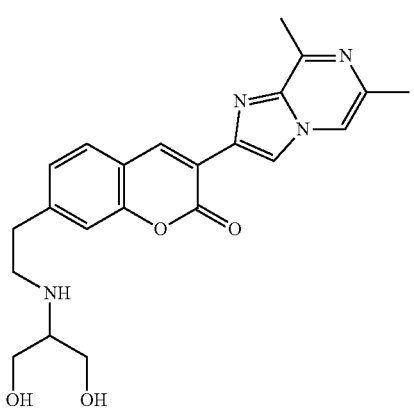 | 877 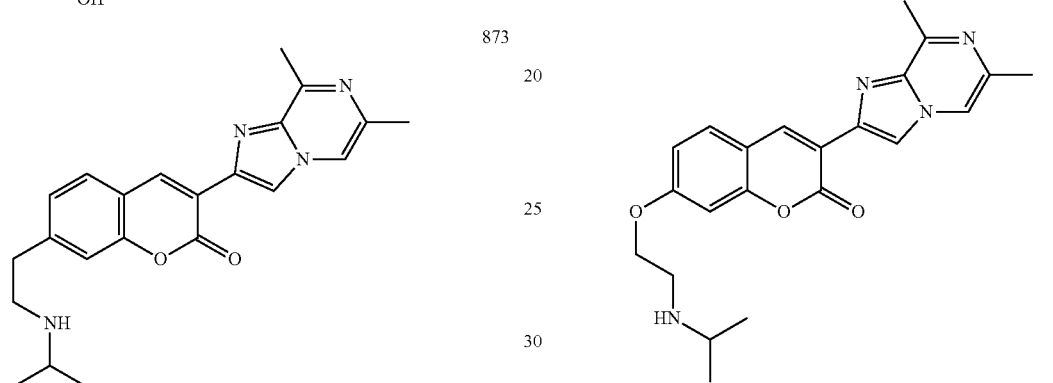 |
| 874 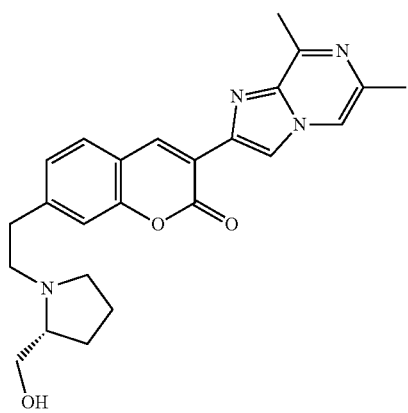 | 878 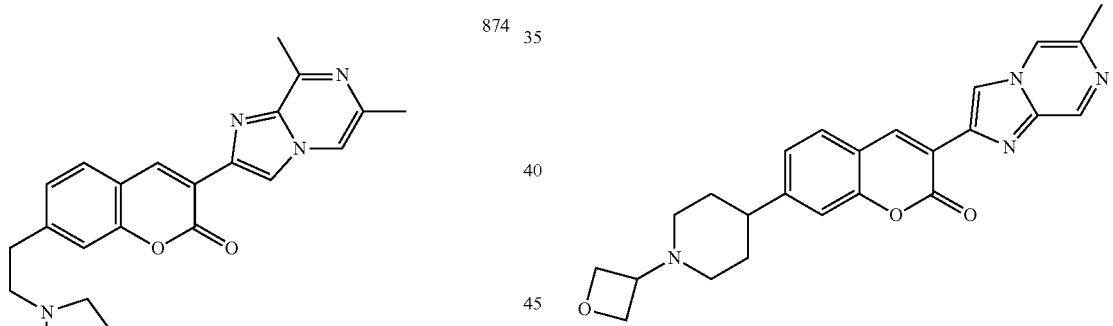 |
| 875 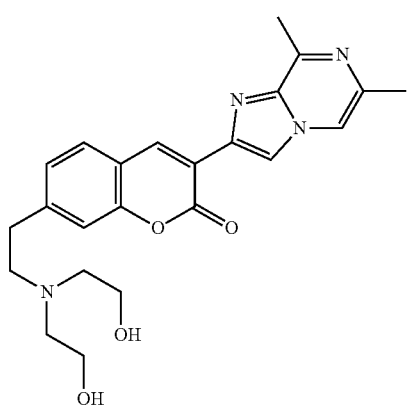 | 879 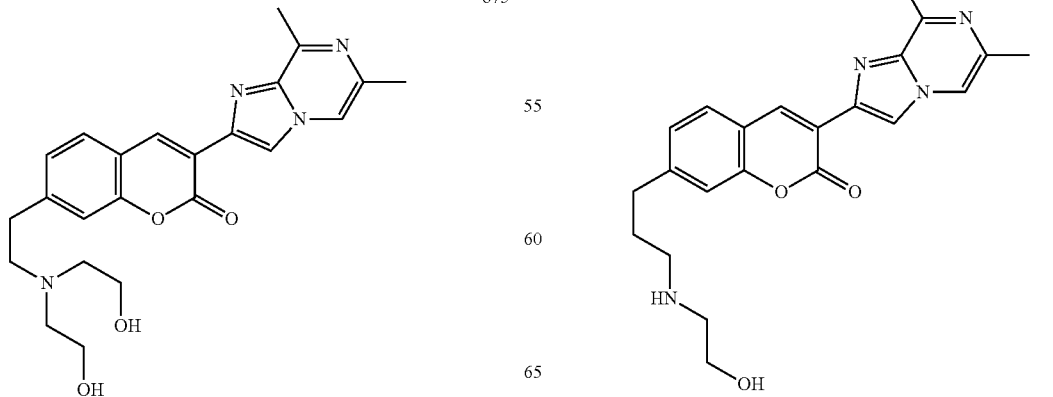 |

880
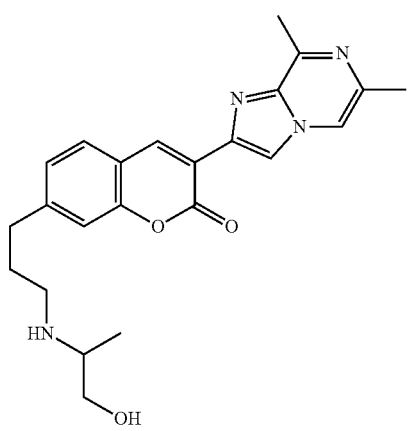
881
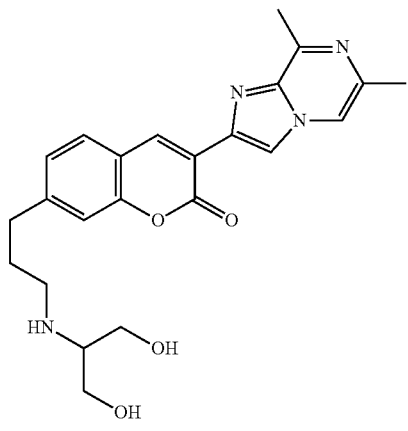
882
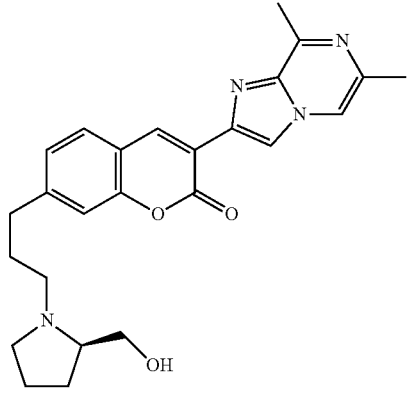
883
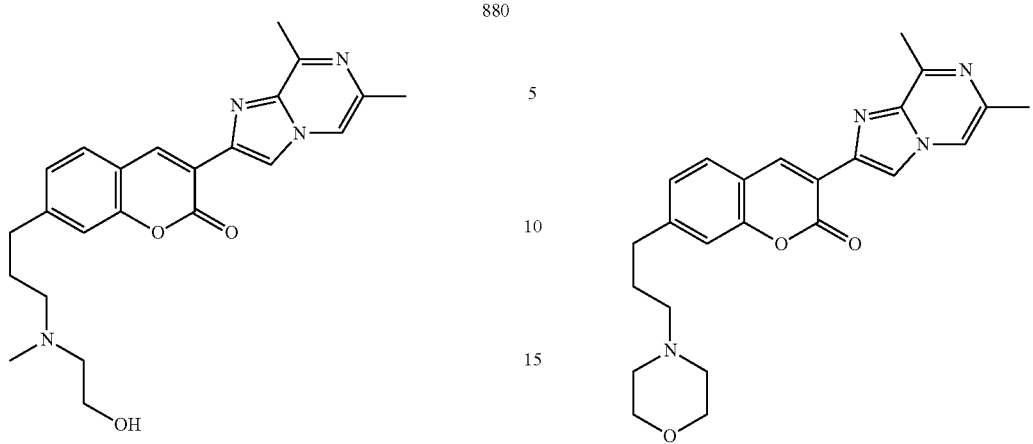
884
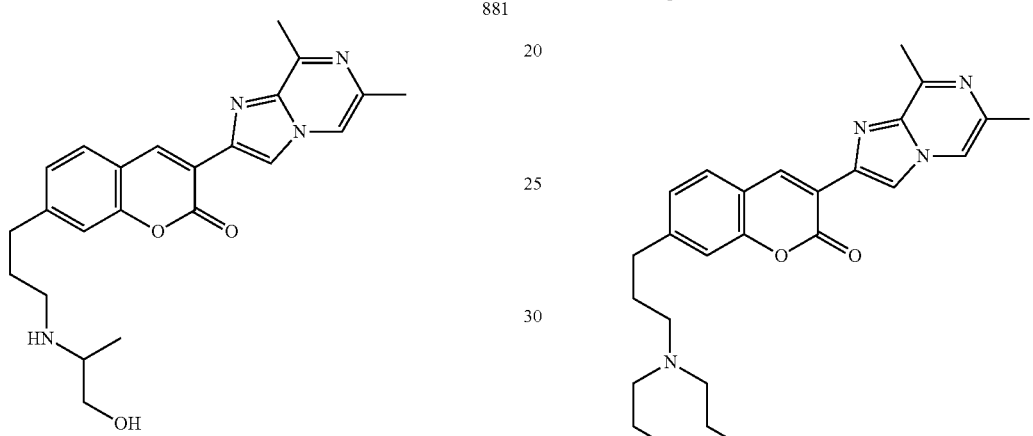
885
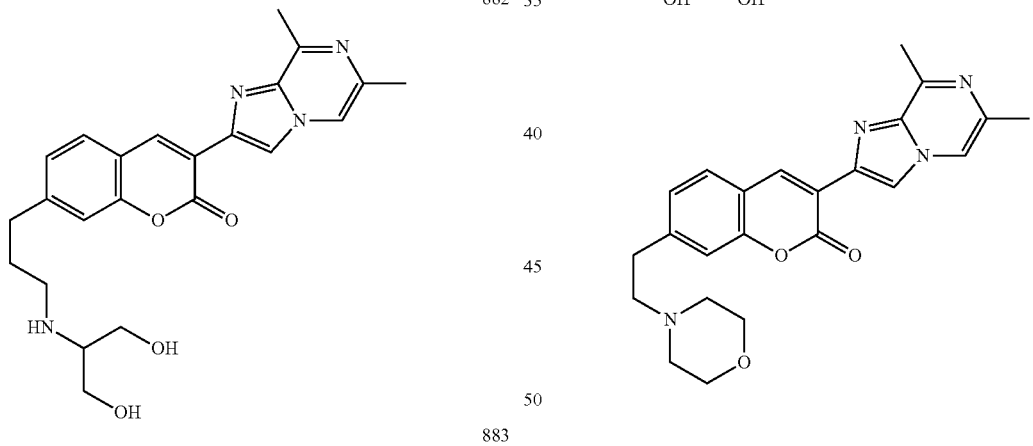
886
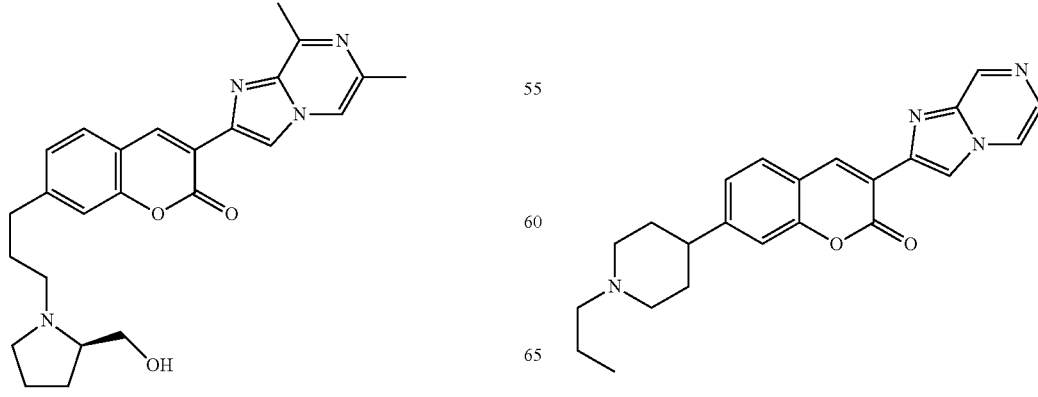
887

888
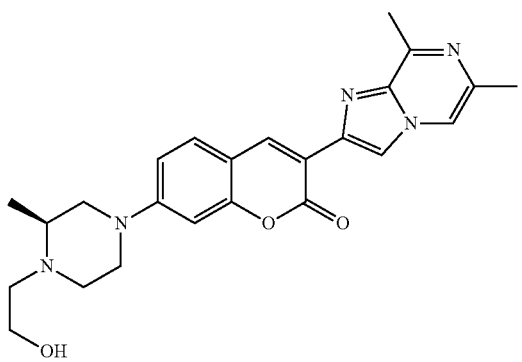
889
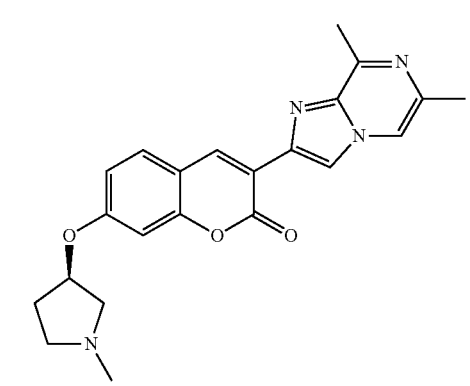
890
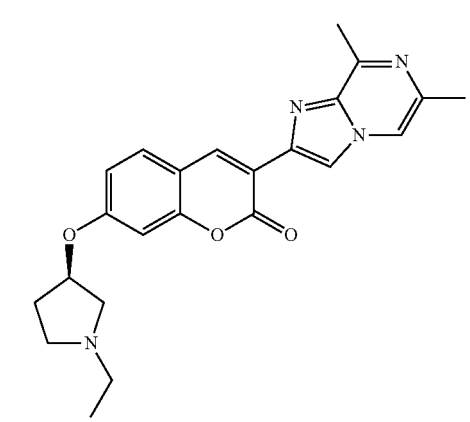
891
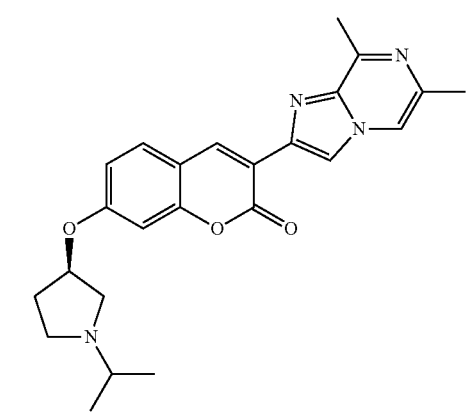
892
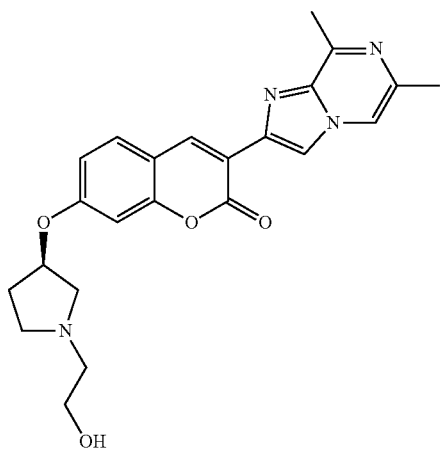
893
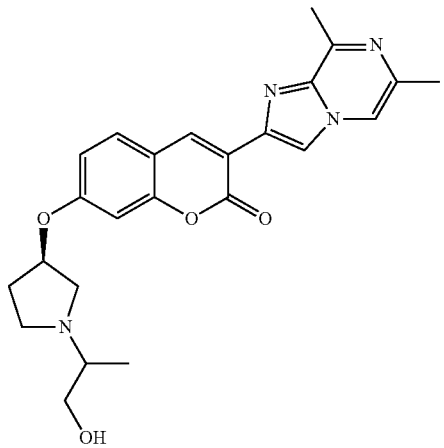
894
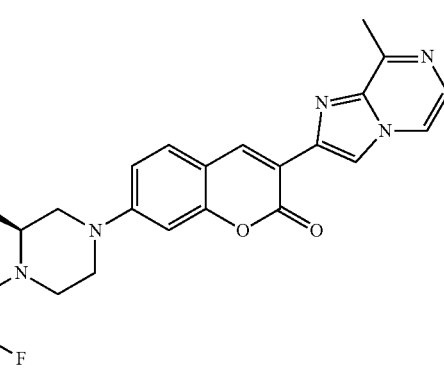

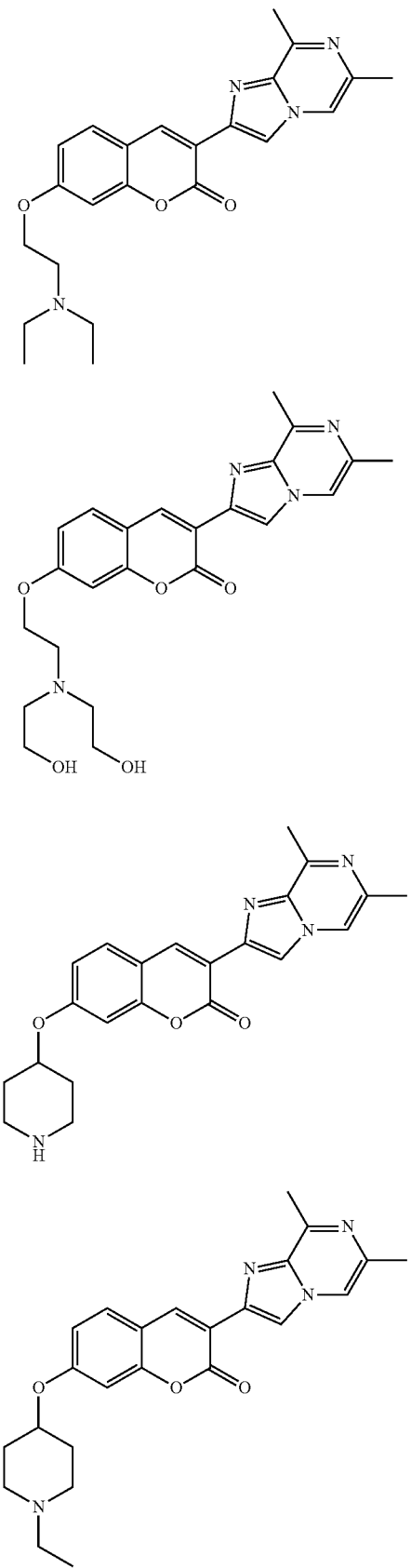
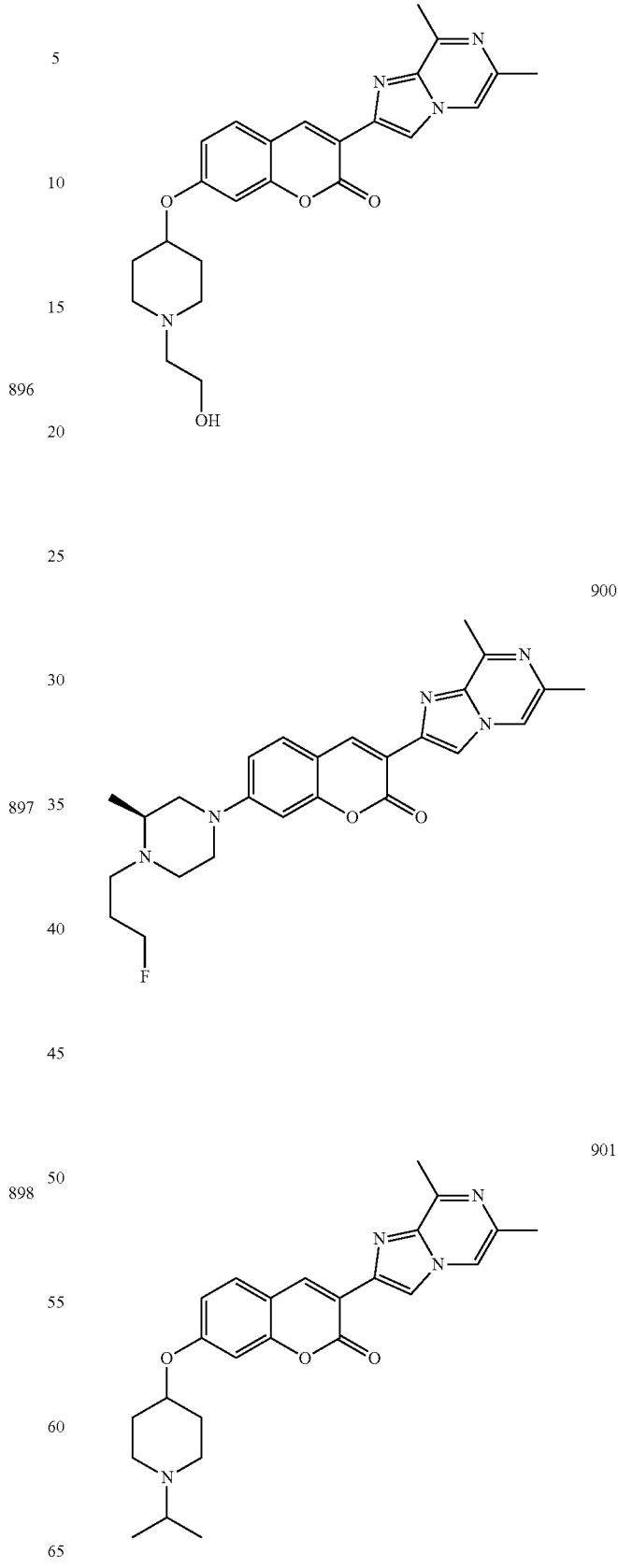

-continued
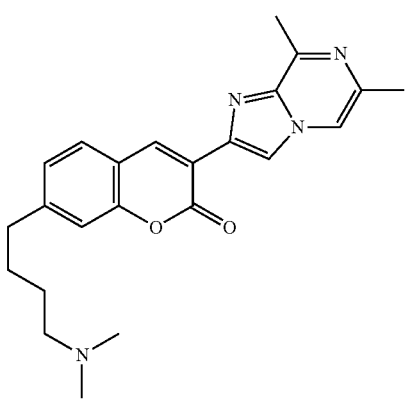
902
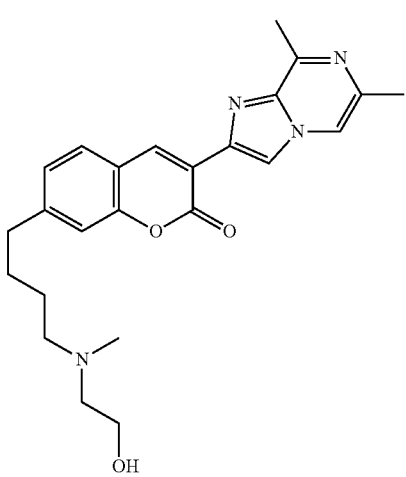
903
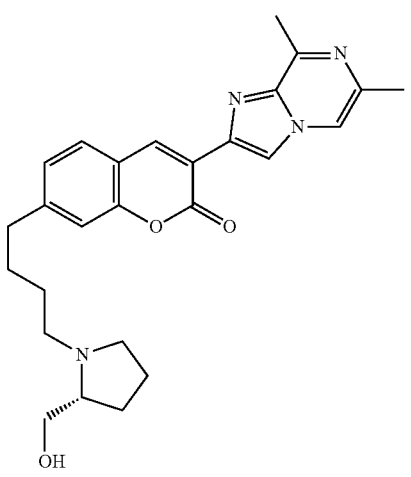
904
-continued
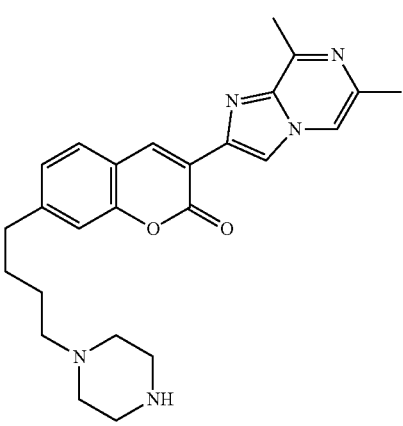
905
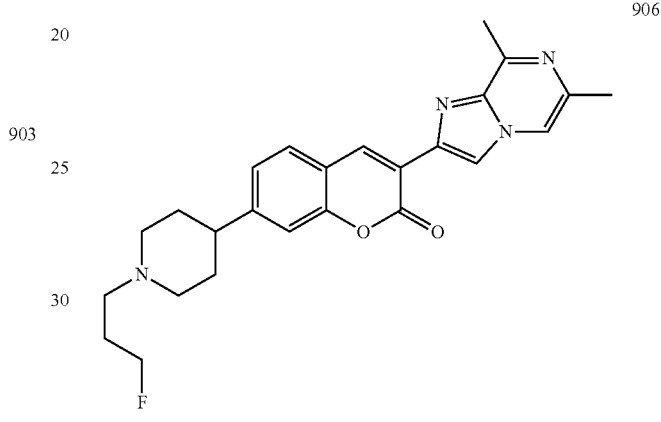
906
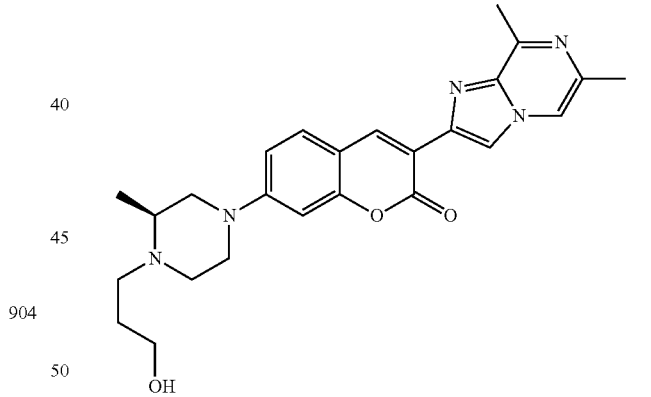
907
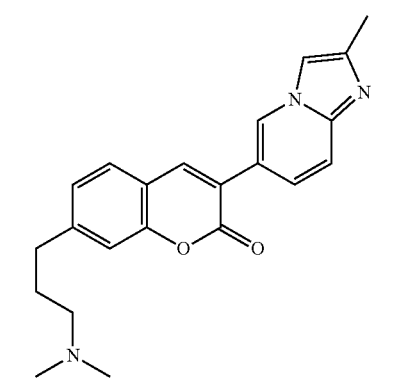
908

-continued
909
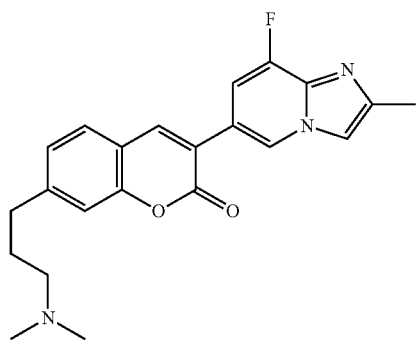
910
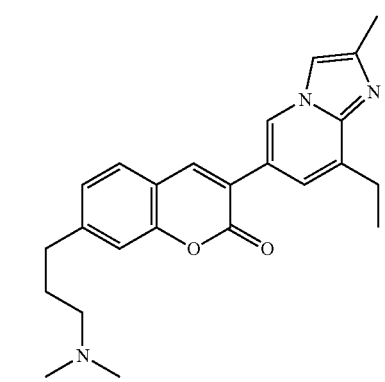
911
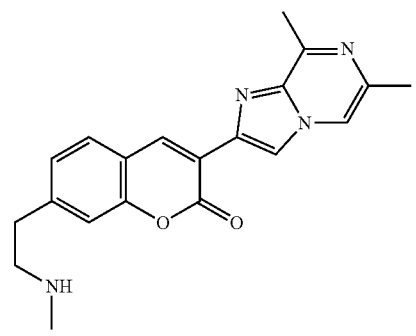
912
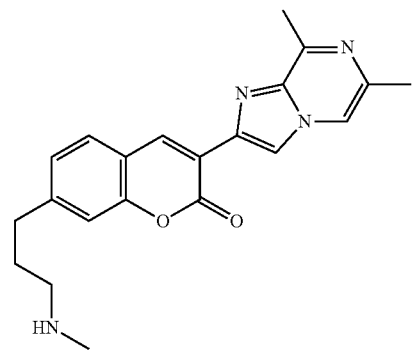
-continued
913
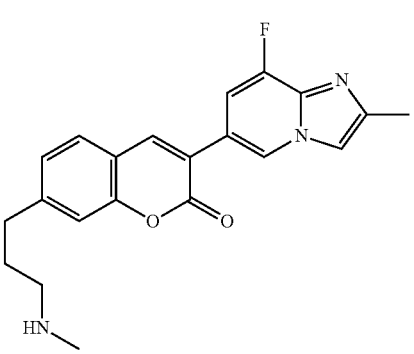
914
915
916
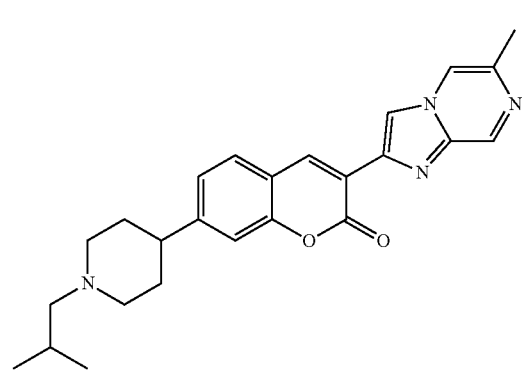

-continued
917
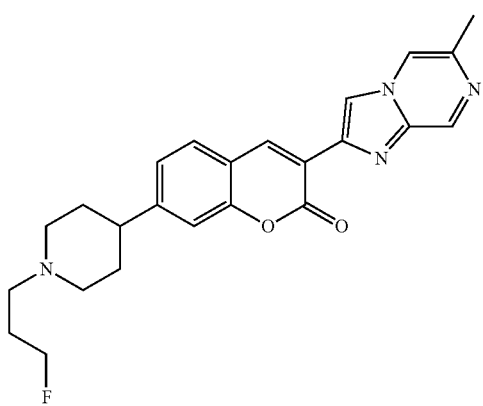
918
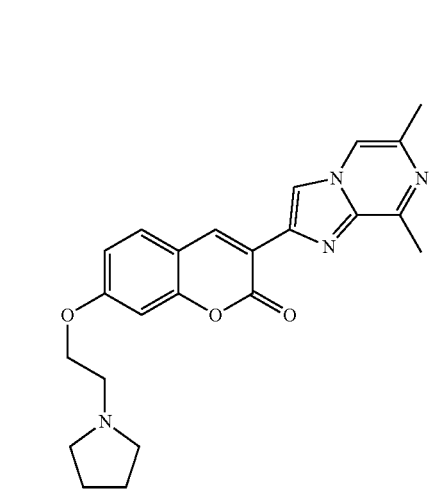
919
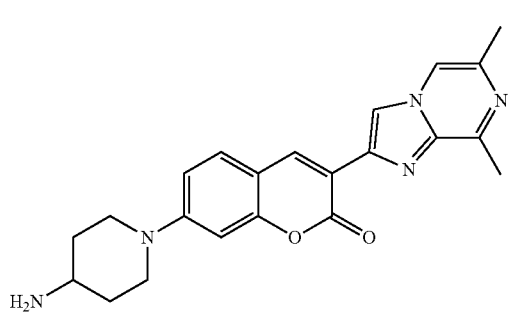
920
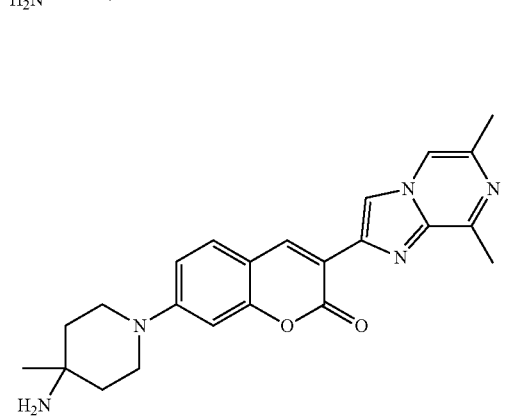
-continued
921
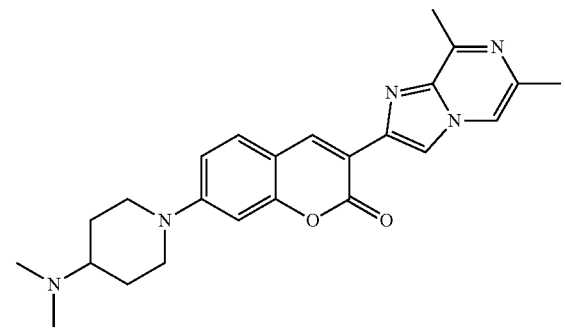
922
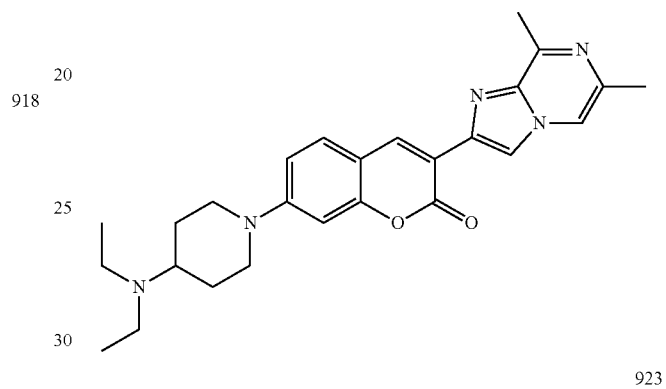
923
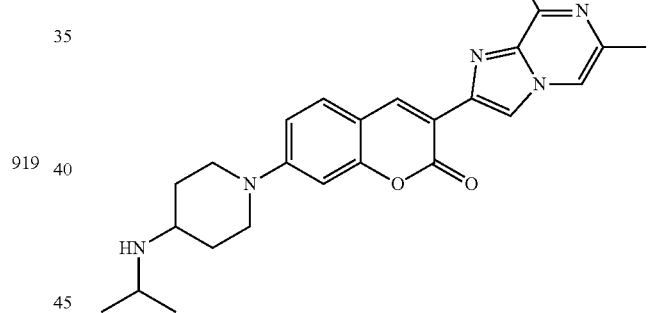
924
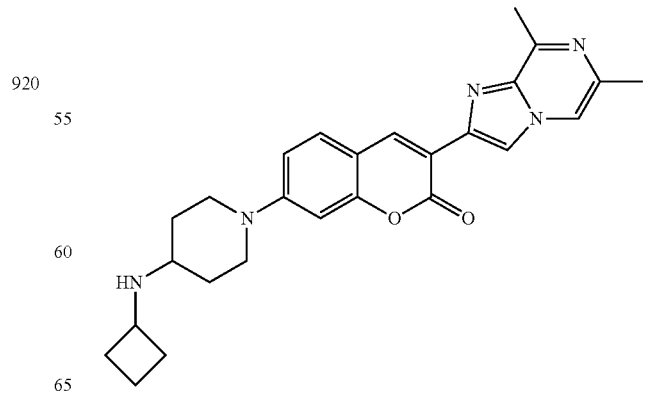

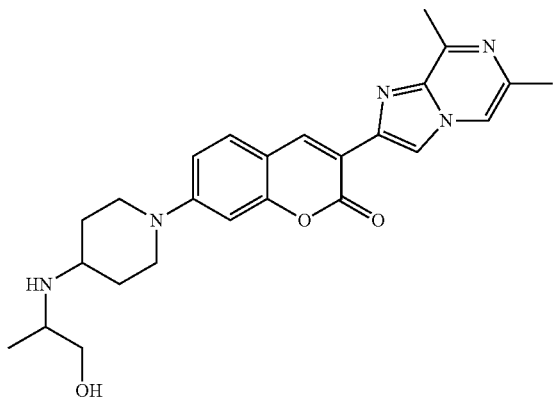
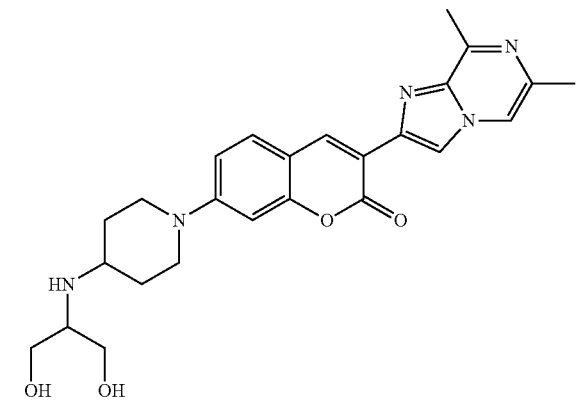

229
-continued
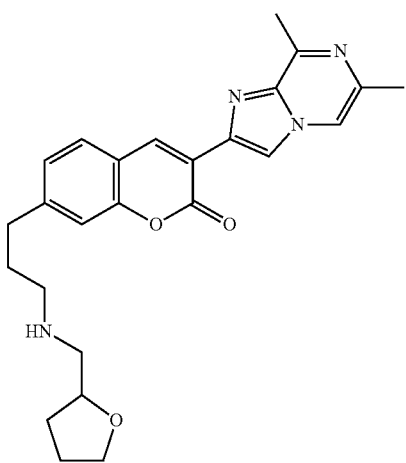
932
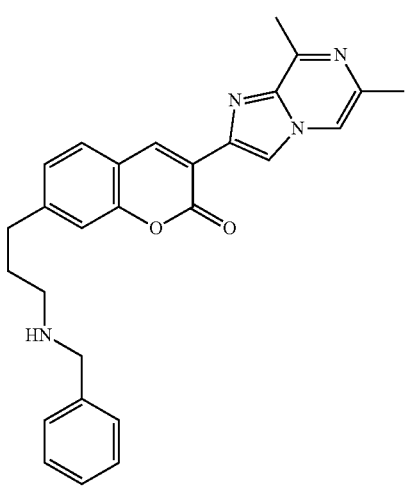
933
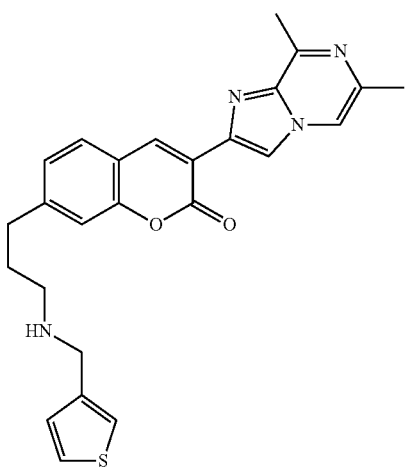
934
230
-continued
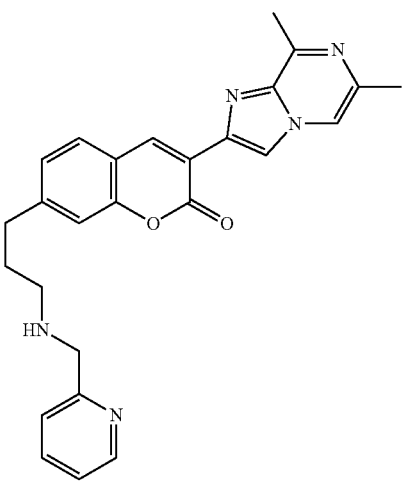
935
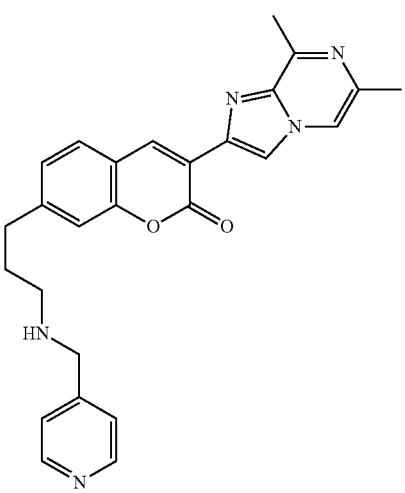
936
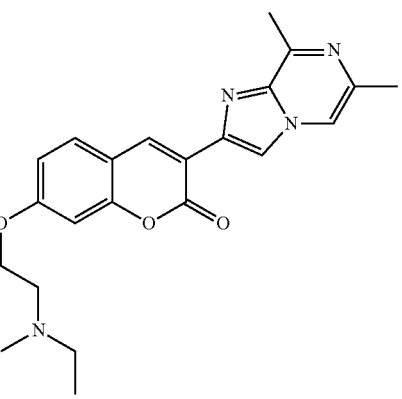
937

-continued
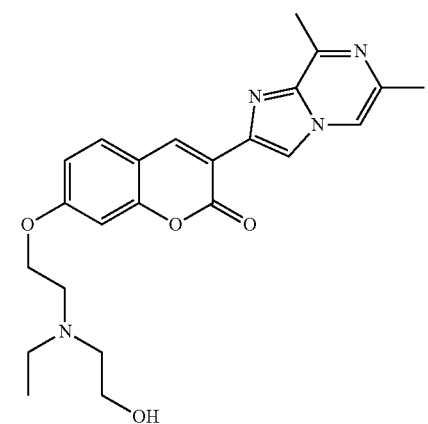
938
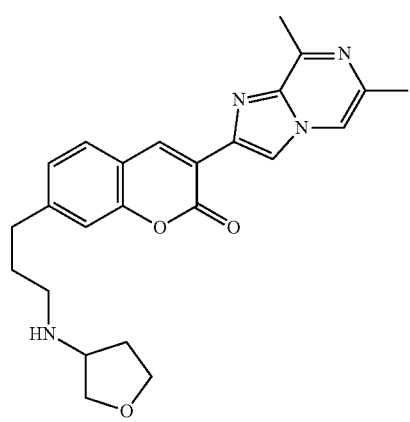
939
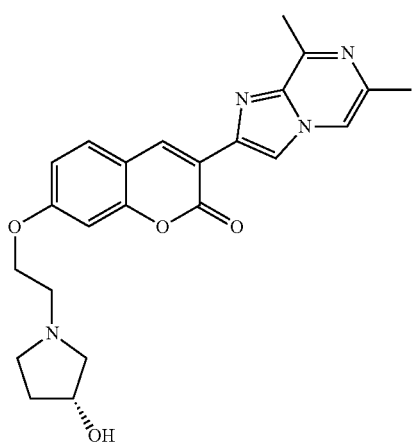
941
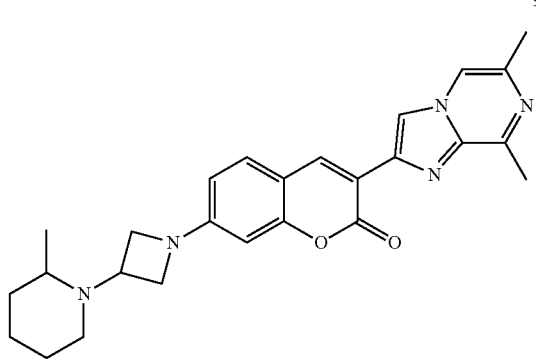
942
-continued
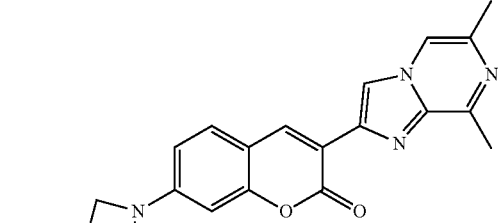
943
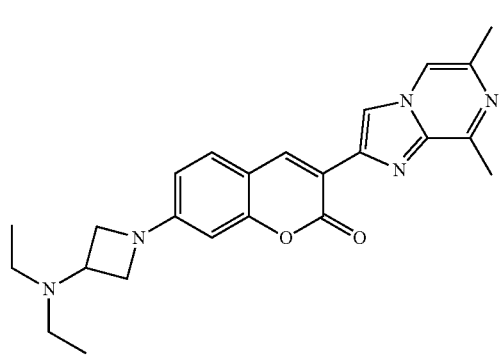
944
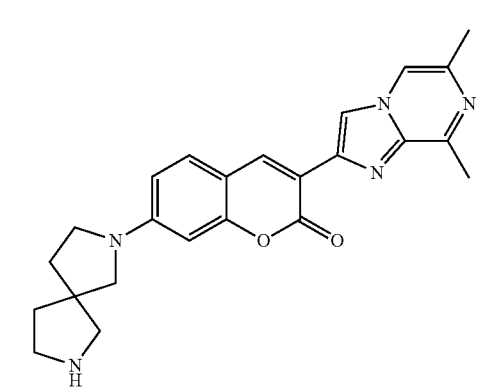
945
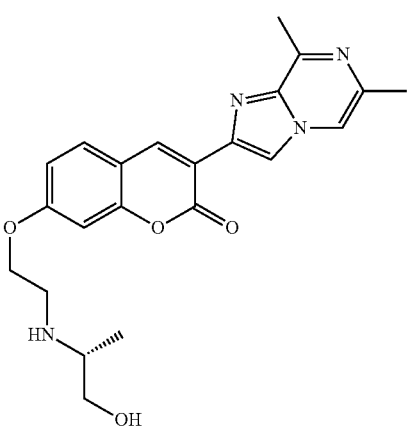
946

233
-continued
947
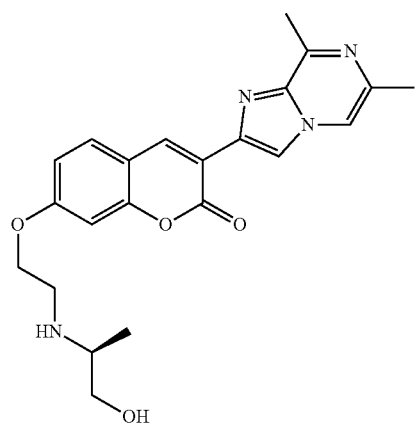
948
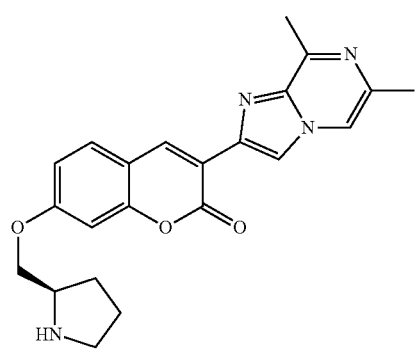
949
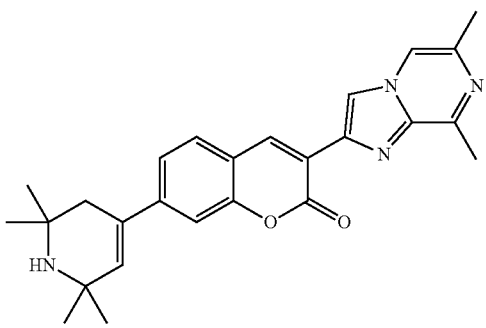
950
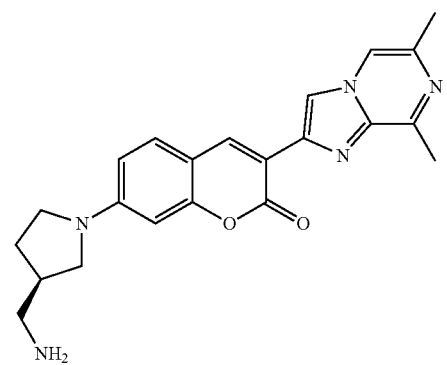
234
-continued
951
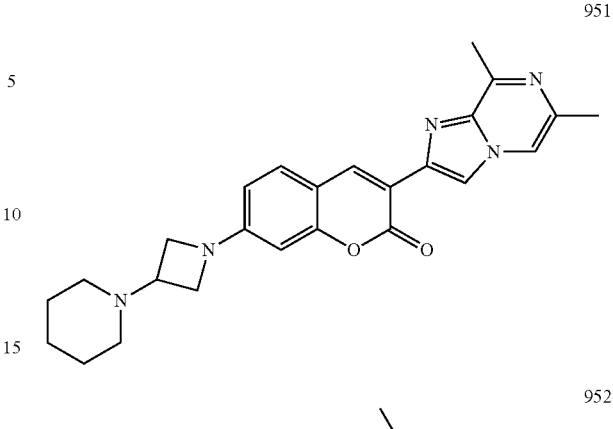
952
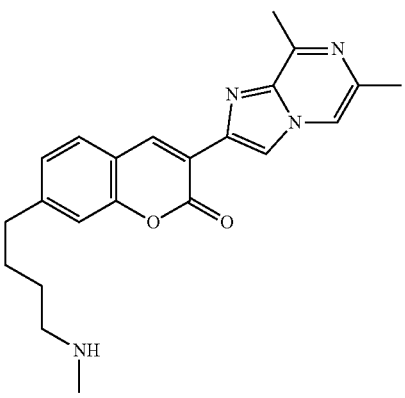
953
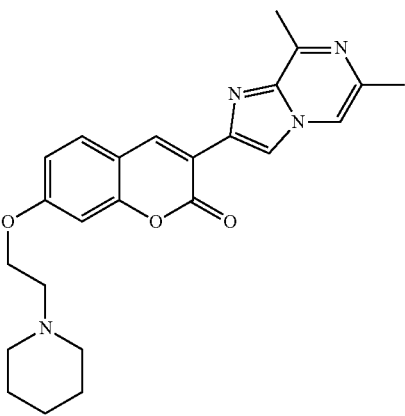
954
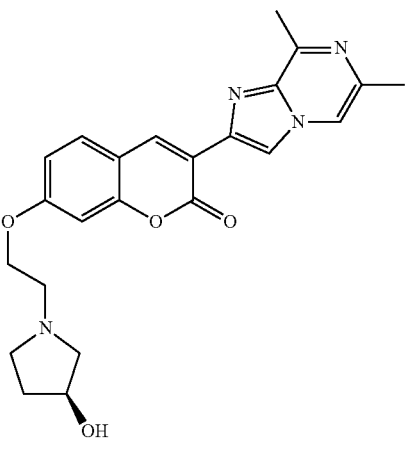

955
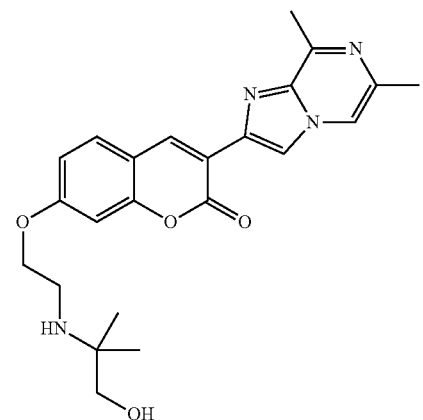
956
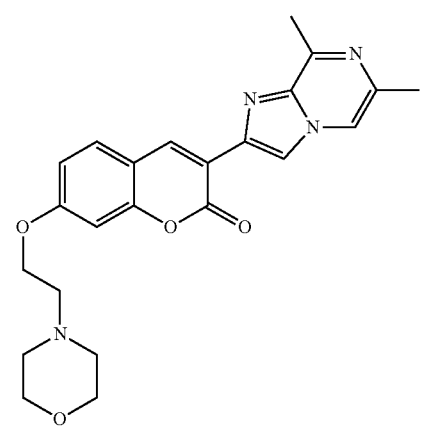
957
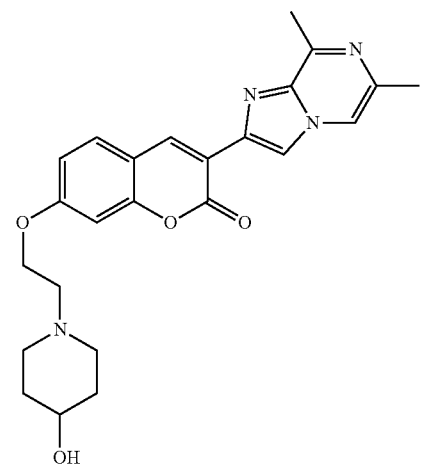
958
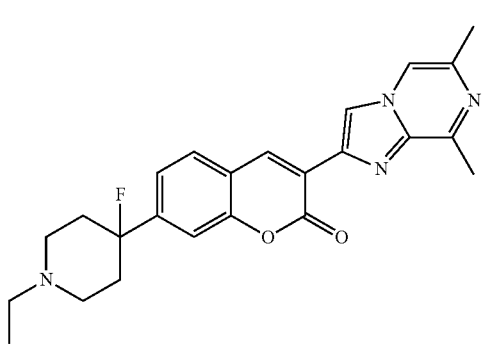
959
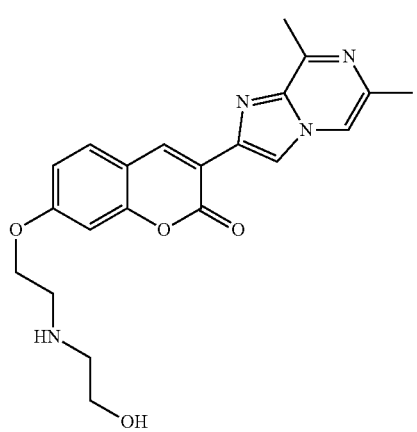
960
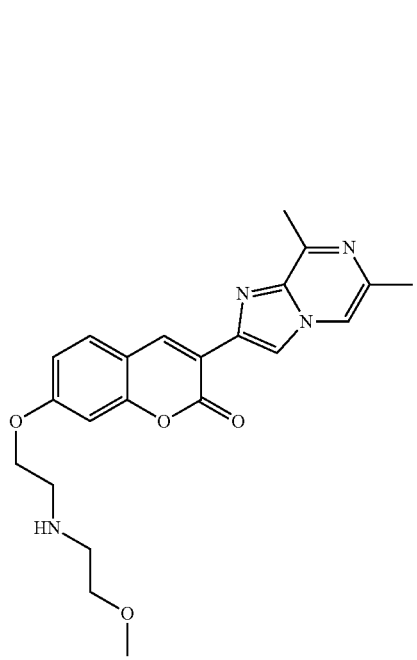
961
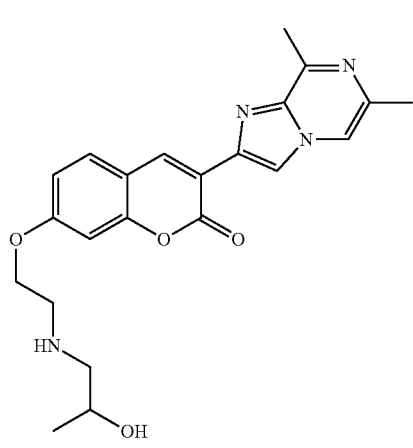

237
-continued
962
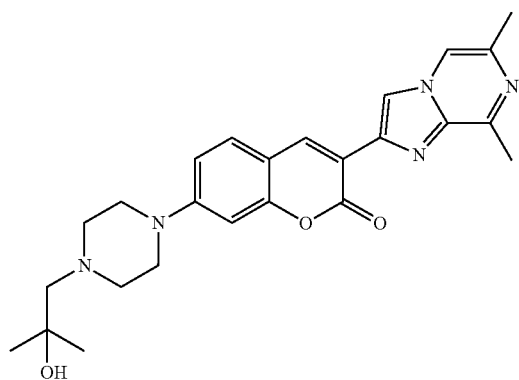
963
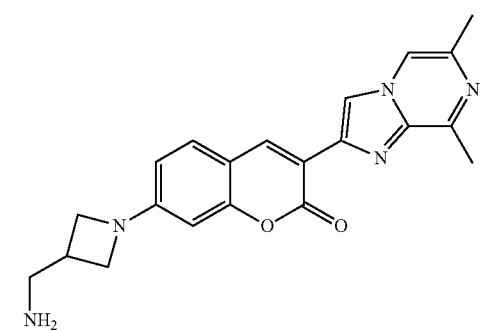
964
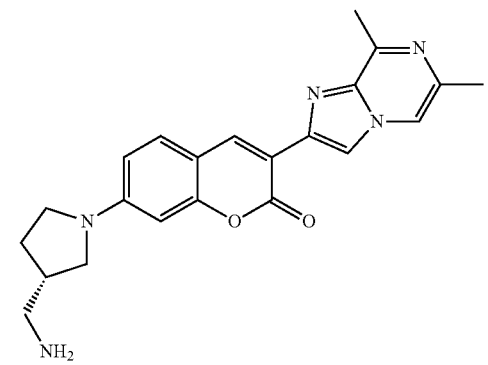
965
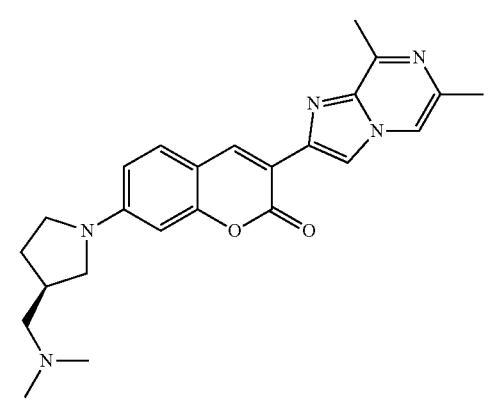
238
-continued
966
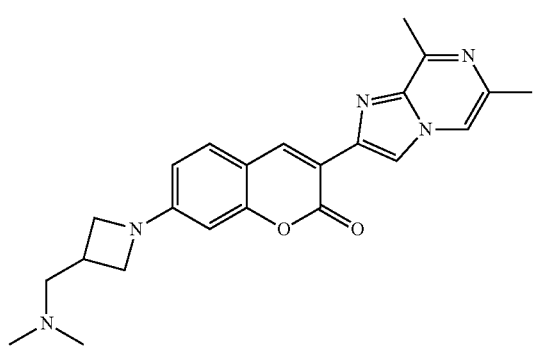
967
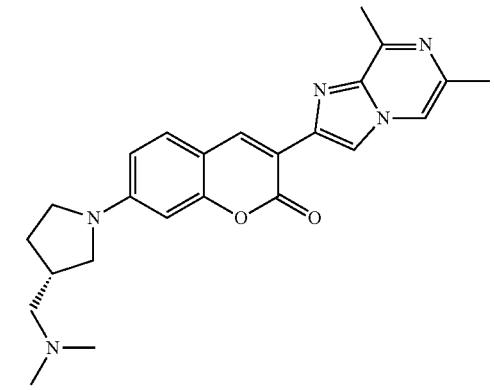
968
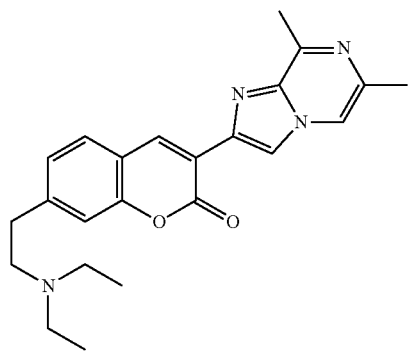
969
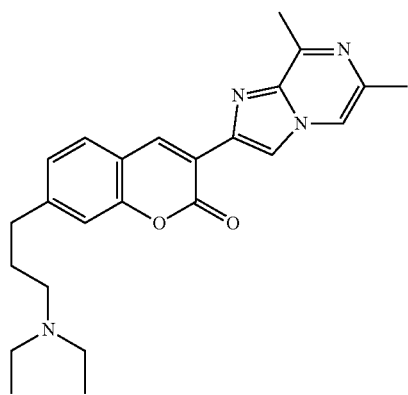

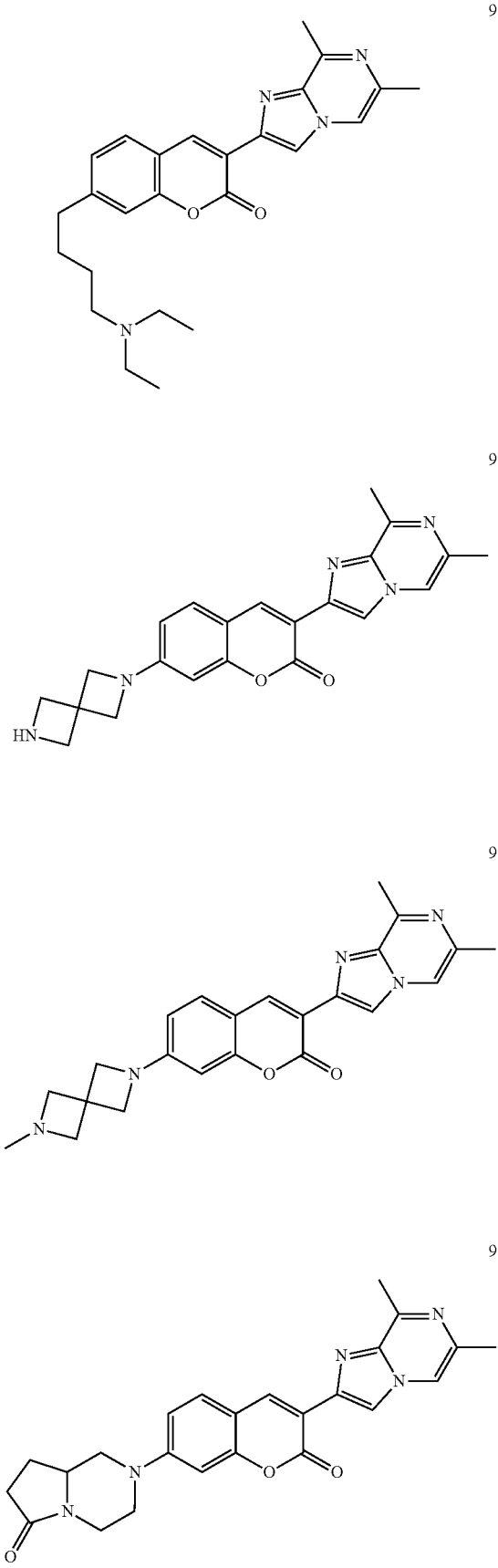

979

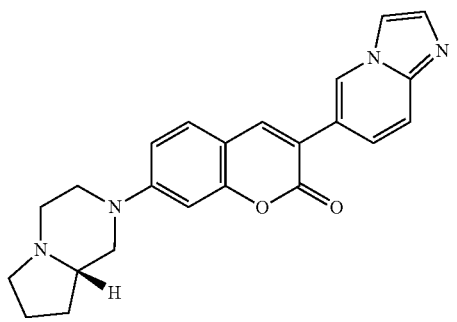

980

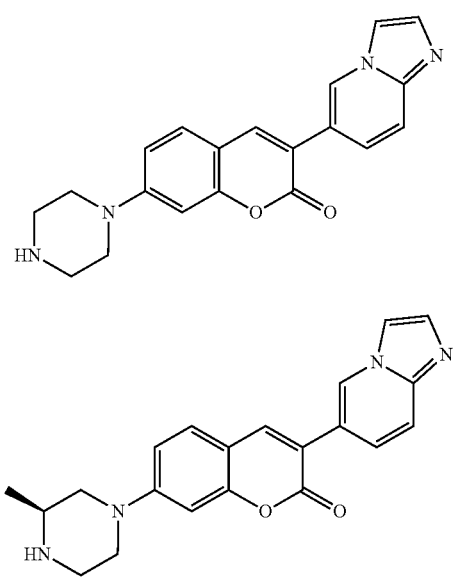

981

982

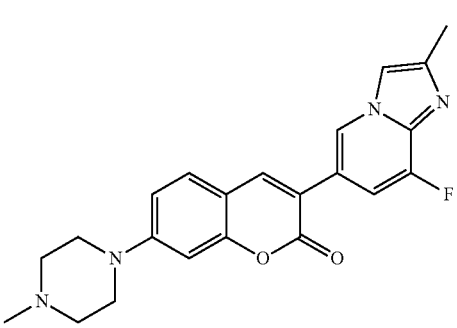

983

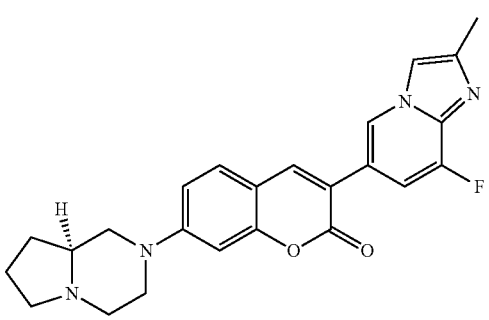

984

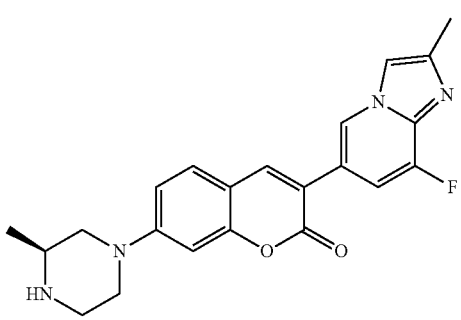

985

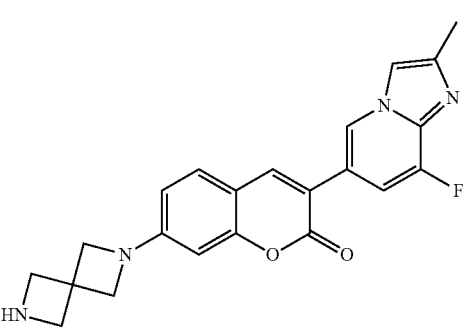

986

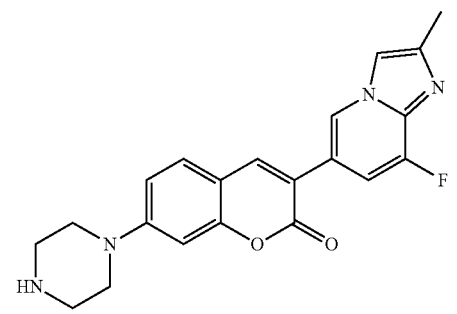

or a form thereof.

Terminology

The chemical terms used above and throughout the description herein, unless specifically defined otherwise, shall be understood by one of ordinary skill in the art to have the following indicated meanings.

As used herein, the term "$C_{1-8}$alkyl" generally refers to saturated hydrocarbon radicals having from one to eight carbon atoms in a straight or branched chain configuration, including, but not limited to, methyl, ethyl, n-propyl (also referred to as propyl or propanyl), isopropyl, n-butyl (also referred to as butyl or butanyl), isobutyl, sec-butyl, tert-butyl, n-pentyl (also referred to as pentyl or pentanyl), n-hexyl (also referred to as hexyl or hexanyl), n-heptyl (also referred to as heptyl or heptanyl), n-octyl and the like. In some embodiments, $C_{1-8}$alkyl includes, but is not limited to, $C_{1-6}$alkyl, $C_{1-4}$alkyl and the like. A $C_{1-8}$alkyl radical is optionally substituted with substituent species as described herein where allowed by available valences.

As used herein, the term "$C_{2-8}$alkenyl" generally refers to partially unsaturated hydrocarbon radicals having from two to eight carbon atoms in a straight or branched chain configuration and one or more carbon-carbon double bonds therein, including, but not limited to, ethenyl (also referred to as vinyl), allyl, propenyl and the like. In some embodiments, $C_{2-8}$alkenyl includes, but is not limited to, $C_{2-6}$alkenyl, $C_{2-4}$alkenyl and the like. A $C_{2-8}$alkenyl radical is optionally substituted with substituent species as described herein where allowed by available valences.

As used herein, the term "$C_{2-8}$alkynyl" generally refers to partially unsaturated hydrocarbon radicals having from two to eight carbon atoms in a straight or branched chain configuration and one or more carbon-carbon triple bonds therein, including, but not limited to, ethynyl, propynyl and the like. In some embodiments, $C_{2-8}$alkynyl includes, but is not limited to, $C_{2-6}$alkynyl, $C_{2-4}$alkynyl and the like. A $C_{2-8}$alkynyl radical is optionally substituted with substituent species as described herein where allowed by available valences.

As used herein, the term "$C_{1-8}$alkoxy" generally refers to saturated hydrocarbon radicals having from one to eight carbon atoms in a straight or branched chain configuration of the formula: —O—$C_{1-8}$alkyl, including, but not limited to, methoxy, ethoxy, n-propoxy, isopropoxy, n-butoxy, isobutoxy, sec-butoxy, tert-butoxy, n-pentoxy, n-hexoxy and the like. In some embodiments, $C_{1-8}$alkoxy includes, but is not limited to, $C_{1-6}$alkoxy, $C_{1-4}$alkoxy and the like. A $C_{1-8}$alkoxy radical is optionally substituted with substituent species as described herein where allowed by available valences.

As used herein, the term "$C_{3-14}$cycloalkyl" generally refers to a saturated monocyclic, bicyclic or polycyclic hydrocarbon radical, including, but not limited to, cyclopropyl, cyclobutyl, cyclopentyl, cyclohexyl, cycloheptyl, cyclooctyl, 1H-indanyl, indenyl, tetrahydro-naphthalenyl and the like. In some embodiments, $C_{3-14}$cycloalkyl includes, but is not limited to, $C_{3-8}$cycloalkyl, $C_{5-8}$cycloalkyl, $C_{3-10}$cycloalkyl and the like. A $C_{3-14}$cycloalkyl radical is optionally substituted with substituent species as described herein where allowed by available valences.

As used herein, the term "aryl" generally refers to a monocyclic, bicyclic or polycyclic aromatic carbon atom ring structure radical, including, but not limited to, phenyl, naphthyl, anthracenyl, fluorenyl, azulenyl, phenanthrenyl and the like. An aryl radical is optionally substituted with substituent species as described herein where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including, but not limited to, furanyl (also referred to as furyl), thienyl (also referred to as thiophenyl), pyrrolyl, 2H-pyrrolyl, 3H-pyrrolyl, pyrazolyl, 1H-pyrazolyl, imidazolyl, 1H-imidazolyl, isoxazolyl, isothiazolyl, oxazolyl, 1,3-thiazolyl, triazolyl (such as 1H-1,2,3-triazolyl and the like), oxadiazolyl (such as 1,2,4-oxadiazolyl, 1,3,4-oxadiazolyl and the like), thiadiazolyl, tetrazolyl (such as 1H-tetrazolyl, 2H-tetrazolyl and the like), pyridinyl (also referred to as pyridyl), pyrimidinyl, pyrazinyl, pyridazinyl, triazinyl, indolyl, indazolyl, 1H-indazolyl, 2H-indazolyl, indolizinyl, isoindolyl, benzofuranyl, benzothienyl (also referred to as benzothiophenyl), benzoimidazolyl, 1H-benzoimidazolyl, 1,3-benzothiazolyl, 1,3-benzoxazolyl (also referred to as 1,3-benzooxazolyl), purinyl, 9H-purinyl, quinolinyl, isoquinolinyl, quinazolinyl, quinoxalinyl, 1,3-diazinyl, 1,2-diazinyl, 1,2-diazolyl, 1,4-diazanaphthalenyl, acridinyl, furo[3,2-b]pyridinyl, furo[3,2-c]pyridinyl, furo[2,3-c]pyridinyl, 6H-thieno[2,3-b]pyrrolyl, thieno[3,2-c]pyridinyl, thieno[2,3-d]pyrimidinyl, 1H-pyrrolo[2,3-b]pyridinyl, 1H-pyrrolo[2,3-c]pyridinyl, 1H-pyrrolo[3,2-b]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, 3H-imidazo[4,5-b]pyridinyl, [1,3]oxazolo[4,5-b]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,2,4]triazolo[1,5-a]pyridinyl, [1,2,4]triazolo[4,3-a]pyridinyl and the like. A heteroaryl radical is optionally substituted on a carbon or nitrogen atom ring member with substituent species as described herein where allowed by available valences.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including, but not limited to, oxiranyl, oxetanyl, azetidinyl, tetrahydrofuranyl, pyrrolinyl, pyrrolidinyl, pyrazolinyl, pyrazolidinyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, pyranyl, dihydro-2H-pyranyl, thiopyranyl, 1,3-dioxanyl, 1,2,5,6-tetrahydropyridinyl, 1,2,3,6-tetrahydropyridinyl, piperidinyl, piperazinyl, morpholinyl, thiomorpholinyl, 1,4-diazepanyl, 1,3-benzodioxolyl (also referred to as benzo[d][1,3]dioxolyl), 1,4-benzodioxanyl, 2,3-dihydro-1,4-benzodioxinyl (also referred to as 2,3-dihydrobenzo[b][1,4]dioxinyl), hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, (3aR,6aR)-hexahydropyrrolo[3,4-b]pyrrol-(2H)-yl, hexahydropyrrolo[3,4-c]pyrrol-(1H)-yl, (3aR,6aS)-hexahydropyrrolo[3,4-c]pyrrol-(1H)-yl, (3aR,6aR)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(1H)-yl, (7R,8aS)-hexahydropyrrolo[1,2-a]pyrazin-(1H)-yl, (8aS)-hexahydropyrrolo[1,2-a]pyrazin-(1H)-yl, (8aR)-hexahydropyrrolo[1,2-a]pyrazin-(1H)-yl, (8aS)-octahydropyrrolo[1,2-a]pyrazin-(1H)-yl, (8aR)-octahydropyrrolo[1,2-a]pyrazin-(1H)-yl, hexahydropyrrolo[1,2-a]pyrazin-(2H)-one, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 8-azabicyclo[3.2.1]oct-2-enyl, 2,6-diazaspiro[3.3]heptyl, 2,7-diazaspiro[3.5]nonyl, 5,8-diazaspiro[3.5]nonyl, 2,7-diazaspiro[4.4]nonyl or 6,9-diazaspiro[4.5]decyl and the like. A heterocyclyl radical is optionally substituted on a carbon or nitrogen atom ring member with substituent species as described herein where allowed by available valences.

As used herein, the term "$C_{1-8}$alkoxy-$C_{1-8}$alkyl" refers to a radical of the formula: —$C_{1-8}$alkyl-O—$C_{1-8}$alkyl.

As used herein, the term "$C_{1-8}$alkoxy-$C_{1-8}$alkyl-amino" refers to a radical of the formula: —NH—$C_{1-8}$alkyl-O—$C_{1-8}$ alkyl.

As used herein, the term "($C_{1-8}$alkoxy-$C_{1-8}$alkyl)$_2$-amino" refers to a radical of the formula: —N($C_{1-8}$alkyl-O—$C_{1-8}$alkyl)$_2$.

As used herein, the term "($C_{1-8}$alkoxy-$C_{1-8}$alkyl)($C_{1-8}$alkyl)amino" refers to a radical of the formula: —N($C_{1-8}$alkyl)($C_{1-8}$alkyl-O—$C_{1-8}$alkyl).

As used herein, the term "$C_{1-8}$alkoxy-$C_{1-8}$alkyl-amino-$C_{1-8}$alkoxy" refers to a radical of the formula: —O—$C_{1-8}$alkyl-NH—$C_{1-8}$alkyl-O—$C_{1-8}$alkyl.

As used herein, the term "($C_{1-8}$alkoxy-$C_{1-8}$alkyl)$_2$-amino-$C_{1-8}$alkoxy" refers to a radical of the formula: —O—$C_{1-8}$alkyl-N($C_{1-8}$alkyl-O—$C_{1-8}$alkyl)$_2$.

As used herein, the term "($C_{1-8}$alkoxy-$C_{1-8}$alkyl)($C_{1-8}$alkyl)amino-$C_{1-8}$alkoxy" refers to a radical of the formula: —O—$C_{1-8}$alkyl-N($C_{1-8}$alkyl)($C_{1-8}$alkyl-O—$C_{1-8}$alkyl).

As used herein, the term "$C_{1-8}$alkoxy-$C_{1-8}$alkyl-amino-$C_{1-8}$alkyl" refers to a radical of the formula: —$C_{1-8}$alkyl-NH—$C_{1-8}$alkyl-O—$C_{1-8}$alkyl.

As used herein, the term "($C_{1-8}$alkoxy-$C_{1-8}$alkyl)$_2$-amino-$C_{1-8}$alkyl" refers to a radical of the formula: —$C_{1-8}$alkyl-N($C_{1-8}$alkyl-O—$C_{1-8}$alkyl)$_2$.

As used herein, the term "($C_{1-8}$alkoxy-$C_{1-8}$alkyl)($C_{1-8}$alkyl)amino-$C_{1-8}$alkyl" refers to a radical of the formula: —$C_{1-8}$alkyl-N($C_{1-8}$alkyl)($C_{1-8}$alkyl-O—$C_{1-8}$alkyl).

As used herein, the term "$C_{1-8}$alkoxy-carbonyl" refers to a radical of the formula: —C(O)—O—$C_{1-8}$alkyl.

As used herein, the term "$C_{1-8}$alkoxy-carbonyl-amino" refers to a radical of the formula: —NH—C(O)—O—$C_{1-8}$alkyl.

As used herein, the term "$C_{1-8}$alkyl-amino" refers to a radical of the formula: —NH—$C_{1-8}$alkyl.

As used herein, the term "($C_{1-8}$alkyl)$_2$-amino" refers to a radical of the formula: —N($C_{1-8}$alkyl)$_2$.

As used herein, the term "$C_{1-8}$alkyl-amino-$C_{2-8}$alkenyl" refers to a radical of the formula: —$C_{2-8}$alkenyl-NH—$C_{1-8}$alkyl.

As used herein, the term "($C_{1-8}$alkyl)$_2$-amino-$C_{2-8}$alkenyl" refers to a radical of the formula: —$C_{2-8}$alkenyl-N($C_{1-8}$alkyl)$_2$.

As used herein, the term "$C_{1-8}$alkyl-amino-$C_{1-8}$alkoxy" refers to a radical of the formula: —O—$C_{1-8}$alkyl-NH—$C_{1-8}$alkyl.

As used herein, the term "($C_{1-8}$alkyl)$_2$-amino-$C_{1-8}$alkoxy" refers to a radical of the formula: —O—$C_{1-8}$alkyl-N($C_{1-8}$alkyl)$_2$.

As used herein, the term "$C_{1-8}$alkyl-amino-$C_{1-8}$alkyl" refers to a radical of the formula: —$C_{1-8}$alkyl-NH—$C_{1-8}$alkyl.

As used herein, the term "($C_{1-8}$alkyl)$_2$-amino-$C_{1-8}$alkyl" refers to a radical of the formula: —$C_{1-8}$alkyl-N($C_{1-8}$alkyl)$_2$.

As used herein, the term "$C_{1-8}$alkyl-amino-$C_{1-8}$alkyl-amino" refers to a radical of the formula: —NH—$C_{1-8}$alkyl-NH—$C_{1-8}$alkyl.

As used herein, the term "($C_{1-8}$alkyl)$_2$-amino-$C_{1-8}$alkyl-amino" refers to a radical of the formula: —NH—$C_{1-8}$alkyl-N($C_{1-8}$alkyl)$_2$.

As used herein, the term "($C_{1-8}$alkyl-amino-$C_{1-8}$alkyl)$_2$-amino" refers to a radical of the formula: —N($C_{1-8}$alkyl-NH—$C_{1-8}$alkyl)$_2$.

As used herein, the term "($C_{1-8}$alkyl-amino-$C_{1-8}$alkyl)($C_{1-8}$alkyl)amino" refers to a radical of the formula: —N($C_{1-8}$alkyl)($C_{1-8}$alkyl-NH—$C_{1-8}$alkyl).

As used herein, the term "[($C_{1-8}$alkyl)$_2$-amino-$C_{1-8}$alkyl]($C_{1-8}$alkyl)amino" refers to a radical of the formula: —N($C_{1-8}$alkyl) [$C_{1-8}$alkyl-N($C_{1-8}$alkyl)$_2$].

As used herein, the term "$C_{1-8}$alkyl-amino-$C_{2-8}$alkynyl" refers to a radical of the formula: —$C_{2-8}$alkynyl-NH—$C_{1-8}$alkyl.

As used herein, the term "($C_{1-8}$alkyl)$_2$-amino-$C_{2-8}$alkynyl" refers to a radical of the formula: —$C_{2-8}$alkynyl-N($C_{1-8}$alkyl)$_2$.

As used herein, the term "$C_{1-8}$alkyl-carbonyl" refers to a radical of the formula: —C(O)—$C_{1-8}$alkyl.

As used herein, the term "$C_{1-8}$alkyl-carbonyl-amino" refers to a radical of the formula: —NH—C(O)—$C_{1-8}$alkyl.

As used herein, the term "$C_{1-8}$alkyl-thio" refers to a radical of the formula: —S—$C_{1-8}$alkyl.

As used herein, the term "amino-$C_{2-8}$alkenyl" refers to a radical of the formula: —$C_{2-8}$alkenyl-NH$_2$.

As used herein, the term "amino-$C_{1-8}$alkoxy" refers to a radical of the formula: —O—$C_{1-8}$alkyl-NH$_2$.

As used herein, the term "amino-$C_{1-8}$alkyl" refers to a radical of the formula: —$C_{1-8}$alkyl-NH$_2$.

As used herein, the term "amino-$C_{1-8}$alkyl-amino" refers to a radical of the formula: —NH—$C_{1-8}$alkyl-NH$_2$.

As used herein, the term "(amino-$C_{1-8}$alkyl)$_2$-amino" refers to a radical of the formula: —N($C_{1-8}$alkyl-NH$_2$)$_2$.

As used herein, the term "(amino-$C_{1-8}$alkyl)($C_{1-8}$alkyl)amino" refers to a radical of the formula: —N($C_{1-8}$alkyl)($C_{1-8}$alkyl-NH$_2$).

As used herein, the term "amino-$C_{2-8}$alkynyl" refers to a radical of the formula: —$C_{2-8}$alkynyl-NH$_2$.

As used herein, the term "aryl-$C_{1-8}$alkoxy-carbonyl" refers to a radical of the formula: —C(O)—O—$C_{1-8}$alkyl-aryl.

As used herein, the term "aryl-$C_{1-8}$alkyl" refers to a radical of the formula: —$C_{1-8}$alkyl-aryl.

As used herein, the term "aryl-$C_{1-8}$alkyl-amino" refers to a radical of the formula: —NH—$C_{1-8}$alkyl-aryl.

As used herein, the term "(aryl-$C_{1-8}$alkyl)$_2$-amino" refers to a radical of the formula: —N($C_{1-8}$alkyl-aryl)$_2$.

As used herein, the term "(aryl-$C_{1-8}$alkyl)($C_{1-8}$alkyl)amino" refers to a radical of the formula: —N($C_{1-8}$alkyl)($C_{1-8}$alkyl-aryl).

As used herein, the term "aryl-$C_{1-8}$alkyl-amino-$C_{1-8}$alkyl" refers to a radical of the formula: —$C_{1-8}$alkyl-NH—$C_{1-8}$alkyl-aryl.

As used herein, the term "(aryl-$C_{1-8}$alkyl)$_2$-amino-$C_{1-8}$alkyl" refers to a radical of the formula: —$C_{1-8}$alkyl-N($C_{1-8}$alkyl-aryl)$_2$.

As used herein, the term "(aryl-$C_{1-8}$alkyl)($C_{1-8}$alkyl)amino-$C_{1-8}$alkyl" refers to a radical of the formula: —$C_{1-8}$alkyl-N($C_{1-8}$alkyl)($C_{1-8}$alkyl-aryl).

As used herein, the term "aryl-amino" refers to a radical of the formula: —NH-aryl.

As used herein, the term "aryl-amino-carbonyl" refers to a radical of the formula: —C(O)—NH-aryl.

As used herein, the term "aryl-sulfonyloxy-$C_{1-8}$alkyl" refers to a radical of the formula: —$C_{1-8}$alkyl-O—SO$_2$-aryl.

As used herein, the term "benzoxy-carbonyl" refers to a radical of the formula: —C(O)O—CH$_2$-phenyl.

As used herein, the term "$C_{3-14}$cycloalkyl-$C_{1-8}$alkyl" refers to a radical of the formula: —$C_{1-8}$alkyl-$C_{3-14}$cycloalkyl.

As used herein, the term "$C_{3-14}$cycloalkyl-amino" refers to a radical of the formula: —NH—$C_{3-14}$cycloalkyl.

As used herein, the term "$C_{3-14}$cycloalkyl-oxy" refers to a radical of the formula: —O—$C_{3-14}$cycloalkyl.

As used herein, the term "halo" or "halogen" generally refers to a halogen atom radical, including fluoro, chloro, bromo and iodo.

As used herein, the term "halo-$C_{1-8}$alkoxy" refers to a radical of the formula: —O—$C_{1-8}$alkyl-halo, wherein $C_{1-8}$alkyl is partially or completely substituted with one or more halogen atoms where allowed by available valences.

As used herein, the term "halo-$C_{1-8}$alkyl" refers to a radical of the formula: —$C_{1-8}$alkyl-halo, wherein $C_{1-8}$alkyl is partially or completely substituted with one or more halogen atoms where allowed by available valences.

As used herein, the term "halo-$C_{1-8}$alkyl-amino" refers to a radical of the formula: —NH—$C_{1-8}$alkyl-halo.

As used herein, the term "(halo-$C_{1-8}$alkyl)($C_{1-8}$alkyl)amino" refers to a radical of the formula: —N($C_{1-8}$alkyl)($C_{1-8}$alkyl-halo).

As used herein, the term "(halo-$C_{1-8}$alkyl)$_2$-amino" refers to a radical of the formula: —N($C_{1-8}$alkyl-halo)$_2$.

As used herein, the term "heteroaryl-$C_{1-8}$alkoxy" refers to a radical of the formula: —O—$C_{1-8}$alkyl-heteroaryl.

As used herein, the term "heteroaryl-$C_{1-8}$alkyl" refers to a radical of the formula: —$C_{1-8}$alkyl-heteroaryl.

As used herein, the term "heteroaryl-$C_{1-8}$alkyl-amino" refers to a radical of the formula: —NH—$C_{1-8}$alkyl-heteroaryl.

As used herein, the term "(heteroaryl-$C_{1-8}$alkyl)$_2$-amino" refers to a radical of the formula: —N($C_{1-8}$alkyl-heteroaryl)$_2$.

As used herein, the term "(heteroaryl-$C_{1-8}$alkyl)($C_{1-8}$alkyl)amino" refers to a radical of the formula: —N($C_{1-8}$alkyl)($C_{1-8}$alkyl-heteroaryl).

As used herein, the term "heteroaryl-$C_{1-8}$alkyl-amino-$C_{1-8}$alkyl" refers to a radical of the formula: —$C_{1-8}$alkyl-NH—$C_{1-8}$alkyl-heteroaryl.

As used herein, the term "(heteroaryl-$C_{1-8}$alkyl)$_2$-amino-$C_{1-8}$alkyl" refers to a radical of the formula: —$C_{1-8}$alkyl-N($C_{1-8}$alkyl-heteroaryl)$_2$.

As used herein, the term "(heteroaryl-$C_{1-8}$alkyl($C_{1-8}$alkyl)amino-$C_{1-8}$alkyl" refers to a radical of the formula: —$C_{1-8}$alkyl-N($C_{1-8}$alkyl)($C_{1-8}$alkyl-heteroaryl).

As used herein, the term "heteroaryl-amino" refers to a radical of the formula: —NH-heteroaryl.

As used herein, the term "heterocyclyl-$C_{1-8}$alkoxy" refers to a radical of the formula: —O—$C_{1-8}$alkyl-heterocyclyl.

As used herein, the term "heterocyclyl-$C_{1-8}$alkyl" refers to a radical of the formula: —$C_{1-8}$alkyl-heterocyclyl.

As used herein, the term "(heterocyclyl)($C_{1-8}$alkyl)amino" refers to a radical of the formula: —N($C_{1-8}$alkyl)(heterocyclyl).

As used herein, the term "heterocyclyl-$C_{1-8}$alkyl-amino" refers to a radical of the formula: —NH—$C_{1-8}$alkyl-heterocyclyl.

As used herein, the term "(heterocyclyl-$C_{1-8}$alkyl)$_2$-amino" refers to a radical of the formula: —N($C_{1-8}$alkyl-heterocyclyl)$_2$.

As used herein, the term "(heterocyclyl-$C_{1-8}$alkyl)($C_{1-8}$alkyl)amino" refers to a radical of the formula: —N($C_{1-8}$alkyl)($C_{1-8}$alkyl-heterocyclyl).

As used herein, the term "heterocyclyl-$C_{1-8}$alkyl-amino-$C_{1-8}$alkyl" refers to a radical of the formula: —$C_{1-8}$alkyl-NH—$C_{1-8}$alkyl-heterocyclyl.

As used herein, the term "(heterocyclyl-$C_{1-8}$alkyl)$_2$-amino-$C_{1-8}$alkyl" refers to a radical of the formula: —$C_{1-8}$alkyl-N($C_{1-8}$alkyl-heterocyclyl)$_2$.

As used herein, the term "(heterocyclyl-$C_{1-8}$alkyl)($C_{1-8}$alkyl)amino-$C_{1-8}$alkyl" refers to a radical of the formula: —$C_{1-8}$alkyl-N($C_{1-8}$alkyl)($C_{1-8}$alkyl-heterocyclyl).

As used herein, the term "heterocyclyl-amino" refers to a radical of the formula: —NH-heterocyclyl.

As used herein, the term "heterocyclyl-amino-$C_{1-8}$alkyl" refers to a radical of the formula: —$C_{1-8}$alkyl-NH-heterocyclyl.

As used herein, the term "heterocyclyl-carbonyl" refers to a radical of the formula: —C(O)-heterocyclyl.

As used herein, the term "heterocyclyl-carbonyl-oxy" refers to a radical of the formula: —O—C(O)-heterocyclyl.

As used herein, the term "heterocyclyl-oxy" refers to a radical of the formula: —O-heterocyclyl.

As used herein, the term "hydroxy" refers to a radical of the formula: —OH.

As used herein, the term "hydroxy-$C_{1-8}$alkoxy-$C_{1-8}$alkyl" refers to a radical of the formula: —$C_{1-8}$alkyl-O—$C_{1-8}$alkyl-OH.

As used herein, the term "hydroxy-$C_{1-8}$alkyl" refers to a radical of the formula: —$C_{1-8}$alkyl-OH, wherein $C_{1-8}$alkyl is partially or completely substituted with one or more hydroxy radicals where allowed by available valences.

As used herein, the term "(hydroxy-$C_{1-8}$alkyl)($C_{1-8}$alkyl)amino" refers to a radical of the formula: —N($C_{1-8}$alkyl)($C_{1-8}$alkyl-OH).

As used herein, the term "hydroxy-$C_{1-8}$alkyl-amino" refers to a radical of the formula: —NH—$C_{1-8}$alkyl-OH.

As used herein, the term "(hydroxy-$C_{1-8}$alkyl)$_2$-amino" refers to a radical of the formula: —N($C_{1-8}$alkyl-OH)$_2$.

As used herein, the term "hydroxy-$C_{1-8}$alkyl-amino-$C_{1-8}$alkyl" refers to a radical of the formula: —$C_{1-8}$alkyl-NH—$C_{1-8}$alkyl-OH.

As used herein, the term "(hydroxy-$C_{1-8}$alkyl)($C_{1-8}$alkyl)amino-$C_{1-8}$alkyl" refers to a radical of the formula: —$C_{1-8}$alkyl-N($C_{1-8}$alkyl)($C_{1-8}$alkyl-OH).

As used herein, the term "(hydroxy-$C_{1-8}$alkyl)$_2$-amino-$C_{1-8}$alkyl" refers to a radical of the formula: —$C_{1-8}$alkyl-N($C_{1-8}$alkyl-OH)$_2$.

As used herein, the term "hydroxy-$C_{1-8}$alkyl-amino-$C_{1-8}$alkoxy" refers to a radical of the formula: —O—$C_{1-8}$alkyl-NH—$C_{1-8}$alkyl-OH.

As used herein, the term "(hydroxy-$C_{1-8}$alkyl)($C_{1-8}$alkyl)amino-$C_{1-8}$alkoxy" refers to a radical of the formula: —O—$C_{1-8}$alkyl-N($C_{1-8}$alkyl)($C_{1-8}$alkyl-OH).

As used herein, the term "(hydroxy-$C_{1-8}$alkyl)$_2$-amino-$C_{1-8}$alkoxy" refers to a radical of the formula: —O—$C_{1-8}$alkyl-N($C_{1-8}$alkyl-OH)$_2$.

As used herein, the term "hydroxy-$C_{1-8}$alkyl-amino-$C_{1-8}$alkyl-amino" refers to a radical of the formula: —NH—$C_{1-8}$alkyl-NH—$C_{1-8}$alkyl-OH.

As used herein, the term "(hydroxy-$C_{1-8}$alkyl-amino-$C_{1-8}$alkyl)$_2$-amino" refers to a radical of the formula: —N($C_{1-8}$alkyl-NH—$C_{1-8}$alkyl-OH)$_2$.

As used herein, the term "(hydroxy-$C_{1-8}$alkyl)$_2$-amino-$C_{1-8}$alkyl-amino" refers to a radical of the formula: —NH—$C_{1-8}$alkyl-N($C_{1-8}$alkyl-OH)$_2$.

As used herein, the term "(hydroxy-$C_{1-8}$alkyl-amino-$C_{1-8}$alkyl)($C_{1-8}$alkyl)amino" refers to a radical of the formula: —N($C_{1-8}$alkyl)($C_{1-8}$alkyl-NH—$C_{1-8}$alkyl-OH).

As used herein, the term "[(hydroxy-$C_{1-8}$alkyl)$_2$-amino-$C_{1-8}$alkyl]($C_{1-8}$alkyl)amino" refers to a radical of the formula: —N($C_{1-8}$alkyl)[$C_{1-8}$alkyl-N($C_{1-8}$alkyl-OH)$_2$].

As used herein, the term "(hydroxy-$C_{1-8}$alkyl)($C_{1-8}$alkyl)amino-$C_{1-8}$alkyl-amino" refers to a radical of the formula: —NH—$C_{1-8}$alkyl-N($C_{1-8}$alkyl,$C_{1-8}$alkyl-OH).

As used herein, the term "[(hydroxy-$C_{1-8}$alkyl)($C_{1-8}$alkyl)amino-$C_{1-8}$alkyl]($C_{1-8}$alkyl)amino" refers to a radical of the formula: —N($C_{1-8}$alkyl)[$C_{1-8}$alkyl-N($C_{1-8}$alkyl)($C_{1-8}$alkyl-OH)].

As used herein, the term "substituent" means positional variables on the atoms of a core molecule that are attached at a designated atom position, replacing one or more hydrogen atoms on the designated atom, provided that the atom of attachment does not exceed the available valence or shared valences, such that the substitution results in a stable compound. Accordingly, combinations of substituents and/or variables are permissible only if such combinations result in stable compounds. It should also be noted that any carbon as well as heteroatom with a valence level that appears to be unsatisfied as described or shown herein is assumed to have a sufficient number of hydrogen atom(s) to satisfy the valences described or shown.

For the purposes of this description, where one or more substituent variables for a compound of Formula (I) encompass functionalities incorporated into a compound of Formula (I), each functionality appearing at any location within the disclosed compound may be independently selected, and as appropriate, independently and/or optionally substituted.

As used herein, the terms "independently selected," or "each selected" refer to functional variables in a substituent list that may be attached more than once on the structure of a core molecule, where the pattern of substitution at each occurrence is independent of the pattern at any other occurrence. Further, the use of a generic substituent on a core structure for a compound provided herein is understood to include the replacement of the generic substituent with specie substituents that are included within the particular genus, e.g., aryl may be independently replaced with phenyl or naphthalenyl (also referred to as naphthyl) and the like, such that the resulting compound is to be included within the scope of the compounds described herein.

As used herein, the term "each instance of" when used in a phrase such as " . . . aryl, aryl-$C_{1-8}$alkyl, heterocyclyl and heterocyclyl-$C_{1-8}$alkyl, wherein each instance of aryl and heterocyclyl is optionally substituted with one or two substituents . . . " is intended to include optional, independent substitution on each of the aryl and heterocyclyl rings and on the aryl and heterocyclyl portions of aryl-$C_{1-8}$alkyl and heterocyclyl-$C_{1-8}$alkyl.

As used herein, the term "optionally substituted" means that the specified substituent variables, groups, radicals or moieties represent the scope of the genus and may be independently chosen as needed to replace one or more hydrogen atoms on the designated atom of attachment of a core molecule.

As used herein, the terms "stable compound" or "stable structure" mean a compound that is sufficiently robust to be isolated to a useful degree of purity from a reaction mixture and formulations thereof into an efficacious therapeutic agent.

Compound names provided herein were obtained using ACD Labs Index Name software provided by ACD Labs and/or ChemDraw Ultra software provided by CambridgeSoft®. When the compound name disclosed herein conflicts with the structure depicted, the structure shown will supercede the use of the name to define the compound intended. Nomenclature for substituent radicals defined herein may differ slightly from the chemical name from which they are derived; one skilled in the art will recognize that the definition of the substituent radical is intended to include the radical as found in the chemical name.

The term "SMN," unless otherwise specified herein, refers to the human SMN1 gene, DNA or RNA, and/or human SMN2 gene, DNA or RNA. In a specific embodiment, the term "SMN1" refers to the human SMN1 gene, DNA or RNA. In another specific embodiment, the term "SMN2" refers to the human SMN2 gene, DNA or RNA.

Nucleic acid sequences for the human SMN1 and SMN2 genes are known in the art. For nucleic acid sequences of human SMN1, see, e.g., GenBank Accession Nos. DQ894095, NM_000344, NM_022874, and BC062723. For nucleic acid sequences of human SMN2, see, e.g., NM_022875, NM_022876, NM_022877, NM_017411, DQ894734 (Life Technologies, Inc. (formerly Invitrogen), Carlsbad, Calif.), BC000908, BC070242, CR595484, CR598529, CR609539, U21914, and BC015308.

The SMN1 gene can be found on the forward strand of human chromosome 5 from approximately nucleotide 70,220,768 to approximately nucleotide 70,249,769. The approximate locations of exons 6, 7 and 8 and introns 6 and 7 of SMN1 on human chromosome 5 are as follows:
70,241,893 to 70,242,003 exon 6;
70,242,004 to 70,247,767 intron 6;
70,247,768 to 70,247,821 exon 7;
70,247,822 to 70,248,265 intron 7; and,
70,248,266 to 70,248,839 exon 8.

The SMN2 gene can be found on the forward strand of human chromosome 5 from approximately nucleotide 69,345,350 to approximately nucleotide 69,374,349.

The approximate locations of exons 6, 7 and 8 and introns 6 and 7 of SMN2 on human chromosome 5 are as follows:
69,366,468 to 69,366,578 exon 6;
69,366,579 to 69,372,347 intron 6;
69,372,348 to 69,372,401 exon 7;
69,372,402 to 69,372,845 intron 7; and,
69,372,846 to 69,373,419 exon 8.

In specific embodiments, the nucleotide sequences delineated above for exons 6, 7 and 8 and introns 6 and 7 of SMN1 are used in the SMN1 minigene nucleic acid constructs described herein. In other specific embodiments, the nucleotide sequences of exons 6, 7 and 8 and introns 6 and 7 of SMN2 in the examples provided herein are used in the SMN2 minigene nucleic acid constructs described herein.

The term "Smn" or "Smn protein," unless otherwise specified herein, refers to a human Smn protein that contains the amino acid residues encoded by exons 1 through 7 of the SMN1 gene and/or SMN2 gene. In a specific embodiment, the Smn protein is stable and functional in vitro and/or in vivo as assessed by methods known to one of skill in the art. In another specific embodiment, the Smn protein is the full-length protein encoded by the human SMN1 gene and/or SMN2 gene. In another specific embodiment, the Smn protein has the amino acid sequence found at GenBank Accession No. NP_000335, AAC50473.1, AAA66242.1, or NP_059107.

As used herein, the term "enhances the inclusion of exon 7 of SMN2 into mRNA that is transcribed from the SMN2 gene," and analogous terms, unless otherwise specified herein, refers to the inclusion of the complete, intact, non-truncated sequence of exon 7 of SMN2 into the mature mRNA that is transcribed from the SMN2 gene (i.e., resulting in the production of full-length SMN2 mRNA) in vitro and/or in vivo, as assessed by methods known to one of skill in the art, such that increased levels of Smn protein are produced from the SMN2 gene in vitro and/or in vivo, as assessed by methods known to one of skill in the art; or, that increased expression of stable and functional Smn protein is produced from the SMN2 gene in vitro and/or in vivo, as assessed by methods known to one of skill in the art; or, that expression of the fusion protein encoded by the minigene is increased in vitro, as assessed by methods known to one of skill in the art; or, that expression of Smn protein produced from the SMN2 gene in a subject (e.g., an animal model for SMA or a human subject) in need thereof is increased.

As used herein, the term "enhances the inclusion of exon 7 of SMN1 into mRNA that is transcribed from the SMN1 gene," and analogous terms, unless otherwise specified herein, refers to the inclusion of the complete, intact, non-truncated sequence of exon 7 of SMN1 into the mature mRNA that is transcribed from the SMN1 gene (i.e., resulting in the production of full-length SMN1 mRNA) in vitro and/or in vivo, as assessed by methods known to one of skill in the art, such that increased levels of Smn protein are produced from the SMN1 gene in vitro and/or in vivo, as assessed by methods known to one of skill in the art; or, that increased expression of stable and functional Smn protein is produced from the SMN1 gene in vitro and/or in vivo, as assessed by methods known to one of skill in the art; or, that expression of the fusion protein encoded by the minigene is increased in vitro, as assessed by methods known to one of skill in the art; or, that expression of Smn protein produced from the SMN1 gene in a subject (e.g., an animal model for SMA or a human subject) in need thereof is increased.

As used herein, the term "substantial change" in the context of the amount of mRNA means that the amount of mRNA changes by a statistically significant amount, e.g., a p value less than a value selected from 0.1, 0.05, 0.01, 0.005, 0.001, 0.0005, 0.0001, 0.00005 or 0.00001.

As used herein, the terms "subject" and "patient" are used interchangeably to refer to an animal or any living organism having sensation and the power of voluntary movement, and which requires for its existence oxygen and organic food. Nonlimiting examples include members of the human, equine, porcine, bovine, rattus, murine, canine and feline species. In some embodiments, the subject is a mammal or a warm-blooded vertebrate animal. In certain embodiments, the subject is a non-human animal. In specific embodiments, the subject is a human.

As used herein, the term "elderly human" refers to a human 65 years old or older.

As used herein, the term "human adult" refers to a human that is 18 years or older.

As used herein, the term "human child" refers to a human that is 1 year to 18 years old.

As used herein, the term "human infant" refers to a newborn to 1 year old year human.

As used herein, the term "human toddler" refers to a human that is 1 year to 3 years old.

Compound Forms

As used herein, the terms "a compound of Formula (Ia)" and "a compound of Formula (Ib)" refer to sub-genuses of the compound of Formula (I) or a form thereof and are defined herein. Rather than repeat embodiments for a compound of Formula (Ia) or a compound of Formula (Ib), in certain embodiments, the term "a compound(s) of Formula (I) or a form thereof" is used to refer to either a compound of Formula (Ia) or a form thereof, a compound of Formula (Ib) or a form thereof, or both. Thus, embodiments and references to "a compound of Formula (I)" are intended to include compounds of Formula (Ia) and Formula (Ib).

As used herein, the term "form" means a compound of Formula (I) selected from a free acid, free base, salt, isotopologue, stereoisomer, racemate, enantiomer, diastereomer, or tautomer thereof.

In certain embodiments described herein, the form of the compound of Formula (I) is a selected from a salt, isotopologue, stereoisomer, racemate, enantiomer, diastereomer or tautomer thereof.

In certain embodiments described herein, the form of the compound of Formula (I) is a selected from a free acid, isotopologue, stereoisomer, racemate, enantiomer, diastereomer or tautomer thereof.

In certain embodiments described herein, the form of the compound of Formula (I) is a selected from a free base, isotopologue, stereoisomer, racemate, enantiomer, diastereomer or tautomer thereof.

In certain embodiments described herein, the form of the compound of Formula (I) is a free acid, free base or salt thereof.

In certain embodiments described herein, the form of the compound of Formula (I) is an isotopologue thereof.

In certain embodiments described herein, the form of the compound of Formula (I) is a stereoisomer, racemate, enantiomer or diastereomer thereof.

In certain embodiments described herein, the form of the compound of Formula (I) is a tautomer thereof.

In certain embodiments described herein, the form of the compound of Formula (I) is a pharmaceutically acceptable form.

In certain embodiments described herein, the compound of Formula (I) or a form thereof is isolated for use.

As used herein, the term "isolated" means the physical state of a compound of Formula (I) or a form thereof after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterizable by standard analytical techniques described herein or well known to the skilled artisan.

As used herein, the term "protected" means that a functional group on a compound of Formula (I) is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

Prodrugs of a compound of Formula (I) or a form thereof are also contemplated herein.

As used herein, the term "prodrug" means that a functional group on a compound of Formula (I) is in a form (e.g., acting as an active or inactive drug precursor) that is transformed in vivo to yield an active or more active compound of Formula (I) or a form thereof. The transformation may occur by various mechanisms (e.g., by metabolic and/or non-metabolic chemical processes), such as, for example, by hydrolysis and/or metabolism in blood, liver and/or other organs and tissues. A discussion of the use of prodrugs is provided by V. J. Stella, et. al., "Biotechnology: Pharmaceutical Aspects, Prodrugs: Challenges and Rewards," American Association of Pharmaceutical Scientists and Springer Press, 2007.

In one example, when a compound of Formula (I) or a form thereof contains a carboxylic acid functional group, a prodrug can comprise an ester formed by the replacement of the hydrogen atom of the acid group with a functional group such as alkyl and the like. In another example, when a compound of Formula (I) or a form thereof contains an alcohol functional group, a prodrug can be formed by the replacement of the hydrogen atom of the alcohol group with a functional group such as alkyl or substituted carbonyl and the like. In another example, when a compound of Formula (I) or a form thereof contains an amine functional group, a prodrug can be formed by the replacement of one or more amine hydrogen atoms with a functional group such as alkyl or substituted carbonyl. In another example, when a compound of Formula (I) or a form thereof contains a hydrogen substituent, a prodrug can be formed by the replacement of one or more hydrogen atoms with an alkyl substituent.

Pharmaceutically acceptable prodrugs of compounds of Formula (I) or a form thereof include those compounds substituted with one or more of the following groups: carboxylic acid esters, sulfonate esters, amino acid esters phosphonate esters, mono-, di- or triphosphate esters or alkyl substituents where appropriate. As described herein, it is understood by a person of ordinary skill in the art that one or more of such substituents may be used to provide a compound of Formula (I) or a form thereof for use as a prodrug.

One or more compounds described herein may exist in unsolvated as well as solvated forms with pharmaceutically acceptable solvents such as water, ethanol, and the like, and the description herein is intended to embrace both solvated and unsolvated forms.

As used herein, the term "solvate" means a physical association of a compound described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

One or more compounds described herein may optionally be converted to a solvate. Preparation of solvates is generally known. A typical, non-limiting process involves dissolving a compound in a desired amount of the desired solvent (organic or water or mixtures thereof) at a higher than ambient temperature, and cooling the solution at a rate sufficient to form crystals which are then isolated by standard methods. Analytical techniques such as, for example infrared spectroscopy, show the presence of the solvent (or water) in the crystals as a solvate (or hydrate).

As used herein, the term "hydrate" means a solvate wherein the solvent molecule is water.

The compounds of Formula (I) can form salts which are intended to be included within the scope of this description. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein.

The term "pharmaceutically acceptable salt(s)", as used herein, means those salts of compounds described herein that are safe and effective (i.e., non-toxic, physiologically acceptable) for use in mammals and that possess biological activity, although other salts are also useful. Salts of the compounds of Formula (I) may be formed, for example, by reacting a compound of Formula (I) with an amount of acid or base, such as an equivalent or stoichiometric amount, in a medium such as one in which the salt precipitates or in an aqueous medium followed by lyophilization.

Pharmaceutically acceptable salts include one or more salts of acidic or basic groups present in compounds described herein. Embodiments of acid addition salts include, and are not limited to, acetate, acid phosphate, ascorbate, benzoate, benzenesulfonate, bisulfate, bitartrate, borate, butyrate, chloride, citrate, camphorate, camphorsulfonate, ethanesulfonate, formate, fumarate, gentisinate, gluconate, glucaronate, glutamate, hydrobromide, hydrochloride, dihydrochloride, hydroiodide, isonicotinate, lactate, maleate, methanesulfonate, naphthalenesulfonate, nitrate, oxalate, pamoate, pantothenate, phosphate, propionate, saccharate, salicylate, succinate, sulfate, tartrate, thiocyanate, toluenesulfonate (also known as tosylate), trifluoroacetate salts and the like. Certain embodiments of mono-acid, di-acid or tri-acid addition salts include a chloride, hydrochloride, dihydrochloride, trihydrochloride, hydrobromide, acetate, diacetate or trifluoroacetate salt. More particular embodiments include a chloride, hydrochloride, dihydrochloride, hydrobromide or trifluoroacetate salt.

Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33, 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Suitable basic salts include, but are not limited to, aluminum, ammonium, calcium, lithium, magnesium, potassium, sodium, zinc, and diethanolamine salts. Certain compounds described herein can also form pharmaceutically acceptable salts with organic bases (for example, organic amines) such as, but not limited to, dicyclohexylamines, tert-butyl amines and the like, and with various amino acids such as, but not limited to, arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the description herein and all acid and base salts are considered equivalent to the free forms of the corresponding compounds for the purposes described herein.

Compounds of Formula I and forms thereof may further exist in a tautomeric form (for example, as a keto or enol form such as an embedded enone system). All such tautomeric forms are contemplated herein as part of the present description.

The compounds of Formula (I) may contain asymmetric or chiral centers, and, therefore, may exist in different stereoisomeric forms. The present description is intended to include all stereoisomeric forms of the compounds of Formula (I) as well as mixtures thereof, including racemic mixtures.

The compounds of Formula (I) described herein may include one or more chiral centers, and as such may exist as racemic mixtures (R/S) or as substantially pure enantiomers and diastereomers. The compounds may also exist as substantially pure (R) or (S) enantiomers (when one chiral center is present). In one embodiment, the compounds of Formula (I) described herein are (S) isomers and may exist as enantiomerically pure compositions substantially comprising only the (S) isomer. In another embodiment, the compounds of Formula (I) described herein are (R) isomers and may exist as enantiomerically pure compositions substantially comprising only the (R) isomer. As one of skill in the art will recognize, when more than one chiral center is present, the compounds of Formula (I) described herein may also include portions described as an (R,R), (R,S), (S,R) or (S,S) isomer, as defined by IUPAC Nomenclature Recommendations.

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect, a compound of Formula (I) is a substantially pure (S) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect, a compound of Formula (I) is a substantially pure (R) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, about 80/20, about 85/15 or about 90/10.

In addition, the present description embraces all geometric and positional isomers. For example, if a compound of Formula (I) incorporates a double bond or a fused ring, both the cis- and trans-forms, as well as mixtures, are embraced within the scope of the description herein.

Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art.

Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered part of this description.

It is also possible that the compounds of Formula (I) may exist in different tautomeric forms, and all such forms are embraced within the scope of this description. Accordingly, all keto-enol and imine-enamine forms of a compound of Formula (I) are included in the description herein.

All stereoisomer forms (for example, geometric isomers, optical isomers, positional isomers and the like) of the present compounds (including salts, solvates, esters and prodrugs and transformed prodrugs thereof) which may exist due to asymmetric carbons on various substituents, including enantiomeric forms (which may exist even in the absence of asymmetric carbons), rotameric forms, atropisomers, diastereomeric forms and regioisomeric forms are contemplated within the scope of the description herein. For example, if a compound of Formula (I) incorporates a double bond or a fused ring, both the cis- and trans-forms, as well as mixtures thereof, are embraced within the scope of the description herein. Also, for example, all keto-enol and imine-enamine tautomeric forms of the compounds are included in the description herein. Individual stereoisomers of the compounds of Formula (I) described herein may, for example, be substantially free of other isomers, or may be present in a racemic mixture, as described supra.

The use of the terms "salt," "prodrug" and "transformed prodrug" are intended to equally apply to the salts, prodrugs and transformed prodrugs of all contemplated isotopologues, stereoisomers, racemates or tautomers of the instant compounds.

The term "isotopologue" refers to isotopically-enriched compounds which are identical to those recited herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, fluorine and chlorine, such as $H^2$, $H^3$, $C^{13}$, $C^{14}$, $N^{15}$, $O^{18}$, $O^{17}$, $P^{31}$, $P^{32}$, $S^{35}$, $F^{18}$, $Cl^{35}$ and $Cl^{36}$, respectively, each of which is also within the scope of this description.

Certain isotopically-enriched compounds described herein (e.g., those labeled with $H^3$ and $C^{14}$) are useful in compound and/or substrate tissue distribution assays. Tritiated (i.e., $H^3$) and carbon-14 (i.e., $C^{14}$) isotopes are particularly preferred for their ease of preparation and detectability. Further, substitution with heavier isotopes such as deuterium (i.e., $H^2$) may afford certain therapeutic advantages resulting from greater metabolic stability (e.g., increased in vivo half-life or reduced dosage requirements) and hence may be preferred in some circumstances. Isotopically-enriched compounds of Formula (I) can generally be prepared using procedures known to persons of ordinary skill in the art by substituting an appropriate isotopically-enriched reagent for a non-isotopically-enriched reagent.

When the compounds are enriched with deuterium, the deuterium-to-hydrogen ratio in the deuterated areas of the molecules substantially exceeds the naturally occurring deuterium-to-hydrogen ratio.

An embodiment described herein may include a compound of Formula (I) and forms thereof, wherein the isotopologue is deuterium.

An embodiment described herein may include a compound of Formula (I) and forms thereof, wherein a carbon atom may have from 1 to 3 hydrogen atoms optionally replaced with deuterium.

Polymorphic crystalline and amorphous forms of the compounds of Formula (I), and of the salts, solvates, esters and prodrugs of the compounds of Formula (I), are further intended to be included in the scope of the compounds described herein.

Compound Uses

Compounds of Formula (I) or a form thereof that enhance inclusion of exon 7 of SMN2 into mRNA that is transcribed from the SMN2 gene are described herein. Such compounds of Formula (I) or a form thereof have been shown to enhance the inclusion of exon 7 of SMN2 into mRNA that is transcribed from the SMN2 gene using the assays described herein (see Biological example section, infra). Accordingly, compounds of Formula (I) or a form thereof have utility as enhancers for the inclusion of exon 7 of SMN2 into mRNA that is transcribed from the SMN2 gene.

Compounds of Formula (I) or a form thereof for enhancing inclusion of exon 7 of SMN1 into mRNA that is transcribed from the SMN1 gene are described herein. Such compounds of Formula (I) or a form thereof may enhance inclusion of exon 7 of SMN1 into mRNA that is transcribed from the SMN1 gene using, e.g., an SMN1 minigene assay. Accordingly, compounds of Formula (I) or a form thereof may have utility as enhancers for the inclusion of exon 7 of SMN1 into mRNA that is transcribed from the SMN1 gene.

In one aspect, provided herein are methods for modulating the inclusion of exon 7 of SMN2 into RNA transcribed from the SMN2 gene, comprising contacting a A method for enhancing the inclusion of exon 7 of SMN2 into mRNA transcribed from the SMN2 gene, comprising contacting a human cell with a compound of Formula (I) or a form thereof. In a specific embodiment, provided herein are methods for modulating the inclusion of exon 7 of SMN2 into RNA transcribed from the SMN2 gene, comprising contacting a human cell with a compound of Formula (I) or a form thereof that modulates the expression of an SMN2 minigene described herein or in International Publication No. WO2009/151546 or U.S. Patent Application Publication No. 2011/0086833, each of which is incorporated herein by reference in its entirety. In one embodiment, the minigene is a minigene described in the Examples of International Publication No. WO2009/151546 or U.S. Patent Application Publication No. 2011/0086833. In another embodiment, the minigene is the minigene described in Biological Example 1, infra. The human cell can be contacted with a compound of Formula (I) or a form thereof in vitro, in a non-human animal or in a human. In a specific embodiment, the human cell is in a human. In another specific embodiment, the human cell is in a human SMA patient. In another specific embodiment, the human cell is in a human SMA patient, wherein SMA is caused by an inactivating mutation or deletion in the SMN1 gene on both chromosomes, resulting in a loss of SMN1 gene function. In another embodiment, the human cell is a human cell from a human SMA patient. In certain embodiments, the human cell is from a cell line, such as GM03813, GM00232, GM09677, and/or GM23240 (available from Coriell Institute).

In a specific embodiment, provided herein is a method for enhancing the inclusion of exon 7 of SMN2 into mRNA that is transcribed from the SMN2 gene, comprising contacting a human cell with a compound of Formula (I) or a form thereof. In another embodiment, provided herein is a method for enhancing the inclusion of exon 7 of SMN2 into mRNA that is transcribed from the SMN2 gene, comprising contacting a human cell with a compound of Formula (I) or a form thereof that enhances the expression of an SMN2 minigene described herein or in International Publication No. WO2009/151546 or U.S. Patent Application Publication No. 2011/0086833, each of which is incorporated herein by reference in its entirety. In one embodiment, the minigene is a minigene described in the Examples of International Publication No. WO2009/151546 or U.S. Patent Application Publication No. 2011/0086833. In another embodiment, the minigene is the minigene described in Biological Example 1, infra. The human cell can be contacted with a compound of Formula (I) or a form thereof in vitro, in a non-human animal or in a human. In a specific embodiment, the human cell is in a human. In another specific embodiment, the human cell is in a human SMA patient. In another specific embodiment, the human cell is in a human SMA patient, wherein SMA is caused by an inactivating mutation or deletion in the SMN1 gene on both chromosomes, resulting in a loss of SMN1 gene function. In another embodiment, the human cell is a human cell from a human SMA patient. In certain embodiments, the human cell is from a cell line, such as GM03813, GM00232, GM09677, and/or GM23240 (available from Coriell Institute).

In another aspect, provided herein are methods for enhancing the inclusion of exon 7 of SMN1 into RNA transcribed from the SMN1 gene, comprising contacting a human cell with a compound of Formula (I) or a form thereof. In a specific embodiment, provided herein are methods for enhancing the inclusion of exon 7 of SMN1 into RNA transcribed from the SMN1 gene, comprising contacting a human cell with a compound of Formula (I) or a form thereof. In another specific embodiment, provided herein are methods for enhancing the inclusion of exon 7 of SMN1 into RNA transcribed from the SMN1 gene, comprising contacting a human cell with a compound of Formula (I) or a form thereof that modulates the expression of an SMN1 minigene described in International Publication No. WO2009/151546 or U.S. Patent Application Publication No. 2011/0086833, each of which is incorporated herein by reference in its entirety. In one embodiment, the minigene is a minigene described in the Examples of International Publication No. WO2009/151546 or U.S. Patent Application Publication No. 2011/0086833. The human cell can be contacted with a compound of Formula (I) or a form thereof in vitro, in a non-human animal or in a human. In a specific embodiment, the human cell is in a human. In another specific embodiment, the human cell is in a human SMA patient.

In specific embodiments, provided herein are methods for enhancing the inclusion of exon 7 of SMN1 and SMN2 into RNA transcribed from the SMN1 and SMN2 genes, comprising contacting a human cell with a compound of Formula (I) or a form thereof. The human cell can be contacted with a compound of Formula (I) or a form thereof in vitro, in a non-human animal or in a human. In a specific embodiment, the human cell is in a human. In another specific embodiment, the human cell is in a human SMA patient.

In another aspect, provided herein is a method for modulating the inclusion of exon 7 of SMN2 into RNA transcribed from the SMN2 gene, comprising administering to a non-human animal model for SMA a compound of Formula (I) or a form thereof. In a specific embodiment, provided herein is a method for modulating the inclusion of exon 7 of SMN2 into RNA transcribed from the SMN2 gene, comprising administering to a non-human animal model for SMA a compound of Formula (I) or a form thereof that modulates the expression of an SMN2 minigene described herein or in International Publication No. WO2009/151546 or U.S. Patent Application Publication No. 2011/0086833, each of which is incorporated herein by reference in its entirety. In one embodiment, the minigene is a minigene described in the Examples of International Publication No. WO2009/151546 or U.S. Patent Application Publication No. 2011/0086833. In another embodiment, the minigene is the minigene described in Biological Example 1, infra.

In a specific embodiment, provided herein is a method for enhancing the inclusion of exon 7 of SMN2 into mRNA that is transcribed from the SMN2 gene, comprising administering to a non-human animal model for SMA a compound of Formula (I) or a form thereof. In another specific embodiment, provided herein is a method for enhancing the inclusion of exon 7 of SMN2 into mRNA that is transcribed from the SMN2 gene, comprising administering to a non-human animal model for SMA a compound of Formula (I) or a form thereof that enhances the expression of an SMN2 minigene described herein or in International Publication No. WO2009/151546 or U.S. Patent Application Publication No. 2011/0086833, each of which is incorporated herein by reference in its entirety. In one embodiment, the minigene is a minigene described in the Examples of International Publication No. WO2009/151546 or U.S. Patent Application Publication No. 2011/0086833. In another embodiment, the minigene is the minigene described in Biological Example 1, infra.

In another aspect, provided herein is a method for enhancing the inclusion of exon 7 of SMN1 into RNA transcribed from the SMN1 gene, comprising administering to a non-human animal model for SMA a compound of Formula (I) or a form thereof. In a specific embodiment, provided herein is a method for enhancing the inclusion of exon 7 of SMN1 into RNA transcribed from the SMN1 gene, comprising administering to a non-human animal model for SMA a compound of Formula (I) or a form thereof that modulates the expression of an SMN1 minigene described herein or in International Publication No. WO2009/151546 or U.S. Patent Application Publication No. 2011/0086833, each of which is incorporated herein by reference in its entirety. In one embodiment, the minigene is a minigene described in the Examples of International Publication No. WO2009/151546 or U.S. Patent Application Publication No. 2011/0086833. In specific embodiments, provided herein is a method for enhancing the inclusion of exon 7 of SMN1 and SMN2 into RNA transcribed from the SMN1 and SMN2 genes, comprising administering to a non-human animal model for SMA a compound of Formula (I) or a form thereof.

In another aspect, provided herein is a method for increasing the amount of Smn protein, comprising contacting a human cell with a compound of Formula (I) or a form thereof. In a specific embodiment, provided herein is a method for increasing the amount of Smn protein, comprising contacting a human cell with a compound of Formula (I) that enhances the inclusion of exon 7 of SMN2 into mRNA that is transcribed from the SMN2 gene. In another specific embodiment, provided herein is a method for increasing the amount of Smn protein, comprising contacting a human cell with a compound of Formula (I) that enhances the inclusion of exon 7 of SMN1 and/or SMN2 into mRNA that is transcribed from the SMN1 and/or SMN2 gene. The human cell can be contacted with a compound of Formula (I) or a form thereof in vitro, in a non-human animal or in a human. In a specific embodiment, the human cell is in a human. In another specific embodiment, the human cell is in a human SMA patient. In another specific embodiment, the human cell is in a human SMA patient, wherein SMA is caused by an inactivating mutation or deletion in the SMN1 gene on both chromosomes, resulting in a loss of SMN1 gene function. In another embodiment, the human cell is a human cell from a human SMA patient. In certain embodiments, the human cell is from a cell line, such as GM03813, GM00232, GM09677, and/or GM23240 (available from Coriell Institute).

In another aspect, provided herein is a method for increasing the amount of Smn protein, comprising administering to a non-human animal model for SMA a compound of Formula (I) or a form thereof. In a specific embodiment, provided herein is a method for increasing the amount of Smn protein, comprising administering to a non-human animal model for SMA a compound of Formula (I) that enhances the inclusion of exon 7 of SMN2 into mRNA that is transcribed from the SMN2 gene in, e.g., a cell-based or cell-free assay, such as described in the Biological Examples, infra. In another specific embodiment, provided herein is a method for increasing the amount of Smn protein, comprising administering to a non-human animal model for SMA a compound of Formula (I) that enhances the inclusion of exon 7 of SMN1 and/or SMN2 into mRNA that is transcribed from the SMN1 and/or SMN2 gene in, e.g., a cell-based or cell-free assay.

In one embodiment, the compound of Formula (I) enhances the expression of a minigene described herein or in International Publication No. WO2009/151546 or U.S. Patent Application Publication No. 2011/0086833, each of which is incorporated herein by reference in its entirety. In a specific embodiment, the compound of Formula (I) enhances the expression of a minigene described in the Examples of International Publication No. WO2009/151546 or U.S. Patent Application Publication No. 2011/0086833. In another specific embodiment, the compound of Formula (I) enhances the expression of a minigene described in Biological Example 1, infra.

In one embodiment, provided herein is the use of a compound of Formula (I) or a form thereof for the preparation of a medicament that enhances the inclusion of exon 7 of SMN2 into mRNA that is transcribed from the SMN2 gene. In another embodiment, provided herein is the use of a compound of Formula (I) or a form thereof for the preparation of a medicament that enhances the inclusion of exon 7 of SMN2 into mRNA that is transcribed from the SMN2 gene, thereby increasing expression of Smn protein in a human subject in need thereof. In a particular embodiment, the compound of Formula (I) or a form thereof enhances the inclusion of exon 7 of SMN2 into mRNA that is transcribed from the SMN2 gene in an assay described herein (see, e.g., the Biological Examples, infra).

In one embodiment, provided herein is the use of a compound of Formula (I) or a form thereof for the preparation of a medicament that enhances the inclusion of exon 7 of SMN1 and/or SMN2 into mRNA that is transcribed from the SMN1 and/or SMN2 gene. In another embodiment, provided herein is the use of a compound of Formula (I) or a form thereof for the preparation of a medicament that enhances the inclusion of exon 7 of SMN1 and/or SMN2 into mRNA that is transcribed from the SMN1 and/or SMN2 gene, thereby increasing expression of Smn protein in a human subject in need thereof.

In another aspect, provided herein are methods for enhancing the inclusion of exon 7 of SMN2 into mRNA that is transcribed from the SMN2 gene in a human subject in need thereof, comprising administering to the human subject an effective amount of a compound of Formula (I) or a form thereof. In a specific embodiment, provided herein is a method for enhancing the inclusion of exon 7 of SMN2 into mRNA that is transcribed from the SMN2 gene in a human subject in need thereof, comprising administering to the human subject an effective amount a compound of Formula (I) or a form thereof that enhances the inclusion of exon 7 of SMN2 into mRNA that is transcribed from the SMN2 gene as determined in an assay described herein (see, e.g., the Biological Examples, infra). In specific embodiments, the effective amount of the compound of Formula (I) or a form thereof is administered to the human subject in a pharmaceutical composition comprising a pharmaceutically acceptable carrier, excipient or diluent. In a particular embodiment, the compound of Formula (I) or a form thereof enhances the inclusion of exon 7 of SMN2 into mRNA that is transcribed from the SMN2 gene in an assay described herein (see, e.g., the Biological Examples, infra). In a specific embodiment, the human subject is a human SMA patient. In another specific embodiment, the human subject is a human SMA patient, wherein SMA is caused by an inactivating mutation or deletion in the SMN1 gene on both chromosomes, resulting in a loss of SMN1 gene function.

In another aspect, provided herein are methods for enhancing the inclusion of exon 7 of SMN1 into mRNA that is transcribed from the SMN1 gene in a human subject in need thereof, comprising administering to the human subject an effective amount of a compound of Formula (I) or a form thereof. In a particular embodiment, the compound of Formula (I) or a form thereof enhances the inclusion of exon 7 of SMN1 into mRNA that is transcribed from the SMN1 gene in an assay described in International Publication No. WO2009/151546 or U.S. Patent Application Publication No. 2011/0086833. In specific embodiments, the effective amount of the compound of Formula (I) or a form thereof is administered to the human subject in a pharmaceutical composition comprising a pharmaceutically acceptable carrier, excipient or diluent. In a specific embodiment, the human subject is a human SMA patient.

In another aspect, provided herein is a method for enhancing the inclusion of exon 7 of SMN1 and SMN2 into mRNA that is transcribed from the SMN1 and SMN2 genes in a human subject in need thereof, comprising administering to the human subject an effective amount a compound of Formula (I) or a form thereof. In a particular embodiment, the compound of Formula (I) or a form thereof enhances the inclusion of exon 7 of SMN1 into mRNA that is transcribed from the SMN1 gene in an assay(s) described in International Publication No. WO2009/151546 or U.S. Patent Application Publication No. 2011/0086833 (see, e.g., the Examples in those publications), each of which is incorporated herein by reference in its entirety. In specific embodiments, the effective amount of the compound of Formula (I) or a form thereof is administered to the human subject in a pharmaceutical composition comprising a pharmaceutically acceptable carrier, excipient or diluent. In a specific embodiment, the human subject is a human SMA patient. In another specific embodiment, the human subject is a human SMA patient, wherein SMA is caused by an inactivating mutation or deletion in the SMN1 gene on both chromosomes, resulting in a loss of SMN1 gene function.

In another aspect, provided herein are methods for enhancing the expression of Smn protein in a human subject in need thereof, comprising administering to the human subject an effective amount of a compound of Formula (I) or a form thereof. In a specific embodiment, provided herein is a method for enhancing the expression of Smn protein in a human subject in need thereof, comprising administering to the human subject an effective amount a compound of Formula (I) or a form thereof that enhances the inclusion of exon 7 of SMN2 into mRNA that is transcribed from the SMN2 gene. In another specific embodiment, provided herein is a method for enhancing the expression of Smn protein in a human subject in need thereof, comprising administering to the human subject an effective amount a compound of Formula (I) or a form thereof that enhances the inclusion of exon 7 of SMN1 and/or SMN2 into mRNA that is transcribed from the SMN1 and/or SMN2 gene. In specific embodiments, the effective amount of the compound of Formula (I) or a form thereof is administered to the human subject in a pharmaceutical composition comprising a pharmaceutically acceptable carrier, excipient or diluent. In a particular embodiment, the compound of Formula (I) or a form thereof enhances the inclusion of exon 7 of SMN1 and/or SMN2 into mRNA that is transcribed from the SMN1 and/or SMN2 gene in an assay described herein (see, e.g., the Biological Examples, infra) or in International Publication No. WO2009/151546 or U.S. Patent Application Publication No. 2011/0086833 (see, e.g., the Examples in those publications), each of which is incorporated herein by reference in its entirety.

In a specific embodiment, the human subject is a human SMA patient. In another specific embodiment, the human subject is a human SMA patient, wherein SMA is caused by an inactivating mutation or deletion in the teleomeric copy of the SMN1 gene in both chromosomes, resulting in a loss of SMN1 gene function.

In another embodiment, provided herein is the use of a compound of Formula (I) or a form thereof for the preparation of a medicament that enhances expression of Smn protein in a human subject in need thereof. In a particular embodiment, the compound of Formula (I) or a form thereof enhances the inclusion of exon 7 of SMN2 into mRNA that is transcribed from the SMN2 gene as determined in an assay described herein (see, e.g., the Biological Examples, infra). In another embodiment, the compound of Formula (I) or a form thereof enhances the inclusion of exon 7 of SMN1 and/or SMN2 into mRNA that is transcribed from the SMN1 and/or SMN2 gene as determined in an assay described herein (see, e.g., the Biological Examples, infra) or in International Publication No. WO2009/151546 or U.S. Patent Application Publication No. 2011/0086833 (see, e.g., the Examples in those publications), each of which is incorporated herein by reference in its entirety.

In another aspect, provided herein are methods for treating spinal muscular atrophy (SMA), comprising administering to a subject an effective amount of a compound of Formula (I) or a form thereof. In a specific embodiment, provided herein is a method for treating SMA in a human subject in need thereof, comprising administering to the subject an effective amount of a compound of Formula (I) or a form thereof. In another specific embodiment, provided herein is a method for treating SMA in a human subject in need thereof, comprising administering to the subject a pharmaceutical composition comprising an effective amount of a compound of Formula (I) or a form thereof, and a pharmaceutically acceptable carrier, excipient or diluent.

In another embodiment, provided herein is a method for treating SMA in a human subject in need thereof, comprising administering to the subject an effective amount of a compound of Formula (I) or a form thereof that enhances the inclusion of exon 7 of SMN2 into mRNA that is transcribed from the SMN2 gene. In a specific embodiment, provided herein is a method for treating SMA in a human subject in need thereof, comprising administering to the subject a pharmaceutical composition comprising an effective amount of a compound of Formula (I) or a form thereof that enhances the inclusion of exon 7 of SMN2 into mRNA that is transcribed from the SMN2 gene, and a pharmaceutically acceptable carrier, excipient or diluent. In another specific embodiment, provided herein is a method for treating SMA in a human subject in need thereof, comprising administering to the human subject a pharmaceutical composition comprising an effective amount of a compound of Formula (I) or a form thereof that enhances the inclusion of exon 7 of SMN1 and/or SMN2 into mRNA that is transcribed from the SMN1 and/or SMN2 gene, and a pharmaceutically acceptable carrier, excipient or diluent. In a particular embodiment, the compound of Formula (I) or a form thereof enhances the inclusion of exon 7 of SMN2 into mRNA that is transcribed from the SMN2 gene in an assay described herein (see, e.g., the Biological Examples, infra). In another embodiment, the compound of Formula (I) or a form thereof enhances the inclusion of exon 7 of SMN1 and/or SMN2 into mRNA that is transcribed from the SMN1 and/or SMN2 gene as determined in an assay described herein (see, e.g., the Biological Examples, infra) or in International Publication No. WO2009/151546 or U.S. Patent Application Publication No. 2011/0086833 (see, e.g., the Examples in those publications), each of which is incorporated herein by reference in its entirety.

In another embodiment, provided herein is the use of a compound of Formula (I) or a form thereof in the manufacture of a medicament for treating SMA in a human subject in need thereof. In a particular embodiment, the compound of Formula (I) or a form thereof enhances the inclusion of exon 7 of SMN2 into mRNA that is transcribed from the SMN2 gene as determined in an assay described herein (see, e.g., the Biological Examples, infra). In another embodiment, the compound of Formula (I) or a form thereof enhances the inclusion of exon 7 of SMN1 and/or SMN2 into mRNA that is transcribed from the SMN1 and/or SMN2 gene as determined in an assay described herein (see, e.g., the Biological Examples, infra) or in International Publication No. WO2009/151546 or U.S. Patent Application Publication No. 2011/0086833 (see, e.g., the Examples in those publications), each of which is incorporated herein by reference in its entirety.

In an embodiment of a use or method provided herein, compounds of Formula (I) or a form thereof are used in combination with one or more additional agents. A compound(s) of Formula (I) or a form thereof can be administered to a subject or contacted with a cell prior to, concurrently with, or subsequent to administering to the subject or contacting the cell with an additional agent(s). A compound(s) of Formula (I) or a form thereof and an additional agent(s) can be administered to a subject or contacted with a cell in single composition or different compositions. In a specific embodiments, a compound(s) of Formula (I) or a form thereof is used in combination with gene replacement of SMN1 (using, e.g., viral delivery vectors). In another specific embodiments, a compound(s) of Formula (I) or a form thereof are used in combination with cell replacement using differentiated SMN1$^{+/+}$ and/or SMN2$^{+/+}$ stem cells. In another specific embodiments, a compound(s) of Formula (I) or a form thereof are used in combination with cell replacement using differentiated SMN1$^{+/+}$ stem cells. In another specific embodiments, a compound(s) of Formula (I) or a form thereof are used in combination with cell replacement using differentiated SMN2$^{+/+}$ stem cells. In another specific embodiment, a compound(s) of Formula (I) or a form thereof are used in combination with aclarubicin. In another specific embodiment, a compound(s) of Formula (I) or a form thereof are used in combination with a transcription activator such as a histone deacetylase ("HDAC") inhibitor (e.g., butyrates, valproic acid, and hydroxyurea), and mRNA stabilizers (e.g., mRNA decapping inhibitor RG3039 from Repligen).

In one embodiment, provided herein is the use of compounds of Formula (I) or a form thereof in combination with supportive therapy, including respiratory, nutritional or rehabilitation care.

In certain embodiments, treating SMA with a compound of Formula (I) or a form thereof (alone or in combination with an additional agent) has a therapeutic effect and/or beneficial effect. In a specific embodiment, treating SMA with a compound of Formula (I) or a form thereof (alone or in combination with an additional agent) results in one, two or more of the following effects: (i) reduces or ameliorates the severity of SMA; (ii) delays onset of SMA; (iii) inhibits the progression of SMA; (iv) reduces hospitalization of a subject; (v) reduces hospitalization length for a subject; (vi) increases the survival of a subject; (vii) improves the quality of life of a subject; (viii) reduces the number of symptoms associated with SMA; (ix) reduces or ameliorates the severity of a symptom(s) associated with SMA; (x) reduces the duration of a symptom associated with SMA; (xi) prevents the recurrence of a symptom associated with SMA; (xii) inhibits the development or onset of a symptom of SMA; and/or (xiii) inhibits of the progression of a symptom associated with SMA.

Symptoms of SMA include muscle weakness, poor muscle tone, weak cry, weak cough, limpness or a tendency to flop, difficulty sucking or swallowing, difficulty breathing, accumulation of secretions in the lungs or throat, clenched fists with sweaty hand, flickering/vibrating of the tongue, head often tilted to one side, even when lying down, legs that tend to be weaker than the arms, legs frequently assuming a "frog legs" position, feeding difficulties, increased susceptibility to respiratory tract infections, bowel/bladder weakness, lower-than-normal weight, inability to sit without support, failure to walk, failure to crawl, and hypotonia, areflexia, and multiple congenital contractures (arthrogryposis) associated with loss of anterior horn cells.

In a specific embodiment, treating SMA with a compound of Formula (I) or a form thereof (alone or in combination with an additional agent) results in one, two or more of the following effects: (i) a reduction in the loss of muscle strength; (ii) an increase in muscle strength; (iii) a reduction in muscle atrophy; (iv) a reduction in the loss of motor function; (v) an increase in motor neurons; (vii) a reduction in the loss of motor neurons; (viii) protection of SMN deficient motor neurons from degeneration; (ix) an increase in motor function; (x) an increase in pulmonary function; and/or (xi) a reduction in the loss of pulmonary function.

In another embodiment, treating SMA with a compound of Formula (I) or a form thereof (alone or in combination with an additional agent) results in the functional ability or helps retain the functional ability for a human infant or a human toddler to sit up. In another embodiment, treating SMA with a compound of Formula (I) or a form thereof (alone or in combination with an additional agent) results in the functional ability or helps retain the functional ability for a human infant, a human toddler, a human child or a human adult to stand up unaided. In another embodiment, treating SMA with a compound of Formula (I) or a form thereof (alone or in combination with an additional agent) results in the functional ability or helps retain the functional ability for a human infant, a human toddler, a human child or a human adult to walk unaided. In another embodiment, treating SMA with a compound of Formula (I) or a form thereof (alone or in combination with an additional agent) results in the functional ability or helps retain the functional ability for a human infant, a human toddler, a human child or a human adult to run unaided. In another embodiment, treating SMA with a compound of Formula (I) or a form thereof (alone or in combination with an additional agent) results in the functional ability or helps retain the functional ability for a human infant, a human toddler, a human child or a human adult to breathe unaided. In another embodiment, treating SMA with a compound of Formula (I) or a form thereof (alone or in combination with an additional agent) results in the functional ability or helps retain the functional ability for a human infant, a human toddler, a human child or a human adult to turn during sleep unaided. In another embodiment, treating SMA with a compound of Formula (I) or a form thereof (alone or in combination with an additional agent) results in the functional ability or helps retain the functional ability for a human infant, a human toddler, a human child or a human adult to swallow unaided.

In certain embodiments, a primer and/or probe described below in the Biological Examples (e.g., SMN primers such as SEQ ID NO. 1, 7, 8, 11 or 13 and/or SEQ ID NO. 2, 9 or 12, and SMN probes such as a SEQ ID NO. 3 or 10) is used in an assay, such as RT-PCR, RT-qPCR, endpoint RT-PCR, PCR, qPCR, rolling circle amplification, Northern blot or Southern blot, to determine whether a compound of Formula (I) or a form thereof enhances the inclusion of exon 7 of SMN1 and/or SMN2 into mRNA that is transcribed from an SMN1 and/or SMN2 gene. In some embodiments, a primer and/or probe described below in the Biological Examples (e.g., SMN primers such as SEQ ID NO. 1, 7, 8, 11 or 13 and/or SEQ ID NO. 2, 9 or 12, and SMN probes such as a SEQ ID NO. 3 or 10) is used in an assay, such as RT-PCR, RT-qPCR, endpoint RT-PCR, PCR, qPCR, rolling circle amplification, Northern blot or Southern blot, or a pharmaceutical or assay kit as described infra, to monitor patient responses to a compound of Formula (I) or a form thereof.

In a specific embodiment, a compound of Formula (I):

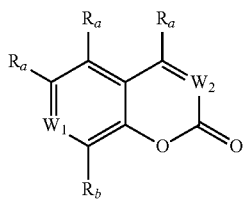

(I)

or a form thereof is used in accordance with a method described herein, wherein:

$w_1$ and $w_2$ are C—$R_1$ or C—$R_2$; wherein, one of $w_1$ and $w_2$ is C—$R_1$ and the other is C—$R_2$, provided that, when $w_1$ is C—$R_1$, then $w_2$ is C—$R_2$; or, when $w_1$ is C—$R_2$, then $w_2$ is C—$R_1$;

$R_1$ is $C_{1-8}$alkyl, amino, $C_{1-8}$alkyl-amino, ($C_{1-8}$alkyl)$_2$-amino, $C_{1-8}$alkoxy-$C_{1-8}$alkyl-amino, ($C_{1-8}$alkoxy-$C_{1-8}$alkyl)$_2$-amino, ($C_{1-8}$alkoxy-$C_{1-8}$alkyl)($C_{1-8}$alkyl)amino, amino-$C_{1-8}$alkyl, $C_{1-8}$alkyl-amino-$C_{1-8}$alkyl, ($C_{1-8}$alkyl)$_2$-amino-$C_{1-8}$alkyl, $C_{1-8}$alkoxy-$C_{1-8}$alkyl-amino-$C_{1-8}$alkyl, ($C_{1-8}$alkoxy-$C_{1-8}$alkyl)$_2$-amino-$C_{1-8}$alkyl, ($C_{1-8}$alkoxy-$C_{1-8}$alkyl)($C_{1-8}$alkyl)amino-$C_{1-8}$alkyl, amino-$C_{1-8}$alkyl-amino, (amino-$C_{1-8}$alkyl)$_2$-amino, (amino-$C_{1-8}$alkyl)($C_{1-8}$alkyl)amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl-amino-$C_{1-8}$alkyl)($C_{1-8}$alkyl)amino, ($C_{1-8}$alkyl)$_2$-amino-$C_{1-8}$alkyl-amino, [($C_{1-8}$alkyl)$_2$-amino-$C_{1-8}$alkyl]($C_{1-8}$alkyl)amino, amino-$C_{1-8}$alkoxy, $C_{1-8}$alkyl-amino-$C_{1-8}$alkoxy, ($C_{1-8}$alkyl)$_2$-amino-$C_{1-8}$alkoxy, $C_{1-8}$alkoxy-$C_{1-8}$alkyl-amino-$C_{1-8}$alkoxy, ($C_{1-8}$alkoxy-$C_{1-8}$alkyl)$_2$-amino-$C_{1-8}$alkoxy, ($C_{1-8}$alkoxy-$C_{1-8}$alkyl)($C_{1-8}$alkyl)amino-$C_{1-8}$alkoxy, amino-$C_{2-8}$alkenyl, $C_{1-8}$alkyl-amino-$C_{2-8}$alkenyl, ($C_{1-8}$alkyl)$_2$-amino-$C_{2-8}$alkenyl, amino-$C_{2-8}$alkynyl, $C_{1-8}$alkyl-amino-$C_{2-8}$alkynyl, ($C_{1-8}$alkyl)$_2$-amino-$C_{2-8}$alkynyl, halo-$C_{1-8}$alkyl-amino, (halo-$C_{1-8}$alkyl)$_2$-amino, (halo-$C_{1-8}$alkyl)($C_{1-8}$alkyl)amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino, (hydroxy-$C_{1-8}$alkyl)($C_{1-8}$alkyl)amino, hydroxy-$C_{1-8}$alkyl-amino-$C_{1-8}$alkyl, (hydroxy-$C_{1-8}$alkyl)$_2$-amino-$C_{1-8}$alkyl, (hydroxy-$C_{1-8}$alkyl)($C_{1-8}$alkyl)amino-$C_{1-8}$alkyl, hydroxy-$C_{1-8}$alkyl-amino-$C_{1-8}$alkoxy, (hydroxy-$C_{1-8}$alkyl)$_2$-amino-$C_{1-8}$alkoxy, (hydroxy-$C_{1-8}$alkyl)($C_{1-8}$alkyl)amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl)$_2$-amino, (hydroxy-$C_{1-8}$alkyl-amino-$C_{1-8}$alkyl)($C_{1-8}$alkyl)amino, (hydroxy-$C_{1-8}$alkyl)$_2$-amino-$C_{1-8}$alkyl-amino, (hydroxy-$C_{1-8}$alkyl)($C_{1-8}$alkyl)amino-$C_{1-8}$alkyl-amino, [(hydroxy-$C_{1-8}$alkyl)$_2$-amino-$C_{1-8}$alkyl]($C_{1-8}$alkyl)amino, [(hydroxy-$C_{1-8}$alkyl)($C_{1-8}$alkyl)amino-$C_{1-8}$alkyl]($C_{1-8}$alkyl)amino, heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl;

wherein, each instance of heterocyclyl and heteroaryl is optionally substituted with one, two or three $R_3$ substituents and one additional, optional $R_4$ substituent; and, wherein, alternatively, each instance of heterocyclyl and heteroaryl is optionally substituted with one, two, three or four $R_3$ substituents;

$R_2$ is aryl, aryl-amino, aryl-amino-carbonyl, heterocyclyl, heteroaryl or heteroaryl-amino;

wherein, each instance of aryl, heterocyclyl and heteroaryl is optionally substituted with one, two or three $R_6$ substituents and one additional, optional $R_7$ substituent;

$R_a$ is, in each instance, independently selected from hydrogen, halogen or $C_{1-8}$alkyl;

$R_b$ is hydrogen, halogen, $C_{1-8}$alkyl or $C_{1-8}$alkoxy;

$R_3$ is, in each instance, independently selected from cyano, halogen, hydroxy, oxo, $C_{1-8}$alkyl, halo-$C_{1-8}$alkyl, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$alkoxy-carbonyl, amino, $C_{1-8}$alkyl-amino, ($C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl, amino-$C_{1-8}$alkyl-amino, $C_{1-8}$alkyl-amino-$C_{1-8}$alkyl-amino, ($C_{1-8}$alkyl)$_2$-amino-$C_{1-8}$alkyl-amino, $C_{1-8}$alkoxy-$C_{1-8}$alkyl-amino, $C_{1-8}$alkyl-carbonyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino or (hydroxy-$C_{1-8}$alkyl)($C_{1-8}$alkyl)amino;

$R_4$ is $C_{3-14}$cycloalkyl, $C_{3-14}$cycloalkyl-$C_{1-8}$alkyl, $C_{3-14}$cycloalkyl-amino, aryl-$C_{1-8}$alkyl, aryl-$C_{1-8}$alkoxy-carbonyl, aryl-sulfonyloxy-$C_{1-8}$alkyl, heterocyclyl or heterocyclyl-$C_{1-8}$alkyl; wherein, each instance of $C_{3-14}$cycloalkyl, aryl and heterocyclyl is optionally substituted with one, two or three $R_5$ substituents;

R$_5$ is, in each instance, independently selected from halogen, hydroxy, cyano, nitro, C$_{1-8}$alkyl, halo-C$_{1-8}$alkyl, C$_{1-8}$alkoxy, halo-C$_{1-8}$alkoxy, amino, C$_{1-8}$alkyl-amino, (C$_{1-8}$alkyl)$_2$-amino or C$_{1-8}$alkyl-thio;

R$_6$ is, in each instance, independently selected from halogen, hydroxy, cyano, nitro, C$_{1-8}$alkyl, C$_{2-8}$alkenyl, halo-C$_{1-8}$alkyl, hydroxy-C$_{1-8}$alkyl, C$_{1-8}$alkoxy, halo-C$_{1-8}$alkoxy, amino, C$_{1-8}$alkyl-amino, (C$_{1-8}$alkyl)$_2$-amino or C$_{1-8}$alkyl-thio; and, R$_7$ is C$_{3-14}$cycloalkyl, C$_{3-14}$cycloalkyl-oxy, aryl, heterocyclyl or heteroaryl.

In another specific embodiment, the compound of Formula (I) used in accordance with a method described herein is a compound selected from Formula (Ia) or Formula (Ib):

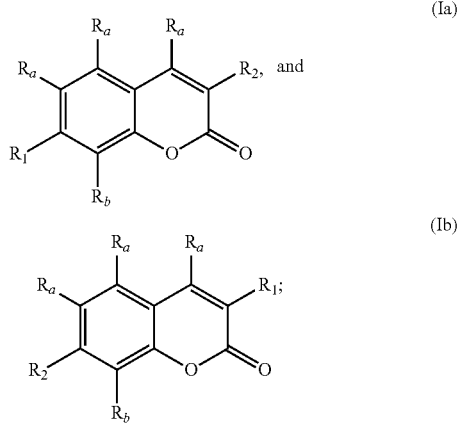

or a form thereof, wherein all variables are as previously defined.

Patient Population

In some embodiments, a compound of Formula (I) or a form thereof, or a pharmaceutical composition thereof is administered to a subject suffering from SMA. In other embodiments, a compound of Formula (I) or a form thereof, is administered to a subject predisposed or susceptible to SMA. In a specific embodiment, a compound of Formula (I) or a form thereof, or a pharmaceutical composition thereof is administered to a human subject, wherein the subject has SMA caused by an inactivating mutation or deletion in the SMN1 gene on both chromosomes, resulting in a loss of SMN1 gene function. In certain embodiments, the human subject is genotyped prior to administration of a compound of Formula (I) or a form thereof, or a pharmaceutical composition thereof to determine whether the subject has an inactivating mutation or deletion in the teleomeric copy of the SMN1 gene in both chromosomes, which results in a loss of SMN1 gene function. In some embodiments, a compound of Formula (I) or a form thereof, or pharmaceutical composition thereof is administered to a subject with Type 0 SMA. In some embodiments, a compound of Formula (I) or a form thereof, or a pharmaceutical composition thereof is administered to a subject with Type 1 SMA. In other embodiments, a compound of Formula (I) or a form thereof, or a pharmaceutical composition thereof is administered to a subject with Type 2 SMA. In other embodiments, a compound of Formula (I) or a form thereof, or a pharmaceutical composition thereof is administered to a subject with Type 3 SMA. In some embodiments, a compound of Formula (I) or a form thereof, or a pharmaceutical composition thereof is administered to a subject with Type 4 SMA.

In certain embodiments, a compound of Formula (I) or a form thereof, or a pharmaceutical composition thereof is administered to a subject that will or might benefit from enhanced inclusion of exon 7 of SMN1 and/or SMN2 into mRNA that is transcribed from the SMN1 and/or SMN2 gene. In specific embodiments, a compound of Formula (I) or a form thereof, or a pharmaceutical composition thereof is administered to a subject that will or may benefit from enhanced Smn protein expression.

In certain embodiments, a compound of Formula (I) or a form thereof, or a pharmaceutical composition thereof is administered to a human that has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In some embodiments, a compound of Formula (I) or a form thereof, or a pharmaceutical composition thereof is administered to a human infant. In other embodiments, a compound of Formula (I) or a form thereof, or a pharmaceutical composition thereof is administered to a human toddler. In other embodiments, a compound of Formula (I) or a form thereof, or a pharmaceutical composition thereof is administered to a human child. In other embodiments, a compound of Formula (I) or a form thereof, or a pharmaceutical composition thereof is administered to a human adult. In yet other embodiments, a compound of Formula (I) or a form thereof, or a pharmaceutical composition thereof is administered to an elderly human.

In some embodiments, a compound of Formula (I) or a form thereof, or a pharmaceutical composition thereof, is administered to a patient to prevent the onset of SMA in a patient at risk of developing SMA. In other embodiments, an effective amount of a compound of Formula (I) or a form thereof, or a pharmaceutical composition thereof, is administered to a patient to prevent the onset of SMA in a patient at risk of developing SMA. In other embodiments, a prophylactically effective amount of a compound of Formula (I) or a form thereof, or a pharmaceutical composition thereof, is administered to a patient to prevent the onset of SMA in a patient at risk of developing SMA. In other embodiments, a therapeutically effective amount of a compound of Formula (I) or a form thereof, or a pharmaceutical composition thereof, is administered to a patient to prevent the onset of SMA in a patient at risk of developing SMA. In a specific embodiment, the patient is an SMA patient.

In some embodiments, a compound of Formula (I) or a form thereof, or a pharmaceutical composition thereof, is administered to a patient to treat or ameliorate SMA in an SMA patient. In other embodiments, an effective amount of a compound of Formula (I) or a form thereof, or a pharmaceutical composition thereof, is administered to a patient to treat or ameliorate SMA in an SMA patient. In other embodiments, a prophylactically effective amount of a compound of Formula (I) or a form thereof, or a pharmaceutical composition thereof, is administered to a patient to prevent advancement of SMA in an SMA patient. In other embodiments, a therapeutically effective amount of a compound of Formula (I) or a form thereof, or a pharmaceutical composition thereof, is administered to a patient to treat or ameliorate SMA in an SMA patient. In a specific embodiment, the patient is an SMA patient.

In some embodiments, a compound of Formula (I) or a form thereof, or a medicament thereof is administered to a subject suffering from SMA. In other embodiments, a compound of Formula (I) or a form thereof, is administered to a subject predisposed or susceptible to SMA. In a specific embodiment, a compound of Formula (I) or a form thereof, or a medicament thereof is administered to a human subject, wherein the subject has SMA caused by an inactivating mutation or deletion in the SMN1 gene on both chromosomes, resulting in a loss of SMN1 gene function. In certain embodiments, the human subject is genotyped prior to administration of a compound of Formula (I) or a form thereof, or a medicament thereof to determine whether the subject has an inactivating mutation or deletion in the teleomeric copy of the SMN1 gene in both chromosomes, which results in a loss of SMN1 gene function. In some embodiments, a compound of Formula (I) or a form thereof, or medicament thereof is administered to a subject with Type 0 SMA. In some embodiments, a compound of Formula (I) or a form thereof, or a medicament thereof is administered to a subject with Type 1 SMA. In other embodiments, a compound of Formula (I) or a form thereof, or a medicament thereof is administered to a subject with Type 2 SMA. In other embodiments, a compound of Formula (I) or a form thereof, or a medicament thereof is administered to a subject with Type 3 SMA. In some embodiments, a compound of Formula (I) or a form thereof, or a medicament thereof is administered to a subject with Type 4 SMA.

In certain embodiments, a compound of Formula (I) or a form thereof, or a medicament thereof is administered to a subject that will or might benefit from enhanced inclusion of exon 7 of SMN1 and/or SMN2 into mRNA that is transcribed from the SMN1 and/or SMN2 gene. In specific embodiments, a compound of Formula (I) or a form thereof, or a medicament thereof is administered to a subject that will or may benefit from enhanced Smn protein expression.

In certain embodiments, a compound of Formula (I) or a form thereof, or a medicament thereof is administered to a human that has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In some embodiments, a compound of Formula (I) or a form thereof, or a medicament thereof is administered to a human infant. In other embodiments, a compound of Formula (I) or a form thereof, or a medicament thereof is administered to a human toddler. In other embodiments, a compound of Formula (I) or a form thereof, or a medicament thereof is administered to a human child. In other embodiments, a compound of Formula (I) or a form thereof, or a medicament thereof is administered to a human adult. In yet other embodiments, a compound of Formula (I) or a form thereof, or a medicament thereof is administered to an elderly human.

In some embodiments, a compound of Formula (I) or a form thereof, or a medicament thereof is administered to a patient to prevent the onset of SMA in a patient at risk of developing SMA. In other embodiments, an effective amount of a compound of Formula (I) or a form thereof, or a medicament thereof, is administered to a patient to prevent the onset of SMA in a patient at risk of developing SMA. In other embodiments, a prophylactically effective amount of a compound of Formula (I) or a form thereof, or a medicament thereof, is administered to a patient to prevent the onset of SMA in a patient at risk of developing SMA. In other embodiments, a therapeutically effective amount of a compound of Formula (I) or a form thereof, or a medicament thereof, is administered to a patient to prevent the onset of SMA in a patient at risk of developing SMA. In a specific embodiment, the patient is an SMA patient.

In some embodiments, a compound of Formula (I) or a form thereof, or a medicament thereof, is administered to a patient to treat or ameliorate SMA in an SMA patient. In other embodiments, an effective amount of a compound of Formula (I) or a form thereof, or a medicament thereof, is administered to a patient to treat or ameliorate SMA in an SMA patient. In other embodiments, a prophylactically effective amount of a compound of Formula (I) or a form thereof, or a medicament thereof, is administered to a patient to prevent advancement of SMA in an SMA patient. In other embodiments, a therapeutically effective amount of a compound of Formula (I) or a form thereof, or a medicament thereof, is administered to a patient to treat or ameliorate SMA in an SMA patient. In a specific embodiment, the patient is an SMA patient.

Mode of Administration

When administered to a patient, a compound of Formula (I) or a form thereof is preferably administered as a component of a composition that optionally comprises a pharmaceutically acceptable carrier, excipient or diluent. The composition can be administered orally, or by any other convenient route, for example, by infusion or bolus injection, by absorption through epithelial or mucocutaneous linings (e.g., oral mucosa, rectal, and intestinal mucosa) and may be administered together with another biologically active agent. Administration can be systemic or local. Various delivery systems are known, e.g., encapsulation in liposomes, microparticles, microcapsules, capsules, and can be used to administer the compound. In a specific embodiment, the patient is an SMA patient.

Methods of administration include but are not limited to parenteral, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of a compound into the bloodstream. In a specific embodiment, a compound is administered orally.

Dosage and Dosage Forms

The amount of a compound of Formula (I) or a form thereof that will be effective in the treatment of SMA depend, e.g., on the route of administration, the type of SMA, the general health of the subject, ethnicity, age, weight, and gender of the subject, diet, time, and the severity of SMA, and should be decided according to the judgment of the practitioner and each patient's or subject's circumstances.

In specific embodiments, an "effective amount," "prophylactically effective amount" or "therapeutically effective amount" in the context of the administration of a compound of Formula (I) or a form thereof, or composition or medicament thereof refers to an amount of a compound of Formula (I) which has a therapeutic effect and/or beneficial effect. In certain specific embodiments, an "effective amount," "prophylactically effective amount" or "therapeutically effective amount" in the context of the administration of a compound of Formula (I) or a form thereof, or composition or medicament thereof results in one, two or more of the following effects: (i) reduces or ameliorates the severity of SMA; (ii) delays onset of SMA; (iii) inhibits the progression of SMA; (iv) reduces hospitalization of a subject; (v) reduces hospitalization length for a subject; (vi) increases the survival of a subject; (vii) improves the quality of life of a subject; (viii) reduces the number of symptoms associated with SMA; (ix) reduces or ameliorates the severity of a symptom(s) associated with SMA; (x) reduces the duration of a symptom associated with SMA; (xi) prevents the recurrence of a symptom associated with SMA; (xii) inhibits the development or onset of a symptom of SMA; and/or (xiii) inhibits of the progression of a symptom associated with SMA. In certain embodiments, an effective amount of a compound of Formula (I) or a form thereof is an amount effective to enhance inclusion of exon 7 of SMN2 into SMN2 mRNA that is transcribed from the SMN2 gene and increases the levels of Smn protein produced from the SMN2 gene and thus producing a desired beneficial effect in a subject in need thereof. In some instances, the desired effect can be determined by analyzing or quantifying: (1) the inclusion of exon 7 of SMN2 into mRNA that is transcribed from the SMN2 gene; or (2) the levels of Smn protein produced from the SMN2 gene. Non-limiting examples of effective amounts of a compound of Formula (I) or a form thereof are described herein.

For example, the effective amount may be the amount required to treat SMA in a human subject in need thereof, or the amount required to enhance inclusion of exon 7 of SMN2 into mRNA that is transcribed from the SMN2 gene in a human subject in need thereof, or the amount required to increase levels of Smn protein produced from the SMN2 gene in a human subject in need thereof.

In general, the effective amount will be in a range of from about 0.001 mg/kg/day to about 500 mg/kg/day for a patient or subject having a weight in a range of between about 1 kg to about 200 kg. The typical adult subject is expected to have a median weight in a range of between about 70 and about 100 kg.

Within the scope of the present description, the "effective amount" of a compound of Formula (I) or a form thereof for use in the manufacture of a medicament, the preparation of a pharmaceutical kit or in a method for treating SMA in a human subject in need thereof, is intended to include an amount in a range of from about 0.001 mg to about 35,000 mg. In a specific embodiment, the human subject is an SMA patient.

The compositions described herein are formulated for administration to the subject via any drug delivery route known in the art. Nonlimiting examples include oral, ocular, rectal, buccal, topical, nasal, ophthalmic, subcutaneous, intramuscular, intravenous (bolus and infusion), intracerebral, transdermal, and pulmonary routes of administration.

Pharmaceutical Compositions

Embodiments described herein include the use of a compound of Formula (I) or a form thereof in a pharmaceutical composition. In a specific embodiment, described herein is the use of a compound of Formula (I) or a form thereof in a pharmaceutical composition for treating SMA in a human subject in need thereof comprising administering an effective amount of a compound of Formula (I) or a form thereof in admixture with a pharmaceutically acceptable carrier, excipient or diluent. In a specific embodiment, the human subject is an SMA patient.

A compound of Formula (I) or a form thereof may optionally be in the form of a composition comprising the compound or a form thereof and an optional carrier, excipient or diluent. Other embodiments provided herein include pharmaceutical compositions comprising an effective amount of a compound of Formula (I) or a form thereof and a pharmaceutically acceptable carrier, excipient, or diluent. In a specific embodiment, the pharmaceutical compositions are suitable for veterinary and/or human administration. The pharmaceutical compositions provided herein can be in any form that allows for the composition to be administered to a subject.

In a specific embodiment and in this context, the term "pharmaceutically acceptable carrier, excipient or diluent" means a carrier, excipient or diluent approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which a therapeutic agent is administered. Such pharmaceutical carriers can be sterile liquids, such as water and oils, including those of petroleum, animal, vegetable or synthetic origin, such as peanut oil, soybean oil, mineral oil, sesame oil and the like. Water is a specific carrier for intravenously administered pharmaceutical compositions. Saline solutions and aqueous dextrose and glycerol solutions can also be employed as liquid carriers, particularly for injectable solutions.

Typical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. Further provided herein are anhydrous pharmaceutical compositions and dosage forms comprising one or more compounds of Formula (I) or a form thereof as described herein. The compositions and single unit dosage forms can take the form of solutions or syrups (optionally with a flavoring agent), suspensions (optionally with a flavoring agent), emulsions, tablets (e.g., chewable tablets), pills, capsules, granules, powder (optionally for reconstitution), taste-masked or sustained-release formulations and the like.

Pharmaceutical compositions provided herein that are suitable for oral administration can be presented as discrete dosage forms, such as, but are not limited to, tablets, caplets, capsules, granules, powder, and liquids. Such dosage forms contain predetermined amounts of active ingredients, and may be prepared by methods of pharmacy well known to those skilled in the art.

Examples of excipients that can be used in oral dosage forms provided herein include, but are not limited to, binders, fillers, disintegrants, and lubricants.

Biomarkers

In certain embodiments, the amount of mRNA that is transcribed from the SMN1 gene and/or SMN2 gene and includes exon 7 of SMN1 and/or SMN2 is used as a biomarker for SMA. In certain embodiments, the amount of mRNA that is transcribed from the SMN1 gene and/or SMN2 gene and does not include exon 7 of SMN1 and/or SMN2 is used as a biomarker for SMA. In a specific embodiment, the patient is an SMA patient.

In other embodiments, the amount of mRNA that is transcribed from the SMN1 and/or SMN2 gene and includes exon 7 of SMN1 and/or SMN2 is used as a biomarker for an SMA patient being treated with a compound, such as disclosed herein. In other embodiments, the amount of mRNA that is transcribed from the SMN1 and/or SMN2 gene and does not include exon 7 of SMN1 and/or SMN2 is used as a biomarker for an SMA patient being treated with a compound, such as disclosed herein. In a specific embodiment, the patient is an SMA patient.

In some embodiments, a change in the amount of mRNA that is transcribed from the SMN1 and/or SMN2 gene and includes exon 7 of SMN1 and/or SMN2 and a corresponding change in the amount of mRNA that is transcribed from the SMN1 and/or SMN2 gene and does not include exon 7 of SMN1 and/or SMN2 is a biomarker for a patient being treated with a compound, such as disclosed herein. In a specific embodiment, the patient is an SMA patient.

In a specific embodiment, an increase in the amount of mRNA that is transcribed from the SMN1 and/or SMN2 gene and includes exon 7 of SMN1 and/or SMN2 and a corresponding decrease in the amount of mRNA that is transcribed from the SMN1 and/or SMN2 gene and does not include exon 7 of SMN1 and/or SMN2, after the administration of a compound (e.g., a compound of Formula (I) disclosed herein), indicates that the compound may be effective to treat SMA. In another specific embodiment, a decrease in the amount of mRNA that is transcribed from the SMN2 gene and includes exon 7 of SMN2 and a corresponding increase in the amount of mRNA that is transcribed from the SMN2 gene and does not include exon 7 of SMN2, after the administration of a compound (e.g., a compound of Formula (I) disclosed herein), indicates that the compound will not be effective to treat SMA. In accordance with these embodiments, an SMN primer(s) and/or an SMN probe described below can be used in assays, such as PCR (e.g., qPCR) and RT-PCR (e.g., RT-qPCR or endpoint RT-PCR) to assess and/or quantify the amount of mRNA that is transcribed from the SMN1 gene and/or SMN2 gene that does or does not include exon 7 of SMN1 and/or SMN2.

In one embodiment, provided herein are SMN primers and/or SMN probes (e.g., a forward primer having the nucleotide sequence of SEQ ID NO. 1, 7, 8, 11 or 13; and/or a reverse primer having the nucleotide sequence of SEQ ID NO. 9 or 12; and/or an SMN probe such as a SEQ ID NO. 3 or 10) for amplifying nucleic acids encoding or encoded by human SMN1 and/or SMN2. These primers can be used as primers in, e.g., RT-PCR (such as RT-PCR, endpoint RT-PCR and/or RT-qPCR as described herein or as known to one skilled in the art), PCR (such as qPCR) or rolling circle amplification, and as probes in hybridization assays, such as a Northern blot and/or a Southern blot assay. As utilized in the Biological Examples herein, endpoint RT-PCR is a reverse transcription-polymerase chain reaction that is carried out for a certain number of amplification cycles (or until starting materials are exhausted) following by a quantification of each of the DNA products using, e.g., gel electrophoretic separation, staining with a fluorescent dye, quantification of fluorescence and the like.

SEQ ID NO. 1 hybridizes to DNA or RNA comprising nucleotides corresponding to nucleotides 22 to 40 of exon 7 of SMN1 and/or SMN2, SEQ ID NO. 2 hybridizes to DNA or RNA comprising nucleotides corresponding to nucleotides 4 to 26 of the firefly luciferase coding sequence; SEQ ID NO. 7 hybridizes to nucleic acid sequences (e.g., the sense strand of DNA) comprising nucleotides corresponding to nucleotides 32 to 54 of exon 7 of SMN1 and/or SMN2 and nucleotides 1 to 4 of exon 8 of SMN1 and/or SMN2, SEQ ID NO. 8 hybridizes to nucleic acid sequences (e.g., the sense strand of DNA) comprising nucleotides corresponding, in order, to nucleotides 87 to 111 of exon 7 of SMN1 and/or SMN2 and nucleotides 1 to 3 of exon 8 of SMN1 and/or SMN2, SEQ ID NO. 9 hybridizes to nucleic acid sequences (e.g., the antisense strand of DNA or RNA) comprising nucleotides corresponding to nucleotides 39 to 62 of exon 8 of SMN1 and/or SMN2, SEQ ID NO. 11 hybridizes to nucleic acid sequences (e.g., the sense strand of DNA) comprising nucleotides corresponding to nucleotides 43 to 63 of exon 6 of SMN1 and/or SMN2, SEQ ID NO. 12 hybridizes to nucleic acid sequences (e.g., the antisense strand of DNA or RNA) comprising nucleotides corresponding to nucleotides 51 to 73 of exon 8 of SMN1 and/or SMN2, and SEQ ID NO. 13 hybridizes to nucleic acid sequence (e.g., the sense strand of DNA) comprising nucleotides corresponding to nucleotides 22 to 46 of exon 6 of SMN1 and/or SMN2.

Accordingly, an oligonucleotide corresponding to SEQ ID NO. 9, 11, 12 and/or 13 can be used in an amplification reaction to amplify nucleic acids encoding or encoded by human SMN1 and/or SMN2 lacking exon 7 of human SMN1 and/or SMN2 and nucleic acid encoding or encoded by human SMN1 and/or SMN2 and includes exon 7 of human SMN1 and/or SMN2. In contrast, an oligonucleotide corresponding to SEQ ID NO. 8 in conjunction with a downstream reverse primer (e.g., SEQ ID NO. 9 or 12) can be used to amplify nucleic acids encoding or encoded by human SMN1 and/or SMN2 lacking exon 7 of human SMN1 and/or SMN2 and an oligonucleotide corresponding to SEQ ID NO. 1 and 7 in conjunction with a downstream reverse primer (e.g., SEQ ID NO. 9 or 12) can be used to amplify nucleic acids encoding or encoded by human SMN1 and/or human SMN2 and includes exon 7 of SMN1 and/or SMN2.

SEQ ID NO. 3 hybridizes to nucleic acid sequences (e.g., the sense strand of DNA) comprising nucleotides corresponding, in order, to nucleotides 50 to 54 of exon 7 of human SMN1 and/or SMN2 and nucleotides 1 to 21 of exon 8 of human SMN1 and/or SMN2, and SEQ ID NO. 10 hybridizes to nucleic acid sequences (e.g., the sense strand of DNA) comprising nucleotides corresponding to nucleotides 7 to 36 of exon 8 of human SMN1 and/or SMN2. SEQ ID NO. 3 is useful as a probe to detect mRNA that is transcribed from the minigene and includes exon 7 of SMN1 and/or SMN2, described herein or described in International Publication No. WO 2009/151546 or U.S. Patent Application Publication No. 2011/0086833 (each of which is incorporated herein by reference in its entirety) and to detect mRNA that is transcribed from human SMN1 and/or SMN2 and includes exon 7 of SMN1 and/or SMN2. In addition, SEQ ID NO. 10 is useful as a probe to detect mRNA that is transcribed from the minigene that does or does not include exon 7 of SMN1 and/or SMN2 and to detect mRNA that is transcribed from human SMN1 and/or SMN2, described herein or as described in International Publication No. WO 2009/151546 or U.S. Patent Application Publication No. 2011/0086833, each of which is incorporated herein by reference in its entirety.

In a specific embodiment, a primer and/or probe described below in the Biological Examples (e.g., SMN primers such as SEQ ID NO. 1, 7, 11 or 13 and/or SEQ ID NO. 2, 9 or 12, and/or SMN probes such as a SEQ ID NO. 3 or 10) is used in an assay, such as RT-PCR, RT-qPCR, endpoint RT-PCR, PCR, qPCR, rolling circle amplification and, as applicable, Northern blot or Southern blot (e.g., an assay such as described below in the Biological Examples), to determine whether a compound (e.g., a compound of Formula (I) or a form thereof) enhances the inclusion of exon 7 of SMN1 and/or SMN2 into mRNA that is transcribed from an SMN1 and/or SMN2 gene.

In another embodiment, a primer and/or probe described below in the Biological Examples (e.g., SMN primers such as SEQ ID NO. 1, 7, 11 or 13 and/or SEQ ID NO. 9 or 12, and/or SMN probes such as a SEQ ID NO. 3 or 10) is used in an assay, such as RT-PCR, RT-qPCR, endpoint RT-PCR, PCR, qPCR, rolling circle amplification and, as applicable, Northern blot or Southern blot (e.g., an assay such as described below in the Biological Examples), to monitor the amount of mRNA that is transcribed from the SMN1 and/or SMN2 gene and includes exon 7 of SMN1 and/or SMN2 in a patient sample. In a specific embodiment, the patient is an SMA patient.

In another embodiment, a primer and/or probe described below in the Biological Examples (e.g., SMN primers such as SEQ ID NO. 1, 7, 11 or 13 and/or SEQ ID NO. 9 or 12, and/or SMN probes such as a SEQ ID NO. 3 or 10) is used in an assay, such as RT-PCR, RT-qPCR, endpoint RT-PCR, PCR, qPCR, rolling circle amplification and, as applicable, Northern blot or Southern blot (e.g., an assay such as described below in the Biological Examples), to monitor a patient's response to a compound (e.g., a compound of Formula (I) or a form thereof). In a specific embodiment, the patient is an SMA patient.

A sample (e.g., a blood sample, PBMC sample, or tissue sample, such as a skin or muscle tissue sample) from a patient can be obtained using techniques known to one skilled in the art and the primers and/or probes described in the Biological Examples below can be used in assays (e.g., PCR, RT-PCR, RT-qPCR, qPCR, endpoint RT-PCR, rolling circle amplification, Northern blot and Southern blot) to determine the amount of mRNA that is transcribed from the SMN1 and/or SMN2 genes (e.g., the amount of mRNA that includes exon 7 of SMN2 transcribed from the SMN2 gene). A sample derived from a patient refers to a sample that is processed and/or manipulated after being obtained from the patient using techniques known to one skilled in the art. For example, a sample from a patient can be processed to, e.g., extract RNA, using techniques known to one of skill in the art. A sample from a patient can be processed to, e.g., extract RNA and the RNA is reversed transcribed to produce cDNA. In a specific embodiment, the patient is an SMA patient.

In a specific embodiment, provided herein is a method for detecting the amount of mRNA that is transcribed from the SMN1 and/or SMN2 gene and includes exon 7 of SMN1 and/or SMN2, comprising: (a) contacting a patient sample (e.g., blood sample or tissue sample) or a sample derived from a patient (e.g., a blood sample or tissue sample that has been processed to extract RNA) with a forward SMN primer described below (e.g., SEQ ID NO. 1, 7, 11 or 13) and/or a reverse SMN primer described herein (e.g., SEQ ID NO. 9 or 12) along with applicable components for, e.g., an RT-PCR (e.g., endpoint RT-PCR and/or RT-qPCR), PCR (e.g., qPCR) or rolling circle amplification; and (b) detecting the amount of mRNA that is transcribed from the SMN1 and/or SMN2 gene and includes exon 7 of SMN1 and/or SMN2. In certain embodiments, the sample is from or derived from a patient administered a compound, such as a compound of Formula (I) or a form thereof as described herein. In a specific embodiment, the patient is an SMA patient.

In another specific embodiment, provided herein is a method for detecting the amount of mRNA that is transcribed from the SMN1 and SMN2 genes, comprising: (a) contacting a patient sample (e.g., blood sample or tissue sample) or a sample derived from a patient (e.g., a blood sample or tissue sample that has been processed to extract RNA) with a forward SMN primer described below (e.g., SEQ ID NO. 1, 7, 11 or 13) and/or a reverse SMN primer described herein (e.g., SEQ ID NO. 9 or 12) along with applicable components for, e.g., an RT-PCR (e.g., endpoint RT-PCR and/or RT-qPCR), PCR (e.g., qPCR) or rolling circle amplification; and (b) detecting the amount of mRNA that is transcribed from the SMN1 and SMN2 genes. In certain embodiments, the sample is from or derived from a patient administered a compound, such as a compound of Formula (I) or a form thereof as described herein. In a specific embodiment, the patient is an SMA patient.

The amount of mRNA that is transcribed from the human SMN1 and SMN2 genes and includes exon 7 of SMN1 and SMN2 and the amount of mRNA that is transcribed from the human SMN1 and SMN2 genes and does not include exon 7 of SMN1 and SMN2 can be differentiated from each other by, e.g., size of the RNA or DNA fragment generated from SMN1 and SMN2 mRNA that includes exon 7 of SMN1 and SMN2 and from SMN1 and SMN2 mRNA that does not include exon 7 of SMN1 and SMN2.

In another specific embodiment, provided herein is a method for detecting the amount of mRNA that is transcribed from the SMN1 and/or SMN2 gene and does not include exon 7 of SMN1 and/or SMN2, comprising: (a) contacting a patient sample (e.g., blood sample or tissue sample) or a sample derived from a patient (e.g., a blood sample or tissue sample that has been processed to extract RNA) with a forward SMN primer described below (e.g., SEQ ID NO. 8, 11 or 13) and/or a reverse SMN primer described herein (e.g., SEQ ID NO. 9 or 12) along with applicable components for, e.g., an RT-PCR (e.g., endpoint RT-PCR and/or RT-qPCR), PCR (e.g., qPCR) or rolling circle amplification; and (b) detecting the amount of mRNA that is transcribed from the SMN1 and/or SMN2 gene and does not include exon 7 of SMN1 and/or SMN2. In certain embodiments, the sample is from or derived from a patient administered a compound, such as a compound of Formula (I) or a form thereof as described herein. In a specific embodiment, the patient is an SMA patient.

In another specific embodiment, provided herein is a method for detecting the amount of mRNA that is transcribed from the SMN1 and/or SMN2 gene and includes exon 7 of SMN1 and/or SMN2, comprising: (a) contacting a patient sample (e.g., blood sample or tissue sample) or a sample derived from a patient (e.g., a blood sample or tissue sample that has been processed to extract RNA) with an SMN probe described below (e.g., SEQ ID NO. 3 or 10) along with applicable components, e.g., of an RT-PCR (e.g., endpoint RT-PCR and/or RT-qPCR), PCR (e.g., qPCR), rolling circle amplification and, as applicable, Northern blot or Southern blot; and (b) detecting the amount of mRNA that is transcribed from the SMN1 and/or SMN2 gene and includes exon 7 of SMN1 and/or SMN2. In certain embodiments, the sample is from or derived from a patient administered a compound, such as a compound of Formula (I) or a form thereof as described herein. In a specific embodiment, the patient is an SMA patient.

In another specific embodiment, provided herein is a method for detecting the amount of mRNA that is transcribed from the SMN1 and SMN2 genes, comprising: (a) contacting a patient sample (e.g., blood sample or tissue sample) or a sample derived from a patient (e.g., a blood sample or tissue sample that has been processed to extract RNA) with an SMN probe described below (e.g., SEQ ID NO. 3 or 10) along with applicable components for, e.g., an RT-PCR (e.g., endpoint RT-PCR and/or RT-qPCR), PCR (e.g., qPCR), rolling circle amplification and, as applicable, Northern blot or Southern blot; and (b) detecting the amount of mRNA that is transcribed from the SMN1 and SMN2 genes. In a specific embodiment, the patient is an SMA patient.

The amount of mRNA that is transcribed from the human SMN1 and SMN2 genes and includes exon 7 of SMN1 and SMN2 and the amount of mRNA that is transcribed from the human SMN1 and SMN2 genes and does not include exon 7 of SMN1 and SMN2 can be differentiated from each other by, e.g., size of the RNA or DNA fragment generated from SMN1 and SMN2 mRNA that includes exon 7 of SMN1 and SMN2 and from SMN1 and SMN2 mRNA that does not include exon 7 of SMN1 and SMN2. In certain embodiments, the sample is from or derived from a patient administered a compound, such as a compound of Formula (I) or a form thereof as described herein. In a specific embodiment, the patient is an SMA patient.

In another specific embodiment, provided herein is a method for detecting the amount of mRNA that is transcribed from the SMN1 and/or SMN2 gene and does not include exon 7 of SMN1 and/or SMN2, comprising: (a) contacting a patient sample (e.g., blood sample or tissue sample) or a sample derived from a patient (e.g., a blood sample or tissue sample that has been processed to extract RNA) with an SMN probe described below (e.g., SEQ ID NO. 10) along with applicable components for, e.g., an RT-PCR (e.g., endpoint RT-PCR and/or RT-qPCR), PCR (e.g., qPCR), rolling circle amplification, or Northern blot or Southern blot; and (b) detecting the amount of mRNA that is transcribed from the SMN1 and/or SMN2 gene and does not include exon 7 of SMN1 and/or SMN2. In certain embodiments, the sample is from or derived from a patient administered a compound, such as a compound of Formula (I) or a form thereof as described herein. In a specific embodiment, the patient is an SMA patient.

In a specific embodiment, provided herein is a method for detecting the amount of mRNA that is transcribed from the SMN1 and/or SMN2 gene and includes exon 7 of SMN1 and/or SMN2, comprising: (a) contacting a patient sample (e.g., blood sample or tissue sample) or a sample derived from a patient (e.g., a blood sample or tissue sample that has been processed to extract RNA) with a forward SMN primer described below (e.g., SEQ ID NO. 1, 7, 11 or 13) and/or a reverse SMN primer described herein (e.g., SEQ ID NO. 9 or 12) and/or an SMN probe described herein (e.g., SEQ ID NO. 3 or 10) along with applicable components for e.g., an RT-PCR (e.g., endpoint RT-PCR and/or RT-qPCR), PCR (e.g., qPCR) or rolling circle amplification; and (b) detecting the amount of mRNA that is transcribed from the SMN1 and/or SMN2 gene and includes exon 7 of SMN1 and/or SMN2. In certain embodiments, the sample is from or derived from a patient administered a compound, such as a compound of Formula (I) or a form thereof as described herein. In a specific embodiment, the patient is an SMA patient.

In a specific embodiment, provided herein is a method for detecting the amount of mRNA that is transcribed from the SMN1 and SMN2 genes, comprising: (a) contacting a patient sample (e.g., blood sample or tissue sample) or a sample derived from a patient (e.g., a blood sample or tissue sample that has been processed to extract RNA) with a forward SMN primer described below (e.g., SEQ ID NO. 1, 7, 8, 11 or 13) and/or a reverse SMN primer described herein (e.g., SEQ ID NO. 9 or 12) and/or an SMN probe described herein (e.g., SEQ ID NO. 3 or 10) along with applicable components for e.g., an RT-PCR (e.g., endpoint RT-PCR and/or RT-qPCR), PCR (e.g., qPCR) or rolling circle amplification, as applicable; and (b) detecting the amount of mRNA that is transcribed from the SMN1 and SMN2 genes. In a specific embodiment, the patient is an SMA patient.

The amount of mRNA that is transcribed from the human SMN1 and SMN2 genes and includes exon 7 of SMN1 and SMN2 and the amount of mRNA that is transcribed from the human SMN1 and SMN2 genes and does not include exon 7 of SMN1 and SMN2 can be differentiated from each other by, e.g., size of the RNA or DNA fragment generated from SMN1 and SMN2 mRNA that includes exon 7 of SMN1 and SMN2 and from SMN1 and SMN2 mRNA that does not include exon 7 of SMN1 and SMN2. In certain embodiments, the sample is from or derived from a patient administered a compound, such as a compound of Formula (I) or a form thereof as described herein. In a specific embodiment, the patient is an SMA patient.

In a specific embodiment, provided herein is a method for detecting the amount of mRNA that is transcribed from the SMN1 and/or SMN2 gene and does not include exon 7 of SMN1 and/or SMN2, comprising: (a) contacting a patient sample (e.g., blood sample or tissue sample) or a sample derived from a patient (e.g., a blood sample or tissue sample that has been processed to extract RNA) with a forward SMN primer described below (e.g., SEQ ID NO. 8) and/or a reverse SMN primer described herein (e.g., SEQ ID NO. 9 or 12) and/or an SMN probe described herein (e.g., SEQ ID NO. 10) along with applicable components for e.g., an RT-PCR (e.g., endpoint RT-PCR and/or RT-qPCR), PCR (e.g., qPCR) or rolling circle amplification; and (b) detecting the amount of mRNA that is transcribed from the SMN1 and/or SMN2 gene and does not include exon 7 of SMN1 and/or SMN2. In certain embodiments, the sample is from or derived from a patient administered a compound, such as a compound of Formula (I) or a form thereof as described herein. In a specific embodiment, the patient is an SMA patient.

In a specific embodiment, provided herein is a method for assessing an SMA patient's response to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 1, 7, 11 or 13) and/or a reverse SMN primer described herein (e.g., SEQ ID NO. 9 or 12) along with applicable components for e.g., RT-PCR (e.g., endpoint RT-PCR and/or RT-qPCR), PCR (e.g., qPCR) or rolling circle amplification, wherein the sample is from or derived from an SMA patient administered a compound (e.g., a compound described herein); and (b) detecting the amount of mRNA that is transcribed from the SMN1 and/or SMN2 gene and includes exon 7 of SMN1 and/or SMN2, wherein (1) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound indicates that the patient is responsive to the compound and that the compound may be or is beneficial and/or of therapeutic value to the patient; and (2) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound indicates that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In another specific embodiment, provided herein is a method for assessing an SMA patient's response to a compound, comprising: (a) administering a compound to an SMA patient; (b) contacting a sample (e.g., blood sample or tissue sample) obtained or derived from the patient with a forward SMN primer described below (e.g., SEQ ID NO. 1, 7, 11 or 13) and/or a reverse SMN primer described herein (e.g., SEQ ID NO. 9 or 12) along with applicable components for e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and includes exon 7 of SMN2, wherein (1) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound indicates that the patient is responsive to the compound and that the compound may be or is beneficial and/or of therapeutic value to the patient; and (2) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound indicates that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In a specific embodiment, provided herein is a method for assessing an SMA patient's response to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 1, 7, 11 or 13) and/or a reverse SMN primer described herein (e.g., SEQ ID NO. 9 or 12) and/or an SMN probe (e.g., SEQ ID NO. 3 or 10) along with applicable components for e.g., RT-PCR (e.g., endpoint RT-PCR and/or RT-qPCR), PCR (e.g., qPCR) or rolling circle amplification, wherein the sample is from or derived from an SMA patient administered a compound (e.g., a compound of Formula (I) or a form thereof as described herein); and (b) detecting the amount of mRNA that is transcribed from the SMN1 and/or SMN2 gene and includes exon 7 of SMN1 and/or SMN2, wherein (1) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound indicates that the patient is responsive to the compound and that the compound may be or is beneficial and/or of therapeutic value to the patient; and (2) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound indicates that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In another specific embodiment, provided herein is a method for assessing an SMA patient's response to a compound, comprising: (a) administering a compound to an SMA patient; (b) contacting a sample (e.g., blood sample or tissue sample) obtained or derived from the patient with a forward SMN primer described below (e.g., SEQ ID NO. 1, 7, 11 or 13) and/or a reverse SMN primer described herein (e.g., SEQ ID NO. 9 or 12) and/or an SMN probe (e.g., SEQ ID NO. 3 or 10) along with applicable components for e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and includes exon 7 of SMN1 and/or SMN2, wherein (1) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound indicates that the patient is responsive to the compound and that the compound may be or is beneficial and/or of therapeutic value to the patient; and (2) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound indicates that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In a specific embodiment, provided herein is a method for assessing an SMA patient's response to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 8, 11 or 13) and/or a reverse SMN primer described herein (e.g., SEQ ID NO. 9 or 12) along with applicable components for e.g., RT-PCR (e.g., endpoint RT-PCR and/or RT-qPCR), PCR (e.g., qPCR) or rolling circle amplification, wherein the sample is from or derived from an SMA patient administered a compound (e.g., a compound of Formula (I) or a form thereof as described herein); and (b) detecting the amount of mRNA that is transcribed from the SMN1 and/or SMN2 gene and does not include exon 7 of SMN1 and/or SMN2, wherein (1) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound indicates that the patient is responsive to the compound and that the compound may be or is beneficial and/or of therapeutic value to the patient; and (2) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound indicates that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In another specific embodiment, provided herein is a method for assessing an SMA patient's response to a compound, comprising: (a) administering a compound to an SMA patient; (b) contacting a sample (e.g., blood sample or tissue sample) obtained or derived from the patient with a forward SMN primer described below (e.g., SEQ ID NO. 8, 11 or 13) and/or a reverse SMN primer described herein (e.g., SEQ ID NO. 9 or 12) along with applicable components for e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and does not include exon 7 of SMN1 and/or SMN2, wherein (1) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound indicates that the patient is responsive to the compound and that the compound may be or is beneficial and/or of therapeutic value to the patient; and (2) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound indicates that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In a specific embodiment, provided herein is a method for assessing an SMA patient's response to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 8, 11 or 13) and/or a reverse SMN primer described herein (e.g., SEQ ID NO. 9 or 12) and/or an SMN probe (e.g., SEQ ID NO. 10) along with applicable components for e.g., RT-PCR (e.g., endpoint RT-PCR and/or RT-qPCR), PCR (e.g., qPCR) or rolling circle amplification, wherein the sample is from or derived from an SMA patient administered a compound (e.g., a compound of Formula (I) or a form thereof as described herein); and (b) detecting the amount of mRNA that is transcribed from the SMN1 and/or SMN2 gene and does not include exon 7 of SMN1 and/or SMN2, wherein (1) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound indicates that the patient is responsive to the compound and that the compound may be or is beneficial and/or of therapeutic value to the patient; and (2) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound indicates that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In another specific embodiment, provided herein is a method for assessing an SMA patient's response to a compound, comprising: (a) administering a compound to an SMA patient; (b) contacting a sample (e.g., blood sample or tissue sample) obtained or derived from the patient with a forward SMN primer described below (e.g., SEQ ID NO. 8, 11 or 13) and/or a reverse SMN primer described herein (e.g., SEQ ID NO. 9 or 12) and/or an SMN probe (e.g., SEQ ID NO. 10) along with applicable components for e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and does not include exon 7 of SMN1 and/or SMN2, wherein (1) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound indicates that the patient is responsive to the compound and that the compound may be or is beneficial and/or of therapeutic value to the patient; and (2) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound indicates that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In a specific embodiment, provided herein is a method for assessing an SMA patient's response to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 11 or 13) and/or a reverse SMN primer described herein (e.g., SEQ ID NO. 9 or 12) along with applicable components for e.g., RT-PCR (e.g., endpoint RT-PCR and/or RT-qPCR), PCR (e.g., qPCR) or rolling circle amplification, wherein the sample is from or derived from an SMA patient administered a compound (e.g., a compound of Formula (I) or a form thereof as described herein); and (b) detecting the amount of mRNA transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1) (i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound, indicate that the patient is responsive to the compound and that the compound may be or is beneficial and/or of therapeutic value to the patient; and (2) (i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound, indicates that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In another specific embodiment, provided herein is a method for assessing an SMA patient's response to a compound, comprising: (a) administering a compound to an SMA patient; (b) contacting a sample (e.g., blood sample or tissue sample) obtained or derived from the patient with a forward SMN primer described below (e.g., SEQ ID NO. 11 or 13) and/or a reverse SMN primer described herein (e.g., SEQ ID NO. 9 or 12) along with applicable components for e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1) (i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound, indicate that the patient is responsive to the compound and that the compound may be or is beneficial and/or of therapeutic value to the patient; and (2) (i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound, indicate that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In a specific embodiment, provided herein is a method for assessing an SMA patient's response to a compound, comprising: (a) contacting an SMA patient sample (e.g., blood sample or tissue sample) or a sample derived from an SMA patient (e.g., a blood sample or tissue sample that has been processed to extract RNA) with an SMN probe (e.g., SEQ ID NO. 10) along with applicable components for e.g., RT-PCR (e.g., endpoint RT-PCR and/or RT-qPCR), PCR (e.g., qPCR) or rolling circle amplification, wherein the sample is from or derived from a patient administered a compound (e.g., a compound of Formula (I) or a form thereof as described herein); and (b) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1) (i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound, indicate that the patient is responsive to the compound and that the compound may be or is beneficial and/or of therapeutic value to the patient; and (2) (i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound, indicate that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In another specific embodiment, provided herein is a method for assessing an SMA patient's response to a compound, comprising: (a) administering a compound to an SMA patient; (b) contacting a sample (e.g., blood sample or tissue sample) obtained or derived from the patient with an SMN probe (e.g., SEQ ID NO. 10) along with applicable components for e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1) (i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound, indicate that the patient is responsive to the compound and that the compound may be or is beneficial and/or of therapeutic value to the patient; and (2) (i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound, indicate that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In a specific embodiment, provided herein is a method for assessing an SMA patient's response to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 11 or 13) and/or a reverse SMN primer described herein (e.g., SEQ ID NO. 9 or 12) and/or an SMN probe (e.g., SEQ ID NO. 10) along with applicable components for e.g., RT-PCR (e.g., endpoint RT-PCR and/or RT-qPCR) or PCR (e.g., qPCR), wherein the sample is from or derived from a patient administered a compound (e.g., a compound of Formula (I) or a form thereof as described herein); and (b) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1) (i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound, indicate that the patient is responsive to the compound and that the compound may be or is beneficial and/or of therapeutic value to the patient; and (2) (i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound, indicate that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In another specific embodiment, provided herein is a method for assessing an SMA patient's response to a compound, comprising: (a) administering a compound to an SMA patient; (b) contacting a sample (e.g., blood sample or tissue sample) obtained or derived from the patient with a forward SMN primer described below (e.g., SEQ ID NO. 11 or 13) and/or a reverse SMN primer described herein (e.g., SEQ ID NO. 9 or 12) and/or an SMN probe (e.g., SEQ ID NO. 10) along with applicable components for, e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1) (i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound, indicate that the SMN1 and/or patient is responsive to the compound and that the compound may be or is beneficial and/or of therapeutic value to the patient; and (2) (i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound, indicate that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In a specific embodiment, provided herein is a method for monitoring an SMA patient's responsiveness to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 1, 7, 11 or 13) and/or a reverse SMN primer described herein (e.g., SEQ ID NO. 9 or 12) along with applicable components for e.g., RT-PCR (e.g., endpoint RT-PCR and/or RT-qPCR), PCR (e.g., qPCR) or rolling circle amplification, wherein the sample is from or derived from a patient administered a compound (e.g., a compound of Formula (I) or a form thereof as described herein); and (b) detecting the amount of mRNA that is transcribed from the SMN1 and/or SMN2 gene and includes exon 7 of SMN1 and/or SMN2, wherein (1) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to the administration of the compound or a certain number of doses of the compound, or a certain earlier date indicates that the patient is responsive to the compound and that the compound may be or is beneficial and/or of therapeutic value to the patient; and (2) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to the administration of the compound or a certain number of doses of the compound, or a certain earlier date indicates that the patient is not responsive to the compound and that the compound is not beneficial and/or of therapeutic value to the patient. In certain embodiments, the patient's response is monitored 1 day, 2 days, 3 days, 4 days, 5 days, 7 days, 14 days, 28 days, 1 month, 2 months, 3 months, 6 months, 9 months, 12 months or more after administration of a compound, such as of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein.

In another specific embodiment, provided herein is a method for monitoring an SMA patient's responsiveness to a compound, comprising: (a) administering a compound to an SMA patient; (b) contacting a sample (e.g., blood sample or tissue sample) obtained or derived from the patient with a forward SMN primer described below (e.g., SEQ ID NO. 1, 7, 11 or 13) and/or a reverse SMN primer described herein (e.g., SEQ ID NO. 9 or 12) along with applicable components for, e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and includes exon 7 of SMN1 and/or SMN2, wherein (1) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to the administration of the compound or a certain number of doses of the compound, or a certain earlier date indicates that the patient is responsive to the compound and that the compound may be or is beneficial and/or of therapeutic value to the patient; and (2) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to the administration of the compound or a certain number of doses of the compound, or a certain earlier date indicates that the patient is not responsive to the compound and that the compound is not beneficial and/or of therapeutic value to the patient. In certain embodiments, the patient's response is monitored 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein.

In a specific embodiment, provided herein is a method for monitoring an SMA patient's responsiveness to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 1, 7, 11 or 13) and/or a reverse SMN primer described herein (e.g., SEQ ID NO. 9 or 12) and/or an SMN probe (e.g., SEQ ID NO. 3 or 10) along with applicable components for e.g., RT-PCR (e.g., endpoint RT-PCR and/or RT-qPCR), PCR (e.g., qPCR) or rolling circle amplification, wherein the sample is from or derived from a patient administered a compound (e.g., a compound of Formula (I) or a form thereof as described herein); and (b) detecting the amount of mRNA that is transcribed from the SMN1 and/or SMN2 gene and includes exon 7 of SMN1 and/or SMN2, wherein (1) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to the administration of the compound or a certain number of doses of the compound, or a certain earlier date indicates that the patient is responsive to the compound and that the compound may be or is beneficial and/or of therapeutic value to the patient; and (2) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to the administration of the compound or a certain number of doses of the compound, or a certain earlier date indicates that the patient is not responsive to the compound and that the compound is not beneficial and/or of therapeutic value to the patient. In certain embodiments, the patient's response is monitored 1 day, 2 days, 3 days, 4 days, 5 days, 7 days, 14 days, 28 days, 1 month, 2 months, 3 months, 6 months, 9 months, 12 months or more after administration of a compound, such as of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein.

In another specific embodiment, provided herein is a method for monitoring an SMA patient's responsiveness to a compound, comprising: (a) administering a compound to an SMA patient; (b) contacting a sample (e.g., blood sample or tissue sample) obtained or derived from the patient with a forward SMN primer described below (e.g., SEQ ID NO. 1, 7, 11 or 13) and/or a reverse SMN primer described herein (e.g., SEQ ID NO. 9 or 12) and/or an SMN probe (e.g., SEQ ID NO. 3 or 10) along with applicable components for, e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and includes exon 7 of SMN1 and/or SMN2, wherein (1) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to the administration of the compound or a certain number of doses of the compound, or a certain earlier date indicates that the patient is responsive to the compound and that the compound may be or is beneficial and/or of therapeutic value to the patient; and (2) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to the administration of the compound or a certain number of doses of the compound, or a certain earlier date indicates that the patient is not responsive to the compound and that the compound is not beneficial and/or of therapeutic value to the patient. In certain embodiments, the patient's response is monitored 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein.

In a specific embodiment, provided herein is a method for monitoring an SMA patient's responsiveness to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 8, 11 or 13) and/or a reverse SMN primer described herein (e.g., SEQ ID NO. 9 or 12) along with applicable components for, e.g., RT-PCR (e.g., endpoint RT-PCR and/or RT-qPCR), PCR (e.g., qPCR) or rolling circle amplification, wherein the sample is from or derived from a patient administered a compound (e.g., a compound of Formula (I) or a form thereof as described herein); and (b) detecting the amount of mRNA that is transcribed from the SMN1 and/or SMN2 gene and does not include exon 7 of SMN1 and/or SMN2, wherein (1) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to the administration of the compound or a certain number of doses of the compound, or a certain earlier date indicates that the patient is responsive to the compound and that the compound may be or is beneficial and/or of therapeutic value to the patient; and (2) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to the administration of the compound or a certain number of doses of the compound, or a certain earlier date indicates that the patient is not responsive to the compound and that the compound is not beneficial and/or of therapeutic value to the patient. In certain embodiments, the patient's response is monitored 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein.

In another specific embodiment, provided herein is a method for monitoring an SMA patient's responsiveness to a compound, comprising: (a) administering a compound to an SMA patient; (b) contacting a sample (e.g., blood sample or tissue sample) obtained or derived from the patient with a forward SMN primer described below (e.g., SEQ ID NO. 8, 11 or 13) and/or a reverse SMN primer described herein (e.g., SEQ ID NO. 9 or 12) along with applicable components for, e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and does not include exon 7 of SMN1 and/or SMN2, wherein (1) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to the administration of the compound or a certain number of doses of the compound, or a certain earlier date indicates that the patient is responsive to the compound and that the compound may be or is beneficial and/or of therapeutic value to the patient; and (2) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to the administration of the compound or a certain number of doses of the compound, or a certain earlier date indicates that the patient is not responsive to the compound and that the compound is not beneficial and/or of therapeutic value to the patient. In certain embodiments, the patient's response is monitored 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein.

In a specific embodiment, provided herein is a method for monitoring an SMA patient's responsiveness to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 8, 11 or 13) and/or a reverse SMN primer described herein (e.g., SEQ ID NO. 9 or 12) and/or an SMN probe (e.g., SEQ ID NO. 10) along with applicable components for, e.g., RT-PCR (e.g., endpoint RT-PCR and/or RT-qPCR), PCR (e.g., qPCR) or rolling circle amplification, wherein the sample is from or derived from a patient administered a compound (e.g., a compound of Formula (I) or a form thereof as described herein); and (b) detecting the amount of mRNA that is transcribed from the SMN1 and/or SMN2 gene and does not include exon 7 of SMN1 and/or SMN2, wherein (1) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to the administration of the compound or a certain number of doses of the compound, or a certain earlier date indicates that the patient is responsive to the compound and that the compound may be or is beneficial and/or of therapeutic value to the patient; and (2) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to the administration of the compound or a certain number of doses of the compound, or a certain earlier date indicates that the patient is not responsive to the compound and that the compound is not beneficial and/or of therapeutic value to the patient. In certain embodiments, the patient's response is monitored 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein.

In another specific embodiment, provided herein is a method for monitoring a SMA patient's responsiveness to a compound, comprising: (a) administering a compound to a SMA patient; (b) contacting a sample (e.g., blood sample or tissue sample) obtained or derived from the patient with a forward SMN primer described below (e.g., SEQ ID NO. 8, 11 or 13) and/or a reverse SMN primer described herein (e.g., SEQ ID NO. 9 or 12) and/or an SMN probe (e.g., SEQ ID NO. 10) along with applicable components for, e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and does not include exon 7 of SMN1 and/or SMN2, wherein (1) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to the administration of the compound or a certain number of doses of the compound, or a certain earlier date indicates that the patient is responsive to the compound and that the compound may be or is beneficial and/or of therapeutic value to the patient; and (2) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to the administration of the compound or a certain number of doses of the compound, or a certain earlier date indicates that the patient is not responsive to the compound and that the compound is not beneficial and/or of therapeutic value to the patient. In certain embodiments, the patient's response is monitored 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein.

In a specific embodiment, provided herein is a method for monitoring an SMA patient's response to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 11 or 13) and/or a reverse SMN primer described herein (e.g., SEQ ID NO. 9 or 12) along with applicable components for, e.g., RT-PCR (e.g., endpoint RT-PCR and/or RT-qPCR), PCR (e.g., qPCR) or rolling circle amplification, wherein the sample is from or derived from a patient administered a compound (e.g., a compound of Formula (I) or a form thereof as described herein); and (b) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1) (i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound or a certain number of doses of the compound, or a certain earlier date, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound or a certain number of doses of the compound, or a certain earlier date, indicate that the patient is responsive to the compound and that the compound may be or is beneficial and/or of therapeutic value to the patient; and (2) (i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound or a certain number of doses of the compound, or a certain earlier date, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound or a certain number of doses of the compound, or a certain earlier date, indicate that the patient is not responsive to the compound and that the compound is not beneficial and/or of therapeutic value to the patient. In certain embodiments, the patient's response is monitored 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein.

In another specific embodiment, provided herein is a method for monitoring an SMA patient's response to a compound, comprising: (a) administering a compound to an SMA patient; (b) contacting a sample (e.g., blood sample or tissue sample) obtained or derived from the patient with a forward SMN primer described below (e.g., SEQ ID NO. 11 or 13) and/or a reverse SMN primer described herein (e.g., SEQ ID NO. 9 or 12) along with applicable components for, e.g., RT-PCR (e.g., endpoint RT-PCR and/or RT-qPCR), PCR (e.g., qPCR), or rolling circle amplification; and (c) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1) (i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound or a certain number of doses of the compound, or a certain earlier date, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound or a certain number of doses of the compound, or a certain earlier date, indicate that the patient is responsive to the compound and that the compound may be or is beneficial and/or of therapeutic value to the patient; and (2) (i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound or a certain number of doses of the compound, or a certain earlier date, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound or a certain number of doses of the compound, or a certain earlier date, indicate that the patient is not responsive to the compound and that the compound is not beneficial and/or of therapeutic value to the patient. In certain embodiments, the patient's response is monitored 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein.

In a specific embodiment, provided herein is a method for monitoring an SMA patient's response to a compound, comprising: (a) contacting an SMA patient sample (e.g., blood sample or tissue sample) or a sample derived from an SMA patient (e.g., a blood sample or tissue sample that has been processed to extract RNA) with an SMN probe (e.g., SEQ ID NO. 10) along with applicable components for, e.g., RT-PCR (e.g., endpoint RT-PCR and/or RT-qPCR), PCR (e.g., qPCR) or rolling circle amplification, wherein the sample is from or derived from a patient administered a compound (e.g., a compound of Formula (I) or a form thereof as described herein); and (b) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1) (i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound or a certain number of doses of the compound, or a certain earlier date, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound or a certain number of doses of the compound, or a certain earlier date, indicate that the patient is responsive to the compound and that the compound may be or is beneficial and/or of therapeutic value to the patient; and (2) (i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound or a certain number of doses of the compound, or a certain earlier date, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound or a certain number of doses of the compound, or a certain earlier date, indicate that the patient is not responsive to the compound and that the compound is not beneficial and/or of therapeutic value to the patient. In certain embodiments, the patient's response is monitored 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein.

In another specific embodiment, provided herein is a method for monitoring an SMA patient's response to a compound, comprising: (a) administering a compound to an SMA patient; (b) contacting a sample (e.g., blood sample or tissue sample) obtained or derived from the patient with an SMN probe (e.g., SEQ ID NO. 10) along with applicable components for, e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1) (i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound or a certain number of doses of the compound, or a certain earlier date, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound or a certain number of doses of the compound, or a certain earlier date, indicate that the patient is responsive to the compound and that the compound may be or is beneficial and/or of therapeutic value to the patient; and (2) (i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound or a certain number of doses of the compound, or a certain earlier date, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound or a certain number of doses of the compound, or a certain earlier date, indicate that the patient is not responsive to the compound and that the compound is not beneficial and/or of therapeutic value to the patient. In certain embodiments, the patient's response is monitored 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein.

In a specific embodiment, provided herein is a method for monitoring an SMA patient's response to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 11 or 13) and/or a reverse SMN primer described herein (e.g., SEQ ID NO. 9 or 12) and/or an SMN probe (SEQ ID NO. 10) along with applicable components for, e.g., RT-PCR (e.g., endpoint RT-PCR and/or RT-qPCR), PCR (e.g., qPCR) or rolling circle amplification, wherein the sample is from or derived from a patient administered a compound (e.g., a compound of Formula (I) or a form thereof as described herein); and (b) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1) (i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN2 in an analogous sample (e.g., from the same type of tissue sample) from the patient prior to administration of the compound or a certain number of doses of the compound, or a certain earlier date, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound or a certain number of doses of the compound, or a certain earlier date, indicate that the patient is responsive to the compound and that the compound may be or is beneficial and/or of therapeutic value to the patient; and (2) (i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound or a certain number of doses of the compound, or a certain earlier date, indicate that the patient is not responsive to the compound and that the compound is not beneficial and/or of therapeutic value to the patient. In certain embodiments, the patient's response is monitored 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein.

In another specific embodiment, provided herein is a method for monitoring an SMA patient's response to a compound, comprising: (a) administering a compound to an SMA patient; (b) contacting a sample (e.g., blood sample or tissue sample) obtained or derived from the patient with a forward SMN primer described below (e.g., SEQ ID NO. 11 or 13) and/or a reverse SMN primer described herein (e.g., SEQ ID NO. 9 or 12) and/or an SMN probe (SEQ ID NO. 10) along with applicable components for, e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1) (i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound or a certain number of doses of the compound, or a certain earlier date, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound or a certain number of doses of the compound, or a certain earlier date, indicate that the patient is responsive to the compound and that the compound may be or is beneficial and/or of therapeutic value to the patient; and (2) (i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound or a certain number of doses of the compound, or a certain earlier date, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN2 gene and does not include exon 7 of SMN1 and/or SMN2 in an analogous sample (e.g., the same type of tissue sample) from the patient prior to administration of the compound or a certain number of doses of the compound, or a certain earlier date, indicate that the patient is not responsive to the compound and that the compound is not beneficial and/or of therapeutic value to the patient. In certain embodiments, the patient's response is monitored 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein.

In specific embodiments, the SMA in the patient is caused by an inactivating mutation or deletion in the SMN1 gene on both chromosomes, resulting in a loss of SMN1 gene function.

Kits

In one aspect, provided herein are pharmaceutical or assay kits comprising an SMN primer or probe described herein, in one or more containers, and instructions for use. In one embodiment, a pharmaceutical or assay kit comprises, in a container, one or more SMN reverse primers (e.g., SEQ ID NO. 2, 9 and/or 12) and/or one or more SMN forward primers (SEQ ID NO. 1, 7, 8, 11 and/or 13)) and instructions for use. In another embodiment, a pharmaceutical or assay kit comprises, in one container, an SMN reverse primer (e.g., SEQ ID NO. 2, 9 or 12), an SMN forward primer (SEQ ID NO. 1, 7, 8, 11 or 13)) and instructions for use.

In one embodiment, a pharmaceutical or assay kit comprises, in separate containers, one SMN reverse primer (e.g., SEQ ID NO. 2, 9 or 12) in one container, another SMN forward primer (e.g., SEQ ID NO. 1, 7, 8, 11 or 13)) in another container, and instructions for use.

In certain embodiments, applicable components needed for a PCR (e.g., qPCR), RT-PCR (e.g., endpoint RT-PCR and/or RT-qPCR) or rolling circle amplification, such as polymerase, deoxynucleoside triphosphates, etc., are included in such kits. In some embodiments, components needed for hybridization are included in such kits. A pharmaceutical or assay kit containing such primers can be used in PCR and RT-PCR to, e.g.,: (i) assess whether a therapeutic agent (e.g., a compound of Formula (I) or a form thereof) enhances inclusion of exon 7 of SMN1 and/or SMN2 into mRNA that is transcribed from the SMN1 and/or SMN2 gene, (ii) monitor the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, and/or (iii) monitor a subject's response to a therapeutic agent (e.g., a compound of Formula (I) or a form thereof).

In a specific embodiment, a pharmaceutical or assay kit comprises the forward primer with the sequence found in SEQ ID NO. 1, in a container, and the reverse primer with the sequence found in SEQ ID NO. 2, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by a human SMN1 minigene or human SMN2 minigene, such as described those described herein or in International Publication No. WO 2009/151546 or U.S. Patent Application Publication No. 2011/0086833, each of which is incorporated herein by reference in its entirety. In other embodiments, these primers are used as probes in, e.g., hybridization assays, such as Southern blot or Northern blot.

In a specific embodiment, a pharmaceutical or assay kit comprises the forward primer with the nucleotide sequence found in SEQ ID NO. 7, in a container, and the reverse primer with the nucleotide sequence found in SEQ ID NO. 9, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by endogenous human SMN1 and SMN2 genes. In other embodiments, these primers are used as probes in, e.g., hybridization assays, such as Southern blot or Northern blot.

In another specific embodiment, a pharmaceutical or assay kit comprises the forward primer with the nucleotide sequence found in SEQ ID NO. 8, in a container, and the reverse primer with the nucleotide sequence found in SEQ ID NO. 9, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by the endogenous human SMN2 gene. In other embodiments, these primers are used as probes in, e.g., hybridization assays, such as Southern blot or Northern blot.

In a specific embodiment, a pharmaceutical or assay kit comprises the forward primer with the nucleotide sequence found in SEQ ID NO. 7, in a container, the forward primer with the nucleotide sequence found in SEQ ID NO. 8, in another container, and the reverse primer with the nucleotide sequence found in SEQ ID NO. 9, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by endogenous human SMN1 and SMN2 genes. In other embodiments, these primers are used as probes in, e.g., hybridization assays, such as Southern blot or Northern blot.

In a specific embodiment, a pharmaceutical or assay kit comprises the forward primer with the nucleotide sequence found in SEQ ID NO. 11, in a container, and the reverse primer with the nucleotide sequence found in SEQ ID NO. 12, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by endogenous human SMN1 and SMN2 genes. In other embodiments, these primers are used as probes in, e.g., hybridization assays, such as Southern blot or Northern blot.

In a specific embodiment, a pharmaceutical or assay kit comprises the forward primer with the nucleotide sequence found in SEQ ID NO. 11, in a container, and the reverse primer with the nucleotide sequence found in SEQ ID NO. 9, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by endogenous human SMN1 and SMN2 genes. In other embodiments, these primers are used as probes in, e.g., hybridization assays, such as Southern blot or Northern blot.

In a specific embodiment, a pharmaceutical or assay kit comprises the forward primer with the nucleotide sequence found in SEQ ID NO. 13, in a container, and the reverse primer with the nucleotide sequence found in SEQ ID NO.

12, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by endogenous human SMN1 and SMN2 genes. In other embodiments, these primers are used as probes in, e.g., hybridization assays, such as Southern blot or Northern blot.

In a specific embodiment, a pharmaceutical or assay kit comprises the forward primer with the nucleotide sequence found in SEQ ID NO. 13, in a container, and the reverse primer with the nucleotide sequence found in SEQ ID NO. 9, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by endogenous human SMN1 and SMN2 genes. In other embodiments, these primers are used as probes in, e.g., hybridization assays, such as Southern blot or Northern blot.

In a specific embodiment, a pharmaceutical or assay kit comprises the forward primer with the nucleotide sequence found in SEQ ID NO. 1, in a container, and the reverse primer with the nucleotide sequence found in SEQ ID NO. 9, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by endogenous human SMN1 and SMN2 genes. In other embodiments, these primers are used as probes in, e.g., hybridization assays, such as Southern blot or Northern blot.

In a specific embodiment, a pharmaceutical or assay kit comprises the forward primer with the nucleotide sequence found in SEQ ID NO. 1, in a container, and the reverse primer with the nucleotide sequence found in SEQ ID NO. 12, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by endogenous human SMN1 and SMN2 genes. In other embodiments, these primers are used as probes in, e.g., hybridization assays, such as Southern blot or Northern blot.

In another embodiment, a pharmaceutical or assay kit comprises an SMN probe described herein (e.g., SEQ ID NO. 3 or 10), in one container. In other embodiments, the probe is used in, e.g., a hybridization assay, such as a Southern blot or Northern blot. In a specific embodiment, the probe is used in RT-qPCR or qPCR. In certain embodiments, components needed for a PCR (e.g., qPCR), RT-PCR (e.g., endpoint RT-PCR and/or RT-qPCR) or rolling circle amplification, such as polymerase, deoxynucleoside triphosphates, primers, etc., are included in such kits. In some embodiments, components needed for hybridization are included in such kits.

In one embodiment, a pharmaceutical or assay kit comprises an SMN reverse primer (e.g., SEQ ID NO. 2, 9 or 12) in one container, an SMN forward primer (e.g., SEQ ID NO. 1, 7, 8, 11 or 13) in another container, and an SMN probe (e.g., SEQ ID NO. 3 or 10) in another container, and instructions for use. In another embodiment, a pharmaceutical or assay kit comprises one or more SMN reverse primers (e.g., SEQ ID NO. 2, 9 and/or 12) in one container, one or more SMN forward primers (e.g., SEQ ID NO. 1, 7, 8, 11 and/or 13) in another container, and one or more SMN probe (e.g., SEQ ID NO. 3 and/or 10) in another container, and instructions for use.

In certain embodiments, components needed to run a PCR, RT-PCR or rolling circle amplification, such as polymerase, deoxynucleoside triphosphates, etc., are included in such kits. A pharmaceutical or assay kit containing such probes and/or primers can be used in PCR and RT-PCR to, e.g.,: (i) assess whether a therapeutic agent (e.g., a compound of Formula (I) or a form thereof) enhances inclusion of exon 7 of SMN1 and/or SMN2 into mRNA that is transcribed from the SMN1 and/or SMN2 gene, (ii) monitor the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, and/or (iii) monitor a subject's response to a therapeutic agent (e.g., a compound of Formula (I) or a form thereof).

In another aspect, provided herein is a pharmaceutical kit comprising a compound of Formula (I) or a form thereof, in a container, and instructions for use of the compound or form thereof. In a specific embodiment, provided herein is a pharmaceutical kit comprising a pharmaceutical composition comprising a compound of Formula (I) or a form thereof and a pharmaceutically acceptable carrier, excipient or diluent, and instructions for use. In another specific embodiment, provided herein is a pharmaceutical kit comprising a pharmaceutical composition comprising an effective amount of a compound of Formula (I) or a form thereof and a pharmaceutically acceptable carrier, excipient or diluent, and instructions for use. In one embodiment, the instructions for use explain one, two or more of the following: the dose, route of administration, frequency of administration and side effects of administration of a compound of Formula (I) or a form thereof to a subject.

General Synthetic Methods

As disclosed herein, general methods for preparing the compounds of Formula (I) or a form thereof as described herein are available via standard, well-known synthetic methodology. Many of the starting materials are commercially available or, when not available, can be prepared using the routes described below using techniques known to those skilled in the art. The synthetic schemes provided herein comprise multiple reaction steps, each of which is intended to stand on its own and can be carried out with or without any preceding or succeeding step(s). In other words, each of the individual reactions steps of the synthetic schemes provided herein in isolation is contemplated.

Scheme A

Compounds of Formula (I), wherein $R_2$ is an aryl or heteroaryl monocyclic or bicyclic ring system, can be prepared as described in Scheme A below.

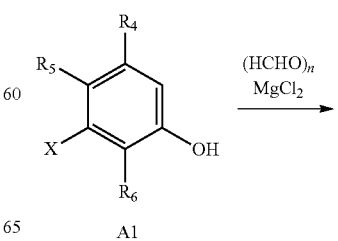

A1

-continued

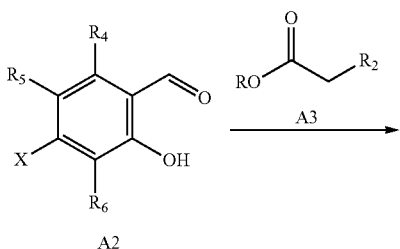

A2

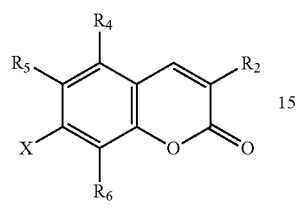

A4

Compound A1 (where X represents various reactive groups which may be used to prepare $R_1$ substituents via functional group substitution reactions using techniques known to a person of ordinary skill in the art) can be regioselectively formylated by treatment with a Lewis acid (such as $MgCl_2$ and the like) and paraformaldehyde in a suitable solvent (such as acetonitrile or THF and the like) to afford Compound A2. Compound A2 is reacted with Compound A3, where R is a $C_{1-4}$alkyl group (such as methyl, ethyl, t-butyl and the like), and in the presence of condensation reagents (such as piperidine/acetic acid and the like) will undergo Knoevenagel condensation followed by lactone formation to afford Compound A4.

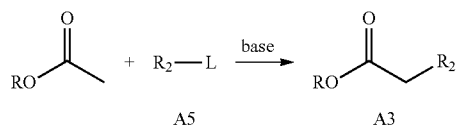

Compound A3 can be prepared by combining a mixture of acetic acid ester (such as t-butyl acetate and the like) and a base (such as LiHMDS and the like) in a suitable solvent (such as THF and the like) with Compound A5, wherein $R_2$ represents an aryl, heterocycle or heteroaryl and L represents a leaving group.

Scheme B

Compounds of Formula (I), wherein $R_2$ is a bicyclic heteroaryl ring system, can be prepared as described in Scheme B below.

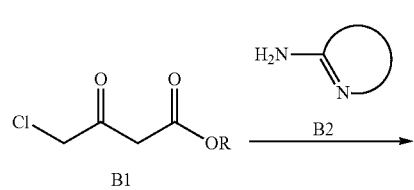

-continued

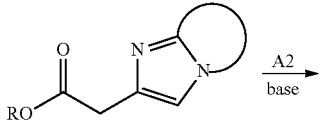

B3

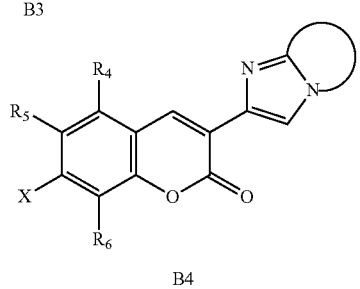

B4

Compound B2, an optionally substituted monocyclic heteroaryl ring system containing an amidine-like moiety (such as but not limited to 2-aminopyridine, 2-aminopyrimidine, 2-aminopyrazine, 3-aminopyridazine, 2-aminothiazole, 4-aminothiazole, 4-aminopyrimidine and the like) is reacted with Compound B1 (where R represents a $C_{1-4}$alkyl group such as methyl, ethyl and the like) in a suitable solvent (such as EtOH and the like) to give Compound B3. Compound B3, is reacted with Compound A2, and in the presence of condensation reagents (such as piperidine/acetic acid and the like), will undergo Knoevenagel condensation followed by lactone formation to afford Compound B4.

Scheme C

Compounds of Formula (I), wherein $R_2$ is a bicyclic heteroaryl ring system, can be prepared as described in Scheme C below.

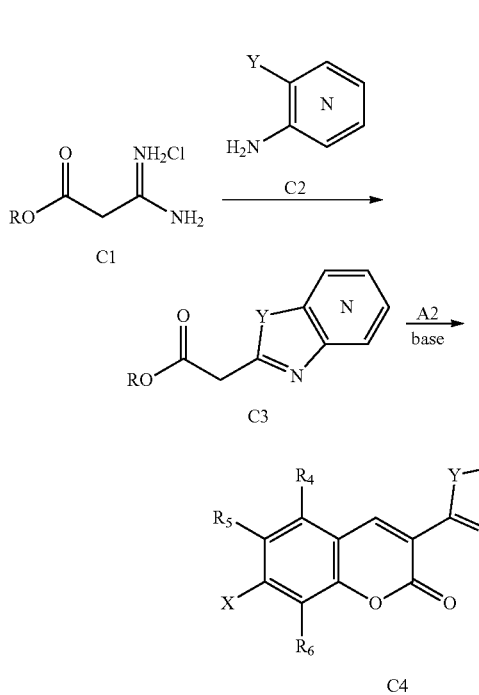

Compound C1 (where R represents a $C_{1-4}$alkyl group such as methyl, ethyl and the like) is reacted with Compound C2, an optionally substituted aniline (where Y can be OH, NH₂, or SH; and, where the aniline ring may have one or more carbon atom ring members replaced with one or more nitrogen atoms, thus making Compound C2 an optionally substituted ring system such as a pyridine, pyrimidine, pyrazine and the like), and in a suitable solvent (such as EtOH or acetonitrile and the like) affords Compound C3. Compound C3 is reacted with Compound A2, and in the presence of condensation reagents (such as piperidine/acetic acid and the like), will undergo Knoevenagel condensation followed by lactone formation to afford Compound C4.

Scheme D

Compounds of Formula (I), wherein $R_2$ is a monocyclic heteroaryl ring system, can be prepared as described in Scheme D below.

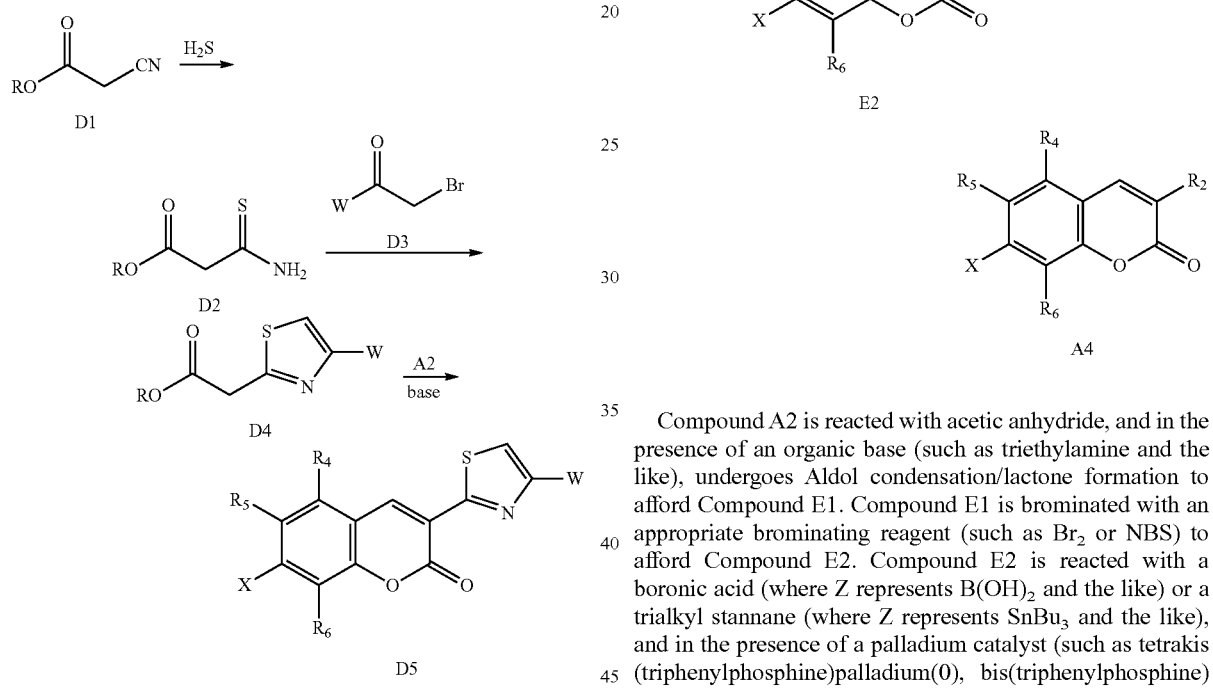

Compound D1 (where R represents a $C_{1-4}$alkyl group such as methyl, ethyl and the like) is reacted with hydrogen sulfide in the presence of an organic base (such as triethylamine and the like) and a suitable solvent (such as pyridine and the like) to give Compound D2. Compound D2 is reacted with Compound D3, an α-bromoketone (where W represents a $C_{1-4}$alkyl or halo-$C_{1-4}$alkyl group such as methyl, ethyl, trifluoromethyl and the like), and in an appropriate solvent (such as DMF and the like), undergoes a tandem alkylation dehydrative condensation to give Compound D4. Compound D4 is reacted with Compound A2, and in the presence of condensation reagents (such as piperidine/acetic acid and the like), will undergo Knoevenagel condensation followed by lactone formation to afford Compound D5.

Scheme E

Compounds of Formula (I), wherein $R_2$ is a monocyclic or bicyclic aryl or heteroaryl ring system, can be prepared as described in Scheme E below.

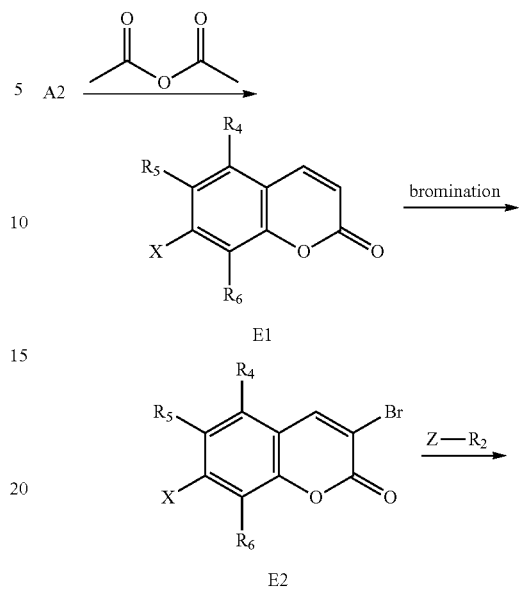

Compound A2 is reacted with acetic anhydride, and in the presence of an organic base (such as triethylamine and the like), undergoes Aldol condensation/lactone formation to afford Compound E1. Compound E1 is brominated with an appropriate brominating reagent (such as Br₂ or NBS) to afford Compound E2. Compound E2 is reacted with a boronic acid (where Z represents B(OH)₂ and the like) or a trialkyl stannane (where Z represents SnBu₃ and the like), and in the presence of a palladium catalyst (such as tetrakis(triphenylphosphine)palladium(0), bis(triphenylphosphine)palladium(II) dichloride, palladium acetate and the like) and an appropriate phospine ligand will undergo Suzuki or Stille cross coupling to give Compound A4.

Scheme F

Compounds of Formula (I), wherein $R_2$ is a monocyclic or bicyclic aryl-amino or heteroaryl-amino, can be prepared as described in Scheme F below.

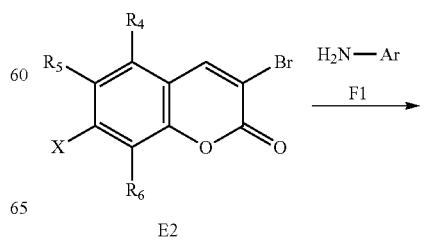

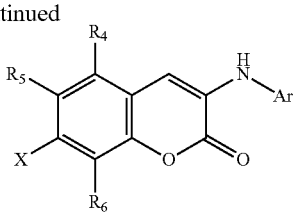

F2

Compound E2 is reacted with Compound F1, where Ar represents an optionally substituted monocyclic or bicyclic aryl or heteroaryl ring system such as an optionally substituted aniline or amino-heteroaryl, in the presence of a palladium catalyst (such as tris(dibenzylideneacetone)dipalladium(0) and the like), phosphine ligand (such as xantphos and the like), and an inorganic base (such as cesium carbonate and the like) in an appropriate solvent (such as 1,4-dioxane or toluene and the like) to afford Compound F2.

Scheme G

Compounds of Formula (I), wherein $R_2$ is a bicyclic heteroaryl ring system, can be prepared as described in Scheme G below.

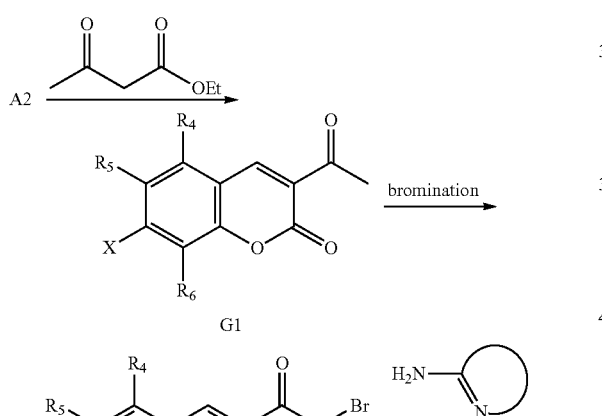

Compound A2 is reacted with ethyl acetoacetate, and in the presence of condensation reagents (such as piperidine/acetic acid and the like), will undergo Knoevenagel condensation followed by lactone formation to afford Compound G1. The α-methyl group of Compound G1 can be selectively brominated with an appropriate brominating reagent (such as $Br_2$ or NBS and the like) to afford Compound G2. Compound G2 is reacted with Compound B2, an optionally substituted monocyclic heteroaryl ring system containing an amidine-like moiety (such as but not limited to 2-aminopyridine, 2-aminopyrimidine, 2-aminopyrazine, 3-aminopyridazine, 2-aminothiazole, 4-aminothiazole, 4-aminopyrimidine and the like) in a suitable solvent (such as acetonitrile and the like) to give Compound B4.

Scheme H

Compounds of Formula (I), wherein $R_2$ is a bicyclic heteroaryl ring system, can be prepared as described in Scheme H below.

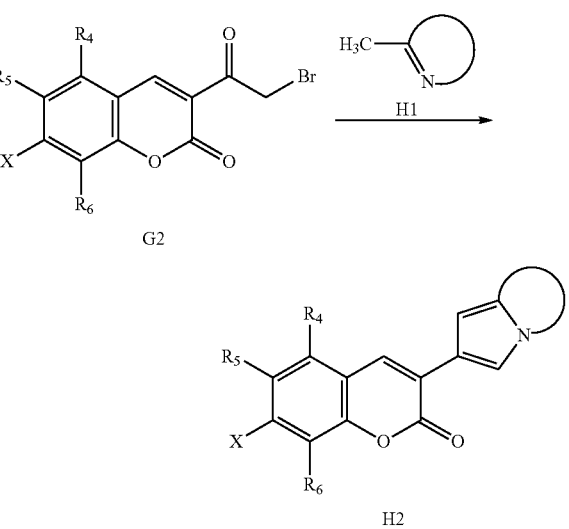

Compound G2 is reacted with Compound H1, an optionally substituted monocyclic heteroaryl ring system containing a ketimine-like moiety (such as but not limited to 2-methylpyridine, 2-methylpyrimidine, 2-methylpyrazine, 3-methylpyridazine and the like), and in a suitable solvent (such as acetonitrile and the like), undergoes a tandem alkylation dehydrative cyclization reaction to give Compound H2.

Scheme I

Compounds of Formula (I), wherein $R_2$ is a bicyclic heteroaryl ring system, can be prepared as described in Scheme I below.

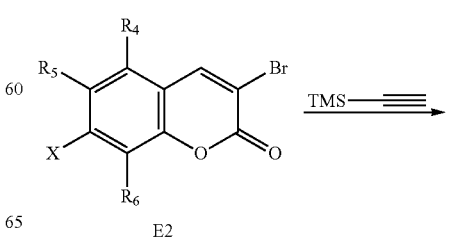

311

-continued

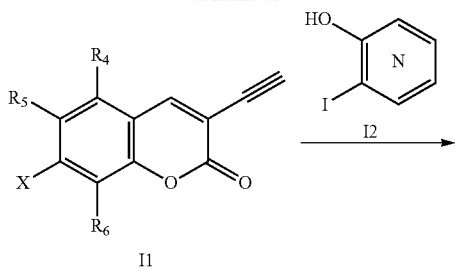

I1

I3

Compound E2 is reacted with trimethylsilylacetylene and an organic base (such as triethylamine and the like) in the presence of copper(I) iodide and a palladium catalyst (such as tetrakis(triphenylphosphine)palladium(0), bis(triphenylphosphine)palladium(II) dichloride, palladium acetate and the like) and, in the presence of an appropriate phospine ligand undergoes a Sonogashira coupling. The resulting trimethylsilylacetylene product when treated with an inorganic base (such as potassium carbonate and the like) in an appropriate solvent (such as methanol and the like) yields Compound I1. Compound I1 can undergo an additional Sonogashira coupling with Compound I2, an iodo-hydroxy-substituted monocyclic heteroaryl ring system (where the heteroaryl ring may have one or more additional nitrogen atom ring members, thus making Compound I2 an iodo-hydroxy-substituted ring system such as a pyridine, pyrimidine, pyrazine and the like, and where the iodo and hydroxy substituents are in an ortho orientation with respect to one another, such as 2-iodopyridin-3-ol, 4-iodopyridin-3-ol and the like) to give Compound I3.

Scheme J

Compounds of Formula (I), wherein $R_2$ is a monocyclic or bicyclic heteroaryl ring system, can be prepared as described in Scheme J below.

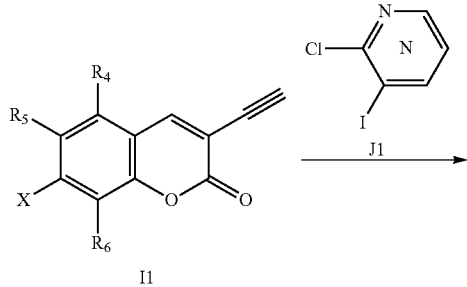

I1

312

-continued

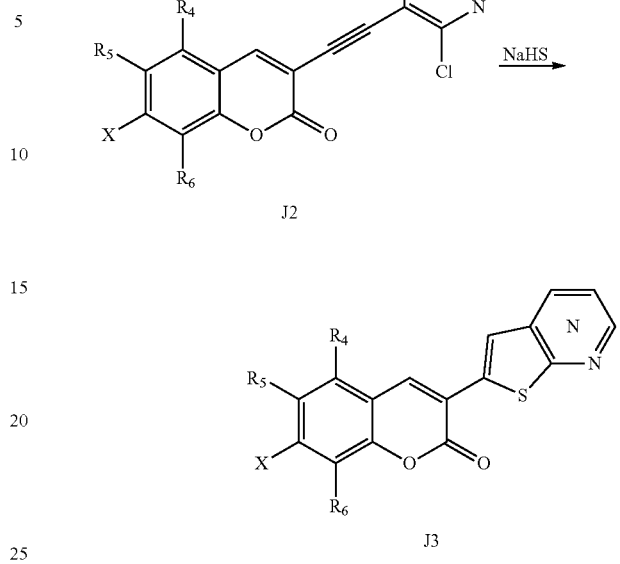

J2

J3

Compound I1 is reacted with Compound J1, a chloro-iodo-substituted monocyclic heteroaryl ring system (where the heteroaryl ring may have one or more additional nitrogen atom ring members, thus making Compound J1 a chloro-iodo-substituted ring system such as a pyridine, pyrimidine, pyrazine and the like, and where the chloro- and iodo-substituents are in an ortho orientation with respect to one another, such as 2-chloro-3-iodopyridine or 4-chloro-3-iodopyridine and the like), and an organic base (such as triethylamine and the like) in the presence of copper(I) iodide and a palladium catalyst (such as tetrakis(triphenylphosphine) palladium(0), bis(triphenylphosphine)palladium (II) dichloride, palladium acetate and the like) and, in the presence of an appropriate phospine ligand undergoes a Sonogashira coupling to afford Compound J2. Compound J2 treated with sodium hydrosulfide in a suitable solvent (such as EtOH and the like) affords Compound J3.

Scheme K

Compounds of Formula (I), wherein $R_2$ is an optionally substituted 1,2,4-oxadiazole ring system, can be prepared as described in Scheme K below.

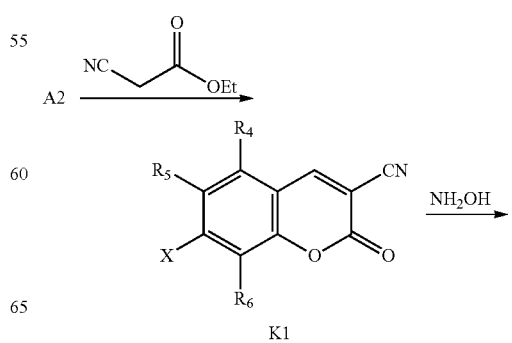

K1

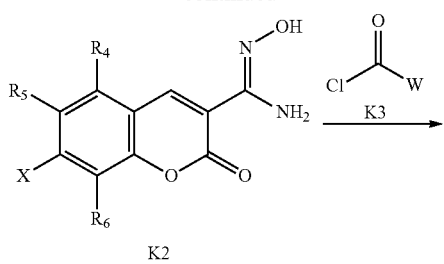

K2

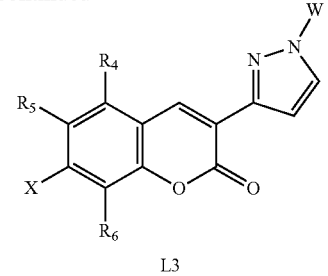

L3

Compound A2 is reacted with ethyl cyanoacetate, and in the presence of condensation reagents (such as piperidine/acetic acid and the like) will undergo Knoevenagel condensation followed by lactone formation to afford Compound K1. Compound K1 is reacted with hydroxylamine in a suitable solvent (such as CH$_2$Cl$_2$) to give Compound K2. Compound K2 is reacted with Compound K3 (where W represents a C$_{1-4}$alkyl, aryl or heteroaryl group), and in the presence of an organic base (such as triethylamine and the like), affords an O-acyl-hydroxyamidine intermediate, that undergoes dehydrative cyclization at elevated temperatures (>100° C.) to yield Compound K4.

Compound G1 is reacted with dimethylformamide dimethyl acetal and an organic base (such as pyrrolidine and the like) to give an enaminone intermediate, which is then reacted with hydrazine in the presence of an organic acid (such as acetic acid and the like) to afford Compound L1. Compound L1 is reacted with Compound L2 (where W represents a C$_{1-4}$alkyl, aryl, or heteroaryl group and L represents a leaving group (such as I or Br and the like), in a suitable solvent (such as DMF and the like), in the presence of an inorganic base (such as Cs$_2$CO$_3$ and the like), and an optional catalyst (such as CuI and the like) to afford Compound L3.

Scheme M

Compounds of Formula (I), wherein R$_2$ is a monocyclic heteroaryl ring system, can be prepared as described in Scheme M below.

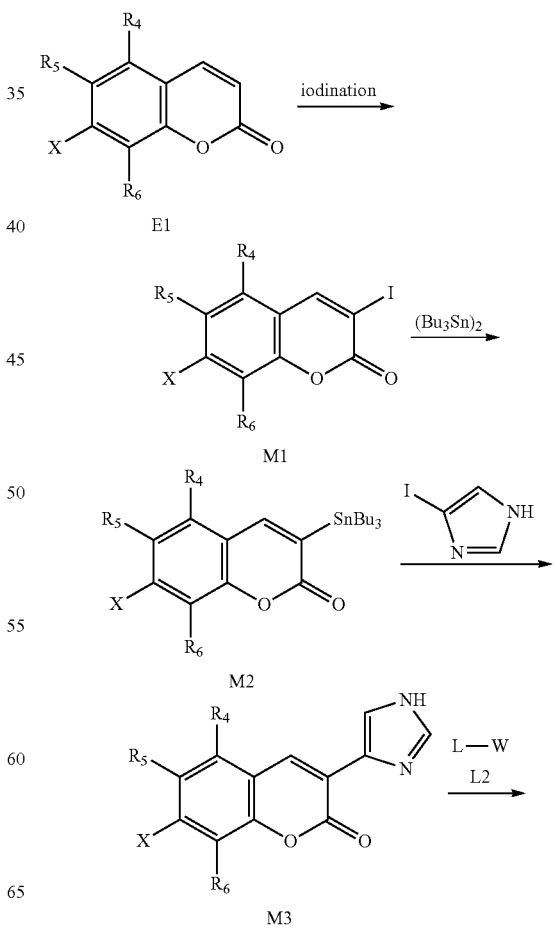

Scheme L

Compounds of Formula (I), wherein R$_2$ is a monocyclic heteroaryl ring system, can be prepared as described in Scheme L below.

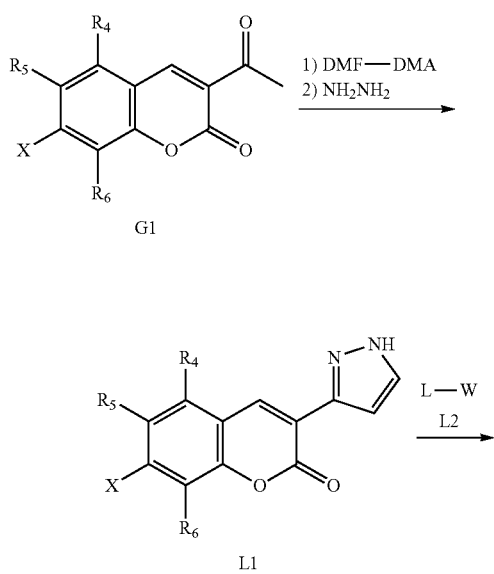

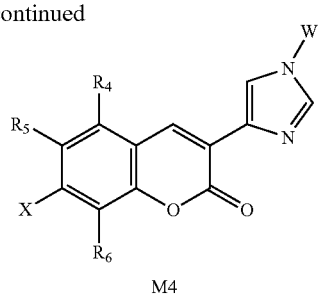

M4

Compound E1 can be regioselectively iodinated with an appropriate iodinating agent (such as iodine or bis(trifluoroacetoxy)iodo]benzene and the like) in an appropriate solvent (such as $CHCl_3$ and the like). Compound M1, when treated with hexabutylditin in the presence of a palladium catalyst (such as tetrakis(triphenylphosphine)palladium(0), bis(triphenylphosphine) palladium(II) dichloride, palladium acetate and the like) in an appropriate solvent (such as 1,4-dioxane or toluene), affords Compound M2. Compound M2 is reacted with 5-iodoimidazole, in the presence of a catalyst (such as tetrakis(triphenylphosphine)palladium(0), bis(triphenylphosphine)palladium(II) dichloride, palladium acetate and the like) and a cocatalyst (such as CuI and the like), in an appropriate solvent (such as 1,4-dioxane or toluene and the like) to afford Compound M3. Compound M3 is reacted with Compound L2 (where W represents a $C_{1-4}$alkyl, aryl, or heteroaryl group and L represents a leaving group (such as I or Br and the like), in a suitable solvent (such as DMF and the like), in the presence of an inorganic base (such as $Cs_2CO_3$ and the like), and an optional catalyst (such as CuI and the like) to afford Compound M4.

Scheme N

Compounds of Formula (I), wherein $R_2$ is a monocyclic or bicyclic aryl or heteroaryl ring system and $R_3$ is hydrogen or alkyl, can be prepared as described in Scheme N below.

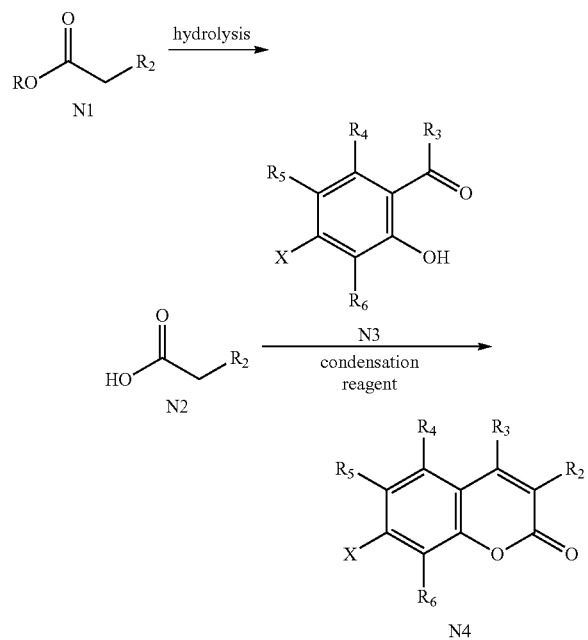

Compound N1 is treated under the conditions for ester hydrolysis (such as aqueous NaOH), to afford Compound N2. Compound N2 is reacted with Compound N3 (where R represents a hydrogen or $C_{1-4}$alkyl group), and in the presence of a coupling reagent (such as N-(3-dimethylaminopropyl)-N'-ethylcarbodiimide hydrochloride and the like) and an organic base (such as triethylamine and the like), undergoes ester formation followed by Knoevenagel condensation to give Compound N4.

SPECIFIC SYNTHETIC EXAMPLES

To describe in more detail and assist in understanding, the following non-limiting examples are offered to more fully illustrate the scope of compounds described herein and are not to be construed as specifically limiting the scope thereof. Such variations of the compounds described herein that may be now known or later developed, which would be within the purview of one skilled in the art to ascertain, are considered to fall within the scope of the compounds as described herein and hereinafter claimed. These examples illustrate the preparation of certain compounds. Those of skill in the art will understand that the techniques described in these examples represent techniques, as described by those of ordinary skill in the art, that function well in synthetic practice, and as such constitute preferred modes for the practice thereof. However, it should be appreciated that those of skill in the art should, in light of the present disclosure, appreciate that many changes can be made in the specific methods that are disclosed and still obtain a like or similar result without departing from the spirit and scope of the present description.

Other than in the following examples of the embodied compounds, unless indicated to the contrary, all numbers expressing quantities of ingredients, reaction conditions, experimental data, and so forth used in the specification and claims are to be understood as being modified by the term "about". Accordingly, all such numbers represent approximations that may vary depending upon the desired properties sought to be obtained by a reaction or as a result of variable experimental conditions. Therefore, within an expected range of experimental reproducibility, the term "about" in the context of the resulting data, refers to a range for data provided that may vary according to a standard deviation from the mean. As well, for experimental results provided, the resulting data may be rounded up or down to present data consistently, without loss of significant figures. At the very least, and not as an attempt to limit the application of the doctrine of equivalents to the scope of the claims, each numerical parameter should be construed in light of the number of significant digits and rounding techniques used by those of skill in the art.

While the numerical ranges and parameters setting forth the broad scope of the present description are approximations, the numerical values set forth in the examples set forth below are reported as precisely as possible. Any numerical value, however, inherently contains certain errors necessarily resulting from the standard deviation found in their respective testing measurements.

COMPOUND EXAMPLES

As used above, and throughout the present description, the following abbreviations, unless otherwise indicated, shall be understood to have the following meanings:

| Abbreviation | Meaning |
| --- | --- |
| Δ | with heating |
| AcOH or HOAc | acetic acid |
| Ac$_2$O | acetic anhydride |
| Ar | argon |
| ACN | acetonitrile |
| BINAP | 2,2'-bis(diphenylphosphino)-1,1'-binaphthalene |
| B(OiPr)$_3$ | triisopropyl borate |
| Boc | tert-butoxy-carbonyl |
| Boc$_2$O | di-tert-butyl dicarbonate |
| BuOH | n-butanol |
| BrettPhos | 2-(dicyclohexylphosphino)3,6-dimethoxy-2',4',6'-triisopropyl-1,1'-biphenyl |
| °C. | degrees Centigrade |
| CDI | 1,1-carbonyldiimidazole or N,N'-carbonyldiimidazole |
| (CHO)$_n$, (HCHO)$_n$ or HCHO | paraformaldehyde |
| Cs$_2$CO$_3$ | cesium carbonate |
| d/h/hr/hrs/min/s | day(d)/hour(h, hr or hrs)/minute(min)/second(s) |
| DavePhos | 2-dicyclohexylphosphino-2'-(N,N-dimethylamino)biphenyl |
| DCE | 1,2-dichloroethane |
| DCM | dichloromethane (CH$_2$Cl$_2$) |
| DIAD | diisopropyl azodicarboxylate |
| DIEA or DIPEA | N,N-diisopropylethylamine |
| DMA | dimethyl acetal |
| DMAc | dimethylacetamide |
| DMAP | 4-(dimethylamino)pyridine |
| DME | 1,2-dimethoxyethane |
| DMF | dimethylformamide |
| DMSO | dimethylsulfoxide |
| EDC or EDCI | N-(3-dimethylaminopropyl)-N'-ethylcarbodiimide hydrochloride |
| EtOAc | ethyl acetate |
| EtOH | ethanol |
| Et$_2$O | diethyl ether |
| HCOH | formaldehyde |
| iPrI | iodopropane |
| JohnPhos | (2-biphenyl)-di-t-butylphosphine |
| KOAc | potassium acetate |
| LAH | lithium aluminum hydride |
| LC/MS, LCMS or LC-MS | liquid chromatographic mass spectroscopy |
| LDA | lithium diisopropylamine |
| LiHMDS or LHMDS | lithium bis(trimethylsilyl)amide |
| MeOH | methanol |
| MeI | iodomethane |
| Me—THF | 2-methyltetrahydrofuran |
| Me$_2$Zn | dimethylzinc |
| MnO$_2$ | manganese dioxide |
| MS | mass spectroscopy |
| NaH | sodium hydride |
| NaHS | sodium hydrosulfide |
| NaHMDS | sodium bis(trimethylsilyl)amide or sodium hexamethyldisilazide |
| NaI | sodium iodide |
| NaOAc | sodium acetate |
| NaOMe | sodium methoxide |
| NBS | N-bromosuccinimide |
| NMP | N-methylpyrrolidone |
| NMR | nuclear magnetic resonance |
| o/n | overnight |
| Pd | palladium |
| Pd/C | palladium on carbon |
| Pd(dba)$_2$ | bis(dibenzylideneacetone)palladium(0) |
| Pd$_2$(dba)$_3$ or Pd$_2$dba$_3$ | tris(dibenzylideneacetone)dipalladium(0) |
| PdCl$_2$(PhCN)$_2$ | trans-bis(benzonitrile)dichloropalladium(II) |
| PdCl$_2$(dppf), PdCl$_2$dppf or Pd(dppf)Cl$_2$ | [1,1'-bis(diphenylphosphino)ferrocene]dichloropalladium(II) |
| Pd(OAc)$_2$ | palladium(II) acetate |
| Pd(PPh$_3$)$_4$ or Pd(pph$_3$)$_4$ | tetrakis(triphenylphosphine)palladium(0) |
| Pd(PPh$_3$)$_2$Cl$_2$, PdCl$_2$(PPh$_3$)$_2$ or PdCl$_2$(Ph$_3$P)$_2$ | bis(triphenylphosphine)palladium(II) dichloride |
| PHBu$_3$BF$_4$ or tBu$_3$PHBF$_4$ | tri-tert-butylphosphonium tetrafluoroborate |
| PhI | iodobenzene |
| PhI(OTFA)$_2$ | [bis(trifluoroacetoxy)iodo]benzene |
| PhMe | toluene |
| POCl$_3$ | phosphoryl chloride |
| PPh$_3$ | triphenylphosphine |
| PPA | polyphosphoric acid |
| PPTs | pyridinium p-toluenesulfonate |
| psi | pounds per square inch pressure |

| Abbreviation | Meaning |
| --- | --- |
| PyBOP | (benzotriazol-1-yloxy)tripyrrolidinophosphonium hexafluorophosphate |
| rt | room temperature |
| RuPhos | 2-dicyclohexylphosphino-2',6'-diisopropoxybiphenyl |
| S-Phos, SPhos or Sphos | 2-dicyclohexylphosphino-2',6'-dimethoxybiphenyl |
| $T_3P$ | propylphosphonic anhydride |
| TEA, $Et_3N$ or $NEt_3$ | triethylamine |
| $Tf_2O$ | triflic anhydride |
| TFA | trifluoroacetic acid |
| THF | tetrahydrofuran |
| TLC | thin layer chromatography |
| TMS | trimethylsilane |
| TMSCl | trimethylchlorosilane or trimethylsilyl chloride |
| TMSOK | potassium trimethylsilanolate |
| t-Bu | tert-butyl |
| t-BuOAc | tert-butyl acetate |
| t-BuXPhos Palladacycle | chloro[2-(di-tert-butylphosphino)-2',4',6'-triisopropyl-1,1'-biphenyl][2-(2-aminoethyl)phenyl)]palladium(II) |
| TsOH, p-TsOH or pTSA | tosylic acid or p-toluenesulfonic acid |
| xantphos | 4,5-bis(diphenylphosphino)-9,9-dimethylxanthene |

Example 1

Preparation of Cpd 4

Part 1: Preparation of ethyl 2-(benzo[d]thiazol-2-yl)acetate

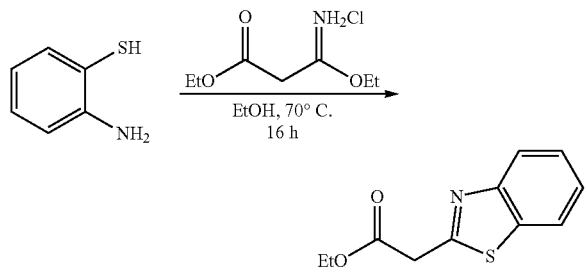

A mixture of 2-aminobenzenethiol (5.34 mL, 50 mmol) and 3-ethoxy-3-iminopropanoate hydrochloride (9.75 g, 50 mmol) in EtOH (50 mL) was heated at 70° C. for 16 h. The mixture was partitioned in EtOAc (200 mL) and water (200 mL). The organic layer was washed with brine, dried over $MgSO_4$, filtered and concentrated. The residue was purified by silica gel column chromatography (10% EtOAc in hexanes) to give the title compound (6.0 g, 54%) as a yellow oil. MS m/z 222.1 [M+H]$^+$; $^1$H NMR (500 MHz, DMSO-$d_6$): δ 8.05 (1H, d, J=8.1 Hz), 7.91 (1H, d, J=8.0 Hz), 7.51 (1H, t, J=8 Hz), 7.43 (1H, t, J=8 Hz), 4.28 (2H, q, J=7.2 Hz), 4.22 (2H, s), 1.33 (3H, t, J=7.1 Hz).

Part 2: Preparation of tert-butyl 4-(4-formyl-3-hydroxyphenyl)piperazine-1-carboxylate

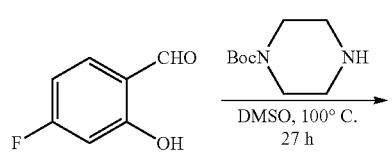

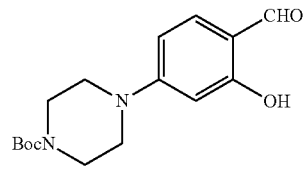

A mixture of 4-fluoro-2-hydroxybenzaldehyde (10 g, 71.4 mmol), 1-boc-piperazine (15.3 g, 82.2 mmol), and DMSO (100 mL) was heated at 100° C. for 27 h. The reaction mixture was diluted in an aqueous $K_2CO_3$ solution and extracted with EtOAc. The organic layer was washed with $H_2O$ and brine, dried over $MgSO_4$, filtered, and concentrated under vacuum. The residue was triturated with hexane/ether (1:1), yielding the title compound (18.8 g, 86%) as a yellow solid. MS m/z 307.2 [M+H]$^+$; $^1$H NMR (500 MHz, CDCl$_3$): δ 11.50 (1H, s), 9.60 (1H, s), 7.36 (1H, d, J=9 Hz), 6.27 (1H, d, J=2 Hz), 6.45 (1H, dd, J=9 Hz, 2 Hz), 3.58 (4H, m), 3.42 (4H, m), 1.49 (9H, s).

Part 3: Preparation of Cpd 4

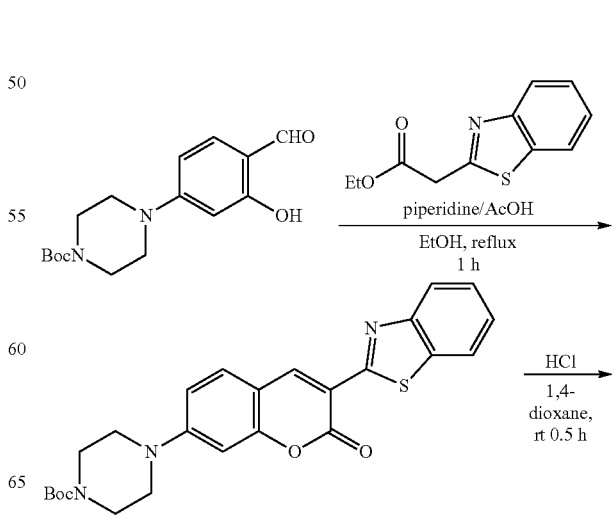

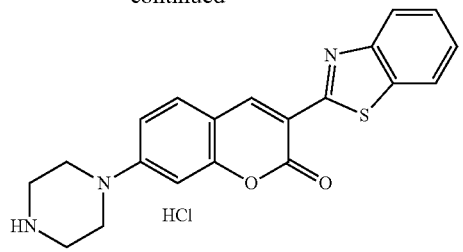

Step A: tert-Butyl 4-(4-formyl-3-hydroxyphenyl)piperazine-1-carboxylate (49 mg, 0.16 mmol) and ethyl 2-(benzo[d]thiazol-2-yl)acetate (35 mg, 0.16 mmol) were combined with piperidine (10 µL, 0.1 mmol) and acetic acid (6 µL, 0.1 mmol) in EtOH (1 mL). The mixture was heated at reflux for 1 h. After cooling the mixture to room temperature, a precipitate formed. The solid was collected by vacuum filtration, washed with 1:1 EtOH:H$_2$O (1 mL) and dried under vacuum to afford tert-butyl 4-(3-(benzo[d]thiazol-2-yl)-2-oxo-2H-chromen-7-yl)piperazine-1-carboxylate.

Step B: tert-butyl 4-(3-(benzo[d]thiazol-2-yl)-2-oxo-2H-chromen-7-yl)piperazine-1-carboxylate was suspended in 4N HCl in 1,4-dioxane (1 mL). After stirring the mixture for 30 min at room temperature, the solvent was removed with a stream of nitrogen, to give the title compound (40 mg, 69%) as a yellow powder: m.p. 250° C. (decomp.); MS m/z 364.4 [M+H]$^+$; $^1$H NMR (500 MHz, DMSO-d$_6$): δ 9.26 (2H, br s), 9.14 (1H, s), 8.16 (1H, d, J=7.9 Hz), 8.04 (1H, d, J=8.1 Hz), 7.93 (1H, d, J=9.0 Hz), 7.56 (1H, m), 7.47 (1H, m), 7.16 (1H, dd, J=8.9 Hz, 2.3 Hz), 7.09 (1H, d, J=2.3 Hz), 3.76-3.74 (4H, m), 3.25-3.23 (4H, m).

As shown in Table 1 below, additional compounds disclosed herein may be prepared according to Example 1 by substituting the appropriate starting materials, reagents and reaction conditions.

Example 2

Preparation of Cpd 5

Part 1: Preparation of tert-butyl 2-(4-chlorobenzo[d]thiazol-2-yl)acetate

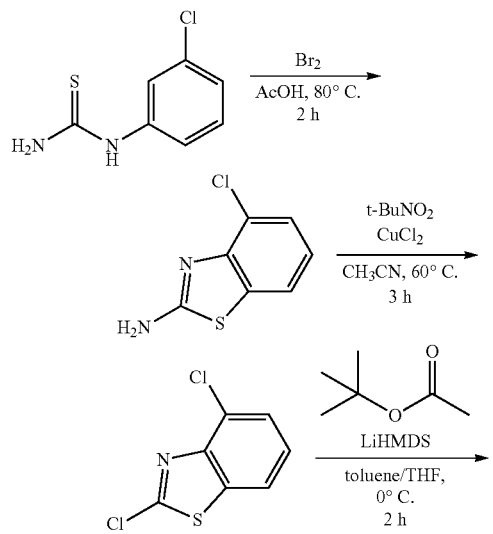

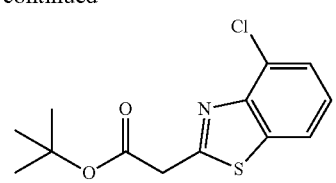

Step A: To a solution of 1-(3-chlorophenyl)thiourea (5.09 g, 27.2 mmol) in acetic acid (100 mL) was added bromine (1.82 mL, 35.4 mmol) dropwise at 60° C. The mixture was heated at 80° C. for 2 h and the solvent was removed under reduced pressure. Diethyl ether was added to the mixture to produce a precipitate. The solid was collected and dried to give 4-chlorobenzo[d]thiazol-2-amine (5.7 g, 79%). MS m/z 185.9 [M+H]$^+$.

Step B: To a mixture of 4-chlorobenzo[d]thiazol-2-amine (4.78 g, 25.8 mmol) and copper(II) chloride (4.16 g, 31 mmol) in CH$_3$CN (25 mL) was added t-butyl nitrite (4.61 mL, 38.8 mmol) at room temperature. The reaction mixture was heated at 60° C. for 30 min, then the solvent was removed from the mixture. The residue was suspended in water, collected by filtration and dried to give 2,4-dichlorobenzo[d]thiazole. (5.3 g, 81%). MS m/z 205.9 [M+H]$^+$.

Step C: To a mixture of t-butyl acetate (4.93 mL, 36.6 mmol) and 2,4-dichlorobenzo[d]thiazole (5 g, 24.4 mmol) in toluene (20 mL) was added lithium bis(trimethylsilyl)amide (1M in THF, 66 mL, 66 mmol) at 0° C. The mixture was stirred at room temperature overnight. Excess reagent was quenched with the addition of aqueous saturated NH$_4$Cl. The aqueous mixture was extracted with EtOAc. The organic layer was concentrated and purified by silica gel column chromatography (0-5% EtOAC in hexanes) to give the title compound (5.9 g, 85%) as a yellow oil. MS m/z 282.1 [M−H]$^−$. $^1$H NMR (500 MHz, CDCl$_3$): δ 7.75 (1H, d, J=8.2 Hz), 7.47 (1H, d, J=7.7 Hz), 7.29 (1H, t, J=7.9 Hz), 4.15 (2H, s), 1.48 (9H, s).

Part 2: Preparation of Cpd 5

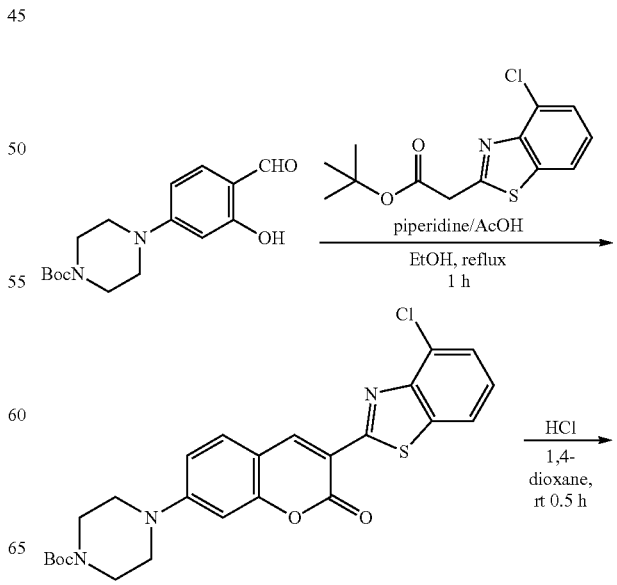

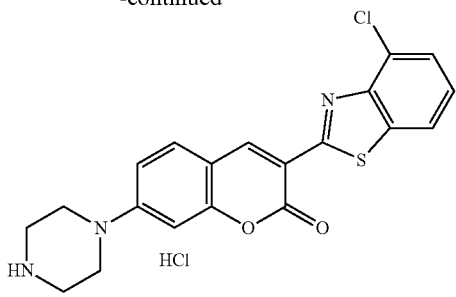

Step A: Following the procedure found in Example 1, Part 3, tert-Butyl 4-(4-formyl-3-hydroxyphenyl)piperazine-1-carboxylate (49 mg, 0.16 mmol), tert-butyl 2-(4-chlorobenzo[d]thiazol-2-yl)acetate (35 mg, 0.16 mmol), piperidine (10 μL, 0.1 mmol) and acetic acid (6 μL, 0.1 mmol) in EtOH (1 mL) gave tert-butyl 4-(3-(4-chlorobenzo[d]thiazol-2-yl)-2-oxo-2H-chromen-7-yl)piperazine-1-carboxylate.

Step B: Following the procedure found in Example 1, Part 3, tert-butyl 4-(3-(4-chlorobenzo [d]thiazol-2-yl)-2-oxo-2H-chromen-7-yl)piperazine-1-carboxylate and 4N HCl in 1,4-dioxane (1 mL) gave the title compound (62 mg, 97%) as a yellow powder: m.p. 290° C. (decomp.); MS m/z 398.1 [M+H]+; 1H NMR (500 MHz, DMSO-d6): δ 9.18 (2H, br s), 9.09 (1H, s), 8.14 (1H, dd, J=8.0 Hz, 1.0 Hz), 7.99 (1H, d, J=9.2 Hz), 7.65 (1H, dd, J=7.7 Hz, 1.0 Hz), 7.44 (1H, t, J=7.8 Hz), 7.17 (1H, dd, J=9.0 Hz, 2.4 Hz), 7.09 (1H, d, J=2.2 Hz), 3.77-3.74 (4H, m), 3.25-3.23 (4H, m).

As shown in Table 1 below, additional compounds disclosed herein may be prepared according to Example 2 by substituting the appropriate starting materials, reagents and reaction conditions.

Example 3

Preparation of Cpd 68

Part 1: Preparation of ethyl 2-(4-chlorobenzo[d]oxazol-2-yl)acetate

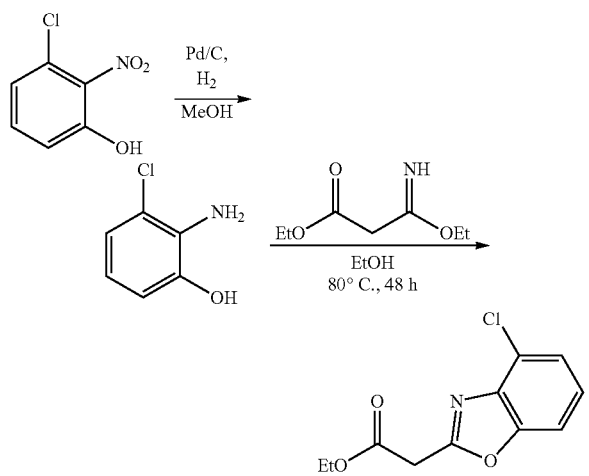

Step A: A mixture of 3-chloro-2-nitrophenol (18.95 g, 100 mmol) and Pd/C (10%, 0.50 g) in MeOH (300 mL) was stirred under H2 (1 atm). After 15 h, the mixture was filtered through Celite. The filtrate was concentrated to give a brown solid, which was washed with CH2Cl2 to give 2-amino-3-chlorophenol (7.39 g, 52%) as a light brown solid. MS m/z 144.1 [M+H]+.

Step B: To a solution of 2-amino-3-chlorophenol (2.0 g, 14 mmol) in EtOH (30 mL) was added ethyl 3-ethoxy-3-iminopropanoate hydrochloride (3.01 g, 15.4 mmol). After heating at 80° C. for 2 d, the mixture was concentrated. The residue was partitioned between EtOAc and water. The organic layer was concentrated and purified by silica gel column chromatography (CH2Cl2) to give ethyl 2-(4-chlorobenzo[d]oxazol-2-yl)acetate (3.17 g, 94%) as an off-white solid. MS m/z 240.1 [M+H]+; 1H NMR (500 MHz, DMSO-d6): δ 7.75 (1H, dd, J=8.0 Hz, 0.9 Hz), 7.49 (1H, dd, J=8.0 Hz, 0.9 Hz), 7.43 (1H, t, J=8.0 Hz), 4.28 (2H, s), 4.16 (2H, q, J=7.2 Hz), 1.21 (3H, t, J=7.2 Hz).

Part 2: Preparation of Cpd 68

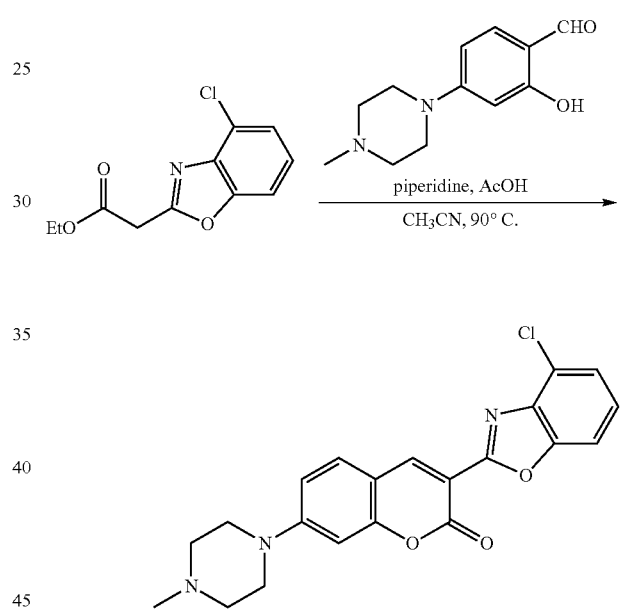

To a solution of ethyl 2-(4-chlorobenzo[d]oxazol-2-yl)acetate (72 mg, 0.3 mmol, prepared according to Example 1) and 2-hydroxy-4-(4-methylpiperazin-1-yl)benzaldehyde (66 mg, 0.3 mmol, prepared following the procedure in Example 1, Part 2) in CH3CN (0.5 mL) were added piperidine (3 uL, 0.03 mmol) and AcOH (3.4 uL, 0.06 mmol). After heating at 90° C. for 2 h, the mixture was cooled to room temperature. The product was collected by vacuum filtration, washed with CH3CN and dried to give the title compound (92 mg, 78%) as a yellow solid: m.p. 229-231° C.; MS m/z 396.2, 398.2 [M+H]+; 1H NMR (500 MHz, CDCl3): δ 8.91 (1H, s), 8.79 (1H, d, J=9.1 Hz), 7.76 (1H, dd, J=8.2 Hz, 0.9 Hz), 7.50 (1H, dd, J=8.0 Hz, 0.8 Hz), 7.42 (1H, t, J=8.0 Hz), 7.08 (1H, dd, J=9.0 Hz, 2.4 Hz), 6.90 (1H, d, J=2.3 Hz), 3.49 (4H, m), 2.43 (4H, m), 2.26 (3H, s).

As shown in Table 1 below, additional compounds disclosed herein may be prepared according to Example 3 by substituting the appropriate starting materials, reagents and reaction conditions.

Example 4

Preparation of Cpd 145

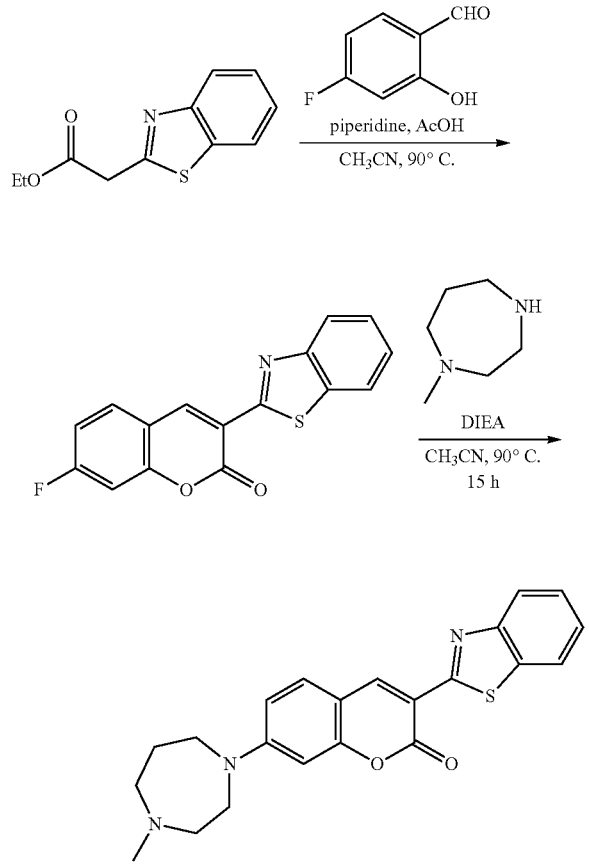

Step A: A mixture of ethyl 2-(benzo[d]thiazol-2-yl)acetate (0.53 g, 2.4 mmol, prepared in Example 1, Part 1), 4-fluoro-2-hydroxybenzaldehyde (0.336 g, 2.4 mmol), piperidine (80 µL, 0.8 mmol) and acetic acid (92 µL, 0.16 mmol) in CH$_3$CN (2 mL) was heated at 60° C. for 1 h. The mixture was filtered. The solid material was washed with CH$_3$CN and dried to give 3-(benzo[d]thiazol-2-yl)-7-fluoro-2H-chromen-2-one (0.57 g, 80%) as a yellow solid. MS m/z 298.1 [M+H]$^+$.

Step B: A mixture of 3-(benzo[d]thiazol-2-yl)-7-fluoro-2H-chromen-2-one (89 mg, 0.3 mmol), 1-methyl-1,4-diazepane (75 µL, 0.6 mmol), N,N-diisopropylethylamine (78 µL, 0.45 mmol) in CH$_3$CN (1 mL) was heated at 90° C. After 15 h, the mixture was cooled to room temperature and filtered. The solid material was washed with CH$_3$CN to give the title compound (110 mg, 94%) as a yellow solid: m.p. 217-220° C.; MS m/z 392.2 [M+H]$^+$; $^1$H NMR (500 MHz, CDCl$_3$): δ 9.04 (1H, s), 8.12 (1H, d, J=7.7 Hz), 7.99 (1H, d, J=8.1 Hz), 7.79 (1H, d, J=9.1), 7.54-7.51 (1H, m), 7.43-7.40 (1H, m), 6.93 (1H, dd, J=9.0 Hz, 2.4 Hz), 6.76 (1H, d, J=2.2 Hz), 3.69 (2H, m), 3.61 (2H, t, J=6.2 Hz), 2.64 (2H, m), 2.46 (2H, m), 2.26 (3H, s), 1.91 (2H, m).

As shown in Table 1 below, additional compounds disclosed herein may be prepared according to Example 4 by substituting the appropriate starting materials, reagents and reaction conditions.

Example 5

Preparation of Cpd 3

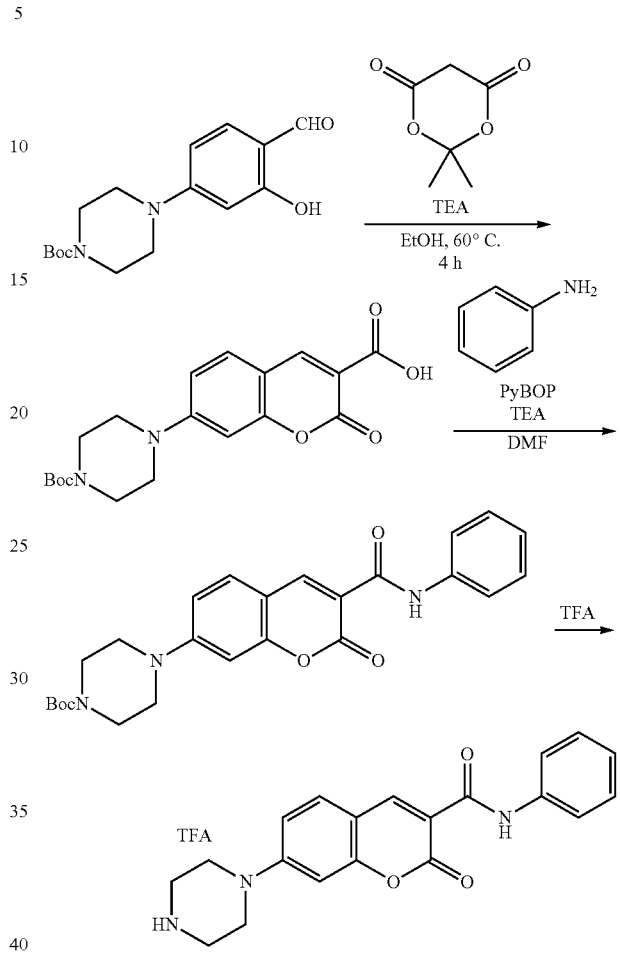

Step A: tert-Butyl 4-(4-formyl-3-hydroxyphenyl)piperazine-1-carboxylate (918 mg, 3 mmol, prepared in Example 1, Part 2), 2,2-dimethyl-1,3-dioxane-4,6-dione (648 mg, 4.5 mmol) and triethylamine (0.14 mL, 1 mmol) were combined in EtOH (6 mL). The mixture was heated at 60° C. for 4 h. The mixture was cooled to room temperature and filtered. The collected material was washed with EtOH and dried under vacuum to afford 7-(4-(tert-butoxycarbonyl)piperazin-1-yl)-2-oxo-2H-chromene-3-carboxylic acid (1.05 g, 94%) as a yellow powder. MS m/z 373.2 [M−H]$^−$.

Step B: 7-(4-(tert-Butoxycarbonyl)piperazin-1-yl)-2-oxo-2H-chromene-3-carboxylic acid (60 mg, 0.16 mmol) was combined with aniline (22 µL, 0.24 mmol), (benzotriazol-1-yloxy)tripyrrolidinophosphonium hexafluorophosphate (100 mg, 0.19 mmol) and triethylamine (45 µL, 0.32 mmol) in DMF (1 mL). The mixture was stirred at room temperature for 2 h. A solution of 4:1 MeOH:H$_2$O (1 mL) was added to the mixture. A precipitate formed and was collected by vacuum filtration. The solid was washed with MeOH:H$_2$O (4:1) and dried under vacuum to afford tert-butyl 4-(2-oxo-3-(phenylcarbamoyl)-2H-chromen-7-yl)piperazine-1-carboxylate.

Step C: A mixture of tert-butyl 4-(2-oxo-3-(phenylcarbamoyl)-2H-chromen-7-yl)piperazine-1-carboxylate in trifluoroacetic acid (1 mL) was stirred at room temperature for 20 min, then the solvent was removed with a stream of nitrogen to afford the title compound (75 mg, 99%) as a yellow powder: MS m/z 350.1 [M+H]+; 1H NMR (500 MHz, DMSO-d6): δ 10.73 (1H, s), 8.81 (1H, s), 7.78 (1H, d, J=9.1 Hz), 7.72 (2H, d, J=8.6 Hz), 7.38 (2H, m), 7.13 (1H, t, J=7.4 Hz), 7.09 (1H, dd, J=9.1 Hz, 2.5 Hz), 6.93 (1H, d, J=2.3 Hz), 3.43 (4H, m), 2.81 (4H, m).

As shown in Table 1 below, additional compounds disclosed herein may be prepared according to Example 5 by substituting the appropriate starting materials, reagents and reaction conditions.

Example 6

Preparation of Cpd 160

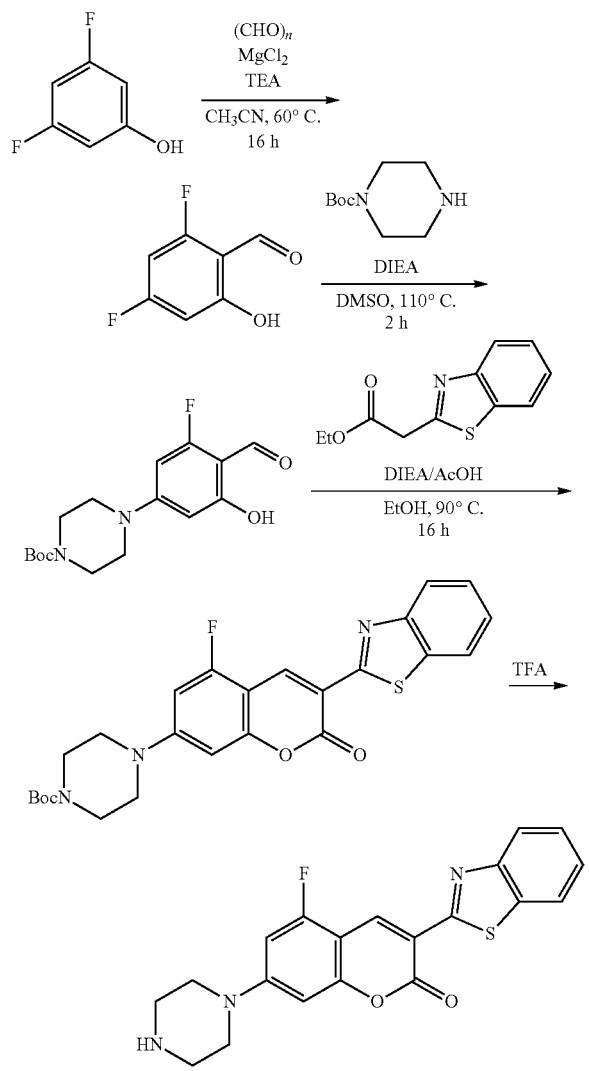

Step A: 3,5-Difluorophenol (2.6 g, 20 mmol) was dissolved in CH3CN (50 mL) with triethylamine (14 mL, 100 mmol). Magnesium chloride (3.8 g, 40 mmol) and paraformaldehyde (6.4 g, 200 mmol) were added sequentially. The heterogeneous mixture was stirred vigorously at 60° C. for 16 h. The mixture was diluted with H2O (200 mL) and the pH was adjusted to <2 with aqueous HCl (1 M). The mixture was extracted with EtOAc (200 mL). The organic layer was washed with brine, dried over Na2SO4, then filtered and concentrated to afford 2,4-difluoro-6-hydroxybenzaldehyde (2.6 g, 82%) as a red oil. MS m/z 157.1 [M–H]−.

Step B: 2,4-Difluoro-6-hydroxybenzaldehyde (16 mmol) was combined with 1-Boc-piperazine (3.57 g, 19.2 mmol) and N,N-diisopropylethylamine (3.34 mL, 19.2 mmol) in DMSO (4 mL). The mixture was heated to 120° C. for 2 h. The mixture was purified by silica gel column chromatography (0-40% EtOAc in hexanes) to afford tert-butyl 4-(3-fluoro-4-formyl-5-hydroxyphenyl)piperazine-1-carboxylate (1.3 g, 25%) as an off white powder. 1H NMR (500 MHz, DMSO-d6): δ 11.93 (1H, s), 9.92 (1H, s), 6.08 (1H, dd, J=14.2 Hz, 2.4 Hz), 6.04 (1H, d, J=2.4 Hz), 3.59 (4H, m), 3.43 (4H, m), 1.49 (9H, s).

Step C: tert-Butyl 4-(3-fluoro-4-formyl-5-hydroxyphenyl)piperazine-1-carboxylate (65 mg, 0.2 mmol) was combined with ethyl 2-(benzo[d]thiazol-2-yl)acetate (22 mg, 0.2 mmol, prepared in Example 1, Part 1), N,N-diisopropylethylamine (35 μL, 0.2 mmol) and acetic acid (11 μL, 0.2 mmol) in EtOH (1 mL). The mixture was heated to 90° C. for 16 h. After cooling the mixture to room temperature, a precipitate was formed. The solid was collected, washed with 1:1 MeOH:H2O (1 mL) and dried under vacuum to afford tert-butyl 4-(3-(benzo[d]thiazol-2-yl)-5-fluoro-2-oxo-2H-chromen-7-yl)piperazine-1-carboxylate.

Step D: A mixture of tert-butyl 4-(3-(benzo[d]thiazol-2-yl)-5-fluoro-2-oxo-2H-chromen-7-yl)piperazine-1-carboxylate and trifluoroacetic acid (1 mL) was stirred at room temperature for 15 min, then the solvent was removed with a stream of nitrogen. The residue was partitioned in CH2Cl2 (5 mL) and aqueous K2CO3 (1 M, 5 mL). The organic layer was collected through a hydrophobic frit and concentrated to afford the title compound (38 mg, 50%) as a yellow powder: m.p. 256-260° C.; MS m/z 382.2 [M+H]+; 1H NMR (500 MHz, DMSO-d6): δ 8.89 (1H, s), 8.15 (1H, d, J=7.8 Hz), 8.05 (1H, d, J=7.3 Hz), 7.55 (1H, m), 7.44 (1H, m), 7.02 (1H, dd, J=13.9 Hz, 2.1 Hz), 6.82 (1H, s), 3.45-3.41 (4H, m), 2.82-2.78 (4H, m), 2.46 (1H, s br).

As shown in Table 1 below, additional compounds disclosed herein may be prepared according to Example 6 by substituting the appropriate starting materials, reagents and reaction conditions.

Example 7

Preparation of Cpd 162

Part 1: Preparation of ethyl 2-(6-methylimidazo[1,2-a]pyridin-2-yl)acetate

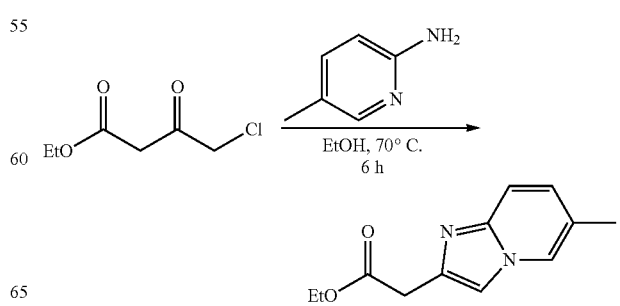

A mixture of ethyl 4-chloroacetoacetate (5.4 mL, 40 mmol) and 5-methylpyridin-2-amine (5.18 g, 48 mmol) in EtOH (100 mL) was heated at 70° C. for 6 h. The mixture was partitioned in EtOAc (300 mL) and an aqueous saturated NaHCO$_3$ solution (300 mL). The organic layer was washed with brine, dried over MgSO$_4$, filtered and concentrated. The residue was purified by silica gel column chromatography (70% EtOAc in hexanes) to give the title compound (1.6 g, 19%) as a brown oil. $^1$H NMR (500 MHz, DMSO-d$_6$): δ 8.31 (1H, s), 7.74 (1H, s), 7.39 (1H, d, J=9.2 Hz), 7.08 (1H, d, J=9.2 Hz), 4.10 (2H, q, J=7.1 Hz), 3.75 (2H, s), 2.27 (3H, s), 1.20 (3H, t, J=7.1 Hz).

Part 2: Preparation of Cpd 162

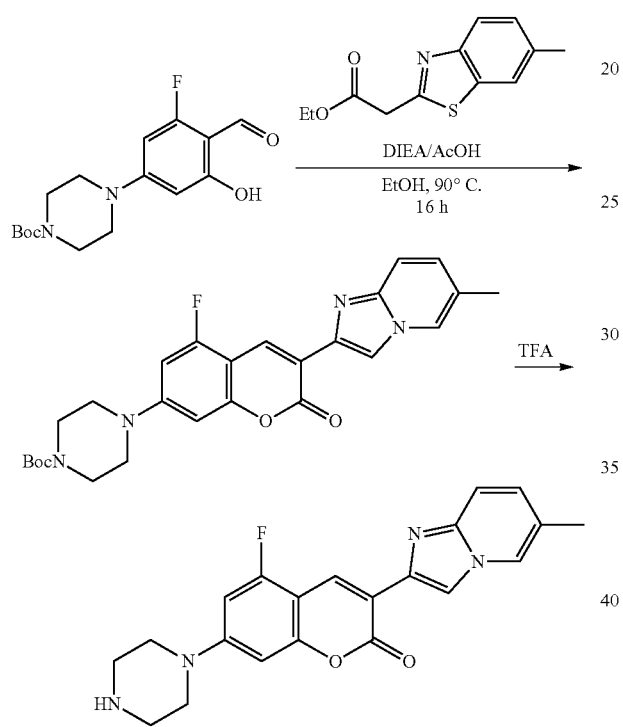

Step A: Following the procedure in Example 6, Step C, tert-butyl 4-(3-fluoro-4-formyl-5-hydroxyphenyl)piperazine-1-carboxylate (65 mg, 0.2 mmol), ethyl 2-(6-methylimidazo[1,2-a]pyridin-2-yl)acetate (22 mg, 0.2 mmol), N,N-diisopropylethylamine (35 μL, 0.2 mmol) and acetic acid (11 μL, 0.2 mmol) in EtOH (1 mL) gave tert-butyl 4-(5-fluoro-3-(6-methylimidazo[1,2-a]pyridin-2-yl)-2-oxo-2H-chromen-7-yl)piperazine-1-carboxylate.

Step B: Following the procedure in Example 6, Step D, tert-butyl 4-(5-fluoro-3-(6-methylimidazo[1,2-a]pyridin-2-yl)-2-oxo-2H-chromen-7-yl)piperazine-1-carboxylate and trifluoroacetic acid (1 mL) gave the title compound (18 mg, 24%) as a yellow powder: m.p. 265-270° C.; MS m/z 379.2 [M+H]$^+$; $^1$H NMR (500 MHz, DMSO-d$_6$): δ 8.60 (1H, s), 8.42 (2H, m), 7.49 (1H, d, J=9.1 Hz), 7.16 (1H, dd, J=9.3 Hz, 1.6 Hz), 6.93 (1H, dd, J=11.6 Hz, 2.2 Hz), 6.75 (1H, d, J=1.9 Hz), 3.33-3.31 (4H, m), 2.82-2.80 (4H, m), 2.28 (3H, s).

As shown in Table 1 below, additional compounds disclosed herein may be prepared according to Example 7 by substituting the appropriate starting materials, reagents and reaction conditions.

Example 8

Preparation of Cpd 290

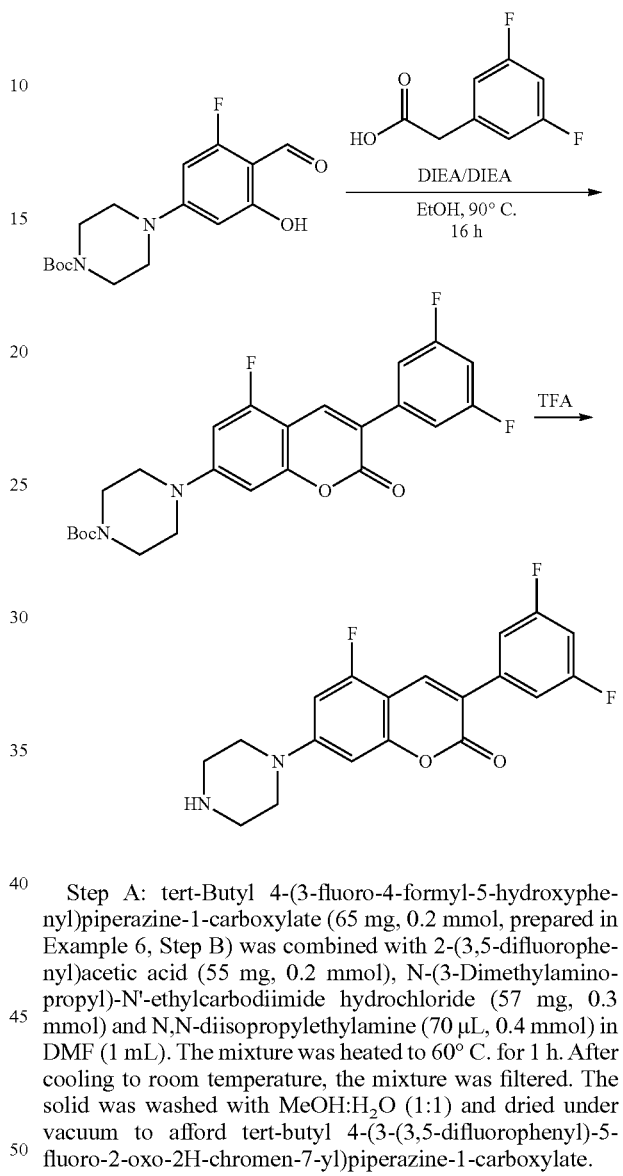

Step A: tert-Butyl 4-(3-fluoro-4-formyl-5-hydroxyphenyl)piperazine-1-carboxylate (65 mg, 0.2 mmol, prepared in Example 6, Step B) was combined with 2-(3,5-difluorophenyl)acetic acid (55 mg, 0.2 mmol), N-(3-Dimethylaminopropyl)-N'-ethylcarbodiimide hydrochloride (57 mg, 0.3 mmol) and N,N-diisopropylethylamine (70 μL, 0.4 mmol) in DMF (1 mL). The mixture was heated to 60° C. for 1 h. After cooling to room temperature, the mixture was filtered. The solid was washed with MeOH:H$_2$O (1:1) and dried under vacuum to afford tert-butyl 4-(3-(3,5-difluorophenyl)-5-fluoro-2-oxo-2H-chromen-7-yl)piperazine-1-carboxylate.

Step B: A mixture of tert-Butyl 4-(3-(3,5-difluorophenyl)-5-fluoro-2-oxo-2H-chromen-7-yl)piperazine-1-carboxylate and trifluoroacetic acid (1 mL) was stirred at room temperature for 15 min, then the solvent was removed with a stream of nitrogen. The residue was partitioned in CH$_2$Cl$_2$ (5 mL) and aqueous K$_2$CO$_3$ (1 M, 5 mL). The organic layer was collected through a hydrophobic frit and concentrated to afford the title compound (24 mg, 33%) as a yellow powder: m.p. 193-198° C.; MS m/z 361.3 [M+H]$^+$; $^1$H NMR (500 MHz, DMSO-d$_6$): δ 8.11 (1H, s), 7.44 (2H, m), 7.16 (1H, tt, J=9.3 Hz, 2.4 Hz), 6.82 (1H, dd, J=13.8 Hz, 2.2 Hz), 6.65 (1H, d, J=2.4 Hz), 3.26 (4H, m), 2.73 (4H, m).

As shown in Table 1 below, additional compounds disclosed herein may be prepared according to Example 8 by substituting the appropriate starting materials, reagents and reaction conditions.

Example 9

Preparation of Cpd 14

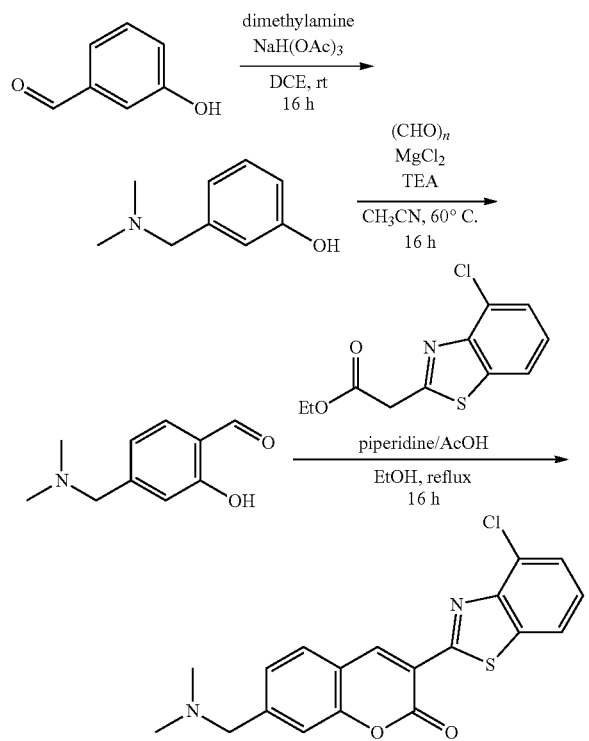

Step A: 3-Hydroxybenzaldehyde (6.1 g, 50 mmol) was combined with dimethylamine (37.5 mL of 2M solution in THF, 75 mmol) in 1,2-dichloroethane (200 mL). Sodium triacetoxyborohydride (15.9 g, 75 mmol) was added slowly at room temperature. Acetic acid (2.86 mL, 50 mmol) was added to the mixture. The mixture was stirred at room temperature for 16 h. To the reaction mixture was added an aqueous saturated NaHCO$_3$ solution (100 mL). The organic layer was removed, dried over Na$_2$SO$_4$, then filtered and concentrated to afford crude 3-((dimethylamino)methyl)phenol (~30 mmol, 60%).

Step B: The crude material (~30 mmol) from Step A was dissolved in CH$_3$CN (300 mL) and triethylamine (21 mL, 150 mmol). To the solution was added anhydrous magnesium chloride (5.7 g, 60 mmol) and paraformaldehyde (9.0 g, 300 mmol). The mixture was stirred vigorously at 60° C. for 16 h, then diluted with aqueous sodium potassium tartrate (0.1 M, 600 mL). The mixture was extracted three times with CH$_2$Cl$_2$ (300 mL). The combined organics were washed with brine, dried over Na$_2$SO$_4$, filtered and concentrated. The residue was purified by silica gel column chromatography (0-10% MeOH in CH$_2$Cl$_2$) to afford 4-((dimethylamino)methyl)-2-hydroxybenzaldehyde (1.7 g, 32%) as a yellow powder. MS m/z 180.1 [M+H]$^+$.

Step C: A mixture of 4-((dimethylamino)methyl)-2-hydroxybenzaldehyde (0.5 mmol), ethyl 2-(4-chlorobenzo[d]thiazol-2-yl)acetate (128 mg, 0.5 mmol, prepared as in Example 2, Part 1), piperidine (40 µL, 0.4 mmol) and acetic acid (12 µL, 0.2 mmol) in EtOH (3 mL) was heated at reflux for 16 h. After cooling the reaction mixture to room temperature, a precipitate formed. The solid was collected by vacuum filtration, washed with 1:1 EtOH:H$_2$O (1 mL) and dried under vacuum to afford the title compound (184 mg, 99%) as a yellow powder: m.p. 179-182° C.; MS m/z 371.1 [M+H]$^+$; $^1$H NMR (500 MHz, DMSO-d$_6$): δ 9.20 (1H, s), 8.18 (1H, d, J=8.0 Hz), 8.10 (1H, d, J=8.0 Hz), 7.69 (1H, d, J=7.7 Hz), 7.48 (2H, m), 7.43 (1H, d, J=8.0 Hz), 3.57 (2H, s), 2.21 (6H, s).

As shown in Table 1 below, additional compounds disclosed herein may be prepared according to Example 9 by substituting the appropriate starting materials, reagents and reaction conditions.

Example 10

Preparation of Cpd 148

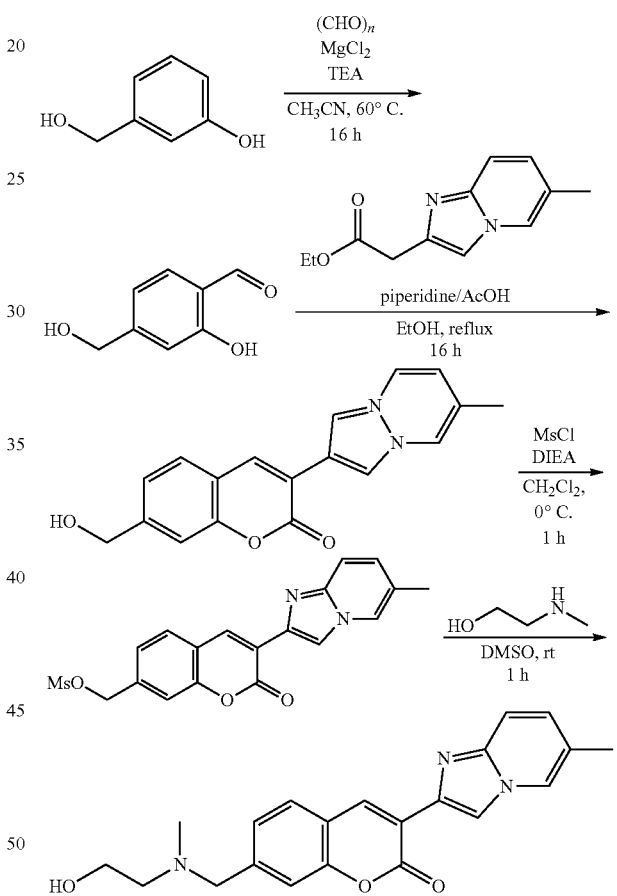

Step A: Following the procedure in Example 6, Step A, 3-(hydroxymethyl)phenol (6.2 g, 50 mmol), triethylamine (35 mL, 250 mmol), anhydrous magnesium chloride (9.5 g, 100 mmol) and paraformaldehyde (15 g, 500 mmol) in CH$_3$CN (500 mL) afforded 2-hydroxy-4-(hydroxymethyl)benzaldehyde (2.2 g, 29%). MS m/z 151.1 [M−H]$^-$.

Step B: Following the procedure in Example 9, Step C, 2-hydroxy-4-(hydroxymethyl)benzaldehyde (608 mg, 4.0 mmol), ethyl 2-(6-methylimidazo[1,2-a]pyridin-2-yl)acetate (872 mg, 4.0 mmol, prepared in Example 7, Part 1), piperidine (0.4 mL, 4.0 mmol) and acetic acid (0.24 mL, 4.0 mmol) in EtOH (4 mL) afforded 7-(hydroxymethyl)-3-(6-methylimidazo[1,2-a]pyridin-2-yl)-2H-chromen-2-one (980 mg, 80%). MS m/z 307.2 [M+H]$^+$.

Step C: 7-(Hydroxymethyl)-3-(6-methylimidazo[1,2-a]pyridin-2-yl)-2H-chromen-2-one (900 mg, 2.9 mmol) was combined with N,N-diisopropylethylamine (1.0 mL, 6 mmol) in CH$_2$Cl$_2$ (15 mL). The mixture was cooled to 0° C., before adding methanesulfonyl chloride (0.28 mL, 3.6 mmol) via syringe. The mixture stirred for 1 h at 0° C., then the solvent was removed from the mixture. The residue was suspended in MeOH (5 mL) and filtered. The collected material was washed with MeOH and dried under vacuum to afford (3-(6-methylimidazo[1,2-a]pyridin-2-yl)-2-oxo-2H-chromen-7-yl)methyl methanesulfonate (1.05 g, 92%) as a tan powder. $^1$H NMR (500 MHz, DMSO-d$_6$): δ 8.86 (1H, s), 8.56 (1H, s), 8.46 (1H, s), 7.99 (1H, d, J=7.9 Hz), 7.56 (1H, s), 7.51 (1H, d, J=9.1 Hz), 7.47 (1H, d, J=8.0 Hz), 7.20 (1H, d, 9.3 Hz), 5.41 (2H, s), 3.32 (3H, s), 2.30 (3H, s).

Step D: (3-(6-Methylimidazo[1,2-a]pyridin-2-yl)-2-oxo-2H-chromen-7-yl)methyl methanesulfonate (77 mg, 0.2 mmol) was combined with 2-(methylamino)ethanol (75 mg, 1.0 mmol) in DMF (2 mL). The mixture was stirred at room temperature for 1 h. To the mixture was added H$_2$O (0.25 mL) to produce a precipitate. The solid was collected by vacuum filtration, washed with MeOH:H$_2$O (1:1) and dried under vacuum to afford the title compound (65 mg, 90%) as an off white powder: m.p. 166-169° C.; MS m/z 364.3 [M+H]$^+$; $^1$H NMR (500 MHz, DMSO-d$_6$): δ 8.83 (1H, s), 8.53 (1H, s), 8.46 (1H, s), 7.87 (1H, d, J=8.0 Hz), 7.50 (1H, d, J=9.4 Hz), 7.43 (1H, s), 7.37 (1H, d, J=7.9 Hz), 7.19 (1H, d, J=9.2 Hz), 4.47 (1H, t, J=5.4 Hz), 3.64 (2H, s), 3.54 (2H, q, J=5.5 Hz), 2.47 (2H, t, J=6.3 Hz), 2.29 (3H, s), 2.21 (3H, s).

As shown in Table 1 below, additional compounds disclosed herein may be prepared according to Example 10 by substituting the appropriate starting materials, reagents and reaction conditions.

Example 11

Preparation of Cpd 18

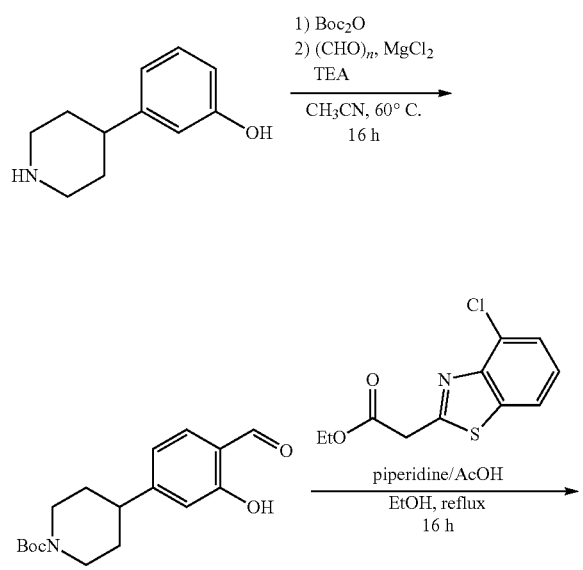

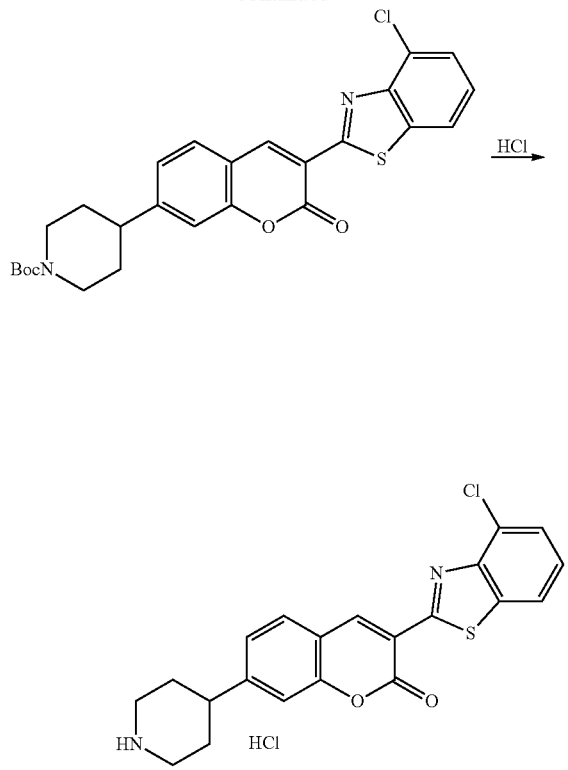

Step A: 4-(3-Hydroxyphenyl)piperidine (1.7 g, 10 mmol) was added to a mixture of CH$_3$CN (20 mL) and di-tert-butyl dicarbonate (2.4 g, 11 mmol). The mixture was stirred for 1 h at room temperature, then triethylamine (7 mL, 50 mmol), anhydrous magnesium chloride (1.9 g, 20 mmol) and paraformaldehyde (3.0 g, 100 mmol) were added. The mixture was stirred vigorously at 60° C. for 2 h, then diluted with H$_2$O (100 mL). Aqueous HCl (1N) was added to adjust the pH of the mixture to ~2. The mixture was extracted with EtOAc (100 mL). The organic layer was washed with brine, dried over Na$_2$SO$_4$, filtered and concentrated. The residue was purified by silica gel column chromatography (0-5% MeOH in CH$_2$Cl$_2$) to afford tert-butyl 4-(4-formyl-3-hydroxyphenyl)piperidine-1-carboxylate (1.44 g, 47%) as a white powder. MS m/z 304.2 [M−H]$^-$.

Step B: Following the procedure in Example 9, Step C, tert-butyl 4-(4-formyl-3-hydroxyphenyl)piperidine-1-carboxylate (61 mg, 0.2 mmol), ethyl 2-(4-chlorobenzo[d]thiazol-2-yl)acetate (50 mg, 0.2 mmol, prepared according to Example 2, Part 1), piperidine (10 μL, 0.1 mmol) and acetic acid (6 μL, 0.1 mmol) in EtOH (1 mL) afforded tert-butyl 4-(3-(4-chlorobenzo[d]thiazol-2-yl)-2-oxo-2H-chromen-7-yl)piperidine-1-carboxylate.

Step C: tert-Butyl 4-(3-(4-chlorobenzo[d]thiazol-2-yl)-2-oxo-2H-chromen-7-yl)piperidine-1-carboxylate was suspended in 4N HCl in 1,4-dioxane (1 mL). The mixture was stirred for 1 h, then the solvent was removed to afford the title compound (73 mg, 92%) as a yellow powder: m.p. 339-341° C.; MS m/z 397.1 [M+H]$^+$; $^1$H NMR (500 MHz, DMSO-d$_6$): δ 9.21 (1H, s), 8.19 (1H, d, J=8.0), 8.14 (1H, d, J=8.1), 7.70 (1H, d, J=7.7 Hz), 7.49 (1H, t, J=7.8 Hz), 7.43 (1H, s), 7.40 (1H, d, J=8.2 Hz) 3.41 (2H, m), 3.01-3.07 (3H, m), 2.03 (2H, m), 1.92 (2H, m).

Example 12

Preparation of Cpd 28

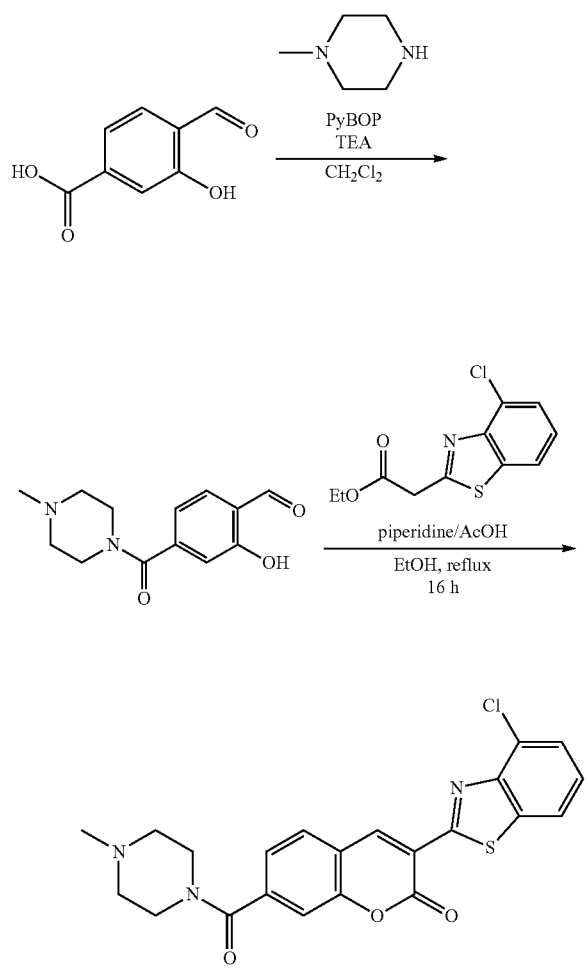

Step A: 4-Formyl-3-hydroxybenzoic acid (830 mg, 5 mmol) was combined with 1-methylpiperazine (0.61 mL, 5.5 mmol), triethylamine (0.77 mL, 5.5 mmol) and (benzotriazol-1-yloxy)tripyrrolidinophosphonium hexafluorophosphate (2.86 g, 5.5 mmol) in $CH_2Cl_2$ (10 mL). The mixture was stirred at room temperature for 3 h, then concentrated and purified by silica gel column chromatography (0-5% MeOH in $CH_2Cl_2$) to afford 2-hydroxy-4-(4-methylpiperazine-1-carbonyl)benzaldehyde (1.24 g, 100%). MS m/z 249.1 $[M+H]^+$.

Step B: Following the procedure in Example 9, Step C, 2-hydroxy-4-(4-methylpiperazine-1-carbonyl)benzaldehyde (50 mg, 0.2 mmol), ethyl 2-(4-chlorobenzo[d]thiazol-2-yl)acetate (50 mg, 0.2 mmol, prepared according to Example 2, Part 1), piperidine (20 μL, 0.2 mmol) and acetic acid (12 μL, 0.2 mmol) in EtOH (1 mL) afforded the title compound (60 mg, 68%) as a yellow powder: m.p. 230-235° C.; MS m/z 440.1 $[M+H]^+$; $^1H$ NMR (500 MHz, DMSO-$d_6$): δ 9.26 (1H, s), 8.24 (1H, d, J=8.0 Hz), 8.21 (1H, d, J=8.0 Hz), 7.72 (1H, d, J=7.6 Hz), 7.59 (1H, s), 7.51 (1H, t, J=7.9 Hz), 7.48 (1H, d, J=7.9 Hz), 3.65 (2H, m), 3.34 (2H, m), 2.42 (2H, m), 2.31 (2H, m), 2.22 (3H, s).

Example 13

Preparation of Cpd 35

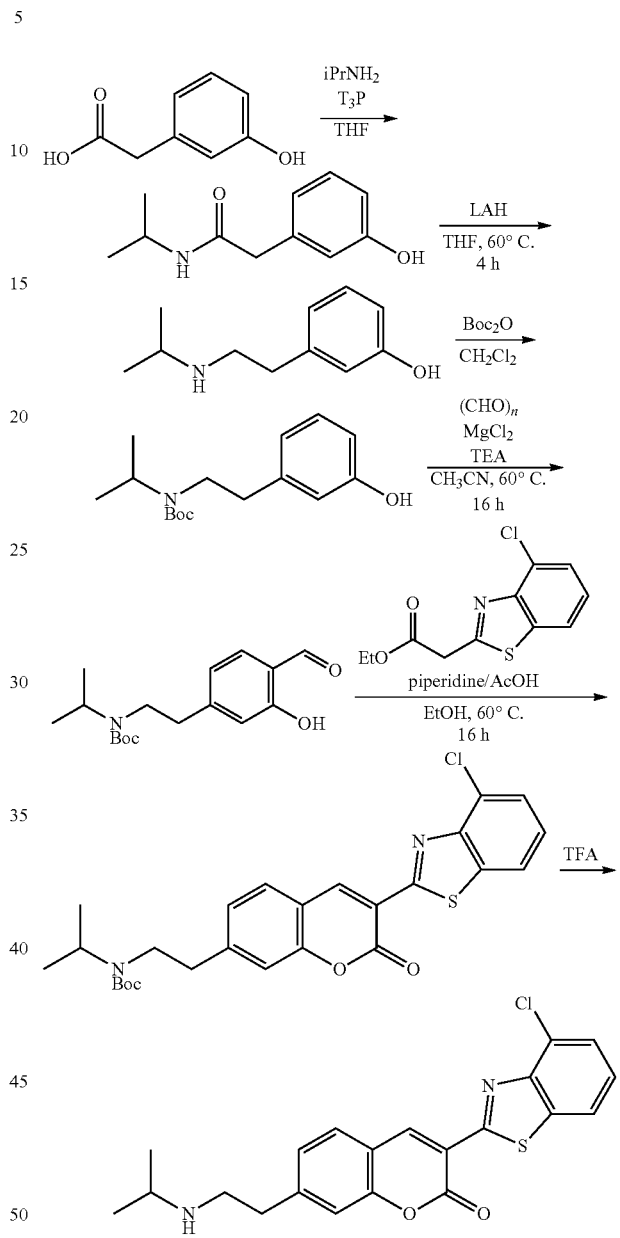

Step A: 3-Hydroxyphenylacetic acid (2.13 g, 14 mmol) was combined with isopropylamine (3.6 mL, 42 mmol) in THF (20 mL). The solution was cooled to 0° C. before adding propylphosphonic anhydride (9.8 mL, ~50% in DMF, 16 mmol). The solution stirred at room temperature for 16 h. The mixture was partitioned in $H_2O$ (300 mL) and EtOAc (300 mL). The organic layer was washed with brine, dried over $Na_2SO_4$, filtered and concentrated. The residue was purified by silica gel column chromatography (50% EtOAc in hexanes) to afford 2-(3-hydroxyphenyl)-N-isopropylacetamide (1.9 g, 70%) as a white powder. MS m/z 194.1 $[M+H]^+$.

Step B: 2-(3-Hydroxyphenyl)-N-isopropylacetamide (1.9 g, 10 mmol) was dissolved in THF (20 mL). Lithium aluminum hydride (10 mL, 1 M in THF, 10 mmol) was added to the solution. The mixture was heated to 60° C. for 2 h with stirring. The excess reagent was quenched by the slow addition of H₂O. After vigorous stirring for 1 h, the mixture was filtered through Celite. The filtrate was concentrated to afford crude 3-(2-(isopropylamino)ethyl)phenol, which was used without further purification.

Step C: 3-(2-(Isopropylamino)ethyl)phenol (716 mg, 4 mmol) was combined with di-tert-butyl dicarbonate (872 mg, 4 mmol) in CH₂Cl₂ (10 mL). The mixture was stirred at room temperature for 16 h, then concentrated and purified by silica gel column chromatography (50% EtOAc in hexanes) to afford tert-butyl 3-hydroxyphenethyl(isopropyl)carbamate (650 mg, 23%) as a white powder.

Step D: Following the procedure in Example 6, Step A, tert-butyl 3-hydroxyphenethyl(isopropyl)carbamate (650 mg, 2.3 mmol), triethylamine (1.6 mL, 11.5 mmol), anhydrous magnesium chloride (437 mg, 4.6 mmol) and paraformaldehyde (690 mg, 23 mmol) in CH₃CN (8 mL) afforded tert-butyl 4-formyl-3-hydroxyphenethyl(isopropyl)carbamate (520 mg, 73%). MS m/z 306.1 [M–H]⁻.

Step E: Following the procedure in Example 9, Step C, tert-butyl 4-formyl-3-hydroxyphenethyl(isopropyl)carbamate (50 mg, 0.16 mmol), ethyl 2-(4-chlorobenzo[d]thiazol-2-yl)acetate (50 mg, 0.2 mmol, prepared according to Example 2, Part 1), piperidine (20 μL, 0.2 mmol) and acetic acid (12 μL, 0.2 mmol) in EtOH (1 mL) afforded tert-butyl 2-(3-(4-chlorobenzo[d]thiazol-2-yl)-2-oxo-2H-chromen-7-yl)ethyl(isopropyl)carbamate.

Step F: A mixture of 2-(3-(4-chlorobenzo[d]thiazol-2-yl)-2-oxo-2H-chromen-7-yl)ethyl(isopropyl)carbamate (0.16 mmol) and trifluoroacetic acid (1 mL) was stirred at room temperature for 15 min, then the solvent was removed with a stream of nitrogen. The residue was partitioned in CH₂Cl₂ (5 mL) and aqueous K₂CO₃ (1 M, 5 mL). The organic layer was collected through a hydrophobic frit and concentrated to afford the title compound (42 mg, 66%) as a yellow powder: m.p. 179-182° C.; MS m/z 399.1 [M+H]⁺; ¹H NMR (500 MHz, DMSO-d₆): δ 9.23 (1H, s), 8.22 (1H, d, J=7.8 Hz), 8.10 (1H, d, J=8.0 Hz), 7.73 (1H, d, J=7.7 Hz), 7.52 (1H, t, J=7.8 Hz), 7.50 (1H, s), 7.42 (1H, d, J=8.0 Hz), 2.89 (4H, m), 2.79 (1H, m), 1.02 (6H, d, J=6.2 Hz).

As shown in Table 1 below, additional compounds disclosed herein may be prepared according to Example 13 by substituting the appropriate starting materials, reagents and reaction conditions.

Example 14

Preparation of Cpd 42

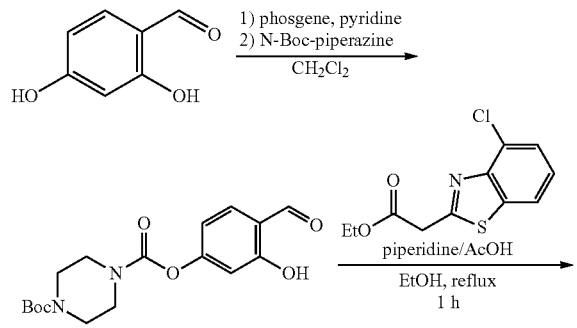

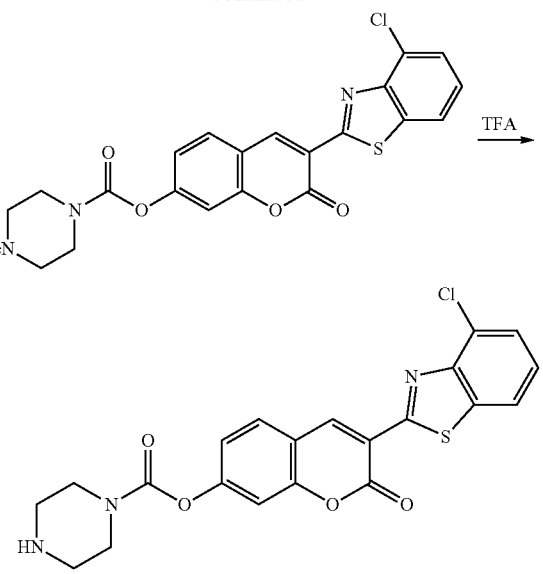

Step A: 2,4-Dihydroxybenzaldehyde (1.38 g, 10 mmol) was dissolved in CH₂Cl₂ (20 mL) and cooled to 0° C. To the mixture was added pyridine (0.81 mL, 10 mmol), followed by phosgene (5.0 mL, 20% in toluene, 10 mmol). The mixture was stirred for 5 min at 0° C. A solution of 1-Boc-piperazine (1.86 g, 10 mmol) and triethylamine (1.4 mL, 10 mmol) in CH₂Cl₂ (5 mL) was added to the mixture at 0° C. After 5 min, the mixture was washed with an aqueous saturated NaHCO₃ solution. The organic layer was dried over Na₂SO₄, filtered and concentrated. The residue was purified by silica gel column chromatography (20% EtOAc in hexanes) to afford 1-tert-butyl 4-(4-formyl-3-hydroxyphenyl) piperazine-1,4-dicarboxylate (480 mg, 14%). MS m/z 349.3 [M–H]⁻.

Step B: Following the procedure in Example 9, Step C, 1-tert-butyl 4-(4-formyl-3-hydroxyphenyl) piperazine-1,4-dicarboxylate (70 mg, 0.2 mmol), ethyl 2-(4-chlorobenzo[d]thiazol-2-yl)acetate (50 mg, 0.2 mmol, prepared according to Example 2, Part 1), piperidine (20 μL, 0.2 mmol) and acetic acid (12 μL, 0.2 mmol) in EtOH (1 mL) afforded 1-tert-butyl 4-(3-(4-chlorobenzo[d]thiazol-2-yl)-2-oxo-2H-chromen-7-yl) piperazine-1,4-dicarboxylate.

Step C: A mixture of 1-tert-butyl 4-(3-(4-chlorobenzo[d]thiazol-2-yl)-2-oxo-2H-chromen-7-yl) piperazine-1,4-dicarboxylate (0.2 mmol) and trifluoroacetic acid (1 mL) was stirred at room temperature for 15 min, then the solvent was removed with a stream of nitrogen. The residue was partitioned in CH₂Cl₂ (5 mL) and aqueous K₂CO₃ (1 M, 5 mL). The organic layer was collected through a hydrophobic frit and concentrated to afford the title compound (62 mg, 70%) as an off white powder: m.p. 236-239° C.; MS m/z 442.1 [M+H]⁺; ¹H NMR (500 MHz, DMSO-d₆): δ 9.23 (1H, s), 8.21-8.18 (2H, m), 7.70 (1H, d, J=7.72 Hz), 7.49 (1H, t, J=7.9 Hz), 7.46 (1H, d, J=2.1 Hz), 7.31 (1H, dd, J=8.5 Hz, 2.1 Hz), 3.55 (2H, m), 3.39 (2H, m), 2.76 (4H, m).

As shown in Table 1 below, additional compounds disclosed herein may be prepared according to Example 14 by substituting the appropriate starting materials, reagents and reaction conditions.

Example 15

Preparation of Cpd 143

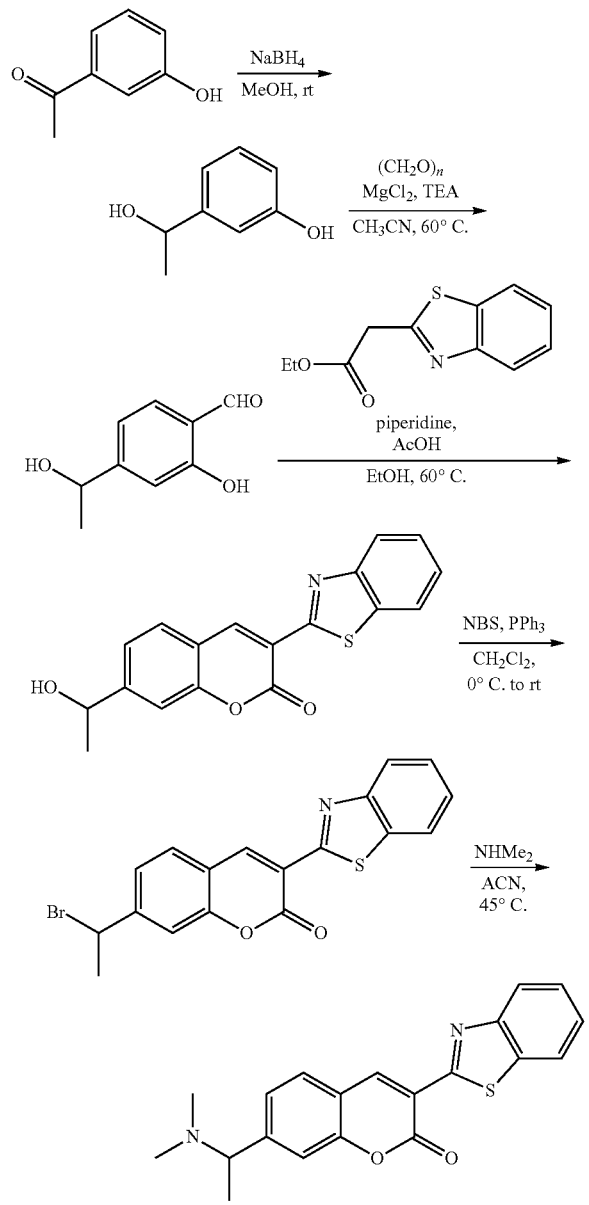

Step A: To a solution of 3-hydroxyacetophenone (2.72 g, 20 mmol) in MeOH (10 mL) was added sodium borohydride (380 mg, 10 mmol). After stirring at room temperature for 2 h, the reaction mixture was acidified to pH<7 with aqueous HCl (1 N). MeOH was removed by rotoevaporation under reduced pressure. The mixture was partitioned in water and EtOAc. The organic layer was washed with water, dried over MgSO$_4$, filtered and concentrated under reduced pressure to provide 3-(1-hydroxyethyl)phenol (2.15 g, 78%). MS m/z 137.1 [M−H]$^-$.

Step B: To a mixture of 3-(1-hydroxyethyl)phenol (1.38 g, 10 mmol), magnesium chloride (1.94 g, 20.4 mmol) and triethylamine (7 mL, 50 mmol) in CH$_3$CN (5 mL) was added paraformaldehyde (3 g, 100 mmol) at room temperature. The reaction mixture was heated at 60° C. overnight, then the solvent was removed by rotoevaporation under reduced pressure. The residual mixture was acidified to pH ~2 with aqueous HCl (1 N). The aqueous mixture was extracted with EtOAc and the organic layer was concentrated. The residue was purified by silica gel column chromatography (0-20% EtOAc in CH$_2$Cl$_2$) to provide 2-hydroxy-4-(1-hydroxyethyl)benzaldehyde (734 mg, 44%).

Step C: To a mixture of 2-hydroxy-4-(1-hydroxyethyl)benzaldehyde (568 mg, 3.4 mmol), piperidine (674 μL, 6.8 mmol) and acetic acid (194 μL, 3.4 mmol) in EtOH (2 mL) was added ethyl 2-(benzo[d]thiazol-2-yl)acetate (800 mg, 4.1 mmol, prepared in Example 1, Part 1). The mixture was heated at 60° C. overnight. After cooling to room temperature, diethyl ether was added to the mixture to produce a precipitate. The solid was collected by filtration, washed with water and dried under vacuum to give 3-(benzo[d]thiazol-2-yl)-7-(1-hydroxyethyl)-2H-chromen-2-one (493 mg, 45%). MS m/z 324.1 [M+H]$^+$.

Step D: To a mixture of 3-(benzo[d]thiazol-2-yl)-7-(1-hydroxyethyl)-2H-chromen-2-one (323 mg, 1 mmol) and triphenylphosphine (525 mg, 2 mmol) in CH$_2$Cl$_2$ (2 mL) was added N-bromosuccinimide (456 mg, 2.6 mmol) at 0° C. The reaction mixture was stirred at room temperature for 3 h. Diethyl ether was added to the mixture to produce a precipitate. The precipitate was collected by vacuum filtration, washed with water and a saturated aqueous NaHCO$_3$ solution, and dried to give 3-(benzo[d]thiazol-2-yl)-7-(1-bromoethyl)-2H-chromen-2-one (193 mg, 50%). MS m/z 386.1, 388.1 [M+H]$^+$.

Step E: To a solution of 3-(benzo[d]thiazol-2-yl)-7-(1-bromoethyl)-2H-chromen-2-one (40 mg, 0.10 mmol) in CH$_3$CN (0.8 mL) was added dimethylamine (16 mg, 0.36 mmol). The reaction mixture was heated at 45° C. for 2 h. Diethyl ether was added to the mixture to produce a precipitate. The solid was collected by vacuum filtration, washed with water and an aqueous saturated NaHCO$_3$ solution, then dried to afford the title compound (14 mg, 27%) as a yellow solid: m.p. 130-133° C.; MS m/z 351.2 [M+H]$^+$; $^1$H NMR (500 MHz, DMSO-d$_6$): δ 9.25 (1H, s), 8.20 (1H, d, J=8.1 Hz), 8.09 (1H, d, J=8.1 Hz), 8.03 (1H, d, J=7.9 Hz), 7.59 (1H, t, J=7.6 Hz), 7.51-7.43 (3H, m), 3.46 (1H, q, J=6.7 Hz), 2.15 (6H, s), 1.32 (3H, d, J=6.7 Hz).

As shown in Table 1 below, additional compounds disclosed herein may be prepared according to Example 15 by substituting the appropriate starting materials, reagents and reaction conditions.

Example 16

Preparation of Cpd 50

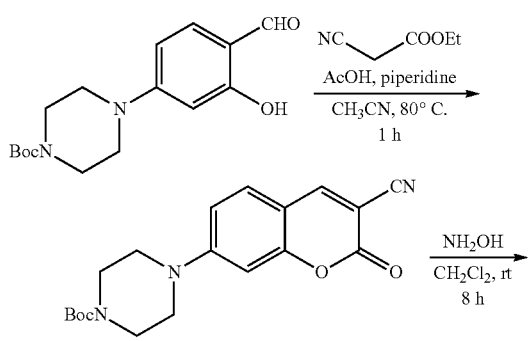

-continued

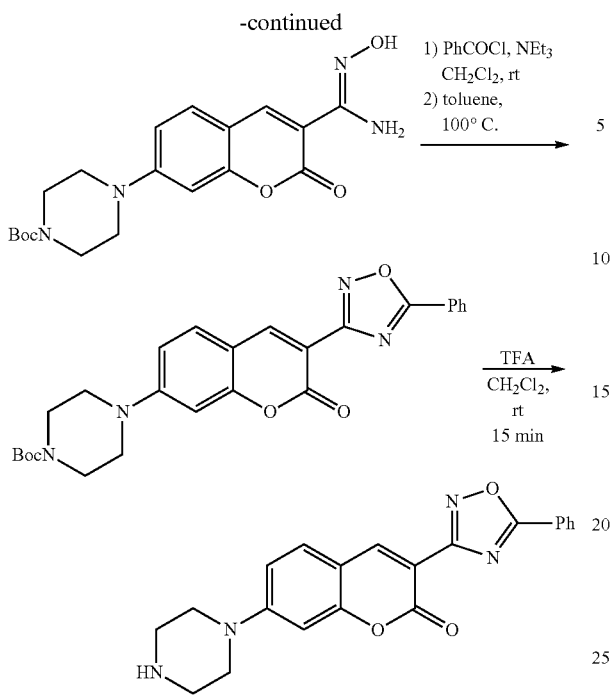

Step A: A mixture of tert-butyl 4-(4-formyl-3-hydroxyphenyl)piperazine-1-carboxylate (6.5 g, 21.2 mmol, prepared in Example 1, Part 2), ethyl cyanoacetate (2.87 mL, 29.6 mmol), piperidine (2.6 mL, 26 mmol), AcOH (1.6 mL, 29.3 mmol) and $CH_3CN$ (50 mL) was heated at 80° C. for 1 h. The reaction mixture was diluted with $H_2O$ and extracted with $CH_2Cl_2$. The organic layer was dried over $MgSO_4$, filtered, and concentrated under vacuum. The residue was purified by silica gel column chromatography (10% EtOAc in $CH_2Cl_2$), followed by trituration with hexane/EtOAc (1:1), yielding tert-butyl 4-(3-cyano-2-oxo-2H-chromen-7-yl)piperazine-1-carboxylate (5.05 g, 67%) as a yellow solid. $^1H$ NMR (500 MHz, $CDCl_3$): δ 8.05 (1H, s), 7.41 (1H, d, J=8.5 Hz), 6.84 (1H, dd, J=8.5 Hz, 2.5 Hz), 6.66 (1H, d, J=2.5 Hz), 3.65 (4H, m), 3.51 (4H, m), 1.52 (9H, s).

Step B: A mixture of tert-butyl 4-(3-cyano-2-oxo-2H-chromen-7-yl)piperazine-1-carboxylate (400 mg, 1.13 mmol), MeOH (2 mL), $CH_2Cl_2$ (2 mL), and $NH_2OH$ (50% aqueous solution, 200 μL, 3.2 mmol) was stirred at room temperature for 8 h. The reaction mixture was concentrated with a stream of nitrogen until the total volume was halved. The reaction mixture was diluted with MeOH (40 mL) and $H_2O$ (5 mL), generating a precipitate. The precipitate was collected by vacuum filtration and dried, affording tert-butyl 4-(3-(N'-hydroxycarbamimidoyl)-2-oxo-2H-chromen-7-yl)piperazine-1-carboxylate (386 mg, 88%) as a tan solid. MS m/z 389.2 $[M+H]^+$.

Step C: tert-Butyl 4-(3-(N'-hydroxycarbamimidoyl)-2-oxo-2H-chromen-7-yl)piperazine-1-carboxylate (190 mg, 0.49 mmol) was suspended in $CH_2Cl_2$ (1.5 mL) and triethylamine (85 μL, 0.6 mmol). Acetyl chloride (40 μL, 0.54 mmol) was added to the mixture. After 10 min, the mixture was diluted in $CH_2Cl_2$ and washed with aqueous HCl, followed by an aqueous saturated $NaHCO_3$ solution. The organic layer was dried over $MgSO_4$, filtered and concentrated under vacuum. The residue was suspended in toluene (1.5 mL) and heated at 100° C. for 30 h, then the solvent was removed with a stream of nitrogen. The residue was purified by silica gel column chromatography (10% EtOAc in $CH_2Cl_2$), followed by trituration with 2:1 hexane/acetone, yielding tert-butyl 4-(2-oxo-3-(5-phenyl-1,2,4-oxadiazol-3-yl)-2H-chromen-7-yl)piperazine-1-carboxylate (187 mg, 50%) as a yellow solid. MS m/z 475.2 $[M+H]^+$.

Step D: tert-Butyl 4-(2-oxo-3-(5-phenyl-1,2,4-oxadiazol-3-yl)-2H-chromen-7-yl)piperazine-1-carboxylate (107 mg, 0.26 mmol) was stirred in a solution of $CH_2Cl_2$ (2.5 mL) and trifluoroacetic acid (1.0 mL) for 15 min. The reaction mixture was partitioned in $CH_2Cl_2$ and aqueous $K_2CO_3$. The organic layer was concentrated under vacuum. The residue was triturated with 2:1 hexane/acetone, yielding the title compound (116 mg, 81%) as a yellow solid: m.p. 214-221° C.; MS m/z 375.2 $[M+H]^+$; $^1H$ NMR (500 MHz, DMSO-$d_6$): δ 8.77 (1H, s), 8.18 (2H, m), 7.75 (2H, m), 7.68 (2H, m), 7.04 (1H, dd, J=9 Hz, 2 Hz), 6.87 (1H, d, J=2 Hz), 3.38 (4H, m), 2.82 (4H, m).

Example 17

Preparation of Cpd 29

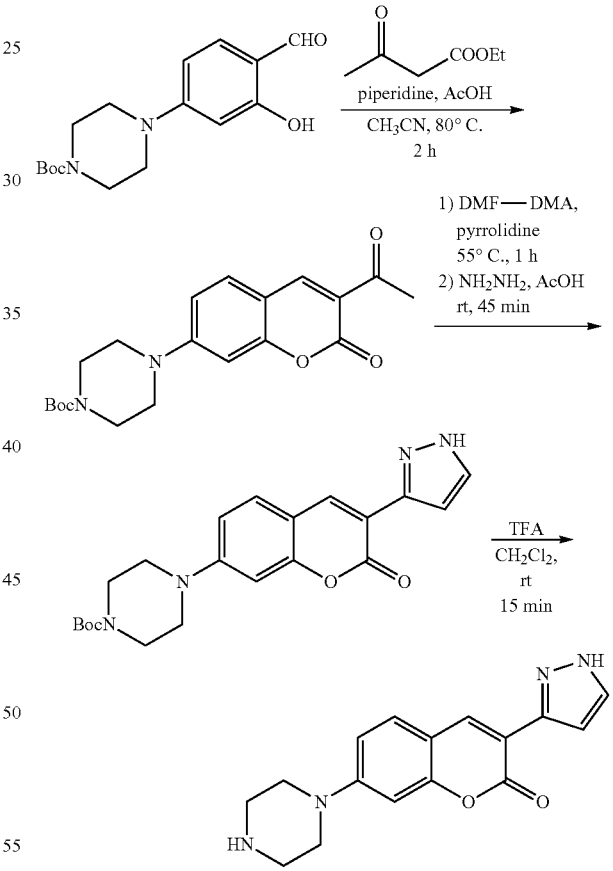

Step A: A mixture of tert-butyl 4-(4-formyl-3-hydroxyphenyl)piperazine-1-carboxylate (2.9 g, 9.5 mmol, prepared in Example 1, Part 2), ethyl acetoacetate (1.28 mL, 11.8 mmol), AcOH (725 μL, 13.3 mmol), piperidine (1.16 mL, 11.8 mmol), and $CH_3CN$ (23 mL) were heated at 80° C. for 2 h. The reaction mixture was partitioned between EtOAc and $H_2O$. The organic layer was dried over $MgSO_4$, filtered, and concentrated under vacuum. The residue was purified by silica gel column chromatography (10% EtOAc in $CH_2Cl_2$), followed by ether trituration, yielding tert-butyl 4-(3-acetyl- 2-oxo-2H-chromen-7-yl)piperazine-1-carboxylate (3.15 g, 89%) as a yellow solid. $^1$H NMR (500 MHz, CDCl$_3$): δ 8.47 (1H, s), 7.49 (1H, d, J=9 Hz), 6.83 (1H, dd, J=9 Hz, 2.5 Hz), 6.67 (1H, d, J=2.5 Hz), 3.64 (4H, m), 3.47 (4H, m), 2.72 (3H, s), 1.52 (9H, s).

Step B: A mixture of tert-butyl 4-(3-acetyl-2-oxo-2H-chromen-7-yl)piperazine-1-carboxylate (300 mg, 0.81 mmol), dimethylformamide dimethyl acetal (900 μL, 7.5 mmol) and pyrrolidine (150 μL, 1.83 mmol) was heated at 55° C. for 1 h, then the solvent was removed with a stream of nitrogen. Hydrazine (70 μL, 2.2 mmol) and AcOH (900 μL) were added. The mixture was stirred at room temperature for 45 min, then partitioned between EtOAc and H$_2$O. The organic layer was dried over MgSO$_4$, then filtered and concentrated under vacuum. The residue was purified by silica gel column chromatography (30% EtOAc in CH$_2$Cl$_2$), followed by trituration with 2:1 hexane/acetone, yielding tert-butyl 4-(2-oxo-3-(1H-pyrazol-3-yl)-2H-chromen-7-yl)piperazine-1-carboxylate (180 mg, 56%) as a yellow solid. MS m/z 397.2 [M+H]$^+$.

Step C: A solution of tert-butyl 4-(2-oxo-3-(1H-pyrazol-3-yl)-2H-chromen-7-yl)piperazine-1-carboxylate (180 mg, 0.45 mmol) in CH$_2$Cl$_2$ (2.5 mL) and trifluoroacetic acid (1.0 mL) was stirred at room temperature for 15 min. The reaction mixture was partitioned between CH$_2$Cl$_2$ and aqueous K$_2$CO$_3$. The organic layer was dried over MgSO$_4$, filtered, and concentrated under vacuum. Trituration of the residue with acetone yielded the title compound (100 mg, 75%) as a yellow solid: m.p. 224-228° C.; MS m/z 297.2 [M+H]$^+$; $^1$H NMR (500 MHz, DMSO-d$_6$:D$_2$O, 100° C.): δ 8.31 (1H, s), 7.63 (1H, br s), 7.54 (1H, d, J=9 Hz), 6.94 (1H, dd, J=9 Hz, 2 Hz), 6.82 (1H, d, J=2 Hz), 6.77 (1H, d, J=2 Hz), 3.32 (4H, t, J=5 Hz), 2.88 (4H, t, J=5 Hz).

Example 18

Preparation of Cpd 38

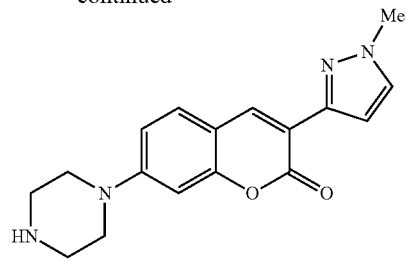

Step A: A mixture of tert-butyl 4-(2-oxo-3-(1H-pyrazol-3-yl)-2H-chromen-7-yl)piperazine-1-carboxylate (300 mg, 0.76 mmol, prepared in Example 17, Step B), Cs$_2$CO$_3$ (515 mg, 1.58 mmol), iodomethane (93 μL, 1.5 mmol), and DMF (2.0 mL) was stirred at 5° C. for 22 h. The reaction mixture was partitioned between EtOAc and H$_2$O. The organic layer was dried over MgSO$_4$, filtered, and concentrated under vacuum. The residue was purified by silica gel column chromatography (15% EtOAc in CH$_2$Cl$_2$), followed by trituration with ether to give tert-butyl 4-(3-(1-methyl-1H-pyrazol-3-yl)-2-oxo-2H-chromen-7-yl)piperazine-1-carboxylate (215 mg, 69%) as a yellow solid. $^1$H NMR (500 MHz, CDCl$_3$): δ 8.32 (1H, s), 7.41 (2H, m), 7.05 (1H, d, J=2 Hz), 6.83 (1H, dd, J=8.5 Hz, 2.5 Hz), 6.74 (1H, d, J=2 Hz), 3.97 (3H, s), 3.62 (4H, m), 3.33 (4H, m), 1.50 (9H, s).

Step B: A solution of tert-butyl 4-(3-(1-methyl-1H-pyrazol-3-yl)-2-oxo-2H-chromen-7-yl)piperazine-1-carboxylate (215 mg, 0.52 mmol) in CH$_2$Cl$_2$ (2.5 mL) and trifluoroacetic acid (1.0 mL) was stirred at room temperature for 1 h. The reaction mixture was partitioned between CH$_2$Cl$_2$ and aqueous K$_2$CO$_3$. The organic layer was dried over MgSO$_4$, filtered, and concentrated under vacuum. The residue was triturated with 1:1 hexane/acetone affording the title compound (142 mg, 92%) as a yellow solid: m.p. 224-228° C.; MS m/z 311.1 [M+H]$^+$; $^1$H NMR (500 MHz, CDCl$_3$): δ 8.32 (1H, s), 7.42 (2H, m), 7.06 (1H, d, J=2 Hz), 6.85 (1H, dd, J=9 Hz, 2.5 Hz), 6.77 (1H, d, J=2 Hz), 3.99 (3H, s), 3.34 (4H, m), 3.06 (4H, m).

Example 19

Preparation of Cpd 74

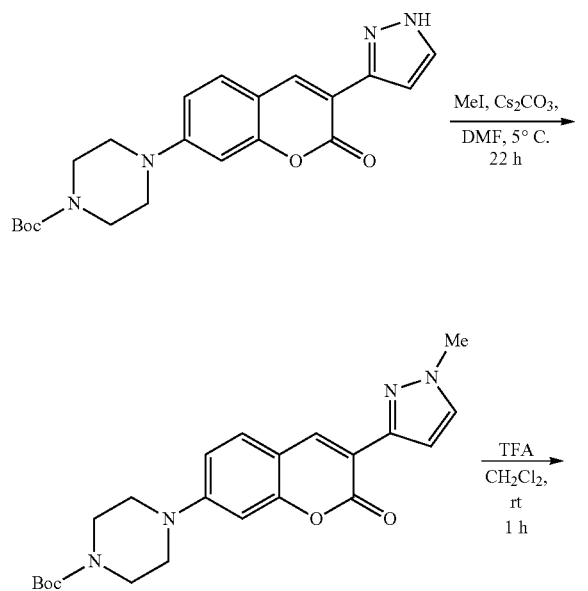

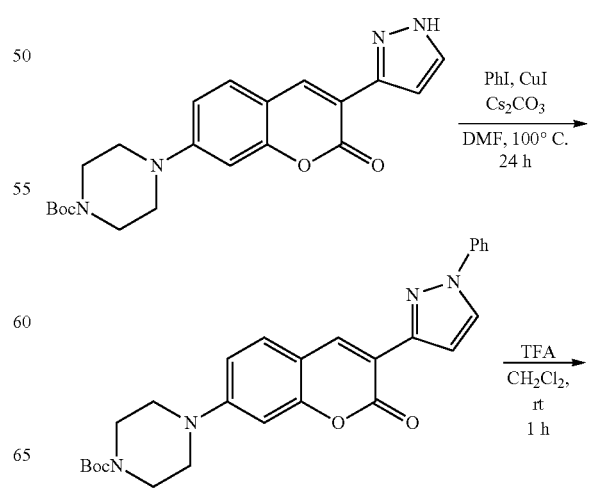

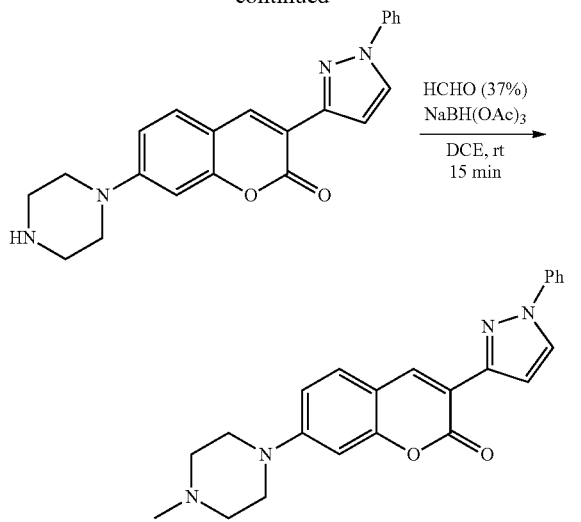

Step A: A mixture of tert-butyl 4-(2-oxo-3-(1H-pyrazol-3-yl)-2H-chromen-7-yl)piperazine-1-carboxylate (250 mg, 0.63 mmol, prepared in Example 17, Step B), Cs$_2$CO$_3$ (650 mg, 1.98 mmol), copper(I) iodide (14 mg, 0.073 mmol), iodobenzene (110 μL, 0.97 mmol), and DMF (1.6 mL) was heated at 100° C. for 24 h. The reaction mixture was partitioned between EtOAc and H$_2$O. The organic layer was dried over MgSO$_4$, filtered, and concentrated under vacuum. The residue was purified by silica gel column chromatography (5% EtOAc in CH$_2$Cl$_2$), followed by ether trituration to yield tert-butyl 4-(2-oxo-3-(1-phenyl-1H-pyrazol-3-yl)-2H-chromen-7-yl)piperazine-1-carboxylate (129 mg, 43%) as a yellow solid. $^1$H NMR (500 MHz, CDCl$_3$): δ 8.52 (1H, s), 7.97 (1H, d, J=2.5 Hz), 7.77 (2H, d, J=8 Hz), 7.49 (3H, m), 7.32 (2H, m), 6.86 (1H, dd, J=8.5 Hz, 2.5 Hz), 6.77 (1H, d, J=2.5 Hz), 3.62 (4H, m), 3.36 (4H, m), 1.50 (9H, s).

Step B: A solution of tert-butyl 4-(2-oxo-3-(1-phenyl-1H-pyrazol-3-yl)-2H-chromen-7-yl)piperazine-1-carboxylate (127 mg, 0.27 mmol) in CH$_2$Cl$_2$ (2.5 mL) and trifluoroacetic acid (1.0 mL) was stirred at room temperature for 1 h. The reaction mixture was partitioned between CH$_2$Cl$_2$ and aqueous K$_2$CO$_3$. The organic layer was dried over MgSO$_4$, filtered, and concentrated under vacuum. The residue was triturated with 2:1 hexane/acetone to afford 3-(1-phenyl-1H-pyrazol-3-yl)-7-(piperazin-1-yl)-2H-chromen-2-one (85 mg, 84%) as a yellow solid. MS m/z 373.3 [M+H]$^+$.

Step C: 3-(1-phenyl-1H-pyrazol-3-yl)-7-(piperazin-1-yl)-2H-chromen-2-one (55 mg, 0.15 mmol) was combined with aqueous formaldehyde (37%, 200 uL, 2.15 mmol) and sodium triacetoxyborohydride (110 mg, 0.52 mmol) in 1,2-dichloroethane (0.5 mL). The mixture was stirred 20 min at room temperature, and then quenched by the addition of an aqueous saturated NaHCO$_3$ solution. The mixture was extracted with CH$_2$Cl$_2$. The organic layer was, dried over NaSO$_4$, filtered, concentrated and purified by silica gel column chromatography (10% MeOH in CH$_2$Cl$_2$) to give the title compound (34 mg, 58%) as a yellow solid: m.p. 152-159° C.; MS m/z 387.3 [M+H]$^+$; $^1$H NMR (500 MHz, CDCl$_3$): δ 8.51 (1H, s), 7.97 (1H, d, J=2.5 Hz), 7.77 (2H, d, J=7.5 Hz), 7.47 (3H, m), 7.32 (2H, m), 6.86 (1H, dd, J=8.5 Hz), 6.77 (1H, d, J=2 Hz), 3.45 (4H, m), 2.66 (4H, br s), 2.43 (3H, s).

Example 20

Preparation of Cpd 80

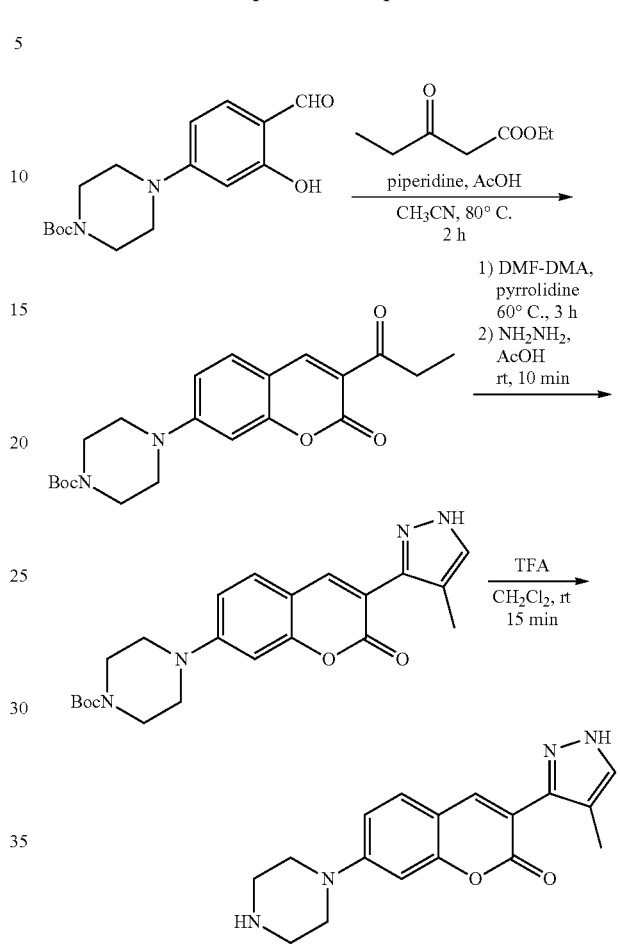

Step A: A mixture of tert-butyl 4-(4-formyl-3-hydroxyphenyl)piperazine-1-carboxylate (3.0 g, 9.8 mmol, prepared in Example 1, Part 2), ethyl 3-oxopentanoate (1.62 mL, 11.3 mmol), AcOH (650 μL, 12 mmol), piperidine (1.1 mL, 11.3 mmol), and CH$_3$CN (24 mL) were heated at 80° C. for 4 h. The reaction mixture was partitioned between CH$_2$Cl$_2$ and H$_2$O. The organic layer was dried over MgSO$_4$, filtered, and concentrated under vacuum. The residue was purified by silica gel column chromatography (10% EtOAc in CH$_2$Cl$_2$), followed by ether trituration, yielding tert-butyl 4-(2-oxo-3-propionyl-2H-chromen-7-yl)piperazine-1-carboxylate (3.6 g, 95%) as a yellow solid. $^1$H NMR (500 MHz, CDCl$_3$): δ 8.49 (1H, s), 7.50 (1H, d, J=8.5 Hz), 6.83 (1H, dd, J=8.5 Hz, 2.5 Hz), 6.67 (1H, d, J=2 Hz), 3.63 (4H, m), 3.47 (4H, m), 3.16 (2H, q, J=7 Hz), 1.52 (9H, s), 1.19 (3H, t, J=7 Hz).

Step B: A mixture of tert-butyl 4-(2-oxo-3-propionyl-2H-chromen-7-yl)piperazine-1-carboxylate (3.3 g, 8.55 mmol), dimethylformamide dimethyl acetal (10 mL, 830 mmol) and pyrrolidine (1.65 mL, 20.1 mmol) was heated at 60° C. for 3 h, then the solvent was removed under vacuum. The reaction mixture was dissolved in AcOH (10 mL) and cooled to 0° C. Hydrazine (820 μL, 26 mmol) was added dropwise (mild exotherm). After the addition was complete, the mixture was stirred at room temperature for 10 min. The reaction mixture was partitioned between CH$_2$Cl$_2$ and aqueous K$_2$CO$_3$. The organic layer was dried over MgSO$_4$, then filtered, and concentrated under vacuum. The residue was purified by silica gel column chromatography (50% EtOAc in $CH_2Cl_2$), followed by trituration with 2:1 hexane/acetone, yielding tert-butyl 4-(3-(4-methyl-1H-pyrazol-3-yl)-2-oxo-2H-chromen-7-yl)piperazine-1-carboxylate (1.01 g, 29%) as a yellow solid. $^1$H NMR (500 MHz, $CDCl_3$): δ 7.95 (1H, s), 7.48 (1H, s), 7.44 (1H, d, J=9 Hz), 6.87 (1H, dd, J=8.5 Hz, 2.5 Hz), 6.74 (1H, d, J=2.5 Hz), 3.63 (4H, m), 3.38 (4H, m), 2.36 (3H, s), 1.50 (9H, s).

Step C: A solution of tert-butyl 4-(3-(4-methyl-1H-pyrazol-3-yl)-2-oxo-2H-chromen-7-yl)piperazine-1-carboxylate (250 mg, 0.61 mmol) in $CH_2Cl_2$ (2.5 mL) and trifluoroacetic acid (1.0 mL) was stirred at room temperature for 15 min. The reaction mixture was partitioned between $CH_2Cl_2$ and aqueous $K_2CO_3$. The organic layer was dried over $MgSO_4$, filtered, and concentrated under vacuum. The residue was triturated with 1:1 hexane/acetone yielding the title compound (155 mg, 82%) as a yellow solid: m.p. 175-200° C. (decomposition range); MS m/z 311.2 [M+H]$^+$; $^1$H NMR (500 MHz, DMSO-$d_6$:$D_2O$, 100° C.): δ 7.91 (1H, s), 7.54 (1H, d, J=9 Hz), 7.41 (1H, br s), 6.95 (1H, d, J=9 Hz), 6.80 (1H, d, J=2.5 Hz), 3.35 (4H, m), 2.92 (4H, m), 2.09 (3H, br s).

Example 21

Preparation of Cpd 283

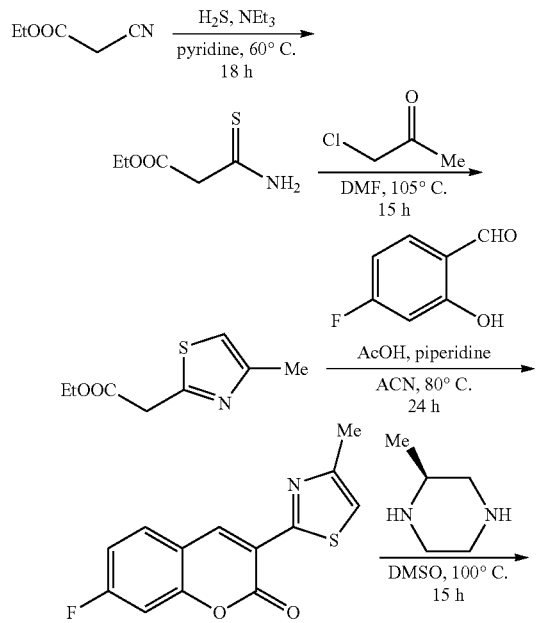

Step A: Hydrogen sulfide gas ($H_2S$) was bubbled into a solution of ethyl cyanoacetate (4.7 mL, 44.3 mmol) in pyridine/triethylamine (500 mL, 1:1 v/v) until it became saturated. The mixture was heated at 60° C. for 18 h, then the solvent was removed under vacuum. The residue was partitioned between EtOAc and aqueous HCl. The organic layer was dried over $MgSO_4$, then filtered and concentrated under vacuum. The resulting oil was filtered to remove solid impurities. Ethyl 3-amino-3-thioxopropanoate (6.25 g, 96%) was obtained as an orange oil. $^1$H NMR (500 MHz, $CDCl_3$): δ 8.92 (1H, br s), 7.75 (1H, br s), 4.21 (2H, q, J=7 Hz), 3.82 (2H, s), 1.29 (3H, t, J=7 Hz).

Step B: A solution of ethyl 3-amino-3-thioxopropanoate (2.0 g, 13.6 mmol) and chloroacetone (1.2 mL, 15.0 mmol) in DMF (230 mL) was heated at 105° C. for 15 h. The reaction mixture was partitioned between EtOAc and $H_2O$. The organic layer was dried over $MgSO_4$, filtered and concentrated under vacuum. The residue was purified by silica gel column chromatography ($CH_2Cl_2$) yielding ethyl 2-(4-methylthiazol-2-yl)acetate (1.22 g, 48%) as a red oil. $^1$H NMR (500 MHz, $CDCl_3$): δ 6.86 (1H, s), 4.24 (2H, q, J=7 Hz), 4.03 (2H, s), 2.44 (3H, s), 1.29 (3H, t, J=7 Hz).

Step C: A mixture of ethyl 2-(4-methylthiazol-2-yl)acetate (650 mg, 3.5 mmol), 4-fluoro-2-hydroxybenzaldehyde (490 mg, 3.5 mmol), piperidine (15 μL, 0.15 mmol), AcOH (15 μL, 0.27 mmol) and $CH_3CN$ (5 mL) was heated at 80° C. for 24 h. The reaction mixture was partitioned between $CH_2Cl_2$ and aqueous $K_2CO_3$. The organic layer was dried over $MgSO_4$, filtered and concentrated under vacuum. The residue was triturated with 7:3 hexane/$CH_2Cl_2$ yielding 7-fluoro-3-(4-methylthiazol-2-yl)-2H-chromen-2-one (642 mg, 70%) as a yellow solid. $^1$H NMR (500 MHz, $CDCl_3$): δ 8.85 (1H, s), 7.69 (1H, dd, J=8.5 Hz, 6 Hz), 7.15 (3H, m), 2.57 (3H, s).

Step D: A mixture of 7-fluoro-3-(4-methylthiazol-2-yl)-2H-chromen-2-one (100 mg, 0.38 mmol), (S)-2-methylpiperazine (46 mg, 0.46 mmol) and DMSO (600 μL) was heated at 80° C. for 15 h. The reaction mixture was diluted in an aqueous saturated $NaHCO_3$ solution and filtered. The collected material was purified by silica gel column chromatography (10% MeOH in $CH_2Cl_2$), followed by trituration with 1:1 hexane/acetone to yield the title compound (103 mg, 79%) as a yellow solid: m.p. 194-199° C.; MS m/z 342.2 [M+H]$^+$; $^1$H NMR (500 MHz, DMSO-$d_6$): δ 8.80 (1H, s), 7.75 (1H, d, J=9 Hz), 7.32 (1H, m), 7.06 (1H, dd, J=9 Hz, 2.5 Hz), 6.91 (1H, d, J=2.5 Hz), 3.88 (2H, t, J=11 Hz), 2.96 (1H, d, J=12 Hz), 2.81 (1H, td, J=12 Hz, 3 Hz), 2.72 (2H, m), 2.45 (4H, m), 2.36 (1H, br s), 1.04 (3H, d, J=6.5 Hz).

As shown in Table 1 below, additional compounds disclosed herein may be prepared according to Example 21 by substituting the appropriate starting materials, reagents and reaction conditions.

Example 22

Preparation of Cpd 452

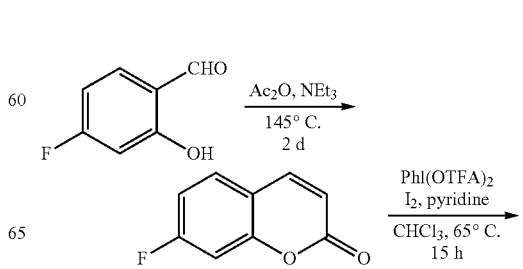

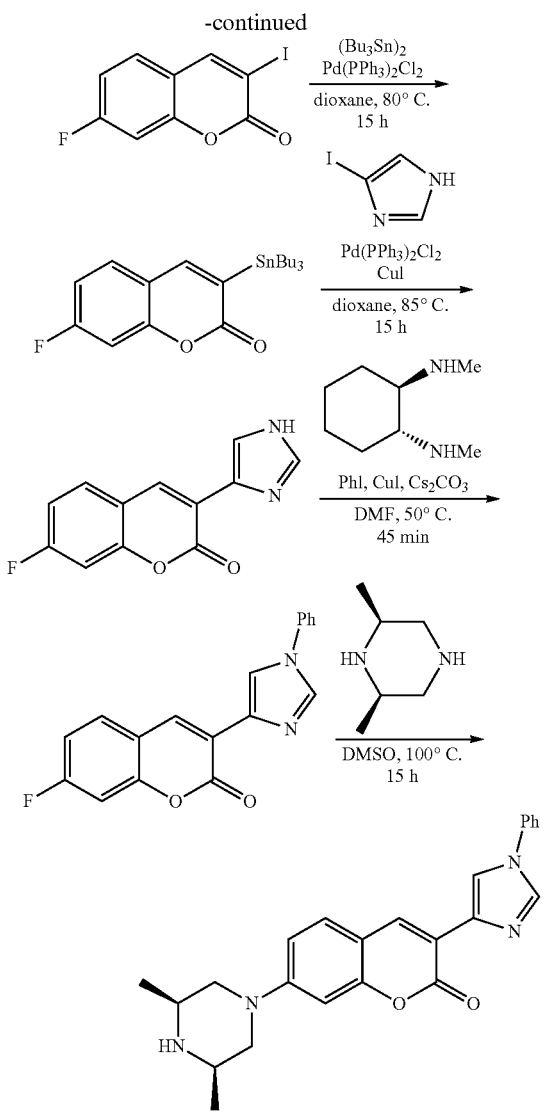

Step A: A mixture of 4-fluoro-2-hydroxybenzaldehyde (10 g, 71.4 mmol), acetic anhydride (34 mL, 360 mmol), and triethylamine (11 mL, 79 mmol) was heated at 145° C. for 2 d. The reaction mixture was diluted in aqueous NH$_4$OH (500 mL) and filtered. The collected material was dried, yielding 7-fluoro-2H-chromen-2-one (10.3 g, 88%) as a brown solid. $^1$H NMR (500 MHz, CDCl$_3$): δ 7.69 (1H, d, J=9.5 Hz), 7.48 (1H, dd, J=8.5 Hz, 6 Hz), 7.07 (1H, dd, J=8.5 Hz, 2.5 Hz), 7.03 (1H, td, J=8.5 Hz, 2.5 Hz), 6.38 (1H, d, J=9.5 Hz).

Step B: A mixture of 7-fluoro-2H-chromen-2-one (4.33 g, 26.4 mmol), [bis(trifluoroacetoxy)iodo]benzene (18.15 g, 42.2 mmol), iodine (10.7 g, 42.2 mmol), pyridine (4.2 mL, 53 mmol), and CHCl$_3$ (25 mL) was heated at 65° C. for 15 h. The reaction mixture was partitioned between aqueous NaHSO$_3$ and CH$_2$Cl$_2$. The organic layer was dried over MgSO$_4$, filtered, and concentrated under vacuum. The residue was purified by silica gel column chromatography (50% CH$_2$Cl$_2$ in hexanes, then CH$_2$Cl$_2$) yielding 7-fluoro-3-iodo-2H-chromen-2-one (5.6 g, 73%) as a tan solid. $^1$H NMR (500 MHz, CDCl$_3$): δ 8.36 (1H, s), 7.46 (1H, dd, J=9 Hz, 6 Hz), 7.07 (2H, m).

Step C: A mixture of 7-fluoro-3-iodo-2H-chromen-2-one (5.6 g, 19.3 mmol), hexabutylditin (13.45 g, 23.2 mmol), bis(triphenylphosphine)palladium(II) dichloride (540 mg, 0.77 mmol) and 1,4-dioxane (55 mL) was heated at 80° C. for 15 h. The reaction mixture was diluted in EtOAc and filtered. The filtrate was concentrated under vacuum. The residue was purified by silica gel column chromatography (20-40% CH$_2$Cl$_2$ in hexanes) yielding 7-fluoro-3-(tributylstannyl)-2H-chromen-2-one (6.79 g, 77%) as a colorless oil.

Step D: A mixture of 7-fluoro-3-(tributylstannyl)-2H-chromen-2-one (1.15 g, 2.53 mmol), 4-iodoimidazole (600 mg, 3.1 mmol), bis(triphenylphosphine)palladium(II) dichloride (285 mg, 0.41 mmol), copper(I) iodide (115 mg, 0.60 mmol), and 1,4-dioxane (7 mL) was heated at 85° C. for 2 d. The reaction mixture was partitioned between NH$_4$OH and CH$_2$Cl$_2$. The organic layer was concentrated under vacuum. The residue was purified by silica gel column chromatography (30% MeOH in CH$_2$Cl$_2$). The product was triturated with CH$_2$Cl$_2$, yielding 7-fluoro-3-(1H-imidazol-4-yl)-2H-chromen-2-one (298 mg, 51%) as a yellow solid. MS m/z 231.1 [M+H]$^+$.

Step E: A mixture of 7-fluoro-3-(1H-imidazol-4-yl)-2H-chromen-2-one (90 mg, 0.39 mmol), iodobenzene (70 µL, 0.62 mmol), CuI (60 mg, 0.32 mmol), trans-1,2-bis(methylamino)cyclohexane (23 µL, 0.15 mmol), Cs$_2$CO$_3$ (585 mg, 1.79 mmol) and DMF (0.9 mL) was heated at 50° C. for 45 min. The reaction mixture was diluted in H$_2$O and filtered. The solid material was partitioned between aqueous NH$_4$OH and CH$_2$Cl$_2$. The organic layer was concentrated under vacuum. The residue was purified by silica gel chromatography (10% EtOAc in CH$_2$Cl$_2$), yielding 7-fluoro-3-(1-phenyl-1H-imidazol-4-yl)-2H-chromen-2-one (52 mg, 43%) as a white solid. $^1$H NMR (500 MHz, CDCl$_3$): δ 8.58 (1H, s), 8.27 (1H, d, J=1.5 Hz), 7.94 (1H, d, J=1.5 Hz), 7.60 (1H, dd, J=8.5 Hz, 6 Hz), 7.52 (4H, m), 7.42 (1H, m), 7.11 (1H, dd, J=9 Hz, 2.5 Hz), 7.06 (1H, td, J=8 Hz, 2.5 Hz).

Step F: A mixture of 7-fluoro-3-(1-phenyl-1H-imidazol-4-yl)-2H-chromen-2-one (50 mg, 0.16 mmol), cis-2,6-dimethylpiperazine (29 mg, 0.25 mmol) and DMSO (300 µL) were heated at 100° C. for 15 h. The reaction mixture was diluted in an aqueous saturated NaHCO$_3$ solution and filtered. The solid material was purified by silica gel column chromatography (5% MeOH in CH$_2$Cl$_2$), yielding the title compound (52 mg, 81%) as a yellow solid: m.p. 260-264° C.; MS m/z 401.3 [M+H]$^+$; $^1$H NMR (500 MHz, DMSO-d$_6$): δ 8.50 (1H, s), 8.41 (1H, d, J=1 Hz), 8.14 (1H, d, J=1 Hz), 7.71 (2H, d, J=8.5 Hz), 7.64 (1H, d, J=9 Hz), 7.55 (2H, t, J=8 Hz), 7.40 (1H, t, J=7.5 Hz), 7.01 (1H, dd, J=9 Hz, 2 Hz), 6.89 (1H, d, J=2 Hz), 3.82 (2H, dd, J=12.5 Hz, 2 Hz), 2.80 (2H, m), 2.31 (2H, t, J=11.5 Hz), 2.25 (1H, br s), 1.04 (6H, d, J=6.5 Hz).

Example 23

Preparation of Cpd 433

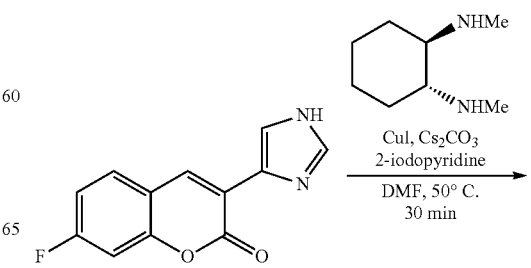

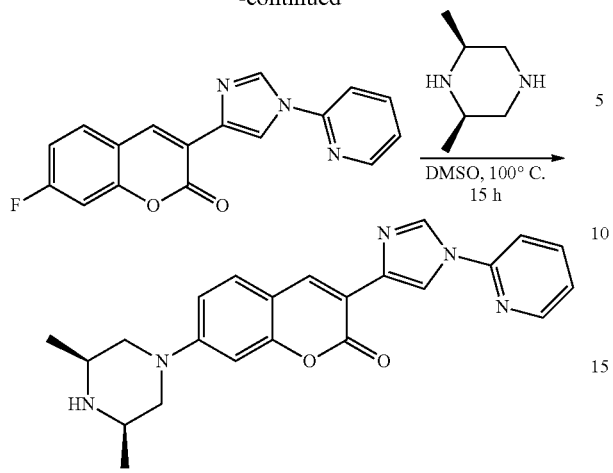

Step A: A mixture of 7-fluoro-3-(1H-imidazol-4-yl)-2H-chromen-2-one (75 mg, 0.32 mmol, prepared in Example 22, Step D), 2-iodopyridine (55 μL, 0.5 mmol), copper(I) iodide (27 mg, 0.14 mmol), trans-1,2-bis(methylamino)cyclohexane (13 μL, 0.08 mmol), $Cs_2CO_3$ (330 mg, 1.01 mmol) and DMF (750 μL) was heated at 50° C. for 30 min. The reaction mixture was diluted with $H_2O$ and filtered. The solid material was partitioned between aqueous $NH_4OH$ and $CH_2Cl_2$. The organic layer was concentrated under vacuum. The residue was purified by silica gel column chromatography (10% acetone in $CH_2Cl_2$), followed by trituration with 1:1 $CH_2Cl_2$/hexane, yielding 7-fluoro-3-(1-(pyridin-2-yl)-1H-imidazol-4-yl)-2H-chromen-2-one (62 mg, 63%) as a white solid. $^1H$ NMR (500 MHz, $CDCl_3$): δ 8.61 (1H, s), 8.56 (1H, d, J=1 Hz), 8.52 (1H, m), 8.50 (1H, d, J=1 Hz), 7.88 (1H, m), 7.60 (1H, dd, J=8.5 Hz, 6 Hz), 7.48 (1H, d, J=8.5 Hz), 7.29 (1H, m), 7.11 (1H, dd, J=9 Hz, 2.5 Hz), 7.06 (1H, td, J=8.5 Hz, 2.5 Hz).

Step B: Following the procedure from Example 22, Step F, 7-fluoro-3-(1-(pyridin-2-yl)-1H-imidazol-4-yl)-2H-chromen-2-one (40 mg, 0.13 mmol), cis-2,6-dimethylpiperazine (23 mg, 0.2 mmol), and DMSO (300 μL) yielded the title compound (46 mg, 88%): m.p. 201-206° C.; MS m/z 402.3 $[M+H]^+$; $^1H$ NMR (500 MHz, DMSO-$d_6$): δ 8.71 (1H, d, J=1 Hz), 8.55 (1H, m), 8.52 (1H, s), 8.45 (1H, d, J=1 Hz), 8.02 (1H, m), 7.92 (1H, d, J=8.5 Hz), 7.64 (1H, d, J=9 Hz), 7.41 (1H, dd, J=6.5 Hz, 5 Hz), 7.02 (1H, dd, J=9 Hz, 2 Hz), 6.88 (1H, d, J=2.5 Hz), 3.82 (2H, d, J=11.5 Hz), 2.80 (2H, m), 2.32 (2H, t, J=11.5 Hz), 2.28 (1H, br s), 1.04 (6H, d, J=6.5 Hz).

As shown in Table 1 below, additional compounds disclosed herein may be prepared according to Example 23 by substituting the appropriate starting materials, reagents and reaction conditions.

Example 24

Preparation of Cpd 32

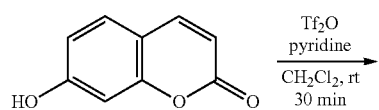

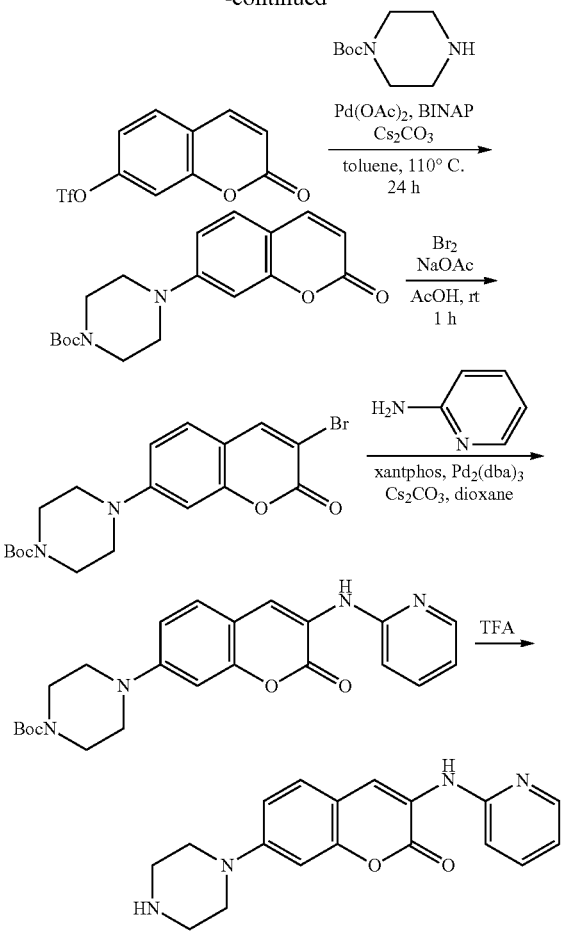

Step A: Into a suspension of 7-hydroxycoumarin (16.2 g, 100 mmol) in pyridine (16.3 mL, 200 mmol) and $CH_2Cl_2$ (250 mL) at 0° C. was added dropwise a solution of triflic anhydride (20.2 mL, 120 mmol) in $CH_2Cl_2$ (50 mL). The mixture warmed to room temperature over 30 min. The mixture was washed with dilute aqueous HCl, water, brine, and then dried over $NaSO_4$ and concentrated to give a solid 2-oxo-2H-chromen-7-yl trifluoromethanesulfonate (28.5 g, 97%) as a tan solid. MS m/z 295.0 $[M+H]^+$.

Step B: A mixture of palladium(II) acetate (0.228 g, 1.02 mmol), 2,2'-bis(diphenylphosphino)-1,1'-binaphthalene (1.27 g, 2.04 mmol) and $Cs_2CO_3$ (8.3 g, 25.5 mmol) in toluene (75 mL) was stirred under Argon at 110° C. for 15 min until a dark red color formed. The mixture was cooled to room temperature, upon which 2-oxo-2H-chromen-7-yl trifluoromethanesulfonate (5.0 g, 17 mmol) and 1-Boc-piperazine (3.8 g, 20.4 mmol) were added. The mixture was stirred at 110° C. for 24 h. The mixture was partitioned in EtOAc and water. The organic layer was dried over $NaSO_4$, filtered, concentrated and purified by silica gel column chromatography (0-15% EtOAc in $CH_2Cl_2$) to give tert-butyl 4-(2-oxo-2H-chromen-7-yl)piperazine-1-carboxylate (2.5 g, 45%) as a yellow solid. MS m/z 331.2 $[M+H]^+$.

Step C: Into a mixture of tert-butyl 4-(2-oxo-2H-chromen-7-yl)piperazine-1-carboxylate (2.5 g, 7.58 mmol) and sodium acetate (1.86 g, 22.7 mmol) in acetic acid (30 mL) at room temperature was added bromine (0.4 mL, 7.95 mmol) dropwise. The mixture was stirred at room temperature for 1 h. Water was added to produce a precipitate. The solid was collected by vacuum filtration, washed with water, dried and purified by silica gel column chromatography (0-25% EtOAc in CH$_2$Cl$_2$) to give tert-butyl 4-(3-bromo-2-oxo-2H-chromen-7-yl)piperazine-1-carboxylate (1.8 g, 58%) as a yellow solid. MS m/z 409.1 [M+H]$^+$, 411.1 [M+2+H]$^+$.

Step D: A mixture of tert-butyl 4-(3-bromo-2-oxo-2H-chromen-7-yl)piperazine-1-carboxylate (80 mg, 0.2 mmol), 2-aminopyridine (26 mg, 0.28 mmol), bis(dibenzylideneacetone)palladium(0) (3.7 mg, 0.004 mmol), 4,5-bis(diphenylphosphino)-9,9-dimethylxanthene (5.1 mg, 0.0088 mmol) and Cs$_2$CO$_3$ (91 mg, 0.28 mmol) in 1,4-dioxane (1.0 mL) was stirred at 100° C. overnight under Argon, then the solvent was removed. The residue was purified by silica gel column chromatography (0-10% EtOAc in CH$_2$Cl$_2$) to give tert-butyl 4-(2-oxo-3-(pyridin-2-ylamino)-2H-chromen-7-yl)piperazine-1-carboxylate (82 mg, 71%) as a yellow solid. MS m/z 423.2 [M+H]$^+$.

Step E: tert-Butyl 4-(2-oxo-3-(pyridin-2-ylamino)-2H-chromen-7-yl)piperazine-1-carboxylate (71 mg, 0.168 mmol) was dissolved in trifluoroacetic acid (2.0 mL). The mixture was stirred for 15 min at room temperature, then the solvent was removed with a stream of nitrogen. The residue was partitioned in CH$_2$Cl$_2$ and aqueous K$_2$CO$_3$. The organic layer was dried over NaSO$_4$, filtered and concentrated to give the title compound (41 mg, 76%) as a yellow solid: m.p. 191-194° C.; MS m/z 323.2 [M+H]$^+$; $^1$H NMR (500 MHz, DMSO-d$_6$): δ 8.78 (1H, s), 8.77 (1H, s), 8.69 (1H, s), 8.24 (1H, dd, J=5.1 Hz, 1.3 Hz), 7.62-7.57 (1H, m), 7.44 (1H, d, J=8.8 Hz), 7.27 (1H, d, J=8.5 Hz), 6.95 (1H, dd, J=8.8 Hz, 2.2 Hz), 6.85-6.80 (2H, m), 3.20-3.13 (4H, m), 2.86-2.78 (4H, m).

As shown in Table 1 below, additional compounds disclosed herein may be prepared according to Example 24 by substituting the appropriate starting materials, reagents and reaction conditions.

Example 25

Preparation of Cpd 274

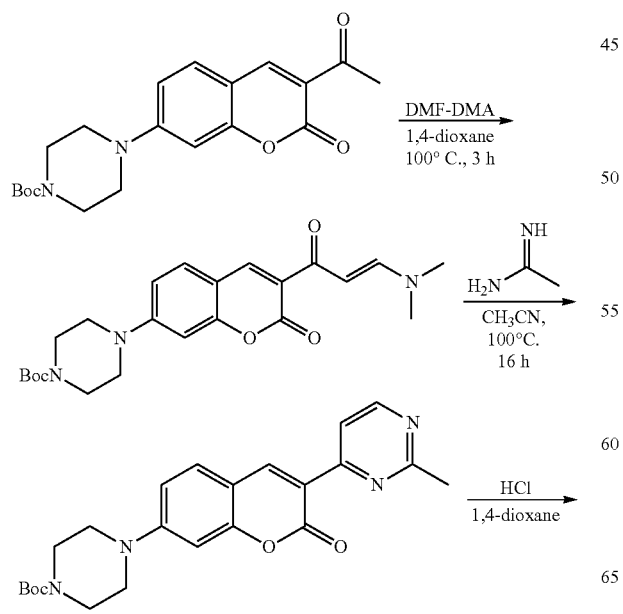

Step A: To a solution of t-butyl 4-(3-acetyl-2-oxo-2H-chromen-7-yl)piperazine-1-carboxylate (1.42 g, 3.8 mmol, prepared in Example 17, Step A) in 1,4-dioxane (8 mL) was added N,N-dimethylformamide dimethylacetal (6 mL, 44.7 mmol). The mixture was heated at 100° C. for 3 h. The reaction mixture was concentrated under reduced pressure. The residue was triturated with ether-hexane (1:1), producing a precipitate. The solid was collected by vacuum filtration, washed with ether-hexane and dried under nitrogen, affording (E)-tert-butyl 4-(3-(3-(dimethylamino)acryloyl)-2-oxo-2H-chromen-7-yl)piperazine-1-carboxylate (1.5 g, 92%) as an orange powder. MS m/z 428.4 [M+H]$^+$.

Step B: To a solution of (E)-t-butyl 4-(3-(3-(dimethylamino)acryloyl)-2-oxo-2H-chromen-7-yl)piperazine-1-carboxylate (171 mg, 0.40 mmol) and acetamidine hydrochloride (151 mg, 1.6 mmol) in CH$_3$CN (2 mL) was added K$_2$CO$_3$ (110 mg, 0.80 mmol). The mixture was heated to 100° C. for 16 h. After cooling to room temperature, water (10 mL) was added to the mixture, producing a precipitate. The precipitate was collected by vacuum filtration, washed with water and dried under nitrogen to afford t-butyl-4-(3-(2-methylpyrimidin-4-yl)-2-oxo-2H-chromen-7-yl)piperazine-1-carboxylate (148 mg, 88%). MS m/z 423.3 [M+H]$^+$.

Step C: To a suspension of t-butyl-4-(3-(2-methylpyrimidin-4-yl)-2-oxo-2H-chromen-7-yl)piperazine-1-carboxylate (182 mg, 0.42 mmol) in CH$_2$Cl$_2$ (1 mL) was added 4N HCl in 1,4-dioxane (1 mL). The mixture was stirred for 2 h at room temperature. The suspension was diluted with ether (10 mL) and filtered. The solid was washed with ether and dried under nitrogen to afford the title compound (140 mg, 91%) as a yellow solid: m.p. 200° C. (decomp.); MS m/z 323.2 [M+H]$^+$; $^1$H NMR (500 MHz, DMSO-d$_6$): δ 9.13 (2H, br), 9.05 (1H, s), 8.78 (1H, d, J=5.4 Hz), 8.22 (1H, d, J=5.4 Hz), 7.88 (1H, d, J=8.8 Hz), 7.12 (1H, dd, J=8.8 Hz, 2.5 Hz), 7.03 (1H, d, J=2.2 Hz), 3.73 (4H, m), 3.24 (4H, m), 2.71 (3H, s).

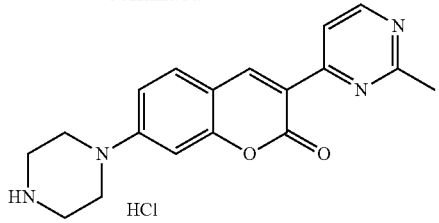

As shown in Table 1 below, additional compounds disclosed herein may be prepared according to Example 25 by substituting the appropriate starting materials, reagents and reaction conditions.

Example 26

Preparation of Cpd 316

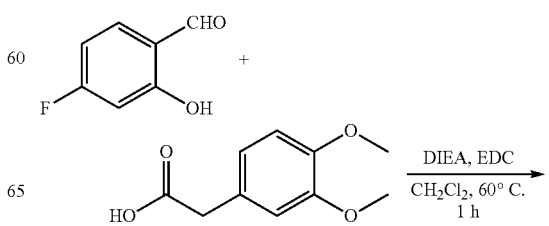

-continued

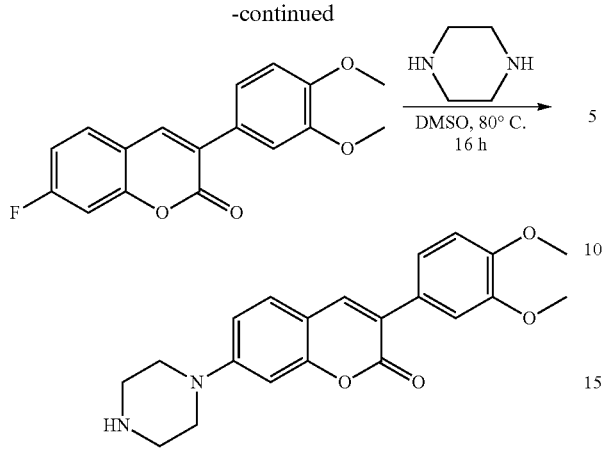

Step A: To a pressure vessel were added, 4-fluoro-2-hydroxybenzaldehyde (0.5 g, 3.6 mmol), 2-(3,4-dimethoxyphenyl)acetic acid (1.4 g, 7.2 mmol), N-(3-dimethylaminopropyl)-N'-ethylcarbodiimide hydrochloride (1.5 g, 7.9 mmol), diisopropylethylamine (2.3 mL, 14.3 mmol) and $CH_2Cl_2$ (10 mL). The mixture was stirred at 60° C. for 1 h, then quenched with an aqueous saturated $NaHCO_3$ solution (50 mL) and extracted with EtOAc three times. The combined extracts were dried over $Na_2SO_4$ and concentrated under vacuum. The residue was purified by silica gel column chromatography (0-5% EtOAc in $CH_2Cl_2$) to give 3-(3,4-dimethoxyphenyl)-7-fluoro-2H-chromen-2-one (1.0 g, 95%). MS m/z 301.0 $[M+H]^+$.

Step B: A mixture of 3-(3,4-dimethoxyphenyl)-7-fluoro-2H-chromen-2-one (40 mg, 0.13 mmol), piperazine (34 mg, 0.40 mmol) and DMSO (0.3 mL) was stirred at 80° C. overnight. After cooling to room temperature, the mixture was diluted with water (5 mL) to produce a precipitate. The precipitate was collected by filtration, washed with water and ethyl ether, and dried to give the title compound (14 mg, 29%) as yellow powder: m.p. 168-170° C.; MS m/z 367.2 $[M+H]^+$; $^1H$ NMR (500 MHz, $CDCl_3$): δ 7.69 (1H, s), 7.38 (1H, d, J=8.8 Hz), 7.31 (1H, d, J=1.9 Hz), 7.25 (1H, d, J=2.2 Hz), 6.93 (1H, d, J=8.5 Hz), 6.85 (1H, dd, J=8.8 Hz, 2.5 Hz), 6.77 (1H, d, J=2.5 Hz), 3.95 (3H, s), 3.93 (3H, s), 3.36-3.32 (4H, m), 3.10-3.05 (4H, m).

As shown in Table 1 below, additional compounds disclosed herein may be prepared according to Example 26 by substituting the appropriate starting materials, reagents and reaction conditions.

Example 27

Preparation of Cpd 385

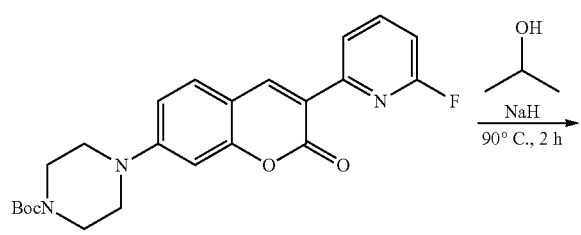

-continued

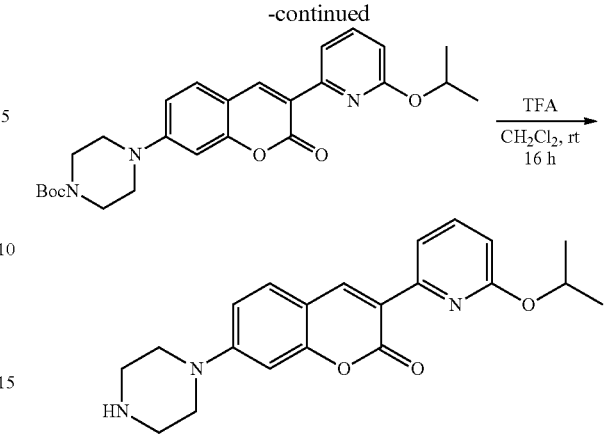

Step A: To a suspension of tert-butyl 4-(3-(6-fluoropyridin-2-yl)-2-oxo-2H-chromen-7-yl)piperazine-1-carboxylate (90 mg, 0.21 mmol, prepared according to Example 26) in isopropanol (1 mL) was added NaH (19 mg, 60% in mineral oil, 0.48 mmol). The mixture was stirred at 90° C. for 2 h, diluted with water and extracted with dichloromethane. The organic layer was concentrated and purified by silica gel column chromatography (0-10% MeOH in $CH_2Cl_2$) to give tert-butyl 4-(3-(6-isopropoxypyridin-2-yl)-2-oxo-2H-chromen-7-yl)piperazine-1-carboxylate (50 mg, 51%). MS 466.3 m/z $[M+H]^+$.

Step B: tert-Butyl 4-(3-(6-isopropoxypyridin-2-yl)-2-oxo-2H-chromen-7-yl)piperazine-1-carboxylate (50 mg, 0.11 mmol) was stirred with 50% TFA in $CH_2Cl_2$ (1.0 mL) at room temperature overnight. Aqueous $K_2CO_3$ (2M solution) was added to the mixture, until the aqueous layer became basic, pH ~9. The organic layer was separated and the aqueous layer was extracted with $CH_2Cl_2$. The combined organics were dried over $Na_2SO_2$ and concentrated to provide the title compound (37 mg, 82%) as a yellow powder: m.p. 177-180° C.; MS 366.3 m/z $[M+H]^+$; $^1H$ NMR (500 MHz, $CDCl_3$): δ 8.67 (1H, s), 8.06 (1H, dd, J=7.6 Hz, 0.6 Hz), 7.63 (1H, dd, J=8.2 Hz, 7.6 Hz), 7.49 (1H, d, J=8.8 Hz), 6.86 (1H, dd, J=8.7 Hz, 2.4 Hz), 6.75 (1H, d, J=2.2 Hz), 6.65 (1H, dd, J=8.2 Hz, 0.6 Hz), 5.43 (1H, t, J=6.3 Hz), 3.41-3.31 (4H, m), 3.10-3.00 (4H, m), 1.42 (6H, d, J=6.3 Hz).

As shown in Table 1 below, additional compounds disclosed herein may be prepared according to Example 27 by substituting the appropriate starting materials, reagents and reaction conditions.

Example 28

Preparation of Cpd 386

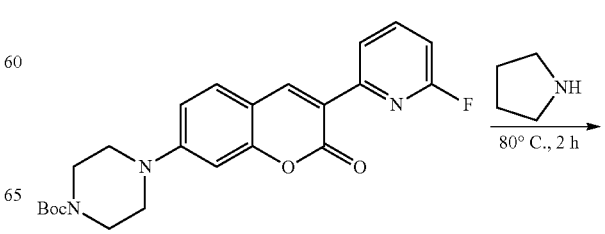

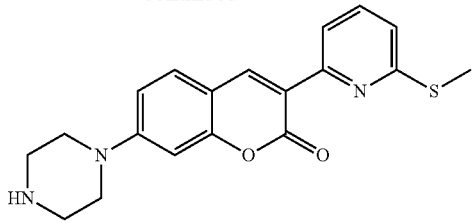

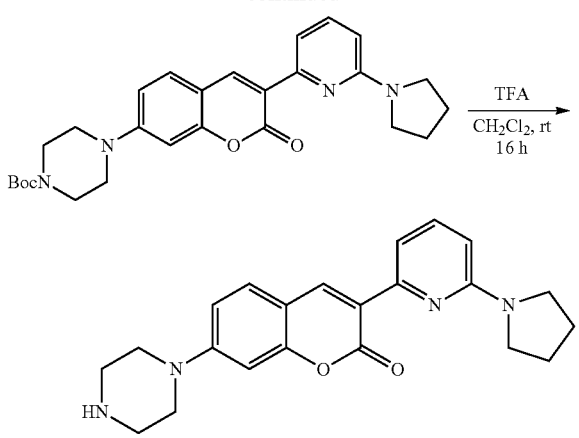

Step A: A mixture of tert-butyl 4-(3-(6-fluoropyridin-2-yl)-2-oxo-2H-chromen-7-yl)piperazine-1-carboxylate (90 mg, 0.21 mmol, prepared according to Example 26) and pyrrolidine (1 mL) was stirred at 80° C. for 2 h. The mixture was diluted with water (10 mL) and extracted with dichloromethane. The organic layer was concentrated and purified by silica gel column chromatography (0-10% MeOH in CH₂Cl₂) to give tert-butyl 4-(2-oxo-3-(6-(pyrrolidin-1-yl)pyridin-2-yl)-2H-chromen-7-yl)piperazine-1-carboxylate (56 mg, 50%). MS 477.0 m/z [M+H]⁺.

Step B: tert-Butyl 4-(2-oxo-3-(6-(pyrrolidin-1-yl)pyridin-2-yl)-2H-chromen-7-yl)piperazine-1-carboxylate was stirred with 50% TFA in CH₂Cl₂ (1.0 mL) at room temperature overnight. Aqueous K₂CO₃ (2M solution) was added to the mixture, until the aqueous layer became basic, pH ~9. The organic layer was separated and the aqueous layer was extracted with CH₂Cl₂. The combined organics were dried over Na₂SO₂ and concentrated to provide the title compound (63 mg, 80%) as yellow powder: m.p. 190-192° C.; MS 377.3 m/z [M+H]⁺; ¹H NMR (500 MHz, CDCl₃): δ 8.72 (1H, s), 7.73 (1H, d, J=7.3 Hz), 7.54-7.44 (2H, m), 6.84 (1H, dd, J=8.8 Hz, 2.5 Hz), 6.75 (1H, d, J=2.2 Hz), 6.40-6.33 (1H, m), 3.60-3.50 (4H, m), 3.33 (4H, dd, J=6.2 Hz, 4.3 Hz), 3.10-3.01 (4H, m), 2.04 (4H, dt, J=6.5 Hz, 3.4 Hz).

Example 29

Preparation of Cpd 445

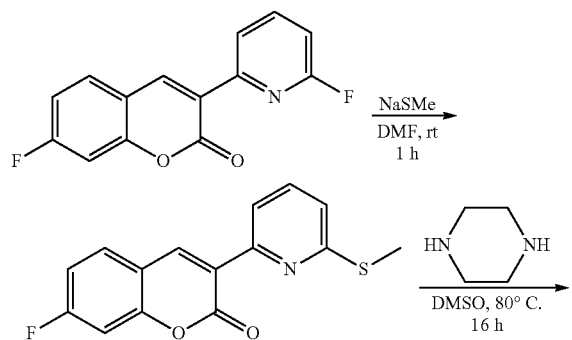

Step A: A mixture of 7-fluoro-3-(6-fluoropyridin-2-yl)-2H-chromen-2-one (260 mg, 1.0 mmol, prepared according to Example 26) and NaSMe (105 mg, 1.5 mmol) in DMF (2 mL) was stirred at room temperature for 1 h. The mixture was diluted with water (10 mL) to produce a precipitate. The precipitate was collected by filtration, washed with water and CH₂Cl₂, and dried to give 7-fluoro-3-(6-(methylthio)pyridin-2-yl)-2H-chromen-2-one (100 mg, 35%). MS 288.3 m/z [M+H]⁺.

Step B: A mixture of 7-fluoro-3-(6-(methylthio)pyridin-2-yl)-2H-chromen-2-one (50 mg, 0.17 mmol), piperazine (44 mg, 0.51 mmol) and DMSO (0.5 mL) was stirred at 80° C. overnight. After cooling to room temperature, the mixture was diluted with water (5 mL) to produce a precipitate. The precipitate was collected by filtration, washed with water and ethyl ether, and dried to give the title compound (18 mg, 30%): m.p. 180-183° C.; MS m/z 354.3 [M+H]⁺; ¹H NMR (500 MHz, CDCl₃): δ 8.69 (1H, s), 7.84 (1H, d, J=7.3 Hz), 7.59 (1H, dd, J=8.5 Hz, 7.6 Hz), 7.53 (1H, d, J=8.8 Hz), 7.17-7.13 (2H, m), 6.71 (1H, s), 3.63-3.61 (4H, m), 3.09-3.03 (4H, m), 2.58-2.54 (3H, m).

Example 30

Preparation of Cpd 187

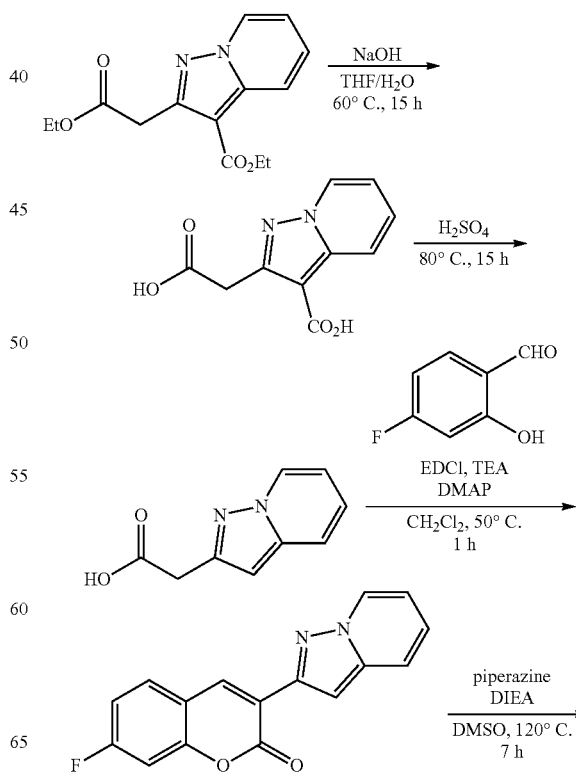

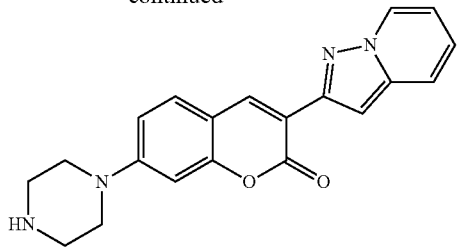

Step A: A mixture of ethyl 2-(2-ethoxy-2-oxoethyl)pyrazolo[1,5-a]pyridine-3-carboxylate (1.2 g, 4.3 mmol, prepared from 1-aminopyridinium iodide and diethyl 3-oxopentanedioate according to the procedure in Japanese Patent 62-267285, 1986), NaOH (3 N, 8.6 mL) and THF (10 mL) was heated at 60° C. for 15 h. The mixture was cooled to room temperature and washed with EtOAc. The aqueous phase was acidified with aqueous HCl (6 N) to pH 3, producing a precipitate. The precipitate was collected by vacuum filtration, washed with water and dried to give 2-(carboxymethyl)pyrazolo[1,5-a]pyridine-3-carboxylic acid (0.63 g, 66%) as a white solid. MS m/z 221.1 [M+H]$^+$.

Step B: To a suspension of 2-(carboxymethyl)pyrazolo[1,5-a]pyridine-3-carboxylic acid (0.63 g, 2.9 mmol) in water (5 mL) was added conc. H$_2$SO$_4$ (5 mL). The clear solution was heated at 80° C. for 15 h. The solution was cooled to room temperature. Aqueous NaOH (1 N) was added to the solution until pH 2-3 was reached. A precipitate formed. The precipitate was collected by vacuum filtration, washed with water and dried to give 2-(pyrazolo[1,5-a]pyridin-2-yl)acetic acid (0.435 g, 86%) as a white solid. MS m/z 177.1 [M+H]$^+$.

Step C: A mixture of 2-(pyrazolo[1,5-a]pyridin-2-yl)acetic acid (0.435 g, 2.47 mmol)), 4-fluoro-2-hydroxybenzaldehyde (0.363 g, 2.59 mmol), N-(3-dimethylaminopropyl)-N'-ethylcarbodiimide hydrochloride (0.57 g, 2.96 mmol), 4-(dimethylamino)pyridine (61 mg, 0.5 mmol) and triethylamine (0.7 mL, 5.0 mmol) in CH$_2$Cl$_2$ (8 mL) was heated at 50° C. After 1 h, the mixture was concentrated. The residue was suspended in CH$_3$CN, collected by vacuum filtration, washed with CH$_3$CN and dried to give 7-fluoro-3-(pyrazolo[1,5-a]pyridin-2-yl)-2H-chromen-2-one (0.66 g, 95%) as a yellow solid. MS m/z 281.1 [M+H]$^+$; $^1$H NMR (500 MHz, DMSO-d$_6$): δ 8.83 (1H, s), 8.71 (1H, dd J=6.9 Hz, 1.0 Hz), 8.03 (1H, dd, J=8.7 Hz, 6.4 Hz), 7.78 (1H, d, J=8.8 Hz), 7.48 (1H, dd, J=9.6 Hz, 2.4 Hz), 7.34-7.24 (1H, m), 7.30 (1H, s), 7.26 (1H, m), 6.98 (1H, td, J=6.9 Hz, 1.4 Hz).

Step D: A mixture of 7-fluoro-3-(pyrazolo[1,5-a]pyridin-2-yl)-2H-chromen-2-one (56 mg, 0.2 mmol), piperazine (52 mg, 0.6 mmol) and N,N-diisopropylethylamine (52 µL, 0.3 mmol) in DMSO (0.5 mL) was heated at 120° C. for 7 h. Upon cooling to room temperature, a precipitate formed. The precipitate was collected by vacuum filtration, washed with CH$_3$CN and dried to give the title compound (60 mg, 87%) as a yellow solid: m.p. 236-238° C.; MS m/z 347.3 [M+H]$^+$; $^1$H NMR (500 MHz, DMSO-d$_6$): δ 8.67 (1H, dd, J=7.0 Hz, 2.3 Hz), 8.5 (1H, s), 7.73 (1H, d, J=8.9 Hz), 7.69 (1H, d, J=8.9 Hz), 7.25-7.20 (2H, m), 7.01 (1H, dd, J=8.9 Hz, 2.4 Hz), 6.92 (1H, td, J=6.8 Hz, 1.4 Hz), 6.86 (1H, d, J=2.3 Hz), 3.32 (4H, m), 2.82 (4H, m).

As shown in Table 1 below, additional compounds disclosed herein may be prepared according to Example 30 by substituting the appropriate starting materials, reagents and reaction conditions.

Example 31

Preparation of Cpd 112

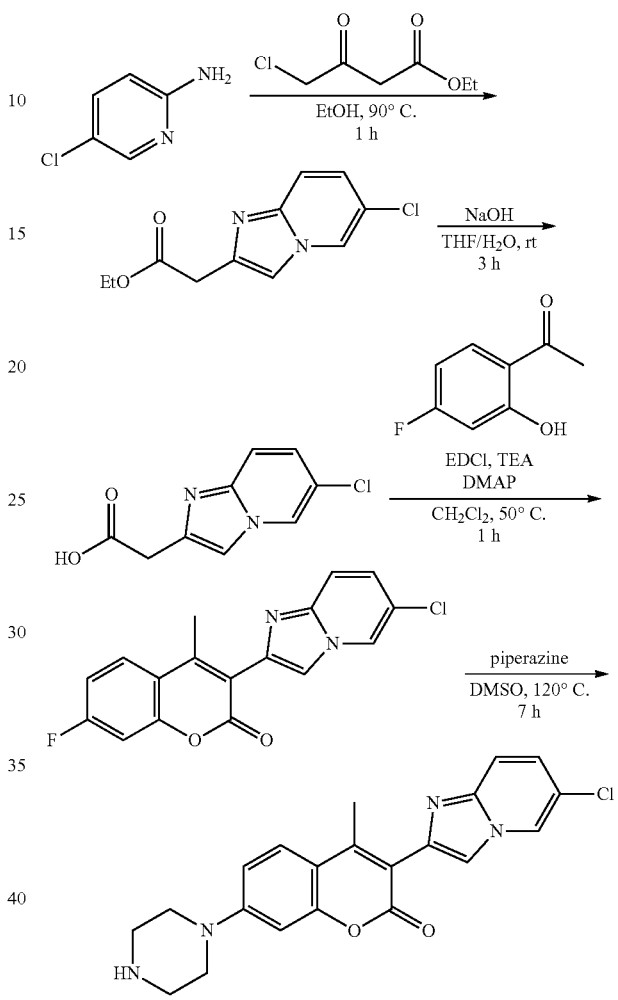

Step A: A mixture of 5-chloropyridin-2-amine (2.57 g, 20 mmol) and ethyl 4-chloro-3-oxobutanoate (3.95 g, 24 mmol) in EtOH (20 mL) was heated at 90° C. for 15 h, then the solvent was removed. The residue was suspended in CH$_3$CN, collected by vacuum filtration, washed with CH$_3$CN and dried to give ethyl 2-(6-chloroimidazo[1,2-a]pyridin-2-yl)acetate (4.14 g, 86%) as a white solid. MS m/z 239.1 [M+H]$^+$.

Step B: To a solution of ethyl 2-(6-chloroimidazo[1,2-a]pyridin-2-yl)acetate (2.38 g, 10 mmol) in THF was added aqueous NaOH (3 N, 6.6 mL, 20 mmol). After stirring at room temperature for 3 h, the mixture was concentrated. The residual mixture was acidified with aqueous HCl (6 N) to pH 3. A precipitate formed. The precipitate was collected by vacuum filtration, washed with water and dried, yielding 2-(6-chloroimidazo[1,2-a]pyridin-2-yl)acetic acid (1.66 g, 79%) as a white solid. MS m/z 211.1 [M+H]$^+$.

Step C: Following the procedure in Example 30, Step C, 2-(6-chloroimidazo[1,2-a]pyridin-2-yl)acetic acid (0.386 g, 2.5 mmol), 1-(4-fluoro-2-hydroxyphenyl)-ethanone (0.525 g, 2.5 mmol), N-(3-dimethylaminopropyl)-N'-ethylcarbodiimide hydrochloride (0.623 g, 3.25 mmol), 4-(dimethylamino)pyridine (92 mg, 0.75 mmol) and triethylamine (0.91 mL, 7.5 mmol) in $CH_2Cl_2$ (4 mL) gave 3-(6-chloroimidazo[1,2-a]pyridin-2-yl)-7-fluoro-4-methyl-2H-chromen-2-one (0.426 g, 52%) as an off-white solid. MS m/z 329.1 $[M+H]^+$.

Step D: Following the procedure in Example 30, Step D, 3-(6-chloroimidazo[1,2-a]pyridin-2-yl)-7-fluoro-4-methyl-2H-chromen-2-one (82 mg, 0.25 mmol), piperazine (65 mg, 0.75 mmol), DIEA (52 μL, 0.3 mmol) in DMSO (0.5 mL) gave the title compound (64 mg, 65%) as a yellow solid: m.p. 224-227° C.; MS m/z 395.2 $[M+H]^+$; $^1$H NMR (500 MHz, DMSO-$d_6$): δ 8.90 (1H, d, J=2.1 Hz), 8.27 (1H, s), 7.69 (1H, d, J=9.1 Hz), 7.63 (1H, d, J=9.6 Hz), 7.30 (1H, dd, J=9.6 Hz, 2.1 Hz), 7.01 (1H, dd, J=9.1 Hz, 2.4 Hz), 6.82 (1H, d, J=2.5 Hz), 3.28 (4H, m), 2.82 (4H, m), 2.66 (3H, s).

As shown in Table 1 below, additional compounds disclosed herein may be prepared according to Example 31 by substituting the appropriate starting materials, reagents and reaction conditions.

Example 32

Preparation of Cpd 124

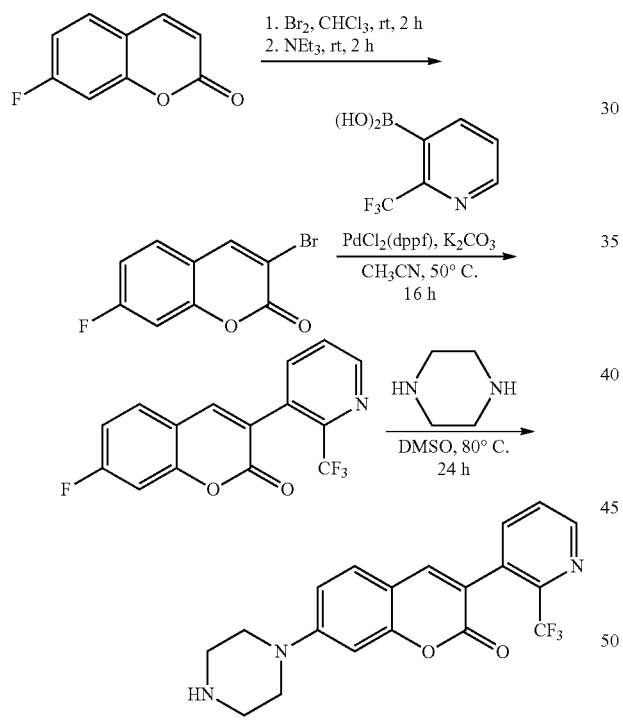

Step A: To a stirred solution of 7-fluorocoumarin (3.04 g, 18.5 mmol, prepared in Example 22, Step A) in chloroform (20 mL), at room temperature, was added dropwise, bromine (11.9 g, 3.81 mL, 74 mmol). After the addition, the mixture was stirred at room temperature for an additional 2 hours, then cooled in an ice-water bath and diluted with dichloromethane (100 mL). Triethylamine (22.4 g, 30.7 mL, 222 mmol) was added carefully while stirring. The mixture was stirred at room temperature for an additional 2 h after the addition. The precipitate present in the mixture was removed by filtration and washed with $CH_2Cl_2$ (3×15 mL). The combined filtrate was concentrated and purified by silica gel column chromatography ($CH_2Cl_2$), yielding 3-bromo-7-fluoro-2H-chromen-2-one (4.07 g, 90%) as white solid. MS m/z 242.4, 244.4 $[M+H]^+$; $^1$H NMR (500 MHz, CDCl$_3$): δ 8.09 (1H, s), 7.47 (1H, dd, J=8.7 Hz, 5.8 Hz), 7.12-7.03 (2H, m).

Step B: A reaction tube, equipped with an open-top cap and a septum was charged with 3-bromo-7-fluoro-2H-chromen-2-one (0.49 g, 2.0 mmol), (2-(trifluoromethyl)pyridin-3-yl)boronic acid (0.42 g, 2.2 mmol), [1,1'-bis(diphenylphosphino)ferrocene]dichloropalladium(II) complex with dichloromethane (0.082 g, 0.1 mmol) and $CH_3CN$ (6.0 mL). After purging three times with nitrogen, aqueous $K_2CO_3$ (2.0 mL, 2.0M, 4.0 mmol) was added and the mixture was stirred at 50° C. overnight, then the solvent was removed. The residue was suspended in $CH_2Cl_2$ and filtered. The filtrate was concentrated and purified by silica gel column chromatography (0-30% EtOAc in $CH_2Cl_2$) to give 7-fluoro-3-(2-(trifluoromethyl)pyridin-3-yl)-2H-chromen-2-one (0.21 g, 34%). MS m/z 310.2 $[M+H]^+$.

Step C: A mixture of 7-fluoro-3-(2-(trifluoromethyl)pyridin-3-yl)-2H-chromen-2-one (93 mg, 0.3 mmol) and piperazine (52 mg, 0.6 mmol) in DMSO (0.6 mL) was stirred at 80° C. for 24 h. After cooling to room temperature, the mixture was diluted with water (5 mL) to produce a precipitate. The solid was collected by filtration, washed with water and ethyl ether, and dried to give the title compound (100 mg, 89%) as yellow powder: m.p. 197-200° C.; MS m/z 376.2 $[M+H]^+$; $^1$H NMR (500 MHz, DMSO-$d_6$): δ 8.71 (1H, s), 8.53 (1H, d, J=2.5 Hz), 8.14 (1H, t, J=7.9 Hz), 7.83 (1H, d, J=8.5 Hz), 7.75 (1H, d, J=9.1 Hz), 7.02 (1H, dd, J=9.0 Hz, 2.4 Hz), 6.85 (1H, d, J=2.2 Hz), 3.40-3.33 (4H, m), 2.85-2.78 (4H, m).

As shown in Table 1 below, additional compounds disclosed herein may be prepared according to Example 32 by substituting the appropriate starting materials, reagents and reaction conditions.

Example 33

Preparation of Cpd 218

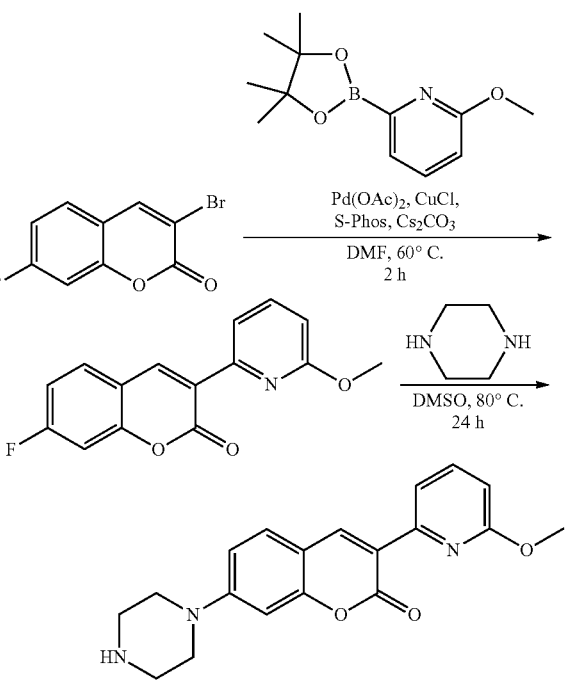

Step A: A mixture of 3-bromo-7-fluorocoumarin (122 mg, 0.5 mmol, prepared in Example 32, Step A), 2-methoxy-6-(4,4,5,5-tetramethyl-1,3,2-dioxaborolan-2-yl)pyridine (235 mg, 1.0 mmol), copper(I) chloride (50 mg, 0.5 mmol), $Cs_2CO_3$ (652 mg, 2.0 mmol), palladium(II) acetate (5.6 mg, 0.025 mmol), 2-dicyclohexylphosphino-2',6'-dimethoxybiphenyl (41 mg, 0.1 mmol) and DMF (2.0 mL) were stirred under an Argon atmosphere at 60° C. for 2 h. After cooling to room temperature, the mixture was diluted with water (10 mL) to produce a precipitate. The solid was washed with water, dried, and purified with silica gel column chromatography (0-10% EtOAc in $CH_2Cl_2$) to give 7-fluoro-3-(6-methoxypyridin-2-yl)-2H-chromen-2-one (52 mg, 38%). MS m/z 272.2 $[M+H]^+$.

Step B: A mixture of 7-fluoro-3-(6-methoxypyridin-2-yl)-2H-chromen-2-one (52 mg, 0.19 mmol), piperazine (50 mg, 0.57 mmol) and DMSO was stirred at 80° C. overnight. After cooling to room temperature, the mixture was diluted with water (5 mL) to produce a precipitate. The precipitate was collected by filtration, dried and purified by silica gel column chromatography (0-20% MeOH in $CH_2Cl_2$) to give the title compound (20 mg, 31%) as yellow powder: m.p. 162-165° C.; MS m/z 338.2 $[M+H]^+$. $^1H$ NMR (500 MHz, DMSO-$d_6$): δ 8.83 (1H, s), 7.96 (1H, dd, J=7.6 Hz, 0.9 Hz), 7.75 (1H, dd, J=8.2, 7.6 Hz), 7.69 (1H, d, J=8.8 Hz), 7.02 (1H, dd, J=9.0, 2.4 Hz), 6.85 (1H, d, J=2.2 Hz), 6.77 (1H, dd, J=8.2 Hz, 0.6 Hz), 3.98 (3H, s), 3.35-3.28 (4H, m), 2.86-2.78 (4H, m).

As shown in Table 1 below, additional compounds disclosed herein may be prepared according to Example 33 by substituting the appropriate starting materials, reagents and reaction conditions.

Example 34

Preparation of Cpd 651

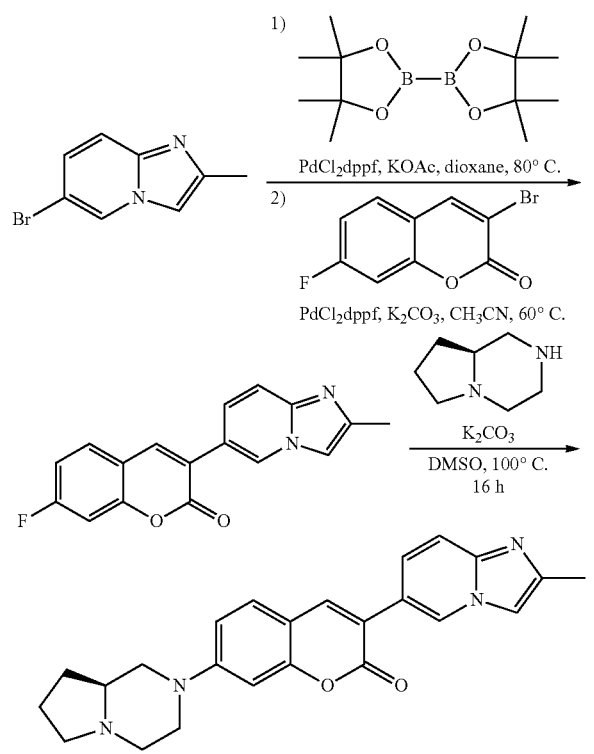

Step A: A mixture of 6-bromo-2-methylimidazo[1,2-a]pyridine (0.79 g, 3.75 mmol), 4,4,4',4',5,5,5',5'-octamethyl-2,2'-bi(1,3,2-dioxaborolane) (1.14 g, 4.49 mmol), [1,1'-bis(diphenylphosphino)ferrocene]dichloropalladium(II) complex with dichloromethane (0.15 g, 0.19 mmol), potassium acetate (1.1 g, 11.5 mmol) in 1,4-dioxane (7.5 mL) was stirred at 80° C. overnight under Argon. The mixture was diluted with THF (20 mL) and filtered. The filtrate was evaporated to give a dark solid residue, which was used without further purification (MS m/z 177.0 $[M+H]^+$). The residue was combined with 3-bromo-7-fluoro-2H-chromen-2-one (0.73 g, 3.0 mmol, prepared in Example 32, Step A), [1,1'-bis(diphenylphosphino)ferrocene]dichloropalladium (II) complex with dichloromethane (0.245 g, 0.3 mmol) and aqueous $K_2CO_3$ (2.0 M×4.5 mL, 9.0 mmol) in $CH_3CN$ (9.0 mL). The mixture was stirred at 60° C. overnight under Argon, then diluted with water and filtered. The solid was dissolved in $CH_2Cl_2$ (10% methanol), dried over $Na_2SO_4$, filtered, concentrated and purified with by silica gel chromatography (0-10% MeOH in $CH_2Cl_2$) to give 7-fluoro-3-(2-methylimidazo[1,2-a]pyridin-6-yl)-2H-chromen-2-one (0.67 g, 76%). MS m/z 295.0 $[M+H]^+$.

Step B: A mixture of 7-fluoro-3-(2-methylimidazo[1,2-a]pyridin-6-yl)-2H-chromen-2-one (90 mg, 0.31 mmol), (S)-octahydropyrrolo[1,2-a]pyrazine (50 mg, 0.40 mmol), $K_2CO_3$ (125 mg, 0.92 mmol) in DMSO (0.6 mL) was stirred at 100° C. overnight. The mixture was diluted with an aqueous saturated $NaHCO_3$ solution and filtered. The solid was dried and purified by silica gel chromatography (0-10% MeOH in $CH_2Cl_2$) to give the title compound (56 mg, 46%) as a yellow solid: m.p. 231-233° C.; MS m/z 401.5 $[M+H]^+$; $^1H$ NMR (500 MHz, $CDCl_3$): δ 8.86 (1H, dd, J=1.7, 0.8 Hz), 7.83 (1H, s), 7.49-7.57 (1H, m), 7.35-7.44 (3H, m), 6.87 (1H, d, J=8.8 Hz), 6.77 (1H, d, J=2.2 Hz), 3.94 (1H, dd, J=12.0, 1.6 Hz), 3.80 (1H, d, J=12.6 Hz), 3.24-3.06 (3H, m), 2.76 (1H, t, J=11.0 Hz), 2.47 (3H, d, J=0.6 Hz), 2.45-2.35 (1H, m), 2.30-2.10 (2H, m), 1.99-1.87 (2H, m), 1.86-1.77 (1H, m), 1.61-1.48 (1H, m).

As shown in Table 1 below, additional compounds disclosed herein may be prepared according to Example 34 by substituting the appropriate starting materials, reagents and reaction conditions.

Example 35

Preparation of Cpd 769

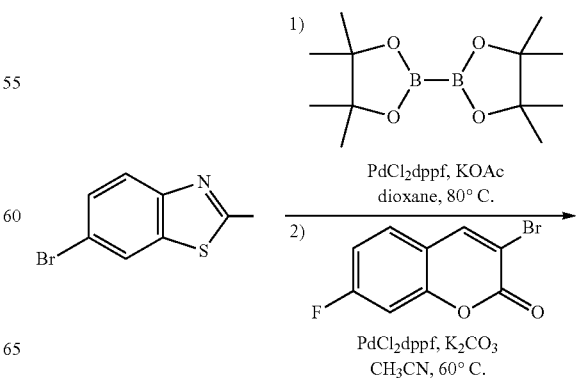

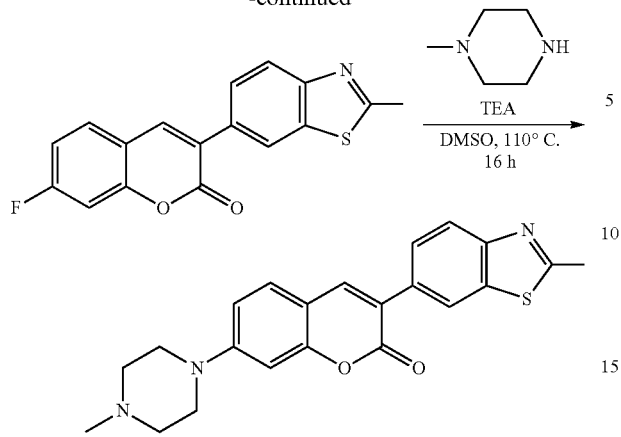

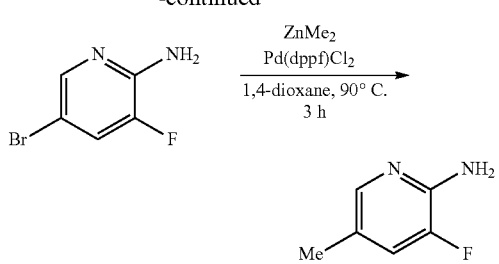

Step A: A solution of 3-fluoropyridin-2-amine (1.0 g, 8.92 mmol) was dissolved in CH₃CN (300 mL) at 0° C. N-Bromosuccinimide (800 mg, 4.5 mmol) was added to the solution. The reaction mixture was stirred at 0° C. for 20 min, then at room temperature for 20 min. The mixture was cooled to 0° C. Additional N-bromosuccinimide (800 mg, 4.5 mmol) was added. The mixture warmed to room temperature over 40 minutes. An aqueous NaHSO₃ solution was added to the mixture to quench excess reagent, then the solvent was removed under vacuum. The residue was dissolved in EtOAc, then washed with aqueous K₂CO₃. The organic layer was dried over MgSO₄, then filtered and concentrated under vacuum. Trituration of the residue with 2:1 hexanes:ether yielded 5-bromo-3-fluoropyridin-2-amine (1.18 g, 69%) as a white solid. ¹H NMR (500 MHz, CDCl₃): δ 7.93 (1H, d, J=2 Hz), 7.37 (1H, dd, J=9.5 Hz, 2 Hz), 4.66 (2H, br s), 2.77 (3H, s).

Step A: Following the procedure in Example 34, Step A, 6-bromo-2-methylbenzo[d]thiazole (0.47 g, 2.1 mmol), 4,4,4',4',5,5,5',5'-octamethyl-2,2'-bi(1,3,2-dioxaborolane) (0.63 g, 2.5 mmol), [1,1'-bis(diphenylphosphino)ferrocene]dichloropalladium(II) complex with dichloromethane (84 mg, 0.1 mmol) in dioxane (4.0 mL) followed by reaction of the intermediate formed with 3-bromo-7-fluoro-2H-chromen-2-one (0.45 g, 1.85 mmol), [1,1'-bis(diphenylphosphino)ferrocene]dichloropalladium(II) complex with dichloromethane (0.16 g, 0.2 mmol), aqueous K₂CO₃ (2.0 M×3.0 mL, 6.0 mmol) in CH₃CN (6.0 mL) yielded 7-fluoro-3-(2-methylbenzo[d]thiazol-6-yl)-2H-chromen-2-one (144 mg, 25%). MS m/z 312.0 [M+H]⁺.

Step B: A solution of dimethylzinc (15 mL, 1.2 M in toluene, 18 mmol) was added to a mixture of 5-bromo-3-fluoropyridin-2-amine (1.48 g, 7.75 mmol) and [1,1'-bis(diphenylphosphino)-ferrocene]dichloropalladium(II) complex with dichloromethane (150 mg, 0.18 mmol) in 1,4-dioxane (30 mL). The mixture was heated at 95° C. for 2 h. The reaction mixture was cooled to room temperature and quenched with MeOH. The mixture was diluted with aqueous saturated NH₄OH and extracted with EtOAc. The organic layer was dried over MgSO₄, filtered and concentrated under vacuum. The residue was purified by silica gel column chromatography (20% acetone in CH₂Cl₂), followed by trituration with hexane to give 3-fluoro-5-methylpyridin-2-amine (668 mg, 68%) as a tan solid. ¹H NMR (500 MHz, CDCl₃): δ 7.69 (1H, s), 7.06 (1H, dd, J=11.5 Hz, 1.5 Hz), 4.43 (2H, br s), 2.21 (3H, s).

Step B: A mixture of 7-fluoro-3-(2-methylbenzo[d]thiazol-6-yl)-2H-chromen-2-one (34 mg, 0.11 mmol), 1-methylpiperazine (22 mg, 0.22 mmol), triethylamine (49 mg, 0.49 mmol) in DMSO (0.25 mL) was stirred at 110° C. overnight. The mixture was diluted with an aqueous saturated NaHCO₃ solution and filtered. The solid was dried and purified by silica gel chromatography (0-10% MeOH in CH₂Cl₂) to give the title compound (41 mg, 95%) as a yellow solid: m.p. 215-217° C.; MS m/z 392.4 [M+H]⁺; ¹H NMR (500 MHz, CDCl₃): δ 8.28 (1H, d, J=1.8 Hz), 7.98 (1H, dd, J=8.5, 0.6 Hz), 7.80 (1H, s), 7.73 (1H, dd, J=8.5, 1.6 Hz), 7.40 (1H, d, J=8.8 Hz), 6.86 (1H, dd, J=8.8, 2.5 Hz), 6.78 (1H, d, J=2.2 Hz), 3.42 (4H, br. s.), 2.86 (3H, s), 2.62 (4H, s), 2.40 (3H, s)

As shown in Table 1 below, additional compounds disclosed herein may be prepared according to Example 35 by substituting the appropriate starting materials, reagents and reaction conditions.

Part 2: Preparation of 3-(2-bromoacetyl)-7-fluoro-2H-chromen-2-one

Example 36

Preparation of Cpd 421

Part 1: Preparation of 3-fluoro-5-methylpyridin-2-amine

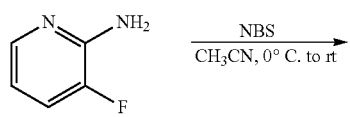

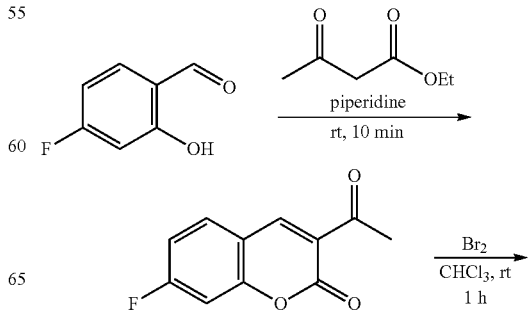

-continued

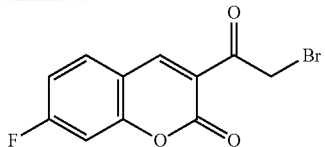

Step A: Into a mixture of 4-fluoro-2-hydroxybenzaldehyde (1.4 g, 10 mmol) and ethyl 3-oxobutanoate (1.3 g, 10 mmol) was added a few drops of piperidine. The mixture was stirred at room temperature for 10 min. A precipitate formed and was collected by vacuum filtration. The solid was washed with ethanol and aqueous HCl (1 N), filtered and dried to give 3-acetyl-7-fluoro-2H-chromen-2-one (1.96 g, 95%) as a pale yellow solid. $^1$H NMR (500 MHz, CDCl$_3$): δ 8.51 (1H, s), 7.68 (1H, m), 7.13-7.07 (2H, m), 2.73 (3H, s).

Step B: Into a solution of 3-acetyl-7-fluoro-2H-chromen-2-one (1.96 g, 9.5 mmol) in CHCl$_3$ (20 mL) was added dropwise a solution of bromine (1.6 g, 10 mmol) in CHCl$_3$ (10 mL). The mixture was stirred at room temperature for 1 h and filtered. The solid was washed with CHCl$_3$ and dried to give the title compound (1.96 g, 72%) as a pale yellow solid. $^1$H NMR (500 MHz, CDCl$_3$): δ 8.63 (1H, s), 7.72 (1H, m), 7.17-7.10 (2H, m), 4.73 (2H, s).

Part 3: Preparation of Cpd 421

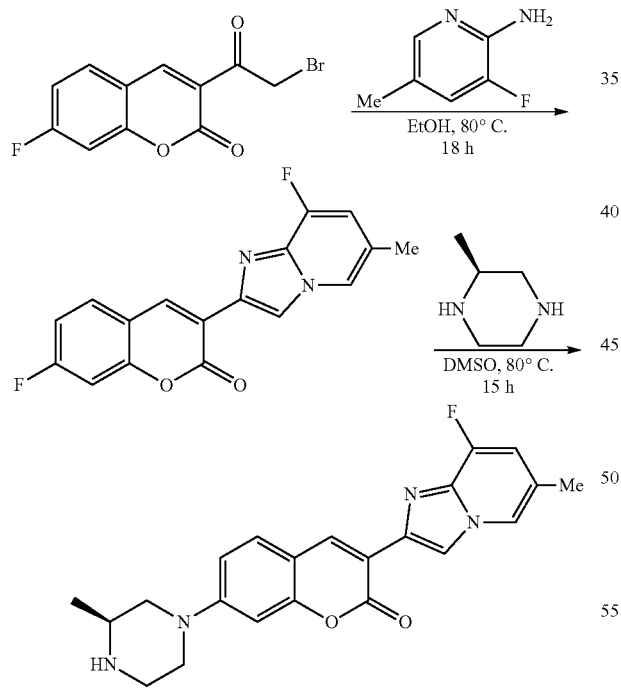

Step A: A mixture of 3-(2-bromoacetyl)-7-fluoro-2H-chromen-2-one (500 mg, 1.75 mmol), 3-fluoro-5-methyl-pyridin-2-amine (240 mg, 1.9 mmol) and EtOH (3 mL) was heated at 95° C. for 18 h. The reaction mixture was partitioned between CH$_2$Cl$_2$ and aqueous K$_2$CO$_3$. The organic layer was dried over MgSO$_4$, filtered, and concentrated under vacuum. The residue was triturated with 1:1 hexane/acetone, yielding 7-fluoro-3-(8-fluoro-6-methylimidazo[1,2-a]pyridin-2-yl)-2H-chromen-2-one (412 mg, 75%) as an orange solid. $^1$H NMR (500 MHz, CDCl$_3$): δ 8.85 (1H, s), 8.50 (1H, d, J=2.5 Hz), 7.77 (1H, m), 7.63 (1H, dd, J=9 Hz, 6 Hz), 7.11 (1H, dd, J=9 Hz, 2 Hz), 7.07 (1H, td, J=8.5 Hz, 2.5 Hz), 6.80 (1H, d, J=6 Hz), 2.34 (3H, s).

Step B: A mixture of 7-fluoro-3-(8-fluoro-6-methylimidazo[1,2-a]pyridin-2-yl)-2H-chromen-2-one (120 mg, 0.38 mmol), (S)-2-methylpiperazine (75 mg, 0.75 mmol) and DMSO (900 μL) was heated at 80° C. for 15 h. The mixture was diluted with an aqueous saturated NaHCO$_3$ solution, causing the product to precipitate from solution. The mixture was filtered. The solid material was purified by silica gel column chromatography (10% MeOH in CH$_2$Cl$_2$), yielding the title compound (133 mg, 89%) as a yellow solid: m.p. 250-255° C.; MS m/z 393.3 [M+H]$^+$; $^1$H NMR (500 MHz, DMSO-d$_6$): δ 8.73 (1H, s), 8.52 (1H, d, J=3 Hz), 8.31 (1H, s), 7.72 (1H, d, J=8.5 Hz), 7.09 (1H, d, J=12 Hz), 7.02 (1H, dd, J=9 Hz, 2 Hz), 6.88 (1H, d, J=2 Hz), 3.81 (2H, m), 2.96 (1H, m), 2.73 (3H, m), 2.39 (1H, t, J=11 Hz), 2.31 (1H, br s), 2.28 (3H, s), 1.04 (3H, d, J=6 Hz).

As shown in Table 1 below, additional compounds disclosed herein may be prepared according to Example 36 by substituting the appropriate starting materials, reagents and reaction conditions.

Example 37

Preparation of Cpd 520

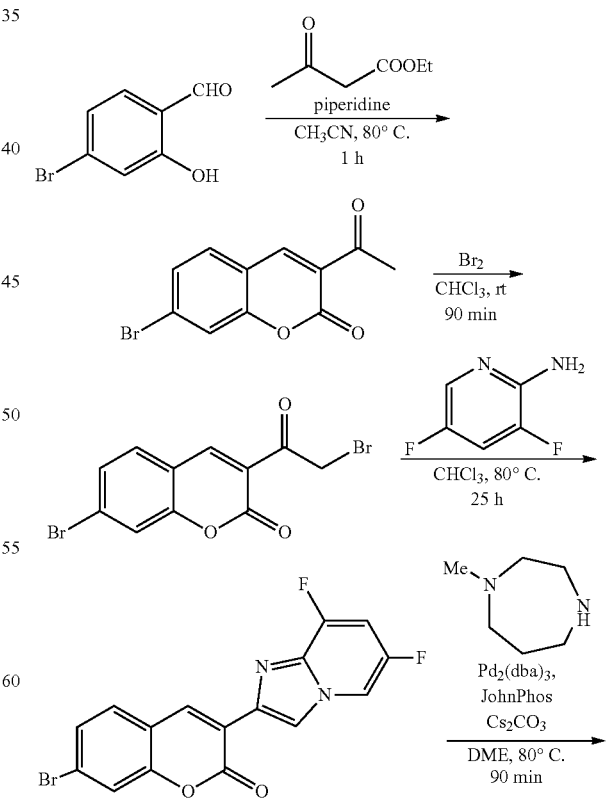

-continued

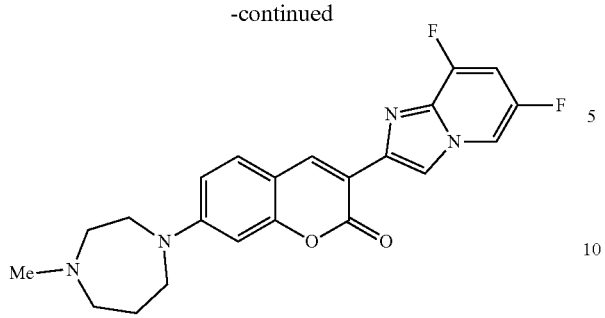

Step A: A mixture of 4-bromo-2-hydroxybenzaldehyde (5.0 g, 24.8 mmol), piperidine (150 μL, 1.5 mmol), ethyl acetoacetate (3.15 mL, 25 mmol) and CH$_3$CN (2.0 mL) was heated at 80° C. for 1 h. The reaction mixture was partitioned between CH$_2$Cl$_2$ and aqueous HCl (1 M). The organic layer was dried over MgSO$_4$, filtered, and concentrated under vacuum. The residue was triturated with MeOH, yielding 3-acetyl-7-bromo-2H-chromen-2-one (5.45 g, 82%) as a yellow solid. $^1$H NMR (500 MHz, CDCl$_3$): δ 8.46 (1H, s), 7.56 (1H, d, J=1.5 Hz), 7.51 (1H, d, J=8 Hz), 7.48 (1H, dd, J=8 Hz, 1.5 Hz), 2.72 (3H, s).

Step B: A solution of Br$_2$ (1.1 mL, 21.4 mmol) in CHCl$_3$ (25 mL) was added dropwise to a solution of 3-acetyl-7-bromo-2H-chromen-2-one (5.4 g, 20.2 mmol) in CHCl$_3$ (90 mL) over a period of 90 min. The mixture was filtered. The solid material was washed with CHCl$_3$, yielding 7-bromo-3-(2-bromoacetyl)-2H-chromen-2-one (5.6 g, 80%) as a light pink solid. $^1$H NMR (500 MHz, CDCl$_3$): δ 8.58 (1H, s), 7.60 (1H, d, J=1.5 Hz), 7.55 (1H, d, J=8.5 Hz), 7.52 (1H, dd, J=8.5 Hz, 1.5 Hz), 4.72 (2H, s).

Step C: A mixture of 7-bromo-3-(2-bromoacetyl)-2H-chromen-2-one (100 mg, 0.29 mmol), 3,5-difluoropyridin-2-amine (48 mg, 0.37 mmol) and CHCl$_3$ (500 μL) was heated at 80° C. for 25 h. The reaction mixture was partitioned between CH$_2$Cl$_2$ and an aqueous saturated NaHCO$_3$ solution. The organic layer was dried over MgSO$_4$, filtered, and concentrated under vacuum. The residue was purified by silica gel column chromatography (CH$_2$Cl$_2$), yielding 7-bromo-3-(8-fluoro-6-methylimidazo[1,2-a]pyridin-2-yl)-2H-chromen-2-one (96 mg, 88%) as a white solid. $^1$H NMR (500 MHz, CDCl$_3$): δ 8.88 (1H, s), 8.64 (1H, d, J=3 Hz), 8.00 (1H, m), 7.59 (1H, d, J=1.5 Hz), 7.53 (1H, d, J=8.5 Hz), 7.47 (1H, dd, J=8.5 Hz, 1.5 Hz), 6.99 (1H, m).

Step D: A mixture of 7-bromo-3-(8-fluoro-6-methylimidazo[1,2-a]pyridin-2-yl)-2H-chromen-2-one (40 mg, 0.11 mmol), (2-biphenyl)-di-t-butylphosphine (6 mg, 0.02 mmol), Pd$_2$(dba)$_3$ (6 mg, 0.0066 mmol), Cs$_2$CO$_3$ (55 mg, 0.17 mmol), 1-methylhomopiperazine (24 μL, 0.18 mmol), and 1,2-dimethoxyethane (450 μL) was heated at 80° C. for 90 min. The reaction mixture was then diluted in CH$_2$Cl$_2$ and filtered. The filtrate was concentrated. The residue was purified by silica gel column chromatography (5-10% MeOH in CH$_2$Cl$_2$), followed by trituration with 3:1 hexane/CH$_2$Cl$_2$, yielding the title compound (24 mg, 53%) as a yellow solid: m.p. 255-260° C.; MS m/z 411.2 [M+H]$^+$; $^1$H NMR (500 MHz, DMSO-d$_6$): δ 8.79 (1H, m), 8.73 (1H, s), 8.63 (1H, d, J=3 Hz), 7.70 (1H, d, J=9 Hz), 7.55 (1H, m), 6.84 (1H, dd, J=9 Hz, 2.5 Hz), 6.67 (1H, d, J=2 Hz), 3.65 (2H, t, J=5 Hz), 3.57 (2H, t, J=5.5 Hz), 2.64 (2H, t, J=5 Hz), 2.46 (2H, t, J=5.5 Hz), 2.27 (3H, s), 1.92 (2H, pentet, J=5.5 Hz).

As shown in Table 1 below, additional compounds disclosed herein may be prepared according to Example 37 by substituting the appropriate starting materials, reagents and reaction conditions.

Example 38

Preparation of Cpd 89

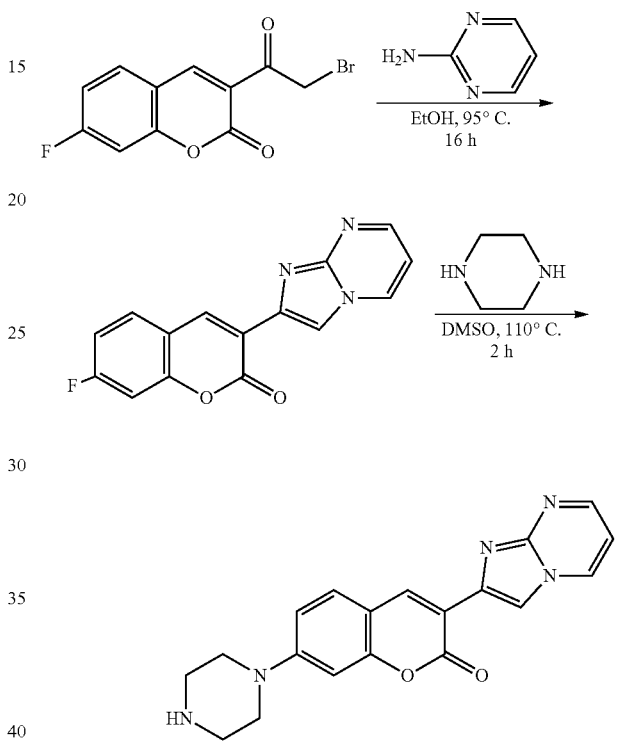

Step A: A mixture of 3-(2-bromoacetyl)-7-fluoro-2H-chromen-2-one (0.285 g, 1.0 mmol, prepared in Example 36, Part 2) and 2-aminopyrimidine (0.19 g, 2.0 mmol) in EtOH (2.0 mL) was stirred at 95° C. overnight. The mixture was diluted with water and filtered. The solid was washed with water and dried to afford 7-fluoro-3-(imidazo[1,2-a]pyrimidin-2-yl)-2H-chromen-2-one hydrobromide (0.28 g, 78%) as a pale yellow solid. MS m/z 282.1 [M+H]$^+$.

Step B: A mixture of 7-fluoro-3-(imidazo[1,2-a]pyrimidin-2-yl)-2H-chromen-2-one hydrobromide (50 mg, 0.18 mmol) and piperazine (61 mg, 0.71 mmol) in DMSO (0.5 mL) was stirred at 110° C. for 2 h. The mixture was diluted with an aqueous saturated NaHCO$_3$ solution and filtered. The solid was washed with water and dried to afford the title compound (40 mg, 64%) as a yellow solid: m.p. 286° C. (decomp.); MS m/z 348.2 [M+H]$^+$; $^1$H NMR (500 MHz, DMSO-d$_6$): δ 8.78 (1H, dd, J=6.8 Hz, 2.2 Hz), 8.55 (1H, s), 8.46 (1H, dd, J=4.2 Hz, 2.2 Hz), 8.40 (1H, s), 7.52 (1H, d, J=8.8 Hz), 6.95-6.91 (2H, m), 6.76 (1H, d, J=2.2 Hz), 3.33-3.28 (4H, m), 2.91-2.86 (4H, m).

As shown in Table 1 below, additional compounds disclosed herein may be prepared according to Example 38 by substituting the appropriate starting materials, reagents and reaction conditions.

Example 39

Preparation of Cpd 241

Part 1: Preparation of 5-methylpyrimidin-2-amine

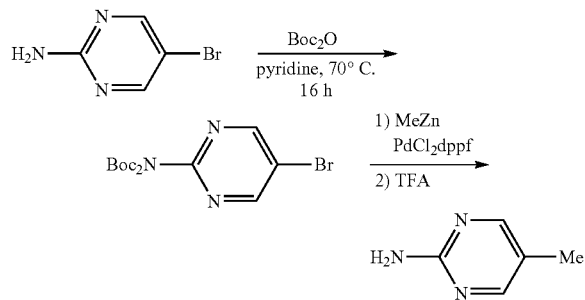

Step A: A mixture of 2-amino-5-bromopyrimidine (2.75 g, 15.8 mmol) and di-tert-butyl dicarbonate (7.58 g, 34.8 mmol) in pyridine (30 mL) was stirred at 70° C. overnight, then the solvent was removed. The residue was partitioned between EtOAc and aqueous HCl (1 N). The aqueous layer was extracted with EtOAc. The combined organics were dried over $NaSO_4$, then filtered and concentrated to give 2-[bis(tert-butoxycarbonyl)amino]-5-bromopyrimidine (5.5 g, 93%) as a white solid. MS m/z 398.2 $[M+Na]^+$.

Step B: A mixture of 2-[bis(tert-butoxycarbonyl)amino]-5-bromopyrimidine (3.0 g, 8.0 mmol), dimethylzinc (1.2 M×8.0 mL, 9.6 mmol) and [1,1'-bis(diphenylphosphino)ferrocene]dichloropalladium(II) (130 mg, 0.16 mmol) in 1,4-dioxane (30 mL) was stirred at 110° C. for 16 h under Argon. The mixture was cooled to room temperature, diluted with ethyl acetate and washed with saturated $NH_4Cl$, water and brine. The organic layer was dried over $NaSO_4$, concentrated and purified by silica gel column chromatography (0-35% EtOAc in hexanes) to give a white solid, which was dissolved in trifluoroacetic acid (5.0 mL). After 5 min, the solvent was removed and the residue was partitioned between ethyl acetate and an aqueous saturated $NaHCO_3$ solution. The organic layer was dried over $NaSO_4$, filtered and concentrated to give the title compound (0.7 g, 80%) as a white solid. MS m/z 110.1 $[M+H]^+$.

Part 2: Preparation of Cpd 241

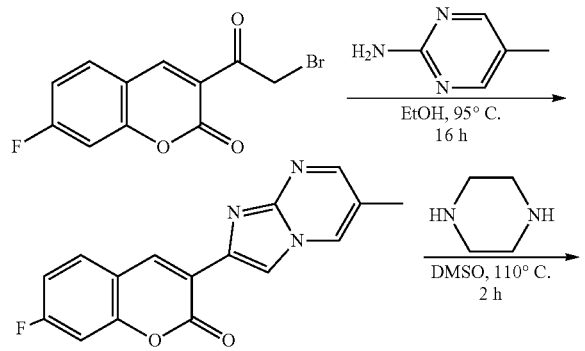

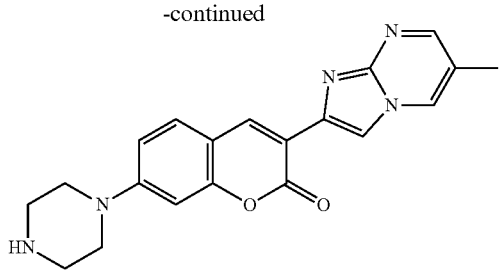

Step A: Following the procedure in Example 36, Part 3, 3-(2-bromoacetyl)-7-fluoro-2H-chromen-2-one (0.855 g, 3.0 mmol) and 5-methylpyrimidin-2-amine (0.327 g, 3.0 mmol) in EtOH (6.0 mL) gave 7-fluoro-3-(6-methylimidazo[1,2-a]pyrimidin-2-yl)-2H-chromen-2-one hydrobromide (0.37 g, 42%) as a pale yellow solid. MS m/z 296.2 $[M+H]^+$.

Step B: Following the procedure in Example 36, Part 3, 7-fluoro-3-(6-methylimidazo[1,2-a]pyrimidin-2-yl)-2H-chromen-2-one hydrobromide (80 mg, 0.21 mmol) and N-methyl piperizine (93 mg, 1.08 mmol) in DMSO (0.5 mL) gave the title compound (66 mg, 84%) as a yellow solid: m.p.>300° C.; MS m/z 362.2 $[M+H]^+$; $^1H$ NMR (500 MHz, DMSO-$d_6$): δ 8.83 (1H, dd, J=2.4 Hz, 1.1 Hz), 8.75 (1H, s), 8.44 (1H, d, J=2.2 Hz), 8.39 (1H, s), 7.71 (1H, d, J=8.8 Hz), 7.02 (1H, dd, J=8.8 Hz, 2.2 Hz), 6.86 (1H, d, J=2.2 Hz), 3.32-3.28 (4H, m), 2.86-2.75 (4H, m), 2.30 (3H, s).

As shown in Table 1 below, additional compounds disclosed herein may be prepared according to Example 39 by substituting the appropriate starting materials, reagents and reaction conditions.

Example 40

Preparation of Cpd 480

Part 1: Preparation of 5-fluoropyrimidin-2-amine

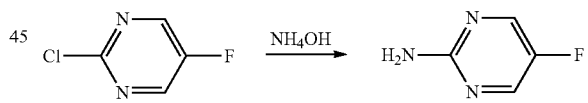

2-Chloro-5-fluoropyrimidine (1.34 g, 10 mmol) was stirred with ammonium hydroxide (30%, 15 mL) at 100° C. in a sealed tube overnight. The mixture was cooled to room temperature and filtered. The solid was washed with water and dried to give the title compound (0.95 g, 80%) as a white solid.

Part 2: Preparation of Cpd 480

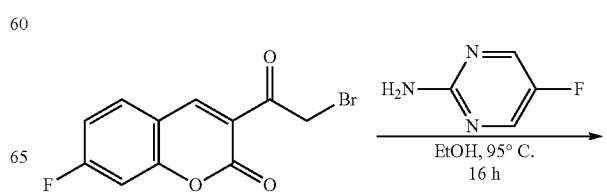

-continued

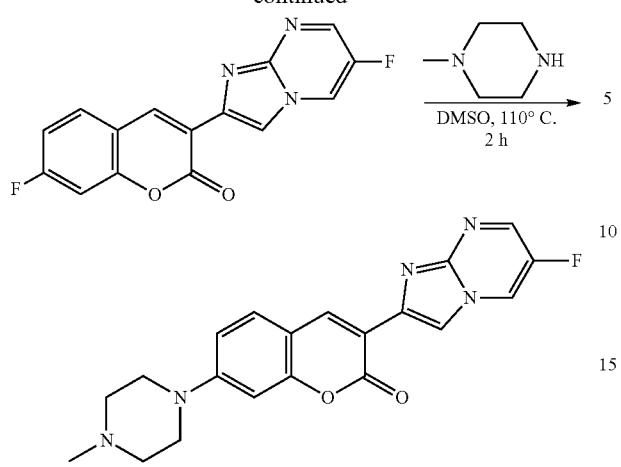

Step A: Following the procedure in Example 36, Part 3, 3-(2-bromoacetyl)-7-fluoro-2H-chromen-2-one (1.32 g, 4.1 mmol) and 5-fluoropyrimidin-2-amine (0.465 g, 4.1 mmol) in EtOH (12.0 mL) gave 7-fluoro-3-(6-fluoroimidazo[1,2-a]pyrimidin-2-yl)-2H-chromen-2-one (0.85 g, 70%) as a pale yellow solid. MS m/z 300.1 [M+H]$^+$.

Step B: Following the procedure in Example 36, Part 3, 7-fluoro-3-(6-fluoroimidazo[1,2-a]pyrimidin-2-yl)-2H-chromen-2-one (70 mg, 0.23 mmol) and N-methyl piperizine (46 mg, 0.46 mmol) in DMSO (0.5 mL) gave the title compound (55 mg, 63%) as a yellow solid: m.p. 275-280° C.; MS m/z 380.8 [M+H]$^+$; $^1$H NMR (500 MHz, methanol-d$_4$): δ 8.95 (1H, dd, J=3.8 Hz, 2.8 Hz), 8.65 (1H, s), 8.61 (1H, d, J=2.8 Hz), 8.53 (1H, s), 7.62 (1H, d, J=8.8 Hz), 7.02 (1H, dd, J=8.7 Hz, 2.4 Hz), 6.86 (1H, d, J=2.2 Hz), 3.51 (4H, br s), 2.81 (4H, br s), 2.50 (3H, br s).

As shown in Table 1 below, additional compounds disclosed herein may be prepared according to Example 40 by substituting the appropriate starting materials, reagents and reaction conditions.

Example 41

Preparation of Cpd 117

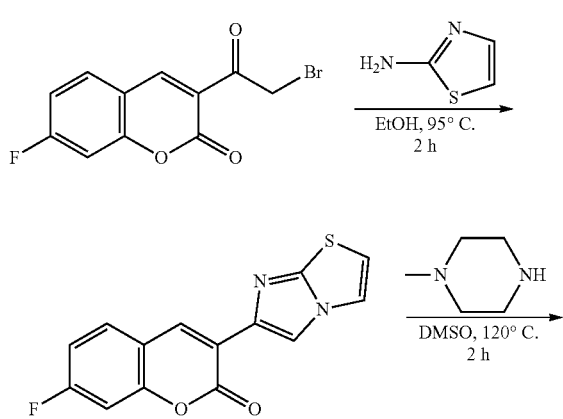

-continued

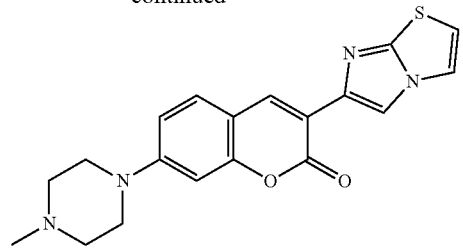

Step A: A mixture of 3-(2-bromoacetyl)-7-fluoro-2H-chromen-2-one (2.85 g, 10 mmol, prepared in Example 36, Part 2) and 2-aminothiazole (1.0 g, 10 mmol) in EtOH (20 mL) was stirred at 95° C. for 6 h. After cooling to room temperature, ethyl acetate was added, causing a precipitate to form. The mixture was filtered. The solid was washed with ethyl acetate and dried, affording 6-(7-fluoro-2-oxo-2H-chromen-3-yl)imidazo[2,1-b]thiazole hydrobromide salt (1.82 g, 64%) as a tan solid. MS m/z 287.1 [M+H]$^+$.

Step B: A mixture of 6-(7-fluoro-2-oxo-2H-chromen-3-yl)imidazo[2,1-b]thiazole hydrobromide salt (286 mg, 1.0 mmol) and 1-methylpiperazine (1.0 mL, 3.0 mmol) in DMSO (1.5 mL) was stirred at 110° C. for 2 h. The mixture was cooled to room temperature and diluted with water, producing a precipitate. The precipitate was collected by vacuum filtration, washed with water, dried and purified by silica gel column chromatography (0-10% MeOH in CH$_2$Cl$_2$) to give the title compound (185 mg, 51%) as a yellow solid: m.p. 256-258° C.; MS m/z 367.2 [M+H]$^+$; $^1$H NMR (500 MHz, DMSO-d$_6$): δ 8.53 (1H, s), 8.31 (1H, s), 7.94 (1H, d, J=4.4 Hz), 7.64 (1H, d, J=8.8 Hz), 7.26 (1H, d, J=4.4 Hz), 7.02 (1H, dd, J=8.8 Hz, 2.5 Hz), 6.87 (1H, d, J=2.2 Hz), 3.45-3.23 (4H, m), 2.47-2.39 (4H, m), 2.22 (3H, s).

As shown in Table 1 below, additional compounds disclosed herein may be prepared according to Example 41 by substituting the appropriate starting materials, reagents and reaction conditions.

Example 42

Preparation of Cpd 429

Preparation of 5-ethylthiazol-2-amine

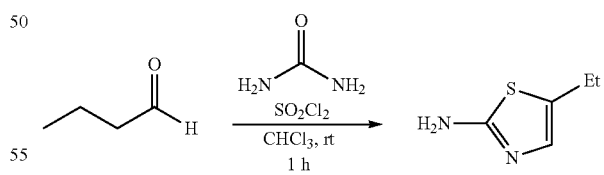

Into a mixture of butyraldehyde (10.8 g, 0.15 mol) and urea (22.8 g, 0.3 mol) in CHCl$_3$ (75 mL) at 0° C. was added sulfuryl chloride (13.5 mL, 0.166 mol) dropwise. The mixture was warmed to room temperature and stirred for 1 h, then the solvent was removed. EtOH (200 mL) was added to the residue, then the mixture was heated at reflux overnight and the solvent was removed. The residue was suspended in water (200 mL) and collected by vacuum filtration to give the title compound (9.5 g, 40%) as a light brown solid. MS m/z 129.1 [M+H]$^+$.

Part 2: Preparation of Cpd 429

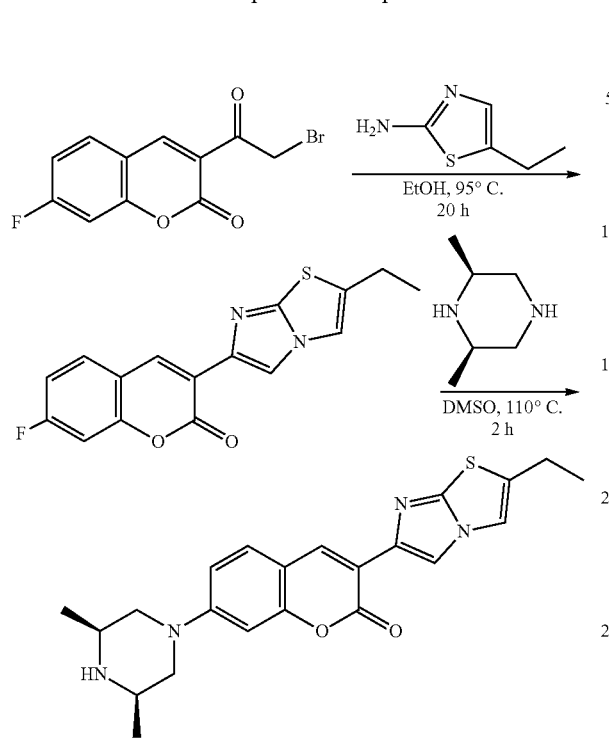

Step A: Following the procedure in Example 41, Step A, 3-(2-bromoacetyl)-7-fluoro-2H-chromen-2-one (0.76 g, 2.7 mmol) and 5-ethylthiazol-2-amine (0.35 g, 2.7 mmol) in EtOH (20 mL) gave 3-(2-ethylimidazo[2,1-b]thiazol-6-yl)-7-fluoro-2H-chromen-2-one hydrobromide (0.55 g, 66%) as a tan solid. MS m/z 315.2 [M+H]$^+$.

Step B: Following the procedure in Example 41, Step B, 3-(2-ethylimidazo[2,1-b]thiazol-6-yl)-7-fluoro-2H-chromen-2-one hydrobromide (42 mg, 0.13 mmol) and 2,6-cis-dimethylpiperizine (30 mg, 0.26 mmol) in DMSO (0.25 mL) gave the title compound (3.8 mg, 7%) as a yellow solid: m.p. 251-253° C.; MS m/z 409.4 [M+H]$^+$; $^1$H NMR (500 MHz, methanol-d$_4$) δ 8.32 (1H, s), 8.21 (1H, s), 7.56-7.48 (2H, m), 7.00 (1H, dd, J=9.0 Hz, 2.4 Hz), 6.82 (1H, d, J=2.2 Hz), 3.82 (2H, dd, J=12.5 Hz, 2.4 Hz), 3.00-2.89 (2H, m), 2.82 (2H, qd, J=7.5, 1.4 Hz), 2.43 (2H, dd, J=12.5 Hz, 10.9 Hz), 1.34 (3H, t, J=7.4 Hz), 1.18 (6H, d, J=6.6 Hz).

As shown in Table 1 below, additional compounds disclosed herein may be prepared according to Example 42 by substituting the appropriate starting materials, reagents and reaction conditions.

Example 43

Preparation of Cpd 536

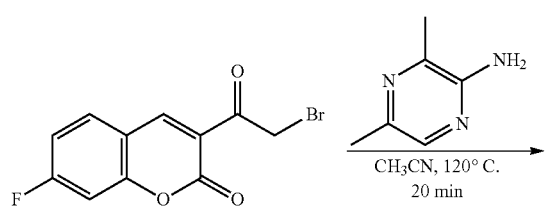

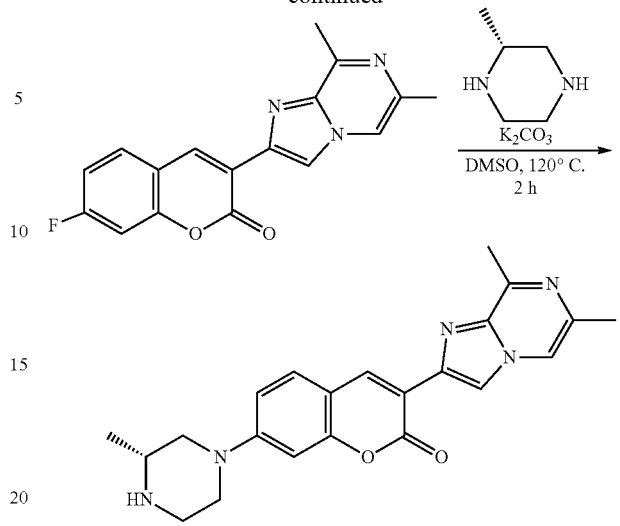

Step A: A mixture of 3-(2-bromoacetyl)-7-fluoro-2H-chromen-2-one (0.684 g, 2.4 mmol, prepared in Example 36, Part 2) and 3,5-dimethylpyrazin-2-amine (0.246 g, 2.0 mmol) in CH$_3$CN (10 mL) was stirred at 120° C. in a sealed tube for 20 min. The mixture was cooled to room temperature and diluted with Et$_2$O to produce a precipitate. The solid was collected by vacuum filtration, washed with Et$_2$O and dried to give 3-(6,8-dimethylimidazo[1,2-a]pyrazin-2-yl)-7-fluoro-2H-chromen-2-one hydrobromide (0.7 g, 90%) as a tan solid. MS m/z 310.1 [M+H]$^+$.

Step B: 3-(6,8-dimethylimidazo[1,2-a]pyrazin-2-yl)-7-fluoro-2H-chromen-2-one hydrobromide (100 mg, 0.25 mmol) was stirred with (R)-2-methylpiperazine (52 mg, 0.52 mmol) in DMSO (0.5 mL) with K$_2$CO$_3$ (0.14 g, 1.0 mmol) at 120° C. for 2 h. The mixture was cooled to room temperature and diluted with water to produce a precipitate. The solid was collected by vacuum filtration and purified by silica gel chromatography (10% MeOH in CH$_2$Cl$_2$) to give the title compound (64 mg, 64%) as a yellow solid. MS m/z 390.2 [M+H]$^+$; $^1$H NMR (500 MHz, CDCl$_3$): δ 8.74 (1H, s), 8.45 (1H, s), 7.77 (1H, s), 7.51 (1H, d, J=8.8 Hz), 6.88 (1H, dd, J=8.8 Hz, 2.5 Hz), 6.77 (1H, d, J=2.5 Hz), 3.77-3.67 (2H, m), 3.21-3.14 (2H, m), 3.06-2.92 (3H, m), 2.91 (3H, s), 2.64-2.56 (1H, m), 2.48 (3H, s), 1.20 (3H, d, J=6.3 Hz).

As shown in Table 1 below, additional compounds disclosed herein may be prepared according to Example 43 by substituting the appropriate starting materials, reagents and reaction conditions.

Example 44

Preparation of Cpd 607

Part 1: Preparation of 5-methyl-3-(trifluoromethyl)pyrazin-2-amine

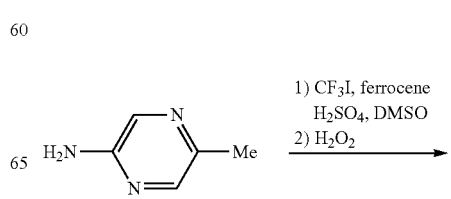

-continued

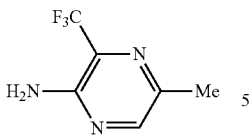

Into a solution of 5-methylpyrazin-2-amine (0.51 g, 4.72 mmol) and ferrocene (0.263 g, 1.42 mmol) in DMSO (12 mL) was added sulfuric acid (12 mL) and a solution of CF$_3$I in DMSO (2.4 M, 5.9 mL, 14.2 mmol). Aqueous hydrogen peroxide (30%, 0.94 mL) was added dropwise to the mixture. After stirring for 30 min at room temperature, excess reagent was quenched with ice water. The mixture was diluted with water and extracted with EtOAc. The organic layer was dried over NaSO$_4$, filtered, concentrated and purified by silica gel column chromatography (0-20% EtOAc in CH$_2$Cl$_2$) to give the title compound (86 mg, 8%) as a white solid. MS m/z 219.1 [M+H]$^+$.

Part 2: Preparation of Cpd 607

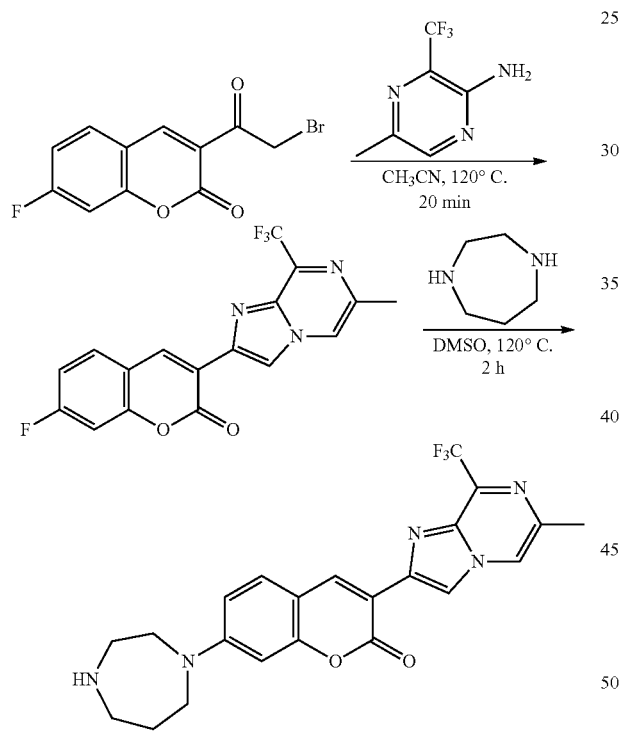

Step A: Following the procedure in Example 43, Step A, 3-(2-bromoacetyl)-7-fluoro-2H-chromen-2-one (138 g, 0.49 mmol) and 5-methyl-3-(trifluoromethyl)pyrazin-2-amine (86 g, 0.49 mmol) in CH$_3$CN (1.0 mL) gave 7-fluoro-3-(6-methyl-8-(trifluoromethyl)imidazo[1,2-a]pyrazin-2-yl)-2H-chromen-2-one hydrobromide (44 mg, 20%) as a tan solid.

Step B: Following the procedure in Example 43, Step B, 7-fluoro-3-(6-methyl-8-(trifluoromethyl)imidazo[1,2-a]pyrazin-2-yl)-2H-chromen-2-one hydrobromide (44 mg, 0.10 mmol) and 1,4-diazepane (44 mg, 0.44 mmol) in DMSO (0.25 mL) gave the title compound (43 mg, 99%) as a yellow solid: m.p.>300° C.; MS m/z 444.2 [M+H]$^+$; $^1$H NMR (500 MHz, CDCl$_3$): δ 8.79 (1H, s), 8.59 (1H, s), 8.09 (1H, s), 7.50 (1H, d, J=9.1 Hz), 6.69 (1H, dd, J=8.8 Hz, 2.2 Hz), 6.57 (1H, d, J=1.9 Hz), 3.70-3.61 (4H, m), 3.10-3.01 (2H, m), 2.88-2.83 (2H, m), 2.55 (3H, s), 2.03-1.90 (2H, m).

Example 45

Preparation of Cpd 712

Part 1: Preparation of 5-chloro-3-methylpyrazin-2-amine

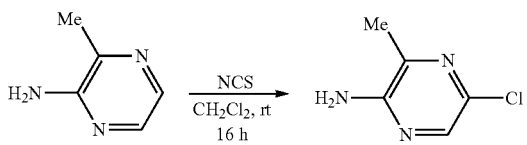 [SMILES: Cc1nccnc1N ; "NCS" ; Cc1nc(Cl)cnc1N]

A mixture of 3-methylpyrazin-2-amine (109 mg, 1.0 mmol) and N-chlorosuccinimide (136 mg, 1.0 mmol) in CH$_2$Cl$_2$ (6.0 mL) was stirred at room temperature overnight. The mixture was washed with aqueous K$_2$CO$_3$ (2.0 M, 6.0 mL). The organic layer was dried over NaSO$_4$, filtered, concentrated and purified by silica gel column chromatography (0-35% EtOAc in hexanes) to give the title compound (136 mg, 80%) as a white solid. MS m/z 144.0 [M+H]$^+$.

Part 2: Preparation of Cpd 712

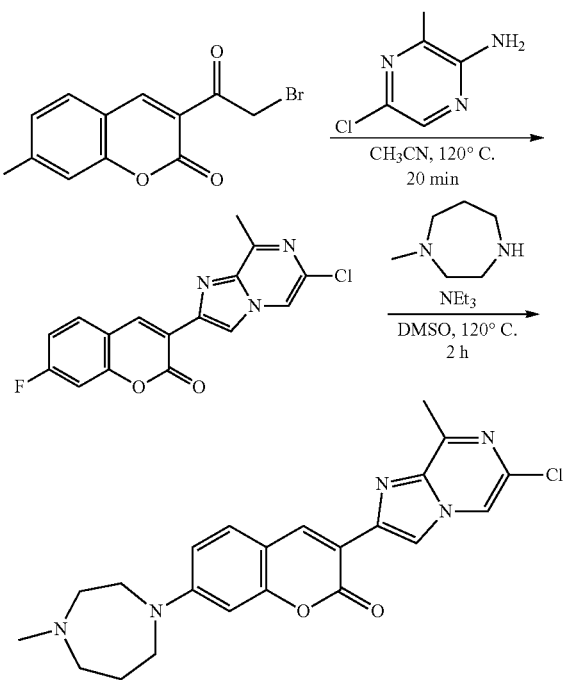

Step A: Following the procedure in Example 43, Step A, 3-(2-bromoacetyl)-7-fluoro-2H-chromen-2-one (0.233 g, 0.81 mmol) and 5-chloro-3-methylpyrazin-2-amine (0.117 g, 0.81 mmol) in CH$_3$CN (3.0 mL) gave 3-(6-chloro-8-methylimidazo[1,2-a]pyrazin-2-yl)-7-fluoro-2H-chromen-2-one hydrobromide (0.18 g, 67%) as a tan solid. MS m/z 330.1 [M+H]$^+$.

Step B: Following the procedure in Example 43, Step B, 3-(6-chloro-8-methylimidazo[1,2-a]pyrazin-2-yl)-7-fluoro- 2H-chromen-2-one hydrobromide (67 mg, 0.2 mmol), N-methyl homopiperizine (28 mg, 0.24 mmol) and triethylamine (100 mg, 1.0 mmol) in DMSO (0.5 mL) gave the title compound (70 mg, 83%) as a yellow solid: m.p. 212-218° C.; MS m/z 424 [M+H]$^+$; $^1$H NMR (500 MHz, methanol-$d_4$) δ 8.71 (1H, s), 8.55 (1H, s), 8.42 (1H, d, J=0.9 Hz), 7.56 (1H, d, J=8.8 Hz), 6.84 (1H, dd, J=8.8 Hz, 2.5 Hz), 6.67 (1H, d, J=2.2 Hz), 3.86-3.77 (2H, m), 3.65 (2H, t, J=6.3 Hz), 3.16 (2H, d, J=1.6 Hz), 3.04 (2H, br s), 2.89-2.82 (3H, m), 2.69 (3H, s), 2.27-2.14 (2H, m).

As shown in Table 1 below, additional compounds disclosed herein may be prepared according to Example 45 by substituting the appropriate starting materials, reagents and reaction conditions.

Example 46

Preparation of Cpd 398

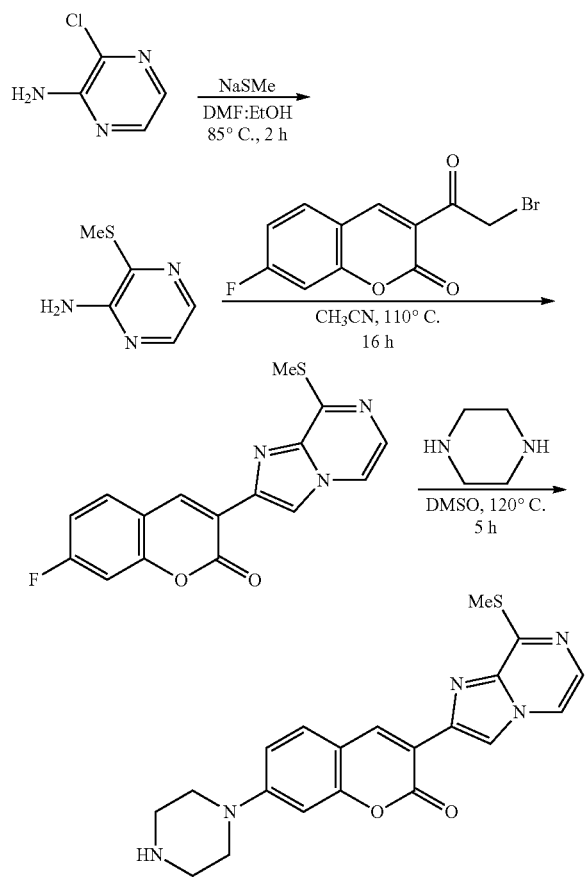

Step A: A mixture of 3-chloropyrazin-2-amine (1.29 g, 10 mmol) and sodium methanethiolate (1.05 g, 15 mmol) in DMF (10 mL) and EtOH (10 mL) was stirred at 85° C. for 2 h, and then concentrated. The mixture was diluted with water and filtered. The filtrate was extracted with ethyl acetate. The organic layer was washed with water, dried over Na$_2$SO$_4$, filtered and concentrated. The residue was combined with the material collected from filtration, affording the desired product 3-(methylthio)pyrazin-2-amine (1.33 g, 94%) as a white solid. MS m/z 142.1 [M+H]$^+$.

Step B: A mixture of 3-(2-bromoacetyl)-7-fluoro-2H-chromen-2-one (2.85 g, 10 mmol, prepared in Example 36, Part 2) and 3-(methylthio)pyrazin-2-amine (1.5 g, 10 mmol) in CH$_3$CN (40 mL) was stirred at 110° C. overnight. The mixture was cooled to room temperature and diluted with ethyl acetate to generate a precipitate. The solid was collected by vacuum filtration, washed with ethyl acetate and dried, yielding 7-fluoro-3-(8-(methylthio)imidazo[1,2-a]pyrazin-2-yl)-2H-chromen-2-one hydrobromide salt (2.15 g, 66%) as a tan solid. MS m/z 328.1 [M+H]$^+$.

Step C: A mixture of 7-fluoro-3-(8-(methylthio)imidazo[1,2-a]pyrazin-2-yl)-2H-chromen-2-one hydrobromide (100 mg, 0.24 mmol) and piperazine (60 mg, 0.6 mmol) in DMSO (0.5 mL) was stirred at 120° C. for 5 h. The mixture was cooled to room temperature and diluted with water to produce a precipitate. The solid was collected by vacuum filtration, washed with water, dried and purified with silica gel column chromatography (5-10% MeOH in CH$_2$Cl$_2$) to give the title compound (52 mg, 55%) as a yellow solid. MS m/z 394.3 [M+H]$^+$; $^1$H NMR (500 MHz, CDCl$_3$): δ 8.81 (1H, s), 8.50 (1H, s), 7.81 (1H, d, J=4.4 Hz), 7.70 (1H, d, J=4.7 Hz), 7.52 (1H, d, J=8.8 Hz), 6.88 (1H, dd, J=8.8 Hz, 2.5 Hz), 6.77 (1H, d, J=2.2 Hz), 3.50 (1H, s), 3.38-3.30 (4H, m), 3.09-3.01 (4H, m), 2.71 (3H, s).

As shown in Table 1 below, additional compounds disclosed herein may be prepared according to Example 46 by substituting the appropriate starting materials, reagents and reaction conditions.

Example 47

Preparation of Cpd 456

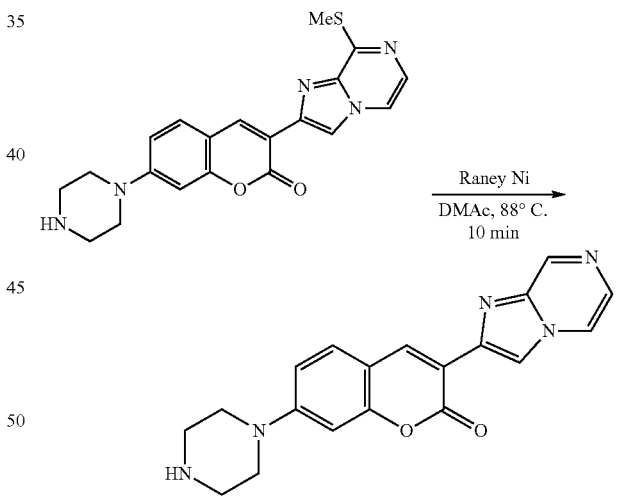

Into a solution of 7-(4-methylpiperazin-1-yl)-3-(7-(methylthio)imidazo[1,2-c]pyrimidin-2-yl)-2H-chromen-2-one (30 mg, 0.076 mmol) in dimethylacetamide (2.0 mL) at 88° C. was added a large excess of Raney Nickle. The mixture was stirred until gas evolution ceased (~10 min). The mixture was diluted with MeOH and filtered through Celite. The filtrate was concentrated under a stream of nitrogen. The residue was purified with silica gel column chromatography (5-10% MeOH in CH$_2$Cl$_2$) to give the title compound (32 mg, 55%) as a yellow solid: m.p. 258-260° C.; MS m/z 348.2 [M+H]$^+$; $^1$H NMR (500 MHz, CDCl$_3$): δ 9.07 (1H, s), 8.75 (1H, s), 8.60 (1H, d, J=0.6 Hz), 8.09 (1H, dd, J=4.6 Hz, 1.4 Hz), 7.88 (1H, d, J=4.4 Hz), 7.50 (1H, d, J=8.8 Hz), 6.88

(1H, dd, J=8.8 Hz, 2.2 Hz), 6.78 (1H, d, J=2.5 Hz), 3.36 (4H, dd, J=6.1 Hz, 4.3 Hz), 3.05 (4H, dd, J=6.1 Hz, 4.3 Hz)

As shown in Table 1 below, additional compounds disclosed herein may be prepared according to Example 47 by substituting the appropriate starting materials, reagents and reaction conditions.

Example 48

Preparation of Cpd 563

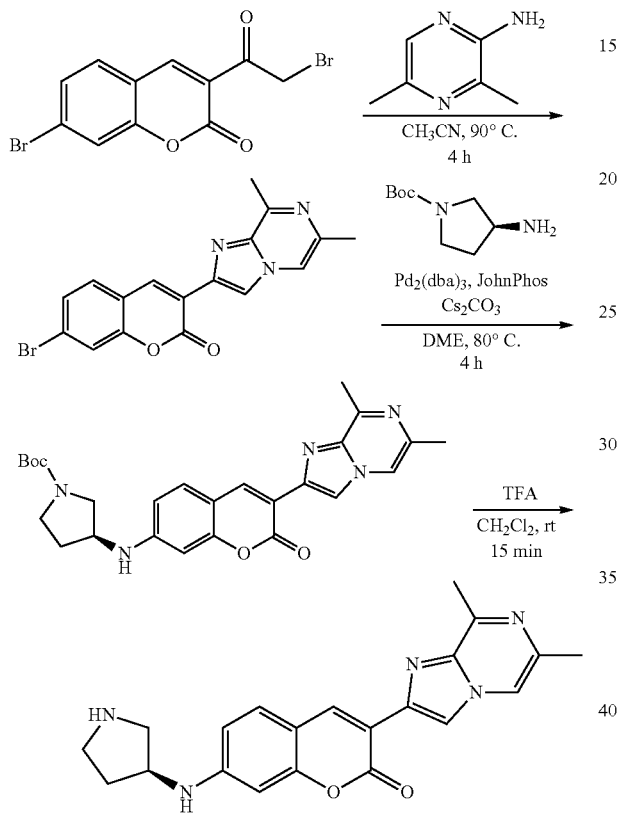

Step A: A mixture of 7-bromo-3-(2-bromoacetyl)-2H-chromen-2-one (2.0 g, 5.78 mmol, prepared in Example 37, Step B), 2-amino-3,5-dimethylpyrazine (825 mg, 6.71 mmol) and CH$_3$CN (22 mL) was heated at 90° C. for 4 h. The addition of an aqueous saturated NaHCO$_3$ solution to the mixture resulted in the formation of a precipitate. The precipitate was collected by vacuum filtration and triturated with 1:1 hexane/acetone, yielding 7-bromo-3-(6,8-dimethylimidazo[1,2-a]pyrazin-2-yl)-2H-chromen-2-one (1.9 g, 88%) as an orange solid. $^1$H NMR (500 MHz, DMSO-d$_6$): δ 8.81 (1H, s), 8.61 (1H, s), 8.31 (1H, s), 7.93 (1H, d, J=8 Hz), 7.76 (1H, d, J=1.5 Hz), 7.58 (1H, dd, J=8 Hz, 1.5 Hz), 2.76 (3H, s), 2.37 (3H, s).

Step B: A mixture of 7-bromo-3-(6,8-dimethylimidazo[1,2-a]pyrazin-2-yl)-2H-chromen-2-one (150 mg, 0.40 mmol), (2-biphenyl)-di-t-butylphosphine (10 mg, 0.033 mmol), Pd$_2$(dba)$_3$ (10 mg, 0.011 mmol), Cs$_2$CO$_3$ (170 mg, 0.52 mmol), (S)-1-Boc-3-aminopyrrolidine (105 μL, 0.60 mmol) and 1,2-dimethoxyethane (1.4 mL) was heated at 80° C. for 4 h. The reaction mixture was diluted with CH$_2$Cl$_2$ and filtered. The filtrate was concentrated. The residue was purified by silica gel column chromatography (30-50% acetone in CH$_2$Cl$_2$), followed by trituration with 1:1 hexane/acetone, yielding (S)-tert-butyl 3-(3-(6,8-dimethylimidazo[1,2-a]pyrazin-2-yl)-2-oxo-2H-chromen-7-ylamino)pyrrolidine-1-carboxylate (109 mg, 57%) as a yellow solid. MS m/z 476.3 [M+H]$^+$.

Step C: A mixture of (S)-tert-butyl 3-(3-(6,8-dimethylimidazo[1,2-a]pyrazin-2-yl)-2-oxo-2H-chromen-7-ylamino)pyrrolidine-1-carboxylate (105 mg, 0.22 mmol) was stirred in a solution of trifluoroacetic acid (1.0 mL) in CH$_2$Cl$_2$ (4.0 mL) for 15 min. The reaction mixture was poured into dilute aqueous NaOH. The mixture was extracted with CH$_2$Cl$_2$ (EtOH added to improve the solubility). The organic layer was collected and concentrated under reduced pressure, yielding the title compound (70 mg, 85%) as a yellow solid: m.p. 132° C. (decomp.); MS m/z 376.1 [M+H]$^+$; $^1$H NMR (500 MHz, DMSO-d$_6$): δ 8.70 (1H, s), 8.50 (1H, s), 8.32 (1H, s), 7.68 (1H, d, J=9 Hz), 7.06 (1H, d, J=6.5 Hz), 6.68 (1H, dd, J=9 Hz, 2 Hz), 6.55 (1H, d, J=2 Hz), 4.12 (1H, m), 3.37 (1H, dd, J=12 Hz, 6 Hz), 3.18 (1H, m), 3.11 (1H, m), 2.94 (1H, dd, J=12 Hz, 4 Hz), 2.76 (3H, s), 2.37 (3H, s), 2.22 (1H, m), 1.82 (1H, m).

As shown in Table 1 below, additional compounds disclosed herein may be prepared according to Example 48 by substituting the appropriate starting materials, reagents and reaction conditions.

Example 49

Preparation of Cpd 620

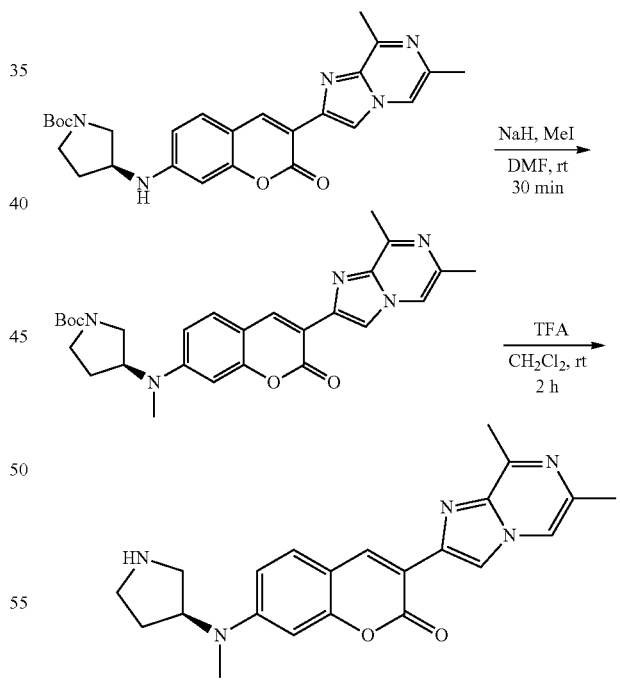

Step A: A mixture of (S)-tert-butyl 3-(3-(6,8-dimethylimidazo[1,2-a]pyrazin-2-yl)-2-oxo-2H-chromen-7-ylamino)pyrrolidine-1-carboxylate (255 mg, 0.54 mmol, prepared in Example 48, Step B), NaH (60% mineral oil suspension, 32 mg, 0.80 mmol) and DMF (2.5 mL) were stirred at room temperature for 10 min. Iodomethane (34 μL, 0.54 mmol) was added to the mixture. After stirring the mixture for 10 min, additional iodomethane (17 μL, 0.27 mmol) was added. After stirring an additional 10 min, water was slowly added to the reaction mixture to quench any remaining NaH. The addition of H$_2$O (15 mL) to the reaction mixture caused a precipitate to form. The precipitate was collected by vacuum filtration and purified by silica gel column chromatography (20-30% acetone in CH$_2$Cl$_2$), followed by ether trituration, yielding (S)-tert-butyl 3-((3-(6,8-dimethylimidazo[1,2-a]pyrazin-2-yl)-2-oxo-2H-chromen-7-yl)(methyl)amino)pyrrolidine-1-carboxylate (84 mg, 32%) as a yellow solid. MS m/z 490.2 [M+H]$^+$.

Step B: A mixture of (S)-tert-butyl 3-((3-(6,8-dimethyl-imidazo[1,2-a]pyrazin-2-yl)-2-oxo-2H-chromen-7-yl)(methyl)amino)pyrrolidine-1-carboxylate (80 mg, 0.16 mmol) was stirred in a solution of trifluoroacetic acid (1.0 mL) in CH$_2$Cl$_2$ (4.0 mL) for 2 h. The reaction mixture was poured into dilute aqueous NaOH. The mixture was extracted with a mixture of CH$_2$Cl$_2$ and EtOH. The organic layer was collected and concentrated under reduced pressure. The residue was purified by silica gel column chromatography (10% 9:1 MeOH:NH$_4$OH in CH$_2$Cl$_2$), yielding the title compound (42 mg, 67%) as a yellow solid: m.p. 192-202° C.; MS m/z 390.1 [M+H]$^+$; $^1$H NMR (500 MHz, DMSO-d$_6$): δ 8.70 (1H, s), 8.49 (1H, s), 8.31 (1H, s), 7.71 (1H, d, J=9 Hz), 6.91 (1H, dd, J=9 Hz, 2.5 Hz), 6.72 (1H, d, J=2 Hz), 4.53 (1H, m), 3.04 (1H, dd, J=11 Hz, 8 Hz), 2.96 (1H, m), 2.93 (3H, s), 2.77 (2H, m), 2.75 (3H, s), 2.37 (3H, s), 2.06 (1H, m), 1.66 (1H, m).

As shown in Table 1 below, additional compounds disclosed herein may be prepared according to Example 49 by substituting the appropriate starting materials, reagents and reaction conditions.

Example 50

Preparation of Cpd 740

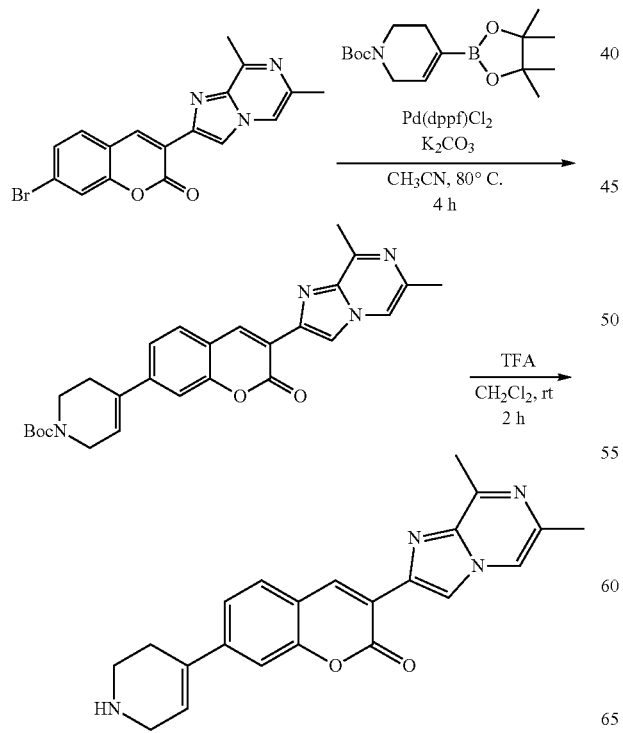

Step A: A mixture of 7-bromo-3-(6,8-dimethylimidazo[1,2-a]pyrazin-2-yl)-2H-chromen-2-one (1.1 g, 2.97 mmol, prepared in Example 48, Step A), tert-butyl 4-(4,4,5,5-tetramethyl-1,3,2-dioxaborolan-2-yl)-5,6-dihydropyridine-1(2H)-carboxylate (1.12 g, 3.62 mmol), K$_2$CO$_3$ (1.24 g, 9.0 mmol), [1,1'-bis(diphenylphosphino)-ferrocene]dichloropalladium(II) complex with dichloromethane (200 mg, 0.24 mmol) and CH$_3$CN (8 mL) was heated at 80° C. for 4 h. The reaction mixture was partitioned between CH$_2$Cl$_2$ and H$_2$O. The organic layer was concentrated under vacuum. The residue was purified by silica gel column chromatography (30-50% acetone in CH$_2$Cl$_2$), followed by trituration with acetone, yielding tert-butyl 4-(3-(6,8-dimethylimidazo[1,2-a]pyrazin-2-yl)-2-oxo-2H-chromen-7-yl)-5,6-dihydropyridine-1(2H)-carboxylate (1.17 g, 83%) as a light yellow solid. $^1$H NMR (500 MHz, DMSO-d$_6$): δ 8.85 (1H, s), 8.62 (1H, s), 8.34 (1H, s), 7.94 (1H, d, J=8.5 Hz), 7.52 (1H, d, J=8.5 Hz), 7.50 (1H, s), 6.47 (1H, br s), 4.07 (2H, br s), 3.58 (2H, t, J=5 Hz), 2.77 (3H, s), 2.53 (2H, br s), 2.38 (3H, s), 1.45 (9H, s).

Step B: A solution of tert-butyl 4-(3-(6,8-dimethylimidazo[1,2-a]pyrazin-2-yl)-2-oxo-2H-chromen-7-yl)-5,6-dihydropyridine-1(2H)-carboxylate (300 mg, 0.63 mmol) in trifluoroacetic acid (1.0 mL) and CH$_2$Cl$_2$ (4 mL) was stirred at room temperature for 30 min. The reaction mixture was poured into dilute aqueous NaOH. The mixture was extracted with CH$_2$Cl$_2$ (EtOH added to improve the solubility). The organic layer was collected and concentrated under reduced pressure. The residue was purified by silica gel column chromatography (30% MeOH in CH$_2$Cl$_2$, followed by 10-20% 9:1 MeOH:NH$_4$OH in CH$_2$Cl$_2$) yielding the title compound (183 mg, 77%) as a light tan solid: m.p. 205-211° C.; MS m/z 373.1 [M+H]$^+$; $^1$H NMR (500 MHz, DMSO-d$_6$): δ 8.83 (1H, s), 8.61 (1H, s), 8.33 (1H, s), 7.91 (1H, d, J=8.5 Hz), 7.50 (1H, dd, J=8 Hz, 1.5 Hz), 7.45 (1H, s), 6.52 (1H, m), 3.42 (2H, m), 2.94 (2H, t, J=6 Hz), 2.77 (3H, s), 2.40 (2H, m), 2.37 (3H, s), 2.28 (1H, br s).

Example 51

Preparation of Cpd 742

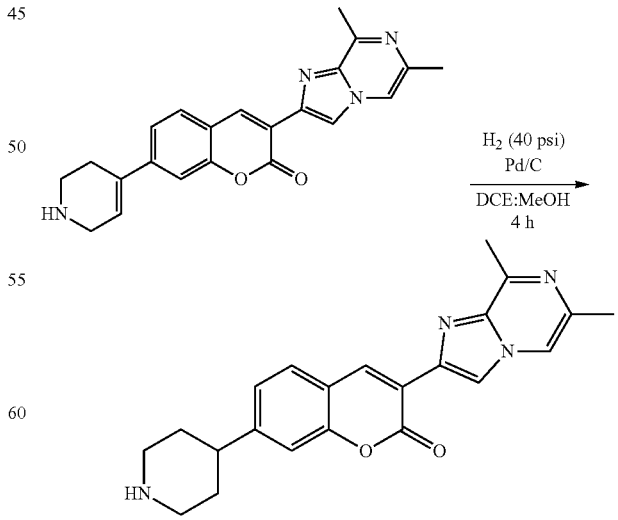

A solution of 3-(6,8-dimethylimidazo[1,2-a]pyrazin-2-yl)-7-(1,2,3,6-tetrahydropyridin-4-yl)-2H-chromen-2-one (133 mg, 0.36 mmol, prepared in Example 50) in 1,2-dichloroethane:MeOH (20 mL, 1:1) was stirred in the presence of 10% palladium on carbon (Pd/C, 107 mg) under hydrogen (40 psi). After 4 h, the reaction mixture was filtered through Celite. The filtrate was concentrated under vacuum. The residue was purified by silica gel column chromatography (10% 9:1 MeOH:NH$_4$OH in CH$_2$Cl$_2$), followed by trituration with 1:1 hexanes/CH$_2$Cl$_2$, yielding the title compound (76 mg, 56%) as an off-white solid: m.p. 224-229° C.; MS m/z 375.1 [M+H]$^+$; $^1$H NMR (500 MHz, DMSO-d$_6$): δ 8.84 (1H, s), 8.61 (1H, s), 8.34 (1H, s), 7.90 (1H, d, J=8 Hz), 7.30 (2H, m), 3.05 (2H, d, J=12 Hz), 2.77 (3H, s), 2.73 (1H, tt, J=12 Hz, 3.5 Hz), 2.59 (2H, td, J=12 Hz, 2.5 Hz), 2.38 (3H, s), 2.20 (1H, br s), 1.73 (2H, d, J=12 Hz), 1.54 (2H, qd, J=12 Hz, 3.5 Hz).

Example 52

Preparation of Cpd 128

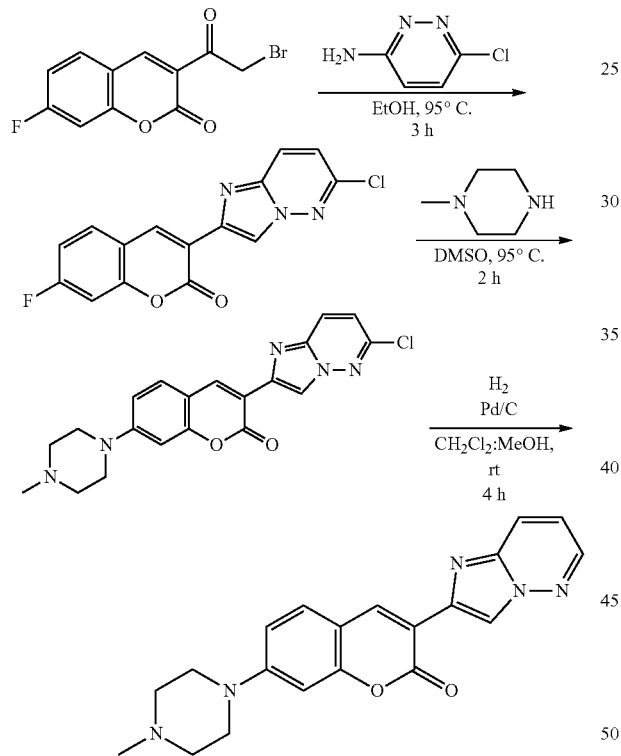

Step A: A mixture of 3-(2-bromoacetyl)-7-fluoro-2H-chromen-2-one (0.285 g, 1.0 mmol, prepared in Example 36, Part 2) and 6-chloropyridazin-3-amine (0.13 g, 1.0 mmol) in EtOH (2.0 mL) was stirred at 95° C. for 3 h. The mixture was cooled to room temperature and diluted with water to produce a precipitate. The solid was collected by vacuum filtration, washed with water and dried to give 3-(6-chloroimidazo[1,2-b]pyridazin-2-yl)-7-fluoro-2H-chromen-2-one hydrobromide (0.26 g, 82%) as a tan solid. MS m/z 316.1 [M+H]$^+$.

Step B: A mixture of 3-(6-chloroimidazo[1,2-b]pyridazin-2-yl)-7-fluoro-2H-chromen-2-one hydrobromide (95 mg, 0.3 mmol), 1-methylpiperazine (75 mg, 0.75 mmol) in DMSO (0.5 mL) was stirred at 95° C. for 2 h. The mixture was cooled to room temperature and diluted with water to produce a precipitate. The solid was collected by vacuum filtration, washed with water, dried and purified with silica gel column chromatography (5-10% MeOH in CH$_2$Cl$_2$) to give 3-(6-chloroimidazo[1,2-b]pyridazin-2-yl)-7-(4-methylpiperazin-1-yl)-2H-chromen-2-one (56 mg, 50%) as a yellow solid. MS m/z 396.2 [M+H]$^+$.

Step C: A suspension of 3-(6-chloroimidazo[1,2-b]pyridazin-2-yl)-7-(4-methylpiperazin-1-yl)-2H-chromen-2-one (50 mg, 0.13 mmol) in a mixed solvent of CH$_2$Cl$_2$ (2.0 mL) and MeOH (5.0 mL) was stirred with 10% Pd/C (20 mg) under hydrogen (1 atm) for 4 h. The mixture was filtered through Celite. The filtrate was concentrated. The residue was suspended in water, collected by vacuum filtration and dried to give the title compound (30 mg, 66%) as a yellow solid: m.p. 284-285° C.; MS m/z 362.3 [M+H]$^+$; $^1$H NMR (500 MHz, DMSO-d$_6$): δ 8.78 (1H, s), 8.63 (1H, s), 8.52 (1H, dd, J=4.4 Hz, 1.6 Hz), 8.11 (1H, d, J=9.5 Hz), 7.74 (1H, d, J=8.2 Hz), 7.28 (1H, dd, J=9.5 Hz, 4.4 Hz), 7.06 (1H, d, J=9.2 Hz), 6.95 (1H, s), 3.53-3.32 (4H, m), 2.48 (3H, s), 2.38-2.15 (4H, m).

Example 53

Preparation of Cpd 617

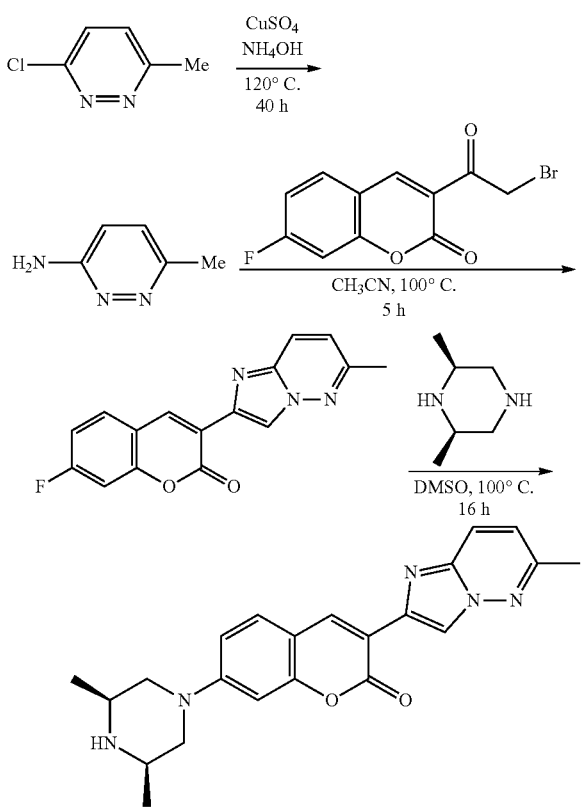

Step A: A mixture of 3-chloro-6-methylpyridazine (516 mg, 4.0 mmol), NH$_4$OH (30%, 3 mL) and copper(II) sulfate pentahydrate (26 mg, 0.2 mmol) was stirred at 120° C. for 40 h. The mixture was cooled to room temperature and partitioned between EtOAc and brine. The aqueous layer was extracted with EtOAc five times. The combined organics were dried over NaSO$_4$, filtered, concentrated and purified by silica gel column chromatography (0-10% MeOH in CH$_2$Cl$_2$) to give 6-methylpyridazin-3-amine (160 mg, 37%) as a white solid. MS m/z 109.9 [M+H]$^+$.

Step B: A mixture of 3-(2-bromoacetyl)-7-fluoro-2H-chromen-2-one (900 mg, 3.0 mmol, prepared in Example 36, Part 2) and 6-methylpyridazin-3-amine (330 mg, 3.0 mmol) was stirred in CH$_3$CN (6.0 mL) at 100° C. for 5 h, then the solvent was removed. The residue was purified by silica gel column chromatography (5% MeOH in CH$_2$Cl$_2$) to give 7-fluoro-3-(6-methylimidazo[1,2-b]pyridazin-2-yl)-2H-chromen-2-one (814 mg, 92%) as a tan solid. MS m/z 296.0 [M+H]$^+$.

Step C: A mixture of 7-fluoro-3-(6-methylimidazo[1,2-b]pyridazin-2-yl)-2H-chromen-2-one (100 mg, 0.34 mmol) and cis-2,6-dimethylpiperazine (155 mg, 1.36 mmol) in DMSO (0.5 mL) was stirred at 100° C. overnight. The mixture was diluted with water to produce a precipitate. The solid was collected by vacuum filtration, dried under vacuum and purified by silica gel column chromatography (5% MeOH in CH$_2$Cl$_2$) to give the title compound (75 mg, 58%) as a yellow solid: m.p. 225-227° C.; MS m/z 390.1 [M+H]$^+$; $^1$H NMR (500 MHz, DMSO-d$_6$): δ 8.64 (1H, s), 8.52 (1H, s), 7.66 (1H, d, J=9.4 Hz), 7.35 (1H, d, J=8.8 Hz), 6.81 (1H, d, J=9.4 Hz), 6.73 (1H, dd, J=8.8 Hz, 2.2 Hz), 6.66 (1H, d, J=2.2 Hz), 3.68-3.56 (2H, m), 3.12-2.96 (2H, m), 2.71-2.54 (2H, m), 2.46 (3H, s), 1.30-1.10 (6H, br s).

As shown in Table 1 below, additional compounds disclosed herein may be prepared according to Example 53 by substituting the appropriate starting materials, reagents and reaction conditions.

Example 54

Preparation of Cpd 458

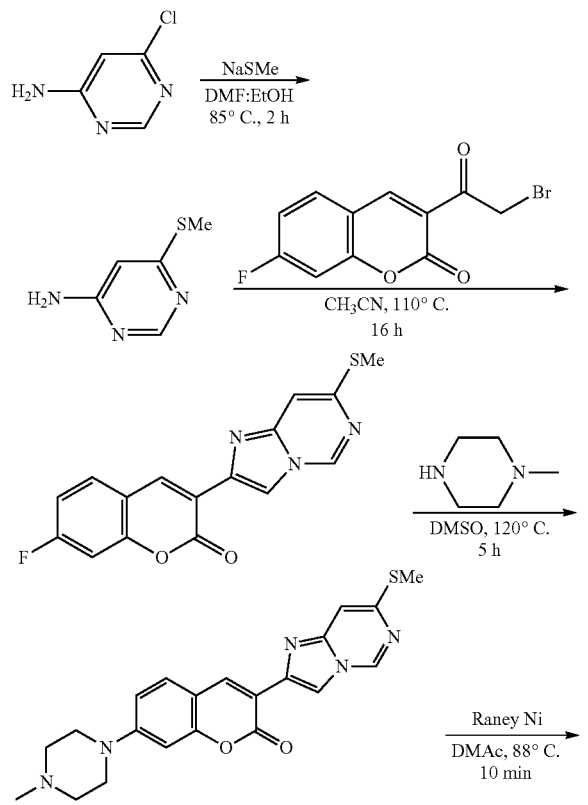

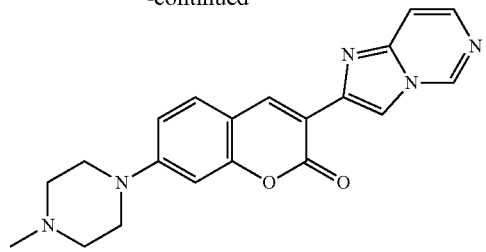

Step A: Following the procedure in Example 46, Step A, 6-chloropyrimidin-4-amine (1.3 g, 10 mmol) and sodium methanethiolate (1.05 g, 15 mmol) in DMF (10 mL) afforded 6-(methylthio)pyrimidin-4-amine (1.06 g, 75%). MS m/z 142.1 [M+H]$^+$.

Step B: A mixture of 3-(2-bromoacetyl)-7-fluoro-2H-chromen-2-one (2.5 g, 8.86 mmol, prepared in Example 36, Part 2) and 6-(methylthio)pyrimidin-4-amine (1.0 g, 7.1 mmol) in CH$_3$CN (35 mL) was stirred at 120° C. overnight. The mixture was cooled to room temperature and diluted with EtOAc to produce a precipitate. The solid was collected by vacuum filtration, washed with EtOAc and dried under vacuum to afford 7-fluoro-3-(7-(methylthio)imidazo[1,2-c]pyrimidin-2-yl)-2H-chromen-2-one hydrobromide salt (2.8 g, 97%) as a tan solid. MS m/z 328.1 [M+H]$^+$.

Step C: A mixture of 7-fluoro-3-(7-(methylthio)imidazo[1,2-c]pyrimidin-2-yl)-2H-chromen-2-one hydrobromide (100 mg, 0.24 mmol) and 1-methylpiperazine (60 mg, 0.6 mmol) in DMSO (0.5 mL) was stirred at 120° C. for 5 h. After cooling to room temperature, the mixture was diluted with water to produce a precipitate. The solid was collected by vacuum filtration, dried under vacuum and purified by silica gel column chromatography (5% MeOH in CH$_2$Cl$_2$) to give 7-(4-methylpiperazin-1-yl)-3-(7-(methylthio)imidazo[1,2-c]pyrimidin-2-yl)-2H-chromen-2-one (68 mg, 69%) as a yellow solid. MS m/z 408.2 [M+H]$^+$.

Step D: Following the procedure in Example 47, 7-(4-methylpiperazin-1-yl)-3-(7-(methylthio)imidazo[1,2-c]pyrimidin-2-yl)-2H-chromen-2-one (66 mg, 0.16 mmol) and excess Raney Ni in dimethylacetamide (2.0 mL) yielded the title compound (32 mg, 55%) as a yellow solid: m.p. 253-255° C.; MS m/z 362.3 [M+H]$^+$; $^1$H NMR (500 MHz, DMSO-d$_6$): δ 9.03 (1H, s), 8.71 (1H, s), 8.56 (1H, s), 7.95 (1H, d, J=6.3 Hz), 7.54-7.44 (2H, m), 6.88 (1H, dd, J=8.8 Hz, 2.2 Hz), 6.79 (1H, d, J=2.2 Hz), 3.48 (4H, br s), 2.67 (4H, br s), 2.44 (3H, br s).

As shown in Table 1 below, additional compounds disclosed herein may be prepared according to Example 54 by substituting the appropriate starting materials, reagents and reaction conditions.

Example 55

Preparation of Cpd 441

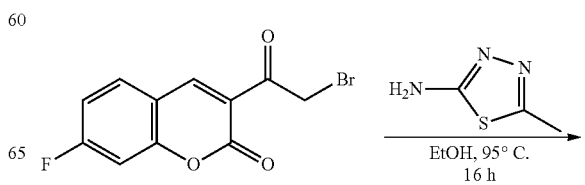

389
-continued

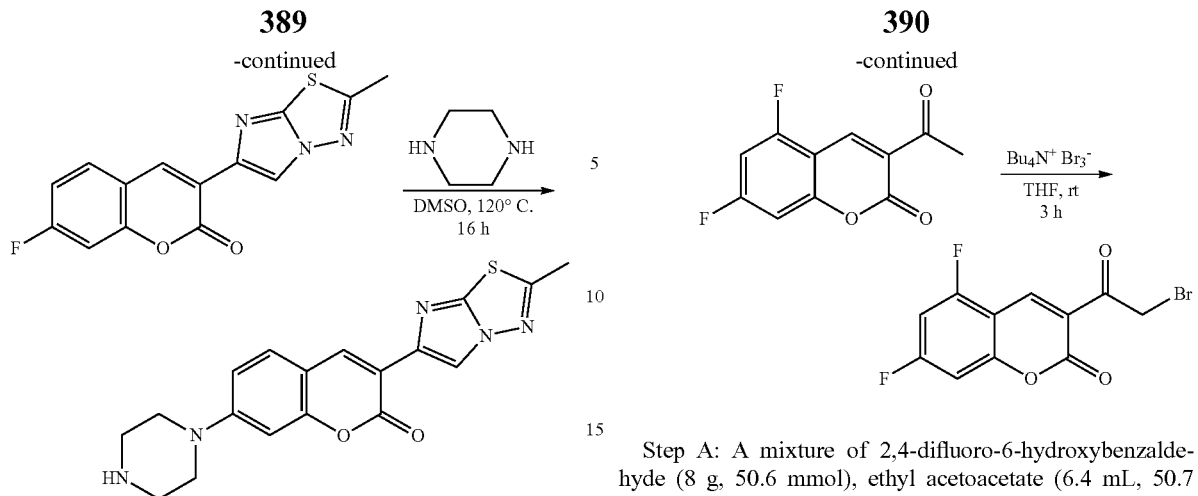

Step A: A mixture of 3-acetyl-7-fluoro-2H-chromen-2-one (600 mg, 2.0 mmol, prepared in Example 36, Part 2) and 5-methyl-1,3,4-thiadiazol-2-amine (241 mg, 2.0 mmol) in EtOH (6.0 mL) was stirred at 95° C. overnight in a sealed tube. The mixture was cooled to room temperature and diluted with an aqueous saturated $NaHCO_3$ solution to produce a precipitate. The solid was collected by vacuum filtration, washed with water and dried under vacuum to give 7-fluoro-3-(2-methylimidazo[2,1-b][1,3,4]thiadiazol-6-yl)-2H-chromen-2-one (1.2 g, 62%) as a tan solid. MS m/z 303.2 $[M+H]^+$.

Step B: A mixture of 7-fluoro-3-(2-methylimidazo[2,1-b][1,3,4]thiadiazol-6-yl)-2H-chromen-2-one (76 mg, 0.25 mmol), piperazine (64 mg, 0.75 mmol), $K_2CO_3$ (104 mg, 0.75 mmol) in DMSO (0.5 mL) was stirred at 120° C. overnight. After cooling to room temperature, the mixture was diluted with water to produce a precipitate. The solid was collected by vacuum filtration, dried under vacuum and purified by silica gel column chromatography (10% MeOH in $CH_2Cl_2$) to afford the title compound (23 mg, 25%) as a yellow solid: m.p. 288-290° C.; MS m/z 368.2 $[M+H]^+$; $^1H$ NMR (500 MHz, MeOD-$d_4$): δ 8.43 (1H, s), 8.40 (1H, s), 7.54 (1H, d, J=8.8 Hz), 7.01 (1H, dd, J=8.8 Hz, 2.5 Hz), 6.84 (1H, d, J=2.2 Hz), 3.39-3.35 (4H, m), 3.00-2.95 (4H, m), 2.74 (3H, s).

As shown in Table 1 below, additional compounds disclosed herein may be prepared according to Example 55 by substituting the appropriate starting materials, reagents and reaction conditions.

Example 56

Preparation of Cpd 391

Part 1: Preparation of 3-(2-bromoacetyl)-5,7-difluoro-2H-chromen-2-one

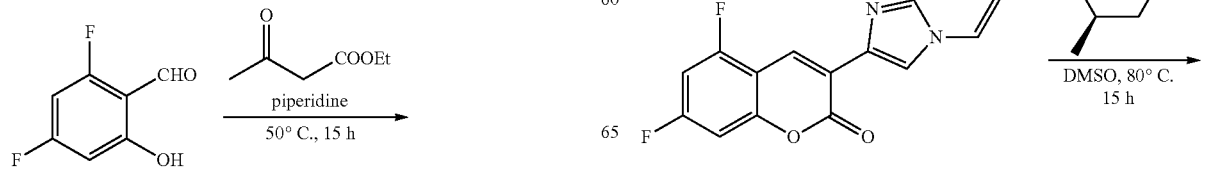

390
-continued

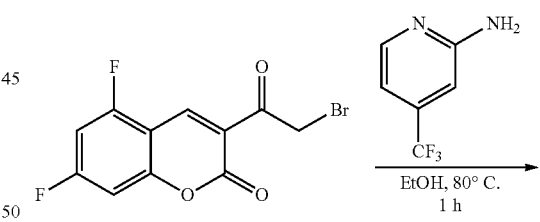

Step A: A mixture of 2,4-difluoro-6-hydroxybenzaldehyde (8 g, 50.6 mmol), ethyl acetoacetate (6.4 mL, 50.7 mmol) and piperidine (240 μL, 2.43 mmol) was heated at 50° C. for 15 h. The reaction mixture was cooled to room temperature, and then suspended in ether. The mixture was filtered. The solid material was purified by silica gel column chromatography (50-70% $CH_2Cl_2$ in hexanes), yielding 3-acetyl-5,7-difluoro-2H-chromen-2-one (4.45 g, 39%) as an off-white solid. $^1H$ NMR (500 MHz, $CDCl_3$): δ 8.69 (1H, s), 6.93 (1H, dt, J=9 Hz, 2 Hz), 6.84 (1H, td, J=9 Hz, 2 Hz), 2.72 (3H, s).

Step B: A mixture of 3-acetyl-5,7-difluoro-2H-chromen-2-one (4.25 g, 19.0 mmol), tetrabutylammonium tribromide (9.85 g, 20.4 mmol) and THF (77 mL) was stirred at room temperature for 3 h, then the solvent was removed under vacuum. The residue was triturated with 1:1 hexane/$CH_2Cl_2$, yielding the title compound (3.31 g, 57%) as an off-white solid: MS m/z [303.0, 305.0]$[M+H]^+$; $^1H$ NMR (500 MHz, $CDCl_3$): δ 8.80 (1H, s), 6.96 (1H, m), 6.87 (1H, td, J=8.5 Hz, 2.5 Hz), 4.69 (2H, s).

Part 2: Preparation of Cpd 391

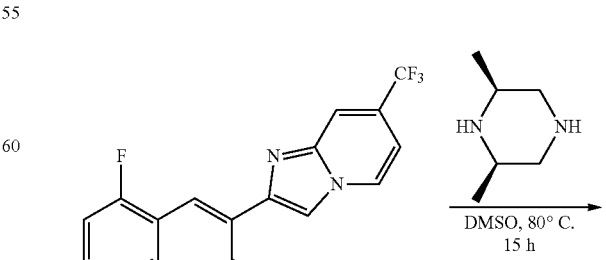

-continued

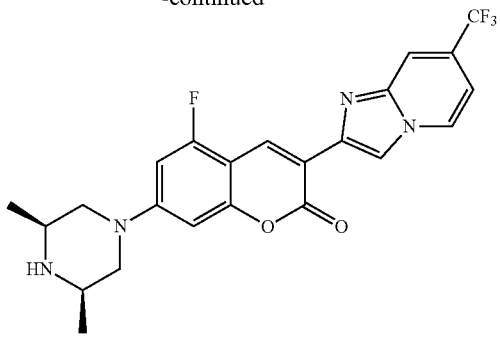

Step A: A mixture of 3-(2-bromoacetyl)-5,7-difluoro-2H-chromen-2-one (160 mg, 0.53 mmol), 4-trifluoromethyl-pyridin-2-amine (100 mg, 0.62 mmol), and EtOH (1 mL) was heated at 80° C. for 1 h. The reaction mixture was partitioned between $CH_2Cl_2$ and an aqueous saturated $NaHCO_3$ solution. The organic layer was dried over $MgSO_4$, filtered, and was concentrated under vacuum. The residue was purified by silica gel column chromatography ($CH_2Cl_2$), followed by trituration with 2:1 hexane/acetone, yielding 5,7-difluoro-3-(7-(trifluoromethyl)imidazo[1,2-a]pyridin-2-yl)-2H-chromen-2-one (92 mg, 47%) as a white solid. $^1$H NMR (500 MHz, $CDCl_3$): δ 8.98 (1H, s), 8.64 (1H, s), 8.27 (1H, d, J=7.5 Hz), 7.95 (1H, s), 7.01 (1H, dd, J=7 Hz, 1.5 Hz), 6.96 (1H, d, J=9 Hz), 6.86 (1H, td, J=9 Hz, 2.5 Hz).

Step B: A mixture of 5,7-difluoro-3-(7-(trifluoromethyl) imidazo[1,2-a]pyridin-2-yl)-2H-chromen-2-one (60 mg, 0.16 mmol), cis-2,6-dimethylpiperazine (27 mg, 0.24 mmol) and DMSO (300 μL) was heated at 80° C. for 15 h. The addition of an aqueous saturated $NaHCO_3$ solution resulted in the formation of a precipitate. The precipitate was collected by vacuum filtration and purified by silica gel column chromatography (5% MeOH in $CH_2Cl_2$), yielding the title compound (58 mg, 79%) as a yellow solid: m.p. 210-219° C.; MS m/z 461.3 [M+H]$^+$; $^1$H NMR (500 MHz, DMSO-d$_6$): δ 8.85 (1H, d, J=7 Hz), 8.72 (1H, s), 8.65 (1H, s), 8.08 (1H, s), 7.20 (1H, dd, J=7 Hz, 2 Hz), 6.96 (1H, dd, J=9 Hz, 2 Hz), 6.78 (1H, d, J=1.5 Hz), 3.88 (2H, d, J=12 Hz), 2.76 (2H, m), 2.37 (2H, t, J=11 Hz), 2.31 (1H, br s), 1.04 (6H, d, J=6.5 Hz).

As shown in Table 1 below, additional compounds disclosed herein may be prepared according to Example 56 by substituting the appropriate starting materials, reagents and reaction conditions.

Example 57

Preparation of Cpd 529

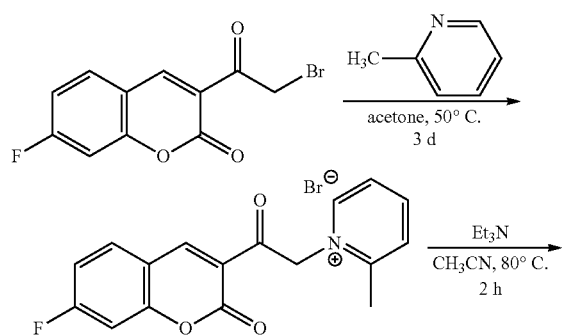

-continued

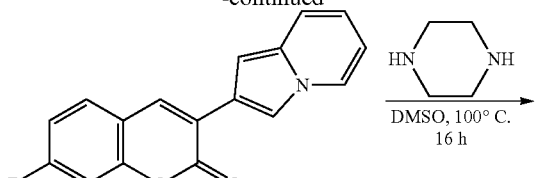

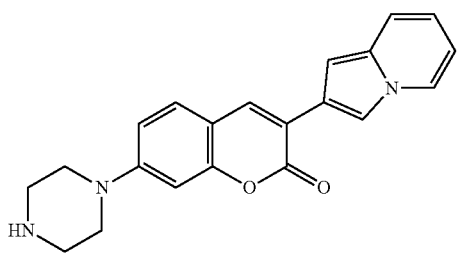

Step A: A mixture of 3-(2-bromoacetyl)-7-fluoro-2H-chromen-2-one (570 mg, 2 mmol, prepared in Example 36, Part 2) and 2-methylpyridine (186 mg, 2 mmol) in anhydrous acetone (2 mL) was heated to 50° C. for 16 h in a sealed tube. After cooling to room temperature, the reaction mixture was filtered. The collected material was washed with a small amount of $CH_3CN$ to provide 1-(2-(7-fluoro-2-oxo-2H-chromen-3-yl)-2-oxoethyl)-2-methyl-pyridinium bromide (590 mg, 78%) as a light brown solid. MS m/z 298.1 [M+H]$^+$.

Step B: 1-(2-(7-Fluoro-2-oxo-2H-chromen-3-yl)-2-oxo-ethyl)-2-methyl-pyridinium bromide (590 mg, 1.6 mmol) was suspended in $CH_3CN$ (10 mL) and triethylamine (2.5 mL). The mixture was heated at reflux for 2 h. After cooling to room temperature, the mixture was filtered. The collected material was washed with $CH_3CN$ to provide 7-fluoro-3-(indolizin-2-yl)-2H-chromen-2-one (360 mg, 83%) as a yellow solid. MS m/z 280.2 [M+H]$^+$; $^1$H NMR (500 MHz, DMSO-d$_6$): δ 8.54 (1H, s), 8.33 (1H, dd, J=7.0 Hz, 1 Hz), 8.29 (1H, d, J=1 Hz), 7.85 (1H, m), 7.45-7.42 (2H, m), 7.30 (1H, td, J=8.5 Hz, 2.5 Hz), 6.94 (1H, s), 6.74 (1H, m), 6.55 (1H, td, J=7.0 Hz, 1.5 Hz).

Step C: A mixture of 7-fluoro-3-(indolizin-2-yl)-2H-chromen-2-one (60 mg, 0.21 mmol) and piperazine (36 mg, 0.42 mmol) in anhydrous DMSO (0.3 mL) was heated to 60° C. for 16 h in a sealed tube. The mixture was purified by column chromatography on basic alumina (0-10% MeOH in $CH_2Cl_2$) to provide the title compound (39 mg, 52%) as a brown solid: m.p. 186-188° C.; MS m/z 346.4 [M+H]$^+$; $^1$H NMR (500 MHz, DMSO-d$_6$): δ 8.35 (1H, s), 8.29 (1H, dd, J=7.0 Hz, 1 Hz), 8.22 (1H, d, J=2.5 Hz), 7.55 (1H, d, J=8.5 Hz), 7.38 (1H, d, J=8.5 Hz), 7.0 (1H, dd, J=8.5 Hz, 2.5 Hz), 6.88 (1H, s), 6.84 (1H, d, J=2.5 Hz), 6.70 (1H, m), 6.52 (1H, m), 3.29-3.27 (4H, m), 2.85-2.84 (4H, m).

As shown in Table 1 below, additional compounds disclosed herein may be prepared according to Example 57 by substituting the appropriate starting materials, reagents and reaction conditions.

Example 58

Preparation of Cpd 588

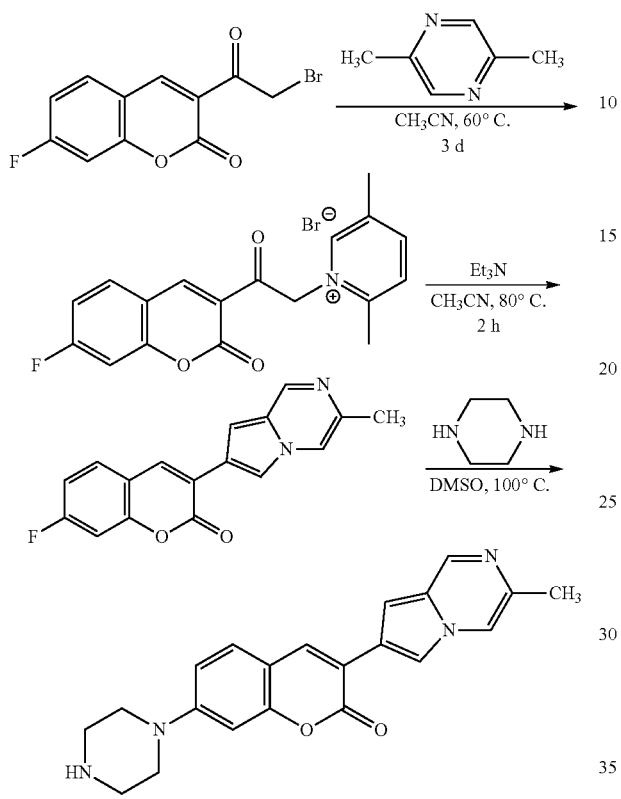

Step A: A mixture of 3-(2-bromoacetyl)-7-fluoro-2H-chromen-2-one (1.0 g, 3.5 mmol) and 2,5-dimethylpyrazine (750 mg, 7.0 mmol, prepared in Example 36, Part 2) in anhydrous $CH_3CN$ (4 mL) was heated to 60° C. for 3 d in a sealed tube. After cooling to room temperature, the reaction mixture was filtered. The collected material was washed with a small amount of $CH_3CN$ to provide crude 1-(2-(7-fluoro-2-oxo-2H-chromen-3-yl)-2-oxoethyl)-2,5-dimethyl-pyrazin-1-ium bromide (1.8 g) as a light brown solid. MS m/z 313.3 $[M+H]^+$.

Step B: The crude intermediate from Step A was suspended in $CH_3CN$ (20 mL) and triethylamine (5 mL). The mixture was heated to reflux for 2 h, then cooled and filtered. The collected material was washed with a small amount of $CH_3CN$ to provide 7-fluoro-3-(indolizin-2-yl)-2H-chromen-2-one (850 mg, 83% over 2 steps) as an orange solid. MS m/z 295.3 $[M+H]^+$; $^1$H NMR (500 MHz, DMSO-$d_6$): δ 8.82 (1H, s), 8.62 (1H, s), 8.34 (1H, s), 8.16 (1H, s), 7.86 (1H, m), 7.47 (1H, d, J=2.5 Hz), 7.34-7.31 (2H, m), 2.37 (3H, s).

Step C: Following the procedure in Example 57, Step C, 7-fluoro-3-(3-methylpyrrolo[1,2-a]pyrazin-7-yl)-2H-chromen-2-one (50 mg, 0.17 mmol) and piperazine (30 mg, 0.34 mmol) in DMSO (0.5 mL) yielded the title compound (21 mg, 34%) as a yellow solid: m.p. 220° C. (dec.); MS m/z 361.4 $[M+H]^+$; $^1$H NMR (500 MHz, DMSO-$d_6$): δ 8.77 (1H, s), 8.45 (1H, s), 8.29 (1H, s), 8.14 (1H, s), 7.58 (1H, d, J=8.5 Hz), 7.28 (1H, s), 7.04 (1H, dd, J=9 Hz, 2.5 Hz), 6.90 (1H, d, J=2.5 Hz), 3.40-3.36 (4H, m), 2.99-2.97 (4H, m), 2.38 (3H, s).

As shown in Table 1 below, additional compounds disclosed herein may be prepared according to Example 58 by substituting the appropriate starting materials, reagents and reaction conditions.

Example 59

Preparation of Cpd 579

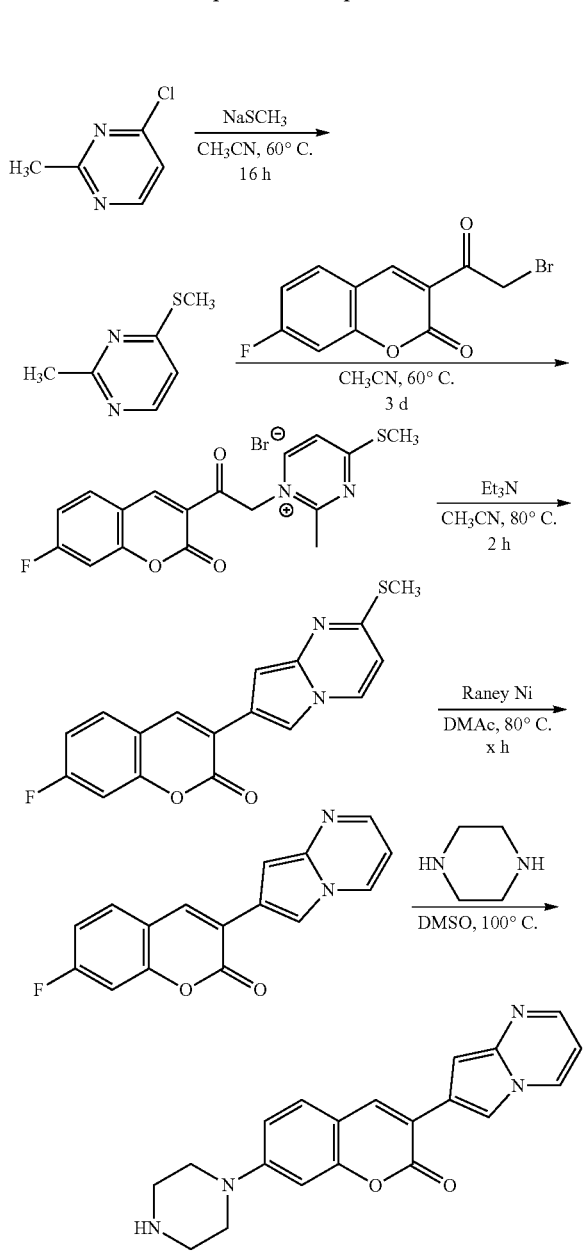

Step A: A mixture of 4-chloro-2-methylpyrimidine (512 mg, 4 mmol) and sodium methanethiolate (280 mg, 4 mmol) in anhydrous $CH_3CN$ (4 mL) was heated to 60° C. for 16 h. After cooling to room temperature, the mixture was filtered. The collected material was washed with $CH_2Cl_2$. The combined filtrate was concentrated to provide crude 2-methyl-4-(methylthio)pyrimidine, which was used in the following step without further purification.

Step B: A mixture of the crude product from Step A and 3-(2-bromoacetyl)-7-fluoro-2H-chromen-2-one (855 mg, 3.0 mmol, prepared in Example 36, Part 2) in anhydrous CH₃CN (4 mL) was heated to 60° C. for 3 days in a sealed tube. The mixture was cooled to room temperature and filtered. The collected material was washed with a small amount of CH$_3$CN to provide crude 1-(2-(7-fluoro-2-oxo-2H-chromen-3-yl)-2-oxoethyl)-2-methyl-4-(methylthio)pyrimidin-1-ium bromide (822 mg) as a light brown solid, which was used in the following step without further purification.

Step C: The crude product from Step B was suspended in CH$_3$CN (10 mL) and triethylamine (2.5 mL). The mixture was heated to reflux for 2 h, then cooled and filtered. The collected material was washed with CH$_3$CN, affording 7-fluoro-3-(2-(methylthio)pyrrolo[1,2-a]pyrimidin-7-yl)-2H-chromen-2-one (1.0 g, 77% over three steps) as a brown solid. MS m/z 327.1 [M+H]$^+$.

Step D: To a solution of 7-fluoro-3-(2-(methylthio)pyrrolo[1,2-a]pyrimidin-7-yl)-2H-chromen-2-one (100 mg, 0.31 mmol) in dimethylacetamide (3 mL) was carefully added Raney Ni (slurry in H$_2$O, ~50 mg) at 60° C. After 15 min, additional Raney Ni was added in small portions until UPLC/MS indicated complete conversion. After cooling to room temperature, the reaction mixture was filtered through Celite. The filter cake was washed with CH$_2$Cl$_2$. The filtrate was concentrated, providing 7-fluoro-3-(pyrrolo[1,2-a]pyrimidin-7-yl)-2H-chromen-2-one (60 mg, 69% yield) as a brown gummy oil. MS m/z 281.1 [M+H]$^+$; $^1$H NMR (500 MHz, DMSO-d$_6$): δ 8.75 (1H, m), 8.65 (1H, s), 8.26 (1H, d, J=1 Hz), 8.13 (1H, m), 7.86 (1H, m), 7.45 (1H, dd, J=9.5 Hz, 2.5 Hz), 7.31 (1H, td, J=8.5 Hz, 2.5 Hz), 7.07 (1H, s), 6.70 (1H, m).

Step E: Following the procedure in Example 57, Step C, 7-fluoro-3-(pyrrolo[1,2-a]pyrimidin-7-yl)-2H-chromen-2-one (60 mg, 0.21 mmol) and piperazine (36 mg, 0.42 mmol) in DMSO (0.5 mL) yielded the title compound (28 mg, 38%) as a yellow solid: m.p. 235-238° C.; MS m/z 347.2 [M+H]$^+$; $^1$H NMR (500 MHz, DMSO-d$_6$): δ 8.70 (1H, dd, J=2 Hz, 1 Hz), 8.47 (1H, s), 8.20 (1H, d, J=1.5 Hz), 8.09 (1H, dd, J=3.5 Hz, 1.5 Hz), 7.57 (1H, d, J=8.5 Hz), 7.04-7.01 (2H, m), 6.86 (1H, d, J=2.5 Hz), 6.67-6.65 (1H, m), 3.31-3.29 (4H, m), 2.87-2.85 (4H, m).

As shown in Table 1 below, additional compounds disclosed herein may be prepared according to Example 59 by substituting the appropriate starting materials, reagents and reaction conditions.

Example 60

Preparation of Cpd 641

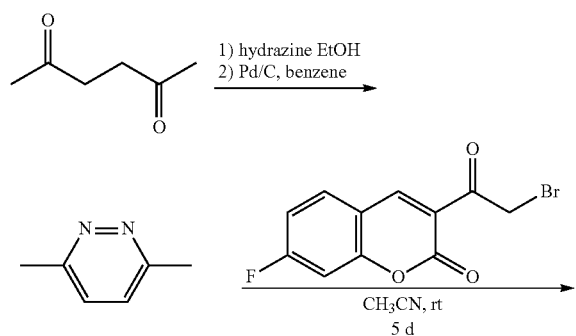

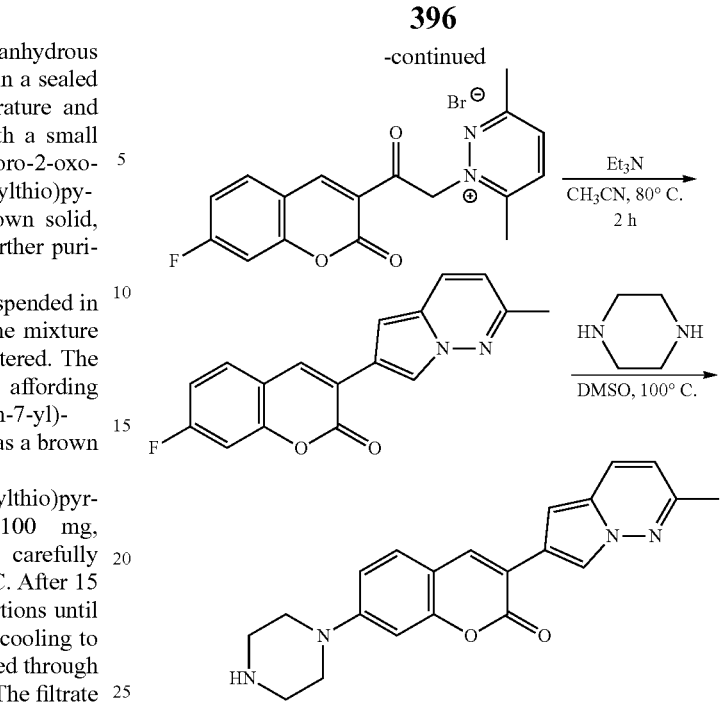

Step A: A mixture of hexane-2,5-dione (6 mL, 51 mmol) and hydrazine monohydrate (2.5 mL, 51 mmol) in ethanol (50 mL) was brought to reflux for 3 h, then the solvent was removed under reduced pressure. The residue was combined with 10% Pd/C (1.1 g) in anhydrous benzene (200 mL). The reaction mixture was heated at reflux overnight, then cooled to room temperature and filtered through a pad of Celite. The filtrate was concentrated and purified by silica gel column chromatography (6% MeOH in CH$_2$Cl$_2$) to provide 3,6-dimethylpyridazine (3.1 g, 56%) as a light brown oil. $^1$H NMR (500 MHz, CDCl$_3$): δ 7.23 (2H, s), 2.69 (6H, s).

Step B: A mixture of 3,6-dimethylpyridazine (81 mg, 0.75 mmol) and 3-(2-bromoacetyl)-7-fluoro-2H-chromen-2-one (143 mg, 0.5 mmol, prepared in Example 36, Part 2) in anhydrous CH$_3$CN (1 mL) was stirred at room temperature for 5 d in a sealed tube to afford 1-(2-(7-fluoro-2-oxo-2H-chromen-3-yl)-2-oxoethyl)-3,6-dimethylpyridazin-1-ium bromide as a crude mixture in CH$_3$CN.

Step C: The crude reaction mixture from Step B was diluted with anhydrous CH$_3$CN (2 mL) and triethylamine (1 mL). The mixture was heated at reflux for 2 h, then cooled and filtered. The collected material was washed with CH$_3$CN, affording 7-fluoro-3-(2-methylpyrrolo[1,2-b]pyridazin-6-yl)-2H-chromen-2-one (103 mg, 70%) as a brown solid. MS m/z 295.0 [M+H]$^+$.

Step D: Following the procedure in Example 57, Step C, 7-Fluoro-3-(2-methylpyrrolo[1,2-b]pyridazin-6-yl)-2H-chromen-2-one (40 mg, 0.13 mmol) and piperazine (22 mg, 0.26 mmol) in DMSO (0.5 mL) yielded the title compound (24 mg, 48%) as a light brown solid: m.p. 213-216° C.; MS m/z 361.1 [M+H]$^+$; $^1$H NMR (500 MHz, DMSO-d$_6$): δ 8.23 (1H, s), 8.15 (1H, d, J=1.5 Hz), 7.68 (1H, d, J=9 Hz), 7.39 (1H, d, J=9 Hz), 6.87-6.83 (2H, m), 6.74 (1H, d, J=2 Hz), 6.43 (1H, d, J=9 Hz), 3.27-3.22 (4H, m), 2.84-2.83 (4, m), 2.33 (3H, s).

As shown in Table 1 below, additional compounds disclosed herein may be prepared according to Example 60 by substituting the appropriate starting materials, reagents and reaction conditions.

Example 61

Preparation of Cpd 630

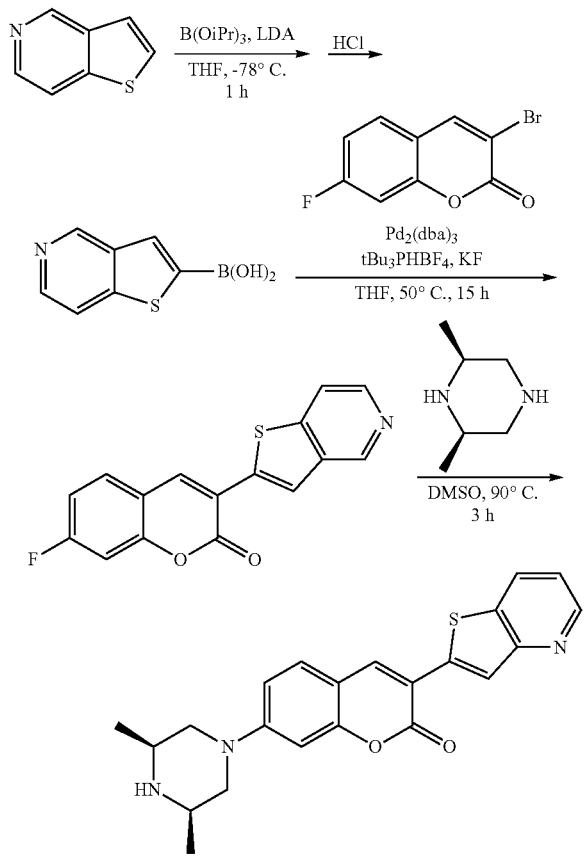

Step A: To an oven dry round bottom flask were added thieno-5-pyridine (0.6 g, 4.4 mmol), triisopropyl borate (1.38 mL, 6.8 mmol) and THF (16 mL). The mixture was cooled to −78° C. under nitrogen before the addition of LDA (3.6 mL, 1.5 M, 5.2 mmol) with stirring. After 1 h the reaction mixture was poured onto ice water (20 mL) and acidified to pH 2 with 2 N HCl. The precipitate was collected by filtration, washed with water and dried to provide thieno-5-pyridine-2-boronic acid (0.7 g, 88%). MS m/z 135.0 [M+H]$^+$.

Step B: A mixture of thieno-5-pyridine-2-boronic acid (0.59 g, 3.29 mmol), 3-bromo-7-fluoro-2H-chromen-2-one (1.0 g, 4.12 mmol, prepared in Example 32, Step A), tris(dibenzylideneacetone)dipalladium(0) (0.19 g, 0.21 mmol), tri-tert-butylphosphonium tetrafluoroborate (0.14 g, 0.49 mmol) and potassium fluoride (1.21 g, 20.57 mmol) in THF (10 mL) was stirred at 50° C. under Argon for 15 h. The mixture was then diluted with 10% MeOH in CH$_2$Cl$_2$ (100 mL) and filtered through Celite. The filtrate was concentrated. The residue was washed with CH$_2$Cl$_2$ and dried to give 7-fluoro-3-(thieno[3,2-c]pyridin-2-yl)-2H-chromen-2-one (0.43 g, 43%). MS m/z 298.0 [M+H]$^+$.

Step C: A mixture of 7-fluoro-3-(thieno[3,2-c]pyridin-2-yl)-2H-chromen-2-one (75 mg, 0.25 mmol), (2S,6R)-2,6-dimethylpiperazine (57 mg, 0.50 mmol) and DMSO (1.0 mL) was stirred at 90° C. overnight. The mixture was cooled to room temperature and diluted with water (10 mL) to produce a precipitate. The precipitate was collected by filtration, washed with water and ethyl ether, and then dried to give the title compound (20 mg, 21%): m.p. 163-165° C.; MS 392.3 m/z [M+H]$^+$; $^1$H NMR (500 MHz, DMSO-d$_6$): δ 9.11 (1H, d, J=1.0 Hz), 8.60 (1H, s), 8.39 (1H, d, J=5.4 Hz), 8.19 (1H, s), 8.03 (1H, d, J=5.7 Hz), 7.62 (1H, d, J=8.8 Hz), 7.07 (1H, dd, J=8.8 Hz, 2.2 Hz), 6.91 (1H, d, J=2.5 Hz), 3.93-3.85 (2H, m), 2.84-2.74 (2H, m), 2.41-2.33 (2H, m), 1.04 (6H, d, J=6.3 Hz).

As shown in Table 1 below, additional compounds disclosed herein may be prepared according to Example 61 by substituting the appropriate starting materials, reagents and reaction conditions.

Example 62

Preparation of Cpd 705

Part 1: Preparation of 4-chloro-5-iodo-2,6-dimethylpyrimidine

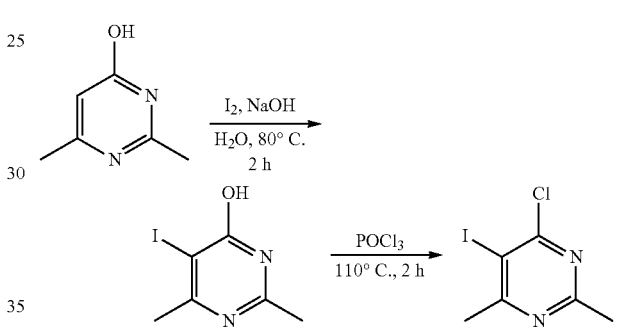

Step A: 2,6-Dimethylpyrimidin-4-ol (5.0 g, 40 mmol) was dissolved in aqueous NaOH solution (50 mL, 1 M, 50 mmol). To the solution was added iodine (10.2 g, 40 mmol). The mixture was gradually heated to 80° C. and stirred for 2 h. After cooling the mixture to room temperature, acetic acid was added to adjust the pH ~6. A precipitate formed and was collected by filtration. The solid was washed with water and dried to give 5-iodo-2,6-dimethylpyrimidin-4-ol (6.51 g, 65%). MS m/z 251.2 [M+H]$^+$.

Step B: 5-Iodo-2,6-dimethylpyrimidin-4-ol (4.6 g, 18.4 mmol) was combined with phosphorus oxychloride (15 mL). The mixture was stirred at 110° C. for 2 h, then the solvent was removed under vacuum. The residue was dissolved in CH$_2$Cl$_2$ and washed with an aqueous saturated NaHCO$_3$ solution and brine. The organic layer was concentrated and purified by silica gel column chromatography (0-10% EtOAc in CH$_2$Cl$_2$) to give the title compound (3.86 g, 78%) as colorless oil that solidified on standing. MS m/z 269.2 [M+H]$^+$.

Part 2: Preparation of Cpd 705

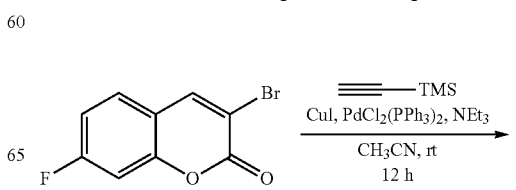

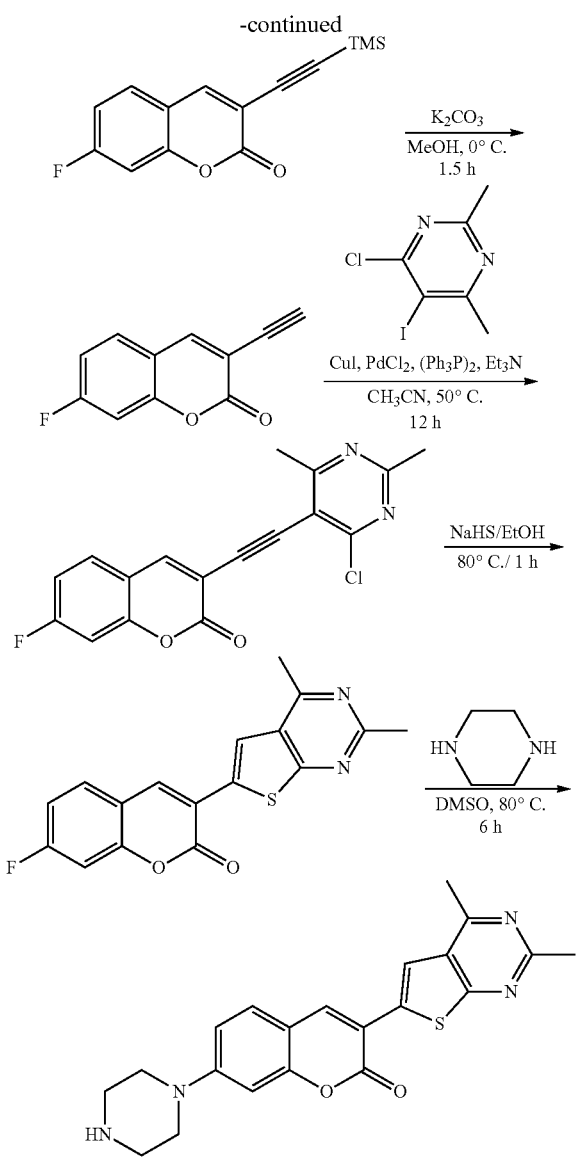

Step A: A mixture of 3-bromo-7-fluorocoumarin (1.82 g, 7.5 mmol, prepared in Example 38, Step A), ethynyltrimethylsilane (0.88 g, 9.0 mmol), copper(I) iodide (0.071 g, 0.38 mmol), bis(triphenylphosphine)palladium(II) dichloride (0.26 g, 0.38 mmol), triethylamine (1.52 g, 15.0 mmol) and CH$_3$CN (15 mL) was stirred under an Argon atmosphere at room temperature for 12 h, then the solvent was removed. The residue was purified by silica gel column chromatography (0-50% EtOAc in hexanes) to give 7-fluoro-3-((trimethylsilyl)ethynyl)-2H-chromen-2-one as white solid, used directly for the next step. MS m/z 261.2 [M+H]$^+$.

Step B: The intermediate obtained in Step A was dissolved in MeOH (50 mL) and cooled in an ice-water bath. K$_2$CO$_3$ (1.55 g, 11.25 mmol) was added and the mixture was stirred at 0° C. for 1.5 h. Saturated aqueous NH$_4$Cl (200 mL) was added to produce a precipitate. The precipitate was collected, washed with water, dried and purified by silica gel column chromatography (0-10% EtOAc in CH$_2$Cl$_2$) to give 3-ethynyl-7-fluoro-2H-chromen-2-one (1.14 g, 81% two steps) as white needles. MS m/z 189.2 [M+H]$^+$.

Step C: A mixture of 3-ethynyl-7-fluoro-2H-chromen-2-one (376 mg, 2.0 mmol), 4-chloro-5-iodo-2,6-dimethylpyrimidine (590 mg, 2.2 mmol), copper(I) iodide (19 mg, 0.1 mmol), bis(triphenylphosphine)palladium(II) dichloride (70 mg, 0.1 mmol), triethylamine (404 mg, 4.0 mmol) and CH$_3$CN (4.0 mL) was stirred at 50° C. under an Argon atmosphere overnight, then the solvent was removed under reduced pressure. The residue was purified by silica gel column chromatography (5% MeOH in CH$_2$Cl$_2$) to give 3-((4-chloro-2,6-dimethylpyrimidin-5-yl)ethynyl)-7-fluoro-2H-chromen-2-one (92 mg, 14%). MS m/z 329.3 [M+H]$^+$.

Step D: 3-((4-Chloro-2,6-dimethylpyrimidin-5-yl)ethynyl)-7-fluoro-2H-chromen-2-one (92 mg, 0.28 mmol) was stirred with sodium hydrosulfide (47 mg, 0.84 mmol) in EtOH (2.0 mL) at 80° C. for 1 h. The mixture was cooled to room temperature and diluted with water (8 mL) to produce a precipitate. The precipitate was collected, washed with water and dried to give 3-(2,4-dimethylthieno[2,3-d]pyrimidin-6-yl)-7-fluoro-2H-chromen-2-one as white powder (66 mg, 73%). MS m/z 327.3 [M+H]$^+$.

Step E: 3-(2,4-Dimethylthieno[2,3-d]pyrimidin-6-yl)-7-fluoro-2H-chromen-2-one (66 mg, 0.2 mmol), piperazine (43 mg, 0.5 mmol) in DMSO (0.5 mL) was stirred at 80° C. for 6 h. The mixture was cooled to room temperature and diluted with water (6 mL) to produce a precipitate. The precipitate was collected, washed with water and dried to give the title compound (75 mg, 96%) as yellow powder: m.p. 275° C. (decomp.); MS m/z 393.1 [M+H]$^+$; $^1$H NMR (500 MHz, DMSO-d$_6$): δ 8.65 (1H, s), 8.15 (1H, s), 7.60 (1H, d, J=8.83 Hz), 7.05 (1H, dd, J=9.0 Hz, 2.4 Hz), 6.89 (1H, d, J=2.5 Hz), 3.38-3.33 (4H, m), 2.84-2.79 (4H, m), 2.74 (3H, s), 2.66 (3H, s).

Example 63

Preparation of Cpd 698

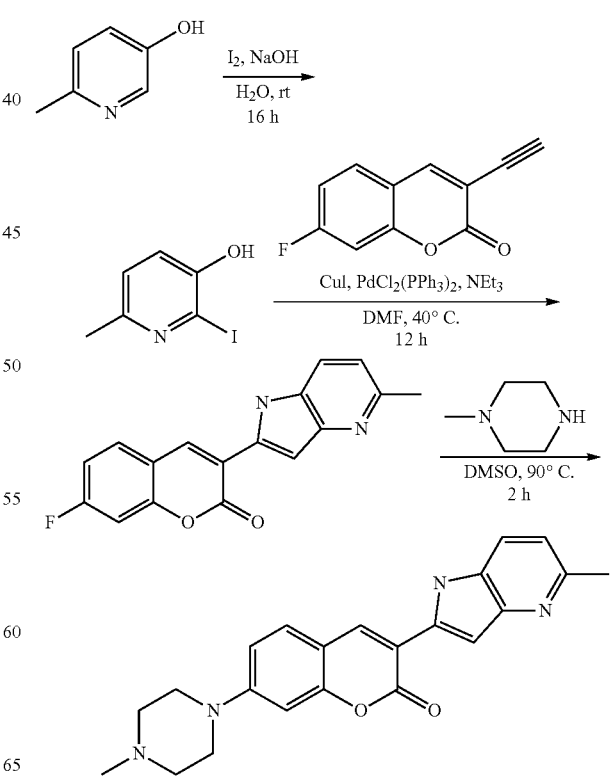

Step A: 6-Methylpyridin-3-ol (0.5 g, 4.58 mmol) was dissolved in aqueous NaOH (4.5 mL, 1 M, 4.5 mmol). To the solution was added iodine (1.28 g, 5.2 mmol) and the mixture was stirred at room temperature overnight. The mixture was neutralized with aqueous HCl (2 M) to pH ~7. A white precipitate formed and was collected by filtration. The solid was washed with water and dried to give 2-iodo-6-methylpyridin-3-ol (0.8 g, 50%). MS m/z 236.0 [M+H]$^+$.

Step B: A mixture of 2-iodo-6-methylpyridin-3-ol (325 mg, 1.38 mmol) and 3-ethynyl-7-fluoro-2H-chromen-2-one (200 mg, 1.06 mmol, prepared in Example 62, Part 2), bis(triphenylphosphine)palladium(II) dichloride (37 mg, 0.05 mmol), copper(I) iodide (10 mg, 0.05 mmol), triethylamine (0.25 mL, 2.12 mmol) in CH$_3$CN (3.0 mL) was stirred under an Argon atmosphere at 40° C. for 4 h. The mixture was diluted with water (50 mL) to produce a precipitate. The precipitate was collected, washed with ethyl ether and dried to give 3-(5-methylfuro[3,2-b]pyridin-2-yl)-7-(piperazin-1-yl)-2H-chromen-2-one (142 mg, 48%). MS m/z 297.2 [M+H]$^+$.

Step C: A mixture of 3-(5-Methylfuro[3,2-b]pyridin-2-yl)-7-(piperazin-1-yl)-2H-chromen-2-one (100 mg, 0.33 mmol), 1-methylpiperazine (67 mg, 0.67 mmol) in DMSO (1 mL) was stirred at 90° C. for 2 h. The mixture was cooled to room temperature and diluted with water (10 mL) to produce a precipitate. The precipitate was collected by filtration, washed with water and dried to give the title compound (99 mg, 80%) as a yellow solid: m.p. 178-180° C.; MS 376.0 m/z [M+H]$^+$; $^1$H NMR (500 MHz, CDCl$_3$): δ 8.22 (1H, s), 7.64 (1H, d, J=0.95 Hz), 7.54 (1H, dd, J=8.5 Hz, 1.0 Hz), 7.39 (1H, d, J=8.8 Hz), 7.00 (1H, d, J=8.5 Hz), 6.80 (1H, dd, J=8.8 Hz, 2.5 Hz), 6.68 (1H, d, J=2.2 Hz), 3.38-3.33 (4H, m), 2.59 (3H, s), 2.54-2.47 (4H, m), 2.30 (3H, s).

As shown in Table 1 below, additional compounds disclosed herein may be prepared according to Example 63 by substituting the appropriate starting materials, reagents and reaction conditions.

Example 64

Preparation of Cpd 723

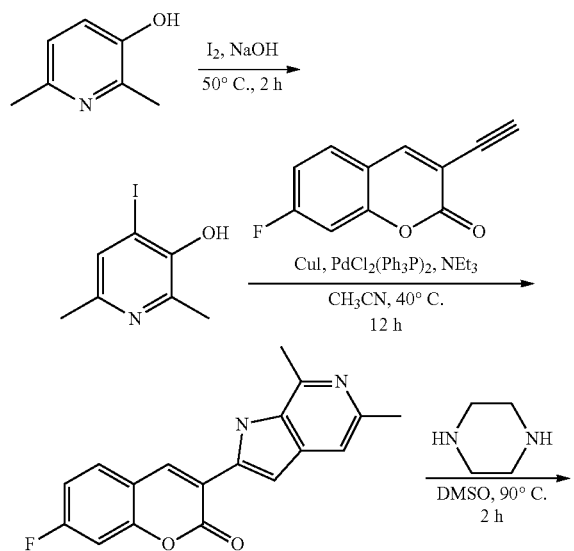

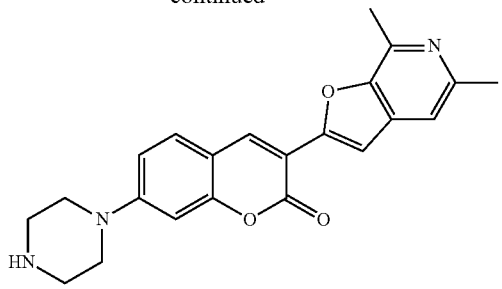

Step A: 2,6-Dimethylpyridin-3-ol (1.0 g, 8.1 mmol) was dissolved in aqueous NaOH (4.05 mL, 2 M, 8.1 mmol). To the solution was added iodine (2.62 g, 10.3 mmol) at room temperature. The mixture was stirred at 50° C. for 2 h, then neutralized (pH ~7) with aqueous HCl (2 N). Excess reagent was quenched with sodium thiosulfate, then the solvent was removed under vacuum. The residue was suspended in 10% MeOH in CH$_2$Cl$_2$ (100 mL) and filtered. The filtrate was concentrated to give 4-iodo-2,6-dimethylpyridin-3-ol (0.96 g, 50%). MS m/z 250.0 [M+H]$^+$.

Step B: A mixture of 4-iodo-2,6-dimethylpyridin-3-ol (343 mg, 1.38 mmol), 3-ethynyl-7-fluoro-2H-chromen-2-one (200 mg, 1.06 mmol, prepared in Example 62, Step B), bis(triphenylphosphine)palladium(II) dichloride (37 mg, 0.05 mmol), copper(I) iodide (10 mg, 0.05 mmol), triethylamine (0.25 mL, 2.12 mmol) in DMF (3.0 mL) was stirred under an Argon atmosphere at 40° C. overnight. The mixture was diluted with water (50 mL) to produce a precipitate. The precipitate was collected to give 3-(5,7-dimethylfuro[2,3-c]pyridin-2-yl)-7-fluoro-2H-chromen-2-one (185 mg, 60%). MS m/z 311.2 [M+H]$^+$.

Step C: A mixture of 3-(5,7-dimethylfuro[2,3-c]pyridin-2-yl)-7-fluoro-2H-chromen-2-one (100 mg, 0.32 mmol), piperazine (58 mg, 0.67 mmol) in DMSO (1.0 mL) was stirred at 90° C. for 2 h. The mixture was cooled to room temperature and diluted with water (10 mL) to produce a precipitate. The precipitate was collected by filtration, washed with water and dried to give the title compound (89 mg, 74%) as yellow powder: m.p. 218-220° C.; MS 376.0 m/z [M+H]$^+$; $^1$H NMR (500 MHz, CDCl$_3$): δ 8.36 (1H, s), 7.56-7.49 (2H, m), 7.21 (1H, s), 6.92-6.87 (1H, m), 6.77-6.74 (1H, m), 3.39 (4H, m, J=10.4 Hz), 3.09-3.03 (4H, m), 2.79 (3H, s), 2.61 (3H, s).

As shown in Table 1 below, additional compounds disclosed herein may be prepared according to Example 64 by substituting the appropriate starting materials, reagents and reaction conditions.

Example 65

Preparation of Cpd 321

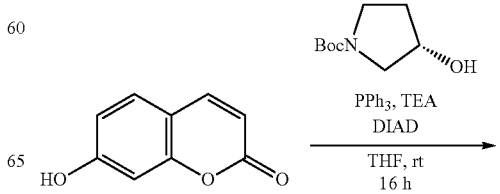

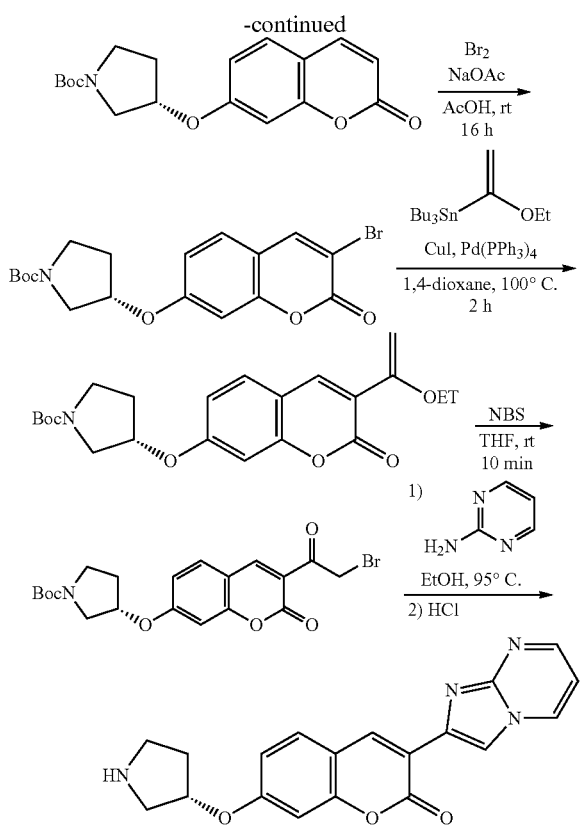

Step A: Diisopropyl azodicarboxylate (5.5 mL, 28 mmol) was added dropwise to a mixture of 7-hydroxycoumarin (4.6 g, 28 mmol), (R)-tert-butyl 3-hydroxypyrrolidine-1-carboxylate (6.0 g, 31 mmol), triphenylphosphine (7.4 g, 28 mmol) and triethylamine (3.9 mL, 28 mmol) in THF (28 mL) at 0° C. The mixture was stirred at room temperature overnight. The solids were removed by filtration and washed with cold THF. The solid was dissolved in EtOAc. The solution was washed with aqueous HCl (0.5 N), dried over $NaSO_4$, then filtered and concentrated to give (S)-tert-butyl 3-(2-oxo-2H-chromen-7-yloxy)pyrrolidine-1-carboxylate (4.85 g, 52%) as a pale yellow solid. MS m/z 232.2 [M-Boc+H]$^+$.

Step B: Into a mixture of (S)-tert-butyl 3-(2-oxo-2H-chromen-7-yloxy)pyrrolidine-1-carboxylate (1.5 g, 3.6 mmol) and sodium acetate (1.0 g, 12.8 mmol) in acetic acid (11.0 mL) was added bromine (0.186 mL, 3.6 mmol) dropwise at room temperature. The mixture was stirred at room temperature overnight, then the solvent was removed and the residue was purified by silica gel column chromatography (0-60% EtOAc in hexanes) to afford (S)-tert-butyl 3-(3-bromo-2-oxo-2H-chromen-7-yloxy)pyrrolidine-1-carboxylate (2.9 g, 80%) as a pale yellow solid. MS m/z 312.1 [M-Boc+H]$^+$.

Step C: A mixture of (S)-tert-butyl 3-(3-bromo-2-oxo-2H-chromen-7-yloxy)pyrrolidine-1-carboxylate (1.2 g, 2.9 mmol), tributyl(1-ethoxyvinyl)stannane (1.2 g, 3.2 mmol), copper(I) iodide (0.13 g, 0.7 mmol) and tetrakis(triphenylphosphine)palladium(0) (0.34 g, 0.29 mmol) in 1,4-dioxane (30 mL) was stirred at 100° C. for 2 h under Argon. The mixture was partitioned between EtOAc and water. The organic layer was washed with brine, dried over $NaSO_4$, filtered and concentrated. The residue was purified by silica gel column chromatography (0-35% EtOAc in $CH_2Cl_2$) to afford (S)-tert-butyl 3-(3-(1-ethoxyvinyl)-2-oxo-2H-chromen-7-yloxy)pyrrolidine-1-carboxylate (1.84 g, 65%) as a pale yellow solid. MS m/z 402.3 [M+H]$^+$.

Step D: Into a solution of (S)-tert-butyl 3-(3-(1-ethoxyvinyl)-2-oxo-2H-chromen-7-yloxy)pyrrolidine-1-carboxylate (0.78 g, 1.84 mmol) in THF (10 mL) and water (1 mL) was added N-bromosuccinimide (0.344 g, 1.93 mmol) portionwise. The mixture was stirred at room temperature for 10 min then partitioned between EtOAc and an aqueous saturated $NaHCO_3$ solution. The organic layer was washed with brine, dried over $NaSO_4$, filtered and concentrated. The residue was purified by silica gel column chromatography (0-30% EtOAc in $CH_2Cl_2$) to afford (S)-tert-butyl 3-(3-(2-bromoacetyl)-2-oxo-2H-chromen-7-yloxy)pyrrolidine-1-carboxylate (0.77 g, 90%) as a pale yellow solid. MS m/z 454.1 [M+H]$^+$.

Step E: A mixture of (S)-tert-butyl 3-(3-(2-bromoacetyl)-2-oxo-2H-chromen-7-yloxy)pyrrolidine-1-carboxylate (100 mg, 0.21 mmol) and 2-aminopyrimidine (20 mg, 0.21 mmol) in EtOH (0.6 mL) was stirred at 95° C. for 10 h in a sealed tube. The mixture was cooled to room temperature and diluted with an aqueous saturated $NaHCO_3$ solution (2.0 mL) to produce a precipitate. The solid was collected by vacuum filtration, washed with water and dried to give (S)-tert-butyl 3-(3-(2-bromoacetyl)-2-oxo-2H-chromen-7-yloxy)pyrrolidine-1-carboxylate, which was dissolved in a solution of 4 N HCl in dioxane (1.0 mL, 4.0 mmol). The mixture was stirred for 1 h at room temperature, then solvent was removed. The residue was suspended in acetone, collected by vacuum filtration and dried to give the title compound as the hydrochloride salt (61 mg, 70%) as an off white solid: m.p. 240-250° C.; MS m/z 349.2 [M+H]$^+$; $^1$H NMR (500 MHz, MeOD-$d_4$): δ 9.27 (1H, dd, J=1.6, 6.8 Hz), 9.07 (1H, dd, J=1.6, 4.4 Hz), 8.83 (1H, s), 8.64 (1H, s), 7.83 (1H, d, J=8.2 Hz), 7.67 (1H, dd, J=4.4, 7.0 Hz), 7.17-7.12 (2H, m), 5.45-5.40 (1H, m), 3.76-3.46 (4H, m), 2.49-2.35 (2H, m).

As shown in Table 1 below, additional compounds disclosed herein may be prepared according to Example 65 by substituting the appropriate starting materials, reagents and reaction conditions.

Example 66

Preparation of Cpd 20

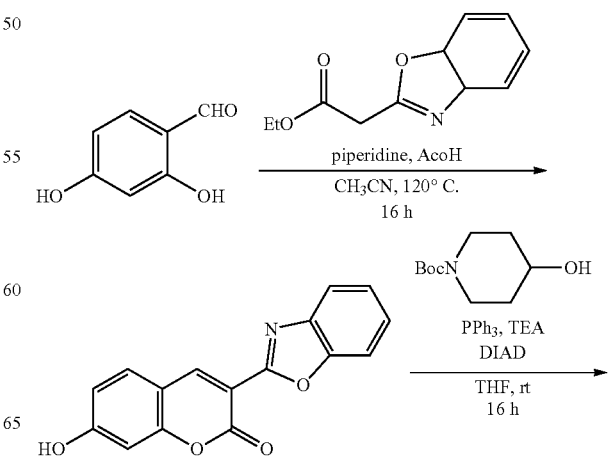

405
-continued

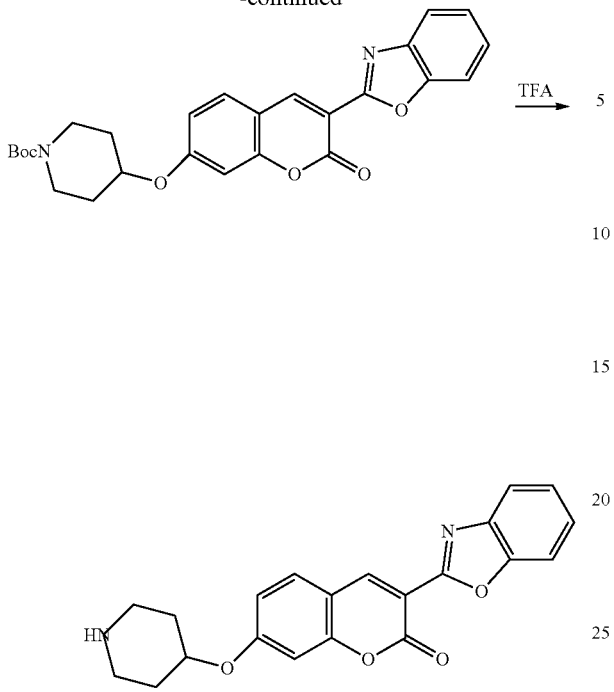

Step A: A mixture of 2,4-dihydroxybenzaldehyde (141 mg, 1.0 mmol), ethyl 2-(benzo[d]oxazol-2-yl)acetate (195 mg, 0.95 mmol, prepared according to Example 1, Part 1), piperidine (86 mg µL, 1.0 mmol) and acetic acid (305 mg, 5.0 mmol) in CH$_3$CN (1.0 mL) was stirred at 120° C. overnight, then the solvent was removed. The residue was suspended in water, collected by vacuum filtration, washed with CH$_3$CN and dried to yield 3-(benzo[d]oxazol-2-yl)-7-hydroxy-2H-chromen-2-one (211 mg, 76%) as a gray solid. MS m/z 280.1 [M+H]$^+$.

Step B: Following the procedure in Example 65, Step A, 3-(benzo[d]oxazol-2-yl)-7-hydroxy-2H-chromen-2-one (280 mg, 1.0 mmol), tert-Butyl 4-hydroxypiperidine-1-carboxylate (227 mg, 1.1 mmol), diisopropyl azodicarboxylate (0.20 mL, 1.0 mmol), triphenylphosphine (0.27 g, 1.0 mmol), triethylamine (0.14 mL, 1.0 mmol) in THF (1.0 mL) yielded tert-Butyl 4-(3-(benzo[d]oxazol-2-yl)-2-oxo-2H-chromen-7-yloxy)piperidine-1-carboxylate (303 mg, 66%) as an off white solid. MS m/z 463.2 [M+H]$^+$.

Step C: tert-Butyl 4-(3-(benzo[d]oxazol-2-yl)-2-oxo-2H-chromen-7-yloxy)piperidine-1-carboxylate was dissolved in CH$_2$Cl$_2$ (2.0 mL) and trifluoroacetic acid (1.0 mL). The mixture was stirred at room temperature for 0.5 h, then the solvent was removed. The residue was suspended in aqueous K$_2$CO$_3$ (2.0 M, 5.0 mL), collected by vacuum filtration, then washed with water, and dried to give the title compound (158 mg, 67%) as a gray solid: m.p. 198-201° C.; MS m/z 363.2 [M+H]$^+$; $^1$H NMR (500 MHz, DMSO-d$_6$): δ 8.90 (1H, s), 7.81-7.76 (2H, m), 7.70 (1H, d, J=7.5 Hz), 7.49-7.39 (2H, m), 7.08-7.03 (2H, m), 4.77-4.69 (1H, m), 3.16-3.08 (2H, m), 2.86-2.78 (2H, m), 2.14-2.06 (2H, m), 1.81-1.69 (2H, m).

As shown in Table 1 below, additional compounds disclosed herein may be prepared according to Example 66 by substituting the appropriate starting materials, reagents and reaction conditions.

406

Example 67

Preparation of Cpd 626

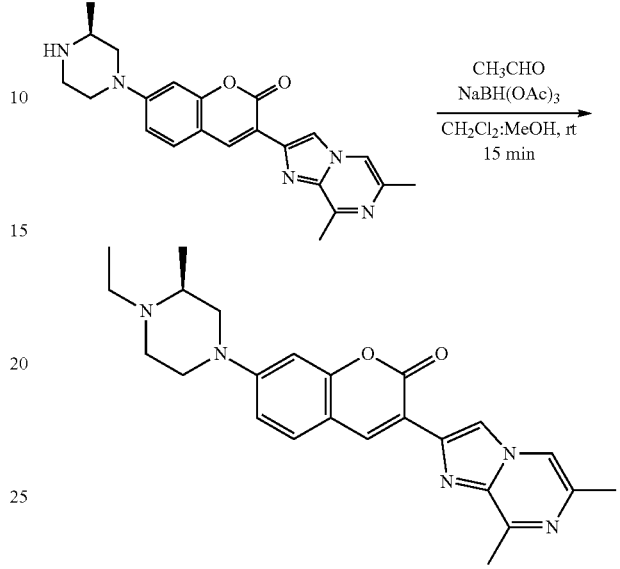

A mixture of (S)-3-(6,8-dimethylimidazo[1,2-a]pyrazin-2-yl)-7-(3-methylpiperazin-1-yl)-2H-chromen-2-one (250 mg, 0.64 mmol, analogously prepared according to the procedure of Example 43), acetaldehyde (71 µL, 1.29 mmol), sodium triacetoxyborohydride (409 mg, 1.93 mmol) in CH$_2$Cl$_2$ (10% MeOH) (10 mL) was stirred at room temperature overnight. The reaction was quenched by the addition of an aqueous saturated NaHCO$_3$ solution. The mixture was extracted with CH$_2$Cl$_2$ (10% MeOH). The organic layer was dried over NaSO$_4$, filtered, concentrated and purified by silica gel column chromatography (10% MeOH in CH$_2$Cl$_2$) to give the title compound (192 mg, 72%) as a yellow solid: m.p. 208-209° C.; MS m/z 418.1 [M+H]$^+$; $^1$H NMR (500 MHz, DMSO-d$_6$): δ 8.70 (1H, s), 8.50 (1H, s), 8.30 (1H, d, J=0.9 Hz), 7.73 (1H, d, J=8.8 Hz), 7.02 (1H, s), 6.88 (1H, d, J=1.9 Hz), 3.73 (2H, s), 3.11-2.97 (1H, m), 2.91-2.82 (1H, m), 2.74 (5H, m), 2.48-2.40 (1H, m), 2.35-2.21 (5H, m), 1.06 (3H, d, J=6.3 Hz), 0.98 (3H, t)

As shown in Table 1 below, additional compounds disclosed herein may be prepared according to Example 67 by substituting the appropriate starting materials, reagents and reaction conditions.

Example 68

Preparation of Cpd 773

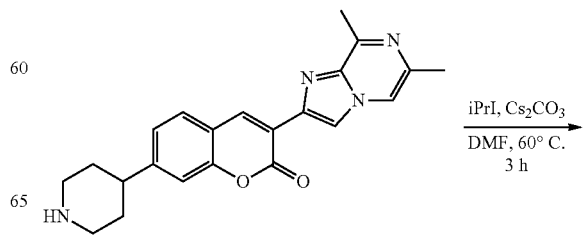

-continued

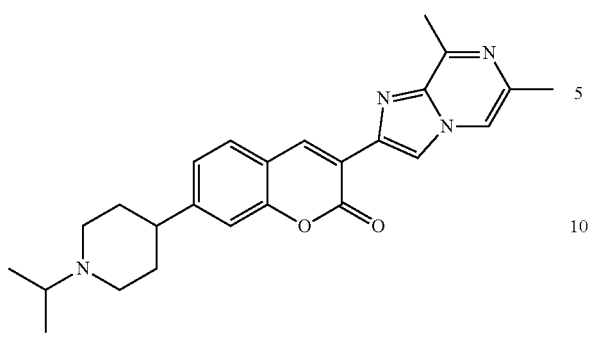

A mixture of 3-(6,8-dimethylimidazo[1,2-a]pyrazin-2-yl)-7-(piperidin-4-yl)-2H-chromen-2-one (50 mg, 0.13 mmol, prepared in Example 51), Cs₂CO₃ (150 mg, 0.46 mmol), 2-iodopropane (20 μL, 0.20 mmol) and DMF (300 μL) was heated at 60° C. for 3 h. The reaction mixture was diluted with H₂O, causing a precipitate to form. The mixture was filtered. The solid material was purified by silica gel column chromatography (5% 10:1 MeOH:NH₄OH in CH₂Cl₂), followed by trituration with 2:1 hexane:CH₂Cl₂, yielding the title compound as a tan solid: m.p. 206-211° C.; MS m/z 417.5 [M+H]⁺; ¹H NMR (500 MHz, DMSO-d₆): δ 8.85 (1H, s), 8.62 (1H, s), 8.34 (1H, s), 7.90 (1H, d, J=8 Hz), 7.34 (1H, s), 7.31 (1H, dd, J=8 Hz, 1.5 Hz), 2.91 (2H, d, J=11 Hz), 2.77 (3H, s), 2.73 (1H, m), 2.62 (1H, m), 2.38 (3H, s), 2.24 (2H, t, J=11 Hz), 1.81 (2H, d, J=12 Hz), 1.67 (2H, qd, J=12 Hz, 3.5 Hz), 1.01 (6H, d, J=6.5 Hz).

As shown in Table 1 below, additional compounds disclosed herein may be prepared according to Example 68 by substituting the appropriate starting materials, reagents and reaction conditions.

Example 69

Preparation of Cpd 825

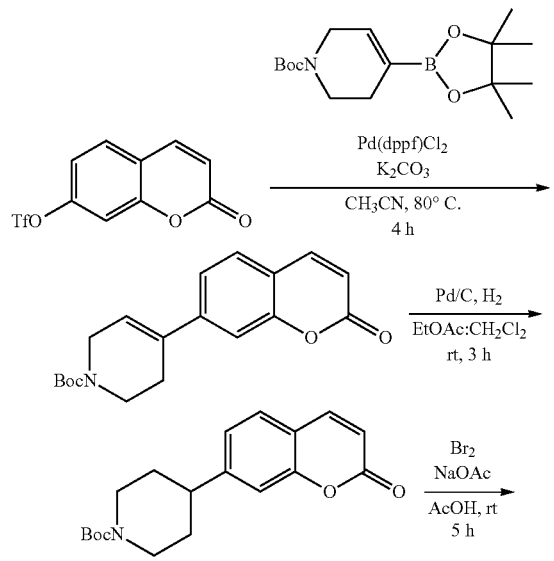

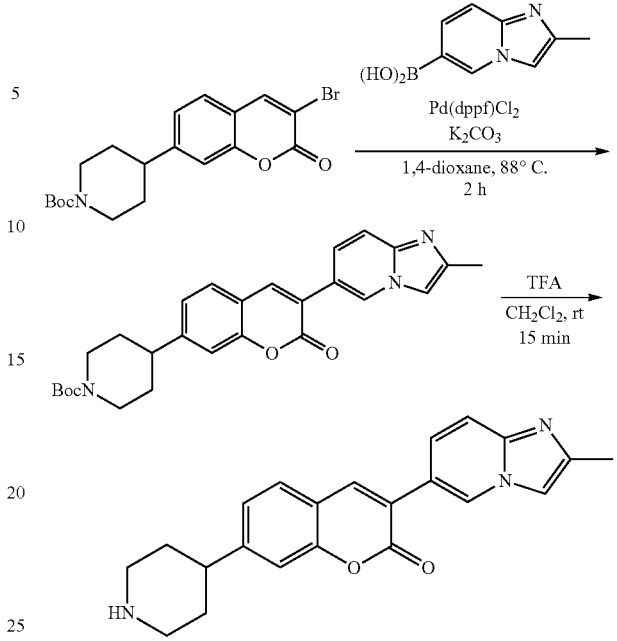

Step A: A mixture of 2-oxo-2H-chromen-7-yl trifluoromethanesulfonate (2.94 g, 10 mmol, prepared in Example 24, Step A), tert-butyl 4-(4,4,5,5-tetramethyl-1,3,2-dioxaborolan-2-yl)-5,6-dihydropyridine-1(2H)-carboxylate (3.7 g, 12 mmol), [1,1'-bis(diphenylphosphino)ferrocene]dichloropalladium(II) complex with dichloromethane (0.81 g, 1.0 mmol) and K₂CO₃ (4.14 g, 30 mmol) in CH₃CN (40 mL) was stirred at 80° C. for 4 h. The mixture was partitioned in water and EtOAc. The organic layer was dried over Na₂SO₄, then concentrated and chromatographed on silica gel, eluting with 0-10% EtOAc in CH₂Cl₂ to give tert-butyl 4-(2-oxo-2H-chromen-7-yl)-5,6-dihydropyridine-1(2H)-carboxylate (3.4 g, 100%). MS m/z 328.2 [M+H]⁺.

Step B: A solution of tert-butyl 4-(2-oxo-2H-chromen-7-yl)-5,6-dihydropyridine-1(2H)-carboxylate (3.4 g, 10 mmol) in CH₂Cl₂ (50 mL) and EtOAc (100 mL) was stirred with 5% Pd/C (0.35 g) under H₂ (1 atm) at room temperature for 3 h. The mixture was filtered. The filtrate was concentrated to give tert-butyl 4-(2-oxo-2H-chromen-7-yl)piperidine-1-carboxylate (3.4 g, 100%). MS m/z 330.2 [M+H]⁺.

Step C: Bromine (2.1 g, 13 mmol) was added dropwise at room temperature into a solution of tert-butyl 4-(2-oxo-2H-chromen-7-yl)piperidine-1-carboxylate (3.4 g, 10 mmol) and sodium acetate (2.46 g, 30 mmol) in acetic acid (15 mL). After stirring 5 h at room temperature, the mixture was diluted with water and filtered. The solid was dissolved in dichloromethane and washed with an aqueous saturated NaHCO₃ solution. The organic layer was dried over Na₂SO₄, concentrated and chromatographed on silica gel, eluting with 0-10% EtOAc in CH₂Cl₂ to give tert-butyl 4-(3-bromo-2-oxo-2H-chromen-7-yl)piperidine-1-carboxylate (0.9 g, 22%).

Step D: A mixture of tert-butyl 4-(3-bromo-2-oxo-2H-chromen-7-yl)piperidine-1-carboxylate (0.5 g, 1.23 mmol), (2-methylimidazo[1,2-a]pyridin-6-yl)boronic acid (300 mg, 1.7 mmol, prepared in Example 34, Step A), [1,1'-bis(diphenylphosphino)ferrocene]dichloropalladium(II) complex with dichloromethane (136 mg, 0.166 mmol) and K₂CO₃ (2.5 mL of a 2.0 M aqueous solution, 5.0 mmol) in 1,4-dioxane (4 mL) was heated at 88° C. for 2 h. The mixture was partitioned in EtOAc and water. The organic layer was concentrated and chromatographed on silica gel, eluting with 20-100% EtOAc in CH$_2$Cl$_2$ to provide tert-butyl 4-(3-(2-methylimidazo[1,2-a]pyridin-6-yl)-2-oxo-2H-chromen-7-yl)piperidine-1-carboxylate (0.4 g, 70%). MS m/z 460.4 [M+H]$^+$.

Step E: A solution of tert-butyl 4-(3-(2-methylimidazo[1,2-a]pyridin-6-yl)-2-oxo-2H-chromen-7-yl)piperidine-1-carboxylate (0.4 g, 0.87 mmol) in CH$_2$Cl$_2$ (2.0 mL) and TFA (2.0 mL) was stirred at room temperature for 15 min. The mixture was concentrated. The residue was partitioned in CH$_2$Cl$_2$ and aqueous K$_2$CO$_3$. The organic layer was concentrated, and then triturated with acetone to provide the title compound (0.25 g, 80%) as a gray powder. MS m/z 360.3 [M+H]$^+$; $^1$H NMR (500 MHz, DMSO-d$_6$): δ 9.01 (1H, m), 8.37 (1H, s), 7.80 (1H, s), 7.71 (1H, d, J=7.9 Hz), 7.54 (2H, m), 7.31 (2H, m), 3.04 (2H, m), 2.74 (1H, m), 2.61 (2H, m), 2.34 (3H, d, J=0.6 Hz), 1.73 (2H, m), 1.57 (2H, m).

As shown in Table 1 below, additional compounds disclosed herein may be prepared according to Example 69 by substituting the appropriate starting materials, reagents and reaction conditions.

Example 70

Preparation of Cpd 845

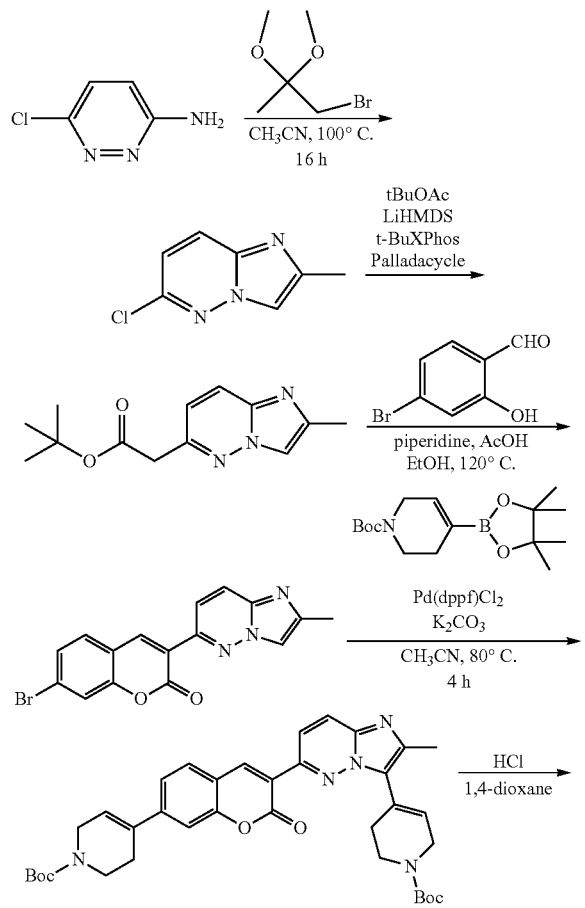

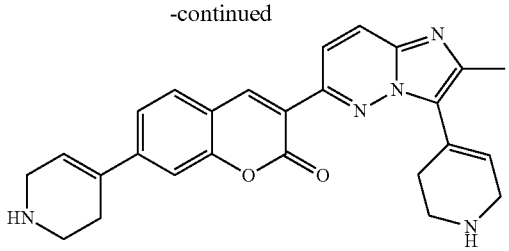

Step A: A mixture of 6-chloropyridazin-3-amine (2.6 g, 20 mmol) and 1-bromo-2,2-dimethoxypropane (4.0 g, 22 mmol) in CH$_3$CN (20 mL) was stirred at 100° C. overnight. The mixture was concentrated and chromatographed on silica gel, eluting with 20-50% EtOAc in CH$_2$Cl$_2$ to give 6-chloro-2-methylimidazo[1,2-b]pyridazine (0.53 g, 16%). MS m/z 168.1 [M+H]$^+$.

Step B: Lithium bis(trimethylsilyl)amide (8.25 mL, 1 M in toluene, 8.25 mmol) was added to a mixture of 6-chloro-2-methylimidazo[1,2-b]pyridazine (0.46 g, 2.75 mmol), t-butyl acetate (0.55 mL, 4.12 mmol) and chloro[2-(di-tert-butylphosphino)-2',4',6'-triisopropyl-1,1'-biphenyl][2-(2-aminoethyl)phenyl)]palladium(II) (47 mg, 0.069 mmol). The mixture was stirred for 5 min at room temperature, and then washed with water. The organic layer was concentrated and chromatographed on silica gel, eluting with 0-35% EtOAc in CH$_2$Cl$_2$ to give tert-butyl 2-(2-methylimidazo[1,2-b]pyridazin-6-yl)acetate (0.12 g, 18%).

Step C: A mixture of 4-bromo-2-hydroxybenzaldehyde (0.12 g, 0.6 mmol), tert-butyl 2-(2-methylimidazo[1,2-b]pyridazin-6-yl)acetate (0.12 g, 0.49 mmol), piperidine (0.145 mL, 1.47 mmol) and acetic acid (42 µL, 0.74 mmol) in ethanol (3.0 mL) was stirred at 120° C. overnight. The mixture was diluted with water and filtered, affording 7-bromo-3-(2-methylimidazo[1,2-b]pyridazin-6-yl)-2H-chromen-2-one.

Step D: 7-Bromo-3-(2-methylimidazo[1,2-b]pyridazin-6-yl)-2H-chromen-2-one was mixed with tert-butyl 4-(4,4,5,5-tetramethyl-1,3,2-dioxaborolan-2-yl)-5,6-dihydropyridine-1(2H)-carboxylate (0.56 g, 0.6 mmol), [1,1'-bis(diphenylphosphino)ferrocene]dichloropalladium(II) complex with dichloromethane (40 mg, 0.049 mmol) and aqueous 2 M K$_2$CO$_3$ (1.0 mL, 2.0 mmol) in CH$_3$CN (2.0 mL). The mixture was stirred at 80° C. for 3 h, then diluted into EtOAc and washed with water. The organic layer was chromatographed on silica gel, eluting with 0-50% EtOAc in CH$_2$Cl$_2$ to give tert-butyl 4-(3-(3-(1-(tert-butoxycarbonyl)-1,2,3,6-tetrahydropyridin-4-yl)-2-methylimidazo[1,2-b]pyridazin-6-yl)-2-oxo-2H-chromen-7-yl)-5,6-dihydropyridine-1(2H)-carboxylate (120 mg, 38%). MS m/z 640.6 [M+H]$^+$.

Step E: The compound from Step D was dissolved in 4 N HCl in dioxane (2.0 mL). The mixture was stirred at room temperature for 15 min, then concentrated, treated with aqueous sodium bicarbonate, and filtered. The solid was washed with water and dried to afford the title compound (15 mg, 18%). MS m/z 440.5 [M+H]$^+$; $^1$H NMR (500 MHz, DMSO-d$_6$) δ 9.26 (1H, s), 8.08 (1H, s), 8.02 (1H, m), 7.81 (1H, m), 7.54 (1H, m), 7.48 (1H, m), 6.70 (1H, m), 6.55 (1H, m), 3.45 (4H, m), 2.90 (4H, m), 2.39 (3H, s), 2.36-2.18 (4H, m).

Example 71

Preparation of Cpd 948

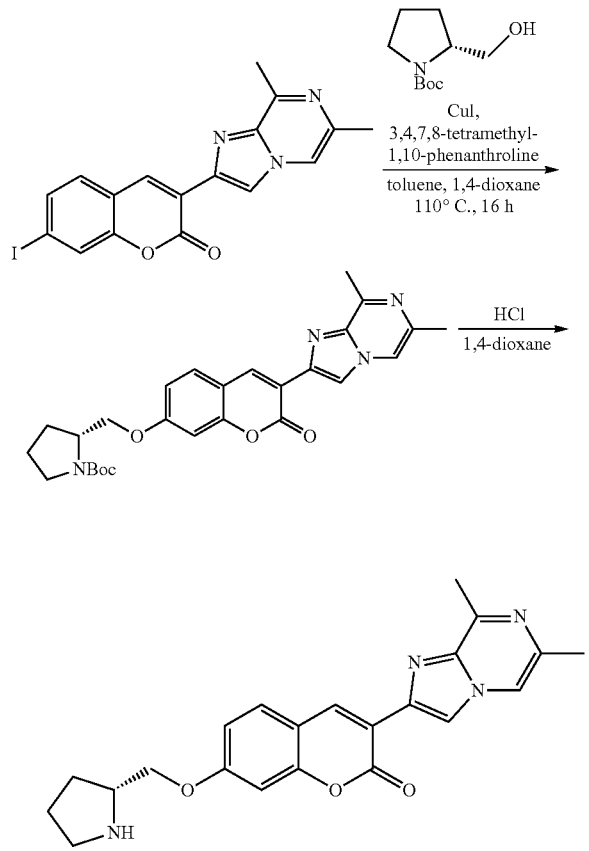

Step A: A mixture of 3-(6,8-dimethylimidazo[1,2-a]pyrazin-2-yl)-7-iodo-2H-chromen-2-one (0.21 g, 0.5 mmol, prepared according to Example 48, Step A), (R)-tert-butyl 2-(hydroxymethyl)pyrrolidine-1-carboxylate (0.145 g, 0.72 mmol), CuI (9.5 mg, 0.05 mmol), 3,4,7,8-tetramethyl-1,10-phenanthroline (24 mg, 0.1 mmol) and $Cs_2CO_3$ (0.33 g, 1.0 mmol) in toluene (1.5 mL) and dioxane (1.0 mL) was stirred at 110° C. for 16 h. The mixture was concentrated and chromatographed on silica gel, eluting with 0-10% MeOH in $CH_2Cl_2$ to give a crude mixture containing (R)-tert-butyl 2-(((3-(6,8-dimethylimidazo[1,2-a]pyrazin-2-yl)-2-oxo-2H-chromen-7-yl)oxy)methyl)pyrrolidine-1-carboxylate (0.21 g). MS m/z 491.2 [M+H]$^+$.

Step B: The mixture from Step A was treated with 4 N HCl in dioxane (2.0 mL). After 1 h, the mixture was concentrated, then dissolved in methanol (7N in $NH_3$). The solvent was removed and the residue was chromatographed on silica gel, eluting with 0-15% MeOH in $CH_2Cl_2$ to give the title compound (25 mg, 13%) as a light yellow powder: m.p. 172-174° C.; MS m/z 391.3 [M+H]$^+$; $^1$H NMR (500 MHz, $CD_3OD$) δ 8.71 (1H, s), 8.46 (1H, s), 8.04 (1H, d, J=0.9 Hz), 7.61 (1H, d, J=8.8 Hz), 6.98 (1H, m), 6.90 (1H, d, J=2.2 Hz), 4.08 (1H, m), 3.99 (1H, m), 3.55 (1H, m), 2.98 (2H, m), 2.83 (3H, s), 2.42 (3H, d, J=0.9 Hz), 2.02 (1H, m), 1.96-1.76 (2H), 1.64 (1H, m).

Example 72

Preparation of Cpd 958

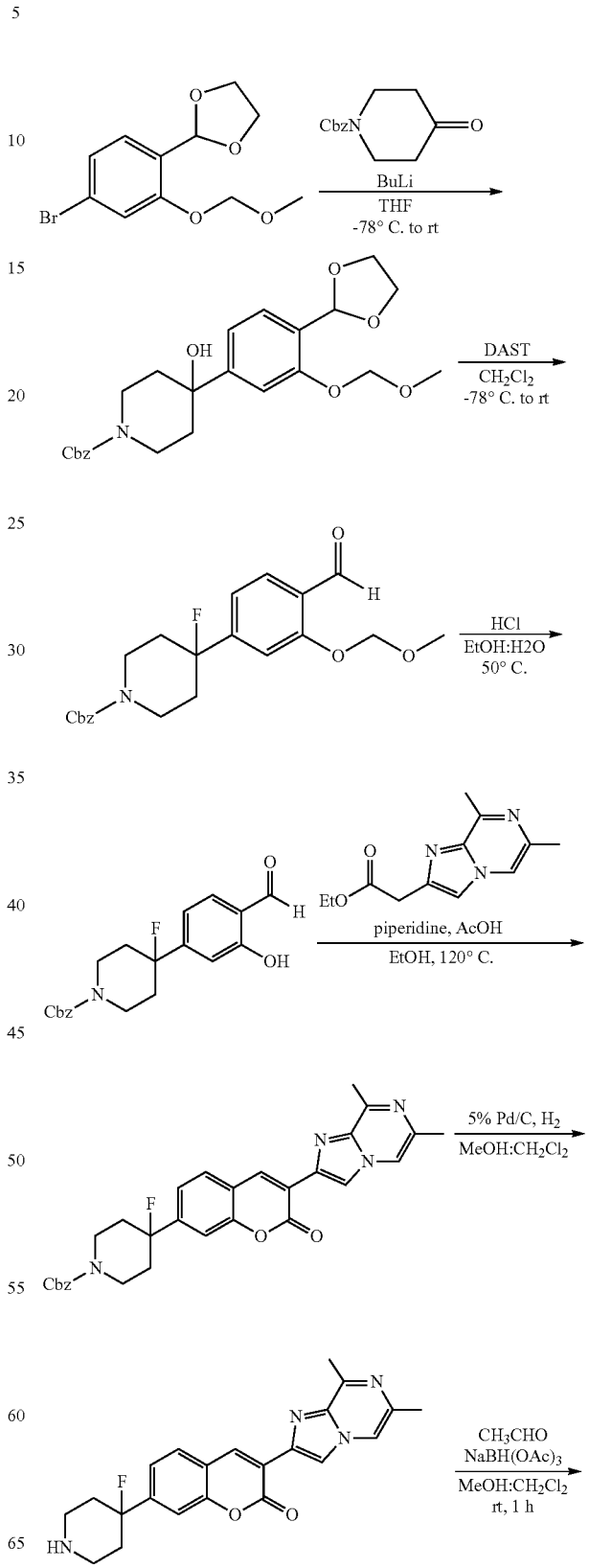

-continued

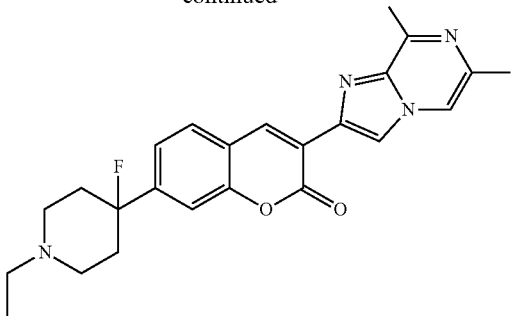

Step A: Into a solution of 2-(4-bromo-2-(methoxymethoxy)phenyl)-1,3-dioxolane (1.45 g, 5.0 mmol) in THF (20 mL) at −78° C. was added BuLi (3.75 mL of a 1.6 M solution in hexane, 6.0 mmol). The mixture was stirred at −78° C. for 30 min, then benzyl 4-oxopiperidine-1-carboxylate (1.75 g, 7.5 mmol) was added to the mixture in one portion. The temperature of the mixture was allowed to rise to room temperature slowly. The mixture was stirred at room temperature for 2 h, then the reaction was quenched with saturated $NH_4Cl$ solution. The mixture was partitioned in EtOAc and water. The organic layer was washed with brine, dried over $Na_2SO_4$, then concentrated and chromatographed on silica gel, eluting with 0-65% EtOAc in $CH_2Cl_2$ to give benzyl 4-(4-(1,3-dioxolan-2-yl)-3-(methoxymethoxy)phenyl)-4-hydroxypiperidine-1-carboxylate (1.2 g, 54%).

Step B: Into a solution of benzyl 4-(4-(1,3-dioxolan-2-yl)-3-(methoxymethoxy)phenyl)-4-hydroxypiperidine-1-carboxylate (1.2 g, 2.7 mmol) in $CH_2Cl_2$ (6.0 mL) at −78° C. was added diethylaminosulfur trifluoride (0.49 mL, 3.0 mmol) dropwise. The temperature of the mixture was allowed to rise to room temperature. The mixture was stirred at room temperature for an additional hour before it was quenched by with saturated $Na_2CO_3$ solution. The organic layer was concentrated and chromatographed on silica gel, eluting with 0-20% EtOAc in $CH_2Cl_2$ to give benzyl 4-fluoro-4-(4-formyl-3-(methoxymethoxy)phenyl)piperidine-1-carboxylate (0.83 g, 76%). $^1H$ NMR (500 MHz, acetone-$d_6$) δ 10.47 (1H, d, J=0.6 Hz), 7.78 (1H, dd, J=8.2, 0.6 Hz), 7.30-7.44 (6H, m), 7.18-7.22 (1H, m), 5.43 (2H, s), 5.15 (2H, s), 4.20 (2H, m), 3.52 (3H, s), 3.33-3.02 (2H, m), 2.22-2.06 (2H, m), 1.95 (2H, m).

Step C: Into a mixture of benzyl 4-fluoro-4-(4-formyl-3-(methoxymethoxy)phenyl)piperidine-1-carboxylate (0.83 g, 2.1 mmol) in ethanol (2.0 mL) and water (2.0 mL) was added concentrated HCl (12 N, 2.0 mL, 24 mmol). The mixture was stirred at 50° C. for 3 h. The mixture was partitioned in EtOAc and water. The organic layer was washed with brine, dried over $Na_2SO_4$, and concentrated to give benzyl 4-fluoro-4-(4-formyl-3-hydroxyphenyl)piperidine-1-carboxylate as a pure product (0.75 g, 100%). MS m/z 356.2 [M−H]$^-$.

Step D: A mixture of benzyl 4-fluoro-4-(4-formyl-3-hydroxyphenyl)piperidine-1-carboxylate (0.75 g, 2.1 mmol), ethyl 2-(6,8-dimethylimidazo[1,2-a]pyrazin-2-yl) acetate (0.54 g, 2.3 mmol), piperidine (1.5 μL, 0.042 mmol), acetic acid (0.5 mL) in ethanol (2.0 mL) was stirred at 120° C. for 2 h. The mixture was concentrated and chromatographed on silica gel, eluting with 30-100% EtOAc in $CH_2Cl_2$ to give benzyl 4-(3-(6,8-dimethylimidazo[1,2-a]pyrazin-2-yl)-2-oxo-2H-chromen-7-yl)-4-fluoropiperidine-1-carboxylate (0.35 g, 47%). MS m/z 527.3 [M+H]$^+$.

Step E: A mixture of benzyl 4-(3-(6,8-dimethylimidazo[1,2-a]pyrazin-2-yl)-2-oxo-2H-chromen-7-yl)-4-fluoropiperidine-1-carboxylate (0.17 g, 0.32 mmol) and 10% Pd/C (17 mg) in methanol and dichloromethane (3:1, 10 mL) was stirred overnight under $H_2$ (1 atm). The mixture was filtered through Celite, concentrated and chromatographed on silica gel, eluting with 10% MeOH in $CH_2Cl_2$ to give 3-(6,8-dimethylimidazo[1,2-a]pyrazin-2-yl)-7-(4-fluoropiperidin-4-yl)-2H-chromen-2-one (75 mg, 60%). MS m/z 393.3 [M+H]$^+$.

Step F: 3-(6,8-Dimethylimidazo[1,2-a]pyrazin-2-yl)-7-(4-fluoropiperidin-4-yl)-2H-chromen-2-one (75 mg, 60%) was dissolved in $CH_3OH:CH_2Cl_2$ 10:1 (2.0 mL). Acetaldehyde (0.1 mL of a 6.5 M solution in isopropanol, 0.65 mmol) was added to the solution, followed by solid sodium triacetoxyborohydride (85 mg, 0.4 mmol). The mixture was stirred at room temperature for 30 min, then quenched with aqueous $K_2CO_3$. The organic layer was concentrated and chromatographed on silica gel, eluting with 0-10% MeOH in $CH_2Cl_2$ to give the title compound (34 mg, 40%) as a gray solid: m.p. 162-164° C.; MS m/z 421.3 [M+H]$^+$; $^1H$ NMR (500 MHz, $CD_3OD$) δ 8.79 (1H, s), 8.53 (1H, s), 8.09 (1H, d, J=0.6 Hz), 7.76 (1H, m), 7.42 (2H, m), 3.03 (2H, m), 2.84 (3H, s), 2.63 (2H, d, J=7.3 Hz), 2.54 (2H, br s), 2.43 (3H, d, J=0.9 Hz), 2.23 (2H, m), 2.05 (2H, br s), 1.20 (3H, t, J=7.3 Hz).

Example 73

Preparation of Cpd 853

Part 1, Preparation of 4,6-dimethyl-2-(trimethylstannyl)pyrazolo[1,5-a]pyrazine

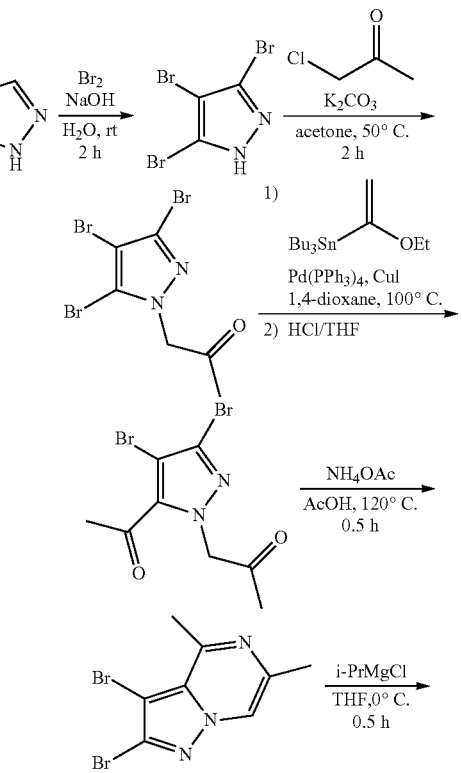

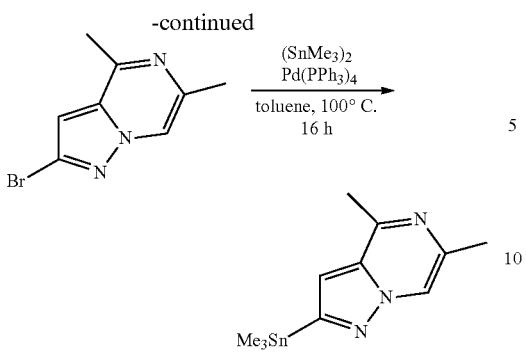

Step A: Into a stirred solution of 1H-pyrazole (6.95 g, 0.1 mmol) and sodium hydroxide (16 g, 0.4 mol) in water (400 mL0 was added bromine (48 g, 0.3 mol) dropwise over 1 h. The mixture was stirred for 1 h, and then filtered. The cake was washed with water and dried to give 3,4,5-tribromo-1H-pyrazole (25.2 g, 81%). MS m/z 302.9 [M+H]$^+$.

Step B: Into a mixture of 3,4,5-tribromo-1H-pyrazole (1.54 g, 5.1 mmol) and K$_2$CO$_3$ (2.1 g, 15.3 mmol) in acetone (20 mL) was added chloroacetone (0.52 g, 5.6 mmol) dropwise. The mixture was stirred at room temperature for 2 h, then partitioned between water and CH$_2$Cl$_2$. The organic layer was dried over Na$_2$SO$_4$ and concentrated to give 1-(3,4,5-tribromo-1H-pyrazol-1-yl)propan-2-one (1.80 g, 99%). MS m/z 361.0 [M+H]$^+$.

Step C: A mixture of 1-(3,4,5-tribromo-1H-pyrazol-1-yl)propan-2-one (3.6 g, 10.0 mmol), tributyl(1-ethoxyvinyl)stannane (3.5 mL, 10.0 mmol) and bis(triphenylphosphine) palladium(II) dichloride (0.35 g, 0.5 mmol) in 1,4-dioxane (25 mL) was stirred at 100° C. overnight. The reaction was cooled to room temperature, and then filtered through Celite. The filtrate was concentrated and partitioned between THF (100 mL) and aqueous 1 N HCl (100 mL). The mixture was stirred at 60° C. for 1 h. The organic layer was separated. The aqueous layer was extracted with ethyl acetate (50 mL×3). The combined organic layers were dried over Na$_2$SO$_4$ and concentrated. The residue was chromatographed on silica gel, eluting with CH$_2$Cl$_2$ to give 1-(5-acetyl-3,4-dibromo-1H-pyrazol-1-yl)propan-2-one (1.1 g, 34%). MS m/z 325.0 [M+H]$^+$.

Step D: A mixture of 1-(5-acetyl-3,4-dibromo-1H-pyrazol-1-yl)propan-2-one (3.24 g, 10 mmol) and ammonium acetate (7.7 g, 100 mmol) in acetic acid (10 mL) was stirred at 120° C. for 30 min. The mixture was cooled to room temperature and diluted with water (150 mL). The mixture was stirred for 20 min and filtered. The solid was dried and chromatographed on silica gel, eluting with CH$_2$Cl$_2$ to give 2,3-dibromo-4,6-dimethylpyrazolo[1,5-a]pyrazine (1.55 g, 50%). MS m/z 305.9 [M+H]$^+$.

Step E: Into a solution of 2,3-dibromo-4,6-dimethylpyrazolo[1,5-a]pyrazine (1.55 g, 5.1 mmol) in THF (50 mL) at 0° C. was added a solution of i-PrMgCl (2.7 mL of a 2.0 M solution in THF, 5.4 mmol). The mixture was stirred at 0° C. for 30 min and excess reagent was quenched with the addition of methanol (25 mL). The mixture was partitioned between EtOAc and water. The organic layer was washed with brine, dried over Na$_2$SO$_4$, concentrated and chromatographed on silica gel, eluting with 0-35% EtOAc in hexanes to provide 2-bromo-4,6-dimethylpyrazolo[1,5-a]pyrazine (0.95 g, 80%). MS m/z 228.1 [M+H]$^+$.

Step F: A mixture of 2-bromo-4,6-dimethylpyrazolo[1,5-a]pyrazine (0.226 mg, 1.0 mmol), hexamethyldistannane (0.397 g, 1.2 mmol) and tetrakis(triphenylphosphine) palladium(0) (0.116 g, 0.1 mmol) in toluene (3.0 mL) was stirred at 100° C. overnight under Argon. The mixture was cooled to room temperature and chromatographed on silica gel, eluting with 0-45% EtOAc in hexanes to give 4,6-dimethyl-2-(trimethylstannyl)pyrazolo[1,5-a]pyrazine (0.212 g, 70%) as a white solid. MS m/z 312.2 [M+H]$^+$; $^1$H NMR (500 MHz, acetone-d$_6$) δ 8.29 (1H, s), 6.95 (1H, s), 2.66 (3H, s), 2.42 (3H, d, J=0.9 Hz), 0.36 (9H, s).

Part 2: Preparation of 3-(4,6-dimethylpyrazolo[1,5-a]pyrazin-2-yl)-7-(1-ethylpiperidin-4-yl)-2H-chromen-2-one

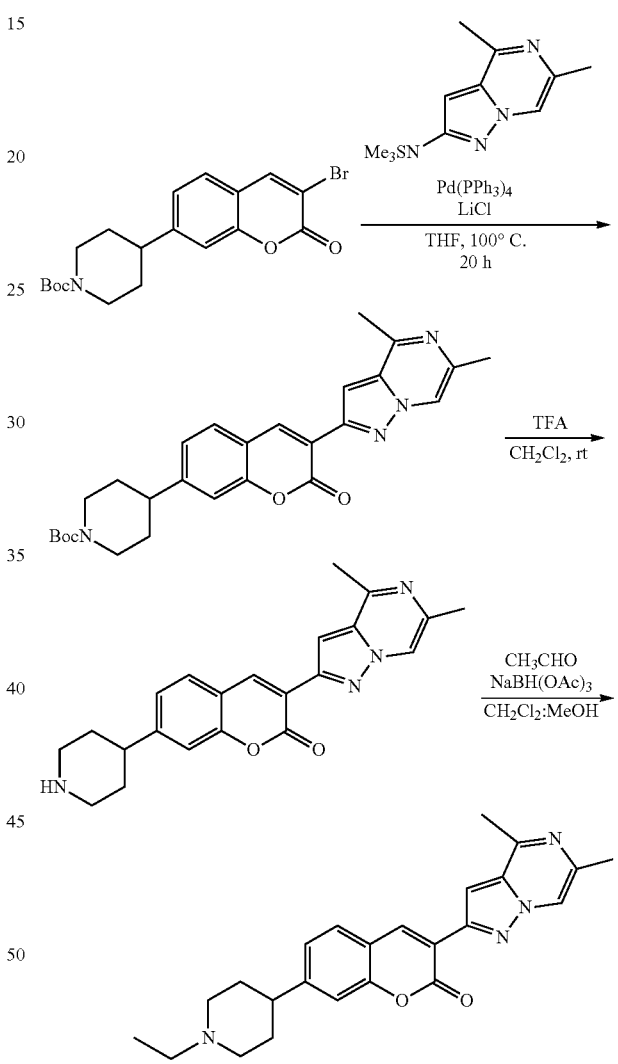

Step A: A mixture of tert-butyl 4-(3-bromo-2-oxo-2H-chromen-7-yl)piperidine-1-carboxylate (110 mg, 0.24 mmol, prepared in Example 69, Step C), 4,6-dimethyl-2-(trimethylstannyl)pyrazolo[1,5-a]pyrazine (75 mg, 0.24 mmol), tetrakis(triphenylphosphine) palladium(0) (28 mg, 0.024 mmol) in a 0.5 M solution of LiCl in THF (1.44 mL, 0.72 mmol) was stirred at 100° C. for 20 h, then the solvent was removed. The residue was chromatographed on silica gel, eluting with 0-60% EtOAc in CH$_2$Cl$_2$ to give tert-butyl 4-(3-(4,6-dimethylpyrazolo[1,5-a]pyrazin-2-yl)-2-oxo-2H-chromen-7-yl)piperidine-1-carboxylate (98 mg, 86%). MS m/z 475.3 [M+H]$^+$.

Step B: Following the procedure in Example 69, Step E, tert-butyl 4-(3-(4,6-dimethylpyrazolo[1,5-a]pyrazin-2-yl)-2-oxo-2H-chromen-7-yl)piperidine-1-carboxylate (98 mg, 0.21 mmol) and TFA (0.4 mL) in dichloromethane (0.4 mL) provided 3-(4,6-dimethylpyrazolo[1,5-a]pyrazin-2-yl)-7-(piperidin-4-yl)-2H-chromen-2-one (80 mg, 100%). MS m/z 375.3 [M+H]+.

Step C: Following the procedure in Example 67, 3-(4,6-dimethylpyrazolo[1,5-a]pyrazin-2-yl)-7-(piperidin-4-yl)-2H-chromen-2-one (61 mg, 0.1 mmol), acetaldehyde (30 μL of a 6.5 M solution in isopropanol, 0.2 mmol) and NaBH(OAc)$_3$ (64 mg, 0.3 mmol) provided the title compound (36 mg, 90%) as a gray solid. MS m/z 403.3 [M+H]+; $^1$H NMR (500 MHz, CD$_3$OD) δ 8.69 (1H, s), 8.23 (1H, s), 7.68 (1H, d, J=8.5 Hz), 7.61 (1H, s), 7.30 (2H, dd, J=3.8 Hz, 2.8 Hz), 3.41 (2H, br), 2.89 (3H, d, J=7.3 Hz), 2.75 (3H, s), 2.66 (2H, m), 2.48 (3H, s), 2.07 (2H, br), 1.95 (2H, m), 1.29 (3H, t, J=7.3 Hz).

Example 74

Preparation of Cpd 876

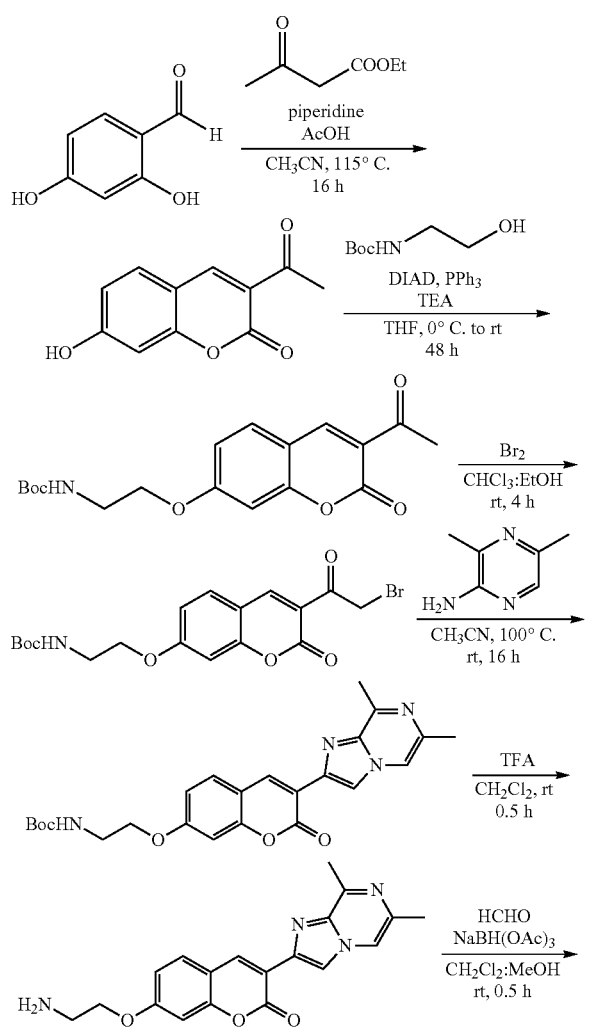

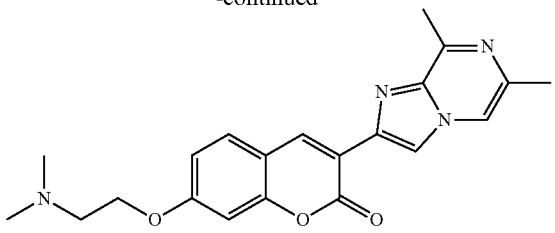

Step A: Following the procedure in Example 37, Step A, 2,4-dihydroxybenzaldehyde (1.4 g, 10 mmol), ethyl acetoacetate (1.28 mL, 10 mmol), piperidine (1.0 mL, 10 mmol) and acetic acid (3 mL, 50 mmol) in CH$_3$CN (20 mL) provided 3-acetyl-7-hydroxy-2H-chromen-2-one (1.77 g, 82%). MS m/z 203.1 [M−H]−.

Step B: Diisopropyl azodicarboxylate (2.0 mL, 10 mmol) was added dropwise into a mixture of 3-acetyl-7-hydroxy-2H-chromen-2-one (2.15 g, 10 mmol), tert-butyl 2-hydroxyethylcarbamate (1.9 mL, 12 mmol), triphenylphosphine (2.62 g, 10 mmol) and triethylamine (1.4 mL, 10 mmol) in THF (10 mL) at 0° C. The mixture warmed to room temperature and stirred 48 h. The mixture was filtered. The solid material was washed with ether and hexane to give tert-butyl 2-(3-acetyl-2-oxo-2H-chromen-7-yloxy)ethylcarbamate (1.81 g, 50%). MS m/z 348.2 [M+H]+.

Step C: Bromine (26 μL, 0.5 mmol) in CH$_2$Cl$_2$ (0.5 mL) was added to a mixture of tert-butyl 2-(3-acetyl-2-oxo-2H-chromen-7-yloxy)ethylcarbamate (183 mg, 0.5 mmol), CHCl$_3$ (3.0 mL) and EtOH (1.0 mL). The mixture was stirred at room temperature for 4 h, then the solvent was removed from the mixture. The residue was chromatographed on silica gel, eluting with 0-15% MeOH in CH$_2$Cl$_2$ to give tert-butyl 2-(3-(2-bromoacetyl)-2-oxo-2H-chromen-7-yloxy)ethylcarbamate (0.108 g, 50%). MS m/z 428.1 [M+H]+.

Step D: Following the procedure in Example 43, Step A, tert-butyl 2-(3-(2-bromoacetyl)-2-oxo-2H-chromen-7-yloxy)ethylcarbamate (108 mg, 0.25 mmol) and 3,5-dimethylpyrazin-2-amine (32 mg, 0.25 mmol) in CH$_3$CN (2.0 mL) provided tert-butyl 2-(3-(6,8-dimethylimidazo[1,2-a]pyrazin-2-yl)-2-oxo-2H-chromen-7-yloxy)ethylcarbamate (88 mg, 80%). MS m/z 451.3 [M+H]+.

Step E: Following the procedure in Example 69, Step E, tert-butyl 2-(3-(6,8-dimethylimidazo[1,2-a]pyrazin-2-yl)-2-oxo-2H-chromen-7-yloxy)ethylcarbamate (88 mg, 0.20 mmol) and TFA (0.3 mL) in CH$_2$Cl$_2$ (0.6 mL) provided 7-(2-aminoethoxy)-3-(6,8-dimethylimidazo[1,2-a]pyrazin-2-yl)-2H-chromen-2-one (66 mg, 95%). MS m/z 351.2 [M+H]+.

Step F: Following the procedure in Example 67, 7-(2-aminoethoxy)-3-(6,8-dimethylimidazo[1,2-a]pyrazin-2-yl)-2H-chromen-2-one (35 mg, 0.1 mmol), formaldehyde (37% aqueous, 0.1 mL) and NaBH(OAc)$_3$ (64 mg, 0.3 mmol) provided the title compound (25 mg, 67%) as a pale yellow solid: m.p. 251-253° C.; MS m/z 379.3 [M+H]+; $^1$H NMR (500 MHz, CD$_3$OD) δ 8.79 (1H, s), 8.51 (1H, s), 8.09 (1H, m), 7.69 (1H, d, J=8.5 Hz), 7.05 (1H, m), 6.99 (1H, m), 4.30 (2H, s), 3.12 (2H, br s), 2.86 (3H, s), 2.59 (6H, s), 2.45 (3H, s).

As shown in Table 1 below, additional compounds disclosed herein may be prepared according to Example 74 by substituting the appropriate starting materials, reagents and reaction conditions.

Example 75

Preparation of Cpd 918

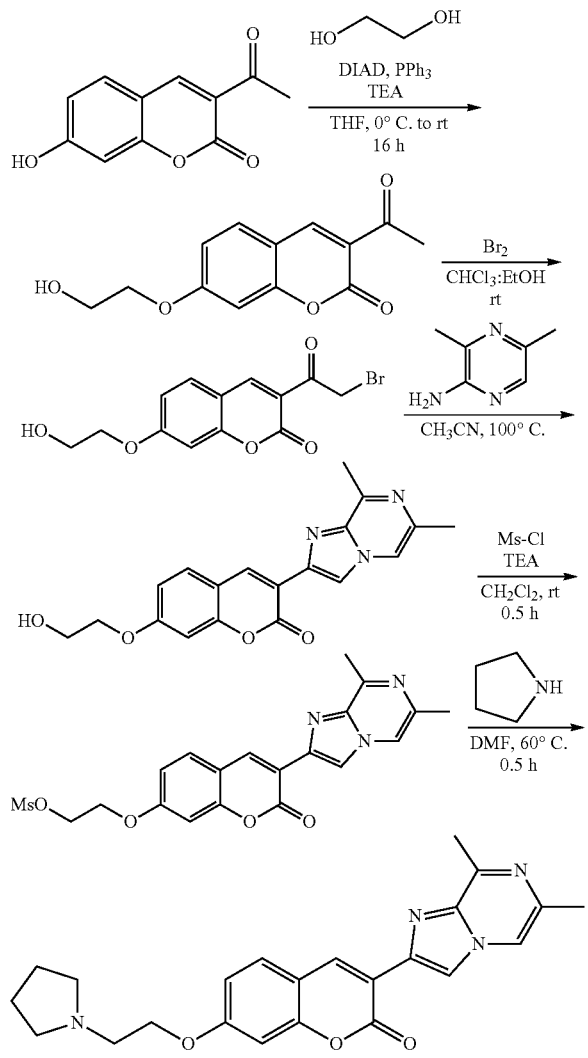

Step A: Into a mixture of 3-acetyl-7-hydroxy-2H-chromen-2-one (2.3 g, 10 mmol), ethylene glycol (1.7 mL, 30 mmol) and triphenylphosphine (2.88 g, 11 mmol) in THF (10 mL) was added triethylamine (1.53 mL, 11 mmol). The mixture was cooled to 0° C. Diisopropyl azodicarboxylate (2.2 mL, 11 mmol) was added dropwise to the mixture. The mixture was stirred at room temperature overnight, after which the solvent was removed. The residue was chromatographed on silica gel, eluting with 0-45% EtOAc in CH$_2$Cl$_2$. The resulting material was chromatographed on silica gel a second time, eluting with 10-100% EtOAc in hexanes to provide 3-acetyl-7-(2-hydroxyethoxy)-2H-chromen-2-one (0.50 g, 20%). MS m/z 249.1 [M+H]$^+$.

Step B: Following the procedure of Example 74, Step C, 3-acetyl-7-(2-hydroxyethoxy)-2H-chromen-2-one (0.5 g, 2.0 mmol) and bromine (0.105 mL, 2.0 mmol) in CHCl$_3$ (18 mL) and EtOH (2.0 mL) provided 3-(2-bromoacetyl)-7-(2-hydroxyethoxy)-2H-chromen-2-one (0.26 g, 40%). MS m/z 329.0 [M+H]$^+$.

Step C: Following the procedure in Example 43, Step A, 3-(2-bromoacetyl)-7-(2-hydroxyethoxy)-2H-chromen-2-one (0.26 g, 0.8 mmol) and 3,5-dimethylpyrazin-2-amine (0.10 g, 0.8 mmol) in CH$_3$CN (2.0 mL) provided 3-(6,8-dimethylimidazo[1,2-a]pyrazin-2-yl)-7-(2-hydroxyethoxy)-2H-chromen-2-one (0.32 g, 88%). MS m/z 352.2 [M+H]$^+$.

Step D: Methanesulfonyl chloride (0.065 mL, 0.81 mmol) in CH$_2$Cl$_2$ (1.5 mL) was added dropwise into a solution of 3-(6,8-dimethylimidazo[1,2-a]pyrazin-2-yl)-7-(2-hydroxyethoxy)-2H-chromen-2-one (0.29 g, 0.66 mmol) and triethylamine (0.28 mL, 1.98 mmol) in CH$_2$Cl$_2$ (1.5 mL) at 0° C. The mixture was stirred at 0° C. for 20 min, and then at room temperature for 30 min, then the solvent was removed. The residue was triturated with methanol, and then filtered to give 2-(3-(6,8-dimethylimidazo[1,2-a]pyrazin-2-yl)-2-oxo-2H-chromen-7-yloxy)ethyl methanesulfonate (0.18 g, 63%). MS m/z 430.2 [M+H]$^+$.

Step E: A mixture of 2-(3-(6,8-dimethylimidazo[1,2-a]pyrazin-2-yl)-2-oxo-2H-chromen-7-yloxy)ethyl methanesulfonate (61 mg, 0.14 mmol) and pyrrolidine (0.07 mL, 0.85 mmol) in DMF (0.3 mL) was stirred at 60° C. for 30 min. The mixture was chromatographed on silica gel, eluting with 0-10% MeOH in CH$_2$Cl$_2$ to give the title compound (25 mg, 40%) as a pale yellow solid: m.p. 201-203° C.; MS m/z 405.2 [M+H]$^+$; $^1$H NMR (500 MHz, CD$_3$OD) δ 8.83 (1H, m), 8.55 (1H, m), 8.11 (1H, m), 7.74 (1H, m), 7.07 (2H, m), 4.46 (2H, m), 3.75 (2H, m), 3.70 (2H, m), 3.23 (2H, m), 2.88 (3H, s), 2.46 (3H, s), 2.22 (2H, m), 2.08 (2H, m).

As shown in Table 1 below, additional compounds disclosed herein may be prepared according to Example 75 by substituting the appropriate starting materials, reagents and reaction conditions.

Example 76

Preparation of Cpd 818

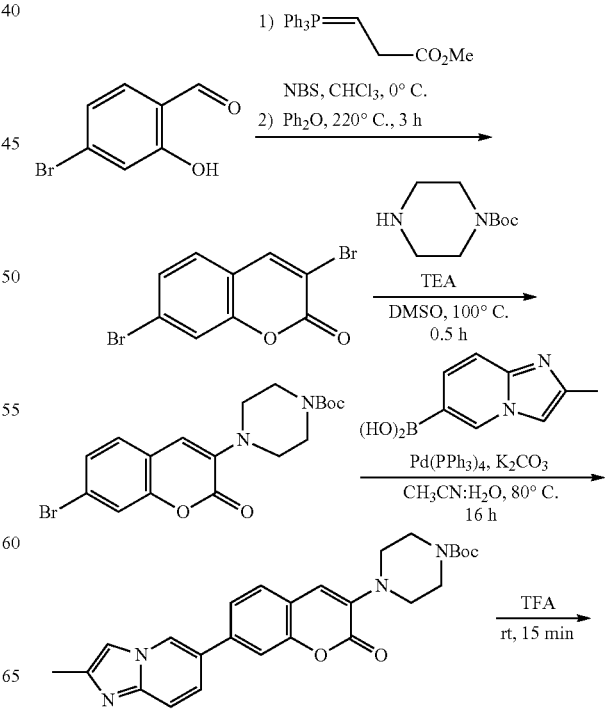

-continued

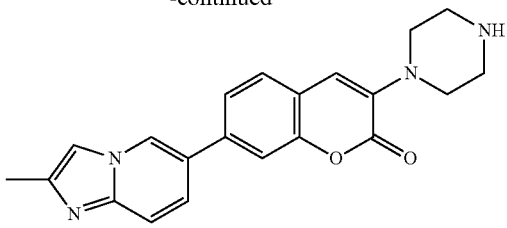

Step A: Methyl 2-(triphenylphosphoranylidene)acetate (1.84 g, 5.5 mmol) was dissolved in CHCl$_3$ (10 mL) and cooled to 0° C. N-Bromosuccinimide (980 mg, 5.5 mmol) was added to the solution. The mixture warmed to room temperature and stirred 20 min. The mixture was concentrated. 4-Bromosalicaldehyde (1.0 g, 5.0 mmol) and diphenyl ether (10 mL) were added to the residue. The mixture was heated at 220° C. for 3 h. The mixture was loaded directly onto silica gel, eluting with 0-30% EtOAc in hexanes to afford 3,7-dibromo-2H-chromen-2-one (650 mg, 43%) as a white solid. $^1$H NMR (500 MHz, DMSO-d$_6$): δ 8.62 (1H, s), 7.78 (1H, d, J=1.8 Hz), 7.65 (1H, d, J=8.3 Hz), 7.60 (1H, dd, J=8.3 Hz, 1.8 Hz).

Step B: 3,7-Dibromo-2H-chromen-2-one (200 mg, 0.66 mmol) was combined with t-Boc-piperazine (186 mg, 1.0 mmol) and triethylamine (0.18 mL, 1.3 mmol) in DMSO (1 mL). The mixture was heated at 100° C. for 30 min. The mixture was partitioned in CH$_2$Cl$_2$ (5 mL) and H$_2$O (5 mL). The organic layer was loaded directly onto silica gel, eluting with 0-50% EtOAc in hexanes to afford tert-butyl 4-(7-bromo-2-oxo-2H-chromen-3-yl)piperazine-1-carboxylate (80 mg, 30%) as a white solid. $^1$H NMR (500 MHz, DMSO-d$_6$): δ 7.72 (1H, s), 7.52 (1H, d, J=8.4 Hz), 7.43 (1H, dd, J=8.4 Hz, 1.6 Hz), 7.31 (1H, d, J=1.6 Hz), 3.81 (4H, m), 3.55 (4H, m), 1.49 (9H, s).

Step C: tert-Butyl 4-(7-bromo-2-oxo-2H-chromen-3-yl)piperazine-1-carboxylate (80 mg, 0.2 mmol) was combined with (2-methylimidazo[1,2-a]pyridin-6-yl)boronic acid (70 mg, 0.4 mmol, prepared in Example 34, Step A) and tetrakis(triphenylphosphine)palladium(0) (23 mg, 0.02 mmol) in CH$_3$CN (1 mL). Aqueous K$_2$CO$_3$ (1 mL, 1 M) was added to the mixture. The mixture was heated under nitrogen at 80° C. for 16 h. The organic layer was removed, concentrated and chromatographed on silica gel, eluting with 0-8% MeOH in CH$_2$Cl$_2$ to afford tert-butyl 4-(7-(2-methylimidazo[1,2-a]pyridin-6-yl)-2-oxo-2H-chromen-3-yl)piperazine-1-carboxylate (57 mg, 62%) as a white powder.

Step D: tert-Butyl 4-(7-(2-methylimidazo[1,2-a]pyridin-6-yl)-2-oxo-2H-chromen-3-yl)piperazine-1-carboxylate (57 mg, 0.12 mmol) was dissolved in TFA (1 mL). The mixture was stirred for 15 min at room temperature, then the solvent was removed with a nitrogen stream. The residue was partitioned in CH$_2$Cl$_2$ and aqueous K$_2$CO$_3$. The organic layer was collected and concentrated to afford the title compound (24 mg, 50%) as a white powder: m.p. 174-178° C.; MS m/z 361.3 [M+H]$^+$; $^1$H NMR (500 MHz, DMSO-d$_6$): δ 8.99 (1H, s), 8.07 (1H, s), 7.89 (1H, d, J=8.1 Hz), 7.76 (1H, s), 7.74 (1H, d, J=8.4 Hz), 7.68 (1H, d, J=9.2 Hz), 7.59 (1H, d, J=9.4 Hz), 7.47 (1H, s), 3.67 (1H, br), 3.35 (4H, m), 2.81 (4H, m), 2.37 (3H, s).

Example 77

Preparation of Cpd 846

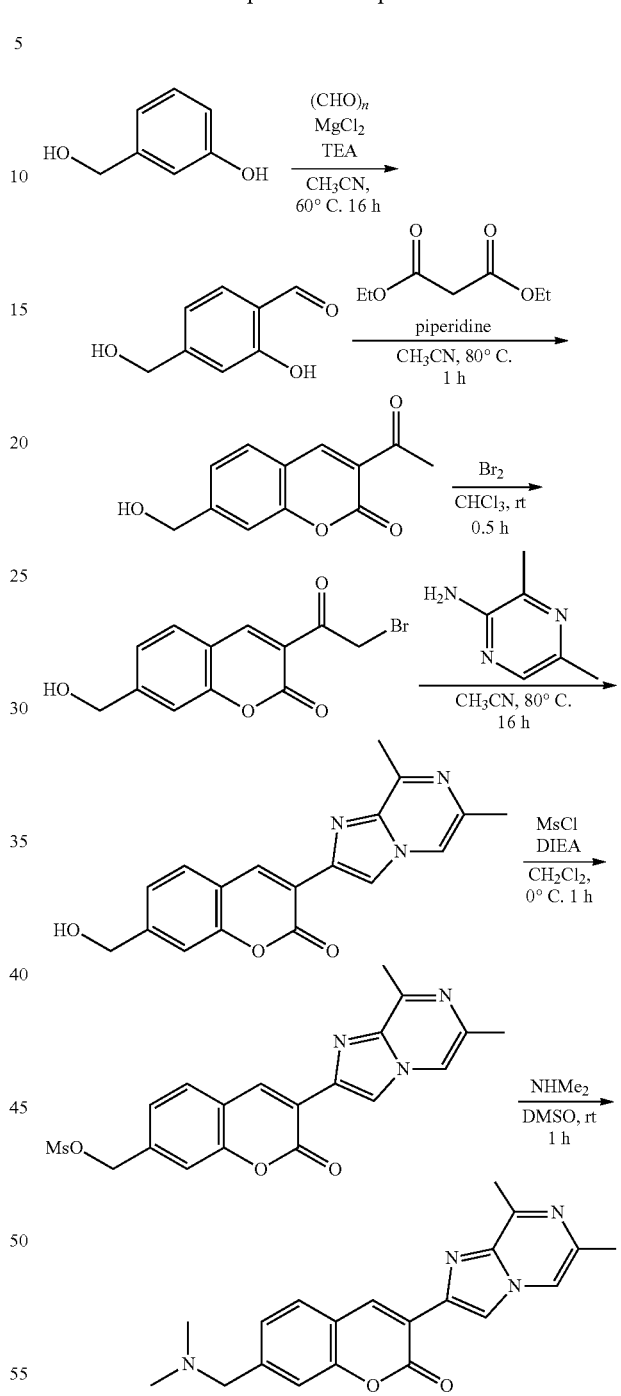

Step A: Following the procedure in Example 6, Step A, 3-(hydroxymethyl)phenol (1.24 g, 100 mmol), triethylamine (70 mL, 500 mmol), anhydrous magnesium chloride (19.0 g, 200 mmol) and paraformaldehyde (30 g, 1000 mmol) in CH$_3$CN (400 mL) afforded 2-hydroxy-4-(hydroxymethyl)benzaldehyde (4.5 g, 29%). MS m/z 151.1 [M−H]$^-$.

Step B: 2-Hydroxy-4-(hydroxymethyl)benzaldehyde (3.04 g, 20 mmol) was combined with ethyl acetoacetate (2.55 mL, 20 mmol) and piperidine (0.2 mL, 2.0 mmol) in CH$_3$CN (10 mL). The mixture was heated at 80° C. for 1 h.

The mixture was concentrated and chromatographed on silica gel, eluting with 0-50% EtOAc in hexanes to afford 3-acetyl-7-(hydroxymethyl)-2H-chromen-2-one (1.88 g, 43%) as a tan powder. $^1$H NMR (500 MHz, DMSO-$d_6$): δ 8.66 (1H, s), 7.90 (1H, d, J=7.7 Hz), 7.36 (2H, m), 5.55 (1H, t, J=5.8 Hz), 4.65 (2H, d, J=5.8 Hz), 2.59 (3H, s).

Step C: 3-Acetyl-7-(hydroxymethyl)-2H-chromen-2-one (1.88 g, 8.3 mmol) was suspended in CHCl$_3$ (8 mL). Bromine (0.43 mL, 8.3 mmol) was added dropwise at room temperature, then the mixture was stirred at room temperature for 30 min. The solid material in the mixture was collected, washed with CHCl$_3$ and dried to afford 3-(2-bromoacetyl)-7-(hydroxymethyl)-2H-chromen-2-one (2.1 g, 85%) as a tan powder. MS m/z 297.1, 299.1 [M+H]$^+$.

Step D: 3-(2-Bromoacetyl)-7-(hydroxymethyl)-2H-chromen-2-one (2.1 g, 7.0 mmol) was combined with 3,5-dimethylpyrazin-2-amine (940 mg, 7.7 mmol) in CH$_3$CN (10 mL). The mixture was heated at 80° C. for 16 h. The mixture was cooled to room temperature and filtered. The solid material was washed with CH$_3$CN and dried to afford 3-(6,8-dimethylimidazo[1,2-a]pyrazin-2-yl)-7-(hydroxymethyl)-2H-chromen-2-one hydrobromide (1.0 g, 35%) as a tan powder. MS m/z 322.3 [M+H]$^+$. $^1$H NMR (500 MHz, DMSO-$d_6$): δ 8.91 (1H, s), 8.73 (1H, s), 8.45 (1H, s), 7.96 (1H, d, J=8.1 Hz), 7.41 (1H, s), 7.37 (1H, d, J=8.1 Hz), 4.65 (2H, s), 2.83 (3H, s), 2.42 (3H, s).

Step E: 3-(6,8-dimethylimidazo[1,2-a]pyrazin-2-yl)-7-(hydroxymethyl)-2H-chromen-2-one hydrobromide (1.0 g, 2.5 mmol) was combined with diisopropylethylamine (1.3 mL, 7.5 mmol) in CH$_2$Cl$_2$ (10 mL). To the mixture was added methanesulfonyl chloride (0.39 mL, 5 mmol) at 0° C. The mixture was stirred 30 min at 0° C., then loaded directly onto silica gel, eluting with 0-30% EtOAc in CH$_2$Cl$_2$ to afford (3-(6,8-dimethylimidazo[1,2-a]pyrazin-2-yl)-2-oxo-2H-chromen-7-yl)methyl methanesulfonate (900 mg, 90%) as a white powder. MS m/z 400.3 [M+H]$^+$. $^1$H NMR (500 MHz, DMSO-$d_6$): δ 8.90 (1H, s), 8.65 (1H, s), 8.36 (1H, s), 8.06 (1H, d, J=8.1 Hz), 7.57 (1H, s), 7.48 (1H, d, J=8.1 Hz), 5.41 (2H, s), 2.78 (3H, s), 2.39 (3H, s).

Step F: (3-(6,8-Dimethylimidazo[1,2-a]pyrazin-2-yl)-2-oxo-2H-chromen-7-yl)methyl methanesulfonate (60 mg, 0.15 mmol) was suspended in THF:DMF (1:1, 1 mL). Dimethylamine (0.75 mmol, 1 M in THF) was added to the mixture. The mixture was stirred at room temperature for 1 h, then loaded directly onto silica gel and eluted with 0-10% MeOH (3% NH$_3$) in CH$_2$Cl$_2$ to afford the title compound (31 mg, 59%) as an off-white powder: m.p. 192-196° C.; MS m/z 349.3 [M+H]$^+$; $^1$H NMR (500 MHz, DMSO-$d_6$): δ 8.88 (1H, s), 8.64 (1H, s), 8.36 (1H, s), 7.95 (1H, d, J=8.1 Hz), 7.38 (1H, s), 7.35 (1H, d, J=8.1 Hz), 3.53 (2H, s), 2.78 (3H, s), 2.38 (3H, s), 2.20 (6H, s).

As shown in Table 1 below, additional compounds disclosed herein may be prepared according to Example 77 by substituting the appropriate starting materials, reagents and reaction conditions.

Example 78

Preparation of Cpd 902

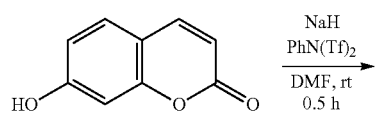

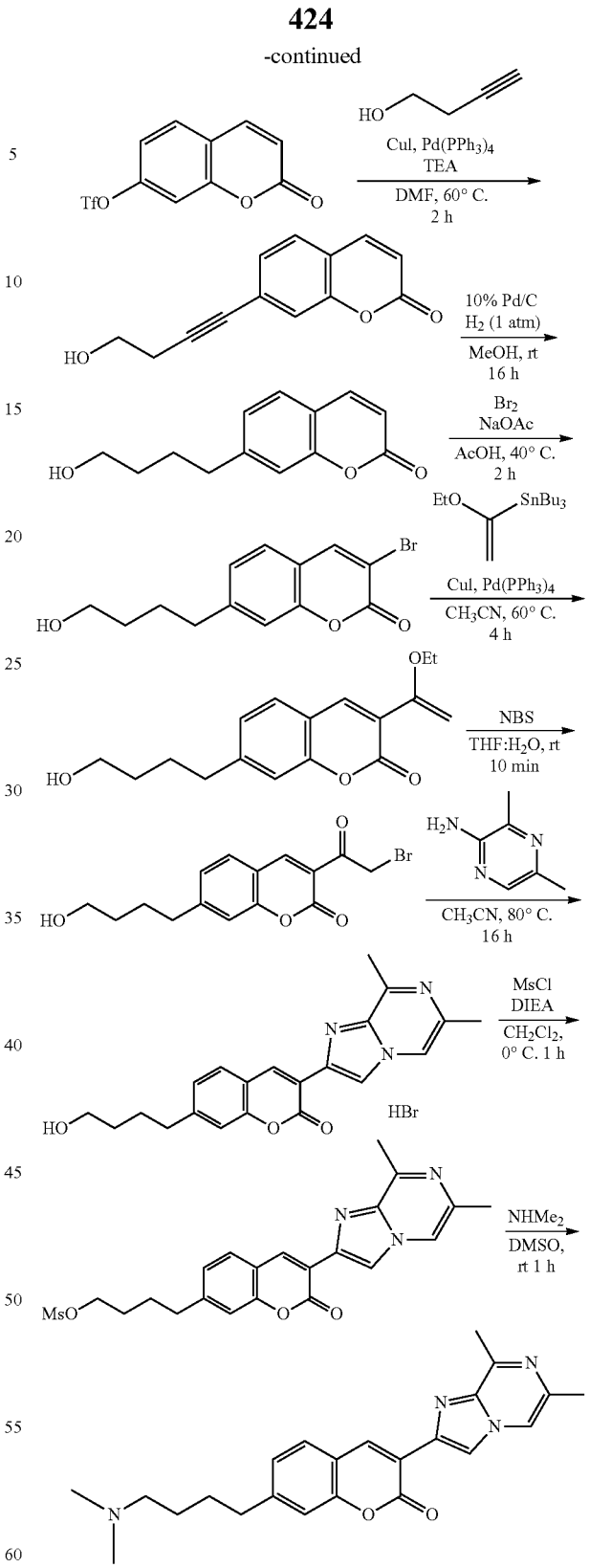

Step A: 7-Hydroxycoumarin (4.86 g, 30 mmol) was dissolved in DMF (60 mL). Sodium hydride (1.8 g, 45 mmol, 60% dispersion in mineral oil) was added to the solution. After 5 min of vigorous stirring, N,N-bis(trifluoromethylsulfonyl)aniline (11.8 g, 33 mmol) was added to the mixture. The mixture was stirred vigorously for 30 min at room temperature, then ice water (120 mL) was added. The mixture was allowed to stand for 30 min, then filtered to remove the solid product. The solid was washed with water and dried, affording 2-oxo-2H-chromen-7-yl trifluoromethanesulfonate (6.9 g, 78%) as a white crystalline solid. MS m/z 295.2 [M+H]$^+$.

Step B: 2-Oxo-2H-chromen-7-yl trifluoromethanesulfonate (2.94 g, 10 mmol) was combined with 3-butyne-1-ol (1.13 mL, 15 mmol), copper(I) iodide (380 mg, 2.0 mmol), tetrakis(triphenylphosphine)palladium(0) (1.16 g, 1.0 mmol) and triethylamine (2.78 mL, 20 mmol) in DMF (30 mL). The mixture was stirred at 60° C. for 2 h, then the solvent was removed by rotary evaporation. The residue was chromatographed on silica gel, eluting with 0-20% EtOAc in $CH_2Cl_2$ to afford 7-(4-hydroxybut-1-yn-1-yl)-2H-chromen-2-one (2.1 g, quant.) as a tan powder. MS m/z 215.2 [M+H]$^+$.

Step C: 7-(4-Hydroxybut-1-yn-1-yl)-2H-chromen-2-one (1.72 g, 8 mmol) was suspended in MeOH (20 mL) with 10% Pd/C (300 mg). The mixture was stirred vigorously under $H_2$ (1 atm) for 16 h, then the catalyst was removed by vacuum filtration. The filtrate was concentrated to afford 7-(4-hydroxybutyl)-2H-chromen-2-one (1.67 g, 96%) as a colorless oil. MS m/z 219.2 [M+H]$^+$.

Step D: 7-(4-Hydroxybutyl)-2H-chromen-2-one (1.67 g, 7.6 mmol) was dissolved in AcOH (20 mL). Sodium acetate (1.87 g, 22.8 mmol) and bromine (1.18 mL, 22.8 mmol) were added sequentially. The mixture was stirred at 40° C. for 2 h., then the solvent was removed by rotary evaporation. MeOH (10 mL) and triethylamine (1 mL) were added to the residue and the mixture was stirred at 70° C. for 10 min. The solvent was removed by rotary evaporation, then the residue was partitioned in water and $CH_2Cl_2$. The organic layer was collected, concentrated and chromatographed on silica gel, eluting with 20-80% EtOAc in hexanes to afford 3-bromo-7-(4-hydroxybutyl)-2H-chromen-2-one (1.2 g, 53%) as a white powder. MS m/z 297.1, 299.1 [M+H]$^+$.

Step E: 3-Bromo-7-(4-hydroxybutyl)-2H-chromen-2-one (1.2 g, 4 mmol) was combined with tributyl(1-ethoxyvinyl)stannane (1.8 g, 5 mmol), copper(I) iodide (190 mg, 1 mmol) and tetrakis(triphenylphosphine)palladium(0) (462 mg, 0.4 mmol) in 1,4-dioxane (20 mL). The mixture was stirred at 60° C. for 4 h, then the solvent was removed by rotary evaporation. The residue was chromatographed on silica gel, eluting with 20-50% EtOAc in hexanes to afford 3-(1-ethoxyvinyl)-7-(4-hydroxybutyl)-2H-chromen-2-one (860 mg, 75%) a colorless oil. MS m/z 261.2 [M+H]$^+$ (hydrolysis during UPLC/MS analysis provides the mass of 3-acetyl-7-(4-hydroxybutyl)-2H-chromen-2-one).

Step F: 3-(1-Ethoxyvinyl)-7-(4-hydroxybutyl)-2H-chromen-2-one (860 mg, 3.0 mmol) was dissolved in THF (12 mL) and $H_2O$ (3 mL). N-Bromosuccinimide (587 mg, 3.3 mmol) was added to the mixture. After 10 min, THF was removed with a nitrogen stream. The residue was suspended in $H_2O$ (10 mL) and filtered. The collected solid was washed with $H_2O$ and dried affording 3-(2-bromoacetyl)-7-(4-hydroxybutyl)-2H-chromen-2-one (1.0 g, 99%) as a tan solid. MS m/z 339.1, 341.1 [M+H]$^+$.

Step G: Following the procedure in Example 77, Step D, 3-(2-bromoacetyl)-7-(4-hydroxybutyl)-2H-chromen-2-one (1.0 g, 3.0 mmol), 3,5-dimethylpyrazin-2-amine (403 mg, 3.3 mmol) in $CH_3CN$ (10 mL) yielded 3-(6,8-dimethylimidazo[1,2-a]pyrazin-2-yl)-7-(4-hydroxybutyl)-2H-chromen-2-one hydrobromide (880 mg, 66%) as a tan powder. MS m/z 364.2 [M+H]$^+$.

Step H: Following the procedure in Example 77, Step E, 3-(6,8-dimethylimidazo[1,2-a]pyrazin-2-yl)-7-(4-hydroxy-butyl)-2H-chromen-2-one hydrobromide, diisopropylethylamine (1.3 mL, 7.5 mmol) and methanesulfonyl chloride (0.39 mL, 5 mmol) in $CH_2Cl_2$ (10 mL) yielded 4-(3-(6,8-dimethylimidazo[1,2-a]pyrazin-2-yl)-2-oxo-2H-chromen-7-yl)butyl methanesulfonate (705 mg, 80%) as a pale yellow solid. MS m/z 442.2 [M+H]$^+$.

Step I: Following the procedure in Example 77, Step F, 4-(3-(6,8-dimethylimidazo[1,2-a]pyrazin-2-yl)-2-oxo-2H-chromen-7-yl)butyl methanesulfonate (36 mg, 0.08 mmol), dimethylamine (2 mmol, 2 M in THF) in DMF (1 mL) yielded the title compound (27 mg, 86%) as an off white powder: m.p. 190-193° C.; MS m/z 391.5 [M+H]$^+$; $^1$H NMR (500 MHz, DMSO-d$_6$): δ 8.86 (1H, s), 8.62 (1H, s), 8.35 (1H, s), 7.90 (1H, d, J=7.9 Hz), 7.32 (1H, s), 7.27 (1H, d, J=7.9 Hz), 2.78 (3H, s), 2.73 (2H, t, J=6.9 Hz), 2.38 (3H, s), 2.22 (2H, t, J=6.9 Hz), 2.10 (6H, s), 1.64 (2H, p, J=7.5 Hz), 1.43 (2H, p, J=7.5 Hz).

As shown in Table 1 below, additional compounds disclosed herein may be prepared according to Example 78 by substituting the appropriate starting materials, reagents and reaction conditions.

Example 79

Preparation of Cpd 908

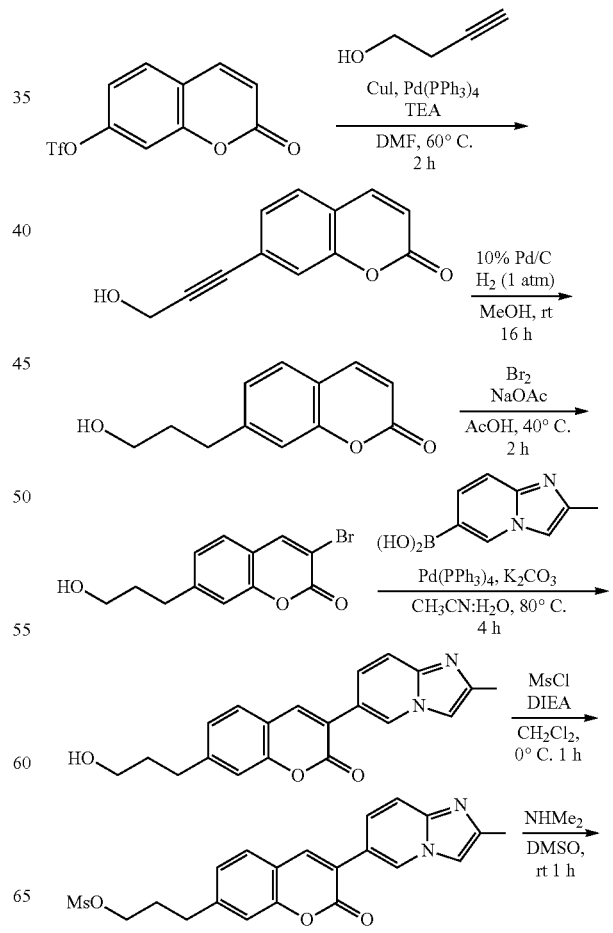

-continued

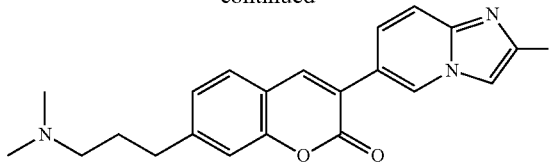

Step A: Following the procedure in Example 78, Step B, 2-oxo-2H-chromen-7-yl trifluoromethanesulfonate (4.2 g, 14.3 mmol, prepared in Example 78, Step A) propargyl alcohol (1.13 mL, 21.4 mmol), copper(I) iodide (266 mg, 1.4 mmol), tetrakis(triphenylphosphine) palladium(0) (1.62 g, 1.4 mmol) and triethylamine (2.98 mL, 21.5 mmol) in DMF (30 mL) yielded 7-(3-hydroxyprop-1-yn-1-yl)-2H-chromen-2-one (1.5 g, 52%) as a tan powder. MS m/z 201.1 [M+H]+.

Step B: Following the procedure in Example 78, Step C, 7-(3-hydroxyprop-1-yn-1-yl)-2H-chromen-2-one (1.5 g, 8 mmol), 10% Pd/C (200 mg) in MeOH (20 mL) yielded 7-(3-hydroxypropyl)-2H-chromen-2-one (1.5 g, quant.) as a white powder. MS m/z 205.2 [M+H]+.

Step C: Following the procedure in Example 78, Step D, 7-(3-hydroxypropyl)-2H-chromen-2-one (1.5 g, 7.3 mmol), sodium acetate (1.74 g, 21.2 mmol) and bromine (1.1 mL, 21.2 mmol) in AcOH (20 mL) yielded 3-bromo-7-(3-hydroxypropyl)-2H-chromen-2-one (595 mg, 29%) as a white powder. MS m/z 283.1, 285.1 [M+H]+.

Step D: 3-bromo-7-(3-hydroxypropyl)-2H-chromen-2-one (142 mg, 0.5 mmol) was combined with (2-methylimidazo[1,2-a]pyridin-6-yl)boronic acid (132 mg, 0.75 mmol, prepared in Example 34, Step A) and tetrakis(triphenylphosphine)palladium(0) (58 mg, 0.05 mmol) in CH₃CN (2 mL). Aqueous K₂CO₃ (2 mL, 1 M) was added to the mixture. The mixture was heated under nitrogen at 80° C. for 2 h. The organic layer was removed, concentrated and chromatographed on silica gel, eluting with 0-8% MeOH in CH₂Cl₂ to afford 7-(3-hydroxypropyl)-3-(2-methylimidazo[1,2-a]pyridin-6-yl)-2H-chromen-2-one (65 mg, 39%) as a tan powder. MS m/z 335.2 [M+H]+.

Step F: Following the procedure in Example 77, Step E, 7-(3-hydroxypropyl)-3-(2-methylimidazo[1,2-a]pyridin-6-yl)-2H-chromen-2-one (65 mg, 0.2 mmol), diisopropylethylamine (0.15 mL, 0.8 mmol) and methanesulfonyl chloride (30 µL, 0.4 mmol) in CH₂Cl₂ (2 mL) yielded 3-(3-(2-methylimidazo[1,2-a]pyridin-6-yl)-2-oxo-2H-chromen-7-yl)propyl methanesulfonate (35 mg, 47%) as a tan powder. MS m/z 413.3 [M+H]+.

Step G: Following the procedure in Example 77, Step F, 3-(3-(2-methylimidazo[1,2-a]pyridin-6-yl)-2-oxo-2H-chromen-7-yl)propyl methanesulfonate (35 mg, 0.08 mmol), dimethylamine (2 mmol, 2 M in THF) in THF (1 mL) yielded the title compound (22 mg, 76%) as an off white powder: m.p. 176-178° C.; MS m/z 362.3 [M+H]+; $^1$H NMR (500 MHz, DMSO-d₆): δ 9.01 (1H, s), 8.38 (1H, s), 7.80 (1H, s), 7.70 (1H, d, J=7.9 Hz), 7.54 (2H, m), 7.34 (1H, s), 7.28 (1H, d, J=7.9 Hz), 2.73 (2H, t, J=7.1 Hz), 2.36 (3H, s), 2.22 (2H, t, J=7.1 Hz), 2.13 (6H, s), 1.76 (2H, p, J=7.3 Hz).

As shown in Table 1 below, additional compounds disclosed herein may be prepared according to Example 79 by substituting the appropriate starting materials, reagents and reaction conditions.

Example 80

Preparation of Cpd 927

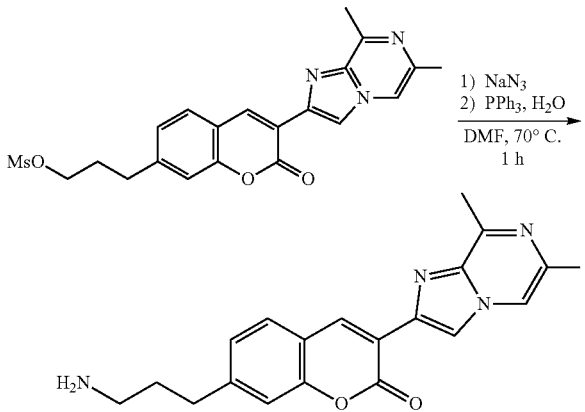

3-(3-(6,8-dimethylimidazo[1,2-a]pyrazin-2-yl)-2-oxo-2H-chromen-7-yl)propyl methanesulfonate (300 mg, 0.70 mmol, prepared according to Example 77) was combined with sodium azide (57 mg, 0.88 mmol) in DMF (5 mL). The mixture was heated at 70° C. for 2 h. Triphenylphosphine (367 mg, 1.4 mmol) and H₂O (63 µL, 3.5 mmol) were added to the solution. The mixture was stirred for an additional 1 h at 70° C., then loaded directly onto silica gel, eluting with 9.7:0.3:90 MeOH:NH₃:CH₂Cl₂ to afford the title compound (160 mg, 66%) as an off white powder: m.p. 212-216° C.; MS m/z 349.3 [M+H]+; $^1$H NMR (500 MHz, DMSO-d₆): δ 8.83 (1H, s), 8.60 (1H, s), 8.33 (1H, s), 7.88 (1H, d, J=7.9 Hz), 7.32 (1H, s), 7.26 (1H, d, J=7.9 Hz), 2.77 (3H, s), 2.75 (2H, t, J=6.9 Hz), 2.57 (2H, t, J=6.9 Hz), 2.37 (3H, s), 1.70 (2H, p, J=7.5 Hz).

Example 81

Preparation of Cpd 933

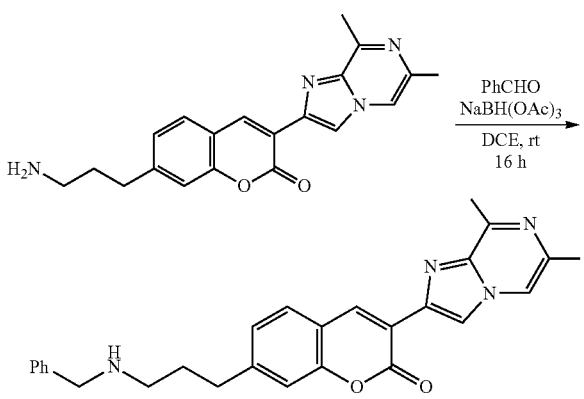

7-(3-aminopropyl)-3-(6,8-dimethylimidazo[1,2-a]pyrazin-2-yl)-2H-chromen-2-one (40 mg, 0.11 mmol, prepared in Example 80) was suspended in 1,2-dichloroethane (1 mL) and EtOH (0.5 mL). To the mixture was added benzaldehyde (122 µL, 1.2 mmol) and sodium triacetoxyborohydride (47 mg, 0.22 mmol). The mixture was stirred at room temperature for 16 h, then loaded directly onto silica gel, eluting with 2-8% MeOH (3% NH$_3$) in CH$_2$Cl$_2$ to afford the title compound (28 mg, 65%) as a tan powder: m.p. 143-147° C.; MS m/z 439.3 [M+H]$^+$; $^1$H NMR (500 MHz, DMSO-d$_6$): δ 8.85 (1H, s), 8.62 (1H, s), 8.35 (1H, s), 7.88 (1H, d, J=7.9 Hz), 7.34-7.19 (7H), 3.69 (2H, s), 2.78 (3H, s), 2.75 (2H, m), 2.52 (2H, m), 2.38 (3H, s), 1.79 (2H, p, J=6.7 Hz).

As shown in Table 1 below, additional compounds disclosed herein may be prepared according to Example 81 by substituting the appropriate starting materials, reagents and reaction conditions.

Example 82

Preparation of Cpd 943

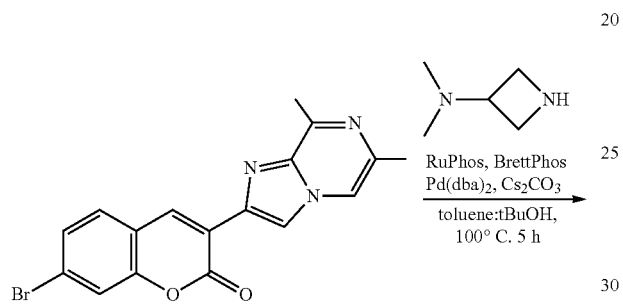

A mixture of 7-bromo-3-(6,8-dimethylimidazo[1,2-a]pyrazin-2-yl)-2H-chromen-2-one (74.4 mg, 0.2 mmol, prepared in Example 48, Step A), 3-(dimethylamino)azetidine dihydrochloride (69.2 mg, 0.4 mmol), bis(dibenzylideneacetone)palladium(0) (11.5 mg, 0.02 mmol), RuPhos (9.3 mg, 0.02 mmol), BrettPhos (10.7 mg, 0.02 mmol) and Cs$_2$CO$_3$ (228.1 mg, 0.7 mmol) in toluene (0.2 mL) and t-butanol (0.2 mL) was heated at 100° C. for 5 h. The solvent was removed by rotary evaporation, then the residue was suspended in diethyl ether and filtered. The solid was washed thoroughly with water and dried to afford the title compound (59.5 mg, 76%) as a yellow solid: m.p. 246-250° C.; MS m/z 390.3 [M+H]$^+$; $^1$H NMR (500 MHz, DMSO-d$_6$): δ 8.72 (1H, s), 8.50 (1H, s), 8.32 (1H, s), 7.74 (1H, d, J=8.6 Hz), 6.47 (1H, dd, J=8.6 Hz, 2.2 Hz), 6.35 (1H, d, J=1.9 Hz), 4.05 (2H, m), 3.78 (2H, m), 3.27 (1H, m), 2.75 (3H, s), 2.37 (3H, s), 2.15 (6H, s).

Example 83

Preparation of Cpd 971

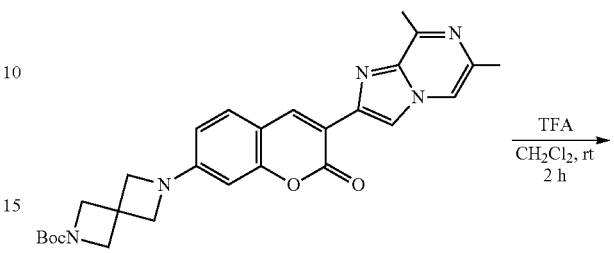

Step A: 6-[3-(6,8-Dimethyl-imidazo[1,2-a]pyrazin-2-yl)-2-oxo-2H-chromen-7-yl]-2,6-diaza-spiro[3.3]heptane-2-carboxylic acid tert-butyl ester (49 mg, 0.100 mmol, prepared according to Example 43) was stirred in CH$_2$Cl$_2$ (5 mL) with trifluoroacetic acid (1.25 mL) at room temperature for 2 h, then the solvent was removed in vacuo. The residue was partitioned in CH$_2$Cl$_2$/MeOH (9/1) and an aqueous saturated NaHCO$_3$ solution (1 M, 5 mL). The organic phase was dried over Na$_2$SO$_4$ and purified by silica gel chromatography (CH$_2$Cl$_2$/MeOH 95/5, 1% aq. NH$_3$) to give the title compound (33 mg, 85%) as a yellow solid. MS m/z 388.3 [M+H]$^+$. $^1$H NMR (300 MHz, CDCl$_3$): δ 8.91 (1H, d, J=1.2 Hz), 8.30 (1H, s), 7.91 (1H, d), 7.53 (1H, d), 7.48 (1H, d), 6.48 (1H, dd), 6.40 (1H, d), 4.14 (4H, s), 4.06 (4H, s), 2.36 (3H, s).

As shown in Table 1 below, additional compounds disclosed herein may be prepared according to Example 83 by substituting the appropriate starting materials, reagents and reaction conditions.

Example 84

Preparation of Cpd 985

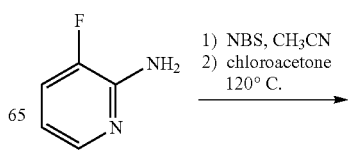

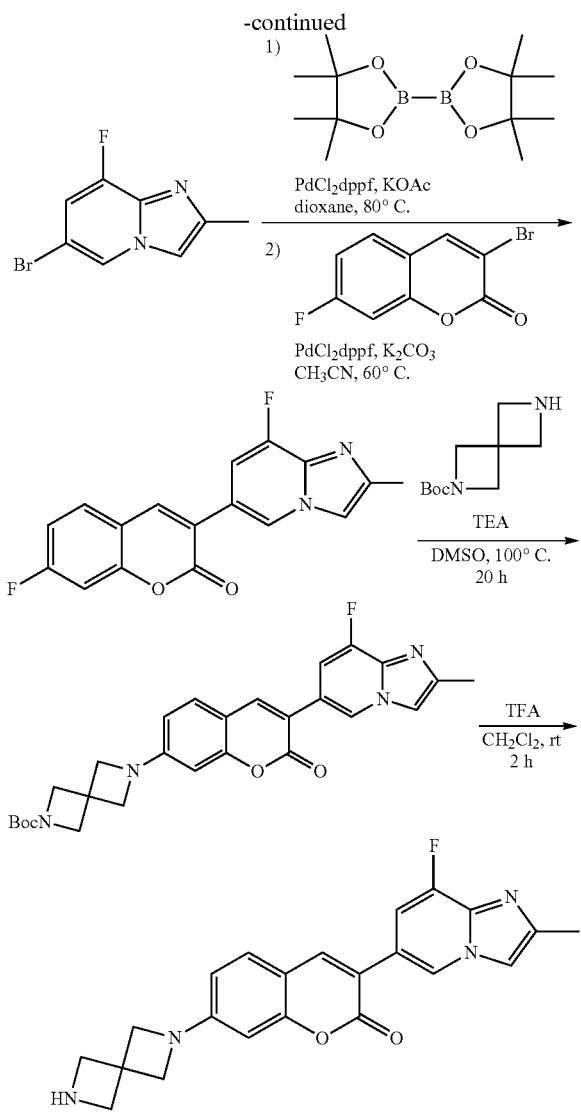

Step A: 3-fluoropyridin-2-amine (5.0 g, 45 mmol) was combined with N-bromosuccinimide (8.0 g, 45 mmol) in $CH_3CN$. The mixture was stirred at room temperature for 30 min. Chloroacetone (4.3 mL, 54 mmol) was added to the mixture, which was heated at 100° C., allowing $CH_3CN$ to evaporate. After 1 h, the temperature was further raised to 120° C. for 2 h. The mixture solidified upon cooling. The solid material was dissolved in $H_2O$ (50 mL) and an aqueous saturated $NaHCO_3$ solution (100 mL) was added. A precipitate formed, and was collected by vacuum filtration. The solid material was washed with $H_2O$ and vacuum dried. The material was chromatographed on silica gel (0-30% EtOAc in $CH_2Cl_2$), providing the title compound as a tan powder (4.65 g, 45%). MS m/z 229.2 $[M+H]^+$.

Step B: A mixture of 6-bromo-8-fluoro-2-methyl-imidazo[1,2-a]pyridine (500 mg, 2.18 mmol), 4,4,4',4',5,5,5',5'-octamethyl-2,2'-bi(1,3,2-dioxaborolane) (665 mg, 2.62 mmol), [1,1'-bis(diphenylphosphino)ferrocene]dichloro-palladium (II) complex with dichloromethane (89.1 mg, 0.109 mmol), and potassium acetate (643 mg, 6.55 mmol) in 1,4-dioxane (4.4 mL) was stirred at 80° C. overnight under Argon. The mixture was diluted with THF (12 mL) and filtered. The filtrate was concentrated to give a dark solid residue, which was used without further purification. The residue was combined with 3-bromo-7-fluoro-2H-chromen-2-one (250 mg, 1.03 mmol, prepared in Example 32, step A), [1,1'-bis(diphenylphosphino)-ferrocene]dichloropalladium(II) complex with dichloromethane (84 mg, 0.101 mmol) and aqueous $K_2CO_3$ (2.0 M×1.55 mL, 3.09 mmol) in $CH_3CN$ (3.5 mL). The mixture was stirred at 60° C. for 5 h under Argon, then cooled to room temperature, diluted with water and filtered. The solid was dissolved in $CH_2Cl_2$ (10% methanol), dried over $Na_2SO_4$, filtered, concentrated and purified by silica gel chromatography (0-5% MeOH in $CH_2Cl_2$) to give 7-fluoro-3-(8-fluoro-2-methyl-imidazo[1,2-a]pyridin-6-yl)-chromen-2-one (286 mg, 89%) as a brown solid.

Step C: A mixture of 7-fluoro-3-(8-fluoro-2-methyl-imidazo[1,2-a]pyridin-6-yl)-chromen-2-one (87 mg, 0.279 mmol), triethyl amine (0.14 mL, 1.00 mmol) and tert-butyl 2,6-diazaspiro[3.3]heptane-2-carboxylate hemioxalate (158 mg, 0.325 mmol) in DMSO (1 mL) was stirred at 100° C. for 20 h. The mixture was diluted with an aqueous saturated $NaHCO_3$ solution and filtered. The solid was dried and purified by silica gel chromatography (0-10% MeOH in $CH_2Cl_2$) to give 6-[3-(8-Fluoro-2-methyl-imidazo[1,2-a]pyridin-6-yl)-2-oxo-2H-chromen-7-yl]-2,6-diazaspiro[3.3]heptane-2-carboxylic acid tert-butyl ester as a yellow solid.

Step D: 6-[3-(8-Fluoro-2-methyl-imidazo[1,2-a]pyridin-6-yl)-2-oxo-2H-chromen-7-yl]-2,6-diazaspiro[3.3]heptane-2-carboxylic acid tert-butyl ester (136 mg, 0.27 mmol) was stirred in $CH_2Cl_2$ (3 mL) with trifluoroacetic acid (0.5 mL) at room temperature for 2 h, then the solvent was removed in vacuo. The residue was partitioned in $CH_2Cl_2$/MeOH (9/1) and an aqueous $NaHCO_3$ solution (1 M, 5 mL). The organic phase was dried over $Na_2SO_4$, concentrated and purified by silica gel chromatography ($CH_2Cl_2$/MeOH 80/20, 1% aq. $NH_3$) to give the title product (32 mg, 29%) as a yellow solid. MS m/z 391.7 $[M+H]^+$. $^1H$ NMR (300 MHz, $CDCl_3$): δ 8.71 (1H, s), 8.42 (1H, s), 7.75 (1H, s), 7.45 (1H, d, J=8.7 Hz), 6.36 (1H, dd, J=8.7 Hz, J=2.1 Hz), 6.28 (1H, d, J=2.1 Hz), 4.10 (4H, s), 3.48 (4H, s), 2.90 (3H, s), 2.17 (3H, s).

As shown in Table 1 below, additional compounds disclosed herein may be prepared according to Example 84 by substituting the appropriate starting materials, reagents and reaction conditions.

Table 1 provides isolated compounds of a free base form of a compound of Formula (I) that may be prepared according to the procedures of the indicated Example by substituting the appropriate starting materials, reagents and reaction conditions. The preparation of any salt, isotopologue, stereoisomer, racemate, enantiomer, diastereomer or tautomer from a free base form of a compound of Formula (I) is also contemplated and further included within the scope of the description herein. Where a free base form of the compound was not isolated from the salt form, a person of ordinary skill in the art could be expected to perform the required reactions to prepare and isolate the free base form of the compound.

The term "Cpd" represents Compound number, the term "Ex" represents "Example Number" (wherein * indicates that the corresponding Example for the Compound is provided above), the term "M.P." represents "Melting Point (° C.)," the term "MS" represents "Mass Spectroscopy Peak(s) m/z $[M+H]^{+/−}$", the term "D" represents "Decomposition/Decomposed," the term "DR" represents "Decomposition Range," the term "S" represents "Softens," the term "ND" indicates that the value was "Not Determined" and the term "NI" indicates that the compound was "Not Isolated."

TABLE 1

| Ex | Cpd | Name | M.P. | MS |
|---|---|---|---|---|
| 1 | 1b | 7-(piperazin-1-yl)-3-[4-(trifluoromethyl)-1,3-benzoxazol-2-yl]-2H-chromen-2-one | ND | 416.3 |
| 1 | 2b | 7-(piperazin-1-yl)-3-[7-(trifluoromethyl)-1,3-benzoxazol-2-yl]-2H-chromen-2-one | ND | 416.2 |
| 5 | 3a | 2-oxo-N-phenyl-7-(piperazin-1-yl)-2H-chromene-3-carboxamide | 238-248 | 350.1 |
| 1 | 4a | 3-(1,3-benzothiazol-2-yl)-7-(piperazin-1-yl)-2H-chromen-2-one | NI | NI |
| 2 | 5a | 3-(4-chloro-1,3-benzothiazol-2-yl)-7-(piperazin-1-yl)-2H-chromen-2-one | NI | NI |
| 2 | 6a | 3-(7-chloro-1,3-benzothiazol-2-yl)-7-(piperazin-1-yl)-2H-chromen-2-one | NI | NI |
| 9 | 7 | 3-(4-chloro-1,3-benzothiazol-2-yl)-7-(piperazin-1-ylmethyl)-2H-chromen-2-one | 222-226 | 412.1 |
| 9 | 8 | 3-(1,3-benzothiazol-2-yl)-7-[(propan-2-ylamino)methyl]-2H-chromen-2-one | 164-168 | 351.2 |
| 9 | 9 | 7-[(propan-2-ylamino)methyl]-3-[4-(trifluoromethyl)-1,3-benzothiazol-2-yl]-2H-chromen-2-one | 191-196 | 419.2 |
| 9 | 10 | 3-(4-chloro-1,3-benzothiazol-2-yl)-7-[(propan-2-ylamino)methyl]-2H-chromen-2-one | 157-161 | 385 |
| 26 | 11 | 7-(4-methylpiperazin-1-yl)-3-[3-(trifluoromethyl)phenyl]-2H-chromen-2-one | 150-156 | 389.3 |
| 26 | 12 | 7-(piperazin-1-yl)-3-(pyridin-3-yl)-2H-chromen-2-one | 170-172 | 308.3 |
| 9 | 13 | 3-(1,3-benzothiazol-2-yl)-7-[(dimethylamino)methyl]-2H-chromen-2-one | 171-176 | 337.1 |
| 9* | 14 | 3-(4-chloro-1,3-benzothiazol-2-yl)-7-[(dimethylamino)methyl]-2H-chromen-2-one | 179-182 | 371.1 |
| 68 | 15 | 3-(1,3-benzothiazol-2-yl)-7-[4-(propan-2-yl)piperazin-1-yl]-2H-chromen-2-one | 238-246 | 406.4 |
| 1 | 16 | 3-(1,3-benzothiazol-2-yl)-7-(4-methylpiperazin-1-yl)-2H-chromen-2-one | 259-262 | 378.1 |
| 2 | 17 | 3-(4-chloro-1,3-benzothiazol-2-yl)-7-(4-methylpiperazin-1-yl)-2H-chromen-2-one | 256-260 | 412.1 |
| 11 | 18a | 3-(4-chloro-1,3-benzothiazol-2-yl)-7-(piperidin-4-yl)-2H-chromen-2-one | NI | NI |
| 1 | 19a | 3-(5-fluoro-1,3-benzoxazol-2-yl)-7-(piperazin-1-yl)-2H-chromen-2-one | NI | NI |
| 66* | 20 | 3-(1,3-benzoxazol-2-yl)-7-(piperidin-4-yloxy)-2H-chromen-2-one | 198-201 | 363.2 |
| 1 | 21 | 3-(4-methyl-1,3-benzoxazol-2-yl)-7-(4-methylpiperazin-1-yl)-2H-chromen-2-one | 217-219 | 376.2 |
| 1 | 22a | 3-(4-methyl-1,3-benzoxazol-2-yl)-7-(piperazin-1-yl)-2H-chromen-2-one | NI | NI |
| 1 | 23 | 3-(1,3-benzoxazol-2-yl)-7-[(3R,5S)-3,5-dimethylpiperazin-1-yl]-2H-chromen-2-one | 230-232 | 376.3 |
| 1 | 24 | 3-(1,3-benzothiazol-2-yl)-7-[(3R,5S)-3,5-dimethylpiperazin-1-yl]-2H-chromen-2-one | 248-252 | 392.1 |
| 2 | 25 | 3-(4-chloro-1,3-benzothiazol-2-yl)-7-[(3R,5S)-3,5-dimethylpiperazin-1-yl]-2H-chromen-2-one | 229-235 | 426.0 428.0 |
| 26 | 26 | 3-(3-fluorophenyl)-7-(piperazin-1-yl)-2H-chromen-2-one | 148-150 | 325.3 |
| 26 | 27 | 7-(piperazin-1-yl)-3-(pyridin-4-yl)-2H-chromen-2-one | 212-214 | 308.4 |
| 12* | 28 | 3-(4-chloro-1,3-benzothiazol-2-yl)-7-[(4-methylpiperazin-1-yl)carbonyl]-2H-chromen-2-one | 230-235 | 440.1 |
| 17* | 29 | 7-(piperazin-1-yl)-3-(1H-pyrazol-5-yl)-2H-chromen-2-one | 224-228 | 297.2 |
| 5 | 30 | 7-[(3R,5S)-3,5-dimethylpiperazin-1-yl]-2-oxo-N-phenyl-2H-chromene-3-carboxamide | 231-233 | 378.3 |
| 1 | 31 | 7-[(3R,5S)-3,5-dimethylpiperazin-1-yl]-3-(4-methyl-1,3-benzoxazol-2-yl)-2H-chromen-2-one | 243-245 | 390.3 |
| 24* | 32 | 7-(piperazin-1-yl)-3-(pyridin-2-ylamino)-2H-chromen-2-one | 191-194 | 323.2 |
| 24 | 33 | 7-(piperazin-1-yl)-3-(pyrimidin-2-ylamino)-2H-chromen-2-one | 193-195 | 324.2 |
| 36 | 34 | 3-(imidazo[1,2-a]pyridin-2-yl)-7-(piperazin-1-yl)-2H-chromen-2-one | 290 (D) | 347.2 |
| 13* | 35 | 3-(4-chloro-1,3-benzothiazol-2-yl)-7-[2-(propan-2-ylamino)ethyl]-2H-chromen-2-one | 179-182 | 399.1 |
| 13 | 36 | 3-(4-chloro-1,3-benzothiazol-2-yl)-7-[3-(propan-2-ylamino)propyl]-2H-chromen-2-one | 262-265 | 413.1 |
| 21 | 37 | 3-(4-methyl-1,3-thiazol-2-yl)-7-(piperazin-1-yl)-2H-chromen-2-one | 244-249 | 328.1 |
| 18* | 38 | 3-(1-methyl-1H-pyrazol-3-yl)-7-(piperazin-1-yl)-2H-chromen-2-one | 224-228 | 311.1 |
| 1 | 39 | 7-[(3R,5S)-3,5-dimethylpiperazin-1-yl]-3-(4-fluoro-1,3-benzoxazol-2-yl)-2H-chromen-2-one | 242-243 | 394.2 |
| 1 | 40a | 3-(4-fluoro-1,3-benzoxazol-2-yl)-7-(piperazin-1-yl)-2H-chromen-2-one | NI | NI |
| 14 | 41 | 3-(1,3-benzothiazol-2-yl)-2-oxo-2H-chromen-7-yl piperazine-1-carboxylate | 221-225 | 408.1 |

TABLE 1-continued

| Ex | Cpd | Name | M.P. | MS |
|---|---|---|---|---|
| 14* | 42 | 3-(4-chloro-1,3-benzothiazol-2-yl)-2-oxo-2H-chromen-7-yl piperazine-1-carboxylate | 236-239 | 442.1 |
| 1 | 43 | benzyl 4-[3-(1-methyl-1H-benzimidazol-2-yl)-2-oxo-2H-chromen-7-yl]piperazine-1-carboxylate | 253-254 | 495.1 |
| 36 | 44 | 3-(8-methylimidazo[1,2-a]pyridin-2-yl)-7-(piperazin-1-yl)-2H-chromen-2-one | 190-193 | 361.2 |
| 21 | 45 | 7-(4-methylpiperazin-1-yl)-3-(4-phenyl-1,3-thiazol-2-yl)-2H-chromen-2-one | 205-210 | 404.2 |
| 66 | 46 | 3-(1,3-benzothiazol-2-yl)-7-(piperidin-4-yloxy)-2H-chromen-2-one | 220-226 | 379.1 |
| 4 | 47 | 3-(1,3-benzoxazol-2-yl)-7-(4-methyl-1,4-diazepan-1-yl)-2H-chromen-2-one | 170-173 | 376.2 |
| 4 | 48 | 3-(1,3-benzoxazol-2-yl)-7-[3-(dimethylamino)pyrrolidin-1-yl]-2H-chromen-2-one | 222-224 | 376.2 |
| 4 | 49 | 3-(1,3-benzoxazol-2-yl)-7-{[2-(dimethylamino)ethyl](methyl)amino}-2H-chromen-2-one | ND | 364.2 |
| 16* | 50 | 3-(5-phenyl-1,2,4-oxadiazol-3-yl)-7-(piperazin-1-yl)-2H-chromen-2-one | 214-221 | 375.2 |
| 36 | 51 | 3-(6-methylimidazo[1,2-a]pyridin-2-yl)-7-(piperazin-1-yl)-2H-chromen-2-one | 229-232 | 361.2 |
| 21 | 52b | 7-(piperazin-1-yl)-3-[4-(trifluoromethyl)-1,3-thiazol-2-yl]-2H-chromen-2-one | 221-229 | 382.2 |
| 21 | 53a | 7-(4-methylpiperazin-1-yl)-3-[4-(trifluoromethyl)-1,3-thiazol-2-yl]-2H-chromen-2-one | NI | NI |
| 66 | 54 | 3-(1,3-benzothiazol-2-yl)-7-[(3S)-pyrrolidin-3-yloxy]-2H-chromen-2-one | 205-211 | 365.2 |
| 66 | 55 | 3-(1,3-benzothiazol-2-yl)-7-[(3R)-pyrrolidin-3-yloxy]-2H-chromen-2-one | 205-211 | 365.2 |
| 66 | 56 | 3-(1,3-benzothiazol-2-yl)-7-[(2S)-pyrrolidin-2-ylmethoxy]-2H-chromen-2-one | 195-199 | 379.2 |
| 9 | 57 | 3-(1,3-benzothiazol-2-yl)-7-[(diethylamino)methyl]-2H-chromen-2-one | 116-119 | 365.2 |
| 9 | 58 | 3-(4-chloro-1,3-benzothiazol-2-yl)-7-[(diethylamino)methyl]-2H-chromen-2-one | 147-151 | 399.2 |
| 9 | 59 | 3-(1,3-benzothiazol-2-yl)-7-(piperidin-1-ylmethyl)-2H-chromen-2-one | 201-205 | 377.2 |
| 9 | 60 | 3-(4-chloro-1,3-benzothiazol-2-yl)-7-(piperidin-1-ylmethyl)-2H-chromen-2-one | 191-195 | 411.2 |
| 24 | 61 | 3-[(3-methylpyridin-2-yl)amino]-7-(piperazin-1-yl)-2H-chromen-2-one | 164-167 | 337.3 |
| 24 | 62 | 3-[(4-methylpyridin-2-yl)amino]-7-(piperazin-1-yl)-2H-chromen-2-one | 182-185 | 337.3 |
| 24 | 63 | 3-[(5-methylpyridin-2-yl)amino]-7-(piperazin-1-yl)-2H-chromen-2-one | 225-228 | 337.3 |
| 24 | 64 | 3-[(6-methylpyridin-2-yl)amino]-7-(piperazin-1-yl)-2H-chromen-2-one | 135-137 | 337.3 |
| 24 | 65 | 3-[(5-chloropyridin-2-yl)amino]-7-(piperazin-1-yl)-2H-chromen-2-one | 253-255 | 357.2 |
| 24 | 66 | 7-(piperazin-1-yl)-3-(pyridin-3-ylamino)-2H-chromen-2-one | 172-175 | 323.3 |
| 3 | 67a | 3-(4-iodo-1,3-benzoxazol-2-yl)-7-(piperazin-1-yl)-2H-chromen-2-one | NI | NI |
| 3* | 68 | 3-(4-chloro-1,3-benzoxazol-2-yl)-7-(4-methylpiperazin-1-yl)-2H-chromen-2-one | 229-231 | 396.2 398.2 |
| 3 | 69 | 3-(4-chloro-1,3-benzoxazol-2-yl)-7-[(3R,5S)-3,5-dimethylpiperazin-1-yl]-2H-chromen-2-one | 238-240 | 410.3 412.3 |
| 3 | 70a | 3-(4-chloro-1,3-benzoxazol-2-yl)-7-(piperazin-1-yl)-2H-chromen-2-one | NI | NI |
| 36 | 71 | 3-(6-chloroimidazo[1,2-a]pyridin-2-yl)-7-(piperazin-1-yl)-2H-chromen-2-one | 233 (D) | 381.2 383.2 |
| 36 | 72 | 3-(imidazo[1,2-a]pyridin-2-yl)-7-(4-methylpiperazin-1-yl)-2H-chromen-2-one | 265-268 | 361.2 |
| 67 | 73 | 7-(4-methylpiperazin-1-yl)-3-(1-methyl-1H-pyrazol-3-yl)-2H-chromen-2-one | 183-186 | 325.3 |
| 19* | 74 | 7-(4-methylpiperazin-1-yl)-3-(1-phenyl-1H-pyrazol-3-yl)-2H-chromen-2-one | 152-159 | 387.3 |
| 24 | 75 | 3-(phenylamino)-7-(piperazin-1-yl)-2H-chromen-2-one | 140-143 | 322.3 |
| 26 | 76 | 7-(piperazin-1-yl)-3-[4-(trifluoromethyl)pyridin-2-yl]-2H-chromen-2-one | 185-190 | 376.3 |
| 26 | 77 | 3-(3-methoxyphenyl)-7-(piperazin-1-yl)-2H-chromen-2-one | 127-130 | 337.3 |
| 10 | 78 | 3-(1,3-benzothiazol-2-yl)-7-[(methylamino)methyl]-2H-chromen-2-one | 156-160 | 323.2 |
| 10 | 79 | 3-(1,3-benzothiazol-2-yl)-7-{[(2-hydroxyethyl)(methyl)amino]methyl}-2H-chromen-2-one | 182-184 | 367.2 |
| 20* | 80 | 3-(4-methyl-1H-pyrazol-3-yl)-7-(piperazin-1-yl)-2H-chromen-2-one | 175-200 (DR) | 311.2 |

TABLE 1-continued

| Ex | Cpd | Name | M.P. | MS |
|---|---|---|---|---|
| 36 | 81 | 3-(6-methylimidazo[1,2-a]pyridin-2-yl)-7-(4-methylpiperazin-1-yl)-2H-chromen-2-one | 267 (D) | 375.2 |
| 68 | 82 | 3-(6-methylimidazo[1,2-a]pyridin-2-yl)-7-[4-(propan-2-yl)piperazin-1-yl]-2H-chromen-2-one | 260 (D) | 403.3 |
| 36 | 83 | 3-(8-chloroimidazo[1,2-a]pyridin-2-yl)-7-(piperazin-1-yl)-2H-chromen-2-one | 196-198 | 381.2 |
| 36 | 84 | 3-(8-methylimidazo[1,2-a]pyridin-2-yl)-7-(4-methylpiperazin-1-yl)-2H-chromen-2-one | 224-226 | 375.2 |
| 4 | 85 | 3-(1,3-benzoxazol-2-yl)-7-(2,5-diazabicyclo[2.2.1]hept-2-yl)-2H-chromen-2-one | ND | 360.2 |
| 4 | 86 | 3-(1,3-benzoxazol-2-yl)-7-(2,5-dimethylpiperazin-1-yl)-2H-chromen-2-one | ND | 376.3 |
| 38 | 87 | 3-(imidazo[1,2-a]pyrimidin-2-yl)-7-(4-methylpiperazin-1-yl)-2H-chromen-2-one | >310 | 362.3 |
| 41 | 88 | 3-(imidazo[2,1-b][1,3]thiazol-6-yl)-7-(piperazin-1-yl)-2H-chromen-2-one | 275-280 | 353.2 |
| 38* | 89 | 3-(imidazo[1,2-a]pyrimidin-2-yl)-7-(piperazin-1-yl)-2H-chromen-2-one | 286 (D) | 348.2 |
| 26 | 90 | 7-(piperazin-1-yl)-3-[6-(trifluoromethyl)pyridin-2-yl]-2H-chromen-2-one | 158-160 | 376.3 |
| 32 | 91 | 3-(1H-indazol-5-yl)-7-(piperazin-1-yl)-2H-chromen-2-one | 250-252 | 347.2 |
| 36 | 92 | 3-(6-chloroimidazo[1,2-a]pyridin-2-yl)-7-(4-methyl-1,4-diazepan-1-yl)-2H-chromen-2-one | 186-189 | 409.2 |
| 36 | 93 | 3-(6-chloroimidazo[1,2-a]pyridin-2-yl)-7-[(2R,5S)-2,5-dimethylpiperazin-1-yl]-2H-chromen-2-one | 245-247 | 409.2 |
| 36 | 94 | 3-(6-chloroimidazo[1,2-a]pyridin-2-yl)-7-(4-methylpiperazin-1-yl)-2H-chromen-2-one | 290-292 | 395.2 397.2 |
| 67 | 95 | 7-(4-ethylpiperazin-1-yl)-3-(6-methylimidazo[1,2-a]pyridin-2-yl)-2H-chromen-2-one | 266-269 | 389.3 |
| 41 | 96 | 3-(2-methylimidazo[2,1-b][1,3]thiazol-6-yl)-7-(piperazin-1-yl)-2H-chromen-2-one | >310 | 367.2 |
| 41 | 97 | 3-(2-methylimidazo[2,1-b][1,3]thiazol-6-yl)-7-(4-methylpiperazin-1-yl)-2H-chromen-2-one | >300 | 381.3 |
| 41 | 98 | 3-(3-methylimidazo[2,1-b][1,3]thiazol-6-yl)-7-(piperazin-1-yl)-2H-chromen-2-one | >300 | 367.2 |
| 10 | 99 | 3-(1,3-benzothiazol-2-yl)-7-{[(1,3-dihydroxypropan-2-yl)amino]methyl}-2H-chromen-2-one | 194-197 | 383.2 |
| 67 | 100 | 7-(4-ethylpiperazin-1-yl)-3-(8-methylimidazo[1,2-a]pyridin-2-yl)-2H-chromen-2-one | 211-213 | 389.3 |
| 36 | 101 | 3-(8-methylimidazo[1,2-a]pyridin-2-yl)-7-(4-propylpiperazin-1-yl)-2H-chromen-2-one | 249-251 | 403.3 |
| 67 | 102 | 7-[4-(2-hydroxyethyl)piperazin-1-yl]-3-(8-methylimidazo[1,2-a]pyridin-2-yl)-2H-chromen-2-one | 210-212 | 405.3 |
| 36 | 103 | 3-(6-fluoroimidazo[1,2-a]pyridin-2-yl)-7-(piperazin-1-yl)-2H-chromen-2-one | 237-240 | 365.2 |
| 67 | 104 | 3-(6-chloroimidazo[1,2-a]pyridin-2-yl)-7-[4-(2-hydroxyethyl)piperazin-1-yl]-2H-chromen-2-one | 245-250 | 425.2 |
| 36 | 105 | 3-(6-chloroimidazo[1,2-a]pyridin-2-yl)-7-[(3R,5S)-3,5-dimethylpiperazin-1-yl]-2H-chromen-2-one | 220-225 | 409.3 |
| 36 | 106 | tert-butyl {(3S)-1-[3-(6-chloroimidazo[1,2-a]pyridin-2-yl)-2-oxo-2H-chromen-7-yl]pyrrolidin-3-yl}carbamate | >300 | 418.3 |
| 38 | 107 | 7-[(3R,5S)-3,5-dimethylpiperazin-1-yl]-3-(imidazo[1,2-a]pyrimidin-2-yl)-2H-chromen-2-one | 256-258 | 376.3 |
| 67 | 108 | 7-(4-ethylpiperazin-1-yl)-3-(imidazo[1,2-a]pyrimidin-2-yl)-2H-chromen-2-one | 300-302 | 376.3 |
| 38 | 109 | 3-(imidazo[1,2-a]pyrimidin-2-yl)-7-(4-propylpiperazin-1-yl)-2H-chromen-2-one | 291-293 | 390.3 |
| 1 | 110a | 3-([1,3]oxazolo[4,5-b]pyridin-2-yl)-7-(piperazin-1-yl)-2H-chromen-2-one | NI | NI |
| 67 | 111 | 7-(4-methylpiperazin-1-yl)-3-([1,3]oxazolo[4,5-b]pyridin-2-yl)-2H-chromen-2-one | ND | 363.3 |
| 31* | 112 | 3-(6-chloroimidazo[1,2-a]pyridin-2-yl)-4-methyl-7-(piperazin-1-yl)-2H-chromen-2-one | 224-227 | 395.2 |
| 32 | 113 | 3-(5-chloropyridin-2-yl)-7-(piperazin-1-yl)-2H-chromen-2-one | 180-182 | 342.3 |
| 36 | 114 | 7-(piperazin-1-yl)-3-[7-(trifluoromethyl)imidazo[1,2-a]pyridin-2-yl]-2H-chromen-2-one | 277-287 | 415.2 |
| 36 | 115 | 7-(4-methylpiperazin-1-yl)-3-[7-(trifluoromethyl)imidazo[1,2-a]pyridin-2-yl]-2H-chromen-2-one | 274-280 | 429.3 |
| 36 | 116 | 7-[(3R,5S)-3,5-dimethylpiperazin-1-yl]-3-[7-(trifluoromethyl)imidazo[1,2-a]pyridin-2-yl]-2H-chromen-2-one | 257-264 | 443.3 |
| 41* | 117 | 3-(imidazo[2,1-b][1,3]thiazol-6-yl)-7-(4-methylpiperazin-1-yl)-2H-chromen-2-one | 256-258 | 367.2 |
| 38 | 118 | 3-(imidazo[1,2-a]pyrimidin-2-yl)-7-(4-methyl-1,4-diazepan-1-yl)-2H-chromen-2-one | 252-254 | 376.3 |

TABLE 1-continued

| Ex | Cpd | Name | M.P. | MS |
|---|---|---|---|---|
| 36 | 119 | 3-(8-chloroimidazo[1,2-a]pyridin-2-yl)-7-(4-propylpiperazin-1-yl)-2H-chromen-2-one | 245-247 | 423.3 425.3 |
| 36 | 120 | 3-(8-chloroimidazo[1,2-a]pyridin-2-yl)-7-[(3R,5S)-3,5-dimethylpiperazin-1-yl]-2H-chromen-2-one | 286 (D) | 409.2 411.2 |
| 67 | 121 | 3-(8-chloroimidazo[1,2-a]pyridin-2-yl)-7-[4-(2-hydroxyethyl)piperazin-1-yl]-2H-chromen-2-one | 247-250 | 425.2 427.2 |
| 36 | 122 | 3-(8-chloroimidazo[1,2-a]pyridin-2-yl)-7-[(3S)-3-(dimethylamino)pyrrolidin-1-yl]-2H-chromen-2-one | 238-241 | 409.2 411.2 |
| 36 | 123 | 3-(7-chloroimidazo[1,2-a]pyridin-2-yl)-7-[(3R,5S)-3,5-dimethylpiperazin-1-yl]-2H-chromen-2-one | 223-231 | 409.3 |
| 32* | 124 | 7-(piperazin-1-yl)-3-[2-(trifluoromethyl)pyridin-3-yl]-2H-chromen-2-one | 197-200 | 376.2 |
| 32 | 125 | 7-(4-methylpiperazin-1-yl)-3-[2-(trifluoromethyl)pyridin-3-yl]-2H-chromen-2-one | 180-182 | 390.3 |
| 32 | 126 | 3-(3-fluoropyridin-4-yl)-7-(piperazin-1-yl)-2H-chromen-2-one | 202-204 | 326.3 |
| 67 | 127 | 3-(1,3-benzothiazol-2-yl)-7-{[(3R)-1-ethylpyrrolidin-3-yl]oxy}-2H-chromen-2-one | 195-198 | 393.3 |
| 52* | 128 | 3-(imidazo[1,2-b]pyridazin-2-yl)-7-(4-methylpiperazin-1-yl)-2H-chromen-2-one | 284-285 | 362.3 |
| 38 | 129a | 7-[(1S,4S)-2,5-diazabicyclo[2.2.1]hept-2-yl]-3-(imidazo[1,2-a]pyrimidin-2-yl)-2H-chromen-2-one | NI | NI |
| 38 | 130 | 7-{[2-(dimethylamino)ethyl](methyl)amino}-3-(imidazo[1,2-a]pyrimidin-2-yl)-2H-chromen-2-one | 175-180 | 364.2 |
| 36 | 131 | 3-(7-methylimidazo[1,2-a]pyridin-2-yl)-7-(piperazin-1-yl)-2H-chromen-2-one | 260-270 | 361.2 |
| 36 | 132 | 3-(5-methylimidazo[1,2-a]pyridin-2-yl)-7-(piperazin-1-yl)-2H-chromen-2-one | 239-249 | 361.2 |
| 36 | 133 | 7-[(3R,5S)-3,5-dimethylpiperazin-1-yl]-3-(7-methylimidazo[1,2-a]pyridin-2-yl)-2H-chromen-2-one | 210-217 | 389.3 |
| 36 | 134 | 3-(7-methylimidazo[1,2-a]pyridin-2-yl)-7-(4-methylpiperazin-1-yl)-2H-chromen-2-one | 252-262 | 375.2 |
| 36 | 135 | 3-(5-methylimidazo[1,2-a]pyridin-2-yl)-7-(4-methylpiperazin-1-yl)-2H-chromen-2-one | 263-272 | 375.2 |
| 36 | 136 | 7-[(3R,5S)-3,5-dimethylpiperazin-1-yl]-3-(8-methylimidazo[1,2-a]pyridin-2-yl)-2H-chromen-2-one | 243-246 | 389.3 |
| 67 | 137 | 3-(8-chloroimidazo[1,2-a]pyridin-2-yl)-7-[(3R,5S)-3,4,5-trimethylpiperazin-1-yl]-2H-chromen-2-one | 244-247 | 423.3 425.3 |
| 36 | 138 | 3-(6-fluoroimidazo[1,2-a]pyridin-2-yl)-7-(4-methylpiperazin-1-yl)-2H-chromen-2-one | 266-269 | 379.2 |
| 36 | 139 | 7-[(3R,5S)-3,5-dimethylpiperazin-1-yl]-3-(imidazo[1,2-a]pyridin-2-yl)-2H-chromen-2-one | 261 (D) | 375.3 |
| 67 | 140 | 3-(imidazo[1,2-a]pyridin-2-yl)-7-[(3R,5S)-3,4,5-trimethylpiperazin-1-yl]-2H-chromen-2-one | ND | 389.4 |
| 41 | 141a | 3-(3-methylimidazo[2,1-b][1,3]thiazol-6-yl)-7-(piperazin-1-yl)-2H-chromen-2-one | ND | 367.3 |
| 36 | 142 | 7-(4-methyl-1,4-diazepan-1-yl)-3-(6-methylimidazo[1,2-a]pyridin-2-yl)-2H-chromen-2-one | 175-180 | 389.2 |
| 15* | 143 | 3-(1,3-benzothiazol-2-yl)-7-[1-(dimethylamino)ethyl]-2H-chromen-2-one | 130-133 | 351.2 |
| 15 | 144 | 3-(1,3-benzothiazol-2-yl)-7-[1-(propan-2-ylamino)ethyl]-2H-chromen-2-one | 135-137 | 365.2 |
| 4* | 145 | 3-(1,3-benzothiazol-2-yl)-7-(4-methyl-1,4-diazepan-1-yl)-2H-chromen-2-one | 217-220 | 392.2 |
| 4 | 146 | 3-(1,3-benzothiazol-2-yl)-7-{[2-(dimethylamino)ethyl](methyl)amino}-2H-chromen-2-one | 155-157 | 380.3 |
| 31 | 147 | 3-(1,3-benzothiazol-2-yl)-4-methyl-7-(piperazin-1-yl)-2H-chromen-2-one | 234-236 | 378.2 |
| 10* | 148 | 7-{[(2-hydroxyethyl)(methyl)amino]methyl}-3-(6-methylimidazo[1,2-a]pyridin-2-yl)-2H-chromen-2-one | 166-169 | 364.3 |
| 36 | 149 | 3-(8-fluoroimidazo[1,2-a]pyridin-2-yl)-7-(piperazin-1-yl)-2H-chromen-2-one | 236-238 | 365.2 |
| 36 | 150 | 3-(8-fluoroimidazo[1,2-a]pyridin-2-yl)-7-(4-methylpiperazin-1-yl)-2H-chromen-2-one | 278-280 | 379.3 |
| 67 | 151 | 7-(4-ethylpiperazin-1-yl)-3-(2-methylimidazo[2,1-b][1,3]thiazol-6-yl)-2H-chromen-2-one | 205-208 | 395.3 |
| 41 | 152 | 7-[(3R,5S)-3,5-dimethylpiperazin-1-yl]-3-(2-methylimidazo[2,1-b][1,3]thiazol-6-yl)-2H-chromen-2-one | 210-212 | 395.3 |
| 41 | 153 | 7-(4-methyl-1,4-diazepan-1-yl)-3-(2-methylimidazo[2,1-b][1,3]thiazol-6-yl)-2H-chromen-2-one | 179-184 | 395.3 |
| 41 | 154 | 7-[3-(dimethylamino)pyrrolidin-1-yl]-3-(2-methylimidazo[2,1-b][1,3]thiazol-6-yl)-2H-chromen-2-one | 180-183 | 395.3 |
| 6 | 155 | 8-fluoro-7-(piperazin-1-yl)-3-(pyridin-2-yl)-2H-chromen-2-one | 147-153 | 326.3 |
| 7 | 156 | 8-fluoro-3-(6-methylimidazo[1,2-a]pyridin-2-yl)-7-(piperazin-1-yl)-2H-chromen-2-one | 313-319 | 379.3 |
| 6 | 157 | 3-(1,3-benzothiazol-2-yl)-6-fluoro-7-(piperazin-1-yl)-2H-chromen-2-one | 255-260 | 382.3 |

TABLE 1-continued

| Ex | Cpd | Name | M.P. | MS |
|---|---|---|---|---|
| 7 | 158 | 6-fluoro-3-(6-methylimidazo[1,2-a]pyridin-2-yl)-7-(piperazin-1-yl)-2H-chromen-2-one | 245-250 | 379.2 |
| 6 | 159 | 3-(1,3-benzoxazol-2-yl)-5-fluoro-7-(piperazin-1-yl)-2H-chromen-2-one | 245-250 | 366.3 |
| 6* | 160 | 3-(1,3-benzothiazol-2-yl)-5-fluoro-7-(piperazin-1-yl)-2H-chromen-2-one | 256-260 | 382.2 |
| 6 | 161 | 5-fluoro-7-(piperazin-1-yl)-3-(pyridin-2-yl)-2H-chromen-2-one | 221-225 | 326.2 |
| 7* | 162 | 5-fluoro-3-(6-methylimidazo[1,2-a]pyridin-2-yl)-7-(piperazin-1-yl)-2H-chromen-2-one | 265-270 | 379.2 |
| 32 | 163 | 3-(6-methylpyridin-3-yl)-7-(piperazin-1-yl)-2H-chromen-2-one | 148-150 | 322.3 |
| 32 | 164 | 7-(4-methylpiperazin-1-yl)-3-(6-methylpyridin-3-yl)-2H-chromen-2-one | 158-160 | 336.3 |
| 32 | 165 | 3-(2-methoxypyridin-4-yl)-7-(4-methylpiperazin-1-yl)-2H-chromen-2-one | 169-171 | 352.3 |
| 36 | 166 | 7-[(2R,5S)-2,5-dimethylpiperazin-1-yl]-3-(8-methylimidazo[1,2-a]pyridin-2-yl)-2H-chromen-2-one | ND | 389.3 |
| 41 | 167 | 7-[(3R,5S)-3,5-dimethylpiperazin-1-yl]-3-(imidazo[2,1-b][1,3]thiazol-6-yl)-2H-chromen-2-one | 263-265 | 381.3 |
| 67 | 168 | 3-[7-(trifluoromethyl)imidazo[1,2-a]pyridin-2-yl]-7-[(3R,5S)-3,4,5-trimethylpiperazin-1-yl]-2H-chromen-2-one | 267-275 | 457.4 |
| 38 | 169 | 3-(imidazo[1,2-a]pyrimidin-2-yl)-7-[(3R)-3-methylpiperazin-1-yl]-2H-chromen-2-one | 285-287 | 362.3 |
| 38 | 170 | 3-(imidazo[1,2-a]pyrimidin-2-yl)-7-[(3S)-3-methylpiperazin-1-yl]-2H-chromen-2-one | 282-285 | 362.3 |
| 36 | 173 | 7-[(1S,4S)-2,5-diazabicyclo[2.2.1]hept-2-yl]-3-(6-methylimidazo[1,2-a]pyridin-2-yl)-2H-chromen-2-one | 212-215 | 373.3 |
| 36 | 174 | 7-[(3R,5S)-3,5-dimethylpiperazin-1-yl]-3-(6-methylimidazo[1,2-a]pyridin-2-yl)-2H-chromen-2-one | 235-237 | 389.3 |
| 36 | 175 | 7-{[2-(dimethylamino)ethyl](methyl)amino}-3-(6-methylimidazo[1,2-a]pyridin-2-yl)-2H-chromen-2-one | 140-180 (D) | 377.3 |
| 36 | 176 | 7-(1,4-diazepan-1-yl)-3-(6-methylimidazo[1,2-a]pyridin-2-yl)-2H-chromen-2-one | 218-220 | 375.2 |
| 36 | 177 | tert-butyl {(3S)-1-[3-(6-methylimidazo[1,2-a]pyridin-2-yl)-2-oxo-2H-chromen-7-yl]pyrrolidin-3-yl}carbamate | 225-230 | 461.3 |
| 67 | 178 | 7-(4-ethylpiperazin-1-yl)-3-(3-methylimidazo[2,1-b][1,3]thiazol-6-yl)-2H-chromen-2-one | 178-180 | 395.3 |
| 41 | 179 | 7-(4-methyl-1,4-diazepan-1-yl)-3-(3-methylimidazo[2,1-b][1,3]thiazol-6-yl)-2H-chromen-2-one | 182-185 | 395.3 |
| 32 | 180 | 3-(2-chloropyridin-4-yl)-7-(piperazin-1-yl)-2H-chromen-2-one | 190-192 | 342.3 |
| 38 | 181 | 3-(imidazo[1,2-a]pyrimidin-2-yl)-7-[methyl(1-methylpyrrolidin-3-yl)amino]-2H-chromen-2-one | 215-217 | 376.3 |
| 41 | 182 | 7-[(3R,5S)-3,5-dimethylpiperazin-1-yl]-3-(3-methylimidazo[2,1-b][1,3]thiazol-6-yl)-2H-chromen-2-one | 211-215 | 395.3 |
| 36 | 183 | 3-(8-chloroimidazo[1,2-a]pyridin-2-yl)-7-[(3R)-3-methylpiperazin-1-yl]-2H-chromen-2-one | 215-218 | 395.3 397.3 |
| 36 | 184 | 3-(8-chloroimidazo[1,2-a]pyridin-2-yl)-7-[(3S)-3-methylpiperazin-1-yl]-2H-chromen-2-one | 215-217 | 395.3 397.3 |
| 41 | 185 | 3-(3-methylimidazo[2,1-b][1,3]thiazol-6-yl)-7-(4-methylpiperazin-1-yl)-2H-chromen-2-one | 213-216 | 381.3 |
| 38 | 186a | 7-(1,4-diazepan-1-yl)-3-(imidazo[1,2-a]pyrimidin-2-yl)-2H-chromen-2-one | NI | NI |
| 30* | 187 | 7-(piperazin-1-yl)-3-(pyrazolo[1,5-a]pyridin-2-yl)-2H-chromen-2-one | 236-238 | 347.3 |
| 30 | 188 | 7-(4-methylpiperazin-1-yl)-3-(pyrazolo[1,5-a]pyridin-2-yl)-2H-chromen-2-one | 235-237 | 361.3 |
| 30 | 189 | 7-[(3R,5S)-3,5-dimethylpiperazin-1-yl]-3-(pyrazolo[1,5-a]pyridin-2-yl)-2H-chromen-2-one | 188-190 | 375.3 |
| 67 | 190 | 7-[4-(2-hydroxyethyl)piperazin-1-yl]-3-(pyrazolo[1,5-a]pyridin-2-yl)-2H-chromen-2-one | 201-205 | 391.3 |
| 30 | 191 | 7-(2,5-diazabicyclo[2.2.2]oct-2-yl)-3-(pyrazolo[1,5-a]pyridin-2-yl)-2H-chromen-2-one | 182-185 | 391.3 |
| 30 | 192 | 7-(1,4-diazepan-1-yl)-3-(pyrazolo[1,5-a]pyridin-2-yl)-2H-chromen-2-one | 178-180 | 361.3 |
| 30 | 193 | 7-(4-methyl-1,4-diazepan-1-yl)-3-(pyrazolo[1,5-a]pyridin-2-yl)-2H-chromen-2-one | 159-163 | 375.3 |
| 67 | 194 | 7-(4-ethylpiperazin-1-yl)-3-(pyrazolo[1,5-a]pyridin-2-yl)-2H-chromen-2-one | 246-248 | 375.3 |
| 30 | 195 | 7-(4-propylpiperazin-1-yl)-3-(pyrazolo[1,5-a]pyridin-2-yl)-2H-chromen-2-one | 206-208 | 359.3 |
| 68 | 196 | 7-[4-(propan-2-yl)piperazin-1-yl]-3-(pyrazolo[1,5-a]pyridin-2-yl)-2H-chromen-2-one | 243-246 | 389.3 |
| 65 | 197a | 3-(imidazo[1,2-a]pyrimidin-2-yl)-7-(piperidin-4-yloxy)-2H-chromen-2-one | NI | NI |
| 9 | 198 | 7-[(dimethylamino)methyl]-3-(imidazo[2,1-b][1,3]thiazol-6-yl)-2H-chromen-2-one | 135-140 | 326.2 |

TABLE 1-continued

| Ex | Cpd | Name | M.P. | MS |
|---|---|---|---|---|
| 9 | 199 | 3-(imidazo[2,1-b][1,3]thiazol-6-yl)-7-[(propan-2-ylamino)methyl]-2H-chromen-2-one | 141-145 | 340.3 |
| 36 | 200 | 7-[3-(dimethylamino)piperidin-1-yl]-3-(6-methylimidazo[1,2-a]pyridin-2-yl)-2H-chromen-2-one | 167-169 | 403.3 |
| 67 | 201 | 7-(4-ethylpiperazin-1-yl)-3-(imidazo[2,1-b][1,3]thiazol-6-yl)-2H-chromen-2-one | 202-205 | 381.3 |
| 41 | 202 | 7-{[2-(dimethylamino)ethyl](methyl)amino}-3-(imidazo[2,1-b][1,3]thiazol-6-yl)-2H-chromen-2-one | 185-188 | 369.3 |
| 41 | 203 | 3-(imidazo[2,1-b][1,3]thiazol-6-yl)-7-(4-methyl-1,4-diazepan-1-yl)-2H-chromen-2-one | 228-231 | 381.3 |
| 41 | 204 | 3-(imidazo[2,1-b][1,3]thiazol-6-yl)-7-[(3R)-3-methylpiperazin-1-yl]-2H-chromen-2-one | 233-237 | 367.2 |
| 41 | 205 | 3-(imidazo[2,1-b][1,3]thiazol-6-yl)-7-[(3S)-3-methylpiperazin-1-yl]-2H-chromen-2-one | 230-233 | 367.2 |
| 41 | 206 | 7-(1,4-diazepan-1-yl)-3-(imidazo[2,1-b][1,3]thiazol-6-yl)-2H-chromen-2-one | 225-230 | 367.2 |
| 36 | 207 | 3-(6-methylimidazo[1,2-a]pyridin-2-yl)-7-(4-propylpiperazin-1-yl)-2H-chromen-2-one | 220-222 | 403.3 |
| 36 | 208 | 2-[7-(4-methylpiperazin-1-yl)-2-oxo-2H-chromen-3-yl]imidazo[1,2-a]pyridine-6-carbonitrile | 291 (D) | 386.3 |
| 36 | 209 | 7-(piperazin-1-yl)-3-[8-(trifluoromethyl)imidazo[1,2-a]pyridin-2-yl]-2H-chromen-2-one | 249-252 | 415.3 |
| 36 | 210 | 7-(4-methylpiperazin-1-yl)-3-[8-(trifluoromethyl)imidazo[1,2-a]pyridin-2-yl]-2H-chromen-2-one | 235-237 | 429.3 |
| 36 | 211 | 7-[(3R,5S)-3,5-dimethylpiperazin-1-yl]-3-[8-(trifluoromethyl)imidazo[1,2-a]pyridin-2-yl]-2H-chromen-2-one | 295-298 | 443.4 |
| 36 | 212 | 3-(8-chloroimidazo[1,2-a]pyridin-2-yl)-7-(1,4-diazepan-1-yl)-2H-chromen-2-one | 170-173 | 395.3 397.3 |
| 36 | 213 | 3-(7-methylimidazo[1,2-a]pyridin-2-yl)-7-[(3S)-3-methylpiperazin-1-yl]-2H-chromen-2-one | 234-244 | 375.3 |
| 36 | 214 | 3-(7-methylimidazo[1,2-a]pyridin-2-yl)-7-[(3R)-3-methylpiperazin-1-yl]-2H-chromen-2-one | 222 (S), 242-244 | 375.3 |
| 36 | 215 | 7-(3,3-dimethylpiperazin-1-yl)-3-(7-methylimidazo[1,2-a]pyridin-2-yl)-2H-chromen-2-one | 217-223 | 389.3 |
| 36 | 216 | 7-(1,4-diazepan-1-yl)-3-(7-methylimidazo[1,2-a]pyridin-2-yl)-2H-chromen-2-one | 236 (S), 248-252 | 375.3 |
| 36 | 217 | 7-(4-methyl-1,4-diazepan-1-yl)-3-(7-methylimidazo[1,2-a]pyridin-2-yl)-2H-chromen-2-one | 200-206 | 389.3 |
| 33* | 218 | 3-(6-methoxypyridin-2-yl)-7-(piperazin-1-yl)-2H-chromen-2-one | 162-165 | 338.2 |
| 36 | 219 | 7-(4-aminopiperidin-1-yl)-3-(6-methylimidazo[1,2-a]pyridin-2-yl)-2H-chromen-2-one | 250-252 | 375.3 |
| 36 | 220 | 3-(6-methylimidazo[1,2-a]pyridin-2-yl)-7-[(3R)-3-methylpiperazin-1-yl]-2H-chromen-2-one | 185-188 | 375.3 |
| 36 | 221 | 3-(6-methylimidazo[1,2-a]pyridin-2-yl)-7-[methyl(pyridin-3-ylmethyl)amino]-2H-chromen-2-one | 220-223 | 397.4 |
| 36 | 222 | 7-(3,3-dimethylpiperazin-1-yl)-3-(6-methylimidazo[1,2-a]pyridin-2-yl)-2H-chromen-2-one | 177-180 | 389.4 |
| 38 | 223 | 3-(7-methylimidazo[1,2-a]pyrimidin-2-yl)-7-(piperazin-1-yl)-2H-chromen-2-one | 295-298 | 362.3 |
| 38 | 224 | 3-(7-methylimidazo[1,2-a]pyrimidin-2-yl)-7-(4-methylpiperazin-1-yl)-2H-chromen-2-one | ND | 376.4 |
| 38 | 225 | 7-[(3R,5S)-3,5-dimethylpiperazin-1-yl]-3-(7-methylimidazo[1,2-a]pyrimidin-2-yl)-2H-chromen-2-one | 246-252 | 390.4 |
| 38 | 226 | 7-{[2-(dimethylamino)ethyl](methyl)amino}-3-(7-methylimidazo[1,2-a]pyrimidin-2-yl)-2H-chromen-2-one | 188-191 | 378.3 |
| 38 | 227 | 7-(4-methyl-1,4-diazepan-1-yl)-3-(7-methylimidazo[1,2-a]pyrimidin-2-yl)-2H-chromen-2-one | 232-236 | 390.3 |
| 38 | 228 | 3-(7-methylimidazo[1,2-a]pyrimidin-2-yl)-7-[(3R)-3-methylpiperazin-1-yl]-2H-chromen-2-one | 297-300 | 376.3 |
| 38 | 229 | 3-(7-methylimidazo[1,2-a]pyrimidin-2-yl)-7-[(3S)-3-methylpiperazin-1-yl]-2H-chromen-2-one | 298-301 | 376.3 |
| 38 | 230 | 7-(1,4-diazepan-1-yl)-3-(7-methylimidazo[1,2-a]pyrimidin-2-yl)-2H-chromen-2-one | 286-288 | 376.3 |
| 41 | 231 | 3-(2-methylimidazo[2,1-b][1,3]thiazol-6-yl)-7-[(3R)-3-methylpiperazin-1-yl]-2H-chromen-2-one | 178-181 | 381.3 |
| 41 | 232 | 3-(2-methylimidazo[2,1-b][1,3]thiazol-6-yl)-7-[(3S)-3-methylpiperazin-1-yl]-2H-chromen-2-one | 177-182 | 381.3 |
| 41 | 233 | 7-(1,4-diazepan-1-yl)-3-(2-methylimidazo[2,1-b][1,3]thiazol-6-yl)-2H-chromen-2-one | 188-191 | 381.3 |
| 32 | 234 | 3-(4-methoxypyridin-3-yl)-7-(piperazin-1-yl)-2H-chromen-2-one | 179-181 | 338.3 |
| 32 | 235 | 3-(4-chloropyridin-3-yl)-7-(piperazin-1-yl)-2H-chromen-2-one | 175-177 | 342.3 |
| 21 | 236 | 7-[(3R,5S)-3,5-dimethylpiperazin-1-yl]-3-[4-(trifluoromethyl)-1,3-thiazol-2-yl]-2H-chromen-2-one | 215-219 | 410.3 |

TABLE 1-continued

| Ex | Cpd | Name | M.P. | MS |
|---|---|---|---|---|
| 21 | 237 | 7-(1,4-diazepan-1-yl)-3-[4-(trifluoromethyl)-1,3-thiazol-2-yl]-2H-chromen-2-one | 200 (S), 228-231 | 396.2 |
| 21 | 238 | 7-(4-methyl-1,4-diazepan-1-yl)-3-[4-(trifluoromethyl)-1,3-thiazol-2-yl]-2H-chromen-2-one | 218-225 | 410.2 |
| 21 | 239 | 7-[(3S)-3-methylpiperazin-1-yl]-3-[4-(trifluoromethyl)-1,3-thiazol-2-yl]-2H-chromen-2-one | 234-238 | 396.2 |
| 21 | 240 | 7-[(3R)-3-methylpiperazin-1-yl]-3-[4-(trifluoromethyl)-1,3-thiazol-2-yl]-2H-chromen-2-one | 234-238 | 396.2 |
| 39* | 241 | 3-(6-methylimidazo[1,2-a]pyrimidin-2-yl)-7-(piperazin-1-yl)-2H-chromen-2-one | >300 | 362.2 |
| 39 | 242 | 3-(6-methylimidazo[1,2-a]pyrimidin-2-yl)-7-(4-methylpiperazin-1-yl)-2H-chromen-2-one | >310 | 376.3 |
| 39 | 243 | 7-[(3R,5S)-3,5-dimethylpiperazin-1-yl]-3-(6-methylimidazo[1,2-a]pyrimidin-2-yl)-2H-chromen-2-one | 308-310 | 390.3 |
| 36 | 244 | 3-(8-cyclopropylimidazo[1,2-a]pyridin-2-yl)-7-(4-methylpiperazin-1-yl)-2H-chromen-2-one | 198-202 | 401.1 |
| 36 | 245 | 3-(8-bromoimidazo[1,2-a]pyridin-2-yl)-7-(4-methylpiperazin-1-yl)-2H-chromen-2-one | 217-220 | 440.1 442.1 |
| 36 | 246 | 7-(4-methyl-1,4-diazepan-1-yl)-3-(8-methylimidazo[1,2-a]pyridin-2-yl)-2H-chromen-2-one | 138-140 | 389.3 |
| 36 | 247 | 3-(8-methylimidazo[1,2-a]pyridin-2-yl)-7-[(3R)-3-methylpiperazin-1-yl]-2H-chromen-2-one | 299 (D) | 375.3 |
| 36 | 248 | 3-(8-methylimidazo[1,2-a]pyridin-2-yl)-7-[(3S)-3-methylpiperazin-1-yl]-2H-chromen-2-one | 162-166 | 375.3 |
| 36 | 249 | 3-(8-chloroimidazo[1,2-a]pyridin-2-yl)-7-(3,3-dimethylpiperazin-1-yl)-2H-chromen-2-one | 216-220 | 409.2 411.2 |
| 39 | 250 | 7-(4-methyl-1,4-diazepan-1-yl)-3-(6-methylimidazo[1,2-a]pyrimidin-2-yl)-2H-chromen-2-one | 285-287 | 390.3 |
| 10 | 251 | 7-{[(1-hydroxypropan-2-yl)amino]methyl}-3-(6-methylimidazo[1,2-a]pyridin-2-yl)-2H-chromen-2-one | 224-227 | 364.3 |
| 10 | 252 | 7-[(4-hydroxypiperidin-1-yl)methyl]-3-(6-methylimidazo[1,2-a]pyridin-2-yl)-2H-chromen-2-one | 261-264 | 390.4 |
| 10 | 253 | 7-[(3-hydroxypyrrolidin-1-yl)methyl]-3-(6-methylimidazo[1,2-a]pyridin-2-yl)-2H-chromen-2-one | 227-230 | 376.3 |
| 6 | 254 | 5-fluoro-7-(piperazin-1-yl)-3-[4-(trifluoromethyl)-1,3-benzoxazol-2-yl]-2H-chromen-2-one | 249-253 | 434.3 |
| 36 | 255 | 3-(6-methylimidazo[1,2-a]pyridin-2-yl)-7-(octahydro-6H-pyrrolo[3,4-b]pyridin-6-yl)-2H-chromen-2-one | 220-230 | 401.2 |
| 32 | 256 | 3-(2-ethoxypyridin-3-yl)-7-(piperazin-1-yl)-2H-chromen-2-one | 186-188 | 352.3 |
| 32 | 257 | 3-(6-methoxypyridin-2-yl)-7-(4-methylpiperazin-1-yl)-2H-chromen-2-one | 162-164 | 352.3 |
| 26 | 258 | 3-(1-methyl-1H-indol-3-yl)-7-(piperazin-1-yl)-2H-chromen-2-one | 201-203 | 360.3 |
| 26 | 259 | 3-(1-methyl-1H-indol-3-yl)-7-(4-methylpiperazin-1-yl)-2H-chromen-2-one | 185-187 | 374.3 |
| 36 | 260 | 3-(6,8-dimethylimidazo[1,2-a]pyridin-2-yl)-7-(piperazin-1-yl)-2H-chromen-2-one | 219-229 | 375.4 |
| 36 | 261 | 3-(6,8-dimethylimidazo[1,2-a]pyridin-2-yl)-7-(4-methylpiperazin-1-yl)-2H-chromen-2-one | 232-238 | 389.4 |
| 36 | 262 | 3-(6,8-dimethylimidazo[1,2-a]pyridin-2-yl)-7-[(3R,5S)-3,5-dimethylpiperazin-1-yl]-2H-chromen-2-one | 227-237 | 403.4 |
| 36 | 263 | 3-(6-chloro-8-methylimidazo[1,2-a]pyridin-2-yl)-7-(piperazin-1-yl)-2H-chromen-2-one | 224-233 | 395.3 |
| 36 | 264 | 3-(6-chloro-8-methylimidazo[1,2-a]pyridin-2-yl)-7-(4-methylpiperazin-1-yl)-2H-chromen-2-one | 238 (S), 253-258 | 409.3 |
| 36 | 265 | 3-(6-chloro-8-methylimidazo[1,2-a]pyridin-2-yl)-7-[(3R,5S)-3,5-dimethylpiperazin-1-yl]-2H-chromen-2-one | 271-281 | 423.3 |
| 21 | 266 | 7-[(1S,4S)-2,5-diazabicyclo[2.2.1]hept-2-yl]-3-[4-(trifluoromethyl)-1,3-thiazol-2-yl]-2H-chromen-2-one | 211-220 | 394.2 |
| 36 | 267 | 7-[(3R)-3-methylpiperazin-1-yl]-3-[7-(trifluoromethyl)imidazo[1,2-a]pyridin-2-yl]-2H-chromen-2-one | 252-260 | 429.3 |
| 36 | 268 | 7-[(3S)-3-methylpiperazin-1-yl]-3-[7-(trifluoromethyl)imidazo[1,2-a]pyridin-2-yl]-2H-chromen-2-one | 252-260 | 429.3 |
| 36 | 269 | 7-(3,3-dimethylpiperazin-1-yl)-3-[7-(trifluoromethyl)imidazo[1,2-a]pyridin-2-yl]-2H-chromen-2-one | 221-227 | 444.3 |
| 10 | 270 | 3-(4-chloro-1,3-benzothiazol-2-yl)-7-{[(1-hydroxypropan-2-yl)amino]methyl}-2H-chromen-2-one | 186-190 | 401.2 |
| 10 | 271 | 3-(4-chloro-1,3-benzothiazol-2-yl)-7-{[(2-hydroxyethyl)(methyl)amino]methyl}-2H-chromen-2-one | 193-196 | 401.2 |
| 10 | 272 | 3-(4-chloro-1,3-benzothiazol-2-yl)-7-[(3-hydroxypyrrolidin-1-yl)methyl]-2H-chromen-2-one | 188-192 | 413.2 |
| 10 | 273 | 3-(4-chloro-1,3-benzothiazol-2-yl)-7-[(4-hydroxypiperidin-1-yl)methyl]-2H-chromen-2-one | 193-196 | 427.2 |

TABLE 1-continued

| Ex | Cpd | Name | M.P. | MS |
|---|---|---|---|---|
| 25 | 274a | 3-(2-methylpyrimidin-4-yl)-7-(piperazin-1-yl)-2H-chromen-2-one | NI | NI |
| 36 | 275 | 7-(1,4-diazepan-1-yl)-3-[7-(trifluoromethyl)imidazo[1,2-a]pyridin-2-yl]-2H-chromen-2-one | 253-262 | 429.3 |
| 36 | 276 | 7-(4-methyl-1,4-diazepan-1-yl)-3-[7-(trifluoromethyl)imidazo[1,2-a]pyridin-2-yl]-2H-chromen-2-one | 244-249 | 443.3 |
| 36 | 277 | 7-[(2R,5S)-2,5-dimethylpiperazin-1-yl]-3-[7-(trifluoromethyl)imidazo[1,2-a]pyridin-2-yl]-2H-chromen-2-one | 213-219 | 443.3 |
| 25 | 278a | 3-(2-cyclopropylpyrimidin-4-yl)-7-(piperazin-1-yl)-2H-chromen-2-one | NI | NI |
| 25 | 279a | 7-(piperazin-1-yl)-3-[2-(propan-2-yl)pyrimidin-4-yl]-2H-chromen-2-one | NI | NI |
| 36 | 280 | 3-(8-chloroimidazo[1,2-a]pyridin-2-yl)-7-(4-methyl-1,4-diazepan-1-yl)-2H-chromen-2-one | 161-163 | 409.2 411.2 |
| 36 | 281 | 7-(1,4-diazepan-1-yl)-3-(8-methylimidazo[1,2-a]pyridin-2-yl)-2H-chromen-2-one | 138-140 | 375.3 |
| 36 | 282 | 3-(6-methylimidazo[1,2-a]pyridin-2-yl)-7-[methyl(1-methylpiperidin-4-yl)amino]-2H-chromen-2-one | 181-184 | 403.3 |
| 21* | 283 | 7-[(3S)-3-methylpiperazin-1-yl]-3-(4-methyl-1,3-thiazol-2-yl)-2H-chromen-2-one | 194-199 | 342.2 |
| 21 | 284 | 7-(1,4-diazepan-1-yl)-3-(4-methyl-1,3-thiazol-2-yl)-2H-chromen-2-one | 195-203 | 342.2 |
| 21 | 285 | 7-(4-methyl-1,4-diazepan-1-yl)-3-(4-methyl-1,3-thiazol-2-yl)-2H-chromen-2-one | 190-200 | 356.2 |
| 21 | 286 | 7-[(3R,5S)-3,5-dimethylpiperazin-1-yl]-3-(4-methyl-1,3-thiazol-2-yl)-2H-chromen-2-one | 178-183 | 356.2 |
| 36 | 287 | 3-(7-ethylimidazo[1,2-a]pyridin-2-yl)-7-(piperazin-1-yl)-2H-chromen-2-one | 253-263 | 375.3 |
| 36 | 288 | 3-(7-ethylimidazo[1,2-a]pyridin-2-yl)-7-(4-methylpiperazin-1-yl)-2H-chromen-2-one | 203-211 | 389.3 |
| 36 | 289 | 7-[(3R,5S)-3,5-dimethylpiperazin-1-yl]-3-(7-ethylimidazo[1,2-a]pyridin-2-yl)-2H-chromen-2-one | 183-188 | 403.3 |
| 8* | 290 | 3-(3,5-difluorophenyl)-5-fluoro-7-(piperazin-1-yl)-2H-chromen-2-one | 193-198 | 361.3 |
| 8 | 291 | 3-(3,5-difluorophenyl)-7-(piperazin-1-yl)-2H-chromen-2-one | 202-206 | 343.2 |
| 6 | 292 | 5-fluoro-3-(4-fluoro-1,3-benzoxazol-2-yl)-7-(piperazin-1-yl)-2H-chromen-2-one | 225-230 | 384.3 |
| 36 | 293 | 7-(4-methyl-1,4-diazepan-1-yl)-3-[8-(trifluoromethyl)imidazo[1,2-a]pyridin-2-yl]-2H-chromen-2-one | 196-199 | 443.2 |
| 36 | 294 | 3-(6-fluoroimidazo[1,2-a]pyridin-2-yl)-7-(4-methyl-1,4-diazepan-1-yl)-2H-chromen-2-one | 152-155 | 393.2 |
| 36 | 295 | 3-(8-fluoroimidazo[1,2-a]pyridin-2-yl)-7-(4-methyl-1,4-diazepan-1-yl)-2H-chromen-2-one | 174-176 | 393.2 |
| 67 | 296 | 3-(8-chloroimidazo[1,2-a]pyridin-2-yl)-7-[(3R)-3,4-dimethylpiperazin-1-yl]-2H-chromen-2-one | 199-202 | 409.3 411.3 |
| 67 | 297 | 7-(4-methylpiperazin-1-yl)-3-(2-methylpyrimidin-4-yl)-2H-chromen-2-one | 200~300 (D) | 337.3 |
| 67 | 298 | 3-(2-cyclopropylpyrimidin-4-yl)-7-(4-methylpiperazin-1-yl)-2H-chromen-2-one | 200~300 (D) | 363.3 |
| 21 | 299 | 7-[(2S,5R)-2,5-dimethylpiperazin-1-yl]-3-(4-methyl-1,3-thiazol-2-yl)-2H-chromen-2-one | 184-190 | 356.2 |
| 21 | 300 | 7-[(3R)-3-methylpiperazin-1-yl]-3-(4-methyl-1,3-thiazol-2-yl)-2H-chromen-2-one | 176 (S), 192-198 | 342.3 |
| 21 | 301 | 7-(3,3-dimethylpiperazin-1-yl)-3-(4-methyl-1,3-thiazol-2-yl)-2H-chromen-2-one | 204-209 | 356.3 |
| 30 | 302 | 3-(5-methylpyrazolo[1,5-a]pyridin-2-yl)-7-(piperazin-1-yl)-2H-chromen-2-one | 228-231 | 361.3 |
| 30 | 303 | 7-(4-methylpiperazin-1-yl)-3-(5-methylpyrazolo[1,5-a]pyridin-2-yl)-2H-chromen-2-one | 279-281 | 375.3 |
| 30 | 304 | 7-[(3R,5S)-3,5-dimethylpiperazin-1-yl]-3-(5-methylpyrazolo[1,5-a]pyridin-2-yl)-2H-chromen-2-one | 200-202 | 389.3 |
| 30 | 305 | 7-(3,3-dimethylpiperazin-1-yl)-3-(5-methylpyrazolo[1,5-a]pyridin-2-yl)-2H-chromen-2-one | 203-205 | 389.3 |
| 30 | 306 | 7-[(3R)-3-methylpiperazin-1-yl]-3-(5-methylpyrazolo[1,5-a]pyridin-2-yl)-2H-chromen-2-one | 183-187 | 375.3 |
| 67 | 307 | 7-(4-ethylpiperazin-1-yl)-3-(5-methylpyrazolo[1,5-a]pyridin-2-yl)-2H-chromen-2-one | 257-259 | 389.3 |
| 30 | 308 | 3-(5-methylpyrazolo[1,5-a]pyridin-2-yl)-7-(4-propylpiperazin-1-yl)-2H-chromen-2-one | 228-230 | 403.3 |
| 30 | 309 | 7-(1,4-diazepan-1-yl)-3-(5-methylpyrazolo[1,5-a]pyridin-2-yl)-2H-chromen-2-one | 203-206 | 375.3 |
| 30 | 310 | 7-(4-methyl-1,4-diazepan-1-yl)-3-(5-methylpyrazolo[1,5-a]pyridin-2-yl)-2H-chromen-2-one | 175-177 | 389.3 |

TABLE 1-continued

| Ex | Cpd | Name | M.P. | MS |
|---|---|---|---|---|
| 7 | 311 | 5-fluoro-3-(imidazo[2,1-b][1,3]thiazol-6-yl)-7-(piperazin-1-yl)-2H-chromen-2-one | 278-283 | 371.2 |
| 7 | 312 | 5-fluoro-3-(imidazo[1,2-a]pyrimidin-2-yl)-7-(piperazin-1-yl)-2H-chromen-2-one | 298-302 | 366.2 |
| 1 | 313 | 3-(1H-benzimidazol-2-yl)-7-(piperazin-1-yl)-2H-chromen-2-one | 254-258 | 347.2 |
| 1 | 314 | 7-(piperazin-1-yl)-3-(9H-purin-8-yl)-2H-chromen-2-one | 291-297 | 349.2 |
| 32 | 315 | 7-[(3R,5S)-3,5-dimethylpiperazin-1-yl]-3-(6-methoxypyridin-2-yl)-2H-chromen-2-one | 175-177 | 366.3 |
| 26* | 316 | 3-(3,4-dimethoxyphenyl)-7-(piperazin-1-yl)-2H-chromen-2-one | 168-170 | 367.2 |
| 32 | 317 | 3-(3,4-dimethoxyphenyl)-7-(4-methylpiperazin-1-yl)-2H-chromen-2-one | 189-191 | 381.3 |
| 32 | 318 | 3-(4-methylthiophen-2-yl)-7-(piperazin-1-yl)-2H-chromen-2-one | 218-220 | 327.1 |
| 32 | 319 | 7-(piperazin-1-yl)-3-(thiophen-3-yl)-2H-chromen-2-one | 175-177 | 313.1 |
| 32 | 320 | 7-(4-methylpiperazin-1-yl)-3-(thiophen-3-yl)-2H-chromen-2-one | 151-153 | 327.1 |
| 65 | 321a | 3-(imidazo[1,2-a]pyrimidin-2-yl)-7-[(3R)-pyrrolidin-3-yloxy]-2H-chromen-2-one | NI | NI |
| 65 | 322a | 3-(7-methylimidazo[1,2-a]pyrimidin-2-yl)-7-[(3R)-pyrrolidin-3-yloxy]-2H-chromen-2-one | NI | NI |
| 65 | 323a | 3-(7-methylimidazo[1,2-a]pyridin-2-yl)-7-[(3R)-pyrrolidin-3-yloxy]-2H-chromen-2-one | NI | NI |
| 65 | 324a | 3-(imidazo[2,1-b][1,3]thiazol-6-yl)-7-[(3R)-pyrrolidin-3-yloxy]-2H-chromen-2-one | NI | NI |
| 65 | 325a | 3-(2-methylimidazo[2,1-b][1,3]thiazol-6-yl)-7-[(3R)-pyrrolidin-3-yloxy]-2H-chromen-2-one | NI | NI |
| 65 | 326a | 3-(6-methylimidazo[1,2-a]pyridin-2-yl)-7-[(3R)-pyrrolidin-3-yloxy]-2H-chromen-2-one | NI | NI |
| 65 | 327a | 3-(6-methylimidazo[1,2-a]pyrimidin-2-yl)-7-[(3R)-pyrrolidin-3-yloxy]-2H-chromen-2-one | NI | NI |
| 36 | 328 | 3-(6-fluoro-8-methylimidazo[1,2-a]pyridin-2-yl)-7-(piperazin-1-yl)-2H-chromen-2-one | 223-230 | 379.3 |
| 36 | 329 | 3-(6-fluoro-8-methylimidazo[1,2-a]pyridin-2-yl)-7-(4-methylpiperazin-1-yl)-2H-chromen-2-one | 223-233 | 393.3 |
| 36 | 330 | 3-(6-fluoro-8-methylimidazo[1,2-a]pyridin-2-yl)-7-(4-methyl-1,4-diazepan-1-yl)-2H-chromen-2-one | 191-198 | 407.4 |
| 36 | 331 | 7-[(3R,5S)-3,5-dimethylpiperazin-1-yl]-3-(6-fluoro-8-methylimidazo[1,2-a]pyridin-2-yl)-2H-chromen-2-one | 290-300 | 407.3 |
| 36 | 332 | 3-(8-ethyl-6-methylimidazo[1,2-a]pyridin-2-yl)-7-(4-methyl-1,4-diazepan-1-yl)-2H-chromen-2-one | 172-176 | 417.4 |
| 36 | 333 | 3-(7-ethylimidazo[1,2-a]pyridin-2-yl)-7-(4-methyl-1,4-diazepan-1-yl)-2H-chromen-2-one | 181-187 | 403.4 |
| 36 | 334 | 3-(8-ethyl-6-methylimidazo[1,2-a]pyridin-2-yl)-7-(piperazin-1-yl)-2H-chromen-2-one | 198-208 | 389.4 |
| 56 | 335 | 5-fluoro-3-(imidazo[1,2-a]pyrimidin-2-yl)-7-(4-methyl-1,4-diazepan-1-yl)-2H-chromen-2-one | 300-302 | 394.3 |
| 56 | 336 | 7-(1,4-diazepan-1-yl)-5-fluoro-3-(imidazo[1,2-a]pyrimidin-2-yl)-2H-chromen-2-one | 305-307 | 380.3 |
| 38 | 337 | 3-(6-chloroimidazo[1,2-a]pyrimidin-2-yl)-7-(4-methyl-1,4-diazepan-1-yl)-2H-chromen-2-one | 289-292 | 410.3 |
| 36 | 338 | 7-[(3R,5S)-3,5-dimethylpiperazin-1-yl]-3-(8-fluoroimidazo[1,2-a]pyridin-2-yl)-2H-chromen-2-one | 176-180 | 393.3 |
| 67 | 339 | 3-(8-chloroimidazo[1,2-a]pyridin-2-yl)-7-[(3S)-3,4-dimethylpiperazin-1-yl]-2H-chromen-2-one | 184-186 | 409.3 411.3 |
| 36 | 340 | 3-(8-ethyl-6-methylimidazo[1,2-a]pyridin-2-yl)-7-(4-methylpiperazin-1-yl)-2H-chromen-2-one | 203-210 | 403.4 |
| 36 | 341 | 7-[(3R,5S)-3,5-dimethylpiperazin-1-yl]-3-(8-ethyl-6-methylimidazo[1,2-a]pyridin-2-yl)-2H-chromen-2-one | 203-208 | 417.4 |
| 36 | 342 | 3-(8-chloro-6-methylimidazo[1,2-a]pyridin-2-yl)-7-[(3R,5S)-3,5-dimethylpiperazin-1-yl]-2H-chromen-2-one | 258-263 | 423.3 |
| 36 | 343 | 3-(8-chloro-6-methylimidazo[1,2-a]pyridin-2-yl)-7-(4-methylpiperazin-1-yl)-2H-chromen-2-one | 245-253 | 409.2 |
| 36 | 344 | 3-(8-chloro-6-methylimidazo[1,2-a]pyridin-2-yl)-7-(4-methyl-1,4-diazepan-1-yl)-2H-chromen-2-one | 224-230 | 423.3 |
| 10 | 345 | 7-{[(2-hydroxyethyl)(methyl)amino]methyl}-3-(imidazo[2,1-b][1,3]thiazol-6-yl)-2H-chromen-2-one | 145-148 | 356.2 |
| 10 | 346 | 7-[(4-hydroxypiperidin-1-yl)methyl]-3-(imidazo[2,1-b][1,3]thiazol-6-yl)-2H-chromen-2-one | 248-252 | 382.3 |
| 67 | 347 | 3-(6-chloroimidazo[1,2-a]pyrimidin-2-yl)-7-[4-(2-hydroxyethyl)piperazin-1-yl]-2H-chromen-2-one | 288-296 | 426.3 |
| 38 | 348 | 3-(6-chloroimidazo[1,2-a]pyrimidin-2-yl)-7-(piperazin-1-yl)-2H-chromen-2-one | 275-277 | 410.3 |
| 38 | 349 | 3-(6-chloroimidazo[1,2-a]pyrimidin-2-yl)-7-[(3R,5S)-3,5-dimethylpiperazin-1-yl]-2H-chromen-2-one | 265-271 | 410.3 |
| 38 | 350 | 3-(6-chloroimidazo[1,2-a]pyrimidin-2-yl)-7-[(3R)-3-methylpiperazin-1-yl]-2H-chromen-2-one | 255-259 | 396.3 |

TABLE 1-continued

| Ex | Cpd | Name | M.P. | MS |
|---|---|---|---|---|
| 56 | 351 | 5-fluoro-3-(imidazo[1,2-a]pyrimidin-2-yl)-7-(4-methylpiperazin-1-yl)-2H-chromen-2-one | ND | 380.3 |
| 56 | 352 | 7-[(3R,5S)-3,5-dimethylpiperazin-1-yl]-5-fluoro-3-(imidazo[1,2-a]pyrimidin-2-yl)-2H-chromen-2-one | 290-292 | 394.3 |
| 36 | 353 | 3-(8-fluoro-6-methylimidazo[1,2-a]pyridin-2-yl)-7-(4-methylpiperazin-1-yl)-2H-chromen-2-one | 252-262 | 393.4 |
| 36 | 354 | 7-[(3R,5S)-3,5-dimethylpiperazin-1-yl]-3-(8-fluoro-6-methylimidazo[1,2-a]pyridin-2-yl)-2H-chromen-2-one | 268-275 | 407.3 |
| 36 | 355 | 3-(8-fluoro-6-methylimidazo[1,2-a]pyridin-2-yl)-7-(4-methyl-1,4-diazepan-1-yl)-2H-chromen-2-one | 233-240 | 407.3 |
| 36 | 356 | 3-(8-fluoro-6-methylimidazo[1,2-a]pyridin-2-yl)-7-(piperazin-1-yl)-2H-chromen-2-one | 276-286 | 379.3 |
| 36 | 357 | 7-(1,4-diazepan-1-yl)-3-(8-fluoroimidazo[1,2-a]pyridin-2-yl)-2H-chromen-2-one | 210-213 | 379.2 |
| 36 | 358 | 3-(8-ethylimidazo[1,2-a]pyridin-2-yl)-7-(4-methylpiperazin-1-yl)-2H-chromen-2-one | 137-141 | 389.3 |
| 33 | 359 | 3-(6-methoxypyridin-2-yl)-7-(4-methyl-1,4-diazepan-1-yl)-2H-chromen-2-one | 155-158 | 366.3 |
| 67 | 360 | 7-(4-ethylpiperazin-1-yl)-3-(6-methoxypyridin-2-yl)-2H-chromen-2-one | 145-147 | 366.3 |
| 33 | 361 | 3-(6-methoxypyridin-2-yl)-7-[(3R)-3-methylpiperazin-1-yl]-2H-chromen-2-one | 150-152 | 352.3 |
| 33 | 362 | 3-(6-methoxypyridin-2-yl)-7-[(3S)-3-methylpiperazin-1-yl]-2H-chromen-2-one | 155-157 | 352.3 |
| 32 | 363 | 7-(piperazin-1-yl)-3-(thiophen-2-yl)-2H-chromen-2-one | 193-195 | 313.3 |
| 32 | 364 | 7-[(3R,5S)-3,5-dimethylpiperazin-1-yl]-3-(thiophen-2-yl)-2H-chromen-2-one | 150-152 | 341.3 |
| 8 | 365 | 3-(3,5-difluorophenyl)-5-fluoro-7-(4-methyl-1,4-diazepan-1-yl)-2H-chromen-2-one | 161-164 | 389.2 |
| 6 | 366 | 5-fluoro-3-(4-fluoro-1,3-benzoxazol-2-yl)-7-(4-methylpiperazin-1-yl)-2H-chromen-2-one | 256-260 | 398.3 |
| 6 | 367 | 7-[(3R,5S)-3,5-dimethylpiperazin-1-yl]-5-fluoro-3-(4-fluoro-1,3-benzoxazol-2-yl)-2H-chromen-2-one | 268-272 | 412.3 |
| 6 | 368 | 7-(1,4-diazepan-1-yl)-5-fluoro-3-(4-fluoro-1,3-benzoxazol-2-yl)-2H-chromen-2-one | 240-245 | 398.3 |
| 6 | 369 | 5-fluoro-3-(4-fluoro-1,3-benzoxazol-2-yl)-7-(4-methyl-1,4-diazepan-1-yl)-2H-chromen-2-one | 224-228 | 412.3 |
| 6 | 370 | 3-(1H-benzimidazol-2-yl)-5-fluoro-7-(4-methylpiperazin-1-yl)-2H-chromen-2-one | 281-284 | 379.2 |
| 6 | 371 | 3-(1H-benzimidazol-2-yl)-7-[(3R,5S)-3,5-dimethylpiperazin-1-yl]-5-fluoro-2H-chromen-2-one | 288-294 | 393.3 |
| 56 | 372 | 5-fluoro-3-(imidazo[2,1-b][1,3]thiazol-6-yl)-7-(4-methylpiperazin-1-yl)-2H-chromen-2-one | 268-271 | 385.3 |
| 56 | 373 | 5-fluoro-3-(imidazo[2,1-b][1,3]thiazol-6-yl)-7-(4-methyl-1,4-diazepan-1-yl)-2H-chromen-2-one | 205-207 | 399.3 |
| 6 | 374 | 3-(1H-benzimidazol-2-yl)-7-(1,4-diazepan-1-yl)-5-fluoro-2H-chromen-2-one | 236-242 | 379.3 |
| 6 | 375 | 3-(1H-benzimidazol-2-yl)-5-fluoro-7-(piperazin-1-yl)-2H-chromen-2-one | 245-250 | 365.3 |
| 38 | 376 | 3-(6-chloroimidazo[1,2-a]pyrimidin-2-yl)-7-[(3S)-3-methylpiperazin-1-yl]-2H-chromen-2-one | 260-262 | 396.2 |
| 38 | 377a | 7-[(1-benzylpyrrolidin-3-yl)(methyl)amino]-3-(7-methylimidazo[1,2-a]pyrimidin-2-yl)-2H-chromen-2-one | NI | NI |
| 39 | 378 | 7-(1,4-diazepan-1-yl)-3-(6-methylimidazo[1,2-a]pyrimidin-2-yl)-2H-chromen-2-one | 275-278 | 376.3 |
| 67 | 379 | 7-[(3S)-3,4-dimethylpiperazin-1-yl]-3-(7-methylimidazo[1,2-a]pyridin-2-yl)-2H-chromen-2-one | 231-241 | 389.4 |
| 26 | 380 | 3-(6-fluoropyridin-2-yl)-7-(piperazin-1-yl)-2H-chromen-2-one | 196-198 | 326.3 |
| 33 | 381 | 3-(6-ethoxypyridin-2-yl)-7-(4-methylpiperazin-1-yl)-2H-chromen-2-one | 170-172 | 366.3 |
| 26 | 382 | 3-(3,4-dimethoxyphenyl)-7-[(3R)-3-methylpiperazin-1-yl]-2H-chromen-2-one | 143-145 | 381.3 |
| 26 | 383 | 3-(3,4-dimethoxyphenyl)-7-[(3S)-3-methylpiperazin-1-yl]-2H-chromen-2-one | 140-143 | 381.3 |
| 26 | 384 | 3-(3,4-dimethoxyphenyl)-7-[(3R,5S)-3,5-dimethylpiperazin-1-yl]-2H-chromen-2-one | 130-132 | 395.3 |
| 27* | 385 | 7-(piperazin-1-yl)-3-[6-(propan-2-yloxy)pyridin-2-yl]-2H-chromen-2-one | 177-180 | 366.3 |
| 28* | 386 | 7-(piperazin-1-yl)-3-[6-(pyrrolidin-1-yl)pyridin-2-yl]-2H-chromen-2-one | 190-192 | 377.3 |
| 32 | 387 | 7-(1,4-diazepan-1-yl)-3-(3,5-dimethoxyphenyl)-2H-chromen-2-one | 238-240 | 381.3 |
| 56 | 388 | 3-(8-chloroimidazo[1,2-a]pyridin-2-yl)-7-[(3R,5S)-3,5-dimethylpiperazin-1-yl]-5-fluoro-2H-chromen-2-one | 290-300 | 427.2 |
| 36 | 389 | 3-(6,8-dimethylimidazo[1,2-a]pyridin-2-yl)-7-(4-methyl-1,4-diazepan-1-yl)-2H-chromen-2-one | 164-169 | 403.3 |

TABLE 1-continued

| Ex | Cpd | Name | M.P. | MS |
|---|---|---|---|---|
| 56 | 390 | 3-(8-chloroimidazo[1,2-a]pyridin-2-yl)-5-fluoro-7-[(3R)-3-methylpiperazin-1-yl]-2H-chromen-2-one | 266-276 | 413.2 |
| 56* | 391 | 7-[(3R,5S)-3,5-dimethylpiperazin-1-yl]-5-fluoro-3-[7-(trifluoromethyl)imidazo[1,2-a]pyridin-2-yl]-2H-chromen-2-one | 210-219 | 461.3 |
| 56 | 392 | 3-(8-chloroimidazo[1,2-a]pyridin-2-yl)-5-fluoro-7-(piperazin-1-yl)-2H-chromen-2-one | 241-250 | 399.2 |
| 56 | 393 | 3-(8-chloroimidazo[1,2-a]pyridin-2-yl)-5-fluoro-7-[(3S)-3-methylpiperazin-1-yl]-2H-chromen-2-one | 268-278 | 413.2 |
| 1 | 394 | 3-(4-methyl-1H-benzimidazol-2-yl)-7-(piperazin-1-yl)-2H-chromen-2-one | 206-211 | 361.3 |
| 1 | 395 | 3-(5-fluoro-1H-benzimidazol-2-yl)-7-(piperazin-1-yl)-2H-chromen-2-one | 295-300 | 365.2 |
| 9 | 396 | 3-(1H-benzimidazol-2-yl)-7-[(dimethylamino)methyl]-2H-chromen-2-one | 214-218 | 320.3 |
| 10 | 397 | 5-fluoro-7-(hydroxymethyl)-3-(imidazo[2,1-b][1,3]thiazol-6-yl)-2H-chromen-2-one | 278-282 | 317.2 |
| 46* | 398 | 3-[8-(methylsulfanyl)imidazo[1,2-a]pyrazin-2-yl]-7-(piperazin-1-yl)-2H-chromen-2-one | ND | 394.3 |
| 46 | 399 | 7-(4-methylpiperazin-1-yl)-3-[8-(methylsulfanyl)imidazo[1,2-a]pyrazin-2-yl]-2H-chromen-2-one | ND | 408.3 |
| 46 | 400 | 7-[(3R,5S)-3,5-dimethylpiperazin-1-yl]-3-[8-(methylsulfanyl)imidazo[1,2-a]pyrazin-2-yl]-2H-chromen-2-one | 283-285 | 422.3 |
| 46 | 401 | 7-(4-methyl-1,4-diazepan-1-yl)-3-[8-(methylsulfanyl)imidazo[1,2-a]pyrazin-2-yl]-2H-chromen-2-one | ND | 422.3 |
| 36 | 402 | 3-(8-methoxyimidazo[1,2-a]pyridin-2-yl)-7-(piperazin-1-yl)-2H-chromen-2-one | 236-240 | 377.3 |
| 36 | 403 | 3-(8-methoxyimidazo[1,2-a]pyridin-2-yl)-7-(4-methylpiperazin-1-yl)-2H-chromen-2-one | 202-205 | 391.2 |
| 8 | 404 | 3-(3,4-dimethoxyphenyl)-5-fluoro-7-(piperazin-1-yl)-2H-chromen-2-one | 240 (D) | 385.2 |
| 8 | 405 | 3-(3,4-dimethoxyphenyl)-5-fluoro-7-(4-methylpiperazin-1-yl)-2H-chromen-2-one | ND | 399.3 |
| 8 | 406 | 3-(3,4-dimethoxyphenyl)-5-fluoro-7-(4-methyl-1,4-diazepan-1-yl)-2H-chromen-2-one | 134-140 | 413.2 |
| 32 | 407 | 3-(1-benzothiophen-2-yl)-7-(piperazin-1-yl)-2H-chromen-2-one | 243-245 | 363.3 |
| 32 | 408 | 3-(1-benzothiophen-2-yl)-7-[(3R,5S)-3,5-dimethylpiperazin-1-yl]-2H-chromen-2-one | 271-273 | 391.3 |
| 32 | 409 | 3-(1-benzothiophen-2-yl)-7-[(3R)-3-methylpiperazin-1-yl]-2H-chromen-2-one | 264-266 | 377.3 |
| 32 | 410 | 3-(1-benzothiophen-2-yl)-7-[(3S)-3-methylpiperazin-1-yl]-2H-chromen-2-one | 260-262 | 377.3 |
| 32 | 411 | 3-(3,5-dimethoxyphenyl)-7-(4-methyl-1,4-diazepan-1-yl)-2H-chromen-2-one | 151-153 | 395.3 |
| 32 | 412 | 3-(3,5-dimethoxyphenyl)-7-[(3R)-3-methylpiperazin-1-yl]-2H-chromen-2-one | 148-150 | 381.3 |
| 32 | 413 | 3-(3,5-dimethoxyphenyl)-7-[(3S)-3-methylpiperazin-1-yl]-2H-chromen-2-one | 149-151 | 381.3 |
| 27 | 414 | 3-[6-(cyclobutyloxy)pyridin-2-yl]-7-(piperazin-1-yl)-2H-chromen-2-one | 166-168 | 378.3 |
| 27 | 415 | 3-[6-(cyclobutyloxy)pyridin-2-yl]-7-(4-methylpiperazin-1-yl)-2H-chromen-2-one | 158-160 | 392.3 |
| 26 | 416 | 3-(3,4-dimethoxyphenyl)-5-fluoro-7-[(3R)-3-methylpiperazin-1-yl]-2H-chromen-2-one | 115-117 | 399.3 |
| 47 | 417 | 7-[(3R,5S)-3,5-dimethylpiperazin-1-yl]-3-(imidazo[1,2-a]pyrazin-2-yl)-2H-chromen-2-one | 248-250 | 376.3 |
| 36 | 418 | 7-[(3R,5 S)-3,5-dimethylpiperazin-1-yl]-3-(8-methoxyimidazo[1,2-a]pyridin-2-yl)-2H-chromen-2-one | 184-186 | 405.4 |
| 36 | 419 | 3-(8-methoxyimidazo[1,2-a]pyridin-2-yl)-7-(4-methyl-1,4-diazepan-1-yl)-2H-chromen-2-one | 212-215 | 405.4 |
| 36 | 420 | 3-(8-fluoro-6-methylimidazo[1,2-a]pyridin-2-yl)-7-[(3R)-3-methylpiperazin-1-yl]-2H-chromen-2-one | 246-254 | 393.3 |
| 36* | 421 | 3-(8-fluoro-6-methylimidazo[1,2-a]pyridin-2-yl)-7-[(3S)-3-methylpiperazin-1-yl]-2H-chromen-2-one | 250-255 | 393.3 |
| 56 | 422 | 5-fluoro-3-(imidazo[1,2-a]pyridin-2-yl)-7-(4-methylpiperazin-1-yl)-2H-chromen-2-one | 263-269 | 379.3 |
| 56 | 423 | 5-fluoro-3-(8-methylimidazo[1,2-a]pyridin-2-yl)-7-(4-methylpiperazin-1-yl)-2H-chromen-2-one | 232-237 | 393.3 |
| 56 | 424 | 5-fluoro-3-(7-methylimidazo[1,2-a]pyridin-2-yl)-7-(piperazin-1-yl)-2H-chromen-2-one | 268-278 | 379.3 |
| 36 | 425 | 3-(6,8-dimethylimidazo[1,2-a]pyridin-2-yl)-7-[(3S)-3-methylpiperazin-1-yl]-2H-chromen-2-one | 221-226 | 389.4 |
| 36 | 426 | 7-(3,3-dimethylpiperazin-1-yl)-3-(8-fluoro-6-methylimidazo[1,2-a]pyridin-2-yl)-2H-chromen-2-one | 275-284 | 407.3 |

TABLE 1-continued

| Ex | Cpd | Name | M.P. | MS |
|---|---|---|---|---|
| 36 | 427 | 7-(1,4-diazepan-1-yl)-3-(8-fluoro-6-methylimidazo[1,2-a]pyridin-2-yl)-2H-chromen-2-one | 242-252 | 393.3 |
| 42 | 428 | 3-(2-ethylimidazo[2,1-b][1,3]thiazol-6-yl)-7-(piperazin-1-yl)-2H-chromen-2-one | 231-236 | 381.3 |
| 42* | 429 | 7-[(3R,5S)-3,5-dimethylpiperazin-1-yl]-3-(2-ethylimidazo[2,1-b][1,3]thiazol-6-yl)-2H-chromen-2-one | 251-253 | 409.4 |
| 42 | 430 | 7-(1,4-diazepan-1-yl)-3-(2-ethylimidazo[2,1-b][1,3]thiazol-6-yl)-2H-chromen-2-one | 185-189 | 395.3 |
| 42 | 431 | 3-(2-ethylimidazo[2,1-b][1,3]thiazol-6-yl)-7-(4-methyl-1,4-diazepan-1-yl)-2H-chromen-2-one | 188-191 | 409.3 |
| 36 | 432 | 7-[(3R,5S)-3,5-dimethylpiperazin-1-yl]-3-(7-methoxyimidazo[1,2-a]pyridin-2-yl)-2H-chromen-2-one | 225-230 | 405.3 |
| 23* | 433 | 7-[(3R,5S)-3,5-dimethylpiperazin-1-yl]-3-[1-(pyridin-2-yl)-1H-imidazol-4-yl]-2H-chromen-2-one | 201-206 | 402.3 |
| 36 | 434 | 3-(7-methoxyimidazo[1,2-a]pyridin-2-yl)-7-[(3S)-3-methylpiperazin-1-yl]-2H-chromen-2-one | 250-256 | 391.3 |
| 36 | 435 | 3-(7-methoxyimidazo[1,2-a]pyridin-2-yl)-7-(4-methylpiperazin-1-yl)-2H-chromen-2-one | 251-259 | 391.3 |
| 36 | 436 | 3-(7-methoxyimidazo[1,2-a]pyridin-2-yl)-7-(4-methyl-1,4-diazepan-1-yl)-2H-chromen-2-one | 198-207 | 405.4 |
| 41 | 437 | 7-[(1R,5S,6s)-6-(dimethylamino)-3-azabicyclo[3.1.0]hex-3-yl]-3-(imidazo[2,1-b][1,3]thiazol-6-yl)-2H-chromen-2-one | 233-235 | 393.3 |
| 41 | 438 | 7-(1,4-diazabicyclo[3.2.2]non-4-yl)-3-(imidazo[2,1-b][1,3]thiazol-6-yl)-2H-chromen-2-one | >300 | 393.3 |
| 38 | 439 | 7-[(1R,5S,6s)-6-(dimethylamino)-3-azabicyclo[3.1.0]hex-3-yl]-3-(imidazo[1,2-a]pyrimidin-2-yl)-2H-chromen-2-one | >300 | 388.4 |
| 38 | 440 | 7-(1,4-diazabicyclo[3.2.2]non-4-yl)-3-(imidazo[1,2-a]pyrimidin-2-yl)-2H-chromen-2-one | >300 | 388.4 |
| 55* | 441 | 3-(2-methylimidazo[2,1-b][1,3,4]thiadiazol-6-yl)-7-(piperazin-1-yl)-2H-chromen-2-one | 288-290 | 368.2 |
| 55 | 442 | 3-(2-methylimidazo[2,1-b][1,3,4]thiadiazol-6-yl)-7-(4-methylpiperazin-1-yl)-2H-chromen-2-one | 233-236 | 382.3 |
| 55 | 443 | 7-[(3R,5S)-3,5-dimethylpiperazin-1-yl]-3-(2-methylimidazo[2,1-b][1,3,4]thiadiazol-6-yl)-2H-chromen-2-one | 225-228 | 396.3 |
| 26 | 444 | 7-[(3S)-3-methylpiperazin-1-yl]-3-(pyridin-2-yl)-2H-chromen-2-one | 145-147 | 322.3 |
| 29* | 445 | 3-[6-(methylsulfanyl)pyridin-2-yl]-7-(piperazin-1-yl)-2H-chromen-2-one | 180-183 | 354.3 |
| 26 | 446 | 7-[(1S,4S)-2,5-diazabicyclo[2.2.1]hept-2-yl]-3-(3,4-dimethoxyphenyl)-5-fluoro-2H-chromen-2-one | 239-241 | 397.3 |
| 32 | 447 | 3-(4-methoxyphenyl)-7-(piperazin-1-yl)-2H-chromen-2-one | 211-213 | 337.3 |
| 32 | 448 | 3-(4-methoxyphenyl)-7-[(3R)-3-methylpiperazin-1-yl]-2H-chromen-2-one | 123-126 | 351.3 |
| 32 | 449 | 3-(4-methoxyphenyl)-7-[(3S)-3-methylpiperazin-1-yl]-2H-chromen-2-one | 123-126 | 351.3 |
| 55 | 450 | 7-(1,4-diazepan-1-yl)-3-(2-methylimidazo[2,1-b][1,3,4]thiadiazol-6-yl)-2H-chromen-2-one | 215-218 | 382.2 |
| 55 | 451 | 7-(4-methyl-1,4-diazepan-1-yl)-3-(2-methylimidazo[2,1-b][1,3,4]thiadiazol-6-yl)-2H-chromen-2-one | 191-195 | 396.2 |
| 22* | 452 | 7-[(3R,5S)-3,5-dimethylpiperazin-1-yl]-3-(1-phenyl-1H-imidazol-4-yl)-2H-chromen-2-one | 260-264 | 401.3 |
| 23 | 453 | 7-(4-methyl-1,4-diazepan-1-yl)-3-[2-methyl-1-(pyridin-2-yl)-1H-imidazol-4-yl]-2H-chromen-2-one | 192-196 | 416.3 |
| 47 | 454 | 7-(1,4-diazepan-1-yl)-3-(imidazo[1,2-a]pyrazin-2-yl)-2H-chromen-2-one | 247-249 | 362.2 |
| 47 | 455 | 3-(imidazo[1,2-a]pyrazin-2-yl)-7-(4-methyl-1,4-diazepan-1-yl)-2H-chromen-2-one | ND | 376.2 |
| 47* | 456 | 3-(imidazo[1,2-a]pyrazin-2-yl)-7-(piperazin-1-yl)-2H-chromen-2-one | 258-260 | 348.2 |
| 47 | 457 | 3-(imidazo[1,2-a]pyrazin-2-yl)-7-(4-methylpiperazin-1-yl)-2H-chromen-2-one | 246-249 | 362.3 |
| 54* | 458 | 3-(imidazo[1,2-c]pyrimidin-2-yl)-7-(4-methylpiperazin-1-yl)-2H-chromen-2-one | 253-255 | 362.3 |
| 54 | 459 | 7-[(3R,5S)-3,5-dimethylpiperazin-1-yl]-3-(imidazo[1,2-c]pyrimidin-2-yl)-2H-chromen-2-one | 250-252 | 376.2 |
| 54 | 460 | 3-(imidazo[1,2-c]pyrimidin-2-yl)-7-(4-methyl-1,4-diazepan-1-yl)-2H-chromen-2-one | 225-227 | 376.2 |
| 36 | 461 | 7-[(3R,5S)-3,5-dimethylpiperazin-1-yl]-3-(quinoxalin-2-yl)-2H-chromen-2-one | 234-236 | 387.3 |
| 39 | 462 | 3-(6-methylimidazo[1,2-a]pyrimidin-2-yl)-7-[(3S)-3-methylpiperazin-1-yl]-2H-chromen-2-one | 254-256 | 376.4 |
| 39 | 463 | 3-(6-methylimidazo[1,2-a]pyrimidin-2-yl)-7-[(3R)-3-methylpiperazin-1-yl]-2H-chromen-2-one | 258-261 | 376.4 |
| 26 | 464 | 3-(3,4-dimethoxyphenyl)-5-fluoro-7-[(3S)-3-methylpiperazin-1-yl]-2H-chromen-2-one | 118-120 | 399.3 |

TABLE 1-continued

| Ex | Cpd | Name | M.P. | MS |
|---|---|---|---|---|
| 26 | 465 | 3-(2,4-dimethoxyphenyl)-7-(piperazin-1-yl)-2H-chromen-2-one | 171-173 | 367.3 |
| 26 | 466 | 3-(2,4-dimethoxyphenyl)-7-[(3R)-3-methylpiperazin-1-yl]-2H-chromen-2-one | 101-103 | 381.3 |
| 26 | 467 | 3-(2,4-dimethoxyphenyl)-7-[(3S)-3-methylpiperazin-1-yl]-2H-chromen-2-one | 103-105 | 381.3 |
| 32 | 468 | 5-fluoro-3-(6-methoxypyridin-2-yl)-7-(piperazin-1-yl)-2H-chromen-2-one | 231-236 | 356.3 |
| 32 | 469 | 5-fluoro-3-(6-methoxypyridin-2-yl)-7-[(3S)-3-methylpiperazin-1-yl]-2H-chromen-2-one | 199-201 | 370.3 |
| 37 | 470 | 7-{[2-(dimethylamino)ethyl]amino}-3-(7-methylimidazo[1,2-a]pyridin-2-yl)-2H-chromen-2-one | 156-159 | 363.3 |
| 67 | 471 | 7-[(3S)-3,4-dimethylpiperazin-1-yl]-3-(8-fluoro-6-methylimidazo[1,2-a]pyridin-2-yl)-2H-chromen-2-one | 270-277 | 407.2 |
| 32 | 472 | 3-(3,4-dimethoxyphenyl)-7-[(2S)-2-methylpiperazin-1-yl]-2H-chromen-2-one | ND | 381.3 |
| 41 | 473 | 3-(2-chloroimidazo[2,1-b][1,3]thiazol-6-yl)-7-[(3R,5S)-3,5-dimethylpiperazin-1-yl]-2H-chromen-2-one | 270-273 | 415.2 |
| 37 | 474 | 3-(7-methylimidazo[1,2-a]pyridin-2-yl)-7-[(1-methylpiperidin-4-yl)amino]-2H-chromen-2-one | 224-230 | 389.8 |
| 48 | 475 | 7-{[3-(dimethylamino)propyl]amino}-3-(7-methylimidazo[1,2-a]pyridin-2-yl)-2H-chromen-2-one | 165-170 | 377.8 |
| 43 | 476 | 7-[(3R,5S)-3,5-dimethylpiperazin-1-yl]-3-(6-methylimidazo[1,2-a]pyrazin-2-yl)-2H-chromen-2-one | 249-250 | 390.8 |
| 43 | 477 | 7-(1,4-diazepan-1-yl)-3-(6-methylimidazo[1,2-a]pyrazin-2-yl)-2H-chromen-2-one | ND | 390.8 |
| 41 | 478 | 3-(2-chloroimidazo[2,1-b][1,3]thiazol-6-yl)-7-(4-methylpiperazin-1-yl)-2H-chromen-2-one | 268-270 | 401.2 |
| 41 | 479 | 3-(2-chloroimidazo[2,1-b][1,3]thiazol-6-yl)-7-(4-methyl-1,4-diazepan-1-yl)-2H-chromen-2-one | 229-232 | 415.7 |
| 40* | 480 | 3-(6-fluoroimidazo[1,2-a]pyrimidin-2-yl)-7-(4-methylpiperazin-1-yl)-2H-chromen-2-one | 275-280 | 380.8 |
| 40 | 481 | 3-(6-fluoroimidazo[1,2-a]pyrimidin-2-yl)-7-[(3R)-3-methylpiperazin-1-yl]-2H-chromen-2-one | 232-236 | 380.8 |
| 55 | 482 | 3-(2-methylimidazo[2,1-b][1,3,4]thiadiazol-6-yl)-7-[(3S)-3-methylpiperazin-1-yl]-2H-chromen-2-one | 205-209 | 382.7 |
| 55 | 483 | 3-(2-methylimidazo[2,1-b][1,3,4]thiadiazol-6-yl)-7-[(3R)-3-methylpiperazin-1-yl]-2H-chromen-2-one | 206-210 | 382.7 |
| 32 | 484 | 3-(3-chloro-4-fluorophenyl)-7-(piperazin-1-yl)-2H-chromen-2-one | 186-188 | 359.3 |
| 32 | 485 | 3-(3-chloro-4-fluorophenyl)-7-[(3S)-3-methylpiperazin-1-yl]-2H-chromen-2-one | 143-145 | 373.3 |
| 26 | 486 | 3-(1,3-benzodioxol-5-yl)-7-(piperazin-1-yl)-2H-chromen-2-one | 218-220 | 351.3 |
| 26 | 487 | 3-(1,3-benzodioxol-5-yl)-7-[(3R,5S)-3,5-dimethylpiperazin-1-yl]-2H-chromen-2-one | 123-125 | 379.3 |
| 26 | 488 | 3-(1,3-benzodioxol-5-yl)-7-[(3R)-3-methylpiperazin-1-yl]-2H-chromen-2-one | 135-137 | 365.3 |
| 26 | 489 | 3-(1,3-benzodioxol-5-yl)-7-[(3S)-3-methylpiperazin-1-yl]-2H-chromen-2-one | 134-136 | 365.3 |
| 26 | 490 | 7-[(3S)-3-methylpiperazin-1-yl]-3-[3-(trifluoromethyl)phenyl]-2H-chromen-2-one | 141-143 | 389.3 |
| 40 | 491 | 7-[(3R,5S)-3,5-dimethylpiperazin-1-yl]-3-(6-fluoroimidazo[1,2-a]pyrimidin-2-yl)-2H-chromen-2-one | 275-281 | 394.2 |
| 40 | 492 | 3-(6-fluoroimidazo[1,2-a]pyrimidin-2-yl)-7-[(3S)-3-methylpiperazin-1-yl]-2H-chromen-2-one | 230-236 | 380.8 |
| 43 | 493 | 7-(4-methyl-1,4-diazepan-1-yl)-3-(6-methylimidazo[1,2-a]pyrazin-2-yl)-2H-chromen-2-one | 234-235 | 390.2 |
| 41 | 494 | 3-(2-chloroimidazo[2,1-b][1,3]thiazol-6-yl)-7-(piperazin-1-yl)-2H-chromen-2-one | 240-242 | 387.7 |
| 48 | 495 | 3-(7-methylimidazo[1,2-a]pyridin-2-yl)-7-(piperidin-4-ylamino)-2H-chromen-2-one | 232-239 | 375.8 |
| 48 | 496 | 3-(7-methylimidazo[1,2-a]pyridin-2-yl)-7-[(3R)-pyrrolidin-3-ylamino]-2H-chromen-2-one | 244-254 | 361.7 |
| 36 | 497 | 3-(6-cyclopropyl-8-fluoroimidazo[1,2-a]pyridin-2-yl)-7-[(3R,5S)-3,5-dimethylpiperazin-1-yl]-2H-chromen-2-one | 257-267 | 433.9 |
| 36 | 498 | 3-(6-cyclopropyl-8-fluoroimidazo[1,2-a]pyridin-2-yl)-7-[(3S)-3-methylpiperazin-1-yl]-2H-chromen-2-one | 254-263 | 419.8 |
| 36 | 499 | 3-(6-cyclopropyl-8-fluoroimidazo[1,2-a]pyridin-2-yl)-7-(4-methyl-1,4-diazepan-1-yl)-2H-chromen-2-one | 234-244 | 433.9 |
| 36 | 500 | 3-(6-cyclopropyl-8-fluoroimidazo[1,2-a]pyridin-2-yl)-7-(piperazin-1-yl)-2H-chromen-2-one | 261-271 | 405.8 |
| 36 | 501 | 7-(1,4-diazabicyclo[3.2.2]non-4-yl)-3-(8-fluoroimidazo[1,2-a]pyridin-2-yl)-2H-chromen-2-one | 175-178 | 405.8 |
| 40 | 502 | 3-(6-fluoroimidazo[1,2-a]pyrimidin-2-yl)-7-(piperazin-1-yl)-2H-chromen-2-one | 250-261 | 366.7 |
| 36 | 503 | 3-(6-cyclopropyl-8-fluoroimidazo[1,2-a]pyridin-2-yl)-7-[(3R)-3-methylpiperazin-1-yl]-2H-chromen-2-one | 254-264 | 419.9 |

TABLE 1-continued

| Ex | Cpd | Name | M.P. | MS |
|---|---|---|---|---|
| 36 | 504 | 3-(6-cyclopropyl-8-fluoroimidazo[1,2-a]pyridin-2-yl)-7-(4-methylpiperazin-1-yl)-2H-chromen-2-one | 277-287 | 419.2 |
| 36 | 505 | 7-(1,4-diazabicyclo[3.2.2]non-4-yl)-3-(8-methylimidazo[1,2-a]pyridin-2-yl)-2H-chromen-2-one | 278 (D) | 401.1 |
| 36 | 506 | 7-(3,8-diazabicyclo[3.2.1]oct-3-yl)-3-(8-fluoroimidazo[1,2-a]pyridin-2-yl)-2H-chromen-2-one | 232-235 | 391.8 |
| 36 | 507 | 7-(3,3-dimethylpiperazin-1-yl)-3-(8-fluoroimidazo[1,2-a]pyridin-2-yl)-2H-chromen-2-one | 180-182 | 393.3 |
| 36 | 508 | 7-(3,3-dimethylpiperazin-1-yl)-3-(6-fluoroimidazo[1,2-a]pyridin-2-yl)-2H-chromen-2-one | 182-185 | 393.3 |
| 26 | 509 | 3-(3-chlorophenyl)-7-[(3S)-3-methylpiperazin-1-yl]-2H-chromen-2-one | 149-151 | 355.3 |
| 26 | 510 | 3-(2-chloro-4-fluorophenyl)-7-[(3S)-3-methylpiperazin-1-yl]-2H-chromen-2-one | 109-111 | 373.3 |
| 26 | 511 | 3-(3-methylphenyl)-7-(piperazin-1-yl)-2H-chromen-2-one | 118-120 | 321.3 |
| 26 | 512 | 3-(3-methylphenyl)-7-[(3S)-3-methylpiperazin-1-yl]-2H-chromen-2-one | 101-103 | 335.2 |
| 32 | 513 | 3-(2,3-dihydro-1,4-benzodioxin-6-yl)-7-[(3S)-3-methylpiperazin-1-yl]-2H-chromen-2-one | 196-198 | 379.3 |
| 32 | 514 | 3-(2,3-dihydro-1,4-benzodioxin-6-yl)-7-[(3R,5S)-3,5-dimethylpiperazin-1-yl]-2H-chromen-2-one | 138-140 | 393.2 |
| 43 | 515 | 3-(6,8-dimethylimidazo[1,2-a]pyrazin-2-yl)-7-(piperazin-1-yl)-2H-chromen-2-one | ND | 376.2 |
| 43 | 516 | 3-(6,8-dimethylimidazo[1,2-a]pyrazin-2-yl)-7-(4-methylpiperazin-1-yl)-2H-chromen-2-one | 240-242 | 390.3 |
| 43 | 517 | 3-(6,8-dimethylimidazo[1,2-a]pyrazin-2-yl)-7-[(3R,5S)-3,5-dimethylpiperazin-1-yl]-2H-chromen-2-one | ND | 404.3 |
| 43 | 518 | 7-(1,4-diazepan-1-yl)-3-(6,8-dimethylimidazo[1,2-a]pyrazin-2-yl)-2H-chromen-2-one | 188-190 | 390.3 |
| 43 | 519 | 3-(6,8-dimethylimidazo[1,2-a]pyrazin-2-yl)-7-(4-methyl-1,4-diazepan-1-yl)-2H-chromen-2-one | 253-255 | 404.3 |
| 37* | 520 | 3-(6,8-difluoroimidazo[1,2-a]pyridin-2-yl)-7-(4-methyl-1,4-diazepan-1-yl)-2H-chromen-2-one | 255-260 | 411.2 |
| 36 | 521 | 7-(1,4-diazabicyclo[3.2.2]non-4-yl)-3-(7-methylimidazo[1,2-a]pyridin-2-yl)-2H-chromen-2-one | 216-223 | 401.1 |
| 37 | 522 | 3-(6,8-difluoroimidazo[1,2-a]pyridin-2-yl)-7-(4-methylpiperazin-1-yl)-2H-chromen-2-one | 232-238 | 397.1 |
| 37 | 523 | 3-(6,8-difluoroimidazo[1,2-a]pyridin-2-yl)-7-[(3R,5S)-3,5-dimethylpiperazin-1-yl]-2H-chromen-2-one | 267-277 | 411.1 |
| 37 | 524 | 3-(6,8-difluoroimidazo[1,2-a]pyridin-2-yl)-7-[(3S)-3-methylpiperazin-1-yl]-2H-chromen-2-one | 218-224 | 397.2 |
| 36 | 525 | 3-(8-fluoroimidazo[1,2-a]pyridin-2-yl)-7-[(3S)-3-methylpiperazin-1-yl]-2H-chromen-2-one | 190-193 | 379.1 |
| 36 | 526 | 3-(8-chloroimidazo[1,2-a]pyridin-2-yl)-7-(3,8-diazabicyclo[3.2.1]oct-3-yl)-2H-chromen-2-one | 213-216 | 407.2 409.2 |
| 36 | 527 | 3-(8-chloroimidazo[1,2-a]pyridin-2-yl)-7-(2,5-diazabicyclo[2.2.2]oct-2-yl)-2H-chromen-2-one | 178-182 | 407.2 409.2 |
| 36 | 528 | 3-(8-fluoroimidazo[1,2-a]pyridin-2-yl)-7-[(8aS)-hexahydropyrrolo[1,2-a]pyrazin-2(1H)-yl]-2H-chromen-2-one | 235-238 | 405.2 |
| 57* | 529 | 3-(indolizin-2-yl)-7-(piperazin-1-yl)-2H-chromen-2-one | 186-188 | 346.4 |
| 36 | 530 | 3-(8-fluoroimidazo[1,2-a]pyridin-2-yl)-7-[(3R)-3-methylpiperazin-1-yl]-2H-chromen-2-one | 226-228 | 379.2 |
| 36 | 531 | 3-(8-fluoroimidazo[1,2-a]pyridin-2-yl)-7-[(8aR)-hexahydropyrrolo[1,2-a]pyrazin-2(1H)-yl]-2H-chromen-2-one | 238-241 | 405.8 |
| 37 | 532 | 3-(6,8-difluoroimidazo[1,2-a]pyridin-2-yl)-7-(piperazin-1-yl)-2H-chromen-2-one | 276-286 | 383 |
| 67 | 533 | 7-[(3R)-3,4-dimethylpiperazin-1-yl]-3-(8-fluoro-6-methylimidazo[1,2-a]pyridin-2-yl)-2H-chromen-2-one | 269-277 | 407.1 |
| 36 | 534 | 7-[(8aS)-hexahydropyrrolo[1,2-a]pyrazin-2(1H)-yl]-3-(7-methylimidazo[1,2-a]pyridin-2-yl)-2H-chromen-2-one | 258-265 | 401.1 |
| 36 | 535 | 7-[(1R,5S)-8-methyl-3,8-diazabicyclo[3.2.1]oct-3-yl]-3-(7-methylimidazo[1,2-a]pyridin-2-yl)-2H-chromen-2-one | 224-229 | 401.1 |
| 43* | 536 | 3-(6,8-dimethylimidazo[1,2-a]pyrazin-2-yl)-7-[(3R)-3-methylpiperazin-1-yl]-2H-chromen-2-one | ND | 390.2 |
| 43 | 537 | 3-(6,8-dimethylimidazo[1,2-a]pyrazin-2-yl)-7-[(3S)-3-methylpiperazin-1-yl]-2H-chromen-2-one | ND | 390.2 |
| 32 | 538 | 3-(3,5-difluoro-2-methoxyphenyl)-7-(piperazin-1-yl)-2H-chromen-2-one | 109-111 | 373.2 |
| 32 | 539 | 3-(3,5-difluoro-2-methoxyphenyl)-7-[(3S)-3-methylpiperazin-1-yl]-2H-chromen-2-one | 156-158 | 387.2 |
| 32 | 540 | 3-(3,5-difluoro-2-methoxyphenyl)-7-[(3R,5S)-3,5-dimethylpiperazin-1-yl]-2H-chromen-2-one | 109-111 | 401.3 |
| 26 | 541 | 3-(4-methoxy-3-methylphenyl)-7-(piperazin-1-yl)-2H-chromen-2-one | 171-173 | 351.3 |
| 26 | 542 | 3-(4-methoxy-3-methylphenyl)-7-[(3S)-3-methylpiperazin-1-yl]-2H-chromen-2-one | 127-131 | 365.3 |

TABLE 1-continued

| Ex | Cpd | Name | M.P. | MS |
|---|---|---|---|---|
| 26 | 543 | 7-[(3R,5S)-3,5-dimethylpiperazin-1-yl]-3-(4-methoxy-3-methylphenyl)-2H-chromen-2-one | 111-113 | 379.3 |
| 32 | 544 | 3-(3-fluoro-4-methoxyphenyl)-7-(piperazin-1-yl)-2H-chromen-2-one | 241-243 | 355.2 |
| 32 | 545 | 3-(3-fluoro-4-methoxyphenyl)-7-[(3S)-3-methylpiperazin-1-yl]-2H-chromen-2-one | 141-143 | 369.3 |
| 32 | 546 | 3-(2,3-difluorophenyl)-7-[(3S)-3-methylpiperazin-1-yl]-2H-chromen-2-one | 116-118 | 357.3 |
| 32 | 547 | 3-[6-(dimethylamino)pyridin-3-yl]-7-(piperazin-1-yl)-2H-chromen-2-one | 179-181 | 351.3 |
| 32 | 548 | 3-[6-(dimethylamino)pyridin-3-yl]-7-[(3S)-3-methylpiperazin-1-yl]-2H-chromen-2-one | 194-196 | 365.3 |
| 26 | 549 | 7-[(3S)-3-methylpiperazin-1-yl]-3-(pyridin-4-yl)-2H-chromen-2-one | 210-213 | 322.3 |
| 56 | 550 | 7-(1,4-diazepan-1-yl)-5-fluoro-3-(6-methylimidazo[1,2-a]pyrazin-2-yl)-2H-chromen-2-one | 270-274 | 394 |
| 43 | 551 | 3-(8-methylimidazo[1,2-a]pyrazin-2-yl)-7-(4-methylpiperazin-1-yl)-2H-chromen-2-one | 221-222 | 376.1 |
| 43 | 552 | 7-[(3R,5S)-3,5-dimethylpiperazin-1-yl]-3-(8-methylimidazo[1,2-a]pyrazin-2-yl)-2H-chromen-2-one | 250-258 | 390.2 |
| 57 | 553 | 7-[(3R,5S)-3,5-dimethylpiperazin-1-yl]-3-(indolizin-2-yl)-2H-chromen-2-one | 164-167 | 374.2 |
| 58 | 554 | 7-[(3R,5S)-3,5-dimethylpiperazin-1-yl]-3-(1-methylpyrrolo[1,2-a]pyrazin-7-yl)-2H-chromen-2-one | 200-203 | 389.3 |
| 58 | 555 | 3-(1-methylpyrrolo[1,2-a]pyrazin-7-yl)-7-(piperazin-1-yl)-2H-chromen-2-one | 264-266 | 361.4 |
| 58 | 556 | 7-(4-methyl-1,4-diazepan-1-yl)-3-(1-methylpyrrolo[1,2-a]pyrazin-7-yl)-2H-chromen-2-one | 125-128 | 389.3 |
| 58 | 557 | 7-(4-methylpiperazin-1-yl)-3-(1-methylpyrrolo[1,2-a]pyrazin-7-yl)-2H-chromen-2-one | 190-192 | 375.2 |
| 43 | 558 | 7-(4-methyl-1,4-diazepan-1-yl)-3-(8-methylimidazo[1,2-a]pyrazin-2-yl)-2H-chromen-2-one | 180-182 | 390.2 |
| 43 | 559 | 3-(8-methylimidazo[1,2-a]pyrazin-2-yl)-7-[(3R)-3-methylpiperazin-1-yl]-2H-chromen-2-one | 222-228 | 376.2 |
| 36 | 560 | 3-(8-fluoro-6-methylimidazo[1,2-a]pyridin-2-yl)-7-[(8aS)-hexahydropyrrolo[1,2-a]pyrazin-2(1H)-yl]-2H-chromen-2-one | 296-306 | 419.2 |
| 36 | 561 | 7-(1,4-diazabicyclo[3.2.2]non-4-yl)-3-(8-fluoro-6-methylimidazo[1,2-a]pyridin-2-yl)-2H-chromen-2-one | 287-297 | 419.2 |
| 48 | 562 | 3-(6,8-dimethylimidazo[1,2-a]pyrazin-2-yl)-7-(piperidin-4-ylamino)-2H-chromen-2-one | 255-261 | 390.1 |
| 48* | 563 | 3-(6,8-dimethylimidazo[1,2-a]pyrazin-2-yl)-7-[(3S)-pyrrolidin-3-ylamino]-2H-chromen-2-one | 132-188 (DR) | 376.1 |
| 48 | 564 | 3-(6,8-dimethylimidazo[1,2-a]pyrazin-2-yl)-7-[(3R)-pyrrolidin-3-ylamino]-2H-chromen-2-one | 290-300 | 376.2 |
| 57 | 565 | 3-(indolizin-2-yl)-7-[(3S)-3-methylpiperazin-1-yl]-2H-chromen-2-one | ND | 360.4 |
| 58 | 566 | 7-[(3S)-3-methylpiperazin-1-yl]-3-(1-methylpyrrolo[1,2-a]pyrazin-7-yl)-2H-chromen-2-one | 184-186 | 375.2 |
| 43 | 567 | 3-(6-methylimidazo[1,2-a]pyrazin-2-yl)-7-(piperazin-1-yl)-2H-chromen-2-one | 288-290 | 362.2 |
| 43 | 568 | 3-(6-methylimidazo[1,2-a]pyrazin-2-yl)-7-(4-methylpiperazin-1-yl)-2H-chromen-2-one | 272-275 | 376.2 |
| 43 | 569 | 3-(6-methylimidazo[1,2-a]pyrazin-2-yl)-7-[(3S)-3-methylpiperazin-1-yl]-2H-chromen-2-one | ND | 376.2 |
| 43 | 570 | 3-(6-methylimidazo[1,2-a]pyrazin-2-yl)-7-[(3R)-3-methylpiperazin-1-yl]-2H-chromen-2-one | ND | 376.2 |
| 43 | 571 | 3-(8-methylimidazo[1,2-a]pyrazin-2-yl)-7-(piperazin-1-yl)-2H-chromen-2-one | 213-215 | 362.1 |
| 43 | 572 | 7-(1,4-diazepan-1-yl)-3-(8-methylimidazo[1,2-a]pyrazin-2-yl)-2H-chromen-2-one | 212-216 | 376.2 |
| 43 | 573 | 3-(8-methylimidazo[1,2-a]pyrazin-2-yl)-7-[(3S)-3-methylpiperazin-1-yl]-2H-chromen-2-one | 211-217 | 376.2 |
| 32 | 574 | 3-(3-methoxy-4-methylphenyl)-7-(piperazin-1-yl)-2H-chromen-2-one | 170-174 | 351.2 |
| 32 | 575 | 3-(3-methoxy-4-methylphenyl)-7-[(3S)-3-methylpiperazin-1-yl]-2H-chromen-2-one | 166-170 | 365.3 |
| 26 | 576 | 3-(4-fluoro-3-methoxyphenyl)-7-(piperazin-1-yl)-2H-chromen-2-one | 153-155 | 355.3 |
| 26 | 577 | 3-(4-fluoro-3-methoxyphenyl)-7-[(3S)-3-methylpiperazin-1-yl]-2H-chromen-2-one | 189-191 | 369.1 |
| 36 | 578 | 3-(8-fluoroimidazo[1,2-a]pyridin-2-yl)-7-(octahydro-2H-pyrido[1,2-a]pyrazin-2-yl)-2H-chromen-2-one | 230-233 | 419.1 |
| 59* | 579 | 7-(piperazin-1-yl)-3-(pyrrolo[1,2-a]pyrimidin-7-yl)-2H-chromen-2-one | 235-238 | 347.2 |
| 59 | 580 | 7-[(3R,5S)-3,5-dimethylpiperazin-1-yl]-3-(pyrrolo[1,2-a]pyrimidin-7-yl)-2H-chromen-2-one | ND | 375.2 |

TABLE 1-continued

| Ex | Cpd | Name | M.P. | MS |
|---|---|---|---|---|
| 48 | 581 | 3-(7-methylimidazo[1,2-a]pyridin-2-yl)-7-[(3S)-pyrrolidin-3-ylamino]-2H-chromen-2-one | 243-253 | 361.2 |
| 48 | 582 | 3-(8-fluoro-6-methylimidazo[1,2-a]pyridin-2-yl)-7-[(3S)-pyrrolidin-3-ylamino]-2H-chromen-2-one | 230-240 | 379.1 |
| 48 | 583 | 3-(8-fluoro-6-methylimidazo[1,2-a]pyridin-2-yl)-7-[(3R)-pyrrolidin-3-ylamino]-2H-chromen-2-one | 231-238 | 379.1 |
| 58 | 584 | 7-[(3R,5S)-3,5-dimethylpiperazin-1-yl]-3-(3-methylpyrrolo[1,2-a]pyrazin-7-yl)-2H-chromen-2-one | 172-174 | 389.3 |
| 67 | 585 | 7-[(3S)-3,4-dimethylpiperazin-1-yl]-3-(8-fluoroimidazo[1,2-a]pyridin-2-yl)-2H-chromen-2-one | 188-192 | 393.2 |
| 58 | 586 | 7-[(3R)-3-methylpiperazin-1-yl]-3-(1-methylpyrrolo[1,2-a]pyrazin-7-yl)-2H-chromen-2-one | 212-215 | 375.2 |
| 58 | 587 | 7-(1,4-diazepan-1-yl)-3-(1-methylpyrrolo[1,2-a]pyrazin-7-yl)-2H-chromen-2-one | 210-213 | 375.2 |
| 58* | 588 | 3-(3-methylpyrrolo[1,2-a]pyrazin-7-yl)-7-(piperazin-1-yl)-2H-chromen-2-one | 220 (D) | 361.4 |
| 58 | 589 | 7-(4-methyl-1,4-diazepan-1-yl)-3-(3-methylpyrrolo[1,2-a]pyrazin-7-yl)-2H-chromen-2-one | 148-150 | 389.3 |
| 58 | 590 | 7-(4-methylpiperazin-1-yl)-3-(3-methylpyrrolo[1,2-a]pyrazin-7-yl)-2H-chromen-2-one | 212-214 | 375.2 |
| 56 | 591 | 5-fluoro-7-(4-methyl-1,4-diazepan-1-yl)-3-(6-methylimidazo[1,2-a]pyrazin-2-yl)-2H-chromen-2-one | 210-212 | 408.2 |
| 56 | 592 | 5-fluoro-3-(6-methylimidazo[1,2-a]pyrazin-2-yl)-7-(4-methylpiperazin-1-yl)-2H-chromen-2-one | 283-284 | 394.2 |
| 56 | 593 | 5-fluoro-3-(6-methylimidazo[1,2-a]pyrazin-2-yl)-7-[(3S)-3-methylpiperazin-1-yl]-2H-chromen-2-one | ND | 394.2 |
| 65 | 594 | 3-(6-methylimidazo[1,2-a]pyrazin-2-yl)-7-[(3R)-pyrrolidin-3-yloxy]-2H-chromen-2-one | 254-258 | 363 |
| 36 | 595 | 7-(5,8-diazaspiro[3.5]non-8-yl)-3-(7-methylimidazo[1,2-a]pyridin-2-yl)-2H-chromen-2-one | 226-233 | 401.2 |
| 36 | 596 | 7-(6,9-diazaspiro[4.5]dec-9-yl)-3-(7-methylimidazo[1,2-a]pyridin-2-yl)-2H-chromen-2-one | 180 (S), 204-209 | 415.2 |
| 36 | 597 | 7-(2,5-diazabicyclo[2.2.2]oct-2-yl)-3-(7-methylimidazo[1,2-a]pyridin-2-yl)-2H-chromen-2-one | 196-215 (DR) | 387.1 |
| 36 | 598 | 7-(5,8-diazaspiro[3.5]non-8-yl)-3-(8-fluoro-6-methylimidazo[1,2-a]pyridin-2-yl)-2H-chromen-2-one | 244-254 | 419.1 |
| 36 | 599 | 7-(6,9-diazaspiro[4.5]dec-9-yl)-3-(8-fluoro-6-methylimidazo[1,2-a]pyridin-2-yl)-2H-chromen-2-one | 236-242 | 433.1 |
| 36 | 600 | 7-(2,5-diazabicyclo[2.2.2]oct-2-yl)-3-(8-fluoro-6-methylimidazo[1,2-a]pyridin-2-yl)-2H-chromen-2-one | 246-256 | 405.2 |
| 65 | 601 | 3-(6,8-dimethylimidazo[1,2-a]pyrazin-2-yl)-7-[(3R)-pyrrolidin-3-yloxy]-2H-chromen-2-one | ND | 377.1 |
| 32 | 602 | 3-(1-benzofuran-2-yl)-7-(piperazin-1-yl)-2H-chromen-2-one | 208-211 | 347.1 |
| 32 | 603 | 3-(1-benzofuran-2-yl)-7-[(3S)-3-methylpiperazin-1-yl]-2H-chromen-2-one | 192-194 | 361.2 |
| 32 | 604 | 3-(1-benzofuran-2-yl)-7-[(3R,5S)-3,5-dimethylpiperazin-1-yl]-2H-chromen-2-one | 191-193 | 375.2 |
| 67 | 605 | 3-(6,8-dimethylimidazo[1,2-a]pyrazin-2-yl)-7-[(3R,5S)-3,4,5-trimethylpiperazin-1-yl]-2H-chromen-2-one | 229-232 | 418.3 |
| 67 | 606 | 3-(6,8-dimethylimidazo[1,2-a]pyrazin-2-yl)-7-[(3R)-3,4-dimethylpiperazin-1-yl]-2H-chromen-2-one | 220-221 | 404.3 |
| 44* | 607 | 7-(1,4-diazepan-1-yl)-3-[6-methyl-8-(trifluoromethyl)imidazo[1,2-a]pyrazin-2-yl]-2H-chromen-2-one | >300 | 444.2 |
| 56 | 608 | 7-(1,4-diazepan-1-yl)-3-(6,8-dimethylimidazo[1,2-a]pyrazin-2-yl)-5-fluoro-2H-chromen-2-one | 248-250 | 408.2 |
| 43 | 609 | 7-[(8aS)-hexahydropyrrolo[1,2-a]pyrazin-2(1H)-yl]-3-(6-methylimidazo[1,2-a]pyrazin-2-yl)-2H-chromen-2-one | ND | 402 |
| 65 | 610 | 3-(8-methylimidazo[1,2-a]pyrazin-2-yl)-7-[(3R)-pyrrolidin-3-yloxy]-2H-chromen-2-one | 220-230 | 363 |
| 36 | 611 | 3-(8-fluoro-6-methylimidazo[1,2-a]pyridin-2-yl)-7-[(8aR)-hexahydropyrrolo[1,2-a]pyrazin-2(1H)-yl]-2H-chromen-2-one | 296-306 | 419.2 |
| 36 | 612 | 3-(8-fluoro-6-methylimidazo[1,2-a]pyridin-2-yl)-7-(octahydro-2H-pyrido[1,2-a]pyrazin-2-yl)-2H-chromen-2-one | 268-275 | 433.2 |
| 36 | 613 | 3-(8-fluoro-6-methylimidazo[1,2-a]pyridin-2-yl)-7-(8-methyl-3,8-diazabicyclo[3.2.1]oct-3-yl)-2H-chromen-2-one | 267-274 | 419.2 |
| 56 | 614 | 3-(6,8-dimethylimidazo[1,2-a]pyrazin-2-yl)-5-fluoro-7-(4-methyl-1,4-diazepan-1-yl)-2H-chromen-2-one | 223-225 | 422.1 |
| 43 | 615 | 3-(6,8-dimethylimidazo[1,2-a]pyrazin-2-yl)-7-[methyl(1-methylpyrrolidin-3-yl)amino]-2H-chromen-2-one | 182-184 | 404.2 |
| 43 | 616 | 7-[(1-benzylpyrrolidin-3-yl)(methyl)amino]-3-(6,8-dimethylimidazo[1,2-a]pyrazin-2-yl)-2H-chromen-2-one | 150-152 | 480.3 |
| 53* | 617 | 7-[(3R,5S)-3,5-dimethylpiperazin-1-yl]-3-(6-methylimidazo[1,2-b]pyridazin-2-yl)-2H-chromen-2-one | 225-227 | 390.1 |

TABLE 1-continued

| Ex | Cpd | Name | M.P. | MS |
|---|---|---|---|---|
| 67 | 618 | 7-(4-ethyl-1,4-diazepan-1-yl)-3-(6-methylimidazo[1,2-a]pyrazin-2-yl)-2H-chromen-2-one | ND | 404.2 |
| 48 | 619 | 7-(azetidin-3-ylamino)-3-(6,8-dimethylimidazo[1,2-a]pyrazin-2-yl)-2H-chromen-2-one | 250-256 | 362.1 |
| 49* | 620 | 3-(6,8-dimethylimidazo[1,2-a]pyrazin-2-yl)-7-{methyl[(3S)-pyrrolidin-3-yl]amino}-2H-chromen-2-one | 192-202 | 390.1 |
| 67 | 621 | 3-(6,8-dimethylimidazo[1,2-a]pyrazin-2-yl)-7-(4-ethylpiperazin-1-yl)-2H-chromen-2-one | 215-217 | 404.2 |
| 67 | 622 | 7-(4-ethylpiperazin-1-yl)-3-(6-methylimidazo[1,2-a]pyrazin-2-yl)-2H-chromen-2-one | 242-255 | 390.1 |
| 43 | 623 | 7-[(1S,4S)-2,5-diazabicyclo[2.2.1]hept-2-yl]-3-(6-methylimidazo[1,2-a]pyrazin-2-yl)-2H-chromen-2-one | 225-227 | 374 |
| 53 | 624 | 3-(6-methylimidazo[1,2-b]pyridazin-2-yl)-7-[(3S)-3-methylpiperazin-1-yl]-2H-chromen-2-one | 208-212 | 376 |
| 43 | 625 | 7-[(8aR)-hexahydropyrrolo[1,2-a]pyrazin-2(1H)-yl]-3-(6-methylimidazo[1,2-a]pyrazin-2-yl)-2H-chromen-2-one | 240-245 | 402 |
| 67* | 626 | 3-(6,8-dimethylimidazo[1,2-a]pyrazin-2-yl)-7-[(3S)-4-ethyl-3-methylpiperazin-1-yl]-2H-chromen-2-one | 208-209 | 418.1 |
| 67 | 627 | 7-[(3S)-4-ethyl-3-methylpiperazin-1-yl]-3-(6-methylimidazo[1,2-a]pyrazin-2-yl)-2H-chromen-2-one | 205-208 | 404.1 |
| 67 | 628 | 7-[(3R)-3,4-dimethylpiperazin-1-yl]-3-(6-methylimidazo[1,2-a]pyrazin-2-yl)-2H-chromen-2-one | 256-258 | 390.1 |
| 61 | 629 | 7-[(3S)-3-methylpiperazin-1-yl]-3-(thieno[3,2-c]pyridin-2-yl)-2H-chromen-2-one | ND | 378.2 |
| 61* | 630 | 7-[(3R,5S)-3,5-dimethylpiperazin-1-yl]-3-(thieno[3,2-c]pyridin-2-yl)-2H-chromen-2-one | 163-165 | 392.3 |
| 53 | 631 | 7-(1,4-diazepan-1-yl)-3-(6-methylimidazo[1,2-b]pyridazin-2-yl)-2H-chromen-2-one | 252-255 | 376 |
| 43 | 632 | 3-(6,8-dimethylimidazo[1,2-a]pyrazin-2-yl)-7-[(8aR)-hexahydropyrrolo[1,2-a]pyrazin-2(1H)-yl]-2H-chromen-2-one | 255-258 | 416.1 |
| 43 | 633 | 3-(6,8-dimethylimidazo[1,2-a]pyrazin-2-yl)-7-(octahydro-2H-pyrido[1,2-a]pyrazin-2-yl)-2H-chromen-2-one | 225-227 | 430.1 |
| 43 | 634 | 3-(6,8-dimethylimidazo[1,2-a]pyrazin-2-yl)-7-[(8aS)-hexahydropyrrolo[1,2-a]pyrazin-2(1H)-yl]-2H-chromen-2-one | 261-263 | 416.1 |
| 43 | 635 | 3-(6-methylimidazo[1,2-a]pyrazin-2-yl)-7-(octahydro-2H-pyrido[1,2-a]pyrazin-2-yl)-2H-chromen-2-one | 275-277 | 416.1 |
| 58 | 636 | 7-[(8aR)-hexahydropyrrolo[1,2-a]pyrazin-2(1H)-yl]-3-(1-methylpyrrolo[1,2-a]pyrazin-7-yl)-2H-chromen-2-one | 170-173 | 401.1 |
| 58 | 637 | 7-[(3R)-3-methylpiperazin-1-yl]-3-(3-methylpyrrolo[1,2-a]pyrazin-7-yl)-2H-chromen-2-one | 220-223 | 375.2 |
| 58 | 638 | 7-(1,4-diazepan-1-yl)-3-(3-methylpyrrolo[1,2-a]pyrazin-7-yl)-2H-chromen-2-one | 178-181 | 375.2 |
| 60 | 639 | 7-[(3R,5S)-3,5-dimethylpiperazin-1-yl]-3-(2-methylpyrrolo[1,2-b]pyridazin-6-yl)-2H-chromen-2-one | 105-108 | 389.1 |
| 67 | 640 | 7-(4-ethylpiperazin-1-yl)-3-(3-methylpyrrolo[1,2-a]pyrazin-7-yl)-2H-chromen-2-one | 208-210 | 389.3 |
| 60* | 641 | 3-(2-methylpyrrolo[1,2-b]pyridazin-6-yl)-7-(piperazin-1-yl)-2H-chromen-2-one | 213-216 | 361.1 |
| 58 | 642 | 7-[(8aS)-hexahydropyrrolo[1,2-a]pyrazin-2(1H)-yl]-3-(1-methylpyrrolo[1,2-a]pyrazin-7-yl)-2H-chromen-2-one | 175-178 | 401.1 |
| 58 | 643 | 7-[(8aS)-hexahydropyrrolo[1,2-a]pyrazin-2(1H)-yl]-3-(3-methylpyrrolo[1,2-a]pyrazin-7-yl)-2H-chromen-2-one | 182-184 | 401.1 |
| 58 | 644 | 3-(1,3-dimethylpyrrolo[1,2-a]pyrazin-7-yl)-7-(4-methylpiperazin-1-yl)-2H-chromen-2-one | 127-131 | 389.5 |
| 58 | 645 | 7-[(3R,5S)-3,5-dimethylpiperazin-1-yl]-3-(1,3-dimethylpyrrolo[1,2-a]pyrazin-7-yl)-2H-chromen-2-one | 170-173 | 403.1 |
| 58 | 646 | 3-(3-methylpyrrolo[1,2-a]pyrazin-7-yl)-7-(octahydro-2H-pyrido[1,2-a]pyrazin-2-yl)-2H-chromen-2-one | 218-221 | 415.1 |
| 58 | 647 | 7-[(3S)-3-methylpiperazin-1-yl]-3-(3-methylpyrrolo[1,2-a]pyrazin-7-yl)-2H-chromen-2-one | 202-204 | 375.3 |
| 43 | 648 | 7-[(1S,4S)-2,5-diazabicyclo[2.2.1]hept-2-yl]-3-(6,8-dimethylimidazo[1,2-a]pyrazin-2-yl)-2H-chromen-2-one | ND | 388.5 |
| 34 | 649 | 7-[(8aS)-hexahydropyrrolo[1,2-a]pyrazin-2(1H)-yl]-3-(2-methylimidazo[1,2-a]pyrimidin-6-yl)-2H-chromen-2-one | 295-297 | 402.5 |
| 34 | 650 | 3-(2-methylimidazo[1,2-a]pyrimidin-6-yl)-7-[(3R)-3-methylpiperazin-1-yl]-2H-chromen-2-one | ND | 376.5 |
| 34* | 651 | 7-[(8aS)-hexahydropyrrolo[1,2-a]pyrazin-2(1H)-yl]-3-(2-methylimidazo[1,2-a]pyridin-6-yl)-2H-chromen-2-one | 231-233 | 401.5 |
| 34 | 652 | 3-(2-methylimidazo[1,2-a]pyridin-6-yl)-7-[(3R)-3-methylpiperazin-1-yl]-2H-chromen-2-one | ND | 375.5 |
| 34 | 653 | 7-(4-methyl-1,4-diazepan-1-yl)-3-(2-methylimidazo[1,2-a]pyridin-6-yl)-2H-chromen-2-one | 175-178 | 389.5 |
| 67 | 654 | 3-(6,8-dimethylimidazo[1,2-a]pyrazin-2-yl)-7-[4-(2-hydroxyethyl)piperazin-1-yl]-2H-chromen-2-one | 231-233 | 420.2 |

TABLE 1-continued

| Ex | Cpd | Name | M.P. | MS |
|---|---|---|---|---|
| 43 | 655 | 3-(6,8-dimethylimidazo[1,2-a]pyrazin-2-yl)-7-[(4aR,7aR)-octahydro-6H-pyrrolo[3,4-b]pyridin-6-yl]-2H-chromen-2-one | 259-269 | 416.1 |
| 67 | 656 | 3-(6,8-dimethylimidazo[1,2-a]pyrazin-2-yl)-7-{methyl[(3S)-1-methylpyrrolidin-3-yl]amino}-2H-chromen-2-one | 178-184 | 404.1 |
| 67 | 657 | 3-(6,8-dimethylimidazo[1,2-a]pyrazin-2-yl)-7-{[(3S)-1-methylpyrrolidin-3-yl]amino}-2H-chromen-2-one | 223-233 | 390.1 |
| 67 | 658 | 3-(6,8-dimethylimidazo[1,2-a]pyrazin-2-yl)-7-[(4aR,7aR)-1-methyloctahydro-6H-pyrrolo[3,4-b]pyridin-6-yl]-2H-chromen-2-one | 232 (S), 248-250 | 430.1 |
| 67 | 659 | 7-[(3S)-3,4-dimethylpiperazin-1-yl]-5-fluoro-3-(6-methylimidazo[1,2-a]pyrazin-2-yl)-2H-chromen-2-one | ND | 408.5 |
| 67 | 660 | 7-[(3R)-3,4-dimethylpiperazin-1-yl]-3-(2-methylimidazo[1,2-a]pyrimidin-6-yl)-2H-chromen-2-one | 280-282 | 390.5 |
| 67 | 661 | 7-[(3R)-3,4-dimethylpiperazin-1-yl]-3-(2-methylimidazo[1,2-a]pyridin-6-yl)-2H-chromen-2-one | 206-209 | 389.5 |
| 34 | 662 | 7-(4-methyl-1,4-diazepan-1-yl)-3-(2-methylimidazo[1,2-a]pyrimidin-6-yl)-2H-chromen-2-one | 286-289 | 390.5 |
| 34 | 663 | 7-(1,4-diazepan-1-yl)-3-(2-methylimidazo[1,2-a]pyridin-6-yl)-2H-chromen-2-one | 222-225 | 375.1 |
| 34 | 664 | 3-(2-methylimidazo[1,2-a]pyridin-6-yl)-7-[(3S)-3-methylpiperazin-1-yl]-2H-chromen-2-one | ND | 375.2 |
| 43 | 665 | 3-(6,8-dimethylimidazo[1,2-a]pyrazin-2-yl)-7-(3-ethylpiperazin-1-yl)-2H-chromen-2-one | 211-215 | 404.2 |
| 58 | 666 | 7-[(3S)-3-(dimethylamino)pyrrolidin-1-yl]-3-(3-methylpyrrolo[1,2-a]pyrazin-7-yl)-2H-chromen-2-one | 200-204 | 389.1 |
| 67 | 667 | 7-(4-ethyl-1,4-diazepan-1-yl)-3-(3-methylpyrrolo[1,2-a]pyrazin-7-yl)-2H-chromen-2-one | 130-133 | 403.1 |
| 58 | 668 | 3-(1,3-dimethylpyrrolo[1,2-a]pyrazin-7-yl)-7-[(3R)-3-methylpiperazin-1-yl]-2H-chromen-2-one | 205-209 | 389.1 |
| 58 | 669 | 3-(1,3-dimethylpyrrolo[1,2-a]pyrazin-7-yl)-7-[(8aR)-hexahydropyrrolo[1,2-a]pyrazin-2(1H)-yl]-2H-chromen-2-one | 170-173 | 415.1 |
| 58 | 670 | 3-(1,3-dimethylpyrrolo[1,2-a]pyrazin-7-yl)-7-(piperazin-1-yl)-2H-chromen-2-one | 186-189 | 375.1 |
| 67 | 671 | 3-(1,3-dimethylpyrrolo[1,2-a]pyrazin-7-yl)-7-(4-ethyl-1,4-diazepan-1-yl)-2H-chromen-2-one | 166-169 | 417.1 |
| 67 | 672 | 3-(6,8-dimethylimidazo[1,2-a]pyrazin-2-yl)-7-[(3S)-3,4-dimethylpiperazin-1-yl]-2H-chromen-2-one | 211-215 | 404.1 |
| 58 | 673 | 3-(1,3-dimethylpyrrolo[1,2-a]pyrazin-7-yl)-7-[(8aS)-hexahydropyrrolo[1,2-a]pyrazin-2(1H)-yl]-2H-chromen-2-one | 169-173 | 415.6 |
| 67 | 674 | 3-(1,3-dimethylpyrrolo[1,2-a]pyrazin-7-yl)-7-(4-ethylpiperazin-1-yl)-2H-chromen-2-one | 182-185 | 403.1 |
| 67 | 675 | 7-[(3S)-3,4-dimethylpiperazin-1-yl]-3-(2-methylimidazo[1,2-a]pyridin-6-yl)-2H-chromen-2-one | 205-207 | 389.1 |
| 67 | 676 | 3-(6,8-dimethylimidazo[1,2-a]pyrazin-2-yl)-7-(3-ethyl-4-methylpiperazin-1-yl)-2H-chromen-2-one | 258-262 | 418.1 |
| 34 | 677 | 3-(2-methylimidazo[1,2-a]pyridin-6-yl)-7-(piperazin-1-yl)-2H-chromen-2-one | ND | 361.1 |
| 34 | 678 | 3-(2-methylimidazo[1,2-a]pyridin-6-yl)-7-(4-methylpiperazin-1-yl)-2H-chromen-2-one | 235-238 | 375.2 |
| 67 | 679 | 3-(6,8-dimethylimidazo[1,2-a]pyrazin-2-yl)-7-[(3R)-4-ethyl-3-methylpiperazin-1-yl]-2H-chromen-2-one | 207-209 | 418.5 |
| 58 | 680 | 3-(1,3-dimethylpyrrolo[1,2-a]pyrazin-7-yl)-7-[(3S)-3-methylpiperazin-1-yl]-2H-chromen-2-one | 162-165 | 389.1 |
| 58 | 681 | 3-(1,3-dimethylpyrrolo[1,2-a]pyrazin-7-yl)-7-(4-methyl-1,4-diazepan-1-yl)-2H-chromen-2-one | ND | 403.1 |
| 58 | 682 | 7-(1,4-diazepan-1-yl)-3-(1,3-dimethylpyrrolo[1,2-a]pyrazin-7-yl)-2H-chromen-2-one | 187-190 | 389.5 |
| 58 | 683 | 3-(1,3-dimethylpyrrolo[1,2-a]pyrazin-7-yl)-7-(octahydro-2H-pyrido[1,2-a]pyrazin-2-yl)-2H-chromen-2-one | 145-148 | 429.1 |
| 67 | 684 | 7-[4-(2-hydroxyethyl)piperazin-1-yl]-3-(3-methylpyrrolo[1,2-a]pyrazin-7-yl)-2H-chromen-2-one | 212-215 | 405.4 |
| 67 | 685 | 3-(1,3-dimethylpyrrolo[1,2-a]pyrazin-7-yl)-7-[4-(2-hydroxyethyl)piperazin-1-yl]-2H-chromen-2-one | 160-164 | 419.1 |
| 43 | 686 | 3-(6,8-dimethylimidazo[1,2-a]pyrazin-2-yl)-7-[(3aR,6aS)-hexahydropyrrolo[3,4-c]pyrrol-2(1H)-yl]-2H-chromen-2-one | 250-260 | 402.1 |
| 43 | 687 | 3-(6,8-dimethylimidazo[1,2-a]pyrazin-2-yl)-7-[(3aS,6aS)-hexahydropyrrolo[3,4-b]pyrrol-1(2H)-yl]-2H-chromen-2-one | 243-253 | 402.1 |
| 67 | 688 | 3-(6,8-dimethylimidazo[1,2-a]pyrazin-2-yl)-7-[(3aR,6aS)-5-methylhexahydropyrrolo[3,4-c]pyrrol-2(1H)-yl]-2H-chromen-2-one | 256-264 | 416.5 |

TABLE 1-continued

| Ex | Cpd | Name | M.P. | MS |
|---|---|---|---|---|
| 67 | 689 | 3-(6,8-dimethylimidazo[1,2-a]pyrazin-2-yl)-7-[(3aS,6aS)-5-methylhexahydropyrrolo[3,4-b]pyrrol-1(2H)-yl]-2H-chromen-2-one | 241-248 | 416.1 |
| 43 | 690 | 7-[(3R)-3-(dimethylamino)pyrrolidin-1-yl]-3-(6,8-dimethylimidazo[1,2-a]pyrazin-2-yl)-2H-chromen-2-one | 239-242 | 404.2 |
| 43 | 691 | 7-[(3S)-3-(dimethylamino)pyrrolidin-1-yl]-3-(6,8-dimethylimidazo[1,2-a]pyrazin-2-yl)-2H-chromen-2-one | 244-246 | 404.2 |
| 68 | 692 | 3-(3-methylpyrrolo[1,2-a]pyrazin-7-yl)-7-[4-(propan-2-yl)piperazin-1-yl]-2H-chromen-2-one | 221-225 | 403.1 |
| 58 | 693 | 7-[(3R)-3-(dimethylamino)pyrrolidin-1-yl]-3-(3-methylpyrrolo[1,2-a]pyrazin-7-yl)-2H-chromen-2-one | 206-208 | 389.5 |
| 67 | 694 | 3-(1,3-dimethylpyrrolo[1,2-a]pyrazin-7-yl)-7-[(3S)-4-ethyl-3-methylpiperazin-1-yl]-2H-chromen-2-one | 173-175 | 417.1 |
| 35 | 695 | 3-(2-methyl-1,3-benzoxazol-6-yl)-7-(piperazin-1-yl)-2H-chromen-2-one | 200-205 | 362.5 |
| 67 | 696 | 3-(6,8-dimethylimidazo[1,2-a]pyrazin-2-yl)-7-[(1S,4S)-5-methyl-2,5-diazabicyclo[2.2.1]hept-2-yl]-2H-chromen-2-one | 219-226 | 402.1 |
| 58 | 697 | 7-[(3S)-3-(dimethylamino)pyrrolidin-1-yl]-3-(1,3-dimethylpyrrolo[1,2-a]pyrazin-7-yl)-2H-chromen-2-one | 195-198 | 403.1 |
| 63* | 698 | 3-(5-methylfuro[3,2-b]pyridin-2-yl)-7-(4-methylpiperazin-1-yl)-2H-chromen-2-one | 178-180 | 376 |
| 45 | 699 | 3-(6-chloro-8-methylimidazo[1,2-a]pyrazin-2-yl)-7-[(3R)-3-methylpiperazin-1-yl]-2H-chromen-2-one | 265-268 | 410.1 |
| 49 | 700 | 3-(6,8-dimethylimidazo[1,2-a]pyrazin-2-yl)-7-{methyl[(3R)-pyrrolidin-3-yl]amino}-2H-chromen-2-one | 192-202 | 390.5 |
| 36 | 701 | 7-[(3R,5S)-3,5-dimethylpiperazin-1-yl]-3-(6-methyl-8-nitroimidazo[1,2-a]pyridin-2-yl)-2H-chromen-2-one | 290-300 | 434.5 |
| 48 | 702 | 3-(6,8-dimethylimidazo[1,2-a]pyrazin-2-yl)-7-{[(3-exo)-9-methyl-9-azabicyclo[3.3.1]non-3-yl]amino}-2H-chromen-2-one | 279-287 | 444.1 |
| 36 | 703 | 3-(6-methyl-8-nitroimidazo[1,2-a]pyridin-2-yl)-7-[(3S)-3-methylpiperazin-1-yl]-2H-chromen-2-one | 251-259 | 420 |
| 67 | 704 | 3-(6,8-dimethylimidazo[1,2-a]pyrazin-2-yl)-7-[(3aR,6aR)-1-methylhexahydropyrrolo[3,4-b]pyrrol-5(1H)-yl]-2H-chromen-2-one | 255-263 | 416.5 |
| 62* | 705 | 3-(2,4-dimethylthieno[2,3-d]pyrimidin-6-yl)-7-(piperazin-1-yl)-2H-chromen-2-one | 275 (D) | 393.1 |
| 67 | 706 | 3-(6,8-dimethylimidazo[1,2-a]pyrazin-2-yl)-7-[(3aS,6aS)-1-methylhexahydropyrrolo[3,4-b]pyrrol-5(1H)-yl]-2H-chromen-2-one | 252-262 | 416.1 |
| 67 | 707 | 3-(6,8-dimethylimidazo[1,2-a]pyrazin-2-yl)-7-{methyl[(3R)-1-methylpyrrolidin-3-yl]amino}-2H-chromen-2-one | 179-186 | 404.5 |
| 58 | 708 | 7-[(3R)-3-(dimethylamino)pyrrolidin-1-yl]-3-(1,3-dimethylpyrrolo[1,2-a]pyrazin-7-yl)-2H-chromen-2-one | 155-158 | 403.1 |
| 68 | 709 | 3-(1,3-dimethylpyrrolo[1,2-a]pyrazin-7-yl)-7-[4-(propan-2-yl)piperazin-1-yl]-2H-chromen-2-one | 173-176 | 417.1 |
| 45 | 710 | 3-(6-chloro-8-methylimidazo[1,2-a]pyrazin-2-yl)-7-[(8aR)-hexahydropyrrolo[1,2-a]pyrazin-2(1H)-yl]-2H-chromen-2-one | 268-272 | 436.1 |
| 45 | 711 | 3-(6-chloro-8-methylimidazo[1,2-a]pyrazin-2-yl)-7-[(8aS)-hexahydropyrrolo[1,2-a]pyrazin-2(1H)-yl]-2H-chromen-2-one | 260-262 | 436.1 |
| 45* | 712 | 3-(6-chloro-8-methylimidazo[1,2-a]pyrazin-2-yl)-7-(4-methyl-1,4-diazepan-1-yl)-2H-chromen-2-one | 212-218 | 424 |
| 45 | 713 | 3-(6-chloro-8-methylimidazo[1,2-a]pyrazin-2-yl)-7-[(3S)-3-methylpiperazin-1-yl]-2H-chromen-2-one | 235-238 | 410.1 |
| 58 | 714 | 7-(4-aminopiperidin-1-yl)-3-(1,3-dimethylpyrrolo[1,2-a]pyrazin-7-yl)-2H-chromen-2-one | ND | 389.1 |
| 67 | 715 | 7-[4-(dimethylamino)piperidin-1-yl]-3-(1,3-dimethylpyrrolo[1,2-a]pyrazin-7-yl)-2H-chromen-2-one | 192-195 | 417.1 |
| 67 | 716 | 7-[4-(dimethylamino)piperidin-1-yl]-3-(3-methylpyrrolo[1,2-a]pyrazin-7-yl)-2H-chromen-2-one | 224-227 | 403.1 |
| 34 | 717 | 7-[(3S)-3-(dimethylamino)pyrrolidin-1-yl]-3-(2-methylimidazo[1,2-a]pyridin-6-yl)-2H-chromen-2-one | 230-234 | 389.1 |
| 43 | 718 | 7-[(3aR,6aS)-hexahydropyrrolo[3,4-c]pyrrol-2(1H)-yl]-3-(6-methylimidazo[1,2-a]pyrazin-2-yl)-2H-chromen-2-one | 282-292 | 388.5 |
| 43 | 719 | 3-(6-methylimidazo[1,2-a]pyrazin-2-yl)-7-[(4aR,7aR)-octahydro-6H-pyrrolo[3,4-b]pyridin-6-yl]-2H-chromen-2-one | 282-291 | 402.1 |
| 63 | 720 | 7-[(3R,5S)-3,5-dimethylpiperazin-1-yl]-3-(5-methylfuro[3,2-b]pyridin-2-yl)-2H-chromen-2-one | 179-183 | 390.3 |
| 63 | 721 | 7-[(8aR)-hexahydropyrrolo[1,2-a]pyrazin-2(1H)-yl]-3-(5-methylfuro[3,2-b]pyridin-2-yl)-2H-chromen-2-one | 195-198 | 402.3 |
| 63 | 722 | 7-[(8aS)-hexahydropyrrolo[1,2-a]pyrazin-2(1H)-yl]-3-(5-methylfuro[3,2-b]pyridin-2-yl)-2H-chromen-2-one | 228-230 | 402.3 |

TABLE 1-continued

| Ex | Cpd | Name | M.P. | MS |
|---|---|---|---|---|
| 64* | 723 | 3-(5,7-dimethylfuro[2,3-c]pyridin-2-yl)-7-(piperazin-1-yl)-2H-chromen-2-one | 218-220 | 376 |
| 58 | 724 | tert-butyl {(3S)-1-[3-(1,3-dimethylpyrrolo[1,2-a]pyrazin-7-yl)-2-oxo-2H-chromen-7-yl]pyrrolidin-3-yl}carbamate | 193-196 | 475.1 |
| 67 | 725 | 3-(1,3-dimethylpyrrolo[1,2-a]pyrazin-7-yl)-7-[(3S)-3-(propan-2-ylamino)pyrrolidin-1-yl]-2H-chromen-2-one | 217-220 | 417.1 |
| 67 | 726 | 3-(6-chloro-8-methylimidazo[1,2-a]pyrazin-2-yl)-7-[(3R)-3,4-dimethylpiperazin-1-yl]-2H-chromen-2-one | 250-252 | 424 |
| 67 | 727 | 3-(6-chloro-8-methylimidazo[1,2-a]pyrazin-2-yl)-7-[(3S)-3,4-dimethylpiperazin-1-yl]-2H-chromen-2-one | 251-253 | 424 |
| 58 | 728 | 3-(1,3-dimethylpyrrolo[1,2-a]pyrazin-7-yl)-7-{[(1R,5S)-9-methyl-9-azabicyclo[3.3.1]non-3-yl]amino}-2H-chromen-2-one | 235-238 | 443.1 |
| 67 | 729 | 3-(1,3-dimethylpyrrolo[1,2-a]pyrazin-7-yl)-7-[(3aS,6aS)-1-methylhexahydropyrrolo[3,4-b]pyrrol-5(1H)-yl]-2H-chromen-2-one | 173-175 | 415.1 |
| 67 | 730 | 3-(6,8-dimethylimidazo[1,2-a]pyrazin-2-yl)-7-{[(3R)-1-methylpyrrolidin-3-yl]amino}-2H-chromen-2-one | 226-233 | 390.5 |
| 67 | 731 | 3-(6,8-dimethylimidazo[1,2-a]pyrazin-2-yl)-7-{[(3R)-1-ethylpyrrolidin-3-yl]amino}-2H-chromen-2-one | 209-215 | 404.1 |
| 67 | 732 | 3-(6,8-dimethylimidazo[1,2-a]pyrazin-2-yl)-7-{[(3R)-1-(2-hydroxyethyl)pyrrolidin-3-yl]amino}-2H-chromen-2-one | 211-219 | 420.1 |
| 68 | 733 | 3-(6,8-dimethylimidazo[1,2-a]pyrazin-2-yl)-7-{[(3R)-1-(propan-2-yl)pyrrolidin-3-yl]amino}-2H-chromen-2-one | 200-207 | 418.1 |
| 58 | 734 | 7-[(3R,4R)-3-(dimethylamino)-4-hydroxypyrrolidin-1-yl]-3-(1,3-dimethylpyrrolo[1,2-a]pyrazin-7-yl)-2H-chromen-2-one | 173-176 | 419.1 |
| 67 | 735 | 7-[3-(diethylamino)pyrrolidin-1-yl]-3-(1,3-dimethylpyrrolo[1,2-a]pyrazin-7-yl)-2H-chromen-2-one | 165-168 | 431.1 |
| 43 | 736 | 3-(6,8-dimethylimidazo[1,2-a]pyrazin-2-yl)-7-(3,3-dimethylpiperazin-1-yl)-2H-chromen-2-one | ND | 404.2 |
| 67 | 737 | 3-(6,8-dimethylimidazo[1,2-a]pyrazin-2-yl)-7-(3,3,4-trimethylpiperazin-1-yl)-2H-chromen-2-one | 185-187 | 418.2 |
| 43 | 738 | 7-[(3S,4S)-3-(dimethylamino)-4-hydroxypyrrolidin-1-yl]-3-(6,8-dimethylimidazo[1,2-a]pyrazin-2-yl)-2H-chromen-2-one | 270-272 | 420.2 |
| 43 | 739 | 3-(6,8-dimethylimidazo[1,2-a]pyrazin-2-yl)-7-[(3'S,4'S)-4'-hydroxy-1,3'-bipyrrolidin-1'-yl]-2H-chromen-2-one | 273-275 | 446.1 |
| 50* | 740 | 3-(6,8-dimethylimidazo[1,2-a]pyrazin-2-yl)-7-(1,2,3,6-tetrahydropyridin-4-yl)-2H-chromen-2-one | 205-211 | 373.1 |
| 67 | 741 | 3-(6,8-dimethylimidazo[1,2-a]pyrazin-2-yl)-7-[(3aR,6aS)-5-(2-hydroxyethyl)hexahydropyrrolo[3,4-c]pyrrol-2(1H)-yl]-2H-chromen-2-one | 258-268 | 446.1 |
| 51* | 742 | 3-(6,8-dimethylimidazo[1,2-a]pyrazin-2-yl)-7-(piperidin-4-yl)-2H-chromen-2-one | 224-229 | 375.1 |
| 67 | 743 | 3-(6,8-dimethylimidazo[1,2-a]pyrazin-2-yl)-7-[(3aR,6aS)-5-(propan-2-yl)hexahydropyrrolo[3,4-c]pyrrol-2(1H)-yl]-2H-chromen-2-one | 249-258 | 444.1 |
| 58 | 744 | 7-(2,5-diazabicyclo[2.2.1]hept-2-yl)-3-(3-methylpyrrolo[1,2-a]pyrazin-7-yl)-2H-chromen-2-one | ND | 373.4 |
| 64 | 745 | 3-(5,7-dimethylfuro[2,3-c]pyridin-2-yl)-7-[(8aS)-hexahydropyrrolo[1,2-a]pyrazin-2(1H)-yl]-2H-chromen-2-one | 203-205 | 416.2 |
| 67 | 746 | 3-(6,8-dimethylimidazo[1,2-a]pyrazin-2-yl)-7-(4-ethylpiperazin-1-yl)-5-fluoro-2H-chromen-2-one | 232-234 | 422.1 |
| 67 | 747 | 3-(6,8-dimethylimidazo[1,2-a]pyrazin-2-yl)-7-[(3aR,6aS)-5-ethylhexahydropyrrolo[3,4-c]pyrrol-2(1H)-yl]-2H-chromen-2-one | 231-237 | 430.5 |
| 67 | 748 | 3-(6,8-dimethylimidazo[1,2-a]pyrazin-2-yl)-7-(1-methylpiperidin-4-yl)-2H-chromen-2-one | ND | 389.1 |
| 67 | 749 | 3-(6,8-dimethylimidazo[1,2-a]pyrazin-2-yl)-7-(1-ethylpiperidin-4-yl)-2H-chromen-2-one | 218-223 | 403.5 |
| 67 | 750 | 3-(6,8-dimethylimidazo[1,2-a]pyrazin-2-yl)-7-[1-(2-hydroxyethyl)piperidin-4-yl]-2H-chromen-2-one | 207-212 | 419.1 |
| 58 | 751 | 3-(1,3-dimethylpyrrolo[1,2-a]pyrazin-7-yl)-7-[(3'R,4'R)-4'-hydroxy-1,3'-bipyrrolidin-1'-yl]-2H-chromen-2-one | 264-268 | 445.1 |
| 58 | 752 | 7-(4-cyclopropylpiperazin-1-yl)-3-(1,3-dimethylpyrrolo[1,2-a]pyrazin-7-yl)-2H-chromen-2-one | ND | 415.1 |
| 68 | 753 | 3-(3-methylpyrrolo[1,2-a]pyrazin-7-yl)-7-[4-(propan-2-yl)-1,4-diazepan-1-yl]-2H-chromen-2-one | ND | 417.1 |
| 68 | 754 | 3-(1,3-dimethylpyrrolo[1,2-a]pyrazin-7-yl)-7-[4-(propan-2-yl)-1,4-diazepan-1-yl]-2H-chromen-2-one | 115-118 | 431.1 |
| 67 | 755 | 3-(1,3-dimethylpyrrolo[1,2-a]pyrazin-7-yl)-7-[(3aR,6aR)-1-methylhexahydropyrrolo[3,4-b]pyrrol-5(1H)-yl]-2H-chromen-2-one | 196-198 | 415.1 |
| 67 | 756 | 3-(1,3-dimethylpyrrolo[1,2-a]pyrazin-7-yl)-7-[(3aR,6aS)-5-methylhexahydropyrrolo[3,4-c]pyrrol-2(1H)-yl]-2H-chromen-2-one | 146-150 | 415.1 |

TABLE 1-continued

| Ex | Cpd | Name | M.P. | MS |
|---|---|---|---|---|
| 58 | 757 | 3-(1,3-dimethylpyrrolo[1,2-a]pyrazin-7-yl)-7-[3-(morpholin-4-yl)pyrrolidin-1-yl]-2H-chromen-2-one | 118-122 | 445.1 |
| 43 | 758 | 3-(6,8-dimethylimidazo[1,2-a]pyrazin-2-yl)-7-[(7R,8aS)-7-hydroxyhexahydropyrrolo[1,2-a]pyrazin-2(1H)-yl]-2H-chromen-2-one | 285-287 | 432.4 |
| 67 | 759a | 7-[(3R)-3,4-dimethylpiperazin-1-yl]-3-(8-methoxy-6-methylimidazo[1,2-a]pyrazin-2-yl)-2H-chromen-2-one | NI | NI |
| 67 | 760a | 7-[(3R)-3,4-dimethylpiperazin-1-yl]-3-(8-hydroxy-6-methylimidazo[1,2-a]pyrazin-2-yl)-2H-chromen-2-one | NI | NI |
| 43 | 761 | 7-[(1R,5S,6s)-6-(dimethylamino)-3-azabicyclo[3.1.0]hex-3-yl]-3-(6,8-dimethylimidazo[1,2-a]pyrazin-2-yl)-2H-chromen-2-one | 271-274 | 416.1 |
| 43 | 762 | 7-(4-cyclopropylpiperazin-1-yl)-3-(6,8-dimethylimidazo[1,2-a]pyrazin-2-yl)-2H-chromen-2-one | 263-266 | 416.1 |
| 64 | 763 | 3-(5,7-dimethylfuro[2,3-c]pyridin-2-yl)-7-(4-methylpiperazin-1-yl)-2H-chromen-2-one | 229-232 | 390.3 |
| 45 | 764 | 3-(6-chloro-8-methylimidazo[1,2-a]pyrazin-2-yl)-7-(4-methylpiperazin-1-yl)-2H-chromen-2-one | 217-220 | 410 |
| 45 | 765 | 3-(6-chloro-8-methylimidazo[1,2-a]pyrazin-2-yl)-7-[(3S)-3-(dimethylamino)pyrrolidin-1-yl]-2H-chromen-2-one | 210-215 | 424.1 |
| 67 | 766 | 3-(6-chloro-8-methylimidazo[1,2-a]pyrazin-2-yl)-7-(4-ethylpiperazin-1-yl)-2H-chromen-2-one | 228-230 | 424.1 |
| 58 | 767 | 3-(1,3-dimethylpyrrolo[1,2-a]pyrazin-7-yl)-7-[(7R,8aS)-7-hydroxyhexahydropyrrolo[1,2-a]pyrazin-2(1H)-yl]-2H-chromen-2-one | 185-188 | 431.1 |
| 68 | 768 | 3-(1,3-dimethylpyrrolo[1,2-a]pyrazin-7-yl)-7-[(3S)-3-methyl-4-(propan-2-yl)piperazin-1-yl]-2H-chromen-2-one | 153-156 | 431.1 |
| 35* | 769 | 3-(2-methyl-1,3-benzothiazol-6-yl)-7-(4-methylpiperazin-1-yl)-2H-chromen-2-one | 215-217 | 392.4 |
| 35 | 770 | 3-(2-methyl-1,3-benzothiazol-6-yl)-7-[(3S)-3-methylpiperazin-1-yl]-2H-chromen-2-one | ND | 392.4 |
| 35 | 771 | 7-(1,4-diazepan-1-yl)-3-(2-methyl-1,3-benzothiazol-6-yl)-2H-chromen-2-one | 228-230 | 392.4 |
| 43 | 772 | 3-(6,8-dimethylimidazo[1,2-a]pyrazin-2-yl)-7-[(3S)-3-ethylpiperazin-1-yl]-2H-chromen-2-one | ND | 404.4 |
| 68* | 773 | 3-(6,8-dimethylimidazo[1,2-a]pyrazin-2-yl)-7-[1-(propan-2-yl)piperidin-4-yl]-2H-chromen-2-one | 206-211 | 417.5 |
| 67 | 774 | 3-(5,7-dimethylfuro[2,3-c]pyridin-2-yl)-7-[4-(2-hydroxyethyl)piperazin-1-yl]-2H-chromen-2-one | 203-205 | 420.3 |
| 64 | 775 | 3-(5,7-dimethylfuro[2,3-c]pyridin-2-yl)-7-(4-methyl-1,4-diazepan-1-yl)-2H-chromen-2-one | 243-245 | 404.3 |
| 67 | 776a | 7-[(3S)-3,4-dimethylpiperazin-1-yl]-3-(2-methyl-1,3-benzothiazol-6-yl)-2H-chromen-2-one | NI | NI |
| 67 | 777a | 7-[(3S)-4-ethyl-3-methylpiperazin-1-yl]-3-(2-methyl-1,3-benzothiazol-6-yl)-2H-chromen-2-one | NI | NI |
| 67 | 778a | 3-(6,8-dimethylimidazo[1,2-a]pyrazin-2-yl)-7-[(3S)-3-ethyl-4-methylpiperazin-1-yl]-2H-chromen-2-one | NI | NI |
| 67 | 779a | 7-[(3S)-3,4-diethylpiperazin-1-yl]-3-(6,8-dimethylimidazo[1,2-a]pyrazin-2-yl)-2H-chromen-2-one | NI | NI |
| 45 | 780 | 3-(6-chloro-8-methylimidazo[1,2-a]pyrazin-2-yl)-7-[(1S,4S)-2,5-diazabicyclo[2.2.1]hept-2-yl]-2H-chromen-2-one | ND | 408 |
| 43 | 781 | 3-(6,8-dimethylimidazo[1,2-a]pyrazin-2-yl)-7-[(4aR,7aR)-octahydro-6H-pyrrolo[3,4-b]pyridin-6-yl]-2H-chromen-2-one | 246-252 | 416.1 |
| 67 | 782 | 3-(6,8-dimethylimidazo[1,2-a]pyrazin-2-yl)-7-[(4aR,7aR)-1-methyloctahydro-6H-pyrrolo[3,4-b]pyridin-6-yl]-2H-chromen-2-one | ND | 430.1 |
| 58 | 783 | 7-(2,5-diazabicyclo[2.2.1]hept-2-yl)-3-(1,3-dimethylpyrrolo[1,2-a]pyrazin-7-yl)-2H-chromen-2-one | 236-239 | 387.1 |
| 58 | 784 | 7-[4-(aminomethyl)piperidin-1-yl]-3-(1,3-dimethylpyrrolo[1,2-a]pyrazin-7-yl)-2H-chromen-2-one | 256-259 | 403.1 |
| 67 | 785 | 3-(6,8-dimethylimidazo[1,2-a]pyrazin-2-yl)-7-[(4aR,7aR)-1-(2-hydroxyethyl)octahydro-6H-pyrrolo[3,4-b]pyridin-6-yl]-2H-chromen-2-one | 207-217 | 460.6 |
| 67 | 786 | 3-(6,8-dimethylimidazo[1,2-a]pyrazin-2-yl)-7-[(4aR,7aR)-1-ethyloctahydro-6H-pyrrolo[3,4-b]pyridin-6-yl]-2H-chromen-2-one | 215-221 | 444.5 |
| 67 | 787 | 3-(6-chloro-8-methylimidazo[1,2-a]pyrazin-2-yl)-7-[(1S,4S)-5-methyl-2,5-diazabicyclo[2.2.1]hept-2-yl]-2H-chromen-2-one | ND | 422 |
| 67 | 788 | 3-(5,7-dimethylfuro[2,3-c]pyridin-2-yl)-7-(4-ethylpiperazin-1-yl)-2H-chromen-2-one | 196-198 | 404.3 |
| 68 | 789 | 3-(5,7-dimethylfuro[2,3-c]pyridin-2-yl)-7-[4-(propan-2-yl)piperazin-1-yl]-2H-chromen-2-one | 186-189 | 418.2 |
| 67 | 790 | 3-(1,3-dimethylpyrrolo[1,2-a]pyrazin-7-yl)-7-{4-[(propan-2-ylamino)methyl]piperidin-1-yl}-2H-chromen-2-one | ND | 445.3 |

TABLE 1-continued

| Ex | Cpd | Name | M.P. | MS |
|---|---|---|---|---|
| 67 | 791 | 3-(6-chloro-8-methylimidazo[1,2-a]pyrazin-2-yl)-7-[(1S,4S)-5-ethyl-2,5-diazabicyclo[2.2.1]hept-2-yl]-2H-chromen-2-one | 135-138 | 436.3 |
| 68 | 792 | 3-(6,8-dimethylimidazo[1,2-a]pyrazin-2-yl)-7-[4-(propan-2-yl)piperazin-1-yl]-2H-chromen-2-one | 240-242 | 418.2 |
| 67 | 793 | 3-(6,8-dimethylimidazo[1,2-a]pyrazin-2-yl)-7-[(1S,4S)-5-ethyl-2,5-diazabicyclo[2.2.1]hept-2-yl]-2H-chromen-2-one | 133-135 | 416.3 |
| 43 | 794 | 3-(6,8-dimethylimidazo[1,2-a]pyrazin-2-yl)-7-[(4aS,7aS)-octahydro-6H-pyrrolo[3,4-b]pyridin-6-yl]-2H-chromen-2-one | 246-253 | 416.3 |
| 67 | 795 | 3-(6,8-dimethylimidazo[1,2-a]pyrazin-2-yl)-7-[(4aS,7aS)-1-methyloctahydro-6H-pyrrolo[3,4-b]pyridin-6-yl]-2H-chromen-2-one | ND | 430.3 |
| 67 | 796 | 3-(6,8-dimethylimidazo[1,2-a]pyrazin-2-yl)-7-[(4aS,7aS)-1-(2-hydroxyethyl)octahydro-6H-pyrrolo[3,4-b]pyridin-6-yl]-2H-chromen-2-one | 200-210 | 460.3 |
| 67 | 797 | 7-[(3R,5S)-4-ethyl-3,5-dimethylpiperazin-1-yl]-3-(6-methylimidazo[1,2-a]pyrazin-2-yl)-2H-chromen-2-one | ND | 418.2 |
| 64 | 798 | 7-(4-cyclopropylpiperazin-1-yl)-3-(5,7-dimethylfuro[2,3-c]pyridin-2-yl)-2H-chromen-2-one | ND | 416.2 |
| 68 | 799 | 3-(5,7-dimethylfuro[2,3-c]pyridin-2-yl)-7-[4-(2-methoxyethyl)piperazin-1-yl]-2H-chromen-2-one | 235-237 | 434.2 |
| 67 | 800 | 3-(6,8-dimethylimidazo[1,2-a]pyrazin-2-yl)-7-(1-methyl-1,2,3,6-tetrahydropyridin-4-yl)-2H-chromen-2-one | ND | 387.2 |
| 67 | 801 | 3-(6,8-dimethylimidazo[1,2-a]pyrazin-2-yl)-7-[1-(2-hydroxyethyl)-1,2,3,6-tetrahydropyridin-4-yl]-2H-chromen-2-one | 172-214 (DR) | 417.3 |
| 68 | 802 | 3-(6,8-dimethylimidazo[1,2-a]pyrazin-2-yl)-7-[1-(propan-2-yl)-1,2,3,6-tetrahydropyridin-4-yl]-2H-chromen-2-one | 207-217 | 415.2 |
| 67 | 803 | 3-(6,8-dimethylimidazo[1,2-a]pyrazin-2-yl)-7-[(4aS,7aS)-1-ethyloctahydro-6H-pyrrolo[3,4-b]pyridin-6-yl]-2H-chromen-2-one | 217-221 | 444.3 |
| 64 | 804 | 3-(5,7-dimethylfuro[2,3-c]pyridin-2-yl)-7-[(3S)-3-methylpiperazin-1-yl]-2H-chromen-2-one | 253-257 | 390.2 |
| 67 | 805 | 3-(5,7-dimethylfuro[2,3-c]pyridin-2-yl)-7-[(3S)-3,4-dimethylpiperazin-1-yl]-2H-chromen-2-one | 200-205 | 404.3 |
| 64 | 806 | 3-(5,7-dimethylfuro[2,3-c]pyridin-2-yl)-7-[(3R)-3-methylpiperazin-1-yl]-2H-chromen-2-one | 251-256 | 390.2 |
| 67 | 807 | 3-(5,7-dimethylfuro[2,3-c]pyridin-2-yl)-7-[(3R)-3,4-dimethylpiperazin-1-yl]-2H-chromen-2-one | 199-204 | 404.3 |
| 43 | 808 | 3-(6,8-dimethylimidazo[1,2-a]pyrazin-2-yl)-7-[(3S)-3-(propan-2-yl)piperazin-1-yl]-2H-chromen-2-one | ND | 418.2 |
| 67 | 809 | 3-(6,8-dimethylimidazo[1,2-a]pyrazin-2-yl)-7-[(3S)-4-methyl-3-(propan-2-yl)piperazin-1-yl]-2H-chromen-2-one | ND | 432.3 |
| 67 | 810 | 3-(6,8-dimethylimidazo[1,2-a]pyrazin-2-yl)-7-[(3S)-4-ethyl-3-(propan-2-yl)piperazin-1-yl]-2H-chromen-2-one | ND | 446.3 |
| 43 | 811 | 7-(4-cyclopropylpiperazin-1-yl)-3-(6-methylimidazo[1,2-a]pyrazin-2-yl)-2H-chromen-2-one | 287-289 | 402.5 |
| 43 | 812 | 7-(4-tert-butylpiperazin-1-yl)-3-(6,8-dimethylimidazo[1,2-a]pyrazin-2-yl)-2H-chromen-2-one | 270-272 | 432.3 |
| 67 | 813 | 3-(1,3-dimethylpyrrolo[1,2-a]pyrazin-7-yl)-7-[(3R)-3-methyl-4-(propan-2-yl)piperazin-1-yl]-2H-chromen-2-one | ND | 431.2 |
| 67 | 814 | 7-(4-cyclobutylpiperazin-1-yl)-3-(1,3-dimethylpyrrolo[1,2-a]pyrazin-7-yl)-2H-chromen-2-one | 217-220 | 429.2 |
| 67 | 815 | 3-(5,7-dimethylfuro[2,3-c]pyridin-2-yl)-7-(4-propylpiperazin-1-yl)-2H-chromen-2-one | 259-262 | 418.1 |
| 67 | 816 | 7-[4-(cyclopropylmethyl)piperazin-1-yl]-3-(5,7-dimethylfuro[2,3-c]pyridin-2-yl)-2H-chromen-2-one | ND | 430.3 |
| 62 | 817 | 3-(4,6-dimethylthieno[3,2-c]pyridin-2-yl)-7-(piperazin-1-yl)-2H-chromen-2-one | ND | 392.1 |
| 76* | 818 | 7-(2-methylimidazo[1,2-a]pyridin-6-yl)-3-(piperazin-1-yl)-2H-chromen-2-one | 174-178 | 361.3 |
| 67 | 819 | 3-(4,6-dimethylthieno[3,2-c]pyridin-2-yl)-7-(4-methylpiperazin-1-yl)-2H-chromen-2-one | ND | 406.2 |
| 67 | 820 | 3-(4,6-dimethylthieno[3,2-c]pyridin-2-yl)-7-[4-(2-methoxyethyl)piperazin-1-yl]-2H-chromen-2-one | ND | 450.3 |
| 67 | 821 | 7-(1-cyclobutylpiperidin-4-yl)-3-(6,8-dimethylimidazo[1,2-a]pyrazin-2-yl)-2H-chromen-2-one | 200-205 | 429.4 |
| 67 | 822 | 7-(4-cyclobutylpiperazin-1-yl)-3-(6,8-dimethylimidazo[1,2-a]pyrazin-2-yl)-2H-chromen-2-one | 260-262 | 430.2 |
| 67 | 823 | 3-(6,8-dimethylimidazo[1,2-a]pyrazin-2-yl)-7-[4-(oxetan-3-yl)piperazin-1-yl]-2H-chromen-2-one | 230-235 | 432.3 |
| 43 | 824 | 3-(8-ethyl-6-methylimidazo[1,2-a]pyrazin-2-yl)-7-(piperazin-1-yl)-2H-chromen-2-one | ND | 390.3 |
| 69* | 825 | 3-(2-methylimidazo[1,2-a]pyridin-6-yl)-7-(piperidin-4-yl)-2H-chromen-2-one | ND | 360.3 |
| 67 | 826 | 3-(2-methylimidazo[1,2-a]pyridin-6-yl)-7-(1-methylpiperidin-4-yl)-2H-chromen-2-one | 204-206 | 374.2 |

TABLE 1-continued

| Ex | Cpd | Name | M.P. | MS |
|---|---|---|---|---|
| 67 | 827 | 7-(1-ethylpiperidin-4-yl)-3-(2-methylimidazo[1,2-a]pyridin-6-yl)-2H-chromen-2-one | 268-270 | 388.3 |
| 67 | 828 | 3-(2-methylimidazo[1,2-a]pyridin-6-yl)-7-[1-(oxetan-3-yl)piperidin-4-yl]-2H-chromen-2-one | 198-200 | 416.3 |
| 67 | 829 | 7-[1-(2-hydroxyethyl)piperidin-4-yl]-3-(2-methylimidazo[1,2-a]pyridin-6-yl)-2H-chromen-2-one | 222-226 | 404.3 |
| 67 | 830 | 3-(8-ethyl-6-methylimidazo[1,2-a]pyrazin-2-yl)-7-(4-methylpiperazin-1-yl)-2H-chromen-2-one | 210-215 | 404.2 |
| 64 | 831 | 3-(4,6-dimethylfuro[3,2-c]pyridin-2-yl)-7-(piperazin-1-yl)-2H-chromen-2-one | ND | 376.3 |
| 67 | 832 | 3-(4,6-dimethylfuro[3,2-c]pyridin-2-yl)-7-(4-methylpiperazin-1-yl)-2H-chromen-2-one | ND | 390.2 |
| 67 | 833 | 3-(6-methylimidazo[1,2-a]pyrazin-2-yl)-7-[4-(propan-2-yl)piperazin-1-yl]-2H-chromen-2-one | 275-280 | 404.3 |
| 69 | 834 | 3-(2-methylimidazo[1,2-a]pyrimidin-6-yl)-7-(piperidin-4-yl)-2H-chromen-2-one | 280-281 | 361.3 |
| 67 | 835 | 3-(2-methylimidazo[1,2-a]pyrimidin-6-yl)-7-(1-methylpiperidin-4-yl)-2H-chromen-2-one | 300-302 | 375.3 |
| 67 | 836 | 7-(1-ethylpiperidin-4-yl)-3-(2-methylimidazo[1,2-a]pyrimidin-6-yl)-2H-chromen-2-one | 288-290 | 389.3 |
| 67 | 837 | 7-[4-(2-hydroxyethyl)piperazin-1-yl]-3-(6-methylimidazo[1,2-a]pyrazin-2-yl)-2H-chromen-2-one | 246-252 | 406.3 |
| 67 | 838 | 7-(4-cyclobutylpiperazin-1-yl)-3-(6-methylimidazo[1,2-a]pyrazin-2-yl)-2H-chromen-2-one | 268-274 | 416.2 |
| 67 | 839 | 3-(6-methylimidazo[1,2-a]pyrazin-2-yl)-7-[4-(oxetan-3-yl)piperazin-1-yl]-2H-chromen-2-one | 273-276 | 418.2 |
| 67 | 840 | 3-(4,6-dimethylfuro[3,2-c]pyridin-2-yl)-7-[4-(propan-2-yl)piperazin-1-yl]-2H-chromen-2-one | 186-191 | 418.2 |
| 67 | 841 | 3-(6-methylimidazo[1,2-a]pyrazin-2-yl)-7-(1-methylpiperidin-4-yl)-2H-chromen-2-one | 266-272 | 375.3 |
| 67 | 842 | 3-(6,8-dimethylimidazo[1,2-a]pyrazin-2-yl)-7-(1-propylpiperidin-4-yl)-2H-chromen-2-one | 208-212 | 417.3 |
| 67 | 843 | 7-[1-(2-hydroxyethyl)piperidin-4-yl]-3-(6-methylimidazo[1,2-a]pyrazin-2-yl)-2H-chromen-2-one | 230-236 | 405.4 |
| 67 | 844 | 7-(1-ethylpiperidin-4-yl)-3-(6-methylimidazo[1,2-a]pyrazin-2-yl)-2H-chromen-2-one | 249-259 | 389.4 |
| 70* | 845 | 3-[2-methyl-3-(1,2,3,6-tetrahydropyridin-4-yl)imidazo[1,2-b]pyridazin-6-yl]-7-(1,2,3,6-tetrahydropyridin-4-yl)-2H-chromen-2-one | ND | 440.5 |
| 77* | 846 | 7-[(dimethylamino)methyl]-3-(6,8-dimethylimidazo[1,2-a]pyrazin-2-yl)-2H-chromen-2-one | 192-196 | 349.3 |
| 77 | 847 | 3-(6,8-dimethylimidazo[1,2-a]pyrazin-2-yl)-7-(piperidin-1-ylmethyl)-2H-chromen-2-one | 191-193 | 389.4 |
| 77 | 848 | 3-(6,8-dimethylimidazo[1,2-a]pyrazin-2-yl)-7-(piperazin-1-ylmethyl)-2H-chromen-2-one | 189-195 | 390.4 |
| 77 | 849 | 3-(6,8-dimethylimidazo[1,2-a]pyrazin-2-yl)-7-[(4-methylpiperazin-1-yl)methyl]-2H-chromen-2-one | 220-223 | 404.4 |
| 77 | 850 | 3-(6,8-dimethylimidazo[1,2-a]pyrazin-2-yl)-7-[(propan-2-ylamino)methyl]-2H-chromen-2-one | 285-291 | 363.4 |
| 77 | 851 | 3-(6,8-dimethylimidazo[1,2-a]pyrazin-2-yl)-7-(1H-imidazol-1-ylmethyl)-2H-chromen-2-one | 286-292 | 372.3 |
| 67 | 852 | 3-(6,8-dimethylimidazo[1,2-a]pyrazin-2-yl)-7-(4-ethyl-3-methylpiperazin-1-yl)-2H-chromen-2-one | 203-205 | 418.4 |
| 73* | 853 | 3-(4,6-dimethylpyrazolo[1,5-a]pyrazin-2-yl)-7-(1-ethylpiperidin-4-yl)-2H-chromen-2-one | ND | 403.3 |
| 67 | 854 | 7-(1-cyclopropylpiperidin-4-yl)-3-(6,8-dimethylimidazo[1,2-a]pyrazin-2-yl)-2H-chromen-2-one | 236-243 | 415.4 |
| 67 | 855 | 3-(6,8-dimethylimidazo[1,2-a]pyrazin-2-yl)-7-[1-(oxetan-3-yl)piperidin-4-yl]-2H-chromen-2-one | 217-223 | 431.4 |
| 69 | 856 | 3-(2-methyl-2H-indazol-5-yl)-7-(piperidin-4-yl)-2H-chromen-2-one | 232-238 | 360.3 |
| 77 | 857 | 7-[3-(dimethylamino)propyl]-3-(6,8-dimethylimidazo[1,2-a]pyrazin-2-yl)-2H-chromen-2-one | 194-196 | 377.3 |
| 77 | 858 | 3-(6,8-dimethylimidazo[1,2-a]pyrazin-2-yl)-7-[3-(propan-2-ylamino)propyl]-2H-chromen-2-one | 184-187 | 391.3 |
| 77 | 859 | 3-(6,8-dimethylimidazo[1,2-a]pyrazin-2-yl)-7-[3-(piperazin-1-yl)propyl]-2H-chromen-2-one | 145-153 | 418.4 |
| 77 | 860 | 3-(6,8-dimethylimidazo[1,2-a]pyrazin-2-yl)-7-[3-(4-methylpiperazin-1-yl)propyl]-2H-chromen-2-one | 219-223 | 432.4 |
| 67 | 861 | 7-[1-(2-hydroxyethyl)piperidin-4-yl]-3-(2-methyl-2H-indazol-5-yl)-2H-chromen-2-one | 220-226 | 404.3 |
| 67 | 862 | 3-(2-methyl-2H-indazol-5-yl)-7-(1-methylpiperidin-4-yl)-2H-chromen-2-one | 215-218 | 374.2 |
| 67 | 863 | 7-(1-ethylpiperidin-4-yl)-3-(2-methyl-2H-indazol-5-yl)-2H-chromen-2-one | 196-198 | 388.3 |
| 77 | 864 | 7-[2-(dimethylamino)ethyl]-3-(6,8-dimethylimidazo[1,2-a]pyrazin-2-yl)-2H-chromen-2-one | 219-223 | 363.4 |

TABLE 1-continued

| Ex | Cpd | Name | M.P. | MS |
|---|---|---|---|---|
| 77 | 865 | 3-(6,8-dimethylimidazo[1,2-a]pyrazin-2-yl)-7-[2-(propan-2-ylamino)ethyl]-2H-chromen-2-one | 192-197 | 377.3 |
| 77 | 866 | 3-(6,8-dimethylimidazo[1,2-a]pyrazin-2-yl)-7-[2-(piperazin-1-yl)ethyl]-2H-chromen-2-one | 186-188 | 404.3 |
| 67 | 867 | 3-(6,8-dimethylimidazo[1,2-a]pyrazin-2-yl)-7-[(1-methylpiperidin-4-yl)oxy]-2H-chromen-2-one | 165-168 | 405.3 |
| 51 | 868 | 3-(6-methylimidazo[1,2-a]pyrazin-2-yl)-7-(piperidin-4-yl)-2H-chromen-2-one | 247-253 | 361.3 |
| 67 | 869 | 7-(1-cyclobutylpiperidin-4-yl)-3-(6-methylimidazo[1,2-a]pyrazin-2-yl)-2H-chromen-2-one | 256-268 | 415.5 |
| 77 | 870 | 3-(6,8-dimethylimidazo[1,2-a]pyrazin-2-yl)-7-{2-[(2-hydroxyethyl)amino]ethyl}-2H-chromen-2-one | ND | 379.2 |
| 77 | 871 | 3-(6,8-dimethylimidazo[1,2-a]pyrazin-2-yl)-7-{2-[(2-hydroxyethyl)(methyl)amino]ethyl}-2H-chromen-2-one | 168-172 | 393.3 |
| 77 | 872 | 3-(6,8-dimethylimidazo[1,2-a]pyrazin-2-yl)-7-{2-[(1-hydroxypropan-2-yl)amino]ethyl}-2H-chromen-2-one | 203-206 | 393.3 |
| 77 | 873 | 7-{2-[(1,3-dihydroxypropan-2-yl)amino]ethyl}-3-(6,8-dimethylimidazo[1,2-a]pyrazin-2-yl)-2H-chromen-2-one | 217-221 | 409.3 |
| 77 | 874 | 3-(6,8-dimethylimidazo[1,2-a]pyrazin-2-yl)-7-{2-[(2R)-2-(hydroxymethyl)pyrrolidin-1-yl]ethyl}-2H-chromen-2-one | 166-171 | 419.4 |
| 77 | 875 | 7-{2-[bis(2-hydroxyethyl)amino]ethyl}-3-(6,8-dimethylimidazo[1,2-a]pyrazin-2-yl)-2H-chromen-2-one | 184-188 | 423.4 |
| 74* | 876 | 7-[2-(dimethylamino)ethoxy]-3-(6,8-dimethylimidazo[1,2-a]pyrazin-2-yl)-2H-chromen-2-one | 251-253 | 379.3 |
| 74 | 877 | 3-(6,8-dimethylimidazo[1,2-a]pyrazin-2-yl)-7-[2-(propan-2-ylamino)ethoxy]-2H-chromen-2-one | 202-207 | 393.3 |
| 67 | 878 | 3-(6-methylimidazo[1,2-a]pyrazin-2-yl)-7-[1-(oxetan-3-yl)piperidin-4-yl]-2H-chromen-2-one | ND | 417.3 |
| 77 | 879 | 3-(6,8-dimethylimidazo[1,2-a]pyrazin-2-yl)-7-{3-[(2-hydroxyethyl)amino]propyl}-2H-chromen-2-one | ND | 393.3 |
| 77 | 880 | 3-(6,8-dimethylimidazo[1,2-a]pyrazin-2-yl)-7-{3-[(2-hydroxyethyl)(methyl)amino]propyl}-2H-chromen-2-one | 173-176 | 407.3 |
| 77 | 881 | 3-(6,8-dimethylimidazo[1,2-a]pyrazin-2-yl)-7-{3-[(1-hydroxypropan-2-yl)amino]propyl}-2H-chromen-2-one | 181-184 | 407.3 |
| 77 | 882 | 7-{3-[(1,3-dihydroxypropan-2-yl)amino]propyl}-3-(6,8-dimethylimidazo[1,2-a]pyrazin-2-yl)-2H-chromen-2-one | 195-199 | 423.3 |
| 77 | 883 | 3-(6,8-dimethylimidazo[1,2-a]pyrazin-2-yl)-7-{3-[(2R)-2-(hydroxymethyl)pyrrolidin-1-yl]propyl}-2H-chromen-2-one | 182-185 | 433.3 |
| 77 | 884 | 3-(6,8-dimethylimidazo[1,2-a]pyrazin-2-yl)-7-[3-(morpholin-4-yl)propyl]-2H-chromen-2-one | 168-172 | 419.3 |
| 77 | 885 | 7-{3-[bis(2-hydroxyethyl)amino]propyl}-3-(6,8-dimethylimidazo[1,2-a]pyrazin-2-yl)-2H-chromen-2-one | 158-162 | 437.3 |
| 77 | 886 | 3-(6,8-dimethylimidazo[1,2-a]pyrazin-2-yl)-7-[2-(morpholin-4-yl)ethyl]-2H-chromen-2-one | 180-184 | 405.3 |
| 67 | 887 | 3-(6-methylimidazo[1,2-a]pyrazin-2-yl)-7-(1-propylpiperidin-4-yl)-2H-chromen-2-one | ND | 403.4 |
| 67 | 888 | 3-(6,8-dimethylimidazo[1,2-a]pyrazin-2-yl)-7-[(3S)-4-(2-hydroxyethyl)-3-methylpiperazin-1-yl]-2H-chromen-2-one | ND | 434.4 |
| 67 | 889 | 3-(6,8-dimethylimidazo[1,2-a]pyrazin-2-yl)-7-{[(3R)-1-methylpyrrolidin-3-yl]oxy}-2H-chromen-2-one | 195-202 | 391.2 |
| 67 | 890 | 3-(6,8-dimethylimidazo[1,2-a]pyrazin-2-yl)-7-{[(3R)-1-ethylpyrrolidin-3-yl]oxy}-2H-chromen-2-one | 193-195 | 405.3 |
| 67 | 891 | 3-(6,8-dimethylimidazo[1,2-a]pyrazin-2-yl)-7-{[(3R)-1-(propan-2-yl)pyrrolidin-3-yl]oxy}-2H-chromen-2-one | 176-179 | 419.3 |
| 67 | 892 | 3-(6,8-dimethylimidazo[1,2-a]pyrazin-2-yl)-7-{[(3R)-1-(2-hydroxyethyl)pyrrolidin-3-yl]oxy}-2H-chromen-2-one | 190-196 | 421.2 |
| 67 | 893 | 3-(6,8-dimethylimidazo[1,2-a]pyrazin-2-yl)-7-{[(3R)-1-(1-hydroxypropan-2-yl)pyrrolidin-3-yl]oxy}-2H-chromen-2-one | 196-202 | 435.4 |
| 68 | 894 | 3-(6,8-dimethylimidazo[1,2-a]pyrazin-2-yl)-7-[(3S)-4-(2-fluoroethyl)-3-methylpiperazin-1-yl]-2H-chromen-2-one | 192-195 | 436.4 |
| 74 | 895 | 7-[2-(diethylamino)ethoxy]-3-(6,8-dimethylimidazo[1,2-a]pyrazin-2-yl)-2H-chromen-2-one | 175-177 | 407.3 |
| 74 | 896 | 7-{2-[bis(2-hydroxyethyl)amino]ethoxy}-3-(6,8-dimethylimidazo[1,2-a]pyrazin-2-yl)-2H-chromen-2-one | 199-202 | 439.2 |
| 74 | 897 | 3-(6,8-dimethylimidazo[1,2-a]pyrazin-2-yl)-7-(piperidin-4-yloxy)-2H-chromen-2-one | 172-177 | 391.3 |
| 67 | 898 | 3-(6,8-dimethylimidazo[1,2-a]pyrazin-2-yl)-7-[(1-ethylpiperidin-4-yl)oxy]-2H-chromen-2-one | 175-177 | 419.4 |
| 67 | 899 | 3-(6,8-dimethylimidazo[1,2-a]pyrazin-2-yl)-7-{[1-(2-hydroxyethyl)piperidin-4-yl]oxy}-2H-chromen-2-one | 165-168 | 435.3 |
| 68 | 900 | 3-(6,8-dimethylimidazo[1,2-a]pyrazin-2-yl)-7-[(3S)-4-(3-fluoropropyl)-3-methylpiperazin-1-yl]-2H-chromen-2-one | 215-217 | 450.4 |
| 67 | 901 | 3-(6,8-dimethylimidazo[1,2-a]pyrazin-2-yl)-7-{[1-(propan-2-yl)piperidin-4-yl]oxy}-2H-chromen-2-one | 185-191 | 433.4 |
| 78* | 902 | 7-[4-(dimethylamino)butyl]-3-(6,8-dimethylimidazo[1,2-a]pyrazin-2-yl)-2H-chromen-2-one | 190-193 | 391.5 |

TABLE 1-continued

| Ex | Cpd | Name | M.P. | MS |
|---|---|---|---|---|
| 78 | 903 | 3-(6,8-dimethylimidazo[1,2-a]pyrazin-2-yl)-7-{4-[(2-hydroxyethyl)(methyl)amino]butyl}-2H-chromen-2-one | 156-160 | 421.3 |
| 78 | 904 | 3-(6,8-dimethylimidazo[1,2-a]pyrazin-2-yl)-7-{4-[(2R)-2-(hydroxymethyl)pyrrolidin-1-yl]butyl}-2H-chromen-2-one | 147-151 | 447.4 |
| 78 | 905 | 3-(6,8-dimethylimidazo[1,2-a]pyrazin-2-yl)-7-[4-(piperazin-1-yl)butyl]-2H-chromen-2-one | 187-191 | 432.4 |
| 68 | 906 | 3-(6,8-dimethylimidazo[1,2-a]pyrazin-2-yl)-7-[1-(3-fluoropropyl)piperidin-4-yl]-2H-chromen-2-one | 195-200 | 435.3 |
| 68 | 907 | 3-(6,8-dimethylimidazo[1,2-a]pyrazin-2-yl)-7-[(3S)-4-(3-hydroxypropyl)-3-methylpiperazin-1-yl]-2H-chromen-2-one | 187-190 | 448.4 |
| 79* | 908 | 7-[3-(dimethylamino)propyl]-3-(2-methylimidazo[1,2-a]pyridin-6-yl)-2H-chromen-2-one | 176-178 | 362.3 |
| 79 | 909 | 7-[3-(dimethylamino)propyl]-3-(8-fluoro-2-methylimidazo[1,2-a]pyridin-6-yl)-2H-chromen-2-one | 185-188 | 380.4 |
| 79 | 910 | 7-[3-(dimethylamino)propyl]-3-(8-ethyl-2-methylimidazo[1,2-a]pyridin-6-yl)-2H-chromen-2-one | 123-126 | 390.4 |
| 77 | 911 | 3-(6,8-dimethylimidazo[1,2-a]pyrazin-2-yl)-7-[2-(methylamino)ethyl]-2H-chromen-2-one | 204-208 | 349.3 |
| 77 | 912 | 3-(6,8-dimethylimidazo[1,2-a]pyrazin-2-yl)-7-[3-(methylamino)propyl]-2H-chromen-2-one | 197-201 | 363.3 |
| 79 | 913 | 3-(8-fluoro-2-methylimidazo[1,2-a]pyridin-6-yl)-7-[3-(methylamino)propyl]-2H-chromen-2-one | 163-166 | 366.3 |
| 67 | 914 | 3-(6,8-dimethylimidazo[1,2-a]pyrazin-2-yl)-7-[1-(2-methylpropyl)piperidin-4-yl]-2H-chromen-2-one | 191-198 | 431.5 |
| 67 | 915 | 7-{[1-(1,3-dihydroxypropan-2-yl)piperidin-4-yl]oxy}-3-(6,8-dimethylimidazo[1,2-a]pyrazin-2-yl)-2H-chromen-2-one | 206-210 | 465.3 |
| 67 | 916 | 3-(6-methylimidazo[1,2-a]pyrazin-2-yl)-7-[1-(2-methylpropyl)piperidin-4-yl]-2H-chromen-2-one | 260-270 | 417.3 |
| 68 | 917 | 7-[1-(3-fluoropropyl)piperidin-4-yl]-3-(6-methylimidazo[1,2-a]pyrazin-2-yl)-2H-chromen-2-one | 224-234 | 421.3 |
| 75* | 918 | 3-(6,8-dimethylimidazo[1,2-a]pyrazin-2-yl)-7-[2-(pyrrolidin-1-yl)ethoxy]-2H-chromen-2-one | 201-203 | 405.2 |
| 43 | 919 | 7-(4-aminopiperidin-1-yl)-3-(6,8-dimethylimidazo[1,2-a]pyrazin-2-yl)-2H-chromen-2-one | 262-269 | 390.2 |
| 43 | 920 | 7-(4-amino-4-methylpiperidin-1-yl)-3-(6,8-dimethylimidazo[1,2-a]pyrazin-2-yl)-2H-chromen-2-one | 190-192 | 404.5 |
| 67 | 921 | 7-[4-(dimethylamino)piperidin-1-yl]-3-(6,8-dimethylimidazo[1,2-a]pyrazin-2-yl)-2H-chromen-2-one | 189-193 | 418.3 |
| 67 | 922 | 7-[4-(diethylamino)piperidin-1-yl]-3-(6,8-dimethylimidazo[1,2-a]pyrazin-2-yl)-2H-chromen-2-one | 205-207 | 446.4 |
| 67 | 923 | 3-(6,8-dimethylimidazo[1,2-a]pyrazin-2-yl)-7-[4-(propan-2-ylamino)piperidin-1-yl]-2H-chromen-2-one | 216-218 | 432.4 |
| 67 | 924 | 7-[4-(cyclobutylamino)piperidin-1-yl]-3-(6,8-dimethylimidazo[1,2-a]pyrazin-2-yl)-2H-chromen-2-one | 222-225 | 444.4 |
| 67 | 925 | 3-(6,8-dimethylimidazo[1,2-a]pyrazin-2-yl)-7-{4-[(1-hydroxypropan-2-yl)amino]piperidin-1-yl}-2H-chromen-2-one | 185-189 | 448.4 |
| 77 | 926 | 3-(6,8-dimethylimidazo[1,2-a]pyrazin-2-yl)-7-[3-(ethylamino)propyl]-2H-chromen-2-one | 184-186 | 377.3 |
| 80* | 927 | 7-(3-aminopropyl)-3-(6,8-dimethylimidazo[1,2-a]pyrazin-2-yl)-2H-chromen-2-one | 212-216 | 349.3 |
| 67 | 928 | 7-{4-[bis(2-hydroxyethyl)amino]piperidin-1-yl}-3-(6,8-dimethylimidazo[1,2-a]pyrazin-2-yl)-2H-chromen-2-one | 209-212 | 478.4 |
| 67 | 929 | 7-{4-[(1,3-dihydroxypropan-2-yl)amino]piperidin-1-yl}-3-(6,8-dimethylimidazo[1,2-a]pyrazin-2-yl)-2H-chromen-2-one | 251-256 | 464.4 |
| 75 | 930 | 3-(6,8-dimethylimidazo[1,2-a]pyrazin-2-yl)-7-[2-(ethylamino)ethoxy]-2H-chromen-2-one | 189-193 | 379.4 |
| 77 | 931 | 3-(6,8-dimethylimidazo[1,2-a]pyrazin-2-yl)-7-{3-[(2-methoxyethyl)amino]propyl}-2H-chromen-2-one | 147-150 | 407.3 |
| 77 | 932 | 3-(6,8-dimethylimidazo[1,2-a]pyrazin-2-yl)-7-{3-[(tetrahydrofuran-2-ylmethyl)amino]propyl}-2H-chromen-2-one | 147-150 | 433.3 |
| 81* | 933 | 7-[3-(benzylamino)propyl]-3-(6,8-dimethylimidazo[1,2-a]pyrazin-2-yl)-2H-chromen-2-one | 143-147 | 439.3 |
| 81 | 934 | 3-(6,8-dimethylimidazo[1,2-a]pyrazin-2-yl)-7-{3-[(thiophen-3-ylmethyl)amino]propyl}-2H-chromen-2-one | 149-152 | 445.3 |
| 81 | 935 | 3-(6,8-dimethylimidazo[1,2-a]pyrazin-2-yl)-7-{3-[(pyridin-2-ylmethyl)amino]propyl}-2H-chromen-2-one | 177-180 | 440.4 |
| 81 | 936 | 3-(6,8-dimethylimidazo[1,2-a]pyrazin-2-yl)-7-{3-[(pyridin-4-ylmethyl)amino]propyl}-2H-chromen-2-one | 155-159 | 440.4 |
| 67 | 937 | 3-(6,8-dimethylimidazo[1,2-a]pyrazin-2-yl)-7-{2-[ethyl(methyl)amino]ethoxy}-2H-chromen-2-one | 190-196 | 393.3 |
| 67 | 938 | 3-(6,8-dimethylimidazo[1,2-a]pyrazin-2-yl)-7-{2-[ethyl(2-hydroxyethyl)amino]ethoxy}-2H-chromen-2-one | 165-168 | 423.3 |

TABLE 1-continued

| Ex | Cpd | Name | M.P. | MS |
|---|---|---|---|---|
| 77 | 939 | 3-(6,8-dimethylimidazo[1,2-a]pyrazin-2-yl)-7-[3-(tetrahydrofuran-3-ylamino)propyl]-2H-chromen-2-one | 177-180 | 419.5 |
| 75 | 941 | 3-(6,8-dimethylimidazo[1,2-a]pyrazin-2-yl)-7-{2-[(3R)-3-hydroxypyrrolidin-1-yl]ethoxy}-2H-chromen-2-one | 195-202 | 421.3 |
| 82 | 942 | 3-(6,8-dimethylimidazo[1,2-a]pyrazin-2-yl)-7-[3-(2-methylpiperidin-1-yl)azetidin-1-yl]-2H-chromen-2-one | 220-228 | 444.4 |
| 82* | 943 | 7-[3-(dimethylamino)azetidin-1-yl]-3-(6,8-dimethylimidazo[1,2-a]pyrazin-2-yl)-2H-chromen-2-one | 246-250 | 390.3 |
| 82 | 944 | 7-[3-(diethylamino)azetidin-1-yl]-3-(6,8-dimethylimidazo[1,2-a]pyrazin-2-yl)-2H-chromen-2-one | 218-220 | 418.3 |
| 82 | 945 | 7-(2,7-diazaspiro[4.4]non-2-yl)-3-(6,8-dimethylimidazo[1,2-a]pyrazin-2-yl)-2H-chromen-2-one | 190-200 | 416.3 |
| 75 | 946 | 3-(6,8-dimethylimidazo[1,2-a]pyrazin-2-yl)-7-(2-{[(2R)-1-hydroxypropan-2-yl]amino}ethoxy)-2H-chromen-2-one | 185-188 | 409.3 |
| 75 | 947 | 3-(6,8-dimethylimidazo[1,2-a]pyrazin-2-yl)-7-(2-{[(2S)-1-hydroxypropan-2-yl]amino}ethoxy)-2H-chromen-2-one | 186-188 | 409.3 |
| 71* | 948 | 3-(6,8-dimethylimidazo[1,2-a]pyrazin-2-yl)-7-[(2R)-pyrrolidin-2-ylmethoxy]-2H-chromen-2-one | 172-174 | 391.3 |
| 50 | 949 | 3-(6,8-dimethylimidazo[1,2-a]pyrazin-2-yl)-7-(2,2,6,6-tetramethyl-1,2,3,6-tetrahydropyridin-4-yl)-2H-chromen-2-one | 188-190 | 429.3 |
| 82 | 950 | 7-[(3R)-3-(aminomethyl)pyrrolidin-1-yl]-3-(6,8-dimethylimidazo[1,2-a]pyrazin-2-yl)-2H-chromen-2-one | 196-198 | 390.3 |
| 82 | 951 | 3-(6,8-dimethylimidazo[1,2-a]pyrazin-2-yl)-7-[3-(piperidin-1-yl)azetidin-1-yl]-2H-chromen-2-one | 284-286 | 430.3 |
| 78 | 952 | 3-(6,8-dimethylimidazo[1,2-a]pyrazin-2-yl)-7-[4-(methylamino)butyl]-2H-chromen-2-one | 180-184 | 377.3 |
| 75 | 953 | 3-(6,8-dimethylimidazo[1,2-a]pyrazin-2-yl)-7-[2-(piperidin-1-yl)ethoxy]-2H-chromen-2-one | 178-190 | 419.3 |
| 75 | 954 | 3-(6,8-dimethylimidazo[1,2-a]pyrazin-2-yl)-7-{2-[(3S)-3-hydroxypyrrolidin-1-yl]ethoxy}-2H-chromen-2-one | ND | 421.3 |
| 75 | 955 | 3-(6,8-dimethylimidazo[1,2-a]pyrazin-2-yl)-7-{2-[(1-hydroxy-2-methylpropan-2-yl)amino]ethoxy}-2H-chromen-2-one | 187-191 | 423.3 |
| 75 | 956 | 3-(6,8-dimethylimidazo[1,2-a]pyrazin-2-yl)-7-[2-(morpholin-4-yl)ethoxy]-2H-chromen-2-one | 175-177 | 421.3 |
| 75 | 957 | 3-(6,8-dimethylimidazo[1,2-a]pyrazin-2-yl)-7-[2-(4-hydroxypiperidin-1-yl)ethoxy]-2H-chromen-2-one | 187-190 | 435.4 |
| 72* | 958 | 3-(6,8-dimethylimidazo[1,2-a]pyrazin-2-yl)-7-(1-ethyl-4-fluoropiperidin-4-yl)-2H-chromen-2-one | 162-164 | 421.3 |
| 75 | 959 | 3-(6,8-dimethylimidazo[1,2-a]pyrazin-2-yl)-7-{2-[(2-hydroxyethyl)amino]ethoxy}-2H-chromen-2-one | 175-177 | 395 |
| 75 | 960 | 3-(6,8-dimethylimidazo[1,2-a]pyrazin-2-yl)-7-{2-[(2-methoxyethyl)amino]ethoxy}-2H-chromen-2-one | ND | 409.3 |
| 75 | 961 | 3-(6,8-dimethylimidazo[1,2-a]pyrazin-2-yl)-7-{2-[(2-hydroxypropyl)amino]ethoxy}-2H-chromen-2-one | 185-188 | 409.3 |
| 68 | 962 | 3-(6,8-dimethylimidazo[1,2-a]pyrazin-2-yl)-7-[4-(2-hydroxy-2-methylpropyl)piperazin-1-yl]-2H-chromen-2-one | 212-214 | 448.3 |
| 82 | 963 | 7-[3-(aminomethyl)azetidin-1-yl]-3-(6,8-dimethylimidazo[1,2-a]pyrazin-2-yl)-2H-chromen-2-one | ND | 376.3 |
| 82 | 964 | 7-[(3S)-3-(aminomethyl)pyrrolidin-1-yl]-3-(6,8-dimethylimidazo[1,2-a]pyrazin-2-yl)-2H-chromen-2-one | ND | 390.3 |
| 67 | 965 | 7-{(3R)-3-[(dimethylamino)methyl]pyrrolidin-1-yl}-3-(6,8-dimethylimidazo[1,2-a]pyrazin-2-yl)-2H-chromen-2-one | 206-208 | 418.4 |
| 67 | 966 | 7-{3-[(dimethylamino)methyl]azetidin-1-yl}-3-(6,8-dimethylimidazo[1,2-a]pyrazin-2-yl)-2H-chromen-2-one | 150-152 | 404.4 |
| 67 | 967 | 7-{(3S)-3-[(dimethylamino)methyl]pyrrolidin-1-yl}-3-(6,8-dimethylimidazo[1,2-a]pyrazin-2-yl)-2H-chromen-2-one | 198-200 | 418.4 |
| 77 | 968 | 7-[2-(diethylamino)ethyl]-3-(6,8-dimethylimidazo[1,2-a]pyrazin-2-yl)-2H-chromen-2-one | 190-193 | 391.3 |
| 77 | 969 | 7-[3-(diethylamino)propyl]-3-(6,8-dimethylimidazo[1,2-a]pyrazin-2-yl)-2H-chromen-2-one | 165-168 | 405.4 |
| 78 | 970 | 7-[4-(diethylamino)butyl]-3-(6,8-dimethylimidazo[1,2-a]pyrazin-2-yl)-2H-chromen-2-one | 212-216 | 419.4 |
| 83* | 971 | 7-(2,6-diazaspiro[3.3]hept-2-yl)-3-(6,8-dimethylimidazo[1,2-a]pyrazin-2-yl)-2H-chromen-2-one | ND | 388.3 |
| 67 | 972 | 3-(6,8-dimethylimidazo[1,2-a]pyrazin-2-yl)-7-(6-methyl-2,6-diazaspiro[3.3]hept-2-yl)-2H-chromen-2-one | ND | 402.3 |
| 43 | 973 | 2-[3-(6,8-dimethylimidazo[1,2-a]pyrazin-2-yl)-2-oxo-2H-chromen-7-yl]hexahydropyrrolo[1,2-a]pyrazin-6(2H)-one | ND | 430.3 |
| 43 | 974 | 1-[3-(6,8-dimethylimidazo[1,2-a]pyrazin-2-yl)-2-oxo-2H-chromen-7-yl]piperidine-4-carbonitrile | ND | 400.3 |
| 43 | 975 | 3-(6,8-dimethylimidazo[1,2-a]pyrazin-2-yl)-7-(4-hydroxypiperidin-1-yl)-2H-chromen-2-one | ND | 391.3 |
| 83 | 976 | 7-(2,7-diazaspiro[3.5]non-7-yl)-3-(6,8-dimethylimidazo[1,2-a]pyrazin-2-yl)-2H-chromen-2-one | ND | 416.5 |

TABLE 1-continued

| Ex | Cpd | Name | M.P. | MS |
|---|---|---|---|---|
| 83 | 977 | 7-(6-amino-2-azaspiro[3.3]hept-2-yl)-3-(6,8-dimethylimidazo[1,2-a]pyrazin-2-yl)-2H-chromen-2-one | ND | 402.5 |
| 34 | 978 | 3-(imidazo[1,2-a]pyridin-6-yl)-7-(4-methylpiperazin-1-yl)-2H-chromen-2-one | ND | 360.3 |
| 34 | 979 | 7-[(8aS)-hexahydropyrrolo[1,2-a]pyrazin-2(1H)-yl]-3-(imidazo[1,2-a]pyridin-6-yl)-2H-chromen-2-one | ND | 387.3 |
| 34 | 980 | 3-(imidazo[1,2-a]pyridin-6-yl)-7-(piperazin-1-yl)-2H-chromen-2-one | ND | 374.4 |
| 34 | 981 | 3-(imidazo[1,2-a]pyridin-6-yl)-7-[(3S)-3-methylpiperazin-1-yl]-2H-chromen-2-one | ND | 361.6 |
| 70 | 982 | 3-(8-fluoro-2-methylimidazo[1,2-a]pyridin-6-yl)-7-(4-methylpiperazin-1-yl)-2H-chromen-2-one | ND | 393.2 |
| 70 | 983 | 3-(8-fluoro-2-methylimidazo[1,2-a]pyridin-6-yl)-7-[(8aS)-hexahydropyrrolo[1,2-a]pyrazin-2(1H)-yl]-2H-chromen-2-one | ND | 419.7 |
| 70 | 984 | 3-(8-fluoro-2-methylimidazo[1,2-a]pyridin-6-yl)-7-[(3S)-3-methylpiperazin-1-yl]-2H-chromen-2-one | ND | 393.7 |
| 84* | 985 | 7-(2,6-diazaspiro[3.3]hept-2-yl)-3-(8-fluoro-2-methylimidazo[1,2-a]pyridin-6-yl)-2H-chromen-2-one, and | ND | 391.7 |
| 70 | 986 | 3-(8-fluoro-2-methylimidazo[1,2-a]pyridin-6-yl)-7-(piperazin-1-yl)-2H-chromen-2-one; | ND | 379.7 | or a salt, isotopologue, stereoisomer, racemate, enantiomer, diastereomer or tautomer thereof.

Table 2 further provides certain isolated compounds of a salt form of a compound of Formula (I) that may be prepared according to the procedures of the indicated Example by using the appropriate reactants, reagents and reaction conditions. The preparation of any free base, isotopologue, stereoisomer, racemate, enantiomer, diastereomer or tautomer from a salt form of a compound of Formula (I) is also contemplated and further included within the scope of the description herein. Where a free base form of the compound was not isolated from the salt form, a person of ordinary skill in the art could be expected to perform the required reactions to prepare and isolate the free base form of the compound.

The term "Cpd" represents Compound number, the term "Ex" represents "Example Number" (wherein * indicates that the corresponding Example for the Compound is provided above), the term "M.P." represents "Melting Point (° C.)," the term "MS" represents "Mass Spectroscopy Peak(s) m/z $[M+H]^{+/-}$," the term "D" represents "Decomposition/Decomposed," the term "DR" represents "Decomposition Range," the term "S" represents "Softens" and the term "ND" indicates that the value was "Not Determined."

TABLE 2

| Ex | Cpd | Name | M.P. | MS |
|---|---|---|---|---|
| 1 | 1 | 7-(piperazin-1-yl)-3[4-(trifluoromethyl)-1,3-benzoxazol-2-yl]-2H-chromen-2-one trifluoroacetate | ND | 416.1 |
| 1 | 1a | 7-(piperazin-1-yl)-3[4-(trifluoromethyl)-1,3-benzoxazol-2-yl]-2H-chromen-2-one hydrochloride | 339-341 | 416.1 |
| 1 | 2 | 7-(piperazin-1-yl)-3[7-(trifluoromethyl)-1,3-benzoxazol-2-yl]-2H-chromen-2-one trifluoroacetate | ND | 416.1 |
| 1 | 2a | 7-(piperazin-1-yl)-3[7-(trifluoromethyl)-1,3-benzoxazol-2-yl]-2H-chromen-2-one hydrochloride | 297-307 | 416.1 |
| 5* | 3 | 2-oxo-N-phenyl-7-(piperazin-1-yl)-2H-chromene-3-carboxamide trifluoroacetate | ND | 350.1 |
| 1* | 4 | 3-(1,3-benzothiazol-2-yl)-7-(piperazin-1-yl)-2H-chromen-2-one hydrochloride | 250 (D) | 364.4 |
| 2* | 5 | 3-(4-chloro-1,3-benzothiazol-2-yl)-7-(piperazin-1-yl)-2H-chromen-2-one hydrochloride | 290 (D) | 398.1 |
| 2 | 6 | 3-(7-chloro-1,3-benzothiazol-2-yl)-7-(piperazin-1-yl)-2H-chromen-2-one hydrochloride | 320 (D) | 398.1 |
| 11* | 18 | 3-(4-chloro-1,3-benzothiazol-2-yl)-7-(piperidin-4-yl)-2H-chromen-2-one hydrochloride | 339-341 | 397.1 |
| 1 | 19 | 3-(5-fluoro-1,3-benzoxazol-2-yl)-7-(piperazin-1-yl)-2H-chromen-2-one hydrochloride | 320-325 | 366.1 |
| 1 | 22 | 3-(4-methyl-1,3-benzoxazol-2-yl)-7-(piperazin-1-yl)-2H-chromen-2-one hydrochloride | 257-259 | 362.2 |
| 1 | 40 | 3-(4-fluoro-1,3-benzoxazol-2-yl)-7-(piperazin-1-yl)-2H-chromen-2-one hydrochloride | 230-232 | 366.2 |
| 21 | 52 | 7-(piperazin-1-yl)-3-[4-(trifluoromethyl)-1,3-thiazol-2-yl]-2H-chromen-2-one trifluoroacetate | ND | 382.1 |
| 21 | 52a | 7-(piperazin-1-yl)-3-[4-(trifluoromethyl)-1,3-thiazol-2-yl]-2H-chromen-2-one hydrochloride | ND | 382.2 |
| 21 | 53 | 7-(4-methylpiperazin-1-yl)-3-[4-(trifluoromethyl)-1,3-thiazol-2-yl]-2H-chromen-2-one trifluoroacetate | 260-270 | 396.2 |
| 3 | 67 | 3-(4-iodo-1,3-benzoxazol-2-yl)-7-(piperazin-1-yl)-2H-chromen-2-one hydrochloride | 280-285 | 474.2 |
| 3 | 70 | 3-(4-chloro-1,3-benzoxazol-2-yl)-7-(piperazin-1-yl)-2H-chromen-2-one hydrochloride | 278-282 | 382.2 384.1 |
| 1 | 110 | 3-([1,3]oxazolo[4,5-b]pyridin-2-yl)-7-(piperazin-1-yl)-2H-chromen-2-one hydrochloride | 200~300 (D) | 385.2 |
| 38 | 129 | 7-[(1S,4S)-2,5-diazabicyclo[2.2.1]hept-2-yl]-3-(imidazo[1,2-a]pyrimidin-2-yl)-2H-chromen-2-one hydrochloride (1:3) | >300 | 360.2 |
| 41 | 141 | 3-(3-methylimidazo[2,1-b][1,3]thiazol-6-yl)-7-(piperazin-1-yl)-2H-chromen-2-one hydrochloride (1:3) | ND | 367.2 |
| 38 | 186 | 7-(1,4-diazepan-1-yl)-3-(imidazo[1,2-a]pyrimidin-2-yl)-2H-chromen-2-one hydrochloride | >300 | 362.3 |
| 65 | 197 | 3-(imidazo[1,2-a]pyrimidin-2-yl)-7-(piperidin-4-yloxy)-2H-chromen-2-one hydrochloride | >310 | 363.3 |
| 25* | 274 | 3-(2-methylpyrimidin-4-yl)-7-(piperazin-1-yl)-2H-chromen-2-one hydrochloride | 200 (D) | 323.2 |
| 25 | 278 | 3-(2-cyclopropylpyrimidin-4-yl)-7-(piperazin-1-yl)-2H-chromen-2-one hydrochloride | 200-300 (D) | 349.4 |

TABLE 2-continued

| Ex | Cpd | Name | M.P. | MS |
|---|---|---|---|---|
| 25 | 279 | 7-(piperazin-1-yl)-3-[2-(propan-2-yl)pyrimidin-4-yl]-2H-chromen-2-one hydrochloride | 200-300 | 351.4 (D) |
| 65* | 321 | 3-(imidazo[1,2-a]pyrimidin-2-yl)-7-[(3R)-pyrrolidin-3-yloxy]-2H-chromen-2-one hydrochloride (1:2) | 240-250 | 349.2 |
| 65 | 322 | 3-(7-methylimidazo [1,2-a]pyrimidin-2-yl)-7-[(3R)-pyrrolidin-3-yloxy]-2H-chromen-2-one hydrochloride (1:2) | 292-296 | 363.2 |
| 65 | 323 | 3-(7-methylimidazo[1,2-a]pyridin-2-yl)-7-[(3R)-pyrrolidin-3-yloxy]-2H-chromen-2-one hydrochloride (1:2) | 271-275 | 362.3 |
| 65 | 324 | 3-(imidazo[2,1-b][1,3]thiazol-6-yl)-7-[(3R)-pyrrolidin-3-yloxy]-2H-chromen-2-one hydrochloride (1:2) | 252-256 | 354.2 |
| 65 | 325 | 3-(2-methylimidazo[2,1-b][1,3]thiazol-6-yl)-7-[(3R)-pyrrolidin-3-yloxy]-2H-chromen-2-one hydrochloride (1:2) | 230-235 | 368.2 |
| 65 | 326 | 3-(6-methylimidazo[1,2-a]pyridin-2-yl)-7-[(3R)-pyrrolidin-3-yloxy]-2H-chromen-2-one hydrochloride (1:2) | 261-265 | 362.3 |
| 65 | 327 | 3-(6-methylimidazo[1,2-a]pyrimidin-2-yl)-7-[(3R)-pyrrolidin-3-yloxy]-2H-chromen-2-one hydrochloride (1:2) | 255-258 | 363.3 |
| 38 | 377 | 7-[((1-benzylpyrrolidin-3-yl)(methyl)amino]-3-(7-methylimidazo[1,2-a]pyrimidin-2-yl)-2H-chromen-2-one acetate | ND | 466.4 |
| 67 | 759 | 7-[(3R)-3,4-dimethylpiperazin-1-yl]-3-(8-methoxy-6-methylimidazo[1,2-a]pyrazin-2-yl)-2H-chromen-2-one acetate (1:2) | 227-229 | 420.4 |
| 67 | 760 | 7-[(3R)-3,4-dimethylpiperazin-1-yl]-3-(8-hydroxy-6-methylimidazo[1,2-a]pyrazin-2-yl)-2H-chromen-2-one acetate | 304-306 | 406.0 |
| 67 | 776 | 7-[(3S)-3,4-dimethylpiperazin-1-yl]-3-(2-methyl-1,3-benzothiazol-6-yl)-2H-chromen-2-one acetate (2:1) | 210-211 | 417.5 |
| 67 | 777 | 7-[(3S)-4-ethyl-3-methylpiperazin-1-yl]-3-(2-methyl-1,3-benzothiazol-6-yl)-2H-chromen-2-one acetate | 180-182 | 420.2 |
| 67 | 778 | 3-(6,8-dimethylimidazo [1,2-a]pyrazin-2-yl)-7-[(3S)-3-ethyl-4-methylpiperazin-1-yl]-2H-chromen-2-one acetate, and | 170-172 | 418.2 |
| 67 | 779 | 7-[(3S)-3,4-diethylpiperazin-1-yl]-3-(6,8-dimethylimidazo[1,2-a]pyrazin-2-yl)-2H-chromen-2-one acetate (1:2); | 170-174 | 432.3 | or a free base, isotopologue, stereoisomer, racemate, enantiomer, diastereomer or tautomer thereof.

BIOLOGICAL EXAMPLES

To describe in more detail and assist in understanding the present description, the following non-limiting biological examples are offered to more fully illustrate the scope of the description and are not to be construed as specifically limiting the scope thereof. Such variations of the present description that may be now known or later developed, which would be within the purview of one skilled in the art to ascertain, are considered to fall within the scope of the present description and as hereinafter claimed. These examples illustrate the testing of certain compounds described herein in vitro and/or in vivo and demonstrate the usefulness of the compounds for treating of SMA by enhancing the inclusion of exon 7 of SMN2 into mRNA transcribed from the SMN2 gene. Compounds of Formula (I) enhance inclusion of exon 7 of SMN2 into mRNA transcribed from the SMN2 gene and increase levels of Smn protein produced from the SMN2 gene, and thus can be used to treat SMA in a human subject in need thereof.

Example 1

SMN2 Minigene Construct

Preparation of the Minigene Constructs

DNA corresponding to a region of the SMN2 gene starting from the 5' end of exon 6 (ATAATTCCCCC) (SEQ ID NO. 14) and ending at nucleic acid residue 23 of exon 8 (CAGCAC) (SEQ ID NO. 15) was amplified by PCR using the following primers:

```
Forward primer:
                              (SEQ ID NO. 16)
5'-CGCGGATCCATAATTCCCCCACCACCTC-3'

Reverse primer:
                              (SEQ ID NO. 17)
5'-CGCGGATCCGTGCTGCTCTATGCCAGCA-3'
```

The 5' end of each primer was designed to add a BamHI restriction endonuclease recognition site at both the 5' end of exon 6 (GGATCC) (SEQ ID NO. 18) and the 3' end after the 23$^{rd}$ nucleotide of exon 8. Using the BamHI restriction endonuclease recognition sites, the PCR fragment was cloned into a derivative of the original pcDNA 3.1/Hygro vector which was modified as disclosed in United States Patent Publication US2005/0048549.

New UTRs were added to the modified vector using the HindIII site and the BamHI restriction sites comprising a 5'DEG UTR: 5'-TAGCTTCTTACCCGTACTCCACCGT-TGGCAGCACGATCGCACGTCCCACGT GAACCAT-TGGTAAACCCTG-3' (SEQ ID NO. 19) was cloned into the modified pcDNA3.1/Hygro vector together with a start codon upstream of the BamHI restriction site; and a 3'DEG UTR: 5'-ATCGAAAGTACAGGACTAGCCT-TCCTAGCAACCGCGGGCTGGGAGTCTGA GACAT-CACTCAAGATATATGCTCGGTAACGTATGCTCTAGC-CATCTAACTATTCCCT ATGTCTTATAGGG-3' (SEQ ID NO. 20) was cloned into the modified pcDNA3.1/Hygro vector using the NotI restriction endonuclease recognition site and the XhoI restriction endonuclease recognition site with a stop codon immediately downstream of the NotI restriction site. In addition, a firefly luciferase gene lacking its start codon was cloned into the vector using the BamHI and NotI restriction sites.

The resulting minigene comprises, in 5' to 3' order: the 5'-DEG UTR, the start codon, six additional nucleotides forming a BamHI restriction site, the nucleic acid residues of exon 6, the nucleic acid residues of intron 6 of SMN2, the nucleic acid residues of exon 7 of SMN2, the nucleic acid residues of intron 7 of SMN2, and the first 23 nucleic acid residues of exon 8 of SMN2, an additional six nucleotides forming a BamHI restriction site and the firefly luciferase gene lacking the start codon.

A single adenine residue was inserted after nucleotide 48 of exon 7 of SMN2 by site-directed mutagenesis. This minigene construct is referred to as SMN2-A.

SMN2 transcripts derived from minigenes containing exon 6 through 8 and the intervening introns recapitulate the splicing of their endogenous pre-mRNAs (Lorson et al, Proc. Natl. Acad. Sci. U.S.A., 1999, 96 (11), 6307). An SMN2-alternative splicing reporter construct which contains exons 6 through 8 and the intervening introns followed by a luciferase reporter gene was generated. Salient features of this construct are the lack of the start codon in the luciferase gene, inactivation of the termination codon (in the open reading frame that encodes the SMN protein) of exon 7 by insertion of a nucleotide after nucleic acid 48 of exon 7 and addition of a start codon (ATG) immediately upstream of exon 6. A single adenine (SMN2-A) was inserted after nucleic residue 48 of exon 7.

The SMN2 minigene was designed such that the luciferase reporter is in frame with the ATG start codon immediately upstream of exon 6 when exon 7 is present in the mRNA and the luciferase reporter is out of frame with the ATG start codon immediately upstream of exon 6 if exon 7 of SMN2 is removed during splicing of the pre-mRNA. In addition, in the absence of exon 7, the open reading frame that starts from the ATG start codon immediately upstream of exon 6 contains a stop codon in the fragment of exon 8 of SMN. Thus, in the presence of compounds that increase the inclusion of exon 7 of SMN2 into mRNA transcribed from the SMN2 gene, more transcripts containing exon 7 and more functional reporter are produced. A schematic illustration of this description can be found in FIG. 1.

Figure 2B:
As shown in FIG. 2b, the following subsequences can be found:
  1-70: 5'UTR (deg);
  71-79: exon 6: start codon and BamHI site (atgggatcc);
  80-190: exon 6;
  191-5959: intron 6;
  5960-6014: exon 7 with A insert (position 6008);
  6015-6458: intron 7;
  6459-6481: part of exon 8;
  6482-8146: BamHI site (sequence at 5' end), luciferase coding sequence starting with codon 2 (without initiation codon), NotI site (sequence at 3' end), TAA stop codon; and
  8147-8266: 3'UTR (deg).

The DNA sequence of the minigene from the SMN2-A construct SEQ ID NO. 21 is provided in FIG. 2a. A picture of the minigene SMN2-A subsequences is shown in FIG. 2b.

Example 2

SMN2 Minigene mRNA Splicing RT-qPCR Assay in Cultured Cells

The reverse transcription-quantitative PCR-based (RT-qPCR) assay is used to quantify the level of the full length SMN2 minigene mRNA containing SMN2 exon 7 in a HEK293H cell line stably transfected with said minigene and treated with a test compound.

Materials

| Material | Source |
| --- | --- |
| HEK293H cells | ATCC Catalog No. CRL-1573 |
| Cells-To-Ct lysis buffer | Life Technologies, Inc. (formerly Applied Biosystems) Catalog No.: 4399002 |
| DMEM | Life Technologies, Inc. (formerly Invitrogen) Catalog No.: 11960-044 |
| 96-well flat-bottom plates | Becton Dickinson Catalog No.: 353072 |
| RT-PCR Enzyme Mix | Life Technologies, Inc. (formerly Applied Biosystems) part # 4388520 (also included in AgPath-ID kit Catalog No.: 4387391) |
| RT-PCR buffer | Life Technologies, Inc. (formerly Applied Biosystems) part # 4388519 (also included in AgPath-ID kit Catalog No.: 4387391) |
| AgPath-ID One-Step RT-PCR kit | Life Technologies, Inc. (formerly Applied Biosystems) Catalog No.: 4387391 |
| Thermocycler | Life Technologies, Inc. (formerly Applied Biosystems) 7900HT |

Protocol. HEK293H cells stably transfected with the SMN2-A minigene construct described above (10,000 cells/well) are seeded in 200 μL of cell culture medium (DMEM plus 10% FBS, with 200 μg/mL hygromycin) in 96-well flat-bottom plates and the plate is immediately swirled to ensure proper dispersal of cells, forming an even monolayer of cells. Cells are allowed to attach for at least 4-6 hours. Test compounds are serially diluted 3.16-fold in 100% DMSO to generate a 7-point concentration curve. A solution of test compound (1 μL, 200× in DMSO) is added to each cell-containing well and the plate is incubated for 24 hours in a cell culture incubator (37° C., 5% $CO_2$, 100% relative humidity). 2 replicates are prepared for each test compound concentration. The cells are then lysed in Cells-To-Ct lysis buffer and the lysate is stored at −80° C.

Full length SMN2-A minigene and GAPDH mRNA are quantified using the following primers and probes provided in Table 3. Primer SMN Forward A (SEQ ID NO. 1) hybridizes to a nucleotide sequence in exon 7 (nucleotide 22 to nucleotide 40), primer SMN Reverse A (SEQ ID NO. 2) hybridizes to a nucleotide sequence in the coding sequence of Firefly luciferase, SMN Probe A (SEQ ID NO. 3) hybridizes to a nucleotide sequence in exon 7 (nucleotide 50 to nucleotide 54) and exon 8 (nucleotide 1 to nucleotide 21). The combination of these three oligonucleotides detects only SMN1 or SMN2 minigenes (RT-qPCR) and will not detect endogenous SMN1 or SMN2 genes.

TABLE 3

| Primers/Probes | Sequence | Source |
| --- | --- | --- |
| SMN Forward Primer A | SEQ ID NO. 1:<br>GAAGGAAGGTGCTCACATT | PTC[1] |
| SMN Reverse Primer A | SEQ ID NO. 2:<br>TCTTTATGTTTTTGGCGTCTTC | PTC[1] |
| SMN Forward Probe A | SEQ ID NO. 3:<br>6FAM-<br>AAGGAGAAATGCTGGCAT<br>AGAGCAGC-TAMRA | PTC[1] |
| hGAPDH Forward Probe | SEQ ID NO. 4:<br>VIC-CGCCTGGTCACCAGGGCT<br>GCT-TAMRA | LTI[2] |
| hGAPDH Forward Primer | SEQ ID NO. 5:<br>CAACGGATTTGGTCGTATTGG | LTI[2] |
| hGAPDH Reverse Primer | SEQ ID NO. 6:<br>TGATGGCAACAATATCCACTTT<br>ACC | LTI[2] |

[1]Primers and probes designed by PTC Therapeutics, Inc.;
[2]Commercially available from Life Technologies, Inc. (formerly Invitrogen).

The SMN forward and reverse primers are used at final concentrations of 0.4 μM. The SMN probe is used at a final concentration of 0.15 μM. The GAPDH primers are used at final concentrations of 0.2 μM and the probe at 0.15 μM.

The SMN2-minigene GAPDH mix (15 μL total volume) is prepared by combining 7.5 μL of 2×RT-PCR buffer, 0.4 μL of 25×RT-PCR enzyme mix, 0.75 μL of 20×GAPDH primer-probe mix, 4.0075 μL of water, 2 μL of 10-fold diluted cell lysate, 0.06 μL of 100 μM SMN forward primer, 0.06 μL of 100 μM SMN reverse primer, and 0.225 μL of 100 μM SMN probe.

PCR is carried out at the following temperatures for the indicated time: Step 1: 48° C. (15 min); Step 2: 95° C. (10 min); Step 3: 95° C. (15 sec); Step 4: 60° C. (1 min); then repeat Steps 3 and 4 for a total of 40 cycles.

Each reaction mixture contains both SMN2-A minigene and GAPDH primers/probe sets (multiplex design), allowing simultaneous measurement of the levels of two transcripts.

Two SMN spliced products are generated from the SMN2 minigene. The first spliced product containing exon 7, corresponding to full length SMN2 mRNA, is called SMN2mini FL. The second one lacking exon 7 is called SMN2mini Δ7.

The increase of SMN2mini FL mRNA relative to that in cells treated with vehicle control is determined from real-time PCR data using a modified ΔΔCt method (as described in Livak and Schmittgen, Methods, 2001, 25:402-8). The amplification efficiency E is calculated from the slope of the amplification curve for SMN2mini FL and GAPDH individually. The abundances of SMN2mini FL and GAPDH are then calculated as $(1+E)^{-Ct}$, where Ct is the threshold value for each amplicon. The abundance of SMN2mini FL is normalized to GAPDH abundance. The normalized SMN2mini FL abundance from test compound-treated samples is then divided by normalized SMN2mini FL abundance from vehicle-treated cells to determine the level of SMN2 FL mRNA relative to vehicle control.

Figure 3A:
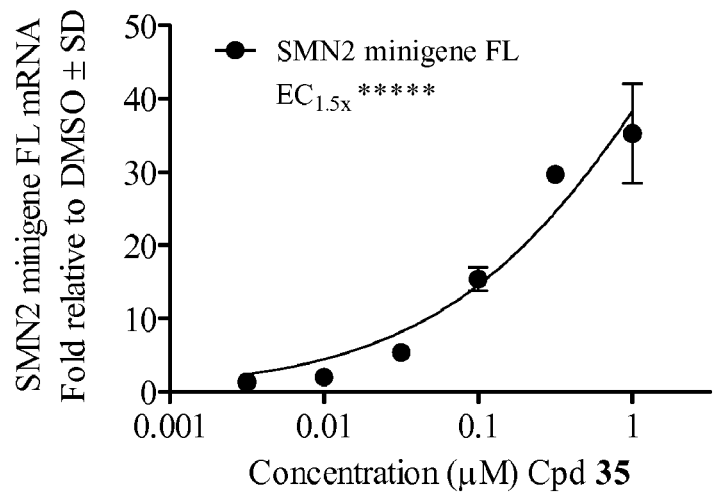
FIG. 3, referenced in Biological Example 2, shows the correction of SMN2 minigene alternative splicing in cells treated with rising concentrations of Compound 35 (FIG. 3a) and Compound 626 (FIG. 3b) over a 24 hr period. The levels of full length SMN2 minigene mRNA were quantified using reverse transcription-quantitative PCR (RT-qPCR). The level of full length SMN2 minigene mRNA in compound-treated samples was normalized to that in vehicle-treated samples and plotted as a function of the compound concentration.
Figure 3B:
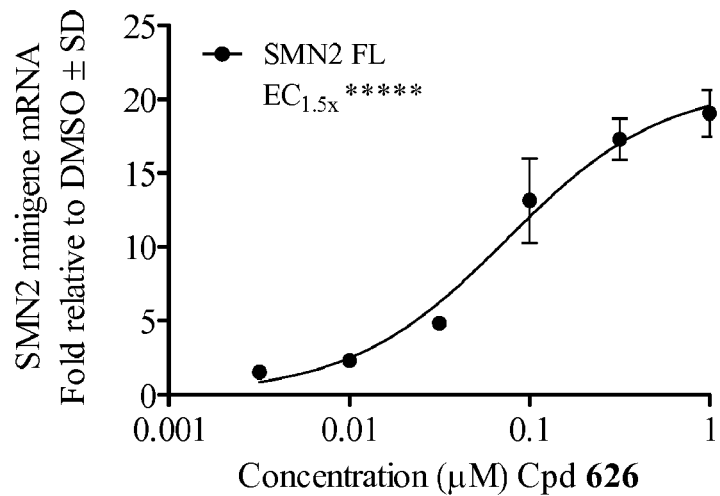

Results. As seen in FIG. 3, cells treated with Compound 35 (FIG. 3a) and Compound 626 (FIG. 3b) increased SMN2mini FL mRNA at low concentrations. The two test compounds fully restored exon 7 inclusion relative to untreated cells.

For compounds of Formula (I) or a form thereof disclosed herein, Table 4 provides the $EC_{1.5x}$ for production of full length SMN2 mRNA that was obtained from the 7-point concentration data generated for each test compound according to the procedure of Biological Example 2. The term "$EC_{1.5x}$ for production of full length SMN2 mRNA" is defined as that concentration of test compound that is effective in increasing the amount of full length SMN2 mRNA to a level 1.5-fold greater relative to that in vehicle-treated cells. An $EC_{1.5x}$ for production of full length SMN2 mRNA between >3 µM and ≤30 µM is indicated by one star (*), an $EC_{1.5x}$ between >1 µM and ≤3 µM is indicated by two stars (), an $EC_{1.5x}$ between >0.3 µM and ≤1 µM is indicated by three stars (*), an $EC_{1.5x}$ between >0.1 µM and ≤0.3 µM is indicated by four stars (**) and an $EC_{1.5x}$≤0.1 µM is indicated by five stars (***).

TABLE 4

| Cpd | $EC_{1.5x}$ |
| --- | --- |
| 1 | *** |
| 2 | *** |
| 3 | ** |
| 4 | ** |
| 5 | *** |
| 6 | ** |
| 7 | * |
| 8 | ** |
| 9 | * |
| 10 | *** |
| 11 | * |
| 12 | * |
| 13 | ** |
| 14 | *** |
| 15 | * |
| 16 | *** |
| 17 | *** |
| 18 | *** |
| 19 | ** |
| 20 | * |
| 21 | * |
| 22 | * |
| 23 | ** |
| 24 | ** |
| 25 | *** |
| 26 | ** |
| 27 | ** |
| 28 | * |
| 29 | * |
| 30 | ** |
| 31 | * |
| 32 | * |
| 33 | * |
| 34 | *** |
| 35 | *** |
| 36 | ** |
| 37 | ** |
| 38 | ** |
| 39 | *** |
| 40 | ** |
| 41 | ** |
| 42 | ** |
| 43 | * |
| 44 | *** |
| 45 | * |
| 46 | *** |
| 47 | * |
| 48 | ** |
| 49 | * |
| 50 | ** |
| 51 | **** |
| 52 | *** |
| 53 | * |
| 54 | ** |
| 55 | ** |
| 56 | * |
| 57 | ** |
| 58 | ** |
| 59 | ** |
| 60 | ** |
| 61 | * |
| 62 | ** |
| 63 | ** |
| 64 | ** |
| 65 | *** |
| 66 | * |
| 67 | *** |
| 68 | ** |
| 69 | **** |
| 70 | *** |
| 71 | ** |
| 72 | *** |
| 73 | * |
| 74 | * |
| 75 | * |
| 76 | ** |
| 77 | * |
| 78 | *** |
| 79 | ** |
| 80 | * |
| 81 | *** |
| 82 | ** |
| 83 | *** |
| 84 | *** |
| 85 | * |
| 86 | * |
| 87 | *** |
| 88 | ***** |
| 89 | **** |
| 90 | *** |
| 91 | *** |
| 92 | ** |
| 93 | ** |
| 94 | * |
| 95 | ** |
| 96 | **** |
| 97 | ** |
| 98 | ** |
| 99 | * |
| 100 | *** |
| 101 | ** |
| 102 | ** |
| 103 | *** |
| 104 | * |
| 105 | ** |
| 106 | * |
| 107 | **** |
| 108 | ** |
| 109 | ** |
| 110 | * |
| 111 | * |
| 112 | * |
| 113 | * |
| 114 | ***** |
| 115 | *** |
| 116 | *** |
| 117 | **** |
| 118 | **** |

TABLE 4-continued

| Cpd | EC$_{1.5x}$ |
|---|---|
| 119 | *** |
| 120 | ***** |
| 121 | *** |
| 122 | ** |
| 123 | ** |
| 124 | *** |
| 125 | ** |
| 126 | * |
| 127 | ** |
| 128 | ** |
| 129 | *** |
| 130 | ** |
| 131 | *** |
| 132 | ** |
| 133 | **** |
| 134 | *** |
| 135 | *** |
| 136 | ** |
| 137 | ** |
| 138 | ** |
| 139 | ** |
| 140 | *** |
| 141 | ** |
| 142 | ** |
| 143 | ** |
| 144 | ** |
| 145 | **** |
| 146 | *** |
| 147 | ** |
| 148 | * |
| 149 | ** |
| 150 | *** |
| 151 | * |
| 152 | ***** |
| 153 | ** |
| 154 | * |
| 155 | * |
| 156 | ** |
| 157 | **** |
| 158 | ** |
| 159 | *** |
| 160 | *** |
| 161 | ** |
| 162 | **** |
| 163 | * |
| 164 | ** |
| 165 | * |
| 166 | ** |
| 167 | *** |
| 168 | ** |
| 169 | *** |
| 170 | *** |
| 171 | * |
| 172 | * |
| 173 | *** |
| 174 | ***** |
| 175 | * |
| 176 | ** |
| 177 | * |
| 178 | * |
| 179 | ** |
| 180 | ***** |
| 181 | ***** |
| 182 | ** |
| 183 | *** |
| 184 | *** |
| 185 | * |
| 186 | **** |
| 187 | *** |
| 188 | *** |
| 189 | ** |
| 190 | ** |
| 191 | *** |
| 192 | *** |
| 193 | **** |
| 194 | *** |
| 195 | ** |
| 196 | ** |
| 197 | *** |
| 198 | *** |
| 199 | ** |
| 200 | * |
| 201 | *** |
| 202 | *** |
| 203 | **** |
| 204 | **** |
| 205 | ***** |
| 206 | *** |
| 207 | ** |
| 208 | ** |
| 209 | *** |
| 210 | *** |
| 211 | *** |
| 212 | *** |
| 213 | **** |
| 214 | *** |
| 215 | ** |
| 216 | *** |
| 217 | *** |
| 218 | *** |
| 219 | * |
| 220 | **** |
| 221 | ** |
| 222 | ** |
| 223 | *** |
| 224 | *** |
| 225 | *** |
| 226 | * |
| 227 | **** |
| 228 | **** |
| 229 | **** |
| 230 | *** |
| 231 | *** |
| 232 | *** |
| 233 | **** |
| 234 | * |
| 235 | ** |
| 236 | ** |
| 237 | ** |
| 238 | ** |
| 239 | ** |
| 240 | ** |
| 241 | *** |
| 242 | *** |
| 243 | *** |
| 244 | *** |
| 245 | **** |
| 246 | **** |
| 247 | **** |
| 248 | **** |
| 249 | *** |
| 250 | **** |
| 251 | * |
| 252 | * |
| 253 | ** |
| 254 | *** |
| 255 | * |
| 256 | * |
| 257 | ** |
| 258 | *** |
| 259 | ** |
| 260 | *** |
| 261 | *** |
| 262 | *** |
| 263 | * |
| 264 | ** |
| 265 | ** |
| 266 | ** |
| 267 | ** |
| 268 | *** |
| 269 | ** |
| 270 | ** |
| 271 | ** |
| 272 | ** |
| 273 | ** |
| 274 | ** |

TABLE 4-continued

| Cpd | $EC_{1.5x}$ |
|---|---|
| 275 | *** |
| 276 | *** |
| 277 | *** |
| 278 | *** |
| 279 | ** |
| 280 | **** |
| 281 | *** |
| 282 | ** |
| 283 | *** |
| 284 | ** |
| 285 | ** |
| 286 | ** |
| 287 | *** |
| 288 | ** |
| 289 | *** |
| 290 | *** |
| 291 | *** |
| 292 | *** |
| 293 | *** |
| 294 | **** |
| 295 | ***** |
| 296 | **** |
| 297 | * |
| 298 | ** |
| 299 | ** |
| 300 | ** |
| 301 | ** |
| 302 | **** |
| 303 | *** |
| 304 | **** |
| 305 | *** |
| 306 | **** |
| 307 | *** |
| 308 | * |
| 309 | *** |
| 310 | *** |
| 311 | ***** |
| 312 | *** |
| 313 | *** |
| 314 | ** |
| 315 | *** |
| 316 | *** |
| 317 | * |
| 318 | ** |
| 319 | ** |
| 320 | ** |
| 321 | ** |
| 322 | *** |
| 323 | *** |
| 324 | *** |
| 325 | *** |
| 326 | **** |
| 327 | *** |
| 328 | *** |
| 329 | *** |
| 330 | *** |
| 331 | *** |
| 332 | *** |
| 333 | *** |
| 334 | **** |
| 335 | **** |
| 336 | *** |
| 337 | ** |
| 338 | **** |
| 339 | **** |
| 340 | *** |
| 341 | *** |
| 342 | **** |
| 343 | **** |
| 344 | *** |
| 345 | ** |
| 346 | * |
| 347 | * |
| 348 | ** |
| 349 | ** |
| 350 | ** |
| 351 | *** |
| 352 | **** |

TABLE 4-continued

| Cpd | $EC_{1.5x}$ |
|---|---|
| 353 | ***** |
| 354 | ***** |
| 355 | ***** |
| 356 | ***** |
| 357 | **** |
| 358 | ** |
| 359 | * |
| 360 | ** |
| 361 | ** |
| 362 | *** |
| 363 | ** |
| 364 | ** |
| 365 | ** |
| 366 | *** |
| 367 | **** |
| 368 | *** |
| 369 | **** |
| 370 | *** |
| 371 | *** |
| 372 | **** |
| 373 | ***** |
| 374 | ** |
| 375 | *** |
| 376 | ** |
| 377 | *** |
| 378 | **** |
| 379 | *** |
| 380 | *** |
| 381 | ** |
| 382 | ** |
| 383 | **** |
| 384 | * |
| 385 | ** |
| 386 | * |
| 387 | * |
| 388 | *** |
| 389 | *** |
| 390 | **** |
| 391 | ** |
| 392 | *** |
| 393 | *** |
| 394 | * |
| 395 | *** |
| 396 | ** |
| 397 | * |
| 398 | ** |
| 399 | * |
| 400 | * |
| 401 | ** |
| 402 | * |
| 403 | * |
| 404 | *** |
| 405 | * |
| 406 | * |
| 407 | *** |
| 408 | *** |
| 409 | ** |
| 410 | ***** |
| 411 | * |
| 412 | * |
| 413 | ** |
| 414 | * |
| 415 | * |
| 416 | ** |
| 417 | **** |
| 418 | ** |
| 419 | *** |
| 420 | ***** |
| 421 | ***** |
| 422 | *** |
| 423 | ** |
| 424 | **** |
| 425 | **** |
| 426 | **** |
| 427 | *** |
| 428 | ** |
| 429 | *** |
| 430 | ** |

TABLE 4-continued

| Cpd | EC$_{1.5x}$ |
|---|---|
| 431 | ** |
| 432 | ** |
| 433 | * |
| 434 | ** |
| 435 | ** |
| 436 | * |
| 437 | ** |
| 438 | **** |
| 439 | * |
| 440 | ** |
| 441 | ***** |
| 442 | * |
| 443 | ***** |
| 444 | * |
| 445 | * |
| 446 | * |
| 447 | ** |
| 448 | ** |
| 449 | ** |
| 450 | ** |
| 451 | ** |
| 452 | * |
| 453 | * |
| 454 | ***** |
| 455 | ***** |
| 456 | ***** |
| 457 | **** |
| 458 | *** |
| 459 | ***** |
| 460 | **** |
| 461 | * |
| 462 | ***** |
| 463 | **** |
| 464 | **** |
| 465 | * |
| 466 | * |
| 467 | * |
| 468 | *** |
| 469 | **** |
| 470 | ** |
| 471 | **** |
| 472 | ** |
| 473 | **** |
| 474 | ** |
| 475 | * |
| 476 | ***** |
| 477 | ***** |
| 478 | *** |
| 479 | *** |
| 480 | * |
| 481 | ** |
| 482 | ***** |
| 483 | **** |
| 484 | *** |
| 485 | ** |
| 486 | * |
| 487 | * |
| 488 | * |
| 489 | * |
| 490 | ** |
| 491 | ** |
| 492 | ** |
| 493 | ***** |
| 494 | **** |
| 495 | ** |
| 496 | *** |
| 497 | *** |
| 498 | *** |
| 499 | *** |
| 500 | *** |
| 501 | **** |
| 502 | ** |
| 503 | *** |
| 504 | ** |
| 505 | * |
| 506 | **** |
| 507 | **** |
| 508 | *** |

TABLE 4-continued

| Cpd | EC$_{1.5x}$ |
|---|---|
| 509 | ** |
| 510 | * |
| 511 | ** |
| 512 | ** |
| 513 | ** |
| 514 | * |
| 515 | ***** |
| 516 | ***** |
| 517 | ***** |
| 518 | ***** |
| 519 | ***** |
| 520 | *** |
| 521 | *** |
| 522 | *** |
| 523 | *** |
| 524 | *** |
| 525 | **** |
| 526 | **** |
| 527 | **** |
| 528 | ** |
| 529 | ** |
| 530 | *** |
| 531 | *** |
| 532 | *** |
| 533 | ***** |
| 534 | ** |
| 535 | ** |
| 536 | ***** |
| 537 | ***** |
| 538 | * |
| 539 | * |
| 540 | * |
| 541 | ** |
| 542 | ** |
| 543 | ** |
| 544 | **** |
| 545 | **** |
| 546 | * |
| 547 | * |
| 548 | * |
| 549 | ** |
| 550 | ***** |
| 551 | *** |
| 552 | ***** |
| 553 | *** |
| 554 | ***** |
| 555 | **** |
| 556 | **** |
| 557 | *** |
| 558 | ***** |
| 559 | *** |
| 560 | **** |
| 561 | *** |
| 562 | ***** |
| 563 | ***** |
| 564 | ***** |
| 565 | ** |
| 566 | ***** |
| 567 | ***** |
| 568 | ***** |
| 569 | ***** |
| 570 | ***** |
| 571 | *** |
| 572 | **** |
| 573 | *** |
| 574 | ** |
| 575 | *** |
| 576 | ** |
| 577 | ** |
| 578 | ** |
| 579 | *** |
| 580 | ** |
| 581 | *** |
| 582 | *** |
| 583 | *** |
| 584 | ***** |
| 585 | *** |
| 586 | ***** |

TABLE 4-continued

| Cpd | EC$_{1.5x}$ |
|---|---|
| 587 | ***** |
| 588 | ***** |
| 589 | ***** |
| 590 | ***** |
| 591 | ***** |
| 592 | ***** |
| 593 | ***** |
| 594 | ***** |
| 595 | *** |
| 596 | *** |
| 597 | ***** |
| 598 | **** |
| 599 | **** |
| 600 | ***** |
| 601 | ***** |
| 602 | *** |
| 603 | *** |
| 604 | *** |
| 605 | ***** |
| 606 | ***** |
| 607 | ***** |
| 608 | ***** |
| 609 | ***** |
| 610 | *** |
| 611 | *** |
| 612 | *** |
| 613 | *** |
| 614 | ***** |
| 615 | ***** |
| 616 | **** |
| 617 | ***** |
| 618 | ***** |
| 619 | ***** |
| 620 | ***** |
| 621 | ***** |
| 622 | ***** |
| 623 | ***** |
| 624 | ***** |
| 625 | ***** |
| 626 | ***** |
| 627 | ***** |
| 628 | ***** |
| 629 | *** |
| 630 | *** |
| 631 | *** |
| 632 | ***** |
| 633 | ***** |
| 634 | ***** |
| 635 | ***** |
| 636 | ***** |
| 637 | ***** |
| 638 | ***** |
| 639 | ***** |
| 640 | ***** |
| 641 | *** |
| 642 | ***** |
| 643 | ***** |
| 644 | ***** |
| 645 | ***** |
| 646 | ***** |
| 647 | ***** |
| 648 | ***** |
| 649 | **** |
| 650 | ***** |
| 651 | ***** |
| 652 | ***** |
| 653 | **** |
| 654 | ***** |
| 655 | ***** |
| 656 | ***** |
| 657 | ***** |
| 658 | ***** |
| 659 | ***** |
| 660 | ***** |
| 661 | ***** |
| 662 | ***** |
| 663 | ***** |
| 664 | ***** |

TABLE 4-continued

| Cpd | EC$_{1.5x}$ |
|---|---|
| 665 | ***** |
| 666 | ***** |
| 667 | ***** |
| 668 | ***** |
| 669 | ***** |
| 670 | ***** |
| 671 | ***** |
| 672 | ***** |
| 673 | ***** |
| 674 | ***** |
| 675 | ***** |
| 676 | ***** |
| 677 | ***** |
| 678 | ***** |
| 679 | ***** |
| 680 | ***** |
| 681 | ***** |
| 682 | ***** |
| 683 | ***** |
| 684 | ***** |
| 685 | ***** |
| 686 | ***** |
| 687 | ***** |
| 688 | ***** |
| 689 | *** |
| 690 | **** |
| 691 | ***** |
| 692 | ***** |
| 693 | ***** |
| 694 | ***** |
| 695 | ***** |
| 696 | ***** |
| 697 | ***** |
| 698 | ** |
| 699 | **** |
| 700 | **** |
| 701 | ** |
| 702 | ** |
| 703 | ** |
| 704 | ***** |
| 705 | **** |
| 706 | ***** |
| 707 | ***** |
| 708 | ***** |
| 709 | ***** |
| 710 | ***** |
| 711 | ***** |
| 712 | ***** |
| 713 | ***** |
| 714 | **** |
| 715 | ***** |
| 716 | ***** |
| 717 | *** |
| 718 | ***** |
| 719 | ***** |
| 720 | *** |
| 721 | ** |
| 722 | ** |
| 723 | ***** |
| 724 | ** |
| 725 | ***** |
| 726 | ***** |
| 727 | **** |
| 728 | *** |
| 729 | ***** |
| 730 | ***** |
| 731 | ***** |
| 732 | ***** |
| 733 | ***** |
| 734 | ***** |
| 735 | ***** |
| 736 | ***** |
| 737 | ***** |
| 738 | ***** |
| 739 | ***** |
| 740 | ***** |
| 741 | ***** |
| 742 | ***** |

TABLE 4-continued

| Cpd | EC$_{1.5x}$ |
|---|---|
| 743 | ***** |
| 744 | ***** |
| 745 | ***** |
| 746 | ***** |
| 747 | ***** |
| 748 | ***** |
| 749 | ***** |
| 750 | ***** |
| 751 | ***** |
| 752 | ***** |
| 753 | ***** |
| 754 | ***** |
| 755 | ***** |
| 756 | ***** |
| 757 | *** |
| 758 | *** |
| 759 | ***** |
| 760 | **** |
| 761 | ***** |
| 762 | ***** |
| 763 | ***** |
| 764 | ***** |
| 765 | *** |
| 766 | ***** |
| 767 | ***** |
| 768 | ***** |
| 769 | *** |
| 770 | ***** |
| 771 | ** |
| 772 | ***** |
| 773 | ***** |
| 774 | ***** |
| 775 | ***** |
| 776 | ** |
| 777 | * |
| 778 | ***** |
| 779 | ***** |
| 780 | ***** |
| 781 | ***** |
| 782 | ***** |
| 783 | ***** |
| 784 | ** |
| 785 | ***** |
| 786 | ***** |
| 787 | ***** |
| 788 | ***** |
| 789 | ***** |
| 790 | *** |
| 791 | ***** |
| 792 | ***** |
| 793 | ***** |
| 794 | ***** |
| 795 | ***** |
| 796 | ***** |
| 797 | ***** |
| 798 | **** |
| 799 | ***** |
| 800 | ***** |
| 801 | ***** |
| 802 | ***** |
| 803 | ***** |
| 804 | ***** |
| 805 | ***** |
| 806 | ***** |
| 807 | ***** |
| 808 | ***** |
| 809 | *** |
| 810 | *** |
| 811 | *** |
| 812 | ***** |
| 813 | ***** |
| 814 | ***** |
| 815 | ***** |
| 816 | ***** |
| 817 | ***** |
| 818 | ** |
| 819 | ***** |
| 820 | *** |
| 821 | ***** |
| 822 | ***** |
| 823 | *** |
| 824 | ***** |
| 825 | ***** |
| 826 | ***** |
| 827 | ***** |
| 828 | **** |
| 829 | ***** |
| 830 | ***** |
| 831 | ** |
| 832 | ** |
| 833 | ***** |
| 834 | ***** |
| 835 | *** |
| 836 | *** |
| 837 | ***** |
| 838 | ***** |
| 839 | **** |
| 840 | *** |
| 841 | ***** |
| 842 | ***** |
| 843 | ***** |
| 844 | ***** |
| 845 | ** |
| 846 | **** |
| 847 | ** |
| 848 | ***** |
| 849 | **** |
| 850 | *** |
| 851 | ** |
| 852 | ***** |
| 853 | ** |
| 854 | ***** |
| 855 | ***** |
| 856 | ***** |
| 857 | ***** |
| 858 | ***** |
| 859 | **** |
| 860 | *** |
| 861 | ***** |
| 862 | ***** |
| 863 | **** |
| 864 | ***** |
| 865 | ***** |
| 866 | **** |
| 867 | ***** |
| 868 | ***** |
| 869 | ***** |
| 870 | ***** |
| 871 | ***** |
| 872 | **** |
| 873 | ***** |
| 874 | ***** |
| 875 | ***** |
| 876 | ***** |
| 877 | ***** |
| 878 | ***** |
| 879 | ***** |
| 880 | ***** |
| 881 | ***** |
| 882 | ***** |
| 883 | ***** |
| 884 | ***** |
| 885 | **** |
| 886 | *** |
| 887 | ***** |
| 888 | ***** |
| 889 | ***** |
| 890 | ***** |
| 891 | **** |
| 892 | ***** |
| 893 | ***** |
| 894 | ***** |
| 895 | ***** |
| 896 | ***** |
| 897 | ***** |
| 898 | ***** |

TABLE 4-continued

| Cpd | EC$_{1.5x}$ |
|---|---|
| 899 | ***** |
| 900 | ***** |
| 901 | ***** |
| 902 | ***** |
| 903 | ***** |
| 904 | **** |
| 905 | ** |
| 906 | ***** |
| 907 | ***** |
| 908 | **** |
| 909 | ***** |
| 910 | ***** |
| 911 | ***** |
| 912 | ***** |
| 913 | ***** |
| 914 | ***** |
| 915 | ***** |
| 916 | **** |
| 917 | ***** |
| 918 | ***** |
| 919 | ***** |
| 920 | ***** |
| 921 | ***** |
| 922 | ***** |
| 923 | ***** |
| 924 | ***** |
| 925 | ***** |
| 926 | ***** |
| 927 | ** |
| 928 | **** |
| 929 | ***** |
| 930 | ***** |
| 931 | ***** |
| 932 | ***** |
| 933 | ***** |
| 934 | ***** |
| 935 | **** |
| 936 | ***** |
| 937 | ***** |
| 938 | ***** |
| 939 | ***** |
| 940 | *** |
| 941 | ***** |
| 942 | ***** |
| 943 | ***** |
| 944 | ***** |
| 945 | ***** |
| 946 | ***** |
| 947 | ***** |
| 948 | ***** |
| 949 | ***** |
| 950 | **** |
| 951 | ***** |
| 952 | ***** |
| 953 | ***** |
| 954 | ***** |
| 955 | **** |
| 956 | **** |
| 957 | ***** |
| 958 | ***** |
| 959 | ***** |
| 960 | ***** |
| 961 | ***** |
| 962 | ***** |
| 963 | *** |
| 964 | **** |
| 965 | ***** |
| 966 | ***** |
| 967 | ***** |
| 968 | ***** |
| 969 | ***** |
| 970 | *** |
| 971 | ***** |
| 972 | *** |
| 973 | * |
| 974 | * |
| 975 | *** |
| 976 | ***** |
| 977 | ** |
| 978 | ** |
| 979 | ** |
| 980 | *** |
| 981 | **** |
| 982 | ***** |
| 983 | ***** |
| 984 | ***** |
| 985 | ***** |
| 986 | ***** |

Example 3

Endogenous SMN2 mRNA RT-qPCR Splicing Assay in Cultured Cells

The reverse transcription-quantitative PCR-based (RT-qPCR) assay is used to quantify the levels of the full length and Δ7 SMN2 mRNAs in primary cells and cell lines containing the SMN2 gene treated with a test compound.

Materials

| Material | Source |
|---|---|
| SMA Type 1 human cells | GM03813 (Coriell Institute) |
| Cells-To-Ct lysis buffer | Life Technologies, Inc. (formerly Applied Biosystems) Catalog No.: 4399002 |
| DMEM | Life Technologies, Inc. (formerly Invitrogen) Catalog No.: 11960-044 |
| 96-well flat-bottom plates | Becton Dickinson Catalog # 353072 |
| RT-PCR Enzyme Mix | Life Technologies, Inc. (formerly Applied Biosystems) part # 4388520 (also included in AgPath-ID kit Catalog No.: 4387391) |
| RT-PCR buffer | Life Technologies, Inc. (formerly Applied Biosystems) part # 4388519 (also included in AgPath-ID kit Catalog No.: 4387391) |
| AgPath-ID One-Step RT-PCR kit | Life Technologies, Inc. (formerly Applied Biosystems) Catalog No.: 4387391 |
| Thermocycler | Life Technologies, Inc. (formerly Applied Biosystems) 7900HT |

Protocol. GM03813 SMA patient cells (5,000 cells/well) are seeded in 200 μL, of cell culture medium (DMEM plus 10% FBS) in 96-well flat-bottom plates and the plate is immediately swirled to ensure proper dispersal of cells, forming an even monolayer of cells. Cells are allowed to attach for at least 4-6 hrs. Test compounds are serially diluted 3.16-fold in 100% DMSO to generate a 7-point concentration curve. A solution of test compound (1 μL, 200× in DMSO) is added to each test well and 1 μL, DMSO is added to each control well. The plate is incubated for 24 hrs in a cell culture incubator (37° C., 5% CO$_2$, 100% relative humidity). The cells are then lysed in Cells-To-Ct lysis buffer and the lysate is stored at −80° C.

SMN2-specific spliced products and GAPDH mRNA are identified using the following primers and probes in Table 5. Primer SMN FL Forward B (SEQ ID NO. 7) hybridizes to a nucleotide sequence in exon 7 (nucleotide 32 to nucleotide 54) and exon 8 (nucleotide 1 to nucleotide 4), primer SMN Δ7 Forward B (SEQ ID NO. 8) hybridizes to a nucleotide sequence in exon 6 (nucleotide 87 to nucleotide 111) and exon 8 (nucleotide 1 to nucleotide 3), primer SMN Reverse B (SEQ ID NO. 9) hybridizes to a nucleotide sequence in exon 8 (nucleotide 39 to nucleotide 62), probe SMN Probe B (SEQ ID NO. 10) hybridizes to a nucleotide sequence in exon 8 (nucleotide 7 to nucleotide 36). These primers and probe hybridize to nucleotide sequences common to human SMN1 and SMN2 mRNAs. Since the SMA patient cells used in Example 3 contain only the SMN2 gene, RT-qPCR can quantify only SMN2 full-length and Δ7 mRNA.

TABLE 5

| Primer/Probe | Sequence | Source |
|---|---|---|
| SMN FL Forward Primer B | SEQ ID NO. 7: GCTCACATTCCTTAAATTAAGG AGAAA | PTC[1] |
| SMN Δ7 Forward Primer B | SEQ ID NO. 8: TGGCTATCATACTGGCTATTAT ATGGAA | PTC[1] |
| SMN Reverse Primer B | SEQ ID NO. 9: TCCAGATCTGTCTGATCGTTTC TT | PTC[1] |
| SMN Forward Probe B | SEQ ID NO. 10: 6FAM-CTGGCATAGAGCAGCACT AAATGACACCAC-TAMRA | PTC[1] |
| hGAPDH Forward Probe | SEQ ID NO. 4: VIC-CGCCTGGTCACCAGGGCT GCT-TAMRA | LTI[2] |
| hGAPDH Forward Primer | SEQ ID NO. 5: CAACGGATTTGGTCGTATTGG | LTI[2] |
| hGAPDH Reverse Primer | SEQ ID NO. 6: TGATGGCAACAATATCCACTTT ACC | LTI[2] |

[1]Primers and probes designed by PTC Therapeutics, Inc.;
[2]Commercially available from Life Technologies, Inc. (formerly Invitrogen).

The SMN forward and reverse primers are used at final concentrations of 0.4 μM. The SMN probe is used at a final concentration of 0.15 μM. GAPDH primers are used at final concentrations of 0.1 μM and the probe at 0.075 μM. TaqMan gene expression assays were conducted at 20× concentrations with the GAPDH primers and Vic labeled probe provided as a 20× mixture. The One-Step RT-PCR kit was used as the Real-Time PCR Mix.

The SMN-GAPDH mix (10 μL total volume) is prepared by combining 5 μL of 2×RT-PCR buffer, 0.4 μL of 25×RT-PCR enzyme mix, 0.25 μL of 20×GAPDH primer-probe mix, 1.755 μL water, 2.5 μL of cell lysate, 0.04 μL of 100 μM SMN FL or SMN Δ7 forward primer, 0.04 μL of 100 μM SMN reverse primer, and 0.015 μL of 100 μM probe.

PCR is carried out at the following temperatures for indicated time: Step 1: 48° C. (15 min); Step 2: 95° C. (10 min); Step 3: 95° C. (15 sec); Step 4: 60° C. (1 min); then, repeat Steps 3 and 4 for a total of 40 cycles.

Each reaction mixture contains either SMN2 FL and GAPDH or SMN2 Δ7 and GAPDH primers/probe sets (multiplex design), allowing simultaneous measurement of the levels of two transcripts.

The endogenous SMN2 gene gives rise to two alternatively spliced mRNAs. The full length SMN2 mRNA contains exon 7 and termed SMN2 FL. The truncated mRNA lacks exon 7 and termed SMN2 Δ7.

The increase of SMN2 FL and decrease in SMN2 Δ7 mRNAs relative to those in cells treated with vehicle control are determined from real-time PCR data using a modified ΔΔCt method (as described in Livak and Schmittgen, Methods, 2001, 25:402-8). The amplification efficiency E is calculated from the slope of the amplification curve for SMN2 FL, SMN2 Δ7, and GAPDH individually. The abundances of SMN2 FL, SMN2 Δ7, and GAPDH are then calculated as $(1+E)^{-Ct}$, where Ct is the threshold value for each amplicon. The abundances of SMN2 FL and SMN2 Δ7 are normalized to GAPDH abundance. The normalized SMN2 FL and SMN2 Δ7 abundances from test compound-treated samples are then divided by normalized SMN2 FL and SMN2 Δ7 abundances, respectively, from vehicle-treated cells to determine the levels of SMN2 FL and SMN2 Δ7 mRNAs relative to vehicle control.

Figure 4A:
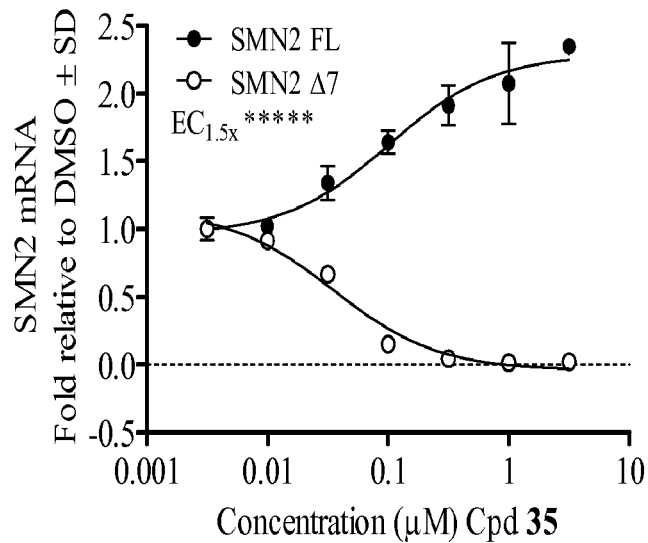
FIG. 4, referenced in Biological Example 3, shows the correction of SMN2 alternative splicing in Type 1 SMA patient fibroblasts treated with rising concentrations of Compound 35 (FIG. 4a) and Compound 626 (FIG. 4b) over a 24 hr period. The levels of full length and Δ7 SMN2 mRNAs were quantified using RT-qPCR. The levels of full length and Δ7 SMN2 mRNAs in compound-treated samples were normalized to those in vehicle-treated samples and plotted as a function of the compound concentration.
Figure 4B:
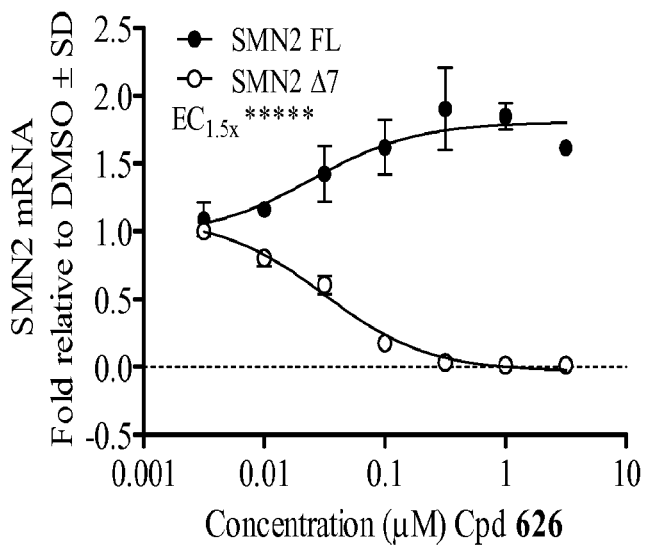

Results. As seen in FIG. 4, cells treated with increasing concentrations of Compound 35 (FIG. 4a) and Compound 626 (FIG. 4b) contain progressively more SMN2 FL mRNA and less SMN2 Δ7 mRNA than those treated with vehicle indicating a correction of SMN2 alternative splicing.

Example 4

Endogenous SMN2 mRNA End-Point Semi-Quantitative RT-PCR Splicing Assay in Cultured Cells The endpoint reverse transcription-PCR splicing assay is used to visualize and quantify the levels of the full length and Δ7 SMN2 mRNAs in primary cells and cell lines containing the SMN2 gene treated with a test compound.

Materials

| Material | Source |
|---|---|
| SMA Type 1 human cells | GM03813 (Coriell Institute) |
| Cells-To-Ct lysis buffer | Life Technologies, Inc. (formerly Applied Biosystems) Catalog No.: 4399002 |
| DMEM | Life Technologies, Inc. (formerly Invitrogen) Catalog No.: 11960-044 |
| 96-well flat-bottom plates | Becton Dickinson Catalog No.: 353072 |
| Platinum Taq HiFi DNA Polymerase Super Mix | Life Technologies, Inc. (formerly Invitrogen) Catalog No.: 11304-016 |
| iScript RT enzyme kit | BioRad Catalog No.: 170-8890 |
| Ethidium bromide 2% agarose E gels 48-Well Double Comb | Life Technologies, Inc. (formerly Invitrogen) Catalog No.: G8008-02 |
| Gel Documentation System | UVP Gel Doc It 310 Imaging system |

Protocol. GM03813 SMA patient cells (5,000 cells/well) are seeded in 200 μL of cell culture medium (DMEM plus 10% FBS) in 96-well flat-bottom plates and the plate is immediately swirled to ensure proper dispersal of cells, forming an even monolayer of cells. Cells are allowed to attach for at least 4-6 hrs. Test compounds are serially diluted 3.16-fold in 100% DMSO to generate a 7-point concentration curve. A solution of test compound (1 μL, 200× in DMSO) is added to each test well and 1 μL DMSO is added to each control well. The plate is incubated for 24 hrs in a cell culture incubator (37° C., 5% $CO_2$, 100% relative humidity). The cells are then lysed in Cells-To-Ct lysis buffer and the lysate is stored at −80° C.

SMN FL and Δ7 mRNAs are identified using the following primers in Table 6. These primers hybridize to a nucleotide sequence in exon 6 (SMN Forward C, SEQ ID NO. 11) (nucleotide 43 to nucleotide 63) and exon 8 (SMN Reverse C, SEQ ID NO. 12) (nucleotide 51 to nucleotide 73) common to human SMN1 and SMN2 mRNAs. Since the SMA patient cells used in Example 4 contain only the SMN2 gene, RT-PCR can visualize and quantify only SMN2 full-length and SMN2 Δ7 mRNAs.

TABLE 6

| Primer | Sequence | Source |
|---|---|---|
| SMN Forward C | SEQ ID NO. 11: GATGCTGATGCTTTGGGAAGT | PTC[1] |
| SMN Reverse C | SEQ ID NO. 12: CGCTTCACATTCCAGATCTGTC | PTC[1] |

[1]Primers designed by PTC Therapeutics, Inc.

To synthesize cDNA, 5 µL of lysate, 4 µL of 5× iScript reaction mix, 1 µL of reverse transcriptase, and 10 µL of water are combined and incubated 5 min at 25° C. followed by 30 min at 42° C., followed by 5 min at 85° C. cDNA solution is stored at −20° C.

To perform endpoint PCR, 5 µL of cDNA, 0.2 µL of 100 µM forward primer, 0.2 µL of 100 µM reverse primer, and 22.5 µL of polymerase super mix are combined in a 96 well semiskirted PCR plate. PCR is carried out at the following temperatures for indicated time: Step 1: 94° C. (2 min), Step 2: 94° C. (30 sec), Step 3: 55° C. (30 sec), Step 4: 68° C. (1 min), then repeat Steps 2 to 4 for a total of 33 cycles, then hold at 4° C.

10 µL of each PCR sample is electrophoretically separated on a 2% agarose E-gel for 14 minutes stained with ds DNA staining reagents (e.g., ethidium bromide) and visualized using a gel imager.

Figure 5A:
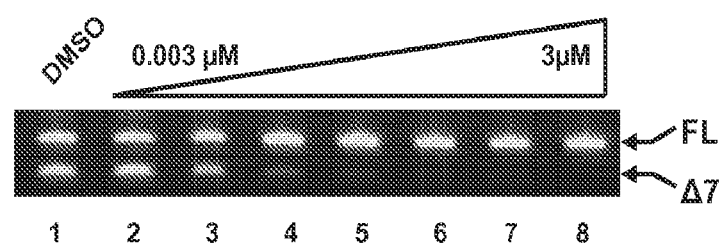
FIG. 5, referenced in Biological Example 4, shows the correction of SMN2 alternative splicing in Type 1 SMA patient fibroblasts treated with rising concentrations of Compound 35 (FIG. 5a) and Compound 626 (FIG. 5b) over a 24 hr period. The full length and Δ7 SMN2 mRNAs were amplified using reverse transcription-end point PCR (RT-PCR) and PCR products were separated using agarose gel electrophoresis. The top and bottom bands correspond to the full length and Δ7 SMN2 mRNAs respectively. The intensity of each band is proportional to the amount of RNA present in the sample.
Figure 5B:
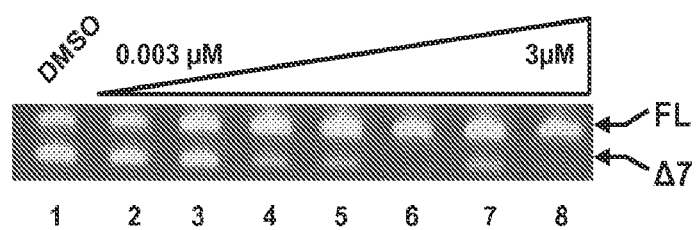

Results. As seen in FIG. 5, cells treated with increasing concentrations of Compound 35 (FIG. 5a) and Compound 626 (FIG. 5b) contain progressively more SMN2 FL mRNA and less SMN2 Δ7 mRNA indicating a correction of SMN2 alternative splicing.

Example 5

SMN2 mRNA RT-qPCR Splicing Assay in Animal Tissues

The reverse transcription-quantitative PCR-based (RT-qPCR) assay is used to quantify the levels of the full length and Δ7 SMN2 mRNAs in tissues from mice treated with test compound.

Materials

| Material | Source |
|---|---|
| Tissues from C/C-allele SMA mice | The Jackson Laboratory, strain # 008714 (B6.129-Smn1$^{tm5(Smn1/SMN2)Mrph}$/J) |
| Tissues from Δ7 SMA mice | The Jackson Laboratory, strain # 005025 (FVB.Cg-Tg(SMN2*delta7)4299Ahmb Tg(SMN2)89Ahmb Smn1$^{tm1Msd}$/J) |
| RT-PCR Enzyme Mix | Life Technologies, Inc. (formerly Applied Biosystems) part # 4388520 (also included in AgPath-ID kit Catalog No.: 4387391) |
| RT-PCR buffer | Life Technologies, Inc. (formerly Applied Biosystems) part # 4388519 (also included in AgPath-ID kit Catalog No.: 4387391) |
| AgPath-ID One-Step RT-PCR kit | Life Technologies, Inc. (formerly Applied Biosystems) Catalog No.: 4387391 |
| Mouse GAPDH primers and probes | Life Technologies, Inc. (formerly Applied Biosystems) Catalog No.: 4352339E |
| QIAzol Lysis Reagent | Qiagen Catalog No.: 79306 |
| RNeasy Lipid Tissue Mini Kit | Qiagen Catalog No.: 74804 |
| 5 mm Stainless Steel Bead | Qiagen Catalog No.: 69989 |
| TissueLyzer II | Qiagen Catalog No.: 85300 |
| Thermocycler | Life Technologies, Inc. (formerly Applied Biosystems) 7900HT |

Protocol. C/C-allele SMA mice are treated by oral gavage two times per day for 10 days with test compounds re-suspended in 0.5% HPMC and 0.1% Tween-80. Tissue samples were collected and snap frozen for RNA purification.

Tissue samples (20-40 mg) are homogenized in QIAzol Lysis Reagent for 2 minutes at 20 Hz in the TissueLyser II using one stainless steel bead. After addition of chloroform, the homogenate is separated into aqueous and organic phases by centrifugation. RNA partitioned to the upper, aqueous phase is extracted and ethanol is added to provide appropriate binding conditions. The sample is then applied to the RNeasy spin column from the RNeasy Mini Kit, where total RNA binds to the membrane. The RNA is eluted in RNase-free water then stored at −20° C. and subsequently analyzed using the TaqMan RT-qPCR on the 7900HT Thermocycler. Total RNA is diluted ten fold and 2.5 µL of the diluted sample is added to the TaqMan RT-qPCR mixture.

SMN2 spliced products are identified using the following primers and probes in Table 7. Primer SMN FL Forward B (SEQ ID NO. 7) hybridizes to a nucleotide sequence in exons 7 and 8, primer SMN Δ7 Forward B (SEQ ID NO. 8) hybridizes to a nucleotide sequence in exons 6 and 8, primer SMN Reverse B (SEQ ID NO. 9) hybridizes to a nucleotide sequence in exon 8, probe SMN Probe B (SEQ ID NO. 10) hybridizes to a nucleotide sequence in exon 8. These primers and probe hybridize to nucleotide sequences common to human SMN1 and SMN2 mRNAs. Since the SMA patient cells used in Example 5 contain only the SMN2 gene, RT-qPCR can quantify only SMN2 full-length and Δ7 mRNAs.

TABLE 7

| Primer/Probe | Sequence | Source |
|---|---|---|
| SMN FL Forward Primer B | SEQ ID NO. 7: GCTCACATTCCTTAAATTAAGG AGAAA | PTC[1] |
| SMN Δ7 Forward Primer B | SEQ ID NO.8: TGGCTATCATACTGGCTATTAT ATGGAA | PTC[1] |
| SMN Reverse Primer B | SEQ ID NO. 9: TCCAGATCTGTCTGATCGTTTC TT | PTC[1] |
| SMN Forward Probe B | SEQ ID NO. 10: 6FAM-CTGGCATAGAGCAGCAC TAAATGACACCAC-TAMRA | PTC[1] |

[1]Primers and probes designed by PTC Therapeutics, Inc.

The SMN forward and reverse primers are used at final concentrations of 0.4 µM. The SMN probe is used at a final concentration of 0.15 µM. The SMN-GAPDH Mix (10 µL total volume) is prepared by combining 5 µL of 2×RT-PCR buffer, 0.4 µL of 25×RT-PCR enzyme mix, 0.5 µL of 20×GAPDH primer-probe mix, 1.505 μL of water, 2.5 μL of RNA solution, 0.04 μL of 100 μM forward primer, 0.04 μL of 100 μM reverse primer, and 0.015 μL of 100 μM SMN probe.

Each PCR cycle was carried out at the following temperatures for indicated time: Step 1: 48° C. (15 min); Step 2: 95° C. (10 min); Step 3: 95° C. (15 sec); Step 4: 60° C. (1 min); then, repeat Steps 3 and 4 for a total of 40 cycles.

Each reaction mixture contains either SMN2 FL and mGAPDH or SMN2 Δ7 and mGAPDH primers/probe sets (multiplex design), allowing simultaneous measurement of the levels of two transcripts.

The increase of SMN2 FL and decrease in SMN2 Δ7 mRNAs relative to those in tissues from animals treated with vehicle control are determined from real-time PCR data using a modified ΔΔCt method (as described in Livak and Schmittgen, Methods, 2001, 25:402-8). The amplification efficiency E is calculated from the slope of the amplification curve for SMN2 FL, SMN2 Δ7, and GAPDH individually. The abundances of SMN2 FL, SMN2 Δ7, and GAPDH are then calculated as $(1+E)^{-Ct}$, where Ct is the threshold value for each amplicon. The abundances of SMN2 FL and SMN2 Δ7 are normalized to GAPDH abundance. The normalized SMN2 FL and SMN2 Δ7 abundances from test compound-treated samples are then divided by normalized SMN2 FL and SMN2 Δ7 abundances, respectively, from vehicle-treated cells to determine the levels of SMN2 FL and SMN2 Δ7 mRNAs relative to vehicle control.

Figure 6A:
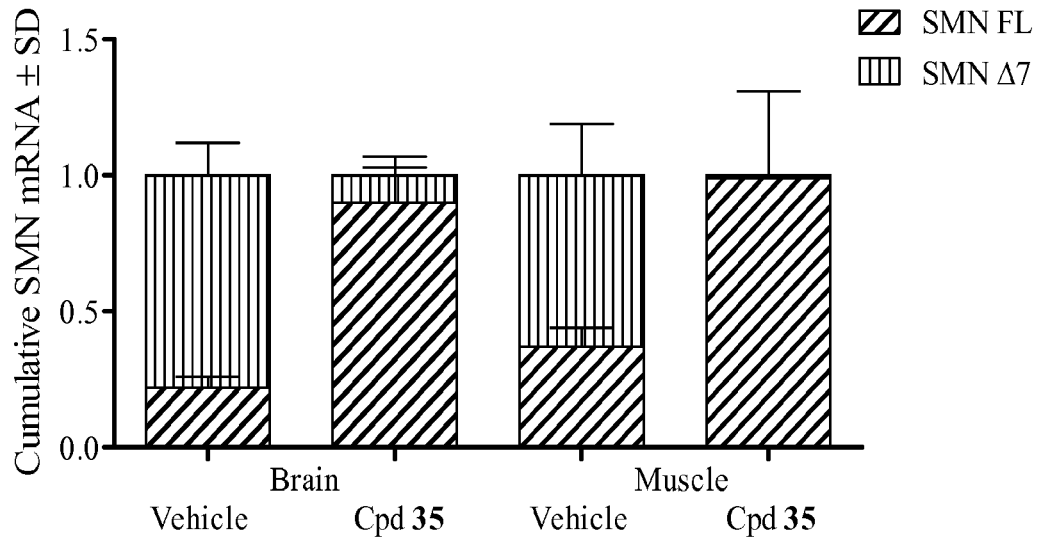
FIG. 6, referenced in Biological Example 5, shows the correction of SMN2 alternative splicing (in both the SMN2 gene and the hybrid mouse Smn1-SMN2 gene) in brain and muscle tissues of C/C-allele SMA mouse model treated for 10 days twice per day with 10 mg/kg of Compound 35 (FIG. 6a) and Compound 626 (FIG. 6b). The levels of full length and Δ7 SMN2 mRNAs were quantified using RT-qPCR, the combined full length and Δ7 SMN2 mRNA quantity was set to 1, and fractional quantities of full length and Δ7 SMN2 were calculated.
Figure 6B:
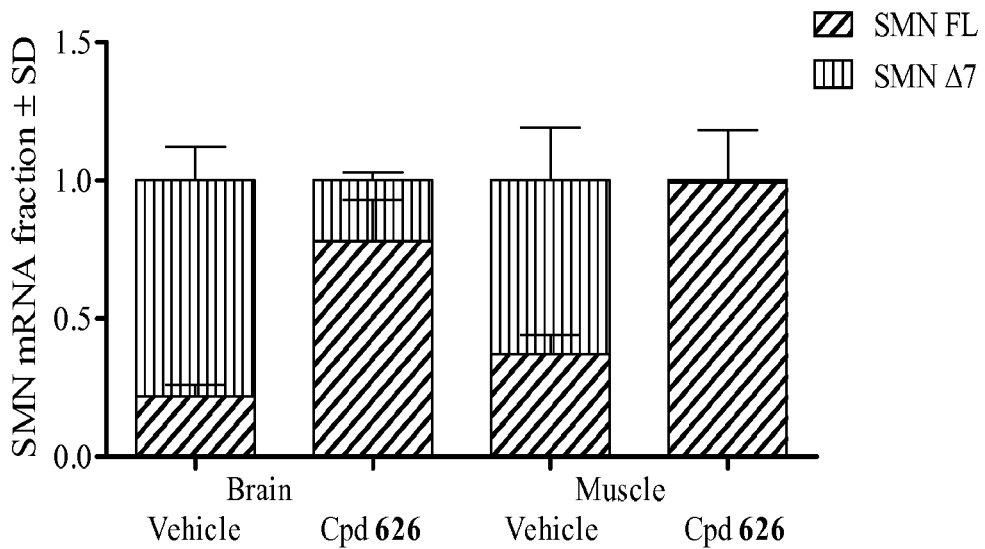

Results. As seen in FIG. 6, tissues of animals treated with Compound 35 (FIG. 6*a*) and Compound 626 (FIG. 6*b*) contain substantially more SMN2 FL mRNA and less SMN2 Δ7 mRNA than those treated with vehicle indicating a correction of SMN2 alternative splicing.

Example 6

Endogenous SMN2 mRNA End-Point Semi-Quantitative RT-PCR Splicing Assay in Animal Tissues The endpoint reverse transcription-PCR (RT-PCR) splicing assay is used to quantify the levels of the full length and Δ7 SMN2 mRNAs in tissues from mice treated with test compound.

Materials

| Material | Source |
| --- | --- |
| Tissues from C/C-allele SMA mice | The Jackson Laboratory, strain # 008714 (B6.129-Smn1$^{tm5(Smn1/SMN2)Mrph}$/J) |
| Tissues from ΔExon7 SMA mice | The Jackson Laboratory, strain # 005025 (FVB.Cg-Tg(SMN2*delta7)4299Ahmb Tg(SMN2)89Ahmb Smn1$^{tm1Msd}$/J) |
| Qiagen RNeasy lipid kit | Qiagen Catalog No.: 74804 |
| Platinum Taq HiFi DNA Polymerase Super Mix | Life Technologies, Inc. (formerly Invitrogen) Catalog No.: 11304-016 |
| iScript RT enzyme kit | BioRad Catalog No.: 170-8890 |
| Twin.tec 96-Well Semiskirted PCR Plate | Eppendorf Catalog No.: 951020389 |
| Ethidium bromide 2% agarose E gels 48-Well Double Comb | Life Technologies, Inc. (formerly Invitrogen) Catalog No.: G8008-02 |
| Gel Documentation System | UVP Gel Doc It 310 Imaging system |

Protocol. C/C-allele SMA mice are treated by oral gavage two times per day for 10 days with test compounds in 0.5% HPMC and 0.1% Tween-80. Tissue samples are collected and snap frozen for RNA purification.

Tissue samples (20-40 mg) are homogenized in QIAzol Lysis Reagent for 2 minutes at 20 Hz in the TissueLyser II using one stainless steel bead. After addition of chloroform, the homogenate is separated into aqueous and organic phases by centrifugation. RNA partitioned to the upper, aqueous phase is extracted and ethanol is added to provide appropriate binding conditions. The sample is then applied to the RNeasy spin column from the RNeasy Mini Kit, where total RNA binds to the membrane. The RNA is eluted in RNase-free water then stored at −20° C.

SMN2 spliced products are identified using the following amplification primers in Table 8. These primers hybridize to a nucleotide sequence in exon 6 (SMN Forward D, SEQ ID NO. 13) (nucleotide 22 to nucleotide 46) and exon 8 (SMN Reverse C, SEQ ID NO. 12) common to human SMN1 and SMN2 mRNAs.

TABLE 8

| Primer | Sequence | Source |
| --- | --- | --- |
| SMN Forward D | SEQ ID NO. 13: ATATGTCCAGATTCTCTTGATGATG | PTC[1] |
| SMN Reverse C | SEQ ID NO. 12: CGCTTCACATTCCAGATCTGTC | PTC[1] |

[1]Primers designed by PTC Therapeutics, Inc.

To synthesize cDNA, combine 1 μL of RNA solution (25-50 ng), 4 μL of 5× iScript reaction mix, 1 μL of reverse transcriptase, and 10 μL of water are combined and incubates 25° C. for 5 min followed by 42° C. for 30 min followed by 85° C. for 5 min. cDNA solution is stored at −20° C.

To perform endpoint PCR, 5 μL of cDNA, 0.2 μL of 100 μM forward primer, 0.2 μL of 100 μM reverse primer, and 22.5 μL of polymerase super mix are combined in a 96 well semiskirted PCR plate. PCR is carried out at the following temperatures for indicated time: Step 1: 94° C. (2 min), Step 2: 94° C. (30 sec), Step 3: 55° C. (30 sec), Step 4: 68° C. (1 min), then repeat Steps 2 to 4 for a total of 33 cycles, then hold at 4° C.

10 μL of each PCR sample is electrophoretically separated on a 2% agarose E-gel for 14 minutes, stained with ds DNA staining reagents (e.g., ethidium bromide) and visualized using a gel imager.

Figure 7A:
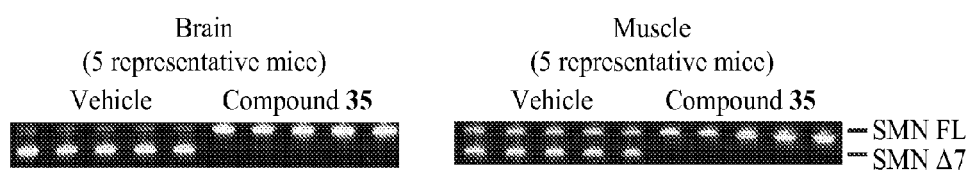
FIG. 7, referenced in Biological Example 6, shows the correction of SMN2 alternative splicing (in both the SMN2 gene and the hybrid mouse Smn1-SMN2 gene) in brain and muscle tissues of C/C-allele SMA mouse model treated for 10 days twice per day with 10 mg/kg of Compound 35 (FIG. 7a) and Compound 626 (FIG. 7b). The full length and Δ7 SMN2 mRNAs were amplified using RT-PCR. The PCR products were separated using agarose gel electrophoresis. The top and bottom bands correspond to the full length and Δ7 SMN2 mRNAs respectively. The intensity of each band is proportional to the amount of RNA present in the sample. The GAPDH loading control is shown for Compound 626.
Figure 7B:
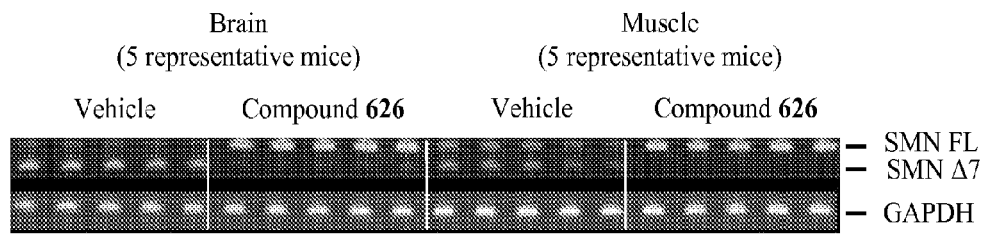

Results. As seen in FIG. 7, tissues from mice treated with increasing concentrations of Compound 35 (FIG. 7*a*) and Compound 626 (FIG. 7*b*) contain progressively more SMN2 FL mRNA and less SMN2 Δ7 mRNA indicating a correction of SMN2 alternative splicing.

Example 7

Smn Protein Assay in Cultured Cells

The SMN HTRF (homogeneous time resolved fluorescence) assay is used to quantify the level of Smn protein in SMA patient fibroblast cells treated with test compounds. The results of the assay are shown in Table 9.

Materials

| Material | Source |
| --- | --- |
| SMA Type 1 human cells | GM03813 (Coriell Institute) |
| Protease inhibitor cocktail | Roche Applied Science Catalog No.: 11836145001 |
| Anti-SMN d2 | Blue cap Cisbio Catalog No.: 63IDC002-SMN |
| Anti-SMN kryptate | Red cap Cisbio Catalog No.: 63IDC002-SMN |
| SMN reconstitution buffer | Cisbio Catalog No.: 63IDC002-SMN-Buffer |
| DMEM | Life Technologies, Inc. (formerly Invitrogen) Catalog No.: 11960-044 |
| RIPA Lysis Buffer | 20 mM Tris-HCl pH 7.5, 150 mM NaCl, 1 mM EDTA, 1% NP-40, 1% Sodium deoxycholate |
| Diluent Buffer | 20 mM Tris-HCl pH 7.5, 150 mM NaCl |
| Envision Plate Reader | Perkin Elmer Model No.: 2103 |

Protocol. Cells are thawed and cultured in DMEM-10% FBS for 72 hours. Cells are trypsinized, counted and re-suspended to a concentration of 25,000 cells/mL in DMEM-10% FBS. The cell suspensions are plated at 5,000 cells per well in a 96 well microtiter plate and incubated for 3 to 5 hours. To provide a control signal, three (3) wells in the 96 well plate do not receive cells and, thus, serve as Blank control wells. Test compounds are serially diluted 3.16-fold in 100% DMSO to generate a 7-point concentration curve. 1 µL of test compound solution is transferred to cell-containing wells and cells are incubated for 48 hours in a cell culture incubator (37° C., 5% $CO_2$, 100% relative humidity). Triplicate samples are set up for each test compound concentration. After 48 hours, the supernatant is removed from the wells and 25 µL of the RIPA lysis buffer, containing protease inhibitors, is added to the wells and incubated with shaking at room temperature for 1 hour. 25 µL of the diluent is added and then 35 µL of the resulting lysate is transferred to a 384-well plate, where each well contains 5 µL of the antibody solution (1:100 dilution of anti-SMN d2 and anti-SMN kryptate in SMN reconstitution buffer). The plate is centrifuged for 1 minute to bring the solution to the bottom of the wells, then incubated overnight at room temperature. Fluorescence for each well of the plate at 665 nm and 620 nm is measured on an EnVision multilabel plate reader (Perkin-Elmer).

The normalized fluorescence signal is calculated for each sample, Blank and vehicle control well by dividing the signal at 665 nm by the signal at 620 nm. Normalizing the signal accounts for possible fluorescence quenching due to the matrix effect of the lysate. The ΔF value (a measurement of Smn protein abundance) for each sample well is calculated by subtracting the normalized average fluorescence for the Blank control wells from the normalized fluorescence for each sample well and then dividing this difference by the normalized average fluorescence for the Blank control wells. The resulting ΔF value for each sample well represents the Smn protein abundance from test compound-treated samples. The ΔF value for each sample well is divided by the ΔF value for the vehicle control wells to calculate the fold increase in Smn protein abundance relative to the vehicle control.

Figure 8A:
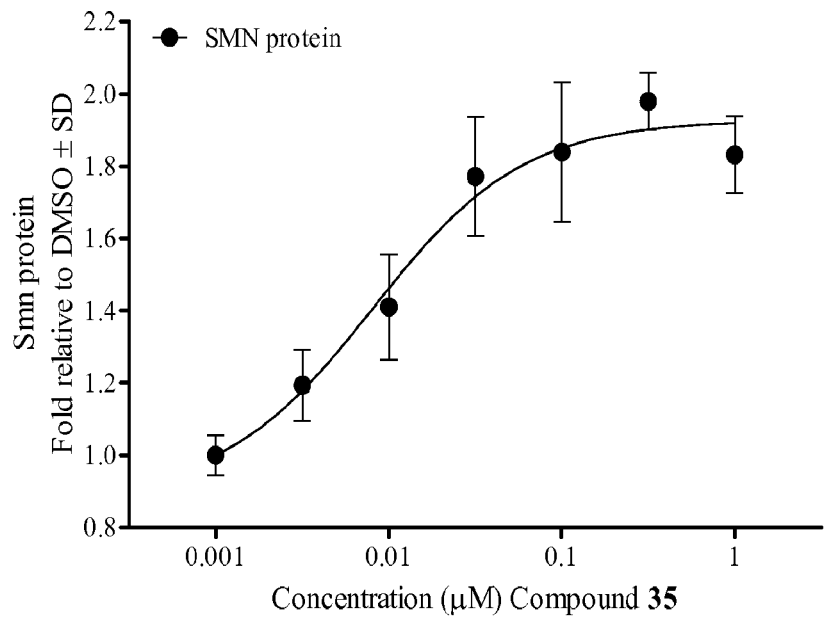
FIG. 8, referenced in Biological Example 7, shows a dose dependent increase in Smn protein expression in SMA Type 1 human fibroblast cells treated over a 48 hour period with Compound 35 (FIG. 8a) and Compound 626 (FIG. 8b).
Figure 8B:
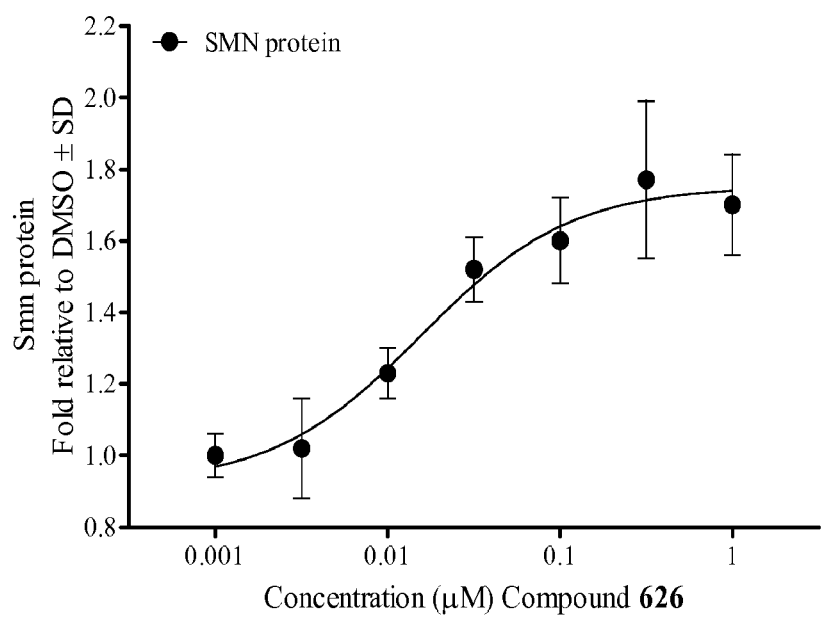

Results. As seen in FIG. 8, SMA Type 1 patient fibroblast cells treated with Compound 35 (FIG. 8a) and Compound 626 (FIG. 8b) show a dose dependent increase in Smn protein expression as measured by the SMN HTRF assay.

For compounds of Formula (I) or a form thereof disclosed herein, Table 9 provides the $EC_{1.5x}$ for Smn protein expression that was obtained from the 7-point concentration data generated for each test compound according to the procedure of Biological Example 7. The term "$EC_{1.5x}$ for Smn protein expression" is defined as that concentration of test compound that is effective in producing 1.5 times the amount of Smn protein in a SMA patient fibroblast cell compared to the amount produced from the DMSO vehicle control. An $EC_{1.5x}$ for Smn protein expression between >3 µM and ≤10 µM is indicated by one star (*), an $EC_{1.5x}$ between >1 and ≤3 µM is indicated by two stars (), an $EC_{1.5x}$ between >0.3 µM and ≤1 µM is indicated by three stars (*) and an $EC_{1.5x}$≤0.3 µM is indicated by four stars (****).

TABLE 9

| Cpd | $EC_{1.5x}$ |
| --- | --- |
| 39 | * |
| 51 | **** |
| 58 | *** |
| 72 | *** |
| 81 | * |
| 83 | ** |
| 84 | ** |
| 87 | ** |
| 88 | ** |
| 89 | *** |
| 95 | **** |
| 96 | * |
| 97 | * |
| 98 | ** |
| 105 | *** |
| 107 | *** |
| 108 | *** |
| 109 | * |
| 117 | *** |
| 118 | **** |
| 120 | **** |
| 123 | *** |
| 128 | * |
| 133 | * |
| 134 | ** |
| 142 | *** |
| 148 | ** |
| 150 | * |
| 152 | ** |
| 161 | * |
| 162 | *** |
| 169 | ** |
| 186 | ** |
| 188 | * |
| 193 | * |
| 198 | * |
| 203 | *** |
| 212 | *** |
| 227 | * |
| 231 | * |
| 243 | * |
| 246 | ** |
| 248 | ** |
| 250 | ** |
| 271 | * |
| 294 | ** |
| 295 | *** |
| 302 | *** |
| 303 | * |
| 304 | ** |
| 307 | * |
| 311 | ** |
| 335 | ** |
| 338 | * |
| 345 | * |

TABLE 9-continued

| Cpd | EC$_{1.5x}$ |
|---|---|
| 353 | ** |
| 354 | ** |
| 355 | *** |
| 373 | *** |
| 383 | ** |
| 404 | ** |
| 417 | **** |
| 418 | *** |
| 420 | **** |
| 421 | **** |
| 424 | **** |
| 425 | ** |
| 438 | ** |
| 443 | *** |
| 450 | ** |
| 454 | * |
| 455 | *** |
| 456 | ** |
| 459 | * |
| 460 | * |
| 462 | ** |
| 471 | *** |
| 476 | **** |
| 477 | **** |
| 482 | **** |
| 483 | ** |
| 493 | **** |
| 507 | **** |
| 515 | **** |
| 516 | **** |
| 517 | **** |
| 518 | **** |
| 519 | **** |
| 527 | **** |
| 530 | **** |
| 533 | **** |
| 536 | **** |
| 537 | **** |
| 550 | **** |
| 551 | **** |
| 552 | **** |
| 554 | **** |
| 555 | **** |
| 556 | *** |
| 558 | *** |
| 560 | **** |
| 561 | **** |
| 562 | **** |
| 563 | **** |
| 564 | **** |
| 566 | **** |
| 567 | **** |
| 568 | **** |
| 569 | **** |
| 570 | **** |
| 572 | *** |
| 573 | **** |
| 584 | **** |
| 586 | **** |
| 587 | **** |
| 588 | **** |
| 589 | **** |
| 590 | **** |
| 591 | **** |
| 592 | **** |
| 593 | **** |
| 594 | **** |
| 597 | **** |
| 600 | **** |
| 601 | **** |
| 605 | **** |
| 606 | **** |
| 607 | *** |
| 608 | **** |
| 609 | **** |
| 611 | ** |
| 614 | **** |
| 615 | **** |

TABLE 9-continued

| Cpd | EC$_{1.5x}$ |
|---|---|
| 618 | **** |
| 619 | **** |
| 620 | **** |
| 621 | **** |
| 622 | **** |
| 623 | *** |
| 625 | *** |
| 626 | **** |
| 627 | **** |
| 628 | **** |
| 632 | **** |
| 634 | **** |
| 635 | **** |
| 638 | **** |
| 640 | **** |
| 643 | **** |
| 644 | **** |
| 645 | **** |
| 646 | **** |
| 647 | **** |
| 648 | **** |
| 649 | *** |
| 650 | *** |
| 651 | **** |
| 652 | **** |
| 654 | **** |
| 655 | **** |
| 656 | **** |
| 657 | **** |
| 658 | **** |
| 659 | **** |
| 660 | *** |
| 661 | **** |
| 662 | ** |
| 664 | **** |
| 665 | **** |
| 666 | **** |
| 667 | **** |
| 668 | **** |
| 669 | **** |
| 670 | **** |
| 671 | **** |
| 672 | **** |
| 673 | **** |
| 674 | **** |
| 675 | ** |
| 676 | **** |
| 677 | **** |
| 678 | **** |
| 679 | **** |
| 680 | **** |
| 681 | **** |
| 682 | ** |
| 683 | **** |
| 684 | **** |
| 685 | **** |
| 686 | **** |
| 687 | ** |
| 688 | **** |
| 690 | *** |
| 691 | **** |
| 692 | **** |
| 693 | *** |
| 694 | **** |
| 696 | **** |
| 697 | *** |
| 699 | *** |
| 700 | **** |
| 704 | **** |
| 706 | *** |
| 707 | *** |
| 709 | *** |
| 711 | ** |
| 713 | **** |
| 716 | ** |
| 718 | **** |
| 723 | **** |
| 725 | *** |

TABLE 9-continued

| Cpd | EC$_{1.5x}$ |
|---|---|
| 726 | *** |
| 727 | ** |
| 729 | ** |
| 732 | **** |
| 734 | **** |
| 735 | *** |
| 736 | **** |
| 737 | **** |
| 738 | **** |
| 739 | **** |
| 740 | **** |
| 741 | **** |
| 742 | **** |
| 743 | **** |
| 745 | **** |
| 746 | **** |
| 747 | **** |
| 748 | **** |
| 749 | **** |
| 750 | **** |
| 752 | *** |
| 753 | ** |
| 757 | ** |
| 761 | **** |
| 762 | *** |
| 763 | **** |
| 767 | **** |
| 768 | **** |
| 770 | **** |
| 772 | **** |
| 773 | **** |
| 774 | **** |
| 775 | **** |
| 778 | **** |
| 779 | **** |
| 780 | **** |
| 782 | **** |
| 785 | ** |
| 786 | **** |
| 787 | *** |
| 788 | **** |
| 791 | ** |
| 792 | **** |
| 793 | **** |
| 794 | **** |
| 795 | **** |
| 796 | *** |
| 797 | **** |
| 798 | *** |
| 799 | **** |
| 800 | **** |
| 801 | **** |
| 802 | **** |
| 804 | **** |
| 805 | **** |
| 806 | **** |
| 807 | **** |
| 808 | **** |
| 809 | ** |
| 810 | ** |
| 811 | *** |
| 813 | **** |
| 814 | **** |
| 815 | **** |
| 816 | *** |
| 821 | **** |
| 822 | **** |
| 823 | ** |
| 824 | **** |
| 825 | **** |
| 826 | **** |
| 827 | **** |
| 828 | *** |
| 829 | **** |
| 830 | **** |
| 833 | **** |
| 834 | **** |
| 835 | *** |

TABLE 9-continued

| Cpd | EC$_{1.5x}$ |
|---|---|
| 836 | *** |
| 837 | **** |
| 838 | **** |
| 839 | *** |
| 841 | **** |
| 842 | **** |
| 843 | **** |
| 844 | *** |
| 846 | *** |
| 848 | *** |
| 849 | *** |
| 852 | **** |
| 854 | **** |
| 855 | **** |
| 856 | **** |
| 857 | **** |
| 858 | **** |
| 859 | *** |
| 860 | ** |
| 861 | *** |
| 862 | *** |
| 863 | *** |
| 864 | **** |
| 865 | ** |
| 866 | *** |
| 867 | **** |
| 868 | **** |
| 869 | **** |
| 870 | **** |
| 871 | **** |
| 872 | *** |
| 873 | *** |
| 874 | **** |
| 875 | **** |
| 876 | **** |
| 877 | *** |
| 878 | *** |
| 879 | **** |
| 880 | **** |
| 881 | **** |
| 882 | **** |
| 883 | **** |
| 884 | **** |
| 885 | *** |
| 886 | *** |
| 887 | **** |
| 888 | **** |
| 889 | **** |
| 890 | **** |
| 891 | *** |
| 892 | **** |
| 893 | **** |
| 894 | *** |
| 895 | **** |
| 896 | **** |
| 897 | **** |
| 898 | **** |
| 899 | **** |
| 900 | **** |
| 901 | **** |
| 902 | **** |
| 903 | *** |
| 904 | *** |
| 905 | ** |
| 906 | **** |
| 907 | **** |
| 908 | *** |
| 909 | **** |
| 910 | **** |
| 911 | **** |
| 912 | **** |
| 913 | **** |
| 914 | **** |
| 915 | *** |
| 916 | *** |
| 917 | **** |
| 918 | *** |
| 919 | **** |

TABLE 9-continued

| Cpd | EC$_{1.5x}$ |
|---|---|
| 920 | **** |
| 921 | **** |
| 922 | *** |
| 923 | *** |
| 924 | **** |
| 925 | ** |
| 926 | **** |
| 929 | ** |
| 930 | **** |
| 931 | *** |
| 932 | **** |
| 935 | *** |
| 936 | **** |
| 937 | **** |
| 938 | **** |
| 939 | **** |
| 941 | ** |
| 942 | ** |
| 943 | **** |
| 944 | *** |
| 945 | **** |
| 946 | **** |
| 947 | **** |
| 949 | **** |
| 950 | ** |
| 951 | ** |
| 952 | **** |
| 953 | **** |
| 954 | **** |
| 956 | ** |
| 957 | *** |
| 958 | **** |
| 959 | *** |
| 960 | ** |
| 961 | **** |
| 962 | **** |
| 965 | **** |
| 966 | **** |
| 967 | **** |
| 968 | **** |
| 969 | **** |
| 970 | *** |
| 971 | **** |
| 972 | * |
| 976 | ** |
| 981 | ** |
| 982 | **** |
| 983 | **** |
| 984 | **** |
| 985 | **** |
| 986 | **** |

For compounds of Formula (I) or a form thereof disclosed herein, Table 10 provides the maximum fold (Fold) increase of Smn protein that was obtained from the 7-point concentration data generated for each test compound according to the procedure of Biological Example 7. A maximum fold increase of ≤1.2 is indicated by one star (*), a fold increase between >1.2 and ≤1.35 is indicated by two stars (), a fold increase between >1.35 and ≤1.5 is indicated by three stars (*), a fold increase between >1.5 and ≤1.65 is indicated by four stars (**) and a fold increase >1.65 is indicated by five stars (***).

TABLE 10

| Cpd | Fold |
|---|---|
| 1 | * |
| 2 | * |
| 3 | * |
| 4 | * |
| 5 | * |
| 6 | * |
| 7 | * |
| 8 | * |
| 9 | * |
| 10 | * |
| 12 | * |
| 13 | ** |
| 14 | *** |
| 15 | * |
| 16 | ** |
| 17 | ** |
| 18 | * |
| 19 | * |
| 20 | * |
| 22 | * |
| 23 | * |
| 24 | * |
| 25 | * |
| 26 | * |
| 27 | * |
| 28 | * |
| 29 | ** |
| 30 | * |
| 31 | * |
| 34 | ** |
| 35 | * |
| 36 | * |
| 37 | ** |
| 39 | *** |
| 40 | ** |
| 41 | * |
| 42 | * |
| 43 | * |
| 45 | * |
| 47 | ** |
| 49 | * |
| 50 | * |
| 51 | ***** |
| 52 | * |
| 53 | ** |
| 54 | * |
| 55 | * |
| 56 | * |
| 57 | ** |
| 58 | **** |
| 59 | ** |
| 60 | ** |
| 61 | ** |
| 62 | * |
| 63 | ** |
| 64 | * |
| 65 | * |
| 67 | * |
| 68 | ** |
| 69 | * |
| 70 | * |
| 71 | ** |
| 72 | *** |
| 73 | ** |
| 75 | * |
| 76 | * |
| 78 | *** |
| 79 | *** |
| 80 | ** |
| 81 | *** |
| 82 | ** |
| 83 | **** |
| 84 | *** |
| 85 | * |
| 86 | * |
| 87 | **** |
| 88 | *** |
| 89 | **** |
| 90 | *** |
| 91 | ** |
| 92 | *** |
| 93 | ** |
| 94 | *** |
| 95 | **** |

TABLE 10-continued

| Cpd | Fold |
|---|---|
| 96 | *** |
| 97 | *** |
| 98 | *** |
| 99 | * |
| 100 | ** |
| 101 | ** |
| 103 | ** |
| 104 | *** |
| 105 | **** |
| 106 | * |
| 107 | **** |
| 108 | **** |
| 109 | *** |
| 110 | ** |
| 111 | ** |
| 112 | * |
| 114 | ** |
| 115 | *** |
| 116 | ** |
| 117 | **** |
| 118 | ***** |
| 119 | ** |
| 120 | **** |
| 121 | *** |
| 122 | * |
| 123 | *** |
| 124 | ** |
| 125 | * |
| 126 | * |
| 128 | *** |
| 129 | ** |
| 130 | * |
| 131 | *** |
| 132 | * |
| 133 | *** |
| 134 | *** |
| 135 | ** |
| 136 | ** |
| 137 | *** |
| 138 | ** |
| 139 | *** |
| 140 | ** |
| 141 | * |
| 142 | **** |
| 143 | *** |
| 144 | * |
| 145 | ** |
| 146 | * |
| 147 | * |
| 148 | ***** |
| 149 | *** |
| 150 | *** |
| 151 | * |
| 152 | *** |
| 153 | *** |
| 154 | * |
| 155 | * |
| 156 | ** |
| 157 | * |
| 158 | ** |
| 159 | *** |
| 160 | * |
| 161 | *** |
| 162 | *** |
| 163 | * |
| 164 | * |
| 165 | ** |
| 166 | ** |
| 167 | ** |
| 168 | * |
| 169 | *** |
| 170 | ** |
| 171 | * |
| 172 | * |
| 173 | ** |
| 174 | *** |
| 175 | * |
| 176 | * |

TABLE 10-continued

| Cpd | Fold |
|---|---|
| 177 | * |
| 178 | * |
| 179 | *** |
| 180 | * |
| 181 | ** |
| 182 | ** |
| 183 | ** |
| 184 | *** |
| 185 | * |
| 186 | *** |
| 187 | ** |
| 188 | *** |
| 189 | ** |
| 190 | ** |
| 191 | ** |
| 192 | ** |
| 193 | ** |
| 194 | * |
| 195 | * |
| 196 | * |
| 197 | ** |
| 198 | **** |
| 199 | ** |
| 200 | * |
| 201 | ** |
| 202 | ** |
| 203 | **** |
| 204 | *** |
| 205 | *** |
| 206 | ** |
| 207 | ** |
| 208 | * |
| 209 | * |
| 210 | * |
| 211 | * |
| 212 | **** |
| 213 | *** |
| 214 | ** |
| 215 | * |
| 216 | *** |
| 217 | *** |
| 218 | ** |
| 219 | * |
| 220 | ** |
| 221 | * |
| 222 | * |
| 223 | * |
| 224 | * |
| 225 | *** |
| 226 | * |
| 227 | *** |
| 228 | ** |
| 229 | *** |
| 230 | *** |
| 231 | ** |
| 232 | * |
| 233 | *** |
| 234 | * |
| 235 | * |
| 236 | * |
| 237 | * |
| 238 | * |
| 239 | * |
| 240 | * |
| 241 | * |
| 242 | *** |
| 243 | ** |
| 244 | * |
| 245 | ** |
| 246 | *** |
| 247 | ** |
| 248 | ** |
| 249 | ** |
| 250 | *** |
| 251 | * |
| 252 | ** |
| 253 | * |
| 254 | * |

TABLE 10-continued

| Cpd | Fold |
|---|---|
| 255 | * |
| 256 | * |
| 257 | * |
| 258 | * |
| 259 | * |
| 260 | * |
| 261 | ** |
| 262 | ** |
| 263 | * |
| 264 | * |
| 265 | * |
| 266 | * |
| 267 | * |
| 268 | * |
| 269 | * |
| 270 | ** |
| 271 | **** |
| 272 | ** |
| 273 | * |
| 274 | ** |
| 275 | * |
| 276 | * |
| 277 | * |
| 278 | * |
| 279 | * |
| 280 | *** |
| 281 | ** |
| 282 | * |
| 283 | * |
| 284 | * |
| 285 | * |
| 286 | * |
| 287 | * |
| 288 | * |
| 289 | * |
| 290 | * |
| 291 | * |
| 292 | *** |
| 293 | * |
| 294 | ** |
| 295 | **** |
| 296 | *** |
| 297 | * |
| 298 | * |
| 299 | * |
| 300 | * |
| 301 | * |
| 302 | *** |
| 303 | *** |
| 304 | *** |
| 305 | ** |
| 306 | *** |
| 307 | *** |
| 308 | ** |
| 309 | ** |
| 310 | ** |
| 311 | *** |
| 312 | ** |
| 313 | * |
| 314 | * |
| 315 | * |
| 316 | ** |
| 317 | * |
| 318 | * |
| 319 | ** |
| 320 | * |
| 321 | ** |
| 322 | ** |
| 323 | ** |
| 324 | *** |
| 325 | * |
| 326 | ** |
| 327 | ** |
| 328 | * |
| 329 | * |
| 330 | * |
| 331 | * |
| 332 | * |

TABLE 10-continued

| Cpd | Fold |
|---|---|
| 333 | * |
| 334 | * |
| 335 | *** |
| 336 | * |
| 337 | * |
| 338 | ** |
| 339 | * |
| 340 | * |
| 341 | * |
| 342 | ** |
| 343 | * |
| 344 | ** |
| 345 | *** |
| 346 | ** |
| 347 | * |
| 348 | * |
| 349 | * |
| 350 | * |
| 351 | * |
| 352 | * |
| 353 | **** |
| 354 | *** |
| 355 | **** |
| 356 | ** |
| 357 | *** |
| 358 | *** |
| 359 | * |
| 360 | * |
| 361 | ** |
| 362 | ** |
| 363 | ** |
| 364 | * |
| 365 | * |
| 366 | ** |
| 367 | *** |
| 368 | ** |
| 369 | ** |
| 370 | * |
| 371 | * |
| 372 | ** |
| 373 | **** |
| 374 | * |
| 375 | ** |
| 376 | * |
| 377 | * |
| 378 | ** |
| 379 | *** |
| 380 | ** |
| 381 | * |
| 382 | * |
| 383 | **** |
| 384 | * |
| 385 | * |
| 386 | * |
| 387 | * |
| 388 | ** |
| 389 | *** |
| 390 | *** |
| 391 | ** |
| 392 | ** |
| 393 | *** |
| 394 | * |
| 395 | * |
| 396 | ** |
| 397 | * |
| 398 | * |
| 399 | * |
| 400 | * |
| 401 | * |
| 402 | * |
| 403 | * |
| 404 | **** |
| 405 | ** |
| 406 | * |
| 407 | * |
| 408 | * |
| 409 | * |
| 410 | * |

TABLE 10-continued

| Cpd | Fold |
|---|---|
| 411 | * |
| 412 | * |
| 413 | * |
| 414 | * |
| 415 | * |
| 416 | ** |
| 417 | *** |
| 418 | **** |
| 419 | ** |
| 420 | **** |
| 421 | *** |
| 422 | ** |
| 423 | * |
| 424 | *** |
| 425 | *** |
| 426 | *** |
| 427 | *** |
| 428 | * |
| 429 | * |
| 430 | * |
| 431 | * |
| 432 | ** |
| 433 | * |
| 434 | ** |
| 435 | * |
| 436 | * |
| 437 | ** |
| 438 | *** |
| 439 | ** |
| 440 | * |
| 441 | *** |
| 442 | ** |
| 443 | **** |
| 444 | * |
| 445 | * |
| 446 | * |
| 447 | * |
| 448 | * |
| 449 | * |
| 450 | *** |
| 451 | *** |
| 452 | * |
| 453 | * |
| 454 | *** |
| 455 | **** |
| 456 | **** |
| 457 | ** |
| 458 | *** |
| 459 | *** |
| 460 | *** |
| 461 | * |
| 462 | *** |
| 463 | * |
| 464 | *** |
| 465 | * |
| 466 | * |
| 467 | * |
| 468 | ** |
| 469 | ** |
| 470 | * |
| 471 | **** |
| 472 | * |
| 473 | ** |
| 474 | * |
| 475 | * |
| 476 | ***** |
| 477 | ***** |
| 478 | * |
| 479 | * |
| 480 | * |
| 481 | * |
| 482 | **** |
| 483 | *** |
| 484 | * |
| 485 | * |
| 486 | * |
| 487 | * |
| 488 | * |

TABLE 10-continued

| Cpd | Fold |
|---|---|
| 489 | * |
| 490 | * |
| 491 | ** |
| 492 | * |
| 493 | ***** |
| 494 | * |
| 495 | * |
| 496 | * |
| 497 | * |
| 498 | * |
| 499 | * |
| 500 | * |
| 501 | ** |
| 502 | * |
| 503 | * |
| 504 | * |
| 505 | * |
| 506 | ** |
| 507 | **** |
| 508 | ** |
| 509 | * |
| 510 | * |
| 511 | * |
| 512 | * |
| 513 | * |
| 514 | * |
| 515 | ***** |
| 516 | ***** |
| 517 | ***** |
| 518 | ***** |
| 519 | ***** |
| 520 | ** |
| 521 | ** |
| 522 | * |
| 523 | ** |
| 524 | * |
| 525 | *** |
| 526 | *** |
| 527 | **** |
| 528 | ** |
| 529 | * |
| 530 | **** |
| 531 | ** |
| 532 | * |
| 533 | **** |
| 534 | *** |
| 535 | * |
| 536 | ***** |
| 537 | ***** |
| 538 | * |
| 539 | * |
| 540 | * |
| 541 | * |
| 542 | * |
| 543 | * |
| 544 | ** |
| 545 | *** |
| 546 | * |
| 547 | * |
| 548 | * |
| 549 | ** |
| 550 | **** |
| 551 | *** |
| 552 | **** |
| 553 | * |
| 554 | ***** |
| 555 | **** |
| 556 | *** |
| 557 | *** |
| 558 | **** |
| 559 | *** |
| 560 | **** |
| 561 | **** |
| 562 | **** |
| 563 | ***** |
| 564 | ***** |
| 565 | * |
| 566 | **** |

TABLE 10-continued

| Cpd | Fold |
|---|---|
| 567 | ***** |
| 568 | ***** |
| 569 | ***** |
| 570 | ***** |
| 571 | ** |
| 572 | **** |
| 573 | **** |
| 574 | * |
| 575 | * |
| 576 | * |
| 577 | ** |
| 578 | * |
| 579 | * |
| 580 | * |
| 581 | * |
| 582 | ** |
| 583 | ** |
| 584 | ***** |
| 585 | *** |
| 586 | *** |
| 587 | **** |
| 588 | ***** |
| 589 | ***** |
| 590 | ***** |
| 591 | ***** |
| 592 | ***** |
| 593 | ***** |
| 594 | ***** |
| 595 | ** |
| 596 | ** |
| 597 | **** |
| 598 | *** |
| 599 | *** |
| 600 | ***** |
| 601 | ***** |
| 602 | * |
| 603 | * |
| 604 | * |
| 605 | ***** |
| 606 | ***** |
| 607 | *** |
| 608 | ***** |
| 609 | ***** |
| 610 | ** |
| 611 | **** |
| 612 | ** |
| 613 | ** |
| 614 | ***** |
| 615 | **** |
| 616 | ** |
| 617 | *** |
| 618 | **** |
| 619 | **** |
| 620 | **** |
| 621 | ***** |
| 622 | **** |
| 623 | *** |
| 624 | *** |
| 625 | *** |
| 626 | **** |
| 627 | ***** |
| 628 | **** |
| 629 | * |
| 630 | * |
| 631 | * |
| 632 | ***** |
| 633 | *** |
| 634 | ***** |
| 635 | **** |
| 636 | ** |
| 638 | **** |
| 639 | * |
| 640 | **** |
| 641 | * |
| 642 | ** |
| 643 | **** |
| 644 | ***** |
| 645 | ***** |
| 646 | **** |
| 647 | **** |
| 648 | ***** |
| 649 | ***** |
| 650 | **** |
| 651 | *** |
| 652 | **** |
| 653 | *** |
| 654 | **** |
| 655 | **** |
| 656 | ***** |
| 657 | **** |
| 658 | ***** |
| 659 | **** |
| 660 | ***** |
| 661 | ***** |
| 662 | *** |
| 663 | *** |
| 664 | ***** |
| 665 | ***** |
| 666 | **** |
| 667 | **** |
| 668 | ***** |
| 669 | ***** |
| 670 | ***** |
| 671 | ***** |
| 672 | **** |
| 673 | ***** |
| 674 | ***** |
| 675 | **** |
| 676 | ***** |
| 677 | **** |
| 678 | ***** |
| 679 | ***** |
| 680 | **** |
| 681 | **** |
| 682 | *** |
| 683 | **** |
| 684 | **** |
| 685 | **** |
| 686 | ***** |
| 687 | *** |
| 688 | ***** |
| 689 | *** |
| 690 | **** |
| 691 | **** |
| 692 | **** |
| 693 | **** |
| 694 | **** |
| 695 | *** |
| 696 | ***** |
| 697 | *** |
| 698 | * |
| 699 | ***** |
| 700 | ***** |
| 701 | ** |
| 702 | * |
| 703 | ** |
| 704 | **** |
| 705 | *** |
| 706 | **** |
| 707 | **** |
| 708 | ** |
| 709 | **** |
| 710 | ** |
| 711 | *** |
| 712 | ** |
| 713 | *** |
| 714 | * |
| 715 | ** |
| 716 | **** |
| 717 | *** |
| 718 | **** |
| 719 | ** |
| 720 | ** |
| 721 | * |
| 722 | * |
| 723 | ***** |

TABLE 10-continued

| Cpd | Fold |
| --- | --- |
| 724 | * |
| 725 | *** |
| 726 | **** |
| 727 | *** |
| 728 | * |
| 729 | *** |
| 730 | *** |
| 731 | *** |
| 732 | *** |
| 733 | *** |
| 734 | **** |
| 735 | **** |
| 736 | ***** |
| 737 | ***** |
| 738 | ***** |
| 739 | **** |
| 740 | ***** |
| 741 | ***** |
| 742 | ***** |
| 743 | ***** |
| 744 | ** |
| 745 | ***** |
| 746 | ***** |
| 747 | ***** |
| 748 | ***** |
| 749 | ***** |
| 750 | ***** |
| 751 | ** |
| 752 | **** |
| 753 | *** |
| 754 | *** |
| 755 | *** |
| 756 | *** |
| 757 | *** |
| 758 | * |
| 759 | *** |
| 760 | *** |
| 761 | **** |
| 762 | **** |
| 763 | **** |
| 764 | ** |
| 765 | * |
| 766 | *** |
| 767 | ***** |
| 768 | **** |
| 769 | ** |
| 770 | **** |
| 771 | * |
| 772 | ***** |
| 773 | **** |
| 774 | **** |
| 775 | **** |
| 776 | ** |
| 777 | * |
| 778 | ***** |
| 779 | ***** |
| 780 | **** |
| 781 | ** |
| 782 | **** |
| 783 | *** |
| 784 | ** |
| 785 | **** |
| 786 | **** |
| 787 | *** |
| 788 | **** |
| 789 | *** |
| 790 | ** |
| 791 | *** |
| 792 | **** |
| 793 | **** |
| 794 | **** |
| 795 | **** |
| 796 | **** |
| 797 | **** |
| 798 | **** |
| 799 | **** |
| 800 | ***** |
| 801 | **** |
| 802 | **** |
| 803 | *** |
| 804 | ***** |
| 805 | ***** |
| 806 | ***** |
| 807 | ***** |
| 808 | **** |
| 809 | **** |
| 810 | **** |
| 811 | **** |
| 812 | *** |
| 813 | **** |
| 814 | ***** |
| 815 | **** |
| 816 | **** |
| 817 | ** |
| 818 | * |
| 819 | *** |
| 820 | ** |
| 821 | ***** |
| 822 | **** |
| 823 | **** |
| 824 | **** |
| 825 | ***** |
| 826 | ***** |
| 827 | ***** |
| 828 | ***** |
| 829 | ***** |
| 830 | ***** |
| 831 | * |
| 832 | * |
| 833 | ***** |
| 834 | ***** |
| 835 | ***** |
| 836 | ***** |
| 837 | ***** |
| 838 | ***** |
| 839 | **** |
| 840 | * |
| 841 | ***** |
| 842 | ***** |
| 843 | **** |
| 844 | **** |
| 845 | * |
| 846 | ***** |
| 847 | ** |
| 848 | ***** |
| 849 | ***** |
| 850 | ** |
| 851 | *** |
| 852 | **** |
| 853 | * |
| 854 | ***** |
| 855 | ***** |
| 856 | ***** |
| 857 | ***** |
| 858 | **** |
| 859 | **** |
| 860 | **** |
| 861 | ***** |
| 862 | ***** |
| 863 | ***** |
| 864 | ***** |
| 865 | **** |
| 866 | *** |
| 867 | **** |
| 868 | ***** |
| 869 | ***** |
| 870 | **** |
| 871 | **** |
| 872 | **** |
| 873 | **** |
| 874 | ***** |
| 875 | **** |
| 876 | **** |
| 877 | *** |
| 878 | ***** |
| 879 | **** |

TABLE 10-continued

| Cpd | Fold |
|---|---|
| 880 | **** |
| 881 | **** |
| 882 | **** |
| 883 | ***** |
| 884 | ***** |
| 885 | ***** |
| 886 | ***** |
| 887 | ***** |
| 888 | ***** |
| 889 | ***** |
| 890 | ***** |
| 891 | ***** |
| 892 | **** |
| 893 | ***** |
| 894 | ***** |
| 895 | ***** |
| 896 | ***** |
| 897 | ***** |
| 898 | ***** |
| 899 | ***** |
| 900 | ***** |
| 901 | ***** |
| 902 | ***** |
| 903 | **** |
| 904 | **** |
| 905 | **** |
| 906 | ***** |
| 907 | **** |
| 908 | ***** |
| 909 | ***** |
| 910 | ***** |
| 911 | ***** |
| 912 | **** |
| 913 | ***** |
| 914 | **** |
| 915 | **** |
| 916 | **** |
| 917 | ***** |
| 918 | **** |
| 919 | **** |
| 920 | ***** |
| 921 | **** |
| 922 | *** |
| 923 | *** |
| 924 | **** |
| 925 | *** |
| 926 | **** |
| 927 | ** |
| 928 | *** |
| 929 | *** |
| 930 | ***** |
| 931 | **** |
| 932 | **** |
| 933 | * |
| 934 | ** |
| 935 | **** |
| 936 | ***** |
| 937 | ***** |
| 938 | ***** |
| 939 | ***** |
| 940 | * |
| 941 | **** |
| 942 | *** |
| 943 | **** |
| 944 | **** |
| 945 | ***** |
| 946 | **** |
| 947 | **** |
| 948 | *** |
| 949 | ***** |
| 950 | *** |
| 951 | **** |
| 952 | ***** |
| 953 | **** |
| 954 | ***** |
| 955 | *** |
| 956 | ***** |
| 957 | **** |
| 958 | ***** |
| 959 | *** |
| 960 | *** |
| 961 | *** |
| 962 | ***** |
| 963 | *** |
| 964 | ** |
| 965 | *** |
| 966 | **** |
| 967 | **** |
| 968 | ***** |
| 969 | **** |
| 970 | ***** |
| 971 | ***** |
| 972 | *** |
| 973 | * |
| 974 | ** |
| 975 | *** |
| 976 | *** |
| 977 | * |
| 978 | ** |
| 979 | ** |
| 980 | *** |
| 981 | **** |
| 982 | ***** |
| 983 | ***** |
| 984 | ***** |
| 985 | ***** |
| 986 | ***** |

Example 8

Gems Count (Smn-dependent Nuclear Speckle Count) Assay

The level of Smn protein directly correlates with the amount of nuclear foci, also known as gems, produced upon staining the cell with a fluorescently labeled anti-Smn antibody (Liu and Dreyfuss, EMBO J., 1996, 15:3555). Gems are multi-protein complexes whose formation is nucleated by the Smn protein and the gems count assay is used to evaluate the level of Smn protein in the cell. As described herein, the gems count assay is used to quantify the level of Smn protein in SMA patient fibroblast cells treated with a test compound.

Materials

| Material | Source |
|---|---|
| SMA Type 1 human cells | GM03813 (Coriell Institute) |
| Primary Antibody-mouse anti-SMN clone 2B1 | Sigma Catalog No.: S2944 |
| Secondary Antibody-anti-mouse Alexa Fluor 555 | Life Technologies, Inc. (formerly Invitrogen) Catalog No.: A21422 |
| Bovine Serum Albumin (BSA) | Sigma Catalog No.: A3294 |
| 4% Paraformaldehyde | Electron Microscopy Sciences Catalog No.: 15710 |
| Bortezomib | LC Labs, Catalog No.: B-1408 |
| 0.05% Triton X-100 | Sigma Catalog No.: 93443-100 mL |
| Mounting medium-ProLong Gold Antifade Reagent with DAPI | Life Technologies, Inc. (formerly Invitrogen) Catalog Nos.: P7481 and P36935 |
| 22 × 22 #1 sterile Cover slips | Fisher Catalog No.: 12-548-B |
| DMEM | Life Technologies, Inc. (formerly Invitrogen) Catalog No.: 11960-044 |
| PBS | Life Technologies, Inc. (formerly Invitrogen) Catalog No.: 10010-031 |
| Clear-coat nail polish | Revlon brand Catalog No.: 1271-76 |
| Zeiss Axovert 135 Fluorescence microscope | Zeiss |

Protocol: Cells are thawed and incubated in DMEM-10% FBS for 72 hours, then trypsinized, counted and resuspended to 100,000 cells/mL in DMEM-10% FBS. 2 mL of the cell suspension is plated in a 6-well cell culture plate with a sterile cover slip and incubated for 3 to 5 hours. Test compounds are serially diluted 3.16-fold in 100% DMSO to generate a 7-point dilution curve. 10 μL of test compound solution is added to each cell-containing well and incubated for 48 hours in a cell culture incubator (37° C., 5% $CO_2$, 100% relative humidity). Duplicates are set up for each test compound concentration. Cells containing DMSO at a final concentration of 0.5% are used as controls.

Cell culture medium is aspirated from the wells containing cover slips and gently washed three times with cold PBS. The cells are fixed by incubation for 20 minutes at room temperature while in paraformaldehyde. The cells are then washed two times with cold PBS followed by incubation for 5 minutes at room temperature with 0.05% Triton X-100 in PBS to permeabilize the cells. After the fixed cells are washed three times with cold PBS, they are blocked with 10% FBS for 1 hour. 60 μL of primary antibody diluted 1:1000 in blocking buffer is added and the mixture is incubated for one hour at room temperature. The cells are washed three times with PBS and 60 μL of secondary antibody diluted 1:5000 in blocking buffer is added, then the mixture is incubated for one hour at room temperature. The cover slips are mounted onto the slides with the aid of mounting medium and allowed to dry overnight. Nail polish is applied to the sides of the cover slip and the slides are stored, protected from light. A Zeiss Axovert 135 with a 63× Plan-Apochromat, NA=1.4 objective is used for immunofluorescence detection and counting. The number of gems is counted per ≥150 nuclei and % activation is calculated using DMSO and 10 nM bortezomib as controls. For each test compound, the cells are examined at all wavelengths to identify test compounds with inherent fluorescence.

Figure 9A:
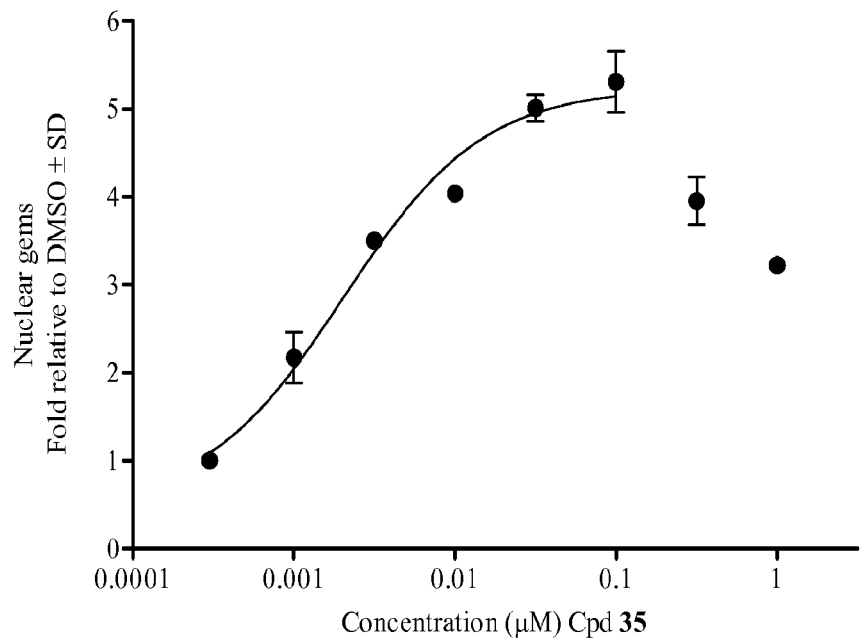
FIG. 9, referenced in Biological Example 8, shows an increase in nuclear speckle counts (gems) in Type 1 SMA patient fibroblasts treated with Compound 35 (FIG. 9a) and Compound 626 (FIG. 9b) over a 48 hour period. Speckles were counted using fluorescence microscopy. The number of speckles in compound-treated samples was normalized to that in vehicle-treated samples and plotted as a function of the compound concentration.
Figure 9B:
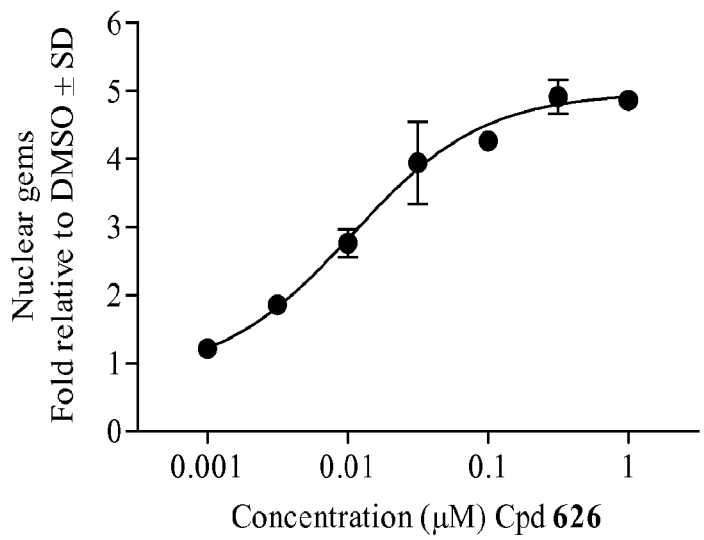

Results. As seen in FIG. 9, SMA Type 1 patient cells treated with Compound 35 (FIG. 9a) and Compound 626 (FIG. 9b) contain progressively more gems relative to cells treated with DMSO.

Example 9

Smn Protein Assay in Human Motor Neurons

Smn immunofluorescent confocal microscopy is used to quantify the level of Smn protein in human motor neurons treated with test compounds.

Protocol. Human motor neurons derived from SMA iPS cells (Ebert et al., Nature, 2009, 457:2770; and, Rubin et al., BMC Biology, 2011, 9:42) are treated with test compound at various concentrations for 72 hours. The level of Smn protein in the cell nucleus is quantified using Smn immunostaining and confocal fluorescence microscopy essentially as described in Makhortova et al., Nature Chemical Biology, 2011, 7:544. The level of Smn protein in compound-treated samples is normalized to that in vehicle-treated samples and plotted as a function of the compound concentration.

Figure 10A:
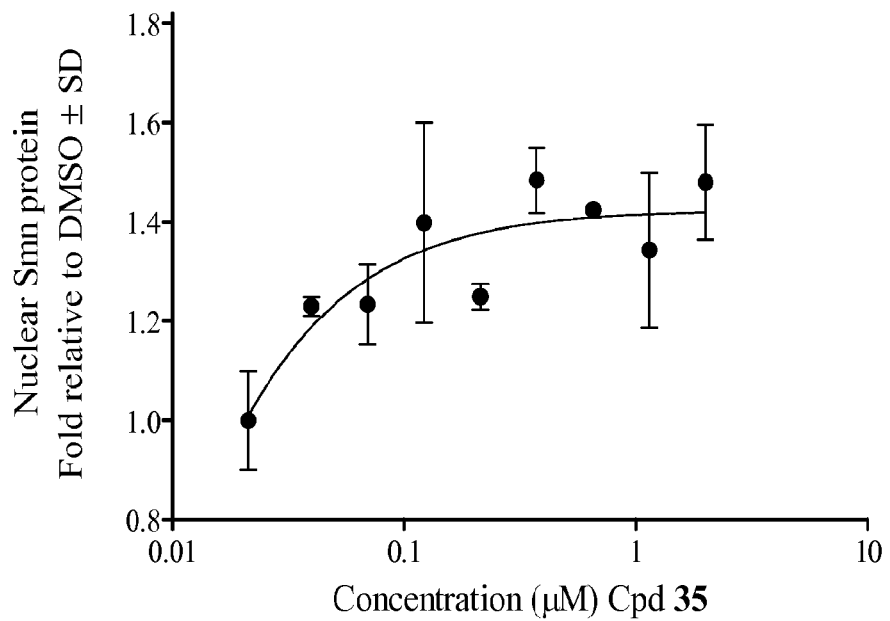
FIG. 10, referenced in Biological Example 9, shows an increase in Smn protein expression (black circles) in motor neurons generated from iPS cells generated from Type 1 SMA patient fibroblasts treated with Compound 35 (FIG. 10a) and Compound 626 (FIG. 10b) over a 72 hour period. The level of Smn protein was quantified using Smn immunostaining and confocal fluorescence microscopy. The level of Smn protein in compound-treated samples was normalized to that in vehicle-treated samples and plotted as a function of the compound concentration.
Figure 10B:
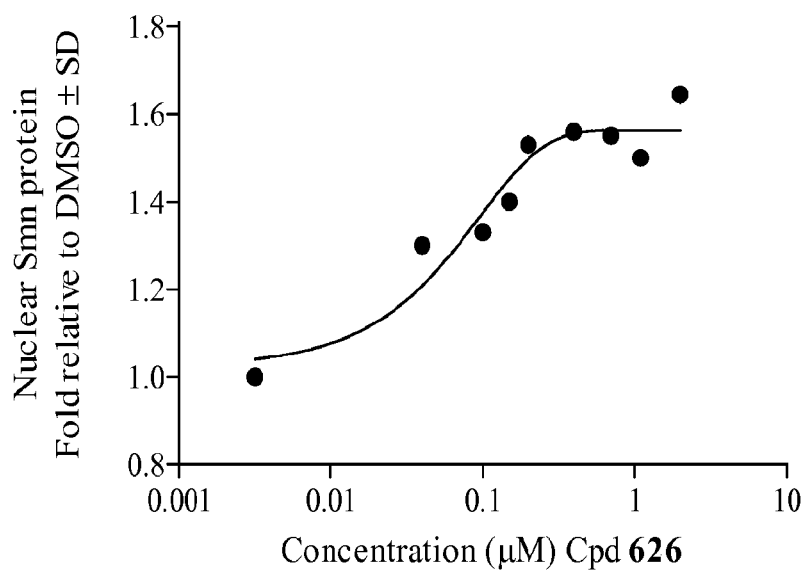

Results. As seen in FIG. 10, human motor neurons treated for 72 hours with increasing concentrations of Compound 35 (FIG. 10a) and Compound 626 (FIG. 10b) contain progressively more Smn protein in the nucleus.

Example 10

Smn Protein Assay in Animal Tissues

This Smn protein assay compares tissues from test compound treated mice with those from DMSO vehicle treated mice to determine the increase in levels of Smn protein produced from the human SMN2 gene.

Materials

| Material | Source |
|---|---|
| Tissues from C/C-allele SMA mice | The Jackson Laboratory, strain # 008714 (B6.129-Smn1$^{tm5(Smn1/SMN2)Mrph}$/J) |
| Tissues from Δ7 SMA mice | The Jackson Laboratory, strain # 005025 (FVB.Cg-Tg(SMN2*delta7)4299Ahmb Tg(SMN2)89Ahmb Smn1$^{tm1Msd}$/J) |
| Protease inhibitor cocktail | Roche Applied Science Catalog No.: 11836145001 |
| Anti-SMN d2 | Blue cap Cisbio Catalog No.: 63IDC002-SMN |
| Anti-SMN kryptate | Red cap Cisbio Catalog No.: 63IDC002-SMN |
| SMN reconstitution buffer | Cisbio Catalog No.: 63IDC002-SMN-Buffer |
| RIPA Lysis Buffer | 20 mM Tris-HCl pH 7.5, 150 mM NaCl, 1 mM EDTA, 1% NP-40, 1% Sodium deoxycholate |
| Diluent Buffer | 20 mM Tris-HCl pH 7.5, 150 mM NaCl |
| BCA protein assay kit | Pierce Catalog No.: 23225 |
| White 384 well plate | Nunc Catalog No.: 351190 |
| Polypropylene V-bottom plate | Falcon Catalog No.: 165195 |
| Clear 96 well polystyrene plate | Nunc Catalog No.: 442404 |
| 5 mm Stainless Steel Beads | Qiagen Catalog No.: 69989 |
| Safe-Lock Tubes 2.0 mL | Eppendorf Catalog No.: 022363352 |
| Twin.tec 96-Well Semiskirted PCR Plate | Eppendorf Catalog No.: 951020389 |
| TissueLyzer II | Qiagen Catalog No.: 85300 |
| Envision Plate Reader | Perkin Elmer Model No.: 2103 |

Protocol. The tissue samples in Safe-Lock tubes are weighed and the volume of RIPA buffer containing the protease inhibitor cocktail is added based on the weight to volume ratios for each type of tissue: Brain (50 mg/mL), Muscle (50 mg/mL) and Spinal Cord (25 mg/mL).

Tissues are homogenized using the TissueLyzer by bead milling. 5 mm stainless steel beads are added to the sample and shaken vigorously for 5 minutes at 30 Hz in the TissueLyzer. The samples are then centrifuged for 20 minutes at 14,000×g in a microcentrifuge and the homogenates transferred to the PCR plate. The homogenates are diluted in RIPA buffer to approximately 1 mg/mL for HTRF and approximately 0.5 mg/mL for total protein measurement using the BCA protein assay. For the SMN HTRF assay, 35 μL of the tissue homogenate is transferred to a 384-well plate containing 5 μL of the antibody solution (1:100 dilution of each of the anti-SMNd2 and anti-SMN Kryptate in reconstitution buffer). To provide a control signal, three (3) wells in the plate contain only RIPA Lysis Buffer and, thus, serve as Blank control wells. The plate is centrifuged for 1 minute to bring the solution to the bottom of the wells and then incubated overnight at room temperature. Fluorescence for each well of the plate at 665 nm and 620 nm is measured on an EnVision multilabel plate reader (Perkin-Elmer). The total protein in the tissue homogenate is measured using the BCA assay according to the manufacturer's protocol.

The normalized fluorescence signal is calculated for each sample, Blank and vehicle control well by dividing the signal at 665 nm by the signal at 620 nm. Normalizing the signal accounts for possible fluorescence quenching due to the matrix effect of the tissue homogenate. The ΔF value (a measurement of Smn protein abundance) for each tissue sample well is calculated by subtracting the normalized average fluorescence for the Blank control wells from the normalized fluorescence for each tissue sample well and then dividing this difference by the normalized average fluorescence for the Blank control wells. The ΔF value for each tissue sample well is divided by the total protein quantity (determined using the BCA assay) for that tissue sample. The change in Smn protein abundance for each tissue sample relative to the vehicle control is calculated as the percent difference in the ΔF value of the tissue sample in the presence of the test compound and the averaged ΔF value of the vehicle control signal divided by the averaged ΔF value of the vehicle control signal.

Example 11

Smn Protein Assay in Tissues of Adult C/C-Allele SMA Mice

The tissues for use in the assay for Smn protein in adult C/C-allele SMA mice are prepared as described in Example 10. The assay assesses whether treatment of C/C-allele SMA mice with a test compound for 10 days increases levels of Smn protein produced from the SMN2 gene.
Materials

| Material | Source |
| --- | --- |
| Tissues from C/C-allele SMA mice | The Jackson Laboratory, strain # 008714 (B6.129-Smn1$^{tm5(Smn1/SMN2)Mrph}$/J) |

Protocol. C/C-allele SMA mice are dosed twice a day orally (in 0.5% hydroxypropylmethyl cellulose (HPMC) with 0.1% Tween-80) with a test compound at 10 mg/kg for 10 days. Age-matched heterozygous mice are dosed with vehicle for use as a control. Tissues are collected for analysis of protein levels according to Example 10.

Figure 11A:
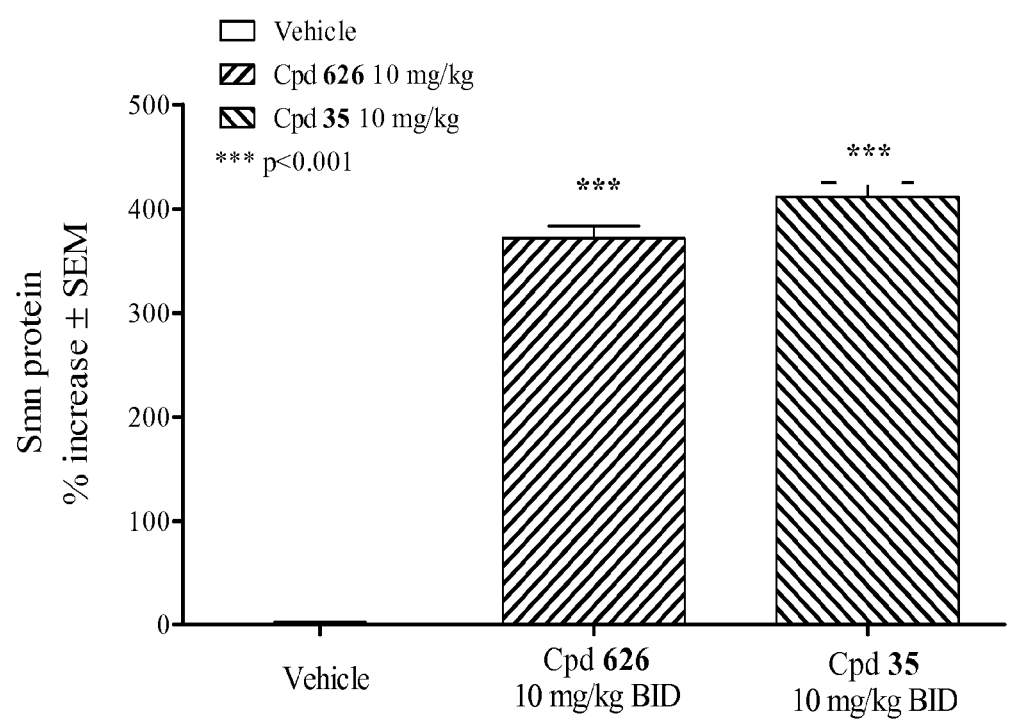
FIG. 11a; Spinal cord.
Figure 11B:
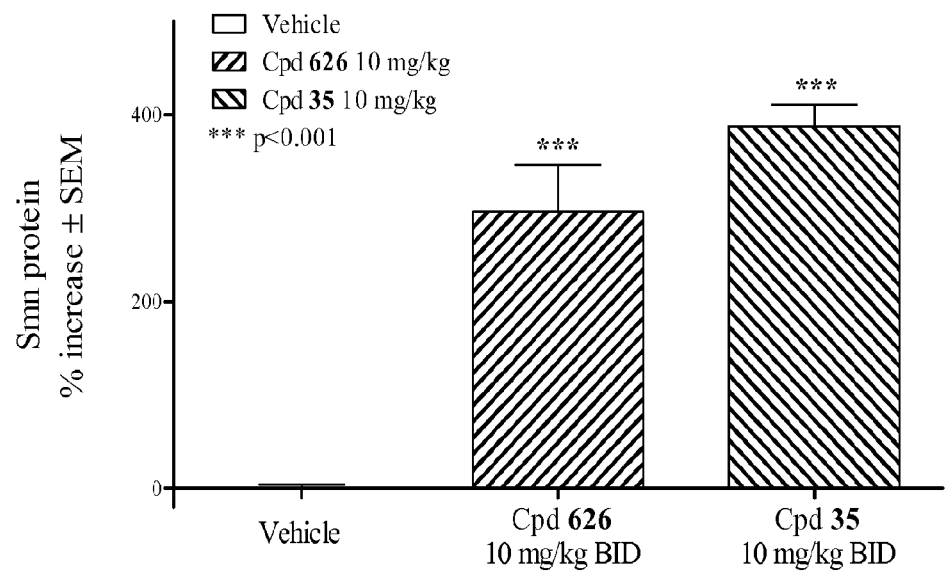
FIG. 11b; and Muscle.
Figure 11C:
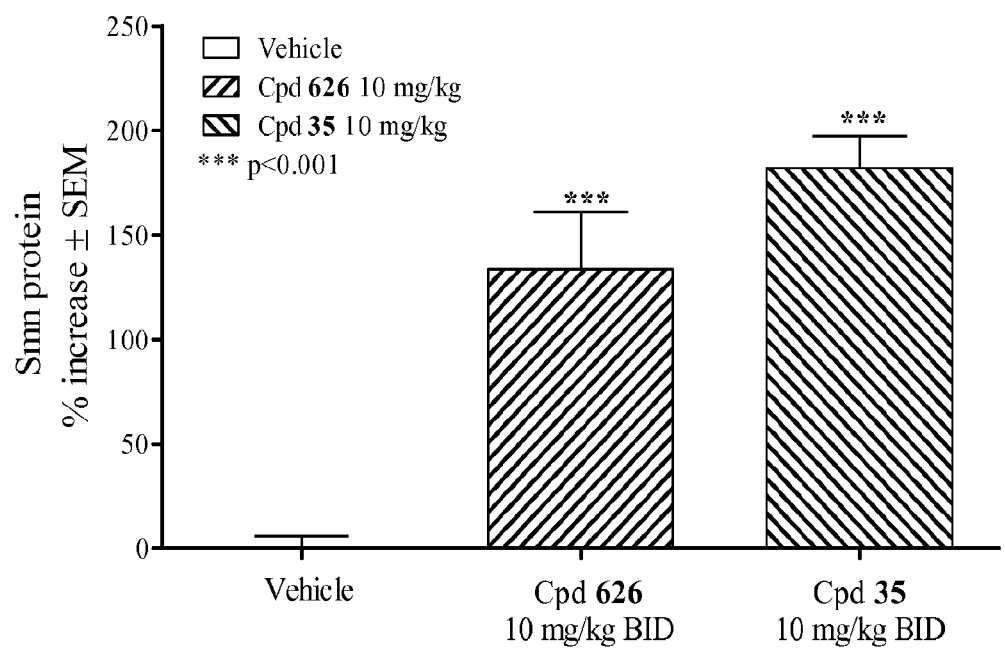
FIG. 11c) of C/C-allele SMA mouse model treated for 10 days twice per day with 10 mg/kg of Compound 35 and Compound 626.

Results. As seen in FIG. 11, total protein normalized Smn level was increased in target tissues (Brain: FIG. 11a; Spinal cord: FIG. 11b; and Muscle: FIG. 11c) of adult C/C-allele SMA mice treated with Compound 35 and Compound 626 relative to the vehicle group. The dashed line in each Figure represents the average increase in normalized Smn levels of heterozygous mice relative to those in the knock out vehicle group. Test compound treatment in the C/C-allele SMA mice increased the Smn protein levels in the target tissues above those observed in the corresponding tissues of the heterozygous mice.

Example 12

Smn Protein in Tissues of Neonatal Δ7 SMA Mice
The assay for Smn protein in neonatal SMA mice tissues is used to determine whether treatment with a test compound increases Smn protein levels produced from the SMN2 gene.
Materials

| Material | Source |
| --- | --- |
| Tissues from Δ7 SMA mice | The Jackson Laboratory, strain # 005025 (FVB.Cg-Tg(SMN2*delta7)4299Ahmb Tg(SMN2)89Ahmb Smn1$^{tm1Msd}$/J) |

Protocol. SMA Δ7 homozygous knockout mice are dosed once a day (QD) intraperitoneally (IP) with a test compound or vehicle (100% DMSO) from postnatal day (PND) 3 to day 9. Tissues are collected for analysis of protein levels according to Example 10.

Figure 12A:
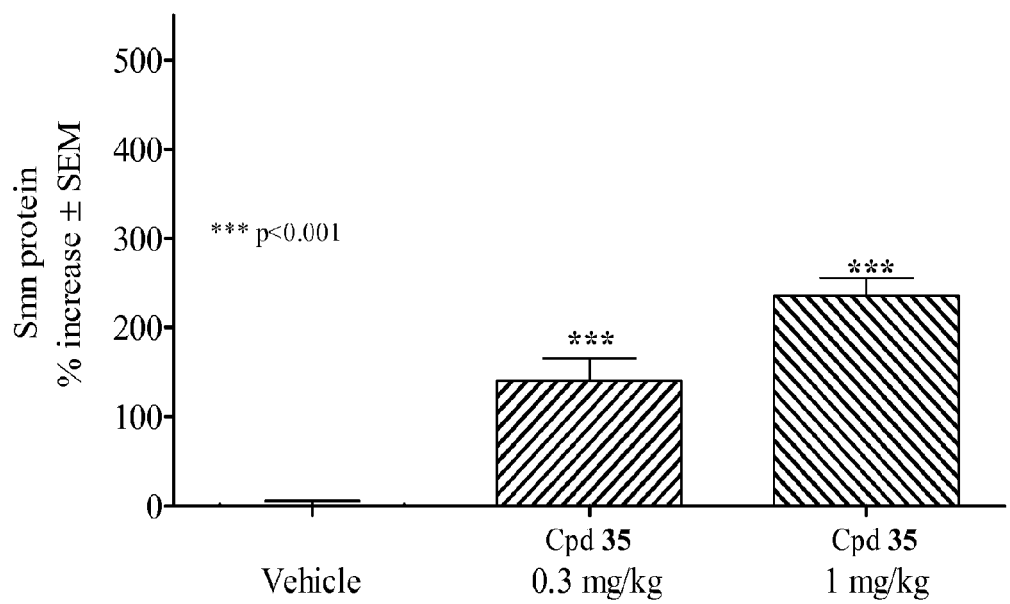
FIG. 12a and FIG. 12b; Spinal cord.
Figure 12B:
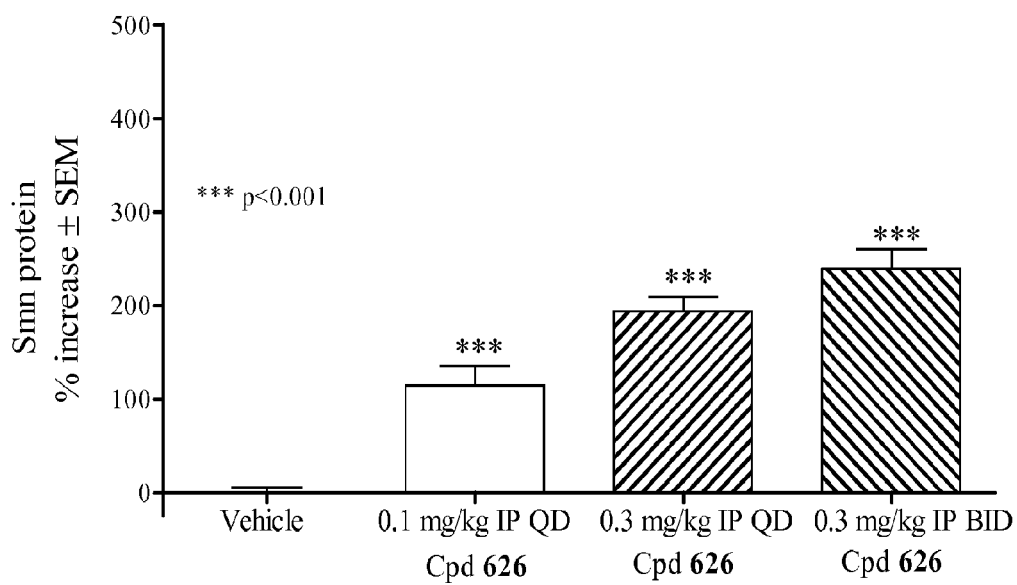
Figure 12C:
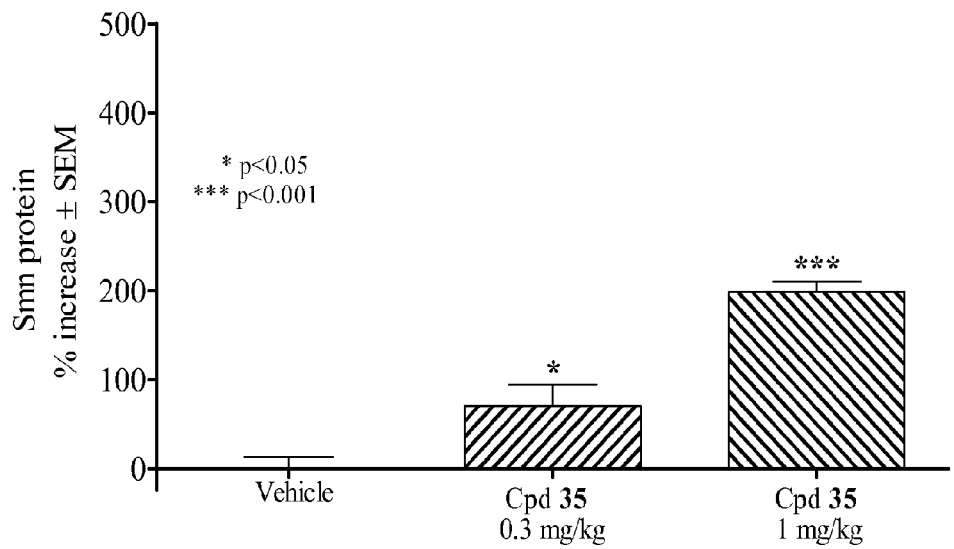
FIG. 12c and FIG. 12d; and Muscle.
Figure 12D:
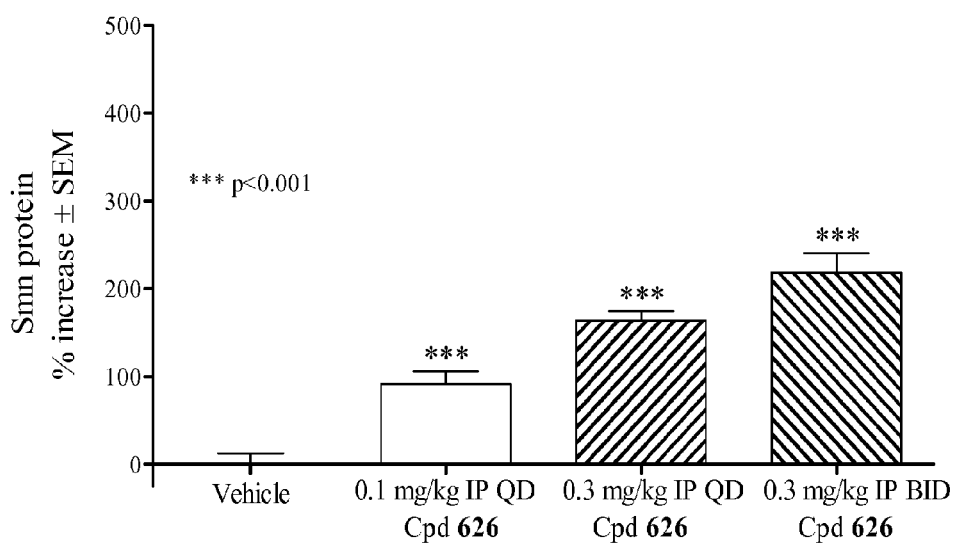
Figure 12E:
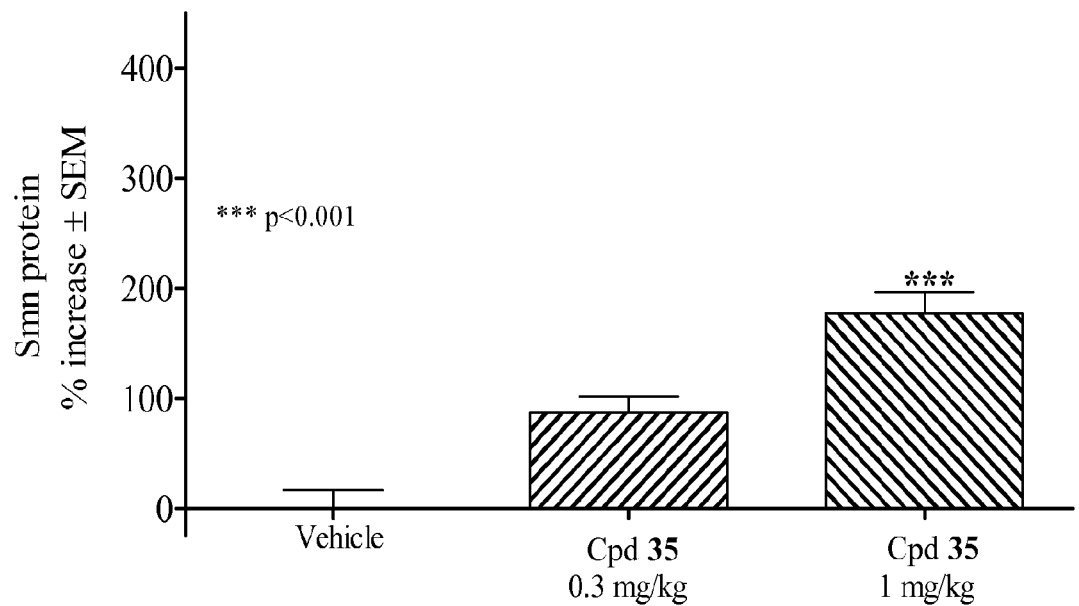
FIG. 12e and FIG. 12f) of neonatal Δ7 SMA mouse model treated for 7 days once per day with indicated doses of Compound 35 and Compound 626, respectively.
Figure 12F:
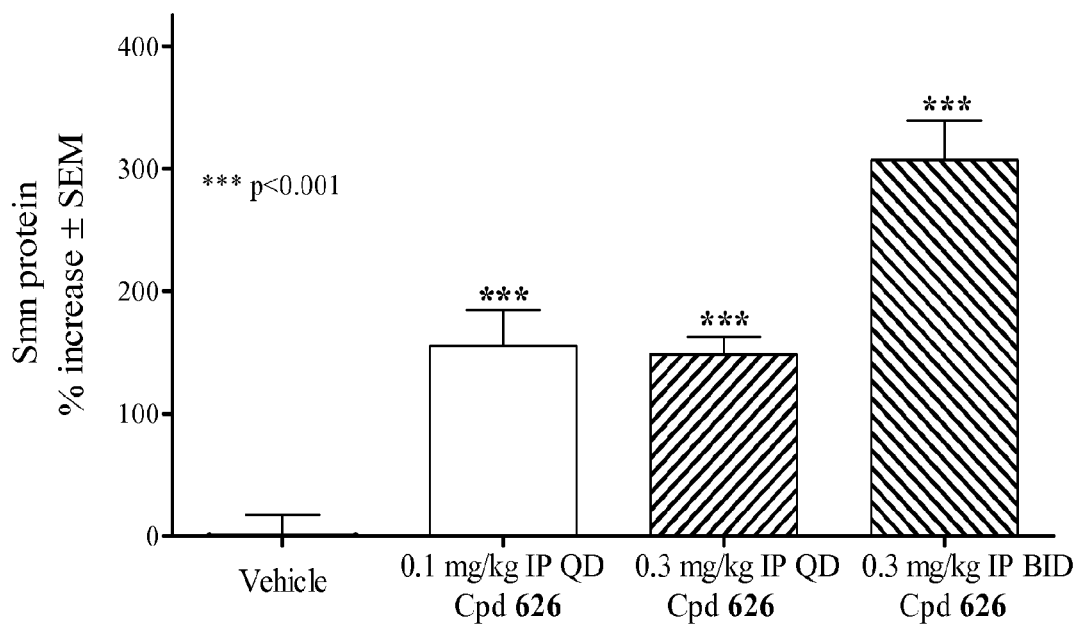

Results. As seen in FIG. 12, total protein normalized Smn level was dose dependently increased in target tissues (Brain: FIG. 12a and FIG. 12b; Spinal cord: FIG. 12c and FIG. 12d; and Muscle: FIG. 12e and FIG. 12f) of neonatal SMA Δ7 homozygous knockout mice treated with Compound 35 and Compound 626, respectively. The dashed line and grey zone in each Figure represent the average and standard deviation of the total protein normalized Smn levels in heterozygous mice.

Example 13

Body Weight of Neonatal Δ7 SMA Mice
The change in body weight of neonatal SMA mice is used to determine whether treatment with a test compound improves body weight.
Materials

| Material | Source |
| --- | --- |
| Tissues from ΔExon7 SMA mice | The Jackson Laboratory, strain # 005025 (FVB.Cg-Tg(SMN2*delta7)4299Ahmb Tg(SMN2)89Ahmb Smn1$^{tm1Msd}$/J) |

Protocol. SMA Δ7 homozygous knockout mice are dosed intraperitoneally (IP) with test compound or vehicle (100% DMSO) once per day (QD) from postnatal day (PND) 3 until the dose regimen is switched to an oral dose twice per day (BID) in 0.5% hydroxypropylmethyl cellulose (HPMC) with 0.1% Tween-80 at a dose 3.16-fold higher than the dose used for IP. Body weights of SMA Δ7 mice treated with test compound or vehicle and age matched heterozygous mice are recorded every day.

Figure 13A:
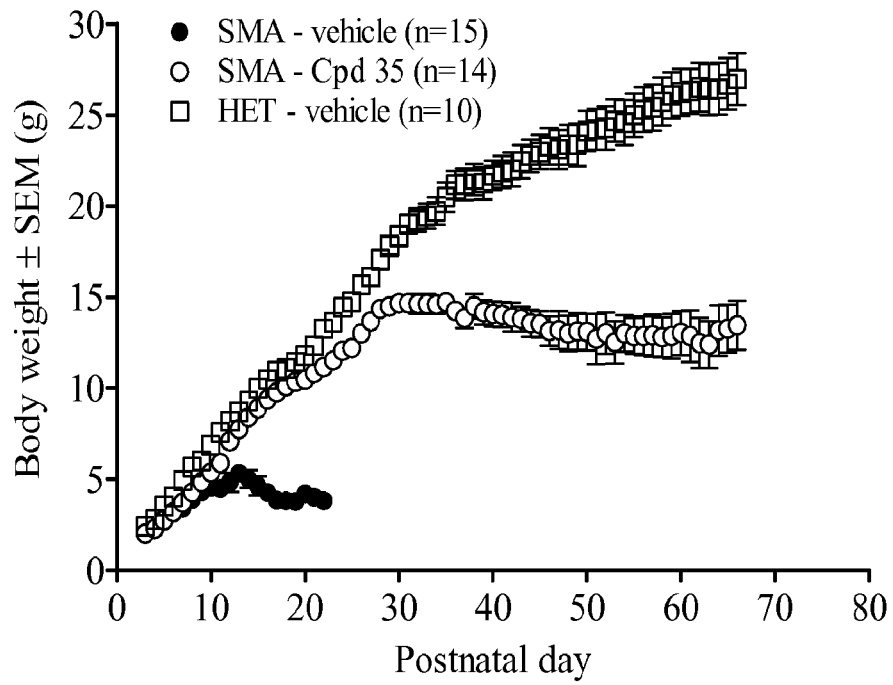
FIG. 13, referenced in Biological Example 13, shows differences in body weight of neonatal Δ7 SMA mouse model treated until postnatal day 66 with Compound 35 (FIG. 13a) and until postnatal day 76 with Compound 626 (FIG. 13b).
Figure 13B:
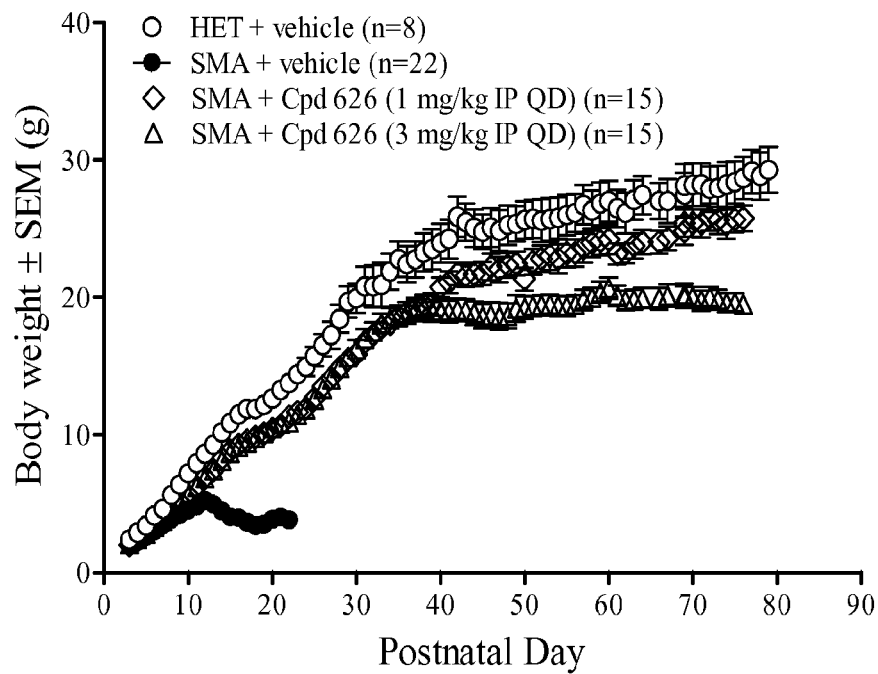

Results. As seen in FIG. 13, body weight of neonatal SMA Δ7 homozygous knockout mice treated with Compound 35, dosed IP QD from PND 3 to day 24, then orally BID from day 25 until study end (FIG. 13a) and Compound 626, dosed IP QD from PND 3 to day 30, then orally BID from day 31 until study end (FIG. 12b) improved compared to vehicle treated mice.

Example 14

Righting Reflex in Neonatal Δ7 SMA Mice
The functional change in righting reflex of neonatal SMA mice is used to determine whether treatment with a test compound improves righting reflex.
Materials

| Material | Source |
| --- | --- |
| Tissues from ΔExon7 SMA mice | The Jackson Laboratory, strain # 005025 (FVB.Cg-Tg(SMN2*delta7)4299Ahmb Tg(SMN2)89Ahmb Smn1$^{tm1Msd}$/J) |

Protocol. SMA Δ7 homozygous knockout mice are dosed intraperitoneally (IP) with test compound or vehicle (100% DMSO) once per day (QD) from postnatal day (PND) 3 until the dose regimen is switched to an oral dose twice per day (BID) in 0.5% hydroxypropylmethyl cellulose (HPMC) with 0.1% Tween-80 at a dose 3.16-fold higher than the dose used for IP. The righting reflex time is measured as the time taken by a mouse to flip over onto its feet after being laid on its back. Righting reflex is measured five times for each mouse (allowing a maximal time of 30 sec for each try) with 5 minutes between each measurement. The righting reflex time for SMA Δ7 homozygous knockout mice treated with test compound or vehicle and age-matched heterozygous mice is measured on PND 10, 14 and 18 and plotted.

Figure 14:
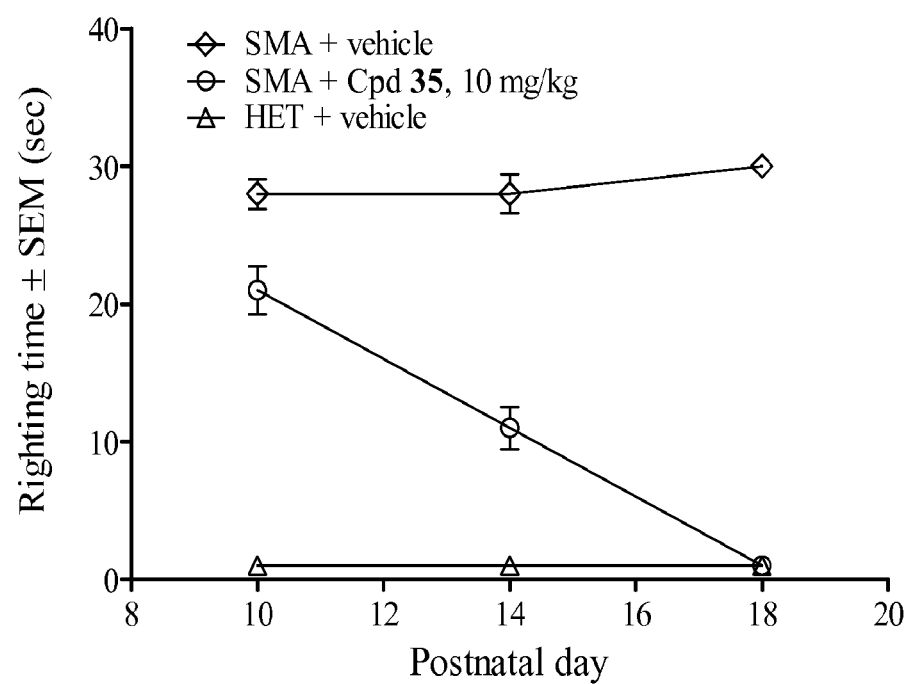
FIG. 14, referenced in Biological Example 14, shows improved righting reflex of neonatal Δ7 SMA mouse model treated with Compound 35.

Results. As seen in FIG. 14, the righting reflex of neonatal SMA Δ7 homozygous knockout mice treated with Compound 35, dosed IP QD from PND 3 to day 24, then orally BID from day 25 until study end, improved compared to vehicle treated mice. The righting time of the compound treated neonatal SMA Δ7 homozygous knockout mice was similar to that of the age matched heterozygous mice on postnatal day 18.

Example 15

Survival of Neonatal Δ7 SMA Mice

The change in the number of surviving mice over time is used to determine whether treatment with a test compound improves survival.

Materials

| Material | Source |
|---|---|
| Tissues from Δ7 SMA mice | The Jackson Laboratory, strain # 005025 (FVB.Cg-Tg(SMN2*delta7)4299Ahmb Tg(SMN2)89Ahmb Smn1$^{tm1Msd}$/J) |

Protocol. SMA Δ7 homozygous knockout mice are dosed intraperitoneally (IP) with test compound or vehicle (100% DMSO) once per day (QD) from postnatal day (PND) 3 until the dose regimen is switched to an oral dose twice per day (BID) in 0.5% hydroxypropylmethyl cellulose (HPMC) with 0.1% Tween-80 at a dose 3.16-fold higher than the dose used for IP. The number of surviving mice in each group is recorded every day and plotted as a percent of total number of mice. Tissues of SMA Δ7 and age-matched heterozygous mice are collected for the measurement of Smn protein levels and processed as detailed in Example 10. The total protein normalized Smn protein levels measured in the tissues are plotted as a percent of those in the age-matched heterozygous mice tissues, with the heterozygous levels represented as 100 percent. The level of Smn protein in the test compound treated mice tissue relative to that in heterozygous mice tissue is indicated as a percent value above each bar in the graph.

Figure 15A:
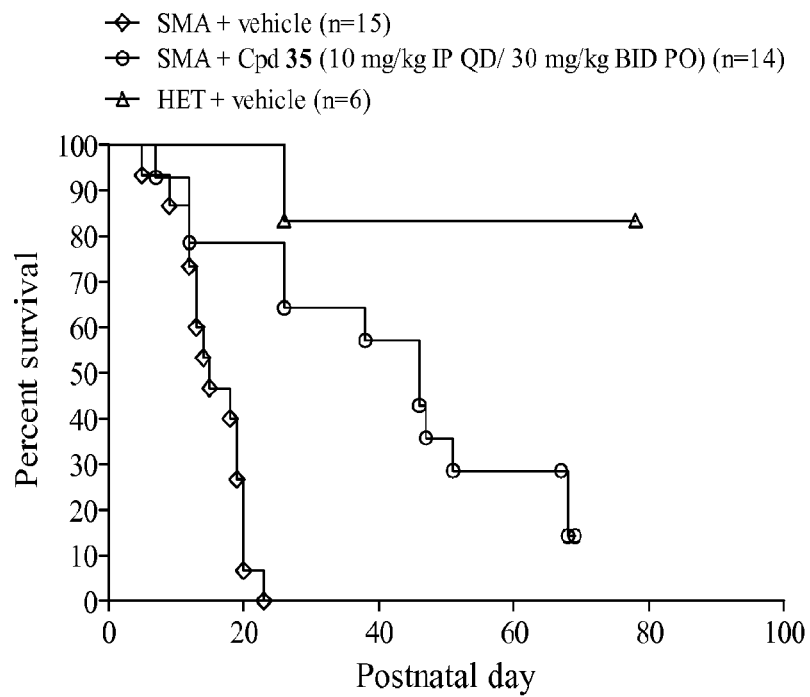
FIG. 15, referenced in Biological Example 15, shows improved survival in a neonatal Δ7 SMA mouse model treated with Compound 35 (FIG. 15a) and Compound 626 (FIG. 15b).
Figure 15B:
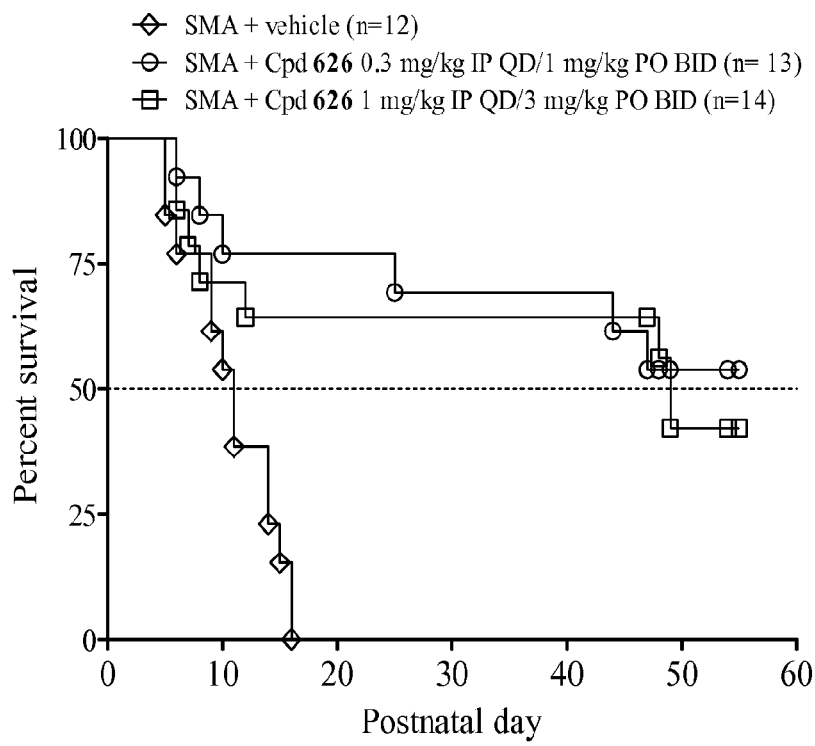

Results. As seen in FIG. 15, survival of neonatal SMA Δ7 homozygous knockout mice treated with Compound 35 (FIG. 15a) dosed IP QD from PND 3 to day 24, then orally BID from day 25 until study end, and Compound 626 (FIG. 15b) dosed IP QD from PND 3 to day 30, then orally BID from day 31 until study end, improved compared to vehicle treated mice.

Figure 16A:
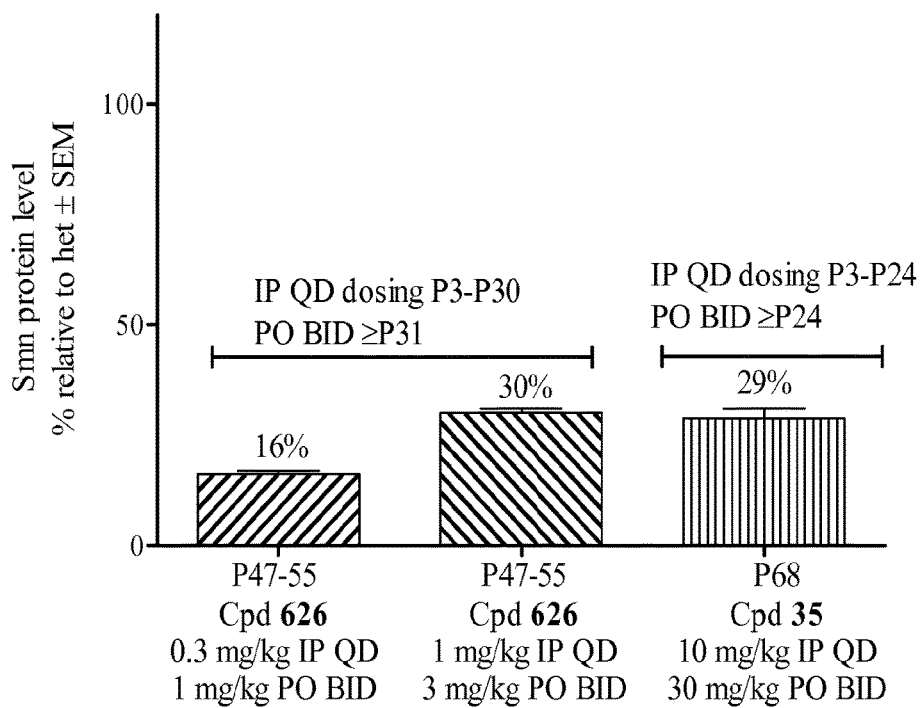
FIG. 16a; and Muscle.
Figure 16B:
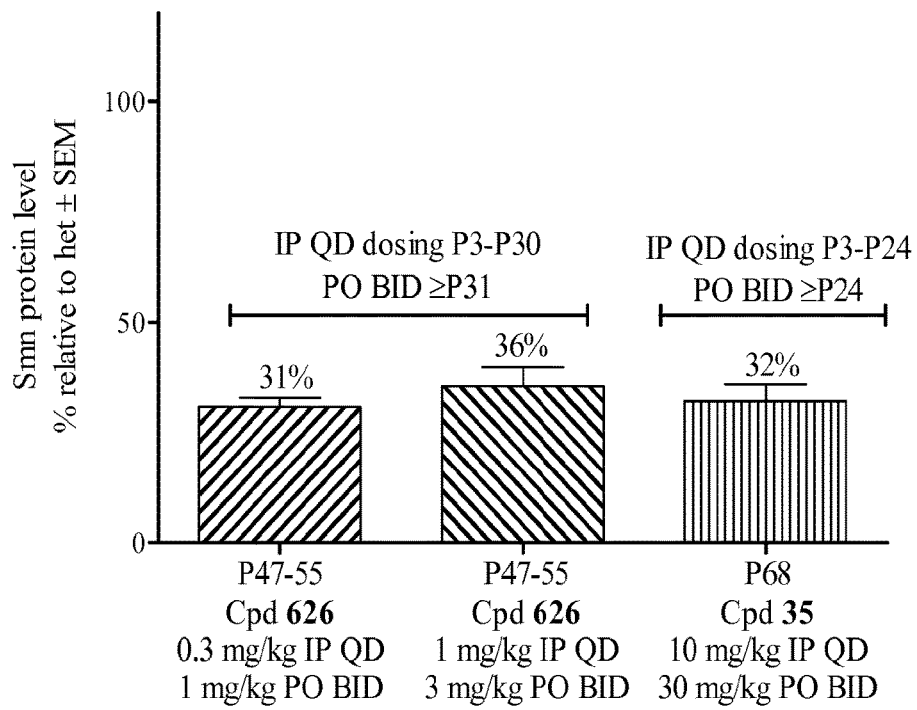
FIG. 16b) in a neonatal Δ7 SMA mouse model treated until postnatal day 47-55 (P47-55) with Compound 35 and until postnatal day 68 (P68) with Compound 626 relative to vehicle treated and age-matched heterozygous mice.

Results. As seen in FIG. 16, Smn protein levels in target tissues (brain, FIG. 16a, and muscle, FIG. 16b) of SMA Δ7 homozygous knockout mice after treatment with Compound 35 and Compound 626 from postnatal day 3 until necropsy was measured and plotted relative to vehicle treated and age-matched heterozygous mice. As seen in FIG. 16a and FIG. 16b, none of the vehicle treated SMA Δ7 homozygous knockout mice survived past day 22.

Without regard to whether a document cited herein was specifically and individually indicated as being incorporated by reference, all documents referred to herein are incorporated by reference into the present application for any and all purposes to the same extent as if each individual reference was fully set forth herein.

Although certain embodiments have been described in detail above, those having ordinary skill in the art will clearly understand that many modifications are possible in the embodiments without departing from the teachings thereof. All such modifications are intended to be encompassed within the claims as described herein.

What is claimed is:

1. A compound selected from Formula (Ia):

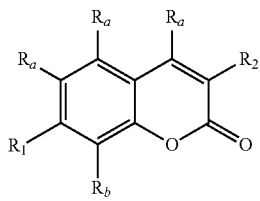

or a free acid, free base, salt, stereoisomer, racemate, enantiomer, diastereomer or tautomer form thereof, wherein:

$R_1$ is heterocyclyl selected from azetidin-1-yl, tetrahydrofuran-3-yl, pyrrolidin-1-yl, piperidin-1-yl, piperidin-4-yl, piperazin-1-yl, 1,4-diazepan-1-yl, 1,2,5,6-tetrahydropyridin-3-yl, 1,2,3,6-tetrahydropyridin-4-yl, hexahydropyrrolo[3,4-b]pyrrol-1(2H)-yl, (3aS,6aS)-hexahydropyrrolo[3,4-b]pyrrol-1(2H)-yl, (3aS,6aS)-hexahydropyrrolo[3,4-b]pyrrol-5(1H)-yl, (3aR,6aR)-hexahydropyrrolo[3,4-b]pyrrol-5(1H)-yl, hexahydropyrrolo[3,4-c]pyrrol-2(1H)-yl, (3aR,6aS)-hexahydropyrrolo[3,4-c]pyrrol-2(1H)-yl, octahydro-5H-pyrrolo[3,2-c]pyridin-5-yl, octahydro-6H-pyrrolo[3,4-b]pyridin-6-yl, (4aR,7aR)-octahydro-6H-pyrrolo[3,4-b]pyridin-6-yl, (4aS,7aS)-octahydro-6H-pyrrolo[3,4-b]pyridin-6-yl, hexahydropyrrolo[1,2-a]pyrazin-2(1H)-yl, hexahydropyrrolo[1,2-a]pyrazin-6(2H)-one, (7R,8aS)-hexahydropyrrolo[1,2-a]pyrazin-2(1H)-yl, (8aS)-hexahydropyrrolo[1,2-a]pyrazin-2(1H)-yl, (8aR)-hexahydropyrrolo[1,2-a]pyrazin-2(1H)-yl, (8aS)-octahydropyrrolo[1,2-a]pyrazin-2(1H)-yl, (8aR)-octahydropyrrolo[1,2-a]pyrazin-2(1H)-yl, octahydro-2H-pyrido[1,2-a]pyrazin-2-yl, 3-azabicyclo[3.1.0]hex-3-yl, 8-azabicyclo[3.2.1]oct-3-yl, (1R,5S)-8-azabicyclo[3.2.1]oct-3-yl, 8-azabicyclo[3.2.1]oct-2-en-3-yl, (1R,5S)-8-azabicyclo[3.2.1]oct-2-en-3-yl, 9-azabicyclo[3.3.1]non-3-yl, (1R,5S)-9-azabicyclo[3.3.1]non-3-yl, 2,5-diazabicyclo[2.2.1]hept-2-yl, (1S,4S)-2,5-diazabicyclo[2.2.1]hept-2-yl, 2,5-diazabicyclo[2.2.2]oct-2-yl, 3,8-diazabicyclo[3.2.1]oct-3-yl, (1R,5S)-3,8-diazabicyclo[3.2.1]oct-3-yl, 1,4-diazabicyclo[3.2.2]non-4-yl, azaspiro[3.3]hept-2-yl, 2,6-diazaspiro[3.3]hept-2-yl, 2,7-diazaspiro[3.5]non-7-yl, 5,8-diazaspiro[3.5]non-8-yl, 2,7-diazaspiro[4.4]non-2-yl and 6,9-diazaspiro[4.5]dec-9-yl optionally substituted with one, two or three $R_3$ substituents and one additional, optional $R_4$ substituent;

$R_2$ is heteroaryl selected from thien-2-yl, thien-3-yl, 1H-pyrazol-4-yl, 1H-pyrazol-5-yl, 1H-imidazol-1-yl, 1H-imidazol-4-yl, 1,2,4-oxadiazol-3-yl, pyridin-2-yl, pyridin-3-yl, pyridine-4-yl, pyrimidin-4-yl, 1H-indol-3-yl, 1H-indol-4-yl, indol-5-yl, indol-6-yl, 1H-indazol-5-yl, 2H-indazol-5-yl, indolizin-2-yl, benzofuran-2-yl, benzothien-2-yl, benzothien-3-yl, 1H-benzimidazol-6-yl, 1,3-benzoxazol-5-yl, 1,3-benzoxazol-6-yl, 1,3-benzothiazol-5-yl, 1,3-benzothiazol-6-yl, 9H-purin-8-yl, furo[3,2-b]pyridine-2-yl, furo[3,2-c]pyridine-2-yl, furo[2,3-c]pyridin-2-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrrolo[1,2-b]pyridazin-6-yl, pyrazolo[1,5-a]pyridin-2-yl, pyrazolo[1,5-a]pyrazin-2-yl, imidazo[2,1-b][1,3]thiazol-6-yl, imidazo[2,1-b][1,3,4]thiadiazol-6-yl, [1,3]oxazolo[4,5-b]pyridin-2-yl, imidazo[1,2-a]pyridin-6-yl, imidazo[1,2-a]pyrimidin-2-yl, imidazo[1,2-a]pyrimidin-6-yl, imidazo[1,2-c]pyrimidin-2-yl, imidazo[1,2-b]pyridazin-2-yl, imidazo[1,2-b]pyridazin-6-yl, imidazo[1,2-a]pyrazin-2-yl and quinoxalin-2-yl;

wherein, each heteroaryl is optionally substituted with one, two or three $R_6$ substituents and one additional, optional $R_7$ substituent;

$R_a$ is, in each instance, independently selected from hydrogen, halogen or $C_{1-8}$alkyl;

$R_b$ is hydrogen, halogen, $C_{1-8}$alkyl or $C_{1-8}$alkoxy;

$R_3$ is, in each instance, independently selected from cyano, halogen, hydroxy, oxo, $C_{1-8}$alkyl, halo-$C_{1-8}$alkyl, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$alkoxy-carbonyl, amino, $C_{1-8}$alkyl-amino, $(C_{1-8}$alkyl$)_2$-amino, amino-$C_{1-8}$alkyl, $C_{1-8}$alkyl-amino-$C_{1-8}$alkyl, $(C_{1-8}$alkyl$)_2$-amino-$C_{1-8}$alkyl, amino-$C_{1-8}$alkyl-amino, $C_{1-8}$alkylamino-$C_{1-8}$alkyl-amino, $(C_{1-8}$alkyl$)_2$-amino-$C_{1-8}$alkyl-amino, $C_{1-8}$alkoxy-$C_{1-8}$alkyl-amino, $C_{1-8}$alkyl-carbonyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl$)_2$-amino or (hydroxy-$C_{1-8}$alkyl)($C_{1-8}$alkyl)amino;

$R_4$ is $C_{3-14}$cycloalkyl, $C_{3-14}$cycloalkyl-$C_{1-8}$alkyl, $C_{3-14}$cycloalkyl-amino, aryl-$C_{1-8}$alkyl, aryl-$C_{1-8}$alkoxy-carbonyl, heterocyclyl or heterocyclyl-$C_{1-8}$alkyl; wherein, each instance of $C_{3-14}$cycloalkyl, aryl and heterocyclyl is optionally substituted with one, two or three $R_5$ substituents;

$R_5$ is, in each instance, independently selected from halogen, hydroxy, cyano, nitro, $C_{1-8}$alkyl, halo-$C_{1-8}$alkyl, $C_{1-8}$alkoxy, halo-$C_{1-8}$alkoxy, amino, $C_{1-8}$alkyl-amino, $(C_{1-8}$alkyl$)_2$-amino or $C_{1-8}$alkyl-thio;

$R_6$ is, in each instance, independently selected from halogen, hydroxy, cyano, nitro, $C_{1-8}$alkyl, halo-$C_{1-8}$alkyl, hydroxy-$C_{1-8}$alkyl, $C_{1-8}$alkoxy, halo-$C_{1-8}$alkoxy, amino, $C_{1-8}$alkyl-amino, $(C_{1-8}$alkyl$)_2$-amino or $C_{1-8}$alkyl-thio; and, $R_7$ is $C_{3-14}$cycloalkyl, $C_{3-14}$cycloalkyl-oxy, aryl, heterocyclyl or heteroaryl.

2. The compound of claim 1, wherein the salt form is a chloride, hydrochloride, dihydrochloride, hydrobromide, acetate or trifluoroacetate salt.

3. A compound, wherein the compound is selected from:
7-(piperazin-1-yl)-3-[4-(trifluoromethyl)-1,3-benzoxazol-2-yl]-2H-chromen-2-one;
7-(piperazin-1-yl)-3-[7-(trifluoromethyl)-1,3-benzoxazol-2-yl]-2H-chromen-2-one;
2-oxo-N-phenyl-7-(piperazin-1-yl)-2H-chromene-3-carboxamide;
3-(1,3-benzothiazol-2-yl)-7-(piperazin-1-yl)-2H-chromen-2-one;
3-(4-chloro-1,3-benzothiazol-2-yl)-7-(piperazin-1-yl)-2H-chromen-2-one;
3-(7-chloro-1,3-benzothiazol-2-yl)-7-(piperazin-1-yl)-2H-chromen-2-one;
3-(4-chloro-1,3-benzothiazol-2-yl)-7-(piperazin-1-ylmethyl)-2H-chromen-2-one;
3-(1,3-benzothiazol-2-yl)-7-[(propan-2-ylamino)methyl]-2H-chromen-2-one;
7-[(propan-2-ylamino)methyl]-3-[4-(trifluoromethyl)-1,3-benzothiazol-2-yl]-2H-chromen-2-one;
3-(4-chloro-1,3-benzothiazol-2-yl)-7-[(propan-2-ylamino)methyl]-2H-chromen-2-one;
7-(4-methylpiperazin-1-yl)-3-[3-(trifluoromethyl)phenyl]-2H-chromen-2-one;
7-(piperazin-1-yl)-3-(pyridin-3-yl)-2H-chromen-2-one;
3-(1,3-benzothiazol-2-yl)-7-[(dimethylamino)methyl]-2H-chromen-2-one;
3-(4-chloro-1,3-benzothiazol-2-yl)-7-[(dimethylamino)methyl]-2H-chromen-2-one;
3-(1,3-benzothiazol-2-yl)-7-[4-(propan-2-yl)piperazin-1-yl]-2H-chromen-2-one;
3-(1,3-benzothiazol-2-yl)-7-(4-methylpiperazin-1-yl)-2H-chromen-2-one;
3-(4-chloro-1,3-benzothiazol-2-yl)-7-(4-methylpiperazin-1-yl)-2H-chromen-2-one;
3-(4-chloro-1,3-benzothiazol-2-yl)-7-(piperidin-4-yl)-2H-chromen-2-one;
3-(5-fluoro-1,3-benzoxazol-2-yl)-7-(piperazin-1-yl)-2H-chromen-2-one;
3-(1,3-benzoxazol-2-yl)-7-(piperidin-4-yloxy)-2H-chromen-2-one;
3-(4-methyl-1,3-benzoxazol-2-yl)-7-(4-methylpiperazin-1-yl)-2H-chromen-2-one;
3-(4-methyl-1,3-benzoxazol-2-yl)-7-(piperazin-1-yl)-2H-chromen-2-one;
3-(1,3-benzoxazol-2-yl)-7-[(3R,5S)-3,5-dimethylpiperazin-1-yl]-2H-chromen-2-one;
3-(1,3-benzothiazol-2-yl)-7-[(3R,5S)-3,5-dimethylpiperazin-1-yl]-2H-chromen-2-one;
3-(4-chloro-1,3-benzothiazol-2-yl)-7-[(3R,5S)-3,5-dimethylpiperazin-1-yl]-2H-chromen-2-one;
3-(3-fluorophenyl)-7-(piperazin-1-yl)-2H-chromen-2-one;
7-(piperazin-1-yl)-3-(pyridin-4-yl)-2H-chromen-2-one;
3-(4-chloro-1,3-benzothiazol-2-yl)-7-[(4-methylpiperazin-1-yl)carbonyl]-2H-chromen-2-one;
7-(piperazin-1-yl)-3-(1H-pyrazol-5-yl)-2H-chromen-2-one;
7-[(3R,5S)-3,5-dimethylpiperazin-1-yl]-2-oxo-N-phenyl-2H-chromene-3-carboxamide;
7-[(3R,5S)-3,5-dimethylpiperazin-1-yl]-3-(4-methyl-1,3-benzoxazol-2-yl)-2H-chromen-2-one;
7-(piperazin-1-yl)-3-(pyridin-2-ylamino)-2H-chromen-2-one;
7-(piperazin-1-yl)-3-(pyrimidin-2-ylamino)-2H-chromen-2-one;
3-(imidazo[1,2-a]pyridin-2-yl)-7-(piperazin-1-yl)-2H-chromen-2-one;
3-(4-chloro-1,3-benzothiazol-2-yl)-7-[2-(propan-2-ylamino)ethyl]-2H-chromen-2-one;
3-(4-chloro-1,3-benzothiazol-2-yl)-7-[3-(propan-2-ylamino)propyl]-2H-chromen-2-one;
3-(4-methyl-1,3-thiazol-2-yl)-7-(piperazin-1-yl)-2H-chromen-2-one;
3-(1-methyl-1H-pyrazol-3-yl)-7-(piperazin-1-yl)-2H-chromen-2-one;
7-[(3R,5S)-3,5-dimethylpiperazin-1-yl]-3-(4-fluoro-1,3-benzoxazol-2-yl)-2H-chromen-2-one;
3-(4-fluoro-1,3-benzoxazol-2-yl)-7-(piperazin-1-yl)-2H-chromen-2-one;
3-(1,3-benzothiazol-2-yl)-2-oxo-2H-chromen-7-yl piperazine-1-carboxylate;
3-(4-chloro-1,3-benzothiazol-2-yl)-2-oxo-2H-chromen-7-yl piperazine-1-carboxylate;
benzyl 4-[3-(1-methyl-1H-benzimidazol-2-yl)-2-oxo-2H-chromen-7-yl]piperazine-1-carboxylate;
3-(8-methylimidazo[1,2-a]pyridin-2-yl)-7-(piperazin-1-yl)-2H-chromen-2-one;
7-(4-methylpiperazin-1-yl)-3-(4-phenyl-1,3-thiazol-2-yl)-2H-chromen-2-one;
3-(1,3-benzothiazol-2-yl)-7-(piperidin-4-yloxy)-2H-chromen-2-one;
3-(1,3-benzoxazol-2-yl)-7-(4-methyl-1,4-diazepan-1-yl)-2H-chromen-2-one;
3-(1,3-benzoxazol-2-yl)-7-[3-(dimethylamino)pyrrolidin-1-yl]-2H-chromen-2-one;
3-(1,3-benzoxazol-2-yl)-7-{[2-(dimethylamino)ethyl](methyl)amino}-2H-chromen-2-one;
3-(5-phenyl-1,2,4-oxadiazol-3-yl)-7-(piperazin-1-yl)-2H-chromen-2-one;
3-(6-methylimidazo[1,2-a]pyridin-2-yl)-7-(piperazin-1-yl)-2H-chromen-2-one;
7-(piperazin-1-yl)-3-(pyridin-3-ylamino)-2H-chromen-2-one;
7-(4-methylpiperazin-1-yl)-3-[4-(trifluoromethyl)-1,3-thiazol-2-yl]-2H-chromen-2-one
3-(1,3-benzothiazol-2-yl)-7-[(3S)-pyrrolidin-3-yloxy]-2H-chromen-2-one 3-(1,3-benzothiazol-2-yl)-7-[(3R)-pyrrolidin-3-yloxy]-2H-chromen-2-one
3-(1,3-benzothiazol-2-yl)-7-[(2S)-pyrrolidin-2-ylmethoxy]-2H-chromen-2-one
3-(1,3-benzothiazol-2-yl)-7-[(diethylamino)methyl]-2H-chromen-2-one
3-(4-chloro-1,3-benzothiazol-2-yl)-7-[(diethylamino)methyl]-2H-chromen-2-one
3-(1,3-benzothiazol-2-yl)-7-(piperidin-1-ylmethyl)-2H-chromen-2-one
3-(4-chloro-1,3-benzothiazol-2-yl)-7-(piperidin-1-ylmethyl)-2H-chromen-2-one
3-[(3-methylpyridin-2-yl)amino]-7-(piperazin-1-yl)-2H-chromen-2-one
3-[(4-methylpyridin-2-yl)amino]-7-(piperazin-1-yl)-2H-chromen-2-one
3-[(5-methylpyridin-2-yl)amino]-7-(piperazin-1-yl)-2H-chromen-2-one
3-[(6-methylpyridin-2-yl)amino]-7-(piperazin-1-yl)-2H-chromen-2-one
3-[(5-chloropyridin-2-yl)amino]-7-(piperazin-1-yl)-2H-chromen-2-one
7-(piperazin-1-yl)-3-(pyridin-3-ylamino)-2H-chromen-2-one
3-(4-iodo-1,3-benzoxazol-2-yl)-7-(piperazin-1-yl)-2H-chromen-2-one;
3-(4-chloro-1,3-benzoxazol-2-yl)-7-(4-methylpiperazin-1-yl)-2H-chromen-2-one;
3-(4-chloro-1,3-benzoxazol-2-yl)-7-[(3R,5S)-3,5-dimethylpiperazin-1-yl]-2H-chromen-2-one;
3-(4-chloro-1,3-benzoxazol-2-yl)-7-(piperazin-1-yl)-2H-chromen-2-one;
3-(6-chloroimidazo[1,2-a]pyridin-2-yl)-7-(piperazin-1-yl)-2H-chromen-2-one;
3-(imidazo[1,2-a]pyridin-2-yl)-7-(4-methylpiperazin-1-yl)-2H-chromen-2-one;
7-(4-methylpiperazin-1-yl)-3-(1-methyl-1H-pyrazol-3-yl)-2H-chromen-2-one;
7-(4-methylpiperazin-1-yl)-3-(1-phenyl-1H-pyrazol-3-yl)-2H-chromen-2-one;
3-(phenylamino)-7-(piperazin-1-yl)-2H-chromen-2-one;
7-(piperazin-1-yl)-3-[4-(trifluoromethyl)pyridin-2-yl]-2H-chromen-2-one;
3-(3-methoxyphenyl)-7-(piperazin-1-yl)-2H-chromen-2-one;
3-(1,3-benzothiazol-2-yl)-7-[(methylamino)methyl]-2H-chromen-2-one;
3-(1,3-benzothiazol-2-yl)-7-{[(2-hydroxyethyl)(methyl)amino]methyl}-2H-chromen-2-one;
3-(4-methyl-1H-pyrazol-3-yl)-7-(piperazin-1-yl)-2H-chromen-2-one;
3-(6-methylimidazo[1,2-a]pyridin-2-yl)-7-(4-methylpiperazin-1-yl)-2H-chromen-2-one;
3-(6-methylimidazo[1,2-a]pyridin-2-yl)-7-[4-(propan-2-yl)piperazin-1-yl]-2H-chromen-2-one;
3-(8-chloroimidazo[1,2-a]pyridin-2-yl)-7-(piperazin-1-yl)-2H-chromen-2-one;
3-(8-methylimidazo[1,2-a]pyridin-2-yl)-7-(4-methylpiperazin-1-yl)-2H-chromen-2-one;
3-(1,3-benzoxazol-2-yl)-7-(2,5-diazabicyclo[2.2.1]hept-2-yl)-2H-chromen-2-one;
3-(1,3-benzoxazol-2-yl)-7-(2,5-dimethylpiperazin-1-yl)-2H-chromen-2-one;
3-(imidazo[1,2-a]pyrimidin-2-yl)-7-(4-methylpiperazin-1-yl)-2H-chromen-2-one;
3-(imidazo[2,1-b][1,3]thiazol-6-yl)-7-(piperazin-1-yl)-2H-chromen-2-one;
3-(imidazo[1,2-a]pyrimidin-2-yl)-7-(piperazin-1-yl)-2H-chromen-2-one;
7-(piperazin-1-yl)-3-[6-(trifluoromethyl)pyridin-2-yl]-2H-chromen-2-one;
3-(1H-indazol-5-yl)-7-(piperazin-1-yl)-2H-chromen-2-one;
3-(6-chloroimidazo[1,2-a]pyridin-2-yl)-7-(4-methyl-1,4-diazepan-1-yl)-2H-chromen-2-one;
3-(6-chloroimidazo[1,2-a]pyridin-2-yl)-7-[(2R,5S)-2,5-dimethylpiperazin-1-yl]-2H-chromen-2-one;
3-(6-chloroimidazo[1,2-a]pyridin-2-yl)-7-(4-methylpiperazin-1-yl)-2H-chromen-2-one;
7-(4-ethylpiperazin-1-yl)-3-(6-methylimidazo[1,2-a]pyridin-2-yl)-2H-chromen-2-one;
3-(2-methylimidazo[2,1-b][1,3]thiazol-6-yl)-7-(piperazin-1-yl)-2H-chromen-2-one;
3-(2-methylimidazo[2,1-b][1,3]thiazol-6-yl)-7-(4-methylpiperazin-1-yl)-2H-chromen-2-one;
3-(3-methylimidazo[2,1-b][1,3]thiazol-6-yl)-7-(piperazin-1-yl)-2H-chromen-2-one;
3-(1,3-benzothiazol-2-yl)-7-{[(1,3-dihydroxypropan-2-yl)amino]methyl}-2H-chromen-2-one;
7-(4-ethylpiperazin-1-yl)-3-(8-methylimidazo[1,2-a]pyridin-2-yl)-2H-chromen-2-one;
3-(8-methylimidazo[1,2-a]pyridin-2-yl)-7-(4-propylpiperazin-1-yl)-2H-chromen-2-one;
7-[4-(2-hydroxyethyl)piperazin-1-yl]-3-(8-methylimidazo[1,2-a]pyridin-2-yl)-2H-chromen-2-one;
3-(6-fluoroimidazo[1,2-a]pyridin-2-yl)-7-(piperazin-1-yl)-2H-chromen-2-one;
3-(6-chloroimidazo[1,2-a]pyridin-2-yl)-7-[4-(2-hydroxyethyl)piperazin-1-yl]-2H-chromen-2-one;
3-(6-chloroimidazo[1,2-a]pyridin-2-yl)-7-[(3R,5S)-3,5-dimethylpiperazin-1-yl]-2H-chromen-2-one;
tert-butyl {(3S)-1-[3-(6-chloroimidazo[1,2-a]pyridin-2-yl)-2-oxo-2H-chromen-7-yl]pyrrolidin-3-yl}carbamate;
7-[(3R,5S)-3,5-dimethylpiperazin-1-yl]-3-(imidazo[1,2-a]pyrimidin-2-yl)-2H-chromen-2-one;
7-(4-ethylpiperazin-1-yl)-3-(imidazo[1,2-a]pyrimidin-2-yl)-2H-chromen-2-one;
3-(imidazo[1,2-a]pyrimidin-2-yl)-7-(4-propylpiperazin-1-yl)-2H-chromen-2-one;
3-([1,3]oxazolo[4,5-b]pyridin-2-yl)-7-(piperazin-1-yl)-2H-chromen-2-one;
7-(4-methylpiperazin-1-yl)-3-([1,3]oxazolo[4,5-b]pyridin-2-yl)-2H-chromen-2-one;
3-(6-chloroimidazo[1,2-a]pyridin-2-yl)-4-methyl-7-(piperazin-1-yl)-2H-chromen-2-one;
3-(5-chloropyridin-2-yl)-7-(piperazin-1-yl)-2H-chromen-2-one;
7-(piperazin-1-yl)-3-[7-(trifluoromethyl)imidazo[1,2-a]pyridin-2-yl]-2H-chromen-2-one;
7-(4-methylpiperazin-1-yl)-3-[7-(trifluoromethyl)imidazo[1,2-a]pyridin-2-yl]-2H-chromen-2-one;
7-[(3R,5S)-3,5-dimethylpiperazin-1-yl]-3-[7-(trifluoromethyl)imidazo[1,2-a]pyridin-2-yl]-2H-chromen-2-one;
3-(imidazo[2,1-b][1,3]thiazol-6-yl)-7-(4-methylpiperazin-1-yl)-2H-chromen-2-one;
3-(imidazo[1,2-a]pyrimidin-2-yl)-7-(4-methyl-1,4-diazepan-1-yl)-2H-chromen-2-one;
3-(8-chloroimidazo[1,2-a]pyridin-2-yl)-7-(4-propylpiperazin-1-yl)-2H-chromen-2-one;
3-(8-chloroimidazo[1,2-a]pyridin-2-yl)-7-[(3R,5S)-3,5-dimethylpiperazin-1-yl]-2H-chromen-2-one;
3-(8-chloroimidazo[1,2-a]pyridin-2-yl)-7-[4-(2-hydroxyethyl)piperazin-1-yl]-2H-chromen-2-one;

3-(8-chloroimidazo[1,2-a]pyridin-2-yl)-7-[(3S)-3-(dimethylamino)pyrrolidin-1-yl]-2H-chromen-2-one;
3-(7-chloroimidazo[1,2-a]pyridin-2-yl)-7-[(3R,5S)-3,5-dimethylpiperazin-1-yl]-2H-chromen-2-one;
7-(piperazin-1-yl)-3-[2-(trifluoromethyl)pyridin-3-yl]-2H-chromen-2-one;
7-(4-methylpiperazin-1-yl)-3-[2-(trifluoromethyl)pyridin-3-yl]-2H-chromen-2-one;
3-(3-fluoropyridin-4-yl)-7-(piperazin-1-yl)-2H-chromen-2-one;
3-(1,3-benzothiazol-2-yl)-7-{[(3R)-1-ethylpyrrolidin-3-yl]oxy}-2H-chromen-2-one;
3-(imidazo[1,2-b]pyridazin-2-yl)-7-(4-methylpiperazin-1-yl)-2H-chromen-2-one;
7-[(1S,4S)-2,5-diazabicyclo[2.2.1]hept-2-yl]-3-(imidazo[1,2-a]pyrimidin-2-yl)-2H-chromen-2-one;
7-{[2-(dimethylamino)ethyl](methyl)amino}-3-(imidazo[1,2-a]pyrimidin-2-yl)-2H-chromen-2-one;
3-(7-methylimidazo[1,2-a]pyridin-2-yl)-7-(piperazin-1-yl)-2H-chromen-2-one;
3-(5-methylimidazo[1,2-a]pyridin-2-yl)-7-(piperazin-1-yl)-2H-chromen-2-one;
7-[(3R,5S)-3,5-dimethylpiperazin-1-yl]-3-(7-methylimidazo[1,2-a]pyridin-2-yl)-2H-chromen-2-one;
3-(7-methylimidazo[1,2-a]pyridin-2-yl)-7-(4-methylpiperazin-1-yl)-2H-chromen-2-one;
3-(5-methylimidazo[1,2-a]pyridin-2-yl)-7-(4-methylpiperazin-1-yl)-2H-chromen-2-one;
7-[(3R,5S)-3,5-dimethylpiperazin-1-yl]-3-(8-methylimidazo[1,2-a]pyridin-2-yl)-2H-chromen-2-one;
3-(8-chloroimidazo[1,2-a]pyridin-2-yl)-7-[(3R,5S)-3,4,5-trimethylpiperazin-1-yl]-2H-chromen-2-one;
3-(6-fluoroimidazo[1,2-a]pyridin-2-yl)-7-(4-methylpiperazin-1-yl)-2H-chromen-2-one;
7-[(3R,5S)-3,5-dimethylpiperazin-1-yl]-3-(imidazo[1,2-a]pyridin-2-yl)-2H-chromen-2-one;
3-(imidazo[1,2-a]pyridin-2-yl)-7-[(3R,5S)-3,4,5-trimethylpiperazin-1-yl]-2H-chromen-2-one;
3-(3-methylimidazo[2,1-b][1,3]thiazol-6-yl)-7-(piperazin-1-yl)-2H-chromen-2-one;
7-(4-methyl-1,4-diazepan-1-yl)-3-(6-methylimidazo[1,2-a]pyridin-2-yl)-2H-chromen-2-one;
3-(1,3-benzothiazol-2-yl)-7-[1-(dimethylamino)ethyl]-2H-chromen-2-one;
3-(1,3-benzothiazol-2-yl)-7-[1-(propan-2-ylamino)ethyl]-2H-chromen-2-one;
3-(1,3-benzothiazol-2-yl)-7-(4-methyl-1,4-diazepan-1-yl)-2H-chromen-2-one;
3-(1,3-benzothiazol-2-yl)-7-{[2-(dimethylamino)ethyl](methyl)amino}-2H-chromen-2-one;
3-(1,3-benzothiazol-2-yl)-4-methyl-7-(piperazin-1-yl)-2H-chromen-2-one;
7-{[(2-hydroxyethyl)(methyl)amino]methyl}-3-(6-methylimidazo[1,2-a]pyridin-2-yl)-2H-chromen-2-one;
3-(8-fluoroimidazo[1,2-a]pyridin-2-yl)-7-(piperazin-1-yl)-2H-chromen-2-one;
3-(8-fluoroimidazo[1,2-a]pyridin-2-yl)-7-(4-methylpiperazin-1-yl)-2H-chromen-2-one;
7-(4-ethylpiperazin-1-yl)-3-(2-methylimidazo[2,1-b][1,3]thiazol-6-yl)-2H-chromen-2-one;
7-[(3R,5S)-3,5-dimethylpiperazin-1-yl]-3-(2-methylimidazo[2,1-b][1,3]thiazol-6-yl)-2H-chromen-2-one;
7-(4-methyl-1,4-diazepan-1-yl)-3-(2-methylimidazo[2,1-b][1,3]thiazol-6-yl)-2H-chromen-2-one;
7-[3-(dimethylamino)pyrrolidin-1-yl]-3-(2-methylimidazo[2,1-b][1,3]thiazol-6-yl)-2H-chromen-2-one;
8-fluoro-7-(piperazin-1-yl)-3-(pyridin-2-yl)-2H-chromen-2-one;
8-fluoro-3-(6-methylimidazo[1,2-a]pyridin-2-yl)-7-(piperazin-1-yl)-2H-chromen-2-one;
3-(1,3-benzothiazol-2-yl)-6-fluoro-7-(piperazin-1-yl)-2H-chromen-2-one;
6-fluoro-3-(6-methylimidazo[1,2-a]pyridin-2-yl)-7-(piperazin-1-yl)-2H-chromen-2-one;
3-(1,3-benzoxazol-2-yl)-5-fluoro-7-(piperazin-1-yl)-2H-chromen-2-one;
3-(1,3-benzothiazol-2-yl)-5-fluoro-7-(piperazin-1-yl)-2H-chromen-2-one;
5-fluoro-7-(piperazin-1-yl)-3-(pyridin-2-yl)-2H-chromen-2-one;
5-fluoro-3-(6-methylimidazo[1,2-a]pyridin-2-yl)-7-(piperazin-1-yl)-2H-chromen-2-one;
3-(6-methylpyridin-3-yl)-7-(piperazin-1-yl)-2H-chromen-2-one;
7-(4-methylpiperazin-1-yl)-3-(6-methylpyridin-3-yl)-2H-chromen-2-one;
3-(2-methoxypyridin-4-yl)-7-(4-methylpiperazin-1-yl)-2H-chromen-2-one;
7-[(2R,5S)-2,5-dimethylpiperazin-1-yl]-3-(8-methylimidazo[1,2-a]pyridin-2-yl)-2H-chromen-2-one;
7-[(3R,5S)-3,5-dimethylpiperazin-1-yl]-3-(imidazo[2,1-b][1,3]thiazol-6-yl)-2H-chromen-2-one;
3-[7-(trifluoromethyl)imidazo[1,2-a]pyridin-2-yl]-7-[(3R,5S)-3,4,5-trimethylpiperazin-1-yl]-2H-chromen-2-one;
3-(imidazo[1,2-a]pyrimidin-2-yl)-7-[(3R)-3-methylpiperazin-1-yl]-2H-chromen-2-one;
3-(imidazo[1,2-a]pyrimidin-2-yl)-7-[(3S)-3-methylpiperazin-1-yl]-2H-chromen-2-one;
7-[(1S,4S)-2,5-diazabicyclo[2.2.1]hept-2-yl]-3-(6-methylimidazo[1,2-a]pyridin-2-yl)-2H-chromen-2-one;
7-[(3R,5S)-3,5-dimethylpiperazin-1-yl]-3-(6-methylimidazo[1,2-a]pyridin-2-yl)-2H-chromen-2-one;
7-{[2-(dimethylamino)ethyl](methyl)amino}-3-(6-methylimidazo[1,2-a]pyridin-2-yl)-2H-chromen-2-one;
7-(1,4-diazepan-1-yl)-3-(6-methylimidazo[1,2-a]pyridin-2-yl)-2H-chromen-2-one;
tert-butyl {(3S)-1-[3-(6-methylimidazo[1,2-a]pyridin-2-yl)-2-oxo-2H-chromen-7-yl]pyrrolidin-3-yl}carbamate;
7-(4-ethylpiperazin-1-yl)-3-(3-methylimidazo[2,1-b][1,3]thiazol-6-yl)-2H-chromen-2-one;
7-(4-methyl-1,4-diazepan-1-yl)-3-(3-methylimidazo[2,1-b][1,3]thiazol-6-yl)-2H-chromen-2-one;
3-(2-chloropyridin-4-yl)-7-(piperazin-1-yl)-2H-chromen-2-one; 3-(imidazo[1,2-a]pyrimidin-2-yl)-7-[methyl(1-methylpyrrolidin-3-yl)amino]-2H-chromen-2-one;
7-[(3R,5S)-3,5-dimethylpiperazin-1-yl]-3-(3-methylimidazo[2,1-b][1,3]thiazol-6-yl)-2H-chromen-2-one;
3-(8-chloroimidazo[1,2-a]pyridin-2-yl)-7-[(3R)-3-methylpiperazin-1-yl]-2H-chromen-2-one;
3-(8-chloroimidazo[1,2-a]pyridin-2-yl)-7-[(3S)-3-methylpiperazin-1-yl]-2H-chromen-2-one;
3-(3-methylimidazo[2,1-b][1,3]thiazol-6-yl)-7-(4-methylpiperazin-1-yl)-2H-chromen-2-one;
7-(1,4-diazepan-1-yl)-3-(imidazo[1,2-a]pyrimidin-2-yl)-2H-chromen-2-one;
7-(piperazin-1-yl)-3-(pyrazolo[1,5-a]pyridin-2-yl)-2H-chromen-2-one;
7-(4-methylpiperazin-1-yl)-3-(pyrazolo[1,5-a]pyridin-2-yl)-2H-chromen-2-one;
7-[(3R,5S)-3,5-dimethylpiperazin-1-yl]-3-(pyrazolo[1,5-a]pyridin-2-yl)-2H-chromen-2-one;

7-[4-(2-hydroxyethyl)piperazin-1-yl]-3-(pyrazolo[1,5-a]pyridin-2-yl)-2H-chromen-2-one;
7-(2,5-diazabicyclo[2.2.2]oct-2-yl)-3-(pyrazolo[1,5-a]pyridin-2-yl)-2H-chromen-2-one;
7-(1,4-diazepan-1-yl)-3-(pyrazolo[1,5-a]pyridin-2-yl)-2H-chromen-2-one;
7-(4-methyl-1,4-diazepan-1-yl)-3-(pyrazolo[1,5-a]pyridin-2-yl)-2H-chromen-2-one;
7-(4-ethylpiperazin-1-yl)-3-(pyrazolo[1,5-a]pyridin-2-yl)-2H-chromen-2-one;
7-(4-propylpiperazin-1-yl)-3-(pyrazolo[1,5-a]pyridin-2-yl)-2H-chromen-2-one;
7-[4-(propan-2-yl)piperazin-1-yl]-3-(pyrazolo[1,5-a]pyridin-2-yl)-2H-chromen-2-one;
3-(imidazo[1,2-a]pyrimidin-2-yl)-7-(piperidin-4-yloxy)-2H-chromen-2-one;
7-[(dimethylamino)methyl]-3-(imidazo[2,1-b][1,3]thiazol-6-yl)-2H-chromen-2-one;
3-(imidazo[2,1-b][1,3]thiazol-6-yl)-7-[(propan-2-ylamino)methyl]-2H-chromen-2-one;
7-[3-(dimethylamino)piperidin-1-yl]-3-(6-methylimidazo[1,2-a]pyridin-2-yl)-2H-chromen-2-one;
7-(4-ethylpiperazin-1-yl)-3-(imidazo[2,1-b][1,3]thiazol-6-yl)-2H-chromen-2-one;
7-{[2-(dimethylamino)ethyl](methyl)amino}-3-(imidazo[2,1-b][1,3]thiazol-6-yl)-2H-chromen-2-one;
3-(imidazo[2,1-b][1,3]thiazol-6-yl)-7-(4-methyl-1,4-diazepan-1-yl)-2H-chromen-2-one;
3-(imidazo[2,1-b][1,3]thiazol-6-yl)-7-[(3R)-3-methylpiperazin-1-yl]-2H-chromen-2-one;
3-(imidazo[2,1-b][1,3]thiazol-6-yl)-7-[(3S)-3-methylpiperazin-1-yl]-2H-chromen-2-one;
7-(1,4-diazepan-1-yl)-3-(imidazo[2,1-b][1,3]thiazol-6-yl)-2H-chromen-2-one;
3-(6-methylimidazo[1,2-a]pyridin-2-yl)-7-(4-propylpiperazin-1-yl)-2H-chromen-2-one;
2-[7-(4-methylpiperazin-1-yl)-2-oxo-2H-chromen-3-yl]imidazo[1,2-a]pyridine-6-carbonitrile;
7-(piperazin-1-yl)-3-[8-(trifluoromethyl)imidazo[1,2-a]pyridin-2-yl]-2H-chromen-2-one;
7-(4-methylpiperazin-1-yl)-3-[8-(trifluoromethyl)imidazo[1,2-a]pyridin-2-yl]-2H-chromen-2-one;
7-[(3R,5S)-3,5-dimethylpiperazin-1-yl]-3-[8-(trifluoromethyl)imidazo[1,2-a]pyridin-2-yl]-2H-chromen-2-one;
3-(8-chloroimidazo[1,2-a]pyridin-2-yl)-7-(1,4-diazepan-1-yl)-2H-chromen-2-one;
3-(7-methylimidazo[1,2-a]pyridin-2-yl)-7-[(3S)-3-methylpiperazin-1-yl]-2H-chromen-2-one;
3-(7-methylimidazo[1,2-a]pyridin-2-yl)-7-[(3R)-3-methylpiperazin-1-yl]-2H-chromen-2-one;
7-(3,3-dimethylpiperazin-1-yl)-3-(7-methylimidazo[1,2-a]pyridin-2-yl)-2H-chromen-2-one;
7-(1,4-diazepan-1-yl)-3-(7-methylimidazo[1,2-a]pyridin-2-yl)-2H-chromen-2-one;
7-(4-methyl-1,4-diazepan-1-yl)-3-(7-methylimidazo[1,2-a]pyridin-2-yl)-2H-chromen-2-one;
3-(6-methoxypyridin-2-yl)-7-(piperazin-1-yl)-2H-chromen-2-one;
7-(4-aminopiperidin-1-yl)-3-(6-methylimidazo[1,2-a]pyridin-2-yl)-2H-chromen-2-one;
3-(6-methylimidazo[1,2-a]pyridin-2-yl)-7-[(3R)-3-methylpiperazin-1-yl]-2H-chromen-2-one;
3-(6-methylimidazo[1,2-a]pyridin-2-yl)-7-[methyl(pyridin-3-ylmethyl)amino]-2H-chromen-2-one;
7-(3,3-dimethylpiperazin-1-yl)-3-(6-methylimidazo[1,2-a]pyridin-2-yl)-2H-chromen-2-one;
3-(7-methylimidazo[1,2-a]pyrimidin-2-yl)-7-(piperazin-1-yl)-2H-chromen-2-one;
3-(7-methylimidazo[1,2-a]pyrimidin-2-yl)-7-(4-methylpiperazin-1-yl)-2H-chromen-2-one;
7-[(3R,5S)-3,5-dimethylpiperazin-1-yl]-3-(7-methylimidazo[1,2-a]pyrimidin-2-yl)-2H-chromen-2-one;
7-{[2-(dimethylamino)ethyl](methyl)amino}-3-(7-methylimidazo[1,2-a]pyrimidin-2-yl)-2H-chromen-2-one;
7-(4-methyl-1,4-diazepan-1-yl)-3-(7-methylimidazo[1,2-a]pyridin-2-yl)-2H-chromen-2-one
3-(7-methylimidazo[1,2-a]pyrimidin-2-yl)-7-[(3R)-3-methylpiperazin-1-yl]-2H-chromen-2-one;
3-(7-methylimidazo[1,2-a]pyrimidin-2-yl)-7-[(3S)-3-methylpiperazin-1-yl]-2H-chromen-2-one;
7-(1,4-diazepan-1-yl)-3-(7-methylimidazo[1,2-a]pyrimidin-2-yl)-2H-chromen-2-one;
3-(2-methylimidazo[2,1-b][1,3]thiazol-6-yl)-7-[(3R)-3-methylpiperazin-1-yl]-2H-chromen-2-one;
3-(2-methylimidazo[2,1-b][1,3]thiazol-6-yl)-7-[(3S)-3-methylpiperazin-1-yl]-2H-chromen-2-one;
7-(1,4-diazepan-1-yl)-3-(2-methylimidazo[2,1-b][1,3]thiazol-6-yl)-2H-chromen-2-one;
3-(4-methoxypyridin-3-yl)-7-(piperazin-1-yl)-2H-chromen-2-one;
3-(4-chloropyridin-3-yl)-7-(piperazin-1-yl)-2H-chromen-2-one;
7-[(3R,5S)-3,5-dimethylpiperazin-1-yl]-3-[4-(trifluoromethyl)-1,3-thiazol-2-yl]-2H-chromen-2-one;
7-(1,4-diazepan-1-yl)-3-[4-(trifluoromethyl)-1,3-thiazol-2-yl]-2H-chromen-2-one;
7-(4-methyl-1,4-diazepan-1-yl)-3-[4-(trifluoromethyl)-1,3-thiazol-2-yl]-2H-chromen-2-one;
7-[(3S)-3-methylpiperazin-1-yl]-3-[4-(trifluoromethyl)-1,3-thiazol-2-yl]-2H-chromen-2-one;
7-[(3R)-3-methylpiperazin-1-yl]-3-[4-(trifluoromethyl)-1,3-thiazol-2-yl]-2H-chromen-2-one;
3-(6-methylimidazo[1,2-a]pyrimidin-2-yl)-7-(piperazin-1-yl)-2H-chromen-2-one;
3-(6-methylimidazo[1,2-a]pyrimidin-2-yl)-7-(4-methylpiperazin-1-yl)-2H-chromen-2-one;
7-[(3R,5S)-3,5-dimethylpiperazin-1-yl]-3-(6-methylimidazo[1,2-a]pyrimidin-2-yl)-2H-chromen-2-one;
3-(8-cyclopropylimidazo[1,2-a]pyridin-2-yl)-7-(4-methylpiperazin-1-yl)-2H-chromen-2-one;
3-(8-bromoimidazo[1,2-a]pyridin-2-yl)-7-(4-methylpiperazin-1-yl)-2H-chromen-2-one;
7-(4-methyl-1,4-diazepan-1-yl)-3-(8-methylimidazo[1,2-a]pyridin-2-yl)-2H-chromen-2-one;
3-(8-methylimidazo[1,2-a]pyridin-2-yl)-7-[(3R)-3-methylpiperazin-1-yl]-2H-chromen-2-one;
3-(8-methylimidazo[1,2-a]pyridin-2-yl)-7-[(3S)-3-methylpiperazin-1-yl]-2H-chromen-2-one;
3-(8-chloroimidazo[1,2-a]pyridin-2-yl)-7-(3,3-dimethylpiperazin-1-yl)-2H-chromen-2-one;
7-(4-methyl-1,4-diazepan-1-yl)-3-(6-methylimidazo[1,2-a]pyrimidin-2-yl)-2H-chromen-2-one;
7-{[(1-hydroxypropan-2-yl)amino]methyl}-3-(6-methylimidazo[1,2-a]pyridin-2-yl)-2H-chromen-2-one;
7-[(4-hydroxypiperidin-1-yl)methyl]-3-(6-methylimidazo[1,2-a]pyridin-2-yl)-2H-chromen-2-one;
7-[(3-hydroxypyrrolidin-1-yl)methyl]-3-(6-methylimidazo[1,2-a]pyridin-2-yl)-2H-chromen-2-one;
5-fluoro-7-(piperazin-1-yl)-3-[4-(trifluoromethyl)-1,3-benzoxazol-2-yl]-2H-chromen-2-one;
3-(6-methylimidazo[1,2-a]pyridin-2-yl)-7-(octahydro-6H-pyrrolo[3,4-b]pyridin-6-yl)-2H-chromen-2-one;

3-(2-ethoxypyridin-3-yl)-7-(piperazin-1-yl)-2H-chromen-2-one;
3-(6-methoxypyridin-2-yl)-7-(4-methylpiperazin-1-yl)-2H-chromen-2-one;
3-(1-methyl-1H-indol-3-yl)-7-(piperazin-1-yl)-2H-chromen-2-one;
3-(1-methyl-1H-indol-3-yl)-7-(4-methylpiperazin-1-yl)-2H-chromen-2-one;
3-(6,8-dimethylimidazo[1,2-a]pyridin-2-yl)-7-(piperazin-1-yl)-2H-chromen-2-one;
3-(6,8-dimethylimidazo[1,2-a]pyridin-2-yl)-7-(4-methylpiperazin-1-yl)-2H-chromen-2-one;
3-(6,8-dimethylimidazo[1,2-a]pyridin-2-yl)-7-[(3R,5S)-3,5-dimethylpiperazin-1-yl]-2H-chromen-2-one;
3-(6-chloro-8-methylimidazo[1,2-a]pyridin-2-yl)-7-(piperazin-1-yl)-2H-chromen-2-one;
3-(6-chloro-8-methylimidazo[1,2-a]pyridin-2-yl)-7-(4-methylpiperazin-1-yl)-2H-chromen-2-one;
3-(6-chloro-8-methylimidazo[1,2-a]pyridin-2-yl)-7-[(3R,5S)-3,5-dimethylpiperazin-1-yl]-2H-chromen-2-one;
7-[(1S,4S)-2,5-diazabicyclo[2.2.1]hept-2-yl]-3-[4-(trifluoromethyl)-1,3-thiazol-2-yl]-2H-chromen-2-one;
7-[(3R)-3-methylpiperazin-1-yl]-3-[7-(trifluoromethyl)imidazo[1,2-a]pyridin-2-yl]-2H-chromen-2-one;
7-[(3S)-3-methylpiperazin-1-yl]-3-[7-(trifluoromethyl)imidazo[1,2-a]pyridin-2-yl]-2H-chromen-2-one;
7-(3,3-dimethylpiperazin-1-yl)-3-[7-(trifluoromethyl)imidazo[1,2-a]pyridin-2-yl]-2H-chromen-2-one;
3-(4-chloro-1,3-benzothiazol-2-yl)-7-{[(1-hydroxypropan-2-yl)amino]methyl}-2H-chromen-2-one;
3-(4-chloro-1,3-benzothiazol-2-yl)-7-{[(2-hydroxyethyl)(methyl)amino]methyl}-2H-chromen-2-one;
3-(4-chloro-1,3-benzothiazol-2-yl)-7-[(3-hydroxypyrrolidin-1-yl)methyl]-2H-chromen-2-one;
3-(4-chloro-1,3-benzothiazol-2-yl)-7-[(4-hydroxypiperidin-1-yl)methyl]-2H-chromen-2-one;
3-(2-methylpyrimidin-4-yl)-7-(piperazin-1-yl)-2H-chromen-2-one;
7-(1,4-diazepan-1-yl)-3-[7-(trifluoromethyl)imidazo[1,2-a]pyridin-2-yl]-2H-chromen-2-one;
7-(4-methyl-1,4-diazepan-1-yl)-3-[7-(trifluoromethyl)imidazo[1,2-a]pyridin-2-yl]-2H-chromen-2-one;
7-[(2R,5S)-2,5-dimethylpiperazin-1-yl]-3-[7-(trifluoromethyl)imidazo[1,2-a]pyridin-2-yl]-2H-chromen-2-one;
3-(2-cyclopropylpyrimidin-4-yl)-7-(piperazin-1-yl)-2H-chromen-2-one; 7-(piperazin-1-yl)-3-[2-(propan-2-yl)pyrimidin-4-yl]-2H-chromen-2-one;
3-(8-chloroimidazo[1,2-a]pyridin-2-yl)-7-(4-methyl-1,4-diazepan-1-yl)-2H-chromen-2-one;
7-(1,4-diazepan-1-yl)-3-(8-methylimidazo[1,2-a]pyridin-2-yl)-2H-chromen-2-one;
3-(6-methylimidazo[1,2-a]pyridin-2-yl)-7-[methyl(1-methylpiperidin-4-yl)amino]-2H-chromen-2-one;
7-[(3S)-3-methylpiperazin-1-yl]-3-(4-methyl-1,3-thiazol-2-yl)-2H-chromen-2-one;
7-(1,4-diazepan-1-yl)-3-(4-methyl-1,3-thiazol-2-yl)-2H-chromen-2-one;
7-(4-methyl-1,4-diazepan-1-yl)-3-(4-methyl-1,3-thiazol-2-yl)-2H-chromen-2-one;
7-[(3R,5S)-3,5-dimethylpiperazin-1-yl]-3-(4-methyl-1,3-thiazol-2-yl)-2H-chromen-2-one;
3-(7-ethylimidazo[1,2-a]pyridin-2-yl)-7-(piperazin-1-yl)-2H-chromen-2-one;
3-(7-ethylimidazo[1,2-a]pyridin-2-yl)-7-(4-methylpiperazin-1-yl)-2H-chromen-2-one;
7-[(3R,5S)-3,5-dimethylpiperazin-1-yl]-3-(7-ethylimidazo[1,2-a]pyridin-2-yl)-2H-chromen-2-one;
3-(3,5-difluorophenyl)-5-fluoro-7-(piperazin-1-yl)-2H-chromen-2-one;
3-(3,5-difluorophenyl)-7-(piperazin-1-yl)-2H-chromen-2-one;
5-fluoro-3-(4-fluoro-1,3-benzoxazol-2-yl)-7-(piperazin-1-yl)-2H-chromen-2-one;
7-(4-methyl-1,4-diazepan-1-yl)-3-[8-(trifluoromethyl)imidazo[1,2-a]pyridin-2-yl]-2H-chromen-2-one;
3-(6-fluoroimidazo[1,2-a]pyridin-2-yl)-7-(4-methyl-1,4-diazepan-1-yl)-2H-chromen-2-one;
3-(8-fluoroimidazo[1,2-a]pyridin-2-yl)-7-(4-methyl-1,4-diazepan-1-yl)-2H-chromen-2-one;
3-(8-chloroimidazo[1,2-a]pyridin-2-yl)-7-[(3R)-3,4-dimethylpiperazin-1-yl]-2H-chromen-2-one;
7-(4-methylpiperazin-1-yl)-3-(2-methylpyrimidin-4-yl)-2H-chromen-2-one;
3-(2-cyclopropylpyrimidin-4-yl)-7-(4-methylpiperazin-1-yl)-2H-chromen-2-one;
7-[(2S,5R)-2,5-dimethylpiperazin-1-yl]-3-(4-methyl-1,3-thiazol-2-yl)-2H-chromen-2-one;
7-[(3R)-3-methylpiperazin-1-yl]-3-(4-methyl-1,3-thiazol-2-yl)-2H-chromen-2-one;
7-(3,3-dimethylpiperazin-1-yl)-3-(4-methyl-1,3-thiazol-2-yl)-2H-chromen-2-one;
3-(5-methylpyrazolo[1,5-a]pyridin-2-yl)-7-(piperazin-1-yl)-2H-chromen-2-one;
7-(4-methylpiperazin-1-yl)-3-(5-methylpyrazolo[1,5-a]pyridin-2-yl)-2H-chromen-2-one;
7-[(3R,5S)-3,5-dimethylpiperazin-1-yl]-3-(5-methylpyrazolo[1,5-a]pyridin-2-yl)-2H-chromen-2-one;
7-(3,3-dimethylpiperazin-1-yl)-3-(5-methylpyrazolo[1,5-a]pyridin-2-yl)-2H-chromen-2-one;
7-[(3R)-3-methylpiperazin-1-yl]-3-(5-methylpyrazolo[1,5-a]pyridin-2-yl)-2H-chromen-2-one;
7-(4-ethylpiperazin-1-yl)-3-(5-methylpyrazolo[1,5-a]pyridin-2-yl)-2H-chromen-2-one;
3-(5-methylpyrazolo[1,5-a]pyridin-2-yl)-7-(4-propylpiperazin-1-yl)-2H-chromen-2-one;
7-(1,4-diazepan-1-yl)-3-(5-methylpyrazolo[1,5-a]pyridin-2-yl)-2H-chromen-2-one;
7-(4-methyl-1,4-diazepan-1-yl)-3-(5-methylpyrazolo[1,5-a]pyridin-2-yl)-2H-chromen-2-one;
5-fluoro-3-(imidazo[2,1-b][1,3]thiazol-6-yl)-7-(piperazin-1-yl)-2H-chromen-2-one;
5-fluoro-3-(imidazo[1,2-a]pyrimidin-2-yl)-7-(piperazin-1-yl)-2H-chromen-2-one;
3-(1H-benzimidazol-2-yl)-7-(piperazin-1-yl)-2H-chromen-2-one;
7-(piperazin-1-yl)-3-(9H-purin-8-yl)-2H-chromen-2-one;
7-[(3R,5S)-3,5-dimethylpiperazin-1-yl]-3-(6-methoxypyridin-2-yl)-2H-chromen-2-one;
3-(3,4-dimethoxyphenyl)-7-(piperazin-1-yl)-2H-chromen-2-one;
3-(3,4-dimethoxyphenyl)-7-(4-methylpiperazin-1-yl)-2H-chromen-2-one;
3-(4-methylthiophen-2-yl)-7-(piperazin-1-yl)-2H-chromen-2-one;
7-(piperazin-1-yl)-3-(thiophen-3-yl)-2H-chromen-2-one;
7-(4-methylpiperazin-1-yl)-3-(thiophen-3-yl)-2H-chromen-2-one;
3-(imidazo[1,2-a]pyrimidin-2-yl)-7-[(3R)-pyrrolidin-3-yloxy]-2H-chromen-2-one;
3-(7-methylimidazo[1,2-a]pyrimidin-2-yl)-7-[(3R)-pyrrolidin-3-yloxy]-2H-chromen-2-one;
3-(7-methylimidazo[1,2-a]pyridin-2-yl)-7-[(3R)-pyrrolidin-3-yloxy]-2H-chromen-2-one;

3-(imidazo[2,1-b][1,3]thiazol-6-yl)-7-[(3R)-pyrrolidin-3-yloxy]-2H-chromen-2-one;
3-(2-methylimidazo[2,1-b][1,3]thiazol-6-yl)-7-[(3R)-pyrrolidin-3-yloxy]-2H-chromen-2-one;
3-(6-methylimidazo[1,2-a]pyridin-2-yl)-7-[(3R)-pyrrolidin-3-yloxy]-2H-chromen-2-one;
3-(6-methylimidazo[1,2-a]pyrimidin-2-yl)-7-[(3R)-pyrrolidin-3-yloxy]-2H-chromen-2-one;
3-(6-fluoro-8-methylimidazo[1,2-a]pyridin-2-yl)-7-(piperazin-1-yl)-2H-chromen-2-one;
3-(6-fluoro-8-methylimidazo[1,2-a]pyridin-2-yl)-7-(4-methylpiperazin-1-yl)-2H-chromen-2-one;
3-(6-fluoro-8-methylimidazo[1,2-a]pyridin-2-yl)-7-(4-methyl-1,4-diazepan-1-yl)-2H-chromen-2-one;
7-[(3R,5S)-3,5-dimethylpiperazin-1-yl]-3-(6-fluoro-8-methylimidazo[1,2-a]pyridin-2-yl)-2H-chromen-2-one;
3-(8-ethyl-6-methylimidazo[1,2-a]pyridin-2-yl)-7-(4-methyl-1,4-diazepan-1-yl)-2H-chromen-2-one;
3-(7-ethylimidazo[1,2-a]pyridin-2-yl)-7-(4-methyl-1,4-diazepan-1-yl)-2H-chromen-2-one;
3-(8-ethyl-6-methylimidazo[1,2-a]pyridin-2-yl)-7-(piperazin-1-yl)-2H-chromen-2-one;
5-fluoro-3-(imidazo[1,2-a]pyrimidin-2-yl)-7-(4-methyl-1,4-diazepan-1-yl)-2H-chromen-2-one;
7-(1,4-diazepan-1-yl)-5-fluoro-3-(imidazo[1,2-a]pyrimidin-2-yl)-2H-chromen-2-one;
3-(6-chloroimidazo[1,2-a]pyrimidin-2-yl)-7-(4-methyl-1,4-diazepan-1-yl)-2H-chromen-2-one;
7-[(3R,5S)-3,5-dimethylpiperazin-1-yl]-3-(8-fluoroimidazo[1,2-a]pyridin-2-yl)-2H-chromen-2-one;
3-(8-chloroimidazo[1,2-a]pyridin-2-yl)-7-[(3S)-3,4-dimethylpiperazin-1-yl]-2H-chromen-2-one;
3-(8-ethyl-6-methylimidazo[1,2-a]pyridin-2-yl)-7-(4-methylpiperazin-1-yl)-2H-chromen-2-one;
7-[(3R,5S)-3,5-dimethylpiperazin-1-yl]-3-(8-ethyl-6-methylimidazo[1,2-a]pyridin-2-yl)-2H-chromen-2-one;
3-(8-chloro-6-methylimidazo[1,2-a]pyridin-2-yl)-7-[(3R,5S)-3,5-dimethylpiperazin-1-yl]-2H-chromen-2-one;
3-(8-chloro-6-methylimidazo[1,2-a]pyridin-2-yl)-7-(4-methylpiperazin-1-yl)-2H-chromen-2-one;
3-(8-chloro-6-methylimidazo[1,2-a]pyridin-2-yl)-7-(4-methyl-1,4-diazepan-1-yl)-2H-chromen-2-one;
7-{[(2-hydroxyethyl)(methyl)amino]methyl}-3-(imidazo[2,1-b][1,3]thiazol-6-yl)-2H-chromen-2-one;
7-[(4-hydroxypiperidin-1-yl)methyl]-3-(imidazo[2,1-b][1,3]thiazol-6-yl)-2H-chromen-2-one;
3-(6-chloroimidazo[1,2-a]pyrimidin-2-yl)-7-[4-(2-hydroxyethyl)piperazin-1-yl]-2H-chromen-2-one;
3-(6-chloroimidazo[1,2-a]pyrimidin-2-yl)-7-(piperazin-1-yl)-2H-chromen-2-one;
3-(6-chloroimidazo[1,2-a]pyrimidin-2-yl)-7-[(3R,5S)-3,5-dimethylpiperazin-1-yl]-2H-chromen-2-one;
3-(6-chloroimidazo[1,2-a]pyrimidin-2-yl)-7-[(3R)-3-methylpiperazin-1-yl]-2H-chromen-2-one;
5-fluoro-3-(imidazo[1,2-a]pyrimidin-2-yl)-7-(4-methylpiperazin-1-yl)-2H-chromen-2-one;
7-[(3R,5S)-3,5-dimethylpiperazin-1-yl]-5-fluoro-3-(imidazo[1,2-a]pyrimidin-2-yl)-2H-chromen-2-one;
3-(8-fluoro-6-methylimidazo[1,2-a]pyridin-2-yl)-7-(4-methylpiperazin-1-yl)-2H-chromen-2-one;
7-[(3R,5S)-3,5-dimethylpiperazin-1-yl]-3-(8-fluoro-6-methylimidazo[1,2-a]pyridin-2-yl)-2H-chromen-2-one;
3-(8-fluoro-6-methylimidazo[1,2-a]pyridin-2-yl)-7-(4-methyl-1,4-diazepan-1-yl)-2H-chromen-2-one;
3-(8-fluoro-6-methylimidazo[1,2-a]pyridin-2-yl)-7-(piperazin-1-yl)-2H-chromen-2-one;
7-(1,4-diazepan-1-yl)-3-(8-fluoroimidazo[1,2-a]pyridin-2-yl)-2H-chromen-2-one;
3-(8-ethylimidazo[1,2-a]pyridin-2-yl)-7-(4-methylpiperazin-1-yl)-2H-chromen-2-one;
3-(6-methoxypyridin-2-yl)-7-(4-methyl-1,4-diazepan-1-yl)-2H-chromen-2-one;
7-(4-ethylpiperazin-1-yl)-3-(6-methoxypyridin-2-yl)-2H-chromen-2-one;
3-(6-methoxypyridin-2-yl)-7-[(3R)-3-methylpiperazin-1-yl]-2H-chromen-2-one;
3-(6-methoxypyridin-2-yl)-7-[(3S)-3-methylpiperazin-1-yl]-2H-chromen-2-one;
7-(piperazin-1-yl)-3-(thiophen-2-yl)-2H-chromen-2-one;
7-[(3R,5S)-3,5-dimethylpiperazin-1-yl]-3-(thiophen-2-yl)-2H-chromen-2-one;
3-(3,5-difluorophenyl)-5-fluoro-7-(4-methyl-1,4-diazepan-1-yl)-2H-chromen-2-one;
5-fluoro-3-(4-fluoro-1,3-benzoxazol-2-yl)-7-(4-methylpiperazin-1-yl)-2H-chromen-2-one;
7-[(3R,5S)-3,5-dimethylpiperazin-1-yl]-5-fluoro-3-(4-fluoro-1,3-benzoxazol-2-yl)-2H-chromen-2-one;
7-(1,4-diazepan-1-yl)-5-fluoro-3-(4-fluoro-1,3-benzoxazol-2-yl)-2H-chromen-2-one;
5-fluoro-3-(4-fluoro-1,3-benzoxazol-2-yl)-7-(4-methyl-1,4-diazepan-1-yl)-2H-chromen-2-one;
3-(1H-benzimidazol-2-yl)-5-fluoro-7-(4-methylpiperazin-1-yl)-2H-chromen-2-one;
3-(1H-benzimidazol-2-yl)-7-[(3R,5S)-3,5-dimethylpiperazin-1-yl]-5-fluoro-2H-chromen-2-one;
5-fluoro-3-(imidazo[2,1-b][1,3]thiazol-6-yl)-7-(4-methylpiperazin-1-yl)-2H-chromen-2-one;
5-fluoro-3-(imidazo[2,1-b][1,3]thiazol-6-yl)-7-(4-methyl-1,4-diazepan-1-yl)-2H-chromen-2-one;
3-(1H-benzimidazol-2-yl)-7-(1,4-diazepan-1-yl)-5-fluoro-2H-chromen-2-one;
3-(1H-benzimidazol-2-yl)-5-fluoro-7-(piperazin-1-yl)-2H-chromen-2-one;
3-(6-chloroimidazo[1,2-a]pyrimidin-2-yl)-7-[(3S)-3-methylpiperazin-1-yl]-2H-chromen-2-one;
7-[(1-benzylpyrrolidin-3-yl)(methyl)amino]-3-(7-methylimidazo[1,2-a]pyrimidin-2-yl)-2H-chromen-2-one;
7-(1,4-diazepan-1-yl)-3-(6-methylimidazo[1,2-a]pyrimidin-2-yl)-2H-chromen-2-one;
7-[(3S)-3,4-dimethylpiperazin-1-yl]-3-(7-methylimidazo[1,2-a]pyridin-2-yl)-2H-chromen-2-one;
3-(6-fluoropyridin-2-yl)-7-(piperazin-1-yl)-2H-chromen-2-one;
3-(6-ethoxypyridin-2-yl)-7-(4-methylpiperazin-1-yl)-2H-chromen-2-one;
3-(3,4-dimethoxyphenyl)-7-[(3R)-3-methylpiperazin-1-yl]-2H-chromen-2-one;
3-(3,4-dimethoxyphenyl)-7-[(3S)-3-methylpiperazin-1-yl]-2H-chromen-2-one;
3-(3,4-dimethoxyphenyl)-7-[(3R,5S)-3,5-dimethylpiperazin-1-yl]-2H-chromen-2-one;
7-(piperazin-1-yl)-3-[6-(propan-2-yloxy)pyridin-2-yl]-2H-chromen-2-one;
7-(piperazin-1-yl)-3-[6-(pyrrolidin-1-yl)pyridin-2-yl]-2H-chromen-2-one;
7-(1,4-diazepan-1-yl)-3-(3,5-dimethoxyphenyl)-2H-chromen-2-one;
3-(8-chloroimidazo[1,2-a]pyridin-2-yl)-7-[(3R,5S)-3,5-dimethylpiperazin-1-yl]-5-fluoro-2H-chromen-2-one;
3-(6,8-dimethylimidazo[1,2-a]pyridin-2-yl)-7-(4-methyl-1,4-diazepan-1-yl)-2H-chromen-2-one;

3-(8-chloroimidazo[1,2-a]pyridin-2-yl)-5-fluoro-7-[(3R)-3-methylpiperazin-1-yl]-2H-chromen-2-one;
7-[(3R,5S)-3,5-dimethylpiperazin-1-yl]-5-fluoro-3-[7-(trifluoromethyl)imidazo[1,2-a]pyridin-2-yl]-2H-chromen-2-one;
3-(8-chloroimidazo[1,2-a]pyridin-2-yl)-5-fluoro-7-(piperazin-1-yl)-2H-chromen-2-one;
3-(8-chloroimidazo[1,2-a]pyridin-2-yl)-5-fluoro-7-[(3S)-3-methylpiperazin-1-yl]-2H-chromen-2-one;
3-(4-methyl-1H-benzimidazol-2-yl)-7-(piperazin-1-yl)-2H-chromen-2-one;
3-(5-fluoro-1H-benzimidazol-2-yl)-7-(piperazin-1-yl)-2H-chromen-2-one;
3-(1H-benzimidazol-2-yl)-7-[(dimethylamino)methyl]-2H-chromen-2-one;
5-fluoro-7-(hydroxymethyl)-3-(imidazo[2,1-b][1,3]thiazol-6-yl)-2H-chromen-2-one;
3-[8-(methylsulfanyl)imidazo[1,2-a]pyrazin-2-yl]-7-(piperazin-1-yl)-2H-chromen-2-one;
7-(4-methylpiperazin-1-yl)-3-[8-(methylsulfanyl)imidazo[1,2-a]pyrazin-2-yl]-2H-chromen-2-one;
7-[(3R,5S)-3,5-dimethylpiperazin-1-yl]-3-[8-(methylsulfanyl)imidazo[1,2-a]pyrazin-2-yl]-2H-chromen-2-one;
7-(4-methyl-1,4-diazepan-1-yl)-3-[8-(methylsulfanyl)imidazo[1,2-a]pyrazin-2-yl]-2H-chromen-2-one;
3-(8-methoxyimidazo[1,2-a]pyridin-2-yl)-7-(piperazin-1-yl)-2H-chromen-2-one;
3-(8-methoxyimidazo[1,2-a]pyridin-2-yl)-7-(4-methylpiperazin-1-yl)-2H-chromen-2-one;
3-(3,4-dimethoxyphenyl)-5-fluoro-7-(piperazin-1-yl)-2H-chromen-2-one;
3-(3,4-dimethoxyphenyl)-5-fluoro-7-(4-methylpiperazin-1-yl)-2H-chromen-2-one;
3-(3,4-dimethoxyphenyl)-5-fluoro-7-(4-methyl-1,4-diazepan-1-yl)-2H-chromen-2-one;
3-(1-benzothiophen-2-yl)-7-(piperazin-1-yl)-2H-chromen-2-one;
3-(1-benzothiophen-2-yl)-7-[(3R,5S)-3,5-dimethylpiperazin-1-yl]-2H-chromen-2-one;
3-(1-benzothiophen-2-yl)-7-[(3R)-3-methylpiperazin-1-yl]-2H-chromen-2-one;
3-(1-benzothiophen-2-yl)-7-[(3S)-3-methylpiperazin-1-yl]-2H-chromen-2-one;
3-(3,5-dimethoxyphenyl)-7-(4-methyl-1,4-diazepan-1-yl)-2H-chromen-2-one;
3-(3,5-dimethoxyphenyl)-7-[(3R)-3-methylpiperazin-1-yl]-2H-chromen-2-one;
3-(3,5-dimethoxyphenyl)-7-[(3S)-3-methylpiperazin-1-yl]-2H-chromen-2-one;
3-[6-(cyclobutyloxy)pyridin-2-yl]-7-(piperazin-1-yl)-2H-chromen-2-one;
3-[6-(cyclobutyloxy)pyridin-2-yl]-7-(4-methylpiperazin-1-yl)-2H-chromen-2-one;
3-(3,4-dimethoxyphenyl)-5-fluoro-7-[(3R)-3-methylpiperazin-1-yl]-2H-chromen-2-one;
7-[(3R,5S)-3,5-dimethylpiperazin-1-yl]-3-(imidazo[1,2-a]pyrazin-2-yl)-2H-chromen-2-one;
7-[(3R,5S)-3,5-dimethylpiperazin-1-yl]-3-(8-methoxyimidazo[1,2-a]pyridin-2-yl)-2H-chromen-2-one;
3-(8-methoxyimidazo[1,2-a]pyridin-2-yl)-7-(4-methyl-1,4-diazepan-1-yl)-2H-chromen-2-one;
3-(8-fluoro-6-methylimidazo[1,2-a]pyridin-2-yl)-7-[(3R)-3-methylpiperazin-1-yl]-2H-chromen-2-one;
3-(8-fluoro-6-methylimidazo[1,2-a]pyridin-2-yl)-7-[(3S)-3-methylpiperazin-1-yl]-2H-chromen-2-one;
5-fluoro-3-(imidazo[1,2-a]pyridin-2-yl)-7-(4-methylpiperazin-1-yl)-2H-chromen-2-one;
5-fluoro-3-(8-methylimidazo[1,2-a]pyridin-2-yl)-7-(4-methylpiperazin-1-yl)-2H-chromen-2-one;
5-fluoro-3-(7-methylimidazo[1,2-a]pyridin-2-yl)-7-(piperazin-1-yl)-2H-chromen-2-one;
3-(6,8-dimethylimidazo[1,2-a]pyridin-2-yl)-7-[(3S)-3-methylpiperazin-1-yl]-2H-chromen-2-one;
7-(3,3-dimethylpiperazin-1-yl)-3-(8-fluoro-6-methylimidazo[1,2-a]pyridin-2-yl)-2H-chromen-2-one;
7-(1,4-diazepan-1-yl)-3-(8-fluoro-6-methylimidazo[1,2-a]pyridin-2-yl)-2H-chromen-2-one;
3-(2-ethylimidazo[2,1-b][1,3]thiazol-6-yl)-7-(piperazin-1-yl)-2H-chromen-2-one;
7-[(3R,5S)-3,5-dimethylpiperazin-1-yl]-3-(2-ethylimidazo[2,1-b][1,3]thiazol-6-yl)-2H-chromen-2-one;
7-(1,4-diazepan-1-yl)-3-(2-ethylimidazo[2,1-b][1,3]thiazol-6-yl)-2H-chromen-2-one;
3-(2-ethylimidazo[2,1-b][1,3]thiazol-6-yl)-7-(4-methyl-1,4-diazepan-1-yl)-2H-chromen-2-one;
7-[(3R,5S)-3,5-dimethylpiperazin-1-yl]-3-(7-methoxyimidazo[1,2-a]pyridin-2-yl)-2H-chromen-2-one;
7-[(3R,5S)-3,5-dimethylpiperazin-1-yl]-3-[1-(pyridin-2-yl)-1H-imidazol-4-yl]-2H-chromen-2-one;
3-(7-methoxyimidazo[1,2-a]pyridin-2-yl)-7-[(3S)-3-methylpiperazin-1-yl]-2H-chromen-2-one;
3-(7-methoxyimidazo[1,2-a]pyridin-2-yl)-7-(4-methylpiperazin-1-yl)-2H-chromen-2-one;
3-(7-methoxyimidazo[1,2-a]pyridin-2-yl)-7-(4-methyl-1,4-diazepan-1-yl)-2H-chromen-2-one;
7-[(1R,5S,6s)-6-(dimethylamino)-3-azabicyclo[3.1.0]hex-3-yl]-3-(imidazo[2,1-b][1,3]thiazol-6-yl)-2H-chromen-2-one;
7-(1,4-diazabicyclo[3.2.2]non-4-yl)-3-(imidazo[2,1-b][1,3]thiazol-6-yl)-2H-chromen-2-one;
7-[(1R,5S,6s)-6-(dimethylamino)-3-azabicyclo[3.1.0]hex-3-yl]-3-(imidazo[1,2-a]pyrimidin-2-yl)-2H-chromen-2-one;
7-(1,4-diazabicyclo[3.2.2]non-4-yl)-3-(imidazo[1,2-a]pyrimidin-2-yl)-2H-chromen-2-one;
3-(2-methylimidazo[2,1-b][1,3,4]thiadiazol-6-yl)-7-(piperazin-1-yl)-2H-chromen-2-one;
3-(2-methylimidazo[2,1-b][1,3,4]thiadiazol-6-yl)-7-(4-methylpiperazin-1-yl)-2H-chromen-2-one;
7-[(3R,5S)-3,5-dimethylpiperazin-1-yl]-3-(2-methylimidazo[2,1-b][1,3,4]thiadiazol-6-yl)-2H-chromen-2-one;
7-[(3S)-3-methylpiperazin-1-yl]-3-(pyridin-2-yl)-2H-chromen-2-one;
3-[6-(methylsulfanyl)pyridin-2-yl]-7-(piperazin-1-yl)-2H-chromen-2-one;
7-[(1S,4S)-2,5-diazabicyclo[2.2.1]hept-2-yl]-3-(3,4-dimethoxyphenyl)-5-fluoro-2H-chromen-2-one;
3-(4-methoxyphenyl)-7-(piperazin-1-yl)-2H-chromen-2-one;
3-(4-methoxyphenyl)-7-[(3R)-3-methylpiperazin-1-yl]-2H-chromen-2-one;
3-(4-methoxyphenyl)-7-[(3S)-3-methylpiperazin-1-yl]-2H-chromen-2-one;
7-(1,4-diazepan-1-yl)-3-(2-methylimidazo[2,1-b][1,3,4]thiadiazol-6-yl)-2H-chromen-2-one;
7-(4-methyl-1,4-diazepan-1-yl)-3-(2-methylimidazo[2,1-b][1,3,4]thiadiazol-6-yl)-2H-chromen-2-one;
7-[(3R,5S)-3,5-dimethylpiperazin-1-yl]-3-(1-phenyl-1H-imidazol-4-yl)-2H-chromen-2-one;
7-(4-methyl-1,4-diazepan-1-yl)-3-[2-methyl-1-(pyridin-2-yl)-1H-imidazol-4-yl]-2H-chromen-2-one;
7-(1,4-diazepan-1-yl)-3-(imidazo[1,2-a]pyrazin-2-yl)-2H-chromen-2-one;

3-(imidazo[1,2-a]pyrazin-2-yl)-7-(4-methyl-1,4-diazepan-1-yl)-2H-chromen-2-one;
3-(imidazo[1,2-a]pyrazin-2-yl)-7-(piperazin-1-yl)-2H-chromen-2-one;
3-(imidazo[1,2-a]pyrazin-2-yl)-7-(4-methylpiperazin-1-yl)-2H-chromen-2-one;
3-(imidazo[1,2-c]pyrimidin-2-yl)-7-(4-methylpiperazin-1-yl)-2H-chromen-2-one;
7-[(3R,5S)-3,5-dimethylpiperazin-1-yl]-3-(imidazo[1,2-c]pyrimidin-2-yl)-2H-chromen-2-one;
3-(imidazo[1,2-c]pyrimidin-2-yl)-7-(4-methyl-1,4-diazepan-1-yl)-2H-chromen-2-one;
7-[(3R,5S)-3,5-dimethylpiperazin-1-yl]-3-(quinoxalin-2-yl)-2H-chromen-2-one;
3-(6-methylimidazo[1,2-a]pyrimidin-2-yl)-7-[(3S)-3-methylpiperazin-1-yl]-2H-chromen-2-one;
3-(6-methylimidazo[1,2-a]pyrimidin-2-yl)-7-[(3R)-3-methylpiperazin-1-yl]-2H-chromen-2-one;
3-(3,4-dimethoxyphenyl)-5-fluoro-7-[(3S)-3-methylpiperazin-1-yl]-2H-chromen-2-one;
3-(2,4-dimethoxyphenyl)-7-(piperazin-1-yl)-2H-chromen-2-one;
3-(2,4-dimethoxyphenyl)-7-[(3R)-3-methylpiperazin-1-yl]-2H-chromen-2-one;
3-(2,4-dimethoxyphenyl)-7-[(3S)-3-methylpiperazin-1-yl]-2H-chromen-2-one;
5-fluoro-3-(6-methoxypyridin-2-yl)-7-(piperazin-1-yl)-2H-chromen-2-one;
5-fluoro-3-(6-methoxypyridin-2-yl)-7-[(3S)-3-methylpiperazin-1-yl]-2H-chromen-2-one;
7-{[2-(dimethylamino)ethyl]amino}-3-(7-methylimidazo[1,2-a]pyridin-2-yl)-2H-chromen-2-one;
7-[(3S)-3,4-dimethylpiperazin-1-yl]-3-(8-fluoro-6-methylimidazo[1,2-a]pyridin-2-yl)-2H-chromen-2-one;
3-(3,4-dimethoxyphenyl)-7-[(2S)-2-methylpiperazin-1-yl]-2H-chromen-2-one;
3-(2-chloroimidazo[2,1-b][1,3]thiazol-6-yl)-7-[(3R,5S)-3,5-dimethylpiperazin-1-yl]-2H-chromen-2-one;
3-(7-methylimidazo[1,2-a]pyridin-2-yl)-7-[(1-methylpiperidin-4-yl)amino]-2H-chromen-2-one;
7-{[3-(dimethylamino)propyl]amino}-3-(7-methylimidazo[1,2-a]pyridin-2-yl)-2H-chromen-2-one;
7-[(3R,5S)-3,5-dimethylpiperazin-1-yl]-3-(6-methylimidazo[1,2-a]pyrazin-2-yl)-2H-chromen-2-one;
7-(1,4-diazepan-1-yl)-3-(6-methylimidazo[1,2-a]pyrazin-2-yl)-2H-chromen-2-one;
3-(2-chloroimidazo[2,1-b][1,3]thiazol-6-yl)-7-(4-methylpiperazin-1-yl)-2H-chromen-2-one;
3-(2-chloroimidazo[2,1-b][1,3]thiazol-6-yl)-7-(4-methyl-1,4-diazepan-1-yl)-2H-chromen-2-one;
3-(6-fluoroimidazo[1,2-a]pyrimidin-2-yl)-7-(4-methylpiperazin-1-yl)-2H-chromen-2-one;
3-(6-fluoroimidazo[1,2-a]pyrimidin-2-yl)-7-[(3R)-3-methylpiperazin-1-yl]-2H-chromen-2-one;
3-(2-methylimidazo[2,1-b][1,3,4]thiadiazol-6-yl)-7-[(3S)-3-methylpiperazin-1-yl]-2H-chromen-2-one;
3-(2-methylimidazo[2,1-b][1,3,4]thiadiazol-6-yl)-7-[(3R)-3-methylpiperazin-1-yl]-2H-chromen-2-one;
3-(3-chloro-4-fluorophenyl)-7-(piperazin-1-yl)-2H-chromen-2-one;
3-(3-chloro-4-fluorophenyl)-7-[(3S)-3-methylpiperazin-1-yl]-2H-chromen-2-one;
3-(1,3-benzodioxol-5-yl)-7-(piperazin-1-yl)-2H-chromen-2-one;
3-(1,3-benzodioxol-5-yl)-7-[(3R,5S)-3,5-dimethylpiperazin-1-yl]-2H-chromen-2-one;
3-(1,3-benzodioxol-5-yl)-7-[(3R)-3-methylpiperazin-1-yl]-2H-chromen-2-one;
3-(1,3-benzodioxol-5-yl)-7-[(3S)-3-methylpiperazin-1-yl]-2H-chromen-2-one;
7-[(3S)-3-methylpiperazin-1-yl]-3-[3-(trifluoromethyl)phenyl]-2H-chromen-2-one;
7-[(3R,5S)-3,5-dimethylpiperazin-1-yl]-3-(6-fluoroimidazo[1,2-a]pyrimidin-2-yl)-2H-chromen-2-one;
3-(6-fluoroimidazo[1,2-a]pyrimidin-2-yl)-7-[(3S)-3-methylpiperazin-1-yl]-2H-chromen-2-one;
7-(4-methyl-1,4-diazepan-1-yl)-3-(6-methylimidazo[1,2-a]pyrazin-2-yl)-2H-chromen-2-one;
3-(2-chloroimidazo[2,1-b][1,3]thiazol-6-yl)-7-(piperazin-1-yl)-2H-chromen-2-one;
3-(7-methylimidazo[1,2-a]pyridin-2-yl)-7-(piperidin-4-ylamino)-2H-chromen-2-one;
3-(7-methylimidazo[1,2-a]pyridin-2-yl)-7-[(3R)-pyrrolidin-3-ylamino]-2H-chromen-2-one;
3-(6-cyclopropyl-8-fluoroimidazo[1,2-a]pyridin-2-yl)-7-[(3R,5S)-3,5-dimethylpiperazin-1-yl]-2H-chromen-2-one;
3-(6-cyclopropyl-8-fluoroimidazo[1,2-a]pyridin-2-yl)-7-[(3S)-3-methylpiperazin-1-yl]-2H-chromen-2-one;
3-(6-cyclopropyl-8-fluoroimidazo[1,2-a]pyridin-2-yl)-7-(4-methyl-1,4-diazepan-1-yl)-2H-chromen-2-one;
3-(6-cyclopropyl-8-fluoroimidazo[1,2-a]pyridin-2-yl)-7-(piperazin-1-yl)-2H-chromen-2-one;
7-(1,4-diazabicyclo[3.2.2]non-4-yl)-3-(8-fluoroimidazo[1,2-a]pyridin-2-yl)-2H-chromen-2-one;
3-(6-fluoroimidazo[1,2-a]pyrimidin-2-yl)-7-(piperazin-1-yl)-2H-chromen-2-one;
3-(6-cyclopropyl-8-fluoroimidazo[1,2-a]pyridin-2-yl)-7-[(3R)-3-methylpiperazin-1-yl]-2H-chromen-2-one;
3-(6-cyclopropyl-8-fluoroimidazo[1,2-a]pyridin-2-yl)-7-(4-methylpiperazin-1-yl)-2H-chromen-2-one;
7-(1,4-diazabicyclo[3.2.2]non-4-yl)-3-(8-methylimidazo[1,2-a]pyridin-2-yl)-2H-chromen-2-one;
7-(3,8-diazabicyclo[3.2.1]oct-3-yl)-3-(8-fluoroimidazo[1,2-a]pyridin-2-yl)-2H-chromen-2-one;
7-(3,3-dimethylpiperazin-1-yl)-3-(8-fluoroimidazo[1,2-a]pyridin-2-yl)-2H-chromen-2-one;
7-(3,3-dimethylpiperazin-1-yl)-3-(6-fluoroimidazo[1,2-a]pyridin-2-yl)-2H-chromen-2-one;
3-(3-chlorophenyl)-7-[(3S)-3-methylpiperazin-1-yl]-2H-chromen-2-one;
3-(2-chloro-4-fluorophenyl)-7-[(3S)-3-methylpiperazin-1-yl]-2H-chromen-2-one;
3-(3-methylphenyl)-7-(piperazin-1-yl)-2H-chromen-2-one;
3-(3-methylphenyl)-7-[(3S)-3-methylpiperazin-1-yl]-2H-chromen-2-one;
3-(2,3-dihydro-1,4-benzodioxin-6-yl)-7-[(3S)-3-methylpiperazin-1-yl]-2H-chromen-2-one;
3-(2,3-dihydro-1,4-benzodioxin-6-yl)-7-[(3R,5S)-3,5-dimethylpiperazin-1-yl]-2H-chromen-2-one;
3-(6,8-dimethylimidazo[1,2-a]pyrazin-2-yl)-7-(piperazin-1-yl)-2H-chromen-2-one;
3-(6,8-dimethylimidazo[1,2-a]pyrazin-2-yl)-7-(4-methylpiperazin-1-yl)-2H-chromen-2-one;
3-(6,8-dimethylimidazo[1,2-a]pyrazin-2-yl)-7-[(3R,5S)-3,5-dimethylpiperazin-1-yl]-2H-chromen-2-one;
7-(1,4-diazepan-1-yl)-3-(6,8-dimethylimidazo[1,2-a]pyrazin-2-yl)-2H-chromen-2-one;
3-(6,8-dimethylimidazo[1,2-a]pyrazin-2-yl)-7-(4-methyl-1,4-diazepan-1-yl)-2H-chromen-2-one;
3-(6,8-difluoroimidazo[1,2-a]pyridin-2-yl)-7-(4-methyl-1,4-diazepan-1-yl)-2H-chromen-2-one;

7-(1,4-diazabicyclo[3.2.2]non-4-yl)-3-(7-methylimidazo[1,2-a]pyridin-2-yl)-2H-chromen-2-one;
3-(6,8-difluoroimidazo[1,2-a]pyridin-2-yl)-7-(4-methylpiperazin-1-yl)-2H-chromen-2-one;
3-(6,8-difluoroimidazo[1,2-a]pyridin-2-yl)-7-[(3R,5S)-3,5-dimethylpiperazin-1-yl]-2H-chromen-2-one;
3-(6,8-difluoroimidazo[1,2-a]pyridin-2-yl)-7-[(3S)-3-methylpiperazin-1-yl]-2H-chromen-2-one;
3-(8-fluoroimidazo[1,2-a]pyridin-2-yl)-7-[(3S)-3-methylpiperazin-1-yl]-2H-chromen-2-one;
3-(8-chloroimidazo[1,2-a]pyridin-2-yl)-7-(3,8-diazabicyclo[3.2.1]oct-3-yl)-2H-chromen-2-one;
3-(8-chloroimidazo[1,2-a]pyridin-2-yl)-7-(2,5-diazabicyclo[2.2.2]oct-2-yl)-2H-chromen-2-one;
3-(8-fluoroimidazo[1,2-a]pyridin-2-yl)-7-[(8aS)-hexahydropyrrolo[1,2-a]pyrazin-2(1H)-yl]-2H-chromen-2-one;
3-(indolizin-2-yl)-7-(piperazin-1-yl)-2H-chromen-2-one;
3-(8-fluoroimidazo[1,2-a]pyridin-2-yl)-7-[(3R)-3-methylpiperazin-1-yl]-2H-chromen-2-one;
3-(8-fluoroimidazo[1,2-a]pyridin-2-yl)-7-[(8aR)-hexahydropyrrolo[1,2-a]pyrazin-2(1H)-yl]-2H-chromen-2-one;
3-(6,8-difluoroimidazo[1,2-a]pyridin-2-yl)-7-(piperazin-1-yl)-2H-chromen-2-one;
7-[(3R)-3,4-dimethylpiperazin-1-yl]-3-(8-fluoro-6-methylimidazo[1,2-a]pyridin-2-yl)-2H-chromen-2-one;
7-[(8aS)-hexahydropyrrolo[1,2-a]pyrazin-2(1H)-yl]-3-(7-methylimidazo[1,2-a]pyridin-2-yl)-2H-chromen-2-one;
7-[(1R,5S)-8-methyl-3,8-diazabicyclo[3.2.1]oct-3-yl]-3-(7-methylimidazo[1,2-a]pyridin-2-yl)-2H-chromen-2-one;
3-(6,8-dimethylimidazo[1,2-a]pyrazin-2-yl)-7-[(3R)-3-methylpiperazin-1-yl]-2H-chromen-2-one;
3-(6,8-dimethylimidazo[1,2-a]pyrazin-2-yl)-7-[(3S)-3-methylpiperazin-1-yl]-2H-chromen-2-one;
3-(3,5-difluoro-2-methoxyphenyl)-7-(piperazin-1-yl)-2H-chromen-2-one;
3-(3,5-difluoro-2-methoxyphenyl)-7-[(3S)-3-methylpiperazin-1-yl]-2H-chromen-2-one;
3-(3,5-difluoro-2-methoxyphenyl)-7-[(3R,5S)-3,5-dimethylpiperazin-1-yl]-2H-chromen-2-one;
3-(4-methoxy-3-methylphenyl)-7-(piperazin-1-yl)-2H-chromen-2-one;
3-(4-methoxy-3-methylphenyl)-7-[(3S)-3-methylpiperazin-1-yl]-2H-chromen-2-one;
7-[(3R,5S)-3,5-dimethylpiperazin-1-yl]-3-(4-methoxy-3-methylphenyl)-2H-chromen-2-one;
3-(3-fluoro-4-methoxyphenyl)-7-(piperazin-1-yl)-2H-chromen-2-one;
3-(3-fluoro-4-methoxyphenyl)-7-[(3S)-3-methylpiperazin-1-yl]-2H-chromen-2-one;
3-(2,3-difluorophenyl)-7-[(3S)-3-methylpiperazin-1-yl]-2H-chromen-2-one;
3-[6-(dimethylamino)pyridin-3-yl]-7-(piperazin-1-yl)-2H-chromen-2-one;
3-[6-(dimethylamino)pyridin-3-yl]-7-[(3S)-3-methylpiperazin-1-yl]-2H-chromen-2-one;
7-[(3S)-3-methylpiperazin-1-yl]-3-(pyridin-4-yl)-2H-chromen-2-one;
7-(1,4-diazepan-1-yl)-5-fluoro-3-(6-methylimidazo[1,2-a]pyrazin-2-yl)-2H-chromen-2-one;
3-(8-methylimidazo[1,2-a]pyrazin-2-yl)-7-(4-methylpiperazin-1-yl)-2H-chromen-2-one;
7-[(3R,5S)-3,5-dimethylpiperazin-1-yl]-3-(8-methylimidazo[1,2-a]pyrazin-2-yl)-2H-chromen-2-one;
7-[(3R,5S)-3,5-dimethylpiperazin-1-yl]-3-(indolizin-2-yl)-2H-chromen-2-one;
7-[(3R,5S)-3,5-dimethylpiperazin-1-yl]-3-(1-methylpyrrolo[1,2-a]pyrazin-7-yl)-2H-chromen-2-one;
3-(1-methylpyrrolo[1,2-a]pyrazin-7-yl)-7-(piperazin-1-yl)-2H-chromen-2-one;
7-(4-methyl-1,4-diazepan-1-yl)-3-(1-methylpyrrolo[1,2-a]pyrazin-7-yl)-2H-chromen-2-one;
7-(4-methylpiperazin-1-yl)-3-(1-methylpyrrolo[1,2-a]pyrazin-7-yl)-2H-chromen-2-one;
7-(4-methyl-1,4-diazepan-1-yl)-3-(8-methylimidazo[1,2-a]pyrazin-2-yl)-2H-chromen-2-one;
3-(8-methylimidazo[1,2-a]pyrazin-2-yl)-7-[(3R)-3-methylpiperazin-1-yl]-2H-chromen-2-one;
3-(8-fluoro-6-methylimidazo[1,2-a]pyridin-2-yl)-7-[(8aS)-hexahydropyrrolo[1,2-a]pyrazin-2(1H)-yl]-2H-chromen-2-one;
7-(1,4-diazabicyclo[3.2.2]non-4-yl)-3-(8-fluoro-6-methylimidazo[1,2-a]pyridin-2-yl)-2H-chromen-2-one;
3-(6,8-dimethylimidazo[1,2-a]pyrazin-2-yl)-7-(piperidin-4-ylamino)-2H-chromen-2-one;
3-(6,8-dimethylimidazo[1,2-a]pyrazin-2-yl)-7-[(3S)-pyrrolidin-3-ylamino]-2H-chromen-2-one;
3-(6,8-dimethylimidazo[1,2-a]pyrazin-2-yl)-7-[(3R)-pyrrolidin-3-ylamino]-2H-chromen-2-one;
3-(indolizin-2-yl)-7-[(3S)-3-methylpiperazin-1-yl]-2H-chromen-2-one;
7-[(3S)-3-methylpiperazin-1-yl]-3-(1-methylpyrrolo[1,2-a]pyrazin-7-yl)-2H-chromen-2-one;
3-(6-methylimidazo[1,2-a]pyrazin-2-yl)-7-(piperazin-1-yl)-2H-chromen-2-one;
3-(6-methylimidazo[1,2-a]pyrazin-2-yl)-7-(4-methylpiperazin-1-yl)-2H-chromen-2-one;
3-(6-methylimidazo[1,2-a]pyrazin-2-yl)-7-[(3S)-3-methylpiperazin-1-yl]-2H-chromen-2-one;
3-(6-methylimidazo[1,2-a]pyrazin-2-yl)-7-[(3R)-3-methylpiperazin-1-yl]-2H-chromen-2-one;
3-(8-methylimidazo[1,2-a]pyrazin-2-yl)-7-(piperazin-1-yl)-2H-chromen-2-one;
7-(1,4-diazepan-1-yl)-3-(8-methylimidazo[1,2-a]pyrazin-2-yl)-2H-chromen-2-one;
3-(8-methylimidazo[1,2-a]pyrazin-2-yl)-7-[(3S)-3-methylpiperazin-1-yl]-2H-chromen-2-one;
3-(3-methoxy-4-methylphenyl)-7-(piperazin-1-yl)-2H-chromen-2-one;
3-(3-methoxy-4-methylphenyl)-7-[(3S)-3-methylpiperazin-1-yl]-2H-chromen-2-one;
3-(4-fluoro-3-methoxyphenyl)-7-(piperazin-1-yl)-2H-chromen-2-one;
3-(4-fluoro-3-methoxyphenyl)-7-[(3S)-3-methylpiperazin-1-yl]-2H-chromen-2-one;
3-(8-fluoroimidazo[1,2-a]pyridin-2-yl)-7-(octahydro-2H-pyrido[1,2-a]pyrazin-2-yl)-2H-chromen-2-one;
7-(piperazin-1-yl)-3-(pyrrolo[1,2-a]pyrimidin-7-yl)-2H-chromen-2-one;
7-[(3R,5S)-3,5-dimethylpiperazin-1-yl]-3-(pyrrolo[1,2-a]pyrimidin-7-yl)-2H-chromen-2-one;
3-(7-methylimidazo[1,2-a]pyridin-2-yl)-7-[(3S)-pyrrolidin-3-ylamino]-2H-chromen-2-one;
3-(8-fluoro-6-methylimidazo[1,2-a]pyridin-2-yl)-7-[(3S)-pyrrolidin-3-ylamino]-2H-chromen-2-one;
3-(8-fluoro-6-methylimidazo[1,2-a]pyridin-2-yl)-7-[(3R)-pyrrolidin-3-ylamino]-2H-chromen-2-one;
7-[(3R,5S)-3,5-dimethylpiperazin-1-yl]-3-(3-methylpyrrolo[1,2-a]pyrazin-7-yl)-2H-chromen-2-one;
7-[(3S)-3,4-dimethylpiperazin-1-yl]-3-(8-fluoroimidazo[1,2-a]pyridin-2-yl)-2H-chromen-2-one;

7-[(3R)-3-methylpiperazin-1-yl]-3-(1-methylpyrrolo[1,2-a]pyrazin-7-yl)-2H-chromen-2-one;

7-(1,4-diazepan-1-yl)-3-(1-methylpyrrolo[1,2-a]pyrazin-7-yl)-2H-chromen-2-one;

3-(3-methylpyrrolo[1,2-a]pyrazin-7-yl)-7-(piperazin-1-yl)-2H-chromen-2-one;

7-(4-methyl-1,4-diazepan-1-yl)-3-(3-methylpyrrolo[1,2-a]pyrazin-7-yl)-2H-chromen-2-one;

7-(4-methylpiperazin-1-yl)-3-(3-methylpyrrolo[1,2-a]pyrazin-7-yl)-2H-chromen-2-one;

5-fluoro-7-(4-methyl-1,4-diazepan-1-yl)-3-(6-methylimidazo[1,2-a]pyrazin-2-yl)-2H-chromen-2-one;

5-fluoro-3-(6-methylimidazo[1,2-a]pyrazin-2-yl)-7-(4-methylpiperazin-1-yl)-2H-chromen-2-one;

5-fluoro-3-(6-methylimidazo[1,2-a]pyrazin-2-yl)-7-[(3S)-3-methylpiperazin-1-yl]-2H-chromen-2-one;

3-(6-methylimidazo[1,2-a]pyrazin-2-yl)-7-[(3R)-pyrrolidin-3-yloxy]-2H-chromen-2-one;

7-(5,8-diazaspiro[3.5]non-8-yl)-3-(7-methylimidazo[1,2-a]pyridin-2-yl)-2H-chromen-2-one;

7-(6,9-diazaspiro[4.5]dec-9-yl)-3-(7-methylimidazo[1,2-a]pyridin-2-yl)-2H-chromen-2-one;

7-(2,5-diazabicyclo[2.2.2]oct-2-yl)-3-(7-methylimidazo[1,2-a]pyridin-2-yl)-2H-chromen-2-one;

7-(5,8-diazaspiro[3.5]non-8-yl)-3-(8-fluoro-6-methylimidazo[1,2-a]pyridin-2-yl)-2H-chromen-2-one;

7-(6,9-diazaspiro[4.5]dec-9-yl)-3-(8-fluoro-6-methylimidazo[1,2-a]pyridin-2-yl)-2H-chromen-2-one;

7-(2,5-diazabicyclo[2.2.2]oct-2-yl)-3-(8-fluoro-6-methylimidazo[1,2-a]pyridin-2-yl)-2H-chromen-2-one;

3-(6,8-dimethylimidazo[1,2-a]pyrazin-2-yl)-7-[(3R)-pyrrolidin-3-yloxy]-2H-chromen-2-one;

3-(1-benzofuran-2-yl)-7-(piperazin-1-yl)-2H-chromen-2-one;

3-(1-benzofuran-2-yl)-7-[(3S)-3-methylpiperazin-1-yl]-2H-chromen-2-one;

3-(1-benzofuran-2-yl)-7-[(3R,5S)-3,5-dimethylpiperazin-1-yl]-2H-chromen-2-one;

3-(6,8-dimethylimidazo[1,2-a]pyrazin-2-yl)-7-[(3R,5S)-3,4,5-trimethylpiperazin-1-yl]-2H-chromen-2-one;

3-(6,8-dimethylimidazo[1,2-a]pyrazin-2-yl)-7-[(3R)-3,4-dimethylpiperazin-1-yl]-2H-chromen-2-one;

7-(1,4-diazepan-1-yl)-3-[6-methyl-8-(trifluoromethyl)imidazo[1,2-a]pyrazin-2-yl]-2H-chromen-2-one;

7-(1,4-diazepan-1-yl)-3-(6,8-dimethylimidazo[1,2-a]pyrazin-2-yl)-5-fluoro-2H-chromen-2-one;

7-[(8aS)-hexahydropyrrolo[1,2-a]pyrazin-2(1H)-yl]-3-(6-methylimidazo[1,2-a]pyrazin-2-yl)-2H-chromen-2-one;

3-(8-methylimidazo[1,2-a]pyrazin-2-yl)-7-[(3R)-pyrrolidin-3-yloxy]-2H-chromen-2-one;

3-(8-fluoro-6-methylimidazo[1,2-a]pyridin-2-yl)-7-[(8aR)-hexahydropyrrolo[1,2-a]pyrazin-2(1H)-yl]-2H-chromen-2-one;

3-(8-fluoro-6-methylimidazo[1,2-a]pyridin-2-yl)-7-(octahydro-2H-pyrido[1,2-a]pyrazin-2-yl)-2H-chromen-2-one;

3-(8-fluoro-6-methylimidazo[1,2-a]pyridin-2-yl)-7-(8-methyl-3,8-diazabicyclo[3.2.1]oct-3-yl)-2H-chromen-2-one;

3-(6,8-dimethylimidazo[1,2-a]pyrazin-2-yl)-5-fluoro-7-(4-methyl-1,4-diazepan-1-yl)-2H-chromen-2-one;

3-(6,8-dimethylimidazo[1,2-a]pyrazin-2-yl)-7-[methyl(1-methylpyrrolidin-3-yl)amino]-2H-chromen-2-one;

7-[(1-benzylpyrrolidin-3-yl)(methyl)amino]-3-(6,8-dimethylimidazo[1,2-a]pyrazin-2-yl)-2H-chromen-2-one;

7-[(3R,5S)-3,5-dimethylpiperazin-1-yl]-3-(6-methylimidazo[1,2-b]pyridazin-2-yl)-2H-chromen-2-one;

7-(4-ethyl-1,4-diazepan-1-yl)-3-(6-methylimidazo[1,2-a]pyrazin-2-yl)-2H-chromen-2-one;

7-(azetidin-3-ylamino)-3-(6,8-dimethylimidazo[1,2-a]pyrazin-2-yl)-2H-chromen-2-one;

3-(6,8-dimethylimidazo[1,2-a]pyrazin-2-yl)-7-{methyl[(3S)-pyrrolidin-3-yl]amino}-2H-chromen-2-one;

3-(6,8-dimethylimidazo[1,2-a]pyrazin-2-yl)-7-(4-ethylpiperazin-1-yl)-2H-chromen-2-one;

7-(4-ethylpiperazin-1-yl)-3-(6-methylimidazo[1,2-a]pyrazin-2-yl)-2H-chromen-2-one;

7-[(1S,4S)-2,5-diazabicyclo[2.2.1]hept-2-yl]-3-(6-methylimidazo[1,2-a]pyrazin-2-yl)-2H-chromen-2-one;

3-(6-methylimidazo[1,2-b]pyridazin-2-yl)-7-[(3S)-3-methylpiperazin-1-yl]-2H-chromen-2-one;

7-[(8aR)-hexahydropyrrolo[1,2-a]pyrazin-2(1H)-yl]-3-(6-methylimidazo[1,2-a]pyrazin-2-yl)-2H-chromen-2-one;

3-(6,8-dimethylimidazo[1,2-a]pyrazin-2-yl)-7-[(3S)-4-ethyl-3-methylpiperazin-1-yl]-2H-chromen-2-one;

7-[(3S)-4-ethyl-3-methylpiperazin-1-yl]-3-(6-methylimidazo[1,2-a]pyrazin-2-yl)-2H-chromen-2-one;

7-[(3R)-3,4-dimethylpiperazin-1-yl]-3-(6-methylimidazo[1,2-a]pyrazin-2-yl)-2H-chromen-2-one;

7-[(3S)-3-methylpiperazin-1-yl]-3-(thieno[3,2-c]pyridin-2-yl)-2H-chromen-2-one;

7-[(3R,5S)-3,5-dimethylpiperazin-1-yl]-3-(thieno[3,2-c]pyridin-2-yl)-2H-chromen-2-one;

7-(1,4-diazepan-1-yl)-3-(6-methylimidazo[1,2-b]pyridazin-2-yl)-2H-chromen-2-one;

3-(6,8-dimethylimidazo[1,2-a]pyrazin-2-yl)-7-[(8aR)-hexahydropyrrolo[1,2-a]pyrazin-2(1H)-yl]-2H-chromen-2-one;

3-(6,8-dimethylimidazo[1,2-a]pyrazin-2-yl)-7-(octahydro-2H-pyrido[1,2-a]pyrazin-2-yl)-2H-chromen-2-one;

3-(6,8-dimethylimidazo[1,2-a]pyrazin-2-yl)-7-[(8aS)-hexahydropyrrolo[1,2-a]pyrazin-2(1H)-yl]-2H-chromen-2-one;

3-(6-methylimidazo[1,2-a]pyrazin-2-yl)-7-(octahydro-2H-pyrido[1,2-a]pyrazin-2-yl)-2H-chromen-2-one;

7-[(8aR)-hexahydropyrrolo[1,2-a]pyrazin-2(1H)-yl]-3-(1-methylpyrrolo[1,2-a]pyrazin-7-yl)-2H-chromen-2-one;

7-[(3R)-3-methylpiperazin-1-yl]-3-(3-methylpyrrolo[1,2-a]pyrazin-7-yl)-2H-chromen-2-one;

7-(1,4-diazepan-1-yl)-3-(3-methylpyrrolo[1,2-a]pyrazin-7-yl)-2H-chromen-2-one;

7-[(3R,5S)-3,5-dimethylpiperazin-1-yl]-3-(2-methylpyrrolo[1,2-b]pyridazin-6-yl)-2H-chromen-2-one;

7-(4-ethylpiperazin-1-yl)-3-(3-methylpyrrolo[1,2-a]pyrazin-7-yl)-2H-chromen-2-one;

3-(2-methylpyrrolo[1,2-b]pyridazin-6-yl)-7-(piperazin-1-yl)-2H-chromen-2-one;

7-[(8aS)-hexahydropyrrolo[1,2-a]pyrazin-2(1H)-yl]-3-(1-methylpyrrolo[1,2-a]pyrazin-7-yl)-2H-chromen-2-one;

7-[(8aS)-hexahydropyrrolo[1,2-a]pyrazin-2(1H)-yl]-3-(3-methylpyrrolo[1,2-a]pyrazin-7-yl)-2H-chromen-2-one;

3-(1,3-dimethylpyrrolo[1,2-a]pyrazin-7-yl)-7-(4-methylpiperazin-1-yl)-2H-chromen-2-one;

7-[(3R,5S)-3,5-dimethylpiperazin-1-yl]-3-(1,3-dimethylpyrrolo[1,2-a]pyrazin-7-yl)-2H-chromen-2-one;

3-(3-methylpyrrolo[1,2-a]pyrazin-7-yl)-7-(octahydro-2H-pyrido[1,2-a]pyrazin-2-yl)-2H-chromen-2-one;

7-[(3S)-3-methylpiperazin-1-yl]-3-(3-methylpyrrolo[1,2-a]pyrazin-7-yl)-2H-chromen-2-one;
7-[(1S,4S)-2,5-diazabicyclo[2.2.1]hept-2-yl]-3-(6,8-dimethylimidazo[1,2-a]pyrazin-2-yl)-2H-chromen-2-one;
7-[(8aS)-hexahydropyrrolo[1,2-a]pyrazin-2(1H)-yl]-3-(2-methylimidazo[1,2-a]pyrimidin-6-yl)-2H-chromen-2-one;
3-(2-methylimidazo[1,2-a]pyrimidin-6-yl)-7-[(3R)-3-methylpiperazin-1-yl]-2H-chromen-2-one;
7-[(8aS)-hexahydropyrrolo[1,2-a]pyrazin-2(1H)-yl]-3-(2-methylimidazo[1,2-a]pyridin-6-yl)-2H-chromen-2-one;
3-(2-methylimidazo[1,2-a]pyridin-6-yl)-7-[(3R)-3-methylpiperazin-1-yl]-2H-chromen-2-one;
7-(4-methyl-1,4-diazepan-1-yl)-3-(2-methylimidazo[1,2-a]pyridin-6-yl)-2H-chromen-2-one;
3-(6,8-dimethylimidazo[1,2-a]pyrazin-2-yl)-7-[4-(2-hydroxyethyl)piperazin-1-yl]-2H-chromen-2-one;
3-(6,8-dimethylimidazo[1,2-a]pyrazin-2-yl)-7-[(4aR,7aR)-octahydro-6H-pyrrolo[3,4-b]pyridin-6-yl]-2H-chromen-2-one;
3-(6,8-dimethylimidazo[1,2-a]pyrazin-2-yl)-7-{methyl[(3S)-1-methylpyrrolidin-3-yl]amino}-2H-chromen-2-one;
3-(6,8-dimethylimidazo[1,2-a]pyrazin-2-yl)-7-{[(3S)-1-methylpyrrolidin-3-yl]amino}-2H-chromen-2-one;
3-(6,8-dimethylimidazo[1,2-a]pyrazin-2-yl)-7-[(4aR,7aR)-1-methyloctahydro-6H-pyrrolo[3,4-b]pyridin-6-yl]-2H-chromen-2-one;
7-[(3S)-3,4-dimethylpiperazin-1-yl]-5-fluoro-3-(6-methylimidazo[1,2-a]pyrazin-2-yl)-2H-chromen-2-one;
7-[(3R)-3,4-dimethylpiperazin-1-yl]-3-(2-methylimidazo[1,2-a]pyrimidin-6-yl)-2H-chromen-2-one;
7-[(3R)-3,4-dimethylpiperazin-1-yl]-3-(2-methylimidazo[1,2-a]pyridin-6-yl)-2H-chromen-2-one;
7-(4-methyl-1,4-diazepan-1-yl)-3-(2-methylimidazo[1,2-a]pyrimidin-6-yl)-2H-chromen-2-one;
7-(1,4-diazepan-1-yl)-3-(2-methylimidazo[1,2-a]pyridin-6-yl)-2H-chromen-2-one;
3-(2-methylimidazo[1,2-a]pyridin-6-yl)-7-[(3S)-3-methylpiperazin-1-yl]-2H-chromen-2-one;
3-(6,8-dimethylimidazo[1,2-a]pyrazin-2-yl)-7-(3-ethylpiperazin-1-yl)-2H-chromen-2-one;
7-[(3S)-3-(dimethylamino)pyrrolidin-1-yl]-3-(3-methylpyrrolo[1,2-a]pyrazin-7-yl)-2H-chromen-2-one;
7-(4-ethyl-1,4-diazepan-1-yl)-3-(3-methylpyrrolo[1,2-a]pyrazin-7-yl)-2H-chromen-2-one;
3-(1,3-dimethylpyrrolo[1,2-a]pyrazin-7-yl)-7-[(3R)-3-methylpiperazin-1-yl]-2H-chromen-2-one;
3-(1,3-dimethylpyrrolo[1,2-a]pyrazin-7-yl)-7-[(8aR)-hexahydropyrrolo[1,2-a]pyrazin-2(1H)-yl]-2H-chromen-2-one;
3-(1,3-dimethylpyrrolo[1,2-a]pyrazin-7-yl)-7-(piperazin-1-yl)-2H-chromen-2-one;
3-(1,3-dimethylpyrrolo[1,2-a]pyrazin-7-yl)-7-(4-ethyl-1,4-diazepan-1-yl)-2H-chromen-2-one;
3-(6,8-dimethylimidazo[1,2-a]pyrazin-2-yl)-7-[(3S)-3,4-dimethylpiperazin-1-yl]-2H-chromen-2-one;
3-(1,3-dimethylpyrrolo[1,2-a]pyrazin-7-yl)-7-[(8aS)-hexahydropyrrolo[1,2-a]pyrazin-2(1H)-yl]-2H-chromen-2-one;
3-(1,3-dimethylpyrrolo[1,2-a]pyrazin-7-yl)-7-(4-ethylpiperazin-1-yl)-2H-chromen-2-one;
7-[(3S)-3,4-dimethylpiperazin-1-yl]-3-(2-methylimidazo[1,2-a]pyridin-6-yl)-2H-chromen-2-one;
3-(6,8-dimethylimidazo[1,2-a]pyrazin-2-yl)-7-(3-ethyl-4-methylpiperazin-1-yl)-2H-chromen-2-one;
3-(2-methylimidazo[1,2-a]pyridin-6-yl)-7-(piperazin-1-yl)-2H-chromen-2-one;
3-(2-methylimidazo[1,2-a]pyridin-6-yl)-7-(4-methylpiperazin-1-yl)-2H-chromen-2-one;
3-(6,8-dimethylimidazo[1,2-a]pyrazin-2-yl)-7-[(3R)-4-ethyl-3-methylpiperazin-1-yl]-2H-chromen-2-one;
3-(1,3-dimethylpyrrolo[1,2-a]pyrazin-7-yl)-7-[(3S)-3-methylpiperazin-1-yl]-2H-chromen-2-one;
3-(1,3-dimethylpyrrolo[1,2-a]pyrazin-7-yl)-7-(4-methyl-1,4-diazepan-1-yl)-2H-chromen-2-one;
7-(1,4-diazepan-1-yl)-3-(1,3-dimethylpyrrolo[1,2-a]pyrazin-7-yl)-2H-chromen-2-one;
3-(1,3-dimethylpyrrolo[1,2-a]pyrazin-7-yl)-7-(octahydro-2H-pyrido[1,2-a]pyrazin-2-yl)-2H-chromen-2-one;
7-[4-(2-hydroxyethyl)piperazin-1-yl]-3-(3-methylpyrrolo[1,2-a]pyrazin-7-yl)-2H-chromen-2-one;
3-(1,3-dimethylpyrrolo[1,2-a]pyrazin-7-yl)-7-[4-(2-hydroxyethyl)piperazin-1-yl]-2H-chromen-2-one;
3-(6,8-dimethylimidazo[1,2-a]pyrazin-2-yl)-7-[(3aR,6aS)-hexahydropyrrolo[3,4-c]pyrrol-2(1H)-yl]-2H-chromen-2-one;
3-(6,8-dimethylimidazo[1,2-a]pyrazin-2-yl)-7-[(3aS,6aS)-hexahydropyrrolo[3,4-b]pyrrol-1(2H)-yl]-2H-chromen-2-one;
3-(6,8-dimethylimidazo[1,2-a]pyrazin-2-yl)-7-[(3aR,6aS)-5-methylhexahydropyrrolo[3,4-c]pyrrol-2(1H)-yl]-2H-chromen-2-one;
3-(6,8-dimethylimidazo[1,2-a]pyrazin-2-yl)-7-[(3aS,6aS)-5-methylhexahydropyrrolo[3,4-b]pyrrol-1(2H)-yl]-2H-chromen-2-one;
7-[(3R)-3-(dimethylamino)pyrrolidin-1-yl]-3-(6,8-dimethylimidazo[1,2-a]pyrazin-2-yl)-2H-chromen-2-one;
7-[(3S)-3-(dimethylamino)pyrrolidin-1-yl]-3-(6,8-dimethylimidazo[1,2-a]pyrazin-2-yl)-2H-chromen-2-one;
3-(3-methylpyrrolo[1,2-a]pyrazin-7-yl)-7-[4-(propan-2-yl)piperazin-1-yl]-2H-chromen-2-one;
7-[(3R)-3-(dimethylamino)pyrrolidin-1-yl]-3-(3-methylpyrrolo[1,2-a]pyrazin-7-yl)-2H-chromen-2-one;
3-(1,3-dimethylpyrrolo[1,2-a]pyrazin-7-yl)-7-[(3S)-4-ethyl-3-methylpiperazin-1-yl]-2H-chromen-2-one;
3-(2-methyl-1,3-benzoxazol-6-yl)-7-(piperazin-1-yl)-2H-chromen-2-one;
3-(6,8-dimethylimidazo[1,2-a]pyrazin-2-yl)-7-[(1S,4S)-5-methyl-2,5-diazabicyclo[2.2.1]hept-2-yl]-2H-chromen-2-one;
7-[(3S)-3-(dimethylamino)pyrrolidin-1-yl]-3-(1,3-dimethylpyrrolo[1,2-a]pyrazin-7-yl)-2H-chromen-2-one;
3-(5-methylfuro[3,2-b]pyridin-2-yl)-7-(4-methylpiperazin-1-yl)-2H-chromen-2-one;
3-(6-chloro-8-methylimidazo[1,2-a]pyrazin-2-yl)-7-[(3R)-3-methylpiperazin-1-yl]-2H-chromen-2-one;
3-(6,8-dimethylimidazo[1,2-a]pyrazin-2-yl)-7-{methyl[(3R)-pyrrolidin-3-yl]amino}-2H-chromen-2-one;
7-[(3R,5S)-3,5-dimethylpiperazin-1-yl]-3-(6-methyl-8-nitroimidazo[1,2-a]pyridin-2-yl)-2H-chromen-2-one;
3-(6,8-dimethylimidazo[1,2-a]pyrazin-2-yl)-7-{[(3-exo)-9-methyl-9-azabicyclo[3.3.1]non-3-yl]amino}-2H-chromen-2-one;
3-(6-methyl-8-nitroimidazo[1,2-a]pyridin-2-yl)-7-[(3S)-3-methylpiperazin-1-yl]-2H-chromen-2-one;
3-(6,8-dimethylimidazo[1,2-a]pyrazin-2-yl)-7-[(3aR,6aR)-1-methylhexahydropyrrolo[3,4-b]pyrrol-5(1H)-yl]-2H-chromen-2-one;
3-(2,4-dimethylthieno[2,3-d]pyrimidin-6-yl)-7-(piperazin-1-yl)-2H-chromen-2-one;

3-(6,8-dimethylimidazo[1,2-a]pyrazin-2-yl)-7-[(3aS,6aS)-1-methylhexahydropyrrolo[3,4-b]pyrrol-5(1H)-yl]-2H-chromen-2-one;

3-(6,8-dimethylimidazo[1,2-a]pyrazin-2-yl)-7-{methyl[(3R)-1-methylpyrrolidin-3-yl]amino}-2H-chromen-2-one;

7-[(3R)-3-(dimethylamino)pyrrolidin-1-yl]-3-(1,3-dimethylpyrrolo[1,2-a]pyrazin-7-yl)-2H-chromen-2-one;

3-(1,3-dimethylpyrrolo[1,2-a]pyrazin-7-yl)-7-[4-(propan-2-yl)piperazin-1-yl]-2H-chromen-2-one;

3-(6-chloro-8-methylimidazo[1,2-a]pyrazin-2-yl)-7-[(8aR)-hexahydropyrrolo[1,2-a]pyrazin-2(1H)-yl]-2H-chromen-2-one;

3-(6-chloro-8-methylimidazo[1,2-a]pyrazin-2-yl)-7-[(8aS)-hexahydropyrrolo[1,2-a]pyrazin-2(1H)-yl]-2H-chromen-2-one;

3-(6-chloro-8-methylimidazo[1,2-a]pyrazin-2-yl)-7-(4-methyl-1,4-diazepan-1-yl)-2H-chromen-2-one;

3-(6-chloro-8-methylimidazo[1,2-a]pyrazin-2-yl)-7-[(3S)-3-methylpiperazin-1-yl]-2H-chromen-2-one;

7-(4-aminopiperidin-1-yl)-3-(1,3-dimethylpyrrolo[1,2-a]pyrazin-7-yl)-2H-chromen-2-one;

7-[4-(dimethylamino)piperidin-1-yl]-3-(1,3-dimethylpyrrolo[1,2-a]pyrazin-7-yl)-2H-chromen-2-one;

7-[4-(dimethylamino)piperidin-1-yl]-3-(3-methylpyrrolo[1,2-a]pyrazin-7-yl)-2H-chromen-2-one;

7-[(3S)-3-(dimethylamino)pyrrolidin-1-yl]-3-(2-methylimidazo[1,2-a]pyridin-6-yl)-2H-chromen-2-one;

7-[(3aR,6aS)-hexahydropyrrolo[3,4-c]pyrrol-2(1H)-yl]-3-(6-methylimidazo[1,2-a]pyrazin-2-yl)-2H-chromen-2-one;

3-(6-methylimidazo[1,2-a]pyrazin-2-yl)-7-[(4aR,7aR)-octahydro-6H-pyrrolo[3,4-b]pyridin-6-yl]-2H-chromen-2-one;

7-[(3R,5S)-3,5-dimethylpiperazin-1-yl]-3-(5-methylfuro[3,2-b]pyridin-2-yl)-2H-chromen-2-one;

7-[(8aR)-hexahydropyrrolo[1,2-a]pyrazin-2(1H)-yl]-3-(5-methylfuro[3,2-b]pyridin-2-yl)-2H-chromen-2-one;

7-[(8aS)-hexahydropyrrolo[1,2-a]pyrazin-2(1H)-yl]-3-(5-methylfuro[3,2-b]pyridin-2-yl)-2H-chromen-2-one;

3-(5,7-dimethylfuro[2,3-c]pyridin-2-yl)-7-(piperazin-1-yl)-2H-chromen-2-one;

tert-butyl {(3S)-1-[3-(1,3-dimethylpyrrolo[1,2-a]pyrazin-7-yl)-2-oxo-2H-chromen-7-yl]pyrrolidin-3-yl}carbamate;

3-(1,3-dimethylpyrrolo[1,2-a]pyrazin-7-yl)-7-[(3S)-3-(propan-2-ylamino)pyrrolidin-1-yl]-2H-chromen-2-one;

3-(6-chloro-8-methylimidazo[1,2-a]pyrazin-2-yl)-7-[(3R)-3,4-dimethylpiperazin-1-yl]-2H-chromen-2-one;

3-(6-chloro-8-methylimidazo[1,2-a]pyrazin-2-yl)-7-[(3S)-3,4-dimethylpiperazin-1-yl]-2H-chromen-2-one;

3-(1,3-dimethylpyrrolo[1,2-a]pyrazin-7-yl)-7-{[(1R,5S)-9-methyl-9-azabicyclo[3.3.1]non-3-yl]amino}-2H-chromen-2-one;

3-(1,3-dimethylpyrrolo[1,2-a]pyrazin-7-yl)-7-[(3aS,6aS)-1-methylhexahydropyrrolo[3,4-b]pyrrol-5(1H)-yl]-2H-chromen-2-one;

3-(6,8-dimethylimidazo[1,2-a]pyrazin-2-yl)-7-{[(3R)-1-methylpyrrolidin-3-yl]amino}-2H-chromen-2-one;

3-(6,8-dimethylimidazo[1,2-a]pyrazin-2-yl)-7-{[(3R)-1-ethylpyrrolidin-3-yl]amino}-2H-chromen-2-one;

3-(6,8-dimethylimidazo[1,2-a]pyrazin-2-yl)-7-{[(3R)-1-(2-hydroxyethyl)pyrrolidin-3-yl]amino}-2H-chromen-2-one;

3-(6,8-dimethylimidazo[1,2-a]pyrazin-2-yl)-7-{[(3R)-1-(propan-2-yl)pyrrolidin-3-yl]amino}-2H-chromen-2-one;

7-[(3R,4R)-3-(dimethylamino)-4-hydroxypyrrolidin-1-yl]-3-(1,3-dimethylpyrrolo[1,2-a]pyrazin-7-yl)-2H-chromen-2-one;

7-[3-(diethylamino)pyrrolidin-1-yl]-3-(1,3-dimethylpyrrolo[1,2-a]pyrazin-7-yl)-2H-chromen-2-one;

3-(6,8-dimethylimidazo[1,2-a]pyrazin-2-yl)-7-(3,3-dimethylpiperazin-1-yl)-2H-chromen-2-one;

3-(6,8-dimethylimidazo[1,2-a]pyrazin-2-yl)-7-(3,3,4-trimethylpiperazin-1-yl)-2H-chromen-2-one;

7-[(3S,4S)-3-(dimethylamino)-4-hydroxypyrrolidin-1-yl]-3-(6,8-dimethylimidazo[1,2-a]pyrazin-2-yl)-2H-chromen-2-one;

3-(6,8-dimethylimidazo[1,2-a]pyrazin-2-yl)-7-[(3'S,4'S)-4'-hydroxy-1,3'-bipyrrolidin-1'-yl]-2H-chromen-2-one;

3-(6,8-dimethylimidazo[1,2-a]pyrazin-2-yl)-7-(1,2,3,6-tetrahydropyridin-4-yl)-2H-chromen-2-one;

3-(6,8-dimethylimidazo[1,2-a]pyrazin-2-yl)-7-[(3aR,6aS)-5-(2-hydroxyethyl)hexahydropyrrolo[3,4-c]pyrrol-2(1H)-yl]-2H-chromen-2-one;

3-(6,8-dimethylimidazo[1,2-a]pyrazin-2-yl)-7-(piperidin-4-yl)-2H-chromen-2-one;

3-(6,8-dimethylimidazo[1,2-a]pyrazin-2-yl)-7-[(3aR,6aS)-5-(propan-2-yl)hexahydropyrrolo[3,4-c]pyrrol-2(1H)-yl]-2H-chromen-2-one;

7-(2,5-diazabicyclo[2.2.1]hept-2-yl)-3-(3-methylpyrrolo[1,2-a]pyrazin-7-yl)-2H-chromen-2-one;

3-(5,7-dimethylfuro[2,3-c]pyridin-2-yl)-7-[(8aS)-hexahydropyrrolo[1,2-a]pyrazin-2(1H)-yl]-2H-chromen-2-one;

3-(6,8-dimethylimidazo[1,2-a]pyrazin-2-yl)-7-(4-ethylpiperazin-1-yl)-5-fluoro-2H-chromen-2-one;

3-(6,8-dimethylimidazo[1,2-a]pyrazin-2-yl)-7-[(3aR,6aS)-5-ethylhexahydropyrrolo[3,4-c]pyrrol-2(1H)-yl]-2H-chromen-2-one;

3-(6,8-dimethylimidazo[1,2-a]pyrazin-2-yl)-7-(1-methylpiperidin-4-yl)-2H-chromen-2-one;

3-(6,8-dimethylimidazo[1,2-a]pyrazin-2-yl)-7-(1-ethylpiperidin-4-yl)-2H-chromen-2-one;

3-(6,8-dimethylimidazo[1,2-a]pyrazin-2-yl)-7-[1-(2-hydroxyethyl)piperidin-4-yl]-2H-chromen-2-one;

3-(1,3-dimethylpyrrolo[1,2-a]pyrazin-7-yl)-7-[(3'R,4'R)-4'-hydroxy-1,3'-bipyrrolidin-1'-yl]-2H-chromen-2-one;

7-(4-cyclopropylpiperazin-1-yl)-3-(1,3-dimethylpyrrolo[1,2-a]pyrazin-7-yl)-2H-chromen-2-one;

3-(3-methylpyrrolo[1,2-a]pyrazin-7-yl)-7-[4-(propan-2-yl)-1,4-diazepan-1-yl]-2H-chromen-2-one;

3-(1,3-dimethylpyrrolo[1,2-a]pyrazin-7-yl)-7-[4-(propan-2-yl)-1,4-diazepan-1-yl]-2H-chromen-2-one;

3-(1,3-dimethylpyrrolo[1,2-a]pyrazin-7-yl)-7-[(3aR,6aR)-1-methylhexahydropyrrolo[3,4-b]pyrrol-5(1H)-yl]-2H-chromen-2-one;

3-(1,3-dimethylpyrrolo[1,2-a]pyrazin-7-yl)-7-[(3aR,6aS)-5-methylhexahydropyrrolo[3,4-c]pyrrol-2(1H)-yl]-2H-chromen-2-one;

3-(1,3-dimethylpyrrolo[1,2-a]pyrazin-7-yl)-7-[3-(morpholin-4-yl)pyrrolidin-1-yl]-2H-chromen-2-one;

3-(6,8-dimethylimidazo[1,2-a]pyrazin-2-yl)-7-[(7R,8aS)-7-hydroxyhexahydropyrrolo[1,2-a]pyrazin-2(1H)-yl]-2H-chromen-2-one;

7-[(3R)-3,4-dimethylpiperazin-1-yl]-3-(8-methoxy-6-methylimidazo[1,2-a]pyrazin-2-yl)-2H-chromen-2-one;

7-[(3R)-3,4-dimethylpiperazin-1-yl]-3-(8-hydroxy-6-methylimidazo[1,2-a]pyrazin-2-yl)-2H-chromen-2-one;

7-[(1R,5S,6s)-6-(dimethylamino)-3-azabicyclo[3.1.0]hex-3-yl]-3-(6,8-dimethylimidazo[1,2-a]pyrazin-2-yl)-2H-chromen-2-one;

7-(4-cyclopropylpiperazin-1-yl)-3-(6,8-dimethylimidazo[1,2-a]pyrazin-2-yl)-2H-chromen-2-one;

3-(5,7-dimethylfuro[2,3-c]pyridin-2-yl)-7-(4-methylpiperazin-1-yl)-2H-chromen-2-one;

3-(6-chloro-8-methylimidazo[1,2-a]pyrazin-2-yl)-7-(4-methylpiperazin-1-yl)-2H-chromen-2-one;

3-(6-chloro-8-methylimidazo[1,2-a]pyrazin-2-yl)-7-[(3S)-3-(dimethylamino)pyrrolidin-1-yl]-2H-chromen-2-one;

3-(6-chloro-8-methylimidazo[1,2-a]pyrazin-2-yl)-7-(4-ethylpiperazin-1-yl)-2H-chromen-2-one;

3-(1,3-dimethylpyrrolo[1,2-a]pyrazin-7-yl)-7-[(7R,8aS)-7-hydroxyhexahydropyrrolo[1,2-a]pyrazin-2(1H)-yl]-2H-chromen-2-one;

3-(1,3-dimethylpyrrolo[1,2-a]pyrazin-7-yl)-7-[(3S)-3-methyl-4-(propan-2-yl)piperazin-1-yl]-2H-chromen-2-one;

3-(2-methyl-1,3-benzothiazol-6-yl)-7-(4-methylpiperazin-1-yl)-2H-chromen-2-one;

3-(2-methyl-1,3-benzothiazol-6-yl)-7-[(3S)-3-methylpiperazin-1-yl]-2H-chromen-2-one;

7-(1,4-diazepan-1-yl)-3-(2-methyl-1,3-benzothiazol-6-yl)-2H-chromen-2-one;

3-(6,8-dimethylimidazo[1,2-a]pyrazin-2-yl)-7-[(3S)-3-ethylpiperazin-1-yl]-2H-chromen-2-one;

3-(6,8-dimethylimidazo[1,2-a]pyrazin-2-yl)-7-[1-(propan-2-yl)piperidin-4-yl]-2H-chromen-2-one;

3-(5,7-dimethylfuro[2,3-c]pyridin-2-yl)-7-[4-(2-hydroxyethyl)piperazin-1-yl]-2H-chromen-2-one;

3-(5,7-dimethylfuro[2,3-c]pyridin-2-yl)-7-(4-methyl-1,4-diazepan-1-yl)-2H-chromen-2-one;

7-[(3S)-3,4-dimethylpiperazin-1-yl]-3-(2-methyl-1,3-benzothiazol-6-yl)-2H-chromen-2-one;

7-[(3S)-4-ethyl-3-methylpiperazin-1-yl]-3-(2-methyl-1,3-benzothiazol-6-yl)-2H-chromen-2-one;

3-(6,8-dimethylimidazo[1,2-a]pyrazin-2-yl)-7-[(3S)-3-ethyl-4-methylpiperazin-1-yl]-2H-chromen-2-one;

7-[(3S)-3,4-diethylpiperazin-1-yl]-3-(6,8-dimethylimidazo[1,2-a]pyrazin-2-yl)-2H-chromen-2-one;

3-(6-chloro-8-methylimidazo[1,2-a]pyrazin-2-yl)-7-[(1S,4S)-2,5-diazabicyclo[2.2.1]hept-2-yl]-2H-chromen-2-one;

3-(6,8-dimethylimidazo[1,2-a]pyrazin-2-yl)-7-[(4aR,7aR)-octahydro-6H-pyrrolo[3,4-b]pyridin-6-yl]-2H-chromen-2-one;

3-(6,8-dimethylimidazo[1,2-a]pyrazin-2-yl)-7-[(4aR,7aR)-1-methyloctahydro-6H-pyrrolo[3,4-b]pyridin-6-yl]-2H-chromen-2-one;

7-(2,5-diazabicyclo[2.2.1]hept-2-yl)-3-(1,3-dimethylpyrrolo[1,2-a]pyrazin-7-yl)-2H-chromen-2-one;

7-[4-(aminomethyl)piperidin-1-yl]-3-(1,3-dimethylpyrrolo[1,2-a]pyrazin-7-yl)-2H-chromen-2-one;

3-(6,8-dimethylimidazo[1,2-a]pyrazin-2-yl)-7-[(4aR,7aR)-1-(2-hydroxyethyl)octahydro-6H-pyrrolo[3,4-b]pyridin-6-yl]-2H-chromen-2-one;

3-(6,8-dimethylimidazo[1,2-a]pyrazin-2-yl)-7-[(4aR,7aR)-1-ethyloctahydro-6H-pyrrolo[3,4-b]pyridin-6-yl]-2H-chromen-2-one;

3-(6-chloro-8-methylimidazo[1,2-a]pyrazin-2-yl)-7-[(1S,4S)-5-methyl-2,5-diazabicyclo[2.2.1]hept-2-yl]-2H-chromen-2-one;

3-(5,7-dimethylfuro[2,3-c]pyridin-2-yl)-7-(4-ethylpiperazin-1-yl)-2H-chromen-2-one;

3-(5,7-dimethylfuro[2,3-c]pyridin-2-yl)-7-[4-(propan-2-yl)piperazin-1-yl]-2H-chromen-2-one;

3-(1,3-dimethylpyrrolo[1,2-a]pyrazin-7-yl)-7-{4-[(propan-2-ylamino)methyl]piperidin-1-yl}-2H-chromen-2-one;

3-(6-chloro-8-methylimidazo[1,2-a]pyrazin-2-yl)-7-[(1S,4S)-5-ethyl-2,5-diazabicyclo[2.2.1]hept-2-yl]-2H-chromen-2-one;

3-(6,8-dimethylimidazo[1,2-a]pyrazin-2-yl)-7-[4-(propan-2-yl)piperazin-1-yl]-2H-chromen-2-one;

3-(6,8-dimethylimidazo[1,2-a]pyrazin-2-yl)-7-[(1S,4S)-5-ethyl-2,5-diazabicyclo[2.2.1]hept-2-yl]-2H-chromen-2-one;

3-(6,8-dimethylimidazo[1,2-a]pyrazin-2-yl)-7-[(4aS,7aS)-octahydro-6H-pyrrolo[3,4-b]pyridin-6-yl]-2H-chromen-2-one;

3-(6,8-dimethylimidazo[1,2-a]pyrazin-2-yl)-7-[(4aS,7aS)-1-methyloctahydro-6H-pyrrolo[3,4-b]pyridin-6-yl]-2H-chromen-2-one;

3-(6,8-dimethylimidazo[1,2-a]pyrazin-2-yl)-7-[(4aS,7aS)-1-(2-hydroxyethyl)octahydro-6H-pyrrolo[3,4-b]pyridin-6-yl]-2H-chromen-2-one;

7-[(3R,5S)-4-ethyl-3,5-dimethylpiperazin-1-yl]-3-(6-methylimidazo[1,2-a]pyrazin-2-yl)-2H-chromen-2-one;

7-(4-cyclopropylpiperazin-1-yl)-3-(5,7-dimethylfuro[2,3-c]pyridin-2-yl)-2H-chromen-2-one;

3-(5,7-dimethylfuro[2,3-c]pyridin-2-yl)-7-[4-(2-methoxyethyl)piperazin-1-yl]-2H-chromen-2-one;

3-(6,8-dimethylimidazo[1,2-a]pyrazin-2-yl)-7-(1-methyl-1,2,3,6-tetrahydropyridin-4-yl)-2H-chromen-2-one;

3-(6,8-dimethylimidazo[1,2-a]pyrazin-2-yl)-7-[1-(2-hydroxyethyl)-1,2,3,6-tetrahydropyridin-4-yl]-2H-chromen-2-one;

3-(6,8-dimethylimidazo[1,2-a]pyrazin-2-yl)-7-[1-(propan-2-yl)-1,2,3,6-tetrahydropyridin-4-yl]-2H-chromen-2-one;

3-(6,8-dimethylimidazo[1,2-a]pyrazin-2-yl)-7-[(4aS,7aS)-1-ethyloctahydro-6H-pyrrolo[3,4-b]pyridin-6-yl]-2H-chromen-2-one;

3-(5,7-dimethylfuro[2,3-c]pyridin-2-yl)-7-[(3S)-3-methylpiperazin-1-yl]-2H-chromen-2-one;

3-(5,7-dimethylfuro[2,3-c]pyridin-2-yl)-7-[(3S)-3,4-dimethylpiperazin-1-yl]-2H-chromen-2-one;

3-(5,7-dimethylfuro[2,3-c]pyridin-2-yl)-7-[(3R)-3-methylpiperazin-1-yl]-2H-chromen-2-one;

3-(5,7-dimethylfuro[2,3-c]pyridin-2-yl)-7-[(3R)-3,4-dimethylpiperazin-1-yl]-2H-chromen-2-one;

3-(6,8-dimethylimidazo[1,2-a]pyrazin-2-yl)-7-[(3S)-3-(propan-2-yl)piperazin-1-yl]-2H-chromen-2-one;

3-(6,8-dimethylimidazo[1,2-a]pyrazin-2-yl)-7-[(3S)-4-methyl-3-(propan-2-yl)piperazin-1-yl]-2H-chromen-2-one;

3-(6,8-dimethylimidazo[1,2-a]pyrazin-2-yl)-7-[(3S)-4-ethyl-3-(propan-2-yl)piperazin-1-yl]-2H-chromen-2-one;

7-(4-cyclopropylpiperazin-1-yl)-3-(6-methylimidazo[1,2-a]pyrazin-2-yl)-2H-chromen-2-one;

7-(4-tert-butylpiperazin-1-yl)-3-(6,8-dimethylimidazo[1,2-a]pyrazin-2-yl)-2H-chromen-2-one;

3-(1,3-dimethylpyrrolo[1,2-a]pyrazin-7-yl)-7-[(3R)-3-methyl-4-(propan-2-yl)piperazin-1-yl]-2H-chromen-2-one;

7-(4-cyclobutylpiperazin-1-yl)-3-(1,3-dimethylpyrrolo[1,2-a]pyrazin-7-yl)-2H-chromen-2-one;

3-(5,7-dimethylfuro[2,3-c]pyridin-2-yl)-7-(4-propylpiperazin-1-yl)-2H-chromen-2-one;
7-[4-(cyclopropylmethyl)piperazin-1-yl]-3-(5,7-dimethylfuro[2,3-c]pyridin-2-yl)-2H-chromen-2-one;
3-(4,6-dimethylthieno[3,2-c]pyridin-2-yl)-7-(piperazin-1-yl)-2H-chromen-2-one;
7-(2-methylimidazo[1,2-a]pyridin-6-yl)-3-(piperazin-1-yl)-2H-chromen-2-one;
3-(4,6-dimethylthieno[3,2-c]pyridin-2-yl)-7-(4-methylpiperazin-1-yl)-2H-chromen-2-one;
3-(4,6-dimethylthieno[3,2-c]pyridin-2-yl)-7-[4-(2-methoxyethyl)piperazin-1-yl]-2H-chromen-2-one;
7-(1-cyclobutylpiperidin-4-yl)-3-(6,8-dimethylimidazo[1,2-a]pyrazin-2-yl)-2H-chromen-2-one;
7-(4-cyclobutylpiperazin-1-yl)-3-(6,8-dimethylimidazo[1,2-a]pyrazin-2-yl)-2H-chromen-2-one;
3-(6,8-dimethylimidazo[1,2-a]pyrazin-2-yl)-7-[4-(oxetan-3-yl)piperazin-1-yl]-2H-chromen-2-one;
3-(8-ethyl-6-methylimidazo[1,2-a]pyrazin-2-yl)-7-(piperazin-1-yl)-2H-chromen-2-one;
3-(2-methylimidazo[1,2-a]pyridin-6-yl)-7-(piperidin-4-yl)-2H-chromen-2-one;
3-(2-methylimidazo[1,2-a]pyridin-6-yl)-7-(1-methylpiperidin-4-yl)-2H-chromen-2-one;
7-(1-ethylpiperidin-4-yl)-3-(2-methylimidazo[1,2-a]pyridin-6-yl)-2H-chromen-2-one;
3-(2-methylimidazo[1,2-a]pyridin-6-yl)-7-[1-(oxetan-3-yl)piperidin-4-yl]-2H-chromen-2-one;
7-[1-(2-hydroxyethyl)piperidin-4-yl]-3-(2-methylimidazo[1,2-a]pyridin-6-yl)-2H-chromen-2-one;
3-(8-ethyl-6-methylimidazo[1,2-a]pyrazin-2-yl)-7-(4-methylpiperazin-1-yl)-2H-chromen-2-one;
3-(4,6-dimethylfuro[3,2-c]pyridin-2-yl)-7-(piperazin-1-yl)-2H-chromen-2-one;
3-(4,6-dimethylfuro[3,2-c]pyridin-2-yl)-7-(4-methylpiperazin-1-yl)-2H-chromen-2-one;
3-(6-methylimidazo[1,2-a]pyrazin-2-yl)-7-[4-(propan-2-yl)piperazin-1-yl]-2H-chromen-2-one;
3-(2-methylimidazo[1,2-a]pyrimidin-6-yl)-7-(piperidin-4-yl)-2H-chromen-2-one;
3-(2-methylimidazo[1,2-a]pyrimidin-6-yl)-7-(1-methylpiperidin-4-yl)-2H-chromen-2-one;
7-(1-ethylpiperidin-4-yl)-3-(2-methylimidazo[1,2-a]pyrimidin-6-yl)-2H-chromen-2-one;
7-[4-(2-hydroxyethyl)piperazin-1-yl]-3-(6-methylimidazo[1,2-a]pyrazin-2-yl)-2H-chromen-2-one;
7-(4-cyclobutylpiperazin-1-yl)-3-(6-methylimidazo[1,2-a]pyrazin-2-yl)-2H-chromen-2-one;
3-(6-methylimidazo[1,2-a]pyrazin-2-yl)-7-[4-(oxetan-3-yl)piperazin-1-yl]-2H-chromen-2-one;
3-(4,6-dimethylfuro[3,2-c]pyridin-2-yl)-7-[4-(propan-2-yl)piperazin-1-yl]-2H-chromen-2-one;
3-(6-methylimidazo[1,2-a]pyrazin-2-yl)-7-(1-methylpiperidin-4-yl)-2H-chromen-2-one;
3-(6,8-dimethylimidazo[1,2-a]pyrazin-2-yl)-7-(1-propylpiperidin-4-yl)-2H-chromen-2-one;
7-[1-(2-hydroxyethyl)piperidin-4-yl]-3-(6-methylimidazo[1,2-a]pyrazin-2-yl)-2H-chromen-2-one;
7-(1-ethylpiperidin-4-yl)-3-(6-methylimidazo[1,2-a]pyrazin-2-yl)-2H-chromen-2-one;
3-[2-methyl-3-(1,2,3,6-tetrahydropyridin-4-yl)imidazo[1,2-b]pyridazin-6-yl]-7-(1,2,3,6-tetrahydropyridin-4-yl)-2H-chromen-2-one;
7-[(dimethylamino)methyl]-3-(6,8-dimethylimidazo[1,2-a]pyrazin-2-yl)-2H-chromen-2-one;
3-(6,8-dimethylimidazo[1,2-a]pyrazin-2-yl)-7-(piperidin-1-ylmethyl)-2H-chromen-2-one;
3-(6,8-dimethylimidazo[1,2-a]pyrazin-2-yl)-7-(piperazin-1-ylmethyl)-2H-chromen-2-one;
3-(6,8-dimethylimidazo[1,2-a]pyrazin-2-yl)-7-[(4-methylpiperazin-1-yl)methyl]-2H-chromen-2-one;
3-(6,8-dimethylimidazo[1,2-a]pyrazin-2-yl)-7-[(propan-2-ylamino)methyl]-2H-chromen-2-one;
3-(6,8-dimethylimidazo[1,2-a]pyrazin-2-yl)-7-(1H-imidazol-1-ylmethyl)-2H-chromen-2-one;
3-(6,8-dimethylimidazo[1,2-a]pyrazin-2-yl)-7-(4-ethyl-3-methylpiperazin-1-yl)-2H-chromen-2-one;
3-(4,6-dimethylpyrazolo[1,5-a]pyrazin-2-yl)-7-(1-ethylpiperidin-4-yl)-2H-chromen-2-one;
7-(1-cyclopropylpiperidin-4-yl)-3-(6,8-dimethylimidazo[1,2-a]pyrazin-2-yl)-2H-chromen-2-one;
3-(6,8-dimethylimidazo[1,2-a]pyrazin-2-yl)-7-[1-(oxetan-3-yl)piperidin-4-yl]-2H-chromen-2-one;
3-(2-methyl-2H-indazol-5-yl)-7-(piperidin-4-yl)-2H-chromen-2-one;
7-[3-(dimethylamino)propyl]-3-(6,8-dimethylimidazo[1,2-a]pyrazin-2-yl)-2H-chromen-2-one;
3-(6,8-dimethylimidazo[1,2-a]pyrazin-2-yl)-7-[3-(propan-2-ylamino)propyl]-2H-chromen-2-one;
3-(6,8-dimethylimidazo[1,2-a]pyrazin-2-yl)-7-[3-(piperazin-1-yl)propyl]-2H-chromen-2-one;
3-(6,8-dimethylimidazo[1,2-a]pyrazin-2-yl)-7-[3-(4-methylpiperazin-1-yl)propyl]-2H-chromen-2-one;
7-[1-(2-hydroxyethyl)piperidin-4-yl]-3-(2-methyl-2H-indazol-5-yl)-2H-chromen-2-one;
3-(2-methyl-2H-indazol-5-yl)-7-(1-methylpiperidin-4-yl)-2H-chromen-2-one;
7-(1-ethylpiperidin-4-yl)-3-(2-methyl-2H-indazol-5-yl)-2H-chromen-2-one;
7-[2-(dimethylamino)ethyl]-3-(6,8-dimethylimidazo[1,2-a]pyrazin-2-yl)-2H-chromen-2-one;
3-(6,8-dimethylimidazo[1,2-a]pyrazin-2-yl)-7-[2-(propan-2-ylamino)ethyl]-2H-chromen-2-one;
3-(6,8-dimethylimidazo[1,2-a]pyrazin-2-yl)-7-[2-(piperazin-1-yl)ethyl]-2H-chromen-2-one;
3-(6,8-dimethylimidazo[1,2-a]pyrazin-2-yl)-7-[(1-methylpiperidin-4-yl)oxy]-2H-chromen-2-one;
3-(6-methylimidazo[1,2-a]pyrazin-2-yl)-7-(piperidin-4-yl)-2H-chromen-2-one;
7-(1-cyclobutylpiperidin-4-yl)-3-(6-methylimidazo[1,2-a]pyrazin-2-yl)-2H-chromen-2-one;
3-(6,8-dimethylimidazo[1,2-a]pyrazin-2-yl)-7-{2-[(2-hydroxyethyl)amino]ethyl}-2H-chromen-2-one;
3-(6,8-dimethylimidazo[1,2-a]pyrazin-2-yl)-7-{2-[(2-hydroxyethyl)(methyl)amino]ethyl}-2H-chromen-2-one;
3-(6,8-dimethylimidazo[1,2-a]pyrazin-2-yl)-7-{2-[(1-hydroxypropan-2-yl)amino]ethyl}-2H-chromen-2-one;
7-{2-[(1,3-dihydroxypropan-2-yl)amino]ethyl}-3-(6,8-dimethylimidazo[1,2-a]pyrazin-2-yl)-2H-chromen-2-one;
3-(6,8-dimethylimidazo[1,2-a]pyrazin-2-yl)-7-{2-[(2R)-2-(hydroxymethyl)pyrrolidin-1-yl]ethyl}-2H-chromen-2-one;
7-{2-[bis(2-hydroxyethyl)amino]ethyl}-3-(6,8-dimethylimidazo[1,2-a]pyrazin-2-yl)-2H-chromen-2-one;
7-[2-(dimethylamino)ethoxy]-3-(6,8-dimethylimidazo[1,2-a]pyrazin-2-yl)-2H-chromen-2-one;
3-(6,8-dimethylimidazo[1,2-a]pyrazin-2-yl)-7-[2-(propan-2-ylamino)ethoxy]-2H-chromen-2-one;
3-(6-methylimidazo[1,2-a]pyrazin-2-yl)-7-[1-(oxetan-3-yl)piperidin-4-yl]-2H-chromen-2-one;
3-(6,8-dimethylimidazo[1,2-a]pyrazin-2-yl)-7-{3-[(2-hydroxyethyl)amino]propyl}-2H-chromen-2-one;

3-(6,8-dimethylimidazo[1,2-a]pyrazin-2-yl)-7-{3-[(2-hydroxyethyl)(methyl)amino]propyl}-2H-chromen-2-one;

3-(6,8-dimethylimidazo[1,2-a]pyrazin-2-yl)-7-{3-[(1-hydroxypropan-2-yl)amino]propyl}-2H-chromen-2-one;

7-{3-[(1,3-dihydroxypropan-2-yl)amino]propyl}-3-(6,8-dimethylimidazo[1,2-a]pyrazin-2-yl)-2H-chromen-2-one;

3-(6,8-dimethylimidazo[1,2-a]pyrazin-2-yl)-7-{3-[(2R)-2-(hydroxymethyl)pyrrolidin-1-yl]propyl}-2H-chromen-2-one;

3-(6,8-dimethylimidazo[1,2-a]pyrazin-2-yl)-7-[3-(morpholin-4-yl)propyl]-2H-chromen-2-one;

7-{3-[bis(2-hydroxyethyl)amino]propyl}-3-(6,8-dimethylimidazo[1,2-a]pyrazin-2-yl)-2H-chromen-2-one;

3-(6,8-dimethylimidazo[1,2-a]pyrazin-2-yl)-7-[2-(morpholin-4-yl)ethyl]-2H-chromen-2-one;

3-(6-methylimidazo[1,2-a]pyrazin-2-yl)-7-(1-propylpiperidin-4-yl)-2H-chromen-2-one;

3-(6,8-dimethylimidazo[1,2-a]pyrazin-2-yl)-7-[(3S)-4-(2-hydroxyethyl)-3-methylpiperazin-1-yl]-2H-chromen-2-one;

3-(6,8-dimethylimidazo[1,2-a]pyrazin-2-yl)-7-{[(3R)-1-methylpyrrolidin-3-yl]oxy}-2H-chromen-2-one;

3-(6,8-dimethylimidazo[1,2-a]pyrazin-2-yl)-7-{[(3R)-1-ethylpyrrolidin-3-yl]oxy}-2H-chromen-2-one;

3-(6,8-dimethylimidazo[1,2-a]pyrazin-2-yl)-7-{[(3R)-1-(propan-2-yl)pyrrolidin-3-yl]oxy}-2H-chromen-2-one;

3-(6,8-dimethylimidazo[1,2-a]pyrazin-2-yl)-7-{[(3R)-1-(2-hydroxyethyl)pyrrolidin-3-yl]oxy}-2H-chromen-2-one;

3-(6,8-dimethylimidazo[1,2-a]pyrazin-2-yl)-7-{[(3R)-1-(1-hydroxypropan-2-yl)pyrrolidin-3-yl]oxy}-2H-chromen-2-one;

3-(6,8-dimethylimidazo[1,2-a]pyrazin-2-yl)-7-[(3S)-4-(2-fluoroethyl)-3-methylpiperazin-1-yl]-2H-chromen-2-one;

7-[2-(diethylamino)ethoxy]-3-(6,8-dimethylimidazo[1,2-a]pyrazin-2-yl)-2H-chromen-2-one;

7-{2-[bis(2-hydroxyethyl)amino]ethoxy}-3-(6,8-dimethylimidazo[1,2-a]pyrazin-2-yl)-2H-chromen-2-one;

3-(6,8-dimethylimidazo[1,2-a]pyrazin-2-yl)-7-(piperidin-4-yloxy)-2H-chromen-2-one;

3-(6,8-dimethylimidazo[1,2-a]pyrazin-2-yl)-7-[(1-ethylpiperidin-4-yl)oxy]-2H-chromen-2-one;

3-(6,8-dimethylimidazo[1,2-a]pyrazin-2-yl)-7-{[1-(2-hydroxyethyl)piperidin-4-yl]oxy}-2H-chromen-2-one;

3-(6,8-dimethylimidazo[1,2-a]pyrazin-2-yl)-7-[(3S)-4-(3-fluoropropyl)-3-methylpiperazin-1-yl]-2H-chromen-2-one;

3-(6,8-dimethylimidazo[1,2-a]pyrazin-2-yl)-7-{[1-(propan-2-yl)piperidin-4-yl]oxy}-2H-chromen-2-one;

7-[4-(dimethylamino)butyl]-3-(6,8-dimethylimidazo[1,2-a]pyrazin-2-yl)-2H-chromen-2-one;

3-(6,8-dimethylimidazo[1,2-a]pyrazin-2-yl)-7-{4-[(2-hydroxyethyl)(methyl)amino]butyl}-2H-chromen-2-one;

3-(6,8-dimethylimidazo[1,2-a]pyrazin-2-yl)-7-{4-[(2R)-2-(hydroxymethyl)pyrrolidin-1-yl]butyl}-2H-chromen-2-one;

3-(6,8-dimethylimidazo[1,2-a]pyrazin-2-yl)-7-[4-(piperazin-1-yl)butyl]-2H-chromen-2-one;

3-(6,8-dimethylimidazo[1,2-a]pyrazin-2-yl)-7-[1-(3-fluoropropyl)piperidin-4-yl]-2H-chromen-2-one;

3-(6,8-dimethylimidazo[1,2-a]pyrazin-2-yl)-7-[(3S)-4-(3-hydroxypropyl)-3-methylpiperazin-1-yl]-2H-chromen-2-one;

7-[3-(dimethylamino)propyl]-3-(2-methylimidazo[1,2-a]pyridin-6-yl)-2H-chromen-2-one;

7-[3-(dimethylamino)propyl]-3-(8-fluoro-2-methylimidazo[1,2-a]pyridin-6-yl)-2H-chromen-2-one;

7-[3-(dimethylamino)propyl]-3-(8-ethyl-2-methylimidazo[1,2-a]pyridin-6-yl)-2H-chromen-2-one;

3-(6,8-dimethylimidazo[1,2-a]pyrazin-2-yl)-7-[2-(methylamino)ethyl]-2H-chromen-2-one;

3-(6,8-dimethylimidazo[1,2-a]pyrazin-2-yl)-7-[3-(methylamino)propyl]-2H-chromen-2-one;

3-(8-fluoro-2-methylimidazo[1,2-a]pyridin-6-yl)-7-[3-(methylamino)propyl]-2H-chromen-2-one;

3-(6,8-dimethylimidazo[1,2-a]pyrazin-2-yl)-7-[1-(2-methylpropyl)piperidin-4-yl]-2H-chromen-2-one;

7-{[1-(1,3-dihydroxypropan-2-yl)piperidin-4-yl]oxy}-3-(6,8-dimethylimidazo[1,2-a]pyrazin-2-yl)-2H-chromen-2-one;

3-(6-methylimidazo[1,2-a]pyrazin-2-yl)-7-[1-(2-methylpropyl)piperidin-4-yl]-2H-chromen-2-one;

7-[1-(3-fluoropropyl)piperidin-4-yl]-3-(6-methylimidazo[1,2-a]pyrazin-2-yl)-2H-chromen-2-one;

3-(6,8-dimethylimidazo[1,2-a]pyrazin-2-yl)-7-[2-(pyrrolidin-1-yl)ethoxy]-2H-chromen-2-one;

7-(4-aminopiperidin-1-yl)-3-(6,8-dimethylimidazo[1,2-a]pyrazin-2-yl)-2H-chromen-2-one;

7-(4-amino-4-methylpiperidin-1-yl)-3-(6,8-dimethylimidazo[1,2-a]pyrazin-2-yl)-2H-chromen-2-one;

7-[4-(dimethylamino)piperidin-1-yl]-3-(6,8-dimethylimidazo[1,2-a]pyrazin-2-yl)-2H-chromen-2-one;

7-[4-(diethylamino)piperidin-1-yl]-3-(6,8-dimethylimidazo[1,2-a]pyrazin-2-yl)-2H-chromen-2-one;

3-(6,8-dimethylimidazo[1,2-a]pyrazin-2-yl)-7-[4-(propan-2-ylamino)piperidin-1-yl]-2H-chromen-2-one;

7-[4-(cyclobutylamino)piperidin-1-yl]-3-(6,8-dimethylimidazo[1,2-a]pyrazin-2-yl)-2H-chromen-2-one;

3-(6,8-dimethylimidazo[1,2-a]pyrazin-2-yl)-7-{4-[(1-hydroxypropan-2-yl)amino]piperidin-1-yl}-2H-chromen-2-one;

3-(6,8-dimethylimidazo[1,2-a]pyrazin-2-yl)-7-[3-(ethylamino)propyl]-2H-chromen-2-one;

7-(3-aminopropyl)-3-(6,8-dimethylimidazo[1,2-a]pyrazin-2-yl)-2H-chromen-2-one;

7-{4-[bis(2-hydroxyethyl)amino]piperidin-1-yl}-3-(6,8-dimethylimidazo[1,2-a]pyrazin-2-yl)-2H-chromen-2-one;

7-{4-[(1,3-dihydroxypropan-2-yl)amino]piperidin-1-yl}-3-(6,8-dimethylimidazo[1,2-a]pyrazin-2-yl)-2H-chromen-2-one;

3-(6,8-dimethylimidazo[1,2-a]pyrazin-2-yl)-7-[2-(ethylamino)ethoxy]-2H-chromen-2-one;

3-(6,8-dimethylimidazo[1,2-a]pyrazin-2-yl)-7-{3-[(2-methoxyethyl)amino]propyl}-2H-chromen-2-one;

3-(6,8-dimethylimidazo[1,2-a]pyrazin-2-yl)-7-{3-[(tetrahydrofuran-2-ylmethyl)amino]propyl}-2H-chromen-2-one;

7-[3-(benzylamino)propyl]-3-(6,8-dimethylimidazo[1,2-a]pyrazin-2-yl)-2H-chromen-2-one;

3-(6,8-dimethylimidazo[1,2-a]pyrazin-2-yl)-7-{3-[(thiophen-3-ylmethyl)amino]propyl}-2H-chromen-2-one;

3-(6,8-dimethylimidazo[1,2-a]pyrazin-2-yl)-7-{3-[(pyridin-2-ylmethyl)amino]propyl}-2H-chromen-2-one;

3-(6,8-dimethylimidazo[1,2-a]pyrazin-2-yl)-7-{3-[(pyridin-4-ylmethyl)amino]propyl}-2H-chromen-2-one;

3-(6,8-dimethylimidazo[1,2-a]pyrazin-2-yl)-7-{2-[ethyl(methyl)amino]ethoxy}-2H-chromen-2-one;

3-(6,8-dimethylimidazo[1,2-a]pyrazin-2-yl)-7-{2-[ethyl(2-hydroxyethyl)amino]ethoxy}-2H-chromen-2-one;

3-(6,8-dimethylimidazo[1,2-a]pyrazin-2-yl)-7-[3-(tetrahydrofuran-3-ylamino)propyl]-2H-chromen-2-one;
3-(6,8-dimethylimidazo[1,2-a]pyrazin-2-yl)-7-{2-[(3R)-3-hydroxypyrrolidin-1-yl]ethoxy}-2H-chromen-2-one;
3-(6,8-dimethylimidazo[1,2-a]pyrazin-2-yl)-7-[3-(2-methylpiperidin-1-yl)azetidin-1-yl]-2H-chromen-2-one;
7-[3-(dimethylamino)azetidin-1-yl]-3-(6,8-dimethylimidazo[1,2-a]pyrazin-2-yl)-2H-chromen-2-one;
7-[3-(diethylamino)azetidin-1-yl]-3-(6,8-dimethylimidazo[1,2-a]pyrazin-2-yl)-2H-chromen-2-one;
7-(2,7-diazaspiro[4.4]non-2-yl)-3-(6,8-dimethylimidazo[1,2-a]pyrazin-2-yl)-2H-chromen-2-one;
3-(6,8-dimethylimidazo[1,2-a]pyrazin-2-yl)-7-(2-{[(2R)-1-hydroxypropan-2-yl]amino}ethoxy)-2H-chromen-2-one;
3-(6,8-dimethylimidazo[1,2-a]pyrazin-2-yl)-7-(2-{[(2S)-1-hydroxypropan-2-yl]amino}ethoxy)-2H-chromen-2-one;
3-(6,8-dimethylimidazo[1,2-a]pyrazin-2-yl)-7-[(2R)-pyrrolidin-2-ylmethoxy]-2H-chromen-2-one;
3-(6,8-dimethylimidazo[1,2-a]pyrazin-2-yl)-7-(2,2,6,6-tetramethyl-1,2,3,6-tetrahydropyridin-4-yl)-2H-chromen-2-one;
7-[(3R)-3-(aminomethyl)pyrrolidin-1-yl]-3-(6,8-dimethylimidazo[1,2-a]pyrazin-2-yl)-2H-chromen-2-one;
3-(6,8-dimethylimidazo[1,2-a]pyrazin-2-yl)-7-[3-(piperidin-1-yl)azetidin-1-yl]-2H-chromen-2-one;
3-(6,8-dimethylimidazo[1,2-a]pyrazin-2-yl)-7-[4-(methylamino)butyl]-2H-chromen-2-one;
3-(6,8-dimethylimidazo[1,2-a]pyrazin-2-yl)-7-[2-(piperidin-1-yl)ethoxy]-2H-chromen-2-one;
3-(6,8-dimethylimidazo[1,2-a]pyrazin-2-yl)-7-{2-[(3S)-3-hydroxypyrrolidin-1-yl]ethoxy}-2H-chromen-2-one;
3-(6,8-dimethylimidazo[1,2-a]pyrazin-2-yl)-7-{2-[(1-hydroxy-2-methylpropan-2-yl)amino]ethoxy}-2H-chromen-2-one;
3-(6,8-dimethylimidazo[1,2-a]pyrazin-2-yl)-7-[2-(morpholin-4-yl)ethoxy]-2H-chromen-2-one;
3-(6,8-dimethylimidazo[1,2-a]pyrazin-2-yl)-7-[2-(4-hydroxypiperidin-1-yl)ethoxy]-2H-chromen-2-one;
3-(6,8-dimethylimidazo[1,2-a]pyrazin-2-yl)-7-(1-ethyl-4-fluoropiperidin-4-yl)-2H-chromen-2-one;
3-(6,8-dimethylimidazo[1,2-a]pyrazin-2-yl)-7-{2-[(2-hydroxyethyl)amino]ethoxy}-2H-chromen-2-one;
3-(6,8-dimethylimidazo[1,2-a]pyrazin-2-yl)-7-{2-[(2-methoxyethyl)amino]ethoxy}-2H-chromen-2-one;
3-(6,8-dimethylimidazo[1,2-a]pyrazin-2-yl)-7-{2-[(2-hydroxypropyl)amino]ethoxy}-2H-chromen-2-one;
3-(6,8-dimethylimidazo[1,2-a]pyrazin-2-yl)-7-[4-(2-hydroxy-2-methylpropyl)piperazin-1-yl]-2H-chromen-2-one;
7-[3-(aminomethyl)azetidin-1-yl]-3-(6,8-dimethylimidazo[1,2-a]pyrazin-2-yl)-2H-chromen-2-one;
7-[(3S)-3-(aminomethyl)pyrrolidin-1-yl]-3-(6,8-dimethylimidazo[1,2-a]pyrazin-2-yl)-2H-chromen-2-one;
7-{(3R)-3-[(dimethylamino)methyl]pyrrolidin-1-yl}-3-(6,8-dimethylimidazo[1,2-a]pyrazin-2-yl)-2H-chromen-2-one;
7-{3-[(dimethylamino)methyl]azetidin-1-yl}-3-(6,8-dimethylimidazo[1,2-a]pyrazin-2-yl)-2H-chromen-2-one;
7-{(3S)-3-[(dimethylamino)methyl]pyrrolidin-1-yl}-3-(6,8-dimethylimidazo[1,2-a]pyrazin-2-yl)-2H-chromen-2-one;
7-[2-(diethylamino)ethyl]-3-(6,8-dimethylimidazo[1,2-a]pyrazin-2-yl)-2H-chromen-2-one;
7-[3-(diethylamino)propyl]-3-(6,8-dimethylimidazo[1,2-a]pyrazin-2-yl)-2H-chromen-2-one;
7-[4-(diethylamino)butyl]-3-(6,8-dimethylimidazo[1,2-a]pyrazin-2-yl)-2H-chromen-2-one;
7-(2,6-diazaspiro[3.3]hept-2-yl)-3-(6,8-dimethylimidazo[1,2-a]pyrazin-2-yl)-2H-chromen-2-one;
3-(6,8-dimethylimidazo[1,2-a]pyrazin-2-yl)-7-(6-methyl-2,6-diazaspiro[3.3]hept-2-yl)-2H-chromen-2-one;
2-[3-(6,8-dimethylimidazo[1,2-a]pyrazin-2-yl)-2-oxo-2H-chromen-7-yl]hexahydropyrrolo[1,2-a]pyrazin-6(2H)-one;
1-[3-(6,8-dimethylimidazo[1,2-a]pyrazin-2-yl)-2-oxo-2H-chromen-7-yl]piperidine-4-carbonitrile;
3-(6,8-dimethylimidazo[1,2-a]pyrazin-2-yl)-7-(4-hydroxypiperidin-1-yl)-2H-chromen-2-one;
7-(2,7-diazaspiro[3.5]non-7-yl)-3-(6,8-dimethylimidazo[1,2-a]pyrazin-2-yl)-2H-chromen-2-one;
7-(6-amino-2-azaspiro[3.3]hept-2-yl)-3-(6,8-dimethylimidazo[1,2-a]pyrazin-2-yl)-2H-chromen-2-one;
3-(imidazo[1,2-a]pyridin-6-yl)-7-(4-methylpiperazin-1-yl)-2H-chromen-2-one;
7-[(8aS)-hexahydropyrrolo[1,2-a]pyrazin-2(1H)-yl]-3-(imidazo[1,2-a]pyridin-6-yl)-2H-chromen-2-one;
3-(imidazo[1,2-a]pyridin-6-yl)-7-(piperazin-1-yl)-2H-chromen-2-one;
3-(imidazo[1,2-a]pyridin-6-yl)-7-[(3S)-3-methylpiperazin-1-yl]-2H-chromen-2-one;
3-(8-fluoro-2-methylimidazo[1,2-a]pyridin-6-yl)-7-(4-methylpiperazin-1-yl)-2H-chromen-2-one;
3-(8-fluoro-2-methylimidazo[1,2-a]pyridin-6-yl)-7-[(8aS)-hexahydropyrrolo[1,2-a]pyrazin-2(1H)-yl]-2H-chromen-2-one;
3-(8-fluoro-2-methylimidazo[1,2-a]pyridin-6-yl)-7-[(3S)-3-methylpiperazin-1-yl]-2H-chromen-2-one;
7-(2,6-diazaspiro[3.3]hept-2-yl)-3-(8-fluoro-2-methylimidazo[1,2-a]pyridin-6-yl)-2H-chromen-2-one; and
3-(8-fluoro-2-methylimidazo[1,2-a]pyridin-6-yl)-7-(piperazin-1-yl)-2H-chromen-2-one, or a salt, isotopologue, stereoisomer, racemate, enantiomer, diastereomer or tautomer thereof.

4. The compound of claim 3, wherein the compound is selected from:
7-(piperazin-1-yl)-3-[4-(trifluoromethyl)-1,3-benzoxazol-2-yl]-2H-chromen-2-one trifluoroacetate;
7-(piperazin-1-yl)-3-[4-(trifluoromethyl)-1,3-benzoxazol-2-yl]-2H-chromen-2-one hydrochloride;
7-(piperazin-1-yl)-3-[7-(trifluoromethyl)-1,3-benzoxazol-2-yl]-2H-chromen-2-one trifluoroacetate;
7-(piperazin-1-yl)-3-[7-(trifluoromethyl)-1,3-benzoxazol-2-yl]-2H-chromen-2-one hydrochloride;
2-oxo-N-phenyl-7-(piperazin-1-yl)-2H-chromene-3-carboxamide trifluoroacetate;
3-(1,3-benzothiazol-2-yl)-7-(piperazin-1-yl)-2H-chromen-2-one hydrochloride;
3-(4-chloro-1,3-benzothiazol-2-yl)-7-(piperazin-1-yl)-2H-chromen-2-one hydrochloride;
3-(7-chloro-1,3-benzothiazol-2-yl)-7-(piperazin-1-yl)-2H-chromen-2-one hydrochloride;
3-(4-chloro-1,3-benzothiazol-2-yl)-7-(piperidin-4-yl)-2H-chromen-2-one hydrochloride;
3-(5-fluoro-1,3-benzoxazol-2-yl)-7-(piperazin-1-yl)-2H-chromen-2-one hydrochloride;
3-(4-methyl-1,3-benzoxazol-2-yl)-7-(piperazin-1-yl)-2H-chromen-2-one hydrochloride;
3-(4-fluoro-1,3-benzoxazol-2-yl)-7-(piperazin-1-yl)-2H-chromen-2-one hydrochloride;

7-(piperazin-1-yl)-3-[4-(trifluoromethyl)-1,3-thiazol-2-yl]-2H-chromen-2-one trifluoroacetate;

7-(piperazin-1-yl)-3-[4-(trifluoromethyl)-1,3-thiazol-2-yl]-2H-chromen-2-one hydrochloride;

7-(4-methylpiperazin-1-yl)-3-[4-(trifluoromethyl)-1,3-thiazol-2-yl]-2H-chromen-2-one trifluoroacetate;

3-(4-iodo-1,3-benzoxazol-2-yl)-7-(piperazin-1-yl)-2H-chromen-2-one hydrochloride;

3-(4-chloro-1,3-benzoxazol-2-yl)-7-(piperazin-1-yl)-2H-chromen-2-one hydrochloride;

3-([1,3]oxazolo[4,5-b]pyridin-2-yl)-7-(piperazin-1-yl)-2H-chromen-2-one hydrochloride;

7-[(1S,4S)-2,5-diazabicyclo[2.2.1]hept-2-yl]-3-(imidazo[1,2-a]pyrimidin-2-yl)-2H-chromen-2-one hydrochloride (1:3);

3-(3-methylimidazo[2,1-b][1,3]thiazol-6-yl)-7-(piperazin-1-yl)-2H-chromen-2-one hydrochloride (1:3);

7-(1,4-diazepan-1-yl)-3-(imidazo[1,2-a]pyrimidin-2-yl)-2H-chromen-2-one hydrochloride;

3-(imidazo[1,2-a]pyrimidin-2-yl)-7-(piperidin-4-yloxy)-2H-chromen-2-one hydrochloride;

3-(2-methylpyrimidin-4-yl)-7-(piperazin-1-yl)-2H-chromen-2-one hydrochloride;

3-(2-cyclopropylpyrimidin-4-yl)-7-(piperazin-1-yl)-2H-chromen-2-one hydrochloride;

7-(piperazin-1-yl)-3-[2-(propan-2-yl)pyrimidin-4-yl]-2H-chromen-2-one hydrochloride;

3-(imidazo[1,2-a]pyrimidin-2-yl)-7-[(3R)-pyrrolidin-3-yloxy]-2H-chromen-2-one hydrochloride (1:2);

3-(7-methylimidazo[1,2-a]pyrimidin-2-yl)-7-[(3R)-pyrrolidin-3-yloxy]-2H-chromen-2-one hydrochloride (1:2);

3-(7-methylimidazo[1,2-a]pyridin-2-yl)-7-[(3R)-pyrrolidin-3-yloxy]-2H-chromen-2-one hydrochloride (1:2);

3-(imidazo[2,1-b][1,3]thiazol-6-yl)-7-[(3R)-pyrrolidin-3-yloxy]-2H-chromen-2-one hydrochloride (1:2);

3-(2-methylimidazo[2,1-b][1,3]thiazol-6-yl)-7-[(3R)-pyrrolidin-3-yloxy]-2H-chromen-2-one hydrochloride (1:2);

3-(6-methylimidazo[1,2-a]pyridin-2-yl)-7-[(3R)-pyrrolidin-3-yloxy]-2H-chromen-2-one hydrochloride (1:2);

3-(6-methylimidazo[1,2-a]pyrimidin-2-yl)-7-[(3R)-pyrrolidin-3-yloxy]-2H-chromen-2-one hydrochloride (1:2);

7-[(1-benzylpyrrolidin-3-yl)(methyl)amino]-3-(7-methylimidazo[1,2-a]pyrimidin-2-yl)-2H-chromen-2-one acetate;

7-[(3R)-3,4-dimethylpiperazin-1-yl]-3-(8-methoxy-6-methylimidazo[1,2-a]pyrazin-2-yl)-2H-chromen-2-one acetate (1:2);

7-[(3R)-3,4-dimethylpiperazin-1-yl]-3-(8-hydroxy-6-methylimidazo[1,2-a]pyrazin-2-yl)-2H-chromen-2-one acetate;

7-[(3S)-3,4-dimethylpiperazin-1-yl]-3-(2-methyl-1,3-benzothiazol-6-yl)-2H-chromen-2-one acetate (2:1);

7-[(3S)-4-ethyl-3-methylpiperazin-1-yl]-3-(2-methyl-1,3-benzothiazol-6-yl)-2H-chromen-2-one acetate;

3-(6,8-dimethylimidazo[1,2-a]pyrazin-2-yl)-7-[(3S)-3-ethyl-4-methylpiperazin-1-yl]-2H-chromen-2-one acetate; and 7-[(3S)-3,4-diethylpiperazin-1-yl]-3-(6,8-dimethylimidazo[1,2-a]pyrazin-2-yl)-2H-chromen-2-one acetate (1:2), or a free base, stereoisomer, racemate, enantiomer, diastereomer or tautomer thereof.

5. A pharmaceutical composition comprising an effective amount of the compound of claim 1 and a pharmaceutically acceptable carrier, excipient or diluent.

\* \* \* \* \*

UNITED STATES PATENT AND TRADEMARK OFFICE
CERTIFICATE OF CORRECTION

PATENT NO. : 9,617,268 B2  Page 1 of 1
APPLICATION NO. : 14/369294
DATED : April 11, 2017
INVENTOR(S) : Woll et al.

It is certified that error appears in the above-identified patent and that said Letters Patent is hereby corrected as shown below:

In the Specification

At Column 1, Line 23, replace "PCT Therapeutics, Inc. and F. Hoffmann-La Roche AG." with
-- F. Hoffmann-La Roche Ltd, Hoffmann-La Roche Inc., PTC Therapeutics, Inc. and Spinal Muscular Atrophy Foundation --

Signed and Sealed this
Eighth Day of October, 2019

Andrei Iancu
*Director of the United States Patent and Trademark Office*